US012606572B2

(12) United States Patent
Ren et al.

(10) Patent No.: US 12,606,572 B2
(45) Date of Patent: Apr. 21, 2026

(54) SUBSTITUTED HETEROCYCLES AND USES THEREOF

(71) Applicant: Kumquat Biosciences Inc., San Diego, CA (US)

(72) Inventors: Pingda Ren, San Diego, CA (US); Baogen Wu, San Diego, CA (US); Xiaoming Li, San Diego, CA (US); Xiaohui He, San Diego, CA (US); Liansheng Li, San Diego, CA (US)

(73) Assignee: Kumquat Biosciences Inc., San Diego, CA (US)

( * ) Notice: Subject to any disclaimer, the term of this patent is extended or adjusted under 35 U.S.C. 154(b) by 0 days.

(21) Appl. No.: 19/352,234

(22) Filed: Oct. 7, 2025

(65) Prior Publication Data

US 2026/0028357 A1 Jan. 29, 2026

Related U.S. Application Data

(63) Continuation of application No. PCT/US2024/032852, filed on Jun. 6, 2024.

(60) Provisional application No. 63/597,315, filed on Nov. 8, 2023, provisional application No. 63/582,474, filed on Sep. 13, 2023, provisional application No. 63/506,493, filed on Jun. 6, 2023.

(51) Int. Cl.

*C07D 519/00* (2006.01)
*A61K 31/553* (2006.01)
*A61P 35/00* (2006.01)

(52) U.S. Cl.

CPC .......... *C07D 519/00* (2013.01); *A61K 31/553* (2013.01); *A61P 35/00* (2018.01)

(58) Field of Classification Search

CPC ...... C07D 519/00; A61P 35/00; A61K 31/553
See application file for complete search history.

(56) References Cited

U.S. PATENT DOCUMENTS

| | | | |
|---|---|---|---|
| 12,209,102 | B2 | 1/2025 | Ren et al. |
| 2024/0116951 | A1 | 4/2024 | Li et al. |
| 2024/0270736 | A1 | 8/2024 | Wu et al. |
| 2024/0368191 | A1 | 11/2024 | Li et al. |
| 2024/0425525 | A1 | 12/2024 | Ren et al. |

FOREIGN PATENT DOCUMENTS

| | | | | |
|---|---|---|---|---|
| CN | 116332948 | A | 6/2023 | |
| WO | WO-2013155223 | A1 | 10/2013 | |
| WO | WO-2015054572 | A1 | 4/2015 | |
| WO | WO-2017172979 | A1 | 10/2017 | |
| WO | WO-2018078360 | A1 * | 5/2018 | .............. A61P 35/00 |
| WO | WO-2018217651 | A1 | 11/2018 | |
| WO | WO-2019099524 | A1 | 5/2019 | |
| WO | WO-2019215203 | A1 | 11/2019 | |
| WO | WO-2020081282 | A1 | 4/2020 | |
| WO | WO-2020097537 | A2 | 5/2020 | |
| WO | WO-2020113071 | A1 | 6/2020 | |
| WO | WO-2021041671 | A1 | 3/2021 | |
| WO | WO-2021108683 | A1 | 6/2021 | |
| WO | WO-2021118877 | A1 | 6/2021 | |
| WO | WO-2022132200 | A1 | 6/2022 | |
| WO | WO-2022216762 | A1 | 10/2022 | |
| WO | WO-2023004102 | A2 | 1/2023 | |
| WO | WO-2023172737 | A1 | 9/2023 | |
| WO | WO-2024009191 | A1 | 1/2024 | |
| WO | WO-2024015262 | A1 | 1/2024 | |
| WO | WO-2024032702 | A1 | 2/2024 | |
| WO | WO-2024032747 | A1 | 2/2024 | |
| WO | WO-2024041573 | A1 | 2/2024 | |
| WO | WO-2024041621 | A1 | 2/2024 | |
| WO | WO-2024083168 | A1 | 4/2024 | |
| WO | WO-2024085661 | A1 | 4/2024 | |
| WO | WO-2024091409 | A1 | 5/2024 | |
| WO | WO-2024104453 | A1 | 5/2024 | |
| WO | WO-2024197503 | A1 | 10/2024 | |
| WO | WO-2024218686 | A1 | 10/2024 | |
| WO | WO-2024227091 | A1 | 10/2024 | |
| WO | WO-2024235286 | A1 | 11/2024 | |
| WO | WO-2024238633 | A2 | 11/2024 | |
| WO | WO-2024254334 | A1 | 12/2024 | |
| WO | WO-2025007000 | A1 | 1/2025 | |
| WO | WO-2025059366 | A1 | 3/2025 | |
| WO | WO-2025076523 | A1 | 4/2025 | |
| WO | WO-2025101776 | A1 | 5/2025 | |
| WO | WO-2025130912 | A1 | 6/2025 | |
| WO | WO-2025167948 | A1 | 8/2025 | |

OTHER PUBLICATIONS

Aaltonen, Niina et al. Piperazine and Piperidine Triazole Ureas as Ultrapotent and Highly Selective Inhibitors of Monoacylglycerol Lipase. Chemistry & Biology 20(3):379-390 (2013).
Adibekian, Alexander et al. Click-generated triazole ureas as ultrapotent in vivo-active serine hydrolase inhibitors. Nature chemical biology 7(7):469-478 (2011).
Cisar, Justin S. et al. Identification of ABX-1431, A Selective Inhibitor of Monoacylglycerol Lipase and Clinical Candidate for Treatment of Neurological Disorders. Journal of Medicinal Chemistry 61(20):9062-9084 (2018).
Co-pending U.S. Appl. No. 19/243,961, filed Jun. 20, 2025.
Co-pending U.S. Appl. No. 19/306,039, filed Aug. 21, 2025.
Co-pending U.S. Appl. No. 19/353,426, filed Oct. 8, 2025.
Deng, Hui, and Weimin Li. Monoacylglycerol Lipase Inhibitors: Modulators for Lipid Metabolism in Cancer Malignancy, Neurological and Metabolic Disorders. Acta Pharmaceutica Sinica B 10(4):582-602 (2020).

(Continued)

*Primary Examiner* — Daniel R Carcanague

(74) *Attorney, Agent, or Firm* — Wilson Sonsini Goodrich & Rosati

(57) ABSTRACT

The present disclosure provides compounds and pharmaceutically acceptable salts thereof, and methods of using the same. The compounds and methods have a range of utilities as therapeutics, diagnostics, and research tools. In particular, the subject compositions and methods are useful for reducing signaling output of oncogenic protein.

20 Claims, 1 Drawing Sheet

Specification includes a Sequence Listing.

(56) References Cited

OTHER PUBLICATIONS

Hensbergen, Albertus Wijnand et al. An Expedient Synthesis of Oxazepino and Oxazocino Quinazolines. Tetrahedron Letters 55(46):6478-6483 (2015).
McAulay, K. et al. Reactivity of Covalent Fragments and Their Role in Fragment Based Drug Discovery. Pharmaceuticals (Basel) 15(11):1366: pp. 1-22 (2022).
McGregor, Lynn M. et al. Expanding the Scope of Electrophiles Capable of Targeting K-Ras Oncogenes. Biochemistry 56(25):3178-3183 (2017).
Niphakis et al. Ace-ylation in the Hole. Nature Chemical Biology 18(11): 1166-1167 ( 2022).
Patel, Jayendra Z. et al. Loratadine Analogues as MAGL Inhibitors. Bioorganic & Medicinal Chemistry Letters 25(7):1436-1442 (2015).
PCT/US2024/032852 International Search Report and Written Opinion dated Sep. 30, 2024.
Shannon et al. Covalent Protein Modification: The Current Landscape of Residue-Specific Electrophiles. Current Opinion in Chemical Biology vol. 24: 18-26 (2015).
Wang, Zhijun and Neidlein, Richard. A Novel Fused Heterocyclic System-synthesis of Substituted 9, 10-dihydro-1,3,4,6,7, 10-hexaazacyclohepta[de]naphthalen-8(7H)-ones. Tetrahedron 54(33):9903-9910 (1998).
Zhang, Z. et al. Chemical Acylation of an Acquired Serine Suppresses Oncogenic Signaling of K-Ras(G12S). Nature Chemical Biology 18(11): 1177-1183 (2022).

* cited by examiner

| | 1 | 20 | 40 | |
|---|---|---|---|---|
| **K-Ras** (SEQ ID No. 9) | mte------- ----ykl vvv gaggvgksal | tiqliqnhfv deydptieds | yrkqvvidge | **49** |
| **H-Ras** (SEQ ID No. 10) | mte------- ----ykl vvv gaggvgksal | tiqliqnhfv deydptieds | yrkqvvidge | **49** |
| **N-Ras** (SEQ ID No. 11) | mte------- ----ykl vvv gaggvgksal | tiqliqnhfv deydptieds | yrkqvvidge | **49** |
| **RalA** (SEQ ID No. 12) | maankpkgqn slalhkvimv gsggvgksal | tlqfmydefv edyeptkads | yrkkvvldge | **60** |
| **RalB** (SEQ ID No. 13) | maankskgqs slalhkvimv gsggvgksal | tlqfmydefv edyeptkads | yrkkvvldge | **60** |

| | 60 | 80 | 100 | |
|---|---|---|---|---|
| **K-Ras** | tclldildta gqeeysamrd qymrtgegfl | cvfainntks fedihhyreq | ikrvkdsed- | **108** |
| **H-Ras** | tclldildta gqeeysamrd qymrtgegfl | cvfainntks fedihqyreq | ikrvkdsdd- | **108** |
| **N-Ras** | tclldildta gqeeysamrd qymrtgegfl | cvfainnsks fadinlyreq | ikrvkdsdd- | **108** |
| **RalA** | evqidildta gqedyaaird nyfrsgegfl | cvfsitemes faatadfreq | ilrvk-eden | **119** |
| **RalB** | evqidildta gqedyaaird nyfrsgegfl | lvfsitehes ftataefreq | ilrvkaeedk | **120** |

SEQUENCE LISTING

```
Sequence total quantity: 13
SEQ ID NO: 1           moltype = AA  length = 188
FEATURE                Location/Qualifiers
source                 1..188
                       mol_type = protein
                       organism = Homo sapiens
SEQUENCE: 1
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ GVDDAFYTLV REIRKHKEKM SKDGKKKKKK  180
SKTKCVIM                                                          188

SEQ ID NO: 2           moltype = AA  length = 188
FEATURE                Location/Qualifiers
source                 1..188
                       mol_type = protein
                       organism = Homo sapiens
SEQUENCE: 2
MTEYKLVVVG ADGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ GVDDAFYTLV REIRKHKEKM SKDGKKKKKK  180
SKTKCVIM                                                          188

SEQ ID NO: 3           moltype = AA  length = 188
FEATURE                Location/Qualifiers
source                 1..188
                       mol_type = protein
                       organism = Homo sapiens
SEQUENCE: 3
MTEYKLVVVG AVGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ GVDDAFYTLV REIRKHKEKM SKDGKKKKKK  180
SKTKCVIM                                                          188

SEQ ID NO: 4           moltype = AA  length = 188
FEATURE                Location/Qualifiers
source                 1..188
                       mol_type = protein
                       organism = Homo sapiens
SEQUENCE: 4
MTEYKLVVVG ASGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ GVDDAFYTLV REIRKHKEKM SKDGKKKKKK  180
SKTKCVIM                                                          188
```

-continued

```
SEQ ID NO: 5            moltype = AA  length = 189
FEATURE                 Location/Qualifiers
source                  1..189
                        mol_type = protein
                        organism = Homo sapiens
SEQUENCE: 5
MTEYKLVVVG AGGVGKSALT IQLIQNHFVD EYDPTIEDSY RKQVVIDGET CLLDILDTAG  60
QEEYSAMRDQ YMRTGEGFLC VFAINNSKSF ADINLYREQI KRVKDSDDVP MVLVGNKCDL  120
PTRTVDTKQA HELAKSYGIP FIETSAKTRQ GVEDAFYTLV REIRQYRMKK LNSSDDGTQG  180
CMGLPCVVM                                                         189

SEQ ID NO: 6            moltype = AA  length = 189
FEATURE                 Location/Qualifiers
source                  1..189
                        mol_type = protein
                        organism = Homo sapiens
SEQUENCE: 6
MTEYKLVVVG ADGVGKSALT IQLIQNHFVD EYDPTIEDSY RKQVVIDGET CLLDILDTAG  60
QEEYSAMRDQ YMRTGEGFLC VFAINNTKSF EDIHQYREQI KRVKDSDDVP MVLVGNKCDL  120
AARTVESRQA QDLARSYGIP YIETSAKTRQ GVEDAFYTLV REIRQHKLRK LNPPDESGPG  180
CMSCKCVLS                                                         189

SEQ ID NO: 7            moltype = AA  length = 189
FEATURE                 Location/Qualifiers
source                  1..189
                        mol_type = protein
                        organism = Homo sapiens
SEQUENCE: 7
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHQYREQI KRVKDSDDVP MVLVGNKCDL  120
AARTVESRQA QDLARSYGIP YIETSAKTRQ GVEDAFYTLV REIRQHKLRK LNPPDESGPG  180
CMSCKCVLS                                                         189

SEQ ID NO: 8            moltype = AA  length = 189
FEATURE                 Location/Qualifiers
source                  1..189
                        mol_type = protein
                        organism = Homo sapiens
SEQUENCE: 8
MTEYKLVVVG ADGVGKSALT IQLIQNHFVD EYDPTIEDSY RKQVVIDGET CLLDILDTAG  60
QEEYSAMRDQ YMRTGEGFLC VFAINNSKSF ADINLYREQI KRVKDSDDVP MVLVGNKCDL  120
PTRTVDTKQA HELAKSYGIP FIETSAKTRQ GVEDAFYTLV REIRQYRMKK LNSSDDGTQG  180
CMGLPCVVM                                                         189

SEQ ID NO: 9            moltype = AA  length = 108
FEATURE                 Location/Qualifiers
source                  1..108
                        mol_type = protein
                        organism = Homo sapiens
SEQUENCE: 9
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSED              108

SEQ ID NO: 10           moltype = AA  length = 108
FEATURE                 Location/Qualifiers
source                  1..108
                        mol_type = protein
                        organism = Homo sapiens
SEQUENCE: 10
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHQYREQI KRVKDSDD              108

SEQ ID NO: 11           moltype = AA  length = 108
FEATURE                 Location/Qualifiers
source                  1..108
                        mol_type = protein
                        organism = Homo sapiens
SEQUENCE: 11
MTEYKLVVVG AGGVGKSALT IQLIQNHFVD EYDPTIEDSY RKQVVIDGET CLLDILDTAG  60
QEEYSAMRDQ YMRTGEGFLC VFAINNSKSF ADINLYREQI KRVKDSDD              108

SEQ ID NO: 12           moltype = AA  length = 119
FEATURE                 Location/Qualifiers
source                  1..119
                        mol_type = protein
                        organism = Homo sapiens
SEQUENCE: 12
MAANKPKGQN SLALHKVIMV GSGGVGKSAL TLQFMYDEFV EDYEPTKADS YRKKVVLDGE  60
EVQIDILDTA GQEDYAAIRD NYFRSGEGFL CVFSITEMES FAATADFREQ ILRVKEDEN   119
```

-continued

```
SEQ ID NO: 13           moltype = AA  length = 120
FEATURE                 Location/Qualifiers
source                  1..120
                        mol_type = protein
                        organism = Homo sapiens
SEQUENCE: 13
MAANKSKGQS SLALHKVIMV GSGGVGKSAL TLQFMYDEFV EDYEPTKADS YRKKVVLDGE  60
EVQIDILDTA GQEDYAAIRD NYFRSGEGFL LVFSITEHES FTATAEFREQ ILRVKAEEDK  120
```

SUBSTITUTED HETEROCYCLES AND USES THEREOF

CROSS-REFERENCE

This application is a continuation of International Application No. PCT/US2024/032852, filed Jun. 6, 2024, which claims the benefit of U.S. Provisional Application No. 63/506,493, filed Jun. 6, 2023; U.S. Provisional Application No. 63/582,474, filed Sep. 13, 2023; and U.S. Provisional Application No. 63/597,315, filed Nov. 8, 2023, each incorporated herein by reference in its entirety.

SEQUENCE LISTING

The instant application contains a Sequence Listing which has been submitted electronically in XML format and is hereby incorporated by reference in its entirety. Said XML copy, created on Sep. 30, 2025, is named 56690_770_301_SL.xml and is 13,995 bytes in size.

BACKGROUND

Cancer (e.g., tumor, neoplasm, metastases) is the second leading cause of death worldwide estimated to be responsible for about 10 million deaths each year. Many types of cancers are marked with mutations in one or more proteins involved in various signaling pathways leading to unregulated growth of cancerous cells. In some cases, about 25 to 30 percent (%) of tumors are known to harbor Rat sarcoma (Ras) mutations. In particular, mutations in the Kirsten Ras oncogene (K-Ras) are one of the most frequent Ras mutations detected in human cancers, including lung adenocarcinomas (LUADs) and pancreatic ductal adenocarcinoma (PDAC).

Ras proteins have long been considered "undruggable," due to, in part, high affinity to their substrate guanosine-5'-triphosphate (GTP) and/or their smooth surfaces without any obvious targeting region. The specific G12C Ras gene mutation has been identified as a druggable target to which a number of G12C specific inhibitors have been developed. However, such therapeutics are still of limited application, as the G12C mutation in Ras exhibits a much lower prevalence rate as compared to other known Ras mutations, such as G12D and G12V. Drug resistance and lack of durability impose further limitations to such therapeutics.

SUMMARY

In view of the foregoing, there remains a considerable need for a new design of therapeutics and diagnostics that can specifically target Ras, including wildtype Ras, mutants and/or associated proteins of Ras to reduce Ras signaling output. Of particular interest are Ras inhibitors, including pan Ras inhibitors capable of inhibiting two or more Ras mutants and/or wildtype Ras, as well as mutant-selective inhibitors targeting mutant Ras proteins such as Ras G12D, G12C, G12S, G13D, and/or G12V, for the treatment of Ras-associated diseases (e.g., cancer). Such compositions and methods can be particularly useful for treating a variety of diseases including, but not limited to, cancers and neoplasia conditions. The present disclosure addresses these needs, and provides additional advantages applicable for diagnosis, prognosis, and/or treatment for a wide diversity of diseases.

In an aspect is provided a compound of Formula (I):

(I)

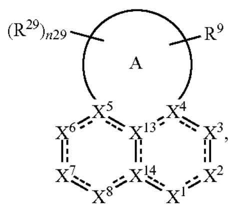

or a pharmaceutically acceptable salt or solvate thereof, wherein:

Ring A is selected from a monocyclic $C_{7-10}$ carbocycle and monocyclic 7- to 10-membered heterocycle;

$X^1$ is selected from $C(R^1)$, $C(R^1)_2$, N, $N(R^{1b})$, O, S, S(O), $S(O)_2$, and C(O);

$X^2$ is selected from $C(R^2)$, $C(R^2)_2$, N, $N(R^{2b})$, O, S, S(O), $S(O)_2$, and C(O);

$X^3$ is selected from $C(R^3)$, $C(R^3)_2$, N, $N(R^{3b})$, O, S, S(O), $S(O)_2$, and C(O);

$X^4$ is selected from C, $C(R^4)$, and N;

$X^5$ is selected from C, $C(R^5)$, and N;

$X^6$ is selected from $C(R^6)$, $C(R^6)_2$, N, $N(R^{6b})$, O, S, S(O), $S(O)_2$, and C(O);

$X^7$ is selected from $C(R^7)$, $C(R^7)(R^{7a})$, and $N(R^{7b})$;

$X^8$ is selected from $C(R^8)$, $C(R^8)_2$, N, $N(R^{8b})$, O, S, S(O), $S(O)_2$, and C(O);

$X^{13}$ is selected from C, $C(R^{13a})$, and N;

$X^{14}$ is selected from C, $C(R^{14a})$, and N;

$R^7$ is $-L^{7a}-R^{17}$; $R^{7b}$ is $-L^{7b}-R^{17}$;

$L^{7a}$ is selected from a bond, $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, —$N(R^{12})$—, —C(O)—, —$N(R^{12})C(O)$—, —$C(O)N(R^{12})$—, —S—, —$S(O)_2$—, —S(O)—, —$P(O)(R^{12})$—, —$N(R^{12})S(O)_2$—, —$N(R^{12})S(O)$—, —$N(R^{12})P(O)(R^{12})$—, —$S(O)_2N(R^{12})$—, —$S(O)N(R^{12})$—, —$P(O)(R^{12})N(R^{12})$—, —$OP(O)(R^{12})$—, and —$P(O)(R^{12})O$—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$;

$L^{7b}$ is selected from a bond, $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —C(O)—, and —$C(O)N(R^{12})$—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$;

$R^9$ is $-L^{19}-R^{19}-L^{19a}-R^{19a}$;

$L^{19}$ is selected from a bond, $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, —$N(R^{12})$—, —C(O)—, —$N(R^{12})C(O)$—, —$C(O)N(R^{12})$—, —S—, —$S(O)_2$—, —S(O)—, —$P(O)(R^{12})$—, —$N(R^{12})S(O)_2$—, —$N(R^{12})S(O)$—, —$N(R^{12})P(O)(R^{12})$—, —$S(O)_2N(R^{12})$—, —$S(O)N(R^{12})$—, —$P(O)(R^{12})N(R^{12})$—, —$OP(O)(R^{12})$—, and —$P(O)(R^{12})O$—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$;

$R^{19}$ is selected from monocyclic $C_{3-8}$ carbocycle and monocyclic 3- to 8-membered heterocycle, wherein the monocyclic $C_{3-8}$ carbocycle and monocyclic 3- to 8-membered heterocycle are optionally substituted with one or more $R^{20}$;

$L^{19a}$ is selected from a bond, $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, —N($R^{12}$)—, —C(O)—, —N($R^{12}$)C(O)—, —C(O)N($R^{12}$)—, —S—, —S(O)$_2$—, —S(O)—, —P(O)($R^{12}$)—, —N($R^{12}$)S(O)$_2$—, —N($R^{12}$)S(O)—, —N($R^{12}$)P(O)($R^{12}$)—, —S(O)$_2$N($R^{12}$)—, —S(O)N($R^{12}$)—, —P(O)($R^{12}$)N($R^{12}$)—, —OP(O)($R^{12}$)—, and —P(O)($R^{12}$)O—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$;

$R^{19a}$ is selected from:

i) 5-membered heteroaryl comprising one or more ring nitrogen atoms, wherein the 5-membered heteroaryl is directly bonded to $L^{19a}$ through an $R^{19a}$ ring nitrogen atom and wherein $R^{19a}$ is optionally substituted with one or more $R^{20}$; and ii) 5- to 12-membered heterocycle comprising three or four ring nitrogen atoms, wherein the 5- to 12-membered heterocycle is optionally substituted with one or more $R^{20}$;

$R^{1b}$, $R^{2b}$, $R^{3b}$, $R^{6b}$, and $R^{8b}$ are independently selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —C(O)O$R^{12}$, —C(O)$R^{12}$, —C(O)N($R^{12}$)($R^{13}$), —C(O)C(O)N($R^{12}$)($R^{13}$), —S(O)$_2R^{12}$, —S(O)(N$R^{12}$)$R^{12}$, —S(O)$_2$N($R^{12}$)($R^{13}$), and —S(═O)(═N$R^{12}$)N($R^{12}$)($R^{13}$), wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$;

$R^1$, $R^2$, $R^3$, $R^4$, $R^5$, $R^6$, $R^{7a}$, $R^8$, $R^{13a}$, $R^{14a}$, and $R^{17}$ are independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —O$R^{12}$, —S$R^{12}$, —N($R^{12}$)($R^{13}$), —C(O)O$R^{12}$, —OC(O)N($R^{12}$)($R^{13}$), —N($R^{12}$)C(O)N($R^{12}$)($R^{13}$), —N($R^{12}$)C(O)O$R^{12}$, —N($R^{12}$)S(O)$_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —S(O)$_2R^{12}$, —S(O)(N$R^{12}$)$R^{12}$, —S(O)$_2$N($R^{12}$)($R^{13}$), and —S(═O)(═N$R^{12}$)N($R^{12}$)($R^{13}$), wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one or more $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one or more $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —O$R^{22}$, —S$R^{22}$, —N($R^{22}$)($R^{23}$), ═N$R^{22}$, ═C($R^{21}$)$_2$, —C(O)O$R^{22}$, —OC(O)N($R^{22}$)($R^{23}$), —N($R^{22}$)C(O)N($R^{22}$)($R^{23}$), —N($R^{22}$)C(O)O$R^{22}$, —N($R^{22}$)S(O)$_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S(O)$_2R^{22}$, —S(O)(N$R^{22}$)$R^{22}$, —S(O)$_2$N($R^{22}$)($R^{23}$)—, and —S(═O)(═N$R^{22}$)N($R^{22}$)($R^{23}$); wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, —O$R^{22}$, —S$R^{22}$, —N($R^{22}$)($R^{23}$), ═N$R^{22}$, ═C($R^{21}$)$_2$, —C(O)O$R^{22}$, —OC(O)N($R^{22}$)($R^{23}$), —N($R^{22}$)C(O)N($R^{22}$)($R^{23}$), —N($R^{22}$)C(O)O$R^{22}$, —N($R^{22}$)S(O)$_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S(O)$_2R^{22}$, —S(O)(N$R^{22}$)$R^{22}$, —S(O)$_2$N($R^{22}$)($R^{23}$), and —S(═O)(═N$R^{22}$)N($R^{22}$)($R^{23}$);

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one or more substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle;

$R^{29}$ is independently selected at each occurrence from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(=O)(=NR^{12})N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$; and wherein two $R^{29}$ attached to the same atom are optionally joined to form oxo;

n29 is selected from 0, 1, 2, 3, 4, 5, 6, 7, 8, 9, 10, 11, 12, and 13; and each ⎓ independently indicates a single or double bond such that all valences are satisfied.

In embodiment of a compound of Formula I, $L^{19a}$ is selected from $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, —$N(R^{12})$—, —C(O)—, —$N(R^{12})C(O)$—, —$C(O)N(R^{12})$—, —S—, —$S(O)_2$—, —S(O)—, —$P(O)(R^{12})$—, —$N(R^{12})S(O)_2$—, —$N(R^{12})S(O)$—, —$N(R^{12})P(O)(R^{12})$—, —$S(O)_2N(R^{12})$—, —$S(O)N(R^{12})$—, —$P(O)(R^{12})N(R^{12})$—, —$OP(O)(R^{12})$—, and —$P(O)(R^{12})O$—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$.

In embodiments of the compound of Formula I, the compound has a formula (IA):

(IA)

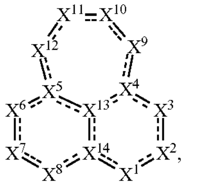

or a pharmaceutically acceptable salt or solvate thereof, wherein:

$X^9$ is selected from $C(R^9)$, $C(R^9)(R^{9a})$, and $N(R^9)$;

$X^{10}$ is selected from $C(R^{10})$, $C(R^{10})_2$, N, $N(R^{10b})$, O, S, S(O), $S(O)_2$, and C(O);

$X^{11}$ is selected from $C(R^{11})$, $C(R^{11})_2$, N, $N(R^{11b})$, O, S, S(O), $S(O)_2$, and C(O);

$X^{12}$ is selected from —$X^{12a}$—, —$X^{12a}$—$X^{12b}$—, —$X^{12a}$—$X^{12b}$—$X^{12c}$—, and —$X^{12a}$—$X^{12b}$—$X^{12c}$—$X^{12d}$—; wherein $X^{12a}$ is directly bonded to $X^5$;

$X^{12a}$, $X^{12b}$, $X^{12c}$, and $X^{12d}$ are independently selected from $C(R^{12})$, $C(R^{12a})_2$, N, $N(R^{12b})$, O, S, S(O), $S(O)_2$, and C(O);

$R^{19a}$ is 5-membered heteroaryl comprising one or more ring nitrogen atoms, wherein the 5-membered heteroaryl is directly bonded to $L^{19a}$ through an $R^{19a}$ ring nitrogen atom and wherein $R^{19a}$ is optionally substituted with one or more $R^{20}$;

$R^{10b}$, $R^{11b}$, and $R^{12b}$ are independently selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-2}$ carbocycle), -(2- to 6-membered heteroalkyl)-($C_{3-2}$ carbocycle), —$C_{0-6}$ alkyl-(3- to 12-membered heterocycle), -(2- to 6-membered heteroalkyl)-(3- to 12-membered heterocycle), —$C(O)OR^{12}$, —$C(O)R^{12}$, —$C(O)N(R^{12})(R^{13})$, —$C(O)C(O)N(R^{12})(R^{13})$, —$S(O)_2R^{12}$, —$S(O)(NR^{12})R^{12}$, —$S(O)_2N(R^{12})(R^{13})$, and —$S(=O)(=NR^{12})N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-2}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$;

$R^{9a}$, $R^{10}$, $R^{11}$, and $R^{12a}$ are independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(=O)(=NR^{12})N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$; and each ⎓ independently indicates a single or double bond such that all valences are satisfied.

In embodiments of a compound of formula I, IA, II, or IIA, $R^{19a}$ is 5-membered heteroaryl having one or two ring nitrogen atoms, wherein the 5-membered heteroaryl is directly bonded to $L^{19a}$ through an $R^{19a}$ ring nitrogen atom and wherein $R^{19a}$ is optionally substituted with one or more $R^{20}$.

In embodiments of a compound of formula I, IA, II, or IIA, $R^{19a}$ is selected from pyrrolyl, imidazolyl, pyrazolyl, oxazolyl, isoxazolyl, thiazolyl, and isothiazolyl; wherein $R^{19a}$ is directly bonded to $L^{19a}$ through an $R^{19a}$ ring nitrogen atom; and wherein $R^{19a}$ is optionally substituted with one or more $R^{20}$.

In embodiments of a compound of formula I, IA, II, or IIA, $R^{19a}$ is selected from pyrrolyl, imidazolyl, and pyrazolyl; wherein $R^{19a}$ is directly bonded to $L^{19a}$ through an $R^{19a}$ ring nitrogen atom; and wherein $R^{19a}$ is optionally substituted with one or more $R^{20}$.

In embodiments of a compound of formula I, the compound has a formula (IB):

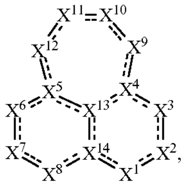

(IB)

or a pharmaceutically acceptable salt or solvate thereof, wherein:

$X^9$ is selected from $C(R^9)$, $C(R^9)(R^{9a})$, and $N(R^9)$;

$X^{10}$ is selected from $C(R^{10})$, $C(R^{10})_2$, N, $N(R^{10b})$, O, S, S(O), $S(O)_2$, and C(O);

$X^{11}$ is selected from $C(R^{11})$, $C(R^{11})_2$, N, $N(R^{11b})$, O, S, S(O), $S(O)_2$, and C(O);

$X^{12}$ is selected from —$X^{12a}$—, —$X^{12a}$—$X^{12b}$—, —$X^{12a}$—$X^{12b}$—$X^{12c}$—, and —$X^{12a}$—$X^{12b}$—$X^{12c}$—$X^{12d}$—; wherein $X^{12a}$ is directly bonded to $X^5$;

$X^{12a}$, $X^{12b}$, $X^{12c}$, and $X^{12d}$ are independently selected from $C(R^{12})$, $C(R^{12a})_2$, N, $N(R^{12b})$, O, S, S(O), $S(O)_2$, and C(O);

$R^{19a}$ is 5- to 12-membered heterocycle comprising three or four ring nitrogen atoms, wherein the 5- to 12-membered heterocycle is optionally substituted with one or more $R^{20}$;

$R^{10b}$, $R^{11b}$, and $R^{12b}$ are independently selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-2}$ carbocycle), -(2- to 6-membered heteroalkyl)-($C_{3-2}$ carbocycle), —$C_{0-6}$ alkyl-(3- to 12-membered heterocycle), -(2- to 6-membered heteroalkyl)-(3- to 12-membered heterocycle), —$C(O)OR^{12}$, —$C(O)R^{12}$, —$C(O)N(R^{12})(R^{13})$, —$C(O)C(O)N(R^{12})(R^{13})$, —$S(O)_2R^{12}$, —$S(O)(NR^{12})R^{12}$, —$S(O)_2N(R^{12})(R^{13})$, and —$S({=}O)({=}NR^{12})N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-2}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$;

$R^{9a}$, $R^{10}$, $R^{11}$, and $R^{12a}$ are independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S({=}O)({=}NR^{12})N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$; and each ═══ independently indicates a single or double bond such that all valences are satisfied.

In embodiments of a compound of formula I, IB, II, or IIA, $R^{19a}$ is a non-aromatic 5- to 12-membered heterocycle comprising three or four ring nitrogen atoms; wherein $R^{19a}$ is optionally substituted with one or more $R^{20}$.

In embodiments of a compound of formula I, IB, II, or IIA, $R^{19a}$ is a 5- to 12-membered heteroaryl comprising three or four ring nitrogen atoms; wherein $R^{19a}$ is optionally substituted with one or more $R^{20}$.

In embodiments of a compound of formula I, IB, II, or IIA, $R^{19a}$ is a 9- to 12-membered heteroaryl comprising three or four ring nitrogen atoms; wherein $R^{19a}$ is optionally substituted with one or more $R^{20}$.

In embodiments of a compound of formula I, IA, IB, II, or IIA, $R^{19a}$ is a 5- to 6-membered heteroaryl comprising three or four ring nitrogen atoms; wherein $R^{19a}$ is optionally substituted with one or more $R^{20}$.

In embodiments of a compound of formula I, IA, IB, II, or IIA, $R^{19a}$ is selected from triazolyl and tetrazolyl; wherein $R^{19a}$ is optionally substituted with one or more $R^{20}$.

In embodiments of a compound of formula I, IA, IB, II, or IIA, $R^{19a}$ is selected from 1,2,3-triazolyl and 1,2,4-triazolyl; wherein $R^{19a}$ is optionally substituted with one or more $R^{20}$.

In embodiments of a compound of formula I, IA, IB, II, or IIA, $R^{19a}$ is optionally substituted with one or more substituents independently selected from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, and 3- to 6-membered heteroalkynyl; wherein $C_{1-6}$ alkyl, $C_{2-6}$ alkenyl, $C_{2-6}$ alkynyl, 2- to 6-membered heteroalkyl, 3- to 6-membered heteroalkenyl, and 3- to 6-membered heteroalkynyl are optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, —$OR^{22}$, —$SR^{22}$, —$N(R^{22})(R^{23})$, ${=}NR^{22}$, ${=}C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —$S({=}O)({=}NR^{22})N(R^{22})(R^{23})$.

In embodiments of a compound of formula I, IA, IB, II, or IIA, $R^{19a}$ is optionally substituted with one or more substituents independently selected from halogen, —CN, and $C_{1-6}$ alkyl, wherein the $C_{1-6}$ alkyl is optionally substituted with one or more substituents independently selected from halogen, oxo, —CN, —$OR^{22}$, —$SR^{22}$, and —$N(R^{22})(R^{23})$.

In embodiments of a compound of formula I, IA, IB, II, or IIA, $R^{19a}$ is optionally substituted with one or more substituents independently selected from —F, —Cl, —Br, and —I.

In embodiments of a compound of formula I, IA, IB, II, or IIA, $R^{19a}$ is optionally substituted with one $R^{20}$ selected from —F and —Cl.

In embodiments of a compound of formula I, IA, IB, II, or IIA, $R^{19a}$ is selected from

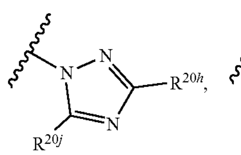

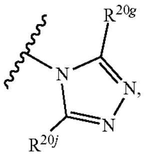

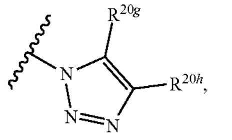

and

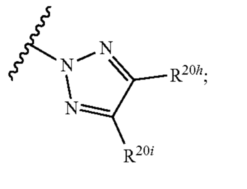

wherein $R^{20g}$, $R^{20h}$, $R^{20i}$, and $R^{20j}$ are independently selected at each occurrence from hydrogen and $R^{20}$.

In embodiments of a compound of formula I, IA, IB, II, or IIA, $R^{19a}$ is selected from

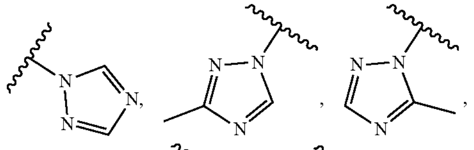

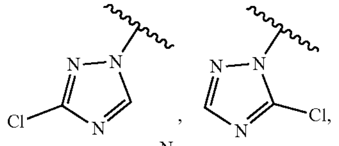

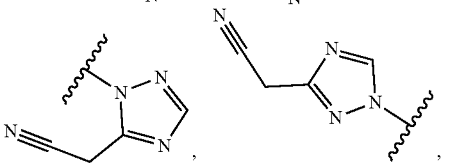

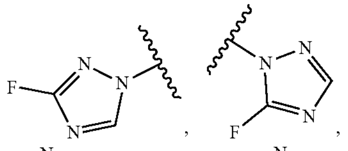

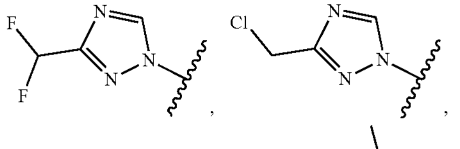

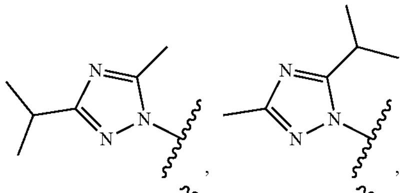

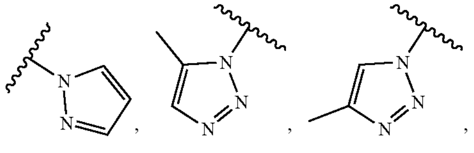

-continued

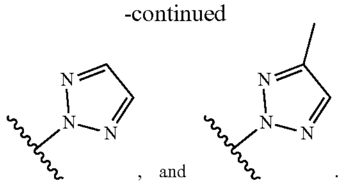

, and .

In embodiments of a compound of formula I, IA, IB, II, or IIA, $L^{19a}$ is selected from —C(O)—, —N($R^{12}$)C(O)—, —C(O)N($R^{12}$)—, —S(O)$_2$—, —S(O)—, —P(O)($R^{12}$)—, —N($R^{12}$)S(O)$_2$—, —N($R^{12}$)S(O)—, —N($R^{12}$)P(O)($R^{12}$)—, —S(O)$_2$N($R^{12}$)—, —S(O)N($R^{12}$)—, and —P(O)($R^{12}$)N($R^{12}$)—.

In embodiments of a compound of formula I, IA, IB, II, or IIA, $L^{19a}$ is selected from —C(O)—, —S(O)$_2$—, and —S(O)—.

In embodiments of a compound of formula I, IA, IB, II, or IIA, $L^{19a}$ is selected from —C(O)— and —N($R^{12}$)C(O)—.

In embodiments of a compound of formula I, IA, IB, II, or IIA, $L^{19a}$ is —C(O)—.

In embodiments of a compound of formula I, IA, IB, II, or IIA, $R^{19}$ is a monocyclic $C_{3-8}$ carbocycle optionally substituted with one or more $R^{20}$.

In embodiments of a compound of formula I, IA, IB, II, or IIA, $R^{19}$ is a monocyclic non-aromatic $C_{4-6}$ carbocycle optionally substituted with one or more $R^{20}$.

In embodiments of a compound of formula I, IA, and IB, $R^{19}$ is a phenyl optionally substituted with one or more $R^{20}$.

In embodiments of a compound of formula I, IA, IB, II, or IIA, $R^{19}$ is a monocyclic 3- to 8-membered heterocycle optionally substituted with one or more $R^{20}$.

In embodiments of a compound of formula I, IA, and IB, $R^{19}$ is a monocyclic 5-membered heteroaryl optionally substituted with one or more $R^{20}$.

In embodiments of a compound of formula I, IA, IB, II, or IIA, $R^{19}$ is a monocyclic, non-aromatic 4- to 5-membered heterocycle optionally substituted with one or more $R^{20}$.

In embodiments of a compound of formula I, IA, IB, II, or IIA, $R^{19}$ is selected from azetidinyl and pyrrolidinyl; wherein the azetidinyl and pyrrolidinyl are optionally substituted with one or more $R^{20}$.

In embodiments of a compound of formula I, IA, IB, II, or IIA, $R^{19}$ is optionally substituted with one or more substituents independently selected from $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), and —$C_{0-6}$ alkyl-(3- to 12-membered heterocycle); wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), and —$C_{0-6}$ alkyl-(3- to 12-membered heterocycle) are optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, —$OR^{22}$, —$SR^{22}$, —N($R^{22}$)($R^{23}$), =$NR^{22}$, =C($R^{21}$)$_2$, —C(O)$OR^{22}$, —OC(O)N($R^{22}$)($R^{23}$), —N($R^{22}$)C(O)N($R^{22}$)($R^{23}$), —N($R^{22}$)C(O)$OR^{22}$, —N($R^{22}$)S(O)$_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S(O)$_2R^{22}$, —S(O)($NR^{22}$)$R^{22}$, —S(O)$_2$N($R^{22}$)($R^{23}$), and —S(=O)(=$NR^{22}$)N($R^{22}$)($R^{23}$).

In embodiments of a compound of formula I, IA, IB, II, or IIA, $R^{19}$ is optionally substituted with one or more substituents independently selected from $C_{1-4}$ alkyl and $C_{3-4}$ carbocycle; wherein $C_{3-4}$ carbocycle is optionally substituted with one or more substituents independently selected from halogen and $C_{1-4}$ alkyl.

In embodiments of a compound of formula I, IA, IB, II, or IIA, $R^{19}$ is optionally substituted with unsubstituted methyl.

In embodiments of a compound of formula I, IA, IB, II, or IIA, $L^{19}$ is a bond.

In embodiments of a compound of formula I, IA, IB, II, or IIA, $L^{19}$ is unsubstituted $C_{1-2}$ alkylene.

In embodiments of a compound of formula I, IA, IB, II, or IIA, $L^{19}$ is unsubstituted methylene.

In embodiments of a compound of formula IA, IB, or IIA, $X^9$ is $N(R^9)$.

In embodiments of a compound of formula IA, IB, or IIA, $X^{10}$ is $C(R^{10})_2$.

In embodiments of a compound of formula IA, IB, or IIA, $X^{10}$ is $CH(R^{10})$.

In embodiments of a compound of formula IA, IB, or IIA, $X^{10}$ is $CH_2$.

In embodiments of a compound of formula IA, IB, or IIA, $R^{10}$ is independently selected at each occurrence from $C_{1-6}$ alkyl, $C_{2-6}$ alkenyl, $C_{2-6}$ alkynyl, $C_{3-12}$ carbocycle, and 3- to 12-membered heterocycle, wherein $C_{1-6}$ alkyl, $C_{2-6}$ alkenyl, $C_{2-6}$ alkynyl, $C_{3-12}$ carbocycle, and 3- to 12-membered heterocycle are optionally substituted with one or more $R^{20}$.

In embodiments of a compound of formula IA, IB, or IIA, $R^{10}$ is independently selected at each occurrence from $C_{1-4}$ alkyl, $C_{2-3}$ alkenyl, $C_{2-3}$ alkynyl, $C_{3-5}$ carbocycle, and 3- to 5-membered heterocycle, wherein $C_{1-4}$ alkyl, $C_{2-3}$ alkenyl, $C_{2-3}$ alkynyl, $C_{3-5}$ carbocycle, and 3- to 5-membered heterocycle are optionally substituted with one or more $R^{20}$.

In embodiments of a compound of formula IA, IB, or IIA, $R^{10}$ is independently selected at each occurrence from $C_{1-4}$ alkyl, $C_{2-3}$ alkenyl, $C_{2-3}$ alkynyl, $C_{3-5}$ carbocycle, and 3- to 5-membered heterocycle, wherein $C_{1-4}$ alkyl, $C_{2-3}$ alkenyl, $C_{2-3}$ alkynyl, $C_{3-5}$ carbocycle, and 3- to 5-membered heterocycle are optionally substituted with one or more $R^{20}$ selected from halogen, —OH, and —CN.

In embodiments of a compound of formula IA, IB, or IIA, $R^{10}$ is independently selected at each occurrence from unsubstituted $C_{1-4}$ alkyl, unsubstituted $C_{2-3}$ alkenyl, unsubstituted $C_{2-3}$ alkynyl, unsubstituted $C_{3-5}$ carbocycle, and unsubstituted 3- to 5-membered heterocycle.

In embodiments of a compound of formula IA, IB, or IIA, $R^{10}$ is independently selected at each occurrence from

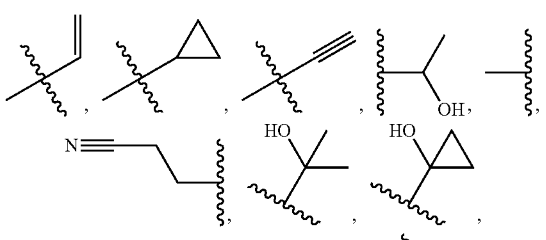

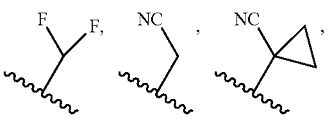

and

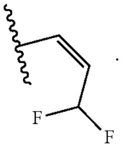

In embodiments of a compound of formula IA, IB, or IIA, $X^{11}$ is $C(R^{11})_2$.

In embodiments of a compound of formula IA, IB, or IIA, $X^{11}$ is $CH(R^{11})$.

In embodiments of a compound of formula IA, IB, or IIA, $X^{11}$ is $CH_2$.

In embodiments of a compound of formula IA, IB, or IIA, $R^{11}$ is independently selected at each occurrence from $C_{1-6}$ alkyl, $C_{2-6}$ alkenyl, $C_{2-6}$ alkynyl, $C_{3-12}$ carbocycle, and 3- to 12-membered heterocycle, wherein $C_{1-6}$ alkyl, $C_{2-6}$ alkenyl, $C_{2-6}$ alkynyl, $C_{3-12}$ carbocycle, and 3- to 12-membered heterocycle are optionally substituted with one or more $R^{20}$.

In embodiments of a compound of formula IA, IB, or IIA, $R^{11}$ is independently selected at each occurrence from $C_{1-4}$ alkyl, $C_{2-3}$ alkenyl, $C_{2-3}$ alkynyl, $C_{3-5}$ carbocycle, and 3- to 5-membered heterocycle, wherein $C_{1-4}$ alkyl, $C_{2-3}$ alkenyl, $C_{2-3}$ alkynyl, $C_{3-5}$ carbocycle, and 3- to 5-membered heterocycle are optionally substituted with one or more $R^{20}$.

In embodiments of a compound of formula IA, IB, or IIA, $R^{11}$ is independently selected at each occurrence from unsubstituted $C_{1-4}$ alkyl, unsubstituted $C_{2-3}$ alkenyl, unsubstituted $C_{2-3}$ alkynyl, unsubstituted $C_{3-5}$ carbocycle, and unsubstituted 3- to 5-membered heterocycle.

In embodiments of a compound of formula IA, IB, or IIA, $X^{12}$ is $—X^{2a}—$.

In embodiments of a compound of formula IA, IB, or IIA, $X^{12a}$ is O.

In embodiments of a compound of formula I, IA, IB, II, or IIA, $X^1$ is N.

In embodiments of a compound of formula I, IA, IB, II, or IIA, $X^2$ is $C(R^2)$.

In embodiments of a compound of formula I, IA, IB, II, or IIA, $R^2$ is $—OR^{12}$.

In embodiments of a compound of formula I, IA, IB, II, or IIA, $R^2$ is $—O(C_{1-3}$ alkylene)(4- to 10-membered heterocycle), wherein 4- to 10-membered heterocycle is optionally substituted with one, two, or three substituents independently selected from halogen, $C_{1-3}$ alkyl, $C_{1-3}$ haloalkyl, and $=C(R^{21})_2$.

In embodiments of a compound of formula I, IA, IB, II, or IIA, $R^2$ is selected from

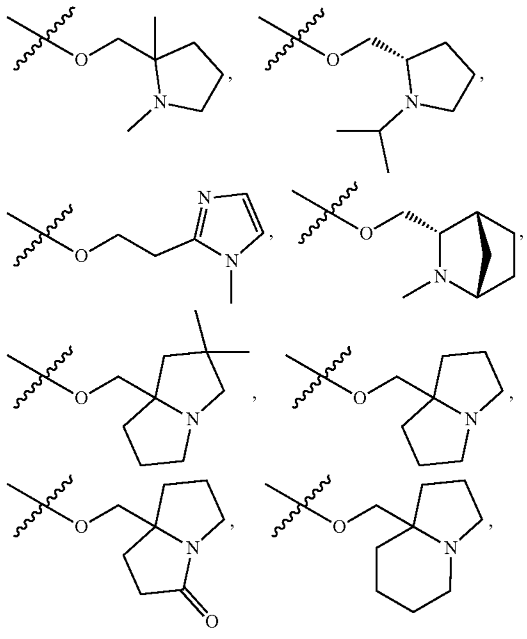

-continued
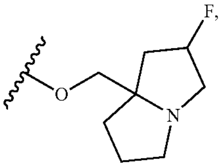
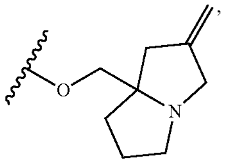
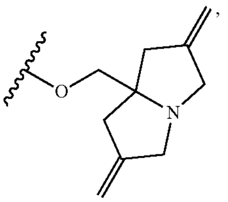
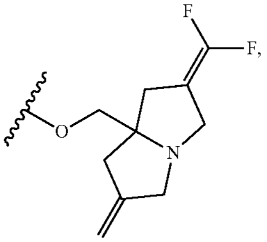
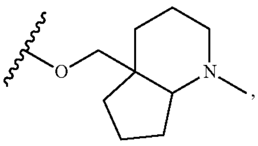
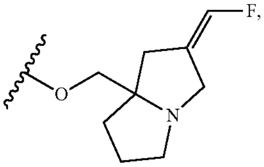
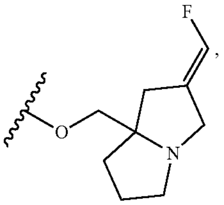
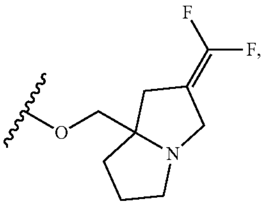
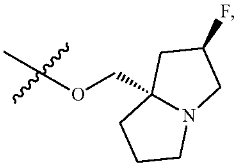
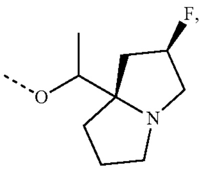
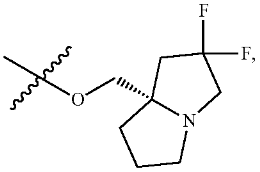
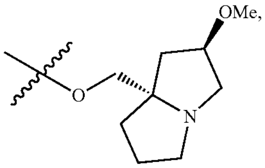
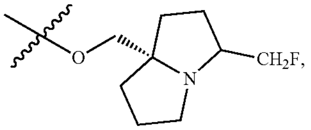
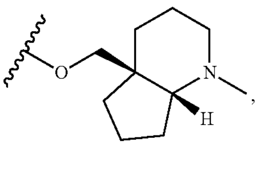
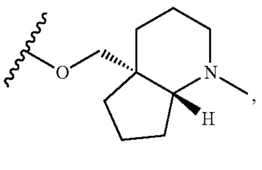
-continued
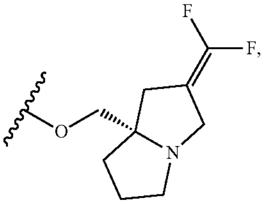
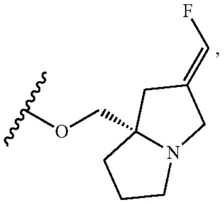
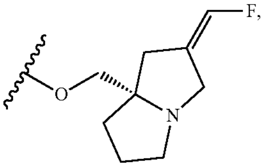
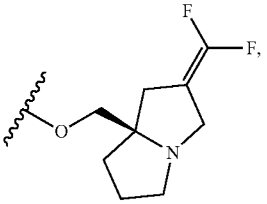
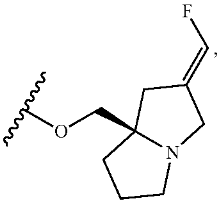
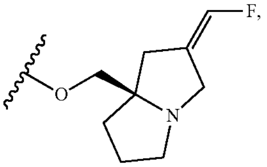
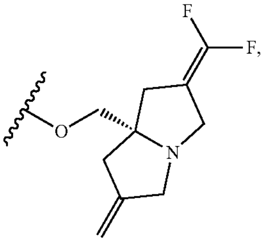
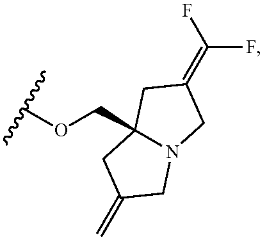
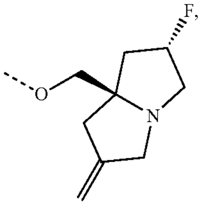
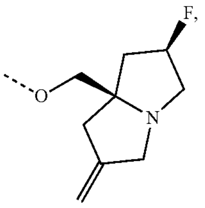
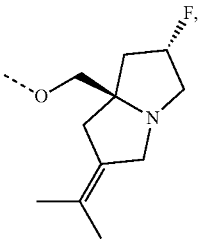
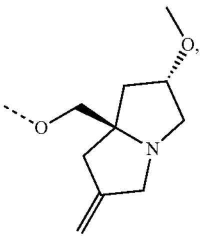
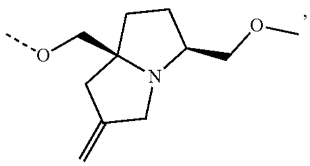

-continued
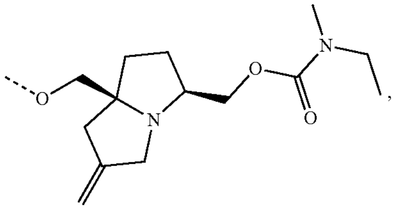
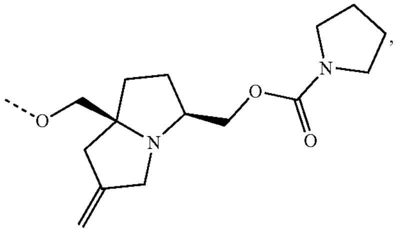
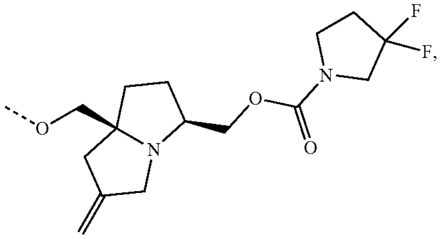
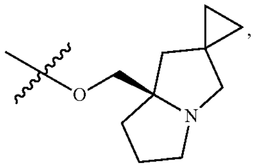
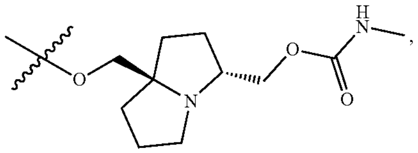
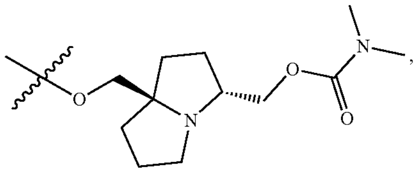
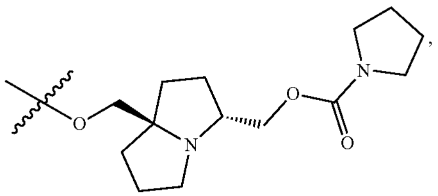
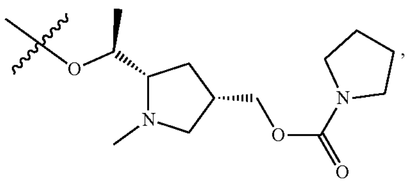
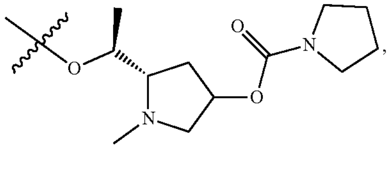
-continued
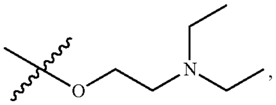
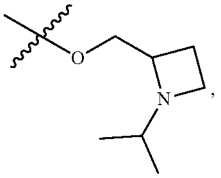
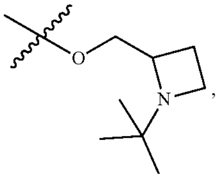
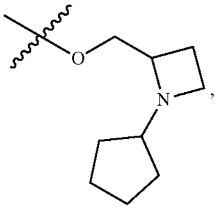
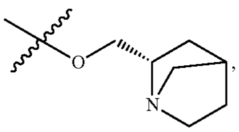
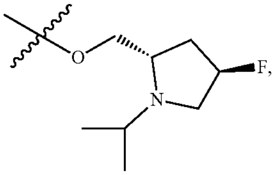
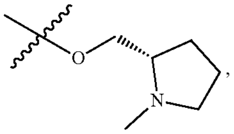
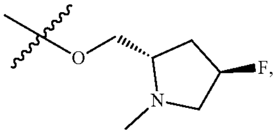
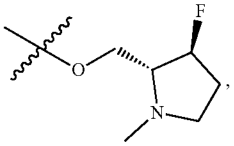
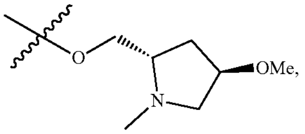
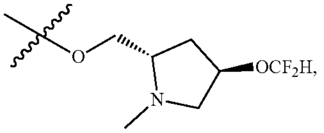
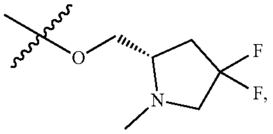
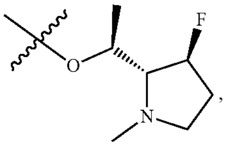
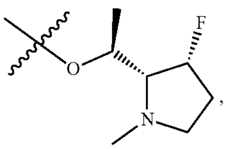
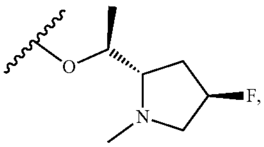
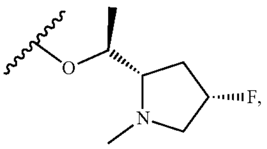
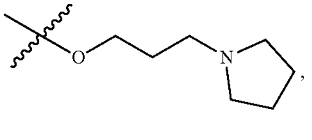

-continued
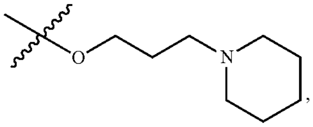
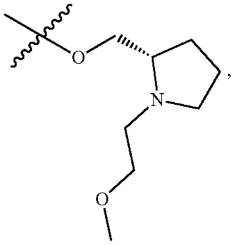
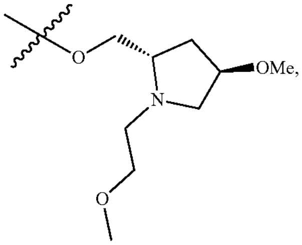
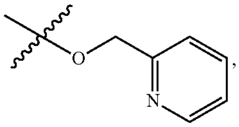
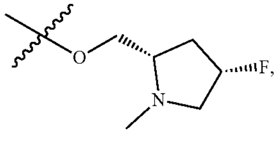
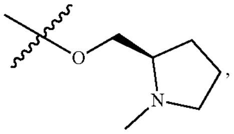
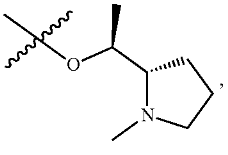
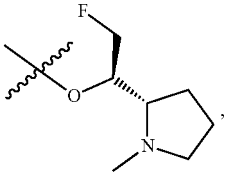
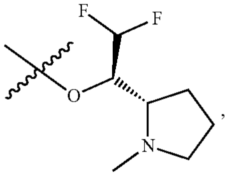
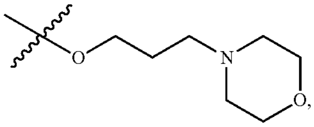
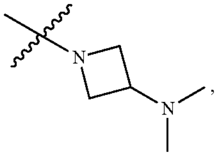
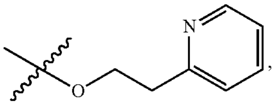
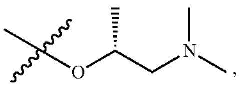
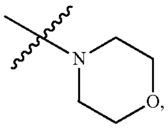
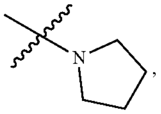
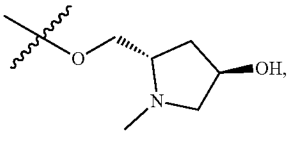
-continued
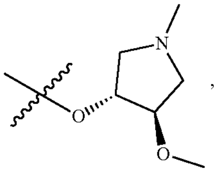
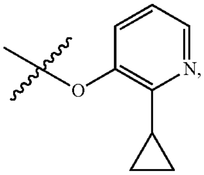
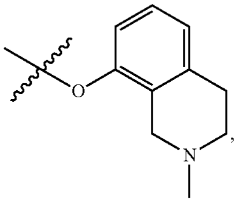
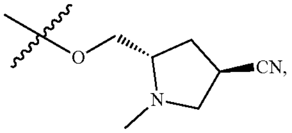
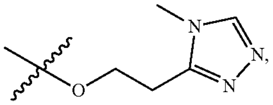
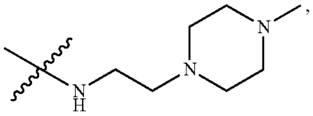
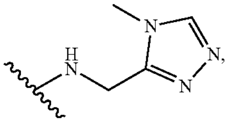
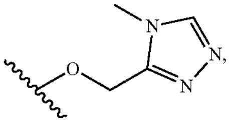
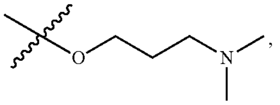
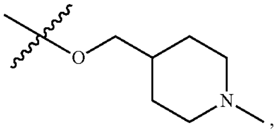
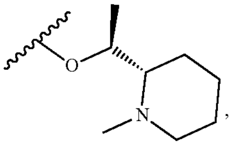
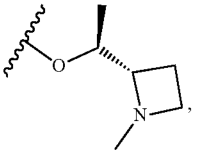
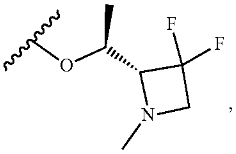
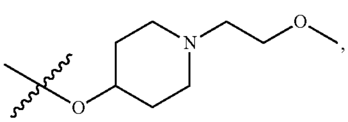
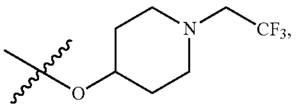
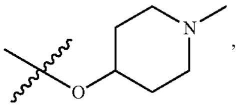
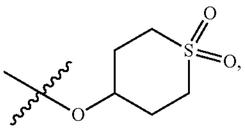

-continued
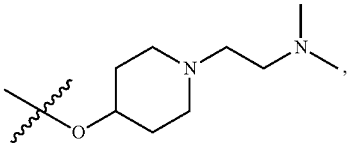
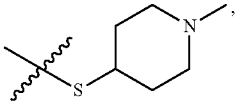
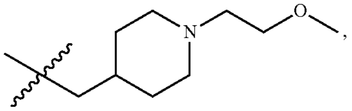
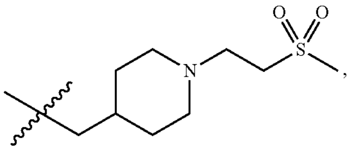
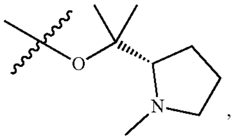
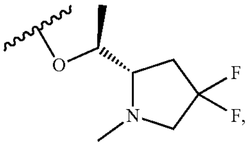
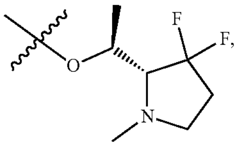
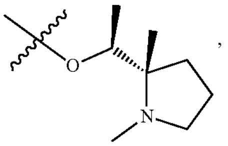
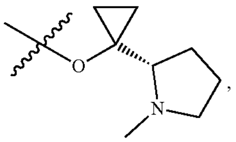
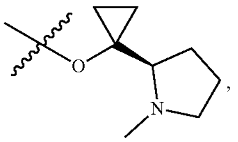
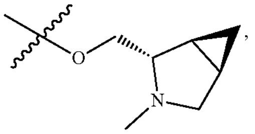
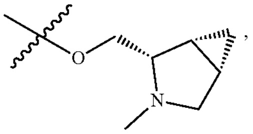
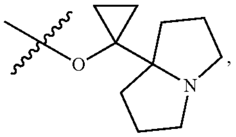
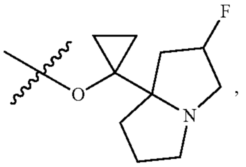
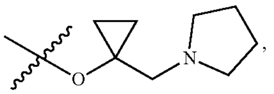
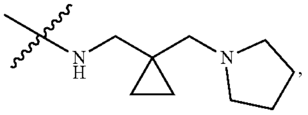
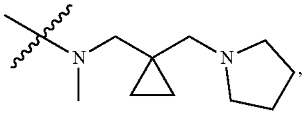
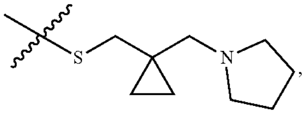
-continued
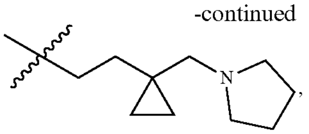
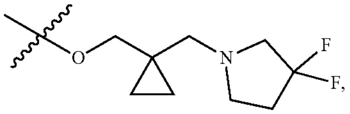
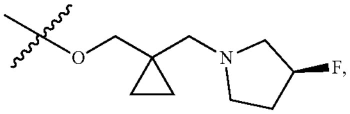
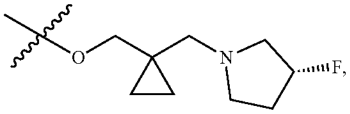
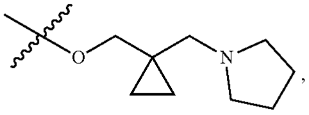
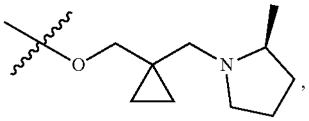
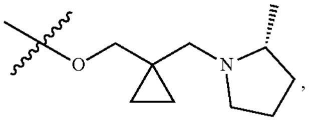
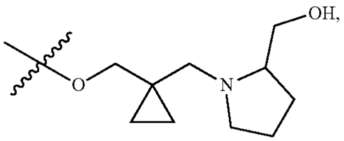
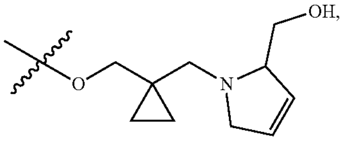
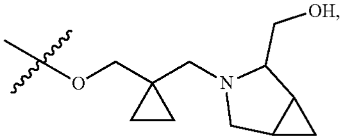
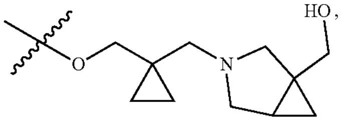
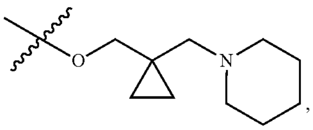
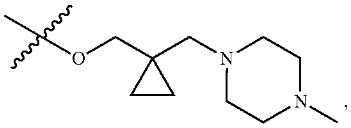
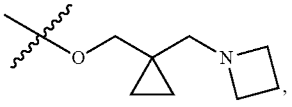

-continued
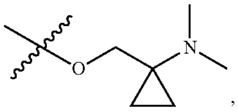,
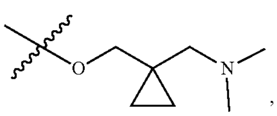,
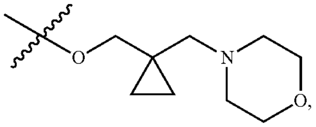,
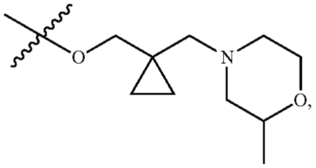,
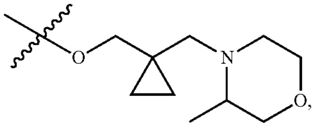,
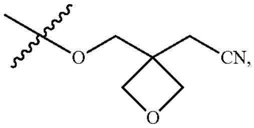,
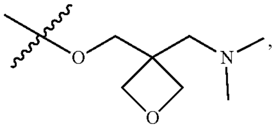,
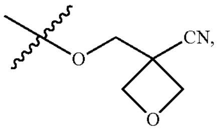,
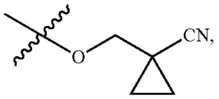,
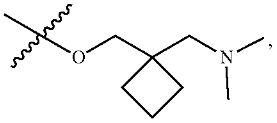,
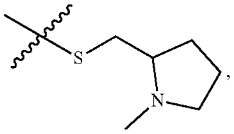,
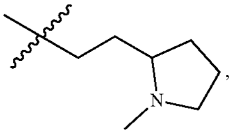,
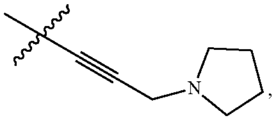,
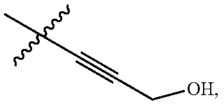,
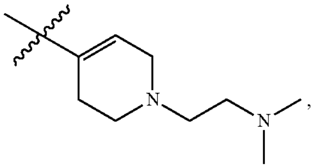,
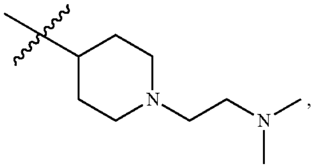,
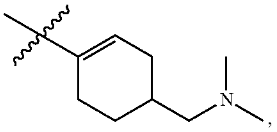,
-continued
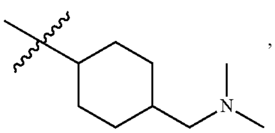,
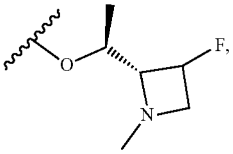,
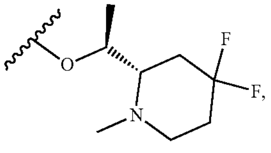,
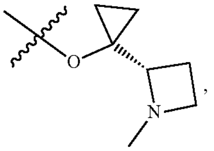,
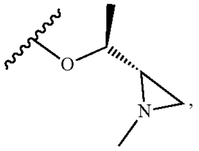,
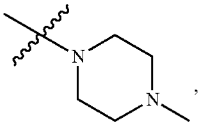,
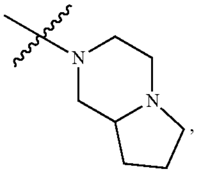,
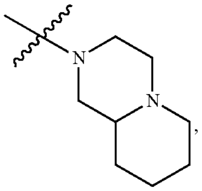,
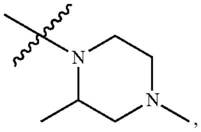,
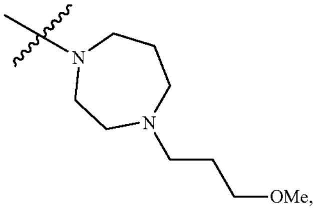,
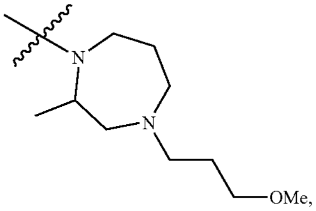,
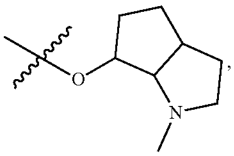,
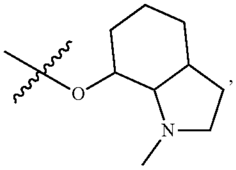,
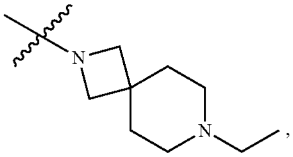,
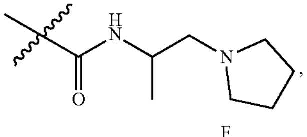,
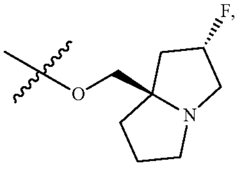,
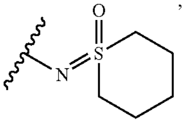, -continued

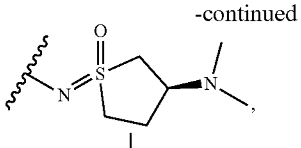

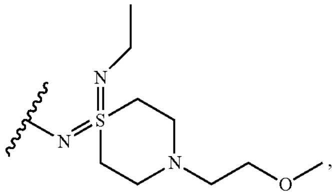

and

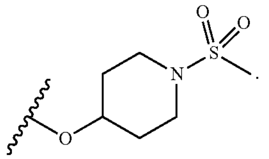

In embodiments of a compound of formula I, IA, IB, II, or IIA, $R^2$ is selected from

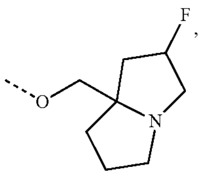

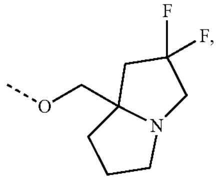

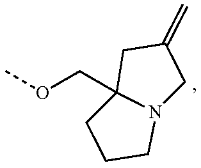

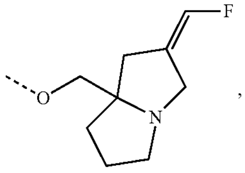

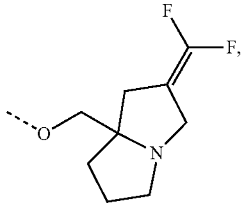

and

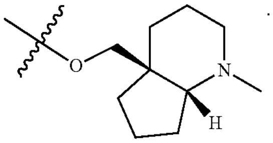

In embodiments of a compound of formula I, IA, IB, II or IIA, $R^2$ is selected from

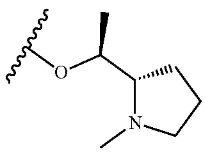

and

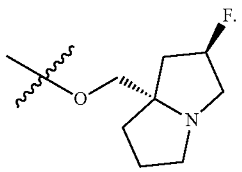

In embodiments of a compound of formula I, IA, IB, II, or IIA, $X^3$ is N.

In embodiments of a compound of formula I, IA, IB, II, or IIA, $X^4$ is C.

In embodiments of a compound of formula I, IA, IB, II, or IIA, $X^5$ is C.

In embodiments of a compound of formula I, IA, IB, II, or IIA, $X^6$ is $C(R^6)$.

In embodiments of a compound of formula I, IA, IB, II, or IIA, $R^6$ is independently selected at each occurrence from hydrogen and halogen.

In embodiments of a compound of formula I, IA, IB, II, or IIA, $X^6$ is N.

In embodiments of a compound of formula I, IA, IB, II, or IIA, $X^6$ is $N(R^{6b})$.

In embodiments of a compound of formula I, IA, IB, II, or IIA, $R^{6b}$ is unsubstituted cyclopropyl.

In embodiments of a compound of formula I, IA, IB, II, or IIA, $X^7$ is $C(R^7)$.

In embodiments of a compound of formula I, IA, IB, II, or IIA, $L^{7a}$ is a bond.

In embodiments of a compound of formula I, IA, IB, II, or IIA, $R^{17}$ is selected from $C_{6-12}$ carbocycle and 5- to 12-membered heterocycle, wherein $C_{6-12}$ carbocycle and 5- to 12-membered heterocycle are optionally substituted with one or more $R^{20}$.

In embodiments of a compound of formula I, IA, IB, II, or IIA, $R^{17}$ is selected from phenyl, pyridyl, naphthyl, quinolinyl, isoquinolinyl, benzothiazolyl, benzothienyl, indazolyl, and benzoxazolyl, wherein phenyl, pyridyl, naphthyl, quinolinyl, isoquinolinyl, benzothiazolyl, benzothienyl, indazolyl, and benzoxazolyl are optionally substituted with one or more $R^{20}$.

In embodiments of a compound of formula I, IA, IB, II, or IIA, $R^{17}$ is selected from:

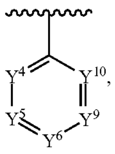

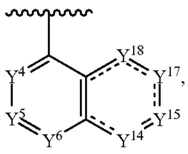

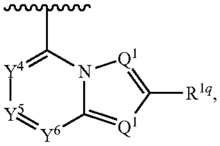

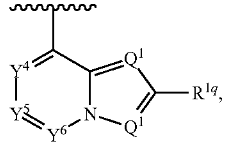

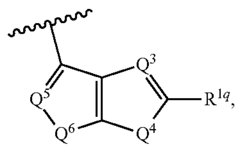

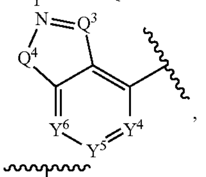

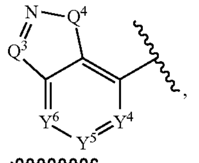

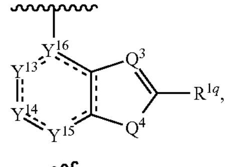

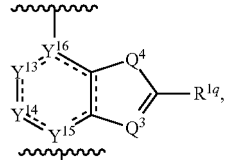

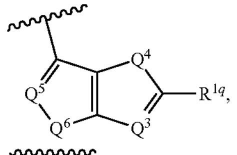

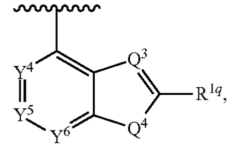

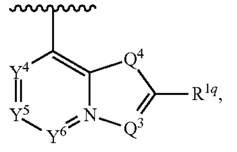

-continued

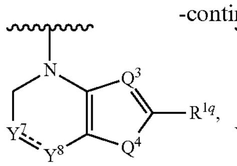,
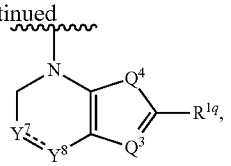,
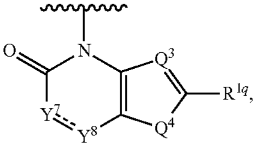, and
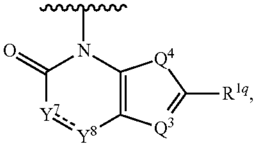, wherein:

$Q^1$, $Q^3$, and $Q^5$ are independently selected from N and $C(R^{1q})$;

$Q^4$ and $Q^6$ are independently selected from O, S, $C(R^{1q})_2$, and $N(R^1)$;

$Y^4$, $Y^5$, $Y^6$, $Y^9$, and $Y^{10}$ are independently selected from $C(R^{1q})$ and N;

$Y^7$ and $Y^8$ are independently selected from $C(R^{1q})$, $C(R^{1q})_2$, N, and $N(R^{1r})$;

$Y^{13}$ is selected from a bond, $C(R^{1q})$, N, C(O), $C(R^{1q})_2$, $C(O)C(R^{1q})_2$, $C(R^{1q})_2C(R^{1q})_2$, $C(R^{1q})_2N(R^{1q})$, and $N(R^{1r})$;

$Y^{14}$, $Y^{15}$, $Y^{17}$, and $Y^{18}$ are independently selected from C(O), $C(R^{1q})$, N, $C(R^{1q})_2$, and $N(R^{1r})$;

$Y^{16}$ is selected from C, N, and $C(R^{1q})$;

each $R^{1q}$ is independently selected from hydrogen, halogen, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(=O)(=NR^{12})N(R^{12})(R^{13})$, wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$; or two $R^{1q}$ bonded to the same carbon are joined to form 3- to 10-membered heterocycle or $C_{3-10}$ carbocycle, wherein 3- to 10-membered heterocycle and $C_{3-10}$ carbocycle are optionally substituted with one or more $R^{20}$; or two $R^{1q}$ bonded to adjacent atoms are joined to form 3- to 10-membered heterocycle or $C_{3-10}$ carbocycle, wherein 3- to 10-membered heterocycle and $C_{3-10}$ carbocycle are optionally substituted with one or more $R^{20}$; or one $R^{1q}$ and one $R^{1r}$ are joined to form 3- to 10-membered heterocycle or $C_{3-10}$ carbocycle, wherein 3- to 10-membered heterocycle and $C_{3-10}$ carbocycle are optionally substituted with one or more $R^{20}$;

each $R^{1r}$ is independently selected from hydrogen, $C_{1-6}$ alkyl, $C_{2-6}$ alkenyl, $C_{2-6}$ alkynyl, 3- to 10-membered heterocycle, and $C_{3-10}$ carbocycle, wherein $C_{1-6}$ alkyl, $C_{2-6}$ alkenyl, $C_{2-6}$ alkynyl, 3- to 10-membered heterocycle, and $C_{3-10}$ carbocycle are optionally substituted with one or more $R^{20}$; and each ⎓ independently indicates a single or double bond such that all valences are satisfied.

In embodiments of a compound of formula I, IA, IB, II, or IIA, $R^{17}$ is selected from

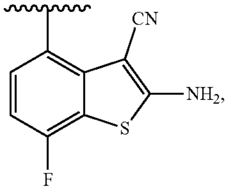,
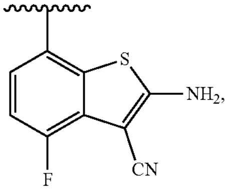,
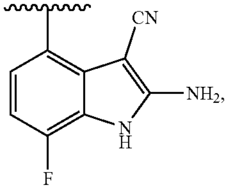,
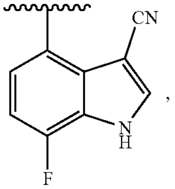,
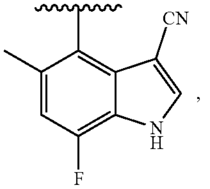,
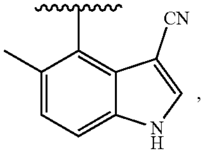,
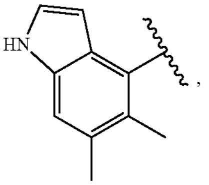,
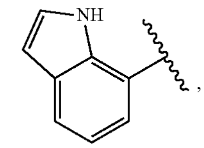,
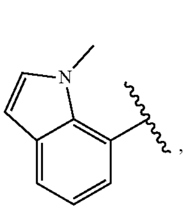,
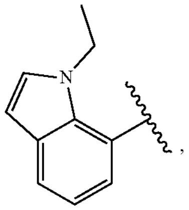,
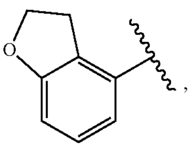,
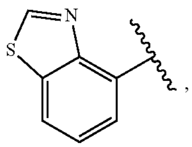,
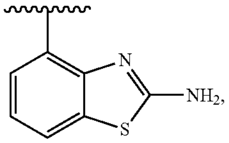,
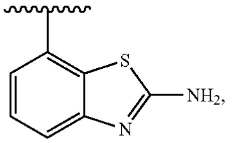,
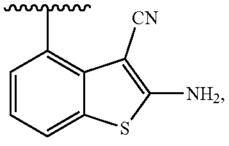,
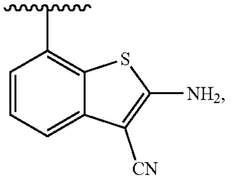, -continued
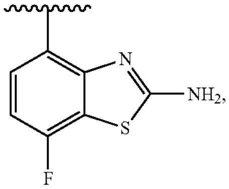
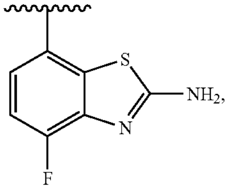
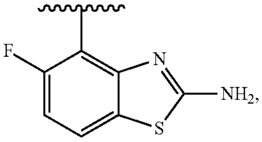
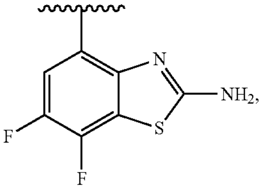
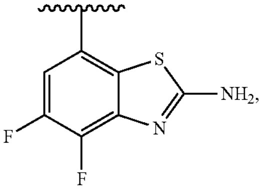
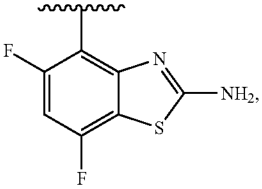
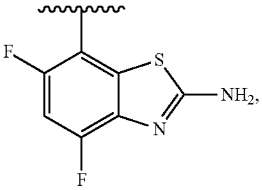
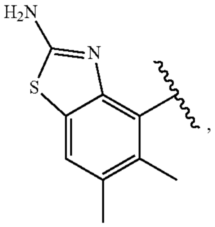
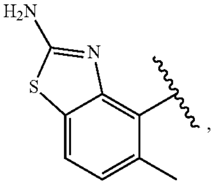
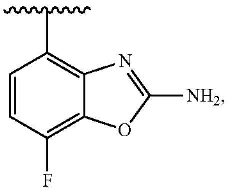
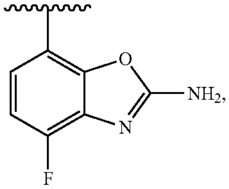
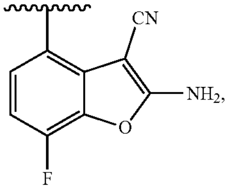
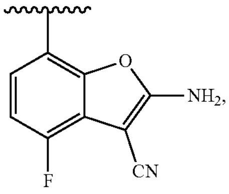
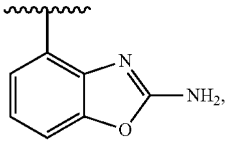
-continued
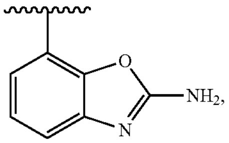
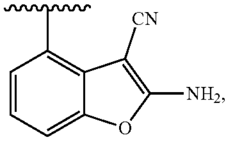
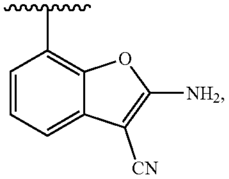
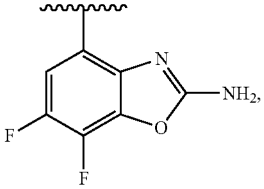
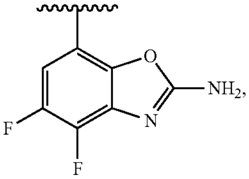
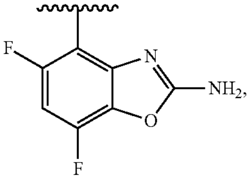
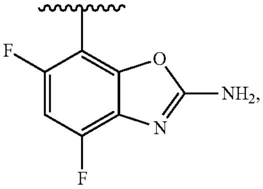
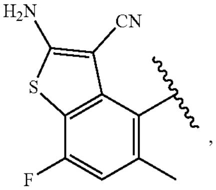
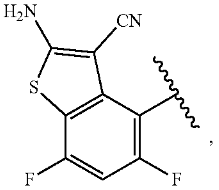
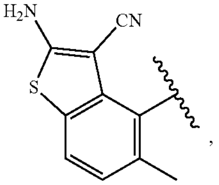
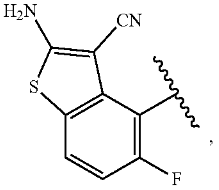
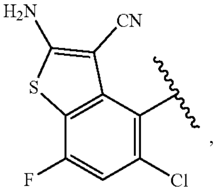
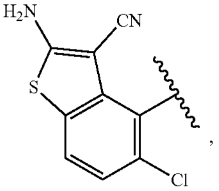
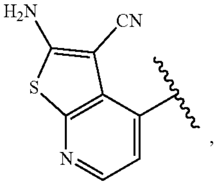
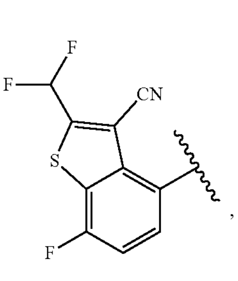
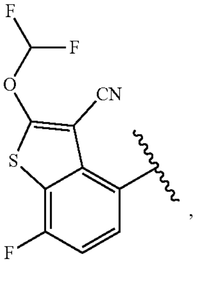

-continued
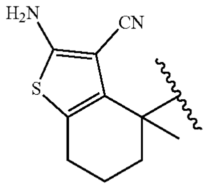,
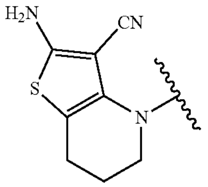,
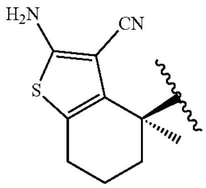,
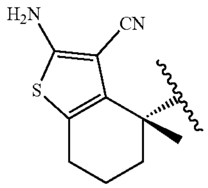,
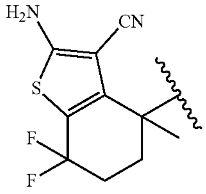,
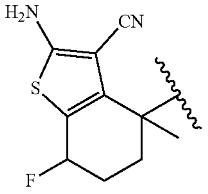,
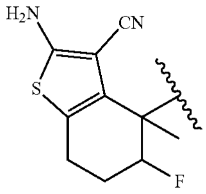,
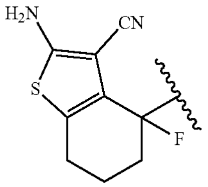,
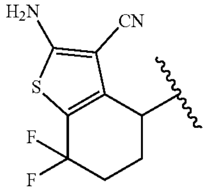,
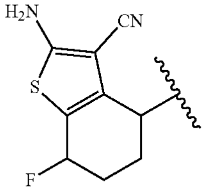,
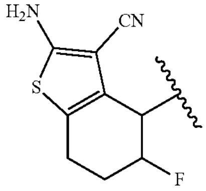,
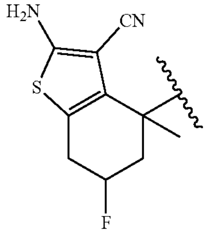,
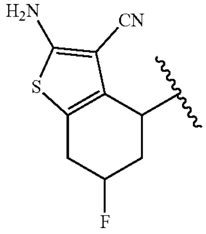,
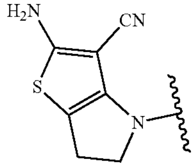,
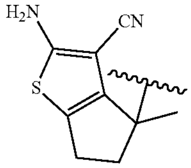,
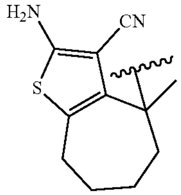,
-continued
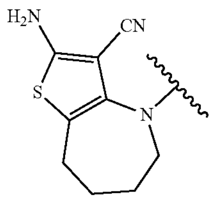,
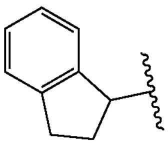,
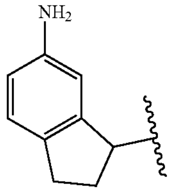,
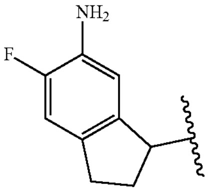,
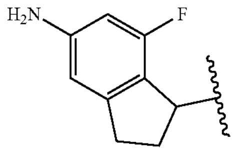,
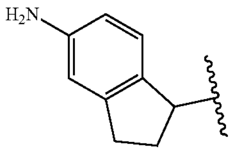,
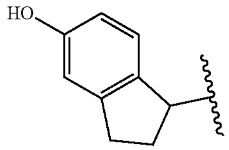,
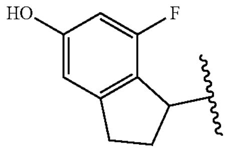,
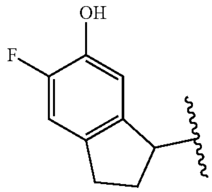,
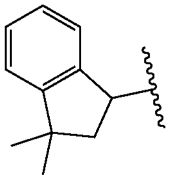,
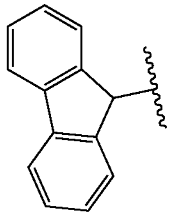,
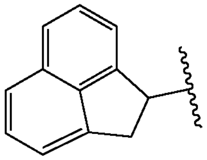,
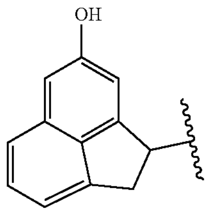,
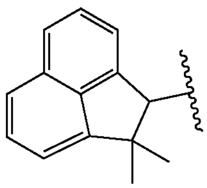,
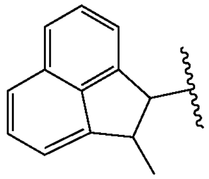,
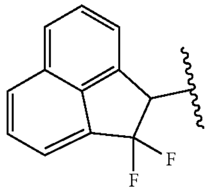, -continued
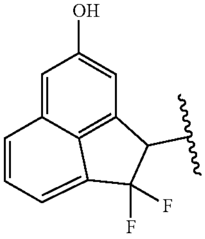, 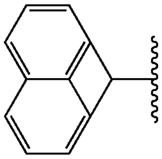,
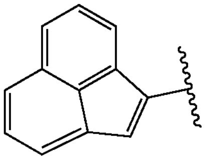, 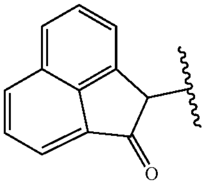,
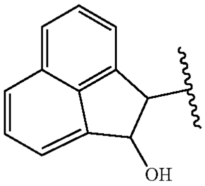, 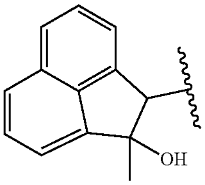,
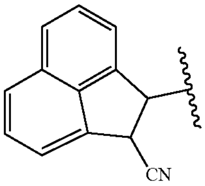, 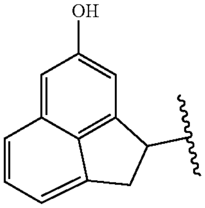,
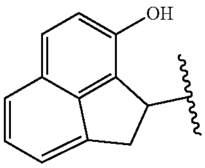, 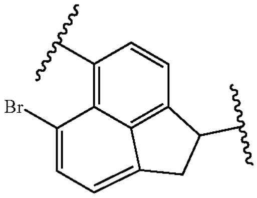,
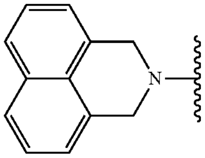, 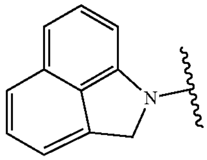,
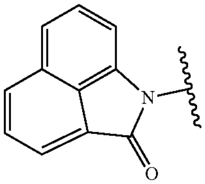, 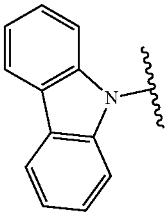,
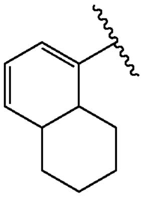, 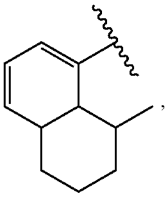,
-continued
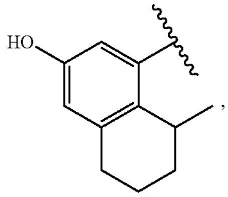, 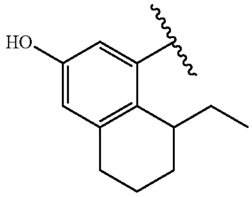,
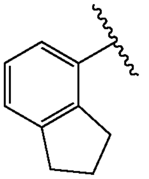, 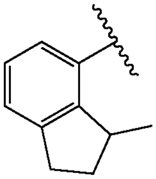,
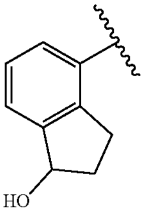, 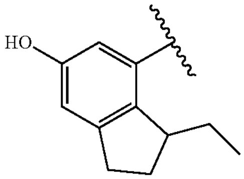,
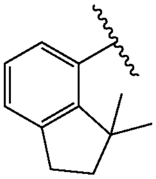, 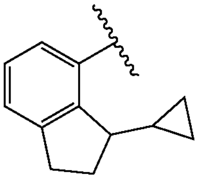,
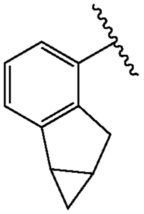, 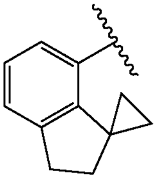, 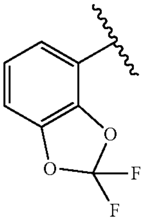,
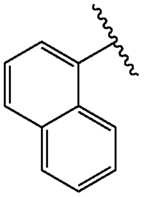, 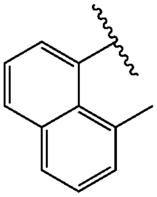, 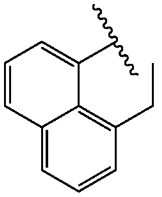,
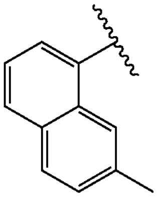, 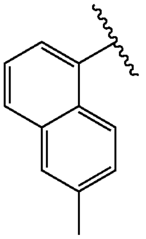,
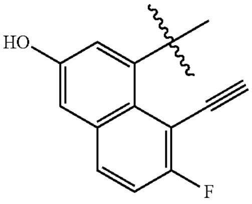, 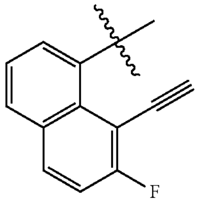, -continued
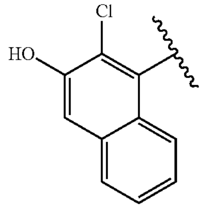
,
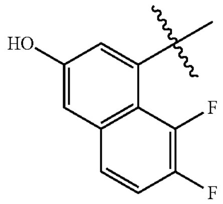
,
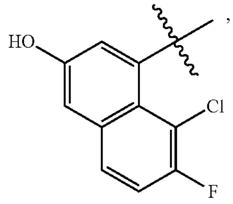
,
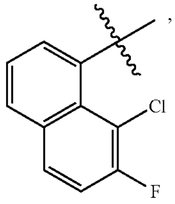
,
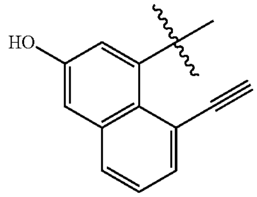
,
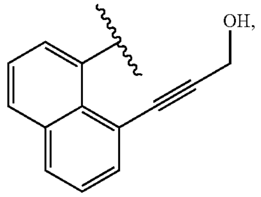
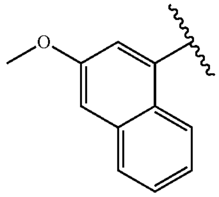
,
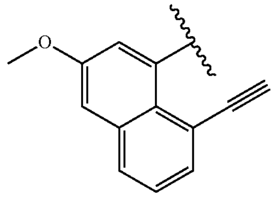
,
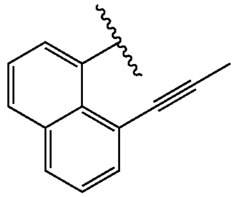
,
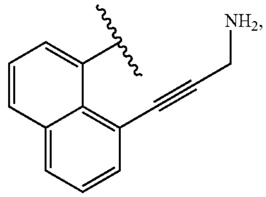
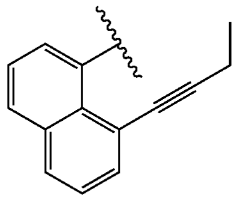
,
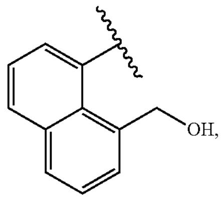
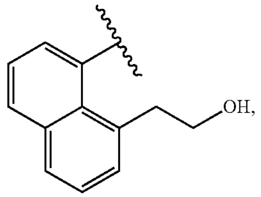
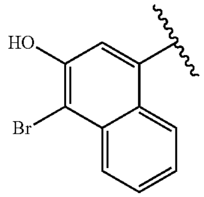
,
-continued
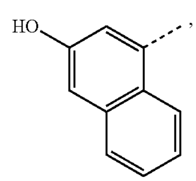
,
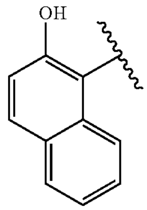
,
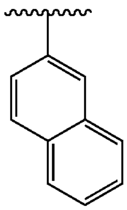
,
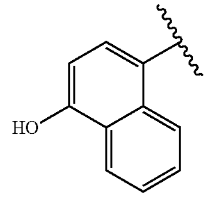
,
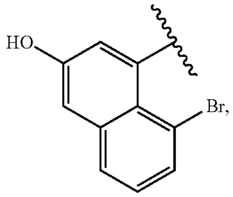
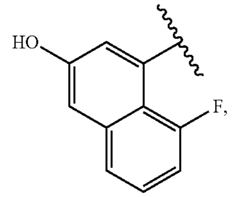
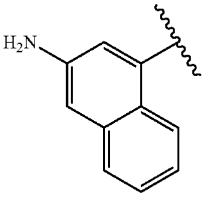
,
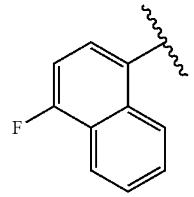
,
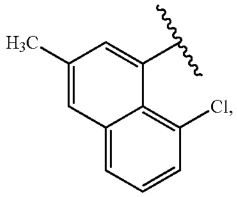
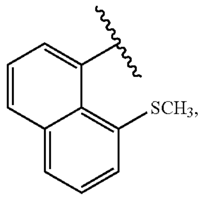
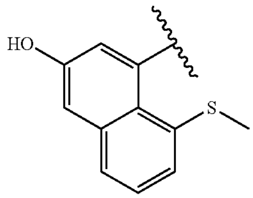
,
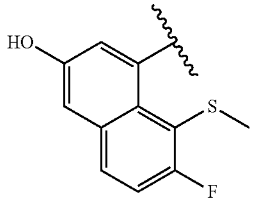
,
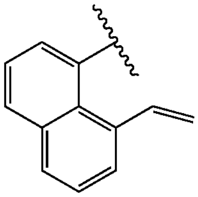
,
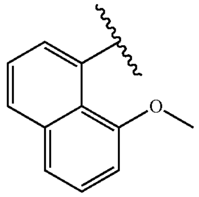
,
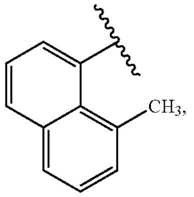
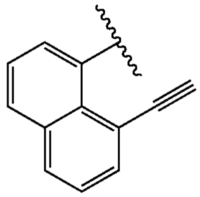
,
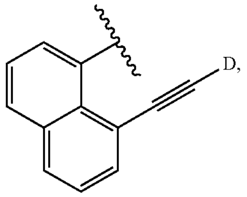

-continued
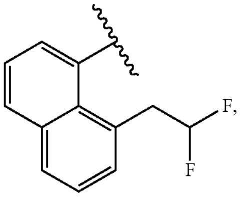
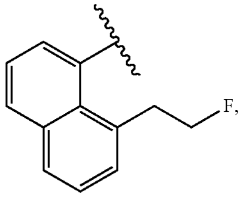
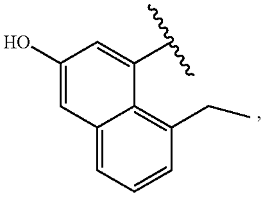
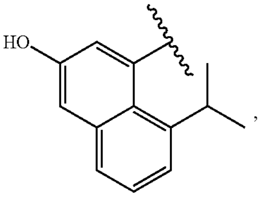
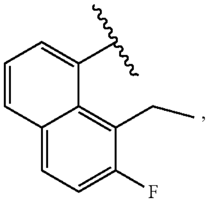
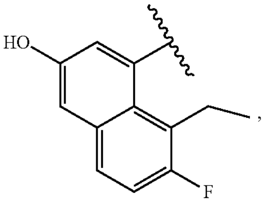
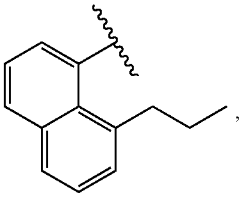
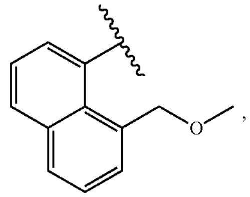
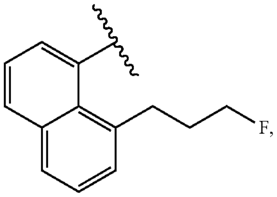
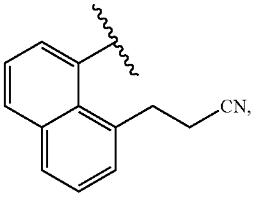
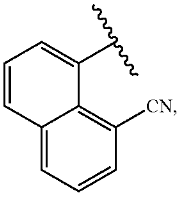
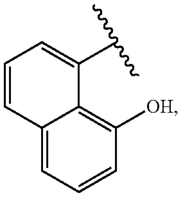
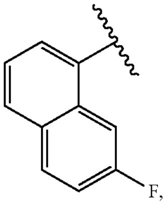
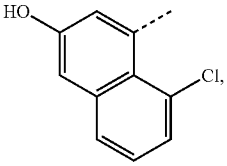
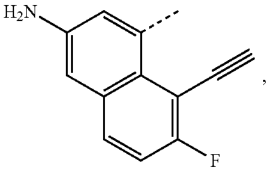
-continued
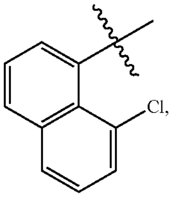
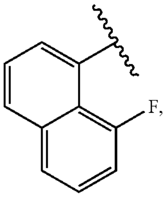
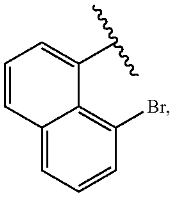
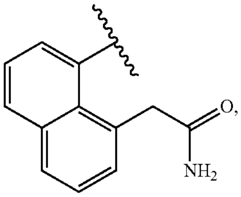
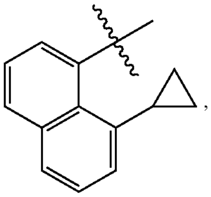
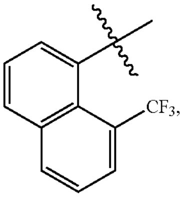
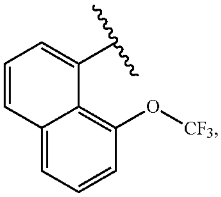
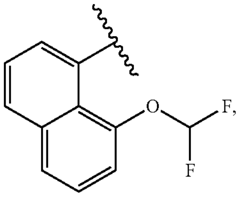
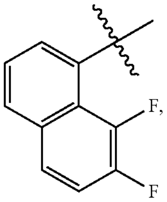
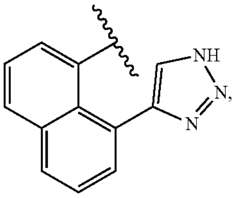
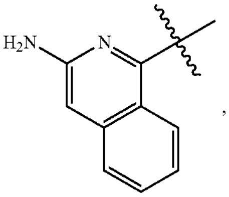
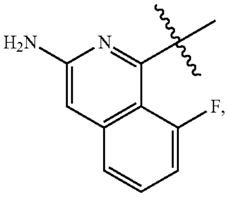
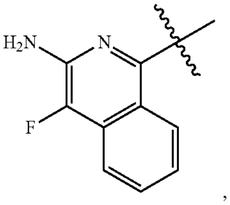
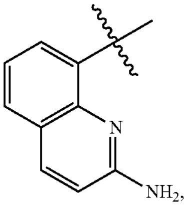
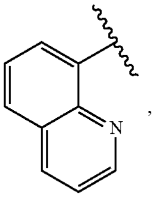
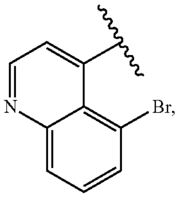

-continued
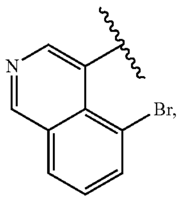 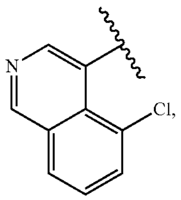
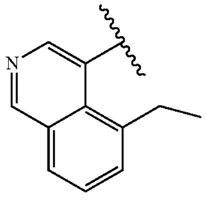, 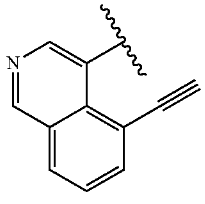,
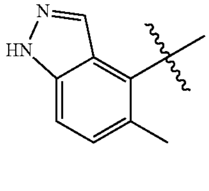, 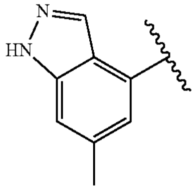,
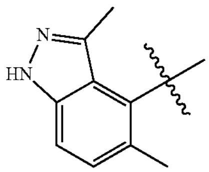, 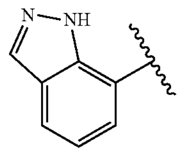,
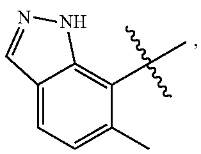, 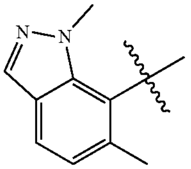,
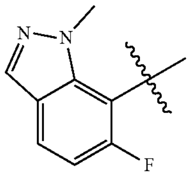, 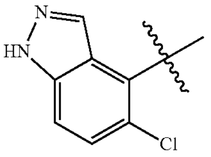,
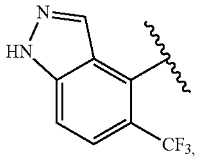 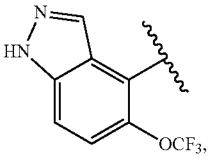
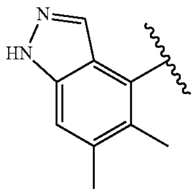, 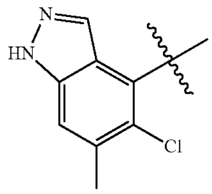,
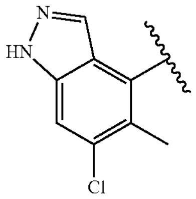, 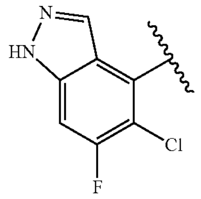,
-continued
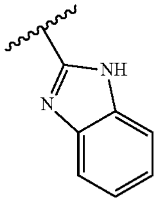, 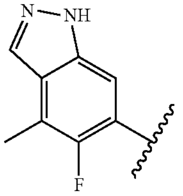,
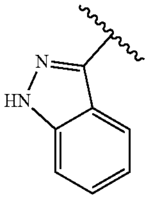, 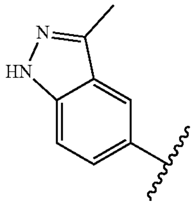,
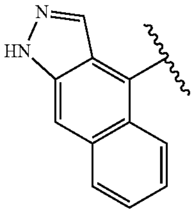, 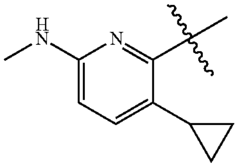,
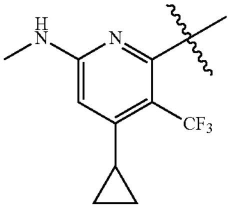, 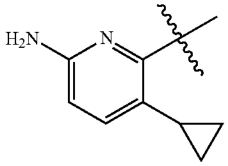,
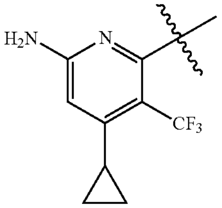, 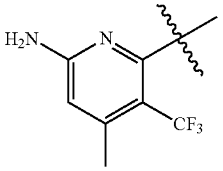,
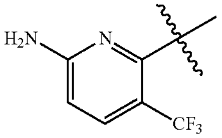, 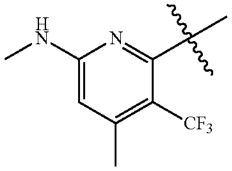,
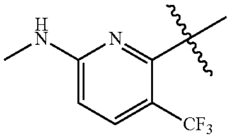, 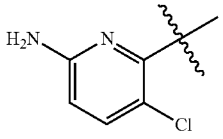,
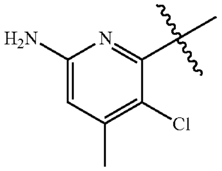, 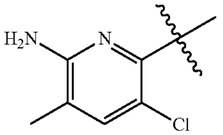,
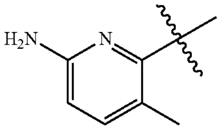, 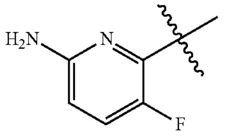, -continued
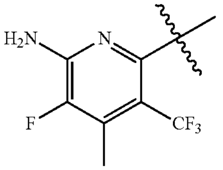,
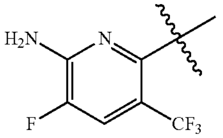,
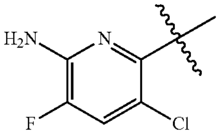,
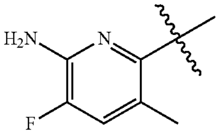,
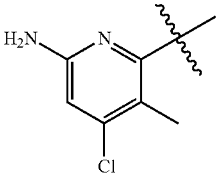,
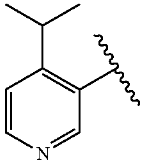,
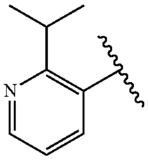,
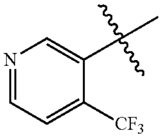,
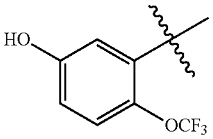,
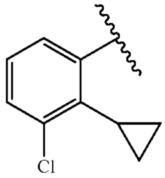,
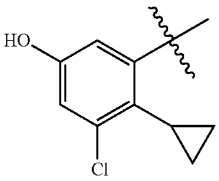,
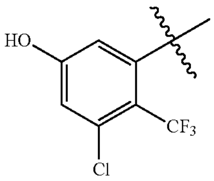,
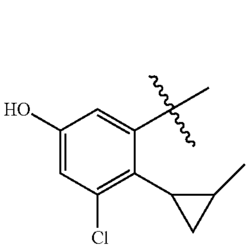,
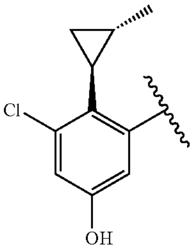,
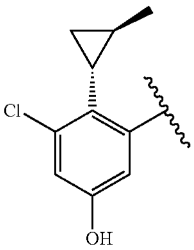,
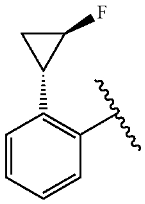,
-continued
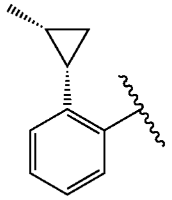,
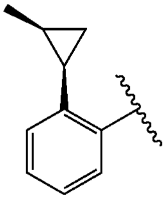,
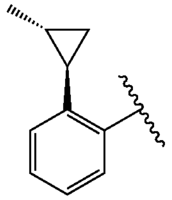,
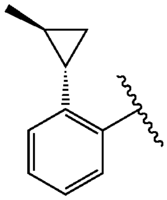,
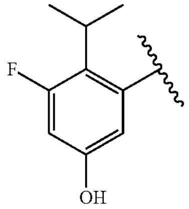,
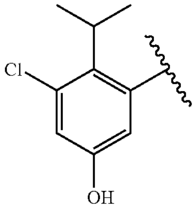,
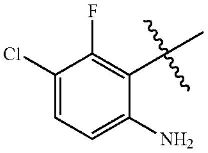,
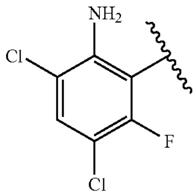,
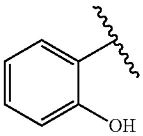,
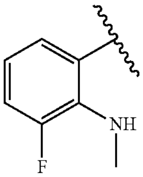,
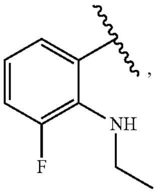,
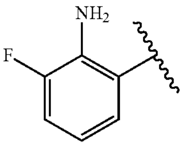,
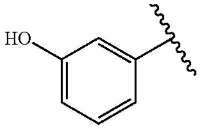,
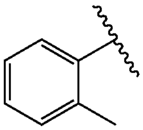,
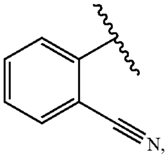,
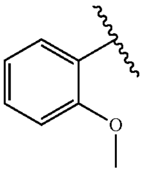,
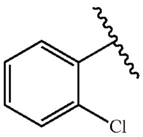,
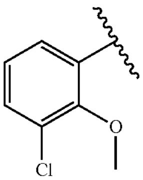,
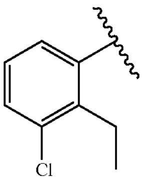, -continued
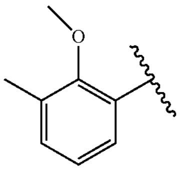,
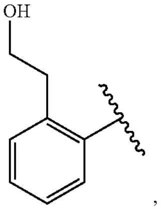,
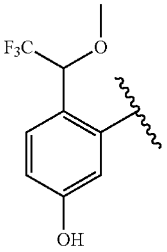,
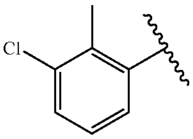,
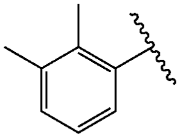,
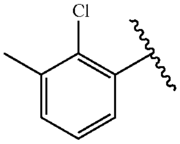,
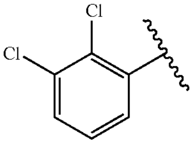,
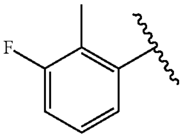,
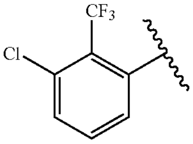,
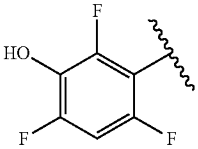,
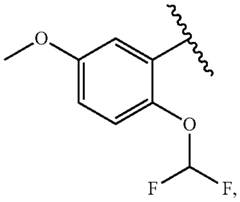,
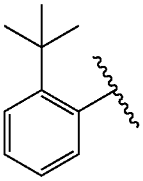,
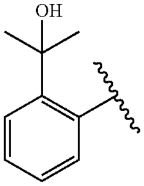,
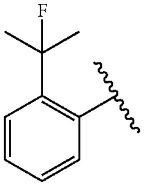,
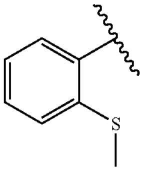,
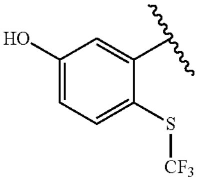,
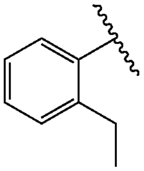,
-continued
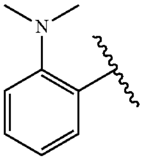,
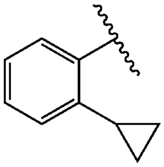,
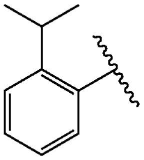,
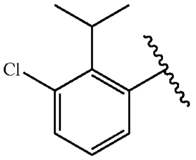,
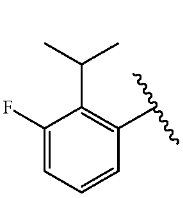,
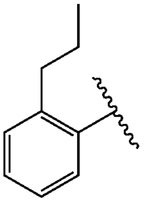,
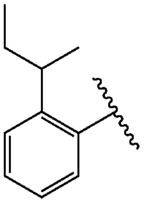,
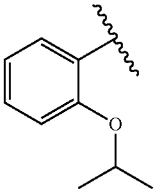,
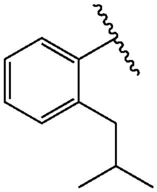,
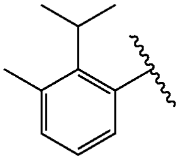,
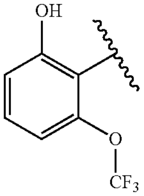,
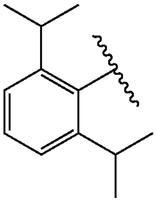,
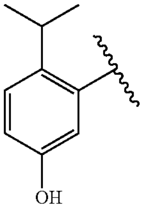,
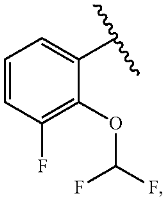,
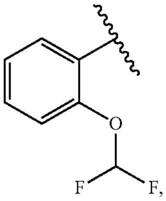,
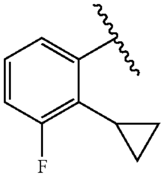,
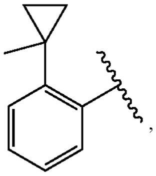,
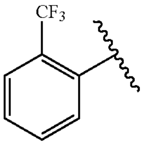, -continued
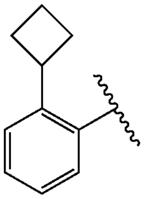,
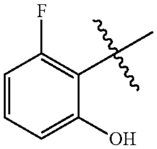,
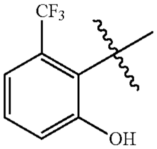,
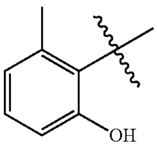,
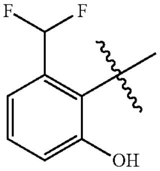,
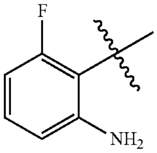,
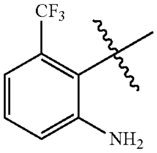,
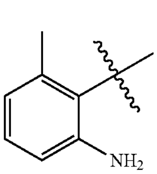,
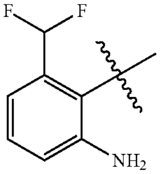,
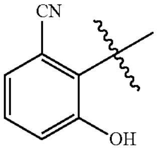,
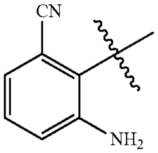,
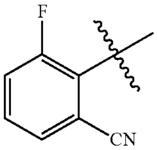,
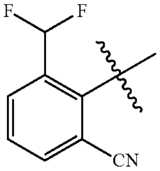,
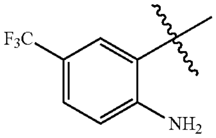,
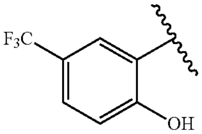,
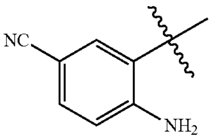,
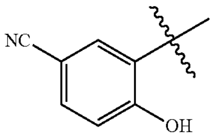,
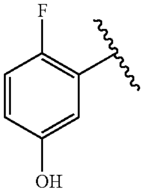,
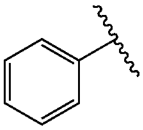,
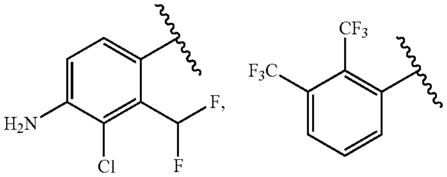,
-continued
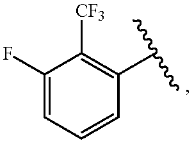,
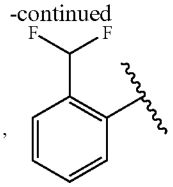,
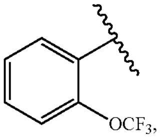
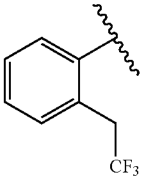,
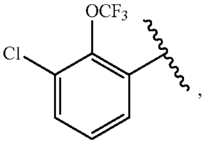,
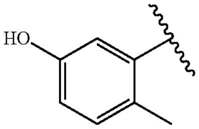,
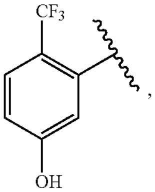,
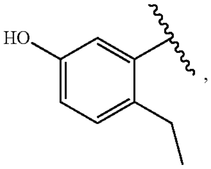,
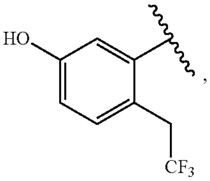,
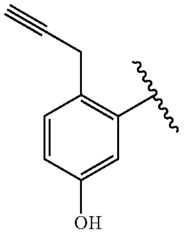,
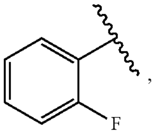,
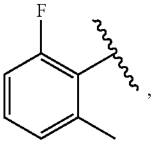,
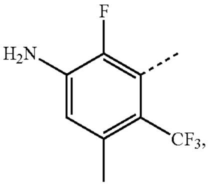
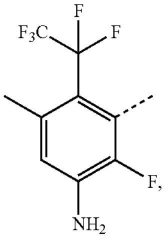
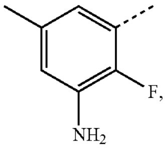
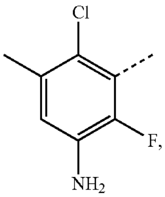
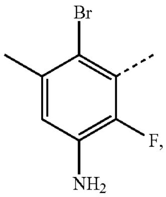
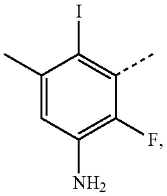
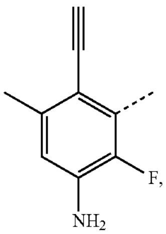
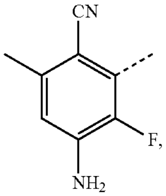

-continued

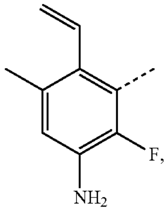

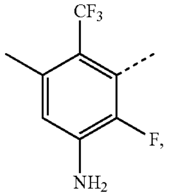

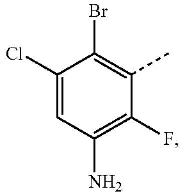

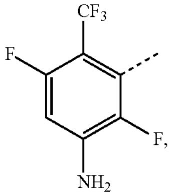

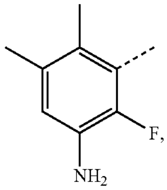

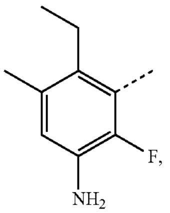

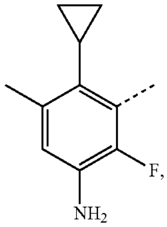

and

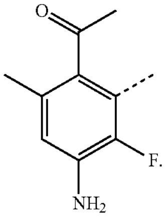

In embodiments of a compound of formula I, IA, IB, II, or IIA, $R^{17}$ is selected from

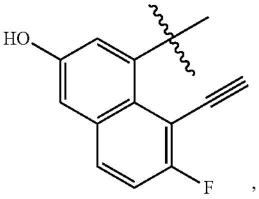

,

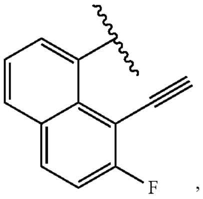

,

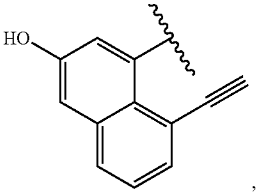

,

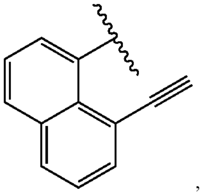

,

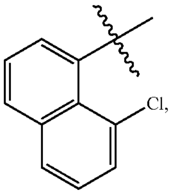

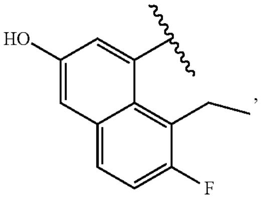

,

-continued

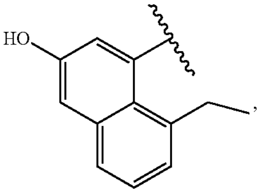

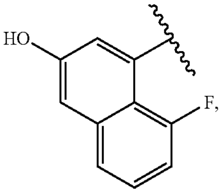

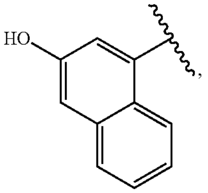

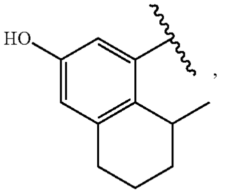

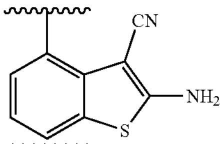

,

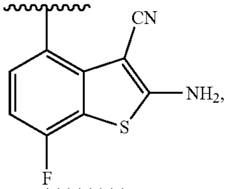

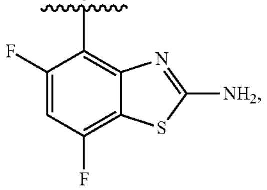

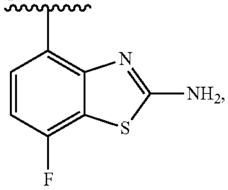

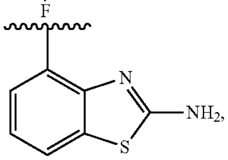

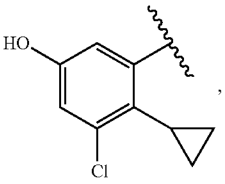

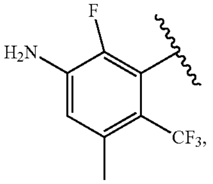

and

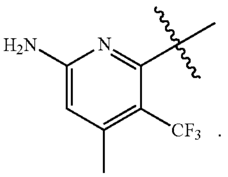

In embodiments of a compound of formula I, IA, IB, II, or IIA, $X^8$ is $C(R^8)$.

In embodiments of a compound of formula I, IA, IB, II, or IIA, $R^8$ is halogen.

In embodiments of a compound of formula I, IA, IB, II, or IIA, $R^8$ is —F.

In embodiments of a compound of formula I, IA, IB, II, or IIA, the compound has the formula:

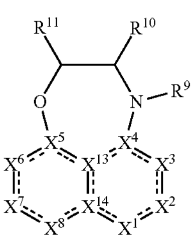

or

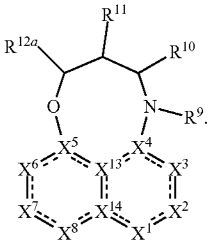

In embodiments of a compound of formula IA, IB, or IIA, the compound has the formula:

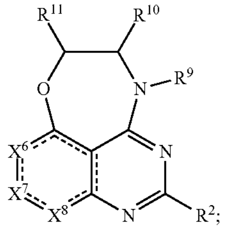

$X^6$ is selected from $C(R^6)$, $C(R^6)_2$, N, and $N(R^{6b})$;

$X^7$ is selected from $C(R^7)$ and $N(R^{7b})$;

$X^8$ is selected from $C(R^8)$ and $C(R^8)_2$; and $L^{7a}$ is a bond; $L^{7b}$ is a bond.

In embodiments of a compound of formula IA, IB, or IIA, the compound has the formula:

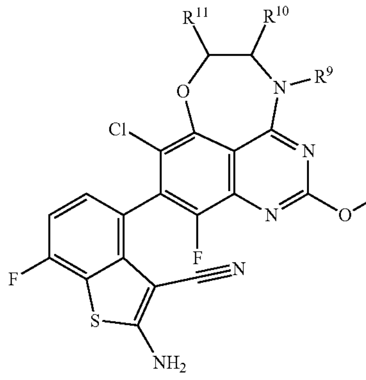

In an aspect is provided a compound having the formula B-$L^{BE}$-E wherein:

B is a monovalent form of a compound described here;

$L^{BE}$ is a covalent linker bonded to B and E; and

E is a monovalent form of a degradation enhancer.

In embodiments of a compound of formula B-$L^{BE}$-E, the degradation enhancer is capable of binding a protein selected from E3A, mdm2, APC, EDD1, SOCS/BC-box/eloBC/CUL5/RING, LNXp80, CBX4, CBLL1, HACE1, HECTD1, HECTD2, HECTD3, HECTD4, HECW1, HECW2, HERC1, HERC2, HERC3, HERC4, HER5, HERC6, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE3D, UBE4A, UBE4B, UBOX5, UBR5, VHL (von-Hippel-Lindau ubiquitin ligase), WWP1, WWP2, Parkin, MKRN1, CMA (chaperon-mediated autophage), SCFb-TRCP (Skip-Cullin-F box (Beta-TRCP) ubiquitin complex), b-TRCP (b-transducing repeat-containing protein), cIAP1 (cellular inhibitor of apoptosis protein 1), APC/C (anaphase-promoting complex/cyclosome), CRBN (cereblon), CUL4-RBX1-DDB1-CRBN ($CRL4^{CRBN}$) ubiquitin ligase, XIAP, IAP, KEAP1, DCAF15, RNF114, DCAF16, AhR, SOCS2, KLHL12, UBR2, SPOP, KLHL3, KLHL20, KLHDC2, SPSB1, SPSB2, SPSB4, SOCS6, FBXO4, FBXO31, BTRC, FBW7, CDC20, PML, TRIM21, TRIM24, TRIM33, GID4, avadomide, iberdomide, and CC-885.

In embodiments of a compound of formula I B-$L^{BE}$-E, the degradation enhancer is capable of binding a protein selected from UBE2A, UBE2B, UBE2C, UBE2D1, UBE2D2, UBE2D3, UBE2DR, UBE2E1, UBE2E2, UBE2E3, UBE2F, UBE2G1, UBE2G2, UBE2H, UBE2I, UBE2J1, UBE2J2, UBE2K, UBE2L3, UBE2L6, UBE2L1, UBE2L2, UBE2L4, UBE2M, UBE2N, UBE20, UBE2Q1, UBE2Q2, UBE2R1, UBE2R2, UBE2S, UBE2T, UBE2U, UBE2V1, UBE2V2, UBE2W, UBE2Z, ATG3, BIRC6, and UFC1.

In embodiments of a compound of formula B-$L^{BE}$-E, $L^{BE}$ is -$L^{BE1}$-$L^{BE2}$-$L^{BE3}$-$L^{BE4}$-$L^{BE5}$-;

$L^{BE1}$, $L^{BE2}$, $L^{BE3}$, $L^{BE4}$, and $L^{BE5}$ are independently a bond, —O—, —$N(R^{12})$—, —C(O)—, —$N(R^{12})C(O)$—, —C(O)$N(R^{12})$—, —S—, —$S(O)_2$—, —S(O)—, —$S(O)_2N(R^{12})$—, —$S(O)N(R^{12})$—, —$N(R^{12})S(O)$—, —$N(R^{12})S(O)_2$—, $C_{1-6}$ alkylene, (—O—$C_{1-6}$ alkyl)$_z$-, (—$C_{1-6}$ alkyl-O)$_z$—, $C_{2-6}$ alkenylene, $C_{2-6}$ alkynylene, $C_{1-6}$ haloalkylene, $C_{3-12}$ cycloalkylene, $C_{1-11}$ heterocycloalkylene, $C_{6-12}$ arylene, or $C_{1-11}$ heteroarylene, wherein $C_{1-6}$ alkylene, $C_{2-6}$ alkenylene, $C_{2-6}$ alkynylene, $C_{1-6}$ haloalkylene, $C_{3-12}$ cycloalkylene, $C_{1-11}$ heterocycloalkylene, $C_{6-12}$ arylene, or $C_{1-11}$ heteroarylene are optionally substituted with one, two, or three $R^{20}$; and wherein each $C_{1-6}$ alkyl of (—O—$C_{1-6}$ alkyl)$_z$- and (—$C_{1-6}$ alkyl-O)$_z$— is optionally substituted with one, two, or three $R^{20}$; and z is independently an integer from 0 to 10.

In embodiments of a compound of formula B-$L^{BE}$-E, $L^{BE}$ is —(O—$C_2$ alkyl)$_z$- and z is an integer from 1 to 10.

In embodiments of a compound of formula B-$L^{BE}$-E, $L^{BE}$ is —($C_2$ alkyl-O—)$_z$— and z is an integer from 1 to 10.

In embodiments of a compound of formula B-$L^{BE}$-E, $L^{BE}$ is —$(CH_2)_{zz1}L^{BE2}(CH_2O)_{zz2}$—, wherein $L^{BE2}$ is a bond, a 5 or 6 membered heterocycloalkylene or heteroarylene, phenylene, —$C_{2-4}$alkynylene, —$SO_2$— or —NH—; and zz1 and zz2 are independently an integer from 0 to 10.

In embodiments of a compound of formula B-$L^{BE}$-E, $L^{BE}$ is —$(CH_2)_{zz1}(CH_2O)_{zz2}$—, wherein zz1 and zz2 are each independently an integer from 0 to 10.

In embodiments of a compound of formula B-$L^{BE}$-E, $L^{BE}$ is a PEG linker.

In embodiments of a compound of formula B-$L^{BE}$-E, E is a monovalent form of a compound selected from

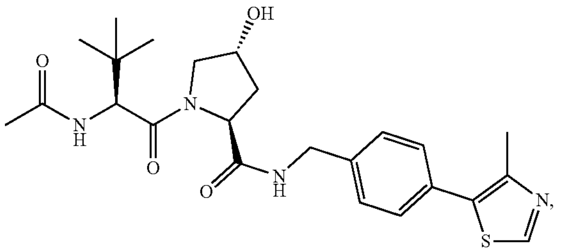

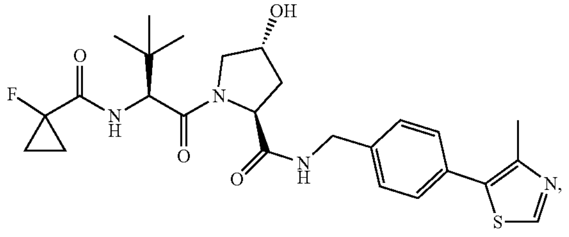

-continued

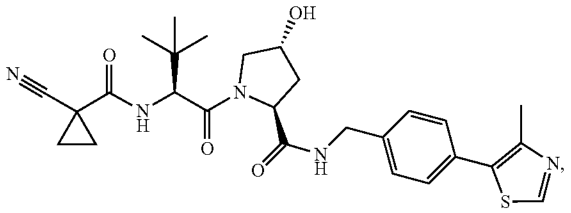

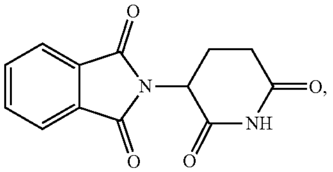

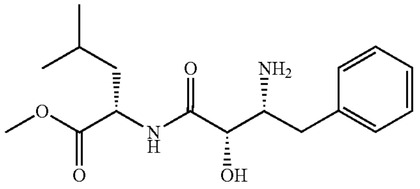

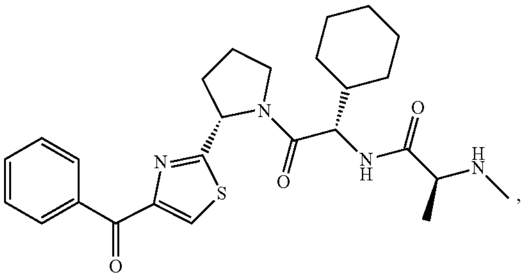

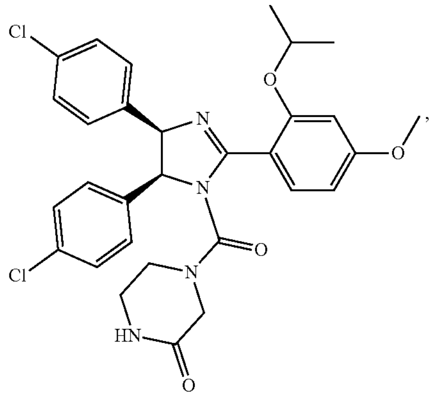

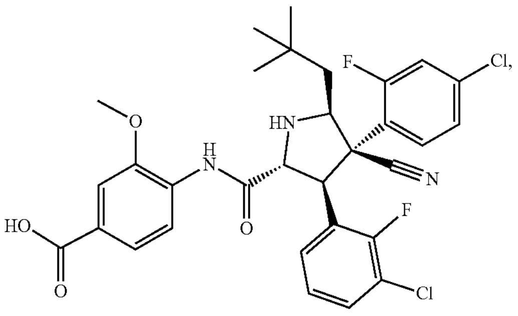

-continued

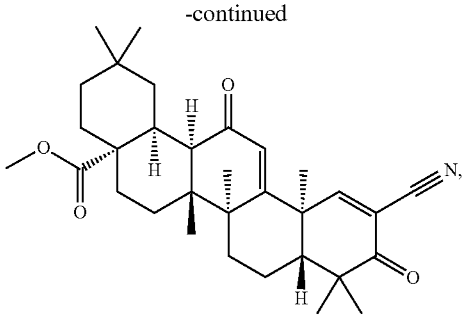

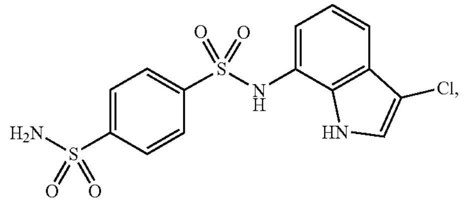

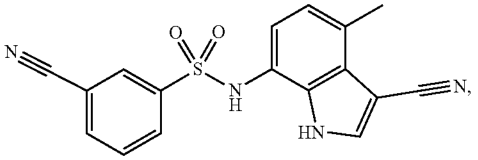

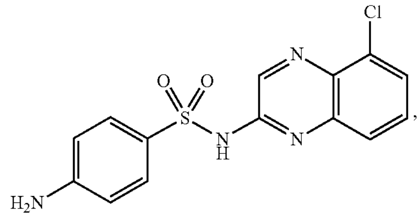

, and

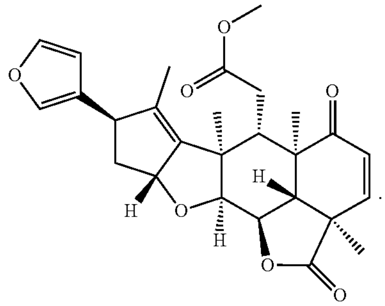

In an aspect is provided a pharmaceutical composition comprising a described herein, or a pharmaceutically acceptable salt or solvate thereof, and a pharmaceutically acceptable excipient.

In an aspect is provided a method of modifying a Ras mutant protein, comprising contacting the Ras mutant protein with an effective amount of the compound, salt, or solvate described herein.

In embodiments of a method described herein, the modified Ras mutant protein exhibits a reduced Ras signaling output.

In embodiments of a method described herein, the reduced Ras signaling output is evidenced by one or more output selected from (i) an increase in steady state level of GDP-bound modified protein; (ii) a reduction in steady state level of GTP-bound modified protein; (iii) a reduction of phosphorylated AKTs473; (iv) a reduction of phosphorylated ERK T202/Y204; (v) a reduction of phosphorylated S6 S235/236; (vi) a reduction of cell growth of a tumor cell expressing a Ras G12S mutant protein; and (vii) a reduction in Ras interaction with a Ras-pathway signaling protein.

In embodiments of a method described herein, the Ras mutant protein comprises an amino acid sequence in SEQ ID No. 4 having a serine residue corresponding to position 12 of SEQ ID No. 1.

In embodiments of a method described herein, the Ras mutant protein comprises an amino acid sequence of SEQ ID No. 4.

In embodiments of a method described herein, the modified Ras mutant protein comprises an amino acid sequence of SEQ ID No. 1, or a fragment thereof that comprises the serine residue corresponding to position 12 of SEQ ID No. 1, and wherein the compound selectively labels the serine residue as compared to (i) an aspartate residue of a K-Ras G12D mutant protein, said aspartate corresponding to position 12 of SEQ ID No. 2; (ii) a valine residue of a K-Ras G12V mutant protein, said valine corresponding to position 12 of SEQ ID No. 3; and/or (iii) a glycine residue of a K-Ras wildtype protein, said glycine corresponding to position 12 of SEQ ID No. 1.

In embodiments of a method described herein, the compound selectively labels the serine residue by at least 2-fold when assayed under comparable conditions.

In embodiments of a method described herein, the compound selectively labels the serine residue by at least 5-fold when assayed under comparable conditions.

In embodiments of a method described herein, the contacting occurs in vivo.

In an aspect is provided a method of treating cancer in a subject in need thereof, comprising administering to the subject a therapeutically effective amount of a compound described herein, or a pharmaceutically acceptable salt or solvate thereof.

In an aspect is provided a method of treating cancer in a subject comprising a Ras mutant protein, the method comprising: inhibiting the Ras mutant protein of said subject by administering to said subject a compound described herein, wherein the compound is characterized in that upon contacting the Ras mutant protein, said Ras mutant protein exhibits reduced Ras signaling output.

In embodiments of a method described herein, the cancer is a solid tumor or a hematological cancer.

In embodiments of a method described herein, the cancer comprises a K-Ras G12S mutant protein.

In an aspect is provided a method of modulating signaling output of a Ras protein, comprising contacting the Ras protein with an effective amount of a compound described herein, or a pharmaceutically acceptable salt or solvate thereof, thereby modulating the signaling output of the Ras protein.

In an aspect is provided a method of inhibiting cell growth, comprising administering an effective amount of a compound described herein, or a pharmaceutically acceptable salt or solvate thereof, to a cell expressing a Ras protein, thereby inhibiting growth of said cells.

In embodiments of a method described herein, the method comprises administering an additional agent.

In embodiments of a method described herein, the additional agent comprises (1) an inhibitor of MEK; (2) an inhibitor of epidermal growth factor receptor (EGFR) and/or mutants thereof; (3) an immunotherapeutic agent; (4) a taxane; (5) an anti-metabolite; (6) an inhibitor of FGFR1 and/or FGFR2 and/or FGFR3 and/or mutants thereof; (7) a mitotic kinase inhibitor; (8) an anti-angiogenic drug; (9) a topoisomerase inhibitor; (10) a platinum-containing compound; (11) an inhibitor of c-MET and/or mutants thereof; (12) an inhibitor of BCR-ABL and/or mutants thereof; (13) an inhibitor of ErbB2 (Her2) and/or mutants thereof; (14) an inhibitor of AXL and/or mutants thereof; (15) an inhibitor of NTRK1 and/or mutants thereof; (16) an inhibitor of RET and/or mutants thereof; (17) an inhibitor of A-Raf and/or B-Raf and/or C-Raf and/or mutants thereof; (18) an inhibitor of ERK and/or mutants thereof; (19) an MDM2 inhibitor; (20) an inhibitor of mTOR; (21) an inhibitor of IGF1/2 and/or IGF1-R; (22) an inhibitor of CDK9; (23) an inhibitor of farnesyl transferase; (24) an inhibitor of SHIP pathway; (25) an inhibitor of SRC; (26) an inhibitor of JAK; (27) a PARP inhibitor, (28) a ROS1 inhibitor; (29) an inhibitor of SHP pathway; (30) an inhibitor of Src, FLT3, HDAC, VEGFR, PDGFR, LCK, Bcr-Abl or AKT; (31) an inhibitor of KRAS G12C; (32) an SHC inhibitor; (33) a GAB inhibitor; (34) a PI-3 kinase inhibitor; (35) a MARPK inhibitor; (36) a CDK4/6 inhibitor; (37) a MAPK inhibitor; (38) a SHP2 inhibitor; (39) a checkpoint immune blockade agent; (40) a SOS1 inhibitor; or (41) a SOS2 inhibitor.

In embodiments of a method described herein, the additional agent comprises an inhibitor of SHP2 selected from RMC-4630, ERAS-601,

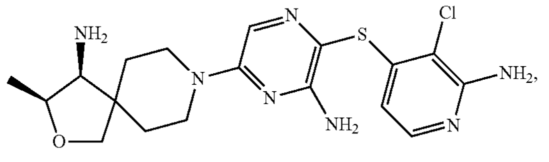

TNO155

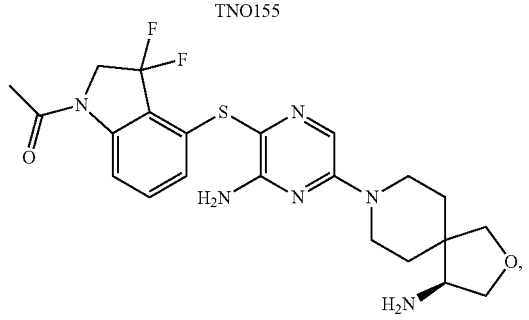

JAB-3068

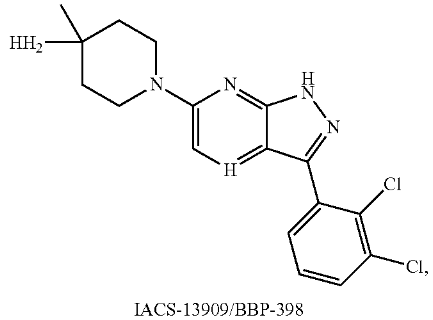

IACS-13909/BBP-398

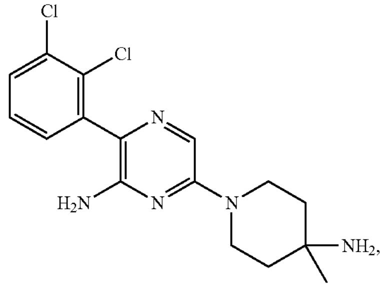

and

SHP099

-continued

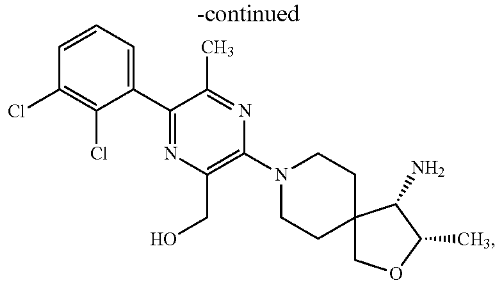

RMC-4550

In embodiments of a method described herein, the additional agent comprises an inhibitor of SOS selected from RMC-5845, BI-1701963,

BI-3406

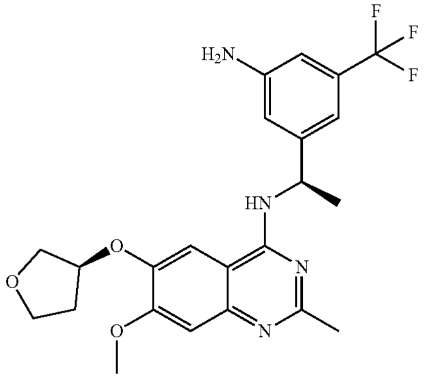

MRTX0902

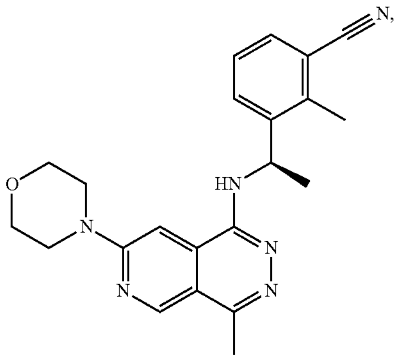

and

BAY 293

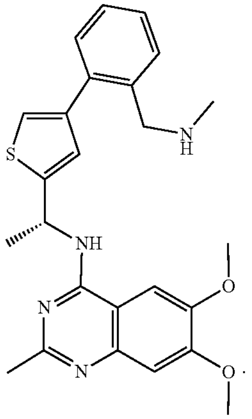

In embodiments of a method described herein, the additional agent comprises an inhibitor of EGFR selected from afatinib, erlotinib, gefitinib, lapatinib, cetuximab panitumumab, osimertinib, olmutinib, and EGF-816.

In embodiments of a method described herein, the additional agent comprises an inhibitor of MEK selected from trametinib, cobimetinib, binimetinib, selumetinib, refametinib, and AZD6244.

In embodiments of a method described herein, the additional agent comprises an inhibitor of ERK selected from ulixertinib, MK-8353, LTT462, AZD0364, SCH772984, BIX02189, LY3214996, and ravoxertinib.

In embodiments of a method described herein, the additional agent comprises an inhibitor of CDK4/6 selected from palbociclib, ribociclib, and abemaciclib.

In embodiments of a method described herein, the additional agent comprises an inhibitor of BRAF selected from Sorafenib, Vemurafenib, Dabrafenib, Encorafenib, regorafenib, and GDC-879.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 depicts a sequence alignment of various wild type Ras proteins including K-Ras, H-Ras, N-Ras, RalA, and RalB, from top to bottom.

DETAILED DESCRIPTION

Unless defined otherwise, all technical and scientific terms used herein have the same meaning as is commonly understood by one of skill in the art to which this disclosure belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Chemical structures are named herein according to IUPAC conventions as implemented in ChemDraw® software (Perkin Elmer, Inc., Cambridge, MA). The section headings used herein are for organizational purposes only and are not to be construed as limiting the subject matter described. As used in the specification and claims, the singular forms "a", "an" and "the" include plural references unless the context clearly dictates otherwise. Furthermore, use of the term "including" as well as other forms, such as "include", "includes", and "included", is not limiting. The section headings used herein are for organizational purposes only and are not to be construed as limiting the subject matter described.

The term "$C_{x-y}$" or "$C_x$-$C_y$" when used in conjunction with a chemical moiety, such as alkyl, alkenyl, or alkynyl, is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups, that contain from x to y carbons in the chain.

"Alkyl" refers to substituted or unsubstituted saturated hydrocarbon groups, including linear and branched alkyl groups. An alkyl group may contain from one to twelve carbon atoms (e.g., $C_{1-12}$ alkyl), such as one to eight carbon atoms ($C_{1-8}$ alkyl) or one to six carbon atoms ($C_{1-6}$ alkyl). Exemplary alkyl groups include methyl, ethyl, n-propyl, isopropyl, n-butyl, isobutyl, sec-butyl, tert-butyl, pentyl, isopentyl, neopentyl, hexyl, septyl, octyl, nonyl, and decyl. An alkyl group is attached to the rest of the molecule by a single bond. Unless stated otherwise specifically in the specification, an alkyl group is optionally substituted by one or more substituents such as those substituents described herein.

"Haloalkyl" refers to an alkyl group that is substituted by one or more halogens. Exemplary haloalkyl groups include trifluoromethyl, difluoromethyl, trichloromethyl, 2,2,2-trifluoroethyl, 1,2-difluoroethyl, 3-bromo-2-fluoropropyl, and 1,2-dibromoethyl.

"Alkenyl" refers to substituted or unsubstituted hydrocarbon groups, including linear and branched alkenyl groups, containing at least one double bond. An alkenyl group may contain from two to twelve carbon atoms (e.g., $C_{2-12}$ alkenyl), such as two to eight carbon atoms ($C_{2-8}$ alkenyl) or two to six carbon atoms ($C_{2-6}$ alkenyl). Exemplary alkenyl groups include ethenyl (i.e., vinyl), prop-1-enyl, but-1-enyl, pent-1-enyl, penta-1,4-dienyl, and the like. Unless stated otherwise specifically in the specification, an alkenyl group is optionally substituted by one or more substituents such as those substituents described herein.

"Alkynyl" refers to substituted or unsubstituted hydrocarbon groups, including linear and branched alkynyl groups, containing at least one triple bond. An alkynyl group may contain from two to twelve carbon atoms (e.g., $C_{2-12}$ alkynyl), such as two to eight carbon atoms ($C_{2-8}$ alkynyl) or two to six carbon atoms ($C_{2-6}$ alkynyl). Exemplary alkynyl groups include ethynyl, propynyl, butynyl, pentynyl, hexynyl, and the like. Unless stated otherwise specifically in the specification, an alkynyl group is optionally substituted by one or more substituents such as those substituents described herein.

"Alkylene" or "alkylene chain" refers to substituted or unsubstituted divalent saturated hydrocarbon groups, including linear alkylene and branched alkylene groups, that contain from one to twelve carbon atoms (e.g., $C_{1-12}$ alkylene), such as one to eight carbon atoms ($C_{1-8}$ alkylene) or one to six carbon atoms ($C_{1-6}$ alkylene). Exemplary alkylene groups include methylene, ethylene, propylene, and n-butylene. Similarly, "alkenylene" and "alkynylene" refer to alkylene groups, as defined above, which comprise one or more carbon-carbon double or triple bonds, respectively. The points of attachment of the alkylene, alkenylene or alkynylene chain to the rest of the molecule can be through one carbon or any two carbons of the chain. Unless stated otherwise specifically in the specification, an alkylene, alkenylene, or alkynylene group is optionally substituted by one or more substituents such as those substituents described herein.

"Heteroalkyl", "heteroalkenyl" and "heteroalkynyl" refer to substituted or unsubstituted alkyl, alkenyl and alkynyl groups, respectively, in which one or more, such as 1, 2 or 3, of the carbon atoms are replaced with a heteroatom, such as O, N, P, Si, S, or combinations thereof. Any nitrogen, phosphorus, and sulfur heteroatoms present in the chain may optionally be oxidized, and any nitrogen heteroatoms may optionally be quaternized. If given, a numerical range refers to the chain length in total. For example, a 3- to 8-membered heteroalkyl group has a chain length of 3 to 8 atoms. Connection to the rest of the molecule may be through either a heteroatom or a carbon in the heteroalkyl, heteroalkenyl, or heteroalkynyl chain. Unless stated otherwise specifically in the specification, a heteroalkyl, heteroalkenyl, or heteroalkynyl group is optionally substituted by one or more substituents such as those substituents described herein.

"Heteroalkylene", "heteroalkenylene" and "heteroalkynylene" refer to substituted or unsubstituted alkylene, alkenylene and alkynylene groups, respectively, in which one or more, such as 1, 2 or 3, of the carbon atoms are replaced with a heteroatom, such as O, N, P, Si, S, or combinations thereof. Any nitrogen, phosphorus, and sulfur heteroatoms present in the chain may optionally be oxidized, and any nitrogen heteroatoms may optionally be quaternized. If given, a numerical range refers to the chain length in total. For example, a 3- to 8-membered heteroalkylene group has a chain length of 3 to 8 atoms. The points of attachment of the heteroalkylene, heteroalkenylene or heteroalkynylene chain to the rest of the molecule can be through either one heteroatom or one carbon, or any two heteroatoms, any two carbons, or any one heteroatom and any one carbon in the heteroalkylene, heteroalkenylene or heteroalkynylene chain. Unless stated otherwise specifically in the specification, a heteroalkylene, heteroalkenylene, or heteroalkynylene group is optionally substituted by one or more substituents such as those substituents described herein.

"Carbocycle" refers to a saturated, unsaturated or aromatic ring in which each atom of the ring is a carbon atom. Carbocycle may include $C_{3-10}$ monocyclic rings, $C_{5-12}$ bicyclic rings, $C_{5-18}$ polycyclic rings, $C_{5-12}$ spirocyclic rings, and $C_{5-12}$ bridged rings. Each ring of a bicyclic or polycyclic carbocycle may be selected from saturated, unsaturated, and aromatic rings. A polycyclic carbocycle contains a number or rings equal to the minimum number of scissions required to convert the carbocycle into an acyclic skeleton (e.g., bicyclic, tricyclic, tetracyclic, etc.). In some embodiments, the carbocycle is a $C_{6-12}$ aryl group, such as $C_{6-10}$ aryl. In some embodiments, the carbocycle is a $C_{3-12}$ cycloalkyl group. In some embodiments, the carbocycle is a $C_{5-12}$ cycloalkenyl group. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic rings, as valence permits, are included in the definition of carbocycle. A carbocycle may comprise a fused ring, a bridged ring, a spirocyclic ring, a saturated ring, an unsaturated ring, an aromatic ring, or any combination thereof. Exemplary carbocycles include cyclopentyl, cyclohexyl, cyclohexenyl, adamantly, phenyl, indanyl, and naphthyl. Unless state otherwise specifically in the specification, a carbocycle is optionally substituted by one or more substituents such as those substituents described herein.

"Heterocycle" refers to a saturated, unsaturated or aromatic ring comprising one or more heteroatoms, for example 1, 2, 3, or 4 heteroatoms selected from O, S, P, and N. Heterocycle may include 3- to 10-membered monocyclic rings, 5- to 12-membered bicyclic rings, 5- to 18-membered polycyclic rings, 5- to 12-membered spirocyclic rings, and 5- to 12-membered bridged rings. Each ring of a bicyclic or polycyclic heterocycle may be selected from saturated, unsaturated, and aromatic rings. A polycyclic heterocycle contains a number or rings equal to the minimum number of scissions required to convert the heterocycle into an acyclic skeleton (e.g., bicyclic, tricyclic, tetracyclic, etc.). The heterocycle may be attached to the rest of the molecule through any atom of the heterocycle, valence permitting, such as a carbon or nitrogen atom of the heterocycle. In some embodiments, the heterocycle is a 5- to 10-membered heteroaryl group, such as 5- or 6-membered heteroaryl. In some embodiments, the heterocycle is a 3- to 12-membered heterocycloalkyl group. A heterocycle may comprise a fused ring, a bridged ring, a spirocyclic ring, a saturated ring, an unsaturated ring, an aromatic ring, or any combination thereof. In an exemplary embodiment, a heterocycle, e.g., pyridyl, may be fused to a saturated or unsaturated ring, e.g., cyclohexane, cyclopentane, or cyclohexene. Exemplary heterocycles include pyrrolidinyl, pyrrolyl, imidazolyl, pyrazolyl, triazolyl, piperidinyl, pyridinyl, pyrimidinyl, pyridazinyl, pyrazinyl, thiophenyl, oxazolyl, thiazolyl, morpholinyl, indazolyl, indolyl, benzothienyl, benzoxazolyl, and quinolinyl. Unless stated otherwise specifically in the specification, a heterocycle is optionally substituted by one or more substituents such as those substituents described herein.

“Heteroaryl” refers to an aromatic ring that comprises at least one heteroatom, for example 1, 2, 3, or 4 heteroatoms selected from O, S and N. Heteroaryl may include 5- to 10-membered monocyclic rings, 6- to 12-membered bicyclic rings, 6- to 18-membered polycyclic rings, 5- to 12-membered spirocyclic rings, and 6- to 12-membered bridged rings. As used herein, the heteroaryl ring may be selected from monocyclic, bicyclic, or polycyclic-including fused, spirocyclic and bridged ring systems—wherein at least one of the rings in the ring system is aromatic and comprises at least one heteroatom. A polycyclic heteroaryl contains a number or rings equal to the minimum number of scissions required to convert the heteroaryl into an acyclic skeleton (e.g., bicyclic, tricyclic, tetracyclic, etc.). The heteroatom(s) in the heteroaryl may optionally be oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryl groups include, but are not limited to, azepinyl, benzimidazolyl, benzisothiazolyl, benzisoxazolyl, benzofuranyl, benzothiazolyl, benzothiophenyl, benzoxazolyl, furanyl, imidazolyl, indazolyl, indolyl, isoquinolinyl, isothiazolyl, isoxazolyl, oxadiazolyl, oxazolyl, purinyl, pyrazinyl, pyrazolidinyl, pyrazolyl, pyridazinyl, pyridazolyl, pyridyl, pyrimidinyl, pyrrolyl, quinazolinyl, quinolinyl, quinoxalinyl, tetrahydroquinolinyl, thiadiazolyl, thiazolyl, and thienyl groups. Unless stated otherwise specifically in the specification, a heteroaryl is optionally substituted by one or more substituents such as those substituents described herein.

Unless stated otherwise, hydrogen atoms are implied in structures depicted herein as necessary to satisfy the valence requirement.

A waved line “∿” drawn across or at the end of a bond or a dashed bond “- - -” are used interchangeably herein to denote where a bond disconnection or attachment occurs. For example, in the structure

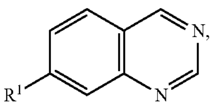

if $R^7$ is 2-fluoro-6-hydroxyphenyl as in

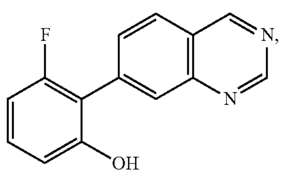 [SMILES: Oc1cccc(F)c1-c1ccc2cncnc2c1]

then $R^7$ may be depicted as

" 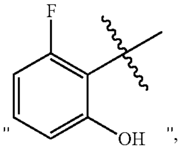 ", " 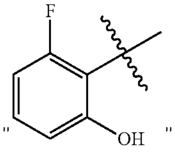 " or " 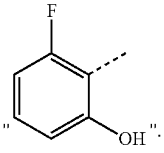 ".

The term “substituted” refers to moieties having substituents replacing a hydrogen on one or more carbons or heteroatoms of the structure. It will be understood that “substitution” or “substituted with” includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term “substituted” is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, heteroatoms such as nitrogen may have any permissible substituents of organic compounds described herein which satisfy the valences of the heteroatoms.

A compound disclosed herein, such as a compound of Formula I, IA, IB, II, or IIA, is optionally substituted by one or more—such as 1, 2 or 3—substituents selected from:

halogen, oxo, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$—, and —$S(=O)(=NR^{22})N(R^{22})(R^{23})$; wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —$S(=O)(=NR^{22})N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein —$C_{0-6}$ alkyl-($C_{3-12}$ carbocycle) and —$C_{0-6}$ alkyl-(3- to 12-membered heterocycle) are optionally substituted with one, two, or three groups independently selected from halogen and $C_{1-6}$ alkyl; and $R^{23}$ is independently selected at each occurrence from hydrogen and $C_{1-6}$ alkyl; or $R^{22}$ and $R^{23}$ attached to the same nitrogen atom form 3- to 10 membered heterocycle.

In some embodiments, a compound disclosed herein, such as a compound of Formula I, IA, IB, II, or IIA, is optionally substituted by one or more—such as 1, 2 or 3—substituents selected from:

halogen, oxo, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, and —$S(O)_2N(R^{22})(R^{23})$—, wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, and =$C(R^{21})_2$;

$R^{21}$ is independently selected at each occurrence from hydrogen, halogen, $C_{1-6}$ alkyl, and $C_{1-6}$ haloalkyl;

$R^{22}$ is independently selected at each occurrence from hydrogen, $C_{1-6}$ alkyl, $C_{1-6}$ haloalkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein —$C_{0-6}$ alkyl-($C_{3-12}$ carbocycle) and —$C_{0-6}$ alkyl-(3- to 12-membered heterocycle) are optionally substituted with one, two, or three groups independently selected from halogen and $C_{1-6}$ alkyl;

$R^{23}$ is independently selected at each occurrence from hydrogen and $C_{1-6}$ alkyl; or $R^{22}$ and $R^{23}$ attached to the same nitrogen atom form 3- to 10 membered heterocycle.

In some embodiments, a compound disclosed herein, such as a compound of Formula I, IA, IB, II, or IIA, is optionally substituted by one or more—such as 1, 2 or 3—substituents selected from halogen, oxo, =NH, —CN, —$NO_2$, $C_{1-6}$ alkyl, $C_{2-6}$ alkenyl, $C_{2-6}$ alkynyl, $C_{3-10}$ carbocycle, —$CH_2$—($C_{3-10}$ carbocycle), 3- to 10-membered heterocycle, —$CH_2$-(3- to 10-membered heterocycle), —OH, —$OCH_3$, —$OCH_2CH_3$, —$NH_2$, —$NHCH_3$, and —$NHCH_2CH_3$, wherein $C_{1-6}$ alkyl, $C_{2-6}$ alkenyl, $C_{2-6}$ alkynyl, $C_{3-10}$ carbocycle, —$CH_2$—($C_{3-10}$ carbocycle), 3- to 10-membered heterocycle, and —$CH_2$-(3- to 10-membered heterocycle) are optionally substituted with one, two, or three groups independently selected from halogen, oxo, =NH, —CN, —$NO_2$, —$CH_3$, —$CH_2CH_3$, —$CH(CH_3)_2$, —$C(CH_3)_3$, —OH, —$OCH_3$, —$OCH_2CH_3$, —$NH_2$, —$NHCH_3$, and —$NHCH_2CH_3$.

It will be understood by those skilled in the art that substituents can themselves be substituted, if appropriate. Unless specifically stated as "unsubstituted", references to chemical moieties herein are understood to include substituted variants. For example, reference to a "heteroaryl" group or moiety implicitly includes both substituted and unsubstituted variants.

Where bivalent substituent groups are specified herein by their conventional chemical formulae, written from left to right, they are intended to encompass the isomer that would result from writing the structure from right to left, e.g., —$CH_2O$— is also intended to encompass —$OCH_2$—.

"Optional" or "optionally" means that the subsequently described event or circumstances may or may not occur, and that the description includes instances where the event or circumstance occurs and instances in which it does not. For example, an "optionally substituted" group may be either unsubstituted or substituted.

Compounds of the present disclosure also include crystalline and amorphous forms of those compounds, pharmaceutically acceptable salts, and active metabolites having the same type of activity, including, for example, polymorphs, pseudopolymorphs, solvates, hydrates, unsolvated polymorphs (including anhydrates), conformational polymorphs, amorphous forms of the compounds, and mixtures thereof.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present disclosure, whether radioactive or not, are encompassed within the scope of the present disclosure. For example, hydrogen has three naturally occurring isotopes, denoted $^1H$ (protium), $^2H$ (deuterium), and $^3H$ (tritium). Protium is the most abundant isotope of hydrogen in nature. Enriching for deuterium may afford certain therapeutic advantages, such as increased in vivo half-life and/or exposure, or may provide a compound useful for investigating in vivo routes of drug elimination and metabolism. Examples of isotopes that may be incorporated into compounds of the present disclosure include, but are not limited to, $^2H$, $^3H$, $^{13}C$, $^{14}C$, $^{15}N$, $^{18}O$, $^{17}O$, $^{35}S$, $^{36}Cl$, and $^{18}F$. Of particular interest are compounds of Formula I, IA, IB, II, or IIA enriched in tritium or carbon-14, which can be used, for example, in tissue distribution studies; compounds of the disclosure enriched in deuterium-especially at a site of metabolism-resulting, for example, in compounds having greater metabolic stability; and compounds of Formula I, IA, IB, II, or IIA enriched in a positron emitting isotope, such as $^{11}C$, $^{18}F$, $^{15}O$ and $^{13}N$, which can be used, for example, in Positron Emission Topography (PET) studies. Isotopically-enriched compounds may be prepared by conventional techniques well known to those skilled in the art.

As used herein, the phrase "of the formula", "having the formula" or "having the structure" is not intended to be limiting and is used in the same way that the term "comprising" is commonly used. For example, if one structure is depicted, it is understood that all stereoisomer and tautomer forms are encompassed, unless stated otherwise.

Certain compounds described herein contain one or more asymmetric centers and can thus give rise to enantiomers, diastereomers, and other stereoisomeric forms, the asymmetric centers of which can be defined, in terms of absolute stereochemistry, as (R)- or (S)-. In some embodiments, in order to optimize the therapeutic activity of the compounds of the disclosure, e.g., to treat cancer, it may be desirable that the carbon atoms have a particular configuration (e.g., (R,R), (S,S), (S,R), or (R,S)) or are enriched in a stereoisomeric form having such configuration. The compounds of the disclosure may be provided as racemic mixtures. Accordingly, the disclosure relates to racemic mixtures, pure stereoisomers (e.g., enantiomers and diastereomers), stereoisomer-enriched mixtures, and the like, unless otherwise indicated. When a chemical structure is depicted herein without any stereochemistry, it is understood that all possible stereoisomers are encompassed by such structure. Similarly, when a particular stereoisomer is shown or named herein, it will be understood by those skilled in the art that minor amounts of other stereoisomers may be present in the compositions of the disclosure unless otherwise indicated, provided that the utility of the composition as a whole is not eliminated by the presence of such other isomers. Individual stereoisomers may be obtained by numerous methods that are known in the art, including preparation using chiral synthons or chiral reagents, resolution using chiral chromatography using a suitable chiral stationary phase or support, or by chemically converting them into diastereomers, separating the diastereoisomers by conventional means such as chromatography or recrystallization, then regenerating the original stereoisomer.

Additionally, where applicable, all cis-trans or E/Z isomers (geometric isomers), tautomeric forms and topoisomeric forms of the compounds described herein are included with the scope of the disclosure unless otherwise specified.

The term "pharmaceutically acceptable" refers to a material that is not biologically or otherwise unacceptable when used in the subject compositions and methods. For example, the term "pharmaceutically acceptable carrier" refers to a material—such as an adjuvant, excipient, glidant, sweetening agent, diluent, preservative, dye, colorant, flavor enhancer, surfactant, wetting agent, dispersing agent, suspending agent, stabilizer, isotonic agent, solvent or emulsifier—that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug Administration.

The terms "salt" and "pharmaceutically acceptable salt" refer to a salt prepared from a base or an acid. Pharmaceutically acceptable salts are suitable for administration to a patient, such as a mammal (for example, salts having acceptable mammalian safety for a given dosage regime). Salts can be formed from inorganic bases, organic bases, inorganic acids and organic acids. In addition, when a compound contains both a basic moiety, such as an amine, pyridine or imidazole, and an acidic moiety, such as a carboxylic acid or tetrazole, zwitterions may be formed and are included within the term "salt" as used herein. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc., and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. An effective amount of an active agent may be administered in a single dose or in multiple doses. A component may be described herein as having at least an effective amount, or at least an amount effective, such as that associated with a particular goal or purpose, such as any described herein. The term "effective amount" also applies to a dose that will provide an image for detection by an appropriate imaging method. The specific dose may vary depending on one or more of: the particular agent chosen, the dosing regimen to be followed, whether it is administered in combination with other compounds, timing of administration, the tissue to be imaged, and the physical delivery system in which it is carried.

As used herein, "treating" or "treatment" refers to an approach for obtaining beneficial or desired results with respect to a disease, disorder, or medical condition (such as cancer) in a subject, including but not limited to the following: (a) preventing the disease or medical condition from occurring, e.g., preventing the reoccurrence of the disease or medical condition or prophylactic treatment of a subject that is pre-disposed to the disease or medical condition; (b) ameliorating the disease or medical condition, e.g., eliminating or causing regression of the disease or medical condition in a subject; (c) suppressing the disease or medical condition, e.g., slowing or arresting the development of the disease or medical condition in a subject; or (d) alleviating symptoms of the disease or medical condition in a subject. For example, "treating cancer" would include preventing cancer from occurring, ameliorating cancer, suppressing cancer, and alleviating the symptoms of cancer. Also, a therapeutic benefit is achieved with the eradication or amelioration of one or more of the physiological symptoms associated with the underlying disorder such that an improvement is observed in the subject, notwithstanding that the subject may still be afflicted with the underlying disorder.

A "therapeutic effect", as that term is used herein, encompasses a therapeutic benefit and/or prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The terms "antagonist" and "inhibitor" are used interchangeably, and they refer to a compound having the ability to inhibit a biological function (e.g., activity, expression, binding, protein-protein interaction) of a target protein (e.g., K-Ras). Accordingly, the terms "antagonist" and "inhibitor" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition.

The term "selective inhibition" or "selectively inhibit" refers to the ability of a biologically active agent to preferentially reduce the target signaling activity as compared to off-target signaling activity, via direct or indirect interaction with the target.

The terms "subject" and "patient" refer to an animal, such as a mammal, for example a human. The methods described herein can be useful in both human therapeutics and veterinary applications. In some embodiments, the subject is a mammal, such as a human. "Mammal" includes humans and both domestic animals such as laboratory animals and household pets (e.g., cats, dogs, swine, cattle, sheep, goats, horses, rabbits), and non-domestic animals such as wildlife and the like.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The terms "polynucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs, such as peptide nucleic acid (PNA), morpholino and locked nucleic acid (LNA), glycol nucleic acid (GNA), threose nucleic acid (TNA), 2'-fluoro, 2'-OMe, and phosphorothiolated DNA. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component or other conjugation target.

As used herein, "expression" refers to the process by which a polynucleotide is transcribed from a DNA template (such as into an mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

An "antigen" is a moiety or molecule that contains an epitope, and, as such, also specifically binds to an antibody. An "antigen binding unit" may be whole or a fragment (or fragments) of a full-length antibody, a structural variant thereof, a functional variant thereof, or a combination thereof. A full-length antibody may be, for example, a monoclonal, recombinant, chimeric, deimmunized, humanized and human antibody. Examples of a fragment of a full-length antibody may include, but are not limited to, variable heavy (VH), variable light (VL), a heavy chain found in camelids, such as camels, llamas, and alpacas (VHH or $V_HH$), a heavy chain found in sharks (V-NAR domain), a single domain antibody (sdAb, e.g., "nanobody") that comprises a single antigen-binding domain, Fv, Fd, Fab, Fab', F(ab')2, and "r IgG" (or half antibody). Examples of modified fragments of antibodies may include, but are not limited to scFv, di-scFv or bi(s)-scFv, scFv-Fc, scFv-zipper, scFab, Fab2, Fab3, diabodies, single chain diabodies, tandem diabodies (Tandab's), tandem di-scFv, tandem tri-scFv, minibodies (e.g., (VH-VL-CH3)2, (scFv-CH3)2, ((scFv)2-CH3+CH3), ((scFv)2-CH3) or (scFv-CH3-scFv)2), and multibodies (e.g., triabodies or tetrabodies).

The term "antibody" and "antibodies" encompass any antigen binding units, including without limitation: monoclonal antibodies, human antibodies, humanized antibodies, camelised antibodies, chimeric antibodies, and any other epitope-binding fragments.

"Prodrug" is meant to indicate a compound that may be converted under physiological conditions or by solvolysis to a biologically active compound described herein (e.g., a compound of Formula I, IA, IB, II, or IIA). Thus, the term "prodrug" refers to a precursor of a biologically active compound that is pharmaceutically acceptable. In some aspects, a prodrug is inactive when administered to a subject but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam); Higuchi, T., et al., "Pro-drugs as Novel Delivery Systems," (1987) A.C.S. Symposium Series, Vol. 14; and Bioreversible Carriers in Drug Design, ed. Edward B. Roche, American Pharmaceutical Association and Pergamon Press each of which is incorporated in full by reference herein). The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound, and the like.

The term "in vivo" refers to an event that takes place in a subject's body. The term "ex vivo" refers to an event that first takes place outside of the subject's body for a subsequent in vivo application into a subject's body. For example, an ex vivo preparation may involve preparation of cells outside of a subject's body for the purpose of introduction of the prepared cells into the same or a different subject's body. The term "in vitro" refers to an event that takes place outside of a subject's body. For example, an in vitro assay encompasses any assay run outside of a subject's body. In vitro assays encompass cell-based assays in which cells alive or dead are employed. In vitro assays also encompass a cell-free assay in which no intact cells are employed.

The disclosure is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the disclosure includes compounds produced by a process comprising administering a compound disclosed herein to a mammal for a period of time sufficient to yield a metabolic product thereof. Such products are typically identified by administering a radiolabeled compound of the disclosure in a detectable dose to an animal, such as rat, mouse, guinea pig, monkey, or to a human, allowing sufficient time for metabolism to occur, and isolating its conversion products from the urine, blood or other biological samples.

The term "Ras" or "RAS" refers to a protein in the Rat sarcoma (Ras) superfamily of small GTPases, such as in the Ras subfamily. The Ras superfamily includes, but is not limited to, the Ras subfamily, Rho subfamily, Rab subfamily, Rap subfamily, Arf subfamily, Ran subfamily, Rheb subfamily, RGK subfamily, Rit subfamily, Miro subfamily, and Unclassified subfamily. In some embodiments, a Ras protein is selected from the group consisting of KRAS (also used interchangeably herein as K-Ras, K-ras, or Kras), HRAS (or H-Ras), NRAS (or N-Ras), MRAS (or M-Ras), ERAS (or E-Ras), RRAS2 (or R-Ras2), RALA (or RalA), RALB (or RalB), RIT1, and any combination thereof, such as from KRAS, HRAS, NRAS, RALA, RALB, and any combination thereof.

The terms "mutant Ras" and "Ras mutant", as used interchangeably herein, refer to a Ras protein with one or more amino acid mutations, such as with respect to a common reference sequence such as a wild-type (WT) sequence. In some embodiments, a mutant Ras is selected from a mutant KRAS, mutant HRAS, mutant NRAS, mutant MRAS, mutant ERAS, mutant RRAS2, mutant RALA, mutant RALB, mutant RIT1, and any combination thereof, such as from a mutant KRAS, mutant HRAS, mutant NRAS, mutant RALA, mutant RALB, and any combination thereof. In some embodiments, a mutation can be an introduced mutation, a naturally occurring mutation, or a non-naturally occurring mutation. In some embodiments, a mutation can be a substitution (e.g., a substituted amino acid), insertion (e.g., addition of one or more amino acids), or deletion (e.g., removal of one or more amino acids). In some embodiments, two or more mutations can be consecutive, non-consecutive, or a combination thereof. In some embodiments, a mutation can be present at any position of Ras. In some embodiments, a mutation can be present at position 12, 13, 62, 92, 95, 96 (e.g., Y96D), or any combination thereof of Ras relative to SEQ ID No. 1 when optimally aligned. In some embodiments, a mutant Ras may comprise about or at least about 1, 2, 3, 4, 5, 6, 7, 8, 9, 10, 11, 12, 13, 14, 15, 16, 17, 18, 19, 20, 25, 30, 35, 40, 45, 50, or more than 50 mutations. In some embodiments, a mutant Ras may comprise up to about 1, 2, 3, 4, 5, 6, 7, 8, 9, 10, 11, 12, 13, 14, 15, 16, 17, 18, 19, 20, 25, 30, 35, 40, 45, or 50 mutations. In some embodiments, the mutant Ras is about or up to about 500, 400, 300, 250, 240, 233, 230, 220, 219, 210, 208, 206, 204, 200, 195, 190, 189, 188, 187, 186, 185, 180, 175, 174, 173, 172, 171, 170, 169, 168, 167, 166, 165, 160, 155, 150, 125, 100, 90, 80, 70, 60, 50, or fewer than 50 amino acids in length. In some embodiments, an amino acid of a mutation is a proteinogenic, natural, standard, non-standard, non-canonical, essential, non-essential, or non-natural amino acid. In some embodiments, an amino acid of a mutation has a positively charged side chain, a negatively charged side chain, a polar uncharged side chain, a non-polar side chain, a hydrophobic side chain, a hydrophilic side chain, an aliphatic side chain, an aromatic side chain, a cyclic side chain, an acyclic side chain, a basic side chain, or an acidic side chain. In some embodiments, a mutation comprises a reactive moiety. In some embodiments, a substituted amino acid comprises a reactive moiety. In some embodiments, a mutant Ras can be further modified, such as by conjugation with a detectable label. In some embodiments, a mutant Ras is a full-length or truncated polypeptide. For example, a mutant Ras can be a truncated polypeptide comprising residues 1-169 or residues 11-183 (e.g., residues 11-183 of a mutant RALA or mutant RALB).

As used herein, the term "corresponding to" or "corresponds to" as applied to an amino acid residue in a polypeptide sequence refers to the correspondence of such amino acid relative to a reference sequence when optimally aligned (e.g., taking into consideration of gaps, insertions and mismatches; wherein alignment may be primary sequence alignment or three-dimensional structural alignment of the folded proteins). For instance, the serine residue in a K-Ras G12S mutant refers to the serine corresponding to residue 12 of SEQ ID No. 4, which can serve as a reference sequence. For instance, the aspartate residue in a K-Ras G12D mutant refers to the aspartate corresponding to residue 12 of SEQ ID No. 2, which can serve as a reference sequence. When an amino acid of a mutant Ras protein corresponds to an amino acid position in the WT Ras protein, it will be understood that although the mutant Ras protein amino acid may be a different amino acid (e.g., G12D, wherein the wildtype G at position 12 is replaced by an aspartate at position 12 of SEQ ID. No. 1), the mutant amino acid is at the position corresponding to the wildtype amino acid (e.g., of SEQ ID No. 1). In embodiments, a modified Ras mutant protein disclosed herein may comprise truncations at the C-terminus, or truncations at the N-terminal end preceding the serine residue. The serine residue in such N-terminal truncated modified mutant is still considered corresponding to position 12 of SEQ ID No. 1. In addition, an aspartate residue at position 12 of SEQ ID No. 2 finds a corresponding residue in SEQ ID Nos. 6 and 8.

The terms "Switch II pocket" and "switch II binding pocket," as used interchangeably herein, refer to a binding pocket formed under the "Switch II" loop of Ras. In some embodiments, the Switch II pocket is located between the central beta-sheet (β-sheet) of Ras and the alpha(α)2- and α3-helices. In some embodiments, the Switch II binding pocket is located about or at least about 5, 10, 20, 30, 40, 50, 60, 70, 80, 90, 100, 110, 120, 130, 140, 150, 160, 170, 180, 190, 200 nanometers (nm), or more from position 12, position 60, position 99, or any combination thereof. In some embodiments, the Switch II binding pocket is located up to about 5, 10, 20, 30, 40, 50, 60, 70, 80, 90, 100, 110, 120, 130, 140, 150, 160, 170, 180, 190, 200 nm, or more from position 12, position 60, position 99, or any combination thereof. In some cases, the Switch II pocket may be formed upon binding to a small molecule (e.g., a small molecule inhibitor). Alternatively, the Switch II pocket may be formed prior to binding to a small molecule.

In some embodiments, the Switch II pocket of Ras comprises three, four, five, six, seven, eight, nine, ten, eleven, twelve, thirteen, fourteen, fifteen or more amino acid residues, or between three to fifteen residues selected from the group consisting of V7, V9, G10, G12, G12X mutant (e.g., G12C, G12S, G12D, or G12V), K14, K16, P34, T58, A59, G60, Q61, E62, E63, Y64, S65, R68, D69, M72, D92, H95, Y96, Q99, I100, R102, and V103 of SEQ ID NO. 1, or corresponding amino acid residues of an HRAS or NRAS protein. In some embodiments, the Switch II pocket of Ras comprises three, four, five, six, seven, eight, nine, ten, eleven, or twelve amino acid residues selected from the group consisting of G10, G12, G12X mutant (e.g., G12C, G12S, G12D, or G12V), K16, P34, T58, A59, E62, R68, D69, H95, Q99, R102, and V103 of SEQ ID NO. 1 or corresponding amino acid residues of an HRAS or NRAS protein.

As used herein, the term "leaving group" refers to an atom or group that becomes detached from an atom in the residual or main part of the substrate in a specified reaction. The residual or main part of the substrate is also referred to herein as the "staying group".

Compounds

In an aspect is provided a compound of Formula (I):

(I)

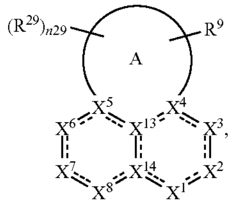

or a pharmaceutically acceptable salt or solvate thereof, wherein:

Ring A is selected from a monocyclic $C_{7-10}$ carbocycle and monocyclic 7- to 10-membered heterocycle;

$X^1$ is selected from $C(R^1)$, $C(R^1)_2$, N, $N(R^{1b})$, O, S, S(O), $S(O)_2$, and C(O);

$X^2$ is selected from $C(R^2)$, $C(R^2)_2$, N, $N(R^{2b})$, O, S, S(O), $S(O)_2$, and C(O);

$X^3$ is selected from $C(R^3)$, $C(R^3)_2$, N, $N(R^{3b})$, O, S, S(O), $S(O)_2$, and C(O);

$X^4$ is selected from C, $C(R^4)$, and N;

$X^5$ is selected from C, $C(R^5)$, and N;

$X^6$ is selected from $C(R^6)$, $C(R^6)_2$, N, $N(R^{6b})$, O, S, S(O), $S(O)_2$, and C(O);

$X^7$ is selected from $C(R^7)$, $C(R^7)(R^{7a})$, and $N(R^{1h})$;

$X^8$ is selected from $C(R^8)$, $C(R^8)_2$, N, $N(R^{8b})$, O, S, S(O), $S(O)_2$, and C(O);

$X^{13}$ is selected from C, $C(R^{13a})$, and N;

$X^{14}$ is selected from C, $C(R^{14a})$, and N;

$R^7$ is $-L^{7a}-R^{17}$; $R^{7b}$ is $-L^{7b}-R^{17}$;

$L^{7a}$ is selected from a bond, $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, —N($R^{12}$)—, —C(O)—, —N($R^{12}$)C(O)—, —C(O)N($R^{12}$)—, —S—, —S(O)$_2$—, —S(O)—, —P(O)($R^{12}$)—, —N($R^{12}$)S(O)$_2$—, —N($R^{12}$)S(O)—, —N($R^{12}$)P(O)($R^{12}$)—, —S(O)$_2$N($R^{12}$)—, —S(O)N($R^{12}$)—, —P(O)($R^{12}$)N($R^{12}$)—, —OP(O)($R^{12}$)—, and —P(O)($R^{12}$)O—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$;

$L^{7b}$ is selected from a bond, $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —C(O)—, and —C(O)N($R^{12}$)—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$;

$R^9$ is -$L^{19}$-$R^{19}$-$L^{19a}$-$R^{19a}$;

$L^{19}$ is selected from a bond, $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, —N($R^{12}$)—, —C(O)—, —N($R^{12}$)C(O)—, —C(O)N($R^{12}$)—, —S—, —S(O)$_2$—, —S(O)—, —P(O)($R^{12}$)—, —N($R^{12}$)S(O)$_2$—, —N($R^{12}$)S(O)—, —N($R^{12}$)P(O)($R^{12}$)—, —S(O)$_2$N($R^{12}$)—, —S(O)N($R^{12}$)—, —P(O)($R^{12}$)N($R^{12}$)—, —OP(O)($R^{12}$)—, and —P(O)($R^{12}$)O—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$;

$R^{19}$ is selected from monocyclic $C_{3-8}$ carbocycle and monocyclic 3- to 8-membered heterocycle, wherein the monocyclic $C_{3-8}$ carbocycle and monocyclic 3- to 8-membered heterocycle are optionally substituted with one or more $R^{20}$;

$L^{19a}$ is selected from a bond, $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, —N($R^{12}$)—, —C(O)—, —N($R^{12}$)C(O)—, —C(O)N($R^{12}$)—, —S—, —S(O)$_2$—, —S(O)—, —P(O)($R^{12}$)—, —N($R^{12}$)S(O)$_2$—, —N($R^{12}$)S(O)—, —N($R^{12}$)P(O)($R^{12}$)—, —S(O)$_2$N($R^{12}$)—, —S(O)N($R^{12}$)—, —P(O)($R^{12}$)N($R^{12}$)—, —OP(O)($R^{12}$)—, and —P(O)($R^{12}$)O—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$;

$R^{19a}$ is selected from:
- i) 5-membered heteroaryl comprising one or more ring nitrogen atoms, wherein the 5-membered heteroaryl is directly bonded to $L^{19a}$ through an $R^{19a}$ ring nitrogen atom and wherein $R^{19a}$ is optionally substituted with one or more $R^{20}$; and
- ii) 5- to 12-membered heterocycle comprising three or four ring nitrogen atoms, wherein the 5- to 12-membered heterocycle is optionally substituted with one or more $R^{20}$;

$R^{1b}$, $R^{2b}$, $R^{3b}$, $R^{6b}$, and $R^{8b}$ are independently selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —C(O)OR$^{12}$, —C(O)R$^{12}$, —C(O)N($R^{12}$)($R^{13}$), —C(O)C(O)N($R^{12}$)($R^{13}$), —S(O)$_2$R$^{12}$, —S(O)(NR$^{12}$)R$^{12}$, —S(O)$_2$N($R^{12}$)($R^{13}$), and —S(=O)(=NR$^{12}$)N($R^{12}$)($R^{13}$), wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$;

$R^1$, $R^2$, $R^3$, $R^4$, $R^5$, $R^6$, $R^{7a}$, $R^8$, $R^{13a}$, $R^{14a}$, and $R^{17}$ are independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —OR$^{12}$, —SR$^{12}$, —N($R^{12}$)($R^{13}$), —C(O)OR$^{12}$, —OC(O)N($R^{12}$)($R^{13}$), —N($R^{12}$)C(O)N($R^{12}$)($R^{13}$), —N($R^{12}$)C(O)OR$^{12}$, —N($R^{12}$)S(O)$_2$R$^{12}$, —C(O)R$^{12}$, —S(O)R$^{12}$, —OC(O)R$^{12}$, —C(O)N($R^{12}$)($R^{13}$), —C(O)C(O)N($R^{12}$)($R^{13}$), —N($R^{12}$)C(O)R$^{12}$, —S(O)$_2$R$^{12}$, —S(O)(NR$^{12}$)R$^{12}$, —S(O)$_2$N($R^{12}$)($R^{13}$), and —S(=O)(=NR$^{12}$)N($R^{12}$)($R^{13}$), wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one or more $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one or more $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —OR$^{22}$, —SR$^{22}$, —N($R^{22}$)($R^{23}$), =NR$^{22}$, =C($R^{21}$)$_2$, —C(O)OR$^{22}$, —OC(O)N($R^{22}$)($R^{23}$), —N($R^{22}$)C(O)N($R^{22}$)($R^{23}$), —N($R^{22}$)C(O)OR$^{22}$, —N($R^{22}$)S(O)$_2$R$^{22}$, —C(O)R$^{22}$, —S(O)R$^{22}$, —OC(O)R$^{22}$, —C(O)N($R^{22}$)($R^{23}$), —C(O)C(O)N($R^{22}$)($R^{23}$), —N($R^{22}$)C(O)R$^{22}$, —S(O)$_2$R$^{22}$, —S(O)(NR$^{22}$)R$^{22}$, —S(O)$_2$N($R^{22}$)($R^{23}$)—, and —S(=O)(=NR$^{22}$)N($R^{22}$)($R^{23}$); wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —C(O)$OR^{22}$, —OC(O)$N(R^{22})(R^{23})$, —$N(R^{22})C(O)N(R^{22})(R^{23})$, —$N(R^{22})C(O)OR^{22}$, —$N(R^{22})S(O)_2R^{22}$, —C(O)$R^{22}$, —S(O)$R^{22}$, —OC(O)$R^{22}$, —C(O)$N(R^{22})(R^{23})$, —C(O)C(O)$N(R^{22})(R^{23})$, —$N(R^{22})C(O)R^{22}$, —$S(O)_2R^{22}$, —S(O)$(NR^{22})R^{22}$, —$S(O)_2N(R^{22})(R^{23})$, and —S(=O)(=$NR^{22}$)$N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one or more substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle;

$R^{29}$ is independently selected at each occurrence from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —C(O)$OR^{12}$, —OC(O)$N(R^{12})(R^{13})$, —$N(R^{12})C(O)N(R^{12})(R^{13})$, —$N(R^{12})C(O)OR^{12}$, —$N(R^{12})S(O)_2R^{12}$, —C(O)$R^{12}$, —S(O)$R^{12}$, —OC(O)$R^{12}$, —C(O)$N(R^{12})(R^{13})$, —C(O)C(O)$N(R^{12})(R^{13})$, —$N(R^{12})C(O)R^{12}$, —$S(O)_2R^{12}$, —S(O)$(NR^{12})R^{12}$, —$S(O)_2N(R^{12})(R^{13})$, and —S(=O)(=$NR^{12}$)$N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$; and wherein two $R^{29}$ attached to the same atom are optionally joined to form oxo;

n29 is selected from 0, 1, 2, 3, 4, 5, 6, 7, 8, 9, 10, 11, 12, and 13; and each ------ independently indicates a single or double bond such that all valences are satisfied.

References herein to Ring A include only those atoms of the depicted ring or ring system in the shortest path between the two points of connectivity with Ring A (i.e., —$X^5$—$X^{13}$—$X^4$ of Formula I). For example, in compounds (a) and (b) shown below, Ring A is (a) a 7-membered monocyclic heterocycle or (b) a 7-membered monocyclic carbocycle.

(a)

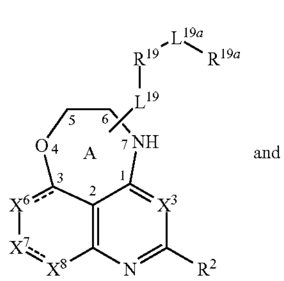

and (b)

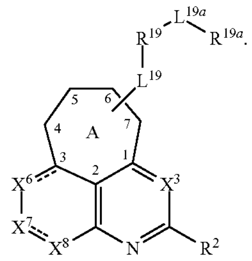

In embodiments of the compound of Formula I, the compound has a formula (IA):

(IA)

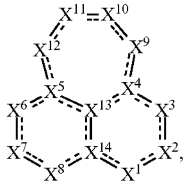

or a pharmaceutically acceptable salt or solvate thereof, wherein:

$X^9$ is selected from $C(R^9)$, $C(R^9)(R^{9a})$, and $N(R^9)$;

$X^{10}$ is selected from $C(R^{10})$, $C(R^{10})_2$, N, $N(R^{10b})$, O, S, S(O), $S(O)_2$, and C(O);

$X^{11}$ is selected from $C(R^{11})$, $C(R^{11})_2$, N, $N(R^{11b})$, O, S, S(O), $S(O)_2$, and C(O);

$X^{12}$ is selected from —$X^{12a}$—, —$X^{12a}$—$X^{12b}$—, —$X^{12a}$—$X^{12b}$—$X^{12c}$—, and —$X^{12a}$—$X^{12b}$—$X^{12c}$—$X^{12d}$—; wherein $X^{12a}$ is directly bonded to $X^5$;

$X^{12a}$, $X^{12b}$, $X^{12c}$, and $X^{12d}$ are independently selected from $C(R^{12a})$, $C(R^{12a})_2$, N, $N(R^{12b})$, O, S, S(O), $S(O)_2$, and C(O);

$R^{19a}$ is 5-membered heteroaryl comprising one or more ring nitrogen atoms, wherein the 5-membered heteroaryl is directly bonded to $L^{19a}$ through an $R^{19a}$ ring nitrogen atom and wherein $R^{19a}$ is optionally substituted with one or more $R^{20}$;

$R^{10b}$, $R^{11b}$, and $R^{12b}$ are independently selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —C(O)$OR^{12}$, —C(O)$R^{12}$, —C(O)$N(R^{12})(R^{13})$, —C(O)C(O)$N(R^{12})(R^{13})$, —$S(O)_2R^{12}$, —S(O)$(NR^{12})R^{12}$, —$S(O)_2N(R^{12})(R^{13})$, and —S(=O)(=$NR^{12}$)$N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$;

$R^{9a}$, $R^{10}$, $R^{11}$, and $R^{12a}$ are independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(=O)(=NR^{12})N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$; and each ═══ independently indicates a single or double bond such that all valences are satisfied.

In embodiments of a compound of formula I, the compound has a formula (IB):

(IB)

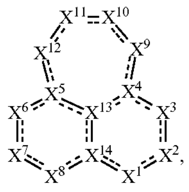

or a pharmaceutically acceptable salt or solvate thereof, wherein:

$X^9$ is selected from $C(R^9)$, $C(R^9)(R^{9a})$, and $N(R^9)$;

$X^{10}$ is selected from $C(R^{10})$, $C(R^{10})_2$, N, $N(R^{10b})$, O, S, S(O), $S(O)_2$, and C(O);

$X^{11}$ is selected from $C(R^{11})$, $C(R^{11})_2$, N, $N(R^{11b})$, O, S, S(O), $S(O)_2$, and C(O);

$X^{12}$ is selected from —$X^{12a}$—, —$X^{12a}$—$X^{12b}$—, —$X^{12a}$—$X^{12b}$—$X^{12c}$—, and —$X^{12a}$—$X^{12b}$—$X^{12c}$—$X^{12d}$—; wherein $X^{12a}$ is directly bonded to $X^5$;

$X^{12a}$, $X^{12b}$, $X^{12c}$, and $X^{12d}$ are independently selected from $C(R^{12a})$, $C(R^{12a})_2$, N, $N(R^{12b})$, O, S, S(O), $S(O)_2$, and C(O);

$R^{19a}$ is 5- to 12-membered heterocycle comprising three or four ring nitrogen atoms, wherein the 5- to 12-membered heterocycle is optionally substituted with one or more $R^{20}$;

$R^{10b}$, $R^{11b}$, and $R^{12b}$ are independently selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$C(O)OR^{12}$, —$C(O)R^{12}$, —$C(O)N(R^{12})(R^{13})$, —$C(O)C(O)N(R^{12})(R^{13})$, —$S(O)_2R^{12}$, —$S(O)(NR^{12})R^{12}$, —$S(O)_2N(R^{12})(R^{13})$, and —$S(=O)(=NR^{12})N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$;

$R^{9a}$, $R^{10}$, $R^{11}$, and $R^{12a}$ are independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(=O)(=NR^{12})N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-2}$ carbocycle), -(2- to 6-membered heteroalkyl)-($C_{3-2}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$; and each ═══ independently indicates a single or double bond such that all valences are satisfied.

In an aspect is provided a compound of Formula (II):

(II)

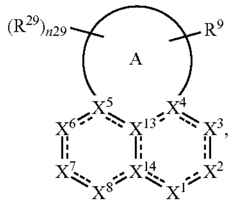

or a pharmaceutically acceptable salt or solvate thereof, wherein:

Ring A is selected from a monocyclic $C_{7-10}$ carbocycle and monocyclic 7- to 10-membered heterocycle;

$X^1$ is selected from $C(R^1)$, $C(R^1)_2$, N, $N(R^{1b})$, O, S, S(O), $S(O)_2$, and C(O);

$X^2$ is selected from $C(R^2)$, $C(R^2)_2$, N, $N(R^{2b})$, O, S, S(O), $S(O)_2$, and C(O);

$X^3$ is selected from $C(R^3)$, $C(R^3)_2$, N, $N(R^{3b})$, O, S, S(O), $S(O)_2$, and C(O);

$X^4$ is selected from C, $C(R^4)$, and N;

$X^5$ is selected from C, $C(R^5)$, and N;

$X^6$ is selected from $C(R^6)$, $C(R^6)_2$, N, $N(R^{6b})$, O, S, S(O), $S(O)_2$, and C(O);

$X^7$ is selected from $C(R^7)$, $C(R^7)(R^{7a})$, and $N(R^{7b})$;

$X^8$ is selected from $C(R^8)$, $C(R^8)_2$, N, $N(R^{8b})$, O, S, S(O), $S(O)_2$, and C(O);

$X^{13}$ is selected from C, $C(R^{13a})$, and N;

$X^{14}$ is selected from C, $C(R^{14a})$, and N;

$R^7$ is $-L^{7a}-R^{17}$; $R^{7b}$ is $-L^{7b}-R^{17}$;

$L^{7a}$ is selected from a bond, $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, —$N(R^{12})$—, —C(O)—, —$N(R^{12})C(O)$—, —$C(O)N(R^{12})$—, —S—, —$S(O)_2$—, —S(O)—, —$P(O)(R^{12})$—, —$N(R^{12})S(O)_2$—, —$N(R^{12})S(O)$—, —$N(R^{12})P(O)(R^{12})$—, —$S(O)_2N(R^{12})$—, —$S(O)N(R^{12})$—, —$P(O)(R^{12})N(R^{12})$—, —$OP(O)(R^{12})$—, and —$P(O)(R^{12})O$—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$;

$L^{7b}$ is selected from a bond, $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —C(O)—, and —$C(O)N(R^{12})$—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$;

$R^{17}$ is independently selected from $C_{3-12}$ carbocycle and 3- to 12-membered heterocycle, wherein $C_{3-12}$ carbocycle and 3- to 12-membered heterocycle are optionally substituted with one or more $R^{20}$;

$R^9$ is $-L^{19}-R^{19}-L^{19a}-R^{19a}$;

$L^{19}$ is selected from a bond, $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, —$N(R^{12})$—, —C(O)—, —$N(R^{12})C(O)$—, —$C(O)N(R^{12})$—, —S—, —$S(O)_2$—, —S(O)—, —$P(O)(R^{12})$—, —$N(R^{12})S(O)_2$—, —$N(R^{12})S(O)$—, —$N(R^{12})P(O)(R^{12})$—, —$S(O)_2N(R^{12})$—, —$S(O)N(R^{12})$—, —$P(O)(R^{12})N(R^{12})$—, —$OS(O)_2$—, —OS(O)—, —$OP(O)(R^{12})$—, —$S(O)_2O$—, —S(O)O—, and —$P(O)(R^{12})O$—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$;

$R^{19}$ is selected from a non-aromatic monocyclic $C_{4-8}$ carbocycle and non-aromatic monocyclic 3- to 8-membered heterocycle, wherein the non-aromatic monocyclic $C_{4-8}$ carbocycle and non-aromatic monocyclic 3- to 8-membered heterocycle are optionally substituted with one or more $R^{20}$;

$L^{19a}$ is selected from a bond, $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, —$N(R^{12})$—, —C(O)—, —$N(R^{12})C(O)$—, —$C(O)N(R^{12})$—, —S—, —$S(O)_2$—, —S(O)—, —$P(O)(R^{12})$—, —$N(R^{12})S(O)_2$—, —$N(R^{12})S(O)$—, —$N(R^{12})P(O)(R^{12})$—, —$S(O)_2N(R^{12})$—, —$S(O)N(R^{12})$—, —$P(O)(R^{12})N(R^{12})$—, —$OP(O)(R^{12})$—, and —$P(O)(R^{12})O$—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$;

$R^{19a}$ is selected from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —S(=O)(=$NR^{12}$)$N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$;

$R^{1b}$, $R^{2b}$, $R^{3b}$, $R^{6b}$, and $R^{8b}$ are independently selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$C(O)OR^{12}$, —$C(O)R^{12}$, —$C(O)N(R^{12})(R^{13})$, —$C(O)C(O)N(R^{12})(R^{13})$, —$S(O)_2R^{12}$, —$S(O)(NR^{12})R^{12}$, —$S(O)_2N(R^{12})(R^{13})$, and —S(=O)(=$NR^{12}$)$N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$;

$R^1$, $R^2$, $R^3$, $R^4$, $R^1$, $R^6$, $R^{7a}$, $R^1$, $R^{13a}$, and $R^{14a}$ are independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —S(=O)(=$NR^{12}$)$N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one or more $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one or more $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$—, and —$S(=O)(=NR^{22})N(R^{22})(R^{23})$; wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —$S(=O)(=NR^{22})N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one or more substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle; and $R^{29}$ is independently selected at each occurrence from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(=O)(=NR^{12})N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$; and wherein two $R^{29}$ attached to the same atom are optionally joined to form oxo;

n29 is selected from 0, 1, 2, 3, 4, 5, 6, 7, 8, 9, 10, 11, 12, and 13; and each ⁚⁚⁚⁚ independently indicates a single or double bond such that all valences are satisfied.

In embodiments of a compound of formula II, the compound has the formula (IIA):

(IIA)

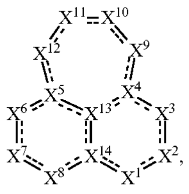

or a pharmaceutically acceptable salt or solvate thereof, wherein:

$X^9$ is selected from $C(R^9)$, $C(R^9)(R^{9a})$, and $N(R^9)$;

$X^{10}$ is selected from $C(R^{10})$, $C(R^{10})_2$, N, $N(R^{10b})$, O, S, S(O), $S(O)_2$, and C(O);

$X^{11}$ is selected from $C(R^{11})$, $C(R^{11})_2$, N, $N(R^{11b})$, O, S, S(O), $S(O)_2$, and C(O);

$X^{12}$ is selected from —$X^{12a}$—, —$X^{12a}$—$X^{12b}$—, —$X^{12a}$—$X^{12b}$—$X^{12c}$—, and —$X^{12a}$—$X^{12b}$—$X^{12c}$—$X^{12d}$—; wherein $X^{12a}$ is directly bonded to $X^5$;

$X^{12a}$, $X^{12b}$, $X^{12c}$, and $X^{12d}$ are independently selected from $C(R^{12a})$, $C(R^{12a})_2$, N, $N(R^{12b})$, O, S, S(O), $S(O)_2$, and C(O);

$R^{10b}$, $R^{11b}$, and $R^{12b}$ are independently selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$C(O)OR^{12}$, —$C(O)R^{12}$, —$C(O)N(R^{12})(R^{13})$, —$C(O)C(O)N(R^{12})(R^{13})$, —$S(O)_2R^{12}$, —$S(O)(NR^{12})R^{12}$, —$S(O)_2N(R^{12})(R^{13})$, and —$S(=O)(=NR^{12})N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$;

$R^{9a}$, $R^{10}$, $R^{11}$, and $R^{12a}$ are independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —S(=O)(=$NR^{12}$)$N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$; and each ═ independently indicates a single or double bond such that all valences are satisfied.

In an aspect is provided a compound of Formula (V):

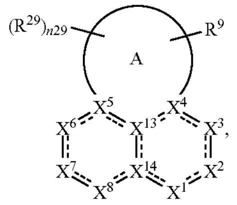

(V)

or a pharmaceutically acceptable salt or solvate thereof, wherein:

Ring A is selected from a monocyclic $C_{7-10}$ carbocycle, monocyclic 7- to 10-membered heterocycle, fused bicyclic $C_{8-12}$ carbocycle, and fused bicyclic 8- to 12-membered heterocycle;

$X^1$ is selected from $C(R^1)$, $C(R^1)_2$, N, $N(R^{1b})$, O, S, S(O), $S(O)_2$, and C(O);

$X^2$ is selected from $C(R^2)$, $C(R^2)_2$, N, $N(R^{2b})$, O, S, S(O), $S(O)_2$, and C(O);

$X^3$ is selected from $C(R^3)$, $C(R^3)_2$, N, $N(R^{3b})$, O, S, S(O), $S(O)_2$, and C(O);

$X^4$ is selected from C, $C(R^4)$, and N;

$X^5$ is selected from C, $C(R^5)$, and N;

$X^6$ is selected from $C(R^6)$, $C(R^6)_2$, N, $N(R^{6*})$, O, S, S(O), $S(O)_2$, and C(O);

$X^7$ is selected from $C(R^7)$, $C(R^7)(R^{7a})$, and $N(R^{7b})$;

$X^8$ is selected from $C(R^8)$, $C(R^8)_2$, N, $N(R^{8b})$, O, S, S(O), $S(O)_2$, and C(O);

$X^{13}$ is selected from C, $C(R^{13a})$, and N;

$X^{14}$ is selected from C, $C(R^{14a})$, and N;

$R^7$ is -$L^{7a}$-$R^{17}$; $R^{7b}$ is -$L^{7b}$-$R^{17}$;

$L^{7a}$ is selected from a bond, $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, —$N(R^{12})$—, —C(O)—, —$N(R^{12})C(O)$—, —$C(O)N(R^{12})$—, —S—, —$S(O)_2$—, —S(O)—, —$P(O)(R^{12})$—, —$N(R^{12})S(O)_2$—, —$N(R^{12})S(O)$—, —$N(R^{12})P(O)(R^{12})$—, —$S(O)_2N(R^{12})$—, —$S(O)N(R^{12})$—, —$P(O)(R^{12})N(R^{12})$—, —$OP(O)(R^{12})$—, and —$P(O)(R^{12})O$—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$;

$L^{7b}$ is selected from a bond, $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —C(O)—, and —$C(O)N(R^{12})$—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$;

$R^9$ is -$L^{19}$-$L^{19a}$-$R^{19a}$;

$L^{19}$ is selected from a bond, $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$;

$L^{19a}$ is selected from a —C(O)— and —$N(R^{12})C(O)$—;

$R^{19a}$ is a 5-membered heteroaryl comprising one or more ring nitrogen atoms, wherein the 5-membered heteroaryl is directly bonded to the C(O) of $L^{19a}$ through an $R^{19a}$ ring nitrogen atom and wherein $R^{19a}$ is optionally substituted with one or more $R^{20}$;

$R^{1b}$, $R^{2b}$, $R^{3b}$, $R^{6b}$, and $R^{8b}$ are independently selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$C(O)OR^{12}$, —$C(O)R^{12}$, —$C(O)N(R^{12})(R^{13})$, —$C(O)C(O)N(R^{12})(R^{13})$, —$S(O)_2R^{12}$, —$S(O)(NR^{12})R^{12}$, —$S(O)_2N(R^{12})(R^{13})$, and —S(=O)(=$NR^{12}$)$N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$;

$R^1$, $R^2$, $R^3$, $R^4$, $R^1$, $R^6$, $R^{7a}$, $R^1$, $R^{13a}$, $R^{14a}$, and $R^{17}$ are independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —S(=O)(=$NR^{12}$)$N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one or more $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one or more $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —C(O)$OR^{22}$, —OC(O)$N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$—, and —S(=O)(=$NR^{22}$)$N(R^{22})(R^{23})$; wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —C(O)$OR^{22}$, —OC(O)$N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —S(=O)(=$NR^{22}$)$N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one or more substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle;

$R^{29}$ is independently selected at each occurrence from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —C(O)$OR^{12}$, —OC(O)$N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —OC(O)$R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —S(=O)(=$NR^{12}$)$N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$; and wherein two $R^{29}$ attached to the same atom are optionally joined to form oxo;

n29 is selected from 0, 1, 2, 3, 4, 5, 6, 7, 8, 9, 10, 11, 12, and 13; and each ⎓ independently indicates a single or double bond such that all valences are satisfied.

In embodiments of a compound of Formula I, IA, IB, II, IIA, or V, the compound has the formula:

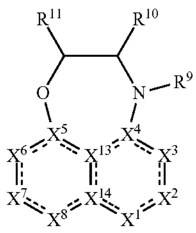

or

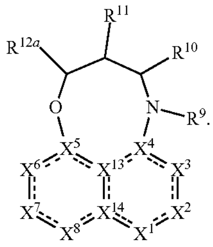

In embodiments of a compound of Formula I, IA, IB, II, IIA, or V, the compound has the formula:

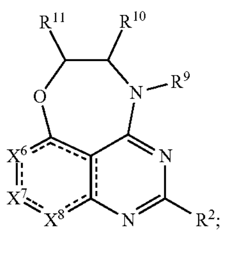

$X^6$ is selected from $C(R^6)$, $C(R^6)_2$, N, and $N(R^{6b})$;

$X^7$ is selected from $C(R^7)$ and $N(R^{7b})$;

$X^8$ is selected from $C(R^8)$ and $C(R^8)_2$; and $L^{7a}$ is a bond; $L^{7b}$ is a bond.

In embodiments of a compound of Formula I, IA, IB, II, IIA, or V, the compound has the formula:

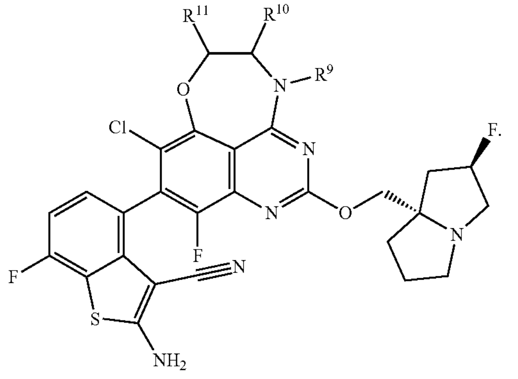

In embodiments of a compound of Formula I, IA, IB, II, IIA, or V, the compound has the formula:

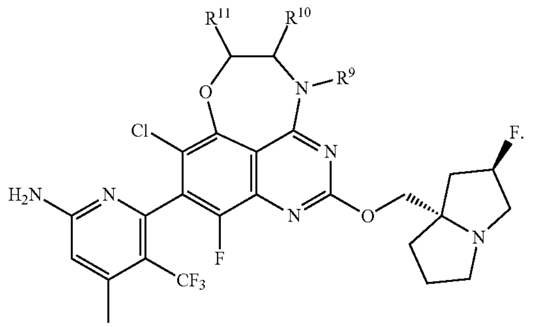

In embodiments of a compound of Formula I, IA, IB, II, IIA, or V, the compound has the formula:

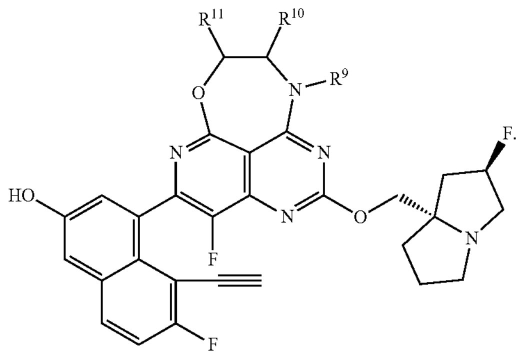

In embodiments of a compound of Formula I, IA, IB, II, IIA, or V, the compound has the formula:

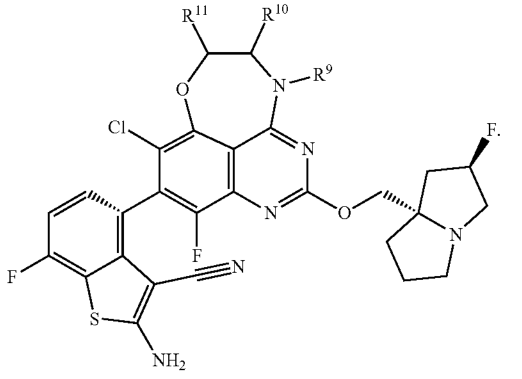

In embodiments of a compound of Formula I, IA, IB, II, IIA, or V, the compound has the formula:

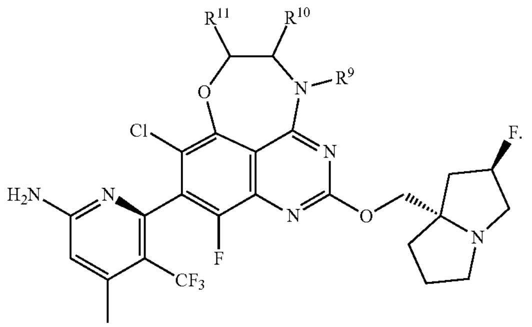

In embodiments of a compound of Formula I, IA, IB, II, IIA, or V, the compound has the formula:

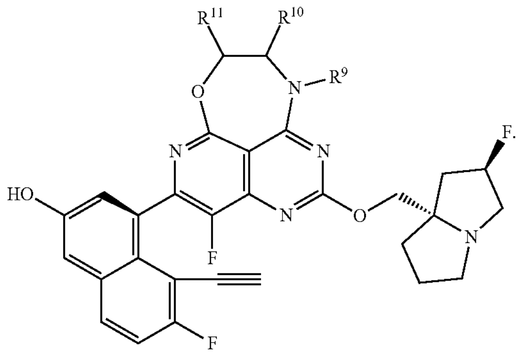

In embodiments of a compound of Formula IA, IB, or IIA, the compound is selected from:

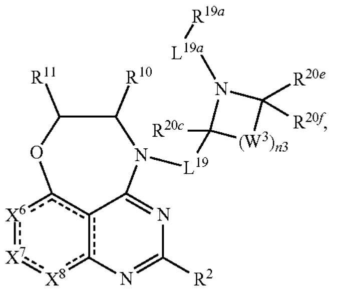
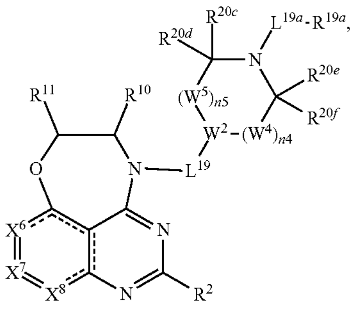
and
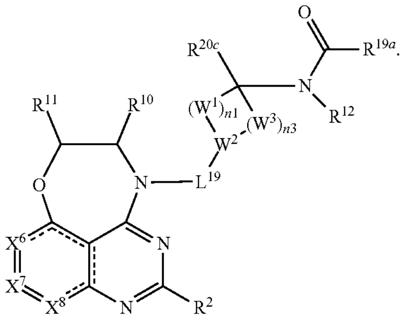
In embodiments of a compound of Formula IA, IB, or IIA, the compound is selected from:
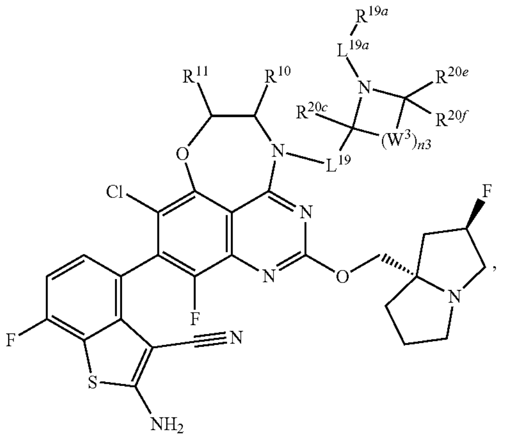
-continued
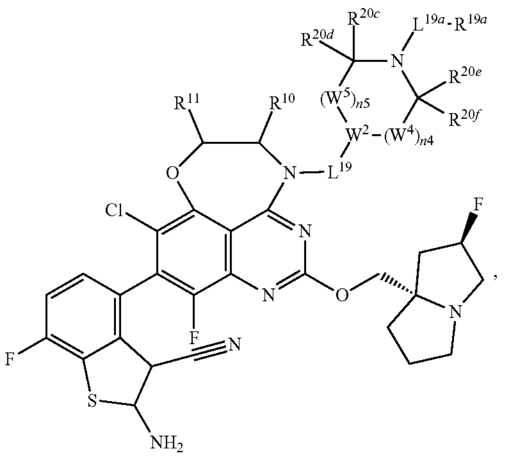
and
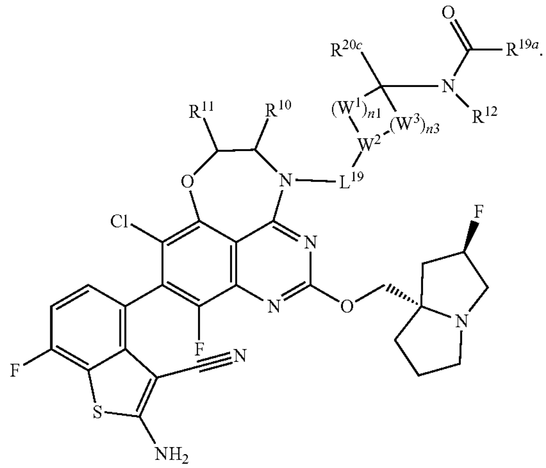
In embodiments of a compound of Formula IA, IB, IIA, the compound is selected from:
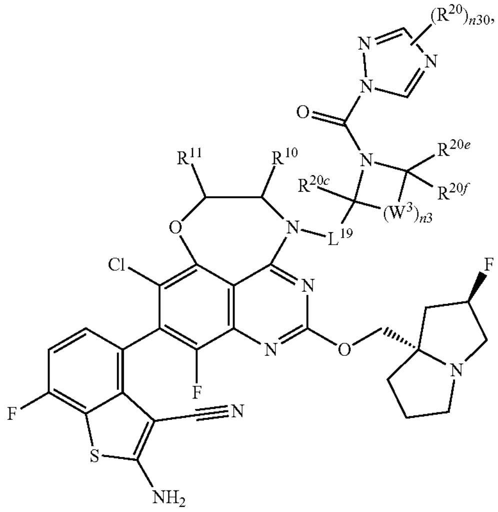

-continued
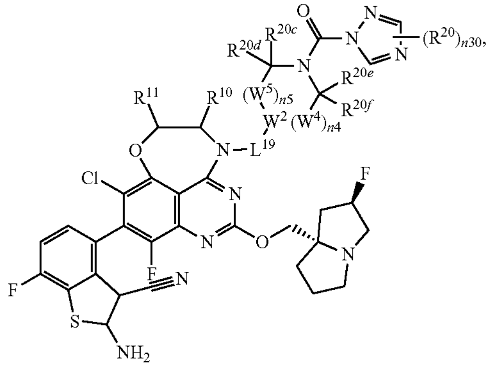
and
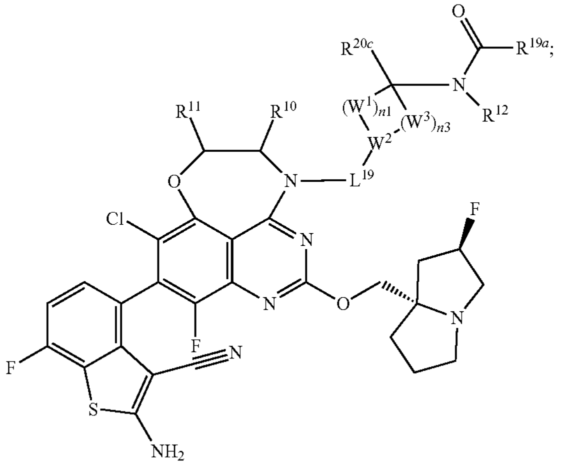
and n30 is 0, 1, or 2. In embodiments, n30 is 0. In embodiments, n30 is 1. In embodiments, n30 is 2.
In embodiments of a compound of Formula IA, IB, or IIA, the compound is selected from:
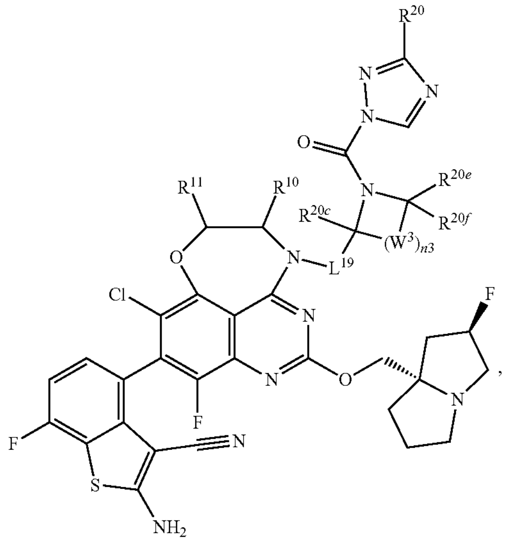
-continued
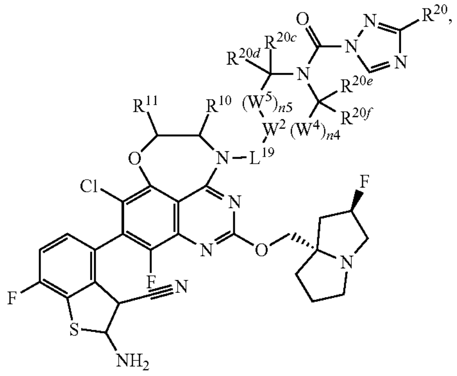
and
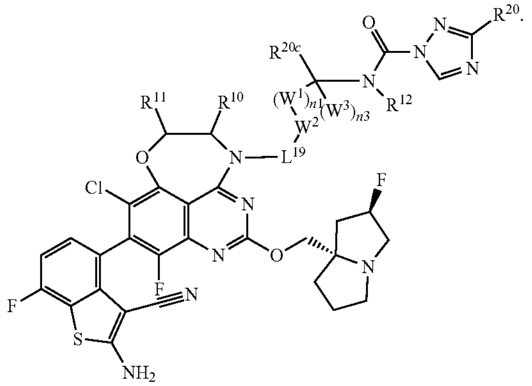
In embodiments of a compound of Formula IA, IB, or IIA, the compound is selected from:
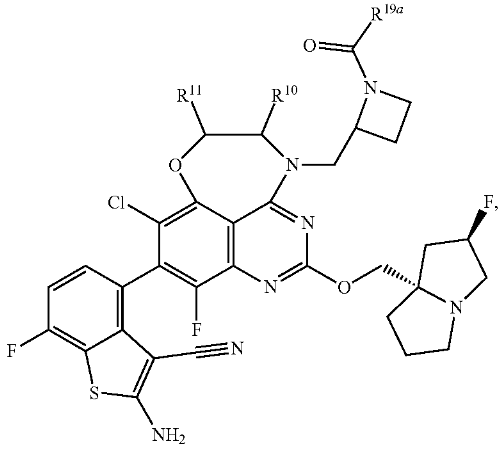

-continued
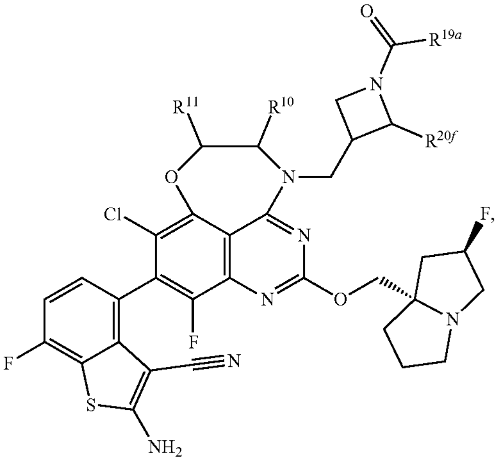
and
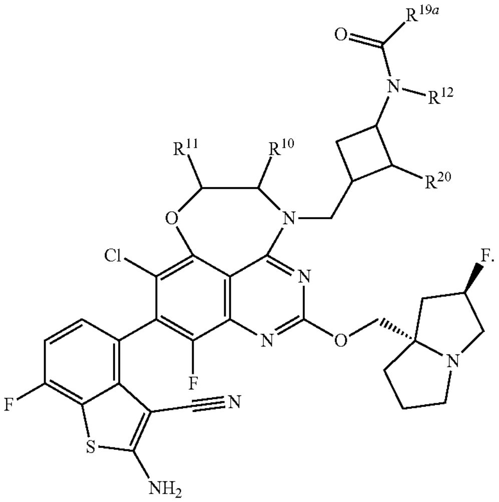
In embodiments of a compound of Formula IA, IB, or IIA, the compound is selected from:
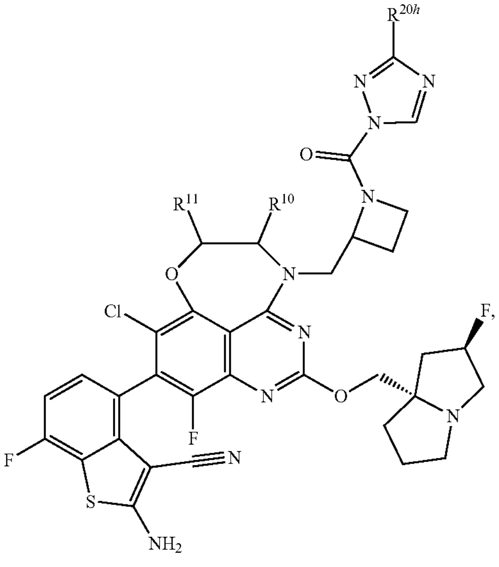
-continued
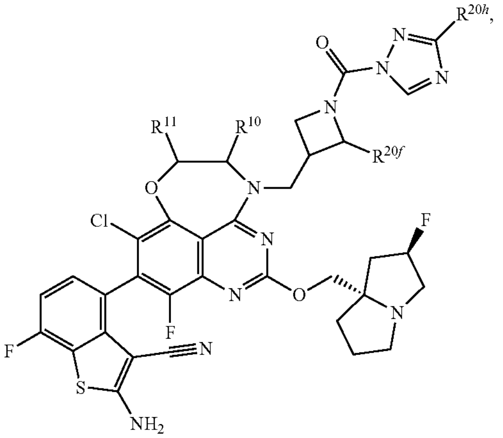
and
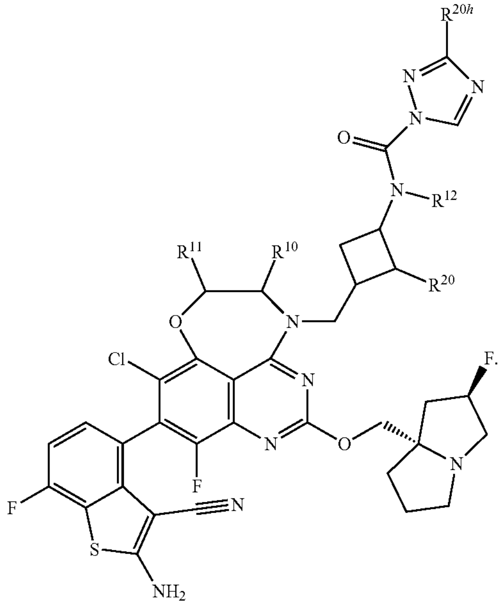
In embodiments of a compound of Formula IA, IB, or IIA, the compound is selected from:
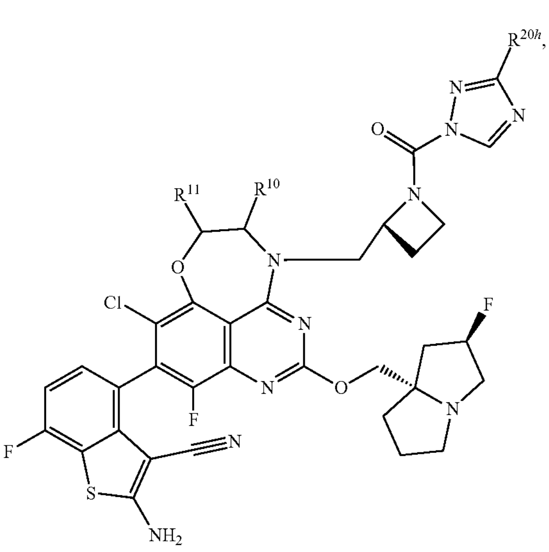

-continued
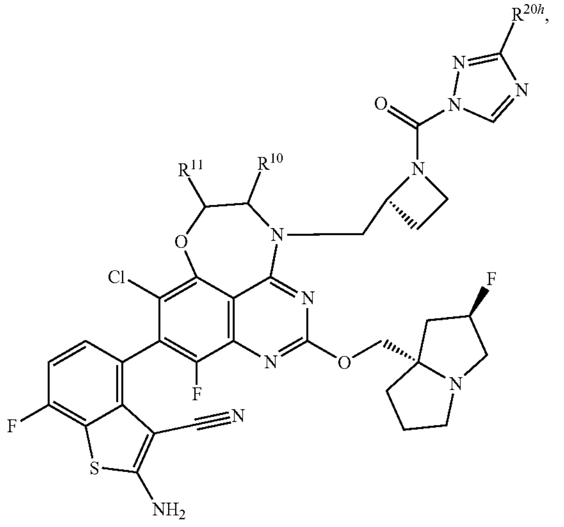
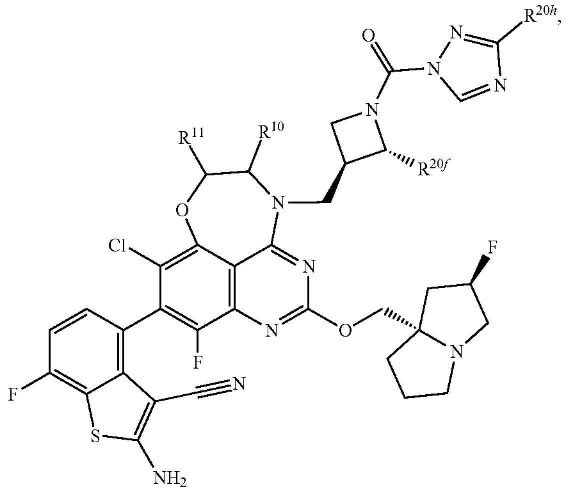
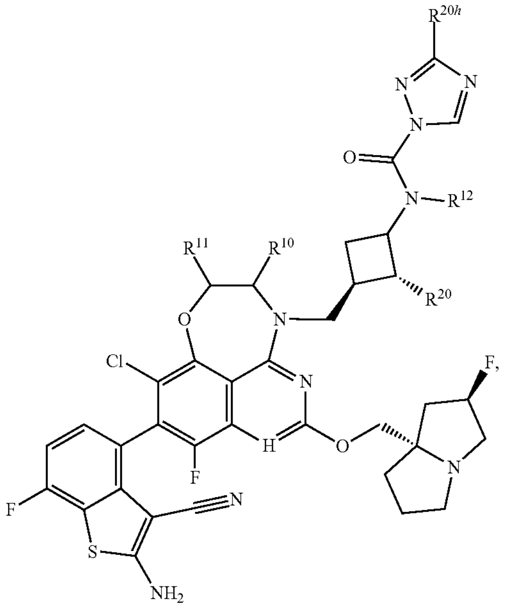
-continued
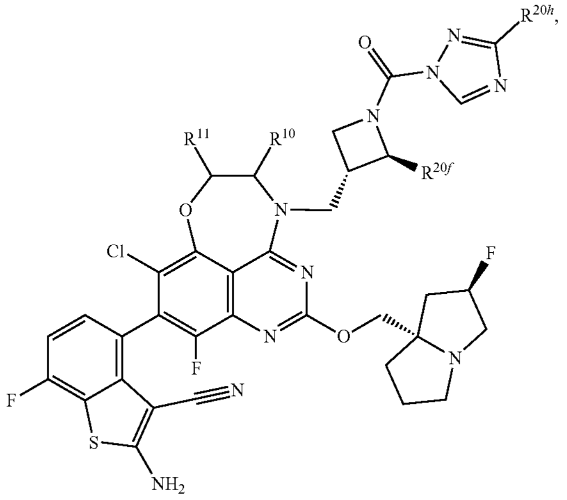
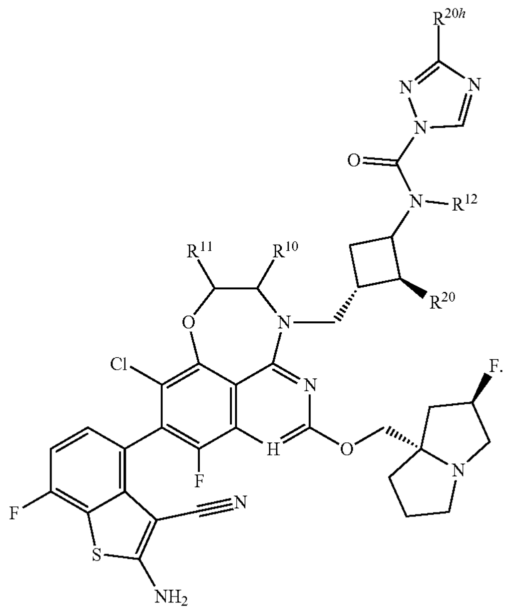
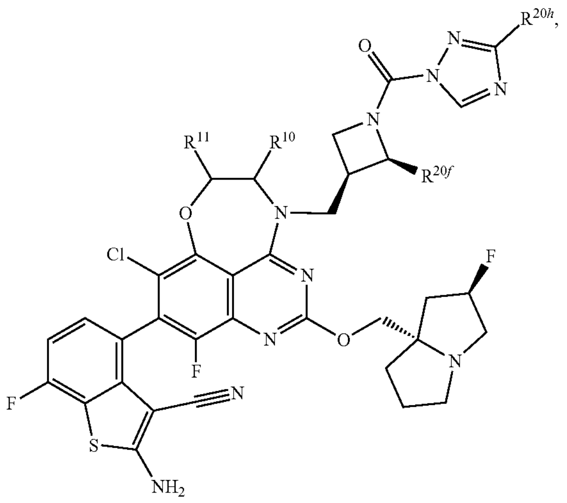

-continued
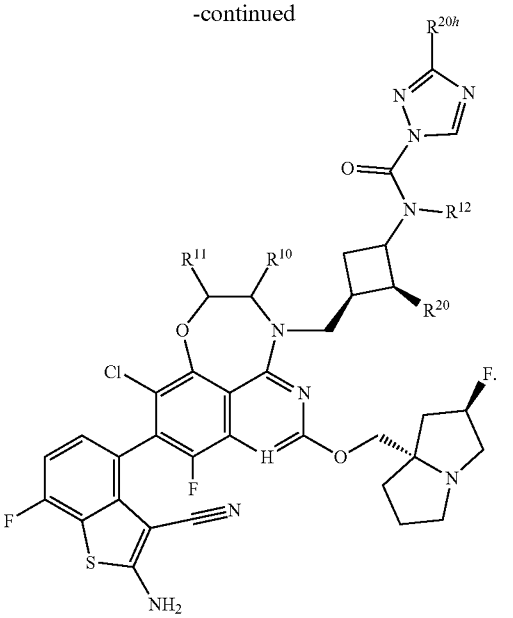
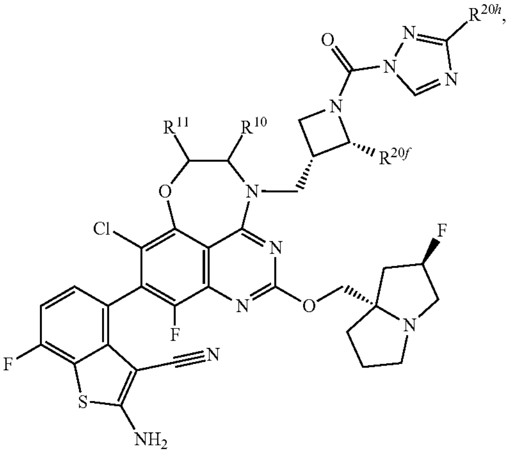
and
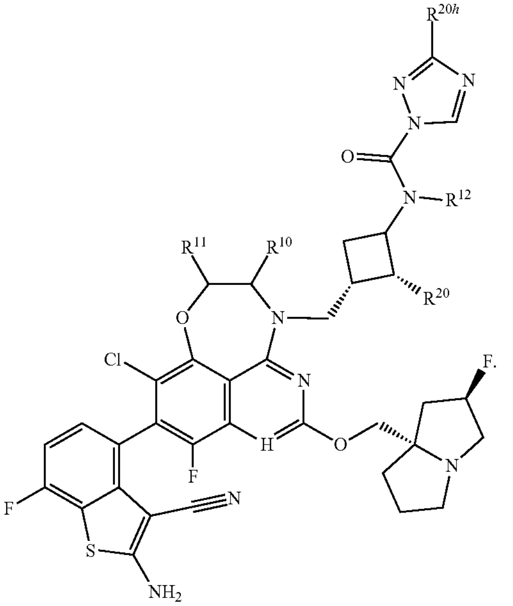
In embodiments of a compound of Formula IA, IB, or IIA, the compound is selected from:
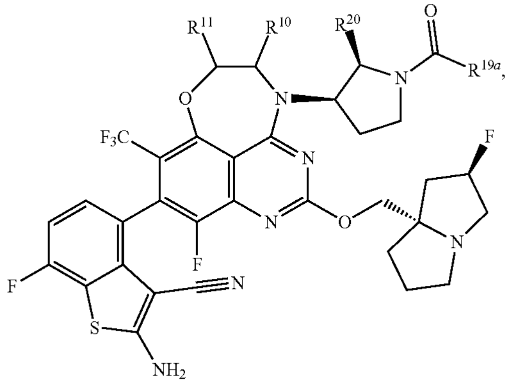
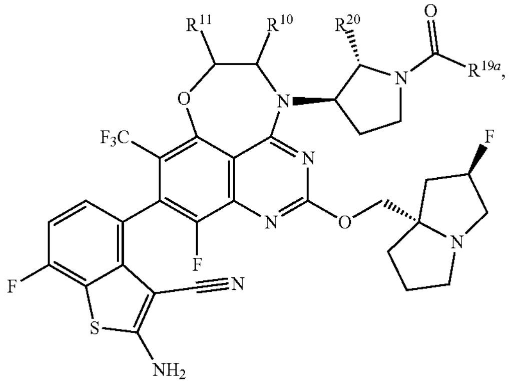
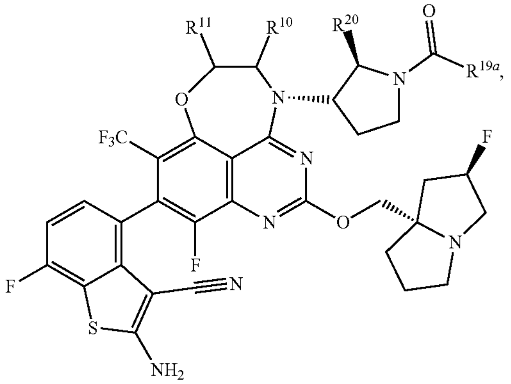
and
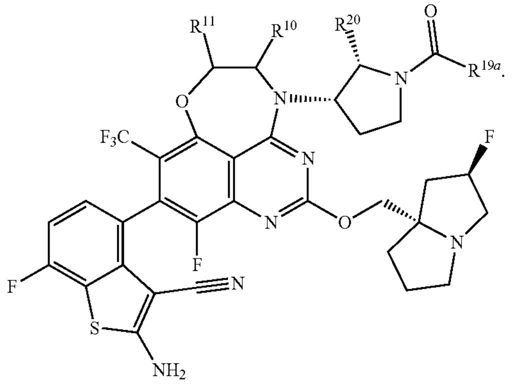
In embodiments of a compound of Formula IA, IB, or IIA, the compound is selected from:

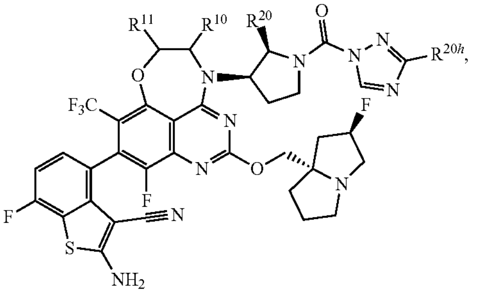
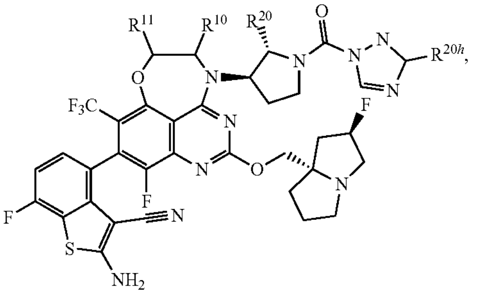
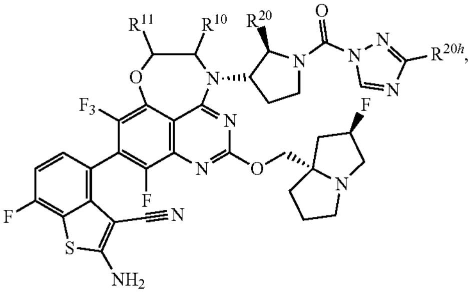
and
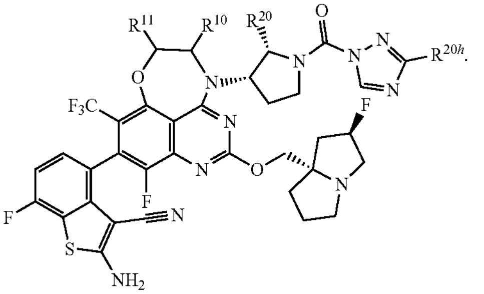
In embodiments of a compound of Formula IA, IB, or IIA, the compound is selected from:
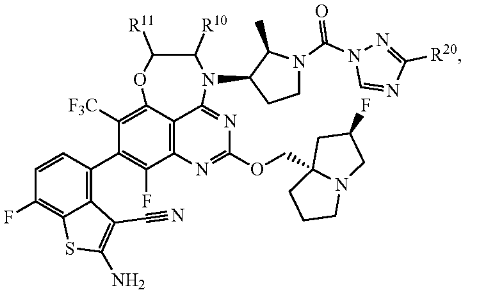
-continued
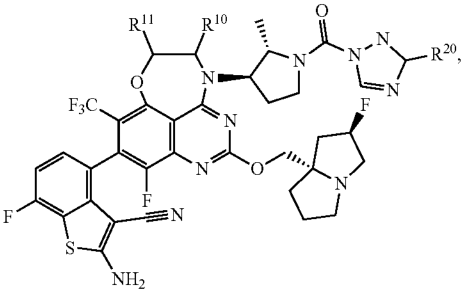
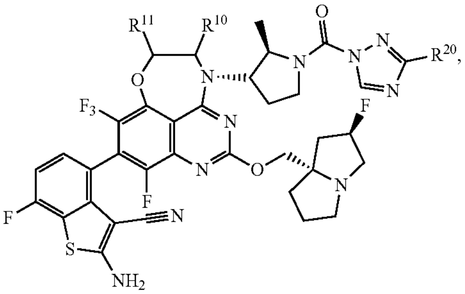
and
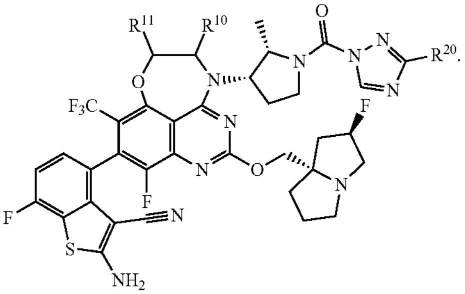
In embodiments of a compound of Formula I, IA, IB, II, IIA, or V, the compound has the formula:
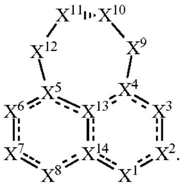
In embodiments of a compound of Formula I, IA, IB, II, IIA, or V, the compound has the formula:
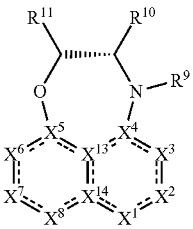
or -continued

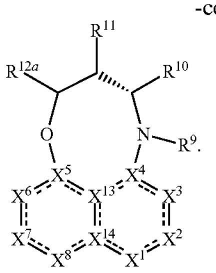

In embodiments of a compound of Formula I, IA, IB, II, IIA, or V, the compound has the formula:

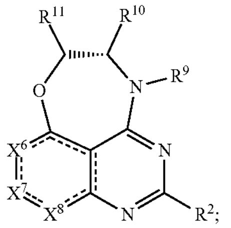

$X^6$ is selected from $C(R^6)$, $C(R^6)_2$, N, and $N(R^{6b})$;
$X^7$ is selected from $C(R^7)$ and $N(R^{7b})$;
$X^8$ is selected from $C(R^8)$ and $C(R^8)_2$; and
$L^{7a}$ is a bond; $L^{7b}$ is a bond.

In embodiments of a compound of Formula I, IA, IB, II, IIA, or V, the compound has the formula:

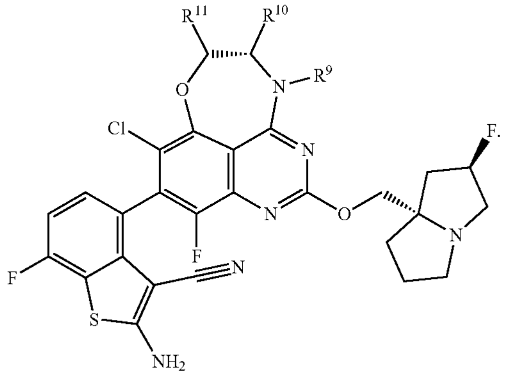

In embodiments of a compound of Formula I, IA, IB, II, IIA, or V, the compound has the formula:

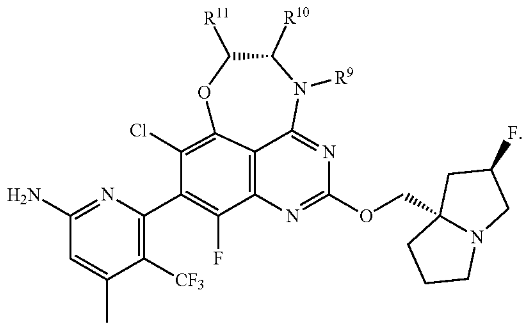

In embodiments of a compound of Formula I, IA, IB, II, IIA, or V, the compound has the formula:

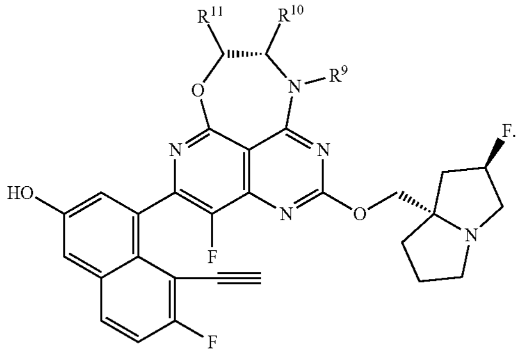

In embodiments of a compound of Formula I, IA, IB, II, IIA, or V, the compound has the formula:

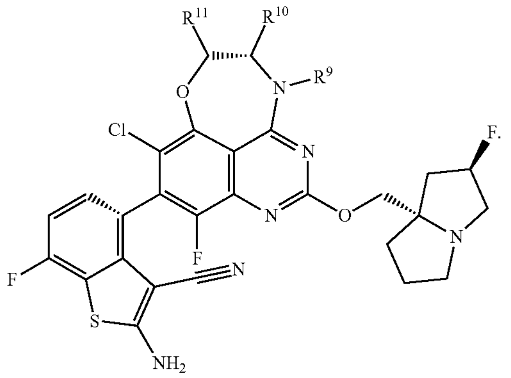

In embodiments of a compound of Formula I, IA, IB, II, IIA, or V, the compound has the formula:

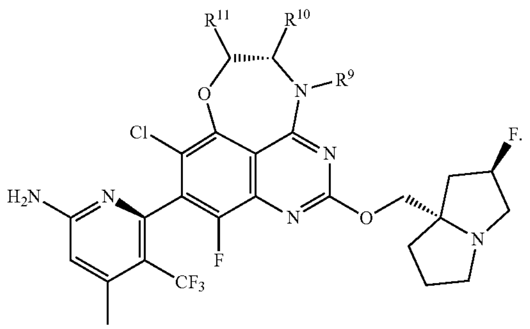

In embodiments of a compound of Formula I, IA, IB, II, IIA, or V, the compound has the formula:

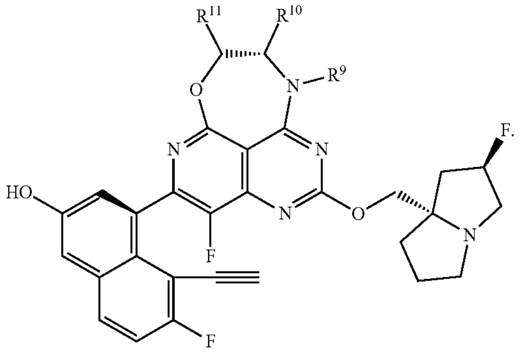
In embodiments of a compound of Formula IA, IB, or IIA, the compound is selected from:
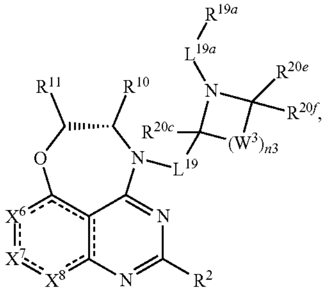
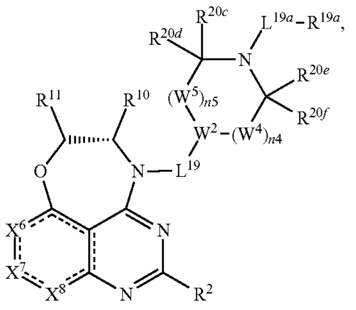
and
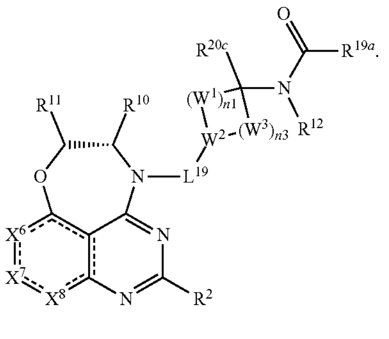
In embodiments of a compound of Formula IA, IB, or IIA, the compound is selected from:
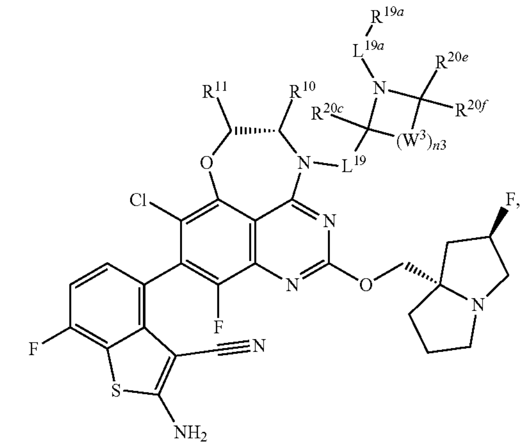
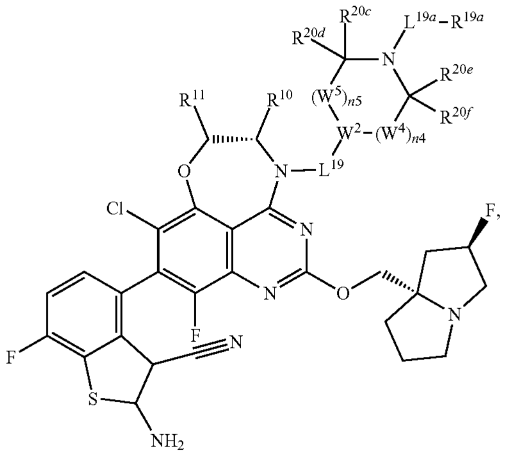
and
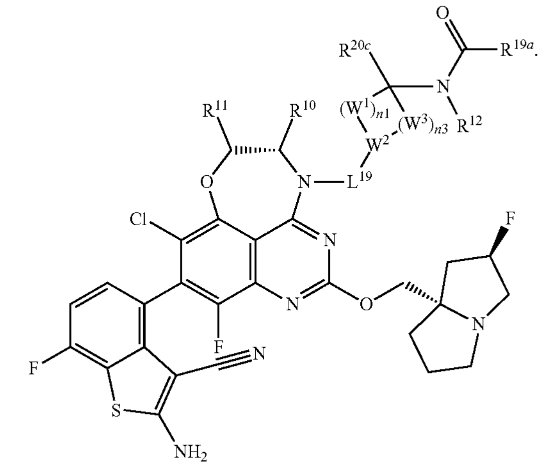
In embodiments of a compound of Formula IA, IB, IIA, the compound is selected from:

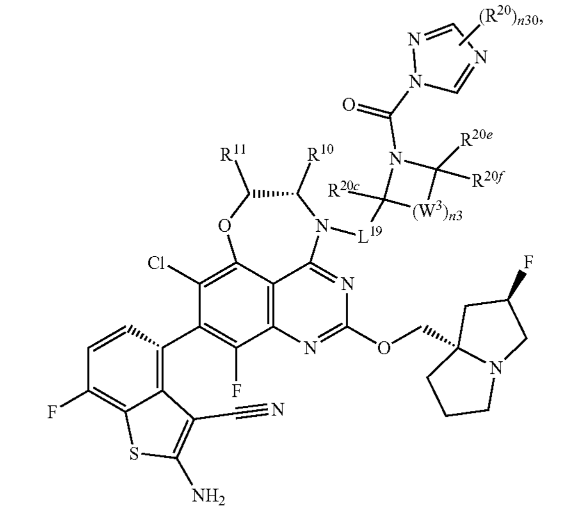
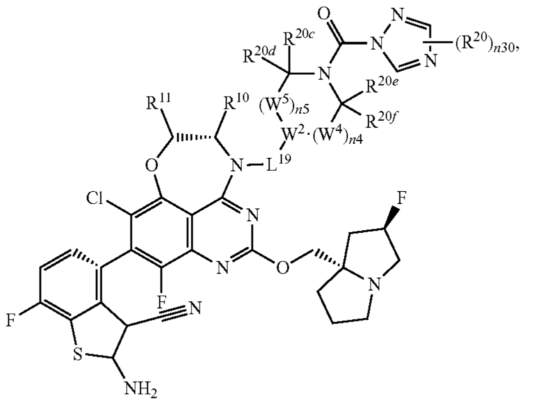
and
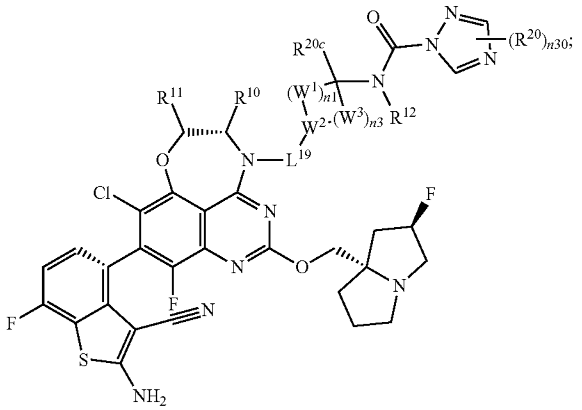
and n30 is 0, 1, or 2. In embodiments, n30 is 0. In embodiments, n30 is 1. In embodiments, n30 is 2.
In embodiments of a compound of Formula IA, IB, or IIA, the compound is selected from:
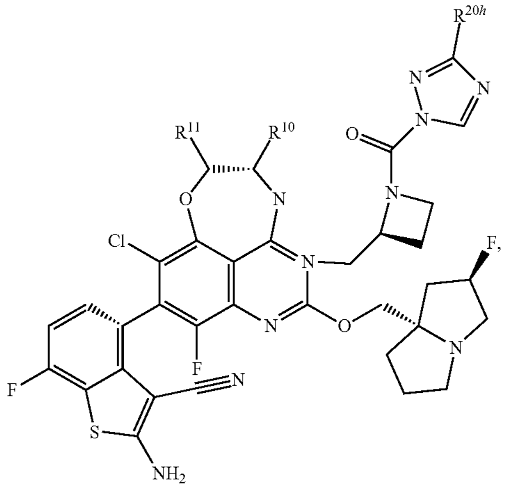
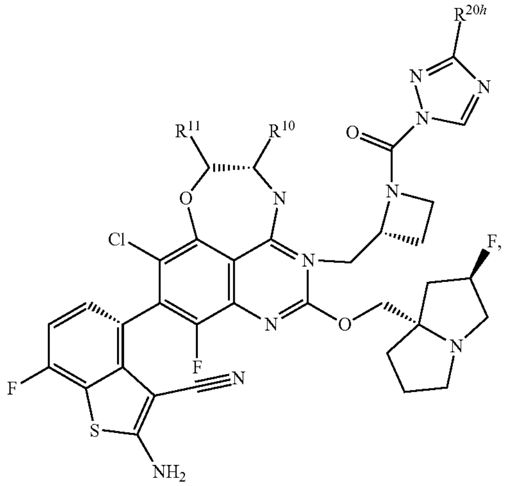
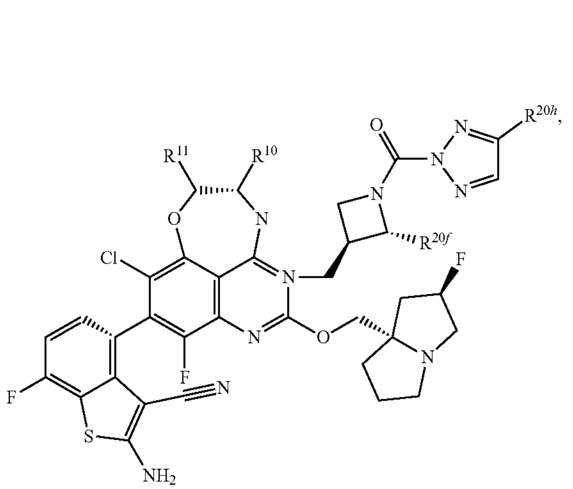

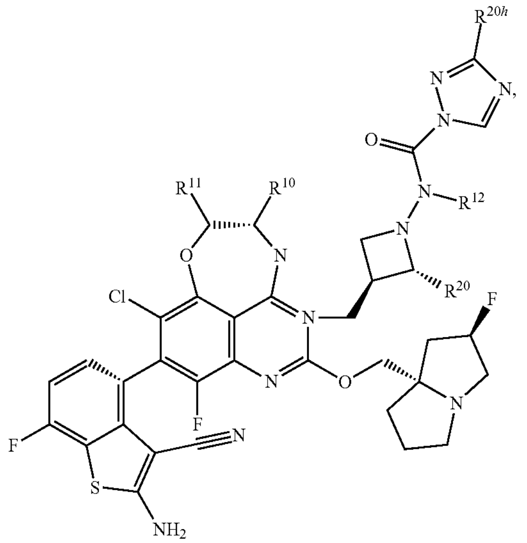
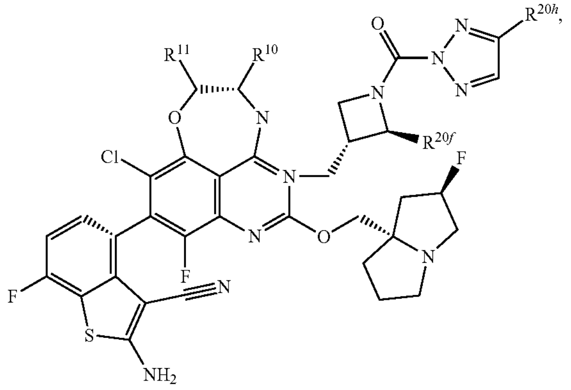
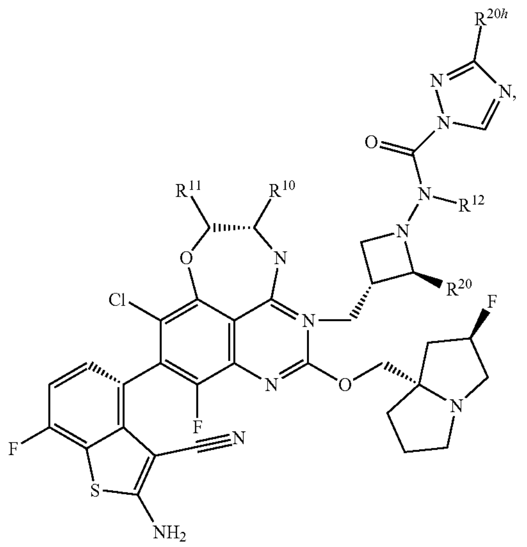
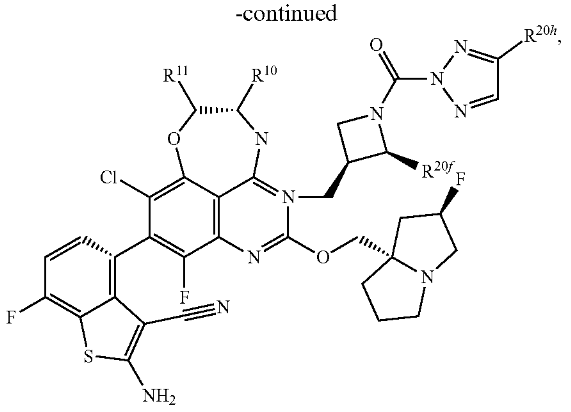
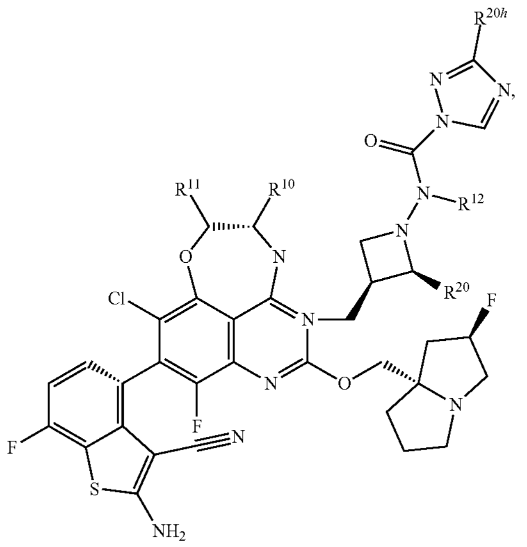
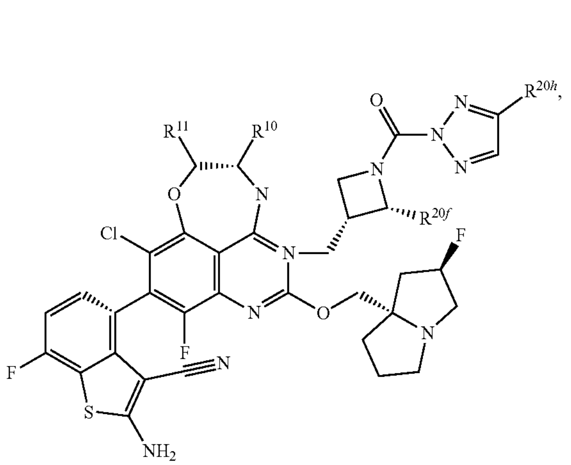

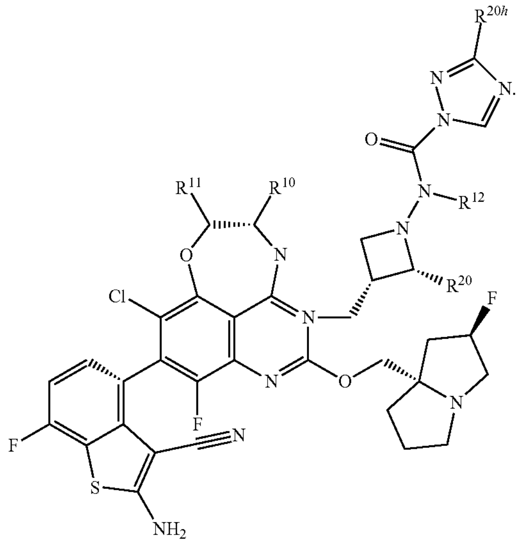
In embodiments of a compound of Formula IA, IB, or IIA, the compound is selected from:
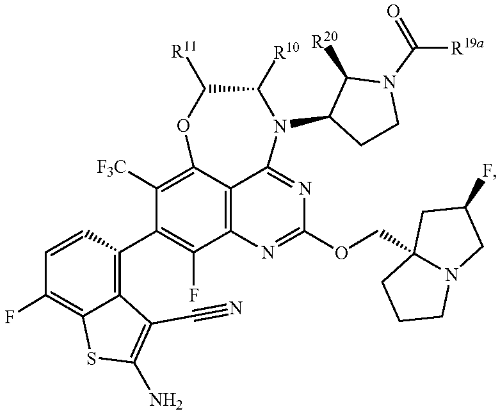
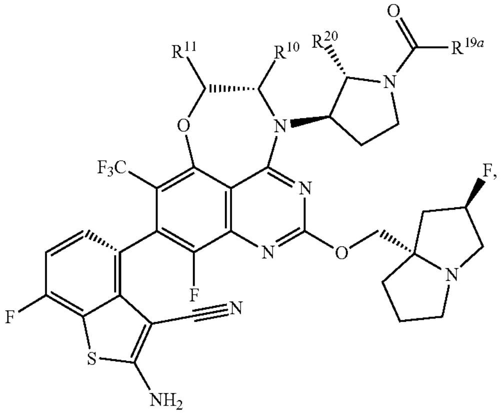
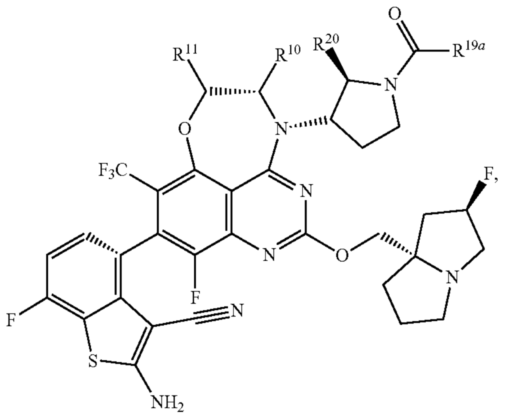
and
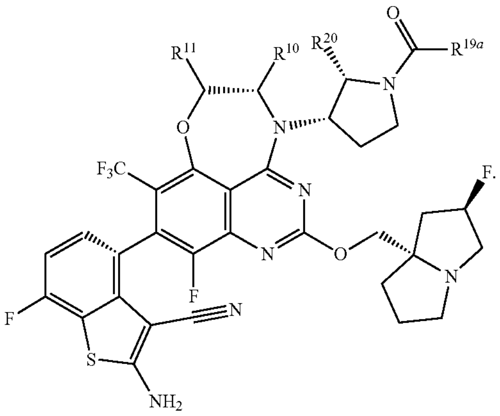
In embodiments of a compound of Formula IA, IB, or IIA, the compound is selected from:
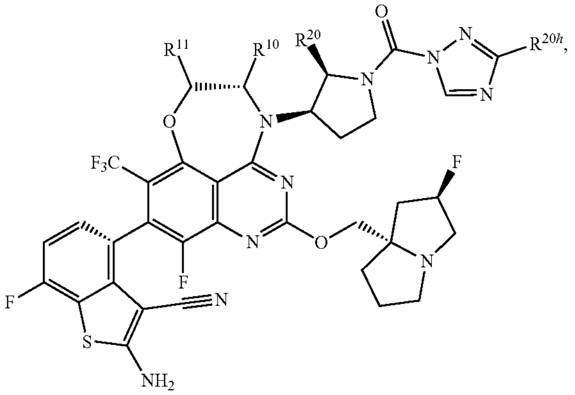

-continued
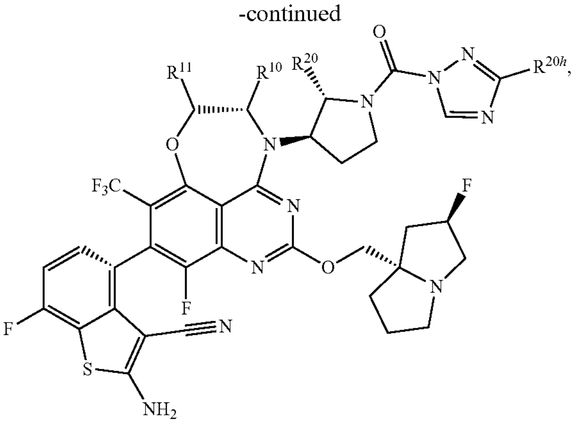
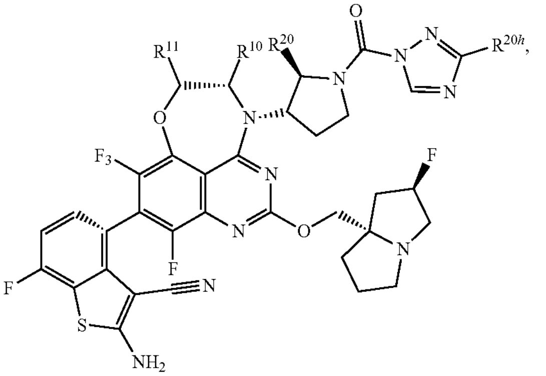
and
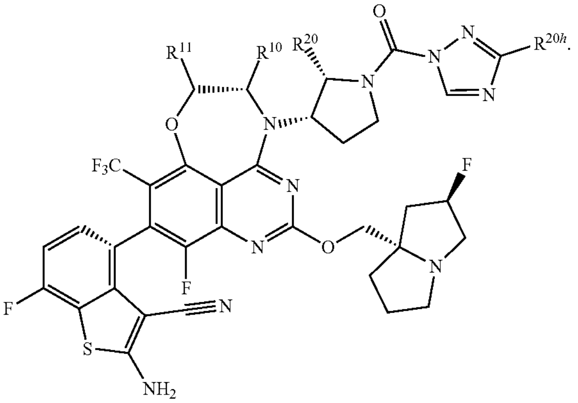
In embodiments of a compound of Formula IA, IB, or IIA, the compound is selected from:
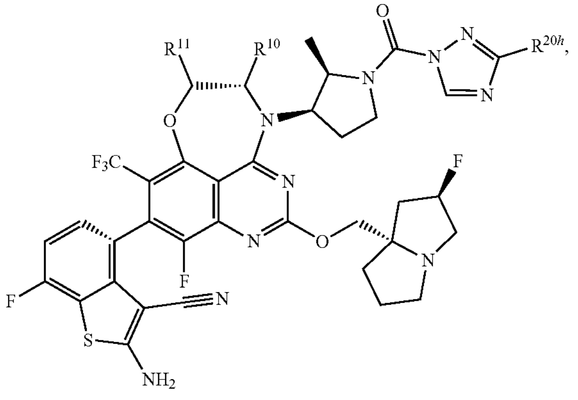
-continued
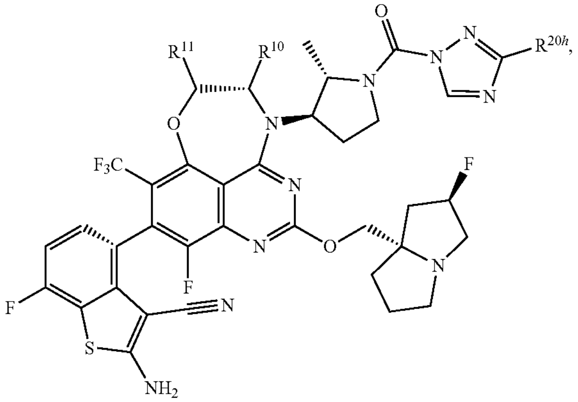
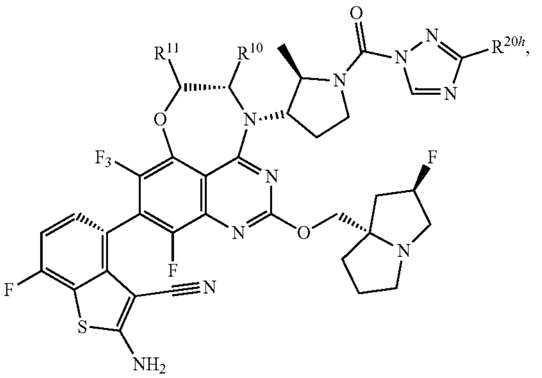
and
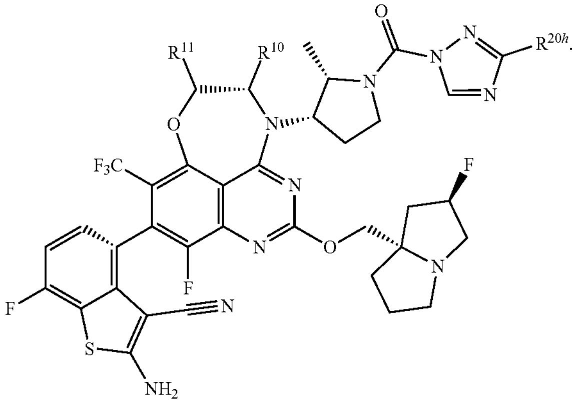
In embodiments of a compound of Formula I, IA, IB, II, IIA, or V, the compound has the formula:
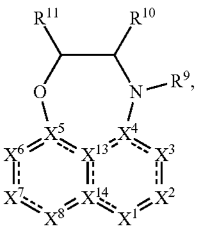
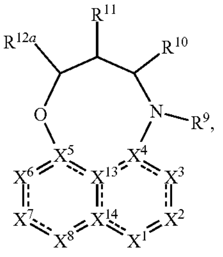

-continued

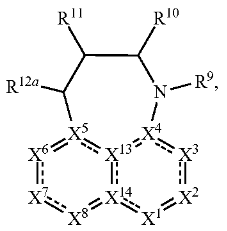

or

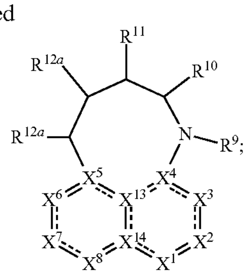

wherein all variables are as described for Formula I, IA, IB, II, IIA, V, or embodiments thereof.

In embodiments of a compound of Formula I, IA, IB, II, IIA, or V, the compound has the formula:

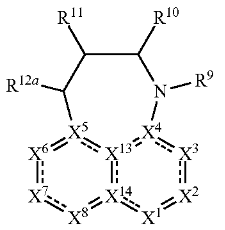

or

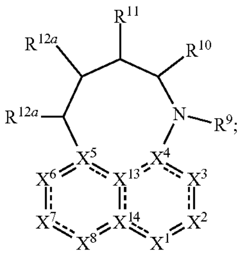

wherein all variables are as described for Formula I, IA, IB, II, IIA, V, or embodiments thereof.

In embodiments of a compound of Formula I, IA, IB, II, IIA, or V, the compound has the formula:

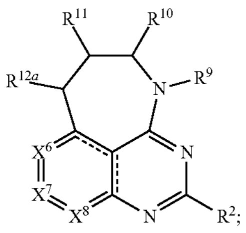

$X^6$ is selected from $C(R^6)$, $C(R^6)_2$, N, and $N(R^{6b})$;

$X^7$ is selected from $C(R^7)$ and $N(R^{7b})$;

$X^8$ is selected from $C(R^8)$ and $C(R^8)_2$; and $L^{7a}$ is a bond; $L^{7b}$ is a bond;

wherein all other variables are as described for Formula I, IA, IB, II, IIA, V, or embodiments thereof.

In embodiments of a compound of Formula I, IA, IB, II, IIA, or V, the compound has a formula selected from:

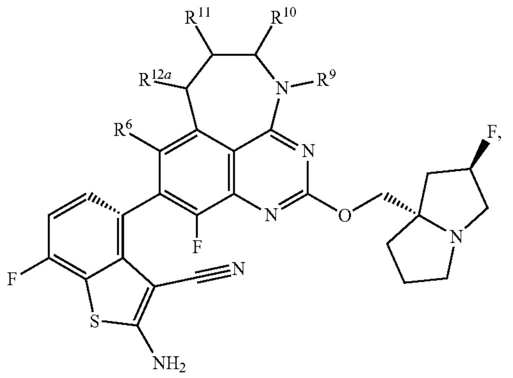

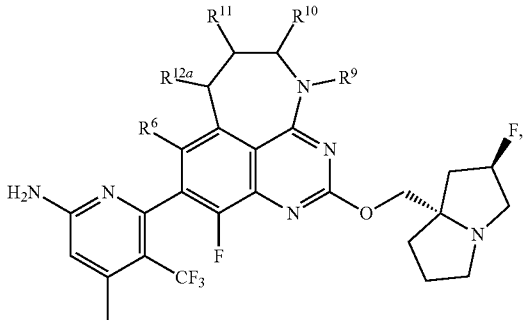

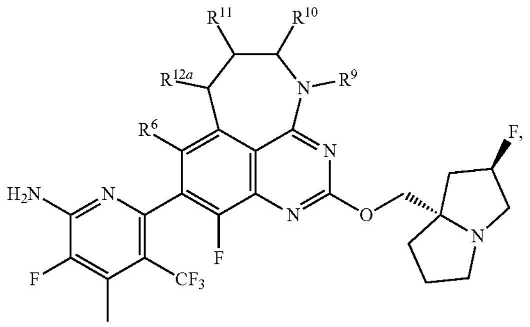

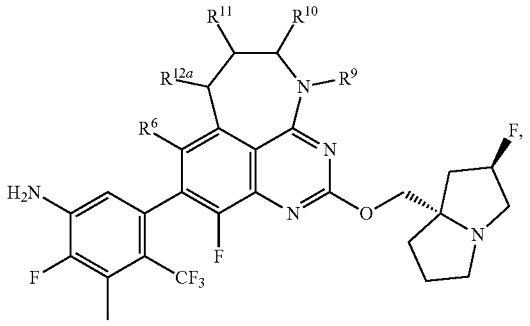

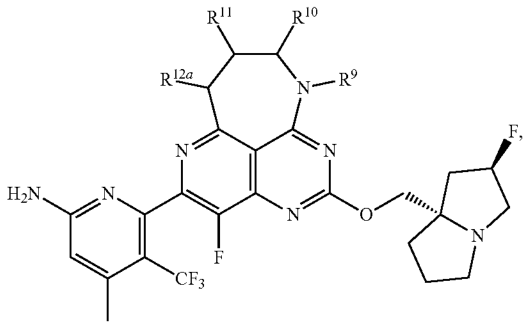

-continued

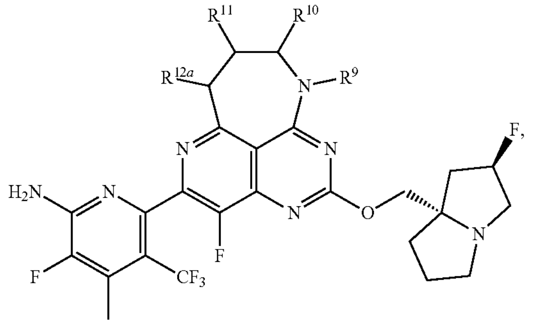

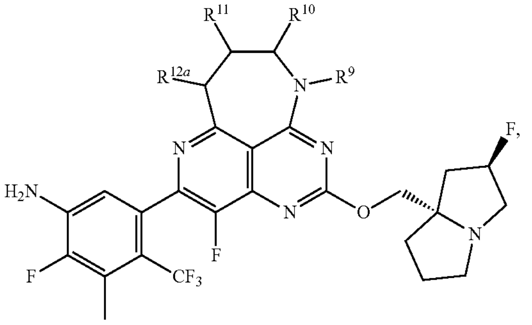

and

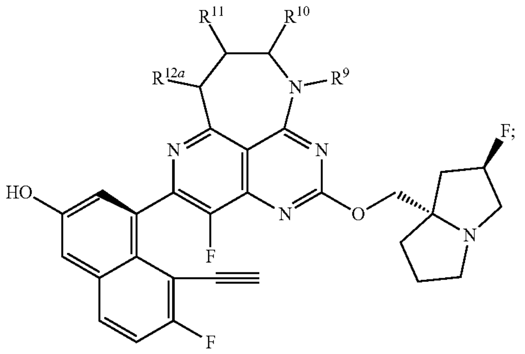

wherein $R^{12a}$ is selected from hydrogen and unsubstituted methyl; and $R^6$ is selected from halogen and —$CF_3$; wherein all other variables are as described for Formula I, IA, IB, II, IIA, V, or embodiments thereof.

In embodiments of a compound of Formula IA, IB, or IIA, the compound is selected from:

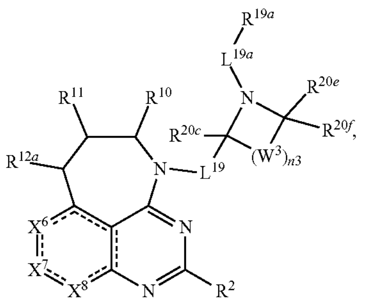

-continued

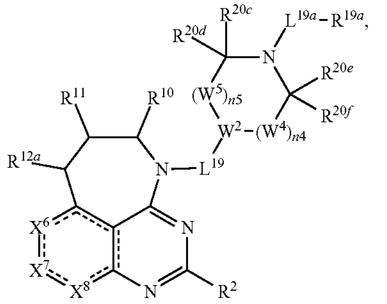

and

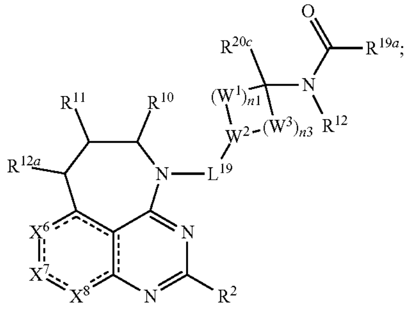

wherein all variables are as described for Formula IA, IB, IIA, or embodiments thereof.

In embodiments of a compound of Formula IA, IB, or IIA, the compound is selected from:

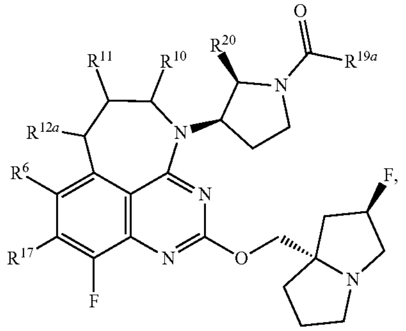

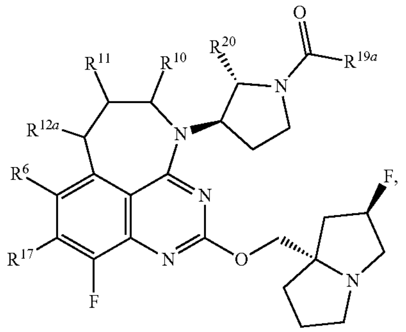

-continued

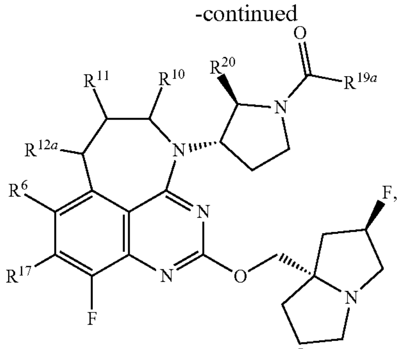

and

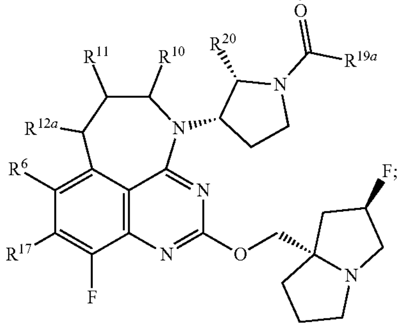

wherein $R^{12a}$ is selected from hydrogen and unsubstituted methyl; and $R^6$ is selected from halogen and $-CF_3$, and $R^{17}$ is selected from

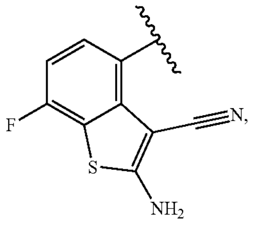

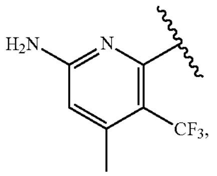

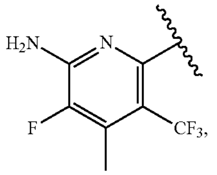

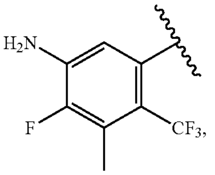

and

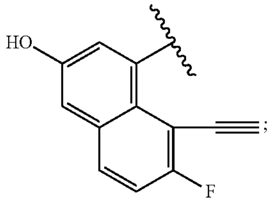

wherein all other variables are as described for Formula IA, IB, IIA, or embodiments thereof.

In embodiments of a compound of Formula I, II, or V, Ring A is a monocyclic $C_7$ carbocycle. In embodiments of a compound of Formula I, II, or V, Ring A is a monocyclic $C_8$ carbocycle. In embodiments of a compound of Formula I, II, or V, Ring A is a monocyclic $C_9$ carbocycle. In embodiments of a compound of Formula I, II, or V, Ring A is a monocyclic $C_{10}$ carbocycle.

In embodiments of a compound of Formula I, II, or V, Ring A is a partially unsaturated monocyclic $C_7$ carbocycle. In embodiments of a compound of Formula I, II, or V, Ring A is a partially unsaturated monocyclic $C_8$ carbocycle. In embodiments of a compound of Formula I, II, or V, Ring A is a partially unsaturated monocyclic $C_9$ carbocycle. In embodiments of a compound of Formula I, II, or V, Ring A is a partially unsaturated monocyclic $C_{10}$ carbocycle.

In embodiments of a compound of Formula I, II, or V, Ring A is a monocyclic 7-membered heterocycle. In embodiments of a compound of Formula I, II, or V, Ring A is a monocyclic 8-membered heterocycle. In embodiments of a compound of Formula I, II, or V, Ring A is a monocyclic 9-membered heterocycle. In embodiments of a compound of formula I or II, Ring A is a monocyclic 10-membered heterocycle.

In embodiments of a compound of Formula I, II, or V, Ring A is a partially unsaturated monocyclic 7-membered heterocycle. In embodiments of a compound of Formula I, II, or V, Ring A is a partially unsaturated monocyclic 8-membered heterocycle. In embodiments of a compound of Formula I, II, or V, Ring A is a partially unsaturated monocyclic 9-membered heterocycle. In embodiments of a compound of Formula I, II, or V, Ring A is a partially unsaturated monocyclic 10-membered heterocycle.

In embodiments of a compound of Formula V, Ring A is a fused bicyclic $C_{8-12}$ carbocycle. In embodiments of a compound of Formula V, Ring A is a fused bicyclic carbocycle comprising a $C_7$ carbocycle and a $C_5$ carbocycle. In embodiments of a compound of Formula V, Ring A is a fused bicyclic carbocycle comprising a $C_8$ carbocycle and a $C_5$ carbocycle. In embodiments of a compound of Formula V, Ring A is a fused bicyclic carbocycle comprising a $C_7$ carbocycle and a $C_6$ carbocycle. In embodiments of a compound of Formula V, Ring A is a fused bicyclic carbocycle comprising a $C_8$ carbocycle and a $C_6$ carbocycle. In embodiments of a compound of Formula V, Ring A is a fused bicyclic 8- to 12-membered heterocycle. In embodiments of a compound of Formula V, Ring A is a fused bicyclic heterocycle comprising a 7-membered ring and a 5-membered ring. In embodiments of a compound of Formula V, Ring A is a fused bicyclic heterocycle comprising an 8-membered ring and a 5-membered ring. In embodiments of a compound of Formula V, Ring A is a fused bicyclic heterocycle comprising a 7-membered ring and a 6-membered ring. In embodiments of a compound of Formula V, Ring A is a fused bicyclic heterocycle comprising a 7-membered ring and a 7-membered ring. In embodiments of a compound of Formula V, Ring A is a fused bicyclic heterocycle comprising an 8-membered ring and a 6-membered ring. In embodiments of a compound of Formula V, Ring A is a fused bicyclic heterocycle comprising a 7-membered ring and a 5-membered ring.

In embodiments of a compound of Formula I, II, or V, n29 is selected from 0, 1, and 2. In embodiments of a compound of Formula I, II, or V, n29 is 0. In embodiments of a compound of Formula I, II, or V, n29 is 1. In embodiments of a compound of Formula I, II, or V, n29 is 2. In embodiments of a compound of Formula I, II, or V, n29 is 3. In embodiments of a compound of Formula I, II, or V, n29 is 4. In embodiments of a compound of Formula I, II, or V, n29 is 5. In embodiments of a compound of Formula I, II, or V, n29 is 6. In embodiments of a compound of Formula I, II, or V, n29 is 7. In embodiments of a compound of Formula I, II, or V, n29 is 8. In embodiments of a compound of Formula I, II, or V, n29 is 9. n embodiments of a compound of Formula I, II, or V, n29 is 10. In embodiments of a compound of Formula I, II, or V, n29 is 11. In embodiments of a compound of Formula I, II, or V, n29 is 12. In embodiments of a compound of Formula I, II, or V, n29 is 13.

In embodiments of a compound of Formula I, IA, IB, II, IIA, or V, $X^1$ is N. In embodiments of a compound of Formula I, IA, IB, II, IIA, or V, $X^1$ is $N(R^{1b})$.

In embodiments of a compound of Formula I, IA, IB, II, IIA, or V, $R^{1b}$ is selected from $C_{3-12}$ carbocycle and 3- to 12-membered heterocycle, wherein $C_{3-12}$ carbocycle and 3- to 12-membered heterocycle are optionally substituted with one or more $R^{20}$. In embodiments of a compound of Formula I, IA, IB, II, IIA, or V, $R^{1b}$ is phenyl optionally substituted with one or more $R^{20}$. In embodiments of a compound of Formula I, IA, IB, II, IIA, or V, $R^{1b}$ is pyridyl optionally substituted with one or more $R^{20}$.

In embodiments of a compound of Formula I, IA, IB, II, IIA, or V, $X^2$ is $C(R^2)$. In embodiments of a compound of Formula I, IA, IB, II, IIA, or V, $X^2$ is C(O). In embodiments of a compound of Formula I, IA, IB, II, IIA, or V, $X^2$ is $N(R^{2b})$.

In some embodiments, for a compound of Formula I, IA, IB, II, IIA, or V, $R^2$ is selected from hydrogen, $C_{1-6}$ alkyl, $C_{2-6}$ alkenyl, $C_{3-10}$ carbocycle, 3- to 10-membered heterocycle, —$OR^{12}$, and —$N(R^{12})(R^{13})$, wherein $C_{1-6}$ alkyl, $C_{2-6}$ alkenyl, $C_{3-10}$ carbocycle, and 3- to 10-membered heterocycle are optionally substituted with one or more $R^{20}$. In some embodiments, $R^2$ is selected from hydrogen, —($C_{0-3}$ alkylene)-O—($C_{0-3}$ alkylene)-$R^{20}$, $C_{1-3}$ alkyl, and 3- to 10-membered heterocycle, wherein each $C_{0-3}$ alkylene, $C_{1-3}$ alkyl, and 3- to 10-membered heterocycle is optionally substituted with one or more $R^{20}$. In some embodiments, $R^2$ is selected from hydrogen, $C_{1-3}$ alkyl, —$OR^{12}$, and 3- to 10-membered heterocycle, wherein $C_{1-3}$ alkyl and 3- to 10-membered heterocycle are optionally substituted with one or more $R^{20}$. In some embodiments, $R^2$ is $OR^{12}$. In some embodiments, $R^2$ is —O($C_{1-3}$ alkylene)(4- to 10-membered heterocycle), wherein 4- to 10-membered heterocycle is optionally substituted with one or more substituents independently selected from halogen, $C_{1-3}$ alkyl, $C_{1-3}$ haloalkyl, and $=C(R^{21})_2$. In some embodiments, $R^2$ is —O($C_{1-3}$ alkylene)(4- to 10-membered heterocycle), wherein 4- to 10-membered heterocycle is optionally substituted with one or more substituents independently selected from halogen, $C_{1-3}$ alkyl, $C_{1-3}$ haloalkyl, and $=C(R^{21})_2$, wherein $R^{21}$ is independently selected at each occurrence from hydrogen, halogen, and $C_{1-3}$ alkyl. In some embodiments, $R^2$ is —$OCH_2$(hexahydro-1H-pyrrolizine) optionally substituted with one or more $R^{20}$. In some embodiments, $R^2$ is —$OCH_2$ (hexahydro-1H-pyrrolizine) optionally substituted with one or more substituents independently selected from halogen, $C_{1-3}$ alkyl, $C_{1-3}$ haloalkyl, and $=C(R^{21})_2$, wherein $R^{21}$ is independently selected at each occurrence from hydrogen, halogen, and $C_{1-3}$ alkyl.

In some embodiments, for a compound of Formula I, IA, IB, II, IIA, or V, $R^2$ is selected from

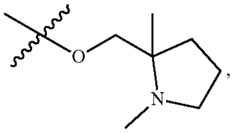,
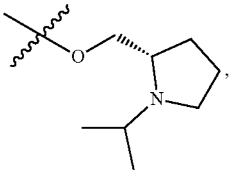,

-continued

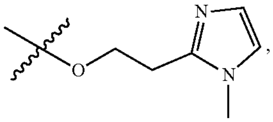,
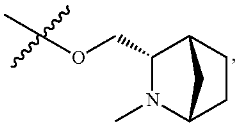,
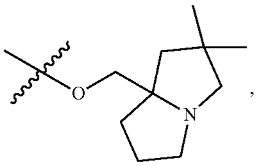,
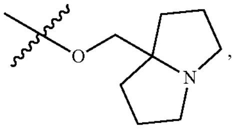,
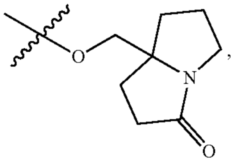,
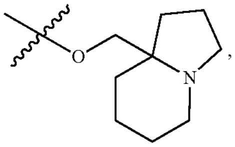,
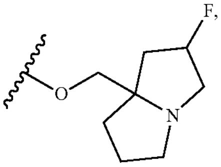,
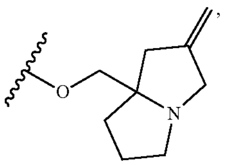,
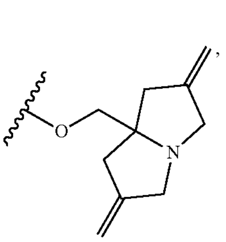,
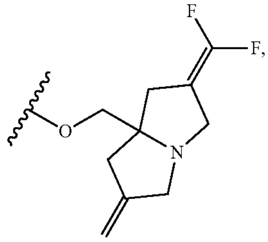,
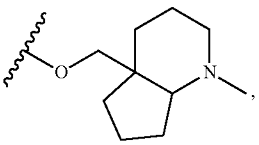,
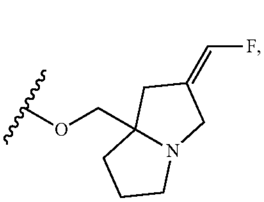,
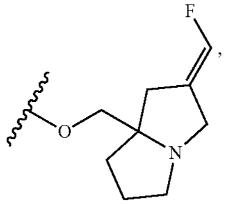,
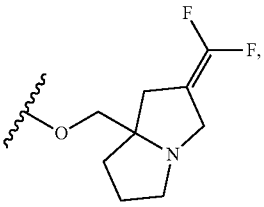,
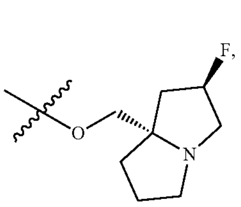,
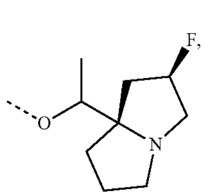,
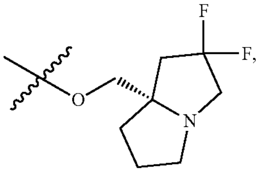, -continued
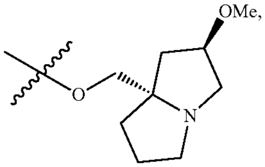
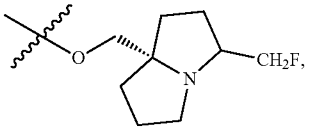
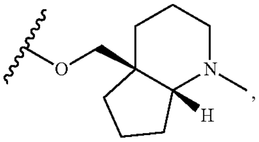
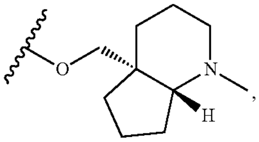
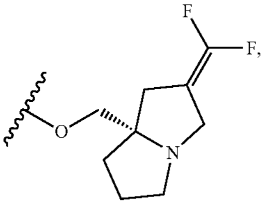
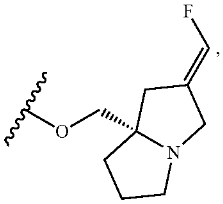
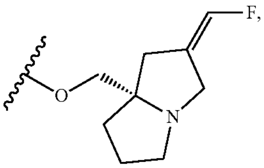
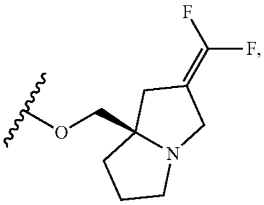
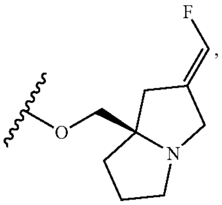
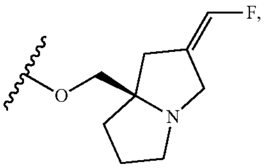
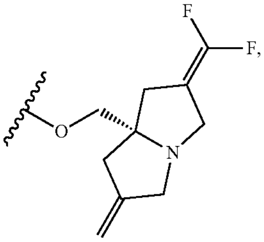
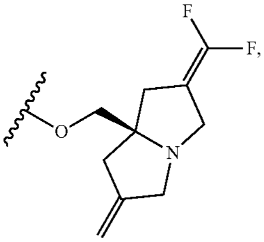
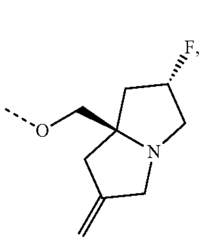
-continued
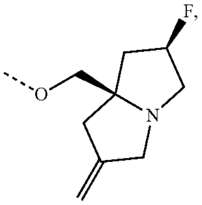
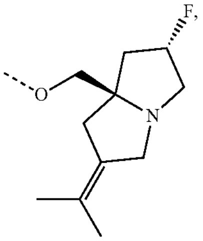
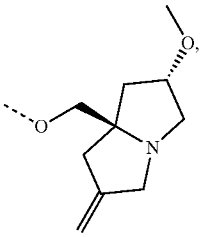
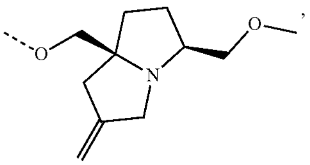
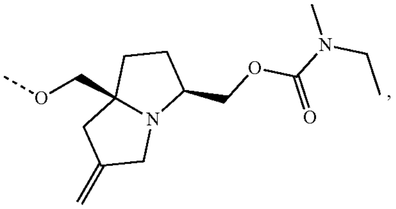
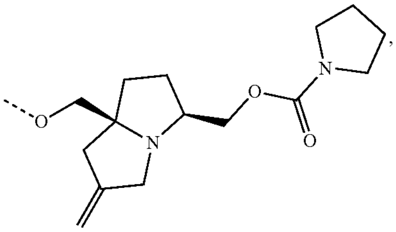
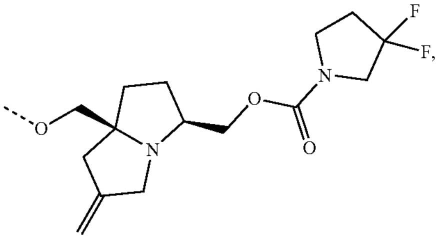
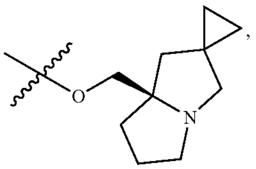
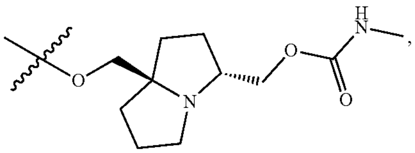
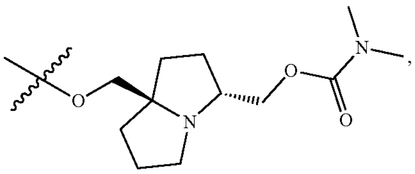

-continued
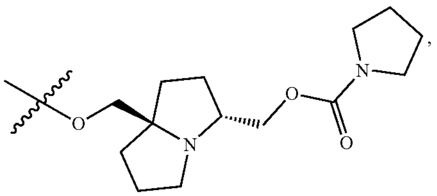,
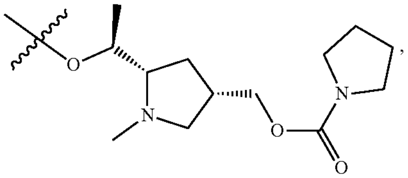,
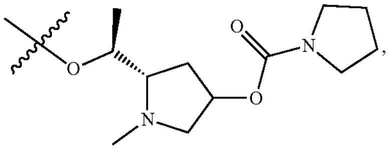,
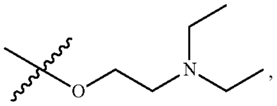, 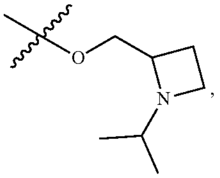,
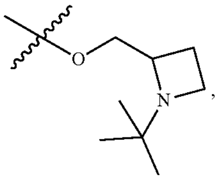, 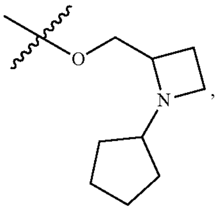,
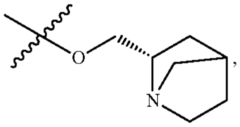, 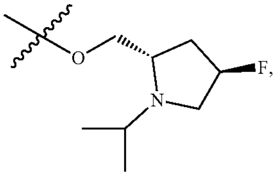,
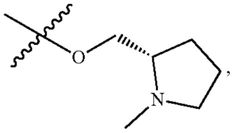, 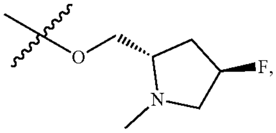,
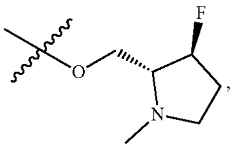,
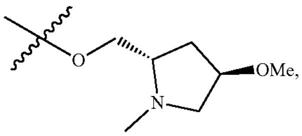,
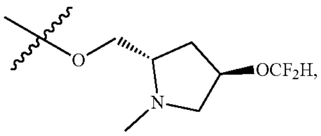,
-continued
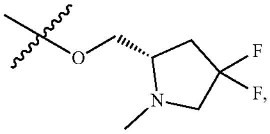, 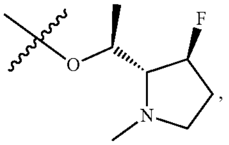,
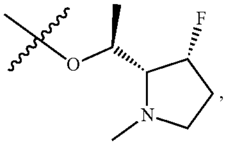, 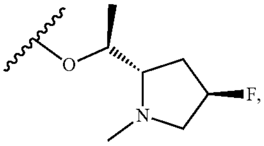,
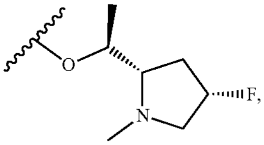,
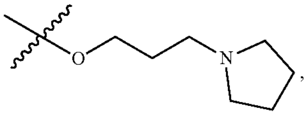,
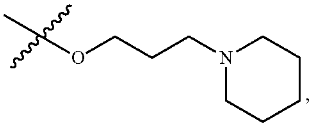,
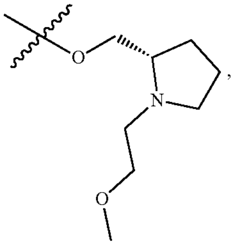,
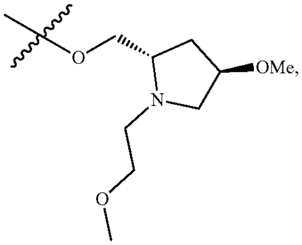,
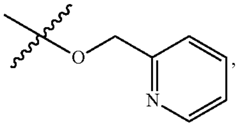, 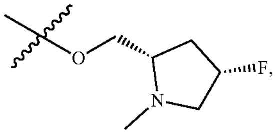,
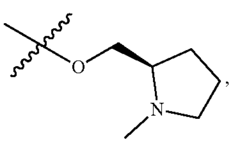, 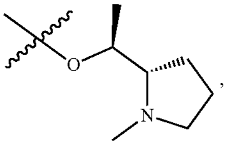,
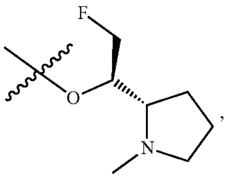, 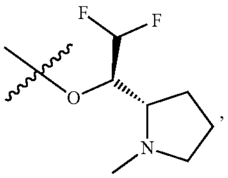, -continued
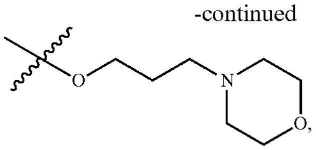
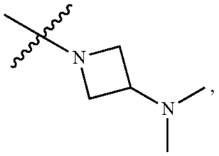 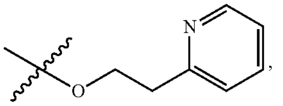
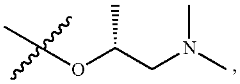 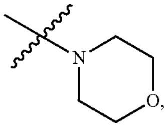
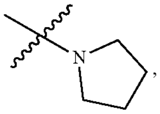 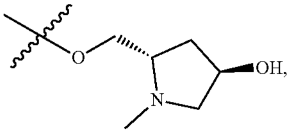
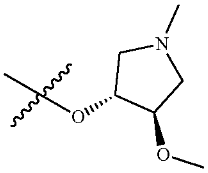 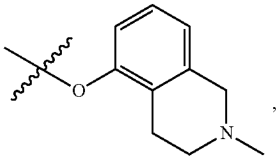
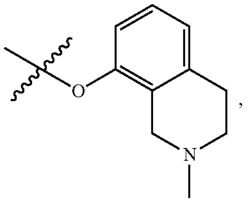 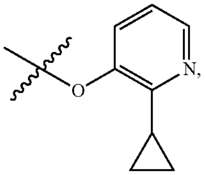
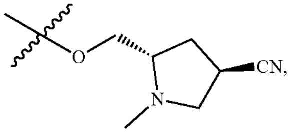
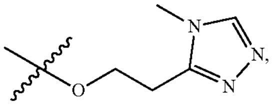
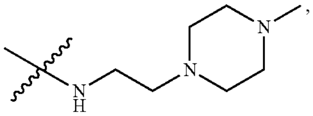
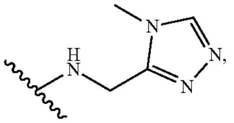 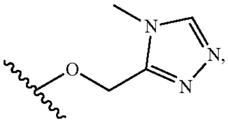
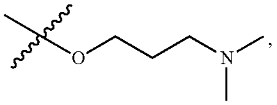
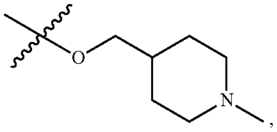 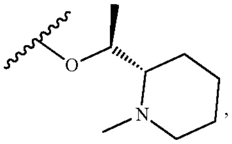
-continued
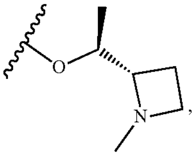 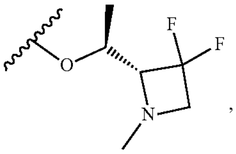
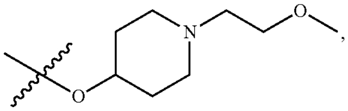
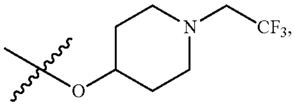
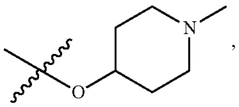 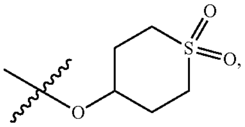
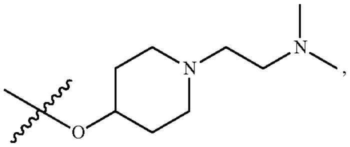
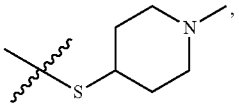
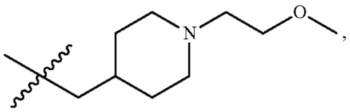
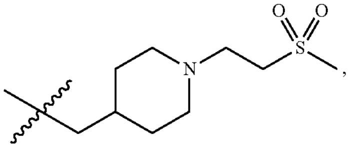
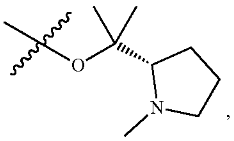 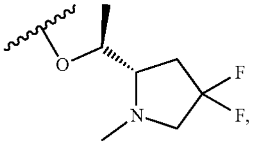
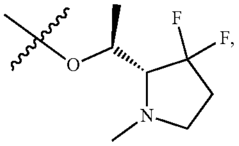 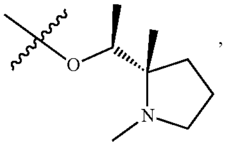
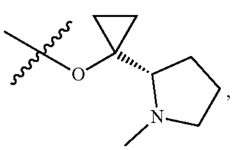 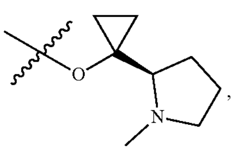
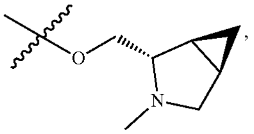 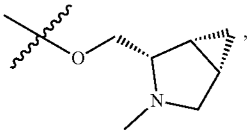

-continued
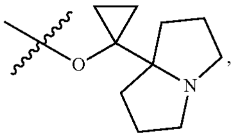,
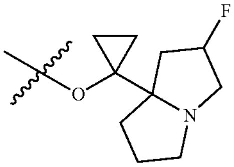,
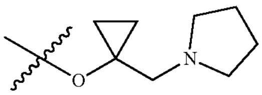,
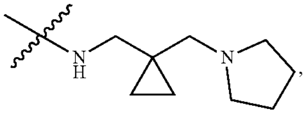,
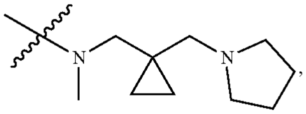,
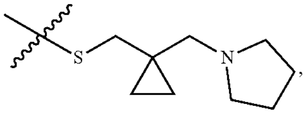,
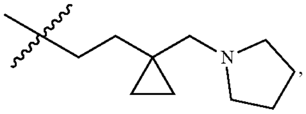,
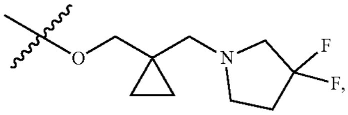,
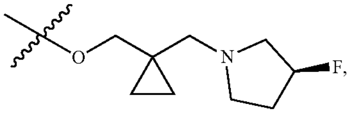,
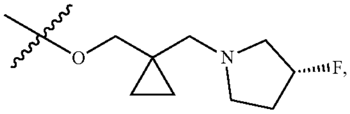,
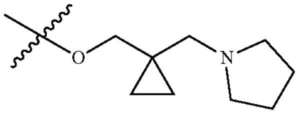,
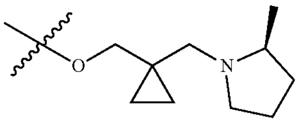,
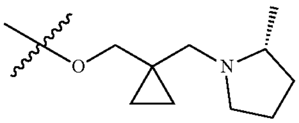,
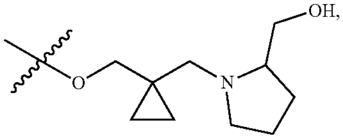,
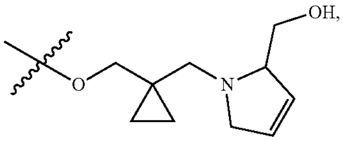
-continued
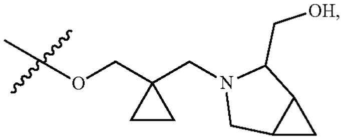,
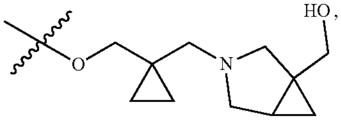,
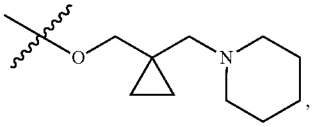,
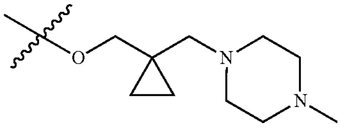,
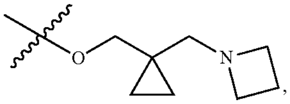,
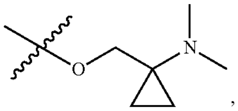,
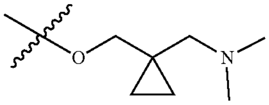,
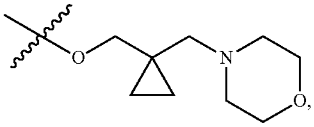,
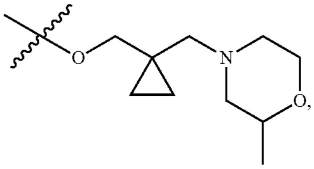,
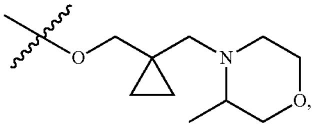,
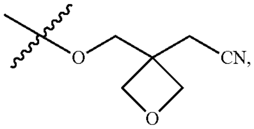,
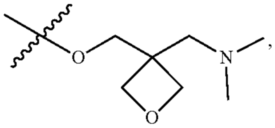,
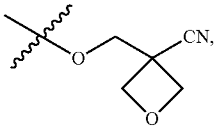,
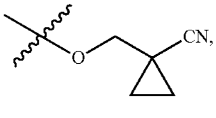,
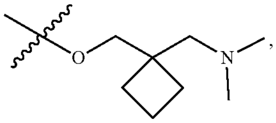,
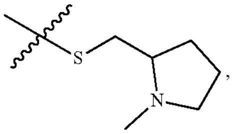,
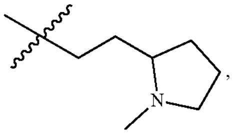, -continued
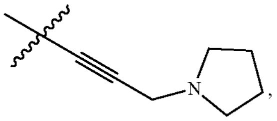
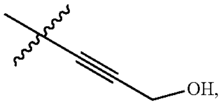
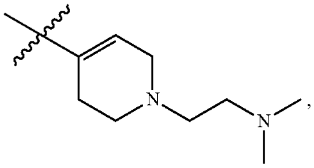
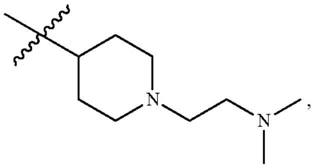
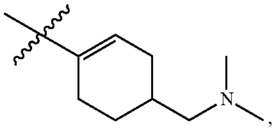
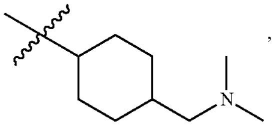
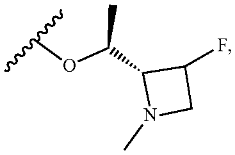
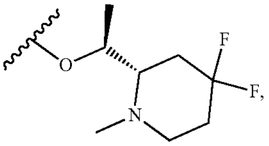
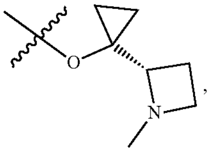
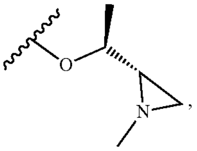
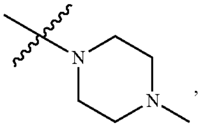
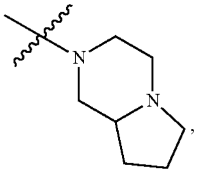
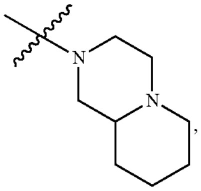
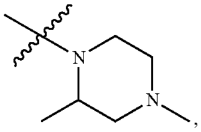
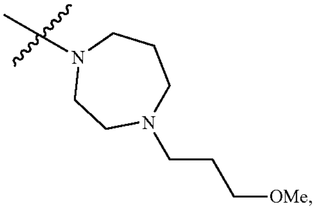
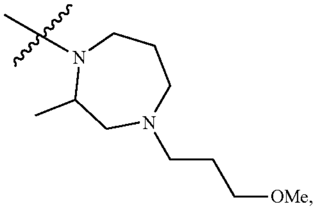
-continued
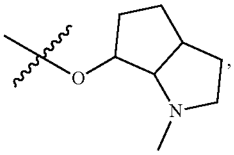
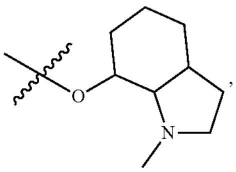
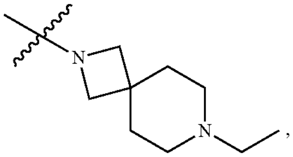
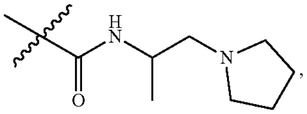
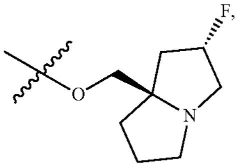
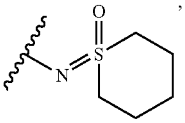
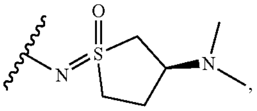
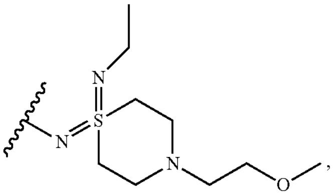
and
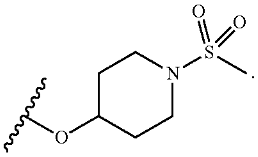
In some embodiments, $R^2$ is selected from
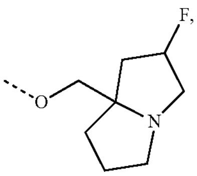
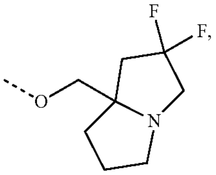
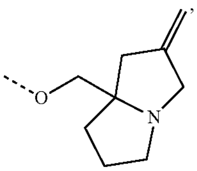
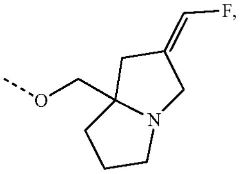

-continued
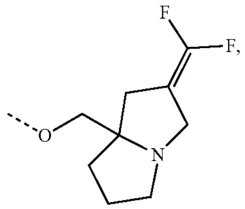
and
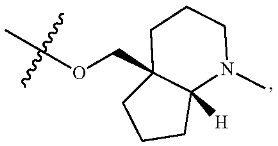
In some embodiments, $R^2$ is selected from
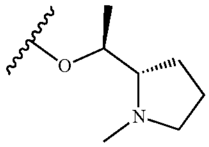
and
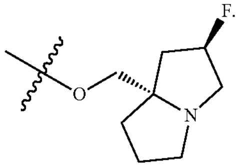
In some embodiments, $R^2$ is
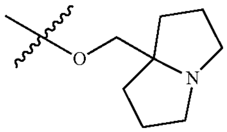 [SMILES: *OCC12CCCN1CCC2]
optionally substituted with one or more $R^{20}$. In some embodiments, $R^2$ is
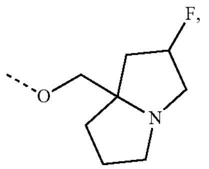
such as
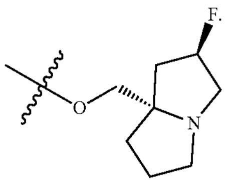 [SMILES: *OC[C@@]12CCCN1C[C@H](F)C2]
In some embodiments, $R^2$ is
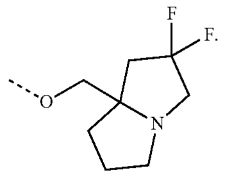
In some embodiments, $R^2$ is
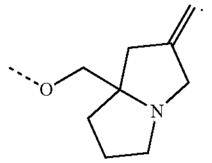
In some embodiments, $R^2$ is
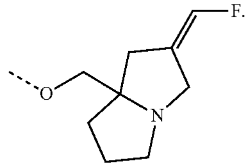
In some embodiments, $R^2$ is
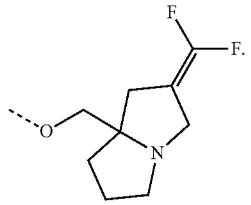
In some embodiments, $R^2$ is
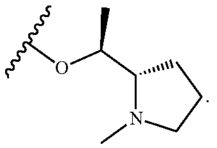 [SMILES: *O[C@@H](C)[C@@H]1CCCN1C]
In some embodiments, $R^2$ is
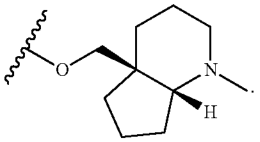 [SMILES: *OC[C@]12CCC[C@H]1N(C)CCC2]

In some embodiments, $R^2$ is selected from

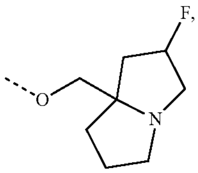
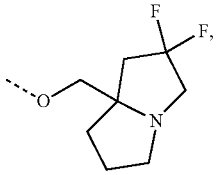
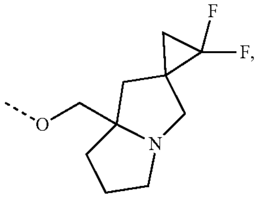
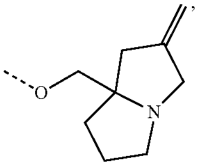
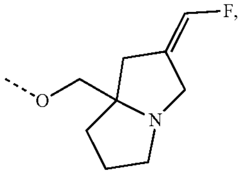
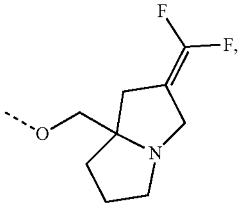
and
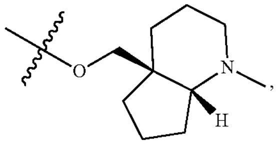

such as

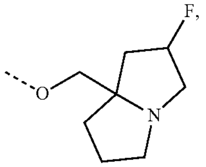

In some embodiments, for a compound of Formula I, IA, IB, II, IIA, or V, $R^2$ is substituted with one, two, three, or four substituents independently selected from halogen, oxo, $C_{1-6}$ alkyl, —$OR^{22}$, —$N(R^{22})(R^{23})$, =$C(R^{21})_2$, and —OC(O)$N(R^{22})(R^{23})$, wherein $C_{1-6}$ alkyl is optionally substituted with one or more substituents independently selected from halogen, —CN, —$OR^{22}$, —$N(R^{22})(R^{23})$, and —OC(O)N$(R^{22})(R^{23})$. In some embodiments, $R^2$ is substituted with one, two, three, or four substituents independently selected from halogen, $C_{1-3}$ alkyl, $C_{1-3}$ haloalkyl, and =$C(R^{21})_2$, wherein $R^{21}$ is independently selected at each occurrence from hydrogen, halogen, and $C_{1-3}$ alkyl. In some embodiments, $R^2$ is substituted with one, two, three, or four substituents independently selected from halogen, $C_{1-3}$ alkyl, $C_{1-3}$ haloalkyl, =$CH_2$, =CHF, and =$CF_2$. In some embodiments, $R^2$ is substituted with halogen, such as fluorine.

In some embodiments, for a compound of Formula I, IA, IB, II, IIA, or V, $R^{2b}$ is selected from hydrogen, $C_{1-6}$ alkyl, $C_{2-6}$ alkenyl, $C_{3-10}$ carbocycle, and 3- to 10-membered heterocycle, wherein $C_{1-6}$ alkyl, $C_{2-6}$ alkenyl, $C_{3-10}$ carbocycle, and 3- to 10-membered heterocycle are optionally substituted with one or more $R^{20}$. In some embodiments, $R^{2b}$ is selected from hydrogen, —($C_{0-3}$ alkylene)-O—($C_{0-3}$ alkylene)-$R^{20}$, $C_{1-3}$ alkyl, and 3- to 10-membered heterocycle, wherein each $C_{0-3}$ alkylene, $C_{1-3}$ alkyl, and 3- to 10-membered heterocycle is optionally substituted with one or more $R^{20}$. In some embodiments, $R^{2b}$ is selected from hydrogen, $C_{1-3}$ alkyl, and 3- to 10-membered heterocycle, wherein $C_{1-3}$ alkyl and 3- to 10-membered heterocycle are optionally substituted with one or more $R^{20}$.

In some embodiments, for a compound of Formula I, IA, IB, II, IIA, or V, $R^{2b}$ is selected from

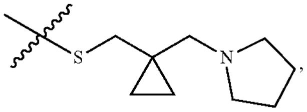
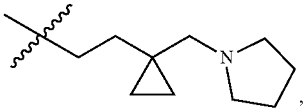
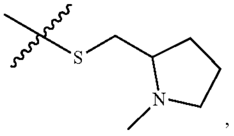
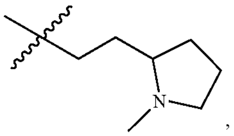
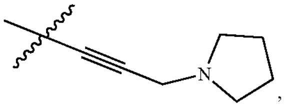
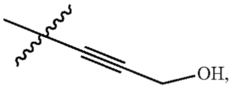
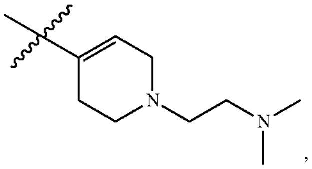
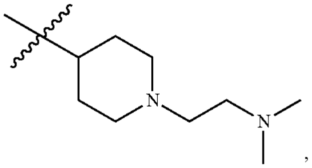
and
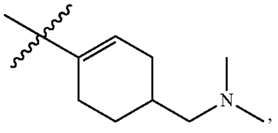
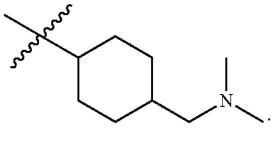

In some embodiments, for a compound of Formula I, IA, IB, II, IIA, or V, $R^{2b}$ is substituted with one, two, three, or four substituents independently selected from halogen, oxo, $C_{1-6}$ alkyl, —$OR^{22}$, —$N(R^{22})(R^{23})$, =$C(R^{21})_2$, and —OC(O)$N(R^{22})(R^{23})$, wherein $C_{1-6}$ alkyl is optionally substituted with one or more substituents independently selected from halogen, —CN, —$OR^{22}$, —$N(R^{22})(R^{23})$, and —OC(O)N$(R^{22})(R^{23})$. In some embodiments, $R^{2b}$ is substituted with one, two, three, or four substituents independently selected from halogen, $C_{1-3}$ alkyl, $C_{1-3}$ haloalkyl, and =$C(R^{21})_2$, wherein $R^{21}$ is independently selected at each occurrence from hydrogen, halogen, and $C_{1-3}$ alkyl. In some embodiments, $R^{2b}$ is substituted with one, two, three, or four substituents independently selected from halogen, $C_{1-3}$ alkyl, $C_{1-3}$ haloalkyl, $=CH_2$, $=CHF$, and $=CF_2$. In some embodiments, $R^2$ is substituted with halogen, such as fluorine.

In embodiments of a compound of Formula I, IA, IB, II, IIA, or V, $X^3$ is N. In embodiments of a compound of Formula I, IA, IB, II, IIA, or V, $X^3$ is $C(R^3)$.

In embodiments of a compound of Formula I, IA, IB, II, IIA, or V, $R^3$ is independently selected at each occurrence from hydrogen, halogen, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more $R^{20}$. In embodiments of a compound of Formula I, IA, IB, II, IIA, or V, $R^3$ is —CN.

In embodiments of a compound of Formula I, IA, IB, II, IIA, or V, $X^4$ is C.

In embodiments of a compound of Formula I, IA, IB, II, IIA, or V, $X^5$ is C.

In embodiments of a compound of Formula I, IA, IB, II, IIA, or V, $X^6$ is $C(R^6)$. In embodiments of a compound of Formula I, IA, IB, II, IIA, or V, $R^6$ is independently selected at each occurrence from hydrogen and halogen. In embodiments of a compound of Formula I, IA, IB, II, IIA, or V, $R^6$ is methyl optionally substituted with one or more $R^{20}$. In embodiments of a compound of Formula I, IA, IB, II, IIA, or V, $R^6$ is methyl independently substituted with one or more halogen. In embodiments of a compound of Formula I, IA, IB, II, IIA, or V, $R^6$ is $—CF_3$. In embodiments of a compound of Formula I, IA, IB, II, IIA, or V, $R^6$ is —Cl. In embodiments of a compound of Formula I, IA, IB, II, IIA, or V, $X^6$ is N. In embodiments of a compound of Formula I, IA, IB, II, IIA, or V, $X^6$ is $N(R^{6b})$. In embodiments of a compound of Formula I, IA, IB, II, IIA, or V, $R^{6b}$ is unsubstituted cyclopropyl. In embodiments of a compound of Formula I, IA, IB, II, IIA, or V, $R^{6b}$ is $C_{1-6}$ alkyl, $C_{2-6}$ alkenyl, $C_{2-6}$ alkynyl, wherein $C_{1-6}$ alkyl, $C_{2-6}$ alkenyl, and $C_{2-6}$ alkynyl are optionally substituted with one or more $R^{20}$ (e.g. CN, halogen, F, or Cl).

In embodiments of a compound of Formula I, IA, IB, II, IIA, or V, $X^7$ is $C(R^7)$. In embodiments of a compound of Formula I, IA, IB, II, IIA, or V, $X^7$ is $N(R^{7b})$.

In embodiments of a compound of Formula I, IA, IB, II, IIA, or V, $R^7$ is $—R^{17}$. In embodiments of a compound of Formula I, IA, IB, II, IIA, or V, $R^{7b}$ is $—R^{17}$.

In some embodiments, for a compound of Formula I, IA, IB, II, IIA, or V, $R^{17}$ is selected from $C_{6-12}$ aryl and 5- to 12-membered heteroaryl, each of which is optionally substituted with one or more $R^{20}$. In some embodiments, $R^{17}$ is selected from $C_{10}$ aryl and 9-membered heteroaryl, each of which is optionally substituted with one or more $R^{20}$. In embodiments of a compound of Formula I, IA, IB, II, IIA, or V, $R^{17}$ is selected from phenyl, pyridyl, naphthyl, quinolinyl, isoquinolinyl, benzothiazolyl, benzothienyl, indazolyl, and benzoxazolyl, wherein phenyl, pyridyl, naphthyl, quinolinyl, isoquinolinyl, benzothiazolyl, benzothienyl, indazolyl, and benzoxazolyl are optionally substituted with one or more $R^{20}$. In some embodiments, $R^{17}$ is selected from naphthalenyl and benzothiophenyl, each of which is optionally substituted with one or more $R^{20}$. In some embodiments, $R^{17}$ is selected from $C_{3-10}$ cycloalkyl, 3- to 10-membered heterocycloalkyl, $C_{6-10}$ aryl, and 5- to 10-membered heteroaryl, each of which is optionally substituted with one or more $R^{20}$. In some embodiments, $R^{17}$ is selected from bicyclic $C_{4-10}$ cycloalkyl, bicyclic 4- to 10-membered heterocycloalkyl, bicyclic $C_{7-10}$ aryl, and bicyclic 7- to 10-membered heteroaryl, each of which is optionally substituted with one or more $R^{20}$. In some embodiments, $R^{17}$ is selected from bridged bicyclic $C_{4-10}$ cycloalkyl, bridged bicyclic 4- to 10-membered heterocycloalkyl, bridged bicyclic $C_{7-10}$ aryl, and bridged bicyclic 7- to 10-membered heteroaryl, each of which is optionally substituted with one or more $R^{20}$. In some embodiments, $R^{17}$ is selected from fused bicyclic $C_{4-10}$ cycloalkyl, fused bicyclic 4- to 10-membered heterocycloalkyl, fused bicyclic $C_{7-10}$ aryl, and fused bicyclic 7- to 10-membered heteroaryl, each of which is optionally substituted with one or more $R^{20}$. In some embodiments, $R^{17}$ is selected from $C_{6-10}$ aryl and 5- to 10-membered heteroaryl, each of which is optionally substituted with one, two, three, four, or five $R^{20}$. In some embodiments, $R^{17}$ is selected from naphthyl, isoquinolinyl, indazolyl, benzothiazolyl, benzothiophenyl, phenyl, and pyridinyl, each of which is optionally substituted with one or more $R^{20}$. In some embodiments, $R^{17}$ is substituted with one, two, three, or four substituents independently selected from halogen, —CN, $C_{1-3}$ alkyl, $C_{1-3}$ haloalkyl, $C_{2-3}$ alkenyl, $C_{2-3}$ alkynyl, $—OR^{22}$, $—N(R^{22})(R^{23})$, and $C_{3-6}$ cycloalkyl. In some embodiments, $R^{17}$ is selected from $C_6$ aryl and 6-membered heteroaryl, each of which is substituted with one, two, three, four, or five $R^{20}$. In some embodiments, $R^{17}$ is optionally substituted with one or more $R^{20}$, such as one, two, three, four, five, six, or seven $R^{20}$.

In some embodiments, for a compound of Formula I, IA, IB, II, IIA, or V, $R^{17}$ is selected from:

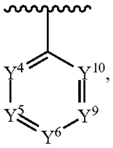
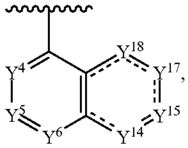
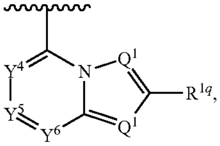
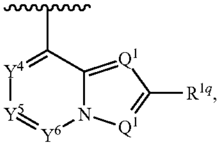
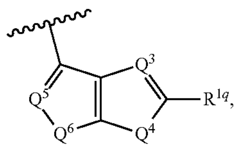
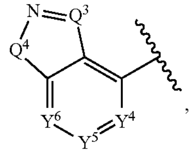
,
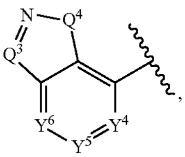
,
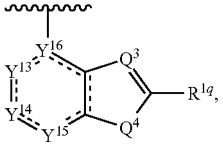
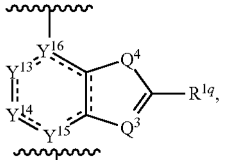
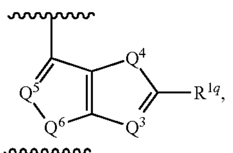
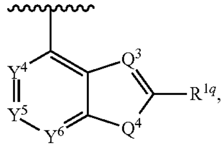
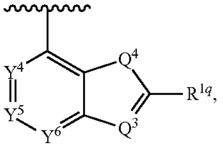

-continued

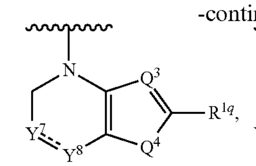

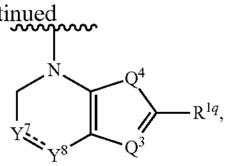

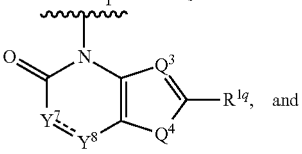

and

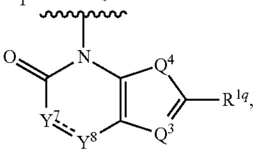

wherein:

$Q^1$, $Q^3$, and $Q^5$ are independently selected from N and $C(R^{1q})$;

$Q^4$ and $Q^6$ are independently selected from O, S, $C(R^{1q})_2$, and $N(R^{1r})$;

$Y^4$, $Y^5$, $Y^6$, $Y^9$, and $Y^{10}$ are independently selected from $C(R^{1q})$ and N;

$Y^7$ and $Y^8$ are independently selected from $C(R^{1q})$, $C(R^{1q})_2$, N, and $N(R^{1r})$;

$Y^{13}$ is selected from a bond, $C(R^{1q})$, N, C(O), $C(R^{1q})_2$, $C(O)C(R^{1q})_2$, $C(R^{1q})_2C(R^{1q})_2$, $C(R^{1q})_2N(R^{1r})$, and $N(R^{1r})$;

$Y^{14}$, $Y^{15}$, $Y^{17}$, and $Y^{18}$ are independently selected from C(O), $C(R^{1q})$, N, $C(R^{1q})_2$, and $N(R^{1r})$;

$Y^{16}$ is selected from C, N, and $C(R^{1q})$;

each $R^{1q}$ is independently selected from hydrogen, halogen, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(=O)(=NR^{12})N(R^{12})(R^{13})$, wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$; or two $R^{1q}$ bonded to the same carbon are joined to form 3- to 10-membered heterocycle or $C_{3-10}$ carbocycle, wherein 3- to 10-membered heterocycle and $C_{3-10}$ carbocycle are optionally substituted with one or more $R^{20}$; or two $R^{1q}$ bonded to adjacent atoms are joined to form 3- to 10-membered heterocycle or $C_{3-10}$ carbocycle, wherein 3- to 10-membered heterocycle and $C_{3-10}$ carbocycle are optionally substituted with one or more $R^{20}$; or one $R^{1q}$ and one $R^{1r}$ are joined to form 3- to 10-membered heterocycle, wherein 3- to 10-membered heterocycle is optionally substituted with one or more $R^{20}$;

each $R^{1r}$ is independently selected from hydrogen, $C_{1-6}$ alkyl, $C_{2-6}$ alkenyl, $C_{2-6}$ alkynyl, 3- to 10-membered heterocycle, and $C_{3-10}$ carbocycle, wherein $C_{1-6}$ alkyl, $C_{2-6}$ alkenyl, $C_{2-6}$ alkynyl, 3- to 10-membered heterocycle, and $C_{3-10}$ carbocycle are optionally substituted with one or more $R^{20}$; and ⁚⁚⁚ indicates a single or double bond such that all valences are satisfied.

In some embodiments, $R^{17}$ is selected from

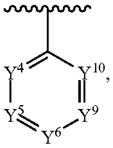

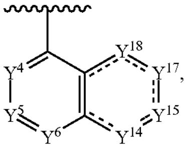

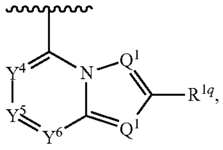

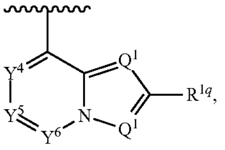

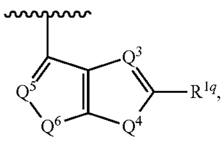

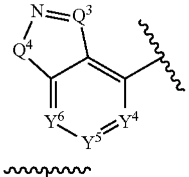

,

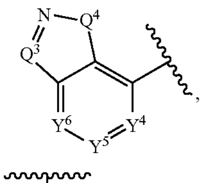

,

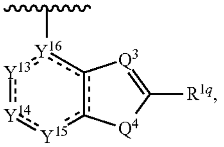

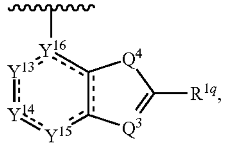

and

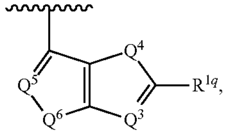

In some embodiments, $R^{17}$ is selected from

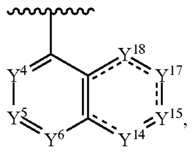

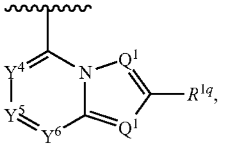

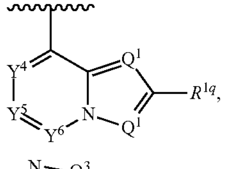

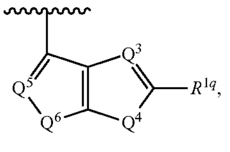

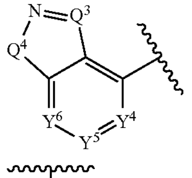

,

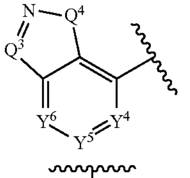

,

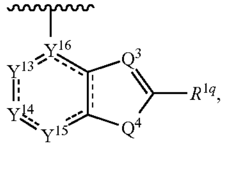

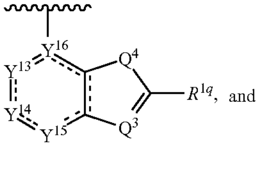

and

-continued
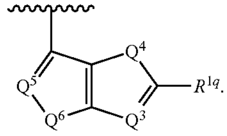
In some embodiments, $R^{17}$ is selected from
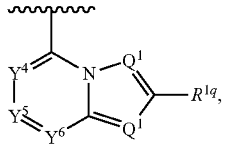
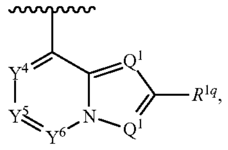
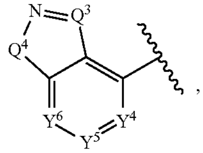
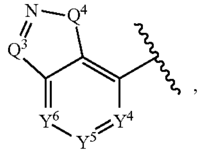
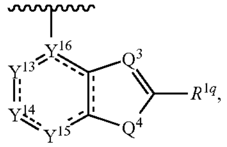 and 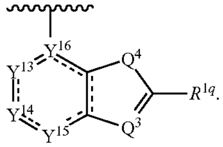
In some embodiments, $R^{17}$ is selected from
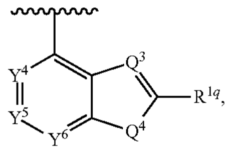
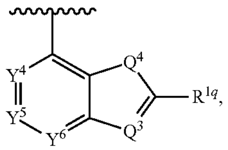
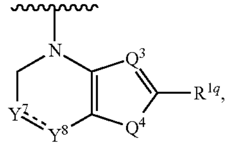
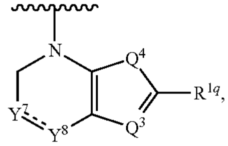
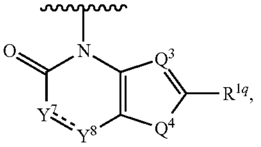 and 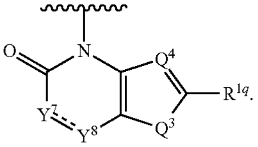
In some embodiments, for a compound of Formula I, IA, IB, II, IIA, or V, $R^{17}$ is selected from
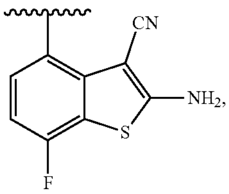
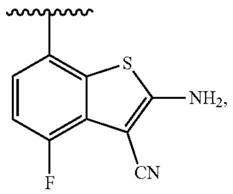
-continued
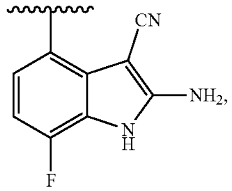
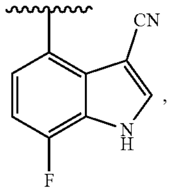
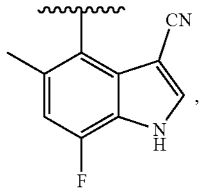
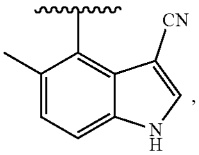
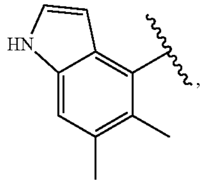
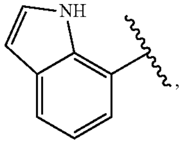
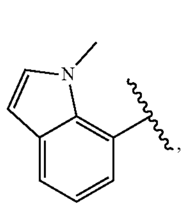
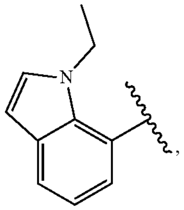
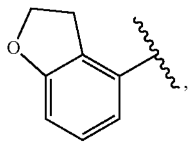
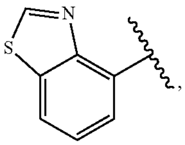
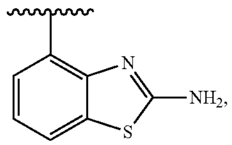
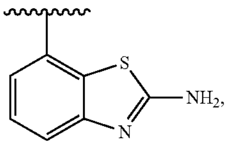
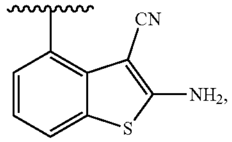
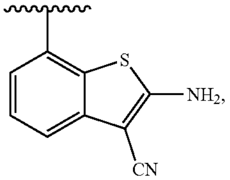
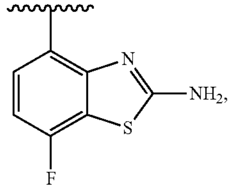
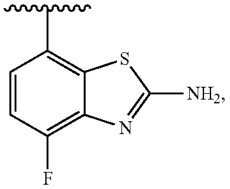
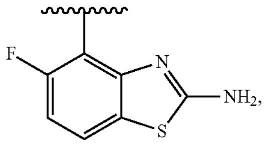
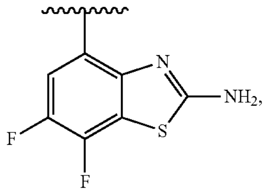

-continued
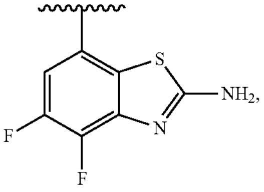
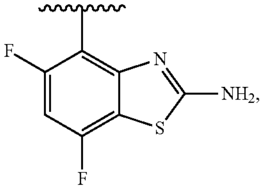
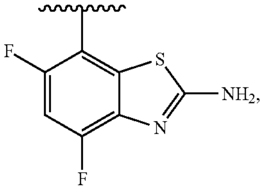
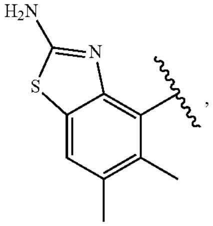
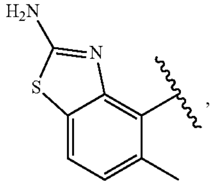
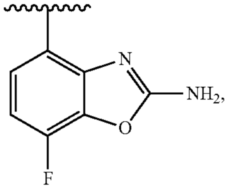
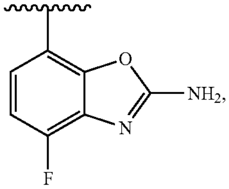
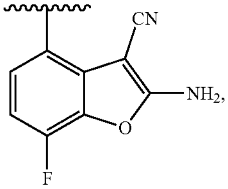 [SMILES: *c1ccc(F)c2sc(N)c(C#N)c12]
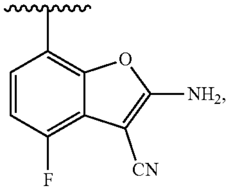
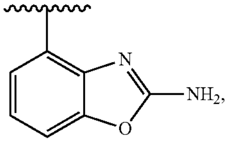
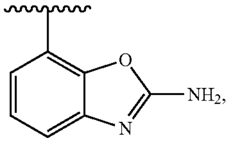
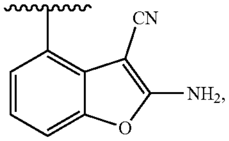
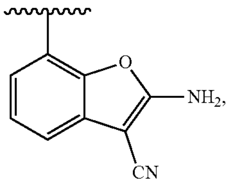
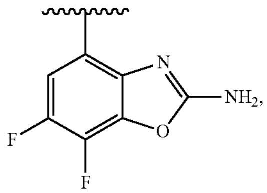
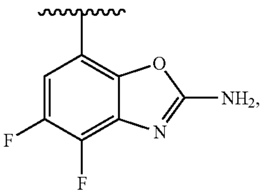
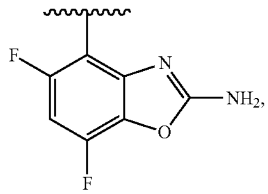
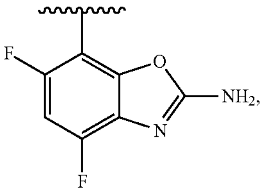
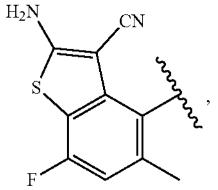
-continued
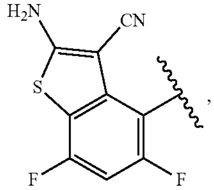
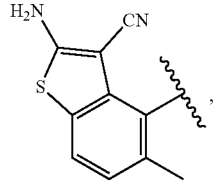
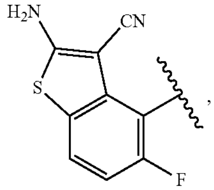
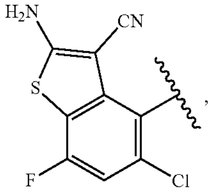
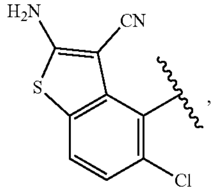
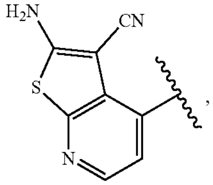
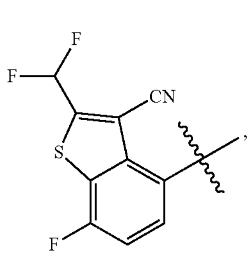
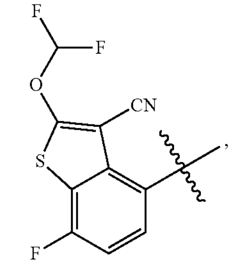
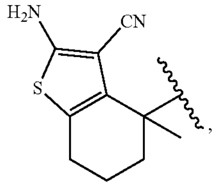
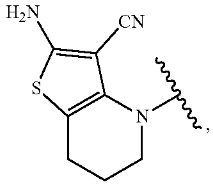
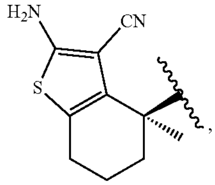
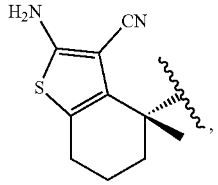
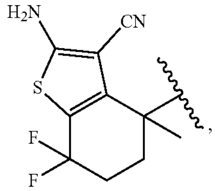
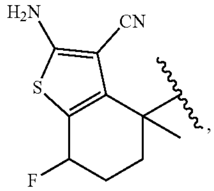
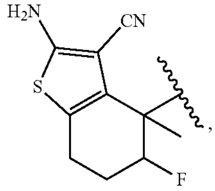
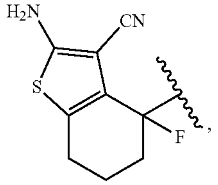

-continued
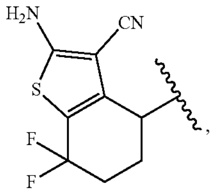,
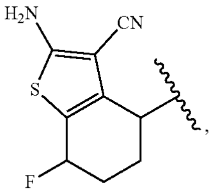,
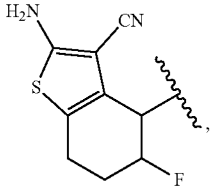,
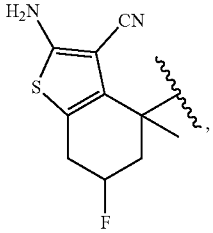,
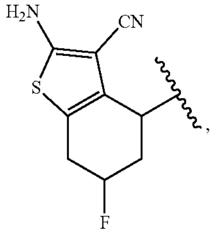,
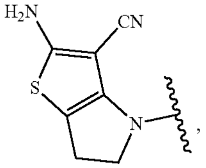,
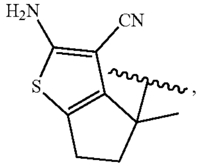,
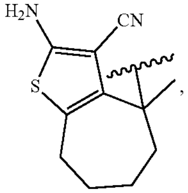,
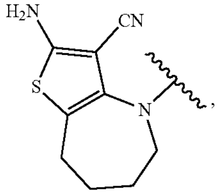,
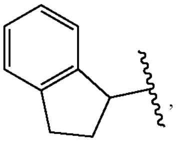,
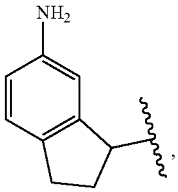,
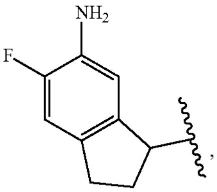,
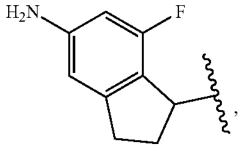,
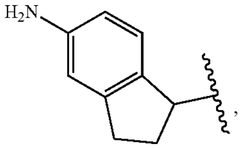,
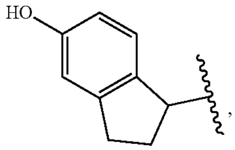,
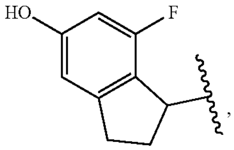,
-continued
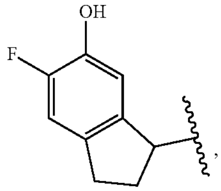,
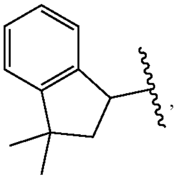,
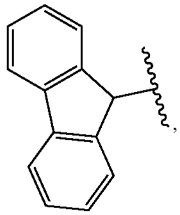,
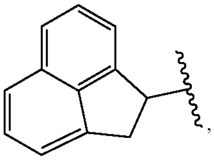,
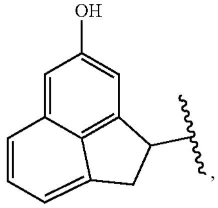,
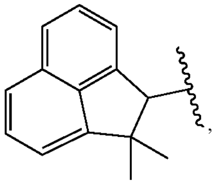,
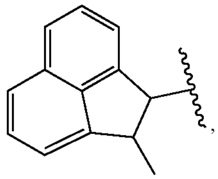,
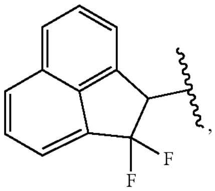,
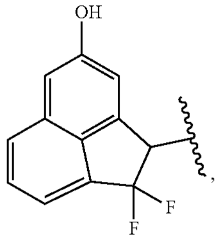,
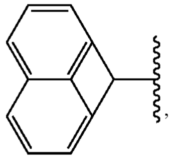,
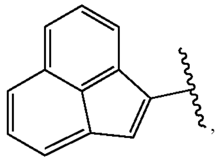,
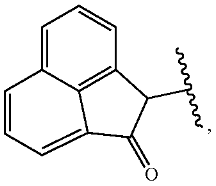,
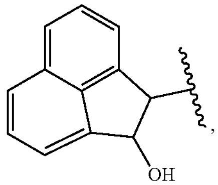,
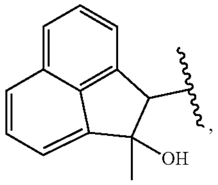,
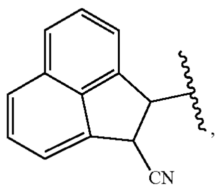,
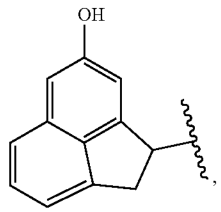, -continued
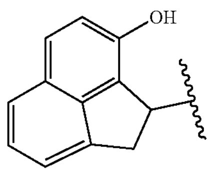, 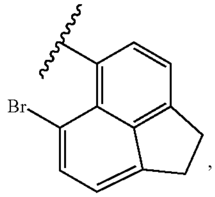,
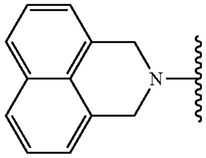, 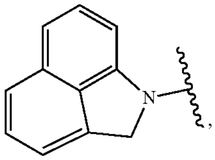,
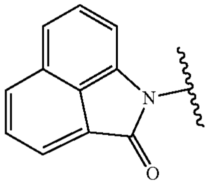, 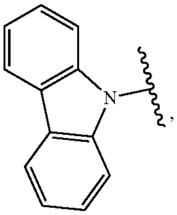,
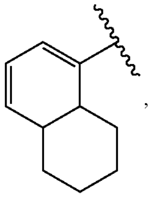, 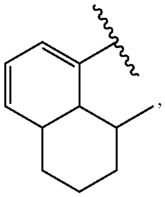,
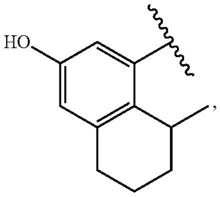, 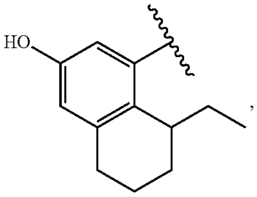,
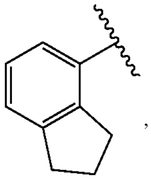, 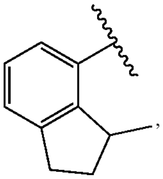, 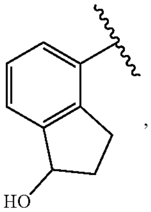,
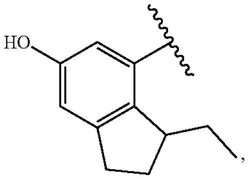, 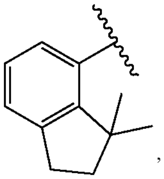,
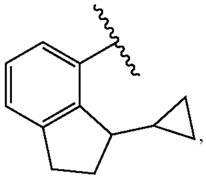, 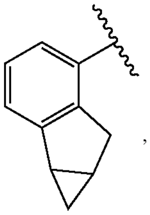,
-continued
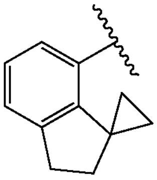, 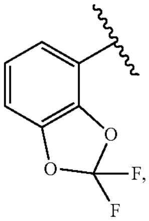 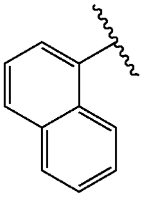,
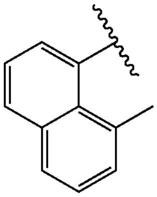, 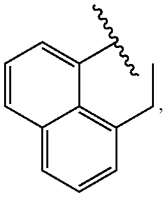,
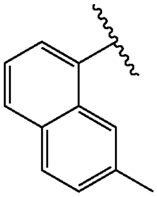, 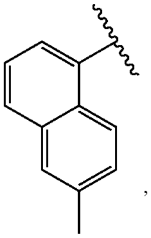,
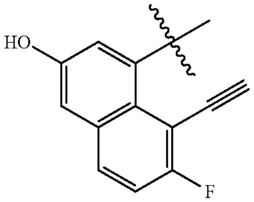 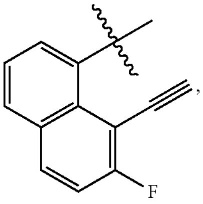
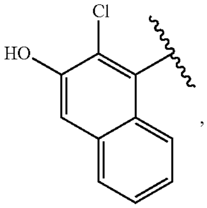, 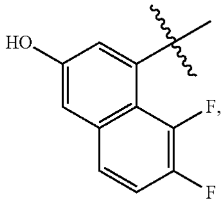
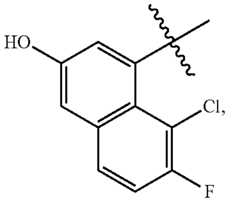 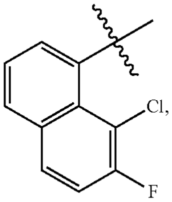
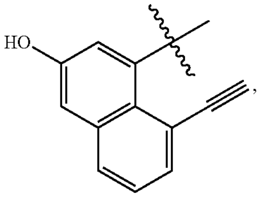 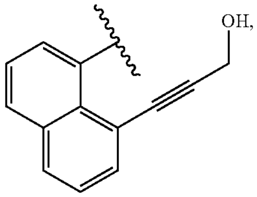

-continued
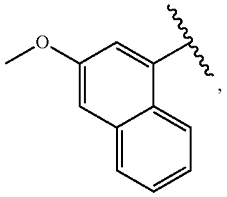
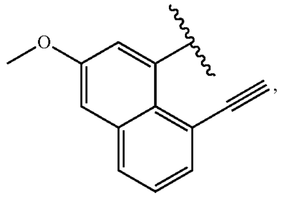
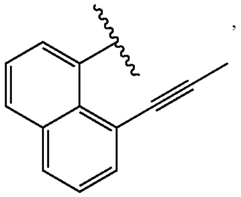
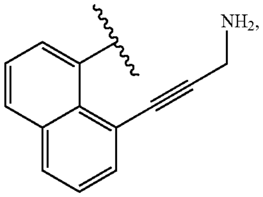
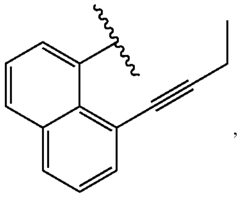
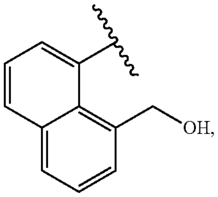
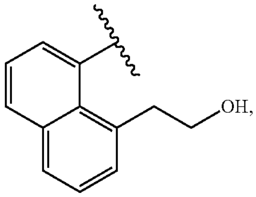
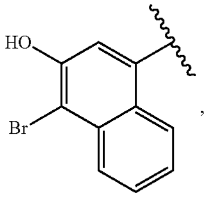
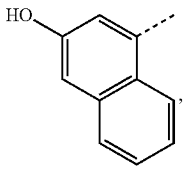
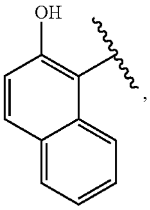
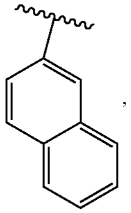
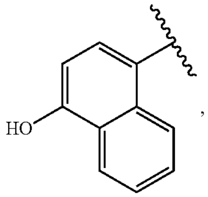
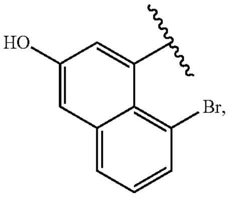
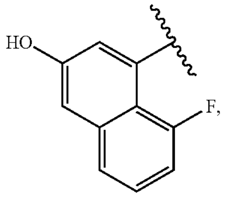
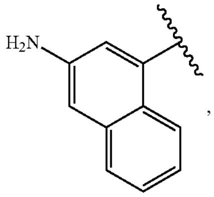
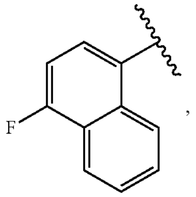
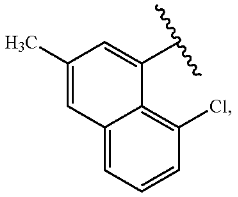
-continued
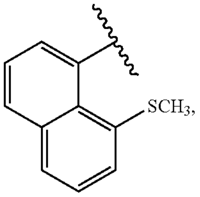
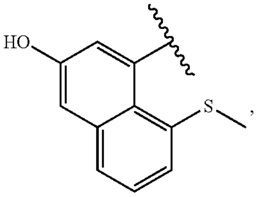
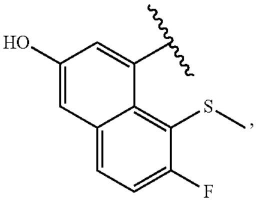
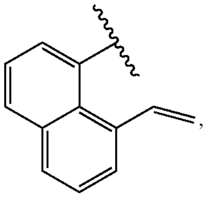
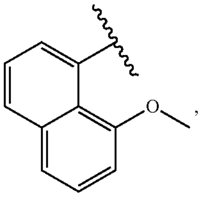
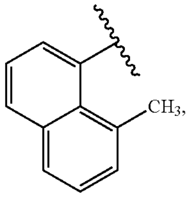
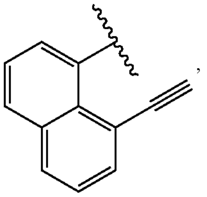
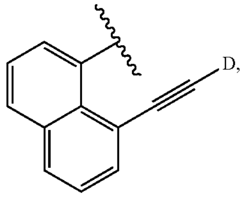
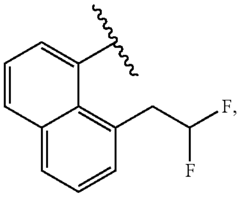
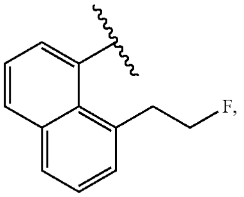
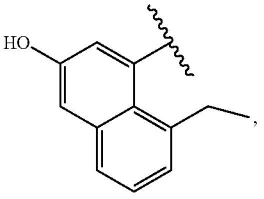
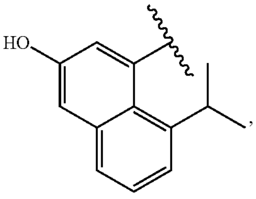
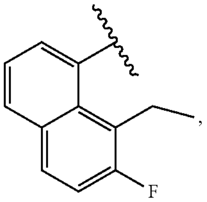
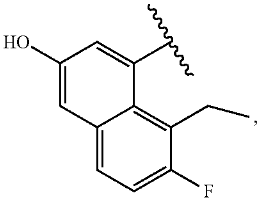
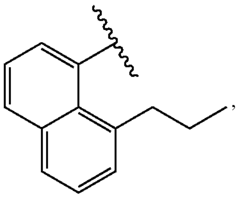
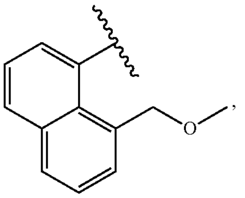

-continued
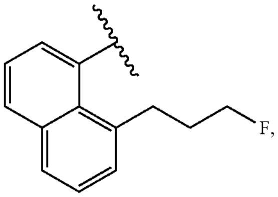
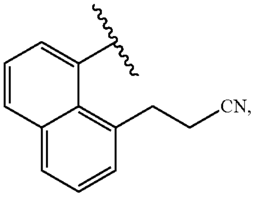
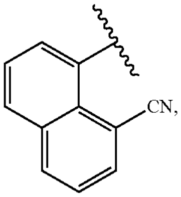
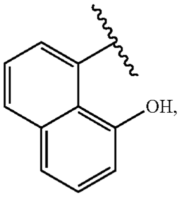
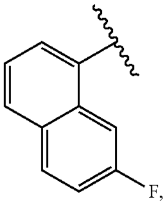
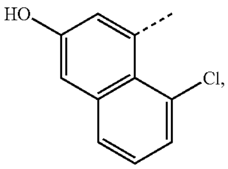
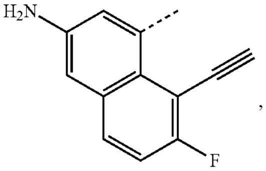
,
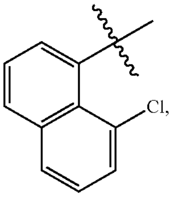
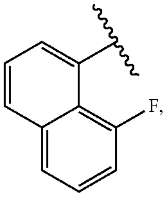
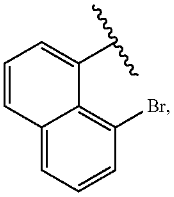
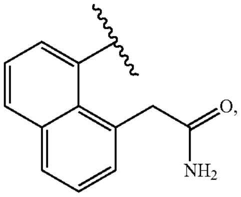
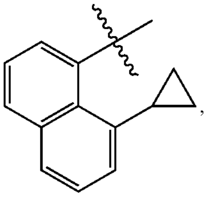
,
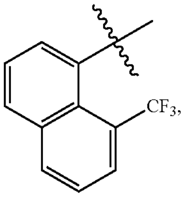
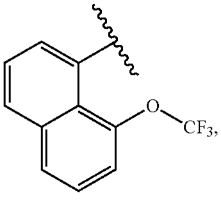
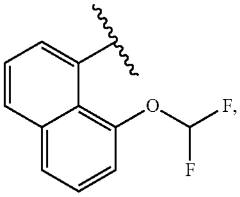
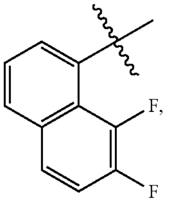
-continued
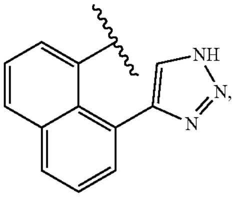
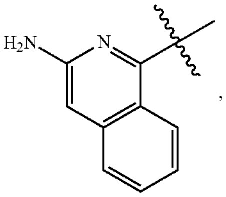
,
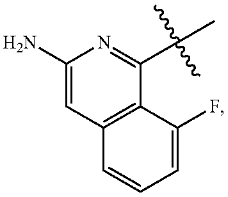
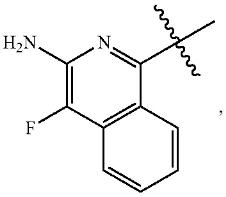
,
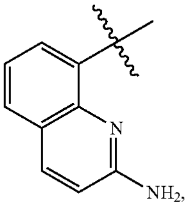
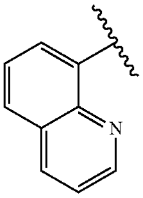
,
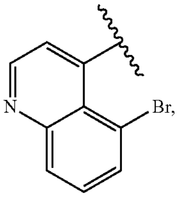
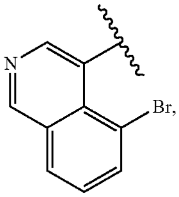
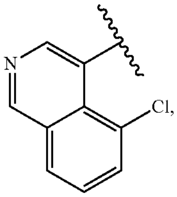
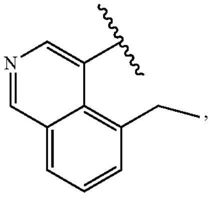
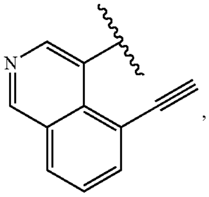
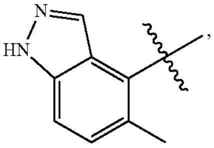
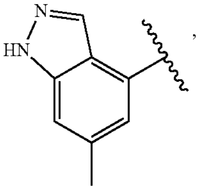
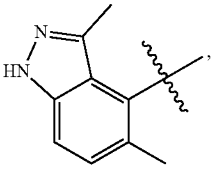
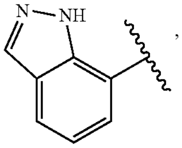
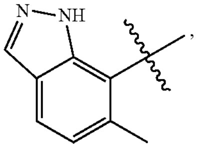
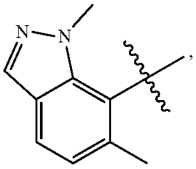
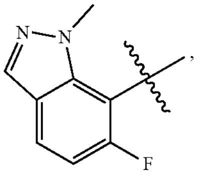
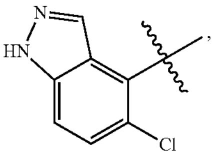

-continued
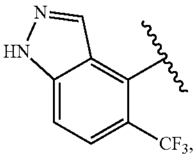,
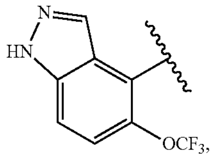,
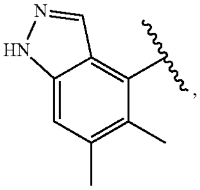,
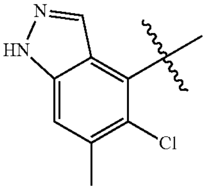,
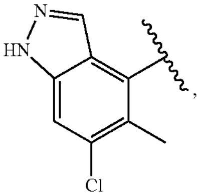,
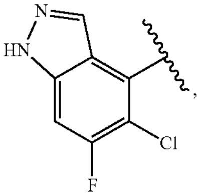,
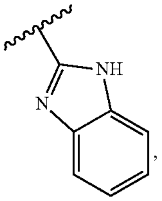,
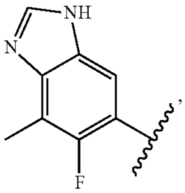,
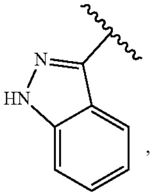,
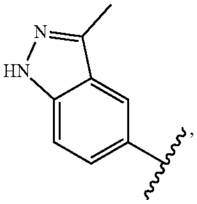,
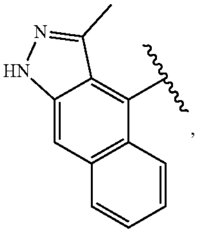,
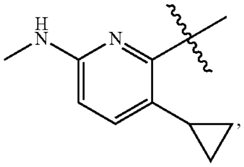,
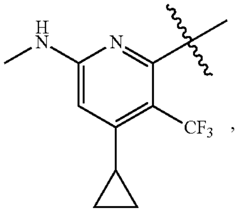,
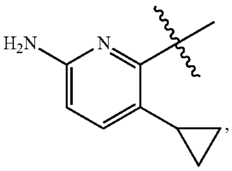,
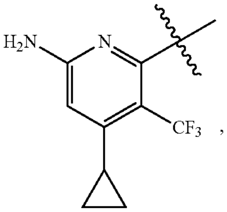,
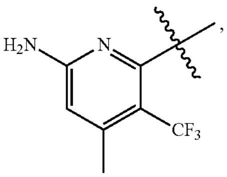,
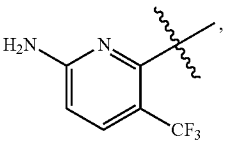,
-continued
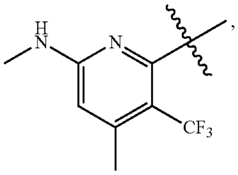,
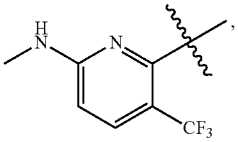,
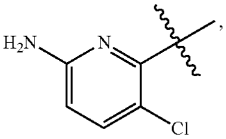,
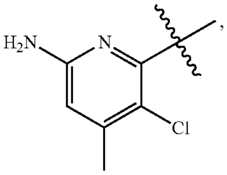,
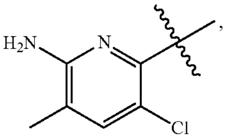,
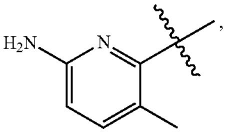,
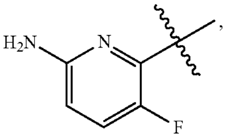,
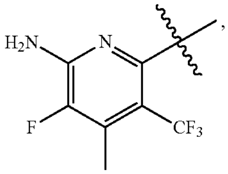,
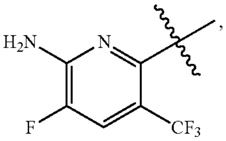,
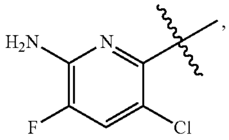,
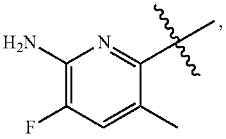,
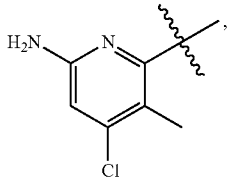,
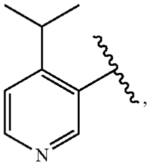,
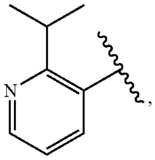,
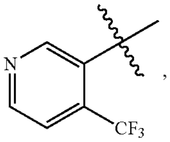,
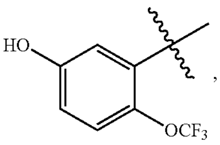,
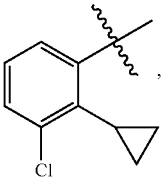,
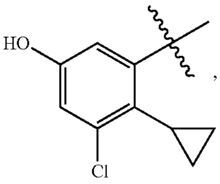,
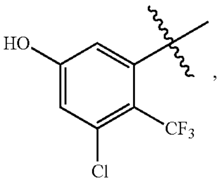, -continued
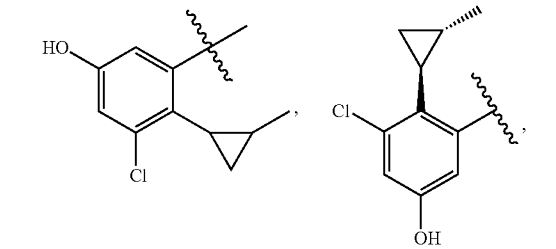
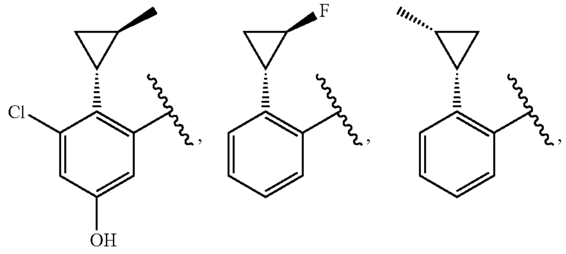
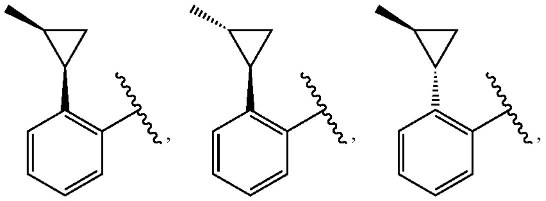
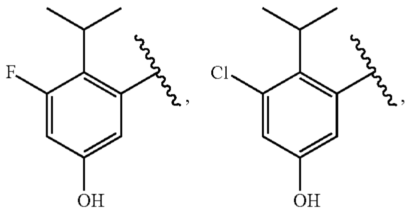
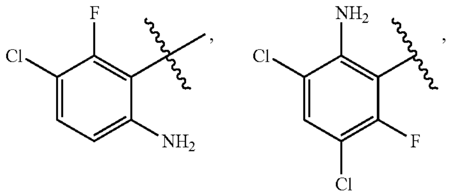
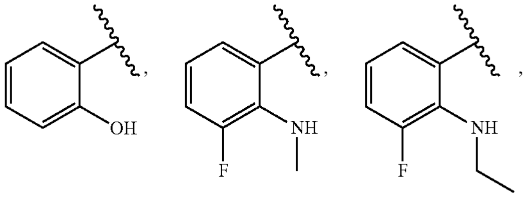
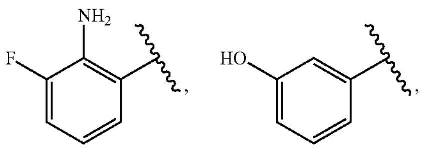
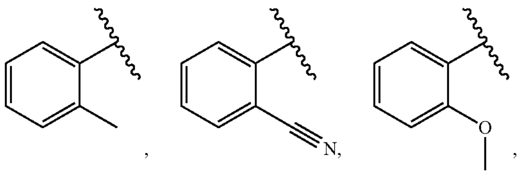
-continued
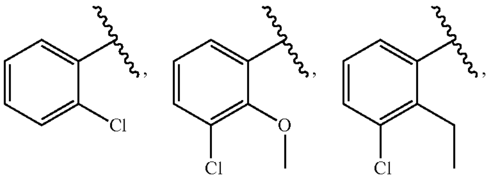
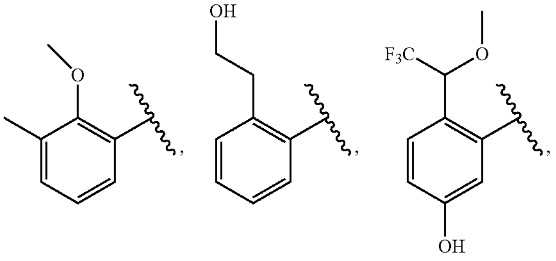
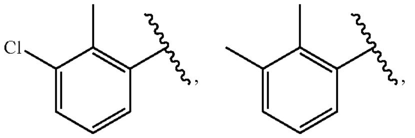
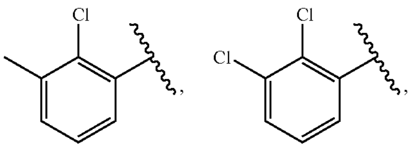
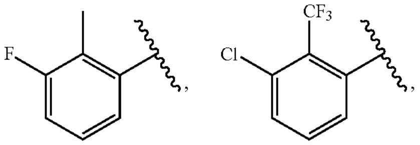
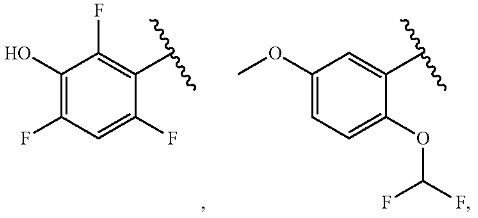
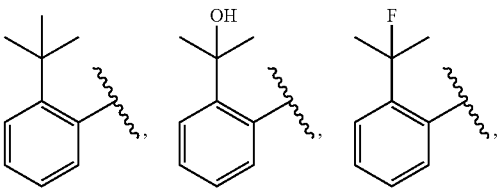
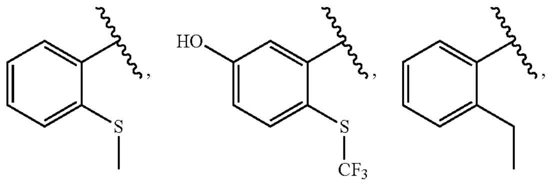
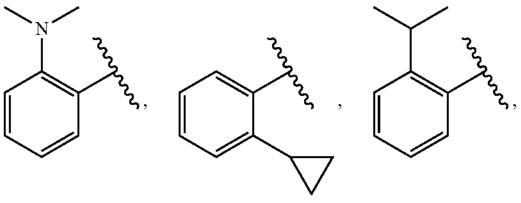

-continued
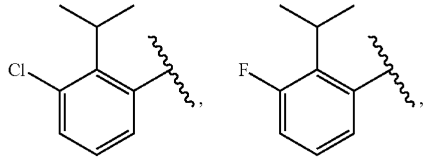
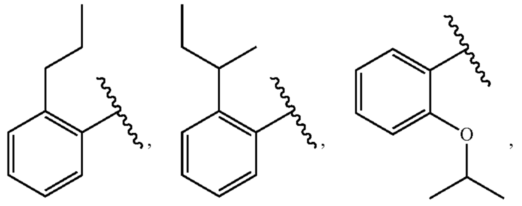
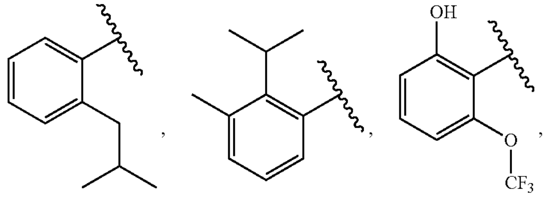
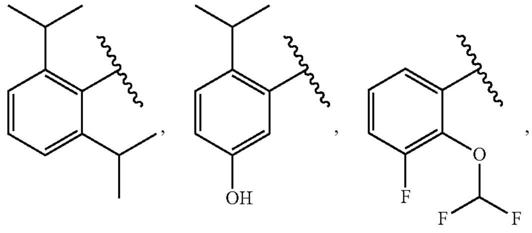
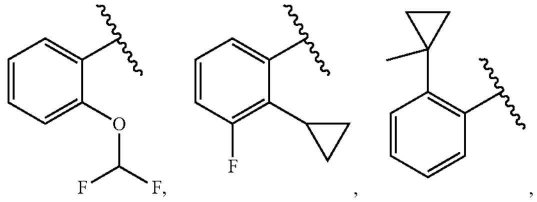
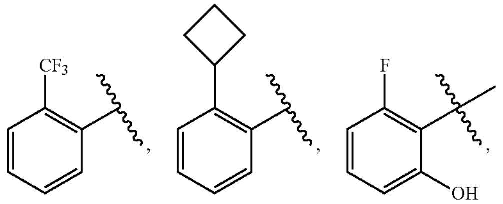
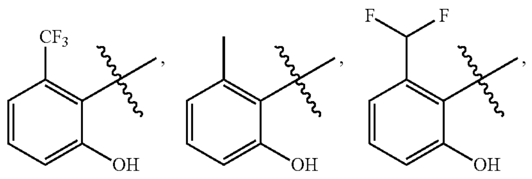
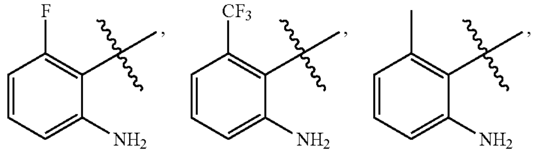
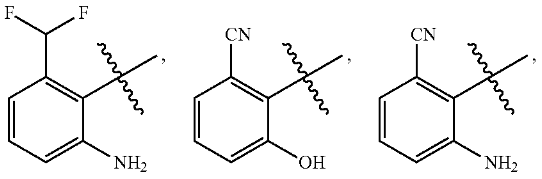
-continued
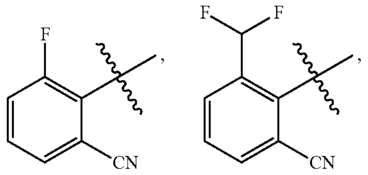
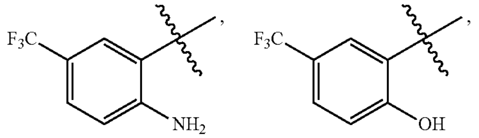
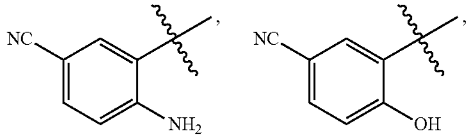
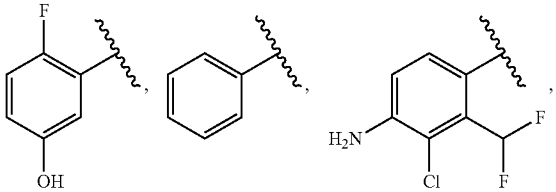
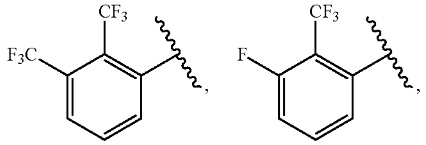
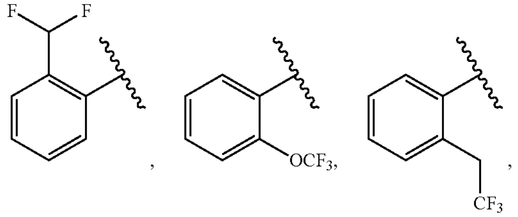
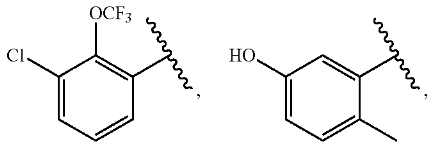
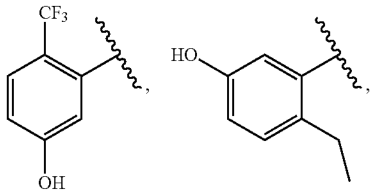
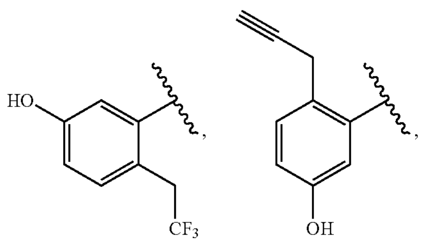

-continued
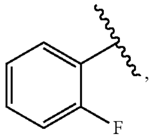, 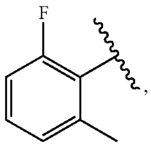, 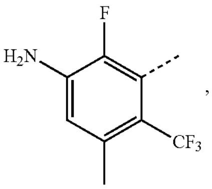,
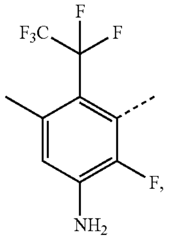 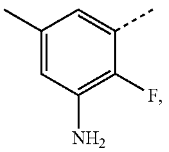 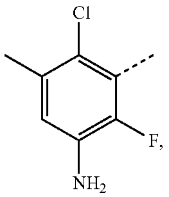
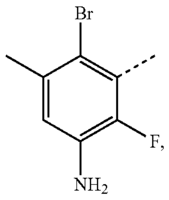 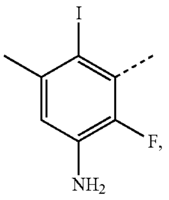 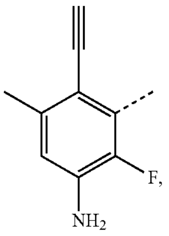
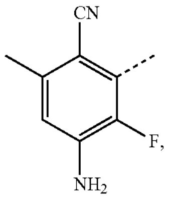 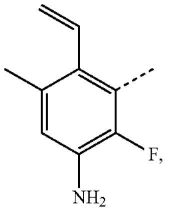 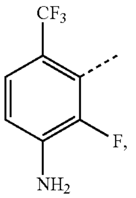
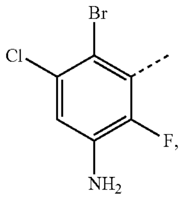 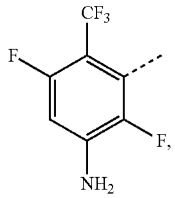
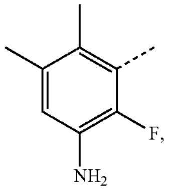 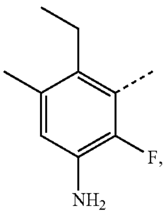
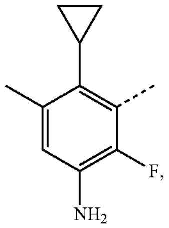 and 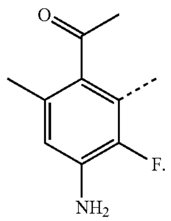
In some embodiments, for a compound of Formula I, IA, IB, II, IIA, or V, $R^{17}$ is
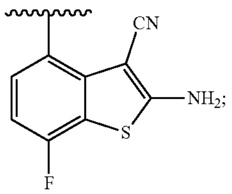 [SMILES: *c1ccc(F)c2sc(N)c(C#N)c12]
In some embodiments, $R^{17}$ is selected from
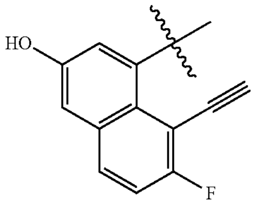, 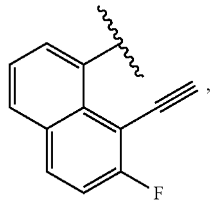,
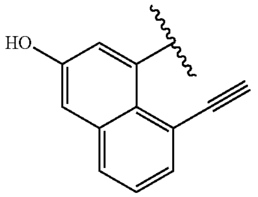, 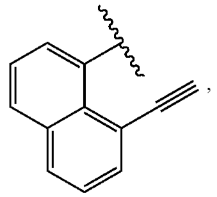,
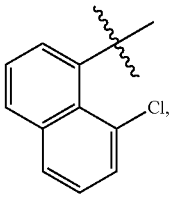 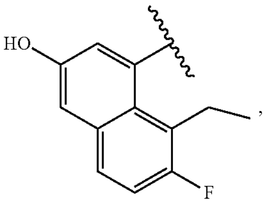,
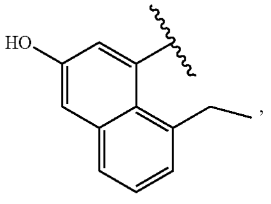, 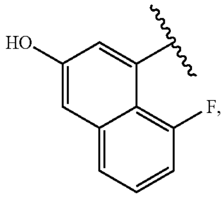
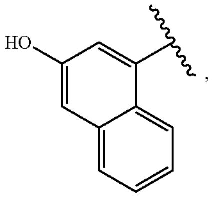, 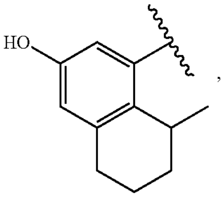,
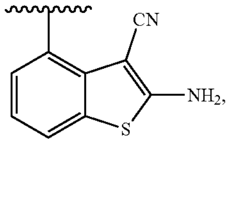 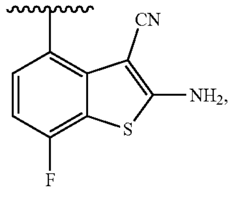
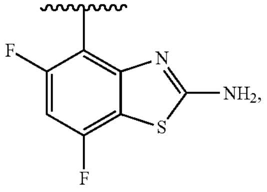 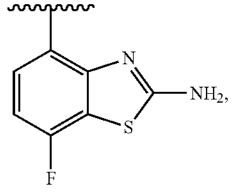

-continued
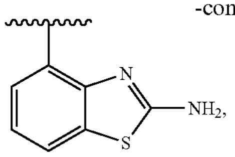
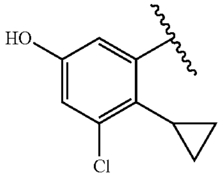
,
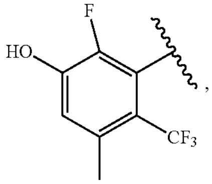
, and
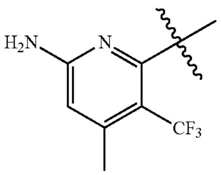
.
In some embodiments, $R^{17}$ is selected from
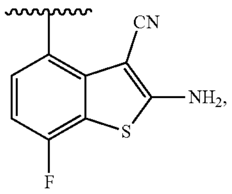
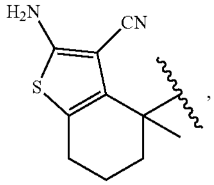
,
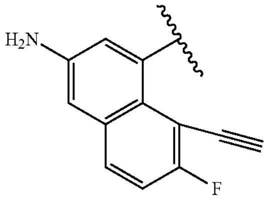
,
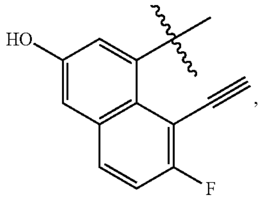
,
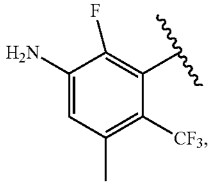
and
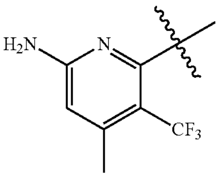
.
In some embodiments, $R^{17}$ is
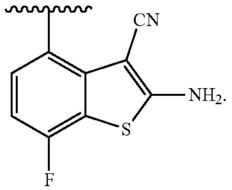
In some embodiments, $R^{17}$ is
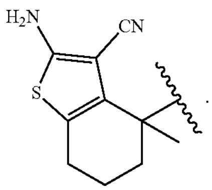
.
In some embodiments, $R^{17}$ is
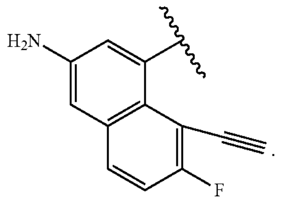 [SMILES: *c1cc(N)cc2ccc(F)c(C#C)c12]
In some embodiments, $R^{17}$ is
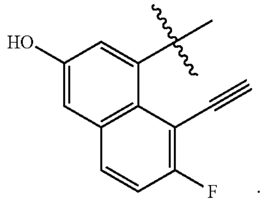
.
In some embodiments, $R^{17}$ is
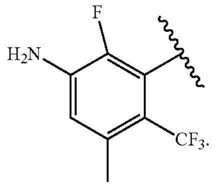 [SMILES: *c1c(F)c(N)cc(C)c1C(F)(F)F]
In some embodiments, $R^{17}$ is
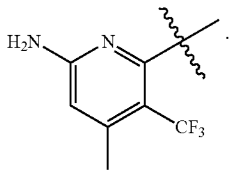 [SMILES: *c1nc(N)cc(C)c1C(F)(F)F]
In some embodiments, for a compound of Formula I, IA, IB, II, IIA, or V, $R^{17}$ is
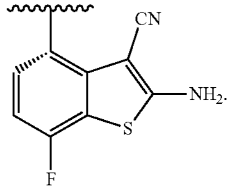

In some embodiments, $R^{17}$ is selected from
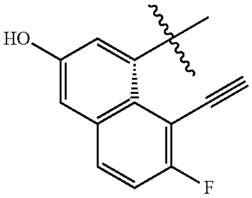,
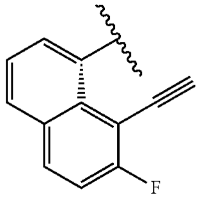,
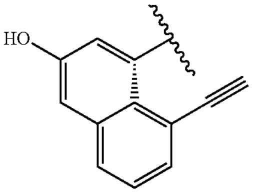,
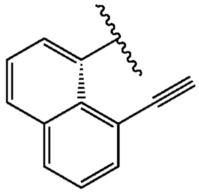,
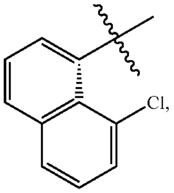
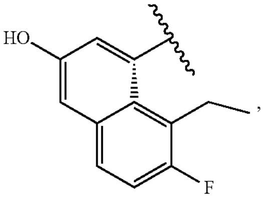
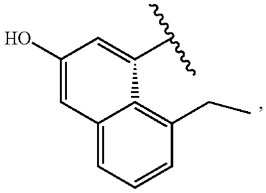
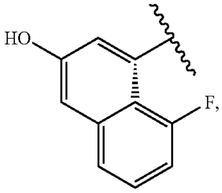
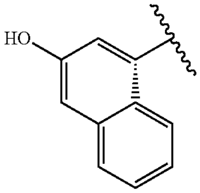,
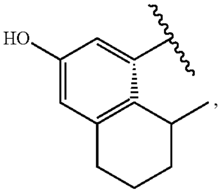
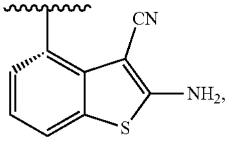
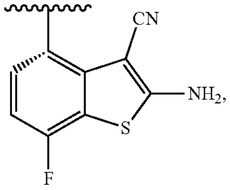
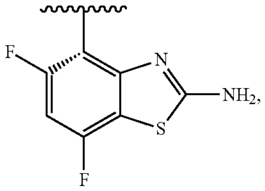
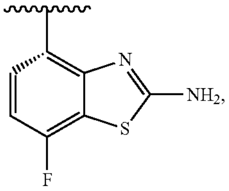
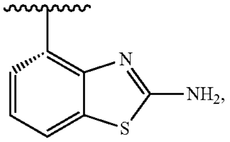
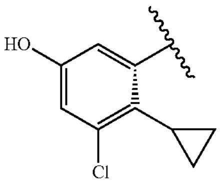,
-continued
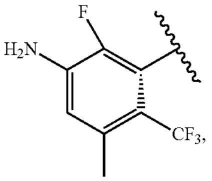 and 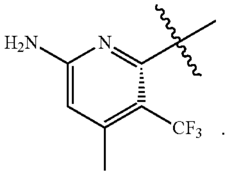.
In some embodiments, $R^{17}$ is selected from
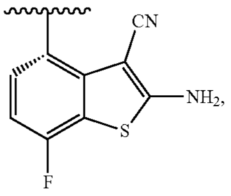
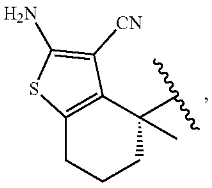,
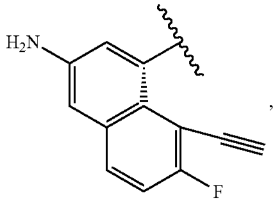,
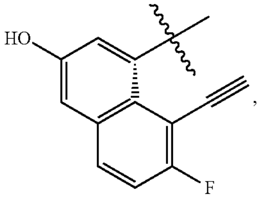
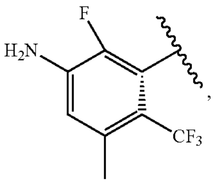 and 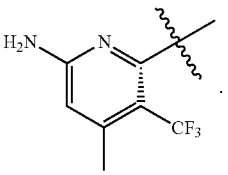.
In some embodiments, $R^{17}$ is
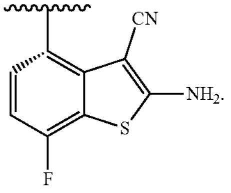
In some embodiments, $R^{17}$ is
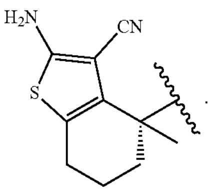 [SMILES: *[C@]1(C)CCCc2sc(N)c(C#N)c21].

In some embodiments, $R^{17}$ is
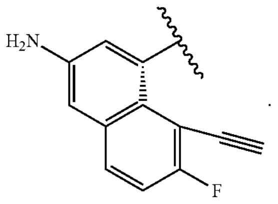
In some embodiments, $R^{17}$ is
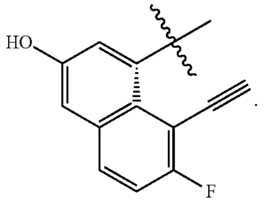
In some embodiments, $R^{17}$ is
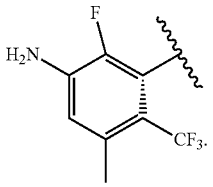
In some embodiments, $R^{17}$ is
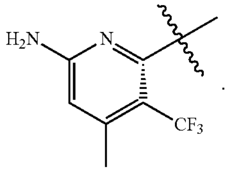
In some embodiments, $R^{17}$ is selected from
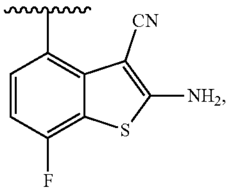
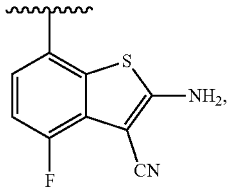
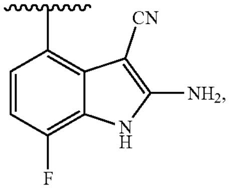
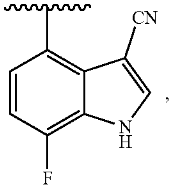
-continued
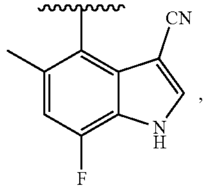
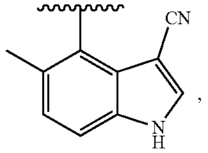
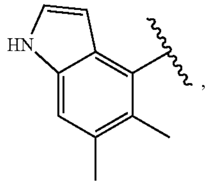
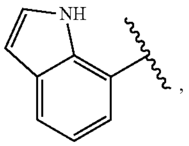
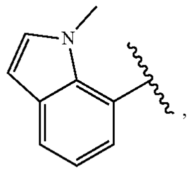
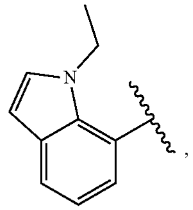
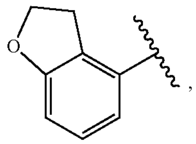
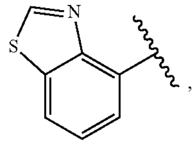
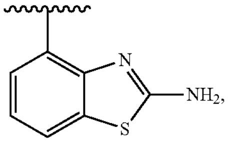
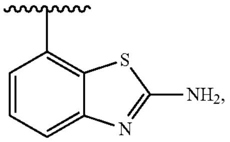
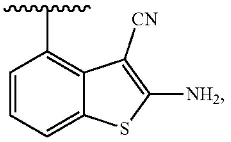
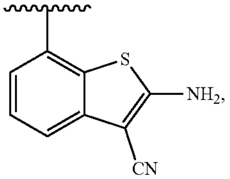
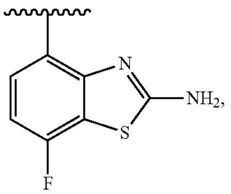
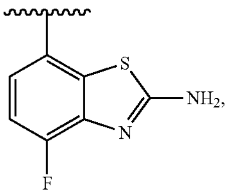
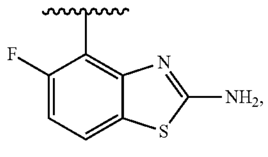
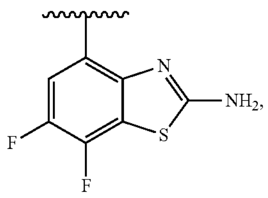

-continued
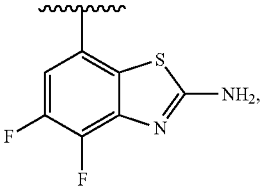
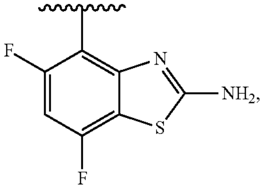
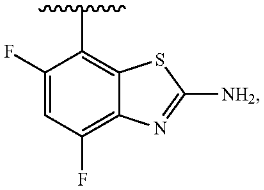
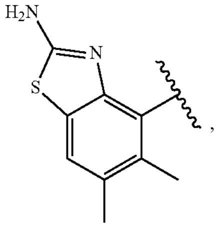
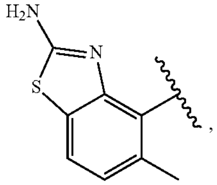
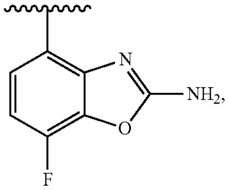
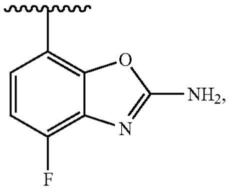
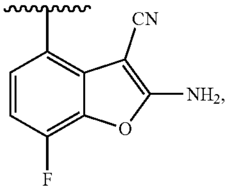
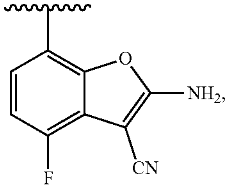
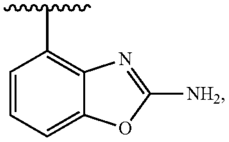
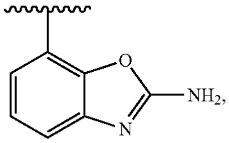
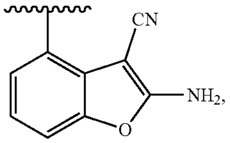
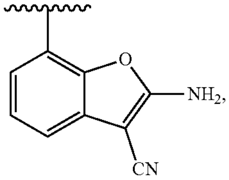
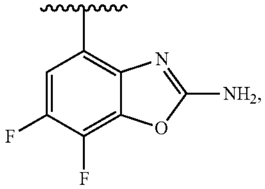
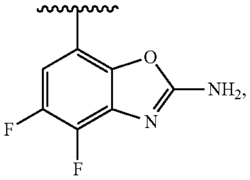
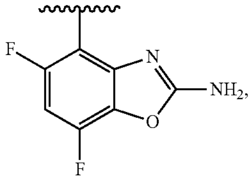
-continued
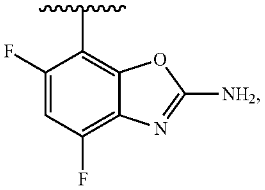
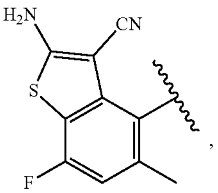
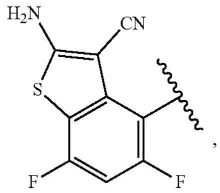
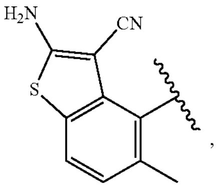
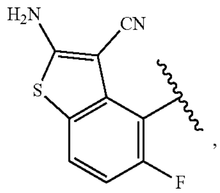
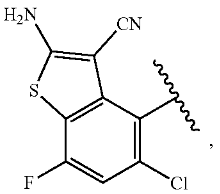
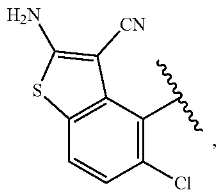
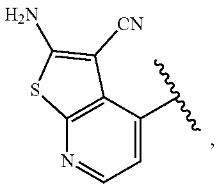
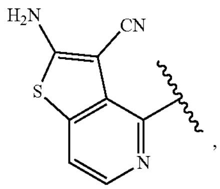
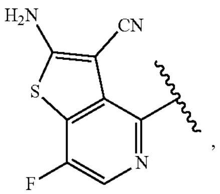
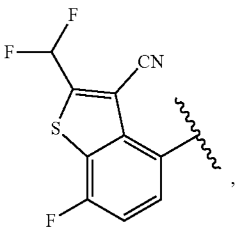
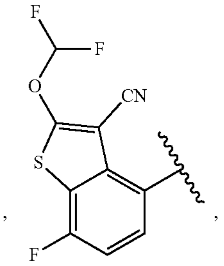
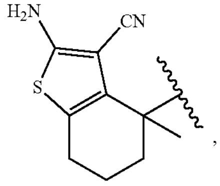
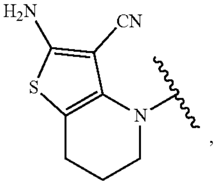
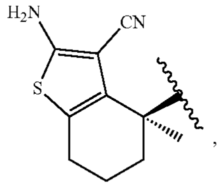
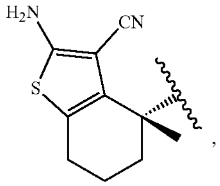

-continued
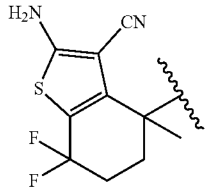,
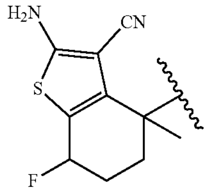,
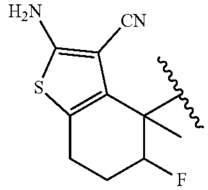,
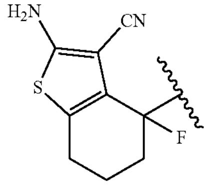,
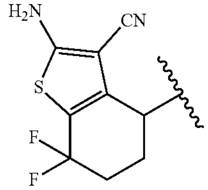,
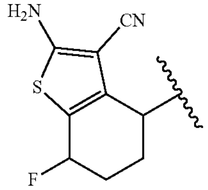,
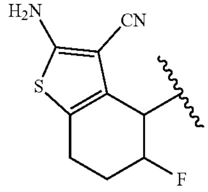,
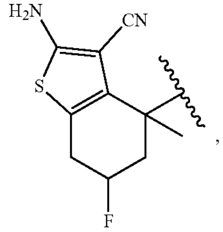,
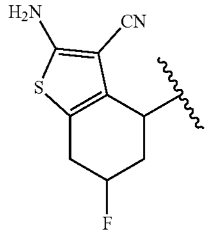,
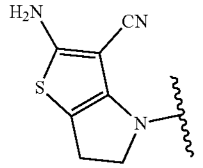,
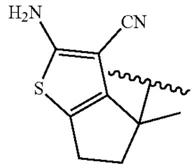,
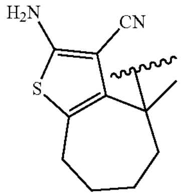,
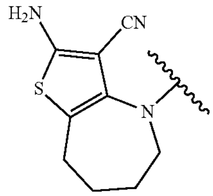,
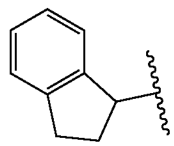,
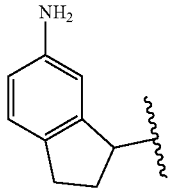,
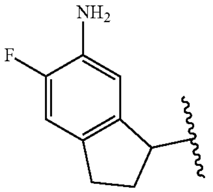,
-continued
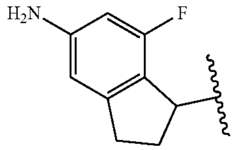,
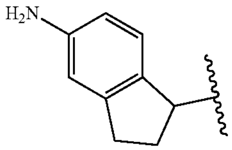,
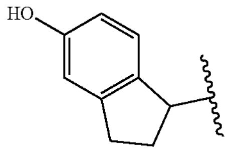,
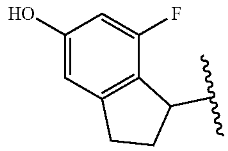,
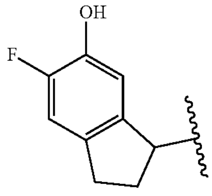,
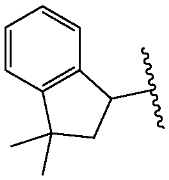,
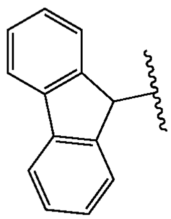,
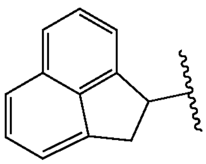,
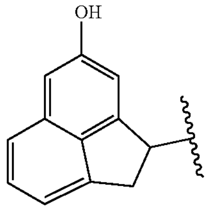,
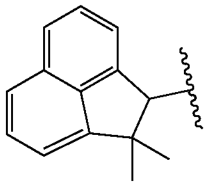,
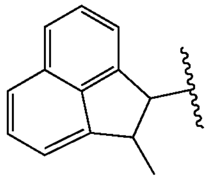,
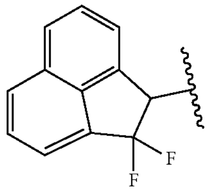,
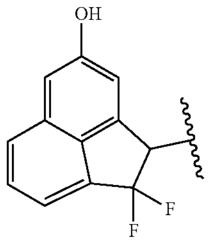,
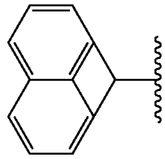,
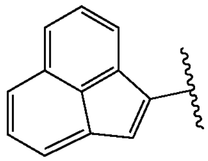,
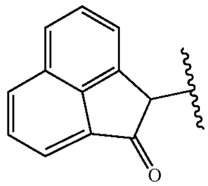, -continued
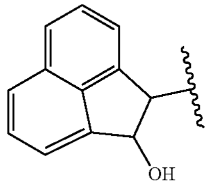,
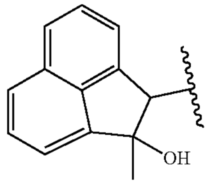,
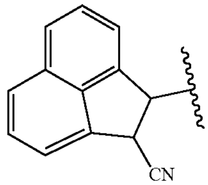,
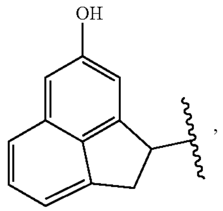,
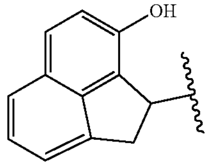,
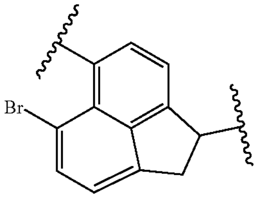,
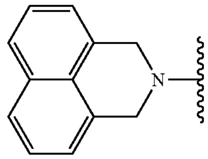,
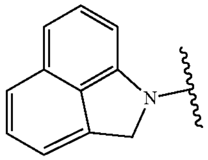,
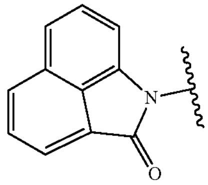,
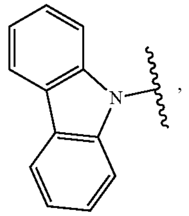,
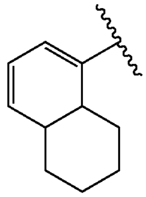,
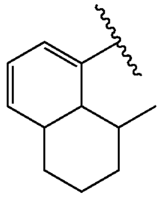,
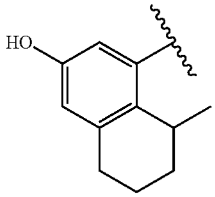,
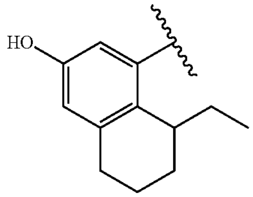,
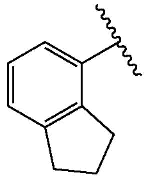,
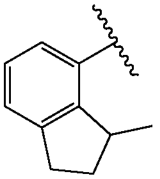,
-continued
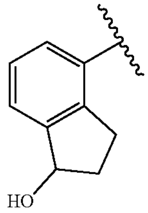,
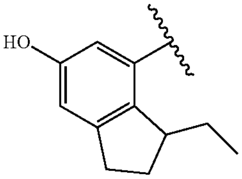,
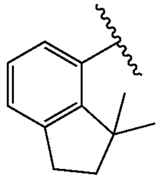,
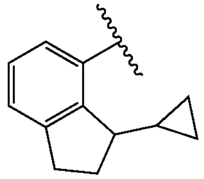,
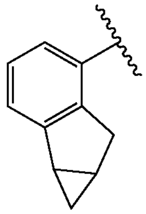,
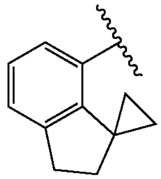,
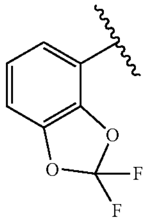,
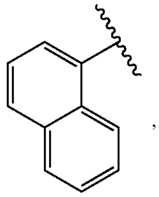,
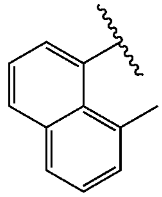,
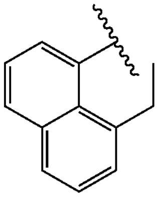,
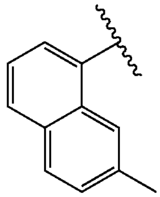,
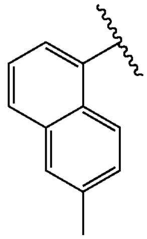,
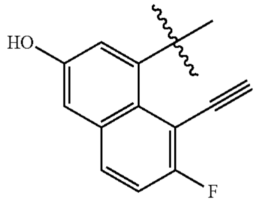,
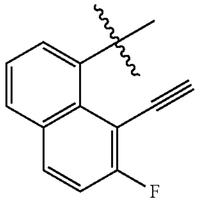,
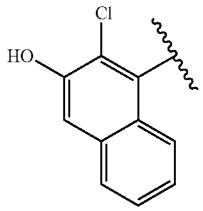,
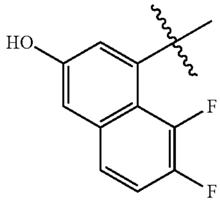,
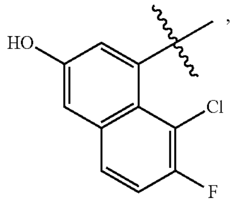,
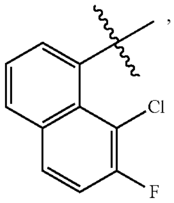, -continued
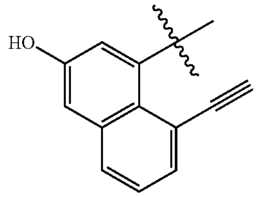
,
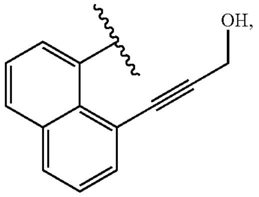
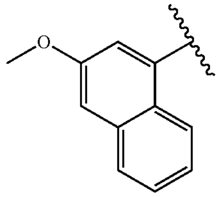
,
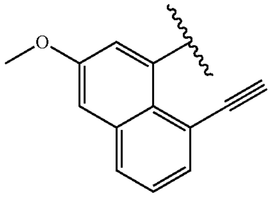
,
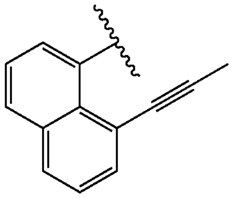
,
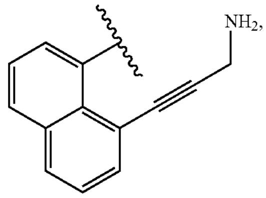
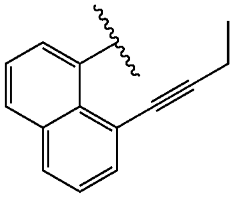
,
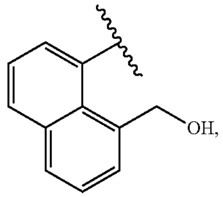
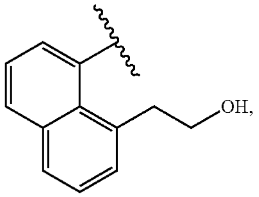
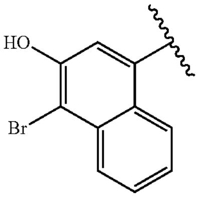
,
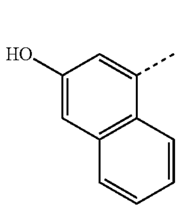
,
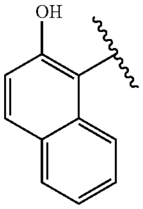
,
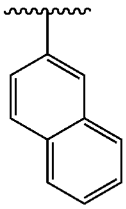
,
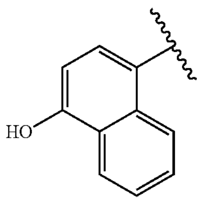
,
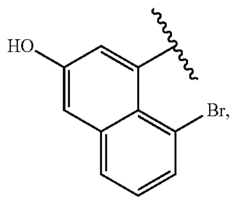
-continued
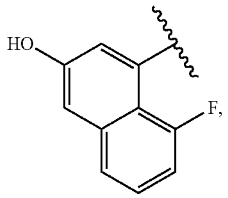
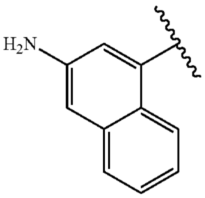
,
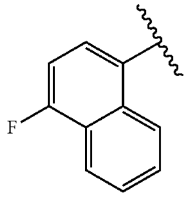
,
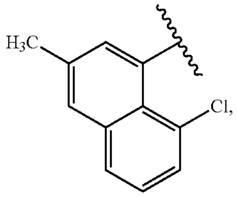
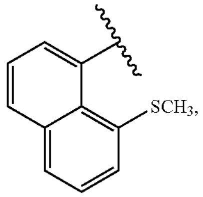
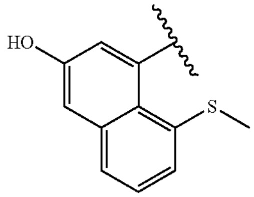
,
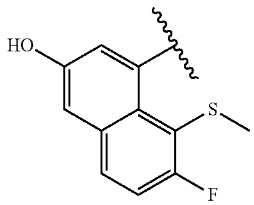
,
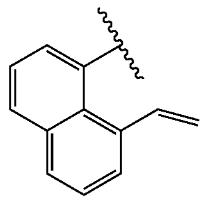
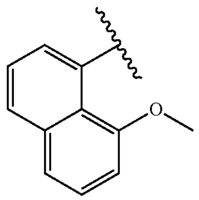
,
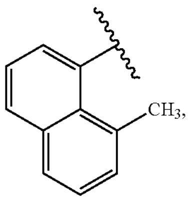
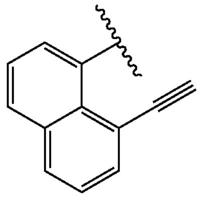
,
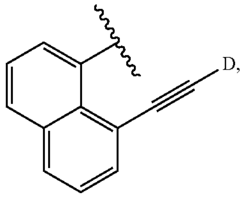
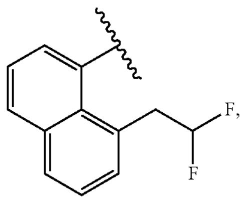
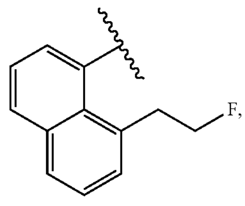
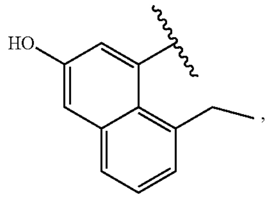
,
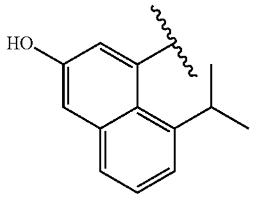
, -continued
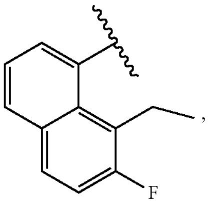 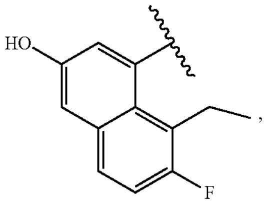
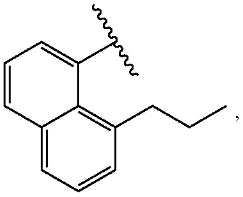 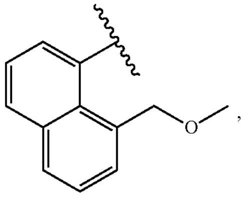
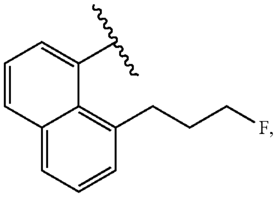
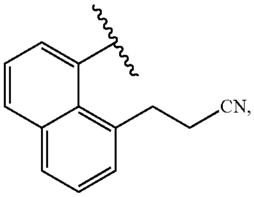 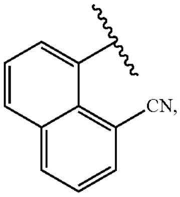
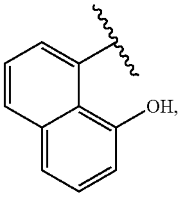 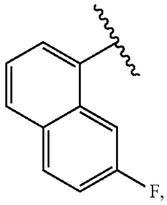
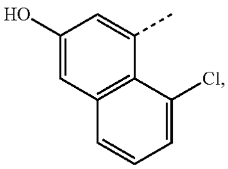 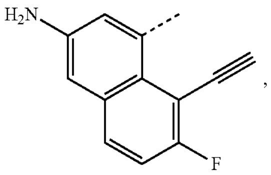
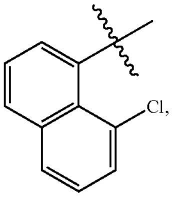 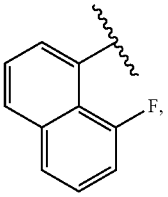
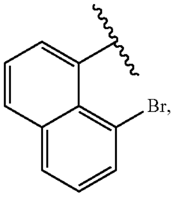 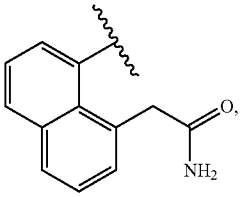
-continued
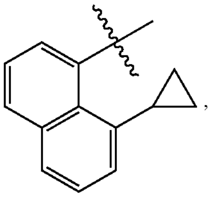 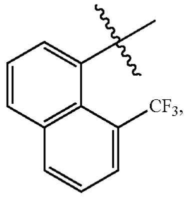
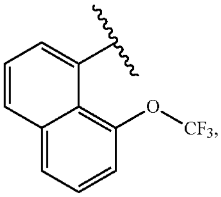 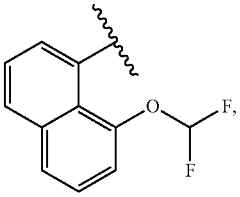
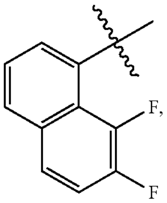 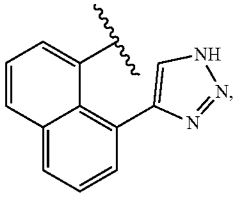
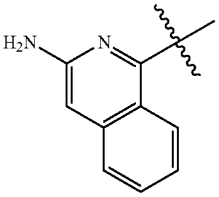 , 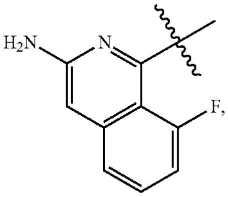
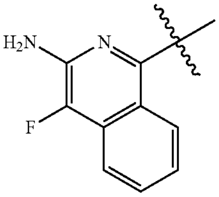 , 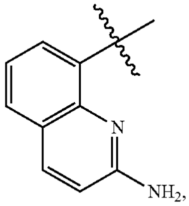
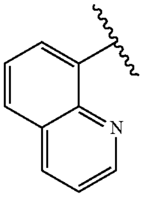 , 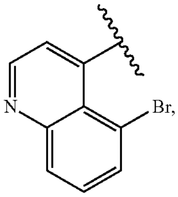
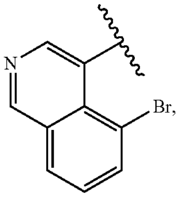 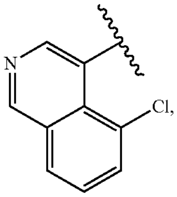
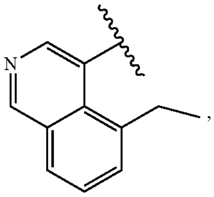 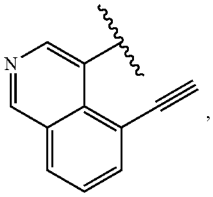

-continued
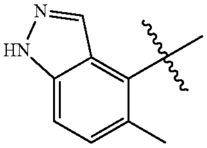,
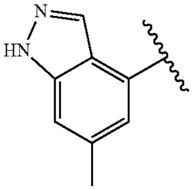,
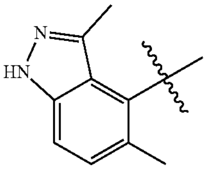,
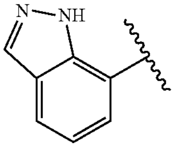,
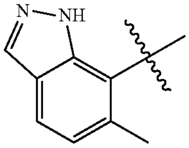,
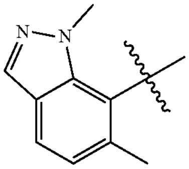,
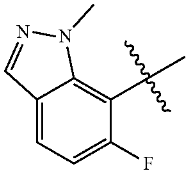,
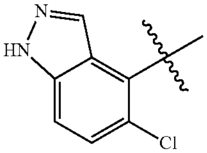,
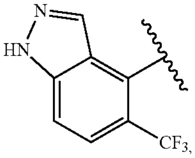
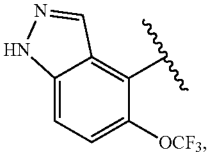
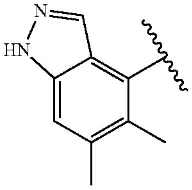,
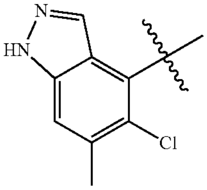,
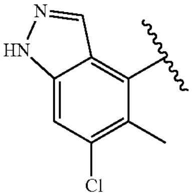,
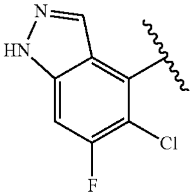,
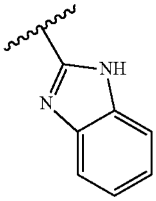,
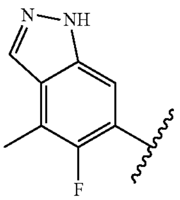,
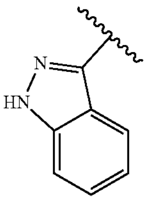,
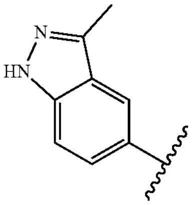,
-continued
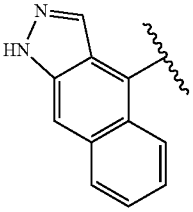,
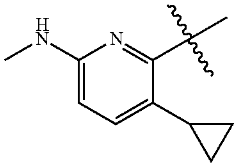,
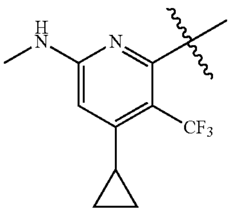,
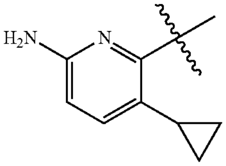,
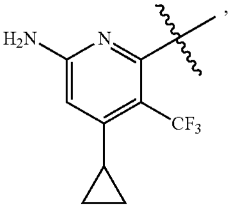,
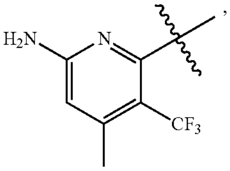,
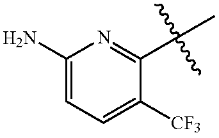,
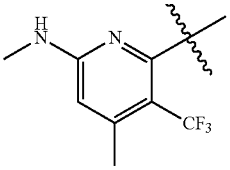,
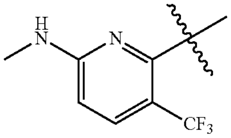,
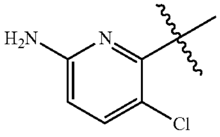,
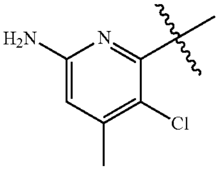,
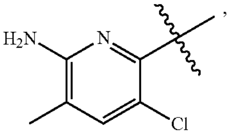,
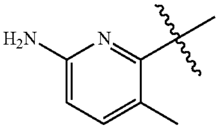,
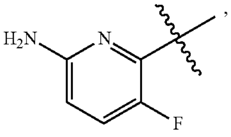,
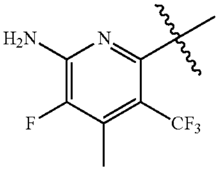,
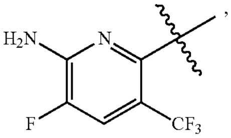,
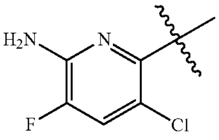,
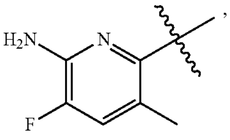, -continued
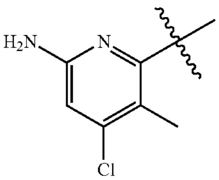,
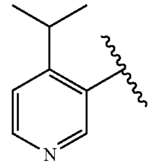,
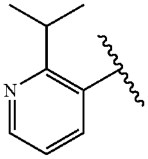,
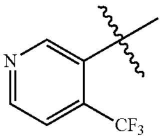,
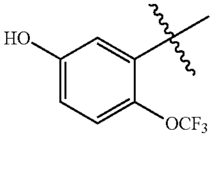,
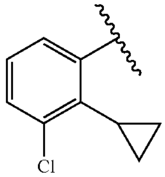,
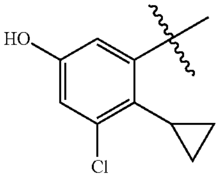,
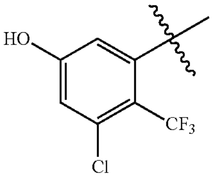,
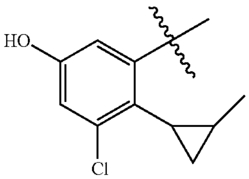,
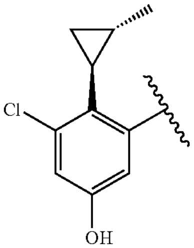,
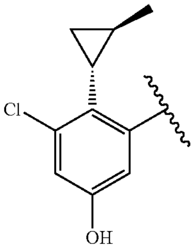,
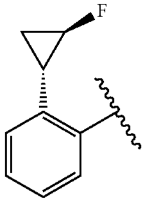,
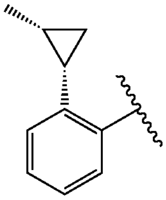,
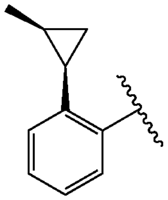,
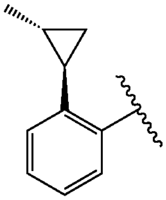,
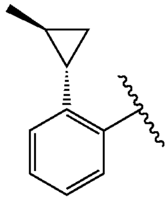,
-continued
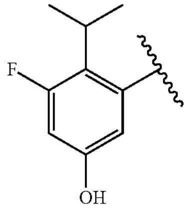,
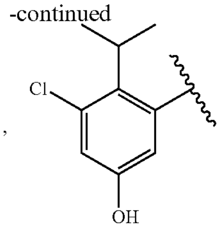,
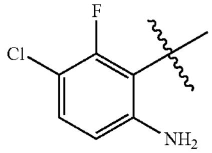,
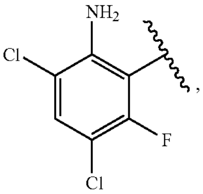,
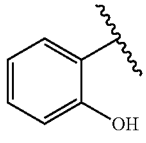,
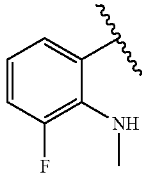,
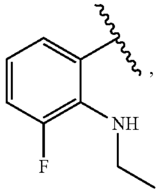,
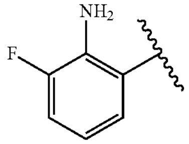,
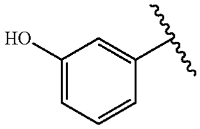,
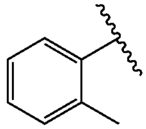,
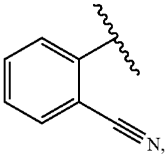,
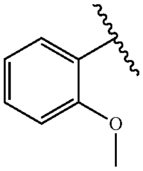,
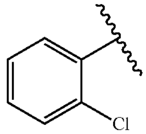,
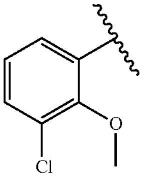,
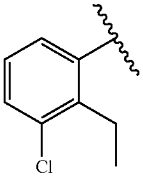,
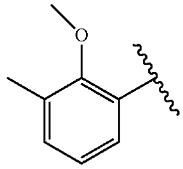,
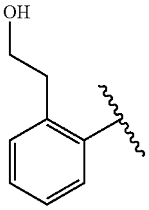,
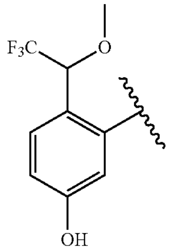,
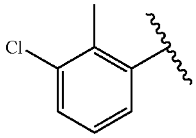,
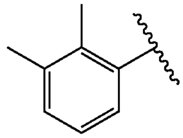,
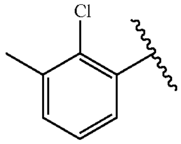, -continued
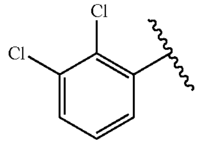,
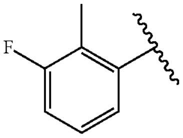,
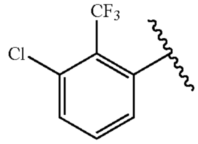,
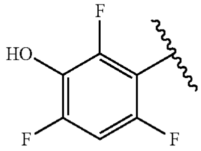,
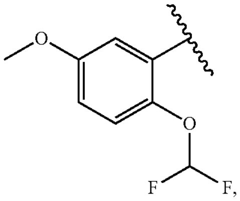,
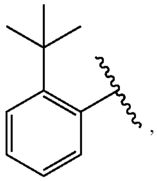,
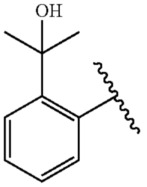,
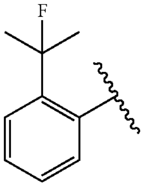,
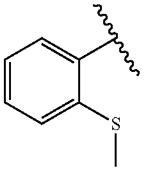,
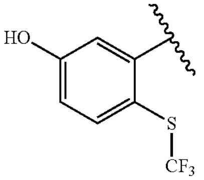,
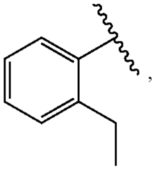,
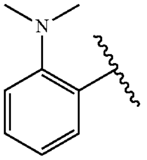,
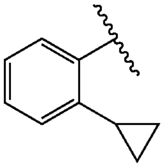,
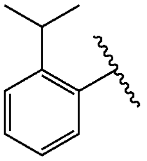,
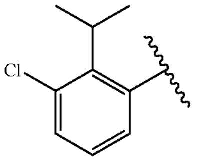,
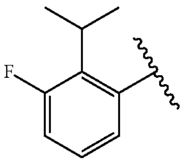,
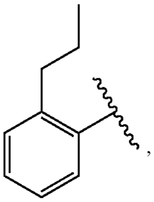,
-continued
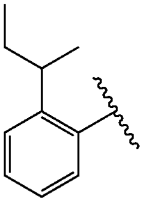,
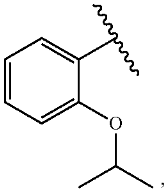,
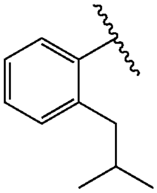,
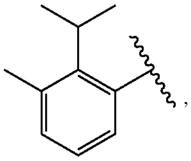,
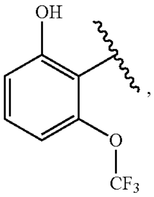,
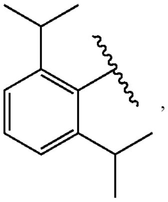,
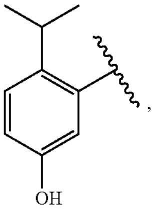,
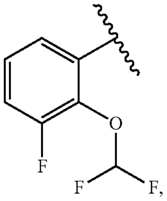,
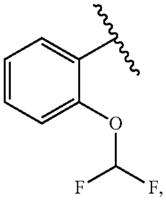,
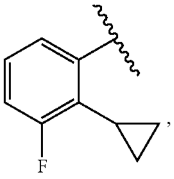,
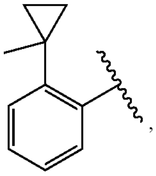,
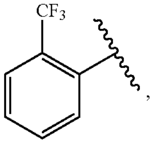,
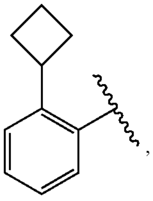,
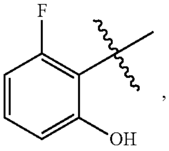,
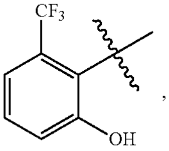,
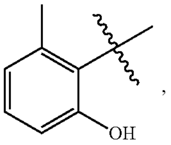,
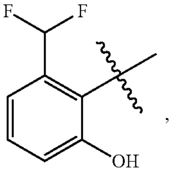,
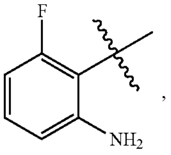,
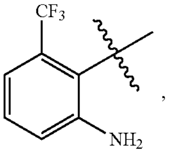, -continued
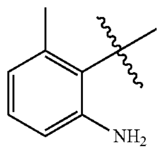, 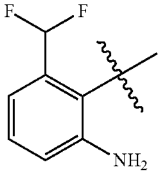,
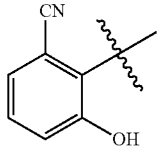, 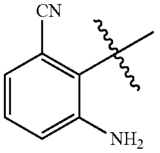,
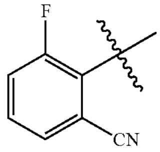, 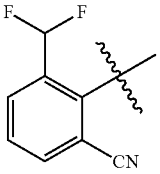,
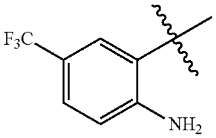, 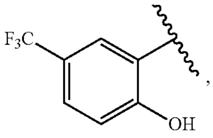
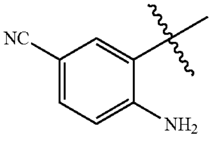, 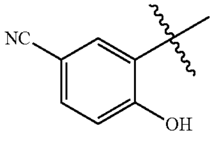,
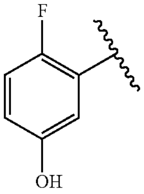, 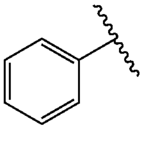
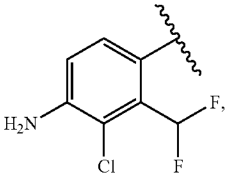 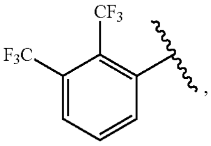
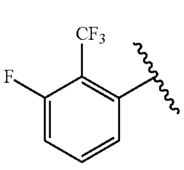, 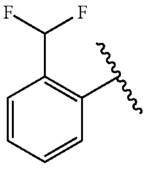
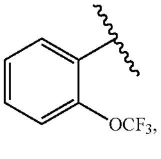 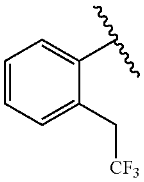,
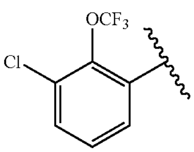, 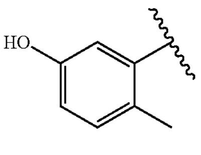
-continued
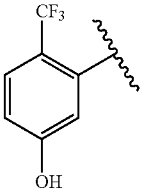, 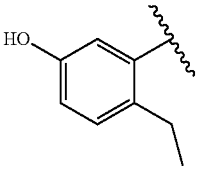,
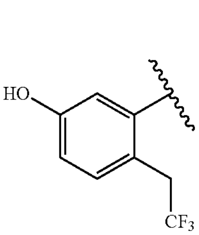, 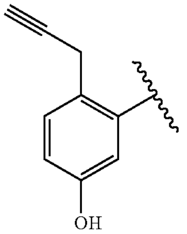,
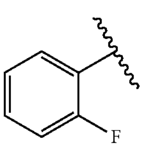, 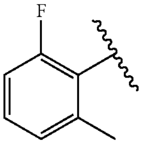,
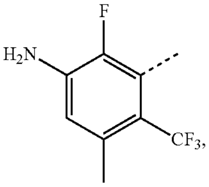 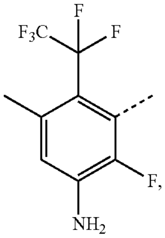
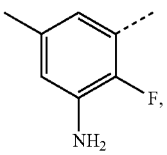 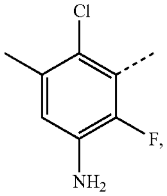 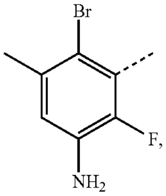
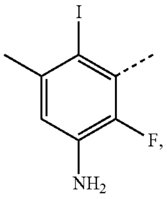 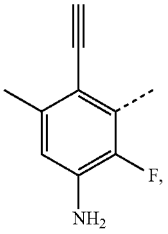 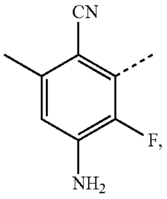
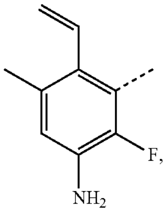 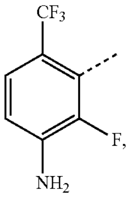
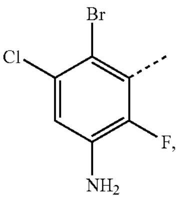 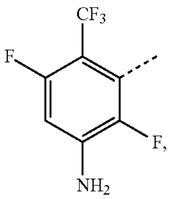

-continued
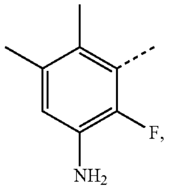
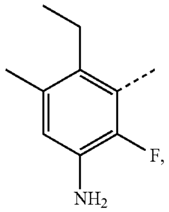
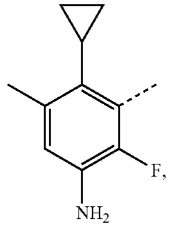
and
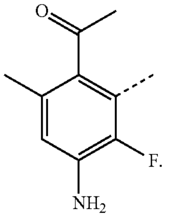
In some embodiments, $R^{17}$ is selected from
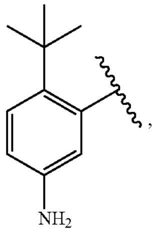
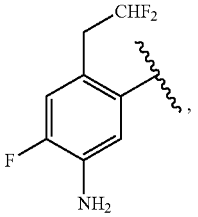
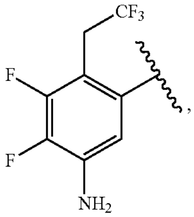
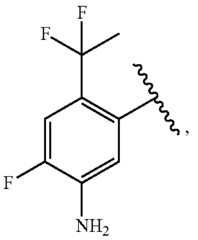
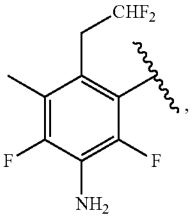
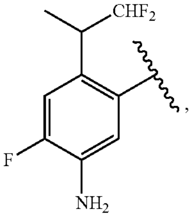
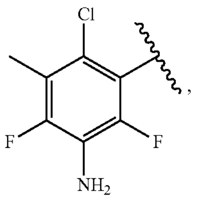
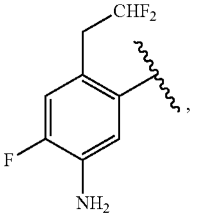
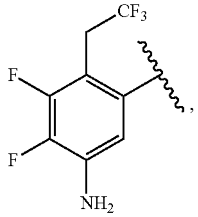
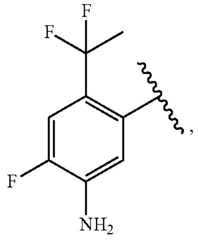
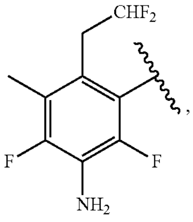
-continued
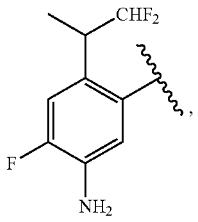
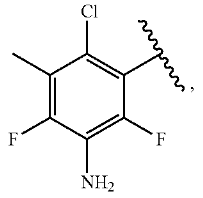
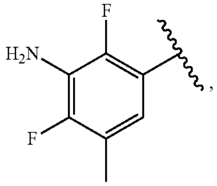
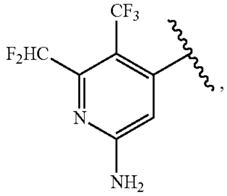
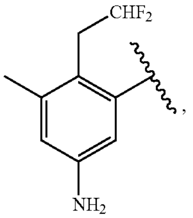
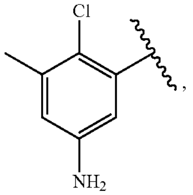
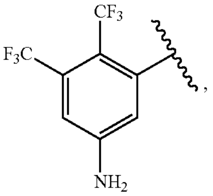
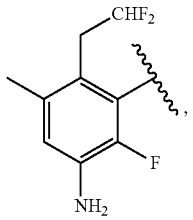
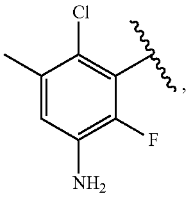
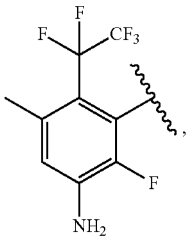
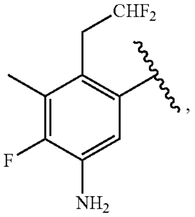
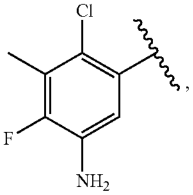
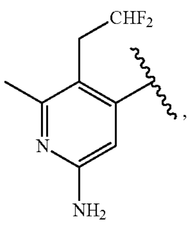
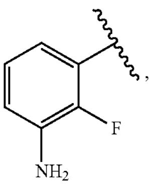
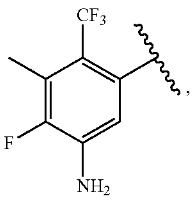

-continued
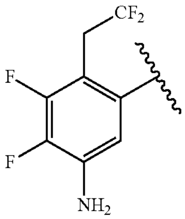,
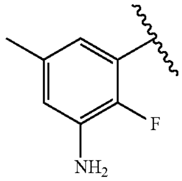,
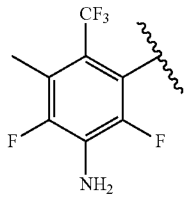,
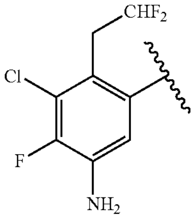,
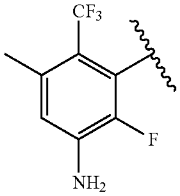,
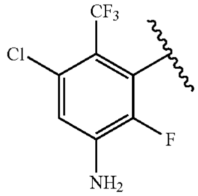,
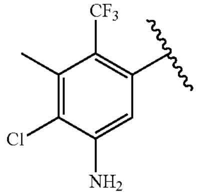,
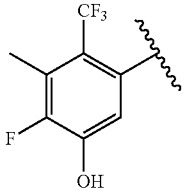,
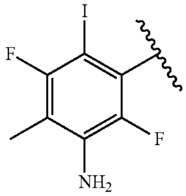,
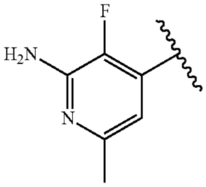,
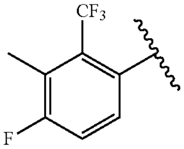,
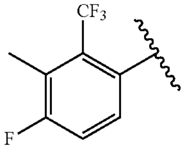,
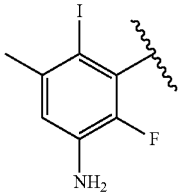,
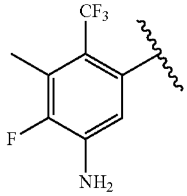,
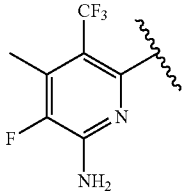,
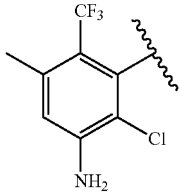,
-continued
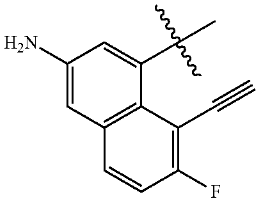,
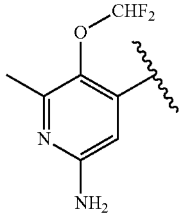,
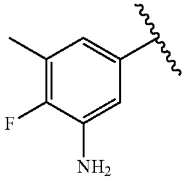,
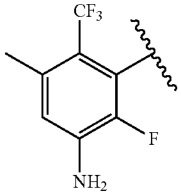,
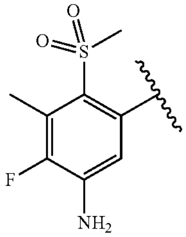,
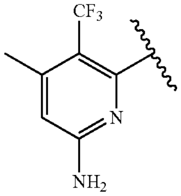,
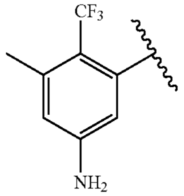,
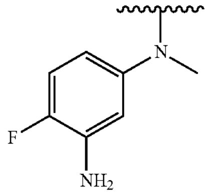,
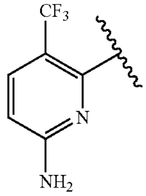,
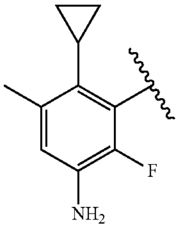,
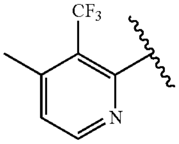,
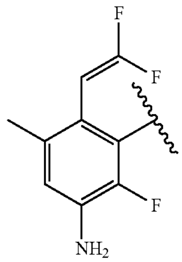,
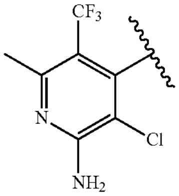,
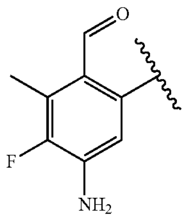,
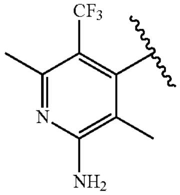, -continued
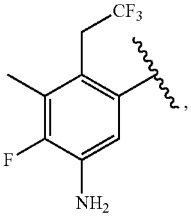, 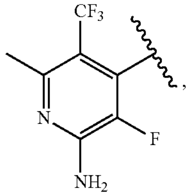, 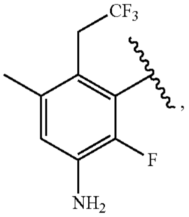, 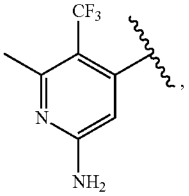, 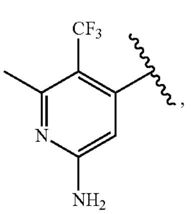, 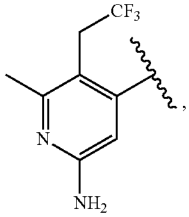, 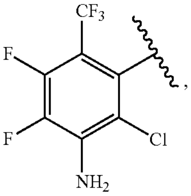, 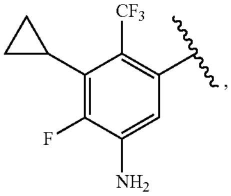, 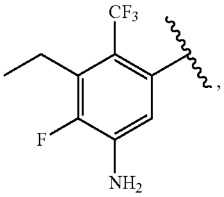, 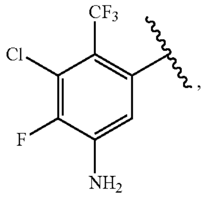, 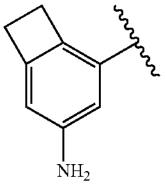, 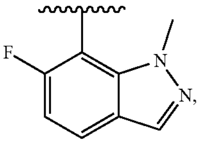 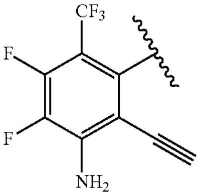 , 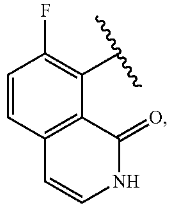 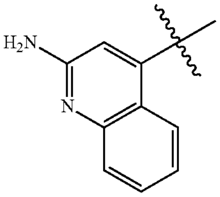 , 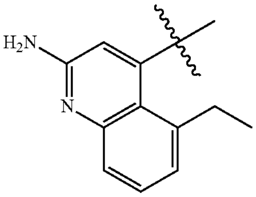 ,
-continued
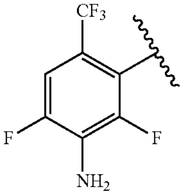, 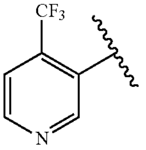, 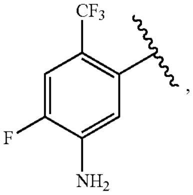, 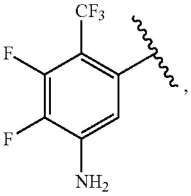, 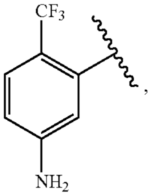, 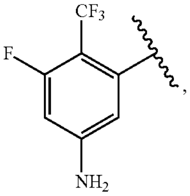, 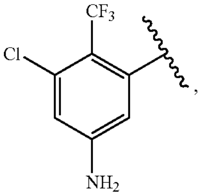, 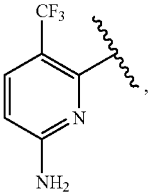, 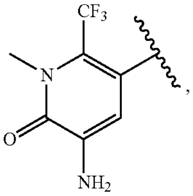, 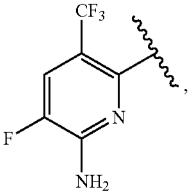, 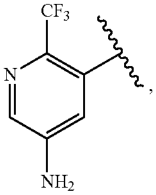, 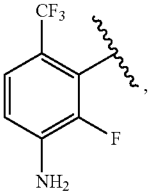, 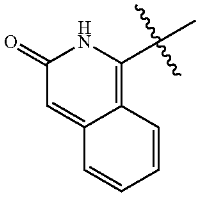 , 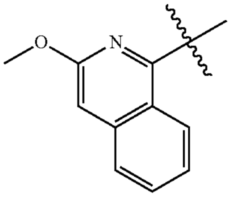 , and
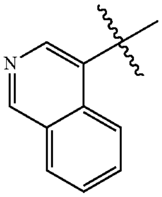 .
In some embodiments, $R^{17}$ is selected from
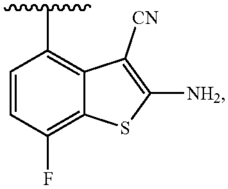 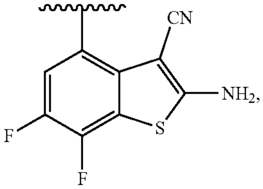 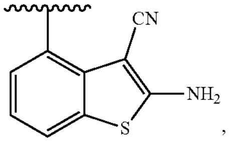 , 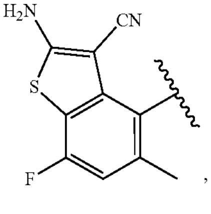 , -continued
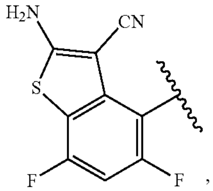
,
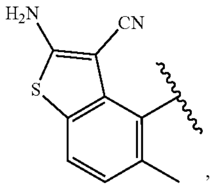
,
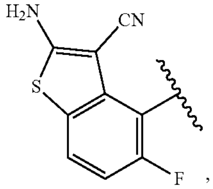
,
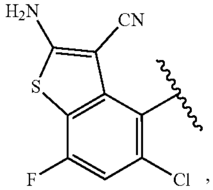
,
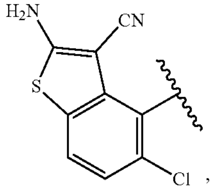
,
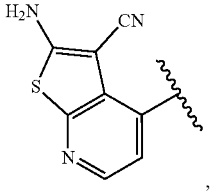
,
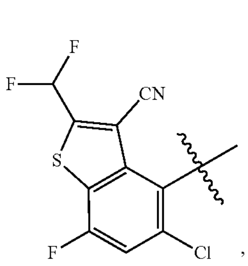
,
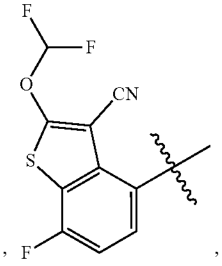
,
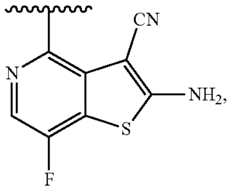
,
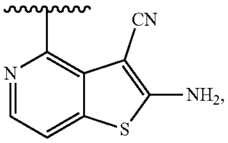
,
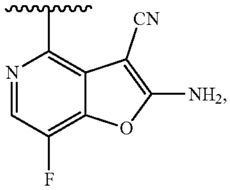
,
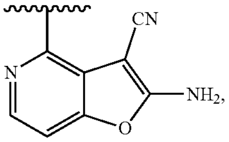
, and
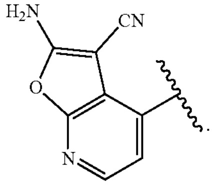 [SMILES: *c1ccnc2oc(N)c(C#N)c12]
.
In some embodiments, $R^{17}$ is
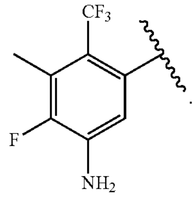
.
In some embodiments, $R^{17}$ is
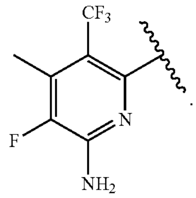
.
In some embodiments, $R^{17}$ is selected from
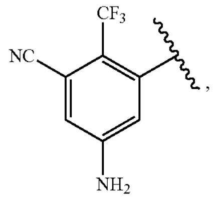
,
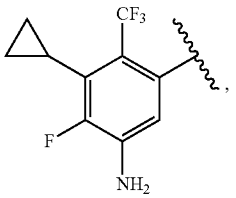
,
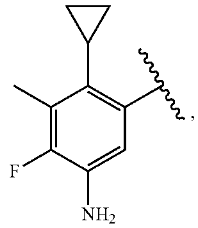
,
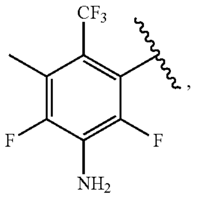
,
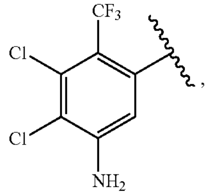
,
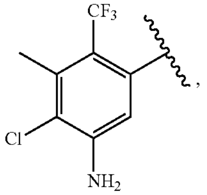
,
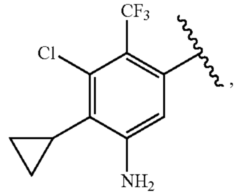
,
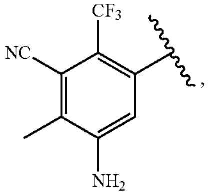
,
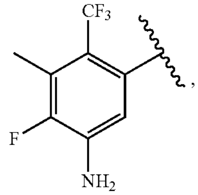
,
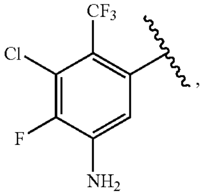
, -continued

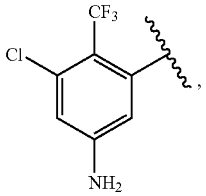

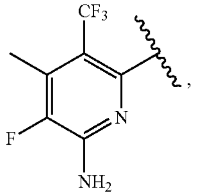

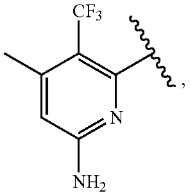

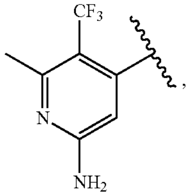

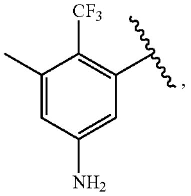

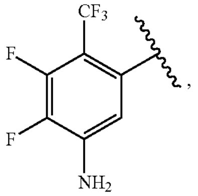

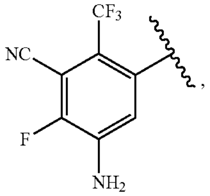

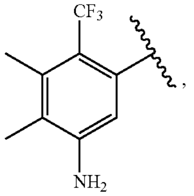

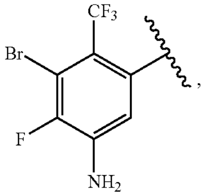

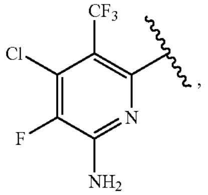

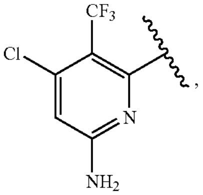

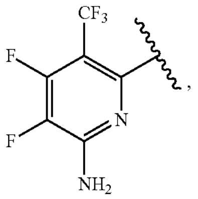

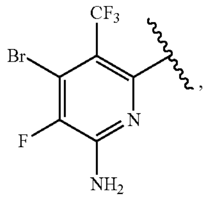

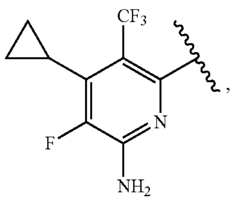

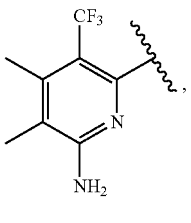

-continued

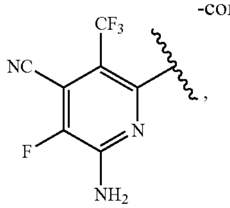

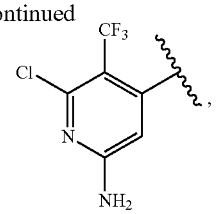

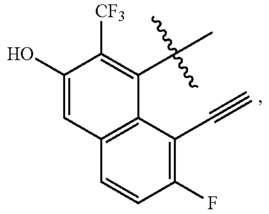

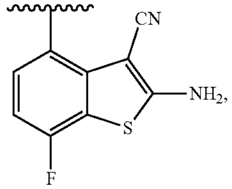

and

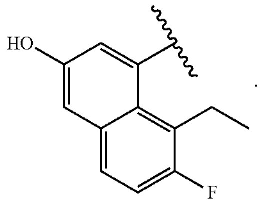

In some embodiments, for a compound of Formula I, IA, IB, II, IIA, or V, $R^{17}$ is substituted with one, two, three, or four substituents independently selected from halogen, —CN, $C_{1-6}$ alkyl, $C_{2-6}$ alkenyl, $C_{2-6}$ alkynyl, $C_{3-6}$ cycloalkyl, —$OR^{22}$, —$SR^{22}$, and —$N(R^{22})(R^{23})$, wherein $C_{1-6}$ alkyl, $C_{2-6}$ alkenyl, $C_{2-6}$ alkynyl, and $C_{3-6}$ cycloalkyl are optionally substituted with one, two, or three substituents independently selected from halogen, $C_{1-6}$ alkyl, $C_{1-6}$ haloalkyl, and —$OR^{22}$. In some embodiments, $R^{17}$ is substituted with one, two, three, or four substituents independently selected from halogen, —CN, $C_{1-3}$ alkyl, $C_{2-3}$ alkenyl, $C_{2-3}$ alkynyl, —$OR^{22}$, and —$N(R^{22})(R^{23})$. In some embodiments, $R^{17}$ is substituted with one, two, three, or four substituents independently selected from halogen, —CN, —$CH_3$, —C≡CH, —OH, and —$NH_2$. In some embodiments, $R^{17}$ is substituted with —F, —CN, and —$NH_2$. In some embodiments, $R^{17}$ is substituted with —F, —C≡CH, and —OH. In some embodiments, $R^{17}$ is substituted with —$CF_3$, —$CH_3$, and —$NH_2$. In some embodiments, $R^{17}$ is substituted with —$CF_3$ and —$NH_2$. In some embodiments, $R^{17}$ is substituted with —$CF_3$, —$CH_3$, —F, and —$NH_2$. In some embodiments, $R^{17}$ is substituted with —$CF_3$, —F, and —$NH_2$. In some embodiments, $R^{17}$ is substituted with one, two, three, or four substituents independently selected from halogen, —CN, —$CH_3$, —$CH_2CH_3$, —CH═$CH_2$, —$CF_3$, —C≡CH, —OH, —$NH_2$, and -cyclopropyl.

In embodiments of a compound of Formula I, IA, IB, II, IIA, or V, $L^{7a}$ is a bond. In embodiments of a compound of Formula I, IA, IB, II, IIA, or V, $L^{7b}$ is a bond.

In embodiments of a compound of Formula I, IA, IB, II, IIA, or V, $X^8$ is $C(R^8)$. In embodiments of a compound of Formula I, IA, IB, II, IIA, or V, $X^8$ is $C(R^8)_2$. In embodiments of a compound of Formula I, IA, IB, II, IIA, or V, $X^8$ is $C(H)_2$. In embodiments of a compound of Formula I, IA, IB, II, IIA, or V, $R^8$ is halogen. In embodiments of a compound of Formula I, IA, IB, II, IIA, or V, $R^8$ is —F. In embodiments of a compound of Formula I, IA, IB, II, IIA, or V, $R^6$ is —Cl and $R^8$ is —F. In embodiments of a compound of Formula I, IA, IB, II, IIA, or V, $R^6$ is —$CF_3$ and $R^8$ is —F. In embodiments of a compound of Formula I, IA, IB, II, IIA, or V, $R^6$ is hydrogen and $R^8$ is —F.

In embodiments of a compound of formula IA, IB, or IIA, $X^9$ is $N(R^9)$. In embodiments of a compound of Formula I, IA, IB, II, IIA, or V, $R^9$ is —$R^{19}$-$L^{19a}$-$R^{19a}$.

In embodiments of a compound of Formula I, IA, IB, II, IIA, or V, $X^1$ is N; $X^2$ is $C(R^2)$; $X^3$ is N; $X^4$ is C; $X^5$ is C; $X^6$ is $C(R^6)$; $X^7$ is $C(R^7)$; $X^8$ is $C(R^8)$, $X^{13}$ is C; and $X^{14}$ is C. In embodiments of a compound of Formula I, IA, IB, II, IIA, or V, $X^1$ is N; $X^2$ is $C(R^2)$; $X^3$ is N; $X^4$ is C; $X^5$ is C; $X^6$ is C(Cl); $X^7$ is $C(R^7)$; $X^8$ is C(F), $X^{13}$ is C; and $X^{14}$ is C. In embodiments of a compound of Formula I, IA, IB, II, IIA, or V, $X^1$ is N; $X^2$ is $C(R^2)$; $X^3$ is N; $X^4$ is C; $X^5$ is C; $X^6$ is N; $X^7$ is $C(R^7)$; $X^8$ is $C(R^8)$, $X^{13}$ is C; and $X^{14}$ is C. In embodiments of a compound of Formula I, IA, IB, II, IIA, or V, $X^1$ is N; $X^2$ is $C(R^2)$; $X^3$ is N; $X^4$ is C; $X^5$ is C; $X^6$ is N; $X^7$ is $C(R^7)$; $X^8$ is C(F), $X^{13}$ is C; and $X^{14}$ is C. In embodiments of a compound of Formula I, IA, IB, II, IIA, or V, $X^1$ is N; $X^2$ is $C(R^2)$; $X^3$ is N; $X^4$ is C; $X^5$ is CH; $X^6$ is $C(H)_2$; $X^7$ is $N(R^{7b})$; $X^8$ is $C(H1)_2$, $X^{13}$ is C; and $X^{14}$ is C. In embodiments of a compound of Formula I, IA, IB, II, IIA, or V, $X^1$ is N; $X^2$ is $C(R^2)$; $X^3$ is N; $X^4$ is C; $X^5$ is $C(R^5)$; $X^6$ is $C(R^6)_2$; $X^7$ is $N(R^1)$; $X^8$ is $C(R^8)_2$, $X^{13}$ is C; and $X^{14}$ is C. In embodiments of a compound of Formula I, IA, IB, II, IIA, or V, $X^1$ is $C(R^1)$. In embodiments of a compound of Formula I, IA, IB, II, IIA, or V, $X^1$ is $C(R^1)_2$. In embodiments of a compound of Formula I, IA, IB, II, IIA, or V, $X^1$ is N. In embodiments of a compound of Formula I, IA, IB, II, IIA, or V, $X^1$ is $N(R^{1b})$. In embodiments of a compound of Formula I, IA, IB, II, IIA, or V, $X^1$ is O. In embodiments of a compound of Formula I, IA, IB, II, IIA, or V, $X^1$ is S. In embodiments of a compound of Formula I, IA, IB, II, IIA, or V, $X^1$ is S(O). In embodiments of a compound of Formula I, IA, IB, II, IIA, or V, $X^1$ is $S(O)_2$. In embodiments of a compound of Formula I, IA, IB, II, IIA, or V, $X^1$ is C(O). In embodiments of a compound of Formula I, IA, IB, II, IIA, or V, $X^2$ is $C(R^2)$. In embodiments of a compound of Formula I, IA, IB, II, IIA, or V, $X^2$ is $C(R^2)_2$. In embodiments of a compound of Formula I, IA, IB, II, IIA, or V, $X^2$ is N. In embodiments of a compound of Formula I, IA, IB, II, IIA, or V, $X^2$ is $N(R^{2b})$. In embodiments of a compound of Formula I, IA, IB, II, IIA, or V, $X^2$ is O. In embodiments of a compound of Formula I, IA, IB, II, IIA, or V, $X^2$ is S. In embodiments of a compound of Formula I, IA, IB, II, IIA, or V, $X^2$ is S(O). In embodiments of a compound of Formula I, IA, IB, II, IIA, or V, $X^2$ is $S(O)_2$. In embodiments of a compound of Formula I, IA, IB, II, IIA, or V, $X^2$ is C(O). In embodiments of a compound of Formula I, IA, IB, II, IIA, or V, $X^3$ is $C(R^3)$. In embodiments of a compound of Formula I, IA, IB, II, IIA, or V, $X^3$ is $C(R^3)_2$. In embodiments of a compound of Formula I, IA, IB, II, IIA, or V, $X^3$ is N. In embodiments of a compound of Formula I, IA, IB, II, IIA, or V, $X^3$ is $N(R^{3b})$. In embodiments of a compound of Formula I, IA, IB, II, IIA, or V, $X^3$ is O. In embodiments of a compound of Formula I, IA, IB, II, IIA, or V, $X^3$ is S. In embodiments of a compound of Formula I, IA, IB, II, IIA, or V, $X^3$ is S(O). In embodiments of a compound of Formula I, IA, IB, II, IIA, or V, $X^3$ is $S(O)_2$. In embodiments of a compound of Formula I, IA, IB, II, IIA, or V, $X^3$ is C(O). In embodiments of a compound of Formula I, IA, IB, II, IIA, or V, $X^4$ is C. In embodiments of a compound of Formula I, IA, IB, II, IIA, or V, $X^4$ is $C(R^4)$. In embodiments of a compound of Formula I, IA, IB, II, IIA, or V, $X^4$ is N. In embodiments of a compound of Formula I, IA, IB, II, IIA, or V, $X^5$ is C. In embodiments of a compound of Formula I, IA, IB, II, IIA, or V, $X^5$ is $C(R^5)$. In embodiments of a compound of Formula I, IA, IB, II, IIA, or V, $X^5$ is N. In embodiments of a compound of Formula I, IA, IB, II, IIA, or V, $X^6$ is $C(R^6)$. In embodiments of a compound of Formula I, IA, IB, II, IIA, or V, $X^6$ is $C(R^6)_2$. In embodiments of a compound of Formula I, IA, IB, II, IIA, or V, $X^6$ is N. In embodiments of a compound of Formula I, IA, IB, II, IIA, or V, $X^6$ is $N(R^{6b})$. In embodiments of a compound of Formula I, IA, IB, II, IIA, or V, $X^6$ is O. In embodiments of a compound of Formula I, IA, IB, II, IIA, or V, $X^6$ is S. In embodiments of a compound of Formula I, IA, IB, II, IIA, or V, $X^6$ is S(O). In embodiments of a compound of Formula I, IA, IB, II, IIA, or V, $X^6$ is $S(O)_2$. In embodiments of a compound of Formula I, IA, IB, II, IIA, or V, $X^6$ is C(O). In embodiments of a compound of Formula I, IA, IB, II, IIA, or V, $X^7$ is $C(R^7)$. In embodiments of a compound of Formula I, IA, IB, II, IIA, or V, $X^7$ is $C(R^7)(R^{7a})$. In embodiments of a compound of Formula I, IA, IB, II, IIA, or V, $X^7$ is $N(R^{7b})$. In embodiments of a compound of Formula I, IA, IB, II, IIA, or V, $X^8$ is $C(R^8)$. In embodiments of a compound of Formula I, IA, IB, II, IIA, or V, $X^8$ is $C(R^8)_2$. In embodiments of a compound of Formula I, IA, IB, II, IIA, or V, $X^8$ is N. In embodiments of a compound of Formula I, IA, IB, II, IIA, or V, $X^8$ is $N(R^{8b})$. In embodiments of a compound of Formula I, IA, IB, II, IIA, or V, $X^1$ is O. In embodiments of a compound of Formula I, IA, IB, II, IIA, or V, $X^8$ is S. In embodiments of a compound of Formula I, IA, IB, II, IIA, or V, $X^8$ is S(O). In embodiments of a compound of Formula I, IA, IB, II, IIA, or V, $X^8$ is $S(O)_2$. In embodiments of a compound of Formula I, IA, IB, II, IIA, or V, $X^8$ is C(O). In embodiments of a compound of Formula I, IA, IB, II, IIA, or V, $X^{13}$ is C. In embodiments of a compound of Formula I, IA, IB, II, IIA, or V, $X^{13}$ is $C(R^{13a})$. In embodiments of a compound of Formula I, IA, IB, II, IIA, or V, $X^{13}$ is N. In embodiments of a compound of Formula I, IA, IB, II, IIA, or V, $X^{14}$ is C. In embodiments of a compound of Formula I, IA, IB, II, IIA, or V, $X^{14}$ is $C(R^{14a})$. In embodiments of a compound of Formula I, IA, IB, II, IIA, or V, $X^{14}$ is N. In embodiments of a compound of formula IA, IB, or IIA, $X^9$ is $C(R^9)$. In embodiments of a compound of formula IA, IB, or IIA, $X^9$ is $C(R^9)(R^{9a})$. In embodiments of a compound of formula IA, IB, or IIA, $X^9$ is $N(R^9)$. In embodiments of a compound of formula IA, IB, or IIA, $X^{10}$ is $C(R^{10})$. In embodiments of a compound of formula IA, IB, or IIA, $X^{10}$ is $C(R^{10})_2$. In embodiments of a compound of formula IA, IB, or IIA, $X^{10}$ is N. In embodiments of a compound of formula IA, IB, or IIA, $X^{10}$ is $N(R^{10b})$. In embodiments of a compound of formula IA, IB, or IIA, $X^{10}$ is O. In embodiments of a compound of formula IA, IB, or IIA, $X^{10}$ is S. In embodiments of a compound of formula IA, IB, or IIA, $X^{10}$ is S(O). In embodiments of a compound of formula IA, IB, or IIA, $X^{10}$ is $S(O)_2$. In embodiments of a compound of formula IA, IB, or IIA, $X^{10}$ is C(O). In embodiments of a compound of formula IA, IB, or IIA, $X^{11}$ is $C(R^{11})$. In embodiments of a compound of formula IA, IB, or IIA, $X^{11}$ is $C(R^{11})_2$. In embodiments of a compound of formula IA, IB, or IIA, $X^{11}$ is N. In embodiments of a compound of formula IA, IB, or IIA, $X^{11}$ is $N(R^{11b})$. In embodiments of a compound of formula IA, IB, or IIA, $X^{11}$ is O. In embodiments of a compound of formula IA, IB, or IIA, $X^{11}$ is S. In embodiments of a compound of formula IA, IB, or IIA, $X^{11}$ is S(O). In embodiments of a compound of formula IA, IB, or IIA, $X^{11}$ is $S(O)_2$. In embodiments of a compound of formula IA, IB, or IIA, $X^{11}$ is C(O). In embodiments of a compound of formula IA, IB, or IIA, $X^{12a}$ is $C(R^{12})$. In embodiments of a compound of formula IA, IB, or IIA, $X^{12a}$ is $C(R^{12a})_2$. In embodiments of a compound of formula IA, IB, or IIA, $X^{12a}$ is N. In embodiments of a compound of formula IA, IB, or IIA, $X^{12a}$ is $N(R^{12b})$. In embodiments of a compound of formula IA, IB, or IIA, $X^{12a}$ is O. In embodiments of a compound of formula IA, IB, or IIA, $X^{12a}$ is S. In embodiments of a compound of formula IA, IB, or IIA, $X^{12a}$ is S(O). In embodiments of a compound of formula IA, IB, or IIA, $X^{12a}$ is $S(O)_2$. In embodiments of a compound of formula IA, IB, or IIA, $X^{12a}$ is C(O). In embodiments of a compound of formula IA, IB, or IIA, $X^{12b}$ is $C(R^{12a})$. In embodiments of a compound of formula IA, IB, or IIA, $X^{12b}$ is $C(R^{12a})_2$. In embodiments of a compound of formula IA, IB, or IIA, $X^{12b}$ is N. In embodiments of a compound of formula IA, IB, or IIA, $X^{12b}$ is $N(R^{12b})$. In embodiments of a compound of formula IA, IB, or IIA, $X^{12a}$ is O. In embodiments of a compound of formula IA, IB, or IIA, $X^{12b}$ is S. In embodiments of a compound of formula IA, IB, or IIA, $X^{12'}$ is S(O). In embodiments of a compound of formula IA, IB, or IIA, $X^{12'}$ is $S(O)_2$. In embodiments of a compound of formula IA, IB, or IIA, $X^{12b}$ is C(O). In embodiments of a compound of formula IA, IB, or IIA, $X^{12}$ is $C(R^{12})$. In embodiments of a compound of formula IA, IB, or IIA, $X^{12c}$ is $C(R^{12})_2$. In embodiments of a compound of formula IA, IB, or IIA, $X^{12c}$ is N. In embodiments of a compound of formula IA, IB, or IIA, $X^{12c}$ is $N(R^{12b})$. In embodiments of a compound of formula IA, IB, or IIA, $X^{12c}$ is O. In embodiments of a compound of formula IA, IB, or IIA, $X^{12c}$ is S. In embodiments of a compound of formula IA, IB, or IIA, $X^{12c}$ is S(O). In embodiments of a compound of formula IA, IB, or IIA, $X^{12c}$ is $S(O)_2$. In embodiments of a compound of formula IA, IB, or IIA, $X^{12c}$ is C(O). In embodiments of a compound of formula IA, IB, or IIA, $X^{12d}$ is $C(R^{12})$. In embodiments of a compound of formula IA, IB, or IIA, $X^{12d}$ is $C(R^{12a})_2$. In embodiments of a compound of formula IA, IB, or IIA, $X^{12d}$ is N. In embodiments of a compound of formula IA, IB, or IIA, $X^{12d}$ is $N(R^{12b})$. In embodiments of a compound of formula IA, IB, or IIA, $X^{12d}$ is O. In embodiments of a compound of formula IA, IB, or IIA, $X^{12d}$ is S. In embodiments of a compound of formula IA, IB, or IIA, $X^{12d}$ is S(O). In embodiments of a compound of formula IA, IB, or IIA, $X^{12d}$ is $S(O)_2$. In embodiments of a compound of formula IA, IB, or IIA, $X^{12d}$ is C(O).

In embodiments of a compound of Formula I, IA, IB, II, IIA, or V, $L^{19}$ is unsubstituted $C_{1-2}$ alkylene. In embodiments of a compound of Formula I, IA, IB, II, IIA, or V, $L^{19}$ is unsubstituted methylene. In embodiments of a compound of Formula I, IA, IB, II, IIA, or V, $L^{19}$ is a bond.

In embodiments of a compound of Formula I, IA, IB, II, IIA, or V, $L^{19}$ is selected from $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, $—N(R^{12})—$, —C(O)—, $—N(R^{12})C(O)—$, $—C(O)N(R^{12})—$, —S—, $—S(O)_2—$, —S(O)—, $—P(O)(R^{12})—$, $—N(R^{12})S(O)_2—$, $—N(R^{12})S(O)—$, $—N(R^{12})P(O)(R^{12})—$, $—S(O)_2N(R^{12})—$, $—S(O)N(R^{12})—$, $—P(O)(R^{12})N(R^{12})—$, $—OP(O)(R^{12})—$, and $—P(O)(R^{12})O—$, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$.

In embodiments of a compound of formula I, IA, or IB, $R^{19}$ is a monocyclic $C_{3-8}$ carbocycle optionally substituted with one or more $R^{20}$. In embodiments of a compound of formula I, IA, IB, II, or IIA, $R^{19}$ is a monocyclic non-aromatic $C_{4-8}$ carbocycle optionally substituted with one or more $R^{20}$. In embodiments of a compound of formula I, IA, IB, II, or IIA, $R^{19}$ is a monocyclic non-aromatic $C_{4-6}$ carbocycle optionally substituted with one or more $R^{20}$. In embodiments of a compound of formula I, IA, IB, II, or IIA, $R^{19}$ is a monocyclic non-aromatic $C_{4-5}$ carbocycle optionally substituted with one or more $R^{20}$. In embodiments of a compound of formula I, IA, IB, II, or IIA, $R^{19}$ is a monocyclic non-aromatic $C_4$ carbocycle optionally substituted with one or more $R^{20}$. In embodiments of a compound of formula I, IA, IB, II, or IIA, $R^{19}$ is a monocyclic non-aromatic $C_5$ carbocycle optionally substituted with one or more $R^{20}$. In embodiments of a compound of formula I, IA, and IB, $R^{19}$ is a phenyl optionally substituted with one or more $R^{20}$. In embodiments of a compound of formula I, IA, IB, II, or IIA, $R^{19}$ is a monocyclic 3- to 8-membered heterocycle optionally substituted with one or more $R^{20}$. In embodiments of a compound of formula I, IA, IB, II, or IIA, $R^{19}$ is a monocyclic non-aromatic 4- to 5-membered heterocycle optionally substituted with one or more $R^{20}$. In embodiments of a compound of formula I, IA, IB, II, or IIA, $R^{19}$ is a monocyclic non-aromatic 4-membered heterocycle optionally substituted with one or more $R^{20}$. In embodiments of a compound of formula I, IA, IB, II, or IIA, $R^{19}$ is a monocyclic non-aromatic 5-membered heterocycle optionally substituted with one or more $R^{20}$. In embodiments of a compound of formula I, IA, IB, II, or IIA, $R^{19}$ is selected from cyclopropyl, cyclobutyl, cyclopentyl, aziridine, azetidine, and pyrrolidine, each of which is optionally substituted with $C_{1-3}$ alkyl. In embodiments of a compound of formula I, IA, IB, II, or IIA, $R^{19}$ is selected from cyclopropyl, cyclobutyl, cyclopentyl, aziridine, azetidine, and pyrrolidine, each of which is optionally substituted with $C_{3-4}$ cycloalkyl, wherein $C_{3-4}$ cycloalkyl is optionally substituted with methyl. In embodiments of a compound of formula I, IA, IB, II, or IIA, $R^{19}$ is cyclobutyl optionally substituted with $C_{1-3}$ alkyl. In embodiments of a compound of formula I, IA, IB, II, or IIA, $R^{19}$ is cyclobutyl, optionally substituted with cyclopropyl, wherein the cyclopropyl is optionally substituted with methyl. In embodiments of a compound of formula I, IA, IB, II, or IIA, $R^{19}$ is cyclobutyl, optionally substituted with cyclopropyl, wherein the cyclopropyl is substituted with methyl. In embodiments of a compound of formula I, IA, IB, II, or IIA, $R^{19}$ is cyclopentyl optionally substituted with $C_{1-3}$ alkyl. In embodiments of a compound of formula I, IA, IB, II, or IIA, $R^{19}$ is cyclopentyl substituted with $C_{1-3}$ alkyl. In embodiments of a compound of formula I, IA, IB, II, or IIA, $R^{19}$ is cyclopentyl substituted with methyl.

In embodiments of a compound of formula I, IA, and IB, $R^{19}$ is a monocyclic 5- to 6-membered heteroaryl optionally substituted with one or more $R^{20}$. In embodiments of a compound of formula I, IA, IB, II, or IIA, $R^{19}$ is a monocyclic, non-aromatic 4- to 5-membered heterocycle optionally substituted with one or more $R^{20}$. In embodiments of a compound of formula I, IA, IB, II, or IIA, $R^{19}$ is selected from azetidinyl and pyrrolidinyl; wherein the azetidinyl and pyrrolidinyl are optionally substituted with one or more $R^{20}$. In embodiments of a compound of formula I, IA, IB, II, or IIA, $R^{19}$ is optionally substituted with one or more substituents independently selected from $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, $—C_{0-6}$ alkyl-($C_{3-12}$ carbocycle), and $—C_{0-6}$ alkyl-(3- to 12-membered heterocycle); wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), and —$C_{0-6}$ alkyl-(3- to 12-membered heterocycle) are optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —$S(=O)(=NR^{22})N(R^{22})(R^{23})$. In embodiments of a compound of formula I, IA, IB, II, or IIA, $R^{19}$ is optionally substituted with one or more substituents independently selected from $C_{1-4}$ alkyl and $C_{3-4}$ carbocycle; wherein $C_{3-4}$ carbocycle is optionally substituted with one or more substituents independently selected from halogen and $C_{1-4}$ alkyl. In embodiments of a compound of formula I, IA, IB, II, or IIA, $R^{19}$ is optionally substituted with unsubstituted methyl.

In embodiments of a compound of formula I, IA, or IB, $R^{19}$ is a monocyclic $C_3$ carbocycle optionally substituted with one or more $R^{20}$. In embodiments of a compound of formula I, IA, IB, II, or IIA, $R^{19}$ is a monocyclic $C_4$ carbocycle optionally substituted with one or more $R^{20}$. In embodiments of a compound of formula I, IA, IB, II, or IIA, $R^{19}$ is a monocyclic $C_5$ carbocycle optionally substituted with one or more $R^{20}$. In embodiments of a compound of formula I, IA, IB, II, or IIA, $R^{19}$ is a monocyclic $C_6$ carbocycle optionally substituted with one or more $R^{20}$. In embodiments of a compound of formula I, IA, IB, II, or IIA, $R^{19}$ is a monocyclic $C_7$ carbocycle optionally substituted with one or more $R^{20}$. In embodiments of a compound of formula I, IA, IB, II, or IIA, $R^{19}$ is a monocyclic $C_8$ carbocycle optionally substituted with one or more $R^{20}$.

In embodiments of a compound of formula I, IA, IB, II, or IIA, $R^{19}$ is a monocyclic $C_{3-8}$ carbocycle substituted with one or more $R^{20}$. In embodiments of a compound of formula I, IA, IB, II, or IIA, $R^{19}$ is a monocyclic $C_3$ carbocycle substituted with one or more $R^{20}$. In embodiments of a compound of formula I, IA, IB, II, or IIA, $R^{19}$ is a monocyclic $C_4$ carbocycle substituted with one or more $R^{20}$. In embodiments of a compound of formula I, IA, IB, II, or IIA, $R^{19}$ is a monocyclic $C_5$ carbocycle substituted with one or more $R^{20}$. In embodiments of a compound of formula I, IA, IB, II, or IIA, $R^{19}$ is a monocyclic $C_6$ carbocycle substituted with one or more $R^{20}$. In embodiments of a compound of formula I, IA, IB, II, or IIA, $R^{19}$ is a monocyclic $C_7$ carbocycle substituted with one or more $R^{20}$. In embodiments of a compound of formula I, IA, IB, II, or IIA, $R^{19}$ is a monocyclic $C_8$ carbocycle substituted with one or more $R^{20}$.

In embodiments of a compound of formula I, IA, IB, II, or IIA, $R^{19}$ is a monocyclic 3-membered heterocycle optionally substituted with one or more $R^{20}$. In embodiments of a compound of formula I, IA, IB, II, or IIA, $R^{19}$ is a monocyclic 4-membered heterocycle optionally substituted with one or more $R^{20}$. In embodiments of a compound of formula I, IA, IB, II, or IIA, $R^{19}$ is a monocyclic 5-membered heterocycle optionally substituted with one or more $R^{20}$. In embodiments of a compound of formula I, IA, IB, II, or IIA, $R^{19}$ is a monocyclic 6-membered heterocycle optionally substituted with one or more $R^{20}$. In embodiments of a compound of formula I, IA, IB, II, or IIA, $R^{19}$ is a monocyclic 7-membered heterocycle optionally substituted with one or more $R^{20}$. In embodiments of a compound of formula I, IA, IB, II, or IIA, $R^{19}$ is a monocyclic 8-membered heterocycle optionally substituted with one or more $R^{20}$.

In embodiments of a compound of formula I, IA, IB, II, or IIA, $R^{19}$ is a monocyclic 3- to 8-membered heterocycle, substituted with one or more $R^{20}$. In embodiments of a compound of formula I, IA, IB, II, or IIA, $R^{19}$ is a monocyclic 3-membered heterocycle substituted with one or more $R^{20}$. In embodiments of a compound of formula I, IA, IB, II, or IIA, $R^{19}$ is a monocyclic 4-membered heterocycle substituted with one or more $R^{20}$. In embodiments of a compound of formula I, IA, IB, II, or IIA, $R^{19}$ is a monocyclic 5-membered heterocycle substituted with one or more $R^{20}$. In embodiments of a compound of formula I, IA, IB, II, or IIA, $R^{19}$ is a monocyclic 6-membered heterocycle substituted with one or more $R^{20}$. In embodiments of a compound of formula I, IA, IB, II, or IIA, $R^{19}$ is a monocyclic 7-membered heterocycle substituted with one or more $R^{20}$. In embodiments of a compound of formula I, IA, IB, II, or IIA, $R^{19}$ is a monocyclic 8-membered heterocycle substituted with one or more $R^{20}$.

In embodiments of a compound of formula I, IA, or IB, $R^{19}$ is a non-aromatic monocyclic $C_3$ carbocycle optionally substituted with one or more $R^{20}$. In embodiments of a compound of formula I, IA, IB, II, or IIA, $R^{19}$ is a non-aromatic monocyclic $C_4$ carbocycle optionally substituted with one or more $R^{20}$. In embodiments of a compound of formula I, IA, IB, II, or IIA, $R^{19}$ is a non-aromatic monocyclic $C_5$ carbocycle optionally substituted with one or more $R^{20}$. In embodiments of a compound of formula I, IA, IB, II, or IIA, $R^{19}$ is a non-aromatic monocyclic $C_6$ carbocycle optionally substituted with one or more $R^{20}$. In embodiments of a compound of formula I, IA, IB, II, or IIA, $R^{19}$ is a non-aromatic monocyclic $C_7$ carbocycle optionally substituted with one or more $R^{20}$. In embodiments of a compound of formula I, IA, IB, II, or IIA, $R^{19}$ is a non-aromatic monocyclic $C_8$ carbocycle optionally substituted with one or more $R^{20}$.

In embodiments of a compound of formula I, IA, or IB, $R^{19}$ is a non-aromatic monocyclic $C_{3-8}$ carbocycle substituted with one or more $R^{20}$. In embodiments of a compound of formula I, IA, IB, II, or IIA, $R^{19}$ is a non-aromatic monocyclic $C_{4-8}$ carbocycle substituted with one or more $R^{20}$. In embodiments of a compound of formula I, IA, or IB, $R^{19}$ is a non-aromatic monocyclic $C_3$ carbocycle substituted with one or more $R^{20}$. In embodiments of a compound of formula I, IA, IB, II, or IIA, $R^{19}$ is a non-aromatic monocyclic $C_4$ carbocycle substituted with one or more $R^{20}$. In embodiments of a compound of formula I, IA, IB, II, or IIA, $R^{19}$ is a non-aromatic monocyclic $C_5$ carbocycle substituted with one or more $R^{20}$. In embodiments of a compound of formula I, IA, IB, II, or IIA, $R^{19}$ is a non-aromatic monocyclic $C_6$ carbocycle substituted with one or more $R^{20}$. In embodiments of a compound of formula I, IA, IB, II, or IIA, $R^{19}$ is a non-aromatic monocyclic $C_7$ carbocycle substituted with one or more $R^{20}$. In embodiments of a compound of formula I, IA, IB, II, or IIA, $R^{19}$ is a non-aromatic monocyclic $C_8$ carbocycle substituted with one or more $R^{20}$.

In embodiments of a compound of formula I, IA, IB, II, or IIA, $R^{19}$ is a non-aromatic monocyclic 3-membered heterocycle optionally substituted with one or more $R^{20}$. In embodiments of a compound of formula I, IA, IB, II, or IIA, $R^{19}$ is a non-aromatic monocyclic 4-membered heterocycle optionally substituted with one or more $R^{20}$. In embodiments of a compound of formula I, IA, IB, II, or IIA, $R^{19}$ is a non-aromatic monocyclic 5-membered heterocycle optionally substituted with one or more $R^{20}$. In embodiments of a compound of formula I, IA, IB, II, or IIA, $R^{19}$ is a non-aromatic monocyclic 6-membered heterocycle optionally substituted with one or more $R^{20}$. In embodiments of a compound of formula I, IA, IB, II, or IIA, $R^{19}$ is a non-aromatic monocyclic 7-membered heterocycle optionally substituted with one or more $R^{20}$. In embodiments of a compound of formula I, IA, IB, II, or IIA, $R^{19}$ is a non-aromatic monocyclic 8-membered heterocycle optionally substituted with one or more $R^{20}$.

In embodiments of a compound of formula I, IA, IB, II, or IIA, $R^{19}$ is a non-aromatic monocyclic 3- to 8-membered heterocycle, substituted with one or more $R^{20}$. In embodiments of a compound of formula I, IA, IB, II, or IIA, $R^{19}$ is a non-aromatic monocyclic 3-membered heterocycle substituted with one or more $R^{20}$. In embodiments of a compound of formula I, IA, IB, II, or IIA, $R^{19}$ is a non-aromatic monocyclic 4-membered heterocycle substituted with one or more $R^{20}$. In embodiments of a compound of formula I, IA, IB, II, or IIA, $R^{19}$ is a non-aromatic monocyclic 5-membered heterocycle substituted with one or more $R^{20}$. In embodiments of a compound of formula I, IA, IB, II, or IIA, $R^{19}$ is a non-aromatic monocyclic 6-membered heterocycle substituted with one or more $R^{20}$. In embodiments of a compound of formula I, IA, IB, II, or IIA, $R^{19}$ is a non-aromatic monocyclic 7-membered heterocycle substituted with one or more $R^{20}$. In embodiments of a compound of formula I, IA, IB, II, or IIA, $R^{19}$ is a non-aromatic monocyclic 8-membered heterocycle substituted with one or more $R^{20}$.

In embodiments of a compound of Formula I, IA, IB, II, or IIA, $-L^{19}-R^{19}-L^{19a}-R^{19a}$ is selected from:

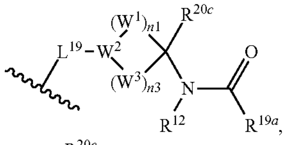

or

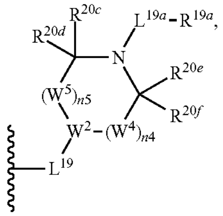

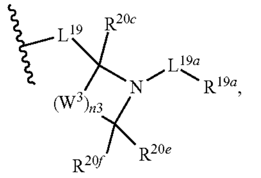

wherein:

$W^1$, $W^3$, $W^4$, and $W^5$ are independently selected at each occurrence from $N(R^{20b})$, $C(R^{20a})_2$, C(O), O, S(O), and $S(O)_2$;

$W^2$ is selected from N and $C(R^{20a})$;

n1 is independently selected from 0, 1, 2, 3, 4, 5, and 6;

n3 is independently selected from 0, 1, 2, 3, 4, and 5;

wherein the sum of n1 and n3 is selected from 1, 2, 3, 4, 5, and 6;

n4 and n5 are each independently selected from 0, 1, 2, 3, and 4;

wherein the sum of n4 and n5 is selected from 0, 1, 2, 3, and 4; and $R^{20a}$, $R^{20b}$, $R^{20}0$, $R^{20d}$, $R^2$, and $R^{20f}$ are independently selected at each occurrence from hydrogen and $R^{20}$.

In embodiments, $R^{20a}$, $R^{20}$, $R^{20d}$, $R^{20e}$, and $R^{20f}$ are independently selected at each occurrence from hydrogen, halogen, —OH, —CN, $C_{1-6}$ alkyl, and $C_{3-6}$ cycloalkyl, wherein $C_{1-6}$ alkyl and $C_{3-6}$ cycloalkyl are optionally substituted with one or more substituents selected from halogen, —OH, —CN, $C_{1-3}$ alkyl, $C_{1-3}$ haloalkyl, and $C_{3-6}$ cycloalkyl.

In embodiments, $R^{20b}$ is independently selected at each occurrence from hydrogen, $C_{1-6}$ alkyl, and $C_{3-6}$ cycloalkyl, wherein $C_{1-6}$ alkyl and $C_{3-6}$ cycloalkyl are optionally substituted with one or more substituents selected from halogen, —OH, —CN, $C_{1-3}$ alkyl, $C_{1-3}$ haloalkyl, and $C_{3-6}$ cycloalkyl.

In embodiments, $W^1$ is independently selected from $N(R^{20b})$, $C(R^{20a})_2$, C(O), O, S(O), and $S(O)_2$. In embodiments, $W^1$ is independently $C(R^{20a})_2$. In embodiments, $W^1$ is independently $CH(R^{20a})$. In embodiments, $W^1$ is independently $C(H)_2$. In embodiments, $W^1$ is independently selected from C(O), S(O), and $S(O)_2$. In embodiments, $W^1$ is independently C(O).

In embodiments, $W^2$ is independently N. In embodiments, $W^2$ is independently $C(R^{20a})$. In embodiments, $W^2$ is independently CH.

In embodiments, $W^3$ is independently selected from $N(R^{20b})$, $C(R^{20a})_2$, C(O), O, S(O), and $S(O)_2$. In embodiments, $W^3$ is independently $C(R^{20a})_2$. In embodiments, $W^3$ is independently $CH(R^{20a})$. In embodiments, $W^3$ is independently $C(H)_2$. In embodiments, $W^3$ is independently selected from C(O), S(O), and $S(O)_2$. In embodiments, $W^3$ is independently C(O). In embodiments, $W^3$ is independently O.

In embodiments, $W^4$ is independently selected from $N(R^{20b})$, $C(R^{20a})_2$, C(O), O, S(O), and $S(O)_2$. In embodiments, $W^4$ is independently $C(R^{20a})_2$. In embodiments, $W^4$ is independently $CH(R^{20a})$. In embodiments, $W^4$ is independently $C(H)_2$. In embodiments, $W^4$ is independently selected from C(O), S(O), and $S(O)_2$. In embodiments, $W^4$ is independently C(O).

In embodiments, $W^5$ is independently selected from $N(R^{20b})$, $C(R^{20a})_2$, C(O), O, S(O), and $S(O)_2$. In embodiments, $W^5$ is independently $C(R^{20a})_2$. In embodiments, $W^5$ is independently $CH(R^{20a})$. In embodiments, $W^5$ is independently $C(H)_2$. In embodiments, $W^5$ is independently selected from C(O), S(O), and $S(O)_2$. In embodiments, $W^5$ is independently C(O).

In embodiments, n1 is 0. In embodiments, n1 is 1. In embodiments, n1 is 2. In embodiments, n1 is 3. In embodiments, n1 is 4. In embodiments, n1 is 5. In embodiments, n1 is 6. In embodiments, n3 is 0. In embodiments, n3 is 1. In embodiments, n3 is 2. In embodiments, n3 is 3. In embodiments, n3 is 4. In embodiments, n3 is 5. In embodiments, n1 is 1 and n3 is 1. In embodiments, n1 is 1 and n3 is 2. In embodiments, n1 is 1 and n3 is 3. In embodiments, n1 is 1 and n3 is 4. In embodiments, n1 is 2 and n3 is 1. In embodiments, n1 is 2 and n3 is 2. In embodiments, n1 is 2 and n3 is 3. In embodiments, n1 is 2 and n3 is 4. In embodiments, n1 is 1 or 2. In embodiments, n3 is 1 or 2. In embodiments, n4 is 0 or 1. In embodiments, n5 is 0 or 1.

In embodiments, n4 is 0. In embodiments, n4 is 1. In embodiments, n4 is 2. In embodiments, n4 is 3. In embodiments, n4 is 4. In embodiments, n5 is 0. In embodiments, n5 is 1. In embodiments, n5 is 2. In embodiments, n5 is 3. In embodiments, n5 is 4. In embodiments, n4 is 1 and n5 is 1. In embodiments, n4 is 1 and n5 is 2. In embodiments, n4 is 1 and n5 is 3. In embodiments, n4 is 2 and n5 is 1. In embodiments, n4 is 2 and n5 is 2.

In embodiments of a compound of Formula I, IA, IB, II, or IIA, $-L^{19}-R^{19}-L^{19a}-R^{19a}$ is selected from:

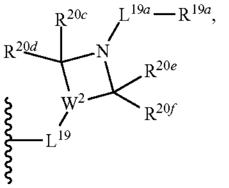
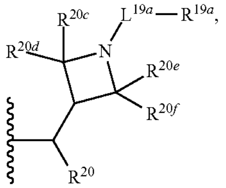
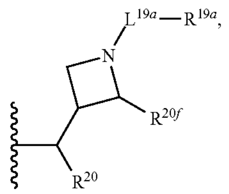
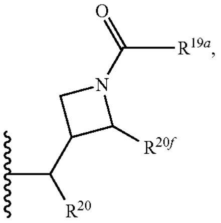
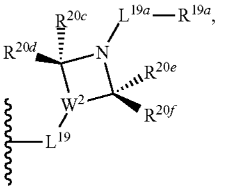
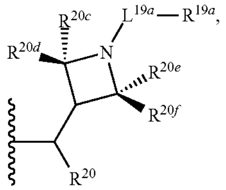
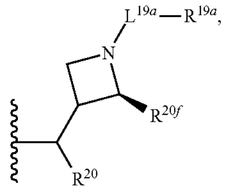
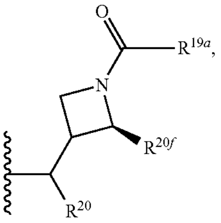
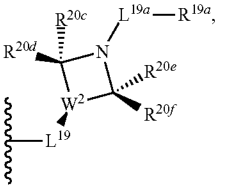
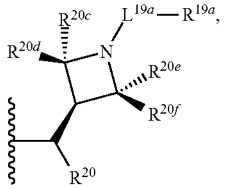
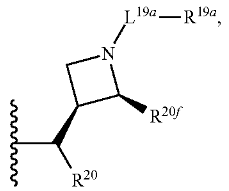
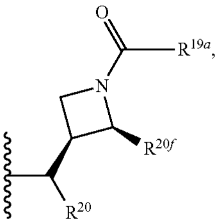
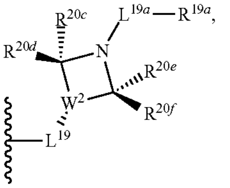
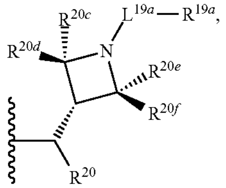
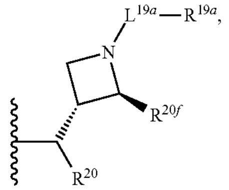
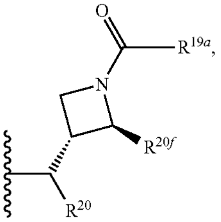
-continued
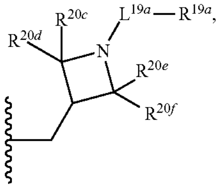
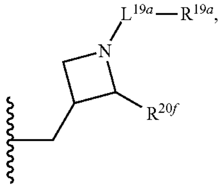
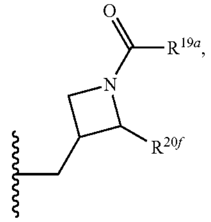
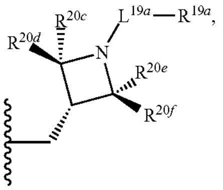
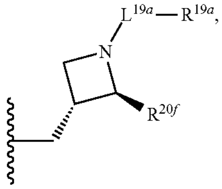
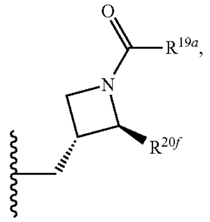
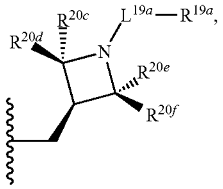
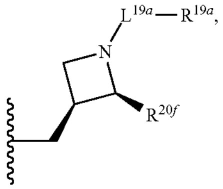
and
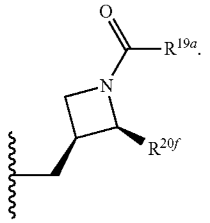
In embodiments of a compound of Formula I, IA, IB, II, or IIA, $-L^{19}-R^{19}-L^{19a}-R^{19a}$ is selected from:
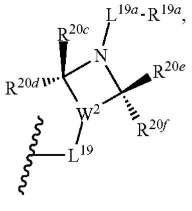
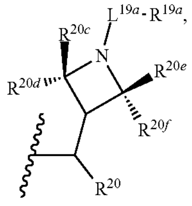
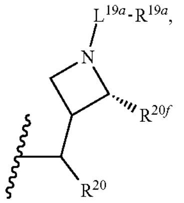
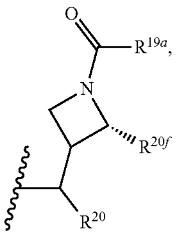

-continued
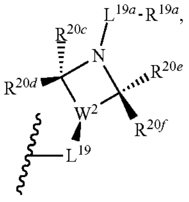
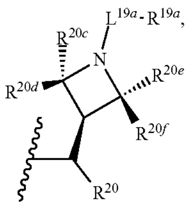
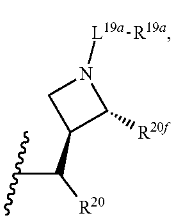
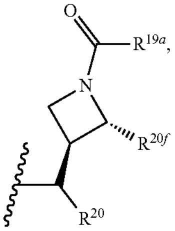
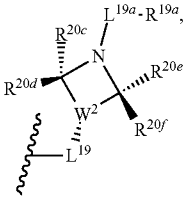
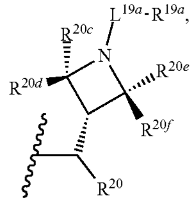
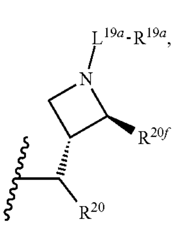
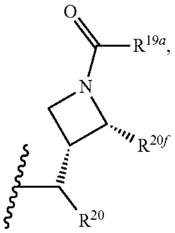
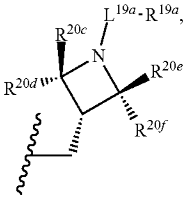
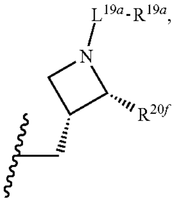
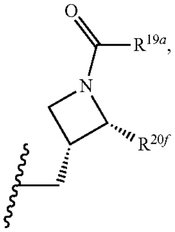
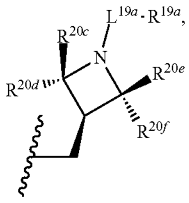
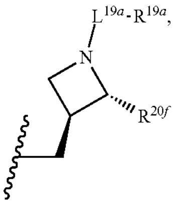
and
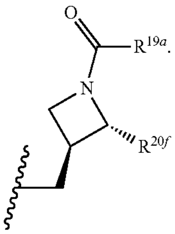
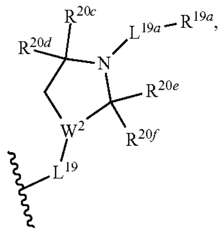
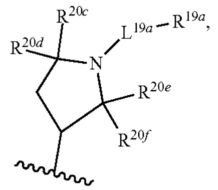
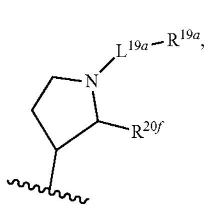
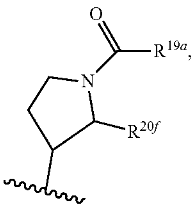
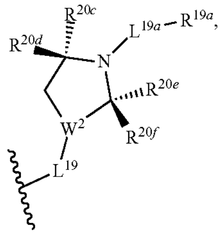
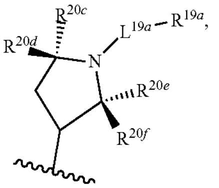
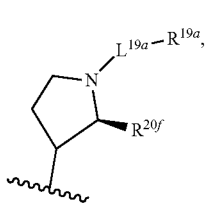
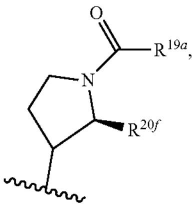
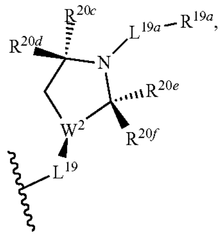
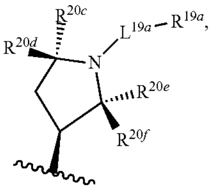
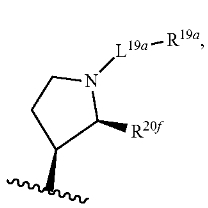
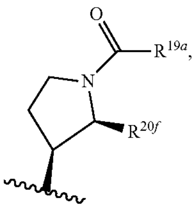
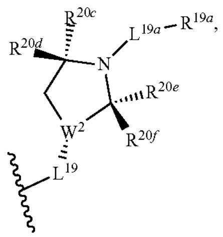
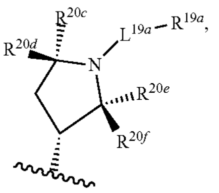
In embodiments of a compound of Formula I, IA, IB, II, or IIA, $-L^{19}-R^{19}-L^{19a}-R^{19a}$ is selected from:

-continued
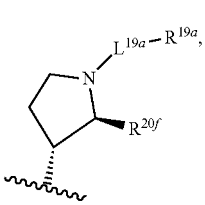
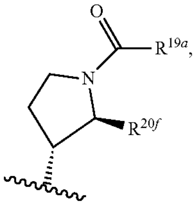
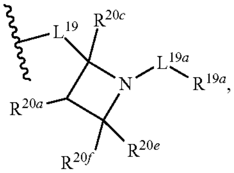
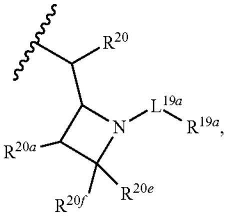
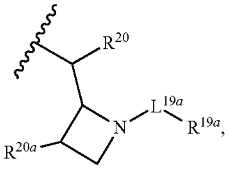
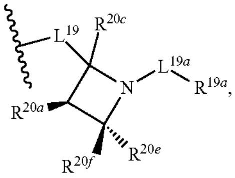
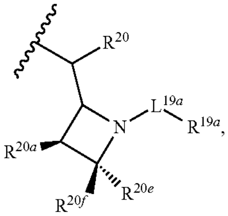
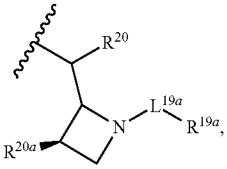
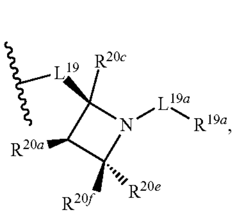
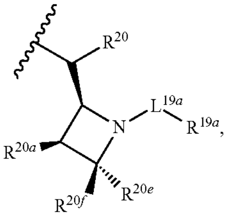
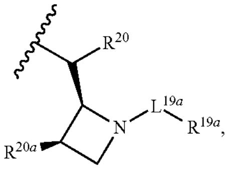
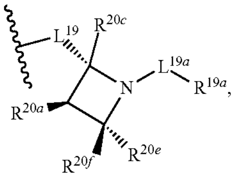
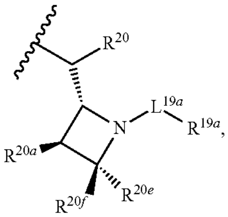
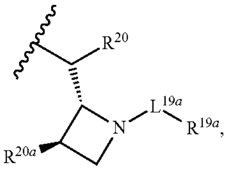
-continued
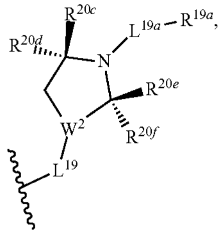
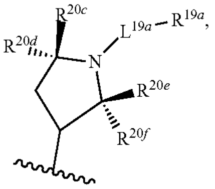
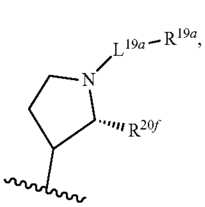
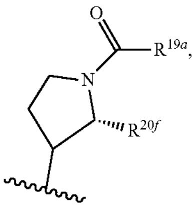
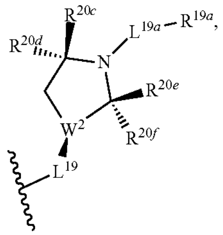
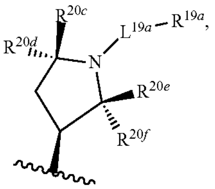
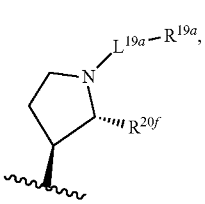
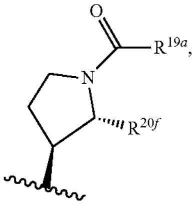
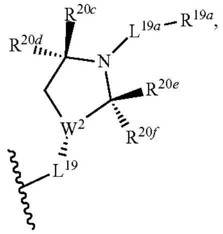
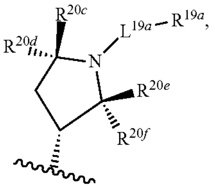
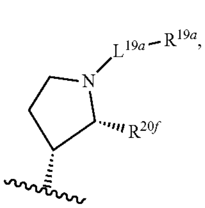
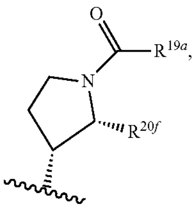
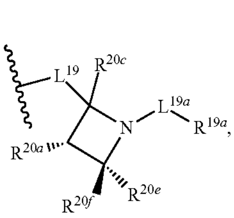
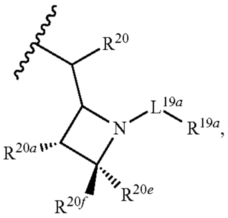

-continued

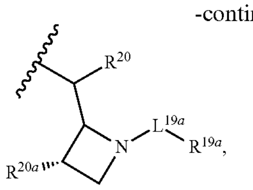

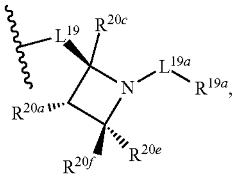

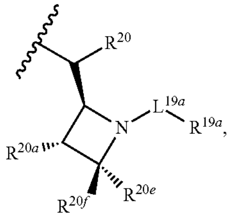

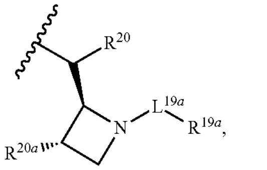

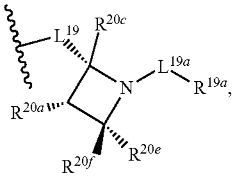

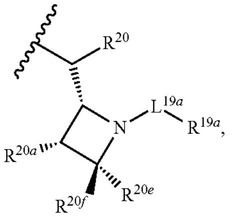

and

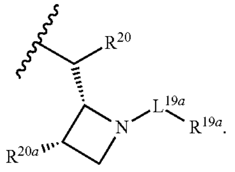

In embodiments of a compound of Formula I, IA, IB, II, or IIA, $-L^{19}-R^{19}-L^{19a}-R^{19a}$ is selected from:

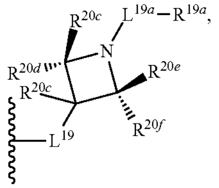

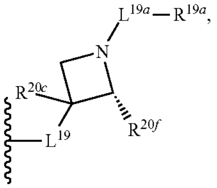

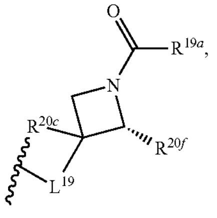

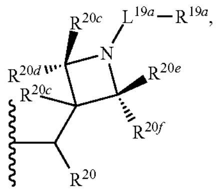

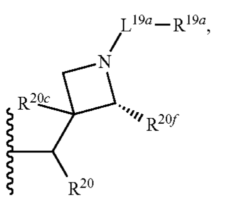

and

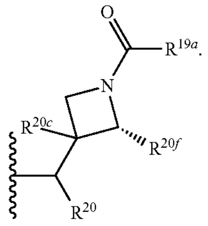

The individual embodiments herein below, or combinations thereof, are applicable to compounds of Formula I, IA, IB, II, IIA, or V, or a pharmaceutically acceptable salt or solvate thereof. It will be understood that wherein the value of a variable is recited as an embodiment of a compound of Formula I, IA, IB, II, IIA, V, or any other formula, it will be understood that such value of the variable may be combined with any compound having a formula selected from a Formula I, IA, IB, II, IIA, V, or any other compound formula (e.g, without a number or label) that is itself recited as an embodiment of a compound of Formula I, IA, IB, II, IIA, and/or V; and is therefore a sub-formula of Formula I, IA, IB, II, IIA, and/or V.

In embodiments, $R^{20a}$ is independently hydrogen. In embodiments, $R^{20a}$ is independently halogen. In embodiments, $R^{20a}$ is independently —OH. In embodiments, $R^{20a}$ is independently —CN. In embodiments, $R^{20a}$ is independently unsubstituted $C_{1-6}$ alkyl. In embodiments, $R^{20a}$ is independently unsubstituted $C_{3-6}$ cycloalkyl.

In embodiments, $R^{20a}$ is independently unsubstituted methyl. In embodiments, $R^{20a}$ is independently unsubstituted ethyl. In embodiments, $R^{20a}$ is independently unsubstituted propyl. In embodiments, $R^{20a}$ is independently unsubstituted isopropyl. In embodiments, $R^{20a}$ is independently unsubstituted butyl. In embodiments, $R^{20a}$ is independently unsubstituted tert-butyl.

In embodiments, $R^{20a}$ is independently methyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20a}$ is independently ethyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20a}$ is independently propyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20a}$ is independently isopropyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20a}$ is independently butyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20a}$ is independently tert-butyl optionally substituted with one, two, or three substituents independently selected from halogen, —OH, —CN, $C_{1-3}$ alkyl, $C_{1-3}$ haloalkyl, and $C_{3-6}$ cycloalkyl.

In embodiments, $R^{20a}$ is independently unsubstituted cyclopropyl. In embodiments, $R^{20a}$ is independently unsubstituted cyclobutyl. In embodiments, $R^{20a}$ is independently unsubstituted cyclopentyl.

In embodiments, $R^{20a}$ is independently cyclopropyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20a}$ is independently cyclopropyl optionally substituted with one, $C_{1-3}$ alkyl. In embodiments, $R^{20a}$ is independently cyclopropyl optionally substituted with one methyl. In embodiments, $R^{20a}$ is independently cyclobutyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20a}$ is independently cyclopentyl optionally substituted with one, two, or three substituents independently selected from halogen, —OH, —CN, $C_{1-3}$ alkyl, $C_{1-3}$ haloalkyl, and $C_{3-6}$ cycloalkyl.

In embodiments, $R^{20b}$ is independently hydrogen. In embodiments, $R^{20b}$ is independently unsubstituted $C_{1-6}$ alkyl. In embodiments, $R^{20b}$ is independently unsubstituted $C_{3-6}$ cycloalkyl.

In embodiments, $R^{20b}$ is independently unsubstituted methyl. In embodiments, $R^{20b}$ is independently unsubstituted ethyl. In embodiments, $R^{20b}$ is independently unsubstituted propyl. In embodiments, $R^{20b}$ is independently unsubstituted isopropyl. In embodiments, $R^{20b}$ is independently unsubstituted butyl. In embodiments, $R^{20b}$ is independently unsubstituted tert-butyl.

In embodiments, $R^{20b}$ is independently methyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20b}$ is independently ethyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20b}$ is independently propyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20b}$ is independently isopropyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20b}$ is independently butyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20b}$ is independently tert-butyl optionally substituted with one, two, or three substituents independently selected from halogen, —OH, —CN, $C_{1-3}$ alkyl, $C_{1-3}$ haloalkyl, and $C_{3-6}$ cycloalkyl.

In embodiments, $R^{20b}$ is independently unsubstituted cyclopropyl. In embodiments, $R^{20b}$ is independently unsubstituted cyclobutyl. In embodiments, $R^{20b}$ is independently unsubstituted cyclopentyl.

In embodiments, $R^{20b}$ is independently cyclopropyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20b}$ is independently cyclopropyl optionally substituted with one, $C_{1-3}$ alkyl. In embodiments, $R^{20b}$ is independently cyclopropyl optionally substituted with one methyl. In embodiments, $R^{20b}$ is independently cyclobutyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20b}$ is independently cyclopentyl optionally substituted with one, two, or three substituents independently selected from halogen, —OH, —CN, $C_{1-3}$ alkyl, $C_{1-3}$ haloalkyl, and $C_{3-6}$ cycloalkyl.

In embodiments, $R^{20c}$ is independently hydrogen. In embodiments, $R^{20c}$ is independently halogen. In embodiments, $R^{20c}$ is independently —OH. In embodiments, $R^{20c}$ is independently —CN. In embodiments, $R^{20c}$ is independently unsubstituted $C_{1-6}$ alkyl. In embodiments, $R^{20c}$ is independently unsubstituted $C_{3-6}$ cycloalkyl.

In embodiments, $R^{20c}$ is independently unsubstituted methyl. In embodiments, $R^{20c}$ is independently unsubstituted ethyl. In embodiments, $R^2$ is independently unsubstituted propyl. In embodiments, $R^{20c}$ is independently unsubstituted isopropyl. In embodiments, $R^2$ is independently unsubstituted butyl. In embodiments, $R^{20c}$ is independently unsubstituted tert-butyl.

In embodiments, $R^{20c}$ is independently methyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20c}$ is independently ethyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20c}$ is independently propyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20c}$ is independently isopropyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20c}$ is independently butyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^2$ is independently tert-butyl optionally substituted with one, two, or three substituents independently selected from halogen, —OH, —CN, $C_{1-3}$ alkyl, $C_{1-3}$ haloalkyl, and $C_{3-6}$ cycloalkyl.

In embodiments, $R^{20c}$ is independently unsubstituted cyclopropyl. In embodiments, $R^{20c}$ is independently unsubstituted cyclobutyl. In embodiments, $R^{20c}$ is independently unsubstituted cyclopentyl.

In embodiments, $R^{20c}$ is independently cyclopropyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20c}$ is independently cyclopropyl optionally substituted with one, $C_{1-3}$ alkyl. In embodiments, $R^{20c}$ is independently cyclopropyl optionally substituted with one methyl. In embodiments, $R^{20c}$ is independently cyclobutyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20c}$ is independently cyclopentyl optionally substituted with one, two, or three substituents independently selected from halogen, —OH, —CN, $C_{1-3}$ alkyl, $C_{1-3}$ haloalkyl, and $C_{3-6}$ cycloalkyl.

In embodiments, $R^{20d}$ is independently hydrogen. In embodiments, $R^{20d}$ is independently halogen. In embodiments, $R^{20d}$ is independently —OH. In embodiments, $R^{20d}$ is independently —CN. In embodiments, $R^{20d}$ is independently unsubstituted $C_{1-6}$ alkyl. In embodiments, $R^{20d}$ is independently unsubstituted $C_{3-6}$ cycloalkyl.

In embodiments, $R^{20d}$ is independently unsubstituted methyl. In embodiments, $R^{20d}$ is independently unsubstituted ethyl. In embodiments, $R^{20d}$ is independently unsubstituted propyl. In embodiments, $R^{20d}$ is independently unsubstituted isopropyl. In embodiments, $R^{20d}$ is independently unsubstituted butyl. In embodiments, $R^{20d}$ is independently unsubstituted tert-butyl.

In embodiments, $R^{20d}$ is independently methyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20d}$ is independently ethyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20d}$ is independently propyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20d}$ is independently isopropyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^2$ is independently butyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^2$ is independently tert-butyl optionally substituted with one, two, or three substituents independently selected from halogen, —OH, —CN, $C_{1-3}$ alkyl, $C_{1-3}$ haloalkyl, and $C_{3-6}$ cycloalkyl.

In embodiments, $R^{20d}$ is independently unsubstituted cyclopropyl. In embodiments, $R^{20d}$ is independently unsubstituted cyclobutyl. In embodiments, $R^{20d}$ is independently unsubstituted cyclopentyl.

In embodiments, $R^{20d}$ is independently cyclopropyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20d}$ is independently cyclopropyl optionally substituted with one, $C_{1-3}$ alkyl. In embodiments, $R^2$ is independently cyclopropyl optionally substituted with one methyl. In embodiments, $R^{20d}$ is independently cyclobutyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20d}$ is independently cyclopentyl optionally substituted with one, two, or three substituents independently selected from halogen, —OH, —CN, $C_{1-3}$ alkyl, $C_{1-3}$ haloalkyl, and $C_{3-6}$ cycloalkyl.

In embodiments, $R^{20e}$ is independently hydrogen. In embodiments, $R^{20e}$ is independently halogen. In embodiments, $R^{20e}$ is independently —OH. In embodiments, $R^{20e}$ is independently —CN. In embodiments, $R^{20e}$ is independently unsubstituted $C_{1-6}$ alkyl. In embodiments, $R^{20e}$ is independently unsubstituted $C_{3-6}$ cycloalkyl.

In embodiments, $R^{20e}$ is independently unsubstituted methyl. In embodiments, $R^{20e}$ is independently unsubstituted ethyl. In embodiments, $R^{20e}$ is independently unsubstituted propyl. In embodiments, $R^{20e}$ is independently unsubstituted isopropyl. In embodiments, $R^{20e}$ is independently unsubstituted butyl. In embodiments, $R^{20e}$ is independently unsubstituted tert-butyl.

In embodiments, $R^{20e}$ is independently methyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20e}$ is independently ethyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20e}$ is independently propyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20e}$ is independently isopropyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20e}$ is independently butyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20e}$ is independently tert-butyl optionally substituted with one, two, or three substituents independently selected from halogen, —OH, —CN, $C_{1-3}$ alkyl, $C_{1-3}$ haloalkyl, and $C_{3-6}$ cycloalkyl.

In embodiments, $R^{20e}$ is independently unsubstituted cyclopropyl. In embodiments, $R^{20e}$ is independently unsubstituted cyclobutyl. In embodiments, $R^{20e}$ is independently unsubstituted cyclopentyl.

In embodiments, $R^{20e}$ is independently cyclopropyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20e}$ is independently cyclopropyl optionally substituted with one, $C_{1-3}$ alkyl. In embodiments, $R^{20e}$ is independently cyclopropyl optionally substituted with one methyl. In embodiments, $R^{20e}$ is independently cyclobutyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20e}$ is independently cyclopentyl optionally substituted with one, two, or three substituents independently selected from halogen, —OH, —CN, $C_{1-3}$ alkyl, $C_{1-3}$ haloalkyl, and $C_{3-6}$ cycloalkyl.

In embodiments, $R^{20f}$ is independently hydrogen. In embodiments, $R^{20f}$ is independently halogen. In embodiments, $R^{20f}$ is independently —OH. In embodiments, $R^{20f}$ is independently —CN. In embodiments, $R^{20f}$ is independently unsubstituted $C_{1-6}$ alkyl. In embodiments, $R^{20}$ is independently unsubstituted $C_{3-6}$ cycloalkyl.

In embodiments, $R^{20}$ is independently unsubstituted methyl. In embodiments, $R^{20}$ is independently unsubstituted ethyl. In embodiments, $R^{20}$ is independently unsubstituted propyl. In embodiments, $R^{20}$ is independently unsubstituted isopropyl. In embodiments, $R^{20f}$ is independently unsubstituted butyl. In embodiments, $R^{20f}$ is independently unsubstituted tert-butyl.

In embodiments, $R^{20f}$ is independently methyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20f}$ is independently ethyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20}$ is independently propyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20}$ is independently isopropyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20}$ is independently butyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20f}$ is independently tert-butyl optionally substituted with one, two, or three substituents independently selected from halogen, —OH, —CN, $C_{1-3}$ alkyl, $C_{1-3}$ haloalkyl, and $C_{3-6}$ cycloalkyl.

In embodiments, $R^{20f}$ is independently unsubstituted cyclopropyl. In embodiments, $R^{20f}$ is independently unsubstituted cyclobutyl. In embodiments, $R^{20}$ is independently unsubstituted cyclopentyl.

In embodiments, $R^{20}$ is independently cyclopropyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20}$ is independently cyclopropyl optionally substituted with one, $C_{1-3}$ alkyl. In embodiments, $R^{20}$ is independently cyclopropyl optionally substituted with one methyl. In embodiments, $R^{20f}$ is independently cyclobutyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20f}$ is independently cyclopentyl optionally substituted with one, two, or three substituents independently selected from halogen, —OH, —CN, $C_{1-3}$ alkyl, $C_{1-3}$ haloalkyl, and $C_{3-6}$ cycloalkyl.

In embodiment of a compound of Formula I, IA, IB, II, or IIA, $L^{19a}$ is selected from $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, —$N(R^{12})$—, —C(O)—, —$N(R^{12})$C (O)—, —C(O)N($R^{12}$)—, —S—, —S(O)$_2$—, —S(O)—, —P(O)($R^{12}$)—, —N($R^{12}$)S(O)$_2$—, —N($R^{12}$)S(O)—, —N($R^{12}$)P(O)($R^{12}$)—, —S(O)$_2$N($R^{12}$)—, —S(O)N($R^{12}$)—, —P(O)($R^{12}$)N($R^{12}$)—, —OP(O)($R^{12}$)—, and —P(O)($R^{12}$)O—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$. In embodiment of a compound of Formula I, IA, IB, II, or IIA, $L^{19a}$ is selected from $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, —N(H)—, —C(O)—, —N(H)C(O)—, —C(O)N(H)—, —S—, —S(O)$_2$—, —S(O)—, —P(O)($R^{12}$)—, —N(H)S(O)$_2$—, —N(H)S(O)—, —N(H)P(O)($R^{12}$)—, —S(O)$_2$N(H)—, —S(O)N(H)—, —P(O)($R^{12}$)N(H)—, —OP(O)($R^{12}$)—, and —P(O)($R^{12}$)O—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$. In embodiment of a compound of Formula I, IA, IB, II, or IIA, $L^{19a}$ is selected from $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, —N($CH_3$)—, —C(O)—, —N($CH_3$)C(O)—, —C(O)N($CH_3$)—, —S—, —S(O)$_2$—, —S(O)—, —P(O)($CH_3$)—, —N($CH_3$)S(O)$_2$—, —N($CH_3$)S(O)—, —N($CH_3$)P(O)($CH_3$)—, —S(O)$_2$N($CH_3$)—, —S(O)N($CH_3$)—, —P(O)($CH_3$)N($CH_3$)—, —OP(O)($CH_3$)—, and —P(O)($CH_3$)O—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$.

In embodiments of a compound of formula I, IA, IB, II, or IIA, $L^{19a}$ is selected from —C(O)—, —N($R^{12}$)C(O)—, —C(O)N($R^{12}$)—, —S(O)$_2$—, —S(O)—, —P(O)($R^{12}$)—, —N($R^{12}$)S(O)$_2$—, —N($R^{12}$)S(O)—, —N($R^{12}$)P(O)($R^{12}$)—, —S(O)$_2$N($R^{12}$)—, —S(O)N($R^{12}$)—, and —P(O)($R^{12}$)N($R^{12}$)—. In embodiments of a compound of formula I, IA, IB, II, or IIA, $L^{19a}$ is selected from —C(O)—, —S(O)$_2$—, and —S(O)—. In embodiments of a compound of formula I, IA, IB, II, or IIA, $L^{19a}$ is selected from —C(O)— and —N($R^{12}$)C(O)—. In embodiments of a compound of formula I, IA, IB, II, IIA, or V, $L^{19a}$ is —N($R^{12}$)C(O)—. In embodiments of a compound of formula I, IA, IB, II, IIA, or V, $L^{19a}$ is —N(H)C(O)—. In embodiments of a compound of formula I, IA, IB, II, IIA, or V, $L^{19a}$ is —N($CH_3$)C(O)—. In embodiments of a compound of formula I, IA, IB, II, IIA, or V, $L^{19a}$ is —C(O)—.

In embodiments of a compound of formula I, IA, IB, II, or IIA, $L^{19a}$ is selected from $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, —N($R^{12}$)—, —C(O)—, —N($R^{12}$)C(O)—, —C(O)N($R^{12}$)—, —S—, —S(O)$_2$—, —S(O)—, —P(O)($R^{12}$)—, —N($R^{12}$)S(O)$_2$—, —N($R^{12}$)S(O)—, —N($R^{12}$)P(O)($R^{12}$)—, —S(O)$_2$N($R^{12}$)—, —S(O)N($R^{12}$)—, —P(O)($R^{12}$)N($R^{12}$)—, —OP(O)($R^{12}$)—, and —P(O)($R^{12}$)O—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$. In embodiments of a compound of formula I, IA, IB, II, or IIA, $L^{19a}$ is selected from —N($R^{12}$)C(O)—, —C(O)N($R^{12}$)—, —N($R^{12}$)S(O)$_2$—, —N($R^{12}$)S(O)—, —N($R^{12}$)P(O)($R^{12}$)—, —S(O)$_2$N($R^{12}$)—, —S(O)N($R^{12}$)—, and —P(O)($R^{12}$)N($R^{12}$)—. In embodiments of a compound of formula I, IA, IB, II, or IIA, $L^{19a}$ is selected from —C(O)—, —S(O)$_2$—, —S(O)—, and —P(O)($R^{12}$)—.

In embodiments of a compound of Formula I, IA, II, IIA, or V, $R^{19a}$ is 5-membered heteroaryl having one or two ring nitrogen atoms, wherein the 5-membered heteroaryl is directly bonded to $L^{19a}$ through an $R^{19a}$ ring nitrogen atom and wherein $R^{19a}$ is optionally substituted with one or more $R^{20}$. In embodiments of a compound of Formula I, IA, II, IIA, or V, $R^{19a}$ is selected from pyrrolyl, imidazolyl, and pyrazolyl; wherein $R^{19a}$ is directly bonded to $L^{19a}$ through an $R^{19a}$ ring nitrogen atom; and wherein $R^{19a}$ is optionally substituted with one or more $R^{20}$. In embodiments of a compound of formula I, IB, II, or IIA, $R^{19a}$ is a non-aromatic 5- to 12-membered heterocycle comprising three or four ring nitrogen atoms; wherein $R^{19a}$ is optionally substituted with one or more $R^{20}$. In embodiments of a compound of formula I, IB, II, or IIA, $R^{19a}$ is a 5- to 12-membered heteroaryl comprising three or four ring nitrogen atoms; wherein $R^{19a}$ is optionally substituted with one or more $R^{20}$. In embodiments of a compound of formula I, IB, II, or IIA, $R^{19a}$ is a 9- to 12-membered heteroaryl comprising three or four ring nitrogen atoms; wherein $R^{19a}$ is optionally substituted with one or more $R^{20}$. In embodiments of a compound of Formula I, IA, IB, II, IIA, or V, $R^{19a}$ is a 5- to 6-membered heteroaryl comprising three or four ring nitrogen atoms; wherein $R^{19a}$ is optionally substituted with one or more $R^{20}$. In embodiments of a compound of Formula I, IA, IB, II, IIA, or V, $R^{19a}$ is selected from triazolyl and tetrazolyl; wherein $R^{19a}$ is optionally substituted with one or more $R^{20}$. In embodiments of a compound of Formula I, IA, IB, II, IIA, or V, $R^{19a}$ is selected from triazolyl and tetrazolyl; wherein $R^{19a}$ is directly bonded to $L^{19a}$ through an $R^{19a}$ ring nitrogen atom; and wherein $R^{19a}$ is optionally substituted with one or more $R^{20}$. In embodiments of a compound of Formula I, IA, IB, II, IIA, or V, $R^{19a}$ is selected from triazolyl and imidazolyl; wherein $R^{19a}$ is directly bonded to $L^{19a}$ through an $R^{19a}$ ring nitrogen atom; and wherein $R^{19a}$ is optionally substituted with one or more $R^{20}$. In embodiments of a compound of Formula I, IA, IB, II, IIA, or V, $R^{19a}$ is selected from 1,2,3-triazolyl and 1,2,4-triazolyl; wherein $R^{19a}$ is optionally substituted with one or more $R^{20}$. In embodiments of a compound of Formula I, IA, IB, II, IIA, or V, $R^{19a}$ is selected from 1,2,3-triazolyl and 1,2,4-triazolyl; wherein $R^{19a}$ is directly bonded to $L^{19a}$ through an $R^{19a}$ ring nitrogen atom; and wherein $R^{19a}$ is optionally substituted with one or more $R^{20}$. In embodiments of a compound of Formula I, IA, IB, II, IIA, or V, $R^{19a}$ is optionally substituted with one or more substituents independently selected from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, and 3- to 6-membered heteroalkynyl; wherein $C_{1-6}$ alkyl, $C_{2-6}$ alkenyl, $C_{2-6}$ alkynyl, 2- to 6-membered heteroalkyl, 3- to 6-membered heteroalkenyl, and 3- to 6-membered heteroalkynyl are optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, —$OR^{22}$, —$SR^{22}$, —N($R^{22}$)($R^{23}$), =$NR^{22}$, =C($R^{21}$)$_2$, —C(O)$OR^{22}$, —OC(O)N($R^{22}$)($R^{23}$), —N($R^{22}$)C(O)N($R^{22}$)($R^{23}$), —N($R^{22}$)C(O)$OR^{22}$, —N($R^{22}$)S(O)$_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S(O)$_2R^{22}$, —S(O)($NR^{22}$)$R^{22}$, —S(O)$_2$N($R^{22}$)($R^{23}$), and —S(=O)(=$NR^{22}$)N($R^{22}$)($R^{23}$). In embodiments of a compound of Formula I, IA, IB, II, IIA, or V, $R^{19a}$ is optionally substituted with one or more substituents independently selected from halogen, —CN, and $C_{1-6}$ alkyl, wherein $C_{1-6}$ alkyl is optionally substituted with one or more substituents independently selected from halogen, oxo, —CN, —$OR^{22}$, —$SR^{22}$, and —$N(R^{22})(R^{23})$. In embodiments of a compound of Formula I, IA, IB, II, IIA, or V, $R^{19a}$ is optionally substituted with one or more substituents independently selected from —F, —Cl, —Br, and —I. In embodiments of a compound of Formula I, IA, IB, II, IIA, or V, $R^{19a}$ is optionally substituted with one $R^{20}$ selected from —F and —Cl. In embodiments of a compound of Formula I, IA, IB, II, IIA, or V, $R^{19a}$ is selected from

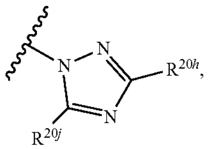

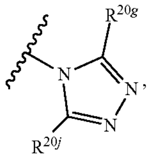

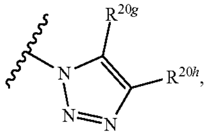

and

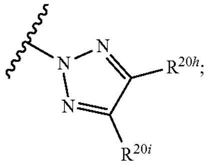

wherein $R^{20g}$, $R^{20h}$, $R^{20i}$, and $R^{20j}$ are independently selected at each occurrence from hydrogen and $R^{20}$.

In embodiments, $R^{20g}$ is independently methyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20g}$ is independently ethyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20g}$ is independently propyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20g}$ is independently isopropyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20g}$ is independently butyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20g}$ is independently tert-butyl optionally substituted with one, two, or three substituents independently selected from halogen, —OH, —CN, $C_{1-3}$ alkyl, $C_{1-3}$ haloalkyl, and $C_{3-6}$ cycloalkyl.

In embodiments, $R^{20g}$ is independently unsubstituted cyclopropyl. In embodiments, $R^{20g}$ is independently unsubstituted cyclobutyl. In embodiments, $R^{20g}$ is independently unsubstituted cyclopentyl.

In embodiments, $R^{20g}$ is independently cyclopropyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20g}$ is independently cyclopropyl optionally substituted with one, $C_{1-3}$ alkyl. In embodiments, $R^{20g}$ is independently cyclopropyl optionally substituted with one methyl. In embodiments, $R^{20g}$ is independently cyclobutyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20g}$ is independently cyclopentyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20g}$ is independently a halogen. In embodiments, $R^{20g}$ is independently F. In embodiments, $R^{20g}$ is independently Cl. In embodiments, $R^{20g}$ is independently I. In embodiments, $R^{20g}$ is independently Br. In embodiments, $R^{20g}$ is independently unsubstituted methyl. In embodiments, $R^{20g}$ is independently unsubstituted ethyl. In embodiments, $R^{20g}$ is independently unsubstituted isopropyl. In embodiments, $R^{20g}$ is independently unsubstituted tert-butyl. In embodiments, $R^{20g}$ is independently CN. In embodiments, $R^{20g}$ is independently $CF_3$. In embodiments, $R^{20g}$ is independently —$CHF_2$. In embodiments, $R^{20g}$ is independently —$CH_2CN$. In embodiments, $R^{20g}$ is independently —$CH_2OH$. In embodiments, $R^{20g}$ is independently —CH2F. In embodiments, $R^{20g}$ is independently —$CH_2Cl$. In embodiments, $R^{20g}$ is independently —CH2I. In embodiments, $R^{20g}$ is independently —$CH_2Br$. In embodiments, $R^{20g}$ is independently hydrogen.

In embodiments, $R^{2h}$ is independently methyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20h}$ is independently ethyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20h}$ is independently propyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20h}$ is independently isopropyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20h}$ is independently butyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20h}$ is independently tert-butyl optionally substituted with one, two, or three substituents independently selected from halogen, —OH, —CN, $C_{1-3}$ alkyl, $C_{1-3}$ haloalkyl, and $C_{3-6}$ cycloalkyl.

In embodiments, $R^{20h}$ is independently unsubstituted cyclopropyl. In embodiments, $R^{20h}$ is independently unsubstituted cyclobutyl. In embodiments, $R^{20h}$ is independently unsubstituted cyclopentyl.

In embodiments, $R^{20h}$ is independently cyclopropyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20h}$ is independently cyclopropyl optionally substituted with one, $C_{1-3}$ alkyl. In embodiments, $R^{20h}$ is independently cyclopropyl optionally substituted with one methyl. In embodiments, $R^{20h}$ is independently cyclobutyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20h}$ is independently cyclopentyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20h}$ is independently a halogen. In embodiments, $R^{20h}$ is independently F. In embodiments, $R^{20h}$ is independently Cl. In embodiments, $R^{20h}$ is independently I. In embodiments, $R^{20h}$ is independently Br. In embodiments, $R^{20h}$ is independently unsubstituted methyl. In embodiments, $R^{20h}$ is independently unsubstituted ethyl. In embodiments, $R^{20h}$ is independently unsubstituted isopropyl. In embodiments, $R^{20h}$ is independently unsubstituted tert-butyl. In embodiments, $R^{20h}$ is independently CN. In embodiments, $R^{20h}$ is independently $CF_3$. In embodiments, $R^{20h}$ is independently —$CHF_2$. In embodiments, $R^{20h}$ is independently —$CH_2CN$. In embodiments, $R^{20h}$ is independently —$CH_2OH$. In embodiments, $R^{20h}$ is independently —$CH_2F$. In embodiments, $R^{20h}$ is independently —$CH_2Cl$. In embodiments, $R^{20h}$ is independently —$CH_2I$. In embodiments, $R^{20h}$ is independently —$CH_2Br$. In embodiments, $R^{20h}$ is independently hydrogen.

In embodiments, $R^{20i}$ is independently methyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20i}$ is independently ethyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20}$ is independently propyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20i}$ is independently isopropyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20i}$ is independently butyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^2$ is independently tert-butyl optionally substituted with one, two, or three substituents independently selected from halogen, —OH, —CN, $C_{1-3}$ alkyl, $C_{1-3}$ haloalkyl, and $C_{3-6}$ cycloalkyl.

In embodiments, $R^{20i}$ is independently unsubstituted cyclopropyl. In embodiments, $R^{20i}$ is independently unsubstituted cyclobutyl. In embodiments, $R^{20i}$ is independently unsubstituted cyclopentyl.

In embodiments, $R^{20i}$ is independently cyclopropyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20i}$ is independently cyclopropyl optionally substituted with one, $C_{1-3}$ alkyl. In embodiments, $R^{20i}$ is independently cyclopropyl optionally substituted with one methyl. In embodiments, $R^{20i}$ is independently cyclobutyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20i}$ is independently cyclopentyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20i}$ is independently a halogen. In embodiments, $R^{20i}$ is independently F. In embodiments, $R^{20i}$ is independently Cl. In embodiments, $R^{20i}$ is independently I. In embodiments, $R^{20i}$ is independently Br. In embodiments, $R^{20i}$ is independently unsubstituted methyl. In embodiments, $R^{20i}$ is independently unsubstituted ethyl. In embodiments, $R^{20i}$ is independently unsubstituted isopropyl. In embodiments, $R^2$ is independently unsubstituted tert-butyl. In embodiments, $R^{20i}$ is independently CN. In embodiments, $R^{20i}$ is independently $CF_3$. In embodiments, $R^{20i}$ is independently —$CHF_2$. In embodiments, $R^{20i}$ is independently —$CH_2CN$. In embodiments, $R^{20i}$ is independently —$CH_2OH$. In embodiments, $R^2$ is independently —$CH_2F$. In embodiments, $R^{20i}$ is independently —$CH_2Cl$. In embodiments, $R^{20i}$ is independently —$CH_2I$. In embodiments, $R^{20}$ is independently —$CH_2Br$. In embodiments, $R^{20i}$ is independently hydrogen.

In embodiments, $R^{20j}$ is independently methyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20j}$ is independently ethyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20j}$ is independently propyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20j}$ is independently isopropyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20j}$ is independently butyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20h}$ is independently tert-butyl optionally substituted with one, two, or three substituents independently selected from halogen, —OH, —CN, $C_{1-3}$ alkyl, $C_{1-3}$ haloalkyl, and $C_{3-6}$ cycloalkyl.

In embodiments, $R^{20j}$ is independently unsubstituted cyclopropyl. In embodiments, $R^{20j}$ is independently unsubstituted cyclobutyl. In embodiments, $R^{20j}$ is independently unsubstituted cyclopentyl.

In embodiments, $R^{20j}$ is independently cyclopropyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20j}$ is independently cyclopropyl optionally substituted with one, $C_{1-3}$ alkyl. In embodiments, $R^{20j}$ is independently cyclopropyl optionally substituted with one methyl. In embodiments, $R^{20j}$ is independently cyclobutyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20j}$ is independently cyclopentyl optionally substituted with one, two, or three substituents independently selected from halogen, —OH, —CN, $C_{1-3}$ alkyl, $C_{1-3}$ haloalkyl, and $C_{3-6}$ cycloalkyl. In embodiments, $R^{20j}$ is independently a halogen. In embodiments, $R^{20j}$ is independently F. In embodiments, $R^{20j}$ is independently Cl. In embodiments, $R^{20j}$ is independently I. In embodiments, $R^{20j}$ is independently Br. In embodiments, $R^{20j}$ is independently unsubstituted methyl. In embodiments, $R^{20j}$ is independently unsubstituted ethyl. In embodiments, $R^{20j}$ is independently unsubstituted isopropyl. In embodiments, $R^{20j}$ is independently unsubstituted tert-butyl. In embodiments, $R^{20j}$ is independently CN. In embodiments, $R^{20j}$ is independently $CF_3$. In embodiments, $R^{20j}$ is independently —$CHF_2$. In embodiments, $R^{20j}$ is independently —$CH_2CN$. In embodiments, $R^{20j}$ is independently —$CH_2OH$. In embodiments, $R^{20j}$ is independently —$CH_2F$. In embodiments, $R^{20j}$ is independently —$CH_2Cl$. In embodiments, $R^{20j}$ is independently —$CH_2I$. In embodiments, $R^{20j}$ is independently —$CH_2Br$. In embodiments, $R^{20j}$ is independently hydrogen.

In embodiments of Formula I, IA, IB, II, IIA, or V, $R^{19a}$ is selected from

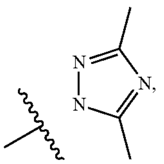 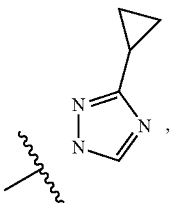 , 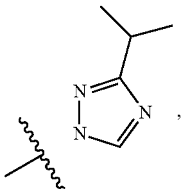 ,

-continued

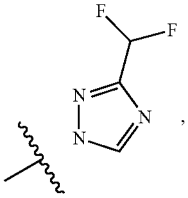 , 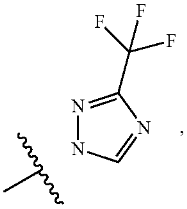 ,

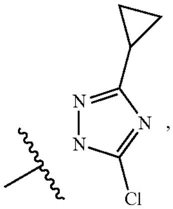 , 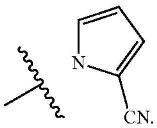

In embodiments of Formula I, IA, IB, II, IIA, or V, $R^{19a}$ is selected from imidazol-1-yl and 1,2,4-triazol-1-yl, each of which is optionally substituted with one or more $R^{20}$. In embodiments of Formula I, IA, IB, II, IIA, or V, $R^{19a}$ is imidazol-1-yl optionally substituted with one or more $R^{20}$. In embodiments of Formula I, IA, IB, II, IIA, or V, $R^{19a}$ is 1,2,4-triazol-1-yl optionally substituted with one or more $R^{20}$. In embodiments of a compound of Formula I, IA, IB, II, IIA, or V, $R^{19a}$ is selected from imidazol-1-yl and 1,2,4-triazol-1-yl; wherein $R^{19a}$ is optionally substituted with one or more $R^{20}$. In embodiments of a compound of Formula I, IA, IB, II, IIA, or V, $R^{19a}$ is selected from imidazol-1-yl and 1,2,4-triazol-1-yl; wherein $R^{19a}$ is directly bonded to $L^{19a}$ through an $R^{19a}$ ring nitrogen atom; and wherein $R^{19a}$ is optionally substituted with one or more $R^{20}$. In embodiments of Formula I, IA, IB, II, IIA, or V, $R^{19a}$ is selected from

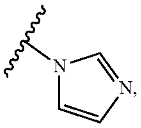 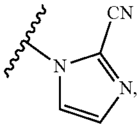 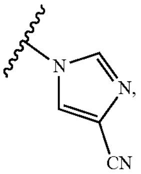

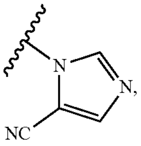 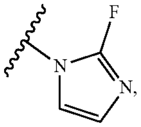 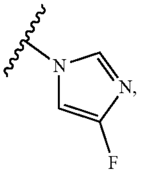

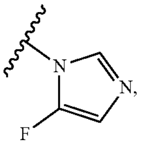 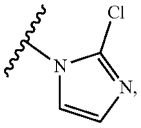 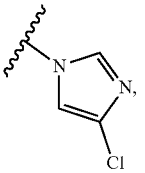

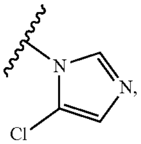 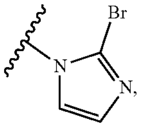 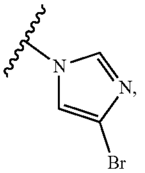

-continued

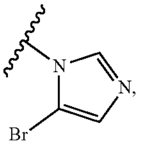 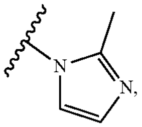 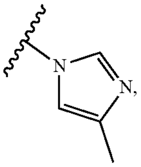

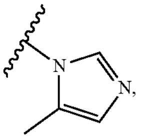 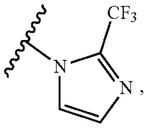 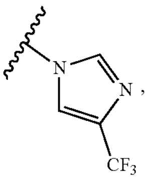

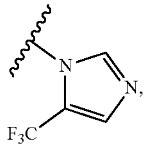 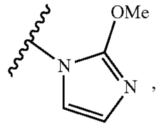 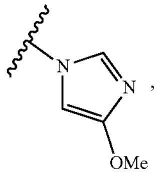

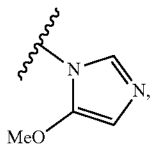 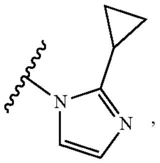 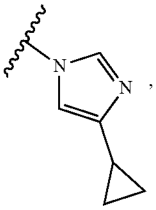

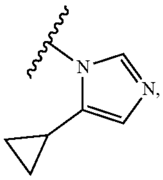 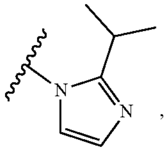 , 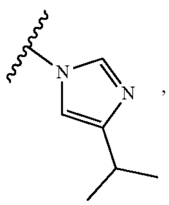 ,

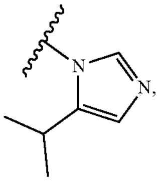 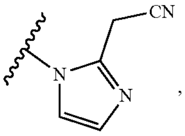 ,

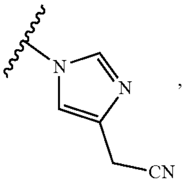 , 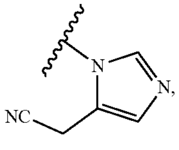 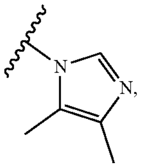

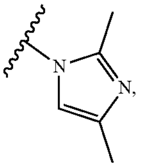 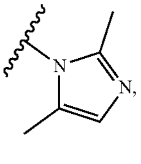 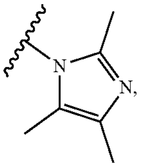

-continued
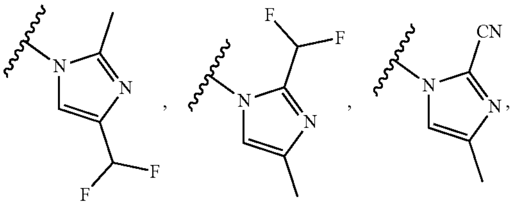
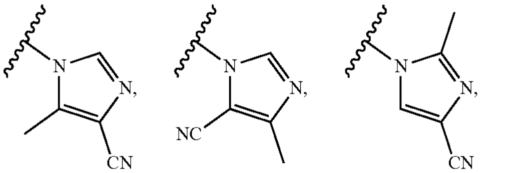
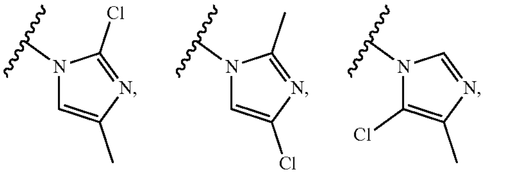
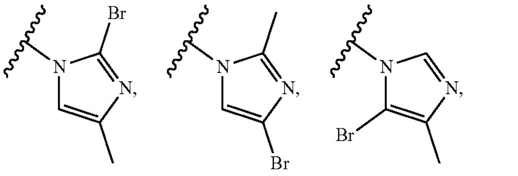
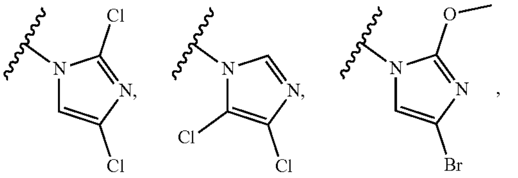
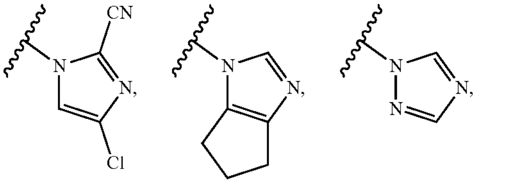
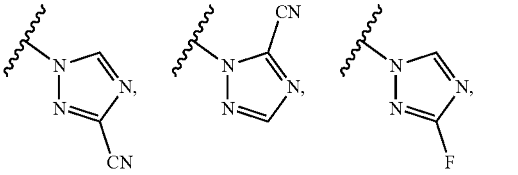
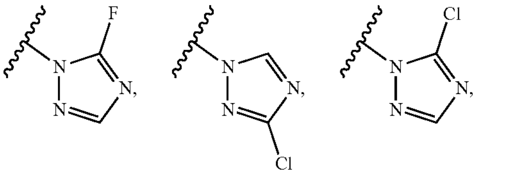
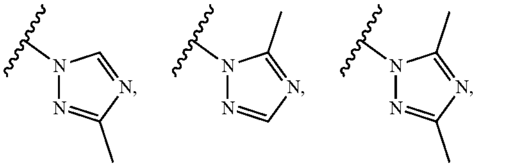
-continued
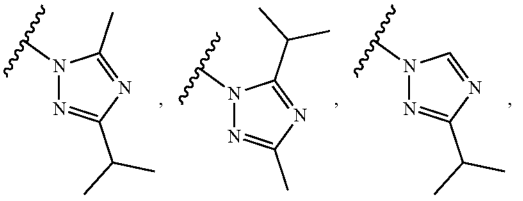
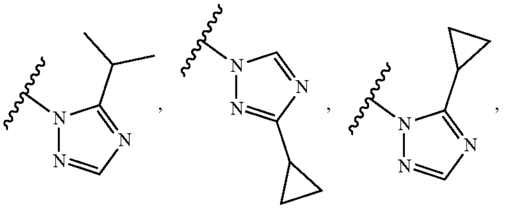
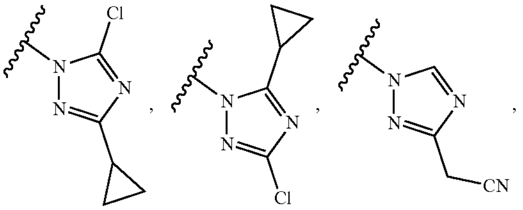
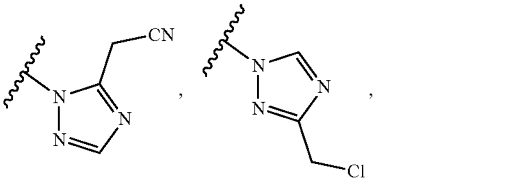
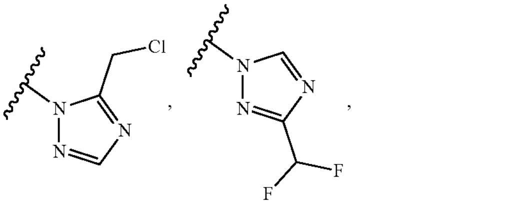
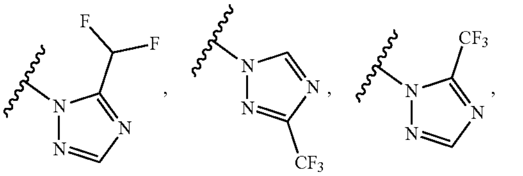
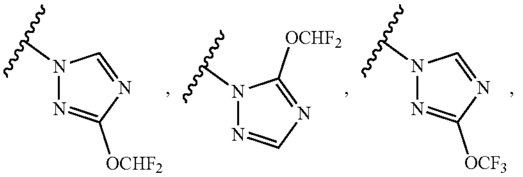
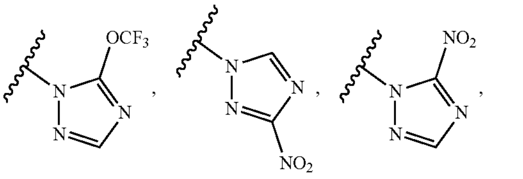
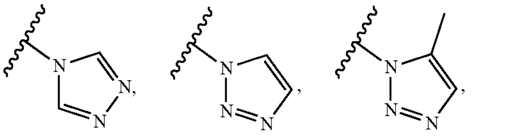

-continued
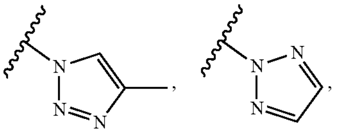
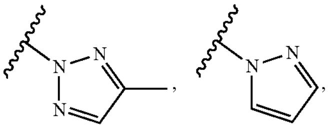
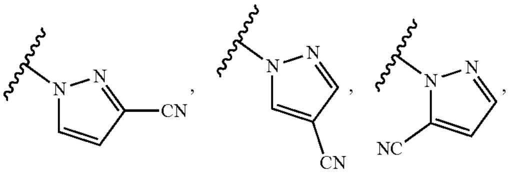
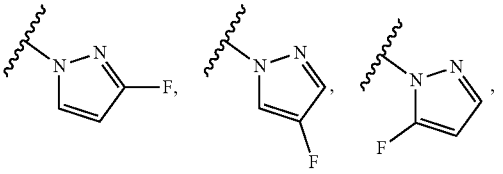
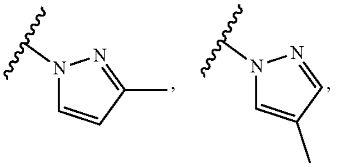
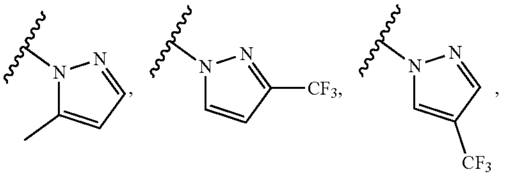
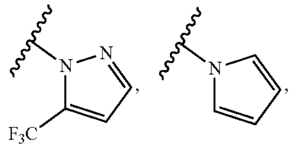
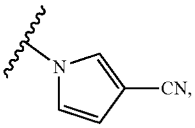
and
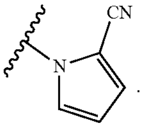
In embodiments of Formula I, IA, IB, II, IIA, or V, $R^{19a}$ is selected from
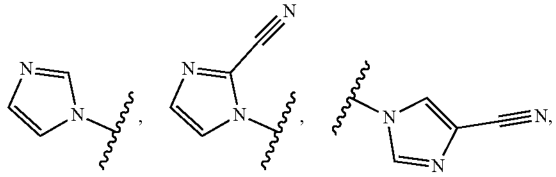
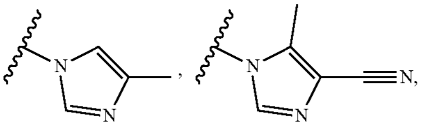
-continued
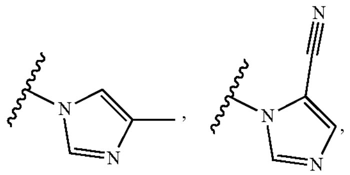
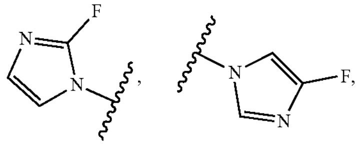
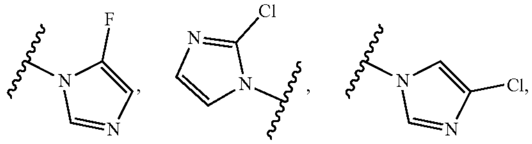
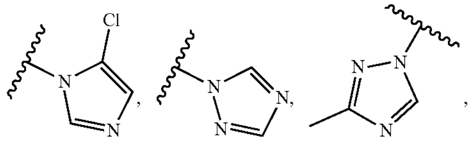
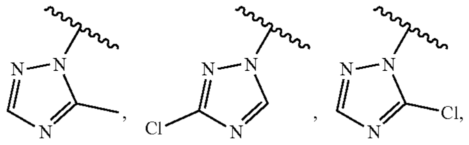
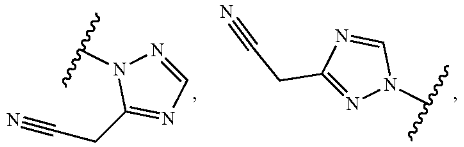
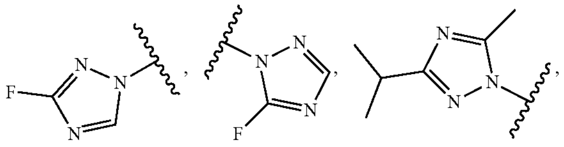
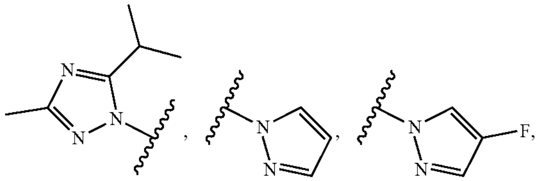
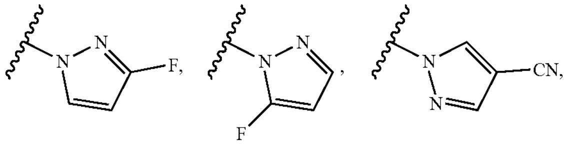
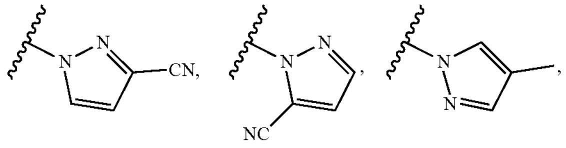
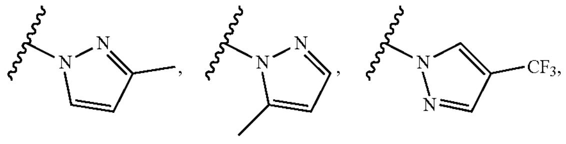

-continued
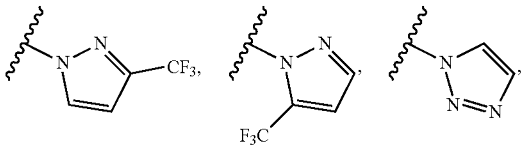
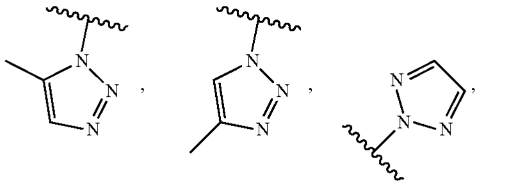
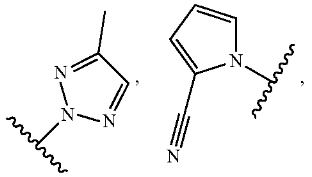
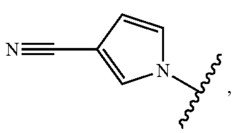
and
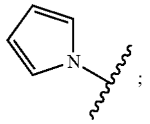
each of which is optionally substituted with one or more $R^{20k}$. In embodiments of Formula I, IA, IB, II, IIA, or V, $R^{19a}$ is selected from
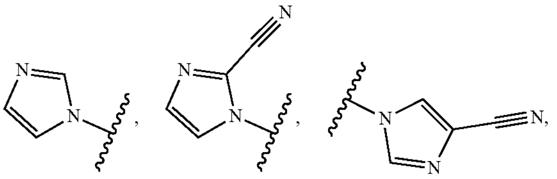
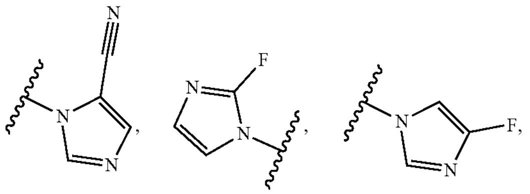
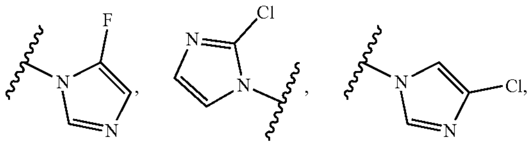
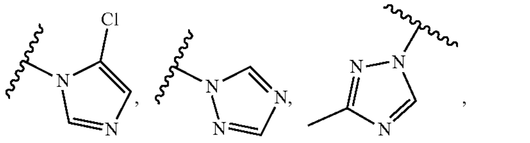
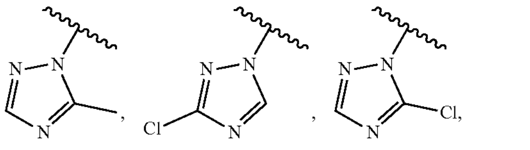
-continued
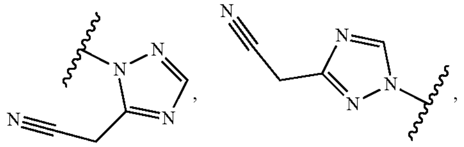
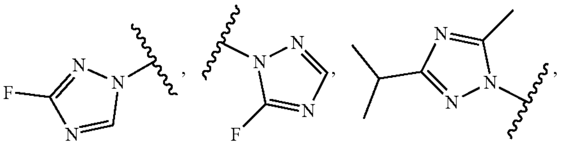
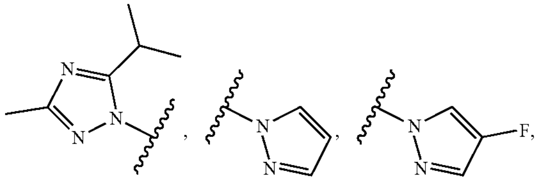
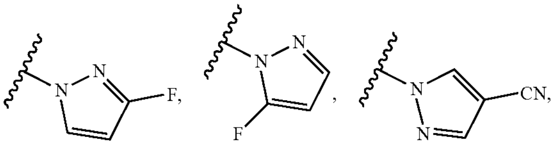
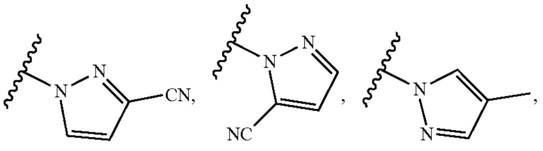
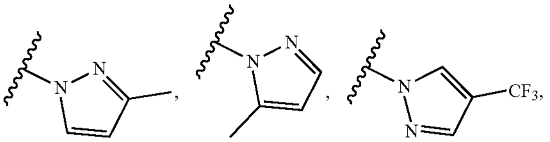
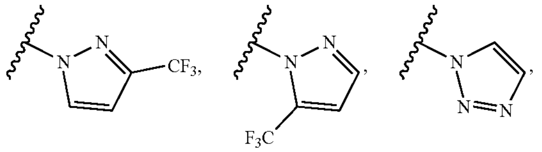
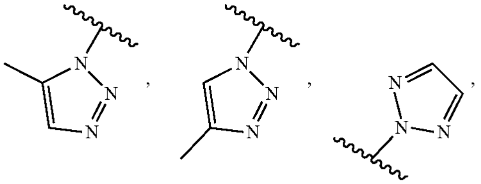
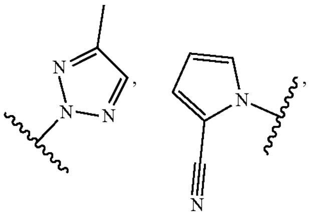
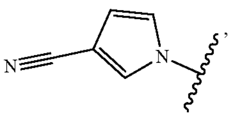
and
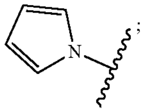
each of which is optionally substituted with one or more $R^{20k}$.
In embodiments of Formula I, IA, IB, II, IIA, or V, $R^{19a}$ is selected from

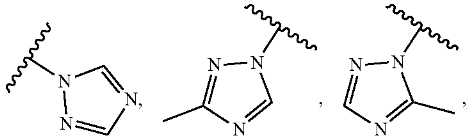
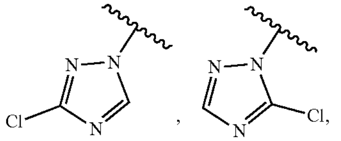
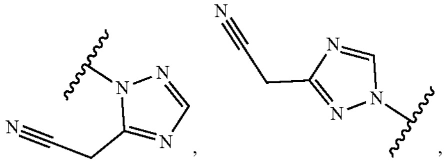
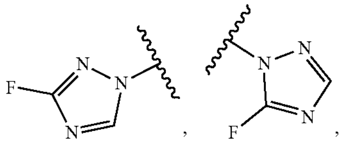
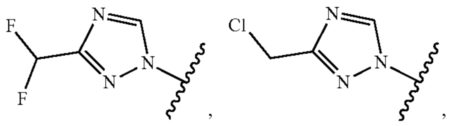
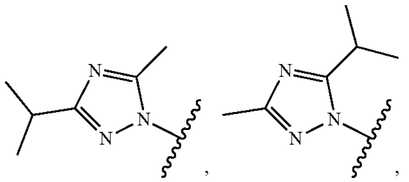
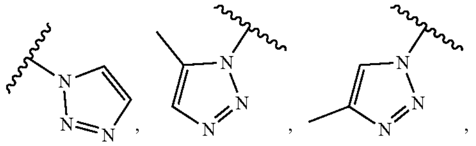
and
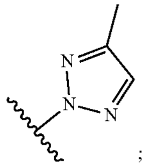
;
each of which is optionally substituted with one or more $R^{20k}$.
In embodiments of Formula I, IA, IB, II, IIA, or V, $R^{19a}$ is selected from
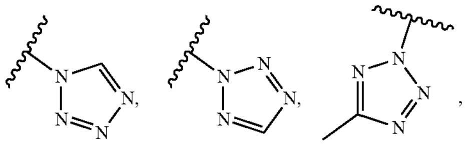
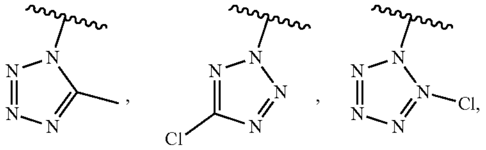
-continued
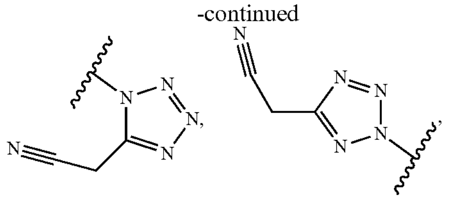
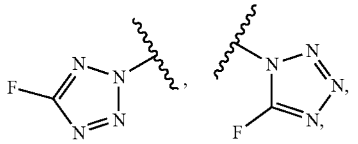
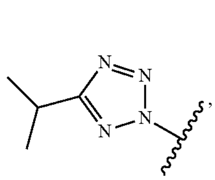
and
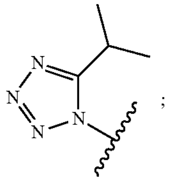
;
each of which is optionally substituted with one or more $R^{20k}$.
In embodiments of a compound of Formula I, IA, IB, II, IIA, or V, $R^{19a}$ is selected from
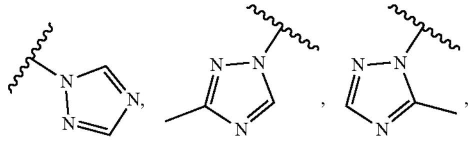
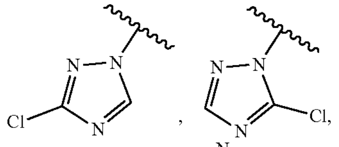
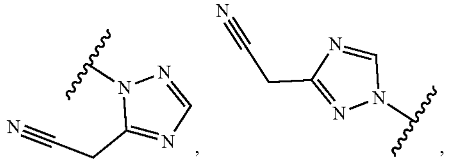
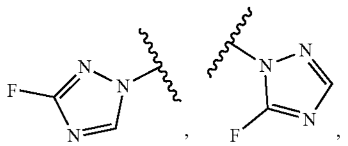
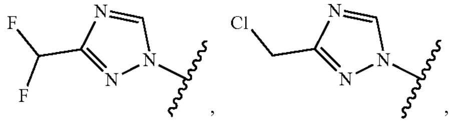
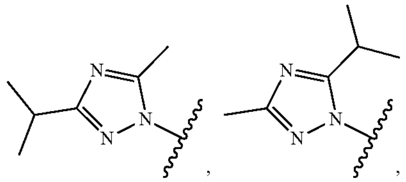
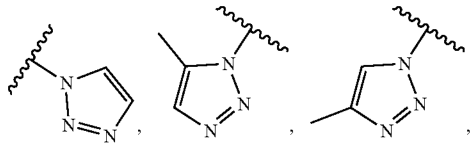

-continued

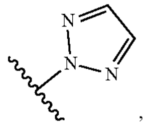

, and

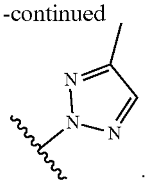

.

In embodiments of a compound of formula II or IIA, $R^{19a}$ is selected from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(=O)(=NR^{12})N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$. In embodiments of a compound of formula II or IIA, $R^{19a}$ is selected from $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, wherein $C_{1-6}$ alkyl, $C_{2-6}$ alkenyl, $C_{2-6}$ alkynyl, 2- to 6-membered heteroalkyl, 3- to 6-membered heteroalkenyl, and 3- to 6-membered heteroalkynyl are optionally substituted with one or more $R^{20}$.

In embodiments of a compound of formula II or IIA, $R^{19a}$ is selected from $C_2$ alkenyl and $C_2$ alkynyl, wherein $C_2$ alkenyl and $C_2$ alkynyl are optionally substituted with one or more $R^{20}$. In embodiments of a compound of formula II or IIA, $R^{19a}$ is -(3- to 12-membered heterocycle), wherein -(3- to 12-membered heterocycle) is optionally substituted with one or more $R^{20}$. In embodiments of a compound of formula II or IIA, $R^{19a}$ is 5-membered heteroaryl, wherein 5-membered heteroaryl is optionally substituted with one or more $R^{20}$. In embodiments of a compound of formula II or IIA, $R^{19a}$ is methyl substituted with one halogen selected from Cl and F.

In embodiments of a compound of Formula I, IA, IB, II, IIA, or V, $R^{19a}$ is a 5-membered heteroaryl comprising one or more nitrogen atoms, wherein the 5-membered heteroaryl is directly bonded to $L^{19a}$ through an $R^{19a}$ ring nitrogen atom and wherein $R^{19a}$ is optionally substituted with one or more $R^{20}$. In embodiments of a compound of Formula I, IA, IB, II, IIA, or V, $R^{19a}$ is a 5-membered heteroaryl comprising one or more ring nitrogen atoms, wherein the 5-membered heteroaryl is directly bonded to $L^{19a}$ through an $R^{19a}$ ring nitrogen atom and wherein $R^{19a}$ is substituted with one or more $R^{20}$. In embodiments of a compound of Formula I, IA, IB, II, IIA, or V, $R^{19a}$ is a 5-membered heteroaryl comprising one or more ring nitrogen atoms, wherein the 5-membered heteroaryl is directly bonded to $L^{19a}$ through an $R^{19a}$ ring nitrogen atom and wherein $R^{19a}$ is substituted with one or more $R^{20}$. In embodiments of a compound of Formula I, IA, IB, II, IIA, or V, $R^{19a}$ is a 5-membered heteroaryl comprising three or four ring nitrogen atoms, wherein the 5-membered heteroaryl is directly bonded to $L^{19a}$ through an $R^{19a}$ ring nitrogen atom and wherein $R^{19a}$ is substituted with one or more $R^{20}$.

In embodiments of a compound of Formula I, IA, IB, II, IIA, or V, $R^{19a}$ is a 5-membered heterocycle comprising three or four ring nitrogen atoms, wherein the 5-membered heterocycle is optionally substituted with one or more $R^{20}$. In embodiments of a compound of Formula I, IA, IB, II, IIA, or V, $R^{19a}$ is a 5-membered heterocycle comprising three or four ring nitrogen atoms, wherein the 5-membered heterocycle is substituted with one or more $R^{20}$. In embodiments of a compound of Formula I, IA, IB, II, IIA, or V, $R^{19a}$ is a 6-membered heterocycle comprising three or four ring nitrogen atoms, wherein the 6-membered heterocycle is optionally substituted with one or more $R^{20}$. In embodiments of a compound of Formula I, IA, IB, II, IIA, or V, $R^{19a}$ is a 6-membered heterocycle comprising three or four ring nitrogen atoms, wherein the 6-membered heterocycle is substituted with one or more $R^{20}$. In embodiments of a compound of formula I, IB, II, or IIA, $R^{19a}$ is a 7-membered heterocycle comprising three or four ring nitrogen atoms, wherein the 7-membered heterocycle is optionally substituted with one or more $R^{20}$. In embodiments of a compound of formula I, IB, II, or IIA, $R^{19a}$ is a 7-membered heterocycle comprising three or four ring nitrogen atoms, wherein the 7-membered heterocycle is substituted with one or more $R^{20}$. In embodiments of a compound of formula I, IB, II, or IIA, $R^{19a}$ is an 8-membered heterocycle comprising three or four ring nitrogen atoms, wherein the 8-membered heterocycle is optionally substituted with one or more $R^{20}$. In embodiments of a compound of formula I, IB, II, or IIA, $R^{19a}$ is an 8-membered heterocycle comprising three or four ring nitrogen atoms, wherein the 8-membered heterocycle is substituted with one or more $R^{20}$. In embodiments of a compound of formula I, IB, II, or IIA, $R^{19a}$ is a 9-membered heterocycle comprising three or four ring nitrogen atoms, wherein the 9-membered heterocycle is optionally substituted with one or more $R^{20}$. In embodiments of a compound of formula I, IB, II, or IIA, $R^{19a}$ is a 9-membered heterocycle comprising three or four ring nitrogen atoms, wherein the 9-membered heterocycle is substituted with one or more $R^{20}$. In embodiments of a compound of formula I, IB, II, or IIA, $R^{19a}$ is a 10-membered heterocycle comprising three or four ring nitrogen atoms, wherein the 10-membered heterocycle is optionally substituted with one or more $R^{20}$. In embodiments of a compound of formula I, IB, II, or IIA, $R^{19a}$ is a 10-membered heterocycle comprising three or four ring nitrogen atoms, wherein the 10-membered heterocycle is substituted with one or more $R^{20}$. In embodiments of a compound of formula I, IB, II, or IIA, $R^{19a}$ is an 11-membered heterocycle comprising three or four ring nitrogen atoms, wherein the 11-membered heterocycle is optionally substituted with one or more $R^{20}$. In embodiments of a compound of formula I, IB, II, or IIA, $R^{19a}$ is an 11-membered heterocycle comprising three or four ring nitrogen atoms, wherein the 11-membered heterocycle is substituted with one or more $R^{20}$. In embodiments of a compound of formula I, IB, II, or IIA, $R^{19a}$ is a 12-membered heterocycle comprising three or four ring nitrogen atoms, wherein the 12-membered heterocycle is optionally substituted with one or more $R^{20}$. In embodiments of a compound of formula I, IB, II, or IIA, $R^{19a}$ is a 12-membered heterocycle comprising three or four ring nitrogen atoms, wherein the 12-membered heterocycle is substituted with one or more $R^{20}$. In embodiments of a compound of formula I, IB, II, or IIA, $R^{19a}$ is a 5- to 12-membered heterocycle comprising three or four ring nitrogen atoms, wherein the 12-membered heterocycle is substituted with one or more $R^{20}$.

In embodiments of a compound of formula II or IIA, $-L^{19a}-R^{19a}$ is selected from

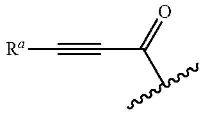,
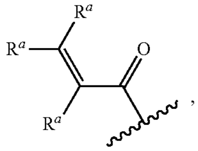,
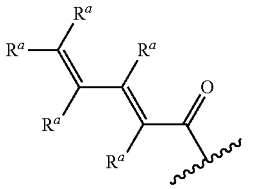,
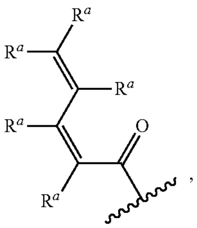,
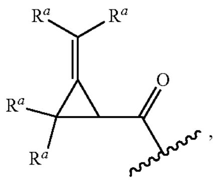,
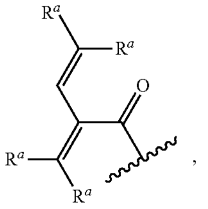,
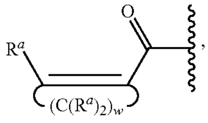,
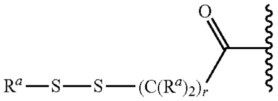,
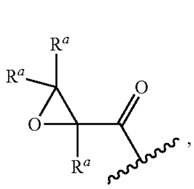,
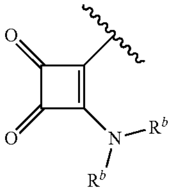,
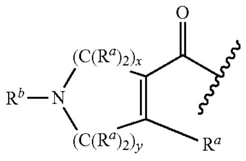,
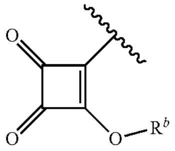,
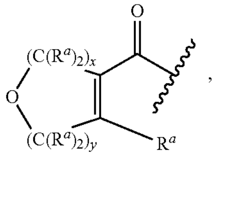,
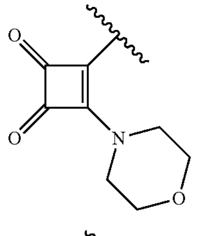,
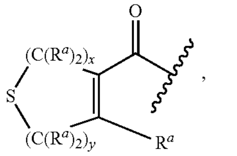,
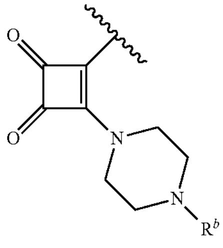, -continued

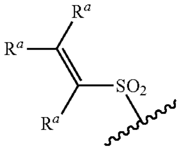,
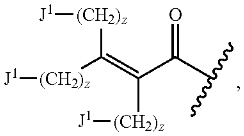,
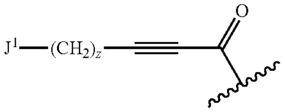,
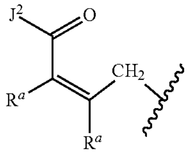,
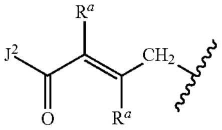,
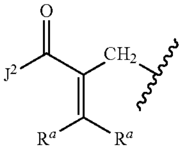,
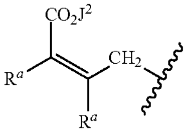,
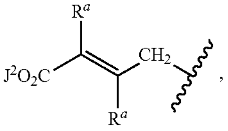, and
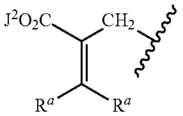, wherein:

$R^a$ is independently selected at each occurrence from hydrogen, $C_{1-6}$ alkyl, carboxy, $C_{1-6}$ carboalkoxy, phenyl, $C_{2-7}$ carboalkyl, $R^c$—$(C(R^b)_2)_z$—, $R^c$—$(C(R^b)_2)_w$-M-$(C(R^b)_2)_r$—, $(R^d)(R^e)$CH-M-$(C(R^b)_2)_r$—, and Het-$J^3$-$(C(R^b)_2)_r$—;

$R^b$ is independently selected at each occurrence from hydrogen, $C_{1-6}$ alkyl, $C_{2-6}$ alkenyl, $C_{2-6}$ alkynyl, $C_{3-6}$ cycloalkyl, $C_{2-7}$ carboalkyl, $C_{2-7}$ carboxyalkyl, phenyl, and phenyl optionally substituted with one or more halogen, $C_{1-6}$ alkoxy, trifluoromethyl, amino, $C_{1-3}$ alkylamino, $C_{2-6}$ dialkylamino, nitro, azido, halomethyl, $C_{2-7}$ alkoxymethyl, $C_{2-7}$ alkanoyloxymethyl, $C_{1-6}$ alkylthio, hydroxy, carboxyl, $C_{2-7}$ carboalkoxy, phenoxy, phenyl, thiophenoxy, benzoyl, benzyl, phenylamino, benzylamino, $C_{1-6}$ alkanoylamino, or $C_{1-6}$alkyl;

$R^c$ is independently selected at each occurrence from —$NR^bR^b$ and —$OR^b$;

$R^d$ and $R^e$ are each independently selected from —$(C(R)_2)_r$—$NR^bR^b$ and —$(C(R^b)_2)_r$—$OR^b$;

$J^1$ is independently selected at each occurrence from hydrogen, chlorine, fluorine, and bromine;

$J^2$ is selected from $C_{1-6}$alkyl and hydrogen;

M is independently selected at each occurrence from —$N(R^b)$—, —O—, —$N[(C(R^b)_2)_w$—$NR^bR^b]$—, and —$N[(C(R^b)_2)_w$—$OR^b]$—;

$J^3$ is independently selected at each occurrence from —$N(R^b)$—, —O—, and a bond;

Het is independently selected at each occurrence from heterocycle, optionally mono- or di-substituted on carbon or nitrogen with $R^b$ and optionally mono-substituted on carbon with —$CH_2OR^b$; wherein the heterocycle is selected from morpholine, thiomorpholine, thiomorpholine S-oxide, thiomorpholine S,S-dioxide, piperidine, pyrrolidine, aziridine, imidazole, 1,2,3-triazole, 1,2,4-triazole, tetrazole, piperazine, tetrahydrofuran, and tetrahydropyran;

each r is independently an integer from 1 to 4;

each w is independently an integer from 2 to 4;

x is 0 or 1;

y is an integer from 0 to 4; and each z is independently an integer from 1 to 6;

wherein the sum of x+y is an integer from 2 to 4.

In embodiments of a compound of formula II or IIA, $-L^{19a}-R^{19a}$ is selected from

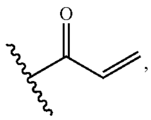, 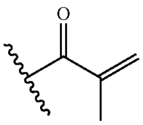, 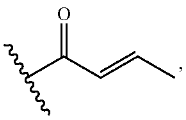,

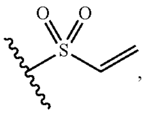, 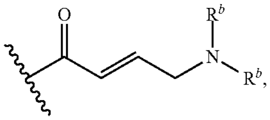

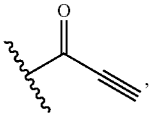, 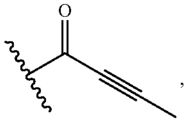,

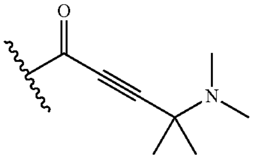, 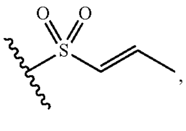,

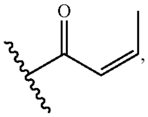, 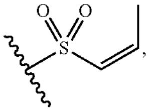, 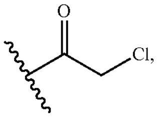

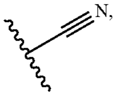

each of which is, valence permitting, optionally substituted with one or more $R^{20}$; and $R^b$ is independently selected at each occurrence from hydrogen, hydroxyl, $C_{1-6}$ alkoxy, and $C_{1-6}$ alkyl.

In embodiments of a compound of formula II or IIA:

i. $L^{19}$ is selected from $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, —$N(R^{12})$—, —C(O)—, —$N(R^{12})C(O)$—, —$C(O)N(R^{12})$—, —S—, —$S(O)_2$—, —S(O)—, —$P(O)(R^{12})$—, —$N(R^{12})S(O)_2$—, —$N(R^{12})S(O)$—, —$N(R^{12})P(O)(R^{12})$—, —$S(O)_2N(R^{12})$—, —$S(O)N(R^{12})$—, —$P(O)(R^{12})N(R^{12})$—, —$OP(O)(R^{12})$—, and —$P(O)(R^{12})O$—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$; and ii. $-L^{19a}-R^{19a}$ is selected from

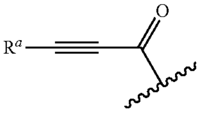, 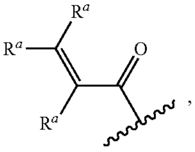,

-continued

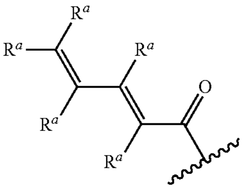, 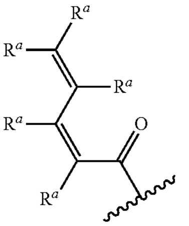,

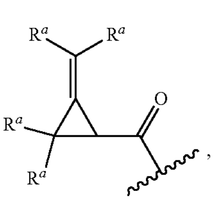, 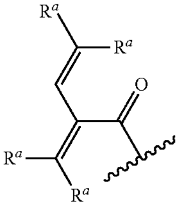,

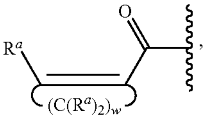, 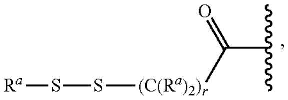,

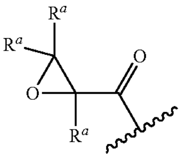, 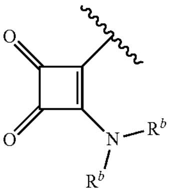,

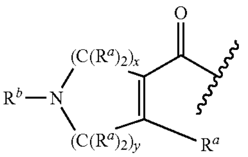, 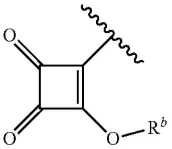,

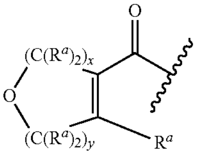, 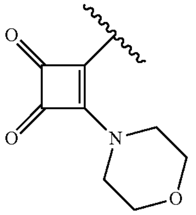,

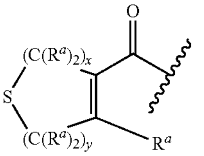, 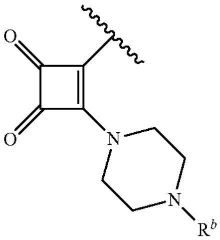,

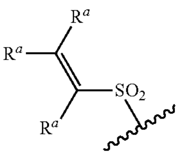, 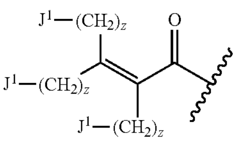,

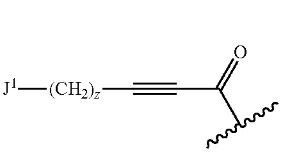, 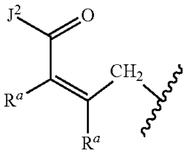,

-continued

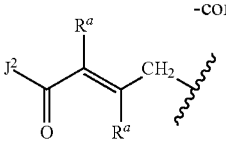
,
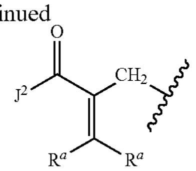
,
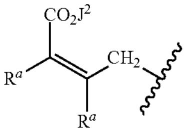
,
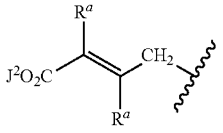
, and
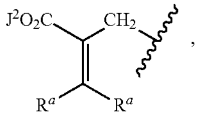
, wherein:

$R^a$ is independently selected at each occurrence from hydrogen, $C_{1-6}$ alkyl, carboxy, $C_{1-6}$ carboalkoxy, phenyl, $C_{2-7}$ carboalkyl, $R^c$—$(C(R^b)_2)_z$—, $R^c$—$(C(R^b)_2)_w$-M-$(C(R^b)_2)_r$-, $(R^d)(R^e)$CH-M-$(C(R^b)_2)_r$-, and Het-$J^3$-$(C(R^b)_2)_r$—;

$R^b$ is independently selected at each occurrence from hydrogen, $C_{1-6}$ alkyl, $C_{2-6}$ alkenyl, $C_{2-6}$ alkynyl, $C_{3-6}$ cycloalkyl, $C_{2-7}$ carboalkyl, $C_{2-7}$ carboxyalkyl, phenyl, and phenyl optionally substituted with one or more halogen, $C_{1-6}$ alkoxy, trifluoromethyl, amino, $C_{1-3}$ alkylamino, $C_{2-6}$ dialkylamino, nitro, azido, halomethyl, $C_{2-7}$ alkoxymethyl, $C_{2-7}$ alkanoyloxymethyl, $C_{1-6}$ alkylthio, hydroxy, carboxyl, $C_{2-7}$ carboalkoxy, phenoxy, phenyl, thiophenoxy, benzoyl, benzyl, phenylamino, benzylamino, $C_{1-6}$ alkanoylamino, or $C_{1-6}$alkyl;

$R^e$ is independently selected at each occurrence from —$NR^bR^b$ and —$OR^b$;

$R^d$ and $R^e$ are each independently selected from —$(C(R^b)_2)_r$—$NR^bR^b$ and —$(C(R^b)_2)_r$—$OR^b$;

$J^1$ is independently selected at each occurrence from hydrogen, chlorine, fluorine, and bromine;

$J^2$ is selected from $C_{1-6}$alkyl and hydrogen;

M is independently selected at each occurrence from —$N(R^b)$—, —O—, —$N[(C(R^b)_2)_w$—$NR^bR^b]$—, and —$N[(C(R^b)_2)_w$—$OR^b]$—;

$J^3$ is independently selected at each occurrence from —$N(R^b)$—, —O—, and a bond;

Het is independently selected at each occurrence from heterocycle, optionally mono- or di-substituted on carbon or nitrogen with $R^b$ and optionally mono-substituted on carbon with —$CH_2OR^b$; wherein the heterocycle is selected from morpholine, thiomorpholine, thiomorpholine S-oxide, thiomorpholine S,S-dioxide, piperidine, pyrrolidine, aziridine, imidazole, 1,2,3-triazole, 1,2,4-triazole, tetrazole, piperazine, tetrahydrofuran, and tetrahydropyran;

each r is independently an integer from 1 to 4;

each w is independently an integer from 2 to 4;

x is 0 or 1;

y is an integer from 0 to 4; and each z is independently an integer from 1 to 6;

wherein the sum of x+y is an integer from 2 to 4.

In embodiments of a compound of formula II or IIA:

i. $L^{19}$ is selected from $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, —$N(R^{12})$—, —C(O)—, —$N(R^{12})C(O)$—, —$C(O)N(R^{12})$—, —S—, —$S(O)_2$—, —S(O)—, —$P(O)(R^{12})$—, —$N(R^{12})S(O)_2$—, —$N(R^{12})S(O)$—, —$N(R^{12})P(O)(R^{12})$—, —$S(O)_2N(R^{12})$—, —$S(O)N(R^{12})$—, —$P(O)(R^{12})N(R^{12})$—, —$OP(O)(R^{12})$—, and —$P(O)(R^{12})O$—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$; and ii. -$L^{19a}$-$R^{19a}$ is selected from

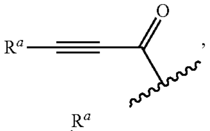
,
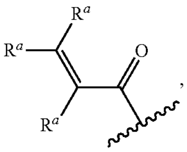
,
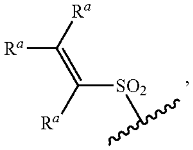
,
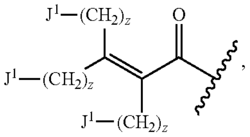
, and
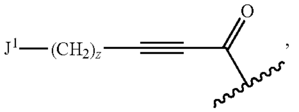
, wherein:

$R^a$ is independently selected at each occurrence from hydrogen, $C_{1-6}$ alkyl, carboxy, $C_{1-6}$ carboalkoxy, phenyl, $C_{2-7}$ carboalkyl, $R^c$—$(C(R^b)_2)_z$—, $R^c$—$(C(R^b)_2)_w$-M-$(C(R^b)_2)_r$-, $(R^d)(R^e)$CH-M-$(C(R^b)_2)_r$—, and Het-$J^3$-$(C(R^b)_2)_r$—;

$R^b$ is independently selected at each occurrence from hydrogen, $C_{1-6}$ alkyl, $C_{2-6}$ alkenyl, $C_{2-6}$ alkynyl, $C_{3-6}$ cycloalkyl, $C_{2-7}$ carboalkyl, $C_{2-7}$ carboxyalkyl, phenyl, and phenyl optionally substituted with one or more halogen, $C_{1-6}$ alkoxy, trifluoromethyl, amino, $C_{1-3}$ alkylamino, $C_{2-6}$ dialkylamino, nitro, azido, halomethyl, $C_{2-7}$ alkoxymethyl, $C_{2-7}$ alkanoyloxymethyl, $C_{1-6}$ alkylthio, hydroxy, carboxyl, $C_{2-7}$ carboalkoxy, phenoxy, phenyl, thiophenoxy, benzoyl, benzyl, phenylamino, benzylamino, $C_{1-6}$ alkanoylamino, or $C_{1-6}$alkyl;

$R^c$ is independently selected at each occurrence from —$NR^bR^b$ and —$OR^b$;

$R^d$ and $R^e$ are each independently selected from —$(C(R^b)_2)_r$—$NR^bR^b$ and —$(C(R^b)_2)_r$—$OR^b$;

$J^1$ is independently selected at each occurrence from hydrogen, chlorine, fluorine, and bromine;

$J^2$ is selected from $C_{1-6}$alkyl and hydrogen;

M is independently selected at each occurrence from —$N(R^b)$—, —O—, —$N[(C(R^b)_2)_w$—$NR^bR^b]$—, and —$N[(C(R^b)_2)_w$—$OR^b]$—; $J^3$ is independently selected at each occurrence from —$N(R^b)$—, —O—, and a bond;

Het is independently selected at each occurrence from heterocycle, optionally mono- or di-substituted on carbon or nitrogen with $R^b$ and optionally mono-substituted on carbon with —$CH_2OR^b$; wherein the heterocycle is selected from morpholine, thiomorpholine, thiomorpholine S-oxide, thiomorpholine S,S-dioxide, piperidine, pyrrolidine, aziridine, imidazole, 1,2,3-triazole, 1,2,4-triazole, tetrazole, piperazine, tetrahydrofuran, and tetrahydropyran;

each r is independently an integer from 1 to 4;

each w is independently an integer from 2 to 4;

x is 0 or 1;

y is an integer from 0 to 4; and each z is independently an integer from 1 to 6;

wherein the sum of x+y is an integer from 2 to 4.

In embodiments of a compound of formula II or IIA:

i. $L^{19}$ is selected from $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, —$N(R^{12})$—, —C(O)—, —$N(R^{12})C(O)$—, —$C(O)N(R^{12})$—, —S—, —$S(O)_2$—, —S(O)—, —$P(O)(R^{12})$—, —$N(R^{12})S(O)_2$—, —$N(R^{12})S(O)$—, —$N(R^{12})P(O)(R^{12})$—, —$S(O)_2N(R^{12})$—, —$S(O)N(R^{12})$—, —$P(O)(R^{12})N(R^{12})$—, —$OP(O)(R^{12})$—, and —$P(O)(R^{12})O$—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$; and ii. -$L^{19a}$-$R^{19a}$ is selected from

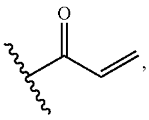, 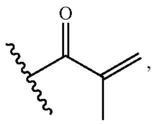, 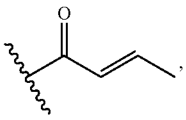,

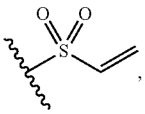, 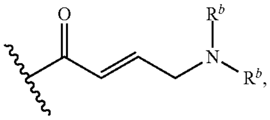

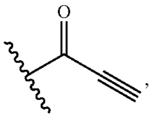, 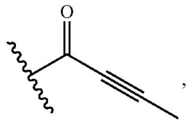,

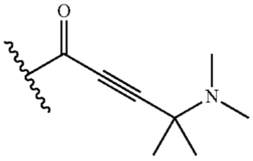, 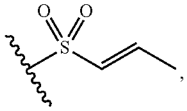,

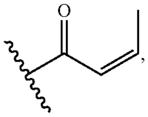, 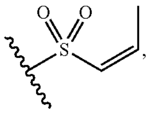, and

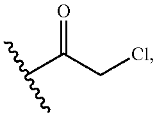

each of which is, valence permitting, optionally substituted with one or more $R^{20}$; and $R^b$ is independently selected at each occurrence from hydrogen, hydroxyl, $C_{1-6}$ alkoxy, and $C_{1-6}$ alkyl.

In embodiments of a compound of formula II or IIA, $L^{19}$ is selected from $C_{2-4}$ alkylene, $C_{2-4}$ alkenylene, $C_{2-4}$ alkynylene, 3- to 4-membered heteroalkenylene, 3- to 4-membered heteroalkynylene, —O—, —$N(R^{12})$—, —C(O)—, —$N(R^{12})C(O)$—, —$C(O)N(R^{12})$—, —S—, —$S(O)_2$—, —S(O)—, —$P(O)(R^{12})$—, —$N(R^{12})S(O)_2$—, —$N(R^{12})S(O)$—, —$N(R^{12})P(O)(R^{12})$—, —$S(O)_2N(R^{12})$—, —$S(O)N(R^{12})$—, —$P(O)(R^{12})N(R^{12})$—, —$OP(O)(R^{12})$—, and —$P(O)(R^{12})O$—, wherein $C_{2-4}$ alkylene, $C_{2-4}$ alkenylene, $C_{2-4}$ alkynylene, 3- to 4-membered heteroalkenylene, and 3- to 4-membered heteroalkynylene are optionally substituted with one or more $R^{20}$.

In embodiments of a compound of formula II or IIA:

i. $L^{19}$ is selected from $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, —$N(R^{12})$—, —C(O)—, —$N(R^{12})C(O)$—, —$C(O)N(R^{12})$—, —S—, —$S(O)_2$—, —S(O)—, —$P(O)(R^{12})$—, —$N(R^{12})S(O)_2$—, —$N(R^{12})S(O)$—, —$N(R^{12})P(O)(R^{12})$—, —$S(O)_2N(R^{12})$—, —$S(O)N(R^{12})$—, —$P(O)(R^{12})N(R^{12})$—, —$OP(O)(R^{12})$—, and —$P(O)(R^{12})O$—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$; and ii. -$L^{19a}$ is selected from a $C_{2-4}$ alkenylene, $C_{2-4}$ alkynylene, 3- to 4-membered heteroalkenylene, 3- to 4-membered heteroalkynylene, —O—, —$N(R^{12})$—, —C(O)—, —S—, —$S(O)_2$—, —S(O)—, —$P(O)R^{12}$—, —$N(R^{12})S(O)_2$—, —$N(R^{12})S(O)$—, —$N(R^{12})P(O)R^{12}$—, —$S(O)_2N(R^{12})$—, —$S(O)N(R^{12})$—, —$P(O)R^{12}N(R^{12})$—, —$OP(O)R^{12}$—, and —$P(O)R^{12}O$—, wherein $C_{2-4}$ alkenylene, $C_{2-4}$ alkynylene, 3- to 4-membered heteroalkenylene, and 3- to 4-membered heteroalkynylene are optionally substituted with one or more $R^{20}$; and iii. $R^{19a}$ is selected from $C_{1-6}$ haloalkyl, $C_{2-6}$ alkenyl, $C_{2-6}$ alkynyl, 3- to 6-membered heteroalkenyl, 3- to 6-membered heteroalkynyl, —$C_{0-6}$ alkyl-($C_{4-12}$ carbocycle), -(2- to 6-membered heteroalkyl)-($C_{3-12}$ carbocycle), —$C_{0-6}$ alkyl-(5- to 12-membered heterocycle), -(2- to 6-membered heteroalkyl)-(5- to 12-membered heterocycle), —$SR^{12}$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$S(O)R^{12}$, —$OC(O)R^{12}$, —$C(O)C(O)N(R^{12})(R^{13})$, —$N(R^{12})C(O)R^{12}$, —$S(O)(NR^{12})R^{12}$, —$S(O)_2N(R^{12})(R^{13})$, and —$S(=O)(=NR^{12})N(R^{12})(R^{13})$, wherein $C_{1-6}$ haloalkyl, $C_{2-6}$ alkenyl, $C_{2-6}$ alkynyl, 3- to 6-membered heteroalkenyl, 3- to 6-membered heteroalkynyl, —$C_{0-6}$ alkyl-($C_{4-12}$ carbocycle), -(2- to 6-membered heteroalkyl)-($C_{3-12}$ carbocycle), —$C_{0-6}$ alkyl-(5- to 12-membered heterocycle), and -(2- to 6-membered heteroalkyl)-(5- to 12-membered heterocycle) are optionally substituted with one or more $R^{20}$.

In embodiments of a compound of formula I, IA, IB, II, or IIA:

i. $L^{19}$ is selected from $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, —$N(R^{12})$—, —C(O)—, —$N(R^{12})C(O)$—, —$C(O)N(R^{12})$—, —S—, —$S(O)_2$—, —S(O)—, —$P(O)(R^{12})$—, —$N(R^{12})S(O)_2$—, —$N(R^{12})S(O)$—, —$N(R^{12})P(O)(R^{12})$—, —$S(O)_2N(R^{12})$—, —$S(O)N(R^{12})$—, —$P(O)(R^{12})N(R^{12})$—, —$OP(O)(R^{12})$—, and —$P(O)(R^{12})O$—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$.

ii. $X^{12}$ is —$X^{12a}$—;

iii. $R^{19}$ is a monocyclic 3- to 8-membered heterocycle, substituted with one or more $R^{20}$; and iv. $R^{19a}$ is a 5-membered heteroaryl comprising one or more ring nitrogen atoms, wherein the 5-membered heteroaryl is directly bonded to $L^{19a}$ through an $R^{19a}$ ring nitrogen atom and wherein $R^{19a}$ is optionally substituted with one or more $R^{20}$.

In embodiments of a compound of formula I, IA, IB, II, or IIA:

i. $L^{19}$ is $C_1$ alkylene optionally substituted with one or more $R^{20}$;

ii. $X^{12}$ is —$X^{12a}$—;

iii. $R^{19}$ is a monocyclic 3- to 8-membered heterocycle, substituted with one or more $R^{20}$; and iv. $R^{19a}$ is a 5-membered heteroaryl comprising one or more ring nitrogen atoms, wherein the 5-membered heteroaryl is directly bonded to $L^{19a}$ through an $R^{19a}$ ring nitrogen atom and wherein $R^{19a}$ is optionally substituted with one or more $R^{20}$.

In embodiments of a compound of formula I, IA, IB, II, or IIA:

i. $L^{19}$ is unsubstituted $C_1$ alkylene;

ii. $X^{12}$ is —$X^{12a}$—;

iii. $R^{19}$ is a monocyclic 3- to 8-membered heterocycle, substituted with one or more $R^{20}$; and iv. $R^{19a}$ is a 5-membered heteroaryl comprising one or more ring nitrogen atoms, wherein the 5-membered heteroaryl is directly bonded to $L^{19a}$ through an $R^{19a}$ ring nitrogen atom and wherein $R^{19a}$ is optionally substituted with one or more $R^{20}$.

In embodiments of Formula II or IIA, $R^{19a}$ is 3 membered heterocycle comprising one ring nitrogen atom, wherein the 3 membered heterocycle is optionally substituted with one, two, or three $R^{20}$. In embodiments of Formula II or IIA, $R^{19a}$ is 3 membered heterocycle comprising one ring nitrogen atom, wherein the 3 membered heterocycle is optionally substituted with $C_{1-6}$alkyl optionally substituted with one, two, or three halogen. In embodiments of Formula II or IIA, $R^{19a}$ is 3 membered heterocycle comprising one ring nitrogen atom, wherein the 3 membered heterocycle is optionally substituted with $C_{1-6}$alkyl, wherein the $C_{1-6}$alkyl is optionally substituted with one, two, or three F. In embodiments of Formula II or IIA, $R^{19a}$ is 3 membered heterocycle comprising one ring nitrogen atom, wherein the 3 membered heterocycle is optionally substituted with methyl and the methyl is optionally substituted with one, two, or three halogen.

In embodiments of Formula II or IIA, $R^{19a}$ is 3 membered heterocycle comprising one ring nitrogen atom, wherein the 3 membered heterocycle is optionally substituted with $C_{3-5}$ non-aromatic carbocycle that is optionally substituted with one, two, or three halogen. In embodiments of Formula II or IIA, $R^{19a}$ is 3 membered heterocycle comprising one ring nitrogen atom, wherein the 3 membered heterocycle is optionally substituted with $C_{3-5}$ non-aromatic carbocycle that is optionally substituted with one, two, or three F. In embodiments of Formula II or IIA, $R^{19a}$ is 3 membered heterocycle comprising one ring nitrogen atom, wherein the 3 membered heterocycle is optionally substituted with cyclopropyl that is optionally substituted with one, two, or three halogen. In embodiments of Formula II or IIA, $R^{19a}$ is 3 membered heterocycle comprising one ring nitrogen atom, wherein the 3 membered heterocycle is optionally substituted with cyclopropyl that is optionally substituted with one, two, or three F.

In embodiments of Formula II or IIA, $R^{19a}$ is 3 membered heterocycle comprising one ring nitrogen atom, wherein the 3 membered heterocycle is optionally substituted with one or more substituents selected from $C_{1-6}$alkyl and $C_{3-5}$ non-aromatic carbocycle. In embodiments of Formula II or IIA, $R^{19a}$ is 3 membered heterocycle comprising one ring nitrogen atom, wherein the 3 membered heterocycle is optionally substituted with one or more substituents selected from $C_{1-6}$alkyl and $C_{3-5}$ non-aromatic carbocycle, wherein the $C_{1-6}$alkyl and $C_{3-5}$ non-aromatic carbocycle are optionally substituted with halogen. In embodiments of Formula II or IIA, $R^{19a}$ is 3 membered heterocycle comprising one ring nitrogen atom, wherein the 3 membered heterocycle is optionally substituted with one or more substituents selected from methyl and cyclopropyl, wherein the methyl and cyclopropyl are optionally substituted with halogen.

In embodiments of Formula II or IIA, $R^{19a}$ is selected from

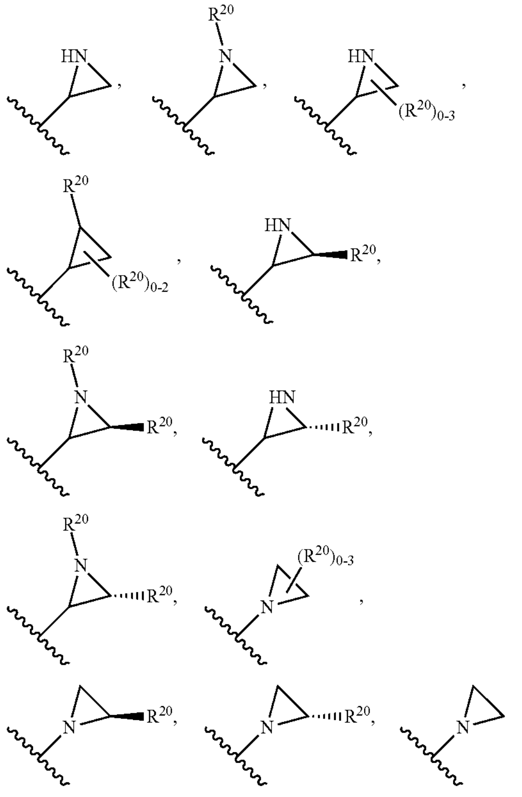

wherein each $R^{20}$ is independently selected and are optionally different.

In embodiments of the formulae above, $R^{19a}$ is selected from

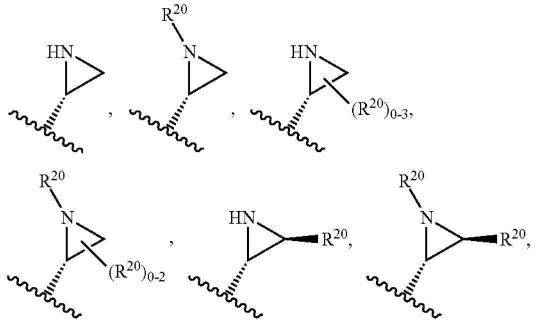

-continued

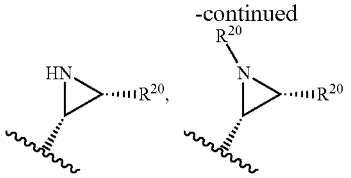

wherein each $R^{20}$ is independently selected and are optionally different.

In embodiments of the formulae above, $R^{19a}$ is selected from

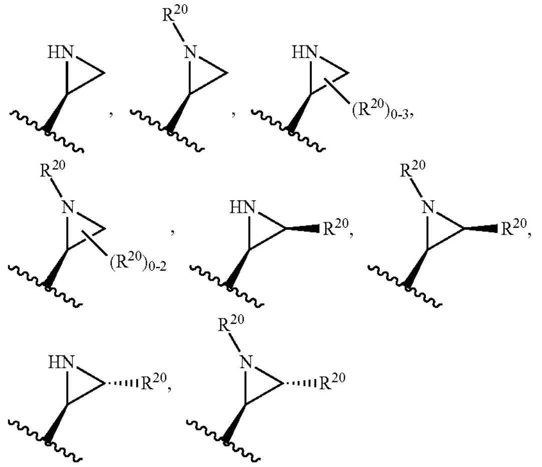

wherein each $R^{20}$ is independently selected and are optionally different.

In embodiments of the formulae above, $R^{19a}$ is selected from

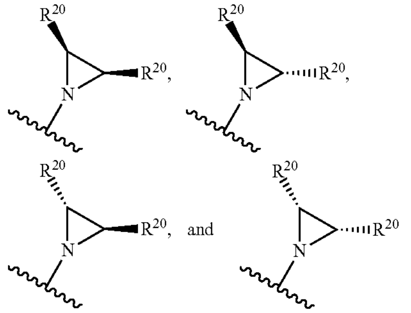

and wherein each $R^{20}$ is independently selected and are optionally different.

In embodiments of the formulae above, $R^{19a}$ is selected from

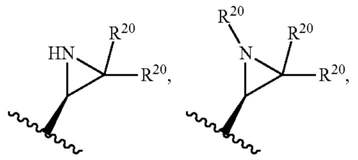

-continued

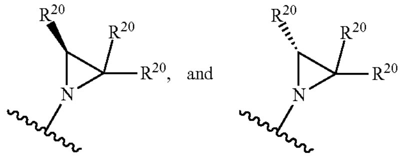

and wherein each $R^{20}$ is independently selected and are optionally different.

In embodiments of the formulae above, $R^{19a}$ is selected from:

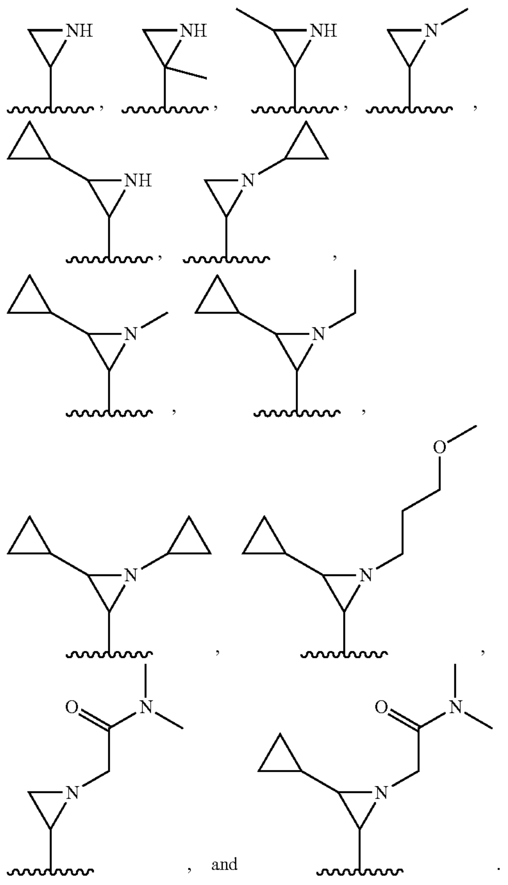

and

In embodiments of the formulae above, each $R^{20}$ is independently halogen. In embodiments of the formulae above, each $R^{20}$ is independently oxo. In embodiments of the formulae above, each $R^{20}$ is independently —CN. In embodiments of the formulae above, each $R^{20}$ is independently $C_{1-6}$alkyl. In embodiments of the formulae above, each $R^{20}$ is independently $C_{2-6}$alkenyl. In embodiments of the formulae above, each $R^{20}$ is independently $C_{2-6}$alkynyl. In embodiments of the formulae above, each $R^{20}$ is independently $C_{3-12}$ carbocycle. In embodiments of the formulae above, each $R^{20}$ is independently $C_{2-11}$ heterocycle. In embodiments of the formulae above, each $R^{20}$ is independently $C_{6-12}$aryl. In embodiments of the formulae above, each $R^{20}$ is independently $C_{1-11}$heteroaryl. In embodiments of the formulae above, each $R^{20}$ is independently $—OR^{22}$. In embodiments of the formulae above, each $R^{20}$ is independently $—SR^{22}$. In embodiments of the formulae above, each $R^{20}$ is independently $—N(R^{22})(R^{23})$.

In embodiments of the formulae above, each $R^{20}$ is independently —OH. In embodiments of the formulae above, each $R^{20}$ is independently —SH. In embodiments of the formulae above, each $R^{20}$ is independently —$NH_2$.

In embodiments, $-L^{19}-R^{19}-L^{19a}-R^{19a}$ is

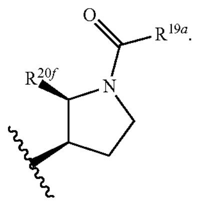

In embodiments, $R^{20f}$ is unsubstituted methyl; and $R^{19a}$ is selected from

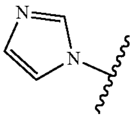, 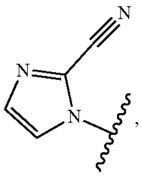, 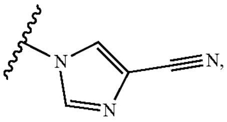

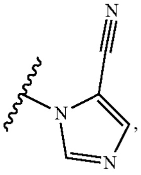, 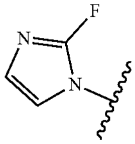, 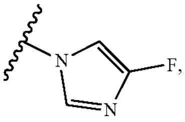

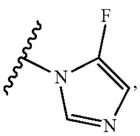, 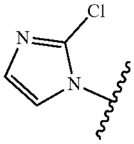, 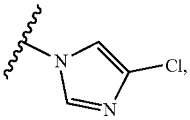

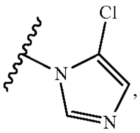, 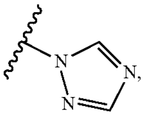, 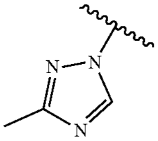,

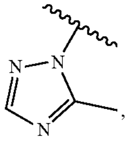, 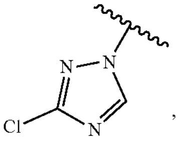, 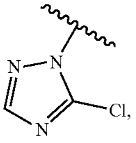

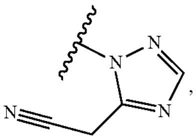, 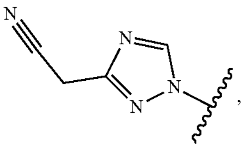,

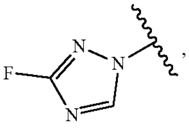, 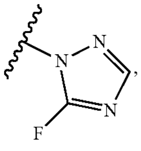, 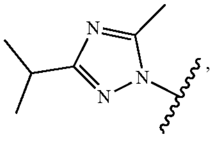,

-continued

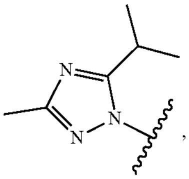, 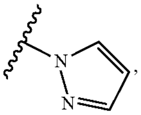, 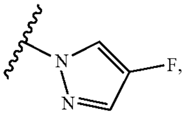

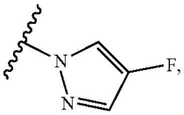, 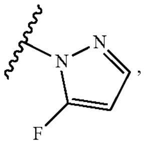, 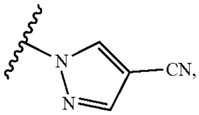

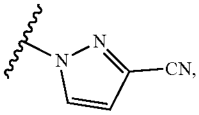, 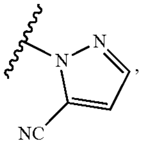, 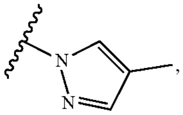

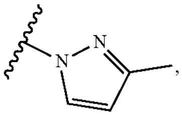, 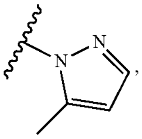, 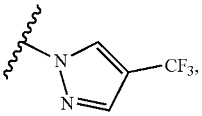

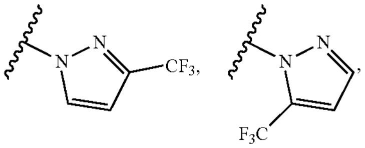

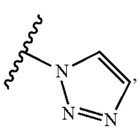, 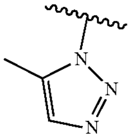,

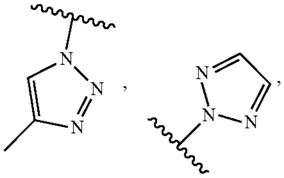

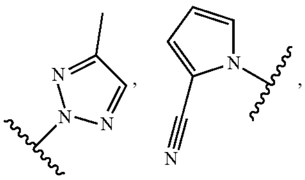

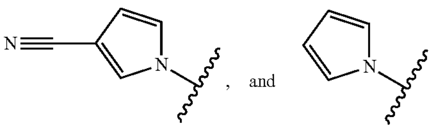.

In embodiments, $R^{20f}$ is unsubstituted $C_{1-3}$ alkyl; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, or unsubstituted $C_{1-3}$ haloalkyl.

In embodiments, $-L^{19}-R^{19}-L^{19a}-R^{19a}$ is

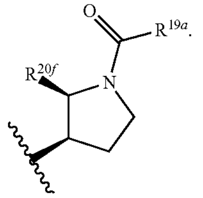

In embodiments, $R^{20f}$ is unsubstituted methyl; and $R^{19a}$ is selected from

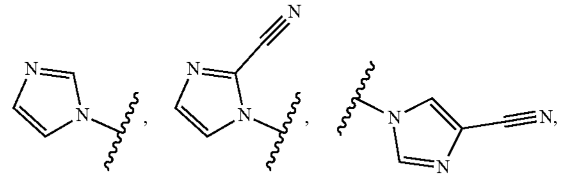

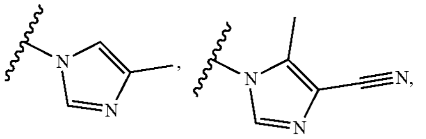

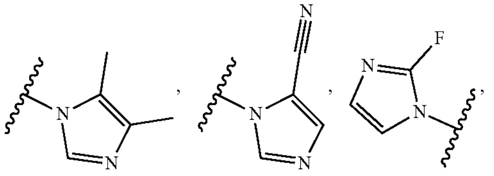

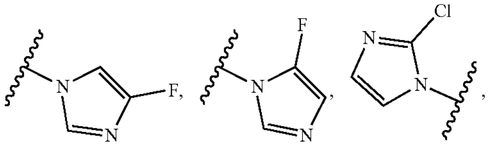

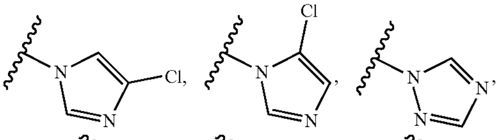

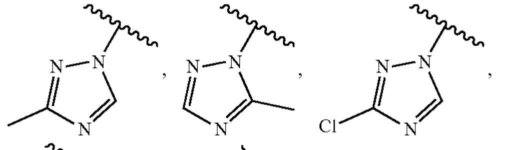

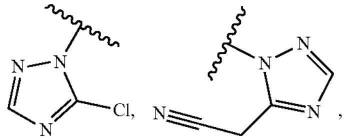

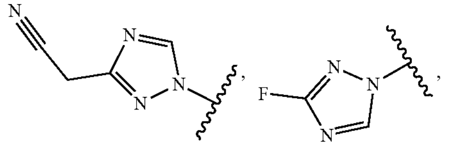

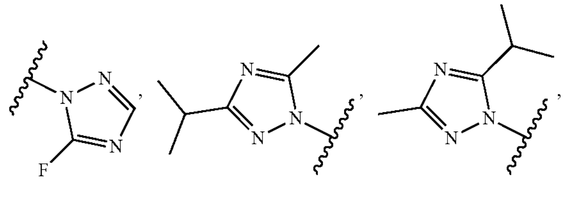

-continued

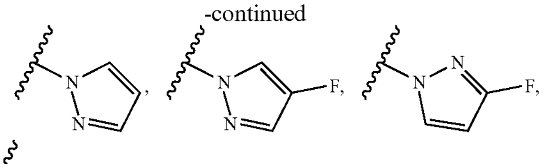

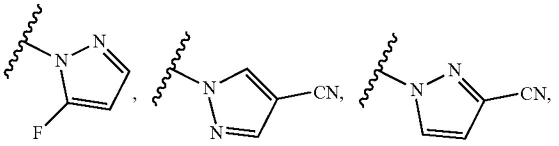

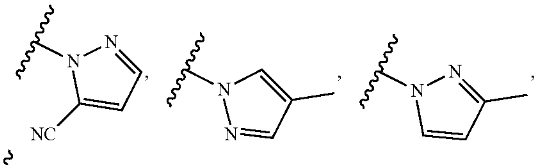

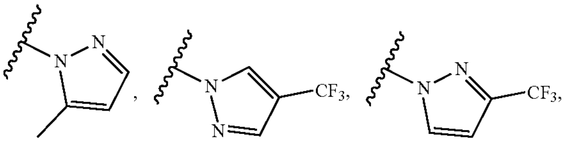

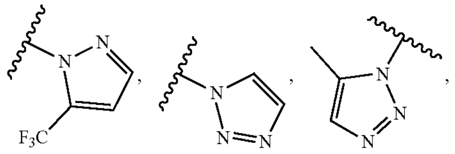

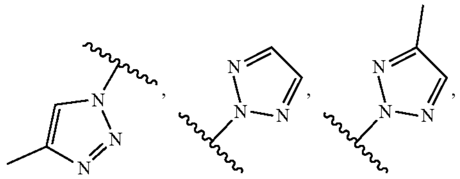

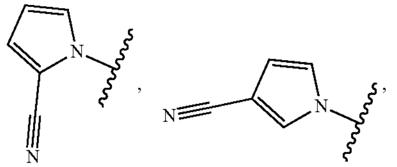

and

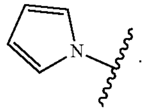

In embodiments, $R^{20f}$ is unsubstituted $C_{1-3}$ alkyl; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

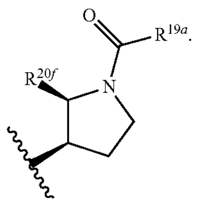

In embodiments, $R^{20f}$ is unsubstituted methyl; and $R^{19a}$ is selected from

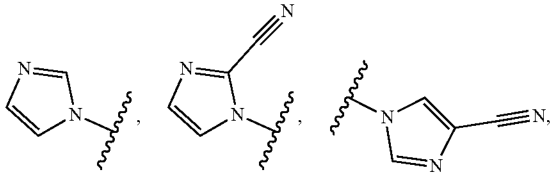
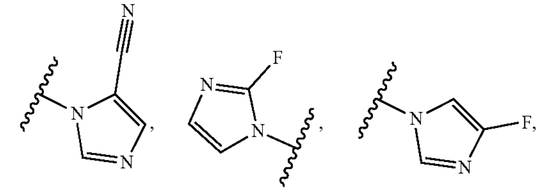
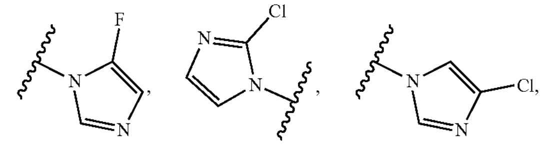
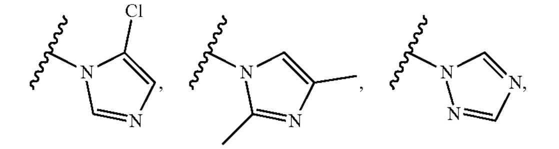
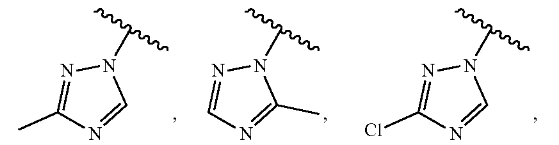
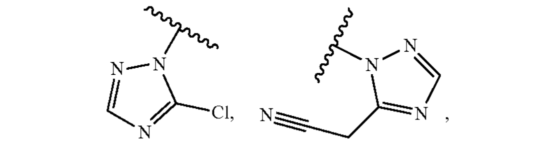
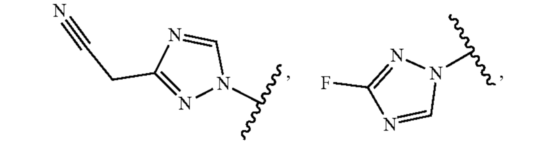
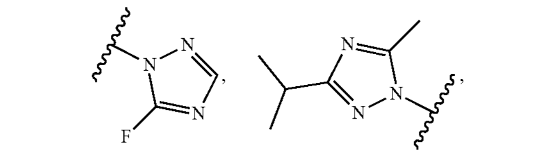
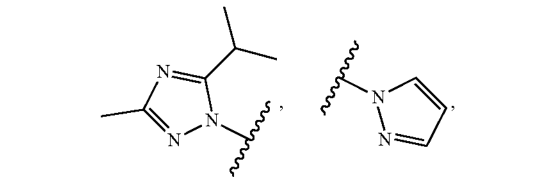
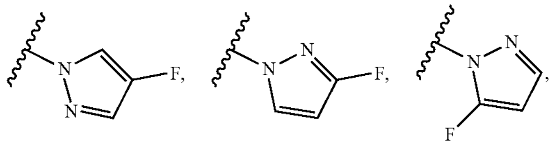
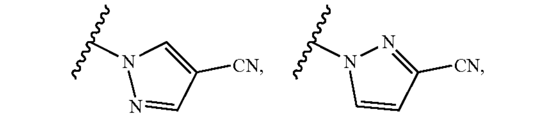

-continued

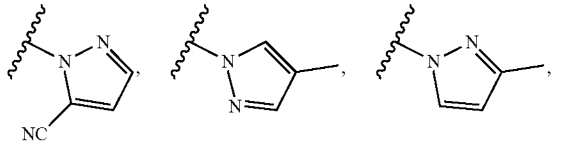
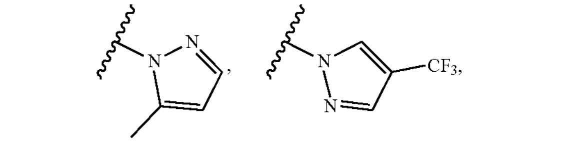
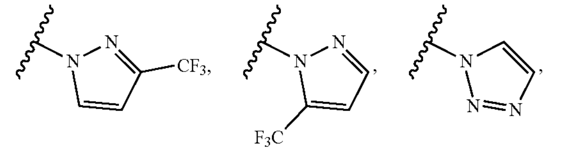
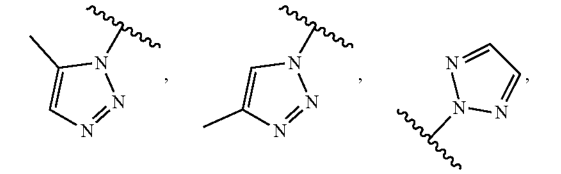
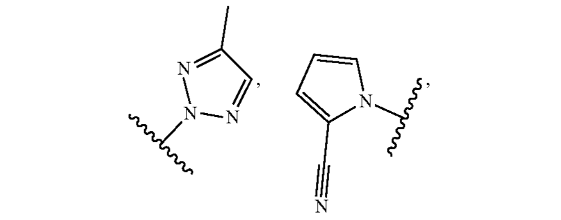
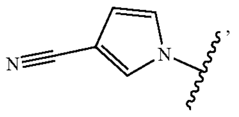

and

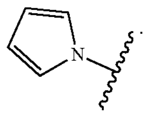

In embodiments, $R^{20f}$ is unsubstituted $C_{1-3}$ alkyl; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, and unsubstituted $C_{1-3}$ haloalkyl.

In embodiments, $-L^{19}-R^{19}-L^{19a}-R^{19a}$ is

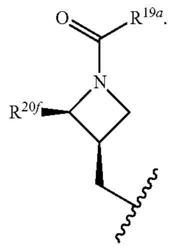

In embodiments, $R^{20f}$ is selected from methyl-substituted cyclopropyl, unsubstituted tert-butyl, unsubstituted isopropyl, and unsubstituted methyl; and $R^{19a}$ is selected from

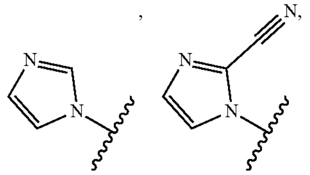
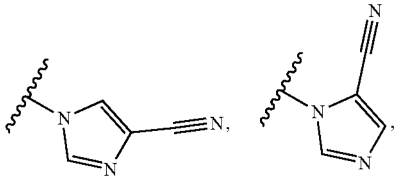
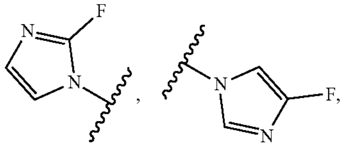
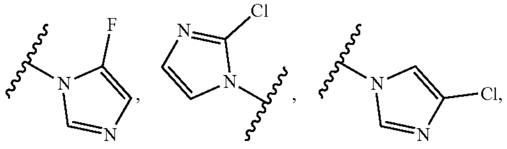
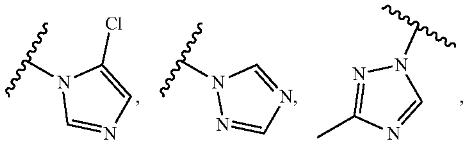
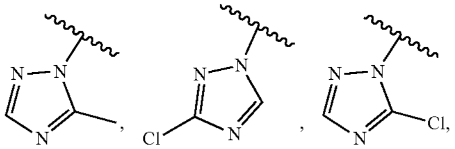
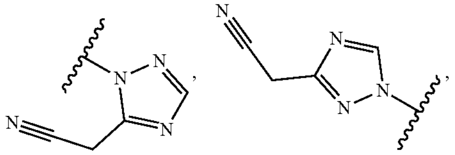
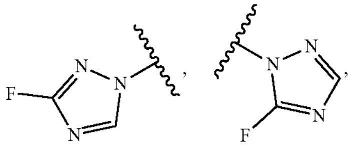
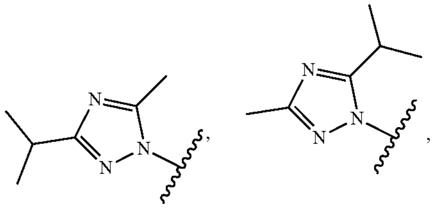
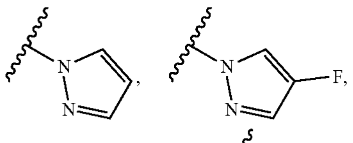
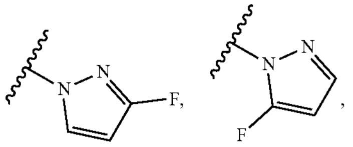

-continued

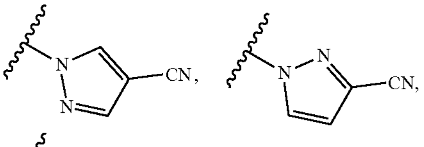
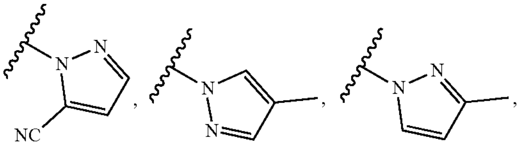
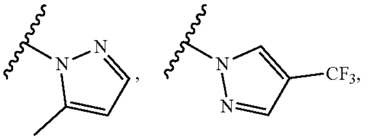
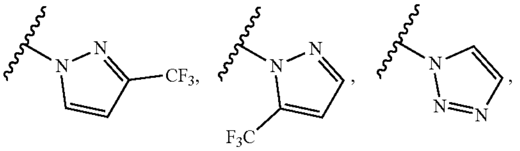
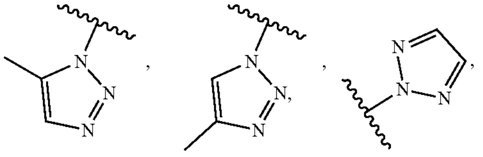
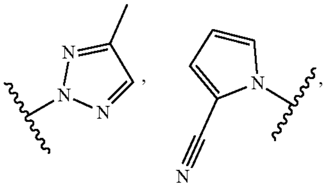
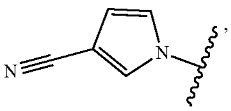
and
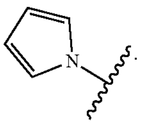

In embodiments, $R^{20f}$ is selected from unsubstituted $C_{1-3}$ alkyl and $C_{3-4}$ non-aromatic carbocycle substituted with $C_{1-3}$ alkyl; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

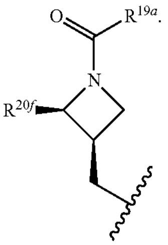

In embodiments, $R^{20f}$ is selected from methyl-substituted cyclopropyl, cyclopropyl substituted with $—CH_2OCH_3$, cyclopropyl substituted with —$CH_2CN$, unsubstituted tert-butyl, unsubstituted isopropyl, and unsubstituted methyl; and $R^{19a}$ is selected from

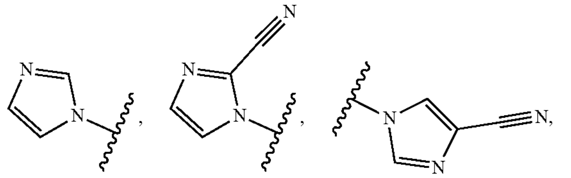
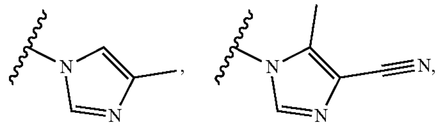
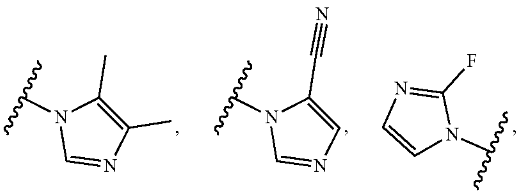
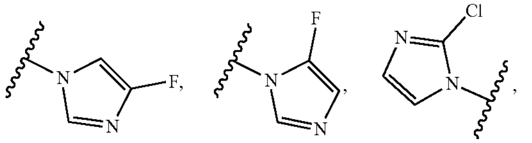
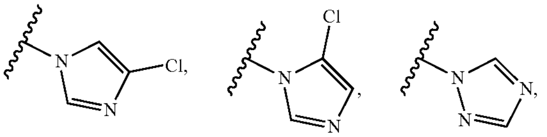
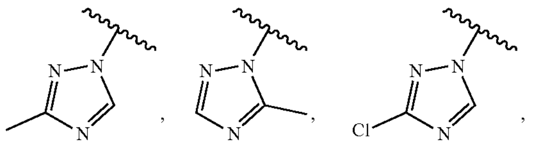
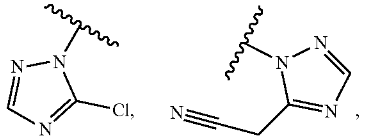
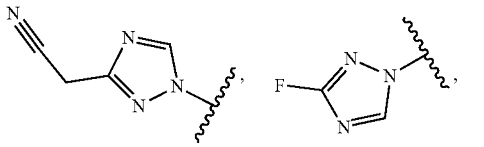
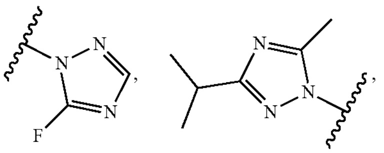
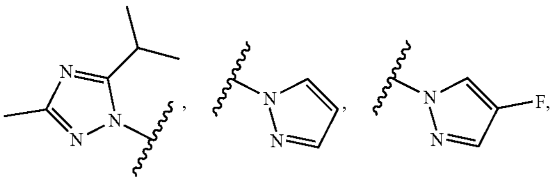

-continued

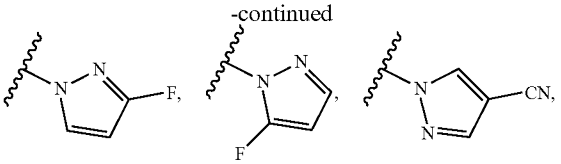
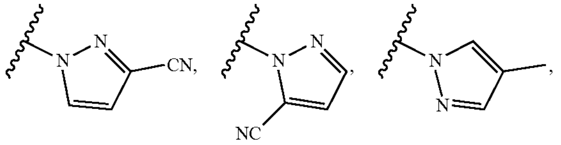
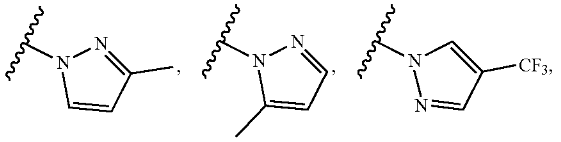
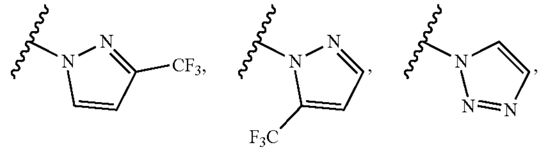
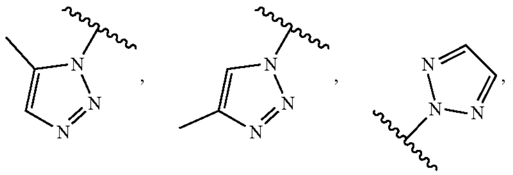
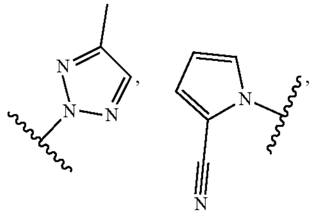
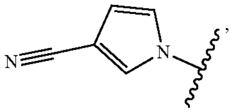

and

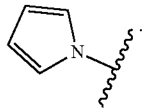

In embodiments, $R^{20f}$ is selected from unsubstituted $C_{1-3}$ alkyl and $C_{3-4}$ non-aromatic carbocycle substituted with $C_{1-3}$ alkyl, wherein the $C_{1-3}$ alkyl is optionally substituted with $C_{1-3}$ alkoxy or CN; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

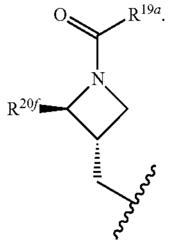

In embodiments, $R^{20f}$ is selected from methyl-substituted cyclopropyl, unsubstituted tert-butyl, unsubstituted isopropyl, and unsubstituted methyl; and $R^{19a}$ is selected from

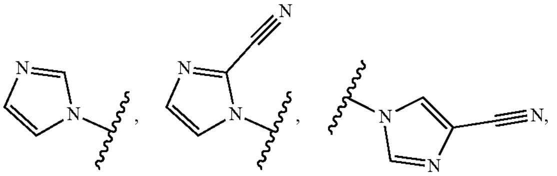

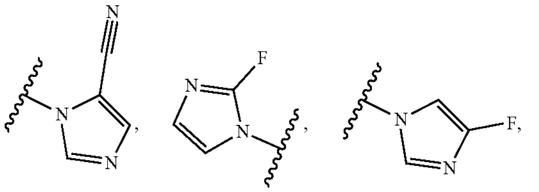

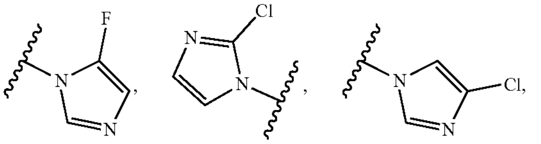

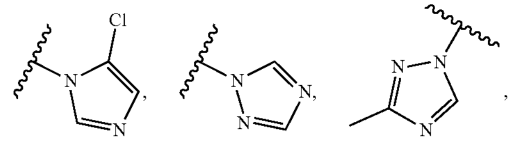

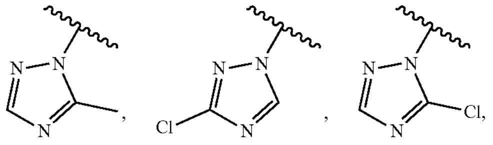

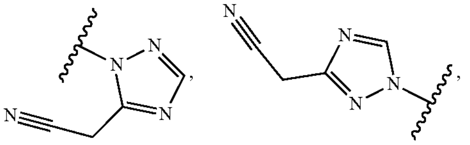

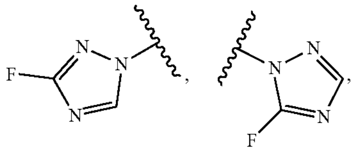

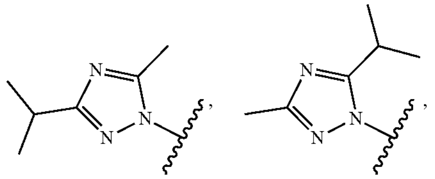

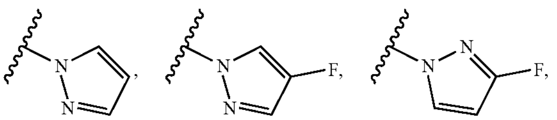

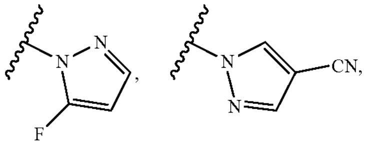

-continued

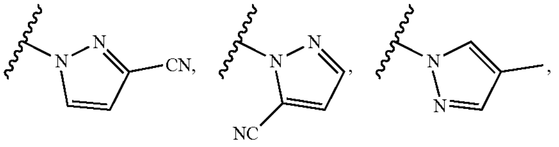

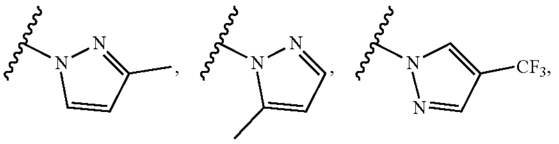

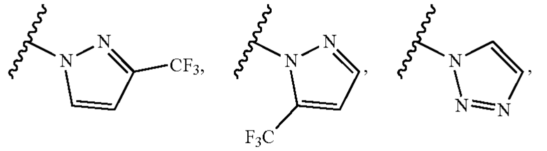

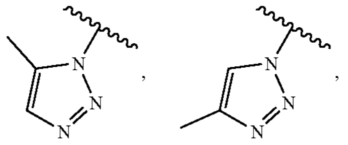

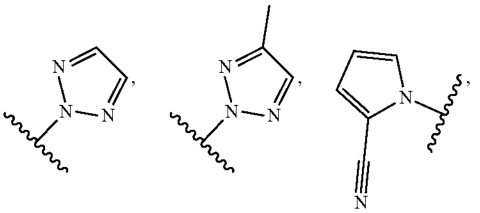

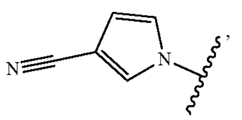

and

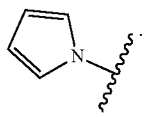

In embodiments, $R^{20f}$ is selected from unsubstituted $C_{1-3}$ alkyl and $C_{3-4}$ non-aromatic carbocycle substituted with $C_{1-3}$ alkyl; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

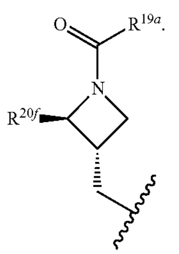

In embodiments, $R^{20f}$ is selected from methyl-substituted cyclopropyl, cyclopropyl substituted with $—CH_2OCH_3$, cyclopropyl substituted with $—CH_2CN$, unsubstituted tert-butyl, unsubstituted isopropyl, and unsubstituted methyl; and $R^{19a}$ is selected from

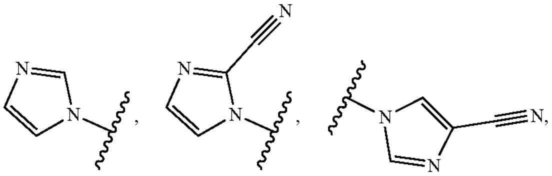
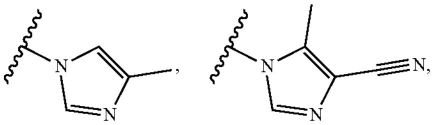
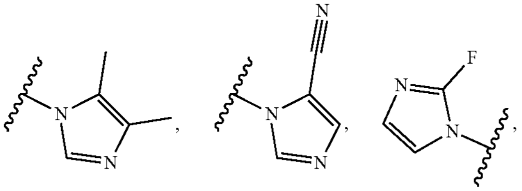
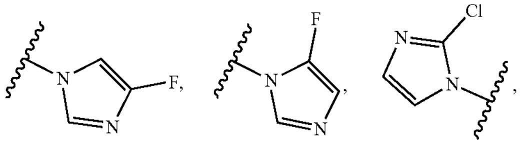
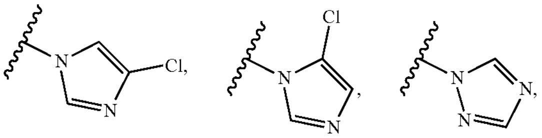
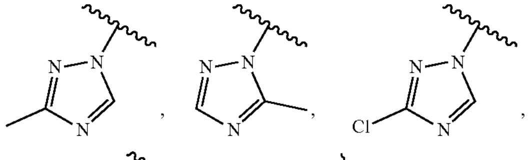
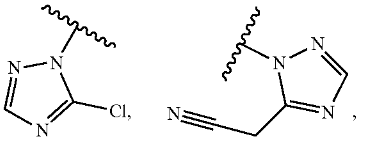
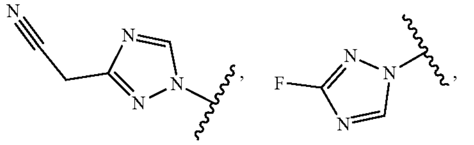
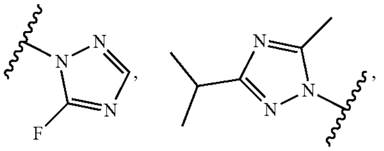
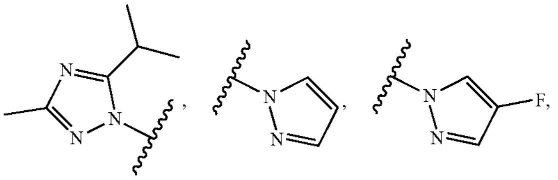
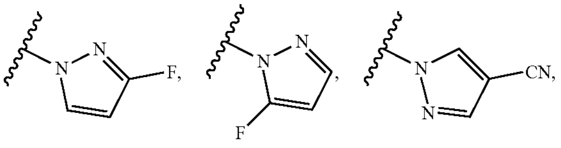

-continued

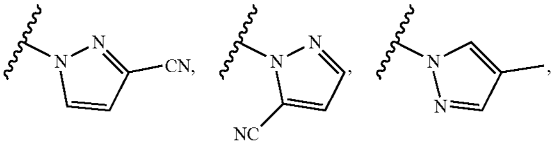
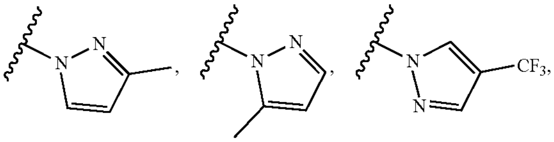
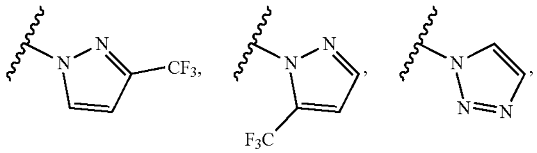
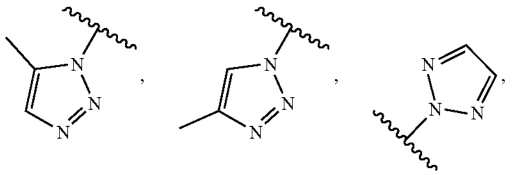
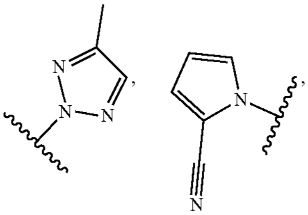
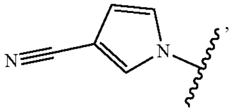

and

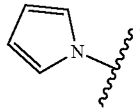

In embodiments, $R^{20f}$ is selected from unsubstituted $C_{1-3}$ alkyl and $C_{3-4}$ non-aromatic carbocycle substituted with $C_{1-3}$ alkyl, wherein the $C_{1-3}$ alkyl is optionally substituted with $C_{1-3}$ alkoxy or CN; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

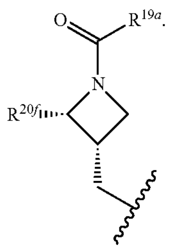

In embodiments, $R^{20f}$ is selected from methyl-substituted cyclopropyl, unsubstituted tert-butyl, unsubstituted isopropyl, and unsubstituted methyl; and $R^{19a}$ is selected from

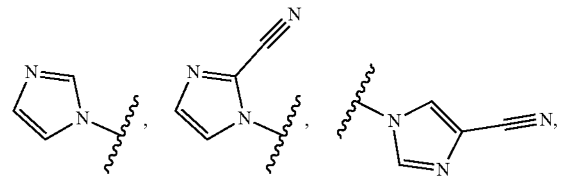
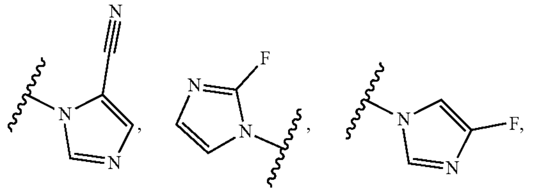
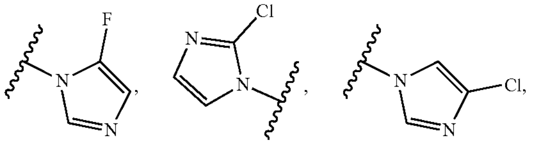
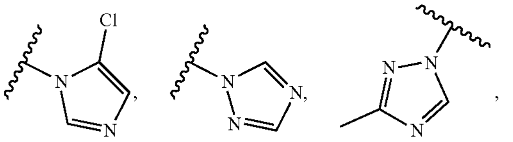
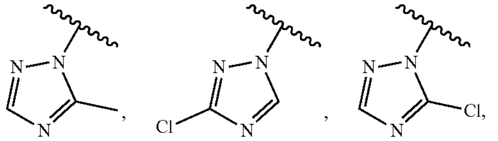
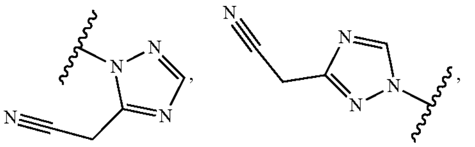
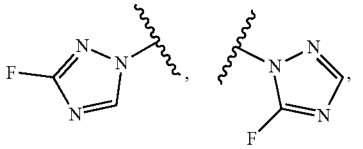
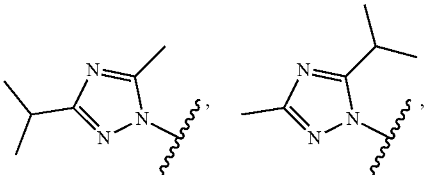
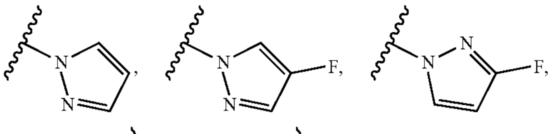
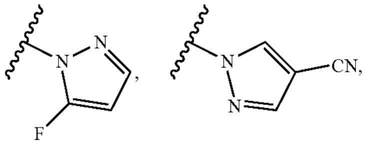
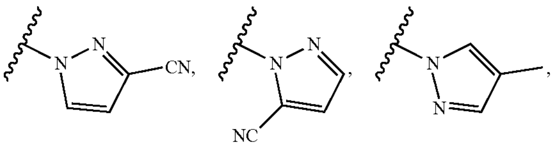

-continued

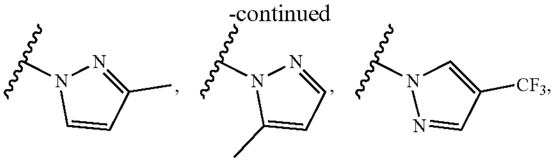
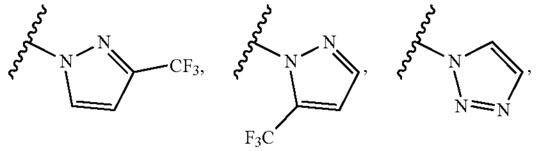
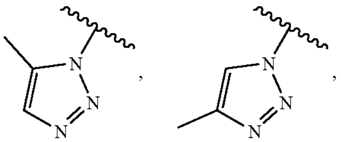
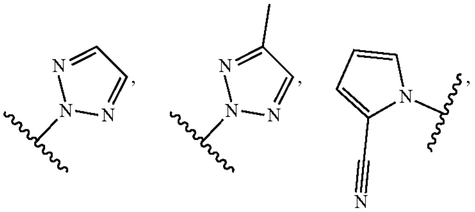
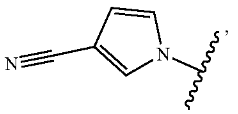

and

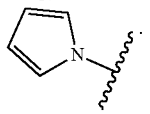

In embodiments, $R^{20f}$ is selected from unsubstituted $C_{1-3}$ alkyl and $C_{3-4}$ non-aromatic carbocycle substituted with $C_{1-3}$ alkyl; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

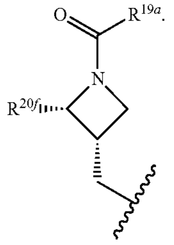

In embodiments, $R^{20f}$ is selected from methyl-substituted cyclopropyl, cyclopropyl substituted with —$CH_2OCH_3$, cyclopropyl substituted with —$CH_2CN$, unsubstituted tert-butyl, unsubstituted isopropyl, and unsubstituted methyl; and $R^{19a}$ is selected from

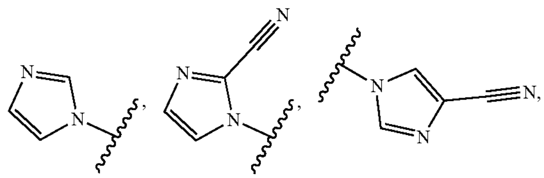

-continued

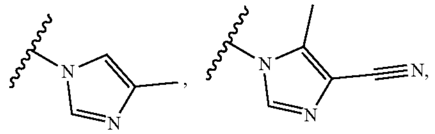
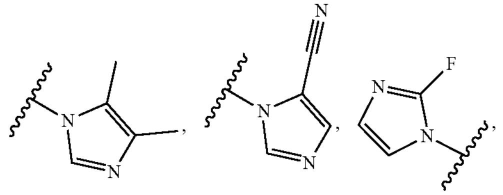
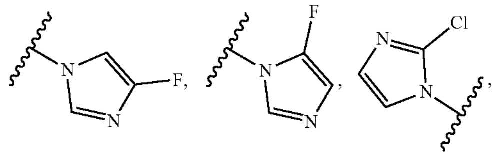
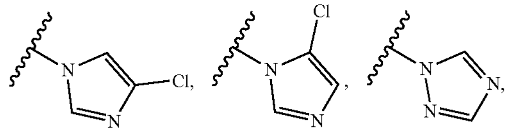
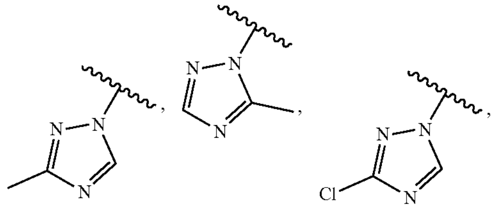
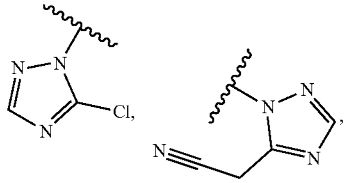
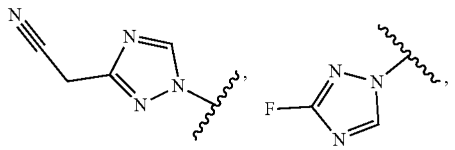
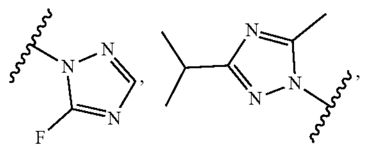
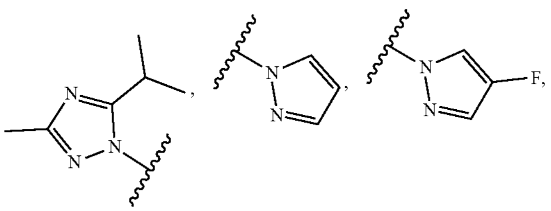
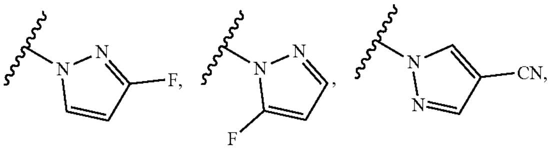

-continued

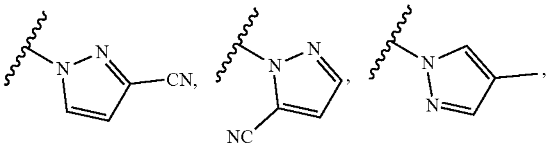
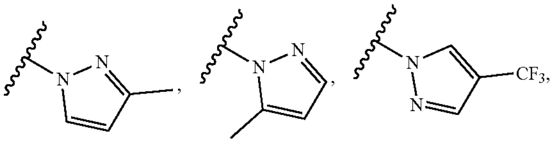
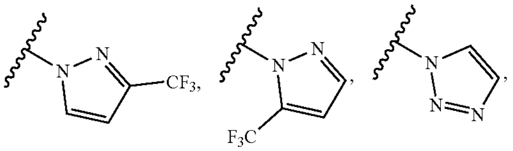
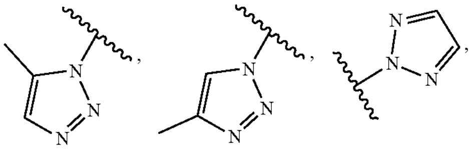
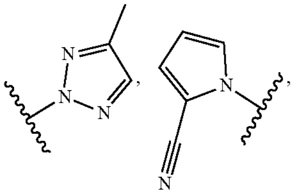
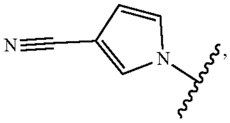
and
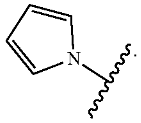

In embodiments, $R^{20f}$ is selected from unsubstituted $C_{1-3}$ alkyl and $C_{3-4}$ non-aromatic carbocycle substituted with $C_{1-3}$ alkyl, wherein the $C_{1-3}$ alkyl is optionally substituted with $C_{1-3}$ alkoxy or CN; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

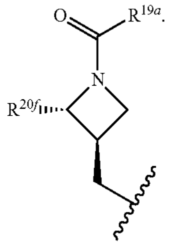

In embodiments, $R^{20f}$ is selected from methyl-substituted cyclopropyl, unsubstituted tert-butyl, unsubstituted isopropyl, and unsubstituted methyl; and $R^{19a}$ is selected

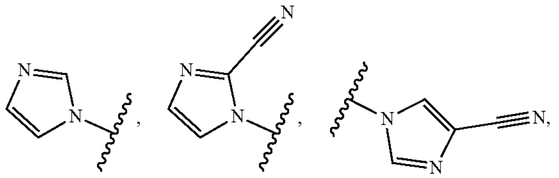
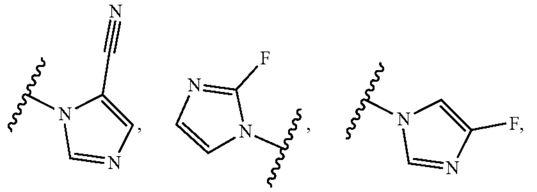
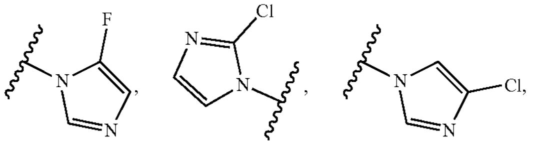
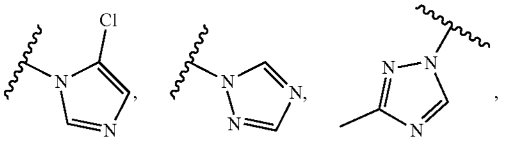
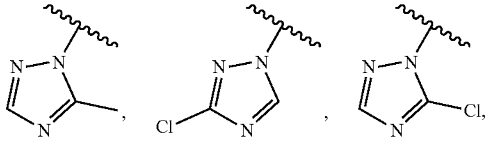
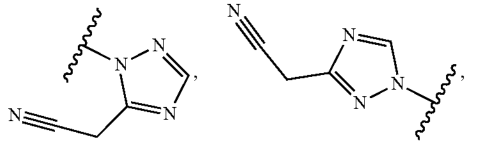
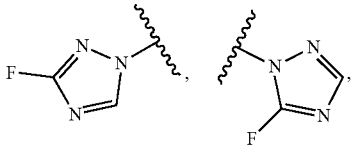
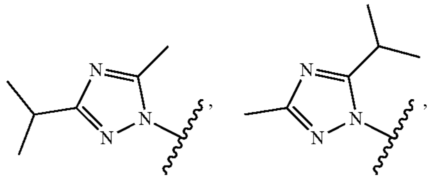
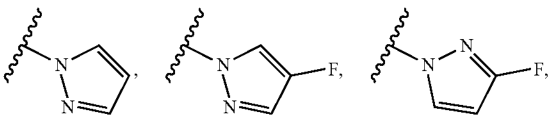
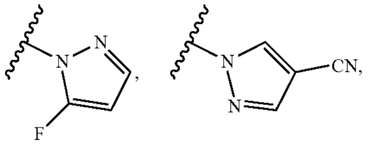
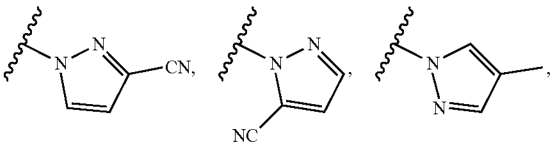

-continued

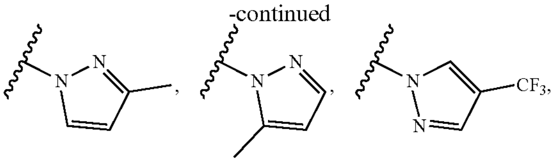
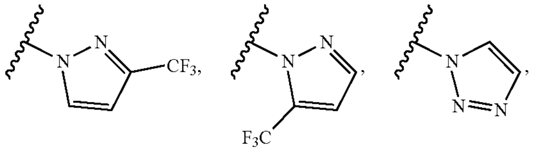
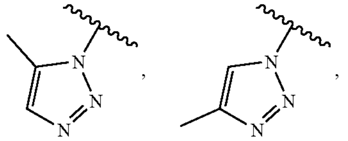
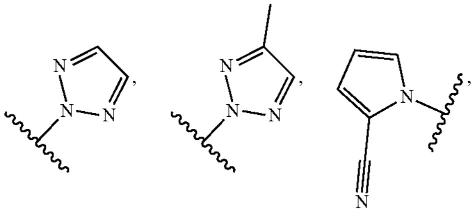

and

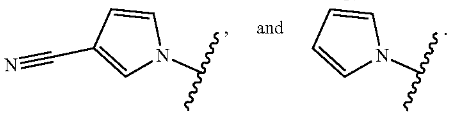

In embodiments, $R^{20f}$ is selected from unsubstituted $C_{1-3}$ alkyl and $C_{3-4}$ non-aromatic carbocycle substituted with $C_{1-3}$ alkyl; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

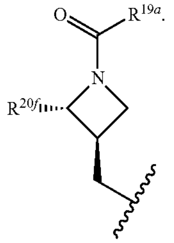

In embodiments, $R^{20f}$ is selected from methyl-substituted cyclopropyl, cyclopropyl substituted with $—CH_2OCH_3$, cyclopropyl substituted with $—CH_2CN$, unsubstituted tert-butyl, unsubstituted isopropyl, and unsubstituted methyl; and $R^{19a}$ is selected from

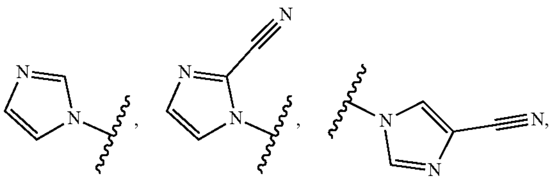

-continued

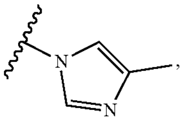, 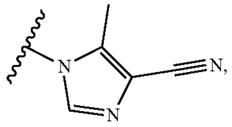

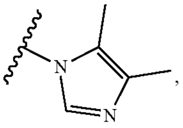, 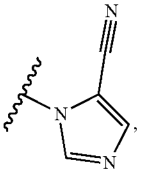, 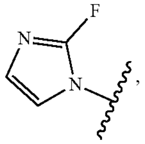,

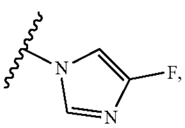 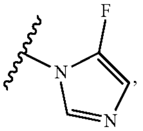, 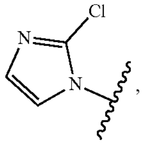,

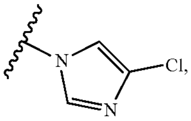 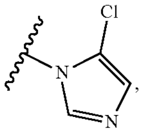, 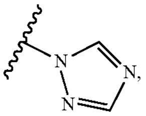

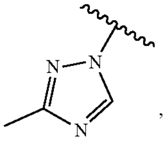, 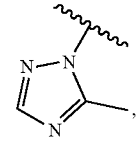, 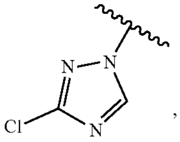,

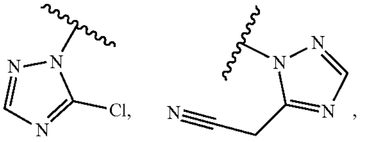

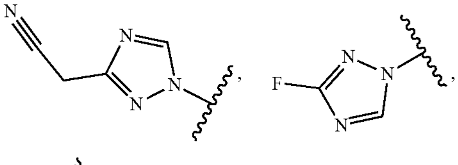

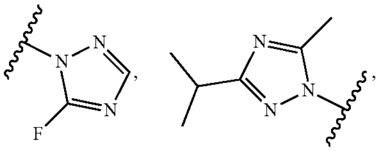

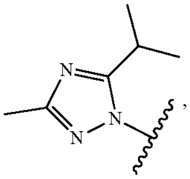, 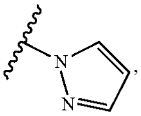, 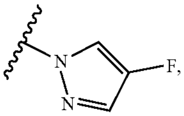

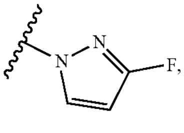 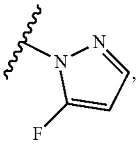, 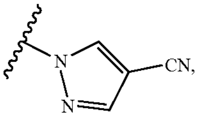

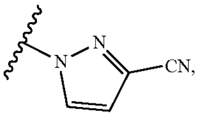 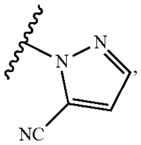, 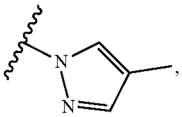,

-continued

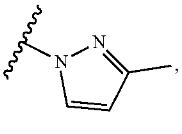, 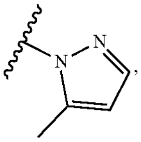, 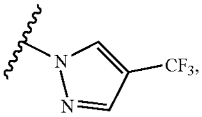

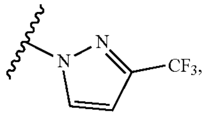 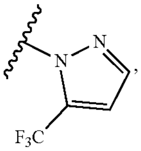, 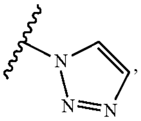,

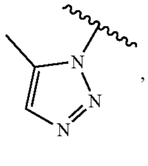, 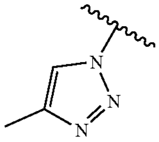, 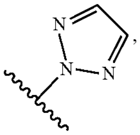,

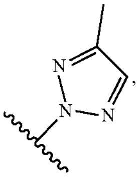, 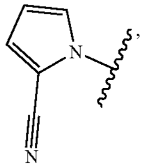,

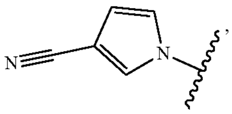, and 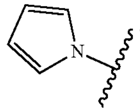.

In embodiments, $R^{20f}$ is selected from unsubstituted $C_{1-3}$ alkyl and $C_{3-4}$ non-aromatic carbocycle substituted with $C_{1-3}$ alkyl, wherein the $C_{1-3}$ alkyl is optionally substituted with $C_{1-3}$ alkoxy or CN; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

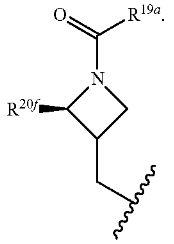

In embodiments, $R^{20f}$ is selected from methyl-substituted cyclopropyl, unsubstituted tert-butyl, unsubstituted isopropyl, and unsubstituted methyl; and $R^{19a}$ is selected from

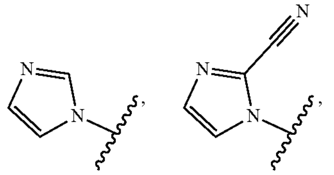

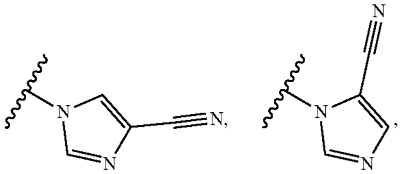

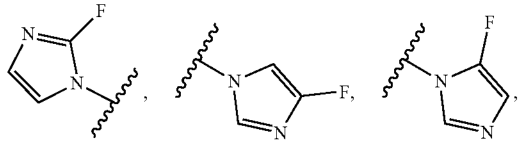

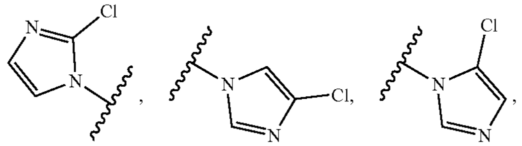

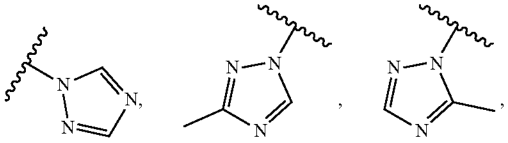

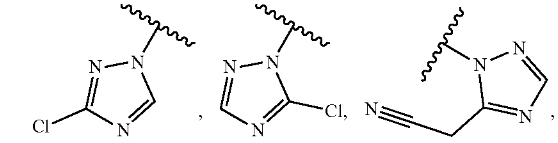

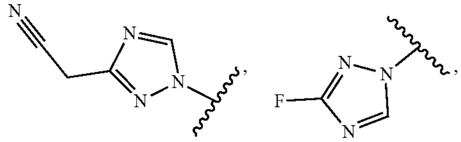

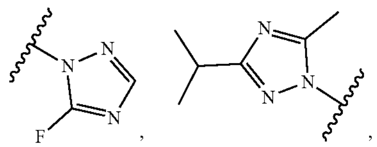

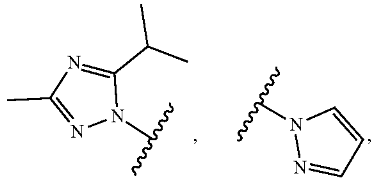

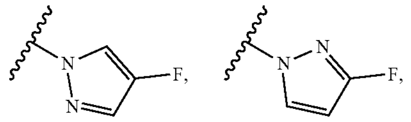

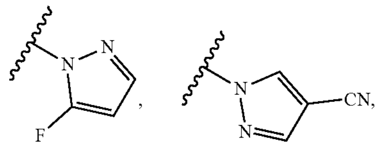

-continued

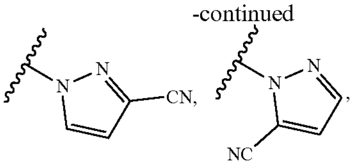

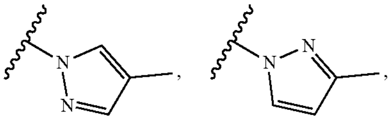

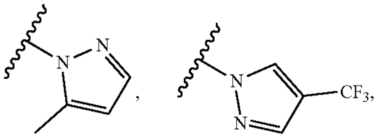

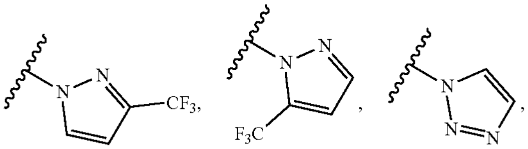

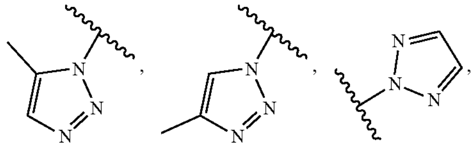

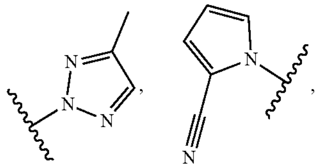

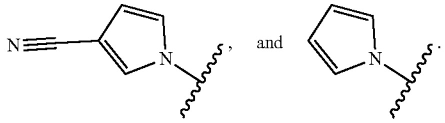

In embodiments, $R^{20f}$ is selected from unsubstituted $C_{1-3}$ alkyl and $C_{3-4}$ non-aromatic carbocycle substituted with $C_{1-3}$ alkyl; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

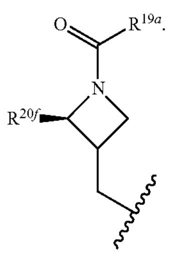

In embodiments, $R^{20f}$ is selected from methyl-substituted cyclopropyl, cyclopropyl substituted with $—CH_2OCH_3$, cyclopropyl substituted with $—CH_2CN$, unsubstituted tert-butyl, unsubstituted isopropyl, and unsubstituted methyl; and $R^{19a}$ is selected from

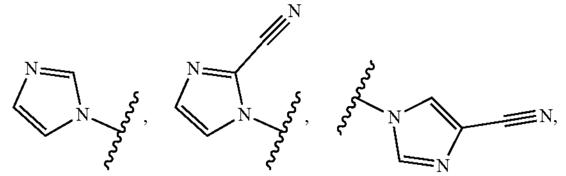

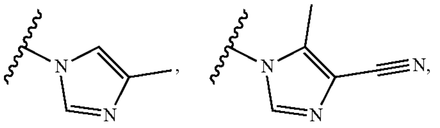

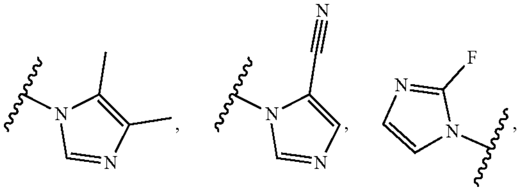

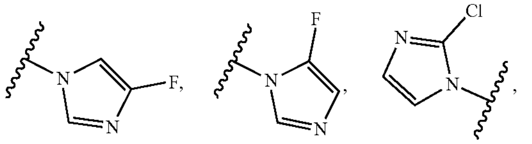

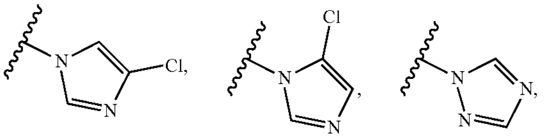

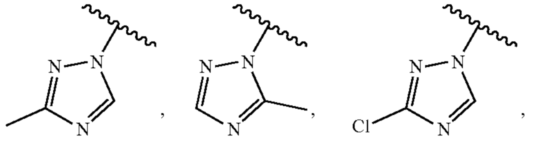

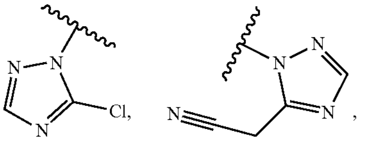

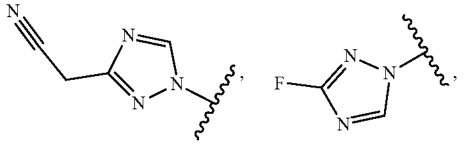

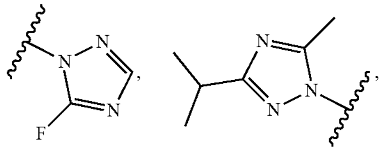

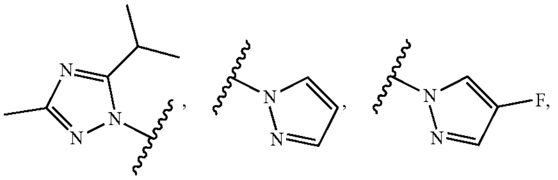

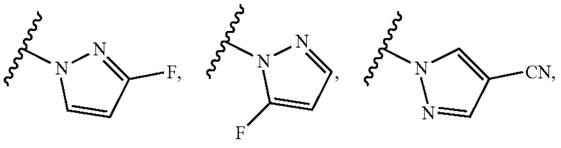

-continued

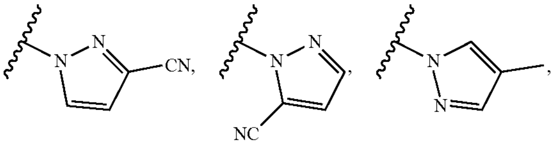

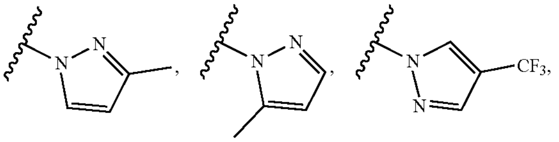

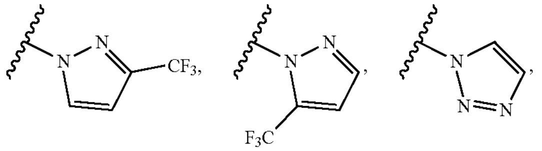

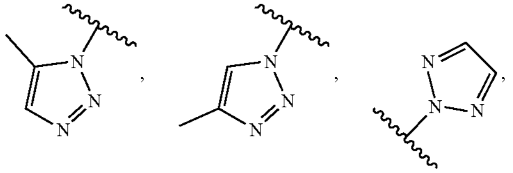

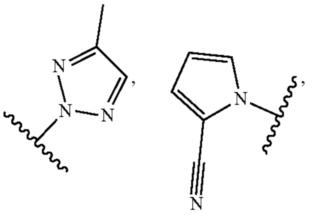

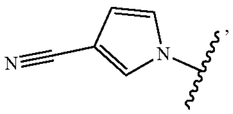

and

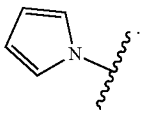

In embodiments, $R^{20f}$ is selected from unsubstituted $C_{1-3}$ alkyl and $C_{3-4}$ non-aromatic carbocycle substituted with $C_{1-3}$ alkyl, wherein the $C_{1-3}$ alkyl is optionally substituted with $C_{1-3}$ alkoxy or CN; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

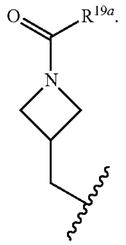

In embodiments, $R^{19a}$ is selected from

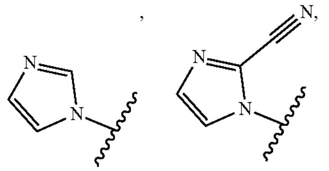

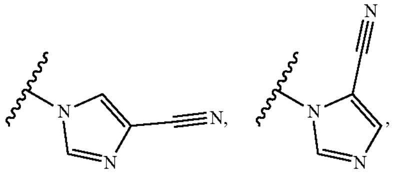

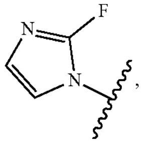 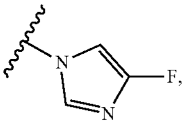 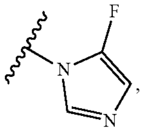

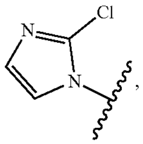 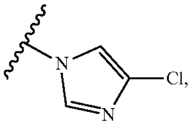 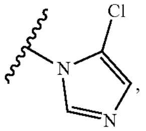

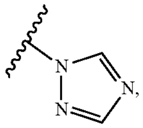 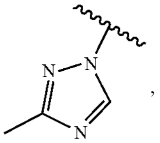 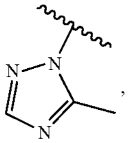

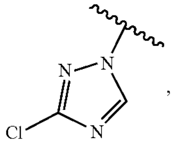 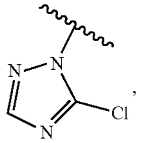

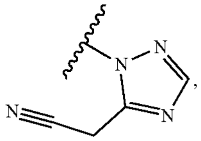 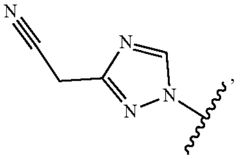

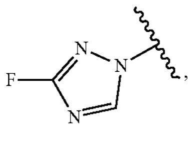 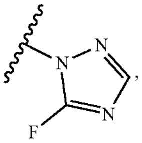

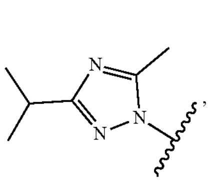 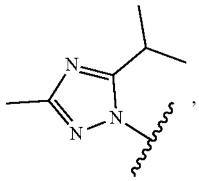

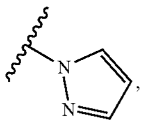 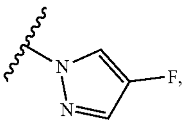 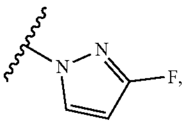

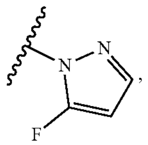 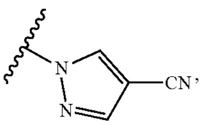

-continued

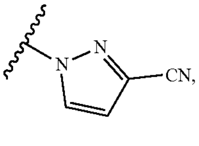 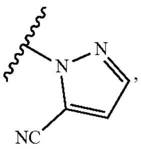

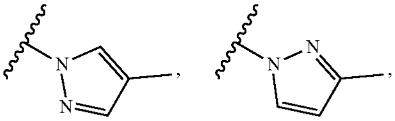

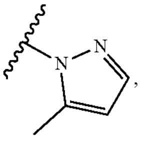 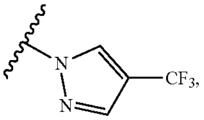

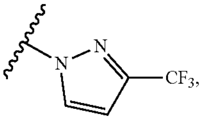 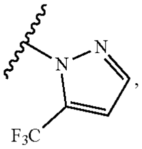

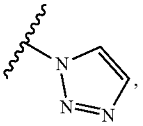 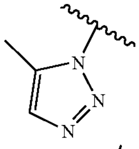 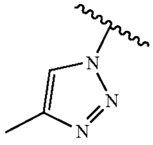

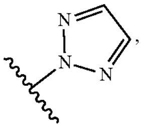 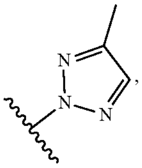

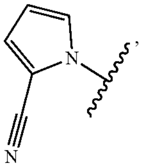 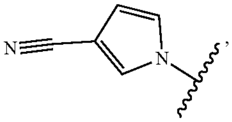 and

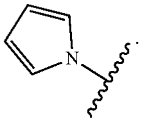

In embodiments, $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

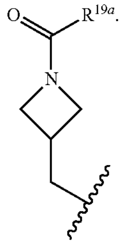

In embodiments, $R^{19a}$ is selected from

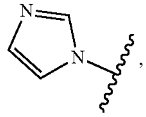, 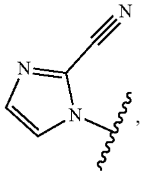, 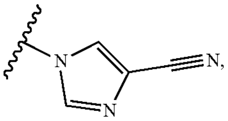

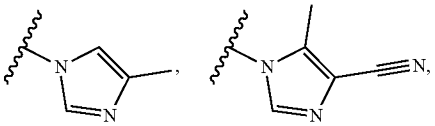

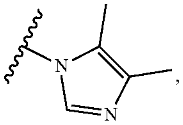, 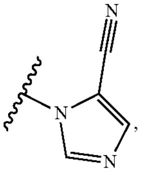, 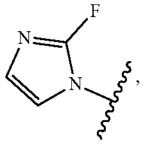,

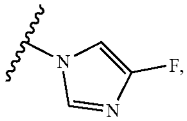, 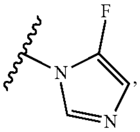, 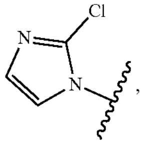,

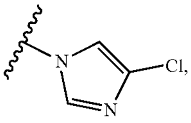, 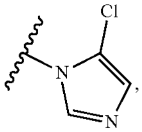, 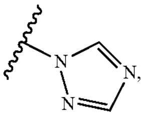

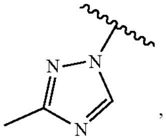, 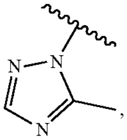, 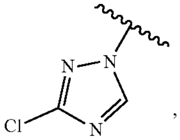,

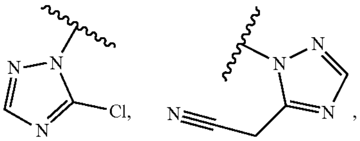

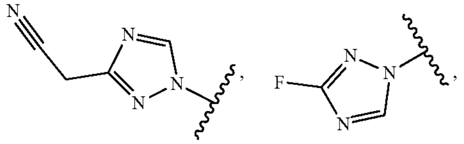

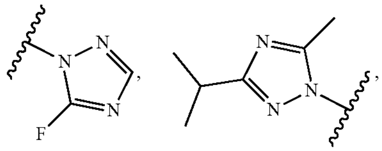

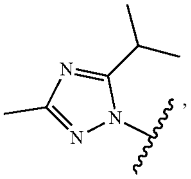, 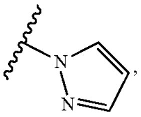, 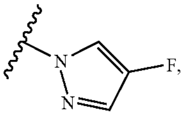

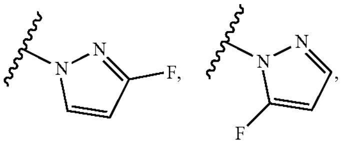, 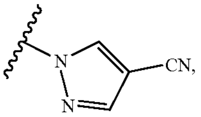

-continued

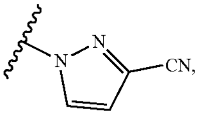, 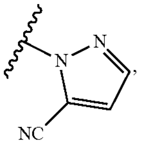, 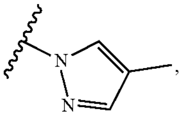,

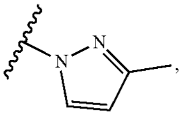, 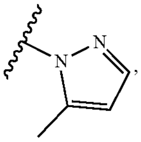, 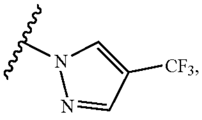

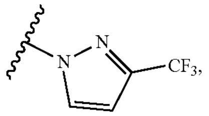, 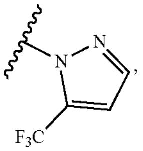, 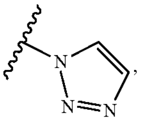,

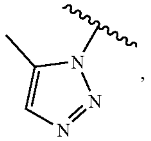, 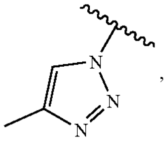, 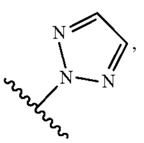,

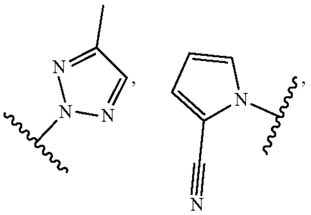,

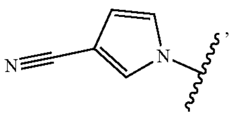, and 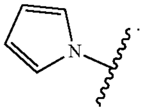.

In embodiments, $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

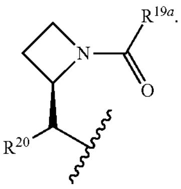

In embodiments, $R^{20}$ is unsubstituted methyl; and $R^{19a}$ is selected from

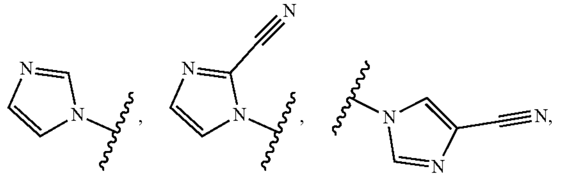
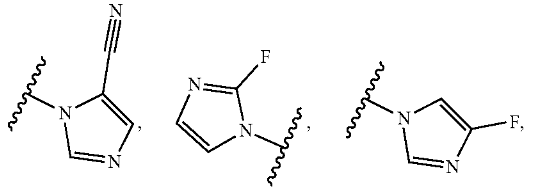
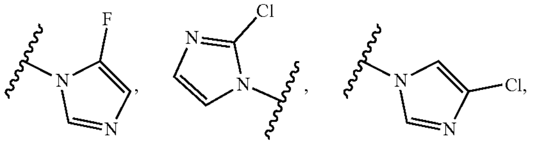
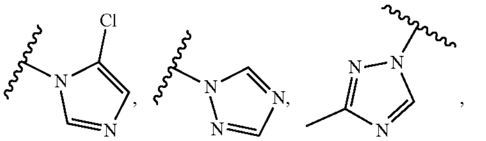
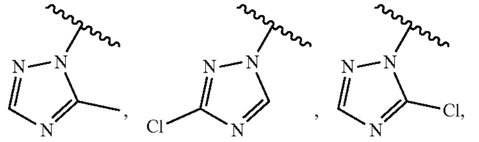
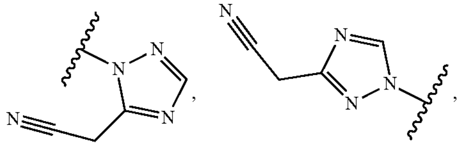
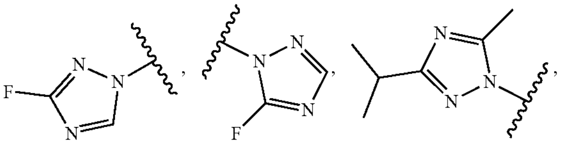
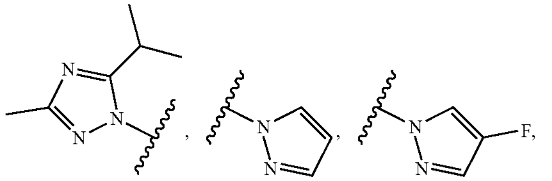
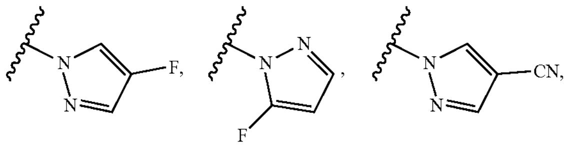
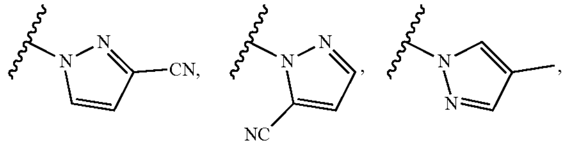
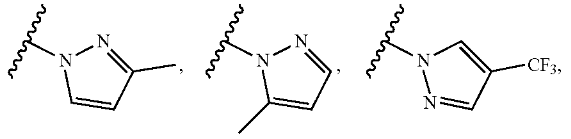

-continued

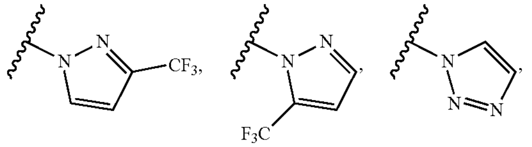
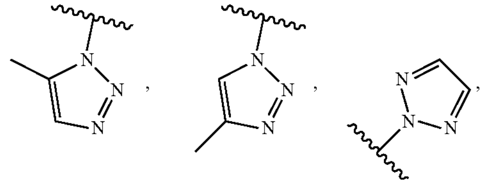
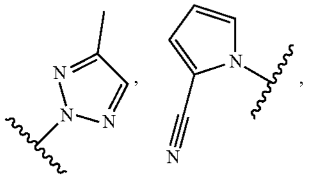
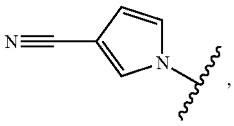
, and
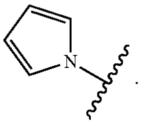

In embodiments, $R^{20}$ is selected from unsubstituted $C_{1-3}$ alkyl; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen.

In embodiments, $-L^{19}-R^{19}-L^{19a}-R^{19a}$ is

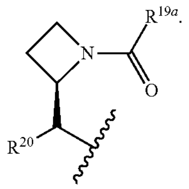

In embodiments, $R^{20}$ is unsubstituted methyl; and $R^{19a}$ is selected from

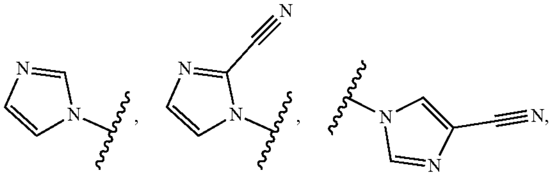
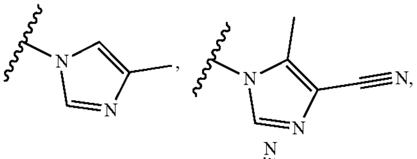
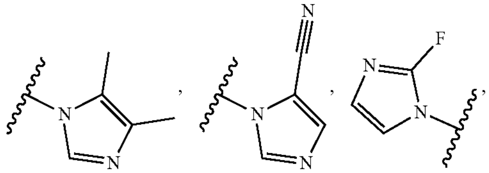

-continued

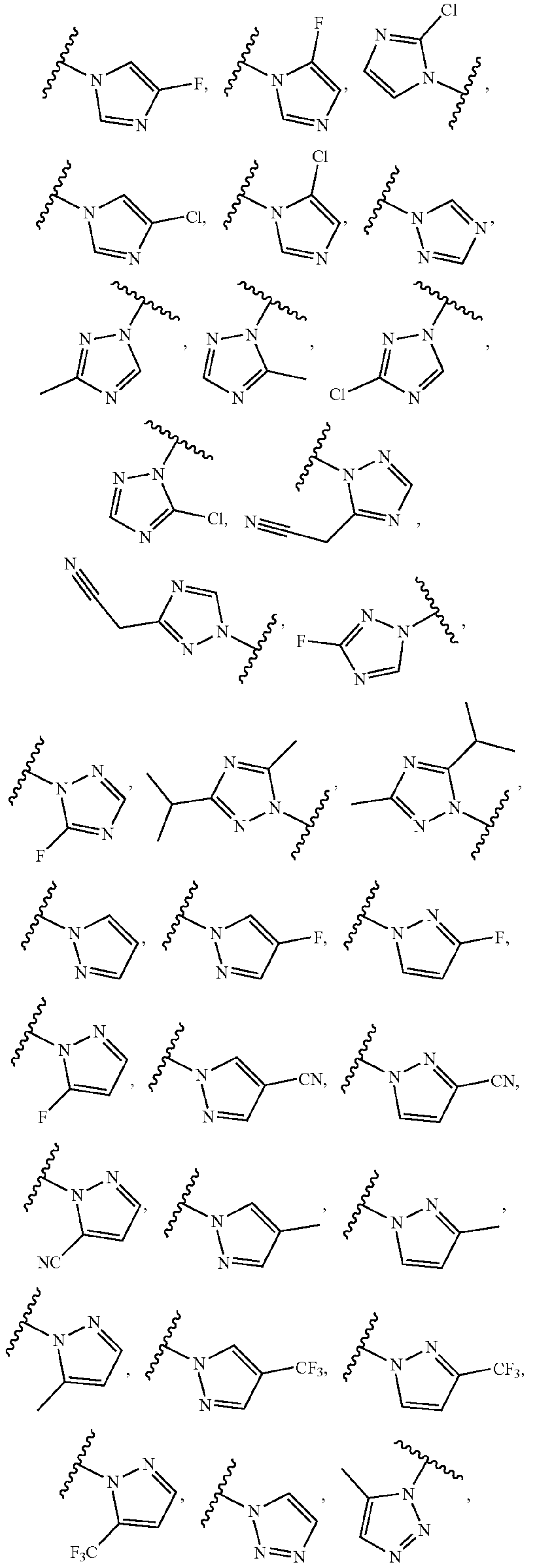

-continued

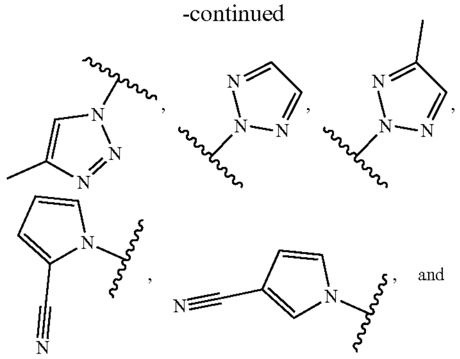

and

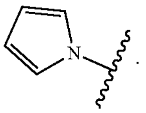

In embodiments, $R^{20}$ is selected from unsubstituted $C_{1-3}$ alkyl; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

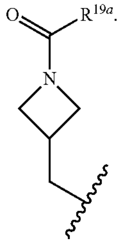

In embodiments, $R^{19a}$ is selected from

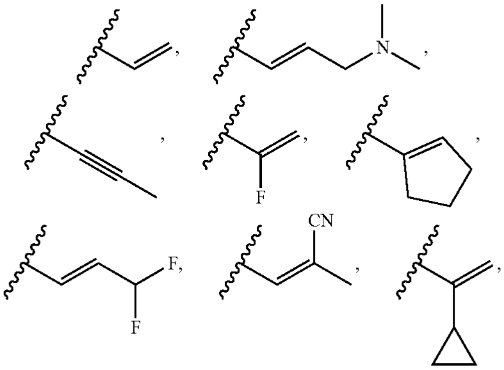

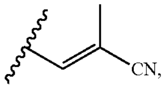

and

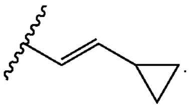

In embodiments, $R^{19a}$ is selected from an unsubstituted cyclopentenyl, unsubstituted $C_{2-3}$ alkynyl, and $C_{2-3}$ alkenyl, wherein the $C_{2-3}$ alkenyl is optionally substituted with one or more halogen, —CN, unsubstituted cyclopropyl, or —$N(CH_3)_2$. In embodiments, $R^{19a}$ is selected from unsubstituted $C_{4-6}$ non-aromatic carbocycle, unsubstituted $C_{2-3}$ alkynyl, and $C_{2-3}$ alkenyl, wherein the $C_{2-3}$ alkenyl is optionally substituted with one or more halogen, —CN, unsubstituted $C_{3-4}$ non-aromatic carbocycle, or —$N(C_{1-3}\ alkyl)_2$.

In embodiments, $-L^{19}-R^{19}-L^{19a}-R^{19a}$ is

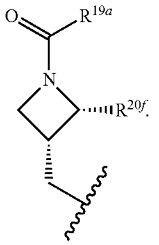

In embodiments, $R^{20f}$ is selected from methyl-substituted cyclopropyl and unsubstituted methyl; and $R^{19a}$ is selected from

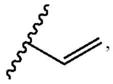, 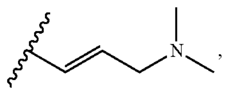, 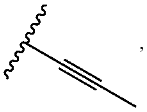, 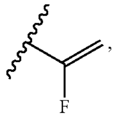, 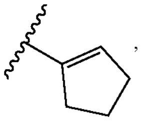, 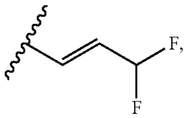, 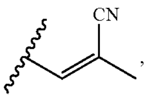, 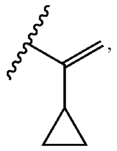, 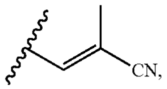, and 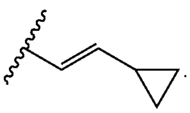.

In embodiments, $R^{20f}$ is selected from unsubstituted $C_{1-3}$ alkyl and $C_{3-4}$ non-aromatic carbocycle that is substituted with $C_{1-3}$ alkyl; and $R^{19a}$ is selected from unsubstituted cyclopentenyl, unsubstituted $C_{2-3}$ alkynyl, and $C_{2-3}$ alkenyl that is optionally substituted with one or more halogen, —CN, unsubstituted cyclopropyl, or —$N(CH_3)_2$. In embodiments, $R^{20f}$ is selected from unsubstituted $C_{1-3}$ alkyl and $C_{3-4}$ non-aromatic carbocycle substituted with $C_{1-3}$ alkyl; and $R^{19a}$ is selected from unsubstituted $C_{4-6}$ non-aromatic carbocycle, unsubstituted $C_{2-3}$ alkynyl, and $C_{2-3}$ alkenyl that is optionally substituted with one or more halogen, —CN, unsubstituted $C_{3-4}$ non-aromatic carbocycle, or —$N(C_{1-3}\ alkyl)_2$.

In embodiments, $-L^{19}-R^{19}-L^{19a}-R^{19a}$ is

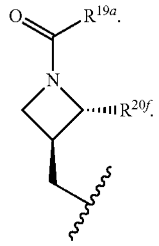

In embodiments, $R^{20f}$ is selected from methyl-substituted cyclopropyl and unsubstituted methyl; and $R^{19a}$ is selected from

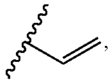, 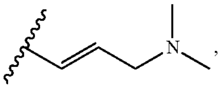, 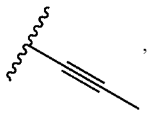, 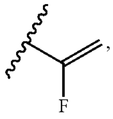, 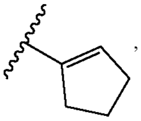, 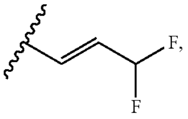, 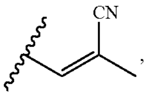, 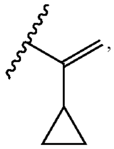, 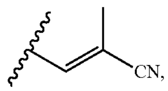, and 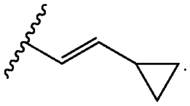.

In embodiments, $R^{20f}$ is selected from unsubstituted $C_{1-3}$ alkyl and $C_{3-4}$ non-aromatic carbocycle substituted with $C_{1-3}$ alkyl; and $R^{19a}$ is selected from unsubstituted cyclopentenyl, unsubstituted $C_{2-3}$ alkynyl, and $C_{2-3}$ alkenyl that is optionally substituted with one or more halogen, —CN, unsubstituted cyclopropyl, or —$N(CH_3)$. In embodiments, $R^{20f}$ is selected from unsubstituted $C_{1-3}$ alkyl and $C_{3-4}$ non-aromatic carbocycle substituted with $C_{1-3}$ alkyl; and $R^{19a}$ is selected from unsubstituted $C_{4-6}$ non-aromatic carbocycle, unsubstituted $C_{2-3}$ alkynyl, and $C_{2-3}$ alkenyl that is optionally substituted with one or more halogen, —CN, unsubstituted $C_{3-4}$ non-aromatic carbocycle, or —$N(C_{1-3}\ alkyl)_2$.

In embodiments, $-L^{19}-R^{19}-L^{19a}-R^{19a}$ is

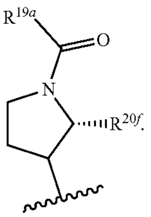

In embodiments, $R^{20f}$ is unsubstituted methyl; and $R^{19a}$ is selected from

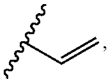, 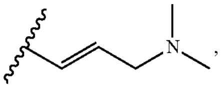,

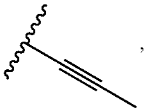, 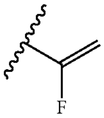, 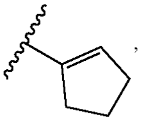,

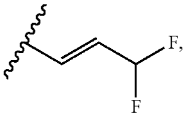 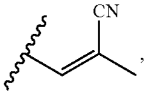, 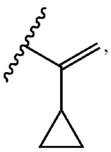

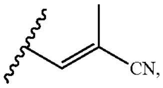 and 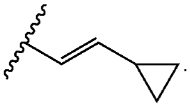

In embodiments, $R^{20f}$ is unsubstituted $C_{1-3}$ alkyl; and $R^{19a}$ is selected from unsubstituted cyclopentenyl, unsubstituted $C_{2-3}$ alkynyl, and $C_{2-3}$ alkenyl that is optionally substituted with one or more halogen, —CN, unsubstituted cyclopropyl, or —$N(CH_3)_2$. In embodiments, $R^{20f}$ is unsubstituted $C_{1-3}$ alkyl and $R^{19a}$ is selected from unsubstituted $C_{4-6}$ non-aromatic carbocycle, unsubstituted $C_{2-3}$ alkynyl, and $C_{2-3}$ alkenyl that is optionally substituted with one or more halogen, —CN, unsubstituted $C_{3-4}$ non-aromatic carbocycle, or —$N(C_{1-3}\ alkyl)_2$.

In embodiments, $-L^{19}-R^{19}-L^{19a}-R^{19a}$ is

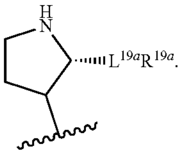

In embodiments, $-L^{19a}-R^{19a}$ is unsubstituted methyl. In embodiments, $-L^{19a}-R^{19a}$ is unsubstituted $C_{1-3}$ alkyl.

In embodiments, $-L^{19}-R^{19}-L^{19a}-R^{19a}$ is

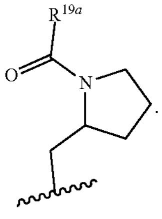

In embodiments, $R^{19a}$ is selected

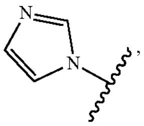, 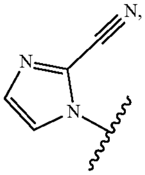 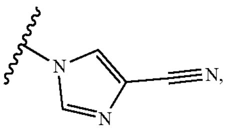

-continued

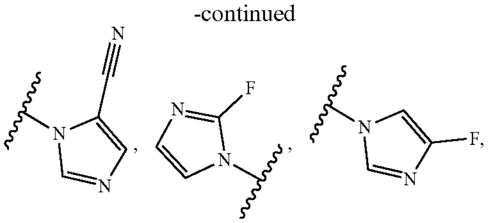

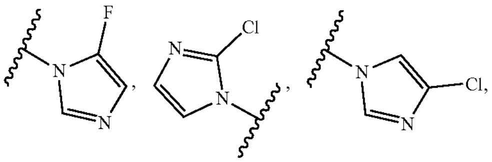

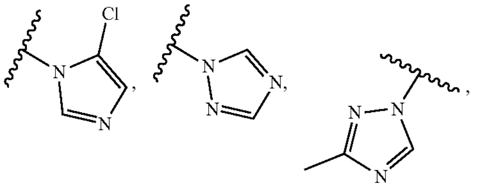

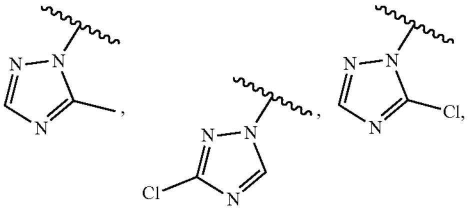

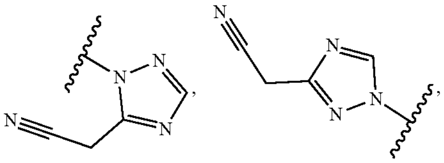

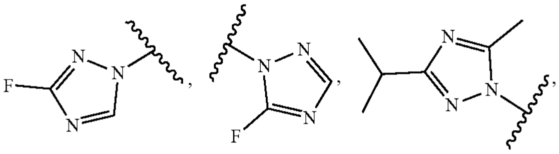

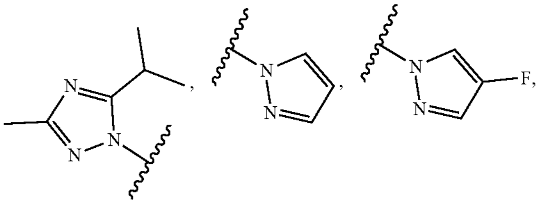

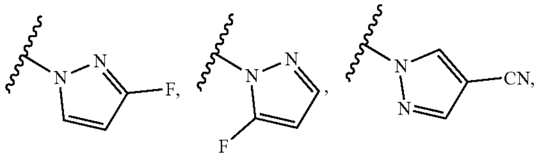

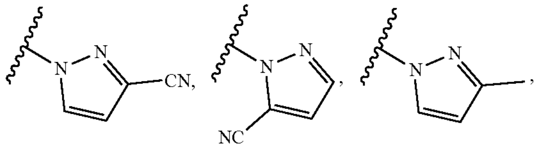

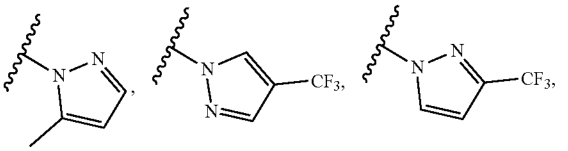

-continued

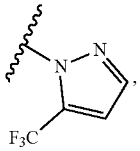, 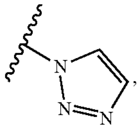, 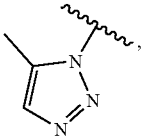,

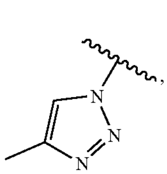, 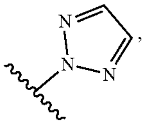, 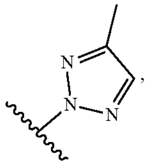,

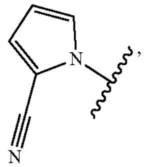, 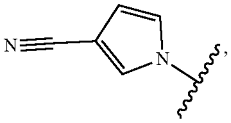, and

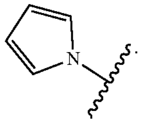.

In embodiments, $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

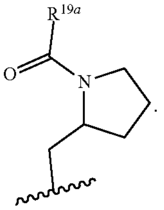.

In embodiments, $R^{19a}$ is selected

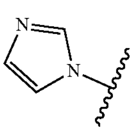, 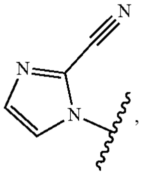, 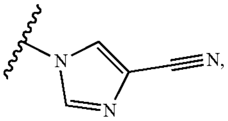,

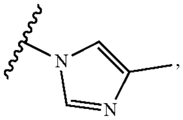, 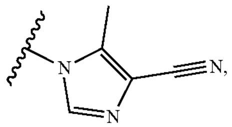,

-continued

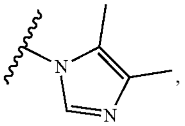, 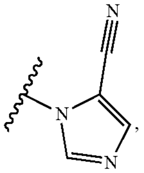, 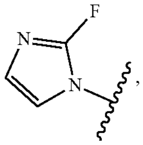,

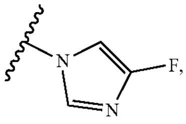, 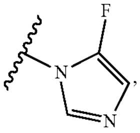, 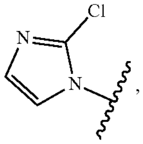,

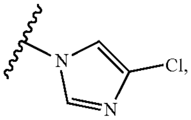, 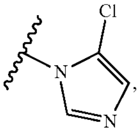, 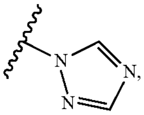,

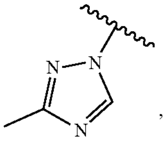, 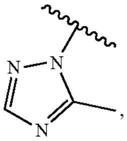, 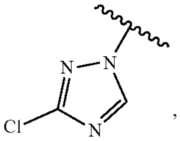,

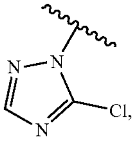, 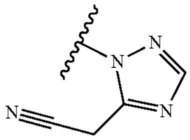,

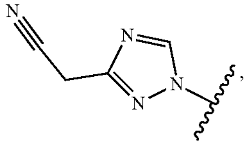, 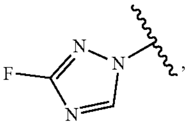,

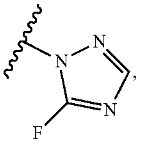, 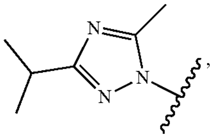,

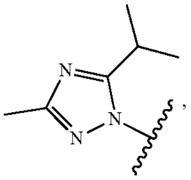, 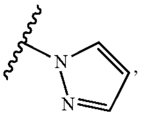, 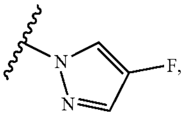,

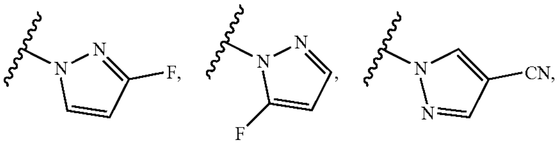

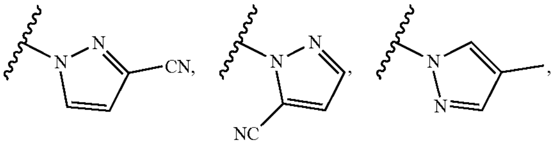

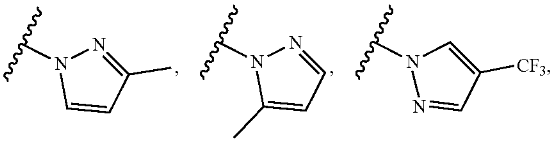

-continued

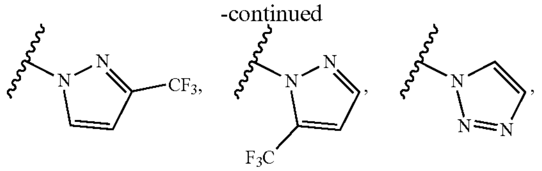

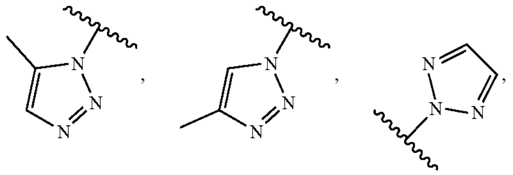

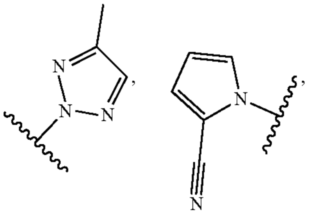

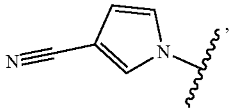

and

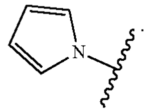

In embodiments, $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

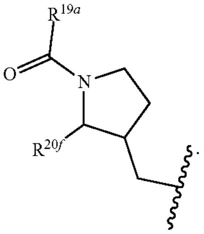

In embodiments, $R^{20f}$ is unsubstituted methyl; and $R^{19a}$ is selected from

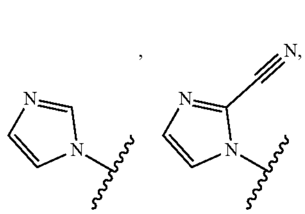

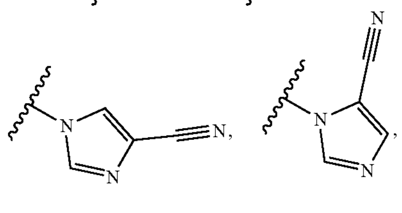

-continued

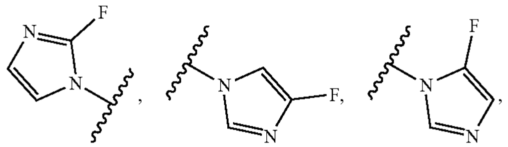

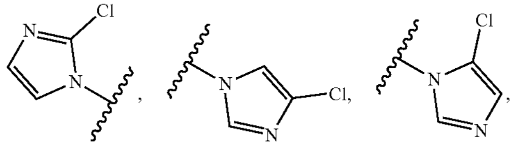

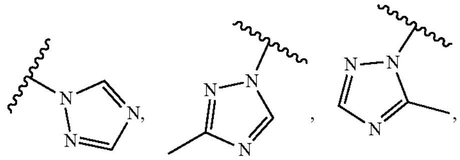

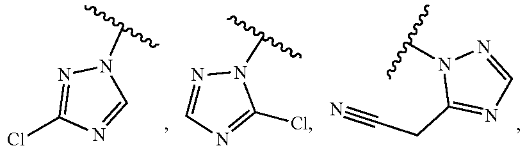

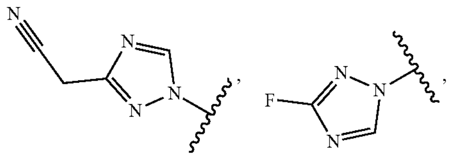

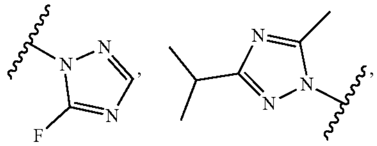

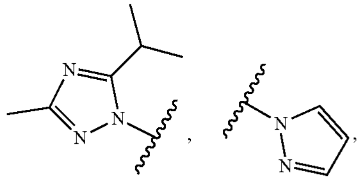

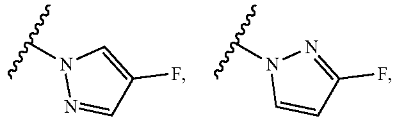

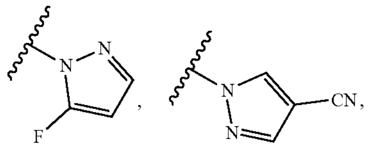

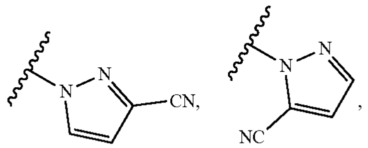

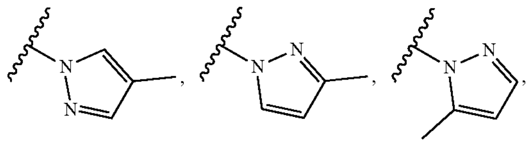

-continued

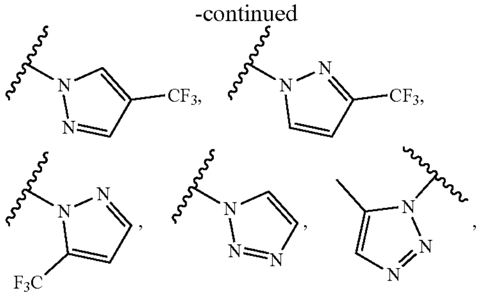

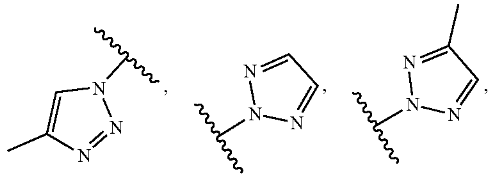

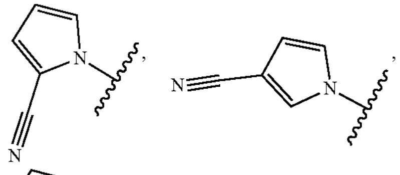

and

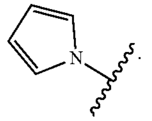

In embodiments, $R^{20f}$ is unsubstituted $C_{1-3}$ alkyl and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

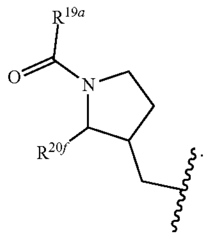

In embodiments, $R^{20f}$ is unsubstituted methyl; and $R^{19a}$ is selected from

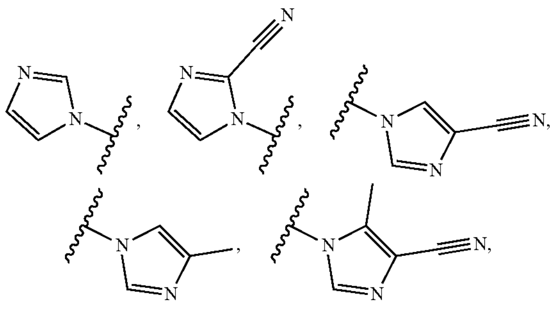

-continued

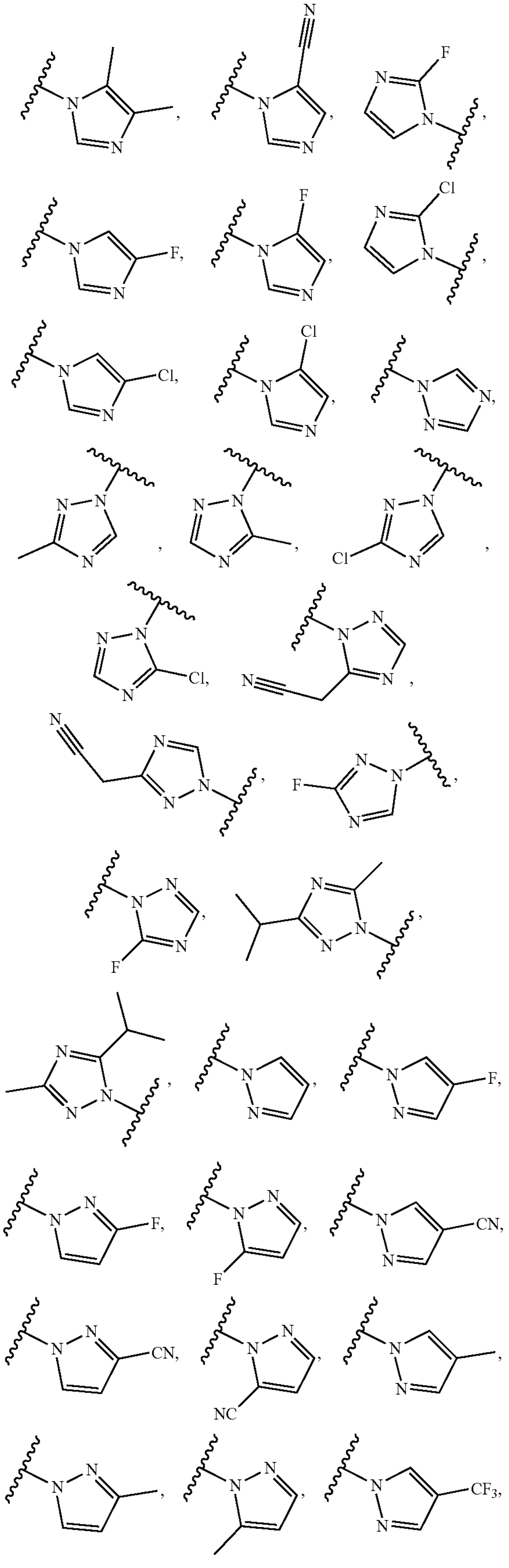

-continued

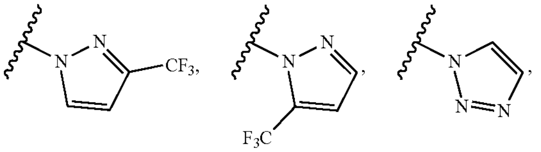

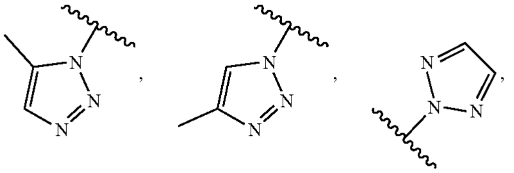

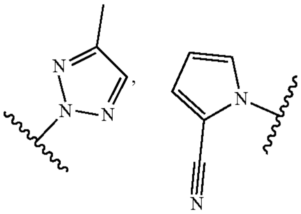

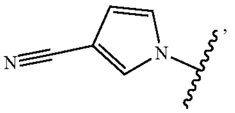

and

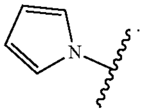

In embodiments, $R^{20f}$ is unsubstituted $C_{1-3}$ alkyl and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

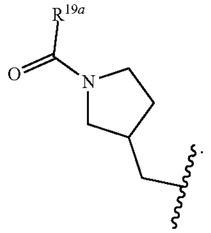

In embodiments, $R^{19a}$ is selected from

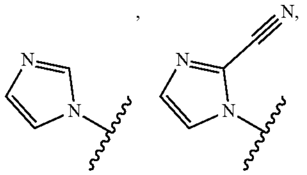

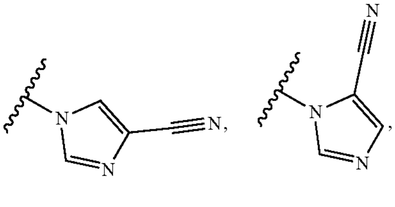

-continued

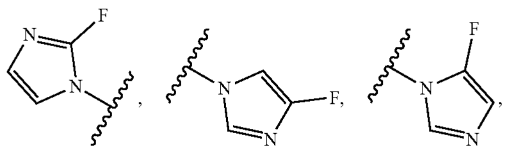

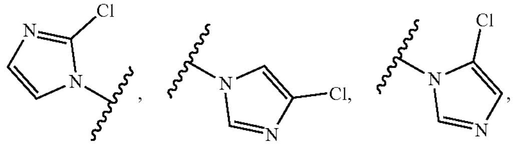

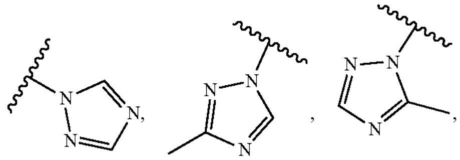

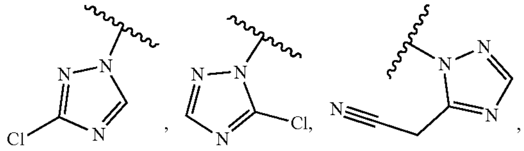

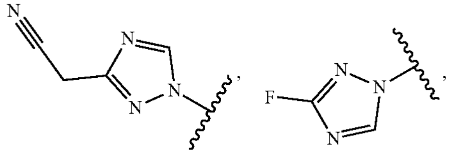

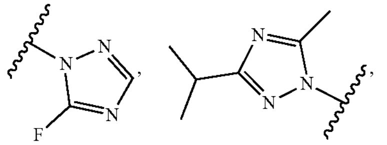

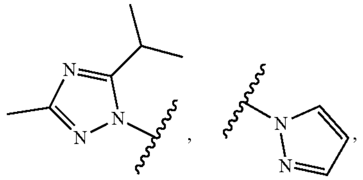

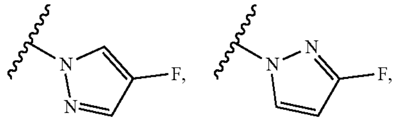

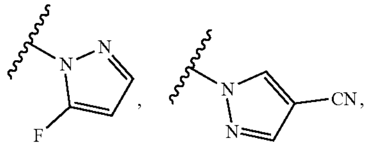

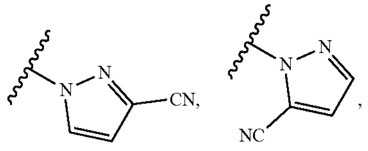

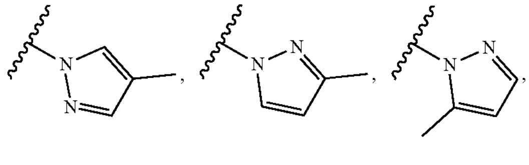

-continued

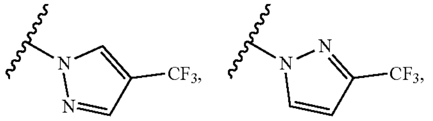

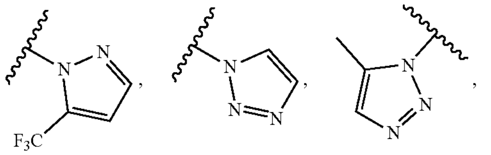

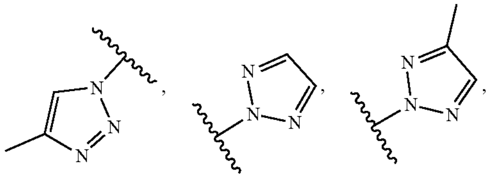

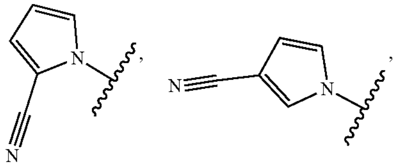

and

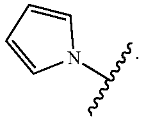

In embodiments, $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

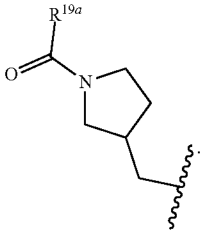

In embodiments, $R^{19a}$ is selected from

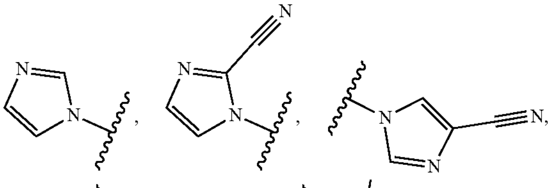

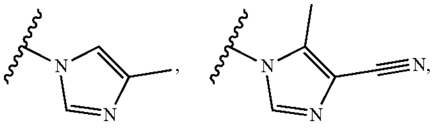

-continued

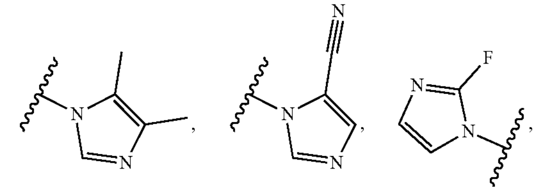

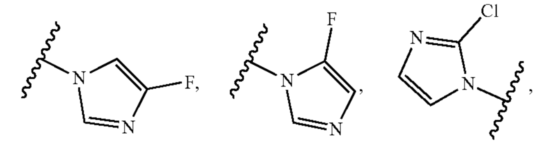

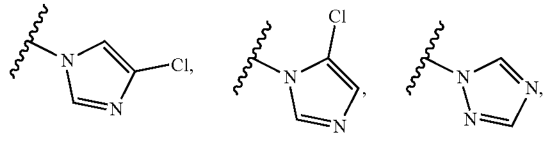

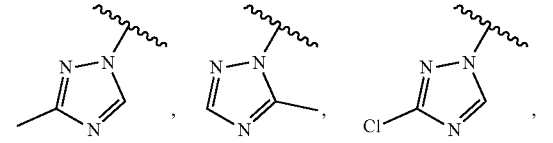

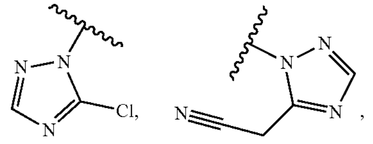

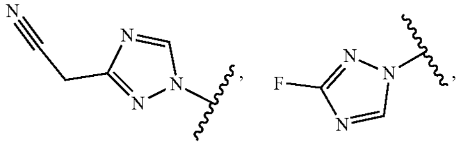

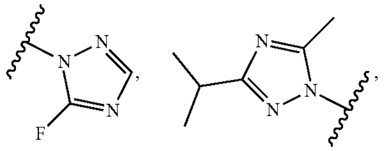

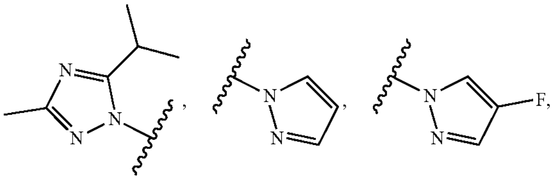

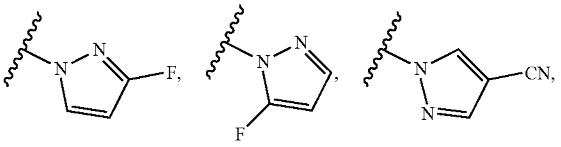

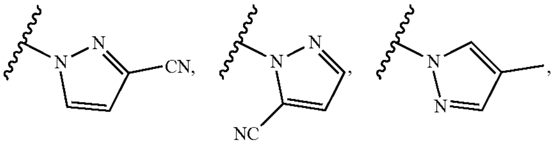

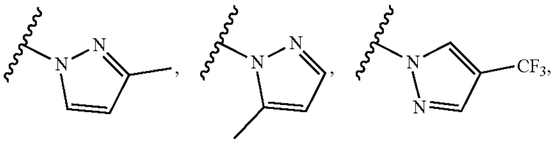

-continued

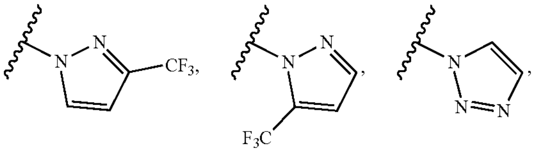

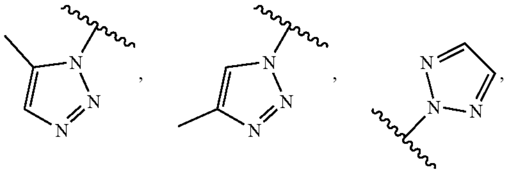

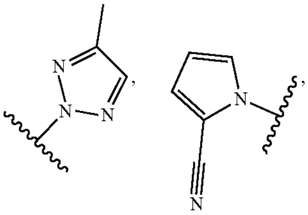

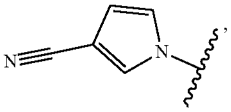

and

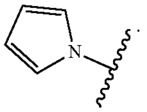

In embodiments, $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

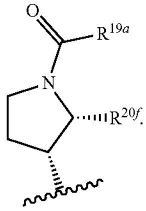

In embodiments, $R^{20f}$ is unsubstituted methyl; and $R^{19a}$ is selected

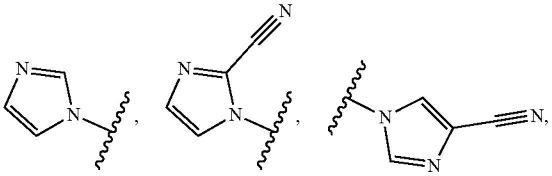

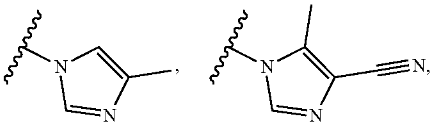

-continued

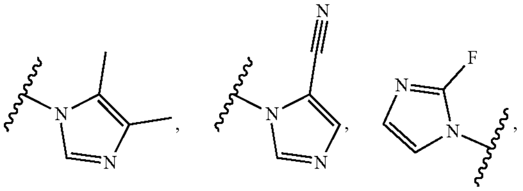

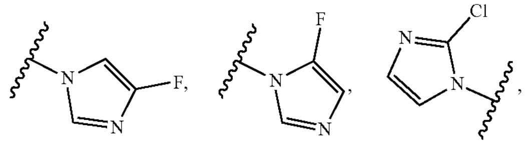

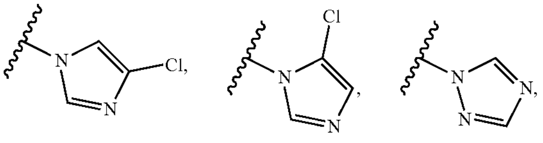

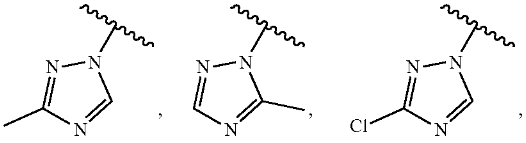

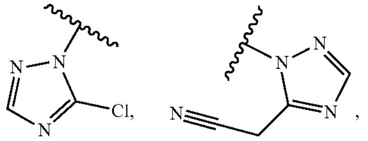

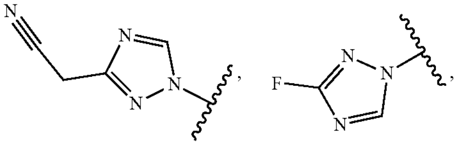

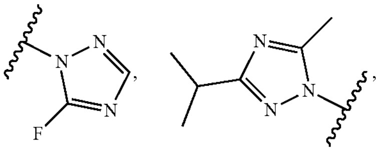

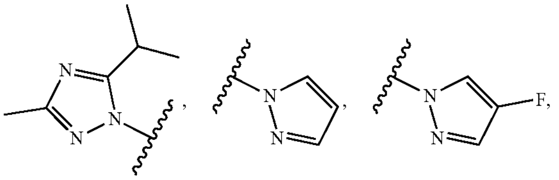

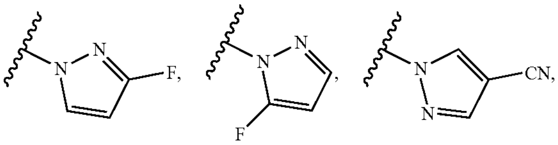

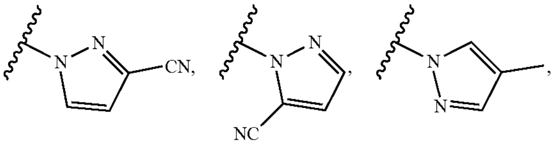

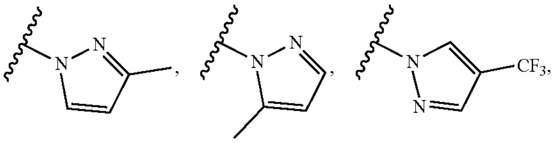

-continued

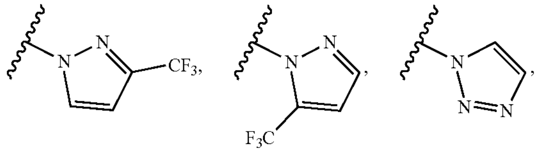

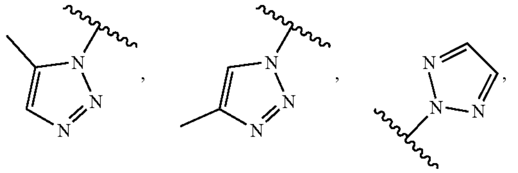

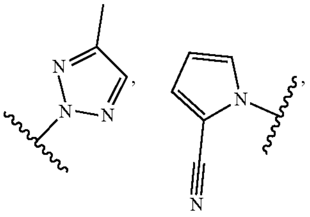

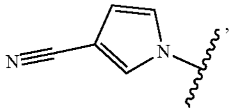

and

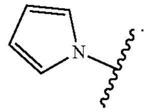

In embodiments, $R^{20f}$ is selected from unsubstituted $C_{1-3}$ alkyl and $C_{3-4}$ non-aromatic carbocycle substituted with $C_{1-3}$ alkyl; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

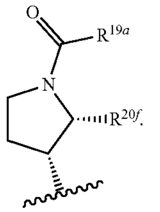

In embodiments, $R^{20f}$ is unsubstituted methyl; and $R^{19a}$ is selected

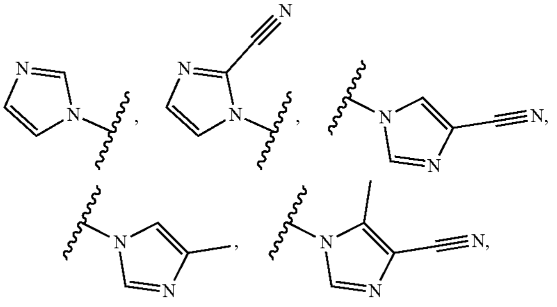

-continued

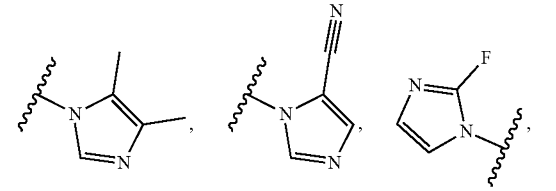

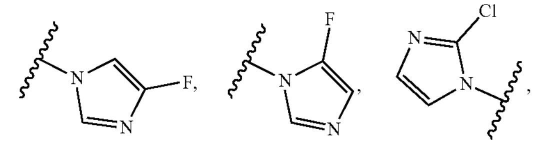

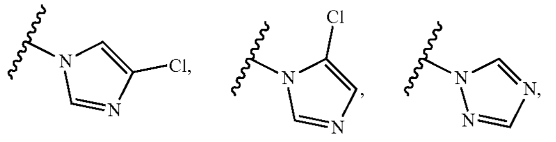

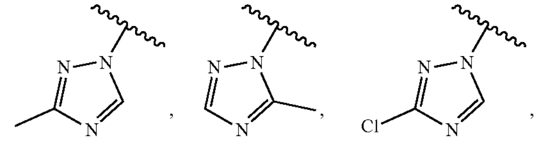

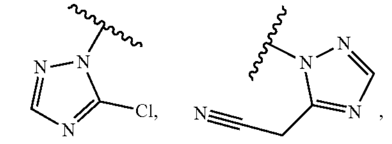

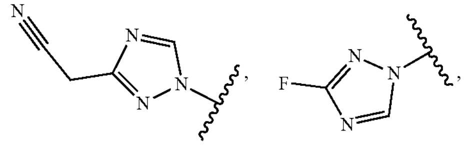

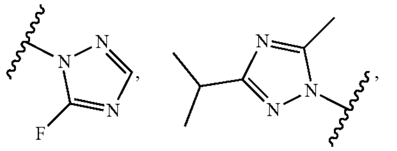

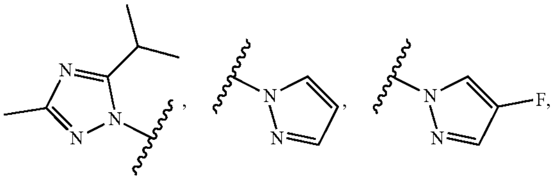

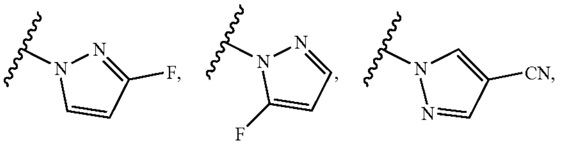

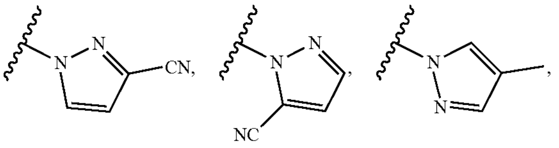

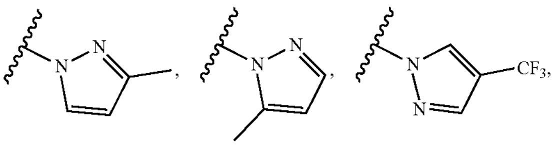

-continued

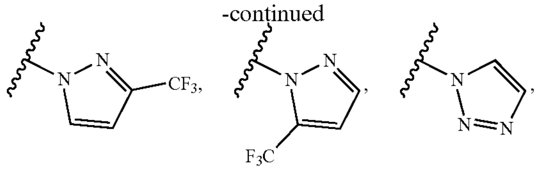

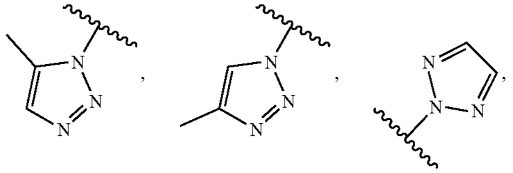

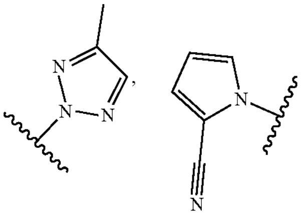

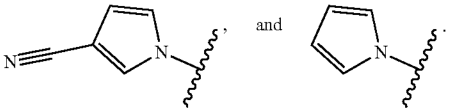

and

In embodiments, $R^{20f}$ is selected from unsubstituted $C_{1-3}$ alkyl and $C_{3-4}$ non-aromatic carbocycle substituted with $C_{1-3}$ alkyl; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

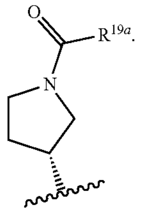

In embodiments, $R^{19a}$ is selected from

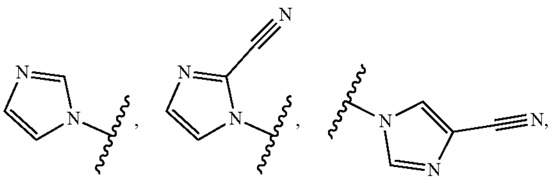

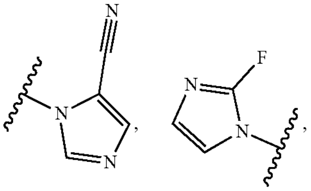

-continued

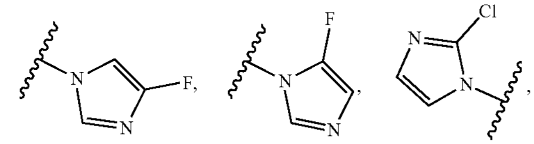

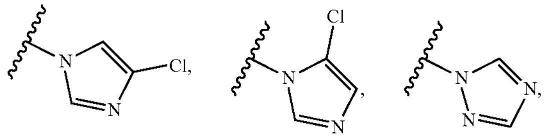

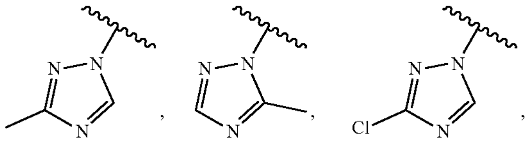

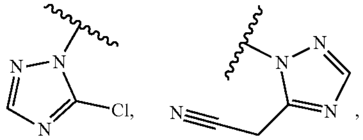

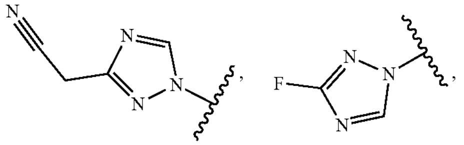

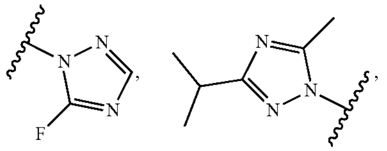

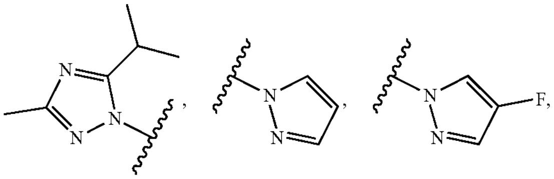

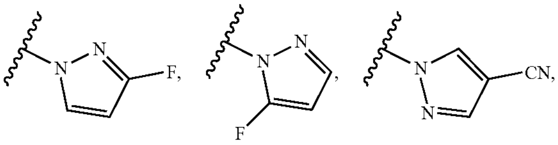

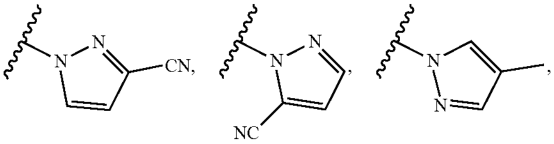

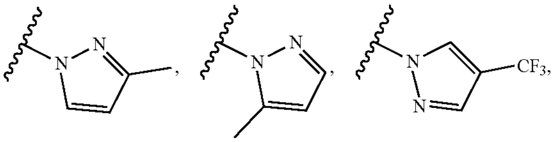

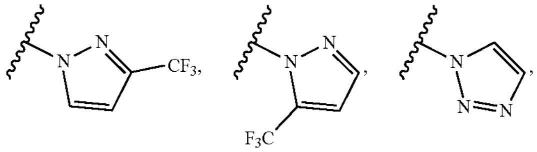

-continued

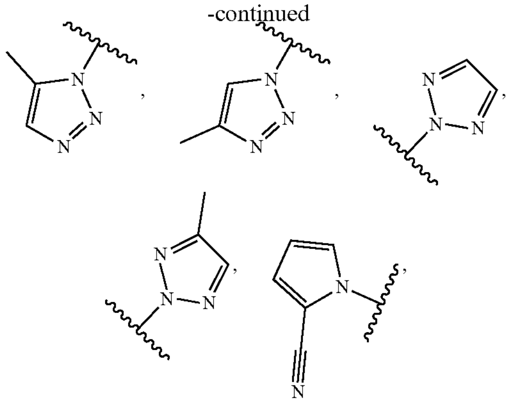

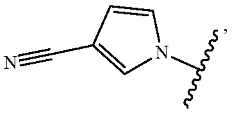

and

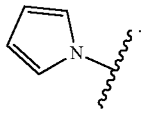

In embodiments, $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

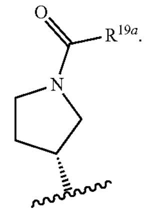

In embodiments, $R^{19a}$ is selected from

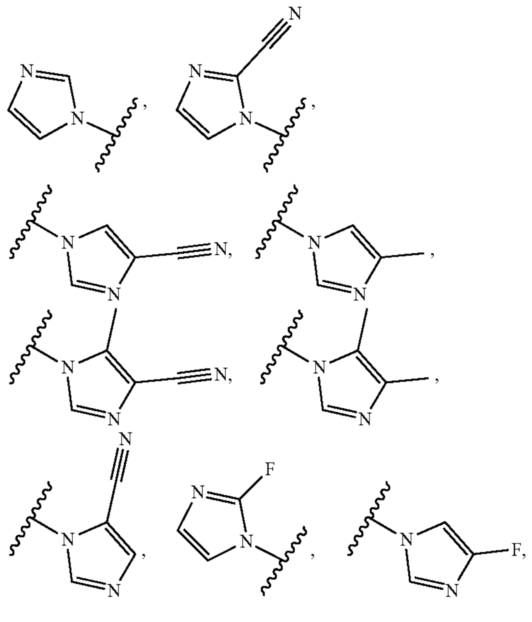

-continued

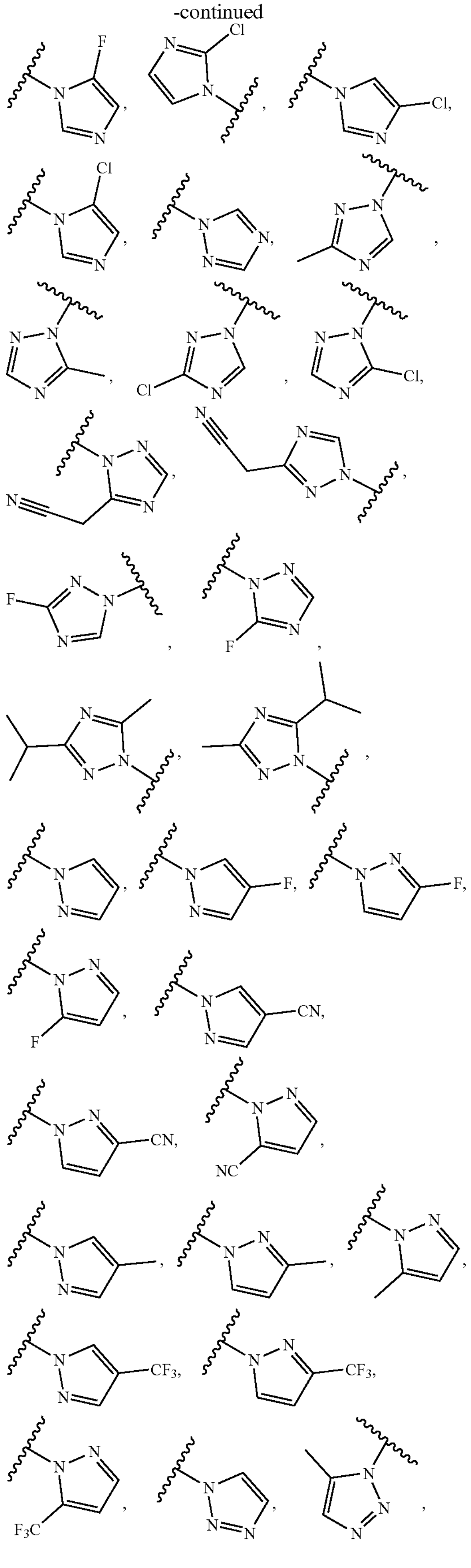

-continued

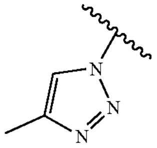, 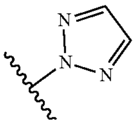, 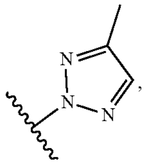,

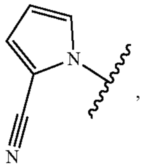, 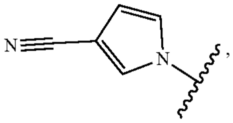, and

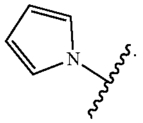.

In embodiments, $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

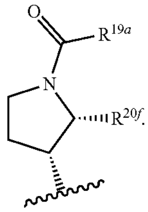.

In embodiments, $R^{20f}$ is unsubstituted methyl; and $R^{19a}$ is

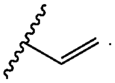 [SMILES: *C=C ; "."].

In embodiments, $R^{20f}$ is selected from unsubstituted $C_{1-3}$ alkyl and $C_{3-4}$ non-aromatic carbocycle substituted with $C_{1-3}$ alkyl; and $R^{19a}$ is selected from unsubstituted cyclopentenyl, unsubstituted $C_{2-3}$ alkynyl, and $C_{2-3}$ alkenyl that is optionally substituted with one or more halogen, —CN, unsubstituted cyclopropyl, or $—N(CH_3)_2$. In embodiments, $R^{20f}$ is selected from unsubstituted $C_{1-3}$ alkyl and $C_{3-4}$ non-aromatic carbocycle substituted with $C_{1-3}$ alkyl; and $R^{19a}$ is selected from unsubstituted $C_{4-6}$ non-aromatic carbocycle, unsubstituted $C_{2-3}$ alkynyl, and $C_{2-3}$ alkenyl that is optionally substituted with one or more halogen, —CN, unsubstituted $C_{3-4}$ non-aromatic carbocycle, or $—N(C_{1-3}\ alkyl)_2$.

In embodiments, $-L^{19}-R^{19}-L^{19a}-R^{19a}$ is

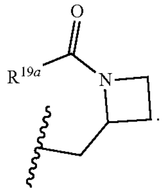.

In embodiments, $R^{19a}$ is selected

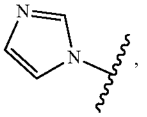, 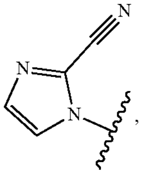, 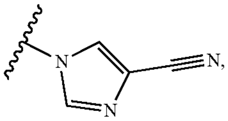,

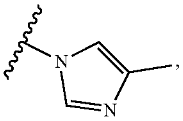, 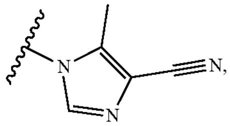,

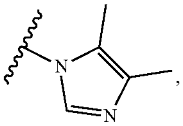, 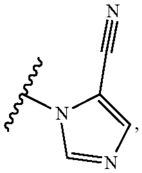, 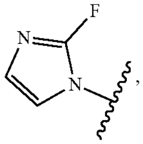,

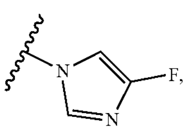, 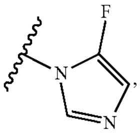, 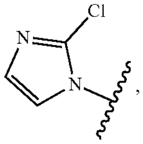,

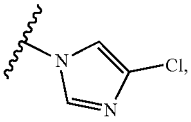, 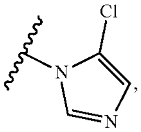, 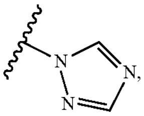,

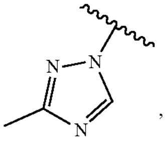, 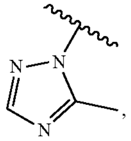, 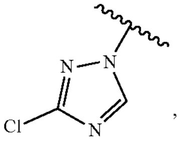,

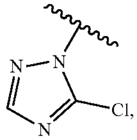, 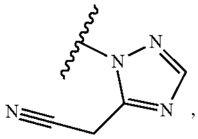,

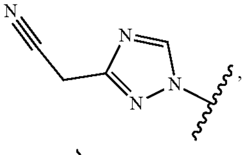, 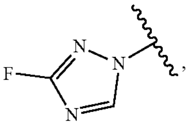,

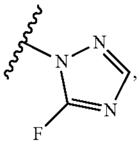, 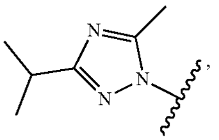,

-continued

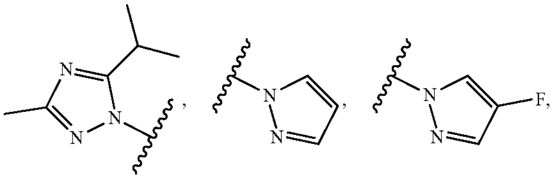

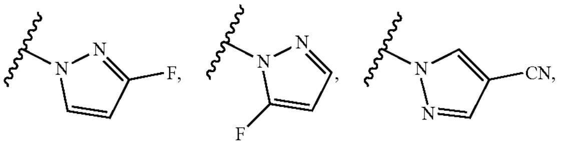

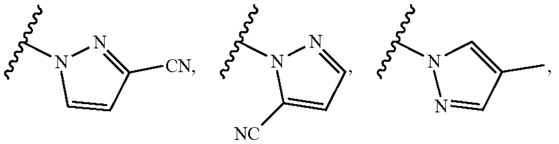

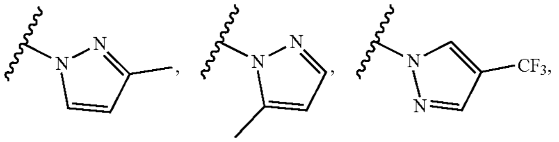

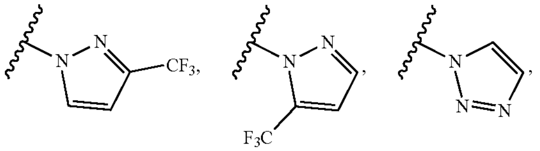

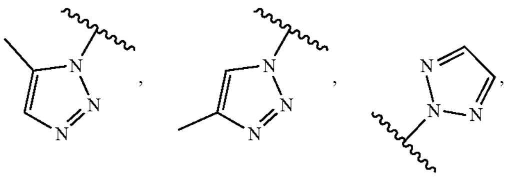

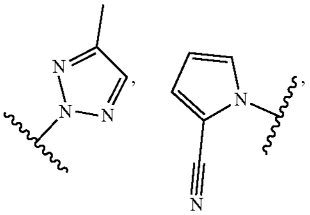

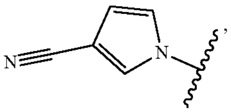

and

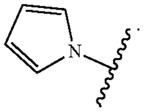

In embodiments, $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

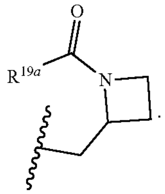

In embodiments, $R^{19a}$ is selected

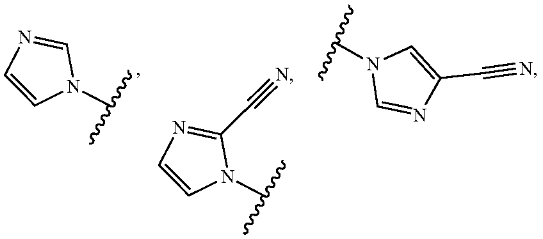

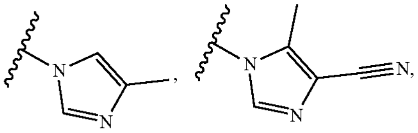

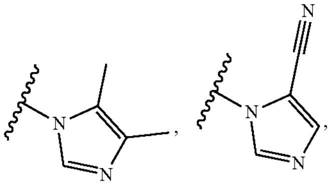

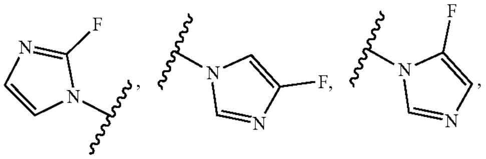

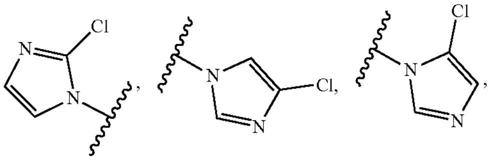

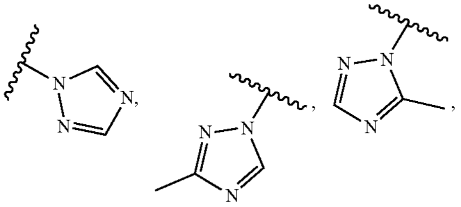

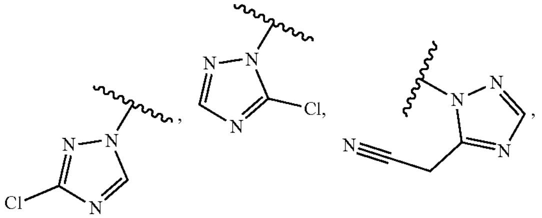

-continued

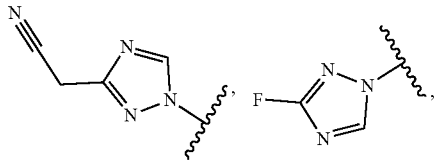

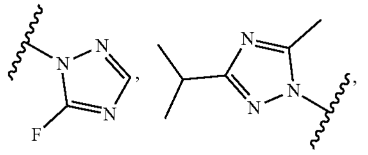

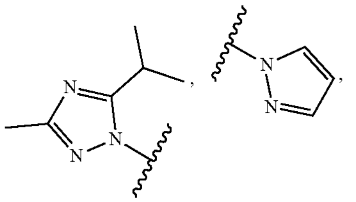

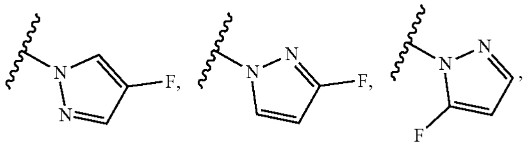

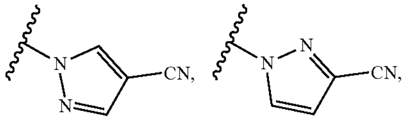

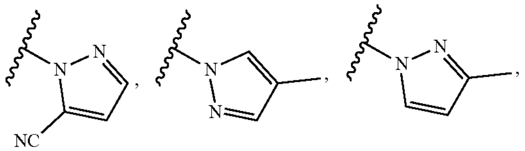

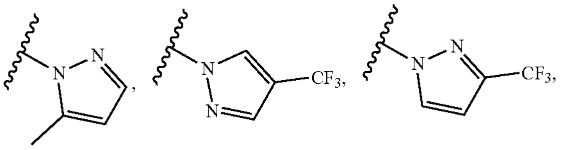

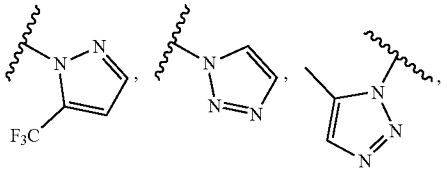

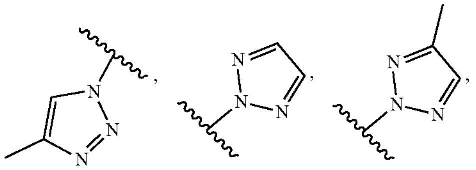

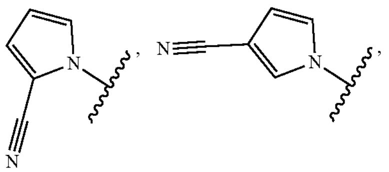

and

-continued

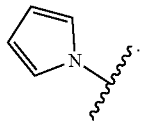

In embodiments, $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

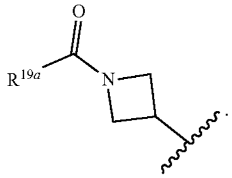

In embodiments, $R^{19a}$ is selected from

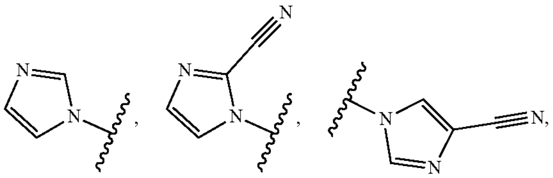

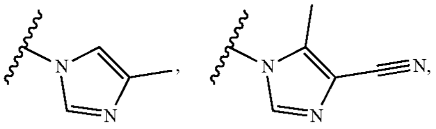

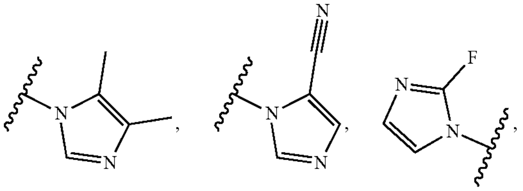

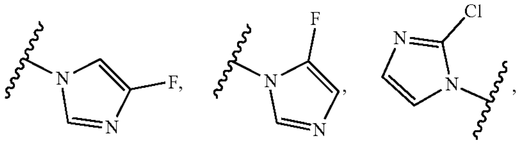

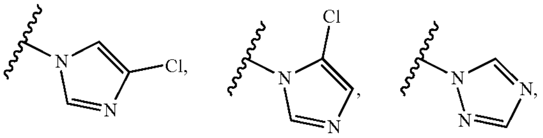

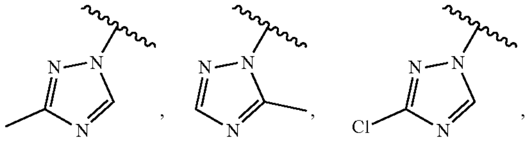

-continued

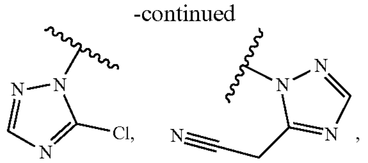
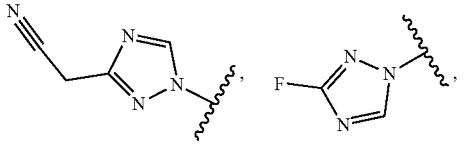
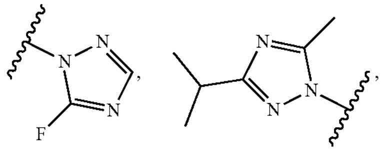
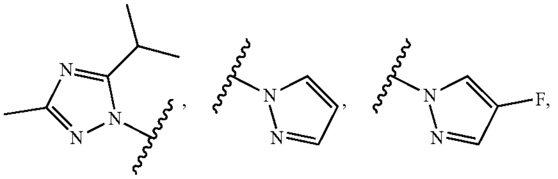
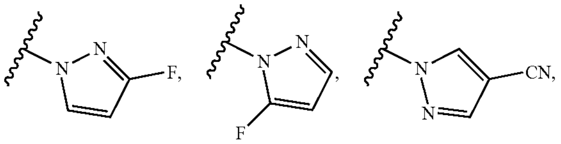
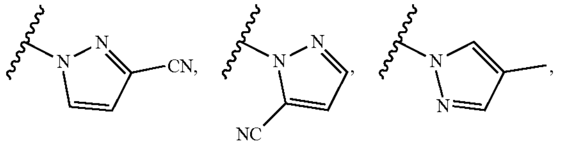
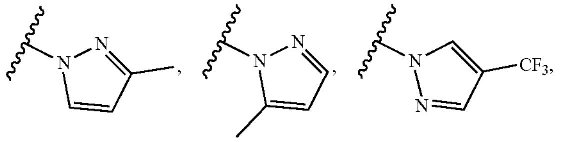
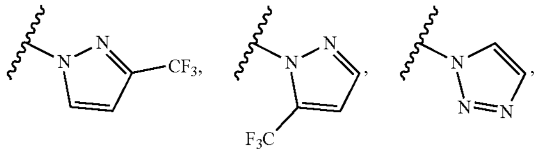
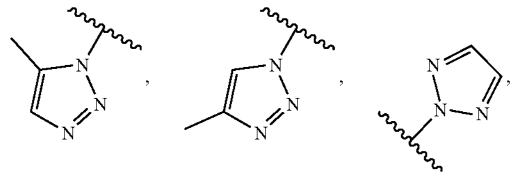
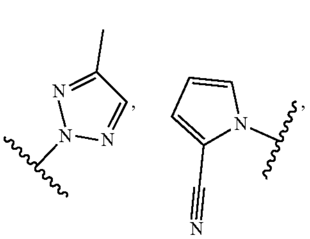
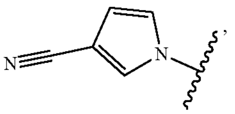

and

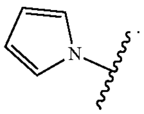

In embodiments, $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

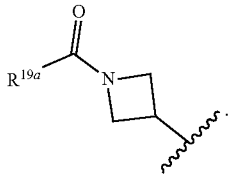

In embodiments, $R^{19a}$ is selected from

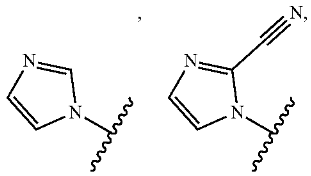
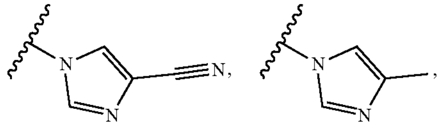
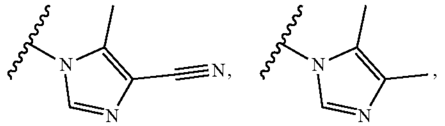
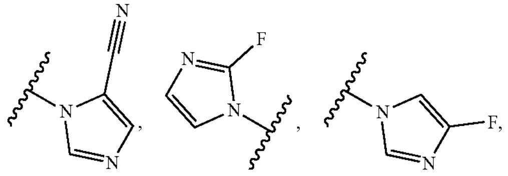
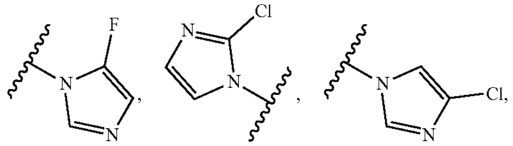
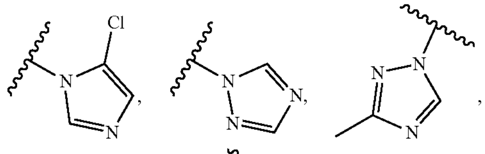
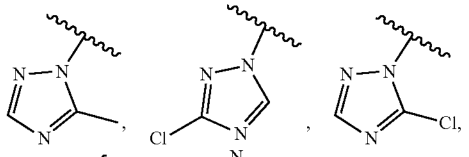
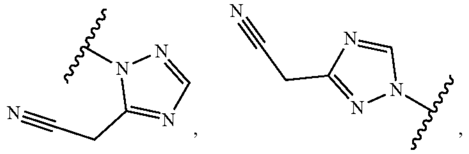

-continued

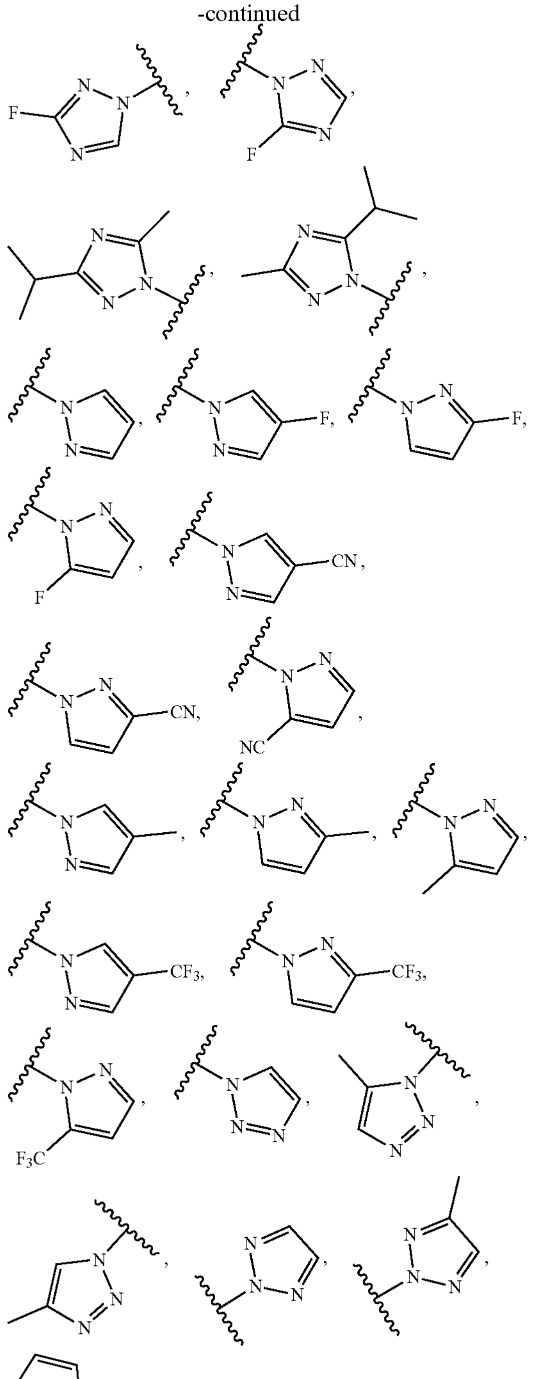

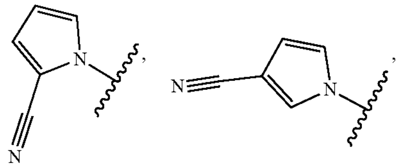

and

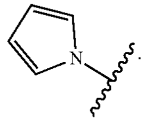

In embodiments, $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

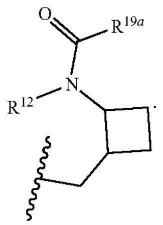

In embodiments, $R^{12}$ is unsubstituted methyl and $R^{19a}$ is selected from

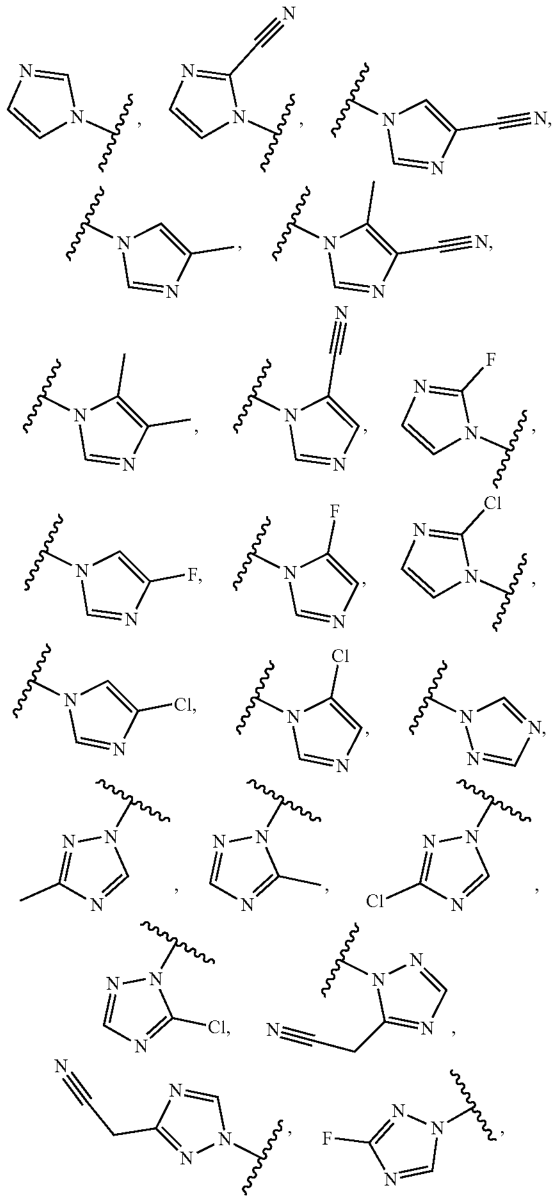

-continued

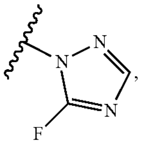 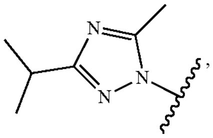

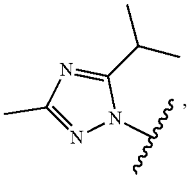 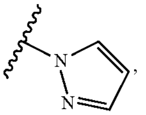 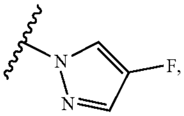

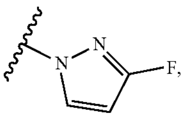 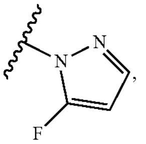 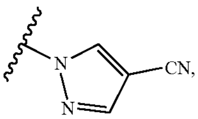

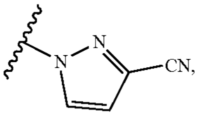 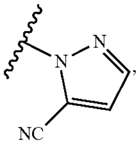 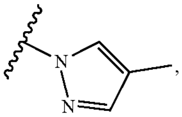

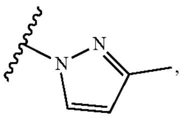 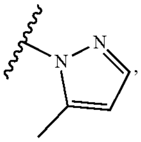 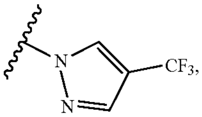

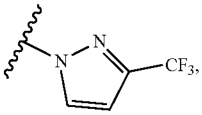 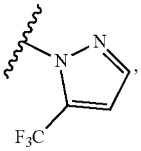 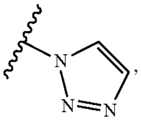

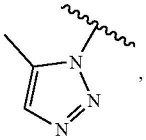 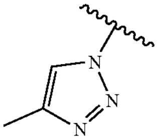 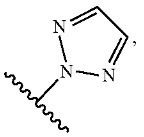

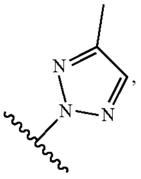 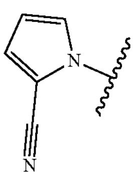

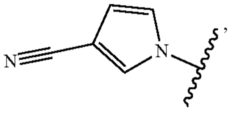 and 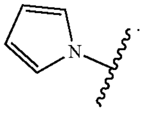

In embodiments, $R^{12}$ is unsubstituted $C_{1-3}$ alkyl and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

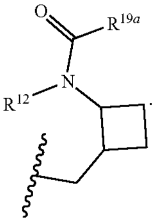

In embodiments, $R^{12}$ is unsubstituted methyl and $R^{19a}$ is selected from

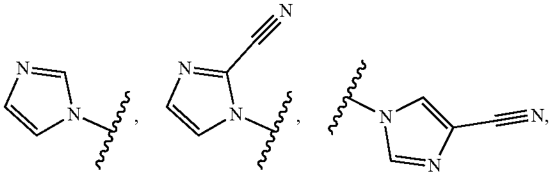

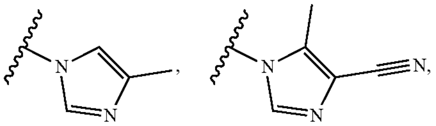

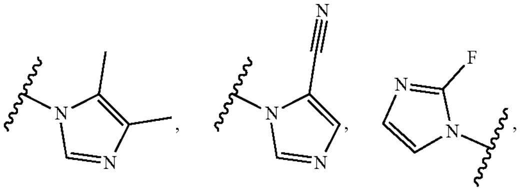

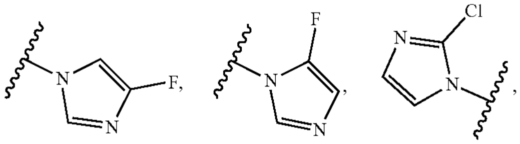

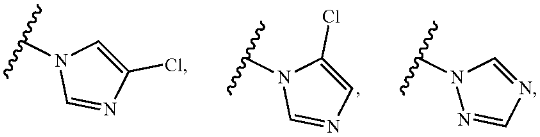

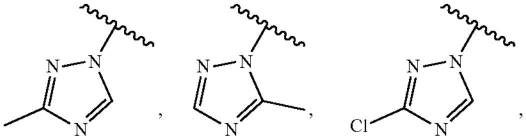

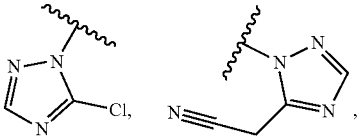

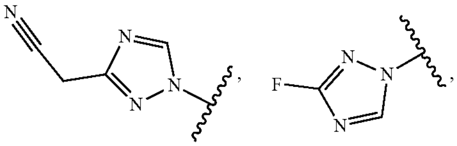

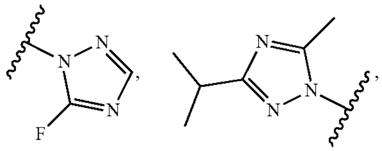

-continued

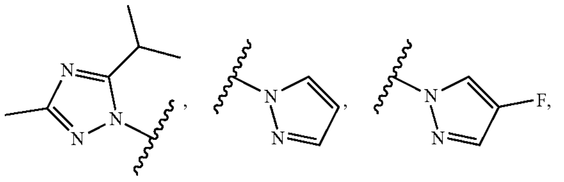

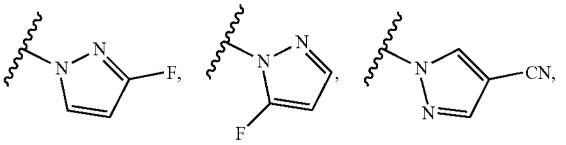

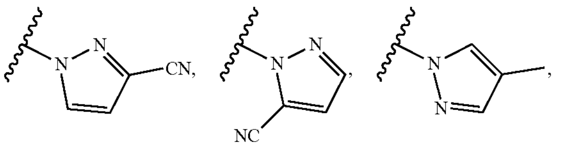

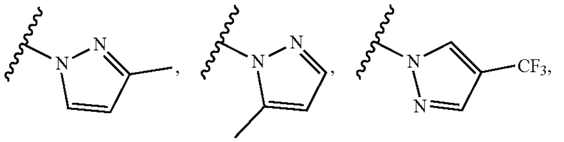

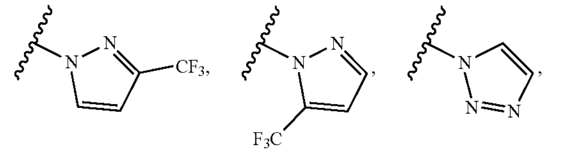

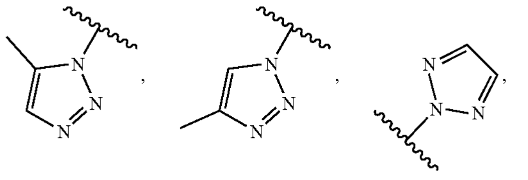

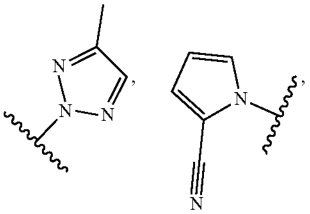

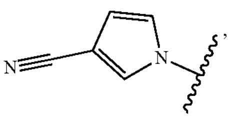 and 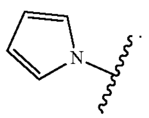

In embodiments, $R^{12}$ is unsubstituted $C_{1-3}$ alkyl and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

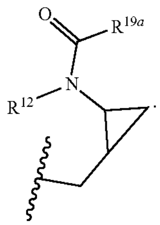

In embodiments, $R^{12}$ is unsubstituted methyl and $R^{19a}$ is selected from

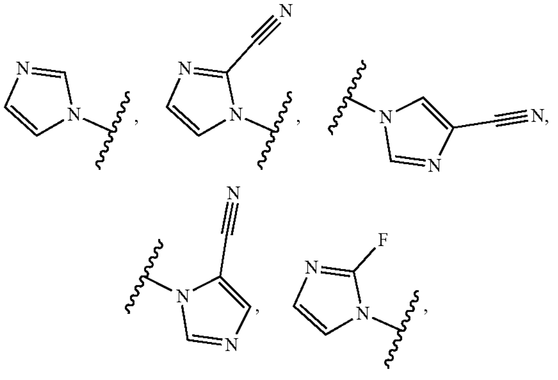

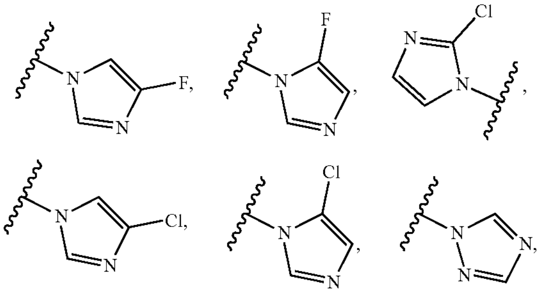

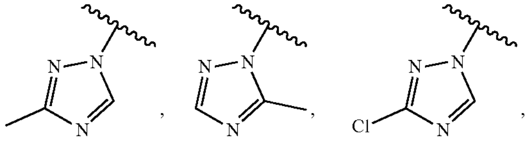

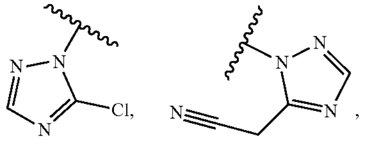

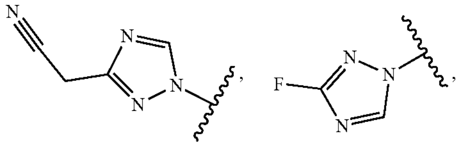

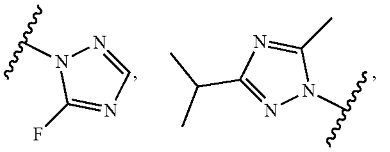

-continued

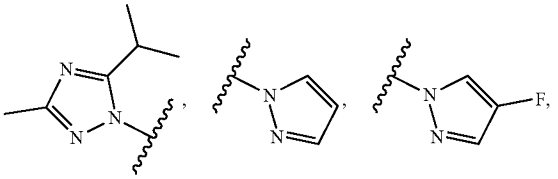

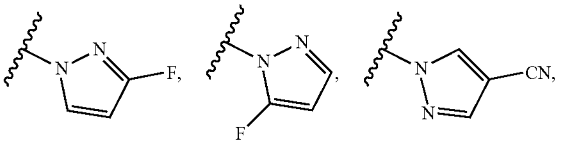

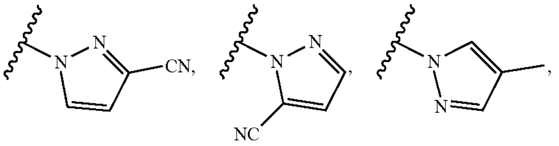

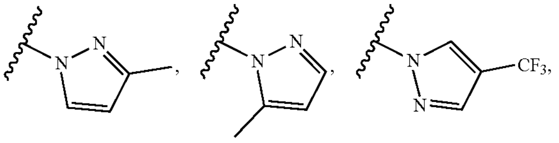

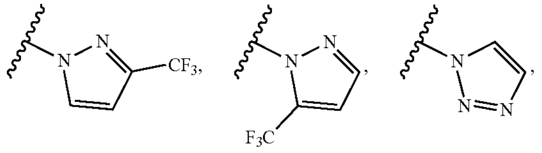

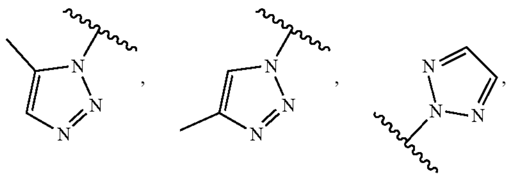

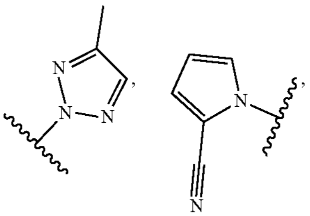

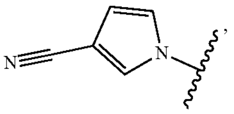 and 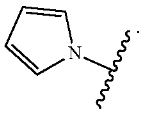

In embodiments, $R^{12}$ is unsubstituted $C_{1-3}$ alkyl and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

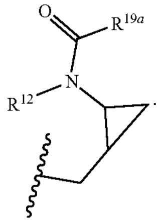

In embodiments, $R^{12}$ is unsubstituted methyl and $R^{19a}$ is selected from

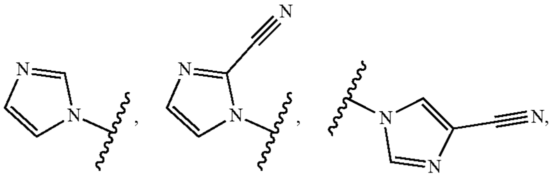

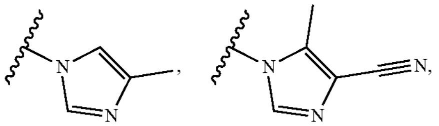

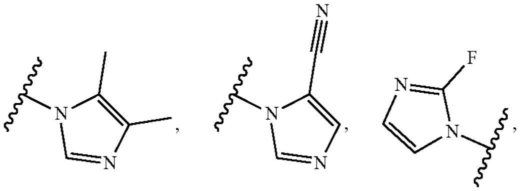

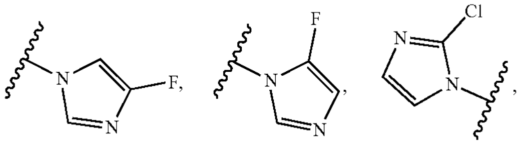

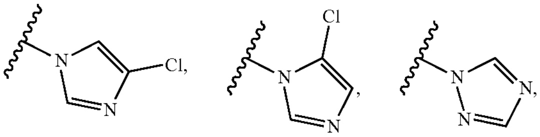

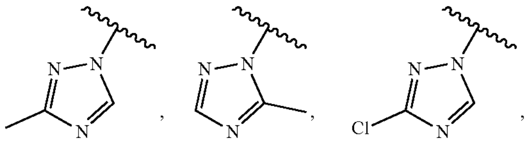

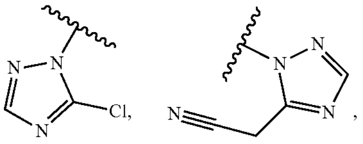

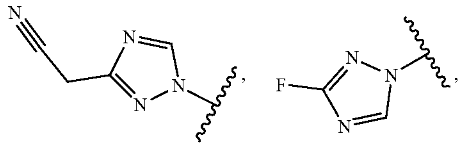

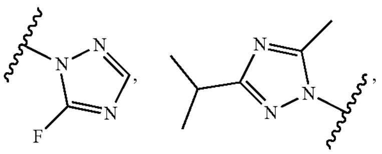

-continued

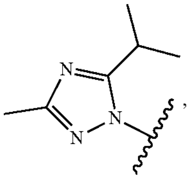,
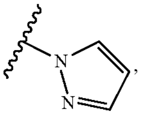,
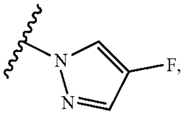
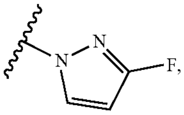
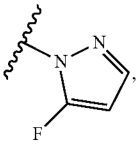,
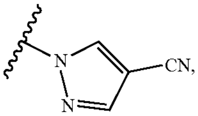
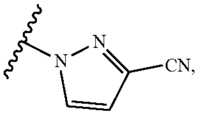
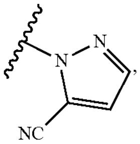,
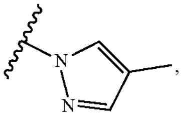,
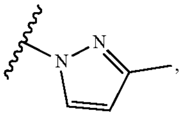,
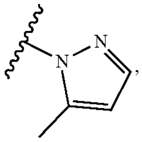,
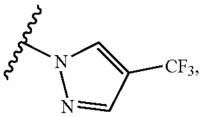
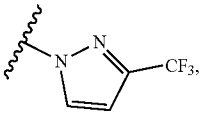
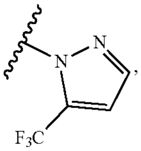,
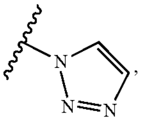,
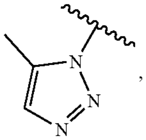,
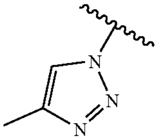,
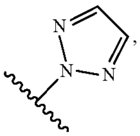,
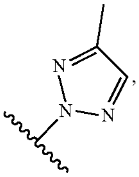,
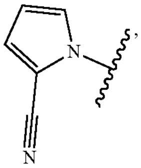,
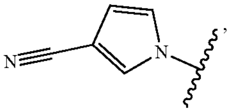, and
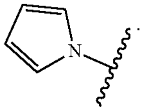.

In embodiments, $R^{12}$ is unsubstituted $C_{1-3}$ alkyl and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

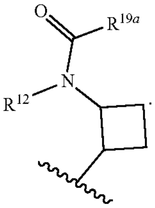.

In embodiments, $R^{12}$ is unsubstituted methyl and $R^{19a}$ is selected from

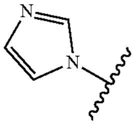,
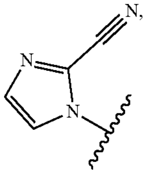,
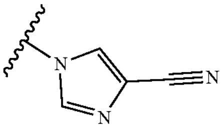
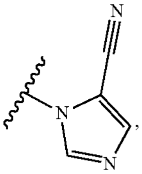,
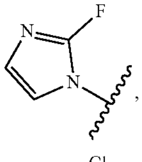,
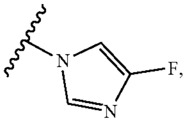
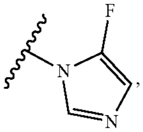,
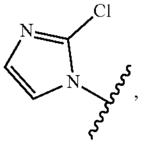,
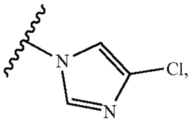
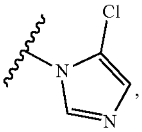,
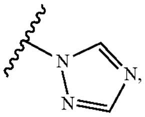
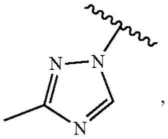,
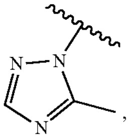,
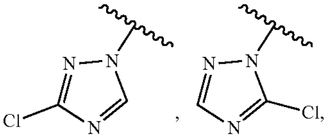
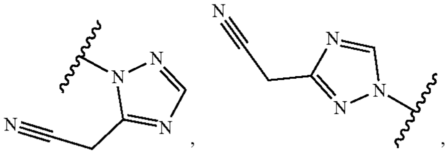,
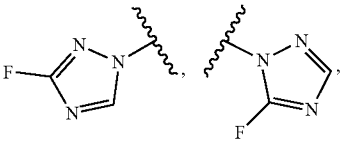,
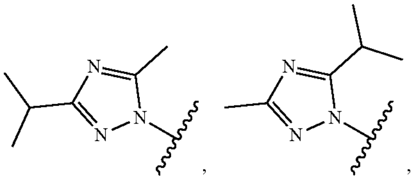, -continued

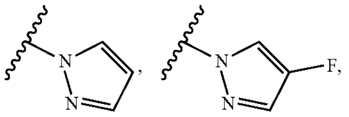

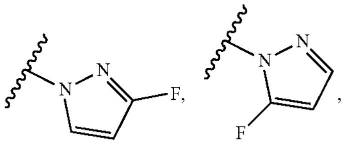

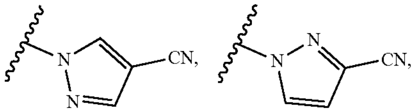

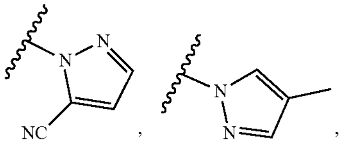

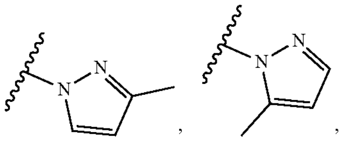

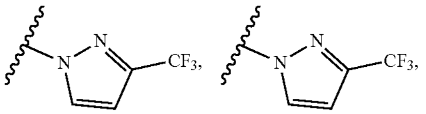

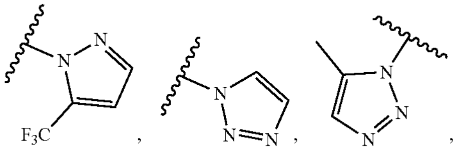

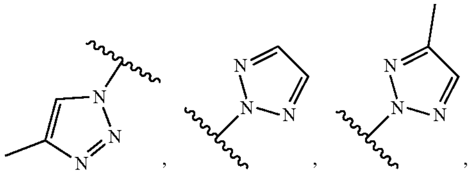

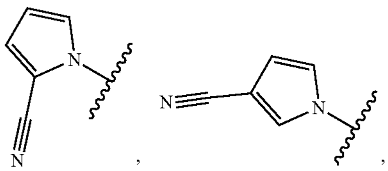

and

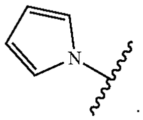

In embodiments, $R^{12}$ is unsubstituted $C_{1-3}$ alkyl and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

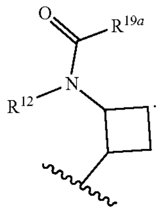

In embodiments, $R^{12}$ is unsubstituted methyl and $R^{19a}$ is selected from

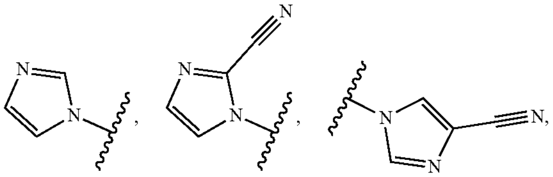

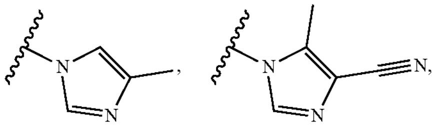

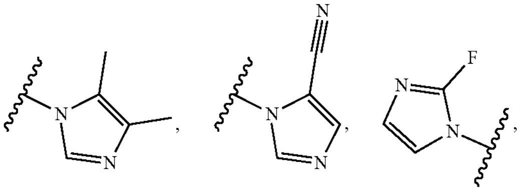

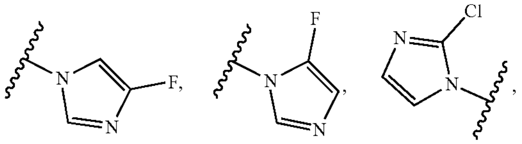

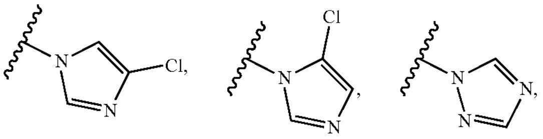

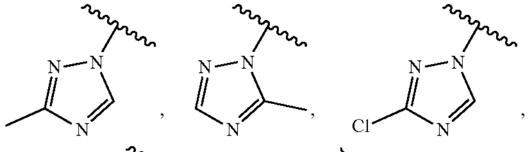

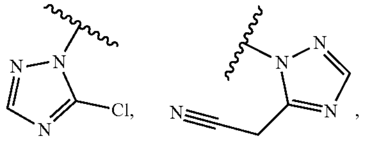

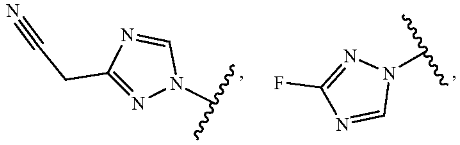

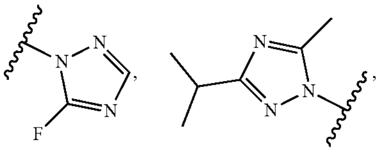

-continued

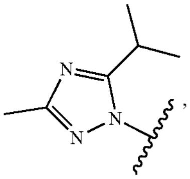
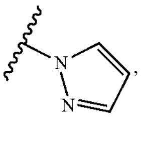
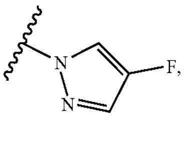
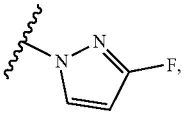
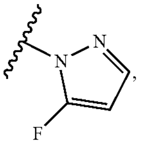
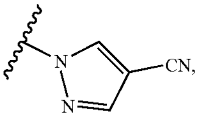
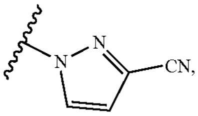
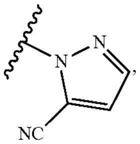
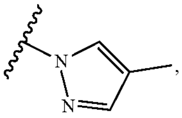
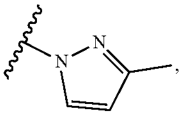
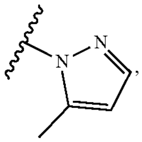
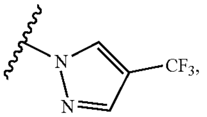
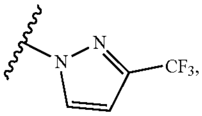
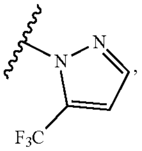
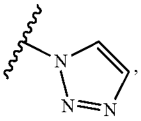
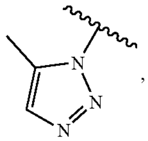
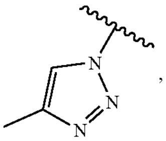
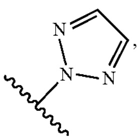
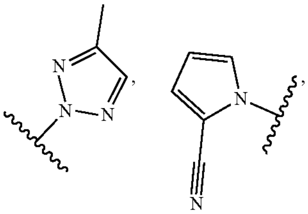
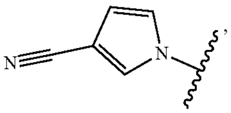
and
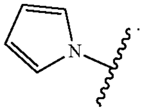

In embodiments, $R^{12}$ is unsubstituted $C_{1-3}$ alkyl and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

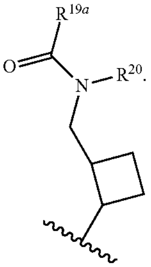

In embodiments, $R^{20}$ is unsubstituted methyl and $R^{1a}$ is selected from

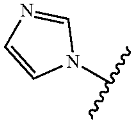
,
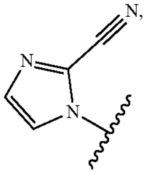
,
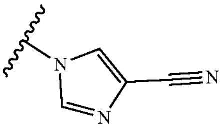
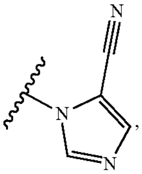
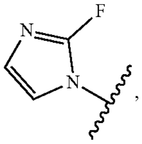
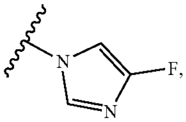
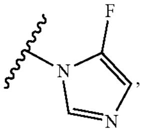
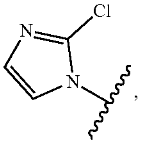
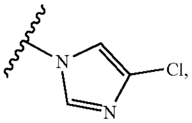
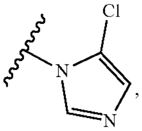
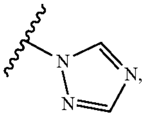
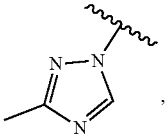
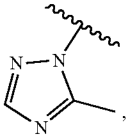
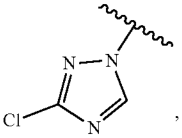
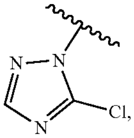
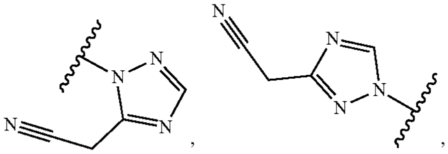
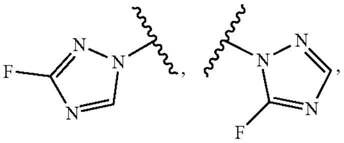
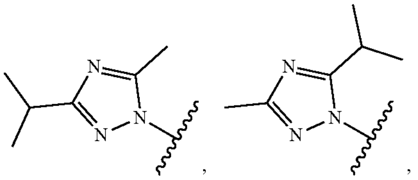

-continued

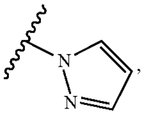, 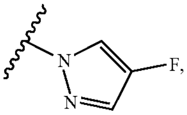,

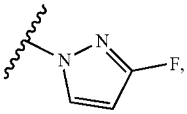, 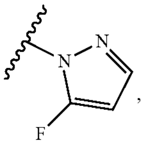,

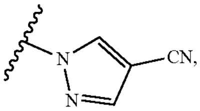, 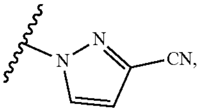,

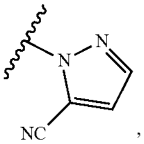, 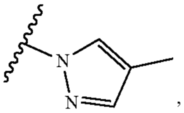,

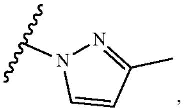, 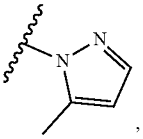,

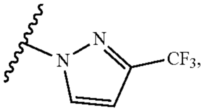, 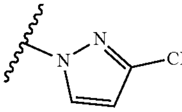,

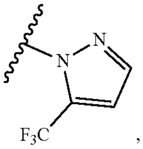, 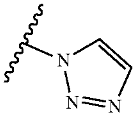, 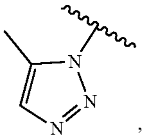,

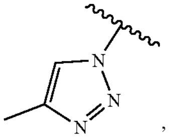, 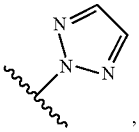, 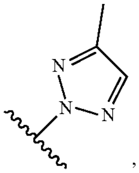,

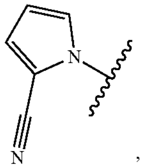, 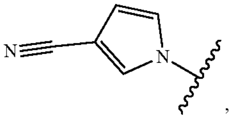, and

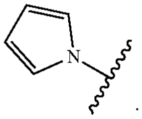.

In embodiments, $R^{20}$ is unsubstituted $C_{1-3}$ alkyl and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

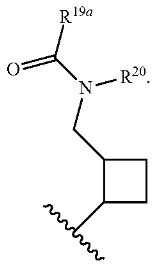

In embodiments, $R^{20}$ is unsubstituted methyl and $R^{19a}$ is selected from

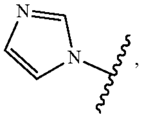, 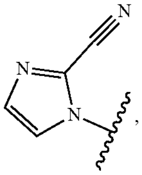, 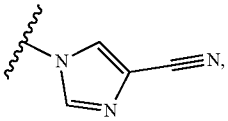,

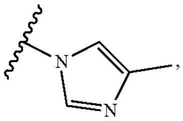, 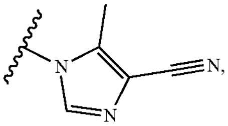,

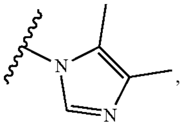, 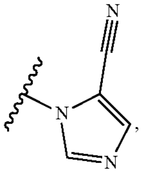, 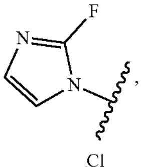,

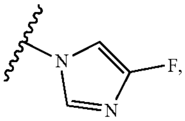, 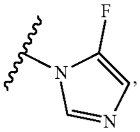, 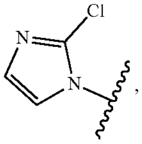,

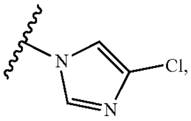, 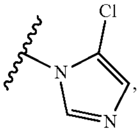, 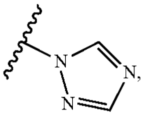,

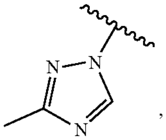, 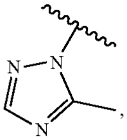, 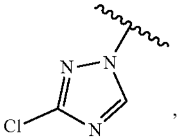,

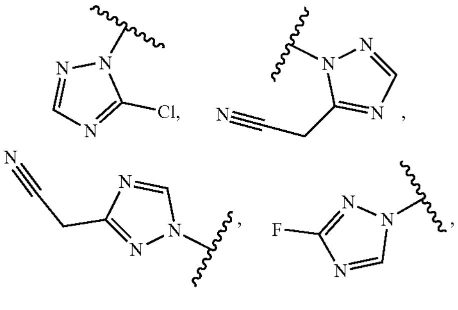

-continued

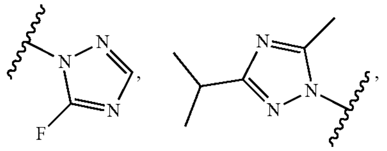

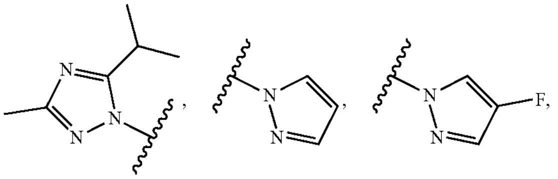

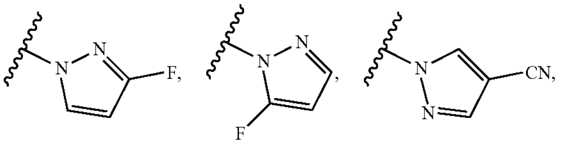

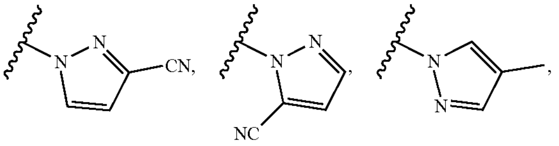

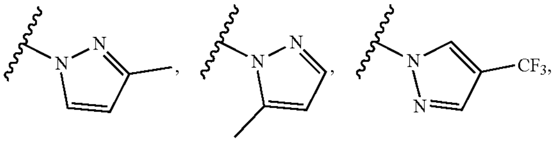

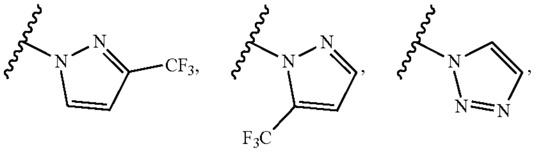

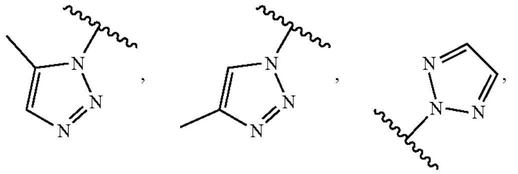

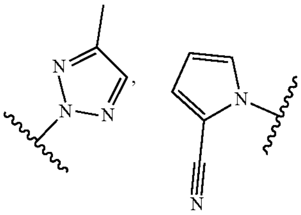

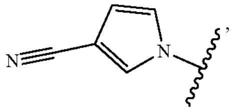

and

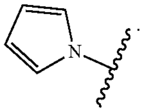

.

In embodiments, $R^{20}$ is unsubstituted $C_{1-3}$ alkyl and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

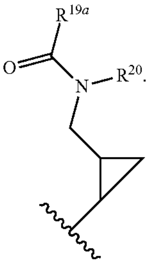

In embodiments, $R^{20}$ is unsubstituted methyl and $R^{19a}$ is selected from

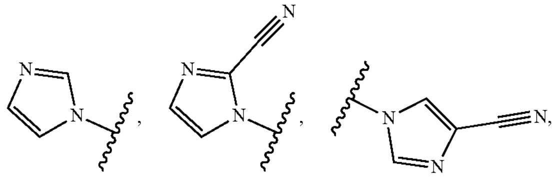

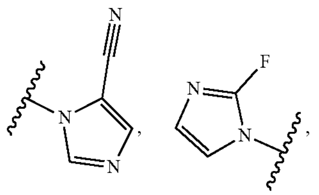

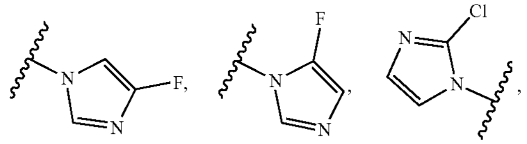

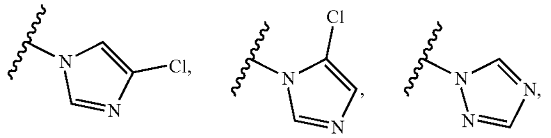

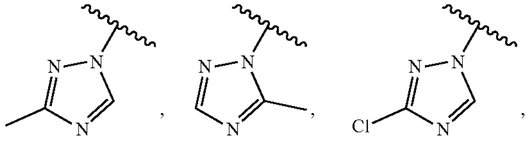

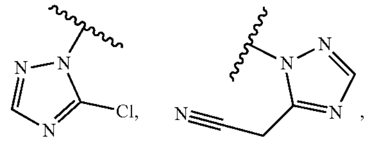

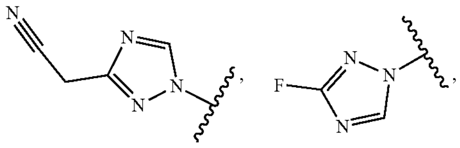

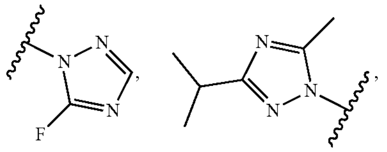

-continued

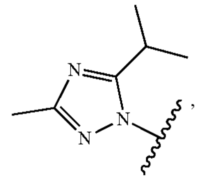 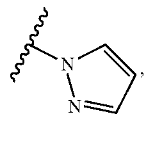 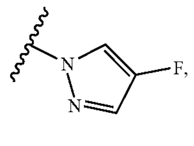

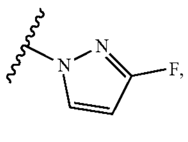 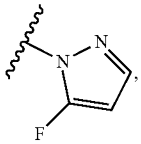 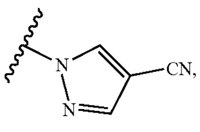

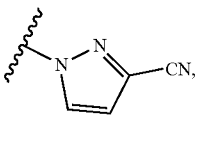 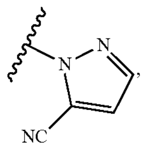 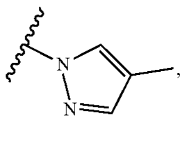

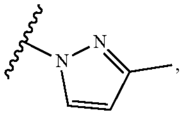 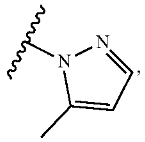 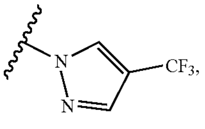

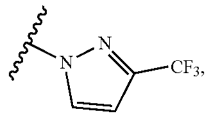 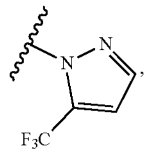 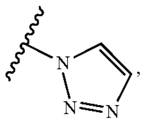

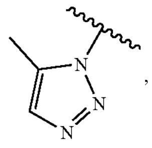 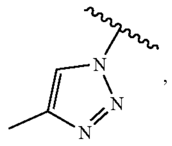 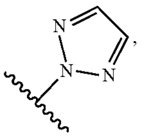

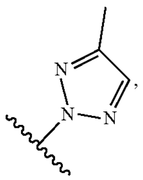 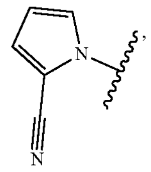

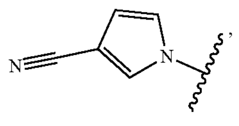 and 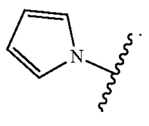

In embodiments, $R^{20}$ is unsubstituted $C_{1-3}$ alkyl and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

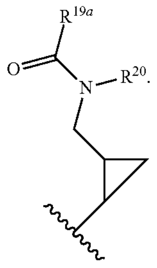

In embodiments, $R^{20}$ is unsubstituted methyl and $R^{19a}$ is selected from

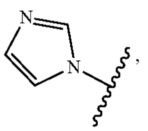 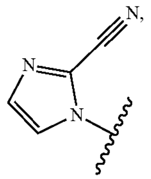 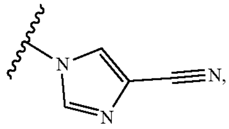

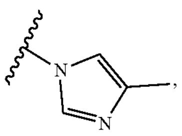 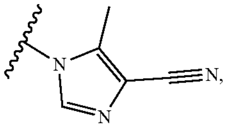

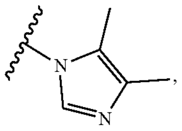 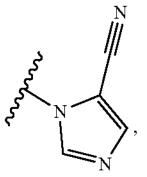 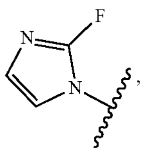

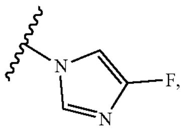 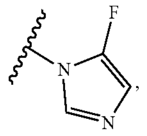 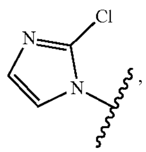

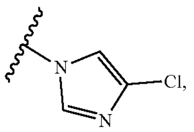 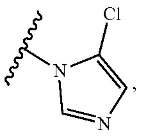 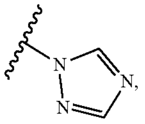

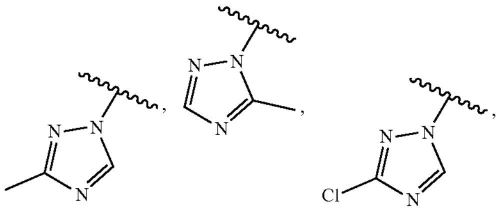

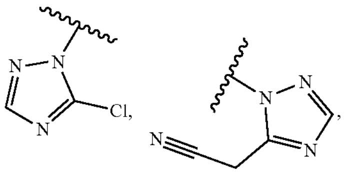

-continued

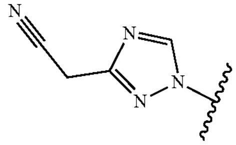, 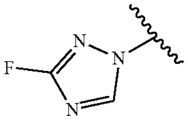,

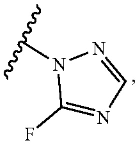, 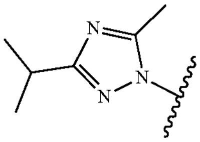,

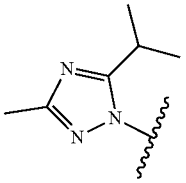, 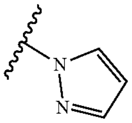, 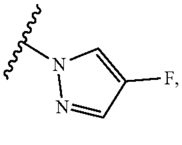

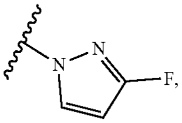 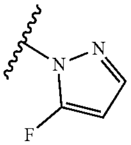, 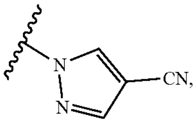

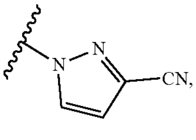 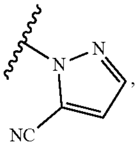,

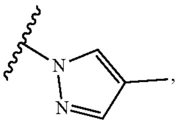, 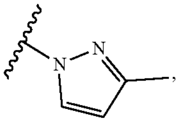,

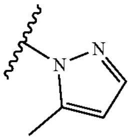, 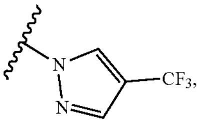 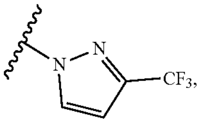

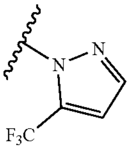, 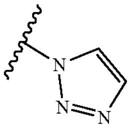, 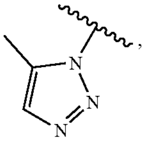,

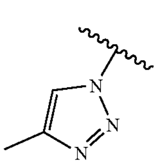, 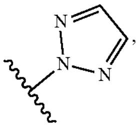, 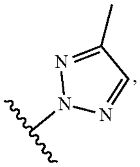,

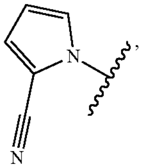, 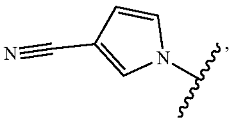, and

-continued

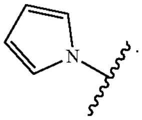.

In embodiments, $R^{20}$ is unsubstituted $C_{1-3}$ alkyl and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

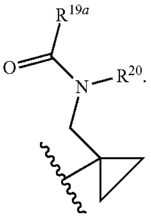

In embodiments, $R^{20}$ is unsubstituted methyl and $R^{19a}$ is selected from

,

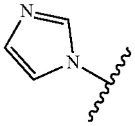 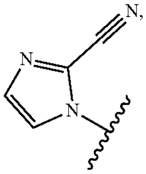

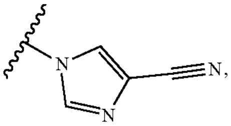 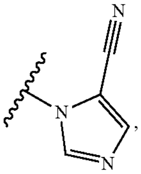,

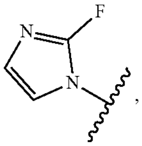 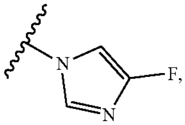

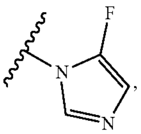, 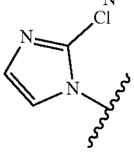, 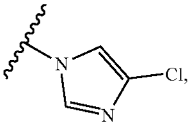

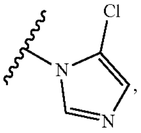, 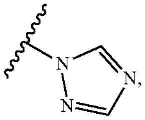 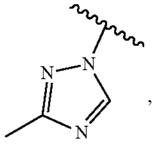,

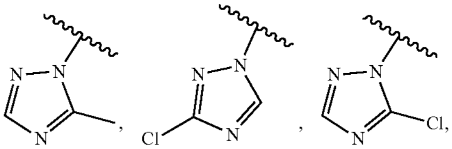

-continued

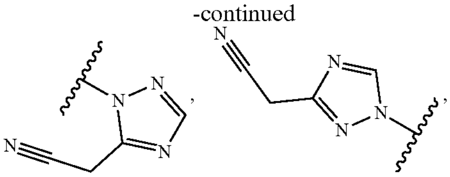

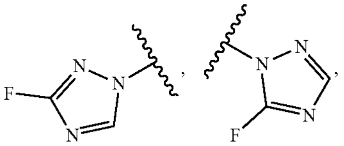

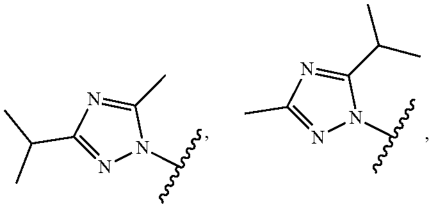

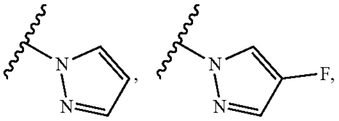

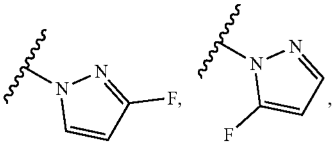

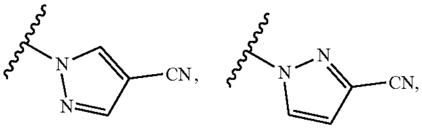

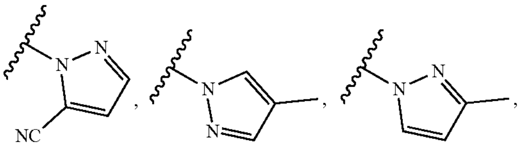

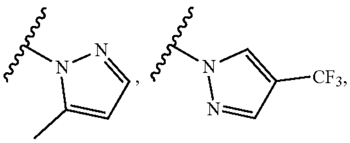

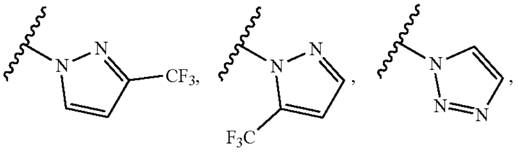

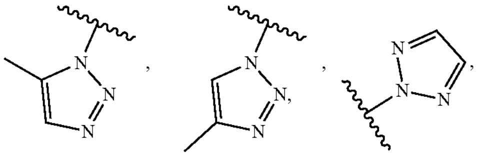

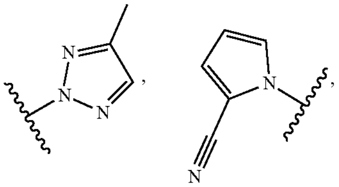

-continued

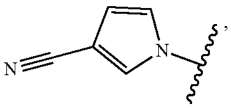

and

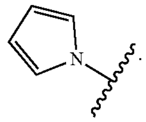

In embodiments, $R^{20}$ is unsubstituted $C_{1-3}$ alkyl and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

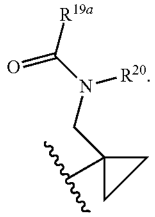

In embodiments, $R^{20}$ is unsubstituted methyl and $R^{19a}$ is selected from

,

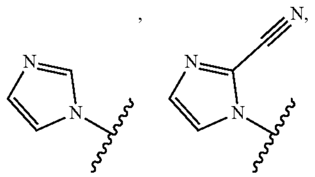

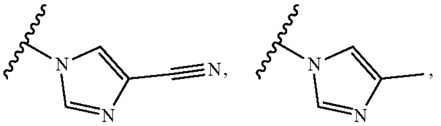

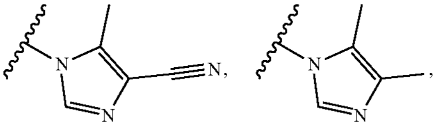

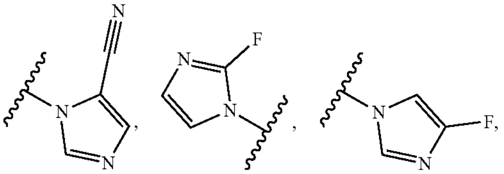

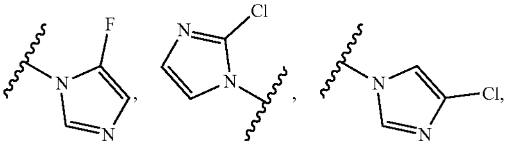

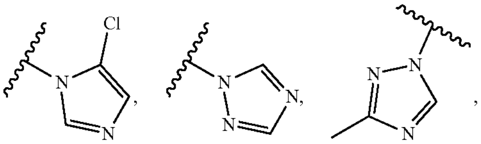

-continued

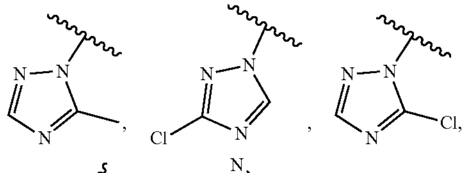

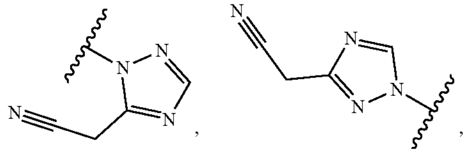

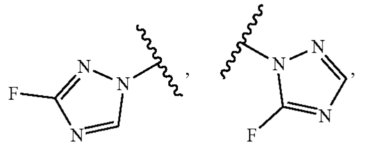

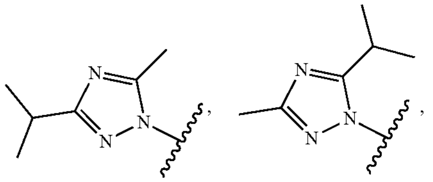

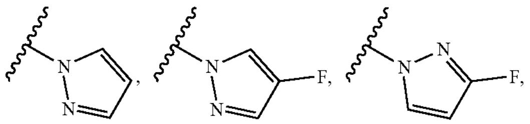

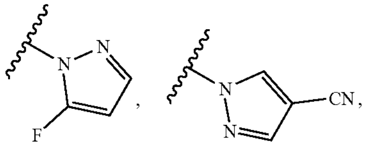

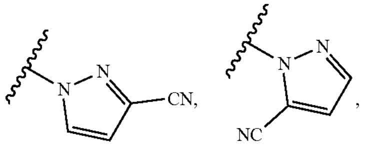

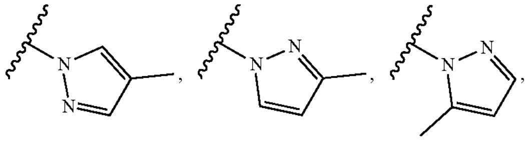

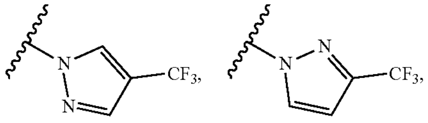

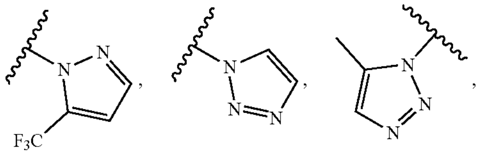

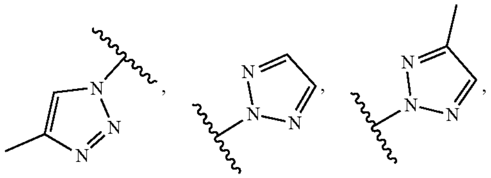

-continued

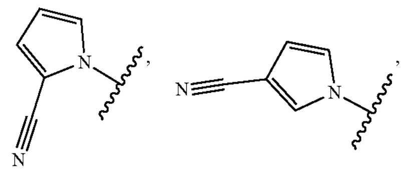

and

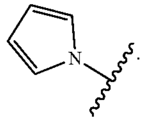

In embodiments, $R^{20}$ is unsubstituted $C_{1-3}$ alkyl and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

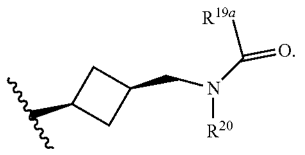

In embodiments, $R^{20}$ is unsubstituted methyl and $R^{19a}$ is selected

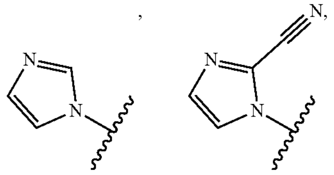

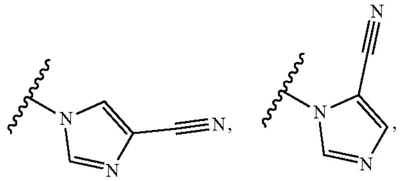

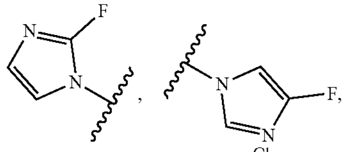

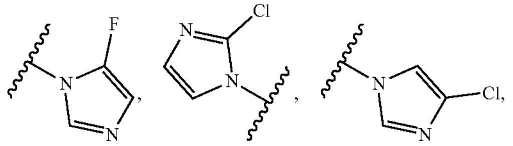

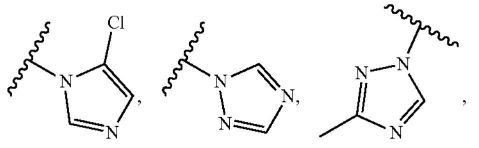

-continued

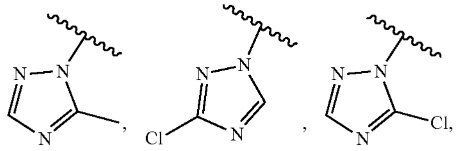

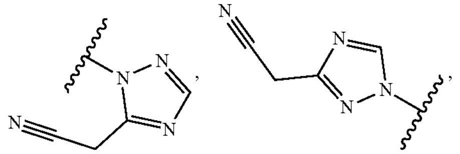

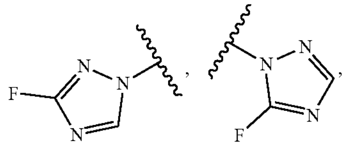

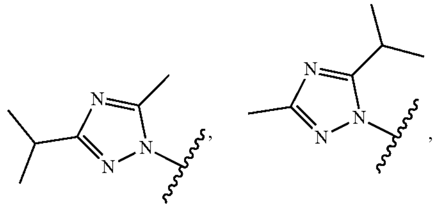

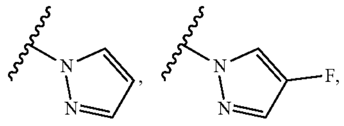

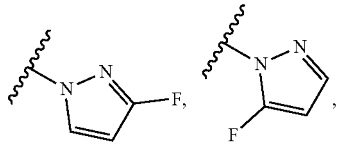

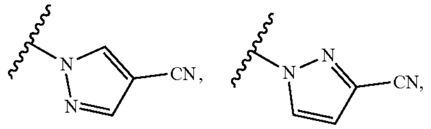

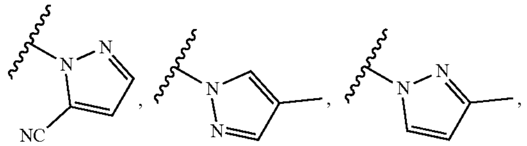

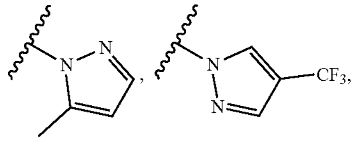

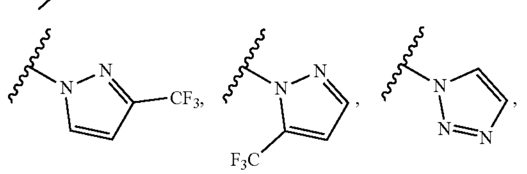

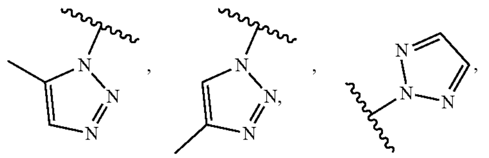

-continued

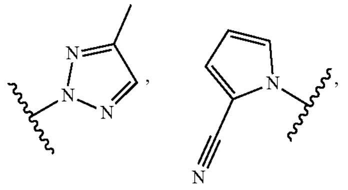

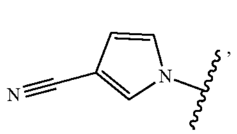

and

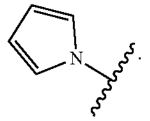

In embodiments, $R^{20}$ is unsubstituted $C_{1-3}$ alkyl and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

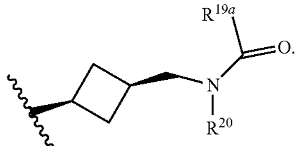

In embodiments, $R^{20}$ is unsubstituted methyl and $R^{19a}$ is selected

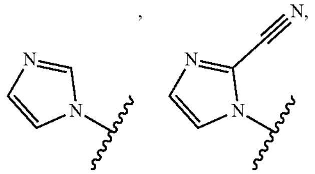

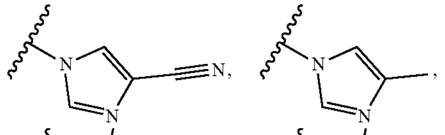

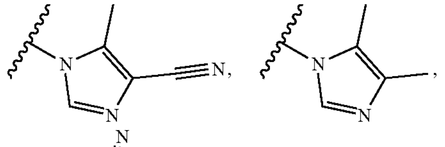

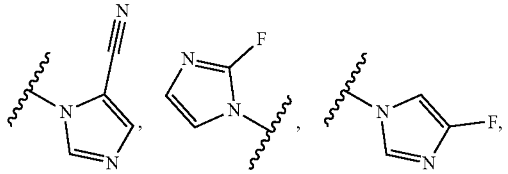

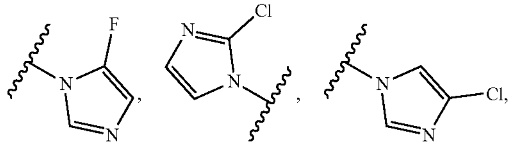

-continued

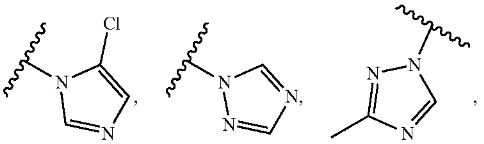
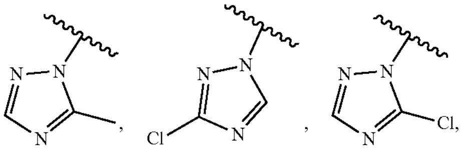
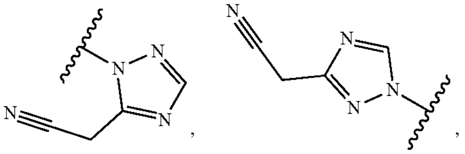
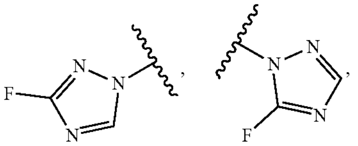
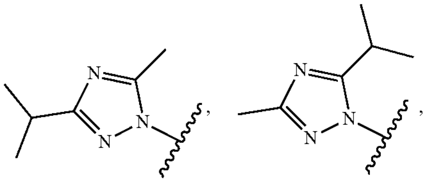
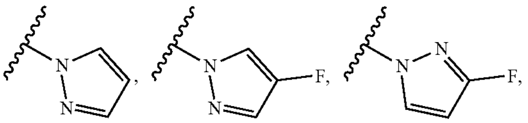
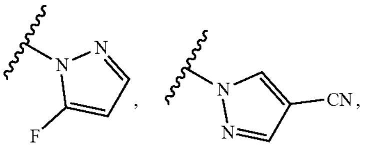
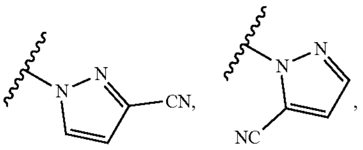
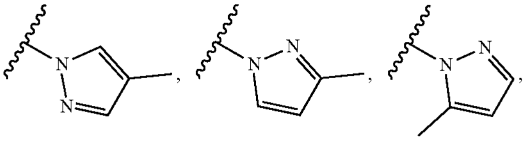
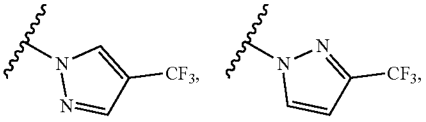
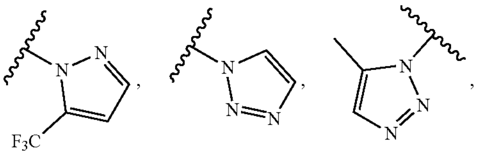

-continued

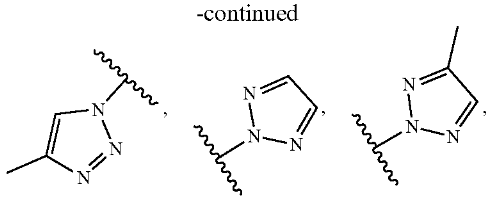
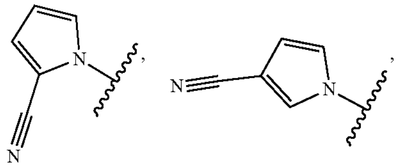
and
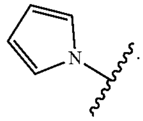

In embodiments, $R^{20}$ is unsubstituted $C_{1-3}$ alkyl and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

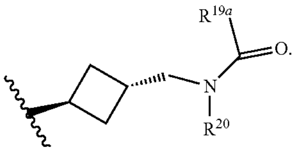

In embodiments, $R^{20}$ is unsubstituted methyl and $R^{19a}$ is selected from

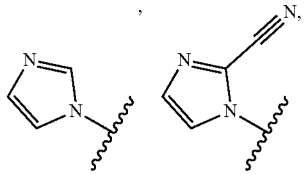
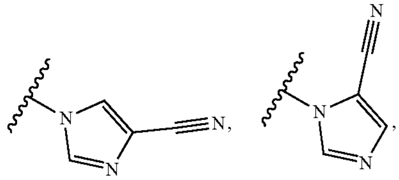
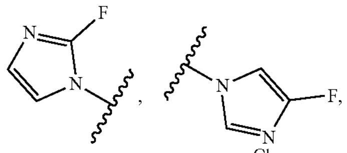
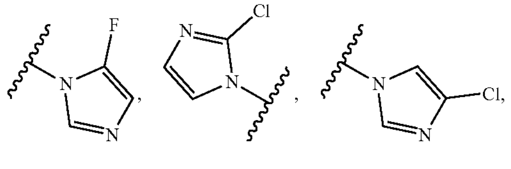

-continued

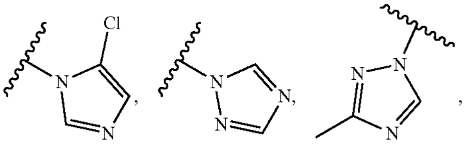
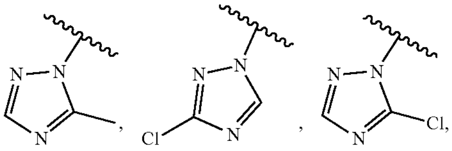
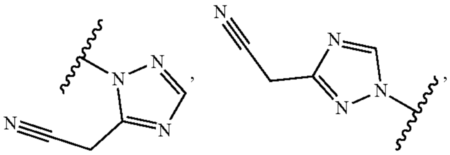
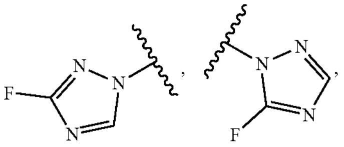
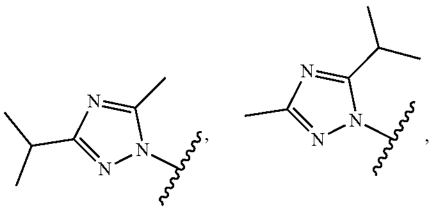
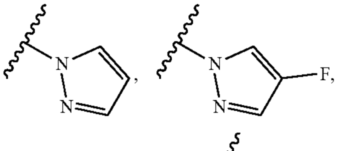
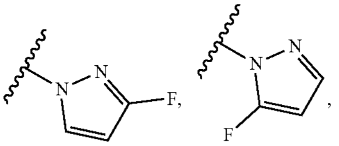
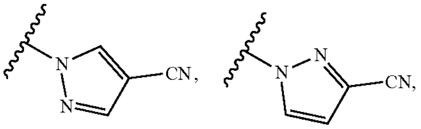
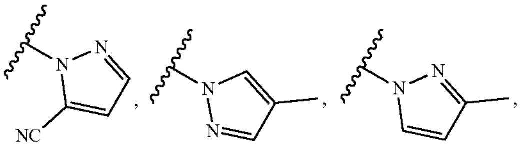
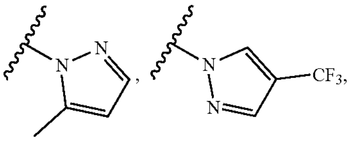
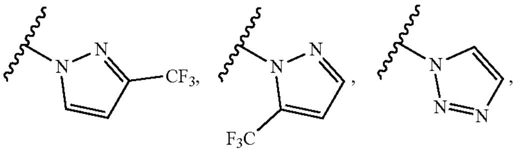

-continued

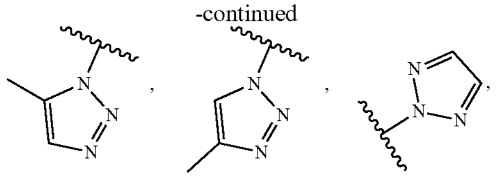
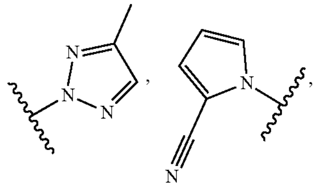
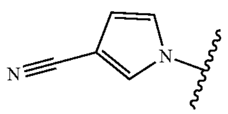
, and
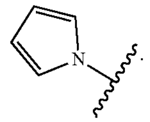

In embodiments, $R^{20}$ is unsubstituted $C_{1-3}$ alkyl and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

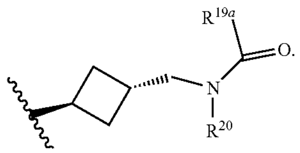

In embodiments, $R^{20}$ is unsubstituted methyl and $R^{19a}$ is selected

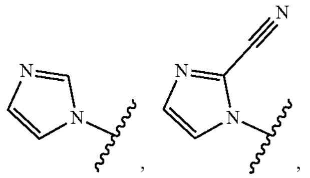
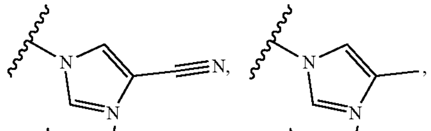
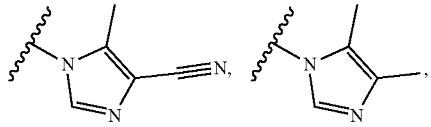
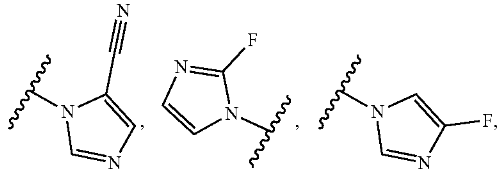

-continued

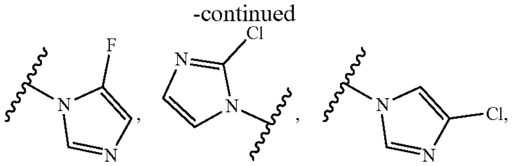

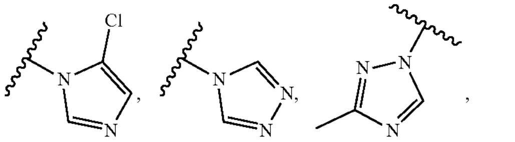

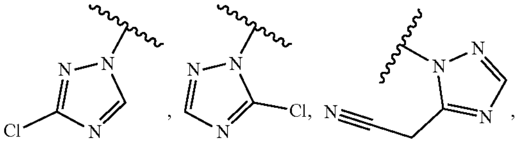

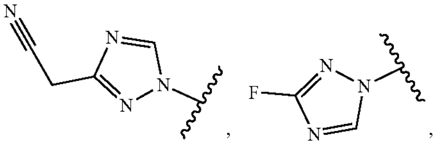

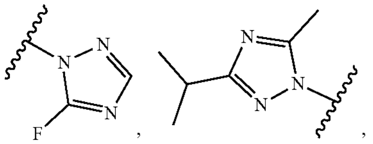

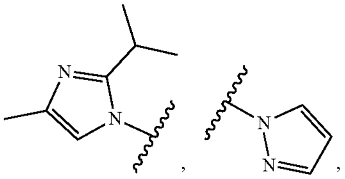

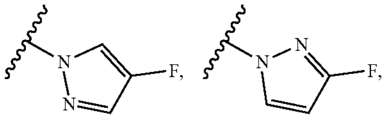

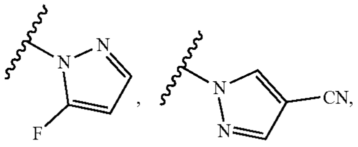

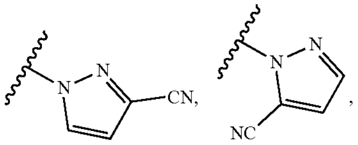

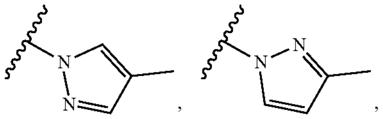

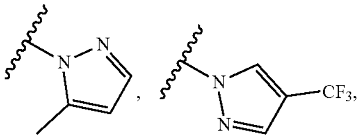

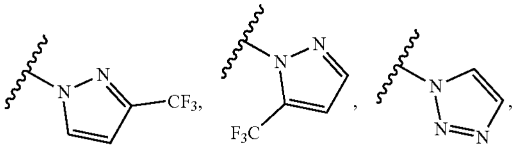

-continued

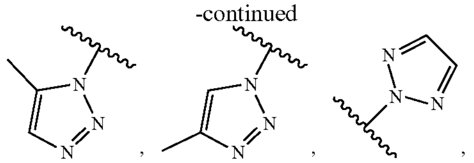

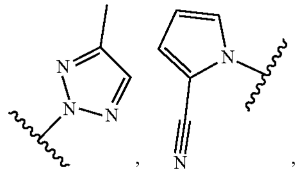

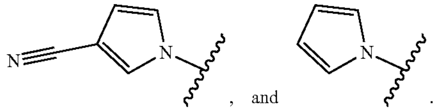

In embodiments, $R^{20}$ is unsubstituted $C_{1-3}$ alkyl and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is from

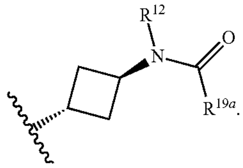

In embodiments, $R^{12}$ is unsubstituted methyl and $R^{19a}$ is selected from

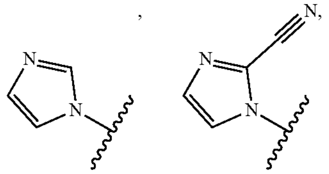

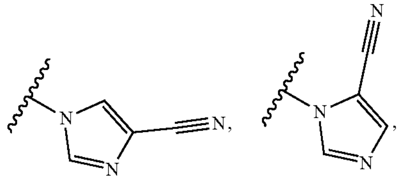

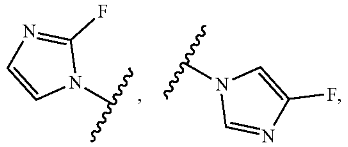

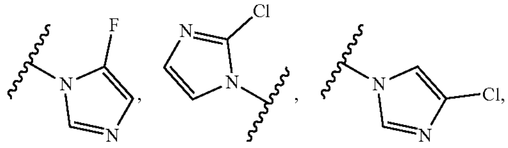

-continued

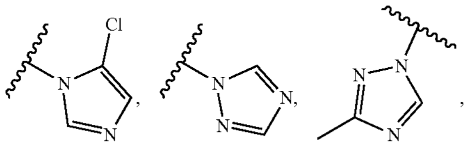

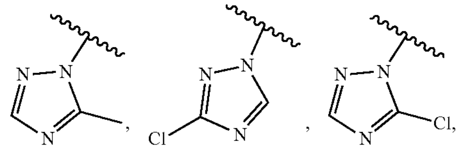

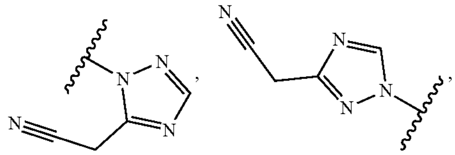

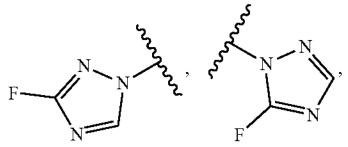

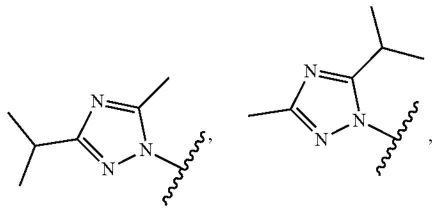

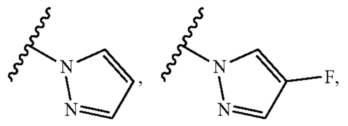

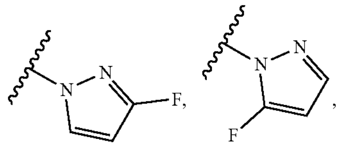

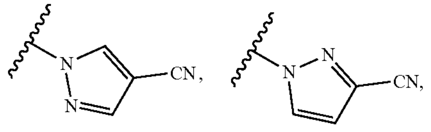

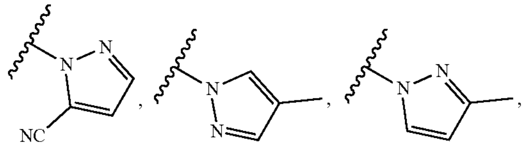

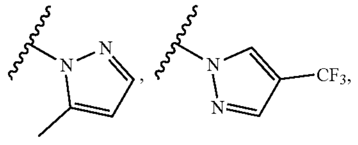

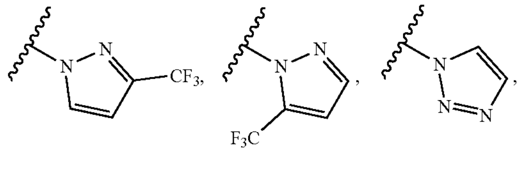

-continued

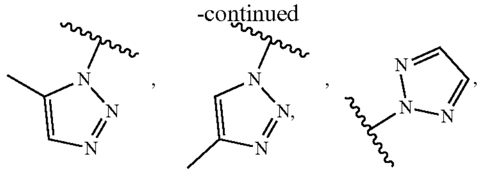

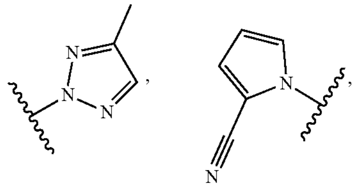

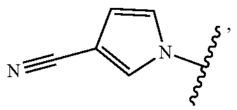

and

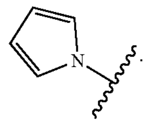

In embodiments, $R^{12}$ is unsubstituted $C_{1-3}$ alkyl and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

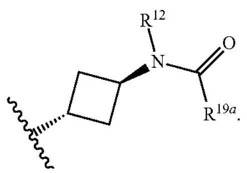

In embodiments, $R^{12}$ is unsubstituted methyl and $R^{19a}$ is selected from

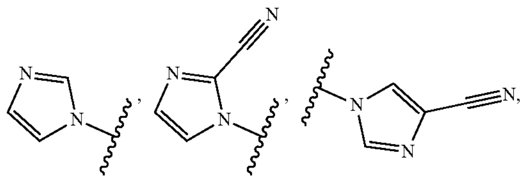

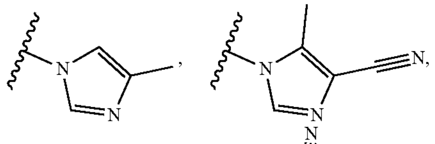

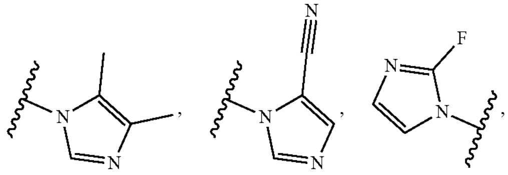

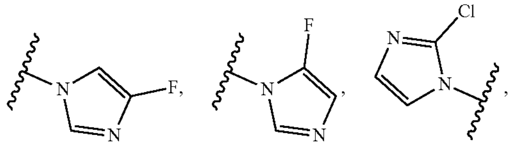

-continued

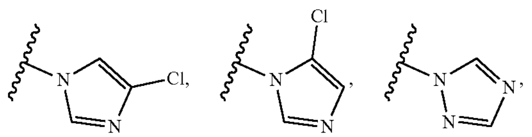

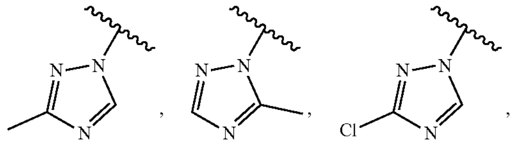

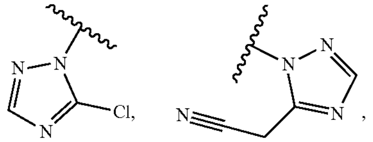

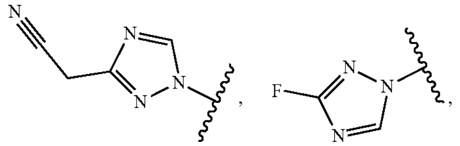

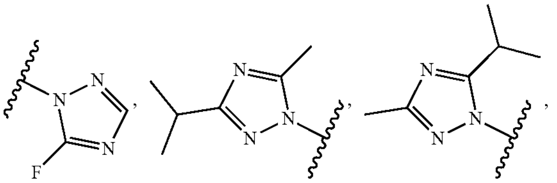

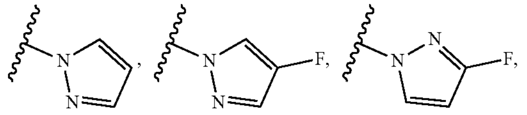

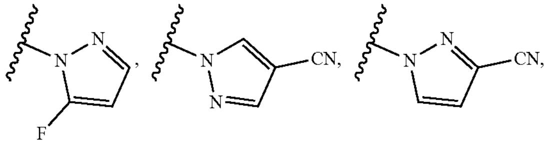

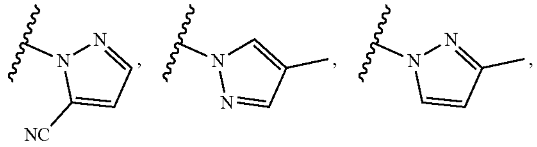

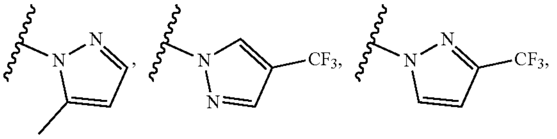

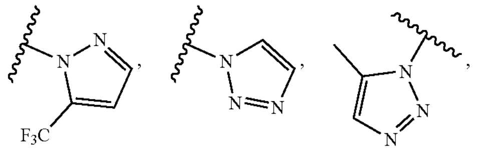

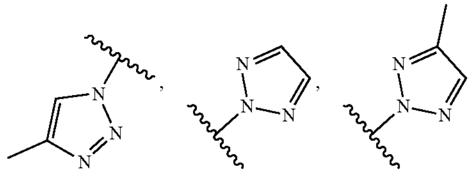

-continued

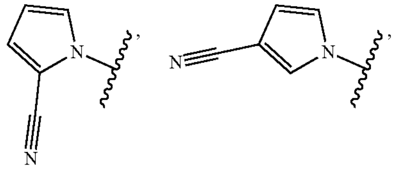

, and

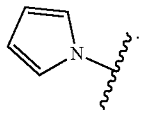

In embodiments, $R^{12}$ is unsubstituted $C_{1-3}$ alkyl and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

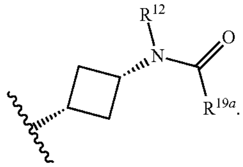

In embodiments, $R^{12}$ is unsubstituted methyl and $R^{19a}$ is selected from

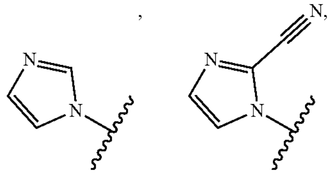

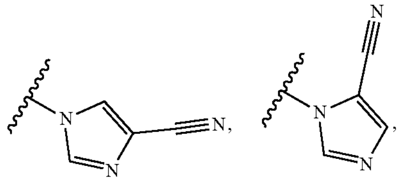

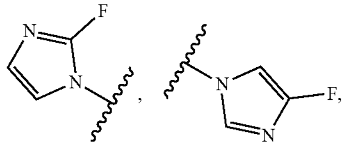

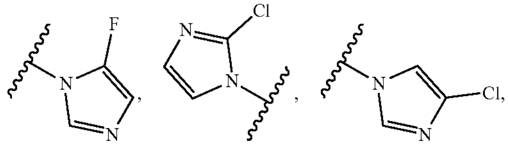

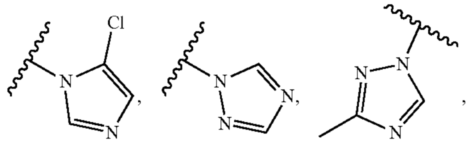

-continued

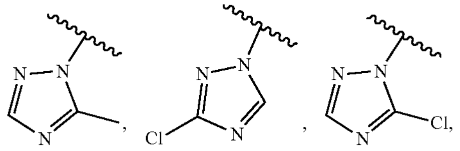

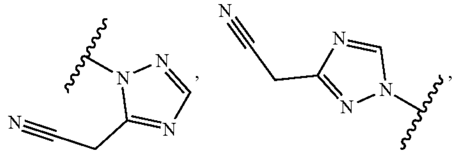

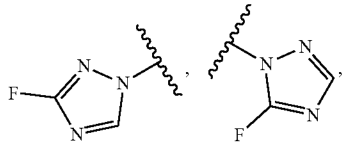

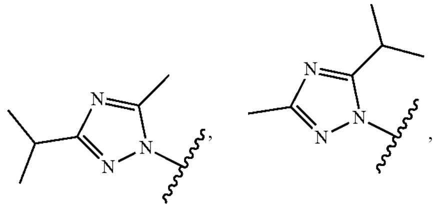

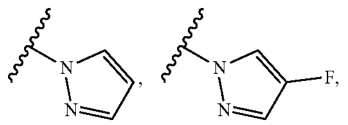

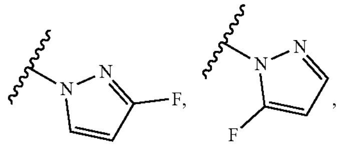

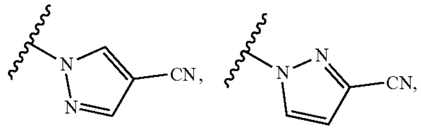

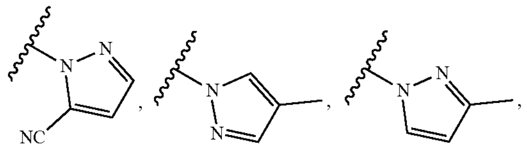

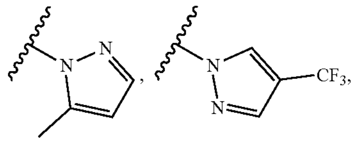

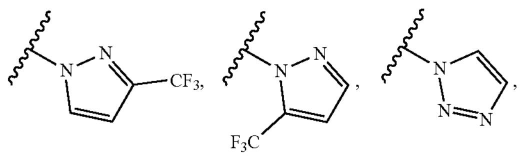

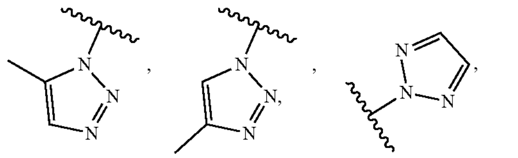

-continued

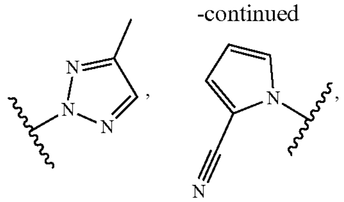

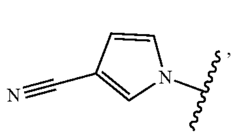

and

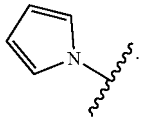

In embodiments, $R^{12}$ is unsubstituted $C_{1-3}$ alkyl and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

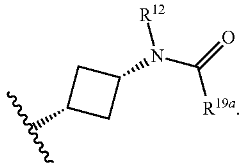

In embodiments, $R^{12}$ is unsubstituted methyl and $R^{19a}$ is selected from

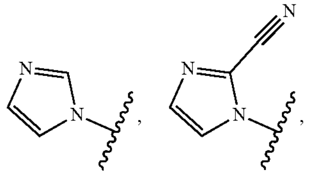

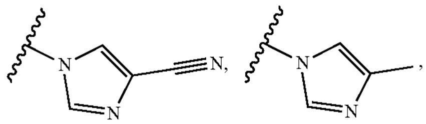

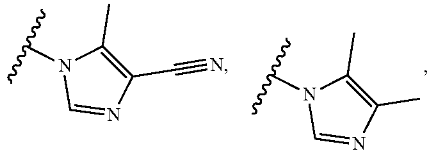

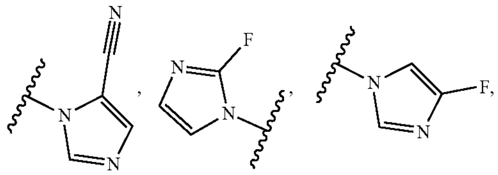

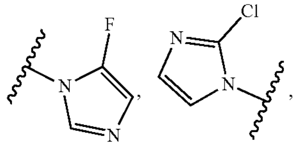

-continued

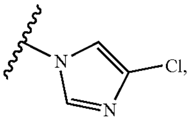 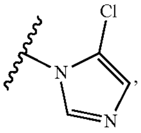 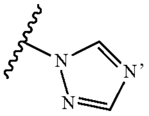

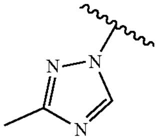, 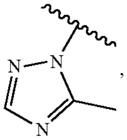, 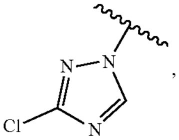,

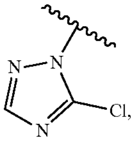 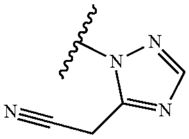,

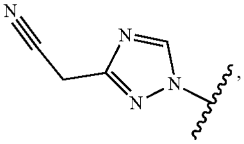, 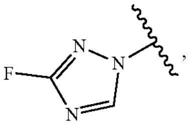,

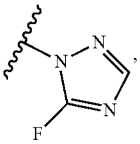, 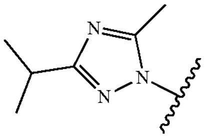,

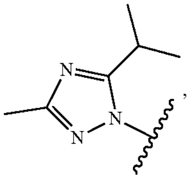, 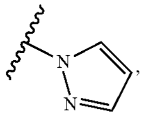,

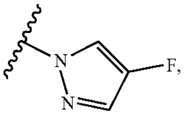 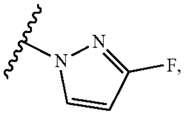

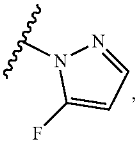, 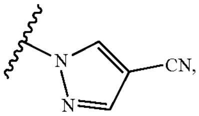

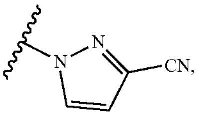 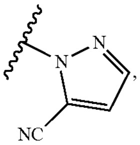,

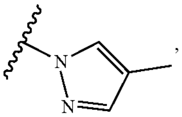, 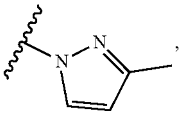,

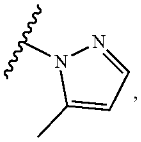, 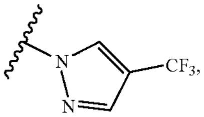

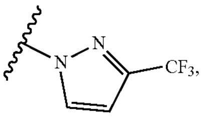 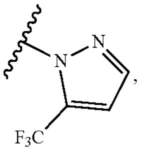,

-continued

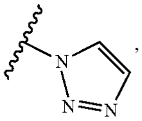, 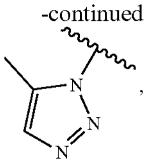,

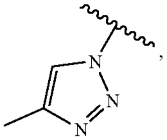, 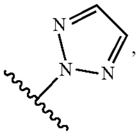, 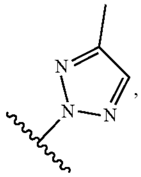,

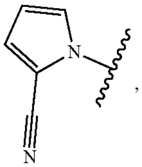, 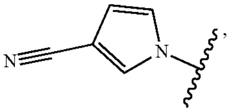, and

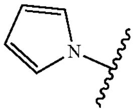.

In embodiments, $R^{12}$ is unsubstituted $C_{1-3}$ alkyl and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

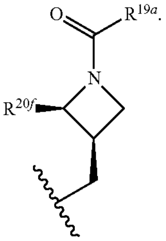

In embodiments, $R^{20f}$ is cyclopropyl substituted with methyl and wherein the methyl is substituted with —OMe, —CN, or F; and $R^{19a}$ is selected from

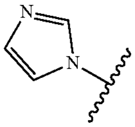, 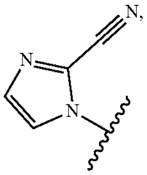

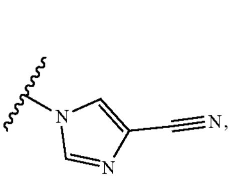 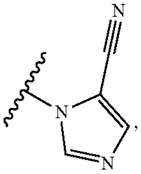

-continued

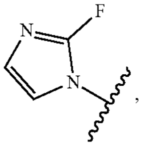, 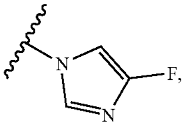

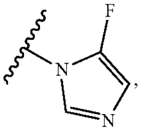, 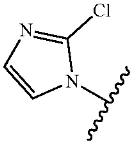, 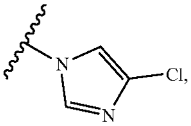

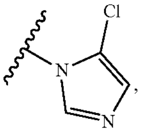, 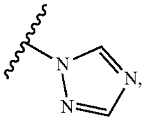, 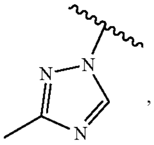,

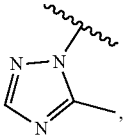, 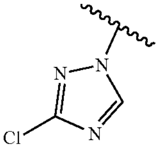, 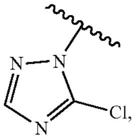

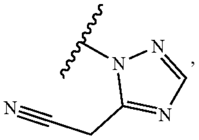, 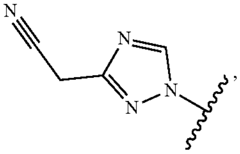

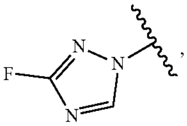, 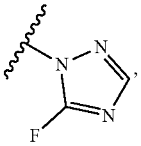

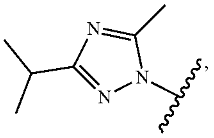, 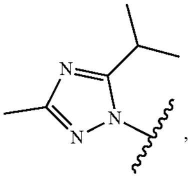,

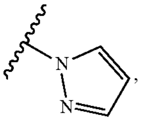, 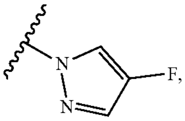

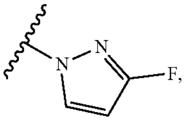, 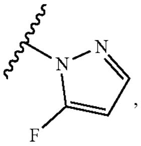,

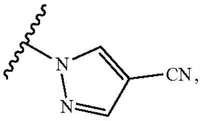, 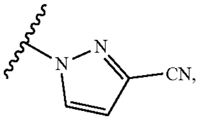

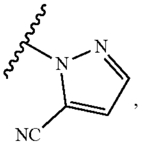, 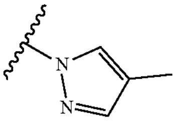, 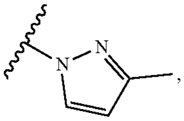

-continued

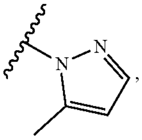, 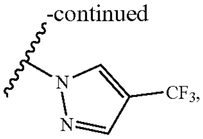

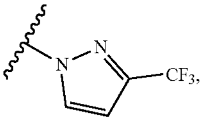, 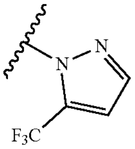, 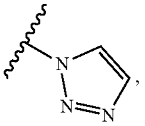

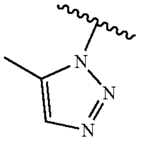, 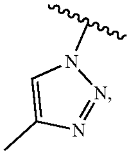, 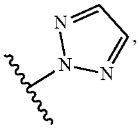

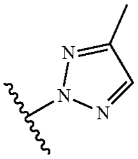, 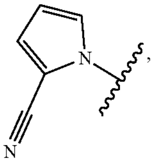

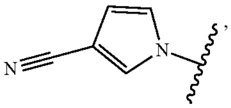, and 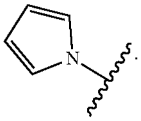

In embodiments, $R^{20f}$ is $C_{3-4}$ non-aromatic carbocycle substituted with $C_{1-3}$ alkyl and wherein the $C_{1-3}$ alkyl is substituted with halogen, —CN, or unsubstituted $C_{1-3}$ alkoxy; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

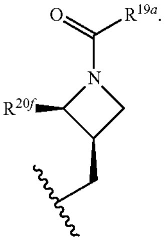

In embodiments, $R^{20f}$ is cyclopropyl substituted with methyl and wherein the methyl is substituted with —OMe, —CN, or F; and $R^{19a}$ is selected from

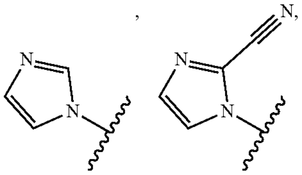

-continued
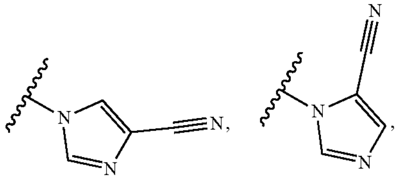
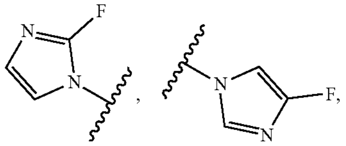
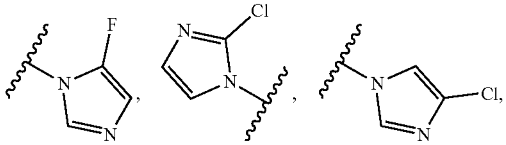
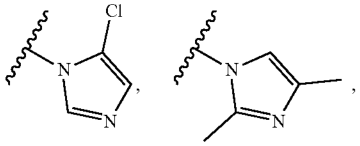
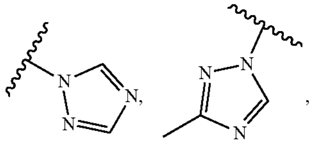
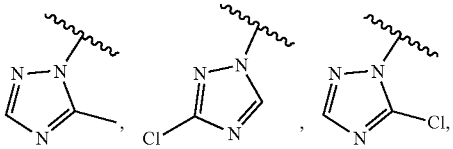
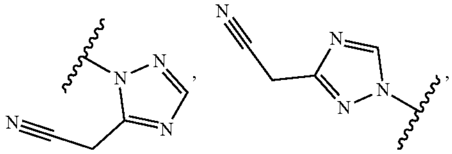
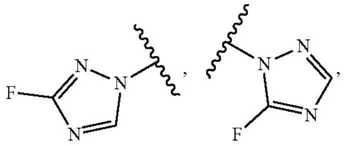
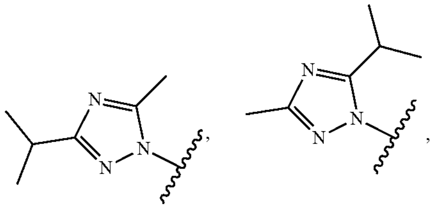
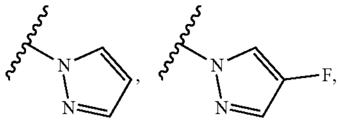
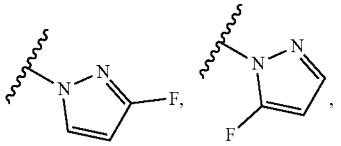
-continued
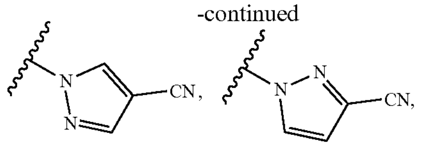
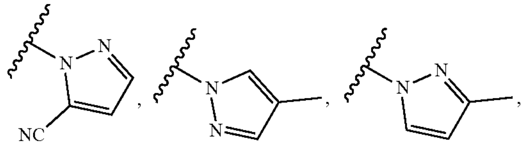
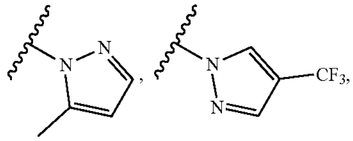
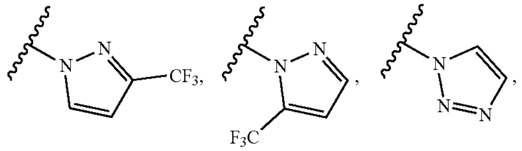
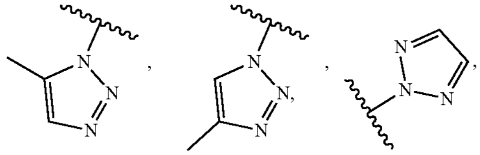
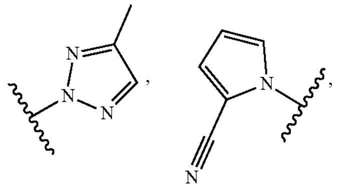
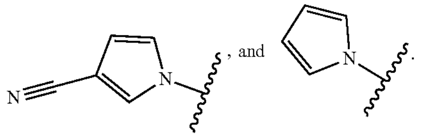
, and
In embodiments, $-L^{19}-R^{19}-L^{19a}-R^{19a}$ is
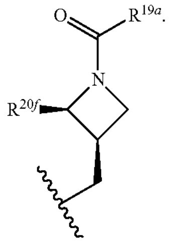
In embodiments, $R^{20f}$ is unsubstituted methyl; and $R^{19a}$ is selected from
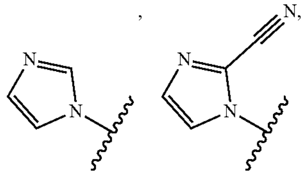

-continued

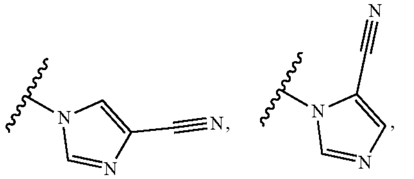
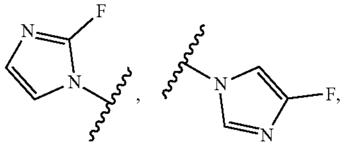
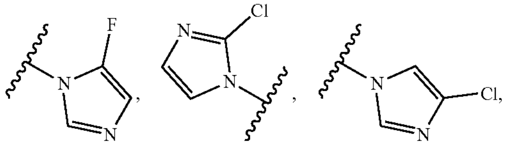
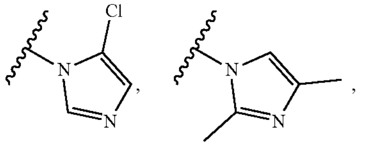
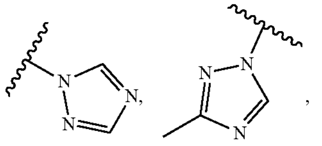
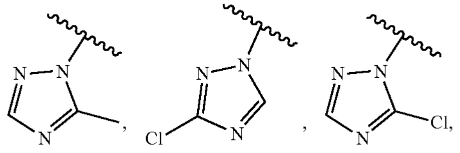
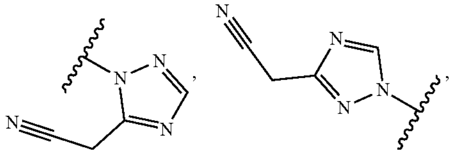
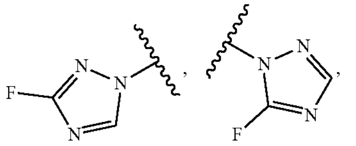
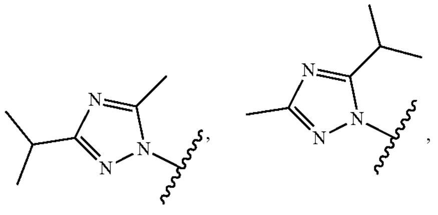
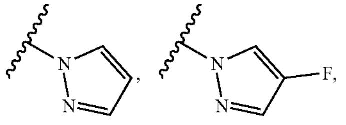
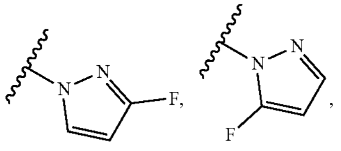

-continued

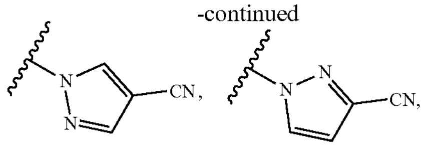
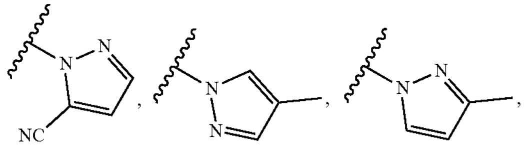
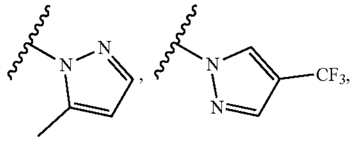
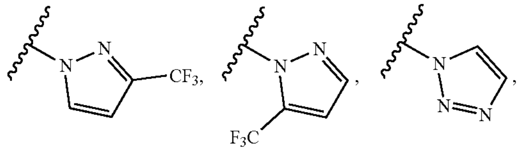
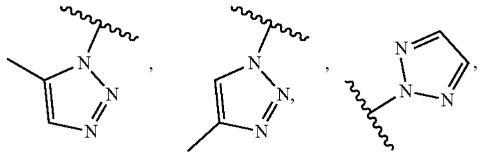
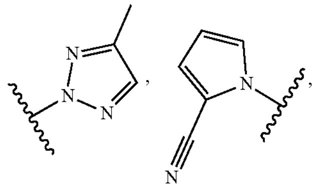
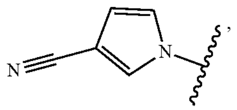
and
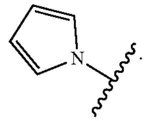

In embodiments, $R^{20f}$ is $C_{3-4}$ non-aromatic carbocycle substituted with $C_{1-3}$ alkyl and wherein the $C_{1-3}$ alkyl is substituted with halogen, —CN, or unsubstituted $C_{1-3}$ alkoxy; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkoxy, or unsubstituted $C_{1-3}$ haloalkyl.

In embodiments, $-L^{19}-R^{19}-L^{19a}-R^{19a}$ is

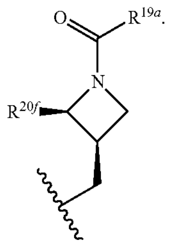

In embodiments, $R^{20f}$ is cyclopropyl substituted with methyl and wherein the methyl is substituted with —OMe, —CN, or F; and $R^{19a}$ is selected from

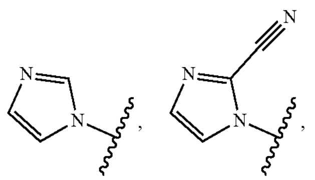
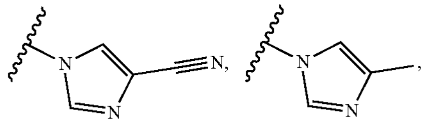
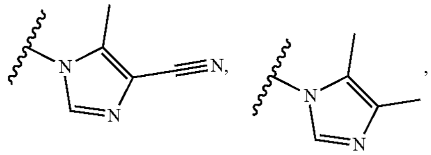
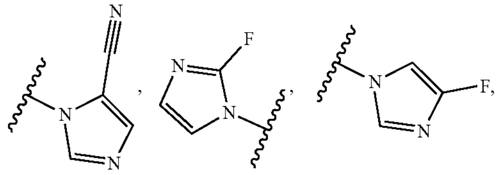
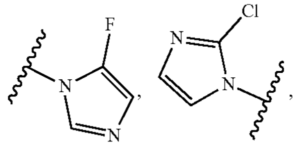
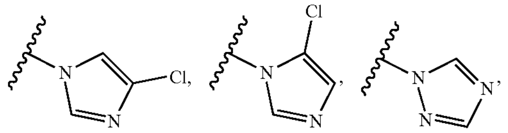
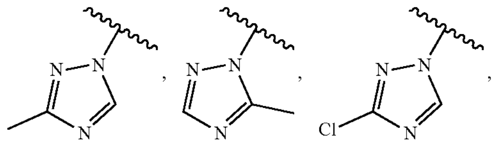
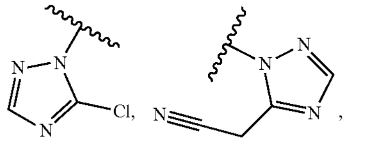
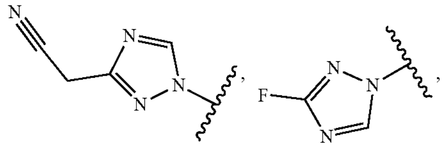
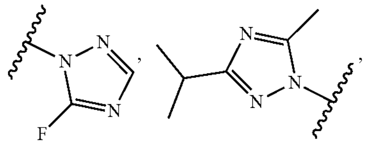
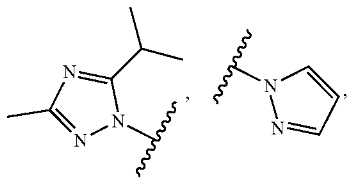

-continued

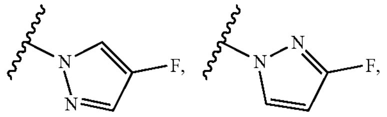
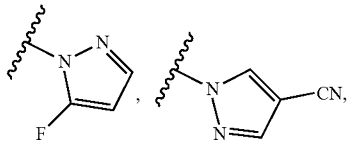
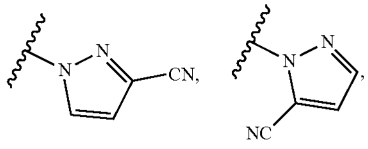
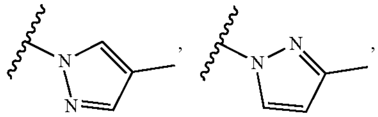
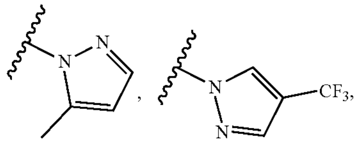
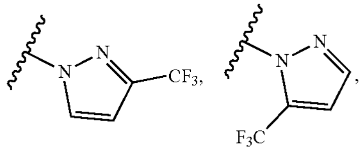
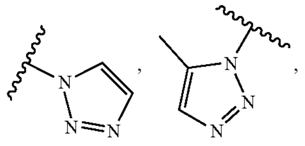
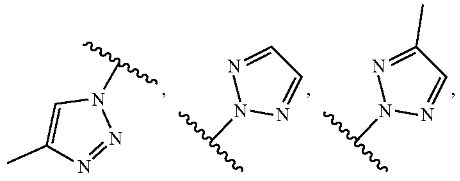
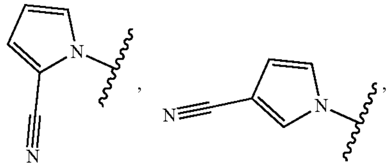
and
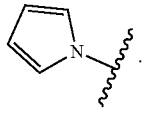

In embodiments, $R^{20f}$ is $C_{3-4}$ non-aromatic carbocycle substituted with $C_{1-3}$ alkyl and wherein the $C_{1-3}$ alkyl is substituted with halogen, —CN, or unsubstituted $C_{1-3}$ alkoxy; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments, $-L^{19}-R^{19}-L^{19a}-R^{19a}$ is

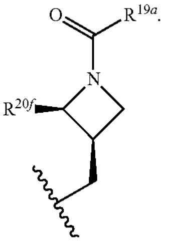

In embodiments, $R^{20f}$ is cyclopropyl substituted with methyl and wherein the methyl is substituted with —OMe, —CN, or F; and $R^{19a}$ is selected from

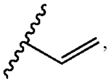, 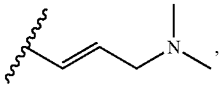, 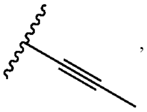, 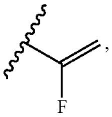, 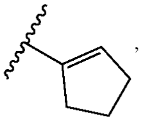, 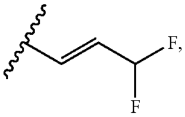, 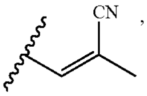, 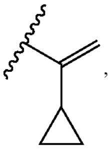, 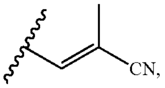, and 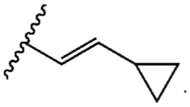.

In embodiments, $R^{20f}$ is $C_{3-4}$ non-aromatic carbocycle substituted with $C_{1-3}$ alkyl and wherein the $C_{1-3}$ alkyl is substituted with halogen, —CN, or unsubstituted $C_{1-3}$ alkoxy; and $R^{19a}$ is selected from unsubstituted cyclopentenyl, unsubstituted $C_{2-3}$ alkynyl, and $C_{2-3}$ alkenyl that is optionally substituted with one or more halogen, —CN, unsubstituted cyclopropyl, or $—N(CH_3)_2$. In embodiments, $R^{20f}$ is $C_{3-4}$ non-aromatic carbocycle substituted with $C_{1-3}$ alkyl and wherein the $C_{1-3}$ alkyl is substituted with halogen, —CN, or unsubstituted $C_{1-3}$ alkoxy; and $R^{19a}$ is selected from unsubstituted $C_{4-6}$ non-aromatic carbocycle, unsubstituted $C_{2-3}$ alkynyl, and $C_{2-3}$ alkenyl that is optionally substituted with one or more halogen, —CN, unsubstituted $C_{3-4}$ non-aromatic carbocycle, or $—N(C_{1-3}\text{ alkyl})_2$.

In embodiments, $-L^{19}-R^{19}-L^{19a}-R^{19a}$ is

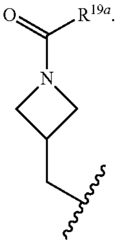

In embodiments, $R^{19a}$ is

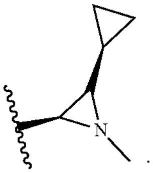

In embodiments, $R^{19a}$ is a 3 membered heterocycle optionally substituted with one or more unsubstituted cyclopropyl or unsubstituted methyl. In embodiments, $R^{19a}$ is a 3-4 membered heterocycle optionally substituted with one or more unsubstituted $C_{3-4}$ non-aromatic carbocycle or unsubstituted $C_{1-3}$ alkyl.

In embodiments, $-L^{19}-R^{19}-L^{19a}-R^{19a}$ is

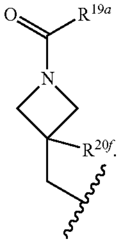

In embodiments, $R^{20f}$ is —OH; and $R^{19a}$ is selected from

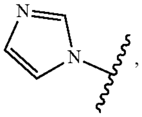, 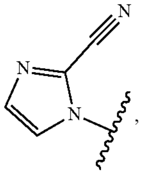, 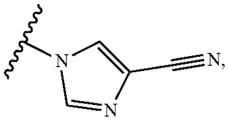, 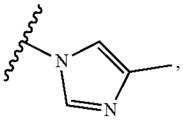, 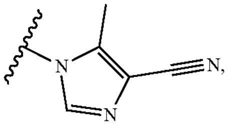, 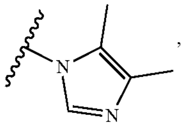, 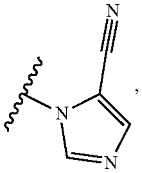, 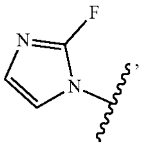, 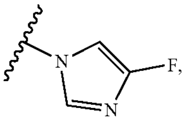, 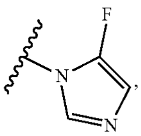, 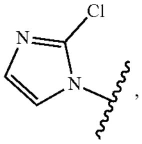, 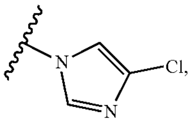, 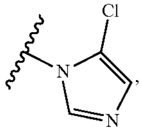, 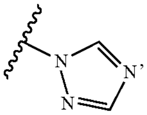, -continued

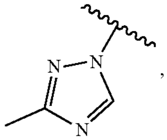, 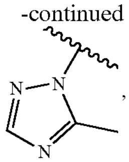, 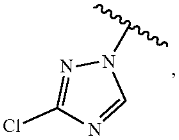,

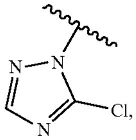, 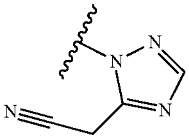,

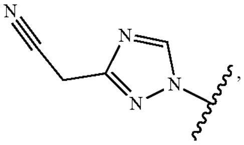, 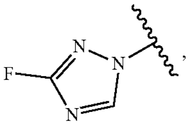,

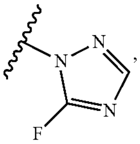, 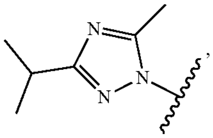,

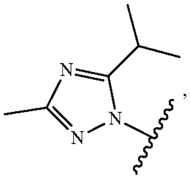, 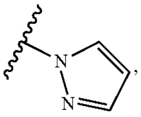,

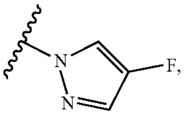, 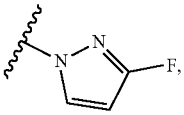,

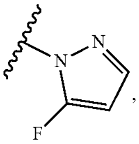, 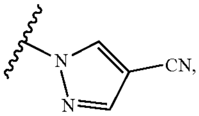,

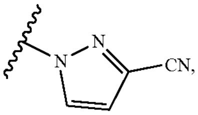, 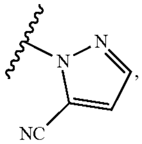,

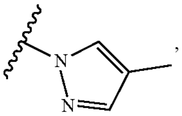, 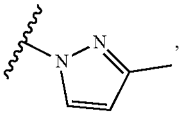,

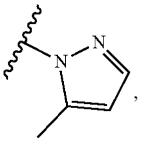, 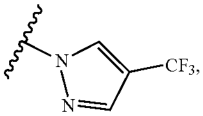,

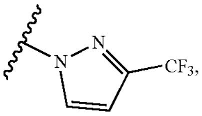, 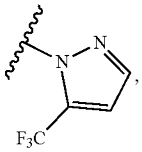,

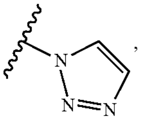, 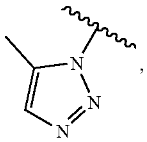,

-continued

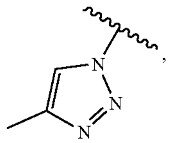, 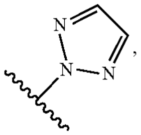, 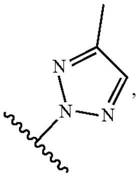,

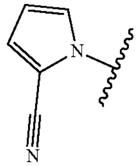, 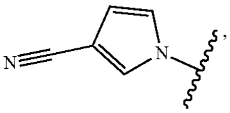, and

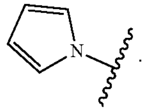.

In embodiments, $R^{20f}$ is —OH; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments of Formula (V), $-L^{19}-L^{19a}-R^{19a}$ is

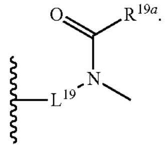

In embodiments of Formula (V), Ring A is a fused bicyclic heterocycle comprising an 8-membered ring and a 5-membered ring, $L^{19}$ is a bond; and $R^{19a}$ is selected from

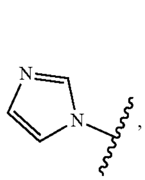, 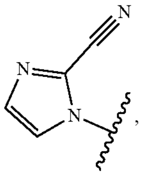,

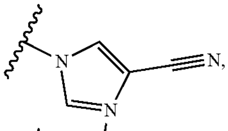, 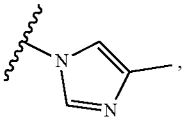,

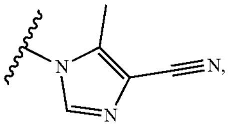, 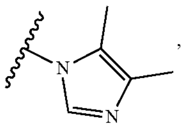,

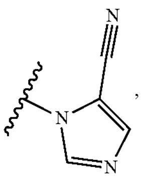, 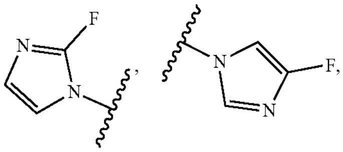,

-continued

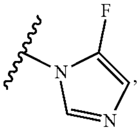, 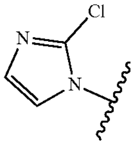,

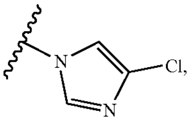, 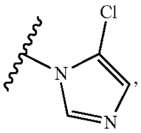, 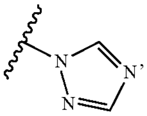,

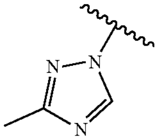, 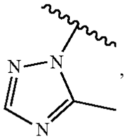, 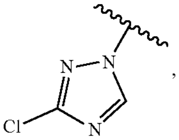,

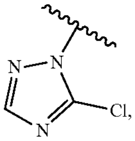, 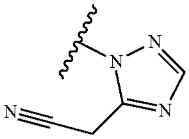,

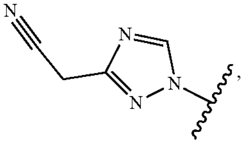, 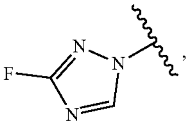,

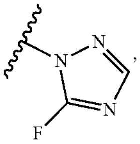, 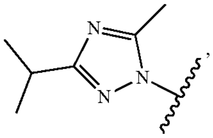,

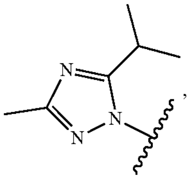, 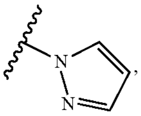,

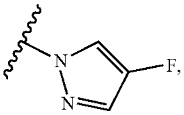, 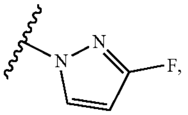,

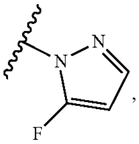, 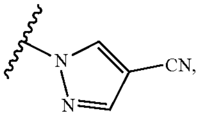,

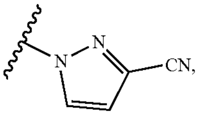, 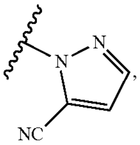,

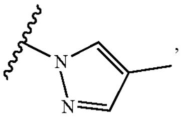, 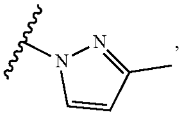,

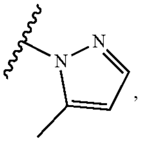, 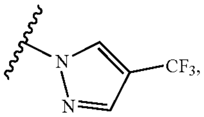,

-continued

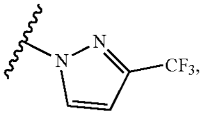, 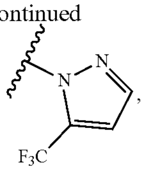,

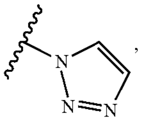, 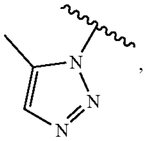,

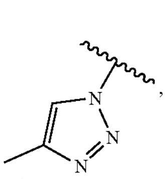, 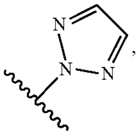, 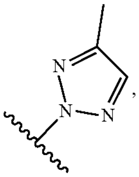,

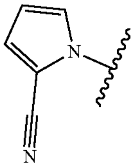, 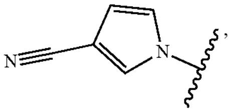, and

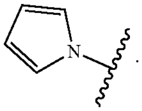.

In embodiments of Formula (V), Ring A is a fused bicyclic heterocycle comprising an 8-membered ring and a 5-membered ring, $L^{19}$ is a bond; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments of Formula (V), $-L^{19}-L^{19a}-R^{19a}$ is

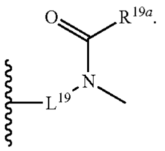

In embodiments of Formula (V), Ring A is a monocyclic 7-membered heterocycle, $L^{19}$ is an unsubstituted $C_{2-3}$ alkylene; and $R^{19a}$ is selected from

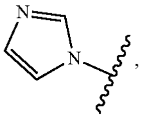, 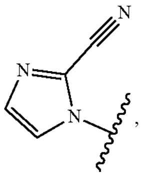,

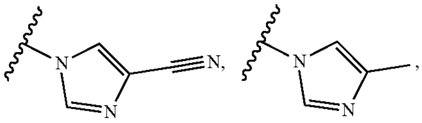

-continued

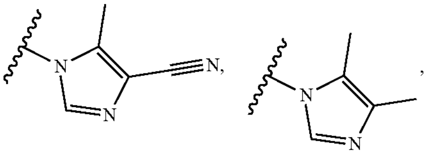,

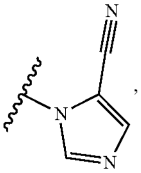, 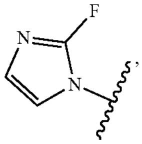, 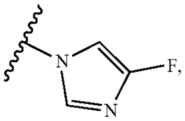

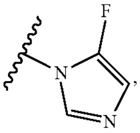, 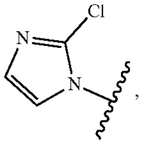,

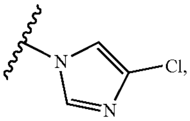 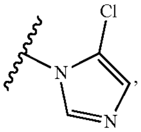, 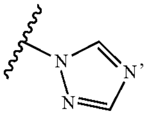

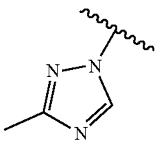, 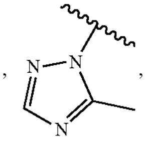, 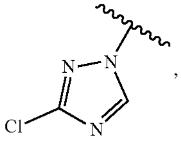,

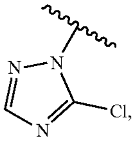 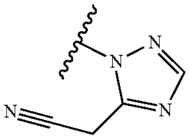,

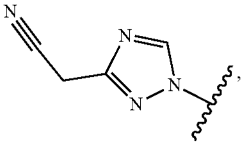, 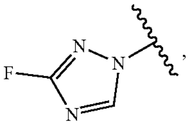,

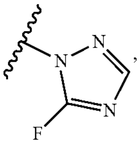, 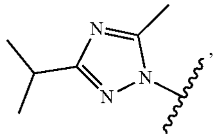,

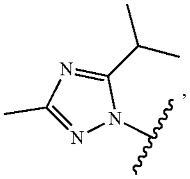, 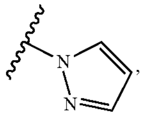,

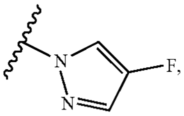 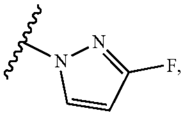,

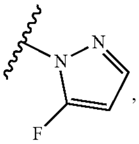, 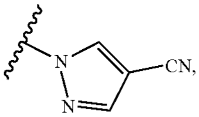

-continued

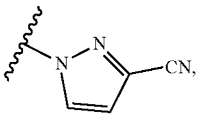 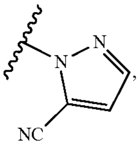

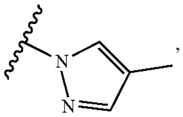, 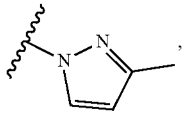,

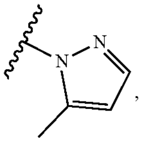, 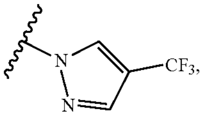

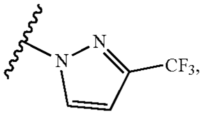 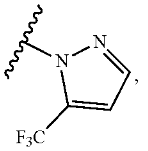

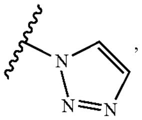, 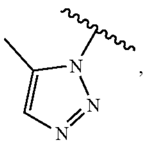,

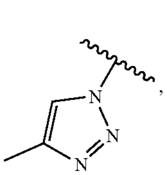, 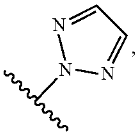, 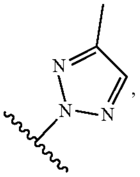

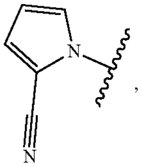, 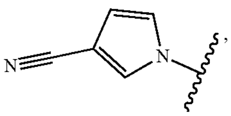, and

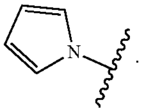.

In embodiments of Formula (V), Ring A is a monocyclic 7-membered heterocycle, $L^{19}$ is an unsubstituted $C_{1-6}$ alkylene; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, unsubstituted $C_{1-3}$ alkoxy, or unsubstituted $C_{1-3}$ haloalkyl.

In embodiments of a compound of formula IA, IB, or IIA, the compound has the formula:

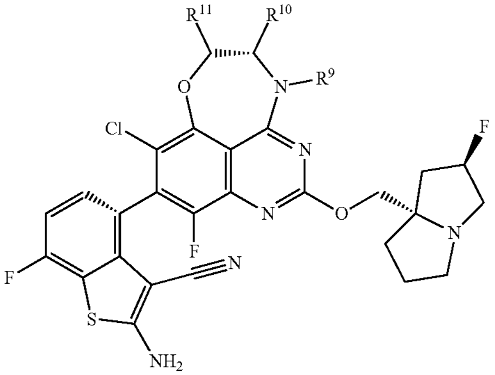
or
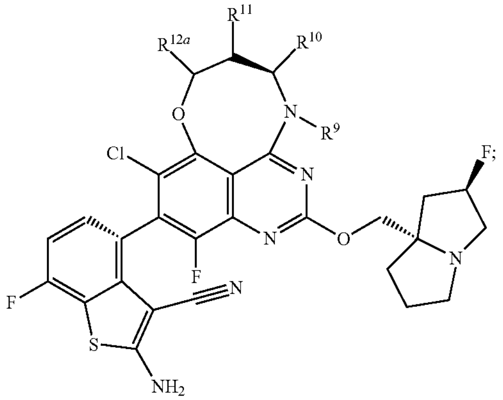
wherein,
$R^9$ is $-L^{19}-R^{19}-L^{19a}-R^{19a}$;
$-L^{19}-R^{19}-L^{19a}-R^{19a}$ is selected from
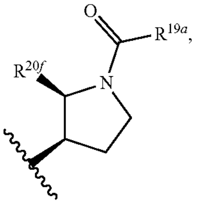
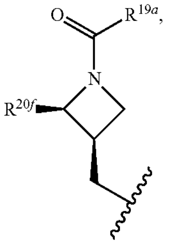
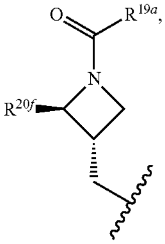
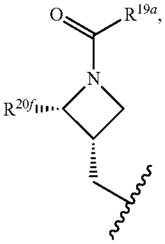
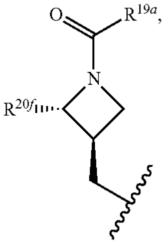
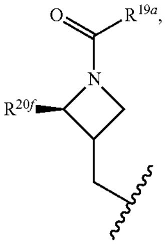
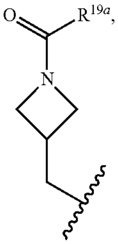
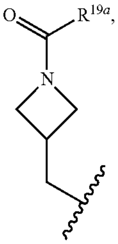
-continued
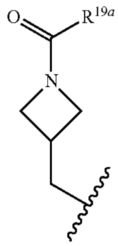
,
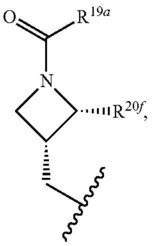
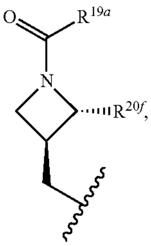
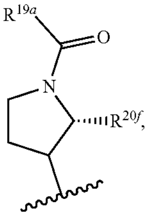
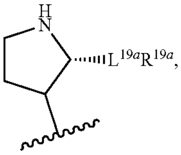
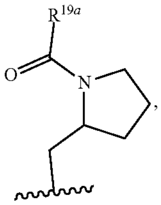
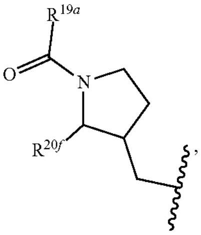
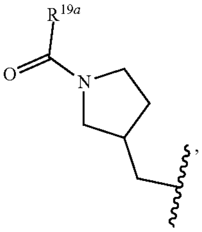
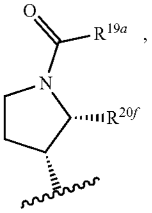
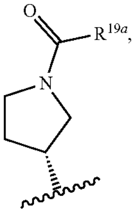
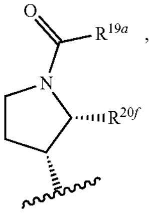
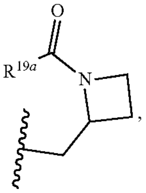
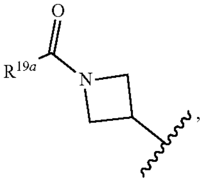
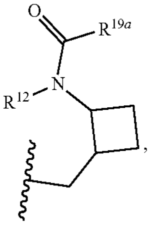
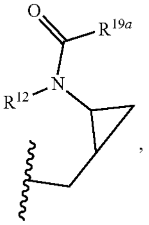
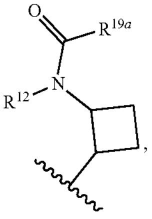
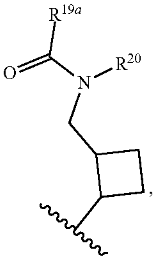
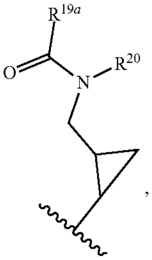
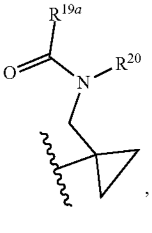

-continued
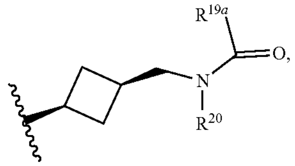
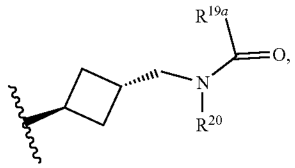
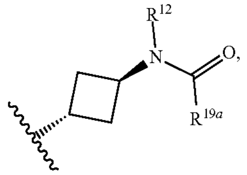
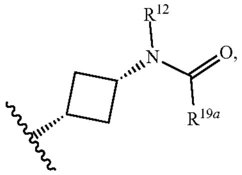
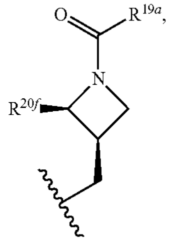
and
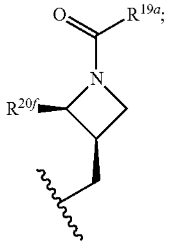
$R^{19a}$ is selected from
,
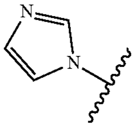
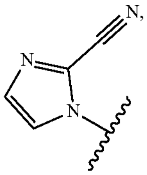
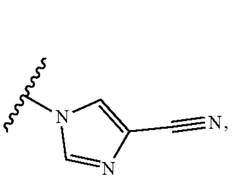
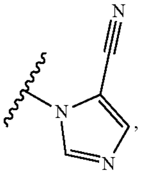
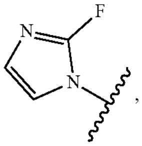
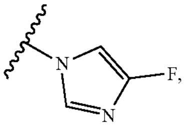
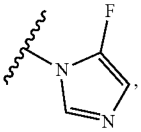
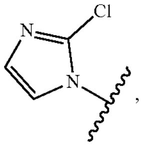
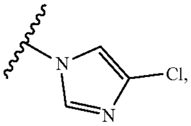
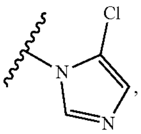
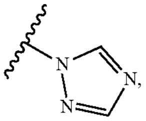
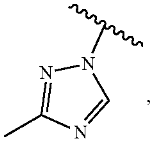
,
-continued
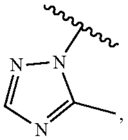
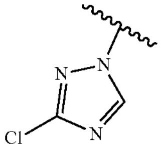
,
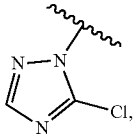
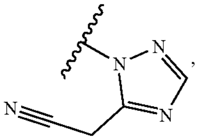
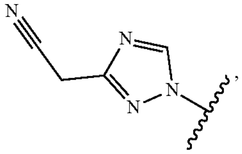
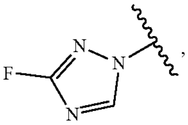
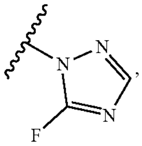
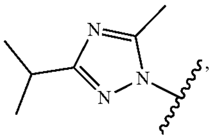
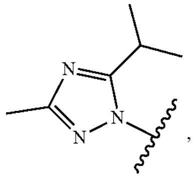
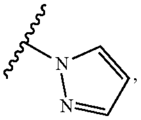
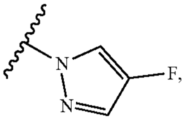
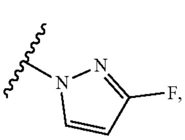
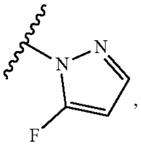
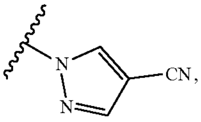
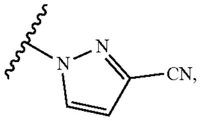
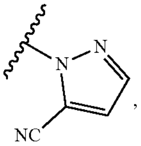
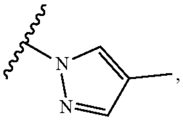
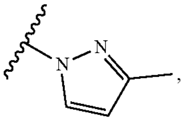
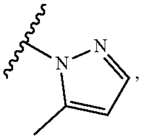
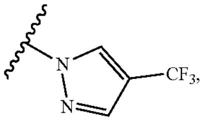
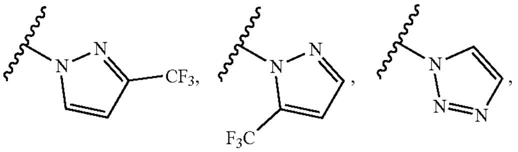
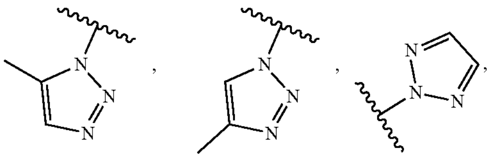

-continued

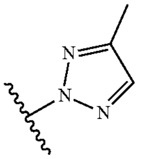

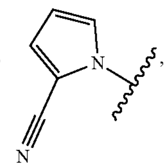

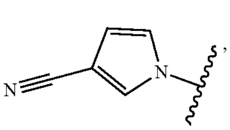

and

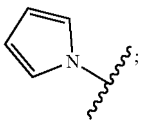

$R^{12}$ is unsubstituted $C_{1-3}$ alkyl;

$R^{20}$ is unsubstituted $C_{1-3}$ alkyl;

$R^{20a}$ is independently selected from —F, —Cl, —OH, and —$CHF_2$;

$R^{20f}$ is independently selected from methyl-substituted cyclopropyl wherein the methyl is optionally substituted with —OMe, —CN, or F, unsubstituted tert-butyl, unsubstituted isopropyl, and unsubstituted methyl; and $R^{10}$, $R^{11}$, and $R^{12a}$ are independently selected at each occurrence from hydrogen,

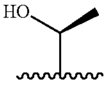

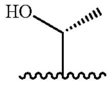

—$CH_3$, and

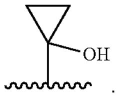

In embodiments of a compound of formula IA, IB, or IIA, the compound has the formula:

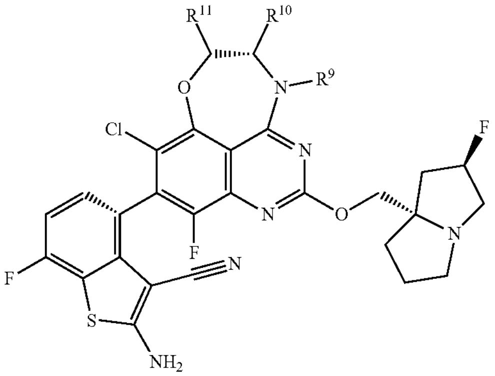

or

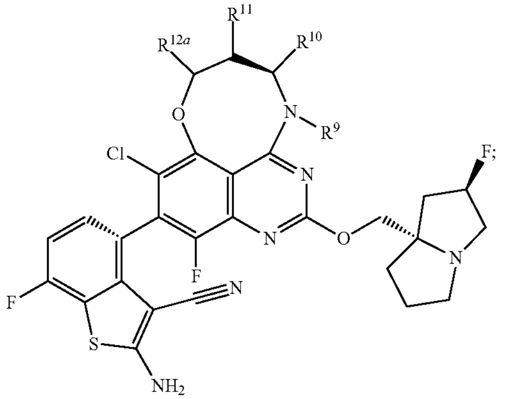

wherein, $R^9$ is $-L^{19}-R^{19}-L^{19a}-R^{19a}$;

$-L^{19}-R^{19}-L^{19a}-R^{19a}$ is selected from

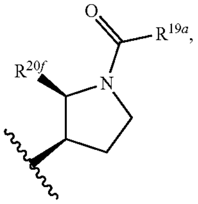

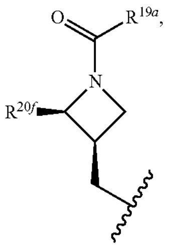

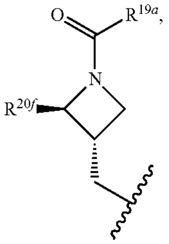

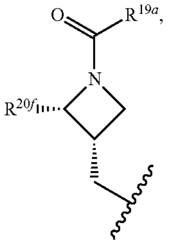

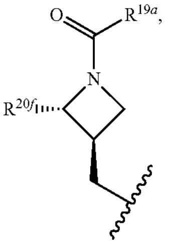

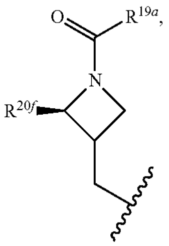

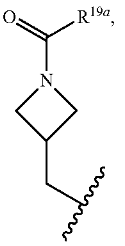

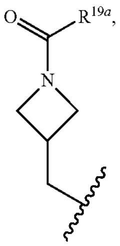

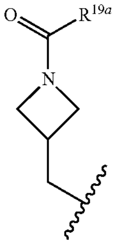

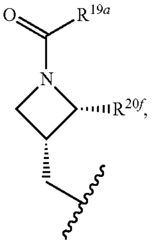

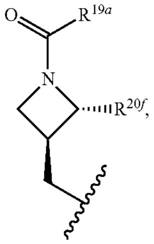

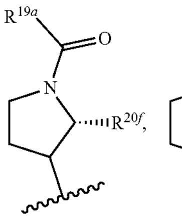

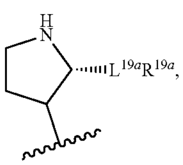

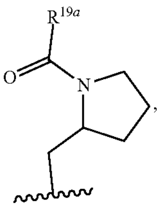

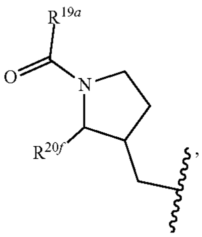

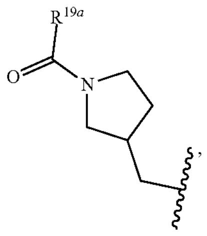

-continued
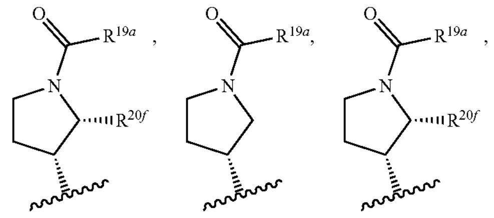
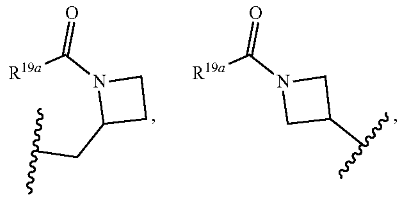
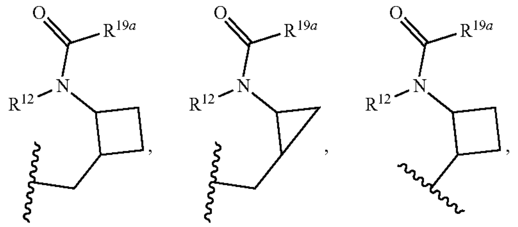
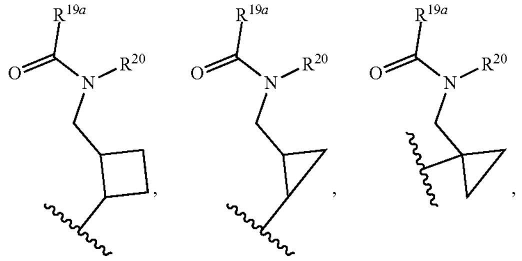
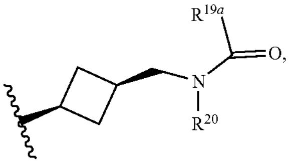
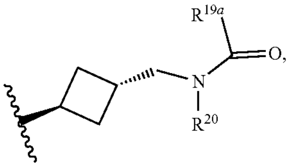
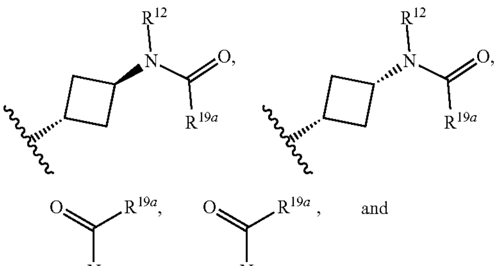
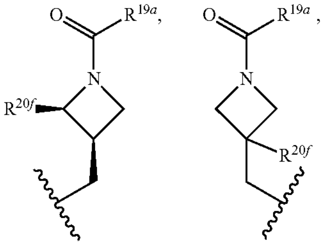
and
-continued
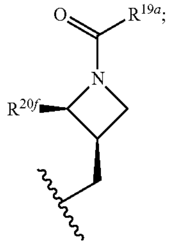
$R^{19a}$ is selected from
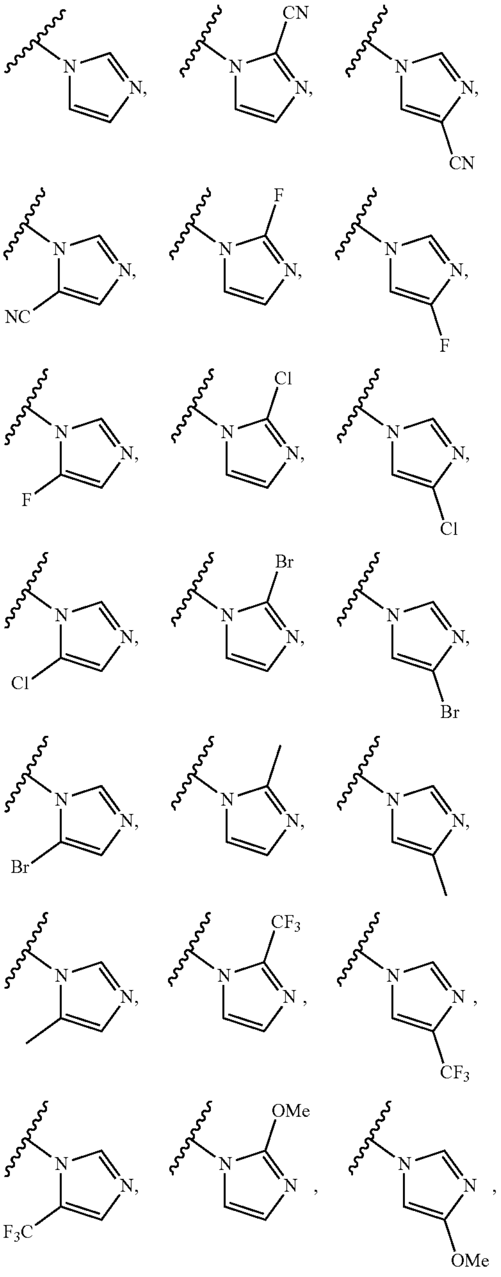

-continued
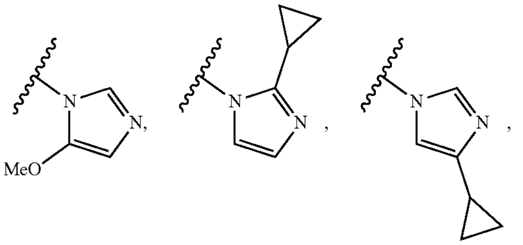
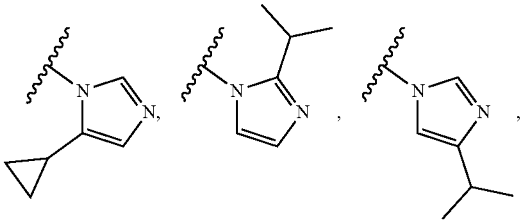
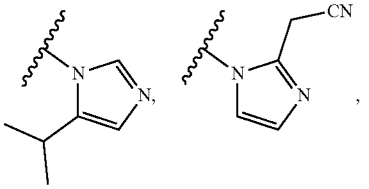
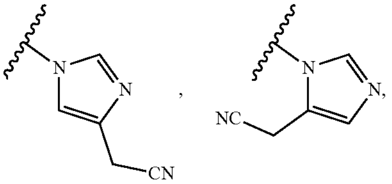
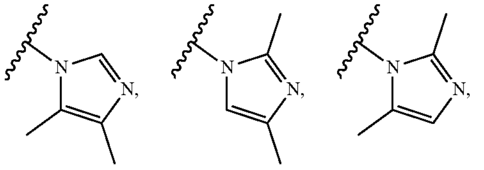
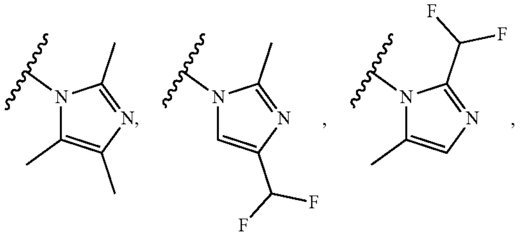
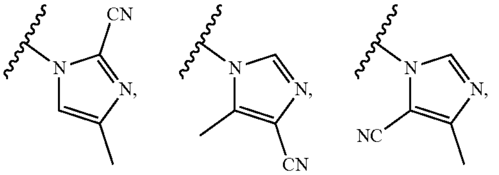
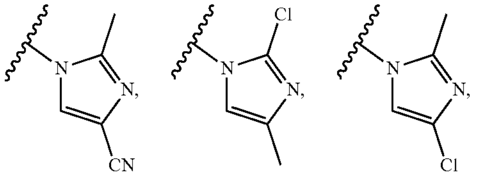
-continued
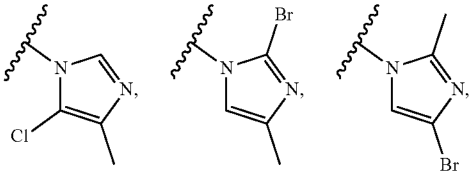
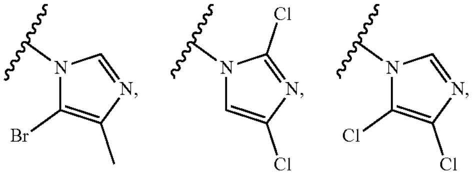
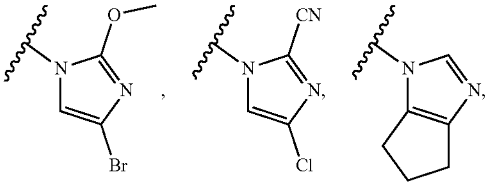
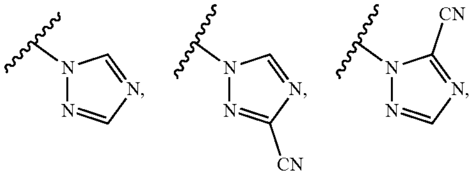
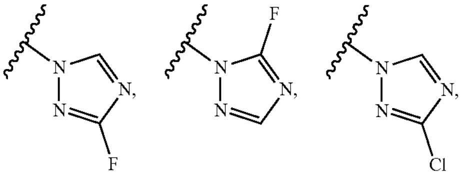
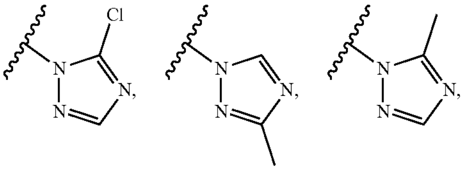
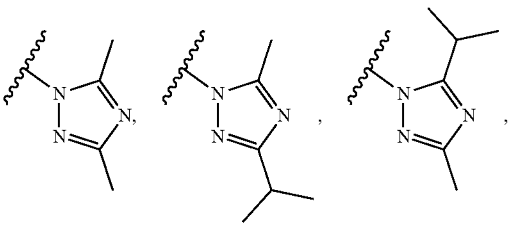
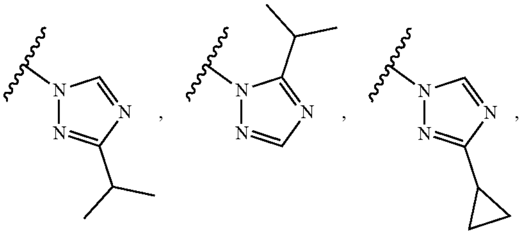

-continued

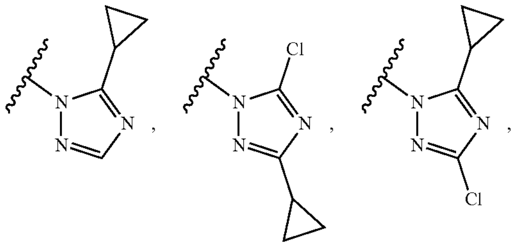

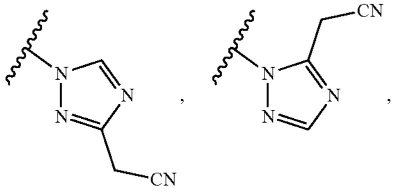

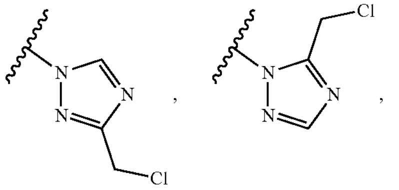

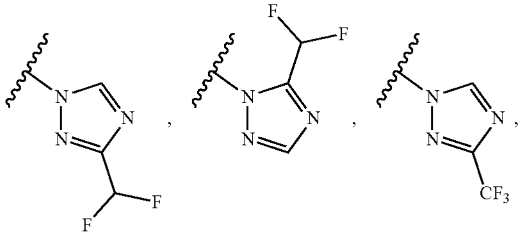

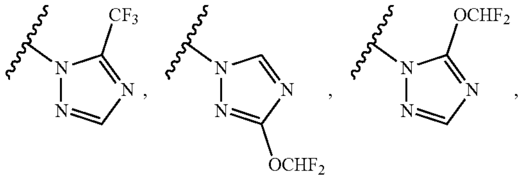

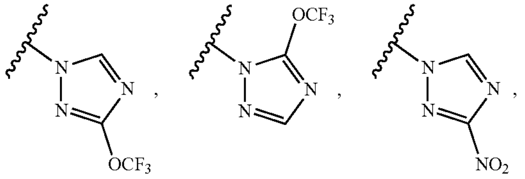

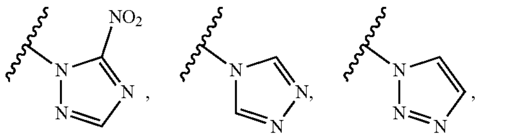

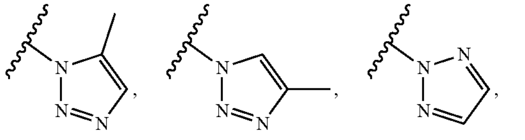

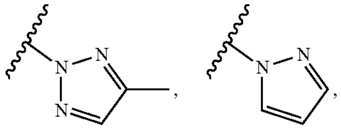

-continued

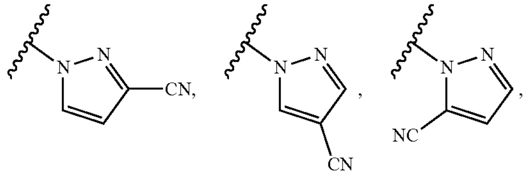

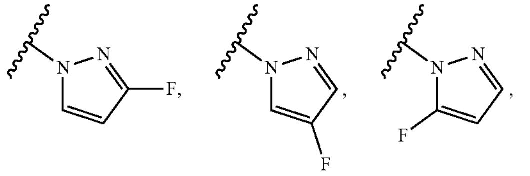

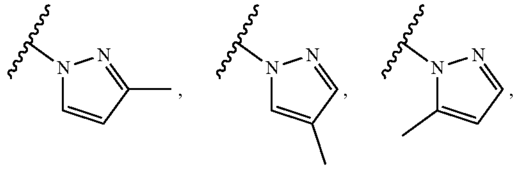

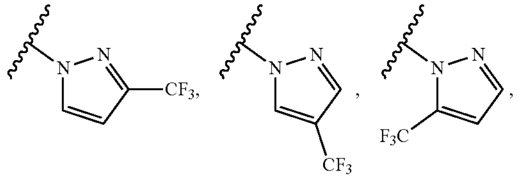

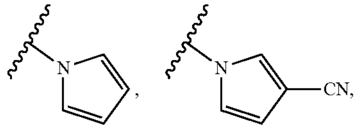

and

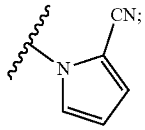

$R^6$ is Cl or —$CF_3$;

$R^{12}$ is unsubstituted $C_{1-3}$ alkyl;

$R^{20}$ is unsubstituted $C_{1-3}$ alkyl;

$R^{20a}$ is independently selected from —F, —Cl, —OH, and —$CHF_2$;

$R^{20}$ is independently selected from —OH, methyl-substituted cyclopropyl wherein the methyl is optionally substituted with —OMe, —CN, or F, unsubstituted tert-butyl, unsubstituted isopropyl, and unsubstituted methyl; and $R^{10}$, $R^{11}$, and $R^{12a}$ are independently selected at each occurrence from hydrogen,

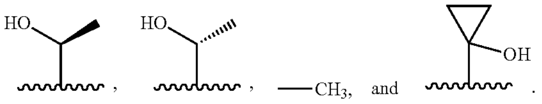

In embodiments of a compound of formula IIA, the compound has the formula:

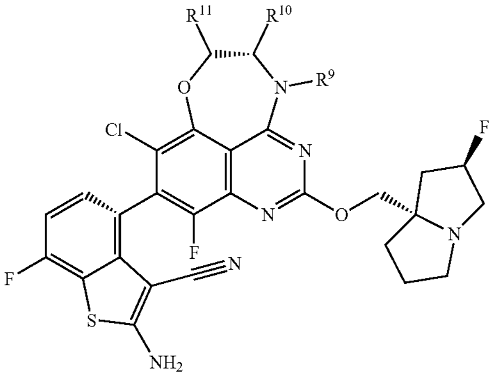
or
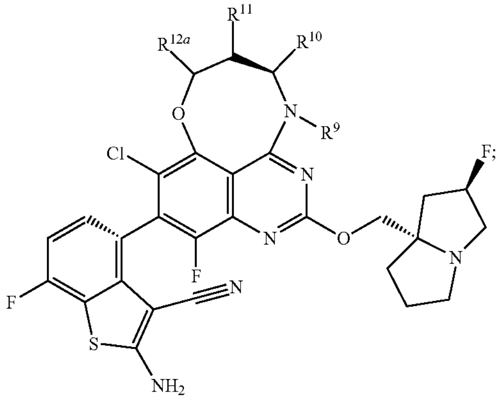
wherein,
$R^9$ is $-L^{19}-R^{19}-L^{19a}-R^{19a}$;
$-L^{19}-R^{19}-L^{19a}-R^{19a}$ is selected from
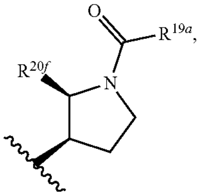 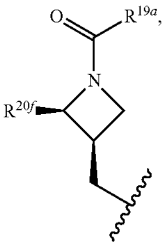 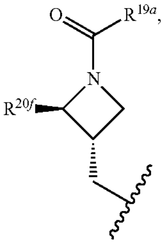
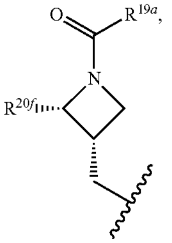 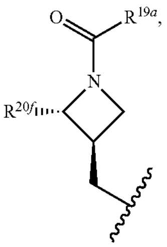 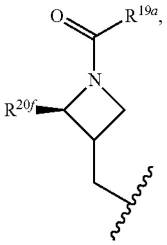
-continued
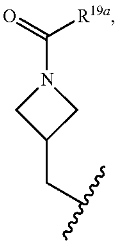 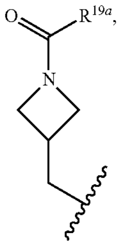 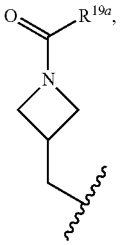 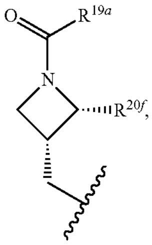
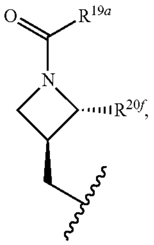 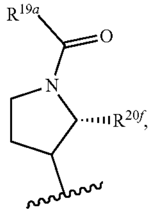 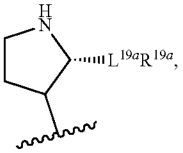
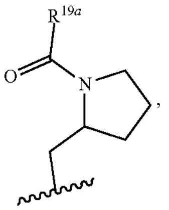 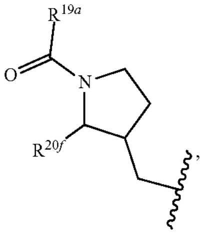
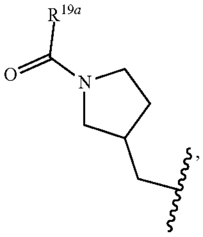 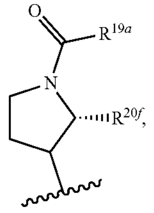 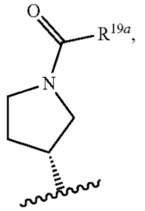
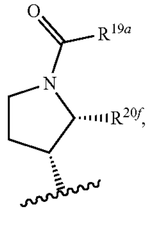 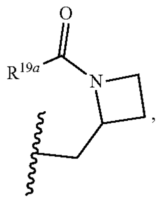 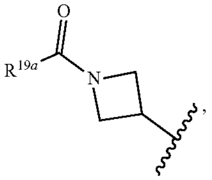
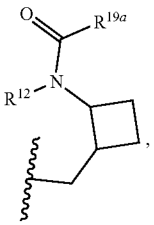 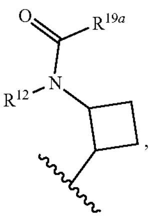 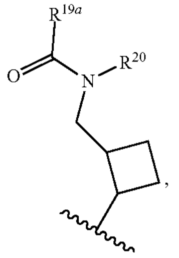

-continued

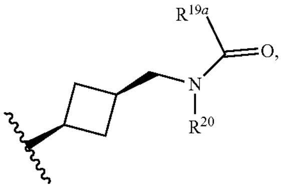
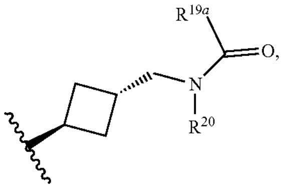

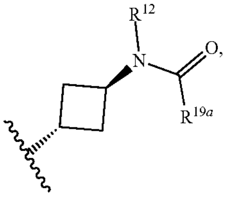
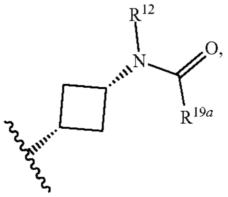

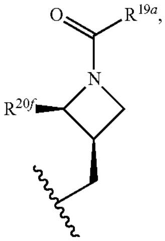 and 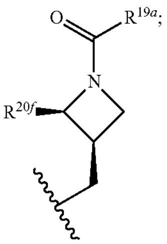

$R^{19a}$ is selected from

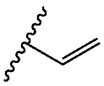, 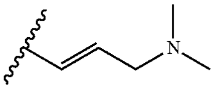, 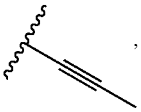,

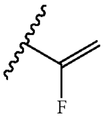, 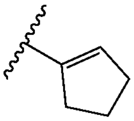, 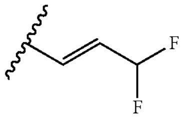

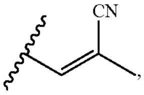, 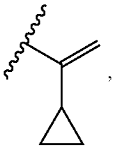, 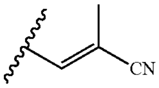

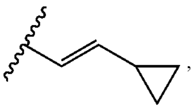, and 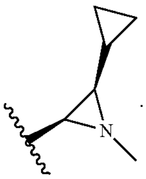.

$R^{12}$ is unsubstituted $C_{1-3}$ alkyl;

$R^{20}$ is unsubstituted $C_{1-3}$ alkyl;

$R^{20a}$ is independently selected from —F, —Cl, —OH, and —$CHF_2$;

$R^{20}$ is independently selected from methyl-substituted cyclopropyl wherein the methyl is optionally substituted with —OMe, —CN, or F, unsubstituted tert-butyl, unsubstituted isopropyl, and unsubstituted methyl; and $R^{10}$, $R^{11}$, and $R^{12a}$ are independently selected at each occurrence from hydrogen,

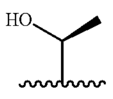, 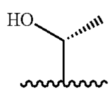, —$CH_3$, and 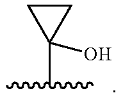.

In embodiments of -$L^{19}$-$R^{19}$-$L^{19a}$-$R^{19a}$ in the paragraphs above, $R^{19a}$ is

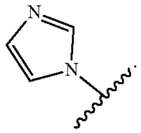

In embodiments of -$L^{19}$-$R^{19}$-$L^{19a}$-$R^{19a}$ in the paragraphs above, $R^{19a}$ is

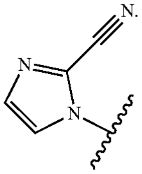 [SMILES: *n1ccnc1C#N]

In embodiments of -$L^{19}$-$R^{19}$-$L^{19a}$-$R^{19a}$ in the paragraphs above, $R^{19a}$ is

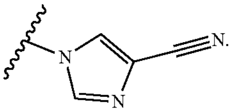 [SMILES: *n1cnc(C#N)c1]

In embodiments of -$L^{19}$-$R^{19}$-$L^{19a}$-$R^{19a}$ in the paragraphs above, $R^{19a}$ is

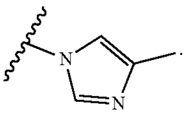 [SMILES: *n1cnc(C)c1]

In embodiments of -$L^{19}$-$R^{19}$-$L^{19a}$-$R^{19a}$ in the paragraphs above, $R^{19a}$ is

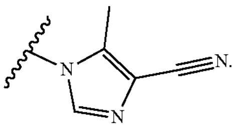 [SMILES: *n1cnc(C#N)c1C]

In embodiments of -$L^{19}$-$R^{19}$-$L^{19a}$-$R^{19a}$ in the paragraphs above, $R^{19a}$ is

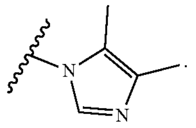 [SMILES: *n1cnc(C)c1C]

In embodiments of $-L^{19}-R^{19}-L^{19a}-R^{19a}$ in the paragraphs above, $R^{19a}$ is

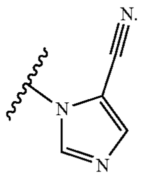

In embodiments of $-L^{19}-R^{19}-L^{19a}-R^{19a}$ in the paragraphs above, $R^{19a}$ is

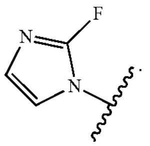 [SMILES: *n1ccnc1F]

In embodiments of $-L^{19}-R^{19}-L^{19a}-R^{19a}$ in the paragraphs above, $R^{19a}$ is

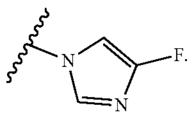 [SMILES: *n1cnc(F)c1]

In embodiments of $-L^{19}-R^{19}-L^{19a}-R^{19a}$ in the paragraphs above, $R^{19a}$ is

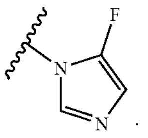 [SMILES: *n1cncc1F]

In embodiments of $-L^{19}-R^{19}-L^{19a}-R^{19a}$ in the paragraphs above, $R^{19a}$ is

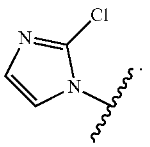

In embodiments of $-L^{19}-R^{19}-L^{19a}-R^{19a}$ in the paragraphs above, $R^{19a}$ is

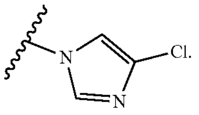 [SMILES: *n1cnc(Cl)c1]

In embodiments of $-L^{19}-R^{19}-L^{19a}-R^{19a}$ in the paragraphs above, $R^{19a}$ is

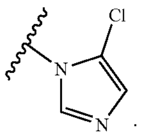 [SMILES: *n1cncc1Cl]

In embodiments of $-L^{19}-R^{19}-L^{19a}-R^{19a}$ in the paragraphs above, $R^{19a}$ is

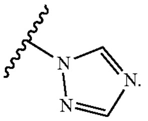 [SMILES: *n1cncn1]

In embodiments of $-L^{19}-R^{19}-L^{19a}-R^{19a}$ in the paragraphs above, $R^{19a}$ is

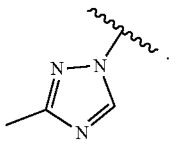 [SMILES: *n1cnc(C)n1]

In embodiments of $-L^{19}-R^{19}-L^{19a}-R^{19a}$ in the paragraphs above, $R^{19a}$ is

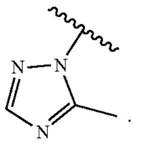 [SMILES: *n1ncnc1C]

In embodiments of $-L^{19}-R^{9}-L^{19a}-R^{19a}$ in the paragraphs above, $R^{19a}$ is

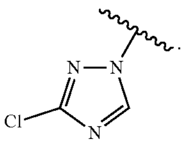 [SMILES: *n1cnc(Cl)n1]

In embodiments of $-L^{19}-R^{19}-L^{19a}-R^{19a}$ in the paragraphs above, $R^{1C}$ is

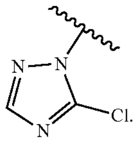 [SMILES: *n1ncnc1Cl]

In embodiments of $-L^{19}$-$R^{19}$-$L^{19a}$-$R^{19a}$ in the paragraphs above, $R^{19a}$ is

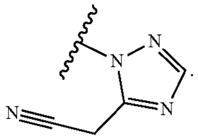 [SMILES: *n1ncnc1CC#N]

In embodiments of $-L^{19}$-$R^{19}$-$L^{19a}$-$R^{19a}$ in the paragraphs above, $R^{19a}$ is

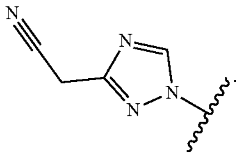 [SMILES: *n1cnc(CC#N)n1]

In embodiments of $-L^{19}$-$R^{19}$-$L^{19a}$-$R^{19a}$ in the paragraphs above, $R^{19a}$ is

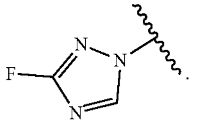 [SMILES: *n1cnc(F)n1]

In embodiments of $-L^{19}$-$R^{19}$-$L^{19a}$-$R^{19a}$ in the paragraphs above, $R^{19a}$ is

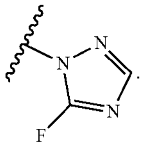 [SMILES: *n1ncnc1F]

In embodiments of $-L^{19}$-$R^{19}$-$L^{19a}$-$R^{19a}$ in the paragraphs above, $R^{19a}$ is

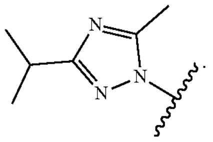 [SMILES: *n1nc(C(C)C)nc1C]

In embodiments of $-L^{19}$-$R^{19}$-$L^{19a}$-$R^{19a}$ in the paragraphs above, $R^{19a}$ is

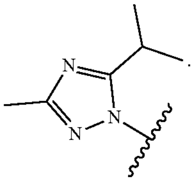 [SMILES: *n1nc(C)nc1C(C)C]

In embodiments of $-L^{19}$-$R^{19}$-$L^{19a}$-$R^{19a}$ in the paragraphs above, $R^{19a}$ is

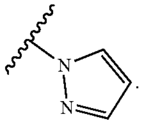 [SMILES: *n1cccn1]

In embodiments of $-L^{19}$-$R^{19}$-$L^{19a}$-$R^{19a}$ in the paragraphs above, $R^{19a}$ is

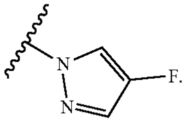 [SMILES: *n1cc(F)cn1]

In embodiments of $-L^{19}$-$R^{19}$-$L^{19a}$-$R^{19a}$ in the paragraphs above, $R^{19a}$ is

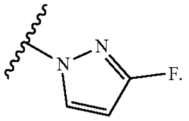 [SMILES: *n1ccc(F)n1]

In embodiments of $-L^{19}$-$R^{19}$-$L^{19a}$-$R^{19a}$ in the paragraphs above, $R^{19a}$ is

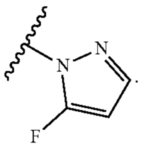

In embodiments of $-L^{19}$-$R^{19}$-$L^{19a}$-$R^{19a}$ in the paragraphs above, $R^{19a}$ is

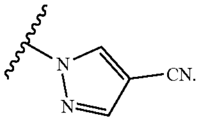 [SMILES: *n1cc(C#N)cn1]

In embodiments of $-L^{19}$-$R^{19}$-$L^{19a}$-$R^{19a}$ in the paragraphs above, $R^{19a}$ is

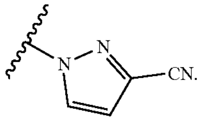 [SMILES: *n1ccc(C#N)n1]

In embodiments of $-L^{19}-R^{19}-L^{19a}-R^{19a}$ in the paragraphs above, $R^{19a}$ is

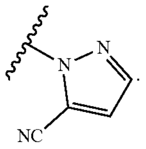 [SMILES: *n1nccc1C#N]

In embodiments of $-L^{19}-R^{19}-L^{19a}-R^{19a}$ in the paragraphs above, $R^{19a}$ is

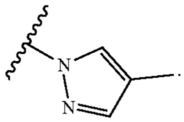 [SMILES: *n1cc(C)cn1]

In embodiments of $-L^{19}-R^{19}-L^{19a}-R^{19a}$ in the paragraphs above, $R^{19a}$ is

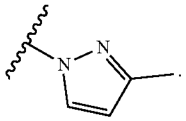 [SMILES: *n1ccc(C)n1]

In embodiments of $-L^{19}-R^{19}-L^{19a}-R^{19a}$ in the paragraphs above, $R^{19a}$ is

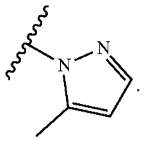 [SMILES: *n1nccc1C ; "."]

In embodiments of $-L^{19}-R^{19}-L^{19a}-R^{19a}$ in the paragraphs above, $R^{19a}$ is

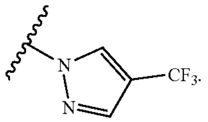 [SMILES: *n1cc(C(F)(F)F)cn1]

In embodiments of $-L^{19}-R^{19}-L^{19a}-R^{19a}$ in the paragraphs above, $R^{19a}$ is

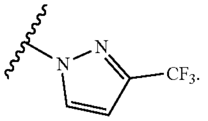 [SMILES: *n1ccc(C(F)(F)F)n1]

In embodiments of $-L^{19}-R^{19}-L^{19a}-R^{19a}$ in the paragraphs above, $R^{19a}$ is

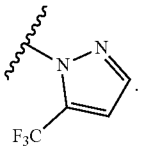

In embodiments of $-L^{19}-R^{19}-L^{19a}-R^{19a}$ in the paragraphs above, $R^{19a}$ is

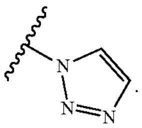 [SMILES: *n1ccnn1 ; "."]

In embodiments of $-L^{19}-R^{19}-L^{19a}-R^{19a}$ in the paragraphs above, $R^{19a}$ is

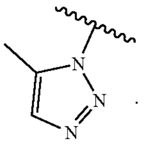 [SMILES: *n1nncc1C]

In embodiments of $-L^{19}-R^{19}-L^{19a}-R^{19a}$ in the paragraphs above, $R^{19a}$ is

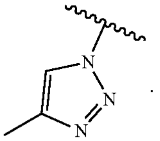 [SMILES: *n1cc(C)nn1]

In embodiments of $-L^{19}-R^{19}-L^{19a}-R^{19a}$ in the paragraphs above, $R^{19a}$ is

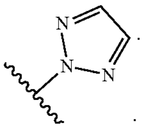 [SMILES: *n1nccn1]

In embodiments of $-L^{19}-R^{19}-L^{19a}-R^{19a}$ in the paragraphs above, $R^{19a}$ is

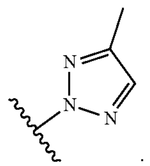 [SMILES: *n1ncc(C)n1]

In embodiments of $-L^{19}-R^{19}-L^{19a}-R^{19a}$ in the paragraphs above, $R^{19a}$ is

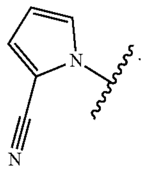 [SMILES: *n1cccc1C#N]

In embodiments of $-L^{19}-R^{19}-L^{19a}-R^{19a}$ in the paragraphs above, $R^{19a}$ is

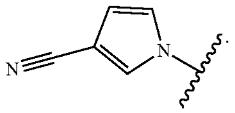

In embodiments of $-L^{19}-R^{19}-L^{19a}-R^{19a}$ in the paragraphs above, $R^{19a}$ is

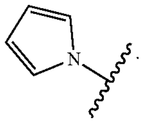 [SMILES: *n1cccc1]

In embodiments of $-L^{19}-L^{19a}-R^{19a}$ in the paragraphs above, $R^{19a}$ is

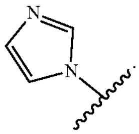

In embodiments of $-L^{19}-L^{19a}-R^{19a}$ in the paragraphs above, $R^{19a}$ is

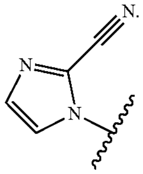 [SMILES: *n1ccnc1C#N]

In embodiments of $-L^{19}-L^{19a}-R^{19a}$ in the paragraphs above, $R^{19a}$ is

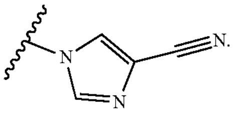

In embodiments of $-L^{19}-L^{19a}-R^{19a}$ in the paragraphs above, $R^{19a}$ is

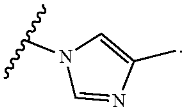 [SMILES: *n1cnc(C)c1]

In embodiments of $-L^{19}-L^{19a}-R^{19a}$ in the paragraphs above, $R^{19}$ is

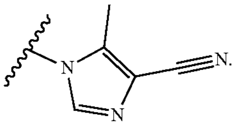 [SMILES: *n1cnc(C#N)c1C]

In embodiments of $-L^{19}-L^{19a}-R^{19a}$ in the paragraphs above, $R^{19a}$ is

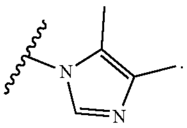

In embodiments of $-L^{19}-L^{19a}-R^{19a}$ in the paragraphs above, $R^{19a}$ is

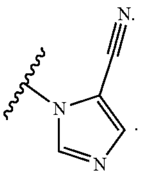 [SMILES: *n1cncc1C#N]

In embodiments of $-L^{19}-L^{19a}-R^{19a}$ in the paragraphs above, $R^{19a}$ is

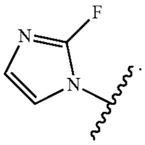 [SMILES: *n1ccnc1F]

In embodiments of $-L^{19}-L^{19a}-R^{19a}$ in the paragraphs above, $R^{19a}$ is

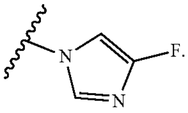 [SMILES: *n1cnc(F)c1]

In embodiments of -$L^{19}$-$L^{19a}$-$R^{19a}$ in the paragraphs above, $R^{19a}$ is

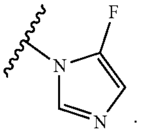 [SMILES: *n1cncc1F]

In embodiments of -$L^{19}$-$L^{19a}$-$R^{19a}$ in the paragraphs above, $R^{19a}$ is

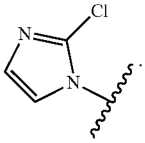 [SMILES: *n1ccnc1Cl]

In embodiments of -$L^{19}$-$L^{19a}$-$R^{19a}$ in the paragraphs above, $R^{19a}$ is

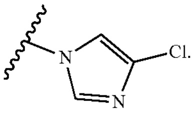 [SMILES: *n1cnc(Cl)c1]

In embodiments of -$L^{19}$-$L^{19a}$-$R^{19a}$ in the paragraphs above, $R^{19a}$ is

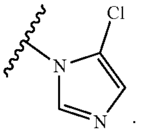

In embodiments of -$L^{19}$-$L^{19a}$-$R^{19a}$ in the paragraphs above, $R^{19a}$ is

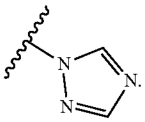 [SMILES: *n1cncn1]

In embodiments of -$L^{19}$-$L^{19a}$-$R^{19a}$ in the paragraphs above, $R^{19a}$ is

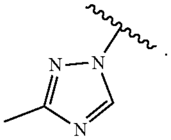 [SMILES: *n1cnc(C)n1]

In embodiments of -$L^{19-}$$L^{19a}$-$R^{19a}$ in the paragraphs above, $R^{19a}$ is

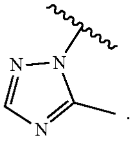 [SMILES: *n1ncnc1C]

In embodiments of -$L^{19}$-$L^{19a}$-$R^{19a}$ in the paragraphs above, $R^{19a}$ is

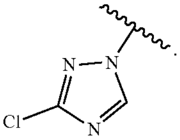 [SMILES: *n1cnc(Cl)n1]

In embodiments of -$L^{19}$-$L^{19a}$-$R^{19a}$ in the paragraphs above, $R^{19a}$ is

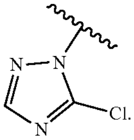 [SMILES: *n1ncnc1Cl]

In embodiments of -$L^{19}$-$L^{19a}$-$R^{19a}$ in the paragraphs above, $R^{19a}$ is

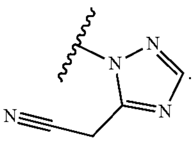 [SMILES: *n1ncnc1CC#N]

In embodiments of -$L^{19}$-$L^{19a}$-$R^{19a}$ in the paragraphs above, $R^{19a}$ is

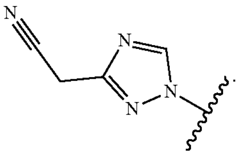 [SMILES: *n1cnc(CC#N)n1]

In embodiments of -$L^{19}$-$L^{19a}$-$R^{19a}$ in the paragraphs above, $R^{19a}$ is

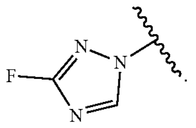

In embodiments of $-L^{19}-L^{19a}-R^{19a}$ in the paragraphs above, $R^{19a}$ is

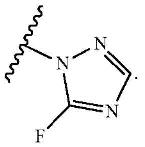 [SMILES: *n1ncnc1F]

In embodiments of $-L^{19}-L^{19a}-R^{19a}$ in the paragraphs above, $R^{19a}$ is

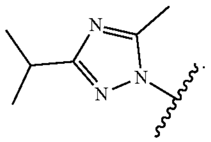 [SMILES: *n1nc(C(C)C)nc1C]

In embodiments of $-L^{19}-L^{19a}-R^{19a}$ in the paragraphs above, $R^{19a}$ is

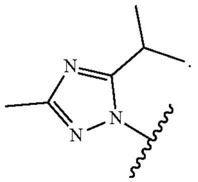 [SMILES: *n1nc(C)nc1C(C)C]

In embodiments of $-L^{19}-L^{19a}-R^{19a}$ in the paragraphs above, $R^{19a}$ is

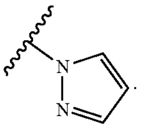 [SMILES: *n1cccn1]

In embodiments of $-L^{19}-L^{19a}-R^{19a}$ in the paragraphs above, $R^{19a}$ is

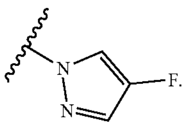 [SMILES: *n1cc(F)cn1]

In embodiments of $-L^{19}-L^{19a}-R^{19a}$ in the paragraphs above, $R^{19a}$ is

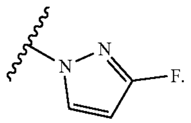 [SMILES: *n1ccc(F)n1]

In embodiments of $-L^{19}-L^{19a}-R^{19a}$ in the paragraphs above, $R^{19a}$ is

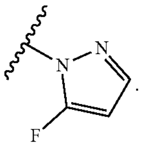

In embodiments of $-L^{19}-L^{19a}-R^{19a}$ in the paragraphs above, $R^{19a}$ is

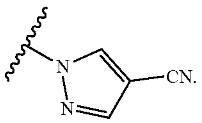 [SMILES: *n1cc(C#N)cn1]

In embodiments of $-L^{19}-L^{19a}-R^{19a}$ in the paragraphs above, $R^{19a}$ is

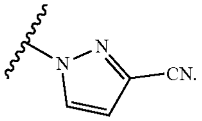

In embodiments of $-L^{19}-L^{19a}-R^{19a}$ in the paragraphs above, $R^{19a}$ is

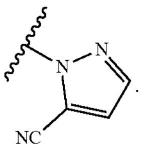 [SMILES: *n1nccc1C#N ; "."]

In embodiments of $-L^{19}-L^{19a}-R^{19a}$ in the paragraphs above, $R^{19a}$ is

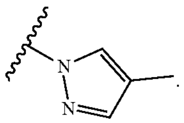 [SMILES: *n1cc(C)cn1]

In embodiments of $-L^{19}-L^{19a}-R^{19a}$ in the paragraphs above, $R^{19a}$ is

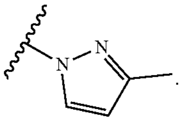 [SMILES: *n1ccc(C)n1]

In embodiments of $-L^{19}-L^{19a}-R^{19a}$ in the paragraphs above, $R^{19a}$ is

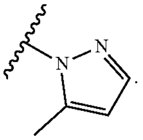 [SMILES: *n1nccc1C]

In embodiments of $-L^{19}-L^{19a}-R^{19a}$ in the paragraphs above, $R^{19a}$ is

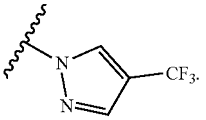 [SMILES: *n1cc(C(F)(F)F)cn1]

In embodiments of $-L^{19}-L^{19a}-R^{19a}$ in the paragraphs above, $R^{19a}$ is

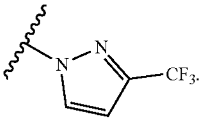 [SMILES: *n1ccc(C(F)(F)F)n1]

In embodiments of $-L^{19}-L^{19a}-R^{19a}$ in the paragraphs above, $R^{19a}$ is

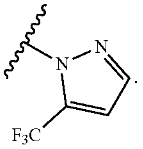

In embodiments of $-L^{19}-L^{19a}-R^{19a}$ in the paragraphs above, $R^{19a}$ is

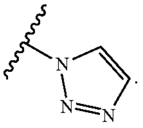 [SMILES: *n1ccnn1]

In embodiments of $-L^{19}-L^{19a}-R^{19a}$ in the paragraphs above, $R^{19a}$ is

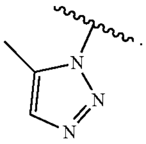 [SMILES: *n1nncc1C]

In embodiments of $-L^{19}-L^{19a}-R^{19a}$ in the paragraphs above, $R^{19a}$ is

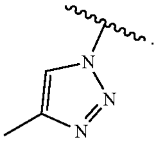 [SMILES: *n1cc(C)nn1]

In embodiments of $-L^{19}-L^{19a}-R^{19a}$ in the paragraphs above, $R^{19a}$ is

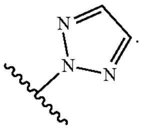 [SMILES: *n1nccn1]

In embodiments of $-L^{19}-L^{19a}-R^{19a}$ in the paragraphs above, $R^{19a}$ is

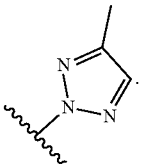 [SMILES: *n1ncc(C)n1]

In embodiments of $-L^{19}-L^{19a}-R^{19a}$ in the paragraphs above, $R^{19a}$ is

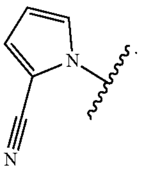 [SMILES: *n1cccc1C#N]

In embodiments of $-L^{19}-L^{19a}-R^{19a}$ in the paragraphs above, $R^{19a}$ is

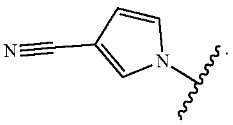 [SMILES: *n1ccc(C#N)c1]

In embodiments of $-L^{19}-L^{19a}-R^{19a}$ in the paragraphs above, $R^{19a}$ is

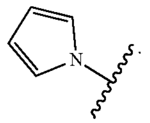 [SMILES: *n1cccc1]

In embodiments of a compound of formula IA, IB, or IIA, $X^{10}$ is $C(R^{10})_2$. In embodiments of a compound of formula IA, IB, or IIA, $X^{10}$ is $CH(R^{10})$. In embodiments of a compound of formula IA, IB, or IIA, $X^{10}$ is $CH_2$. In embodiments of a compound of formula IA, IB, or IIA, $R^{10}$ is independently selected at each occurrence from $C_{1-6}$ alkyl, $C_{2-6}$ alkenyl, $C_{2-6}$ alkynyl, $C_{3-12}$ carbocycle, and 3- to 12-membered heterocycle, wherein $C_{1-6}$ alkyl, $C_{2-6}$ alkenyl, $C_{2-6}$ alkynyl, $C_{3-12}$ carbocycle, and 3- to 12-membered heterocycle are optionally substituted with one or more $R^{20}$. In embodiments of a compound of formula IA, IB, or IIA, $R^{10}$ is independently selected at each occurrence from $C_{1-4}$ alkyl, $C_{2-3}$ alkenyl, $C_{2-3}$ alkynyl, $C_{3-5}$ carbocycle, and 3- to 5-membered heterocycle, wherein $C_{1-4}$ alkyl, $C_{2-3}$ alkenyl, $C_{2-3}$ alkynyl, $C_{3-5}$ carbocycle, and 3- to 5-membered heterocycle are optionally substituted with one or more $R^{20}$. In embodiments of a compound of formula IA, IB, or IIA, $R^{10}$ is independently selected at each occurrence from $C_{1-4}$ alkyl, $C_{2-3}$ alkenyl, $C_{2-3}$ alkynyl, $C_{3-5}$ carbocycle, and 3- to 5-membered heterocycle, wherein $C_{1-4}$ alkyl, $C_{2-3}$ alkenyl, $C_{2-3}$ alkynyl, $C_{3-5}$ carbocycle, and 3- to 5-membered heterocycle are optionally substituted with one or more $R^{20}$ selected from halogen, —OH, unsubstituted methyl, —$CF_3$, $CHF_2$, and —CN. In embodiments of a compound of formula IA, IB, or IIA, $R^{10}$ is independently selected at each occurrence from $C_{1-4}$ alkyl, $C_{2-3}$ alkenyl, $C_{2-3}$ alkynyl, $C_{3-5}$ carbocycle, and 3- to 5-membered heterocycle, wherein $C_{1-4}$ alkyl, $C_{2-3}$ alkenyl, $C_{2-3}$ alkynyl, $C_{3-5}$ carbocycle, and 3- to 5-membered heterocycle are optionally substituted with one or more $R^{20}$ selected from halogen, —OH, and —CN. In embodiments of a compound of formula IA, IB, or IIA, $R^{10}$ is independently selected at each occurrence from unsubstituted $C_{1-4}$ alkyl, unsubstituted $C_{2-3}$ alkenyl, unsubstituted $C_{2-3}$ alkynyl, unsubstituted $C_{3-5}$ carbocycle, and unsubstituted 3- to 5-membered heterocycle. In embodiments of a compound of formula IA, IB, or IIA, $R^{10}$ is independently selected at each occurrence from

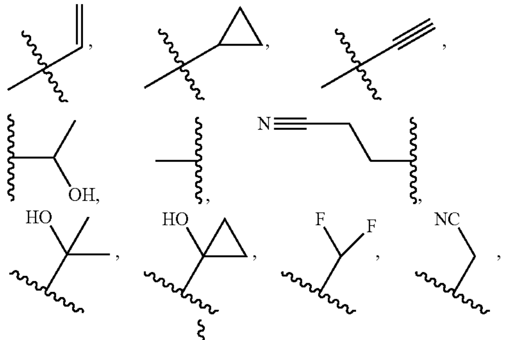

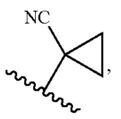 and 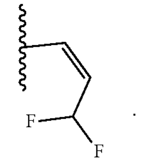

In embodiments of a compound of formula IA, IB, or IIA, $R^{10}$ is hydrogen.

In embodiments of a compound of formula IA, IB, or IIA, $X^{11}$ is $C(R^{11})_2$. In embodiments of a compound of formula IA, IB, or IIA, $X^{11}$ is $CH(R^{11})$. In embodiments of a compound of formula IA, IB, or IIA, $X^{11}$ is $CH_2$. In embodiments of a compound of formula IA, IB, or IIA, $R^{11}$ is independently selected at each occurrence from $C_{1-6}$ alkyl, $C_{2-6}$ alkenyl, $C_{2-6}$ alkynyl, $C_{3-12}$ carbocycle, and 3- to 12-membered heterocycle, wherein $C_{1-6}$ alkyl, $C_{2-6}$ alkenyl, $C_{2-6}$ alkynyl, $C_{3-12}$ carbocycle, and 3- to 12-membered heterocycle are optionally substituted with one or more $R^{20}$. In embodiments of a compound of formula IA, IB, or IIA, $R^{11}$ is independently selected at each occurrence from $C_{1-4}$ alkyl, $C_{2-3}$ alkenyl, $C_{2-3}$ alkynyl, $C_{3-5}$ carbocycle, and 3- to 5-membered heterocycle, wherein $C_{1-4}$ alkyl, $C_{2-3}$ alkenyl, $C_{2-3}$ alkynyl, $C_{3-5}$ carbocycle, and 3- to 5-membered heterocycle are optionally substituted with one or more $R^{20}$. In embodiments of a compound of formula IA, IB, or IIA, $R^{11}$ is independently selected at each occurrence from unsubstituted $C_{1-4}$ alkyl, unsubstituted $C_{2-3}$ alkenyl, unsubstituted $C_{2-3}$ alkynyl, unsubstituted $C_{3-5}$ carbocycle, and unsubstituted 3- to 5-membered heterocycle. In embodiments of a compound of formula IA, IB, or IIA, $R^{11}$ is independently selected at each occurrence from $C_{1-4}$ alkyl, $C_{2-3}$ alkenyl, $C_{2-3}$ alkynyl, $C_{3-5}$ carbocycle, and 3- to 5-membered heterocycle, wherein $C_{1-4}$ alkyl, $C_{2-3}$ alkenyl, $C_{2-3}$ alkynyl, $C_{3-5}$ carbocycle, and 3- to 5-membered heterocycle are optionally substituted with one or more $R^{20}$ selected from halogen, —OH, unsubstituted methyl, —$CF_3$, $CHF_2$, and —CN. In embodiments of a compound of formula IA, IB, or IIA, $R^{11}$ is independently selected at each occurrence from $C_{1-4}$ alkyl, $C_{2-3}$ alkenyl, $C_{2-3}$ alkynyl, $C_{3-5}$ carbocycle, and 3- to 5-membered heterocycle, wherein $C_{1-4}$ alkyl, $C_{2-3}$ alkenyl, $C_{2-3}$ alkynyl, $C_{3-5}$ carbocycle, and 3- to 5-membered heterocycle are optionally substituted with one or more $R^{20}$ selected from halogen, —OH, and —CN.

In embodiments of a compound of formula IA, IB, or IIA, $R^{11}$ is independently selected at each occurrence from

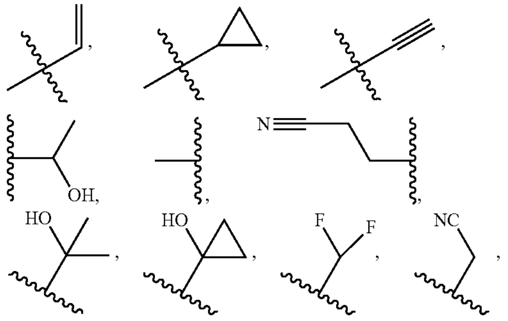

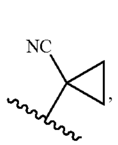 and 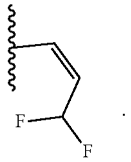

In embodiments of a compound of formula IA, IB, or IIA, $R^{11}$ is hydrogen.

In embodiments of a compound of formula IA, IB, or IIA, $X^{12}$ is —$X^{12a}$—. In embodiments of a compound of formula IA, IB, or IIA, $X^{12a}$ is O.

In embodiments of a compound of formula IA, IB, or IIA, $X^{12}$ is —$X^{12a}$—$X^{12b}$—, wherein $X^{12}$ is directly bonded to $X^5$. In embodiments of a compound of formula IA, IB, or IIA, $X^{12}$ is —$X^{12a}$—$X^{12b}$—, wherein $X^{12a}$ is directly bonded to $X^5$ and —$X^{12a}$—$X^{12b}$— is —O—$X^{12b}$—. In embodiments of a compound of formula IA, IB, or IIA, $X^{12b}$ is $C(R^{12a})_2$. In embodiments of a compound of formula IA, IB, or IIA, $X^{12b}$ is $CH(R^{12a})$. In embodiments of a compound of formula IA, IB, or IIA, $X^{12b}$ is $C(H)_2$.

In embodiments of a compound of formula IA, IB, or IIA, $R^{12a}$ is independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(=O)(=NR^{12})N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$.

In embodiments of a compound of formula IA, IB, or IIA, $R^{12a}$ is independently selected at each occurrence from $C_{1-6}$ alkyl, $C_{2-6}$ alkenyl, $C_{2-6}$ alkynyl, $C_{3-12}$ carbocycle, and 3- to 12-membered heterocycle, wherein $C_{1-6}$ alkyl, $C_{2-6}$ alkenyl, $C_{2-6}$ alkynyl, $C_{3-12}$ carbocycle, and 3- to 12-membered heterocycle are optionally substituted with one or more $R^{20}$. In embodiments of a compound of formula IA, IB, or IIA, $R^{12a}$ is independently selected at each occurrence from $C_{1-4}$ alkyl, $C_{2-3}$ alkenyl, $C_{2-3}$ alkynyl, $C_{3-5}$ carbocycle, and 3- to 5-membered heterocycle, wherein $C_{1-4}$ alkyl, $C_{2-3}$ alkenyl, $C_{2-3}$ alkynyl, $C_{3-5}$ carbocycle, and 3- to 5-membered heterocycle are optionally substituted with one or more $R^{20}$. In embodiments of a compound of formula IA, IB, or IIA, $R^{12a}$ is independently selected at each occurrence from $C_{1-4}$ alkyl, $C_{2-3}$ alkenyl, $C_{2-3}$ alkynyl, $C_{3-5}$ carbocycle, and 3- to 5-membered heterocycle, wherein $C_{1-4}$ alkyl, $C_{2-3}$ alkenyl, $C_{2-3}$ alkynyl, $C_{3-5}$ carbocycle, and 3- to 5-membered heterocycle are optionally substituted with one or more $R^{20}$ selected from halogen, —OH, unsubstituted methyl, —$CF_3$, $CHF_2$, and —CN. In embodiments of a compound of formula IA, IB, or IIA, $R^{12a}$ is independently selected at each occurrence from $C_{1-4}$ alkyl, $C_{2-3}$ alkenyl, $C_{2-3}$ alkynyl, $C_{3-5}$ carbocycle, and 3- to 5-membered heterocycle, wherein $C_{1-4}$ alkyl, $C_{2-3}$ alkenyl, $C_{2-3}$ alkynyl, $C_{3-5}$ carbocycle, and 3- to 5-membered heterocycle are optionally substituted with one or more $R^{20}$ selected from halogen, —OH, and —CN. In embodiments of a compound of formula IA, IB, or IIA, $R^{12a}$ is independently selected at each occurrence from unsubstituted $C_{1-4}$ alkyl, unsubstituted $C_{2-3}$ alkenyl, unsubstituted $C_{2-3}$ alkynyl, unsubstituted $C_{3-5}$ carbocycle, and unsubstituted 3- to 5-membered heterocycle. In embodiments of a compound of formula IA, IB, or IIA, $R^{12a}$ is independently selected at each occurrence from

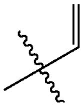, 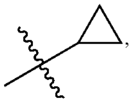, 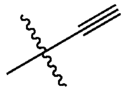,

-continued

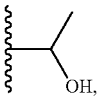, 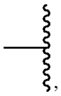, 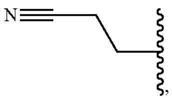, 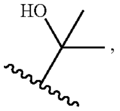, 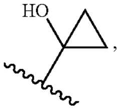, 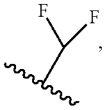, 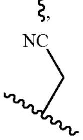, 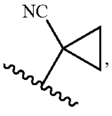, and 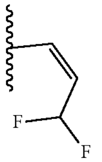.

In embodiments of a compound of formula IA, IB, or IIA, $R^{12a}$ is hydrogen.

In embodiments of a compound of formula IA, IB, or IIA, $R^{10}$, $R^{11}$, and $R^{12a}$ are independently selected at each occurrence from hydrogen,

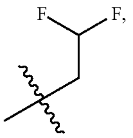, 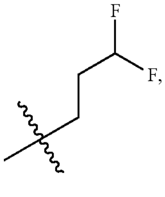, 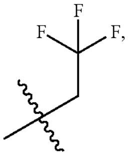, 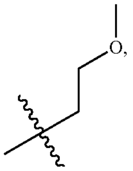, 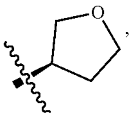, 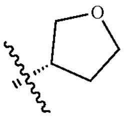, 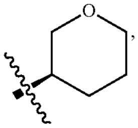, 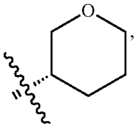, 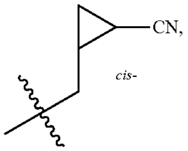

, 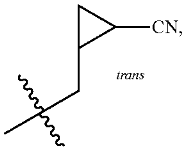

, 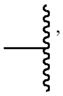, 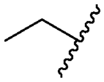, 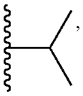, 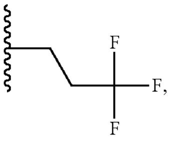, 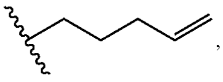, 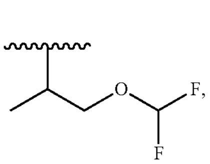, 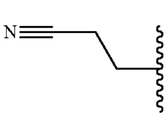, 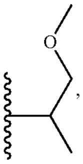, 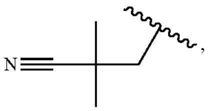, 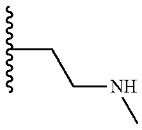, -continued
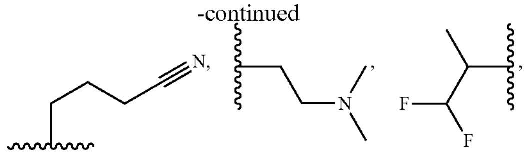
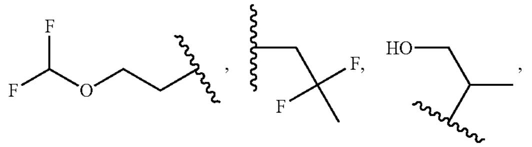
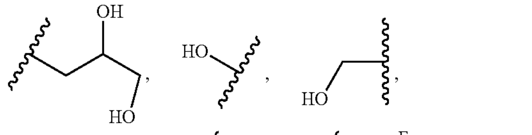
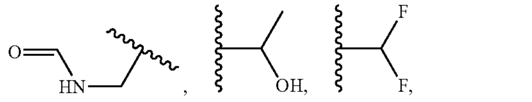
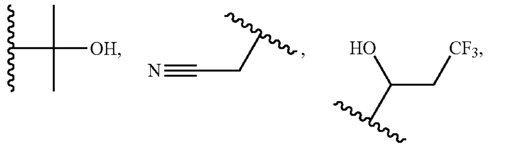
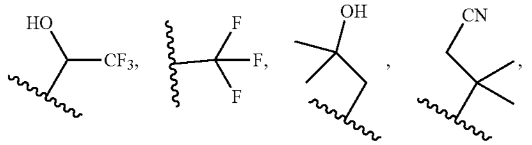
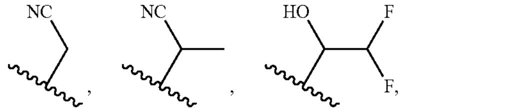
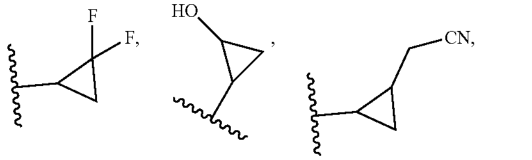
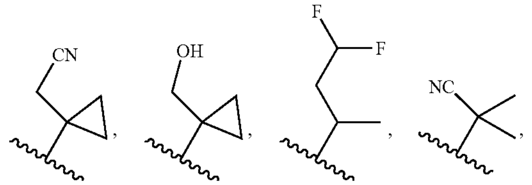
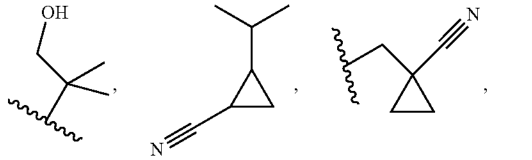
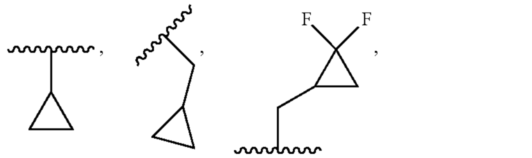
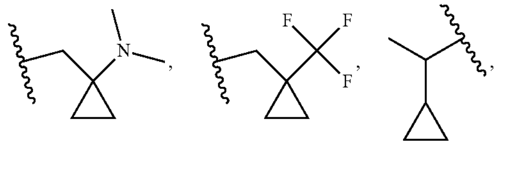
-continued
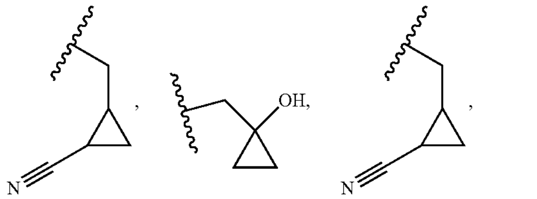
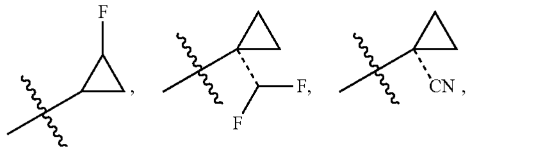
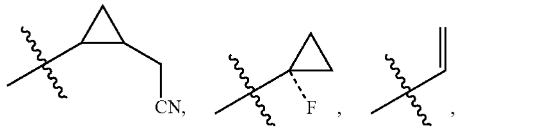
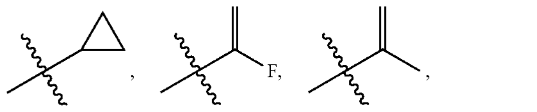
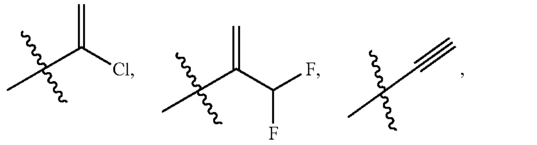
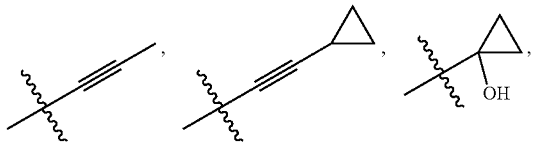
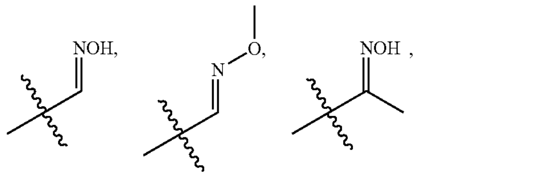
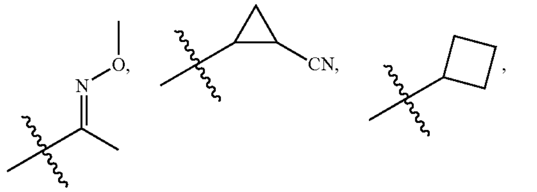
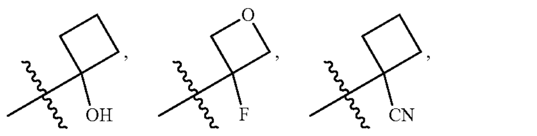
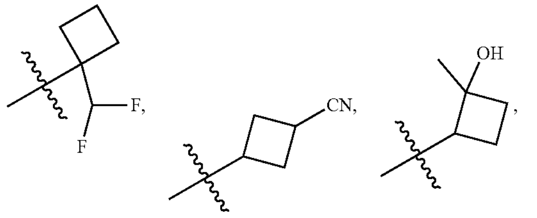

-continued

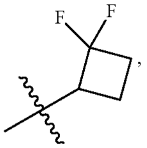, 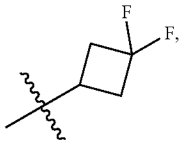 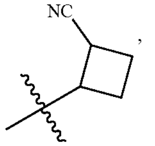,

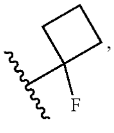, 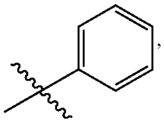, 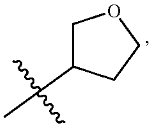,

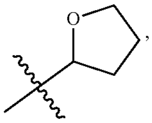, 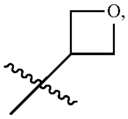 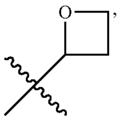,

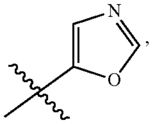, 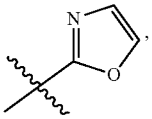, 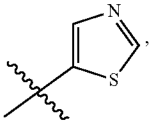,

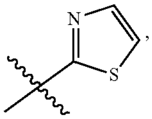, 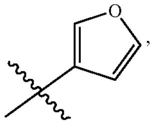, 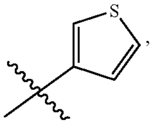,

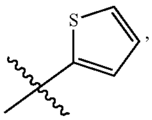, 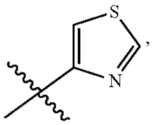, 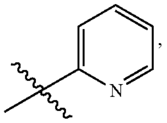,

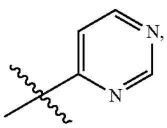 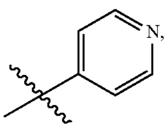 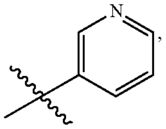,

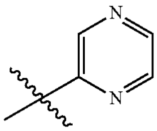, 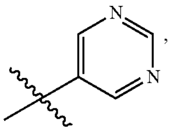, 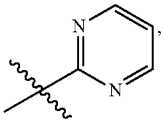,

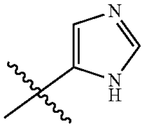, 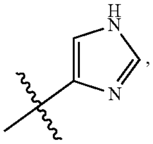, 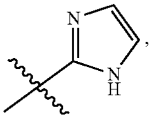,

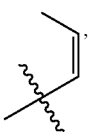, 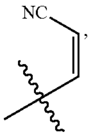, 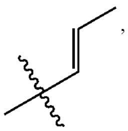, 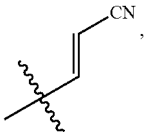,

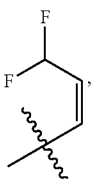, 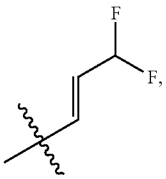 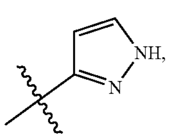

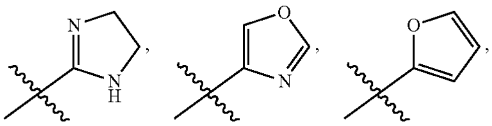

-continued

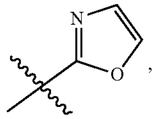, 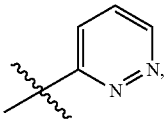 and

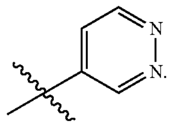 [SMILES: *c1ccnnc1]

In embodiments of a compound of formula IA, IB, or IIA; $R^{10b}$, $R^{11b}$, and $R^{12b}$ are independently selected at each occurrence from hydrogen, $C_{1-6}$ alkyl, $C_{2-6}$ alkenyl, $C_{2-6}$ alkynyl, $C_{3-12}$ carbocycle, and 3- to 12-membered heterocycle, wherein $C_{1-6}$ alkyl, $C_{2-6}$ alkenyl, $C_{2-6}$ alkynyl, $C_{3-12}$ carbocycle, and 3- to 12-membered heterocycle are optionally substituted with one or more $R^{20}$. In embodiments of a compound of formula IA, IB, or IIA; $R^{10b}$, $R^{11b}$, and $R^{12b}$ are independently selected at each occurrence from hydrogen, $C_{1-4}$ alkyl, $C_{2-3}$ alkenyl, $C_{2-3}$ alkynyl, $C_{3-5}$ carbocycle, and 3- to 5-membered heterocycle, wherein $C_{1-4}$ alkyl, $C_{2-3}$ alkenyl, $C_{2-3}$ alkynyl, $C_{3-5}$ carbocycle, and 3- to 5-membered heterocycle are optionally substituted with one or more $R^{20}$. In embodiments of a compound of formula IA, IB, or IIA; $R^{10b}$, $R^{11b}$, and $R^{12b}$ are independently selected at each occurrence from hydrogen, $C_{1-4}$ alkyl, $C_{2-3}$ alkenyl, $C_{2-3}$ alkynyl, $C_{3-5}$ carbocycle, and 3- to 5-membered heterocycle, wherein $C_{1-4}$ alkyl, $C_{2-3}$ alkenyl, $C_{2-3}$ alkynyl, $C_{3-5}$ carbocycle, and 3- to 5-membered heterocycle are optionally substituted with one or more $R^{20}$ selected from halogen, —OH, unsubstituted methyl, —$CF_3$, $CHF_2$, and —CN. In embodiments of a compound of formula IA, IB, or IIA; $R^{10b}$, $R^{11b}$, and $R^{12b}$ are independently selected at each occurrence from hydrogen, $C_{1-4}$ alkyl, $C_{2-3}$ alkenyl, $C_{2-3}$ alkynyl, $C_{3-5}$ carbocycle, and 3- to 5-membered heterocycle, wherein $C_{1-4}$ alkyl, $C_{2-3}$ alkenyl, $C_{2-3}$ alkynyl, $C_{3-5}$ carbocycle, and 3- to 5-membered heterocycle are optionally substituted with one or more $R^{20}$ selected from halogen, —OH, and —CN. In embodiments of a compound of formula IA, IB, or IIA; $R^{10b}$, $R^{11b}$, and $R^{12b}$ are independently selected at each occurrence from hydrogen, unsubstituted $C_{1-4}$ alkyl, unsubstituted $C_{2-3}$ alkenyl, unsubstituted $C_{2-3}$ alkynyl, unsubstituted $C_{3-5}$ carbocycle, and unsubstituted 3- to 5-membered heterocycle. In embodiments of a compound of formula IA, IB, or IIA; $R^{10b}$, $R^{11b}$, and $R^{12b}$ are independently selected at each occurrence from hydrogen,

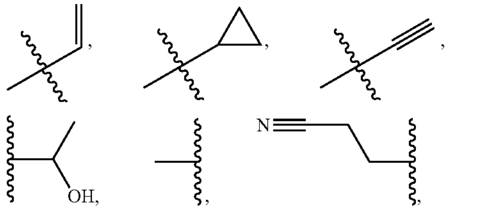

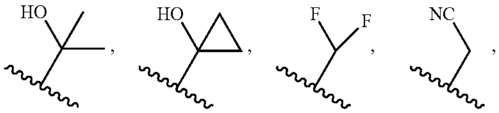

-continued

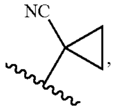, and 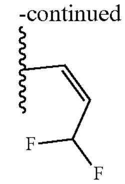.

In embodiments of a compound of formula IA, IB, or IIA; $R^{10b}$, $R^{10b}$, and $R^{12b}$ are hydrogen.

In embodiments of a compound of formula IA, IB, or IIA, $X^{10}$ is selected from $C(R^{10})$, $C(R^{10})_2$, $CH(R^{10})$, N, $N(R^{Ob})$, O, S, S(O), $S(O)_2$, and C(O); wherein $X^{10}$ is not $CH_2$. In embodiments of a compound of formula IA, IB, or IIA, $X^{11}$ is selected from $C(R^{11})$, $C(R^{11})_2$, $CH(R^{11})$, N, $N(R^{11b})$, O, S, S(O), $S(O)_2$, and C(O); wherein $X^{11}$ is not $CH_2$. In embodiments of a compound of formula IA, IB, or IIA, $X^{12}$ is —$X^{12a}$—. In embodiments of a compound of formula IA, IB, or IIA, $X^{12}$ is —$X^{12a}$—$X^{12b}$—; wherein $X^{12a}$ is directly bonded to $X^5$. In embodiments of a compound of formula IA, IB, or IIA, $X^{12}$ is —$X^{12a}$—$X^{12b}$—$X^{12c}$—; wherein $X^{1a}$ is directly bonded to $X^5$. In embodiments of a compound of formula IA, IB, or IIA, $X^{12}$ is —$X^{12a}$—$X^{12b}$—$X^{12c}$—$X^{12d}$—; wherein $X^{12a}$ is directly bonded to $X^5$. In embodiments of a compound of formula IA, IB, or IIA, $X^{12}$ is —$X^{12a}$—$X^{12b}$—; wherein $X^{12a}$ is directly bonded to $X^5$; and $X^{12b}$ is independently selected from $C(R^{12a})$, $CH(R^{12a})$, $C(R^{12a})_2$, N, $N(R^{12b})$, O, S, S(O), $S(O)_2$, and C(O); wherein $X^{12b}$ is not $CH_2$. In embodiments of a compound of formula IA, IB, or IIA, at least one of $R^{9a}$, $R^{10}$, $R^{11}$, $R^{12a}$, $R^{10b}$, $R^{11b}$, and $R^{12b}$ is not hydrogen.

In embodiments of a compound of formula IA, IB, or IIA:

i. at least one of $R^{10b}$, $R^{11b}$, and $R^{12b}$ is independently selected from —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —C(O)$OR^{12}$, —C(O)$R^{12}$, —C(O)N($R^{12}$)($R^{13}$), —C(O)C(O)N($R^{12}$)($R^{13}$), —$S(O)_2R^{12}$, —S(O)($NR^{12}$)$R^{12}$, —$S(O)_2$N($R^{12}$)($R^{13}$), and —S(═O)(═$NR^{12}$)N($R^{12}$)($R^{13}$), wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$; or ii. at least one of $R^{9a}$, $R^{10}$, $R^{11}$, and $R^{12a}$ is independently selected from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —N($R^{12}$)($R^{13}$), —C(O)$OR^{12}$, —OC(O)N($R^{12}$)($R^{13}$), —N($R^{12}$)C(O)N($R^{12}$)($R^{13}$), —N($R^{12}$)C(O)$OR^{12}$, —N($R^{12}$)$S(O)_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —$S(O)_2R^{12}$, —S(O)($NR^{12}$)$R^{12}$, —$S(O)_2$N($R^{12}$)($R^{13}$), and —S(═O)(═$NR^{12}$)N($R^{12}$)($R^{13}$), wherein $C_{1-6}$ alkyl, $C_{2-6}$ alkenyl, $C_{2-6}$ alkynyl, 2- to 6-membered heteroalkyl, 3-to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$.

In embodiments of a compound of formula I, IA, IB, II, IIA, or V, $R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one or more $R^{20}$. In embodiments, $R^{12}$ is hydrogen. In embodiments, $R^{12}$ is $C_{1-6}$ alkyl optionally substituted with one or more $R^{20}$. In embodiments, $R^{12}$ is $C_{2-6}$ alkenyl optionally substituted with one or more $R^{20}$. In embodiments, $R^{12}$ is $C_{2-6}$ alkynyl optionally substituted with one or more $R^{20}$. In embodiments, $R^{12}$ is —$C_{0-6}$ alkyl-($C_{3-12}$ carbocycle) optionally substituted with one or more $R^{20}$. In embodiments, $R^{12}$ is —$C_{0-6}$ alkyl-(3- to 12-membered heterocycle) optionally substituted with one or more $R^{20}$. In embodiments, $R^{12}$ is $C_{3-12}$ carbocycle optionally substituted with one or more $R^{20}$. In embodiments, $R^{12}$ is 3- to 12-membered heterocycle optionally substituted with one or more $R^{20}$. In embodiments, $R^{12}$ is $C_{1-6}$ alkyl. In embodiments, $R^{12}$ is $C_{2-6}$ alkenyl. In embodiments, $R^{12}$ is $C_{2-6}$ alkynyl. In embodiments, $R^{12}$ is —$C_{0-6}$ alkyl-($C_{3-12}$ carbocycle). In embodiments, $R^{12}$ is —$C_{0-6}$ alkyl-(3- to 12-membered heterocycle). In embodiments, $R^{12}$ unsubstituted $C_{3-12}$ carbocycle. In embodiments, $R^{12}$ is unsubstituted 3- to 12-membered heterocycle.

In embodiments of a compound of formula I, IA, IB, II, IIA, or V, $R^{13}$ is independently selected at each occurrence from hydrogen, $C_{1-6}$ alkyl, and $C_{1-6}$ haloalkyl. In embodiments, $R^{13}$ is hydrogen. In embodiments, $R^{13}$ is $C_{1-6}$ alkyl. In embodiments, $R^{13}$ is $C_{1-6}$ haloalkyl. In embodiments of a compound of formula I, IA, IB, II, IIA, or V, $R^{12}$ and $R^{13}$ attached to the same nitrogen atom form 3- to 10-membered heterocycle optionally substituted with one or more $R^{20}$.

In embodiments of a compound of formula I, IA, IB, II, IIA, or V, $R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —N($R^{22}$)($R^{23}$), ═$NR^{22}$, ═C($R^{21}$)$_2$, —C(O)$OR^{22}$, —OC(O)N($R^{22}$)($R^{23}$), —N($R^{22}$)C(O)N($R^{22}$)($R^{23}$), —N($R^{22}$)C(O)$OR^{22}$, —N($R^{22}$)$S(O)_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —$S(O)_2R^{22}$, —S(O)($NR^{22}$)$R^{22}$, —$S(O)_2$N($R^{22}$)($R^{23}$)—, and —S(═O)(═$NR^{22}$)N($R^{22}$)($R^{23}$); wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, —$OR^{22}$, —$SR^{22}$, —N($R^{22}$)($R^{23}$), ═$NR^{22}$, ═C($R^{21}$)$_2$, —C(O)$OR^{22}$, —OC(O)N($R^{22}$)($R^{23}$), —N($R^{22}$)C(O)N($R^{22}$)($R^{23}$), —N($R^{22}$)C(O)$OR^{22}$, —N($R^{22}$)

$S(O)_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S(O)$_2R^{22}$, —S(O)(N$R^{22}$)$R^{22}$, —S(O)$_2$N($R^{22}$)($R^{23}$), and —S(=O)(=N$R^{22}$)N($R^{22}$)($R^{23}$). In embodiments, $R^{20}$ is independently halogen. In embodiments, $R^{20}$ is independently oxo. In embodiments, $R^{20}$ is independently —CN. In embodiments, $R^{20}$ is independently $C_{1-6}$ alkyl optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, —O$R^{22}$, —S$R^{22}$, —N($R^{22}$)($R^{23}$), =N$R^{22}$, =C($R^{21}$)$_2$, —C(O)O$R^{22}$, —OC(O)N($R^{22}$)($R^{23}$), —N($R^{22}$)C(O)N($R^{22}$)($R^{23}$), —N($R^{22}$)C(O)O$R^{22}$, —N($R^{22}$)S(O)$_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S(O)$_2R^{22}$, —S(O)(N$R^{22}$)$R^{22}$, —S(O)$_2$N($R^{22}$)($R^{23}$), and —S(=O)(=N$R^{22}$)N($R^{22}$)($R^{23}$). In embodiments, $R^{20}$ is independently $C_{2-6}$ alkenyl optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, —O$R^{22}$, —S$R^{22}$, —N($R^{22}$)($R^{23}$), =N$R^{22}$, =C($R^{21}$)$_2$, —C(O)O$R^{22}$, —OC(O)N($R^{22}$)($R^{23}$), —N($R^{22}$)C(O)N($R^{22}$)($R^{23}$), —N($R^{22}$)C(O)O$R^{22}$, —N($R^{22}$)S(O)$_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S(O)$_2R^{22}$, —S(O)(N$R^{22}$)$R^{22}$, —S(O)$_2$N($R^{22}$)($R^{23}$), and —S(=O)(=N$R^{22}$)N($R^{22}$)($R^{23}$). In embodiments, $R^{20}$ is independently $C_{2-6}$ alkynyl optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, —O$R^{22}$, —S$R^{22}$, —N($R^{22}$)($R^{23}$), =N$R^{22}$, =C($R^{21}$)$_2$, —C(O)O$R^{22}$, —OC(O)N($R^{22}$)($R^{23}$), —N($R^{22}$)C(O)N($R^{22}$)($R^{23}$), —N($R^{22}$)C(O)O$R^{22}$, —N($R^{22}$)S(O)$_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S(O)$_2R^{22}$, —S(O)(N$R^{22}$)$R^{22}$, —S(O)$_2$N($R^{22}$)($R^{23}$), and —S(=O)(=N$R^{22}$)N($R^{22}$)($R^{23}$). In embodiments, $R^{20}$ is independently 2- to 6-membered heteroalkyl optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, —O$R^{22}$, —S$R^{22}$, —N($R^{22}$)($R^{23}$), =N$R^{22}$, =C($R^{21}$)$_2$, —C(O)O$R^{22}$, —OC(O)N($R^{22}$)($R^{23}$), —N($R^{22}$)C(O)N($R^{22}$)($R^{23}$), —N($R^{22}$)C(O)O$R^{22}$, —N($R^{22}$)S(O)$_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S(O)$_2R^{22}$, —S(O)(N$R^{22}$)$R^{22}$, —S(O)$_2$N($R^{22}$)($R^{23}$), and —S(=O)(=N$R^{22}$)N($R^{22}$)($R^{23}$). In embodiments, $R^{20}$ is independently 3- to 6-membered heteroalkenyl optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, —O$R^{22}$, —S$R^{22}$, —N($R^{22}$)($R^{23}$), =N$R^{22}$, =C($R^{21}$)$_2$, —C(O)O$R^{22}$, —OC(O)N($R^{22}$)($R^{23}$), —N($R^{22}$)C(O)N($R^{22}$)($R^{23}$), —N($R^{22}$)C(O)O$R^{22}$, —N($R^{22}$)S(O)$_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S(O)$_2R^{22}$, —S(O)(N$R^{22}$)$R^{22}$, —S(O)$_2$N($R^{22}$)($R^{23}$), and —S(=O)(=N$R^{22}$)N($R^{22}$)($R^{23}$). In embodiments, $R^{20}$ is independently 3- to 6-membered heteroalkynyl optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, —O$R^{22}$, —S$R^{22}$, —N($R^{22}$)($R^{23}$), =N$R^{22}$, =C($R^{21}$)$_2$, —C(O)O$R^{22}$, —OC(O)N($R^{22}$)($R^{23}$), —N($R^{22}$)C(O)N($R^{22}$)($R^{23}$), —N($R^{22}$)C(O)O$R^{22}$, —N($R^{22}$)S(O)$_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S(O)$_2R^{22}$, —S(O)(N$R^{22}$)$R^{22}$, —S(O)$_2$N($R^{22}$)($R^{23}$), and —S(=O)(=N$R^{22}$)N($R^{22}$)($R^{23}$). In embodiments, $R^{20}$ is independently —$C_{0-6}$ alkyl-($C_{3-12}$ carbocycle) optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, —O$R^{22}$, —S$R^{22}$, —N($R^{22}$)($R^{23}$), =N$R^{22}$, =C($R^{21}$)$_2$, —C(O)O$R^{22}$, —OC(O)N($R^{22}$)($R^{23}$), —N($R^{22}$)C(O)N($R^{22}$)($R^{23}$), —N($R^{22}$)C(O)O$R^{22}$, —N($R^{22}$)S(O)$_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S(O)$_2R^{22}$, —S(O)(N$R^{22}$)$R^{22}$, —S(O)$_2$N($R^{22}$)($R^{23}$), and —S(=O)(=N$R^{22}$)N($R^{22}$)($R^{23}$). In embodiments, $R^{20}$ is independently -(2- to 6-membered heteroalkyl)-($C_{3-12}$ carbocycle) optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, —O$R^{22}$, —S$R^{22}$, —N($R^{22}$)($R^{23}$), =N$R^{22}$, =C($R^{21}$)$_2$, —C(O)O$R^{22}$, —OC(O)N($R^{22}$)($R^{23}$), —N($R^{22}$)C(O)N($R^{22}$)($R^{23}$), —N($R^{22}$)C(O)O$R^{22}$, —N($R^{22}$)S(O)$_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S(O)$_2R^{22}$, —S(O)(N$R^{22}$)$R^{22}$, —S(O)$_2$N($R^{22}$)($R^{23}$), and —S(=O)(=N$R^{22}$)N($R^{22}$)($R^{23}$). In embodiments, $R^{20}$ is independently —$C_{0-6}$ alkyl-(3- to 12-membered heterocycle) optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, —O$R^{22}$, —S$R^{22}$, —N($R^{22}$)($R^{23}$), =N$R^{22}$, =C($R^{21}$)$_2$, —C(O)O$R^{22}$, —OC(O)N($R^{22}$)($R^{23}$), —N($R^{22}$)C(O)N($R^{22}$)($R^{23}$), —N($R^{22}$)C(O)O$R^{22}$, —N($R^{22}$)S(O)$_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S(O)$_2R^{22}$, —S(O)(N$R^{22}$)$R^{22}$, —S(O)$_2$N($R^{22}$)($R^{23}$), and —S(=O)(=N$R^{22}$)N($R^{22}$)($R^{23}$). In embodiments, $R^{20}$ is independently -(2- to 6-membered heteroalkyl)-(3- to 12-membered heterocycle) optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, —O$R^{22}$, —S$R^{22}$, —N($R^{22}$)($R^{23}$), =N$R^{22}$, =C($R^{21}$)$_2$, —C(O)O$R^{22}$, —OC(O)N($R^{22}$)($R^{23}$), —N($R^{22}$)C(O)N($R^{22}$)($R^{23}$), —N($R^{22}$)C(O)O$R^{22}$, —N($R^{22}$)S(O)$_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S(O)$_2R^{22}$, —S(O)(N$R^{22}$)$R^{22}$, —S(O)$_2$N($R^{22}$)($R^{23}$), and —S(=O)(=N$R^{22}$)N($R^{22}$)($R^{23}$). In embodiments, $R^{20}$ is independently $C_{1-6}$ alkyl. In embodiments, $R^{20}$ is independently $C_{2-6}$ alkenyl. In embodiments, $R^{20}$ is independently $C_{2-6}$ alkynyl. In embodiments, $R^{20}$ is independently 2- to 6-membered heteroalkyl. In embodiments, $R^{20}$ is independently 3- to 6-membered heteroalkenyl. In embodiments, $R^{20}$ is independently 3- to 6-membered heteroalkynyl. In embodiments, $R^{20}$ is independently —$C_{0-6}$ alkyl-($C_{3-12}$ carbocycle). In embodiments, $R^{20}$ is independently -(2- to 6-membered heteroalkyl)-($C_{3-12}$ carbocycle). In embodiments, $R^{20}$ is independently —$C_{0-6}$ alkyl-(3- to 12-membered heterocycle). In embodiments, $R^{20}$ is independently -(2- to 6-membered heteroalkyl)-(3- to 12-membered heterocycle). In embodiments, $R^{20}$ is independently —O$R^{22}$. In embodiments, $R^{20}$ is independently —S$R^{22}$. In embodiments, $R^{20}$ is independently —N($R^{22}$)($R^{23}$). In embodiments, $R^{20}$ is independently =N$R^{22}$. In embodiments, $R^{20}$ is independently =C($R^{21}$)$_2$. In embodiments, $R^{20}$ is independently —C(O)O$R^{22}$. In embodiments, $R^{20}$ is independently —OC(O)N($R^{22}$)($R^{23}$). In embodiments, $R^{20}$ is independently —N($R^{22}$)C(O)N($R^{22}$)($R^{23}$). In embodiments, $R^{20}$ is independently —N($R^{22}$)C(O)O$R^{22}$. In embodiments, $R^{20}$ is independently —$N(R^{22})S(O)_2R^{22}$. In embodiments, $R^{20}$ is independently —$C(O)R^{22}$. In embodiments, $R^{20}$ is independently —$S(O)R^{22}$. In embodiments, $R^{20}$ is independently —$OC(O)R^{22}$. In embodiments, $R^{20}$ is independently —$C(O)N(R^{22})(R^{23})$. In embodiments, $R^{20}$ is independently —$C(O)C(O)N(R^{22})(R^{23})$. In embodiments, $R^{20}$ is independently —$N(R^{22})C(O)R^{22}$. In embodiments, $R^{20}$ is independently —$S(O)_2R^{22}$. In embodiments, $R^{20}$ is independently —$S(O)(NR^{22})R^{22}$. In embodiments, $R^{20}$ is independently —$S(O)_2N(R^{22})(R^{23})$—. In embodiments, $R^{20}$ is independently —$S(=O)(=NR^{22})N(R^{22})(R^{23})$. In embodiments, $R^{20a}$ is any of the embodiments of $R^{20}$ in this paragraph. In embodiments, $R^{20b}$ is any of the embodiments of $R^{20}$ in this paragraph. In embodiments, $R^{20c}$ is any of the embodiments of $R^{20}$ in this paragraph. In embodiments, $R^{20d}$ is any of the embodiments of $R^{20}$ in this paragraph. In embodiments, $R^{20b}$ is any of the embodiments of $R^{20}$ in this paragraph. In embodiments, $R^{20f}$ is any of the embodiments of $R^{20}$ in this paragraph. In embodiments, $R^{20g}$ is any of the embodiments of $R^{20}$ in this paragraph. In embodiments, $R^{20h}$ is any of the embodiments of $R^{20}$ in this paragraph. In embodiments, $R^{20i}$ is any of the embodiments of $R^{20}$ in this paragraph. In embodiments, $R^{20i}$ is any of the embodiments of $R^{20}$ in this paragraph.

In embodiments, $R^{20}$ is independently unsubstituted methyl. In embodiments, $R^{20}$ is independently unsubstituted ethyl. In embodiments, $R^{20}$ is independently unsubstituted propyl. In embodiments, $R^{20}$ is independently unsubstituted butyl. In embodiments, $R^{20}$ is independently unsubstituted ethenyl. In embodiments, $R^{20}$ is independently unsubstituted ethynyl. In embodiments, $R^{20}$ is independently —OH. In embodiments, $R^{20}$ is independently —OMe. In embodiments, $R^{20}$ is independently —SH. In embodiments, $R^{20}$ is independently —SMe. In embodiments, $R^{20}$ is independently —$NH_2$. In embodiments, $R^{20}$ is independently =NH. In embodiments, $R^{20}$ is independently =$CH_2$. In embodiments, $R^{20}$ is independently —C(O)OH. In embodiments, $R^{20}$ is independently —$OC(O)NH_2$. In embodiments, $R^{20}$ is independently —$NHC(O)NH_2$. In embodiments, $R^{20}$ is independently —NHC(O)OH. In embodiments, $R^{20}$ is independently —$NHS(O)_2CH_3$. In embodiments, $R^{20}$ is independently —C(O)H. In embodiments, $R^{20}$ is independently —$S(O)CH_3$. In embodiments, $R^{20}$ is independently —OC(O)H. In embodiments, $R^{20}$ is independently —$C(O)NH_2$. In embodiments, $R^{20}$ is independently —NHC(O)H. In embodiments, $R^{20}$ is independently —$S(O)_2CH_3$. In embodiments, $R^{20}$ is independently F. In embodiments, $R^{20}$ is independently Cl. In embodiments, $R^{20}$ is independently Br. In embodiments, $R^{20}$ is independently I. In embodiments, $R^{20}$ is independently —$CHF_2$. In embodiments, $R^{20}$ is independently —$CF_3$. In embodiments, $R^{20a}$ is any of the embodiments of $R^{20}$ in this paragraph. In embodiments, $R^{20b}$ is any of the embodiments of $R^{20}$ in this paragraph. In embodiments, $R^{20c}$ is any of the embodiments of $R^{20}$ in this paragraph. In embodiments, $R^{20d}$ is any of the embodiments of $R^{20}$ in this paragraph. In embodiments, $R^{20e}$ is any of the embodiments of $R^{20}$ in this paragraph. In embodiments, $R^{20f}$ is any of the embodiments of $R^{20}$ in this paragraph. In embodiments, $R^{20g}$ is any of the embodiments of $R^{20}$ in this paragraph. In embodiments, $R^{20h}$ is any of the embodiments of $R^{20}$ in this paragraph. In embodiments, $R^{20i}$ is any of the embodiments of $R^{20}$ in this paragraph. In embodiments, $R^{20j}$ is any of the embodiments of $R^{20}$ in this paragraph.

In embodiments of a compound of formula I, IA, IB, II, IIA, or V, $R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), each of which is optionally substituted with one or more substituents independently selected from halogen, $C_{1-3}$ alkyl, $C_{1-3}$ haloalkyl, and —OH. In embodiments of a compound of formula I, IA, IB, II, IIA, or V, two $R^{21}$ are taken together with the carbon atom to which they are attached to form $C_{3-12}$ carbocycle or 3- to 12-membered heterocycle, each of which is optionally substituted with one or more substituents independently selected from halogen, $C_{1-3}$ alkyl, $C_{1-3}$ haloalkyl, and —OH. In embodiments of a compound of formula I, IA, IB, II, IIA, or V, $R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle). In embodiments of a compound of formula I, IA, IB, II, IIA, or V, two $R^{21}$ are taken together with the carbon atom to which they are attached to form $C_{3-12}$ carbocycle or 3- to 12-membered heterocycle. In embodiments, $R^{21}$ is independently hydrogen. In embodiments, $R^{21}$ is independently halogen. In embodiments, $R^{21}$ is independently $C_{1-6}$ alkyl. In embodiments, $R^{21}$ is independently $C_{1-6}$ haloalkyl. In embodiments, $R^{21}$ is independently —$C_{0-6}$ alkyl-($C_{3-12}$ carbocycle). In embodiments, $R^{21}$ is independently —$C_{0-6}$ alkyl-(3- to 12-membered heterocycle).

In embodiments of a compound of formula I, IA, IB, II, IIA, or V, $R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle). In embodiments, $R^{22}$ is independently hydrogen. In embodiments, $R^{22}$ is independently $C_{1-6}$ alkyl. In embodiments, $R^{22}$ is independently $C_{1-6}$ haloalkyl. In embodiments, $R^{22}$ is independently —$C_{0-6}$ alkyl-($C_{3-12}$ carbocycle). In embodiments, $R^{22}$ is independently —$C_{0-6}$ alkyl-(3- to 12-membered heterocycle).

In embodiments of a compound of formula I, IA, IB, II, IIA, or V, $R^{23}$ is independently selected at each occurrence from hydrogen and $C_{1-6}$ alkyl. In embodiments of a compound of formula I, IA, IB, II, IIA, or V, $R^{22}$ and $R^{23}$ attached to the same nitrogen atom form 3- to 10 membered heterocycle. In embodiments $R^{23}$ is independently hydrogen. In embodiments $R^{23}$ is independently $C_{1-6}$ alkyl.

In embodiments of a compound of formula I, IA, IB, II, IIA, or V, $R^{29}$ is independently selected at each occurrence from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(=O)(=NR^{12})N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$. In embodiments of a compound of formula I, IA, IB, II, IIA, or V, two $R^{29}$ attached to the same atom are joined to form oxo. In embodiments, $R^{29}$ is independently halogen. In embodiments, $R^{29}$ is independently —CN. In embodiments, $R^{29}$ is independently $C_{1-6}$ alkyl optionally substituted with one or more $R^{20}$. In embodiments, $R^{29}$ is independently $C_{2-6}$ alkenyl optionally substituted with one or more $R^{20}$. In embodiments, $R^{29}$ is independently $C_{2-6}$ alkynyl optionally substituted with one or more $R^{20}$. In embodiments, $R^{29}$ is independently 2- to 6-membered heteroalkyl optionally substituted with one or more $R^{20}$. In embodiments, $R^{29}$ is independently 3- to 6-membered heteroalkenyl optionally substituted with one or more $R^{20}$. In embodiments, $R^{29}$ is independently 3- to 6-membered heteroalkynyl optionally substituted with one or more $R^{20}$. In embodiments, $R^{29}$ is independently —$C_{0-6}$ alkyl-($C_{3-12}$ carbocycle) optionally substituted with one or more $R^{20}$. In embodiments, $R^{29}$ is independently -(2- to 6-membered heteroalkyl)-($C_{3-12}$ carbocycle) optionally substituted with one or more $R^{20}$. In embodiments, $R^{29}$ is independently —$C_{0-6}$ alkyl-(3- to 12-membered heterocycle) optionally substituted with one or more $R^{20}$. In embodiments, $R^{29}$ is independently -(2- to 6-membered heteroalkyl)-(3- to 12-membered heterocycle) optionally substituted with one or more $R^{20}$. In embodiments, $R^{29}$ is independently $C_{1-6}$ alkyl. In embodiments, $R^{29}$ is independently $C_{2-6}$ alkenyl. In embodiments, $R^{29}$ is independently $C_{2-6}$ alkynyl. In embodiments, $R^{29}$ is independently 2- to 6-membered heteroalkyl. In embodiments, $R^{29}$ is independently 3- to 6-membered heteroalkenyl. In embodiments, $R^{29}$ is independently 3- to 6-membered heteroalkynyl. In embodiments, $R^{29}$ is independently —$C_{0-6}$ alkyl-($C_{3-12}$ carbocycle). In embodiments, $R^{29}$ is independently -(2- to 6-membered heteroalkyl)-($C_{3-12}$ carbocycle). In embodiments, $R^{29}$ is independently —$C_{0-6}$ alkyl-(3- to 12-membered heterocycle). In embodiments, $R^{29}$ is independently -(2- to 6-membered heteroalkyl)-(3- to 12-membered heterocycle).

In embodiments, $R^{29}$ is independently —$OR^{12}$. In embodiments, $R^{29}$ is independently —$SR^{12}$. In embodiments, $R^{29}$ is independently —$N(R^{12})(R^{13})$. In embodiments, $R^{29}$ is independently —$C(O)OR^{12}$. In embodiments, $R^{29}$ is independently —$OC(O)N(R^{12})(R^{13})$. In embodiments, $R^{29}$ is independently —$N(R^{12})C(O)N(R^{12})(R^{13})$. In embodiments, $R^{29}$ is independently —$N(R^{12})C(O)OR^{12}$. In embodiments, $R^{29}$ is independently —$N(R^{12})S(O)_2R^{12}$. In embodiments, $R^{29}$ is independently —$C(O)R^{12}$. In embodiments, $R^{29}$ is independently —$S(O)R^{12}$. In embodiments, $R^{29}$ is independently —$OC(O)R^{12}$. In embodiments, $R^{29}$ is independently —$C(O)N(R^{12})(R^{13})$. In embodiments, $R^{29}$ is independently —$C(O)C(O)N(R^{12})(R^{13})$. In embodiments, $R^{29}$ is independently —$N(R^{12})C(O)R^{12}$. In embodiments, $R^{29}$ is independently —$S(O)_2R^{12}$. In embodiments, $R^{29}$ is independently —$S(O)(NR^{12})R^{12}$. In embodiments, $R^{29}$ is independently —$S(O)_2N(R^{12})(R^{13})$. In embodiments, $R^{29}$ is independently —$S(=O)(=NR^{12})N(R^{12})(R^{13})$.

In embodiments of a compound of Formula I, IA, IB, II, IIA, or V, $R^{29}$ is independently selected at each occurrence from

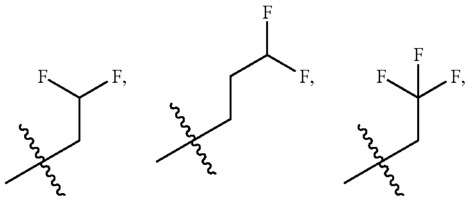

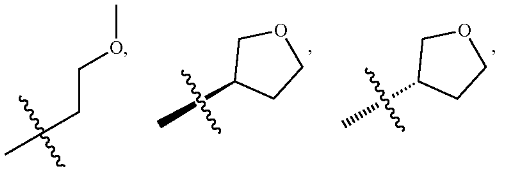

-continued

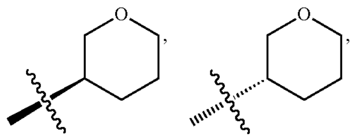

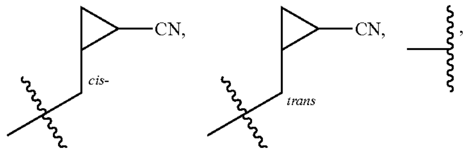

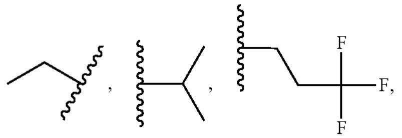

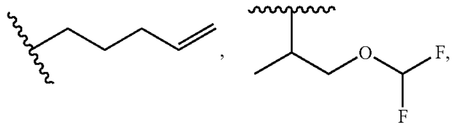

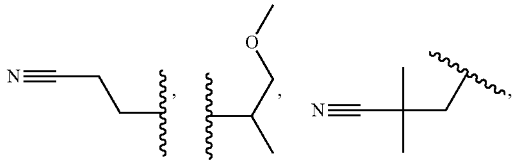

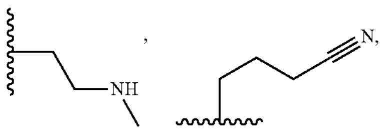

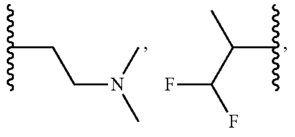

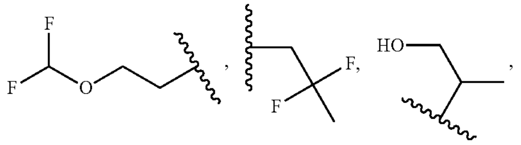

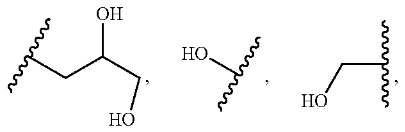

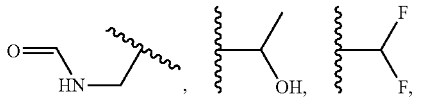

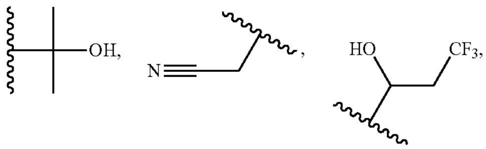

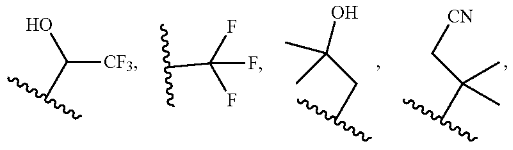

-continued
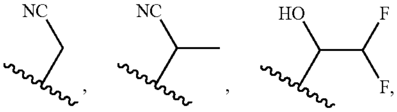
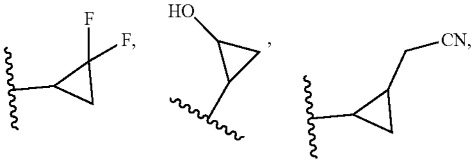
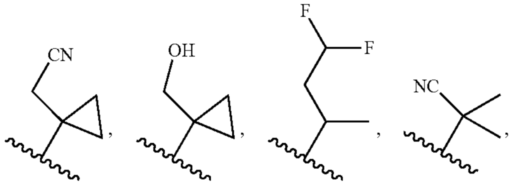
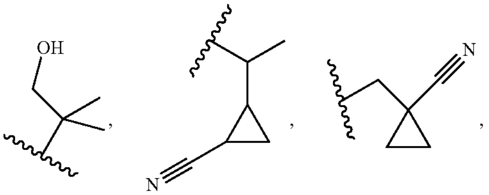
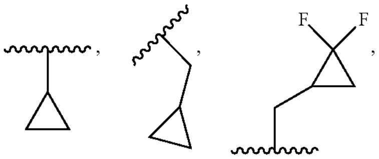
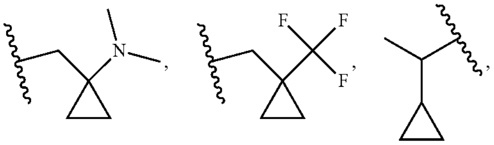
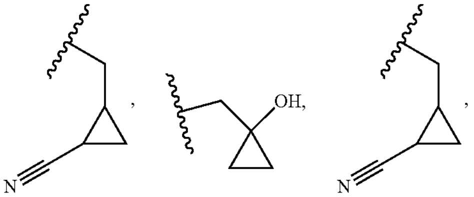
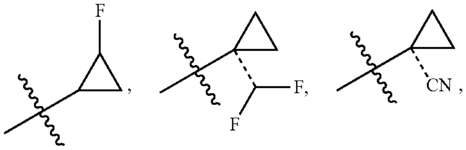
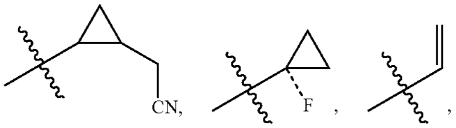
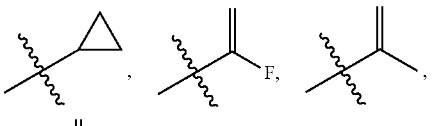
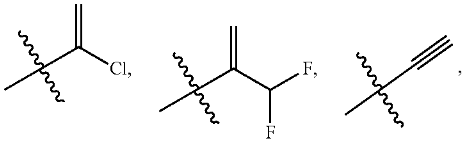
-continued
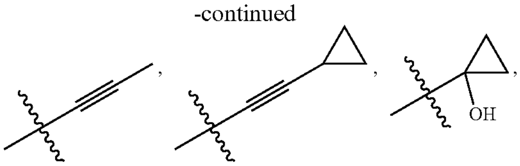
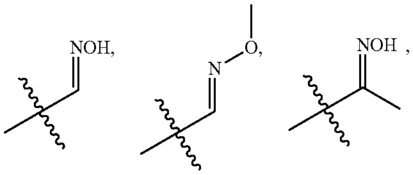
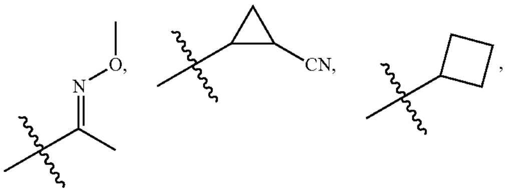
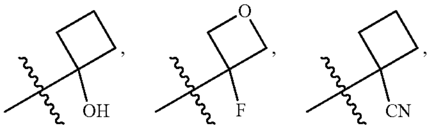
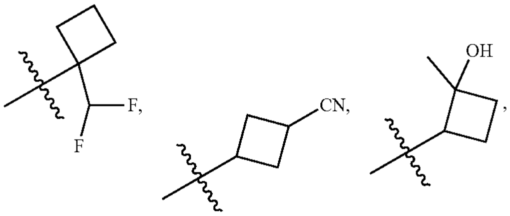
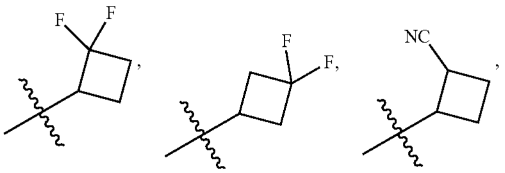
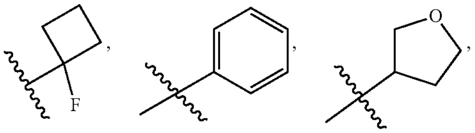
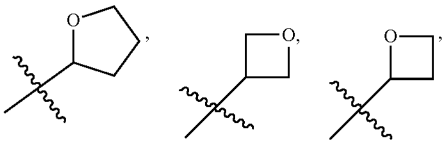
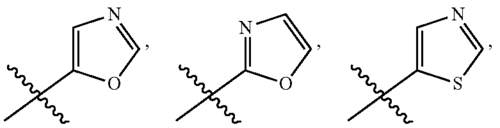
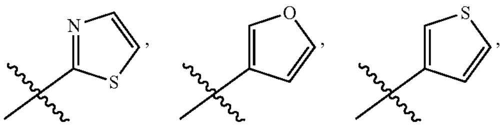
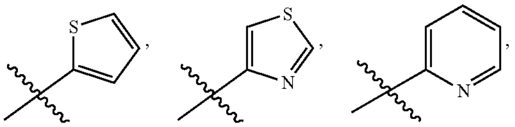

-continued

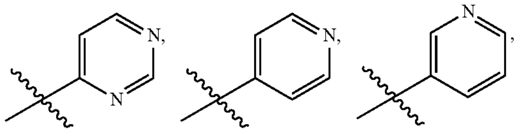

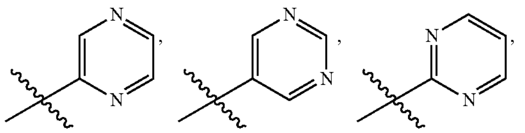

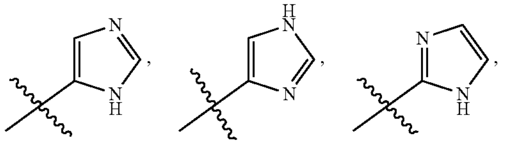

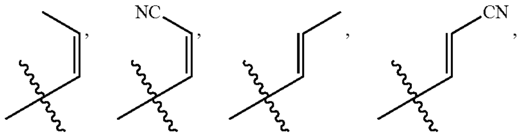

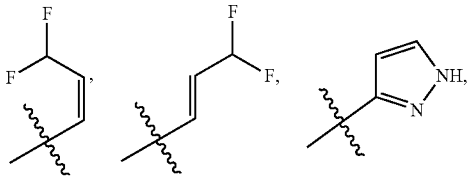

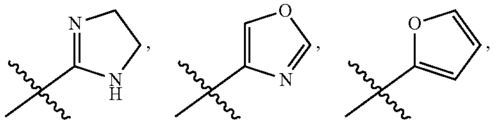

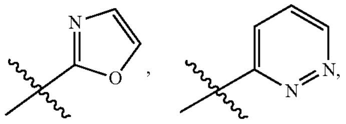

and

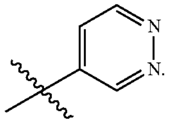

In embodiments, the compound has the formula:

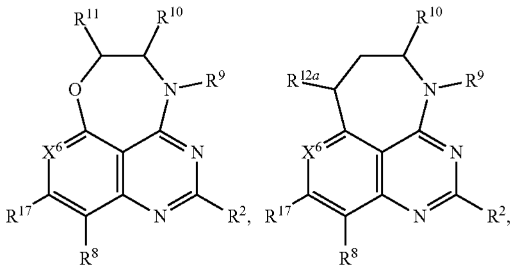

-continued

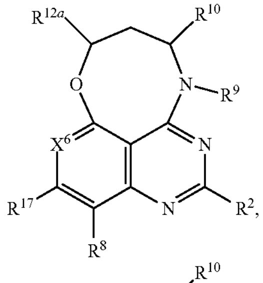

or

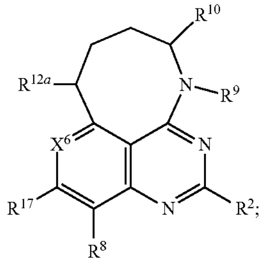

$X^6$ is selected from $C(R^6)$ and N;

$R^6$ is selected from hydrogen, halogen, —CN, $C_{1-3}$ alkyl, $C_{2-3}$ alkenyl, and $C_{2-3}$ alkynyl; wherein $C_{1-3}$ alkyl, $C_{2-3}$ alkenyl, and $C_{2-3}$ alkynyl are each optionally substituted with one, two, or three $R^{20}$;

$R^{10}$, $R^{11}$, and $R^{12}$ are each independently selected from hydrogen, halogen, —CN, $C_{1-3}$ alkyl, $C_{2-3}$ alkenyl, $C_{2-3}$ alkynyl, and $C_{3-6}$ carbocycle; wherein $C_{1-3}$ alkyl, $C_{2-3}$ alkenyl, $C_{2-3}$ alkynyl, and $C_{3-4}$ carbocycle are each optionally substituted with one, two, or three $R^{20}$;

$R^8$ is halogen;

$R^9$ is selected from

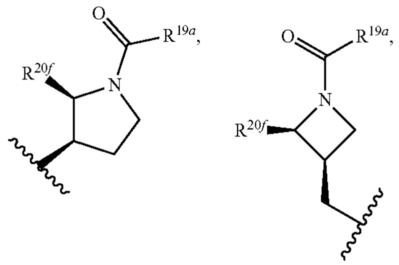

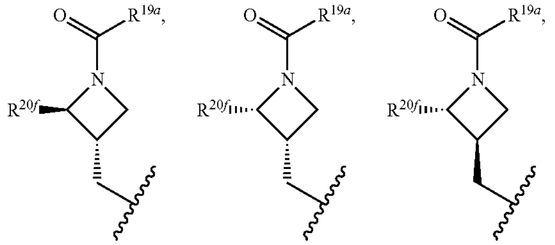

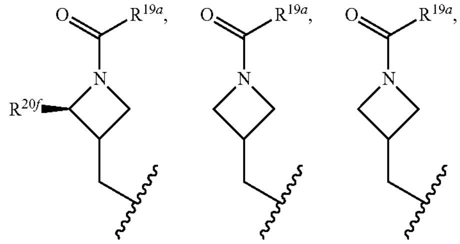

-continued

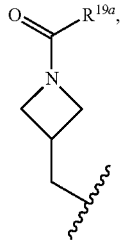 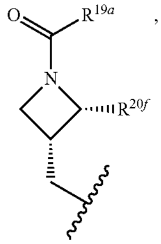 , 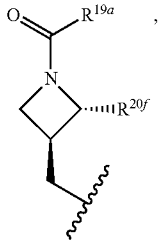 ,

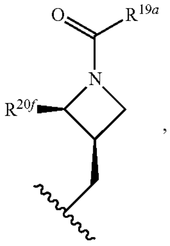 , 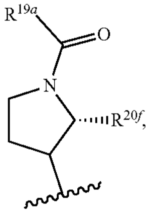 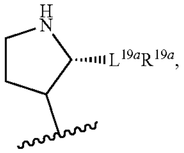

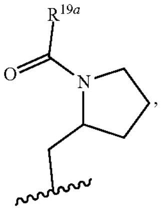 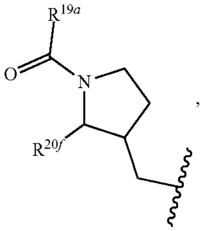 ,

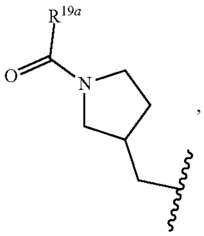 , 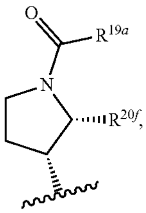 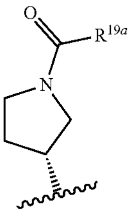 ,

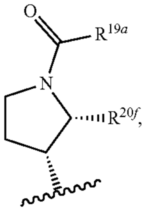 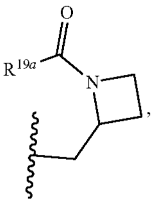 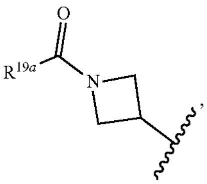

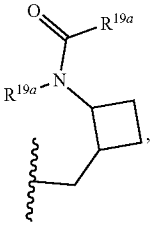 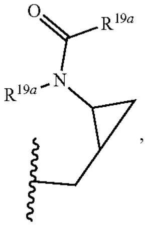 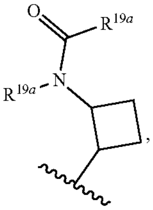

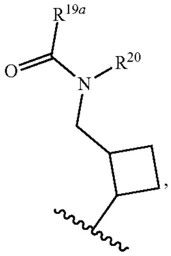 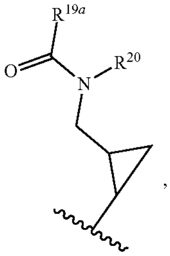 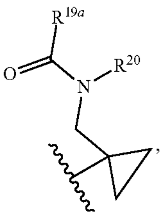

-continued

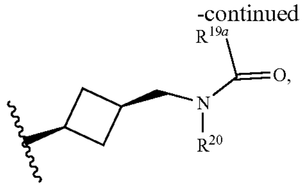

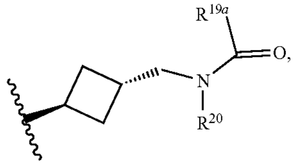

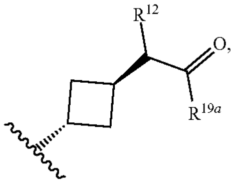 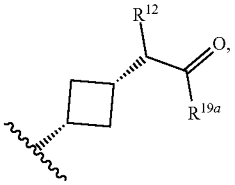 and

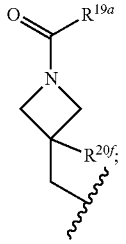

$R^{20f}$ is selected from $C_{1-6}$ alkyl and $C_{3-6}$ carbocycle; wherein $C_{1-6}$ alkyl and $C_{3-6}$ carbocycle are each optionally substituted with one, two, or three $R^{20}$;

$R^{17}$ is selected from

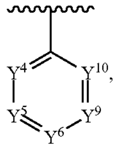 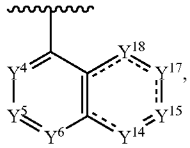 and

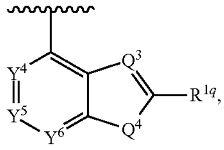

wherein:

$Q^3$ is C(CN);

$Q^4$ is selected from O and S;

$Y^4$, $Y^5$, $Y^6$, $Y^9$, and $Y^{10}$ are independently selected from $C(R^{1q})$ and N;

$Y^{14}$, $Y^{15}$, $Y^{17}$, and $Y^{18}$ are $C(R^{1q})$;

each $R^{1q}$ is independently selected from hydrogen, halogen, —CN, $C_{1-3}$ alkyl, $C_{1-3}$ haloalkyl, $C_{2-3}$ alkenyl, $C_{2-3}$ alkynyl, 2- to 4-membered heteroalkyl, 2- to 4-membered heteroalkenyl, 2- to 4-membered heteroalkynyl, —$C_{0-6}$ alkyl-($C_{3-5}$ carbocycle), —$C_{0-6}$ alkyl-(3- to 5-membered heterocycle), —OH, —$NH_2$, and —$C(O)CH_3$;

$\overline{\underline{\;\;\;\;}}$ indicates a single or double bond such that all valences are satisfied;

$R^2$ is —O($C_{1-3}$ alkylene)(4- to 10-membered heterocycle), wherein 4- to 10-membered heterocycle is optionally substituted with one or more substituents independently selected from halogen, $C_{1-3}$ alkyl, $C_{1-3}$ haloalkyl, and $=C(R^{21})_2$, wherein $R^{21}$ is independently selected at each occurrence from hydrogen, halogen, and $C_{1-3}$ alkyl; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more substituents independently selected from halogen, —CN, unsubstituted $C_{1-3}$ alkyl, and unsubstituted $C_{1-3}$ haloalkyl;

wherein all other variables are as described for Formula I, IA, IB, II, IIA, V, or embodiments thereof.

In embodiments, the compound has the formula:

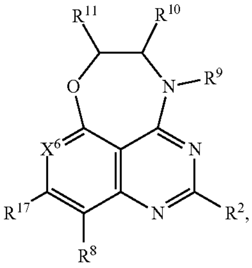
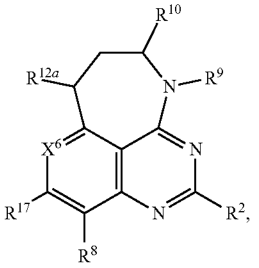
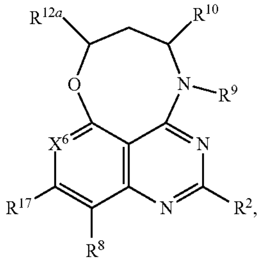
or
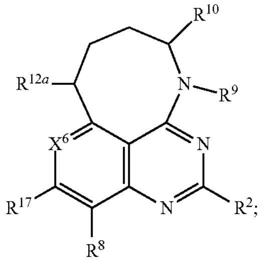

$X^6$ is selected from $C(R^6)$ and N;

$R^6$ is selected from hydrogen, halogen, —CN, $C_{1-3}$ alkyl, $C_{2-3}$ alkenyl, and $C_{2-3}$ alkynyl; wherein $C_{1-3}$ alkyl, $C_{2-3}$ alkenyl, and $C_{2-3}$ alkynyl are each optionally substituted with one, two, or three $R^{20}$;

$R^{10}$, $R^{11}$, and $R^{12a}$ are each independently selected from hydrogen, halogen, —CN, $C_{1-3}$ alkyl, $C_{2-3}$ alkenyl, $C_{2-3}$ alkynyl, and $C_{3-6}$ carbocycle; wherein $C_{1-3}$ alkyl, $C_{2-3}$ alkenyl, $C_{2-3}$ alkynyl, and $C_{3-6}$ carbocycle are each optionally substituted with one, two, or three $R^{20}$;

$R^8$ is halogen;

$R^9$ is selected from

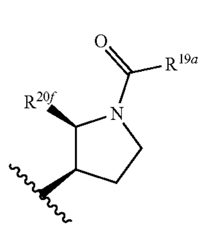
or
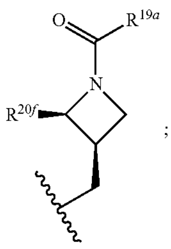
;

$R^{20f}$ is selected from $C_{1-6}$ alkyl and $C_{3-6}$ carbocycle; wherein $C_{1-6}$ alkyl and $C_{3-6}$ carbocycle are each optionally substituted with one, two, or three $R^{20}$;

$R^{17}$ is selected from

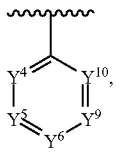
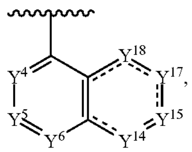
and
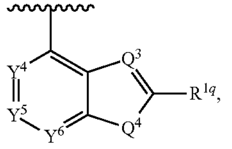

wherein:

$Q^3$ is C(CN);

$Q^4$ is selected from O and S;

$Y^4$, $Y^5$, $Y^6$, $Y^9$, and $Y^{10}$ are independently selected from $C(R^{1q})$ and N;

$Y^{14}$, $Y^{15}$, $Y^{17}$, and $Y^{18}$ are $C(R^{1q})$;

each $R^{1q}$ is independently selected from hydrogen, halogen, —CN, $C_{1-3}$ alkyl, $C_{1-3}$ haloalkyl, $C_{2-3}$ alkenyl, $C_{2-3}$ alkynyl, 2- to 4-membered heteroalkyl, 2- to 4-membered heteroalkenyl, 2- to 4-membered heteroalkynyl, —$C_{0-6}$ alkyl-($C_{3-5}$ carbocycle), —$C_{0-6}$ alkyl-(3- to 5-membered heterocycle), —OH, —$NH_2$, and —$C(O)CH_3$;

╌╌ indicates a single or double bond such that all valences are satisfied;

$R^2$ is —O($C_{1-3}$ alkylene)(4- to 10-membered heterocycle), wherein 4- to 10-membered heterocycle is optionally substituted with one or more substituents independently selected from halogen, $C_{1-3}$ alkyl, $C_{1-3}$ haloalkyl, and $=C(R^{21})_2$, wherein $R^{21}$ is independently selected at each occurrence from hydrogen, halogen, and $C_{1-3}$ alkyl; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more substituents independently selected from halogen, —CN, unsubstituted $C_{1-3}$ alkyl, and unsubstituted $C_{1-3}$ haloalkyl;

wherein all other variables are as described for Formula I, IA, IB, II, IIA, V, or embodiments thereof.

In embodiments, the compound has the formula:

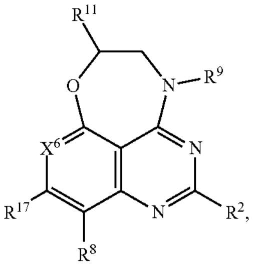

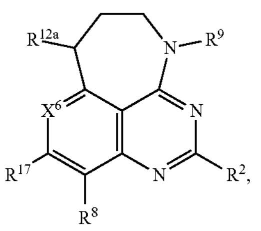

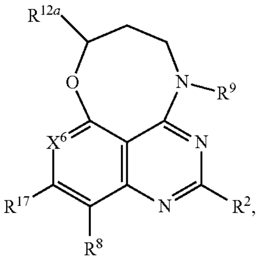

or

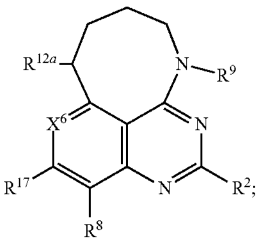

$X^6$ is selected from $C(R^6)$ and N;

$R^6$ is selected from halogen and $—CF_3$;

$R^{11}$ and $R^{12a}$ are each independently selected from hydrogen and $—CH_3$;

$R^8$ is halogen;

$R^9$ is

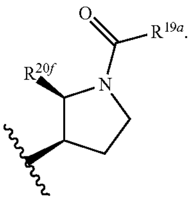

$R^{20f}$ is unsubstituted $C_{1-3}$ alkyl;

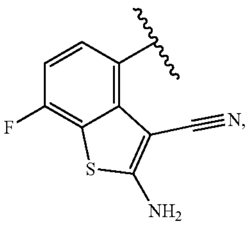

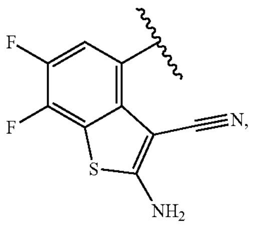

-continued

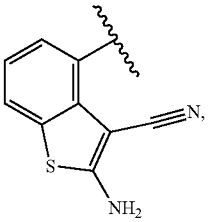

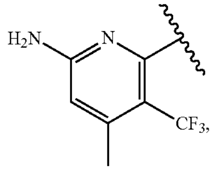

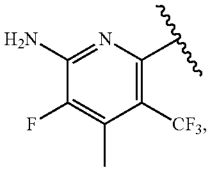

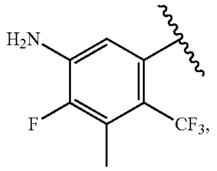

and

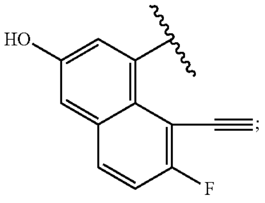

$R^2$ is selected from

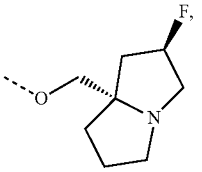

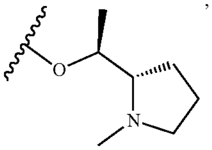

,

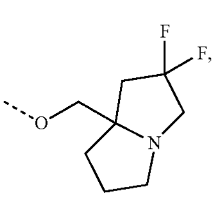

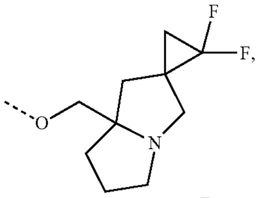

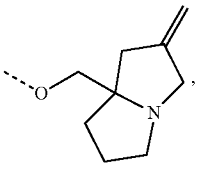

,

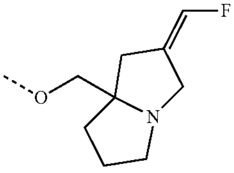

,

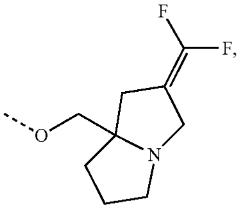

and

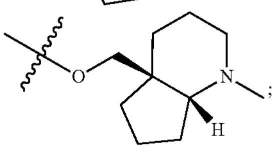

and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more substituents independently selected from halogen, —CN, unsubstituted $C_{1-3}$ alkyl, and unsubstituted $C_{1-3}$ haloalkyl;

wherein all other variables are as described for Formula I, IA, IB, II, IIA, V, or embodiments thereof.

In embodiments, the compound has the formula:

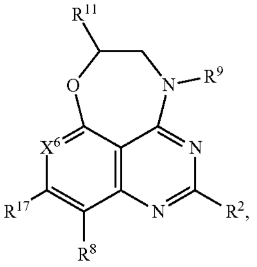

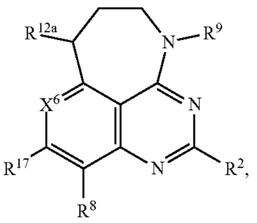

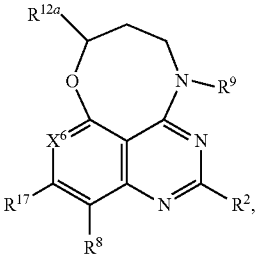

or

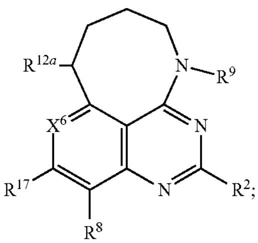

$X^6$ is selected from $C(R^6)$ and N;

$R^6$ is selected from halogen and $-CF_3$;

$R^{11}$ and $R^{12a}$ are each independently selected from hydrogen and $-CH_3$;

$R^8$ is halogen;

$R^9$ is

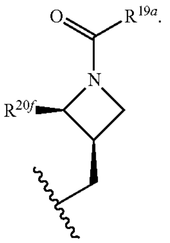

$R^{20f}$ is unsubstituted $C_{1-3}$ alkyl;

$R^{17}$ is selected from

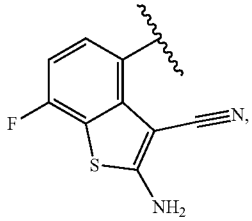

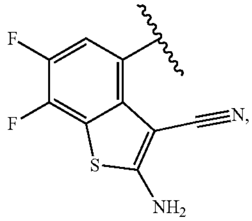

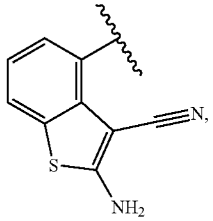

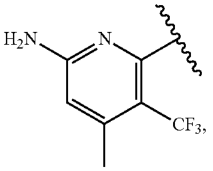

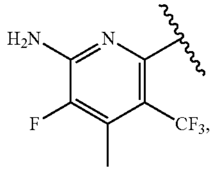

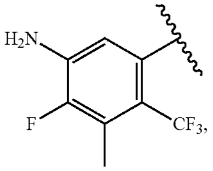

and

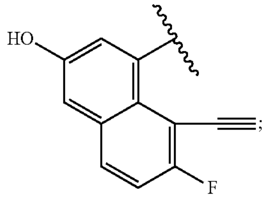

$R^2$ is selected from

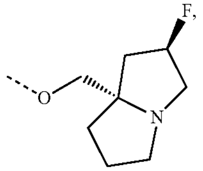

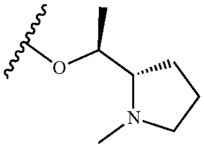

,

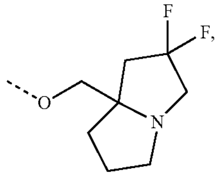

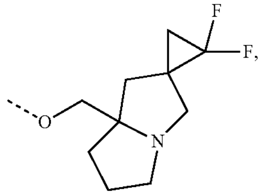

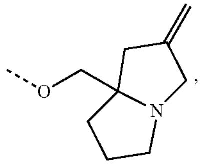

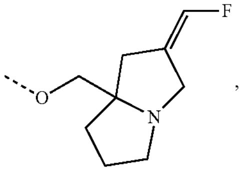

,

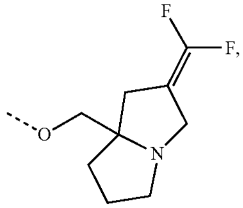

and

-continued

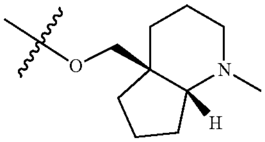
;

and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more substituents independently selected from halogen, —CN, unsubstituted $C_{1-3}$ alkyl, and unsubstituted $C_{1-3}$ haloalkyl;

wherein all other variables are as described for Formula I, IA, IB, II, IIA, V, or embodiments thereof.

In embodiments, $R^{19a}$ is selected from

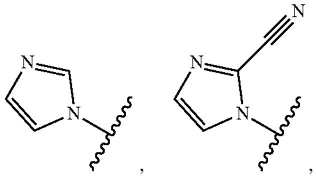
, ,

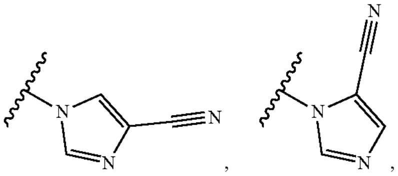
, ,

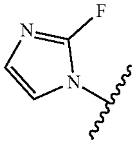
,
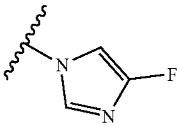
,
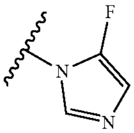
,

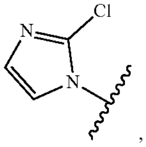
,
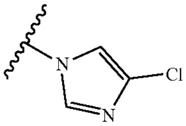
,
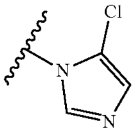
,

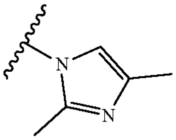
,
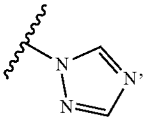
,
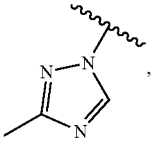
,

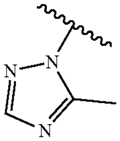
,
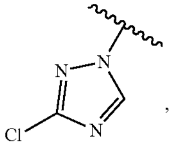
,
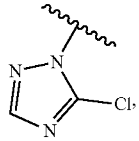
,

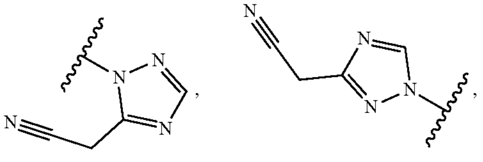
, ,

-continued

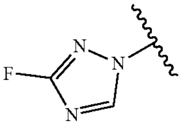
,
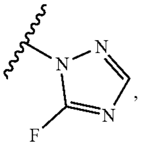
,
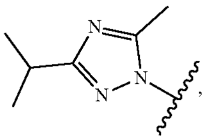
,

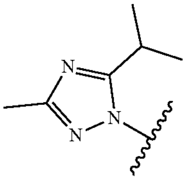
,
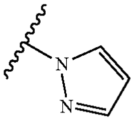
,
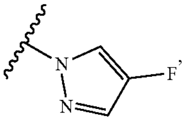
,

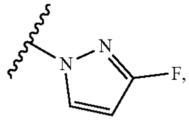
,
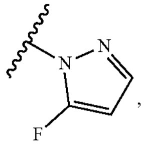
,
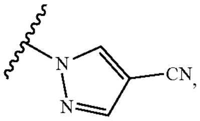
,

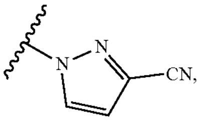
,
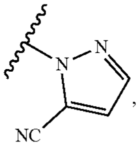
,
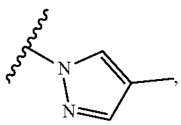
,

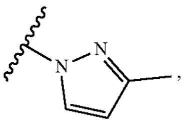
,
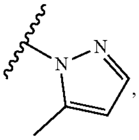
,
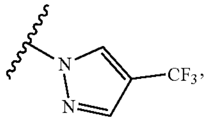
,

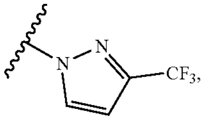
,
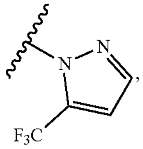
,
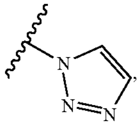
,

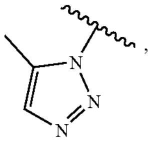
,
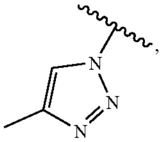
,
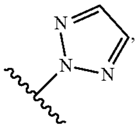
,

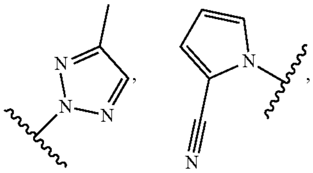
, ,

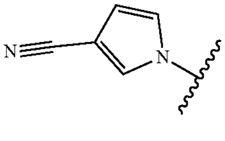
, and
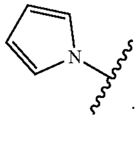
.

In embodiments, $R^{20f}$ is unsubstituted $C_{1-3}$ alkyl; and $R^{19a}$ is a 5-membered heteroaryl comprising one or more ring nitrogen atoms, wherein the 5-membered heteroaryl is directly bonded to —C(O)— through an $R^{19a}$ ring nitrogen atom and wherein $R^{19a}$ is optionally substituted with one or more halogen, —CN, unsubstituted $C_{1-3}$ alkyl, and unsubstituted $C_{1-3}$ haloalkyl. In embodiments, $R^{17}$ is selected from

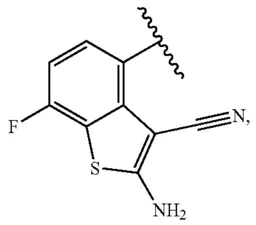
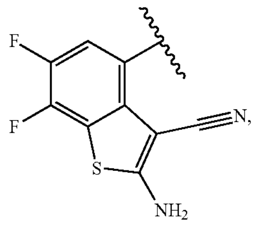
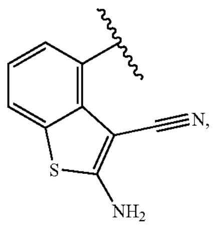
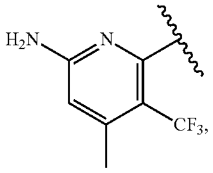
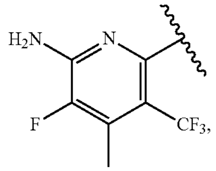
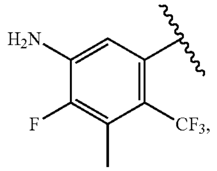
and
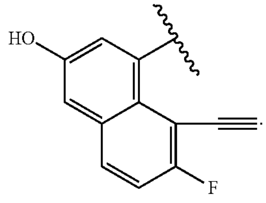
In embodiments, the compound has the formula
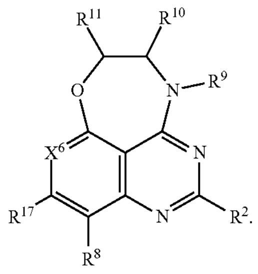
In embodiments the compound has the formula
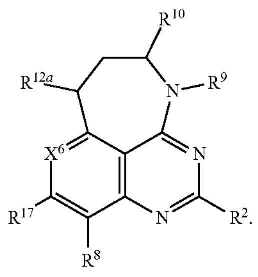
In embodiments, the compound has the formula
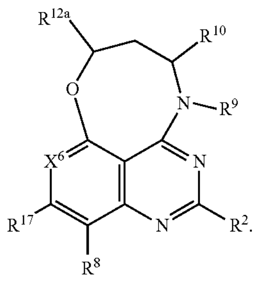
In embodiments, the compound has the formula
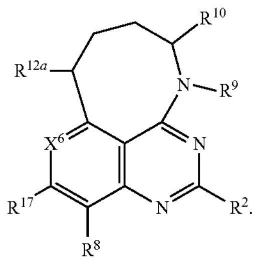
In embodiments, the compound has the formula
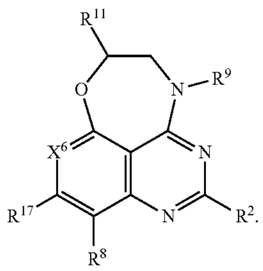
In embodiments, the compound has the formula
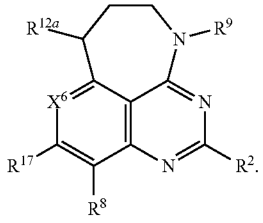
In embodiments, the compound has the formula
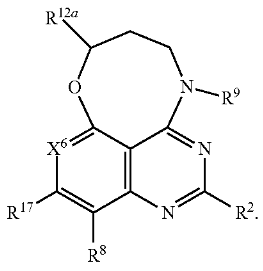

In embodiments, the compound has the formula

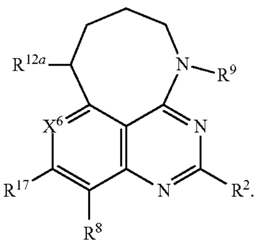

All variables recited in the formula above are as described for Formula I, IA, IB, II, IIA, V, or embodiments thereof.

In embodiments of a compound of Formula I, II, or V, n29 is selected from 0, 1, 2, 3, 4, 5, 6, 7, 8, 9, 10, 11, 12, and 13. In embodiments, n29 is 0. In embodiments, n29 is 1. In embodiments, n29 is 2. In embodiments, n29 is 3. In embodiments, n29 is 4. In embodiments, n29 is 5. In embodiments, n29 is 6. In embodiments, n29 is 7. In embodiments, n29 is 8. In embodiments, n29 is 9. In embodiments, n29 is 10. In embodiments, n29 is 11. In embodiments, n29 is 12. In embodiments, n29 is 13. In embodiments of a compound of Formula I, II, or V, n29 is selected from 0, 1, and 2. In embodiments of a compound of Formula I, II, or V, n29 is selected from 1 and 2. In an aspect is provided a compound selected from

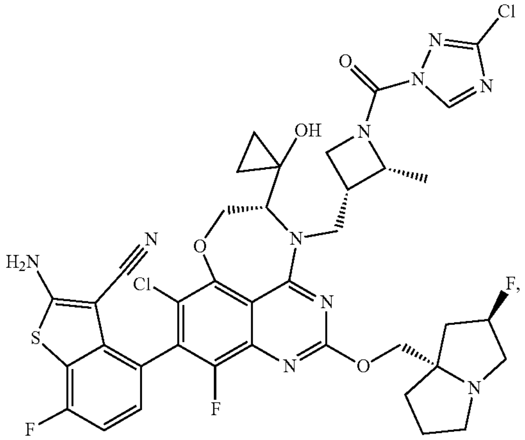

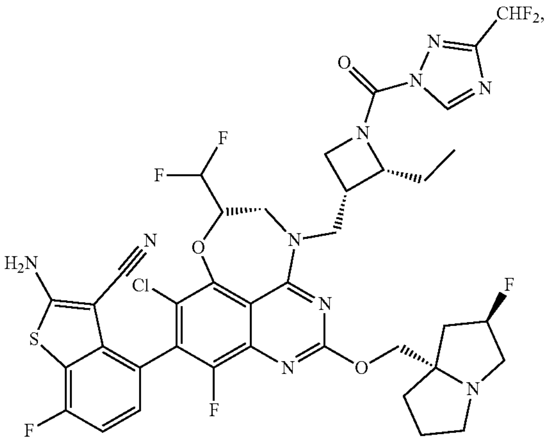

-continued

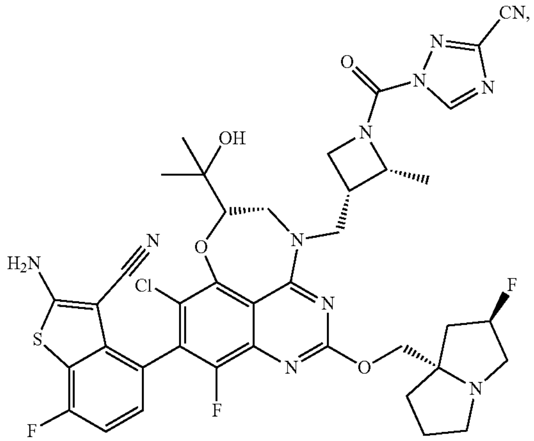

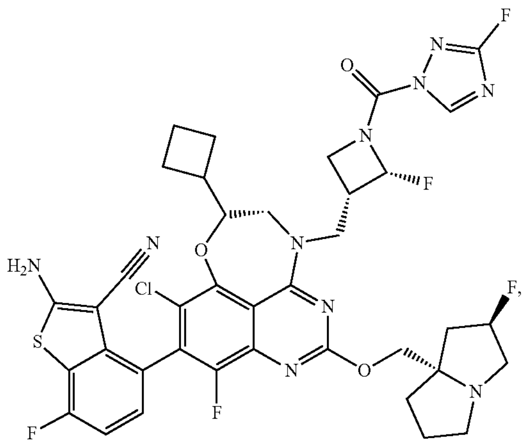

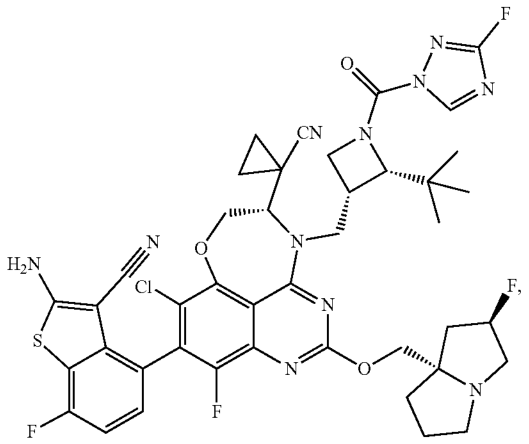

-continued
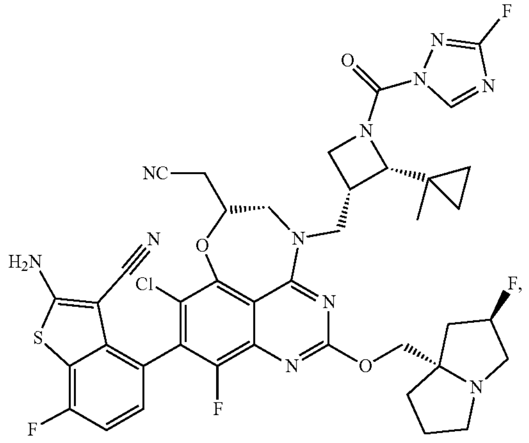
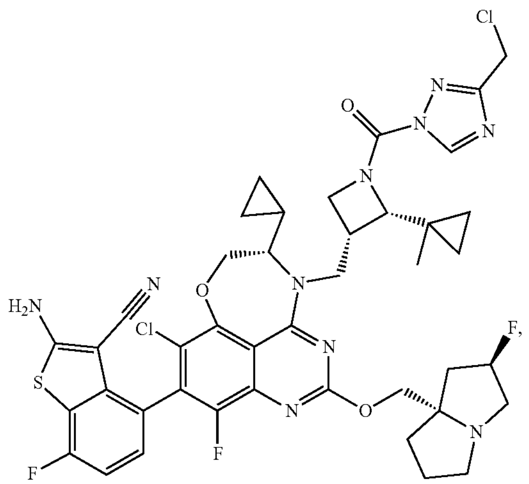
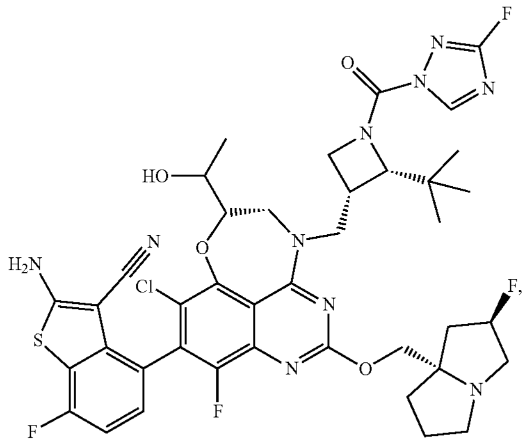
-continued
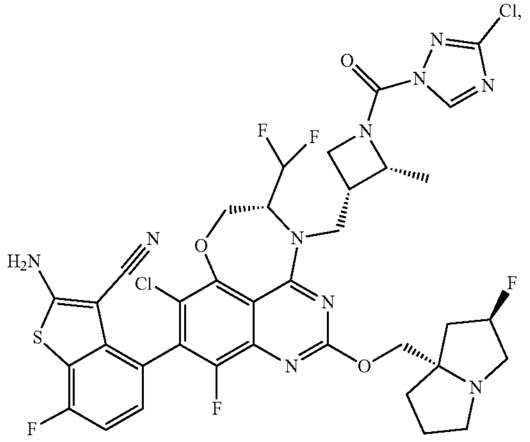
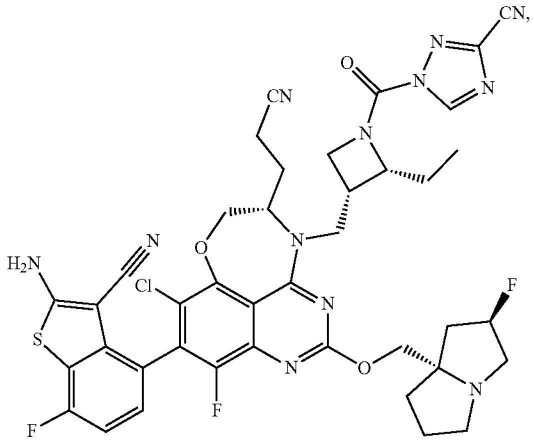
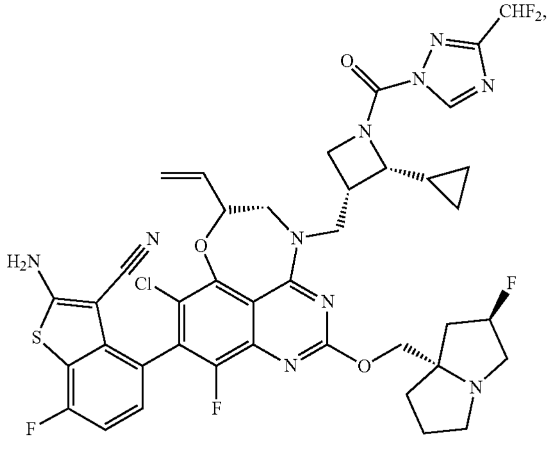

-continued
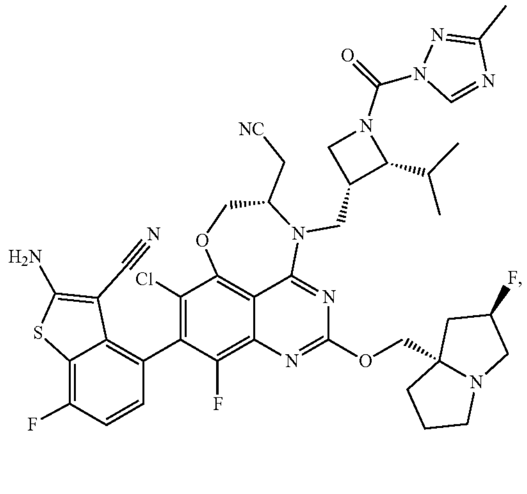
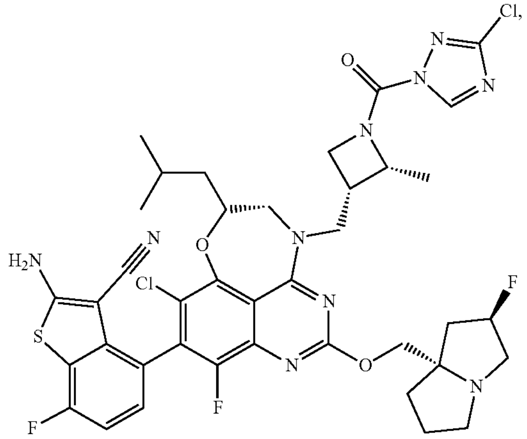
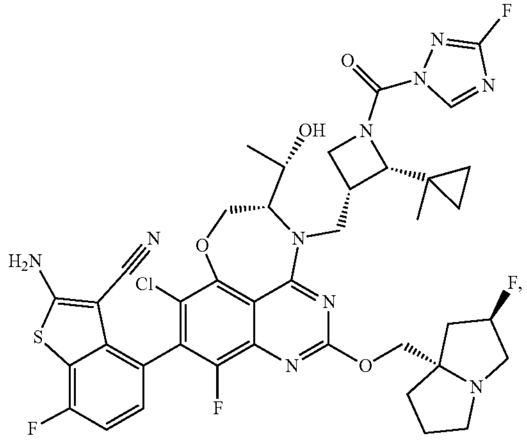
-continued
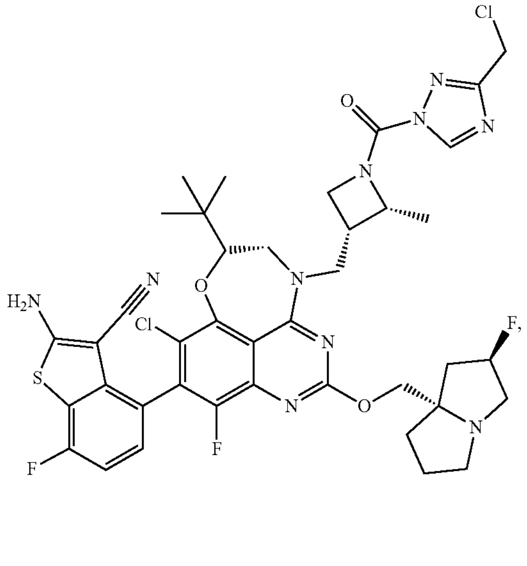
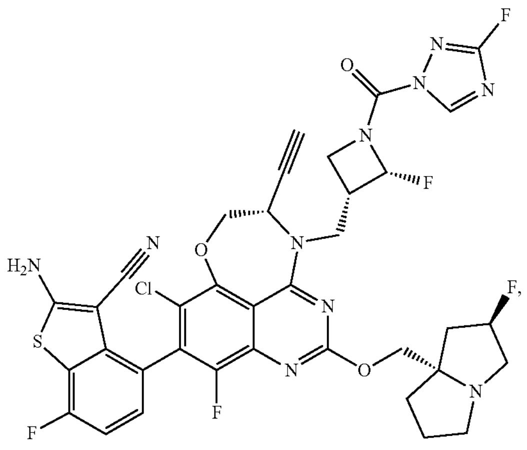
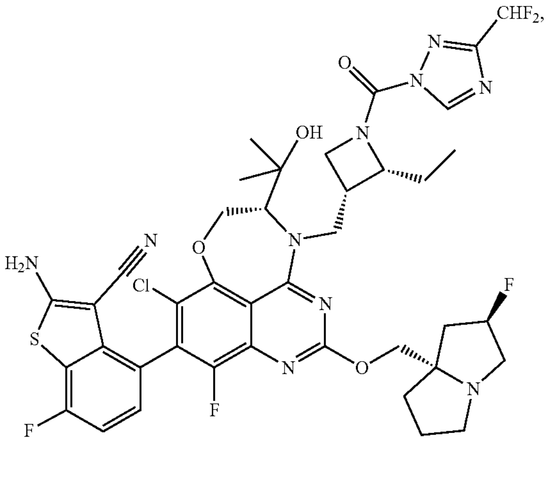

-continued
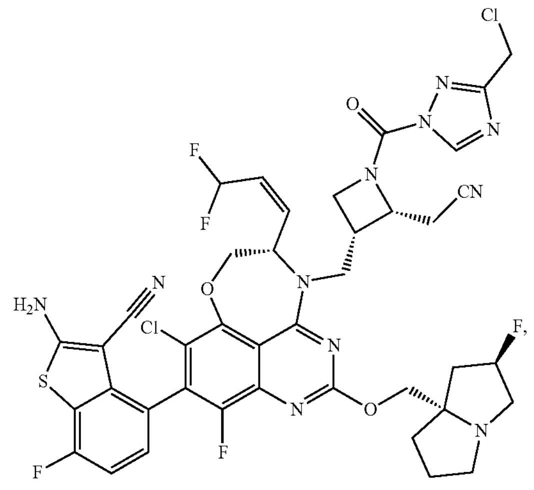
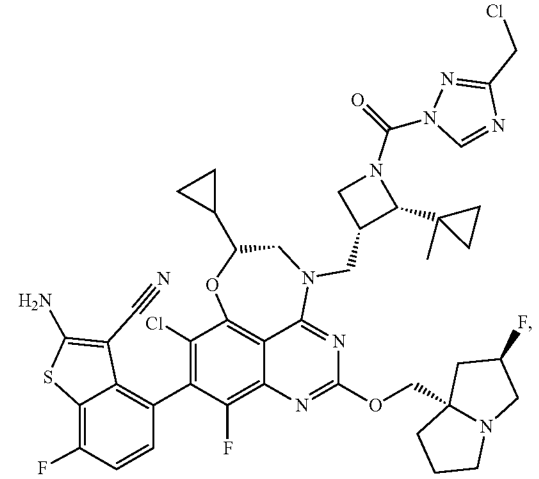
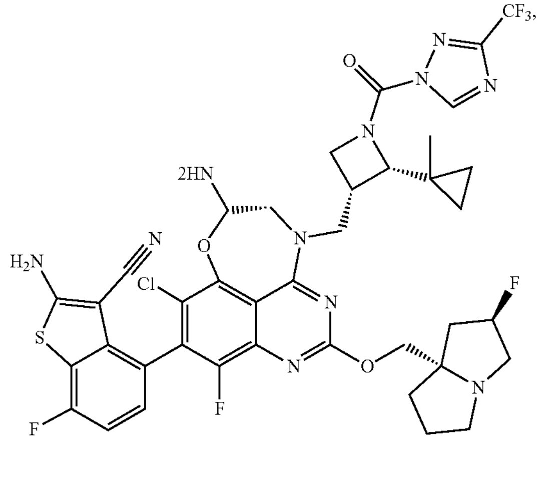
-continued
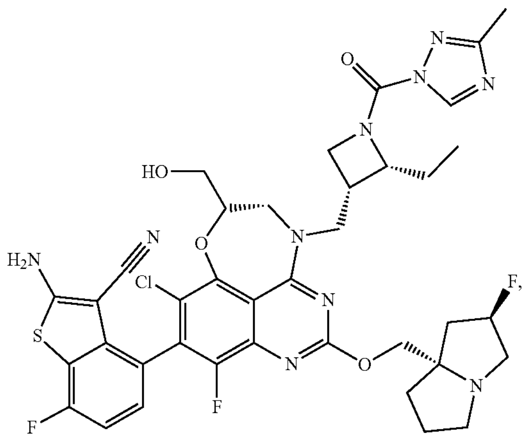
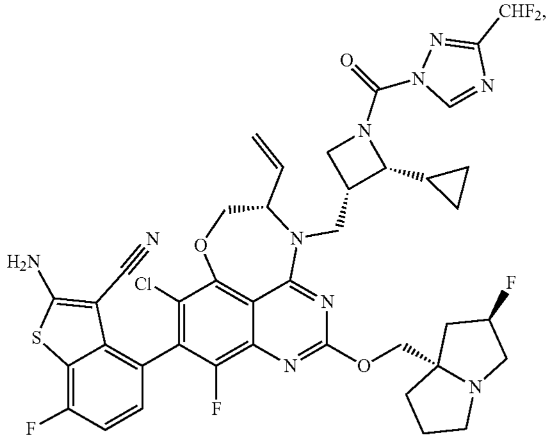
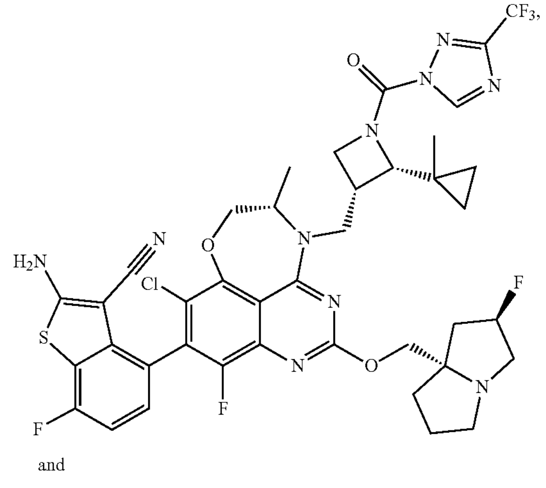
and -continued
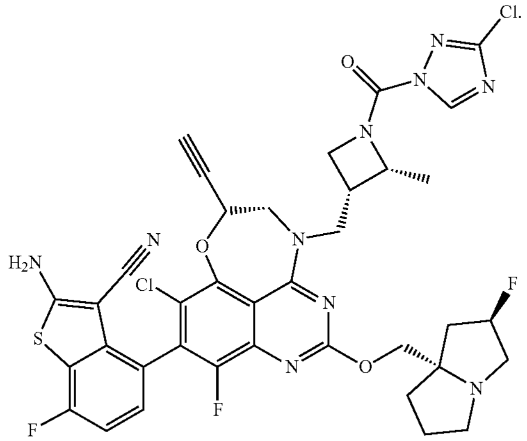
In an aspect is provided a compound selected from
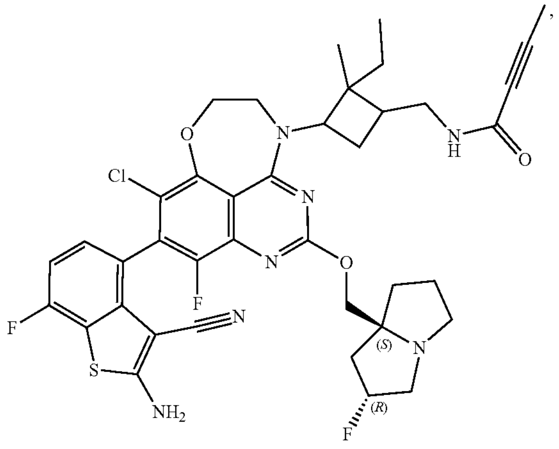
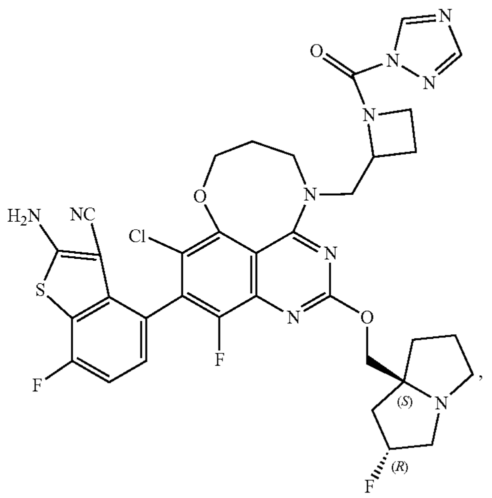
-continued
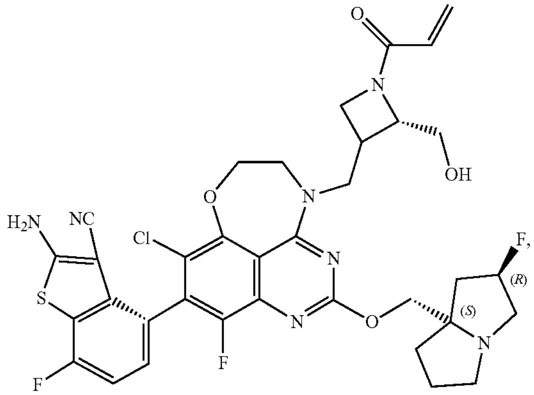
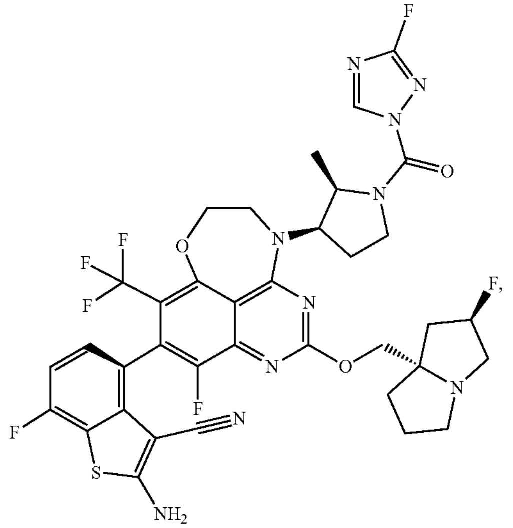
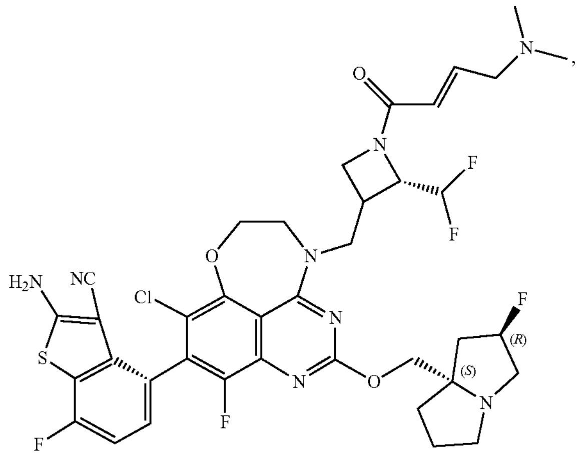

-continued
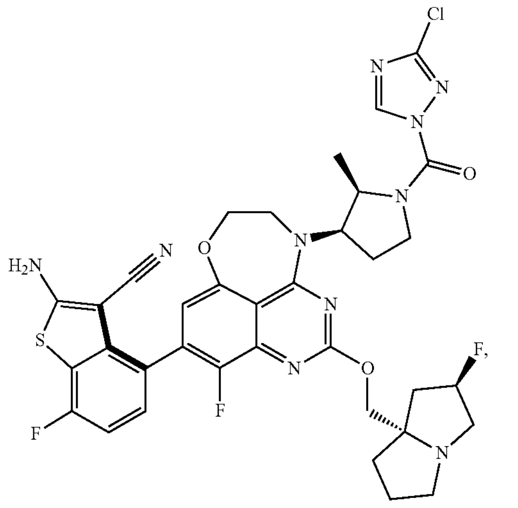
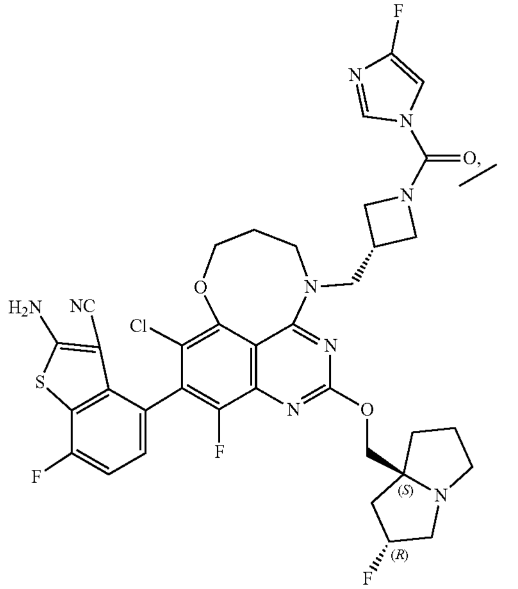
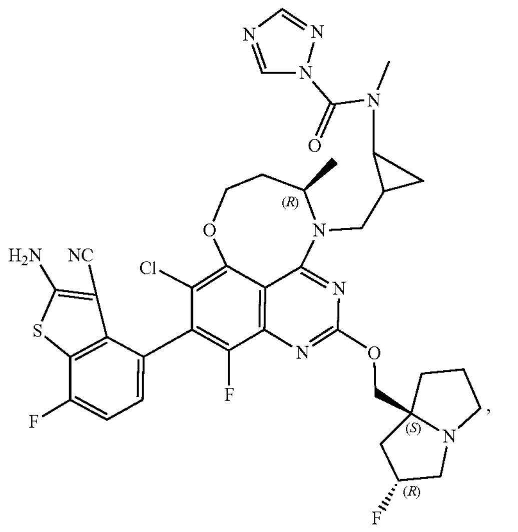
-continued
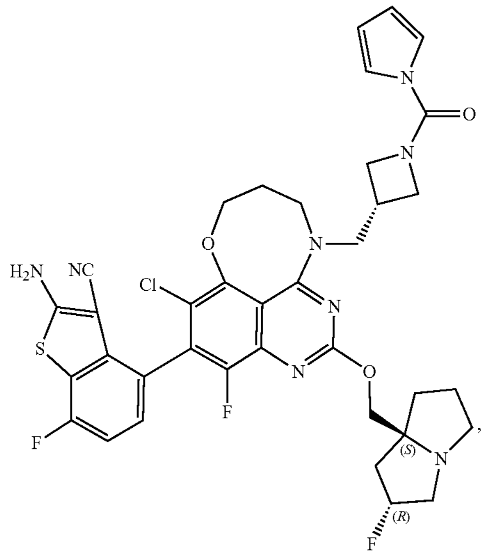
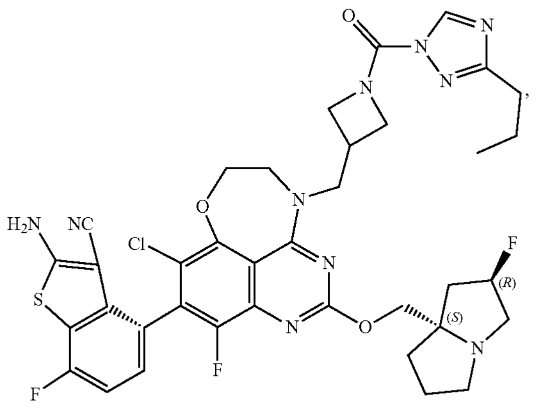
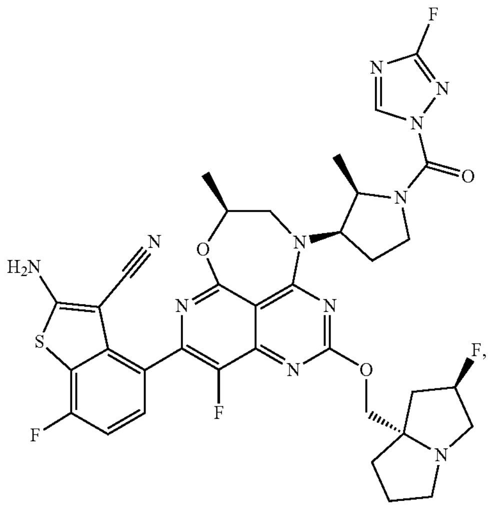

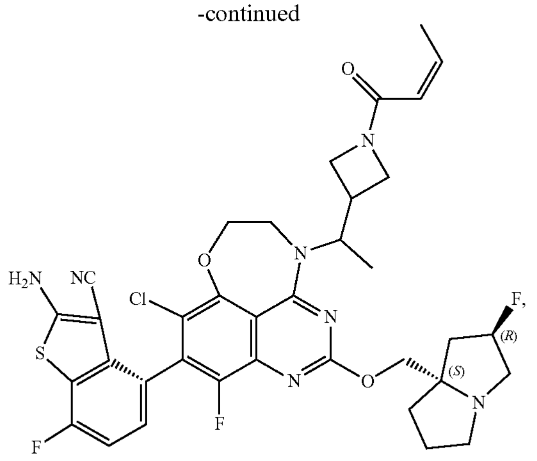
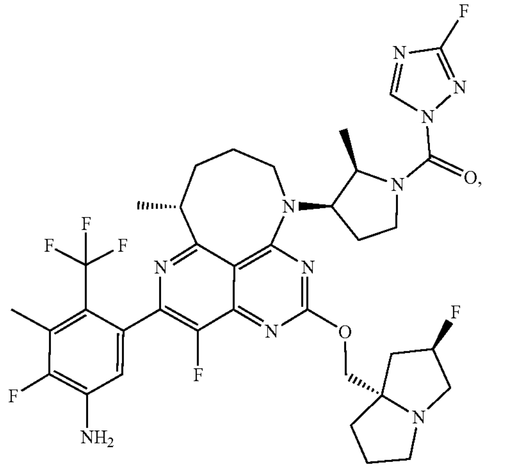
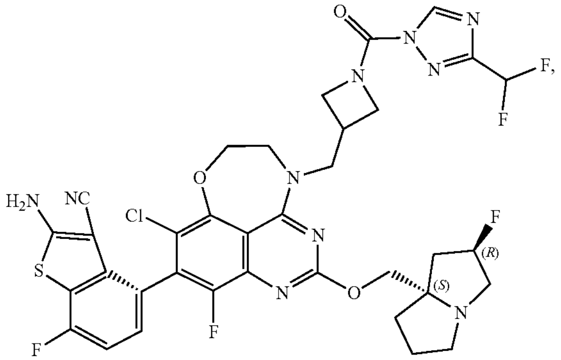
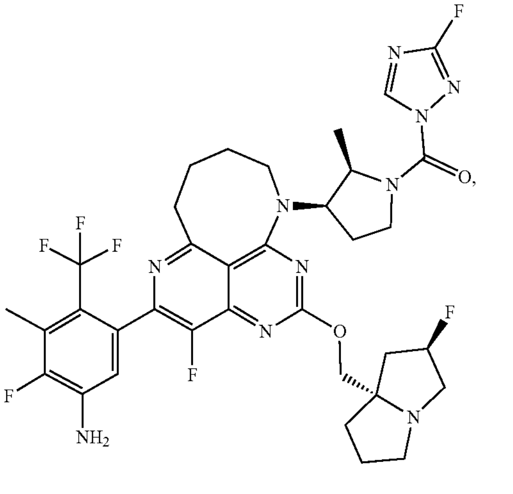
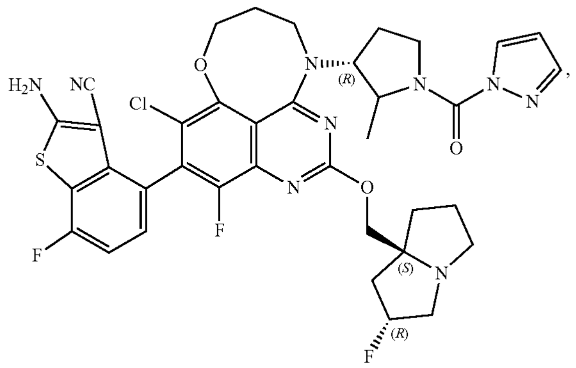
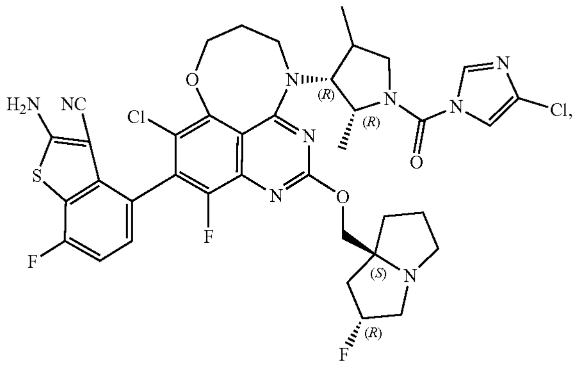
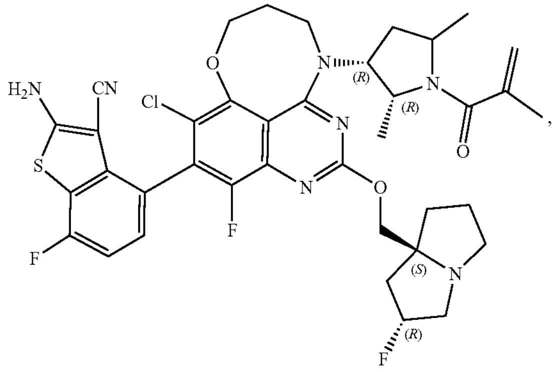
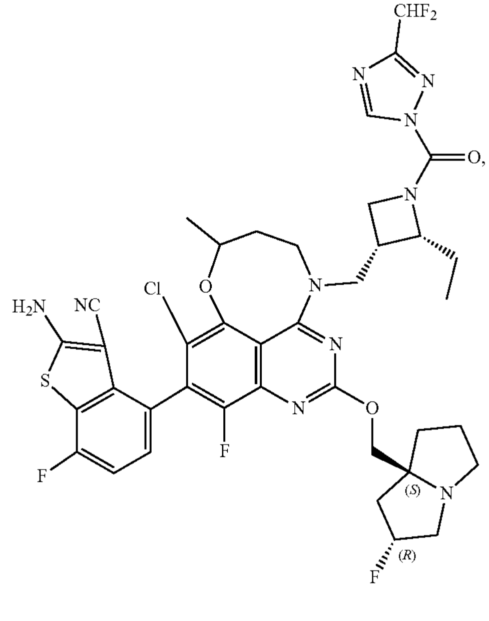

-continued
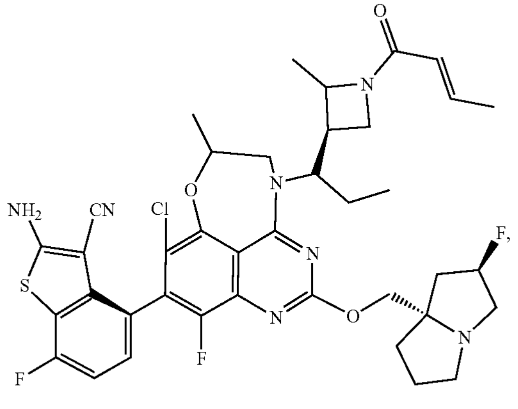
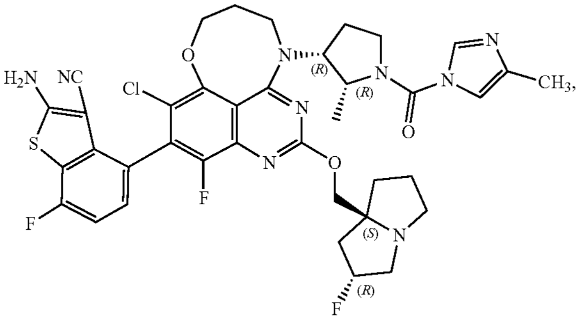
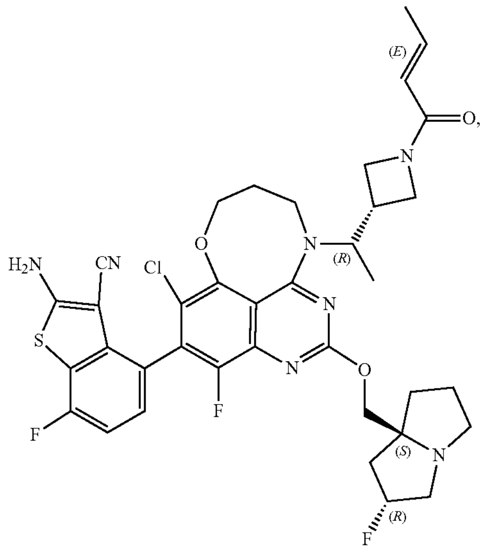
-continued
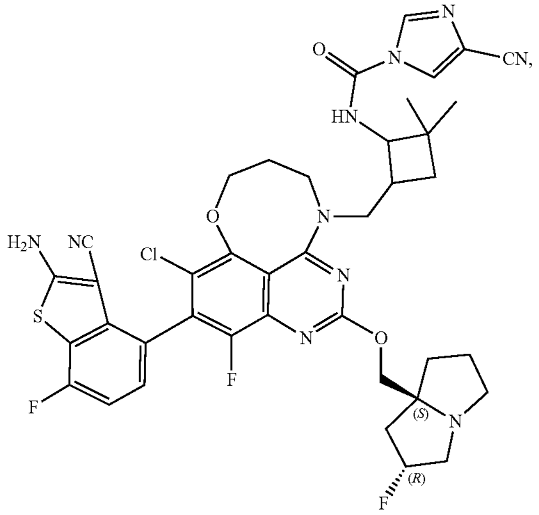
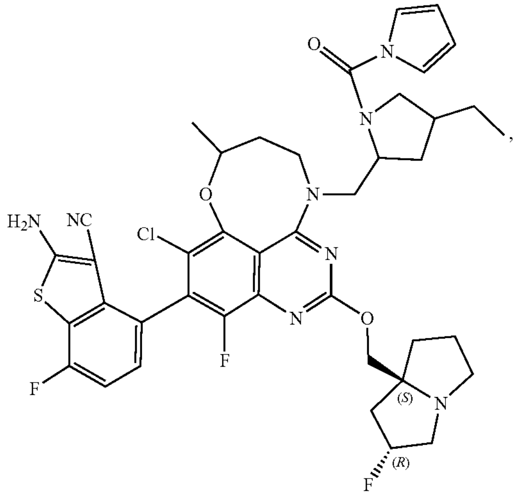
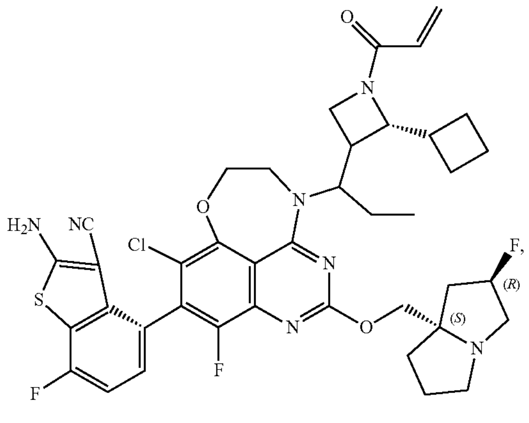

-continued
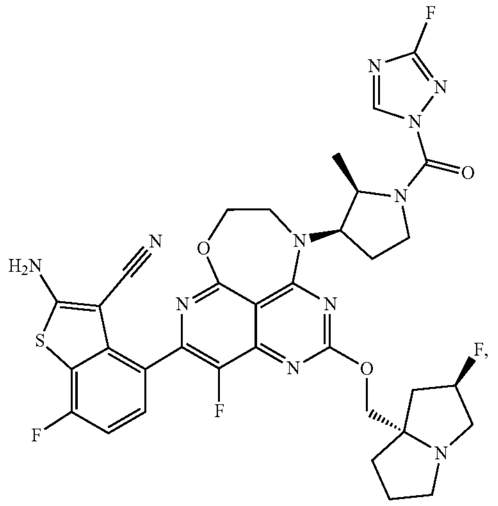
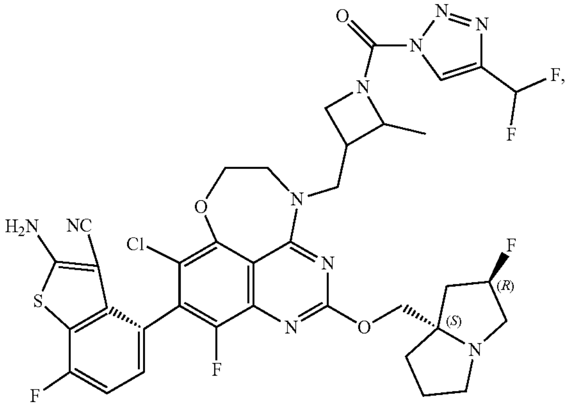
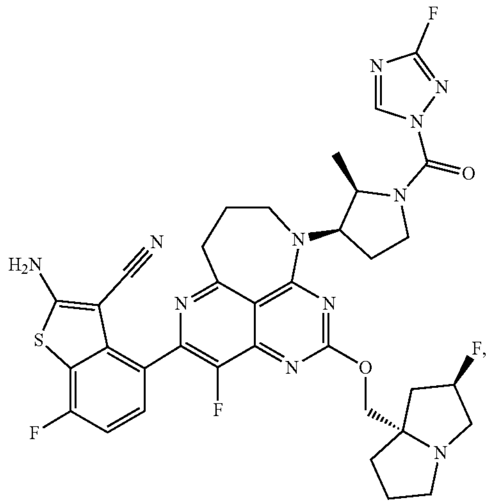
-continued
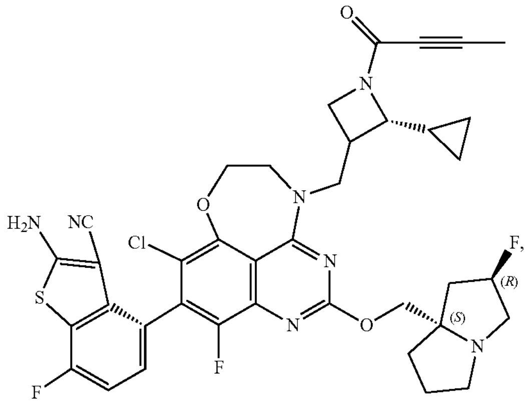
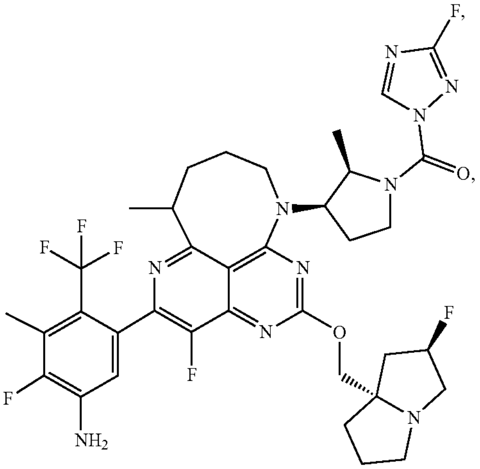
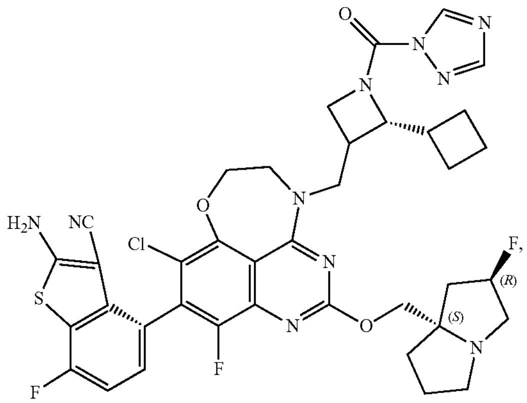
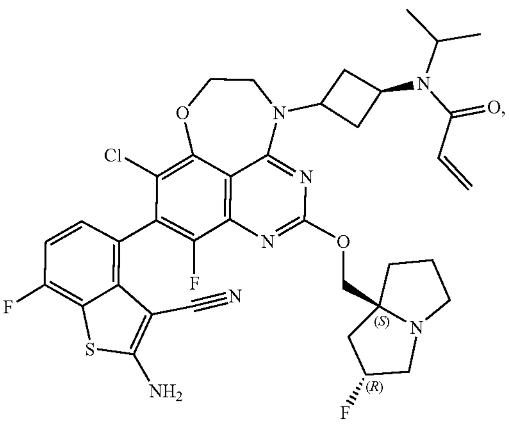

-continued
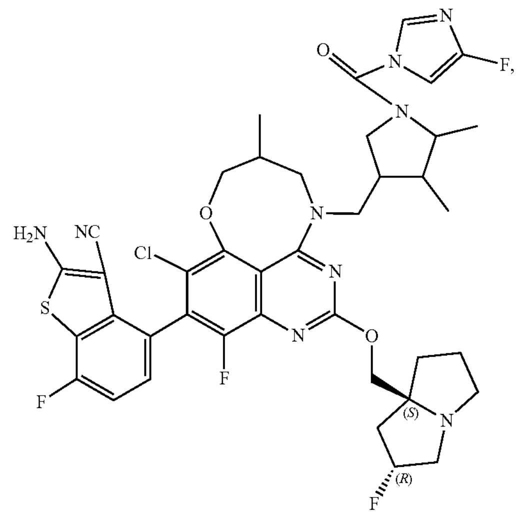
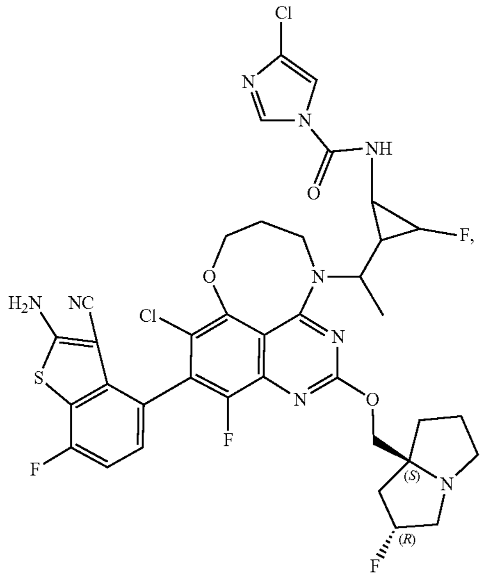
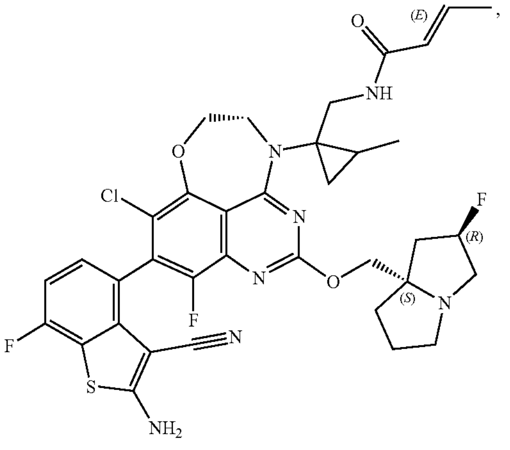
-continued
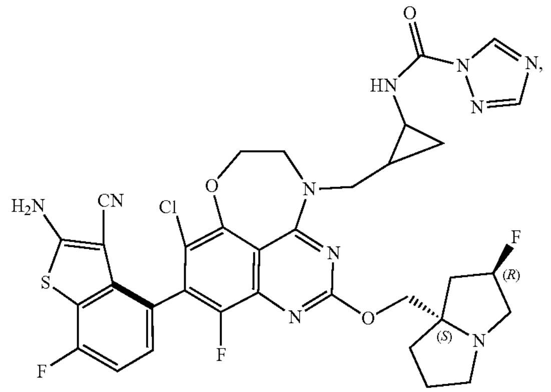
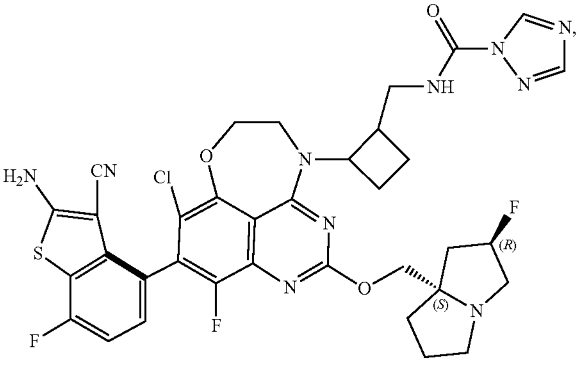
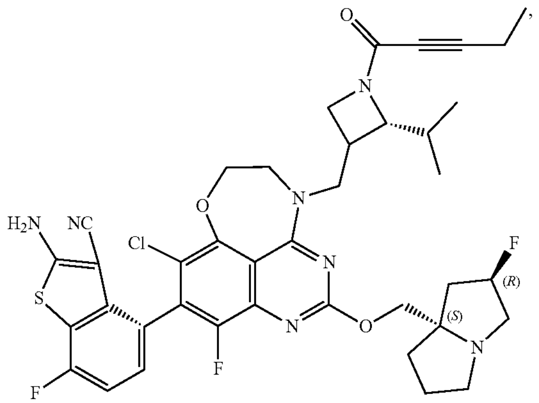
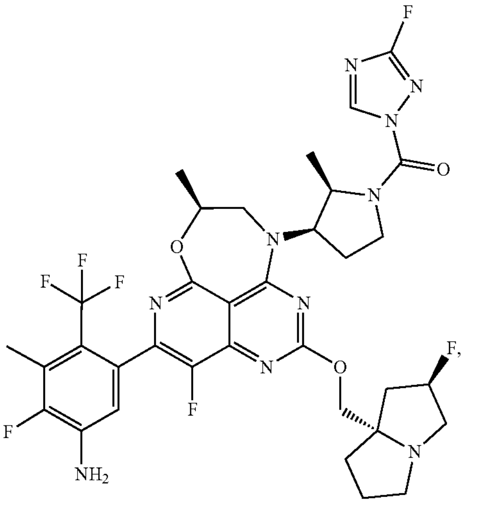

-continued
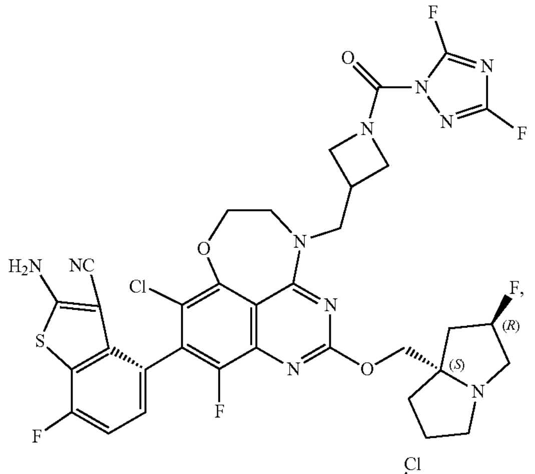
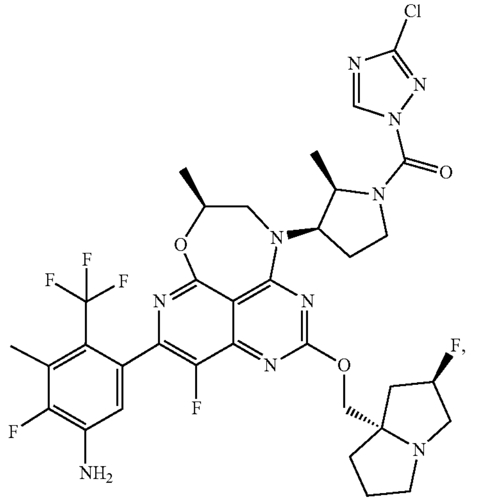
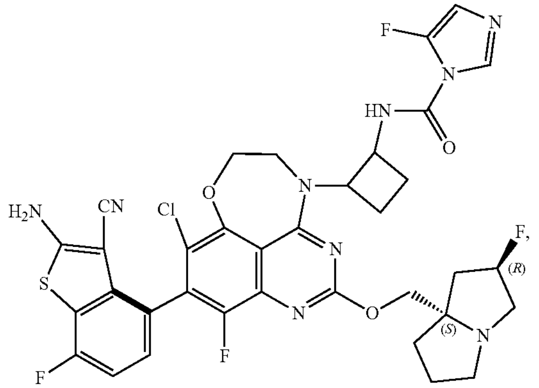
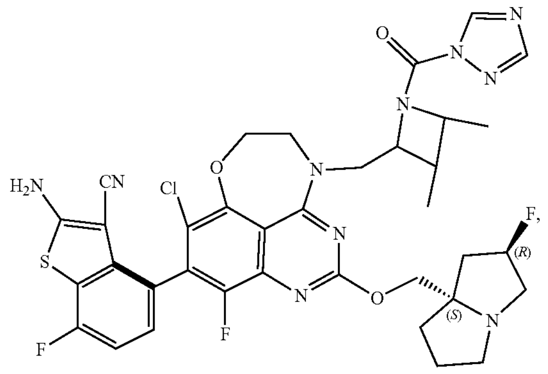
-continued
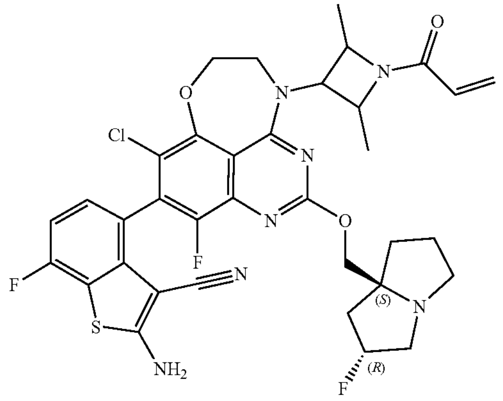
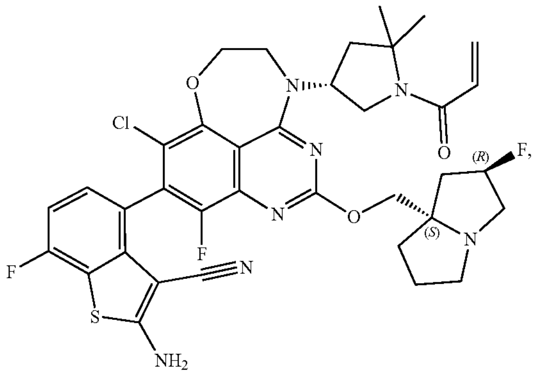
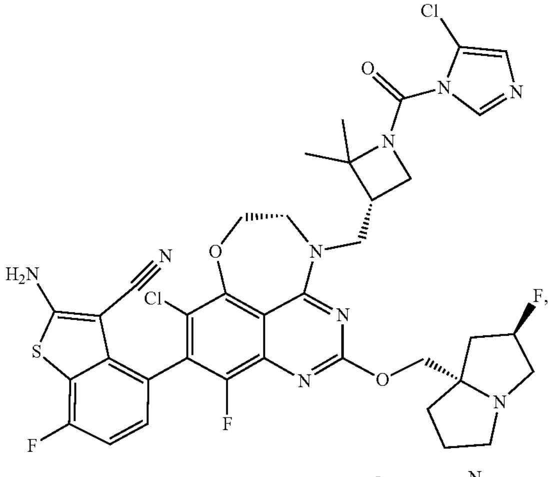
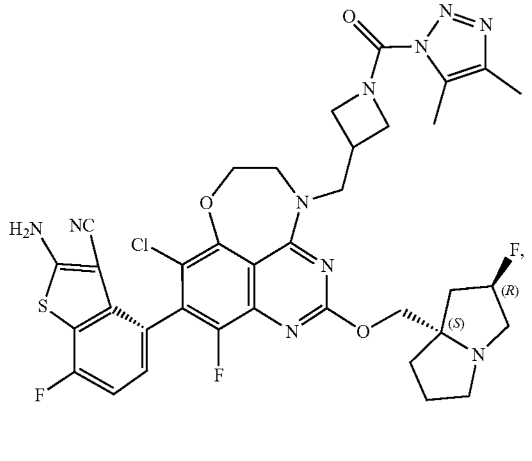

-continued
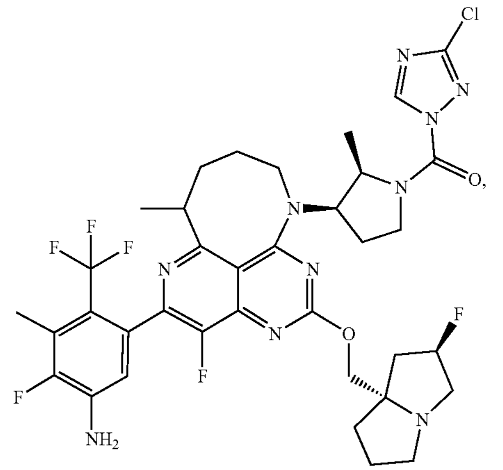
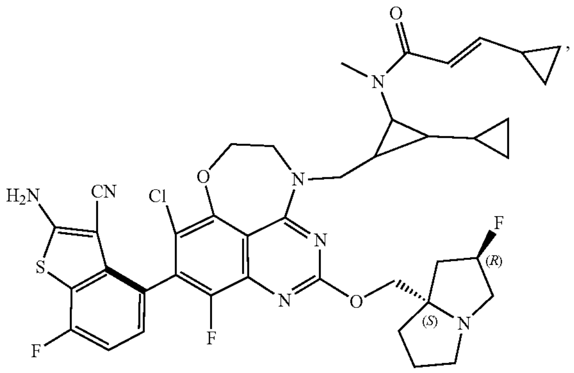
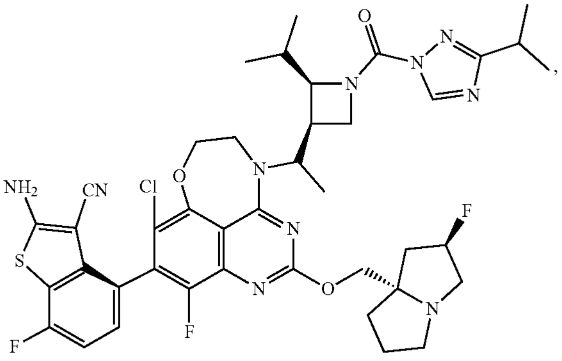
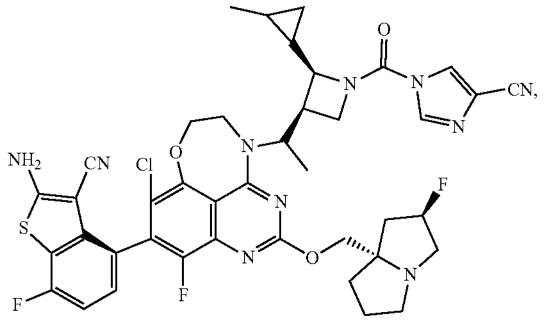
-continued
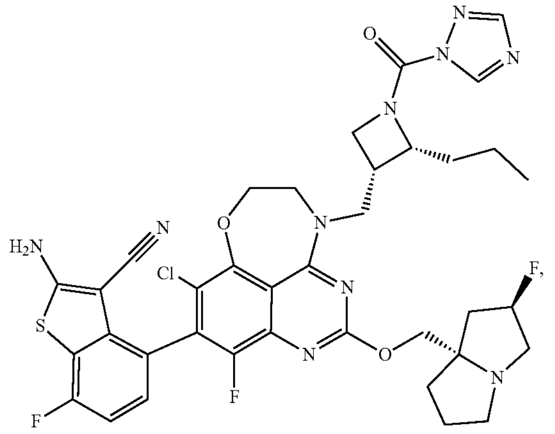
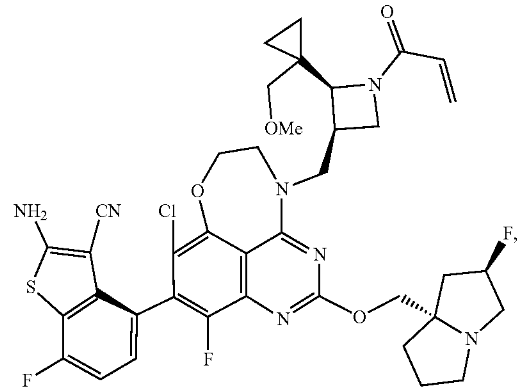
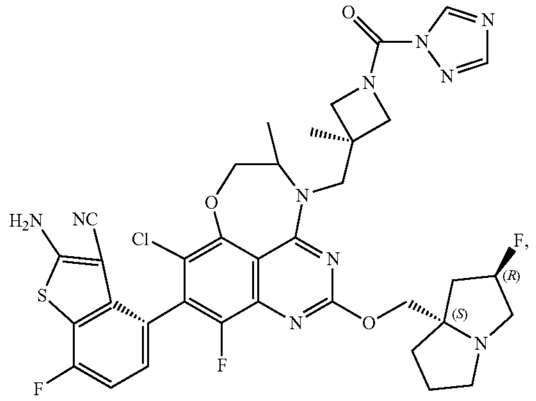
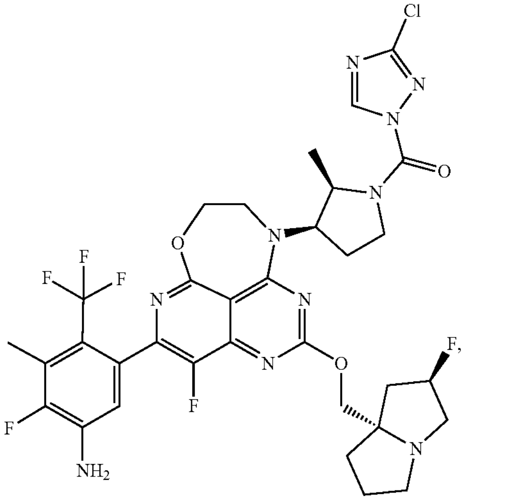

-continued
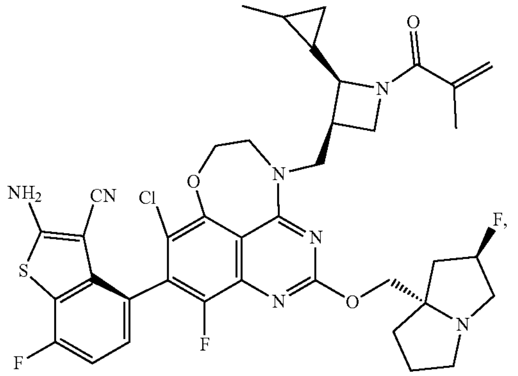
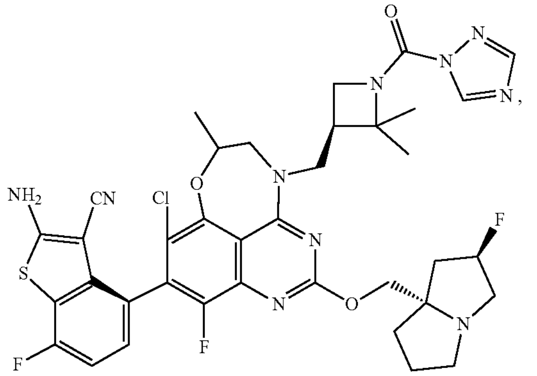
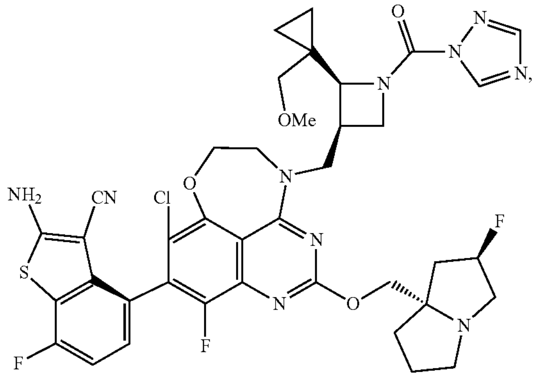
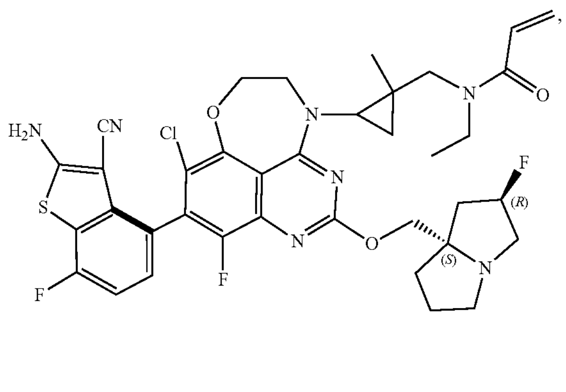
-continued
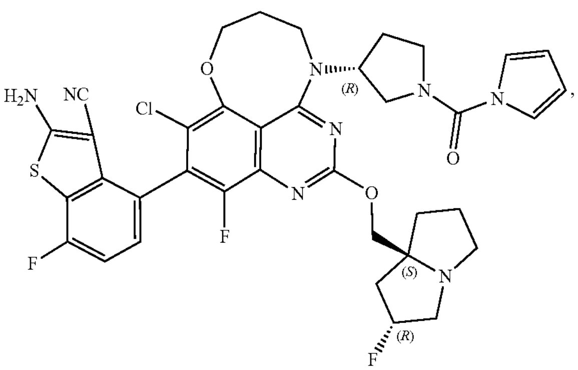
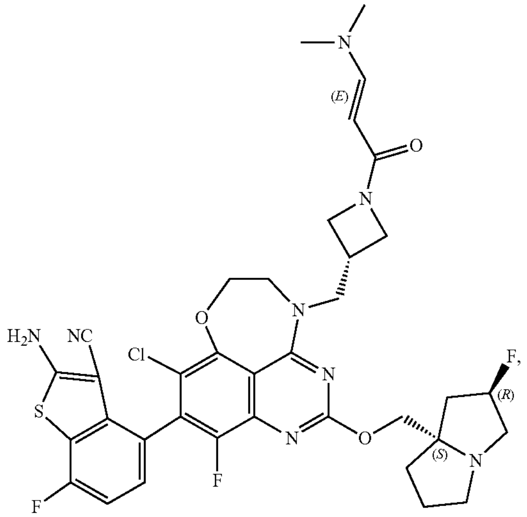
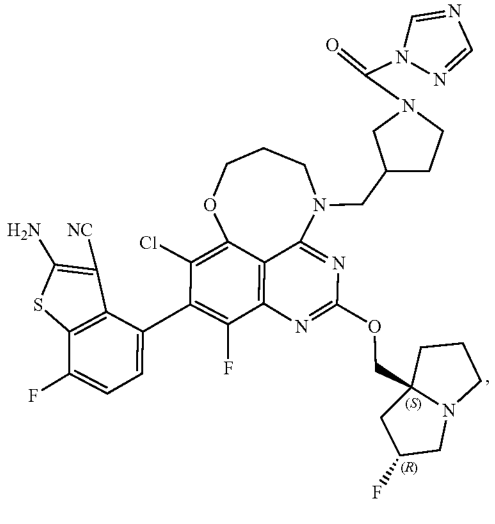

-continued
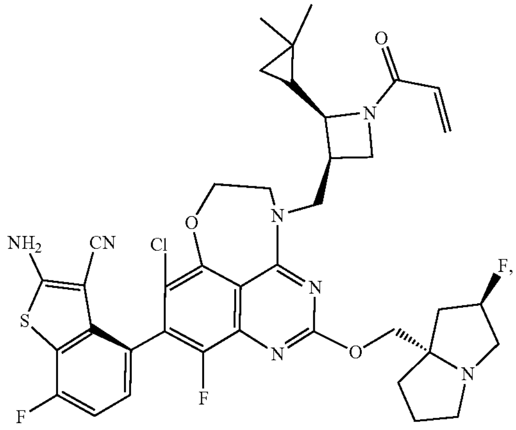
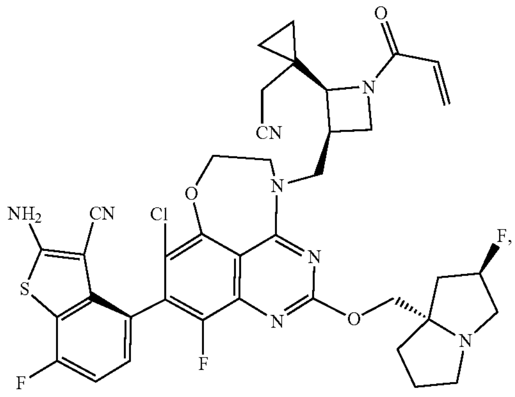
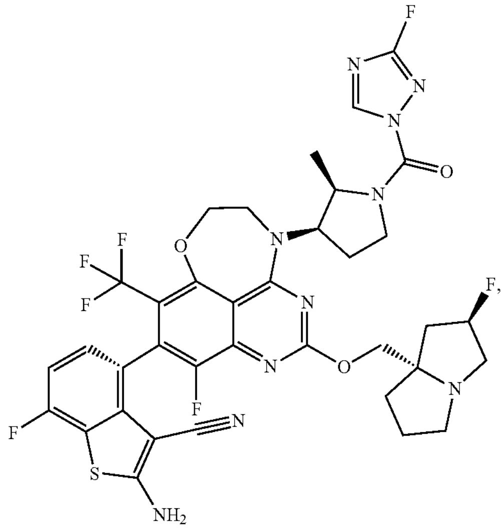
-continued
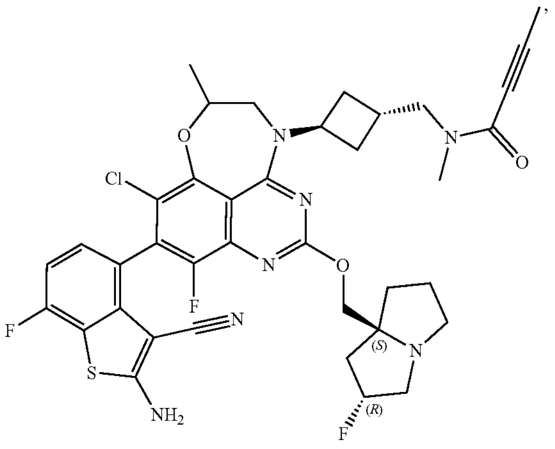
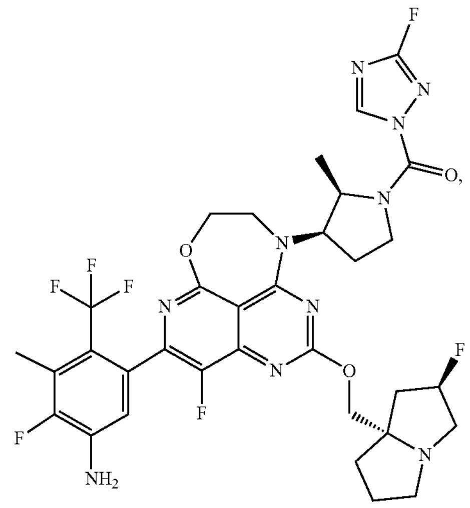
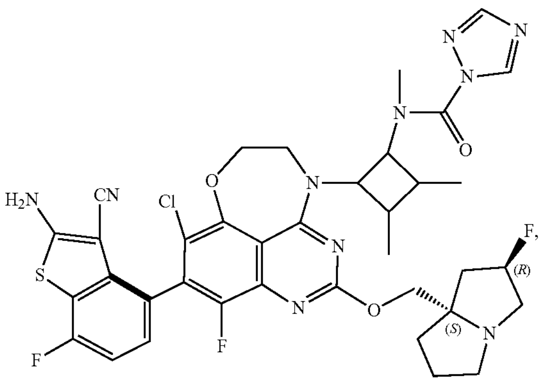

-continued
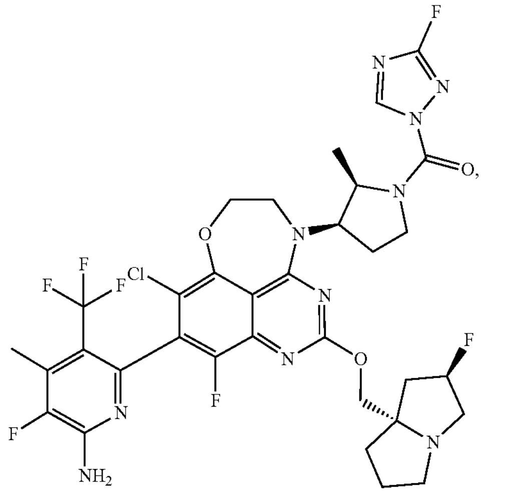
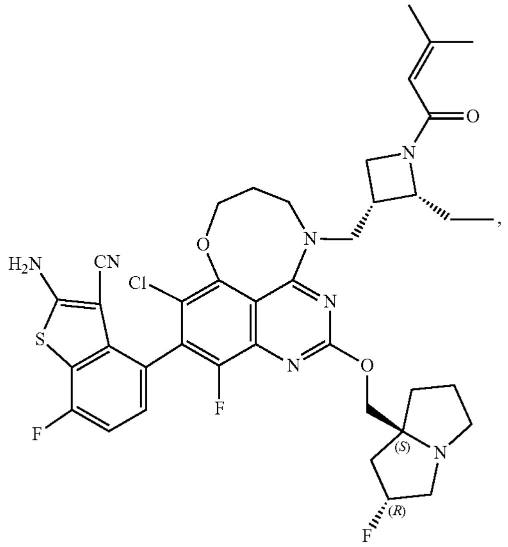
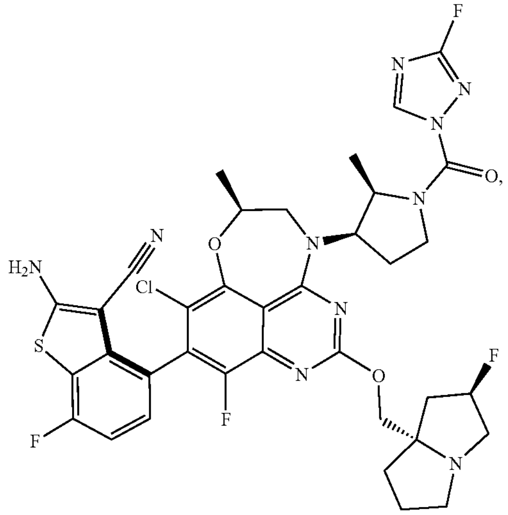
-continued
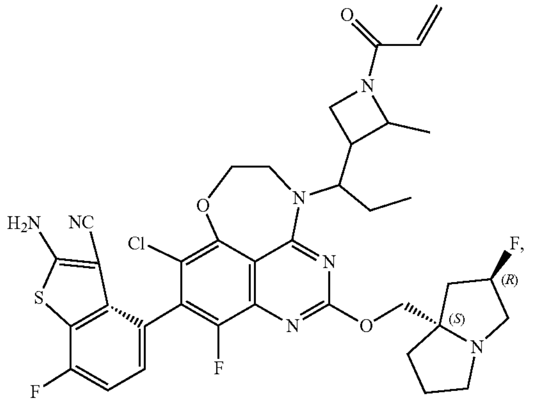
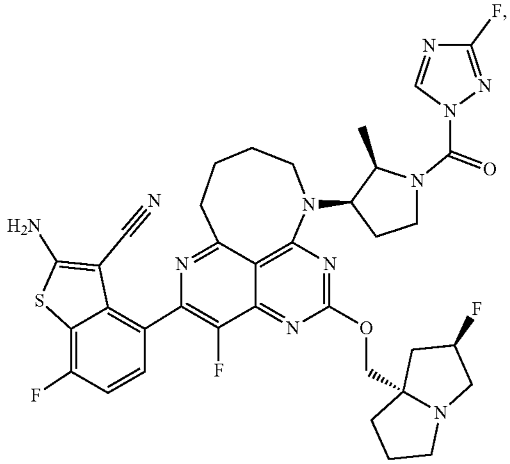
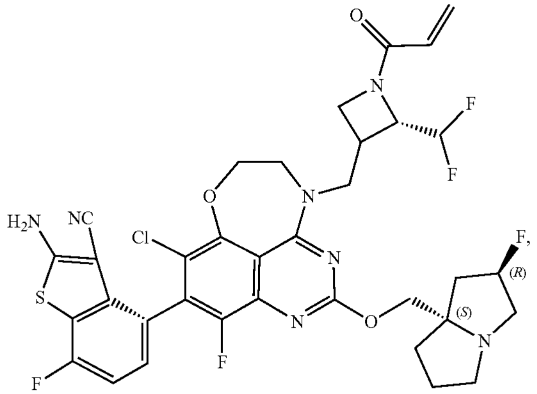

-continued
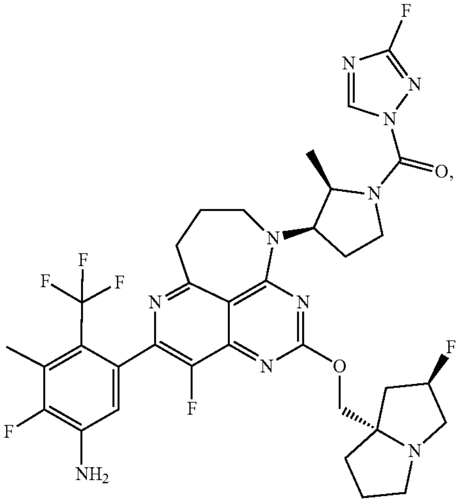
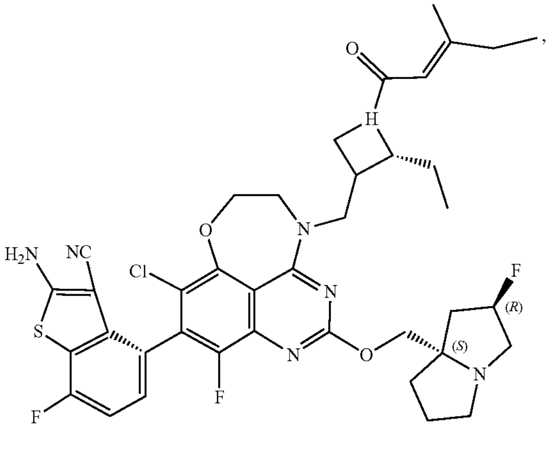
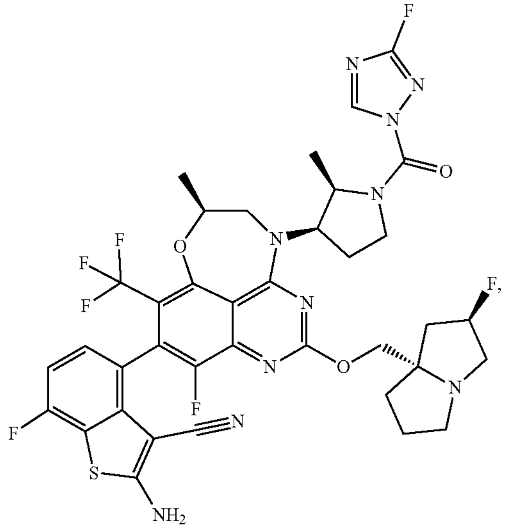
-continued
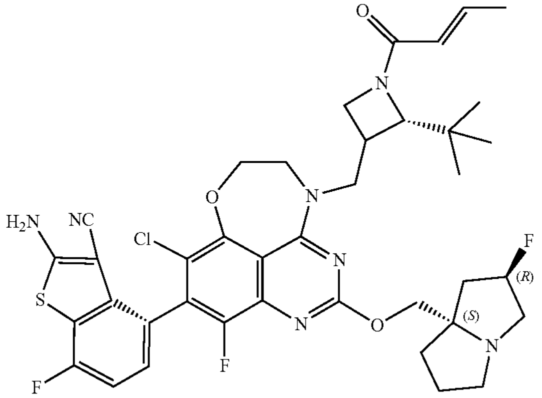
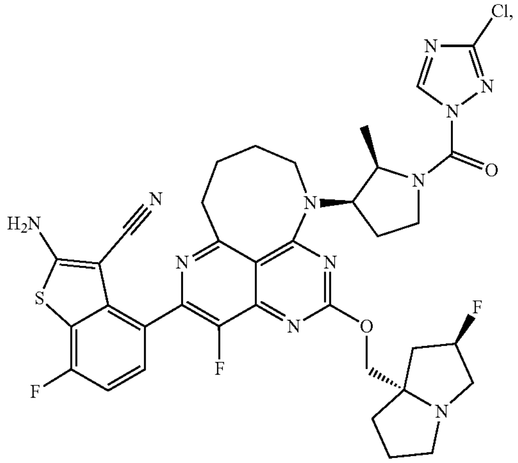
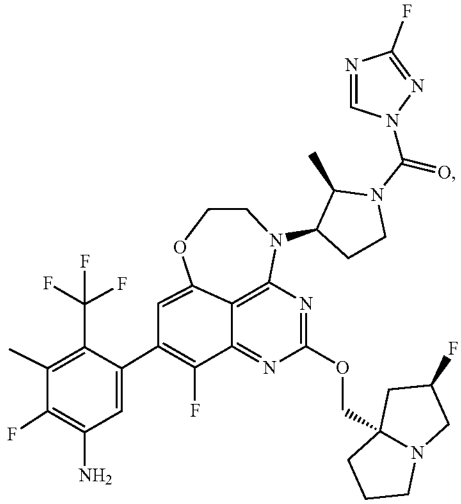
and -continued

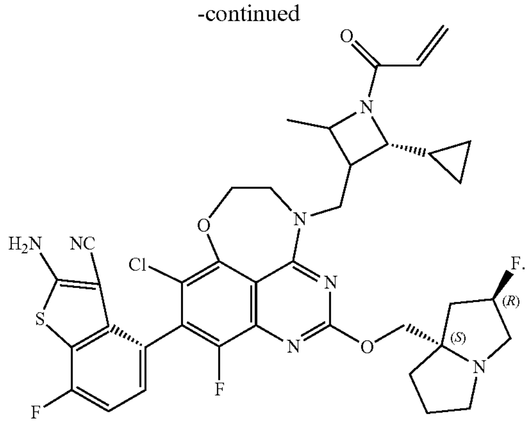

In some embodiments, a compound disclosed herein, such as a compound of Formula I, IA, IB, II, IIA, or V, exhibits selective and potent inhibition of K-Ras G12S relative to wildtype K-Ras or other K-Ras mutants (e.g., K-Ras G12V or K-Ras G12D). In some embodiments, a subject warhead exhibits selective engagement of K-Ras G12S relative to K-Ras G12D or wildtype K-Ras by at least 1-fold, and in some instances greater than 2-, 3-, 4-, 5-, 10-, 15-, or 20-fold, or even higher. In some embodiments, a subject warhead exhibits a selective and rapid engagement of K-Ras G12S yielding at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%, or even higher engagement of G12S within, 10 mins, 20 mins, 30 mins, 1 hr, 2 hrs, 3 hrs, 4 hrs, 5 hrs, 6 hrs, 7 hrs, 8 hrs, 9 hrs, 10 hrs, 20 hrs, or 24 hours. In some embodiments, a selective and rapid engagement of K-Ras G12S is evidenced by at least 50% engagement within 24 hours. In some embodiments, subject compounds specifically engage K-Ras G12S covalently with essentially no detectable labeling of K-Ras G12D when assayed under comparable conditions.

In some embodiments, a compound disclosed herein, such as a compound of Formula I, IA, IB, II, IIA, or V, exhibits selective and potent inhibition of wildtype K-Ras and K-Ras mutants (e.g., K-Ras G12D, K-Ras G12V, K-Ras G12S, and K-Ras G12C). In some embodiments, a subject warhead exhibits engagement of wildtype K-Ras in addition to K-Ras G12D, K-Ras G12V, K-Ras G12S, and K-Ras G12C (e.g., a pan K-Ras inhibitor). In some embodiments, a subject warhead exhibits rapid engagement of wildtype K-Ras, K-Ras G12D, K-Ras G12V, K-Ras G12S, and/or K-Ras G12C, yielding at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%, or even higher engagement of wildtype K-Ras, K-Ras G12D, K-Ras G12V, K-Ras G12S, and/or K-Ras G12C within, 10 mins, 20 mins, 30 mins, 1 hr, 2 hrs, 3 hrs, 4 hrs, 5 hrs, 6 hrs, 7 hrs, 8 hrs, 9 hrs, 10 hrs, 20 hrs, or 24 hours. In some embodiments, rapid engagement of wildtype K-Ras, K-Ras G12D, K-Ras G12V, K-Ras G12S, and/or K-Ras G12C is evidenced by at least 50% engagement within 24 hours.

The inclusion of a warhead of the present disclosure may enhance the efficacy or potency of K-Ras G12S inhibition. In some embodiments, a subject compound comprising a subject warhead inhibits K-Ras G12S with higher potency as evidenced by an IC50 value that is at least 10%, 20%, 50%, 100%, 200%, 300%, 400%, or at least 500% lower than the IC50 value of a corresponding control compound that does not comprise the warhead. In some embodiments, a subject compound comprising a subject warhead inhibits K-Ras G12S with higher potency as evidenced by an IC50 value that is at least 1.1-times, 1.2-times, 1.5-times, 2-times, 3-times, 4-times, 5-times, 6-times, 7-times, 8-times, 9-times, 10-times, 15-times, or at least 20-times lower than the IC50 value of a corresponding control compound that does not comprise the warhead, as ascertained in a biochemical assay exemplified in Example 5.

The inclusion of a warhead of the present disclosure may enhance the efficacy or potency with which a subject compound inhibits the proliferation of cells that express a K-Ras G12S mutation and/or a K-Ras G12C mutation. In some embodiments, a subject compound comprising a subject warhead inhibits the proliferation of cells that express a K-Ras G12S mutation and/or a K-Ras G12C mutation with higher potency as evidenced by an IC50 value that is at least 10%, 20%, 50%, 100%, 200%, 300%, 400%, or at least 500% lower than the IC50 value of a corresponding control compound that does not comprise the warhead. In some embodiments, a subject compound comprising a subject warhead inhibits the proliferation of cells that express a K-Ras G12S mutation and/or a K-Ras G12C mutation with higher potency as evidenced by an IC50 value that is at least 1.1-times, 1.2-times, 1.5-times, 2-times, 3-times, 4-times, 5-times, 6-times, 7-times, 8-times, 9-times, 10-times, 15-times, or at least 20-times lower than the IC50 value of a corresponding control compound that does not comprise the warhead, as ascertained in a cellular inhibition assay exemplified in Example 9.

In some embodiments, a compound described herein, such as a compound of Formula I, IA, IB, II, IIA, or V, is provided as a substantially pure stereoisomer. In some embodiments, the stereoisomer is provided in at least 80% enantiomeric excess, such as at least 85%, at least 90%, at least 95%, at least 96%, at least 97%, at least 98%, at least 99%, or at least 99.9% enantiomeric excess.

In some embodiments, the present disclosure provides an atropisomer of a compound described herein, such as a compound of Formula I, IA, IB, II, IIA, or V. In some embodiments, the atropisomer is provided in enantiomeric excess. In some embodiments, the atropisomer is provided in at least 80% enantiomeric excess, such as at least 85%, at least 90%, at least 95%, at least 96%, at least 97%, at least 98%, at least 99%, or at least 99.9% enantiomeric excess. In some embodiments, the compound or modified protein of Formula I, IA, IB, II, IIA, or V is preferably used as a non-racemic mixture, wherein one atropisomer is present in excess of its corresponding enantiomer or epimer. Typically, such mixture contains a mixture of the two isomers in a ratio of at least 9:1, preferably at least 19:1. In some embodiments, the atropisomer is provided in at least 96% enantiomeric excess, meaning the compound has less than 2% of the corresponding enantiomer. In some embodiments, the atropisomer is provided in at least 96% diastereomeric excess, meaning the compound has less than 2% of the corresponding diastereomer.

The term "atropisomers" refers to conformational stereoisomers which occur when rotation about a single bond in the molecule is prevented, restricted, or greatly slowed as a result of steric interactions with other parts of the molecule and wherein the substituents at both ends of the single bond are asymmetrical (i.e., optical activity arises without requiring an asymmetric carbon center or stereocenter). Where the rotational barrier about the single bond is high enough, and interconversion between conformations is slow enough, separation and isolation of the isomeric species may be permitted. Atropisomers are enantiomers (or epimers) without a single asymmetric atom. Atropisomers are typically considered stable if the barrier to interconversion is high enough to permit the atropisomers to undergo little or no interconversion at room temperature for a least a week, preferably at least a year. In some embodiments, an atropisomeric compound of the disclosure does not undergo more than about 5% interconversion to its opposite atropisomer at room temperature during one week when the atropisomeric compound is in substantially pure form, which is generally a solid state. In some embodiments, an atropisomeric compound of the disclosure does not undergo more than about 5% interconversion to its opposite atropisomer at room temperature (approximately 25° C.) during one year. The present chemical entities, pharmaceutical compositions, and methods are meant to include all such possible atropisomers, including racemic mixtures, diastereomeric mixtures, epimeric mixtures, optically pure forms of single atropisomers, and intermediate mixtures.

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases or inorganic or organic acids to form a pharmaceutically acceptable salt. In some embodiments, such salts are prepared in situ during the final isolation and purification of the compounds described herein, or by separately reacting a purified compound in its free form with a suitable acid or base, and isolating the salt thus formed.

In some embodiments, the compounds described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran, or MeOH. In addition, the compounds provided herein exist in unsolvated as well as solvated forms. In general, the solvated forms are considered equivalent to the unsolvated forms for the purposes of the compounds and methods provided herein.

It will be understood that two or more embodiments of a compound of a formula (e.g., compound of formula I, IA, IB, II, IIA, III, IVA, IVB and/or V) may be combined together (e.g., two separate embodiments of formula I reciting a first and second variable, respectively, may be combined) to yield one new embodiment. For example, a first embodiment of a compound of formula I, wherein $L^{19a}$ is C(O) maybe be combined with a separate second embodiment of a compound of formula I, wherein $R^{19a}$ is an unsubstituted triazole to result in a third embodiment of a compound of formula I, wherein $L^{19a}$ is C(O) and $R^{19a}$ is an unsubstituted triazole.

In certain aspects, the present disclosure provides a compound of the formula B-$L^{BE}$-E wherein:

B is a monovalent form of a compound described herein;

$L^{BE}$ is a covalent linker bonded to B and E; and

E is a monovalent form of a degradation enhancer.

A "degradation enhancer" is a compound capable of binding a ubiquitin ligase protein (e.g., E3 ubiquitin ligase protein) or a compound capable of binding a protein that is capable of binding to a ubiquitin ligase protein to form a protein complex capable of conjugating a ubiquitin protein to a target protein. In some embodiments, the degradation enhancer is capable of binding to an E3 ubiquitin ligase protein or a protein complex comprising an E3 ubiquitin ligase protein. In some embodiments, the degradation enhancer is capable of binding to an E2 ubiquitin-conjugating enzyme. In some embodiments, the degradation enhancer is capable of binding to a protein complex comprising an E2 ubiquitin-conjugating enzyme and an E3 ubiquitin ligase protein.

In some embodiments, the degradation enhancer is capable of binding a protein selected from E3A, mdm2, APC, EDD1, SOCS/BC-box/eloBC/CUL5/RING, LNXp80, CBX4, CBLL1, HACE1, HECTD1, HECTD2, HECTD3, HECTD4, HECW1, HECW2, HERC1, HERC2, HERC3, HERC4, HER5, HERC6, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE3D, UBE4A, UBE4B, UBOX5, UBR5, VHL (von-Hippel-Lindau ubiquitin ligase), WWP1, WWP2, Parkin, MKRN1, CMA (chaperon-mediated autophage), SCFb-TRCP (Skip-Cullin-F box (Beta-TRCP) ubiquitin complex), b-TRCP (b-transducing repeat-containing protein), cIAP1 (cellular inhibitor of apoptosis protein 1), APC/C (anaphase-promoting complex/cyclosome), CRBN (cereblon), CUL4-RBX1-DDB1-CRBN ($CRL4^{CRBN}$) ubiquitin ligase, XIAP, IAP, KEAP1, DCAF15, RNF114, DCAF16, AhR, SOCS2, KLHL12, UBR2, SPOP, KLHL3, KLHL20, KLHDC2, SPSB1, SPSB2, SPSB4, SOCS6, FBXO4, FBXO31, BTRC, FBW7, CDC20, PML, TRIM21, TRIM24, TRIM33, GID4, avadomide, iberdomide, and CC-885. In some embodiments, the degradation enhancer is capable of binding a protein selected from UBE2A, UBE2B, UBE2C, UBE2D1, UBE2D2, UBE2D3, UBE2DR, UBE2E1, UBE2E2, UBE2E3, UBE2F, UBE2G1, UBE2G2, UBE2H, UBE2I, UBE2J1, UBE2J2, UBE2K, UBE2L3, UBE2L6, UBE2L1, UBE2L2, UBE2L4, UBE2M, UBE2N, UBE20, UBE2Q1, UBE2Q2, $UBE2R^1$, $UBE2R^2$, UBE2S, UBE2T, UBE2U, UBE2V1, UBE2V2, UBE2W, UBE2Z, ATG3, BIRC6, and UFC1. In some embodiments, the degradation enhancer is a compound described in Ishida and Ciulli, SLAS Discovery 2021, Vol. 25(4) 484-502, which is incorporated by reference in its entirety for any purpose, for example VH032, VH101, VH298, thalidomide, bestatin, methyl bestatin, nutlin, idasanutlin, bardoxolone, bardoxolone methyl, indisulam (E7070), E7820, chloroquinoxaline sulfonamide (CQS), nimbolide, KB02, ASTX660, lenalidomide, or pomalidomide.

In some embodiments, the degradation enhancer is a compound described in US20180050021, WO2016146985, WO2018189554, WO2018119441, WO2018140809, WO2018119448, WO2018119357, WO2018118598, WO2018102067, WO201898280, WO201889736, WO201881530, WO201871606, WO201864589, WO201852949, WO2017223452, WO2017204445, WO2017197055, WO2017197046, WO2017180417, WO2017176958, WO201711371, WO2018226542, WO2018223909, WO2018189554, WO2016169989, WO2016146985, CN105085620B, CN106543185B, U.S. Ser. No. 10/040,804, U.S. Pat. No. 9,938,302, U.S. Ser. No. 10/144,745, U.S. Ser. No. 10/145,848, U.S. Pat. Nos. 9,938,264, 9,632,089, 9,821,068, 9,758,522, 9,500,653, 9,765,019, 8,507,488, 8,299,057, US20180298027, US20180215731, US20170065719, US20170037004, US20160272639, US20150291562, or US20140356322, each of which is incorporated by reference in its entirety for any purpose.

In some embodiments, $L^{BE}$ is $-L^{BE1}-L^{BE2}-L^{BE3}-L^{BE4}-L^{BE5}-$;

$L^{BE1}$, $L^{BE2}$, $L^{BE3}$, $L^{BE4}$, and $L^{BE5}$ are independently a bond, —O—, —N($R^{12}$)—, —C(O)—, —N($R^{12}$)C(O)—, —C(O)N($R^{12}$)—, —S—, —S$(O)_2$—, —S(O)—, —S$(O)_2$N($R^{12}$)—, —S(O)N($R^{12}$)—, —N($R^{12}$)S(O)—, —N($R^{12}$)S$(O)_2$—, $C_{1-6}$ alkylene, (—O—$C_{1-6}$ alkyl$)_z$-, (—$C_{1-6}$ alkyl-O$)_z$—, $C_{2-6}$ alkenylene, $C_{2-6}$ alkynylene, $C_{1-6}$ haloalkylene, $C_{3-12}$ cycloalkylene, $C_{1-6}$ heterocycloalkylene, $C_{6-12}$ arylene, or $C_{1-11}$ heteroarylene, wherein $C_{1-6}$ alkylene, $C_{2-6}$ alkenylene, $C_{2-6}$ alkynylene, $C_{1-6}$ haloalkylene, $C_{3-12}$ cycloalkylene, $C_{1-11}$ heterocycloalkylene, $C_{6-12}$ arylene, or $C_{1-11}$ heteroarylene are optionally substituted with one, two, or three $R^{20}$; and wherein each $C_{1-6}$ alkyl of (—O—$C_{1-6}$ alkyl$)_z$- and (—$C_{1-6}$ alkyl-O$)_z$— is optionally substituted with one, two, or three $R^{20}$; and z is independently an integer from 0 to 10.

In some embodiments, $L^{BE}$ is —(O—$C_2$ alkyl$)_z$- and z is an integer from 1 to 10. In some embodiments, $L^{BE}$ is —($C_2$ alkyl-O—$)_z$— and z is an integer from 1 to 10. In some embodiments, $L^{BE}$ is —$(CH_2)_{zz1}L^{BE2}(CH_2O)_{zz2}$—, wherein $L^{BE2}$ is a bond, a 5- or 6-membered heterocyclene, phenylene, —$C_{2-4}$ alkynylene, —$SO_2$— or —NH—; and zz1 and zz2 are independently an integer from 0 to 10. In some embodiments, $L^{BE}$ is —$(CH_2)_{zz1}(CH_2O)_{zz2}$—, wherein zz1 and zz2 are each independently an integer from 0 to 10. In some embodiments, $L^{BE}$ is a PEG linker (e.g., divalent linker of 1 to 10 ethylene glycol subunits). In some embodiments, E is a monovalent form of a compound selected from

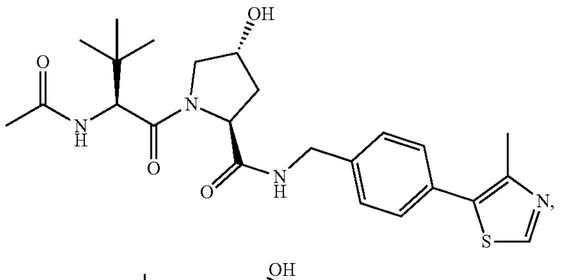

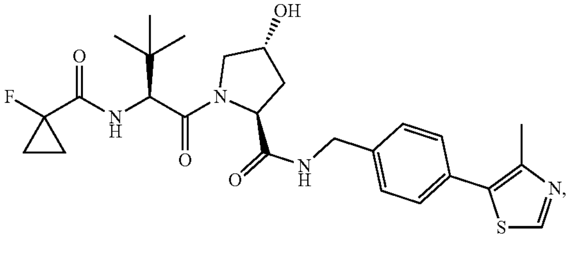

-continued

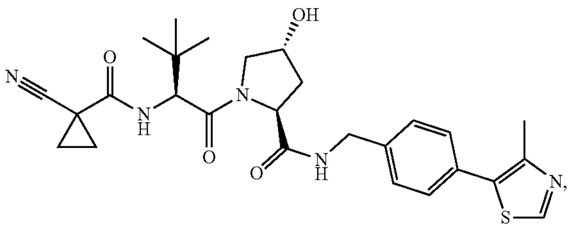

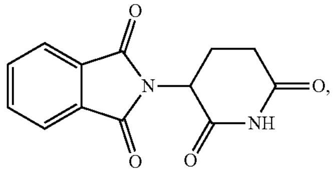

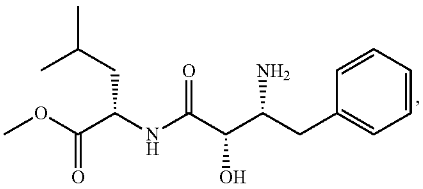

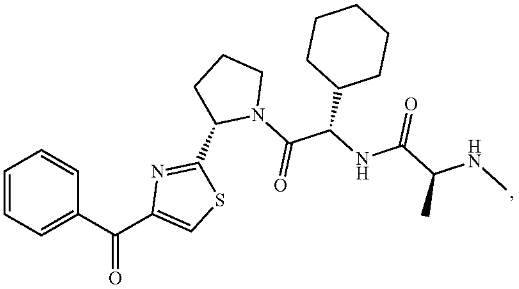

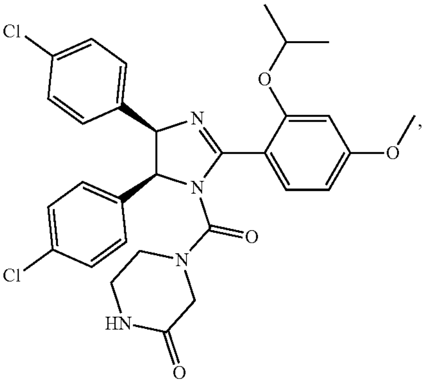

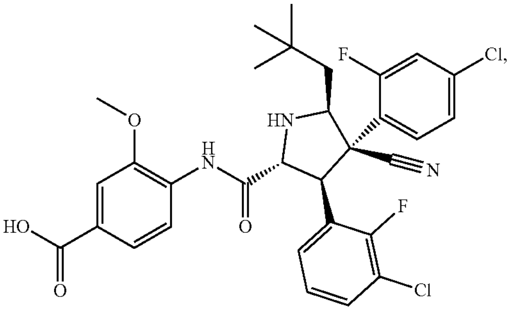

-continued
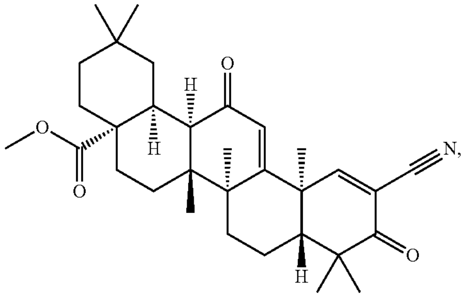
,
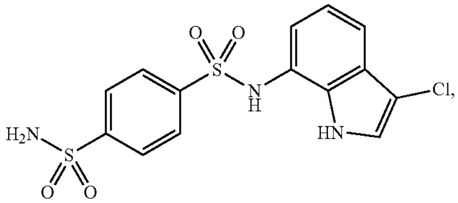
,
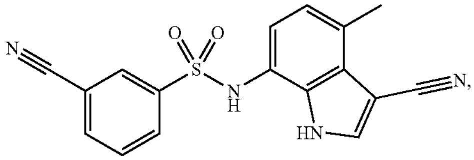
,
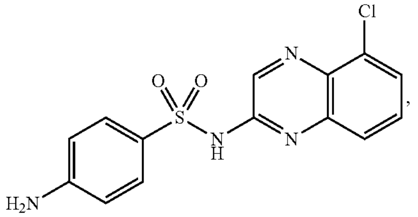
, and
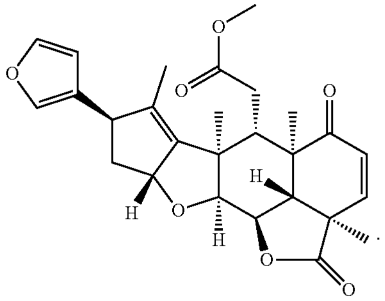
.
In embodiments, E is a monovalent form of a compound selected from
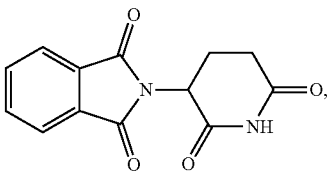
,
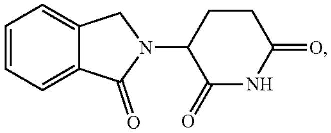
,
-continued
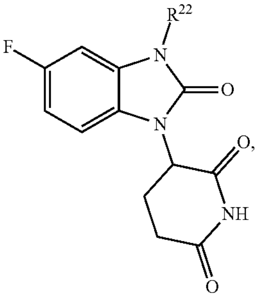
,
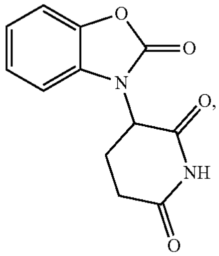
,
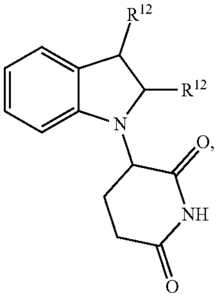
,
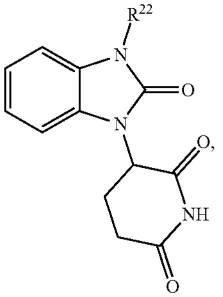
,
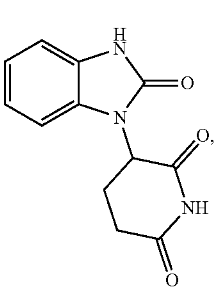
,
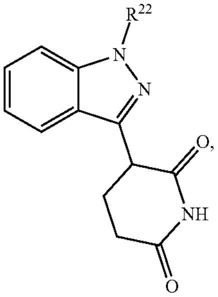
,
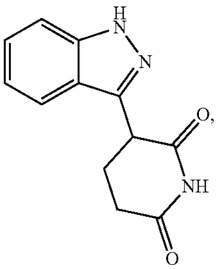
,
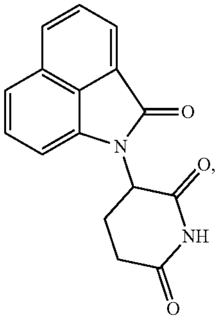
,
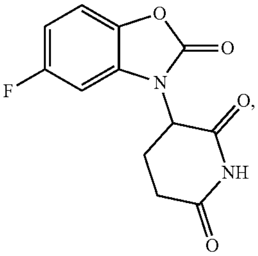
,
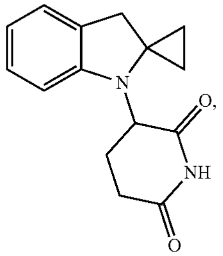
, -continued
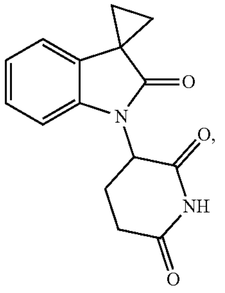
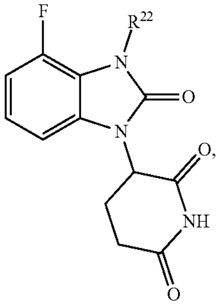
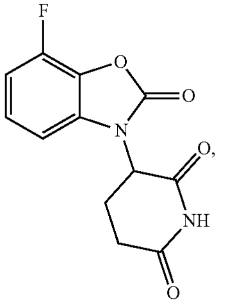
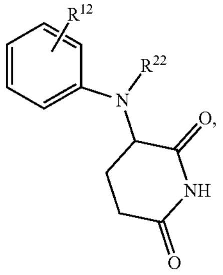
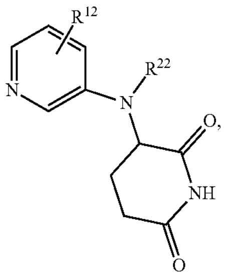
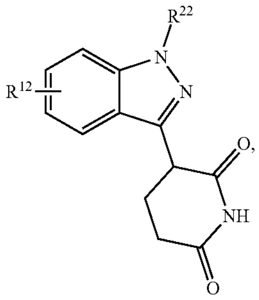
-continued
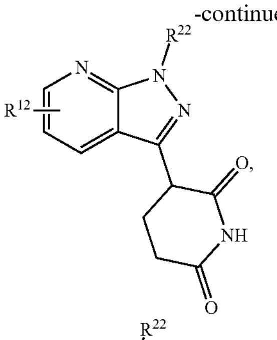
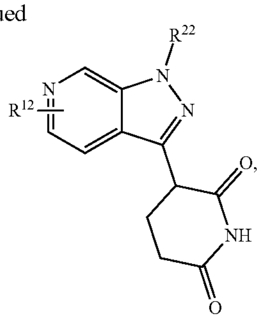
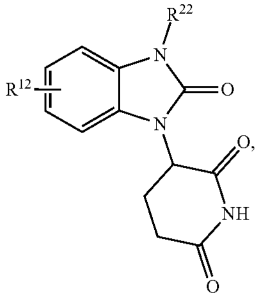
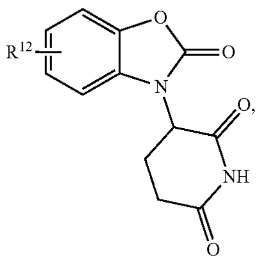
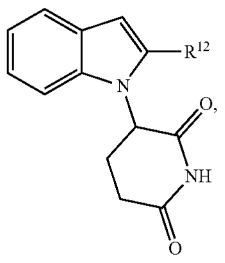
and
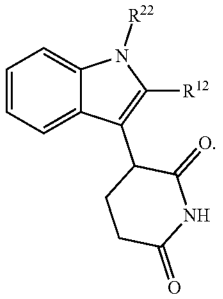
In some embodiments, the compound of formula B-$L^{BE}$-E is selected from
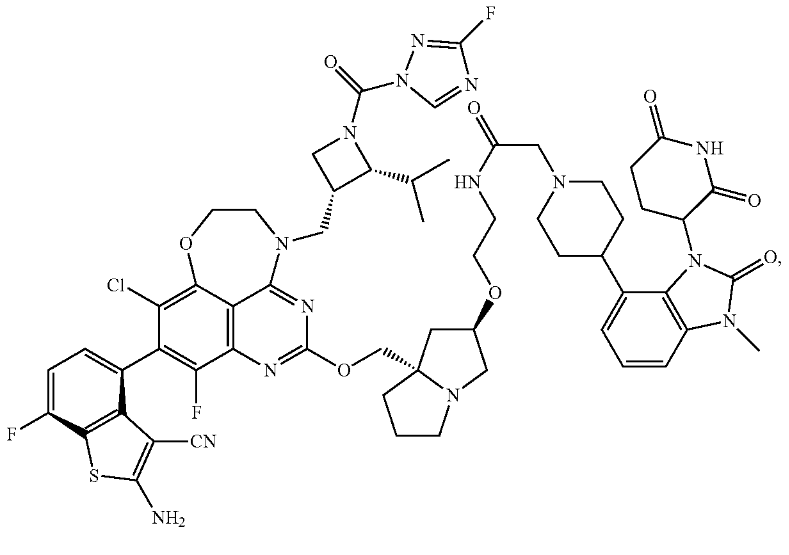

-continued
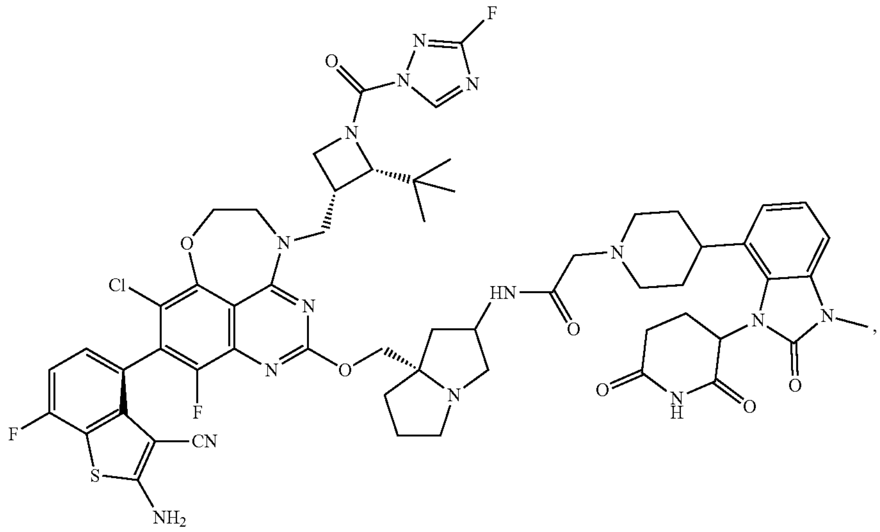
,
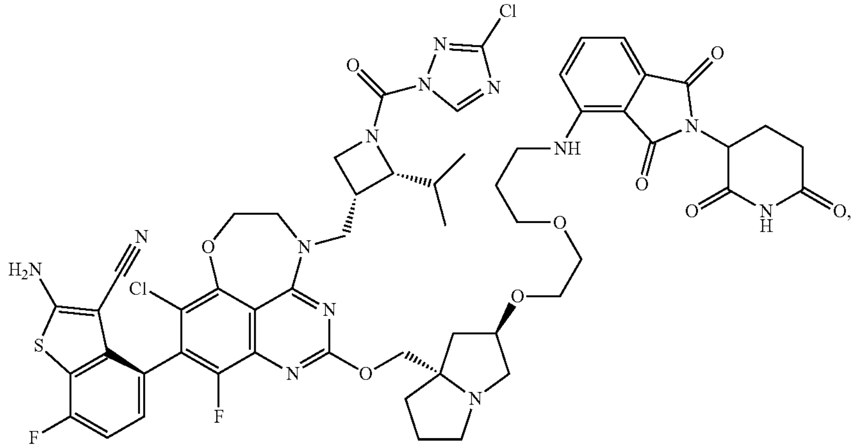
,
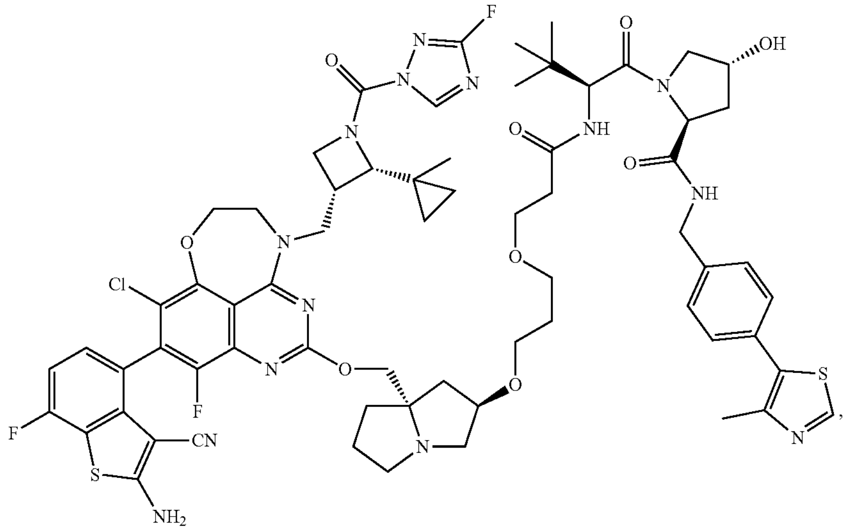
, and

-continued

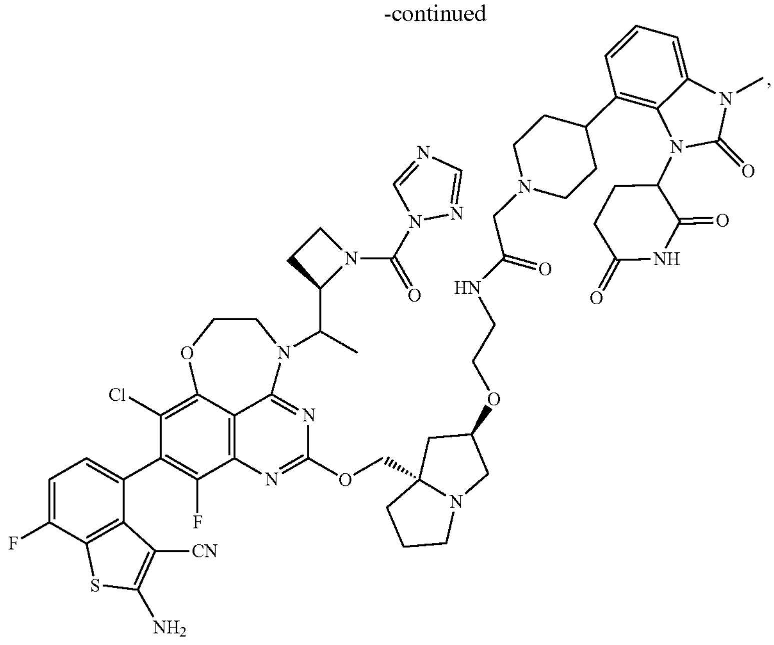

or a pharmaceutically acceptable salt or solvate thereof.

The chemical entities described herein can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes. Although various steps are described and depicted in Schemes 1 and 2, the steps in some cases may be performed in a different order than the order shown in Schemes 1 and 2. Various modifications to these synthetic reaction schemes may be made and will be suggested to one skilled in the art having referred to the present disclosure. Numberings or R groups in each scheme typically have the same meanings as those defined elsewhere herein unless otherwise indicated.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

In general, compounds of the disclosure may be prepared by the following reaction schemes:

Scheme 1

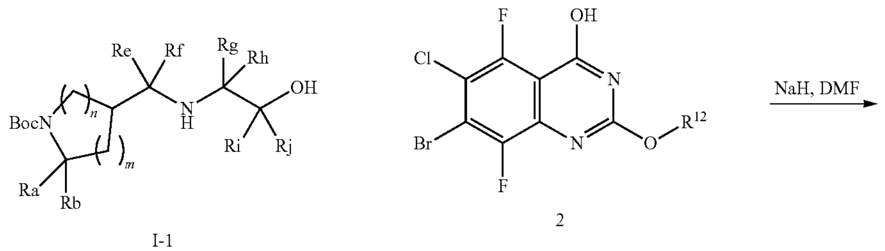

I-1 n = 0, 1, 2, 3, or 4
m = 0, 1, 2, 3, or 4

2

-continued
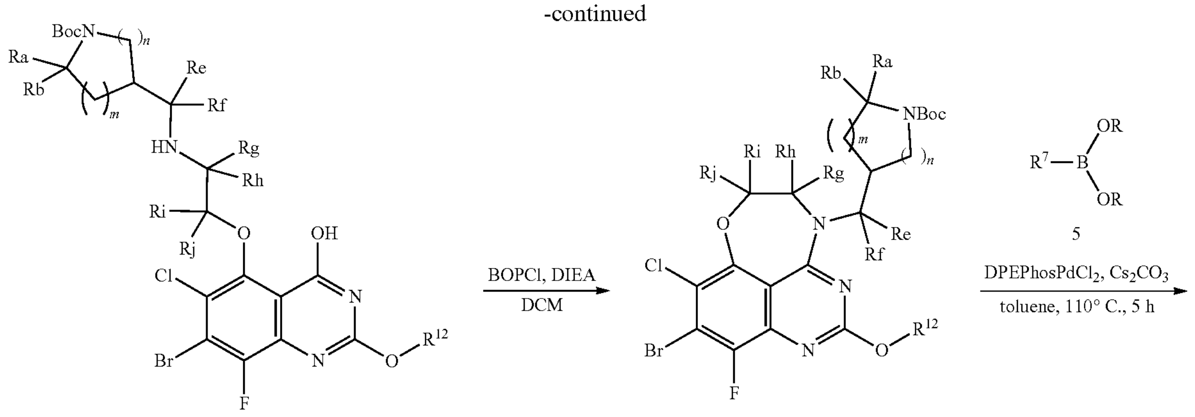
I-3 I-4 5
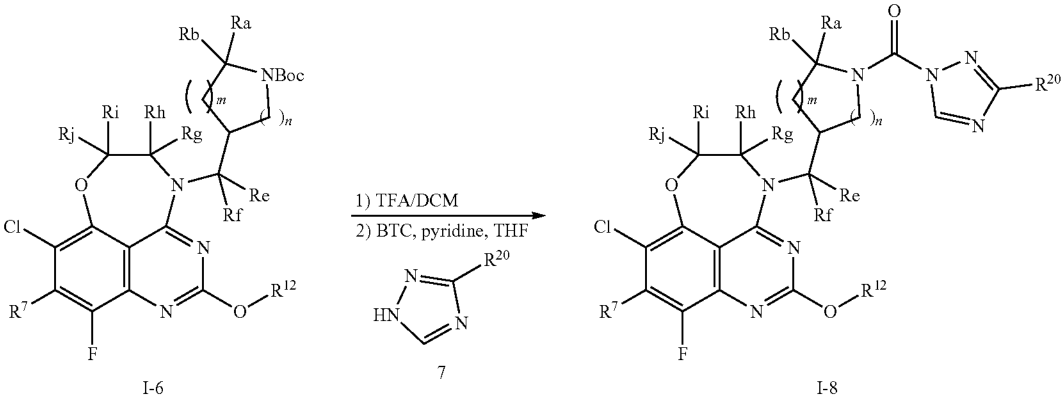
I-6 7 I-8
Scheme 2
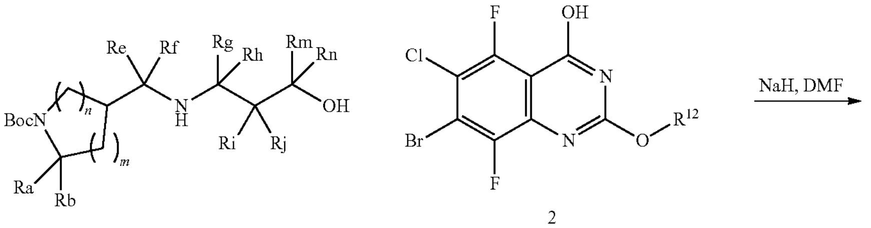
II-1 2
n = 0, 1, 2, 3, or 4
m = 0, 1, 2, 3, or 4

-continued
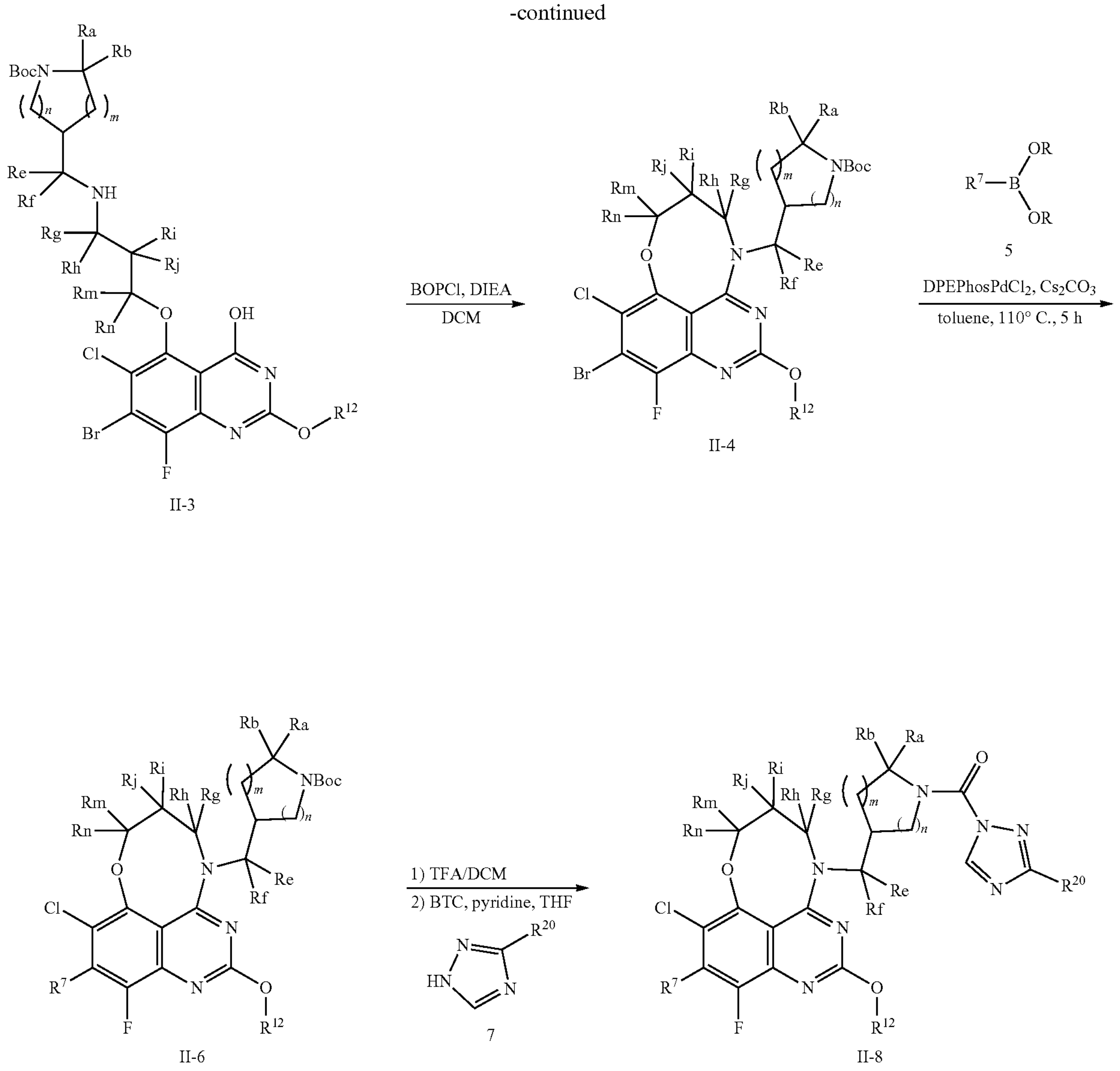
Scheme 3
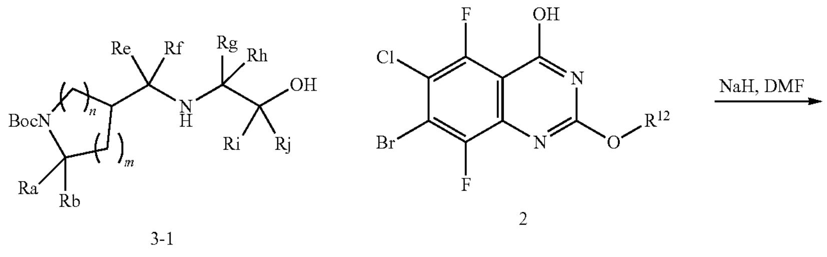
n = 0, 1, 2, 3, or 4
m = 0, 1, 2, 3, or 4

-continued
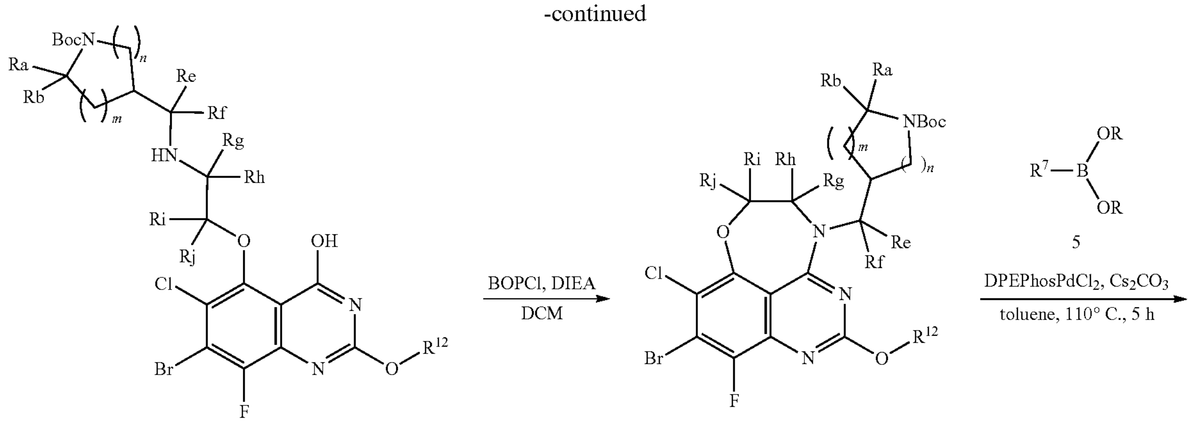
3-3 3-4 5
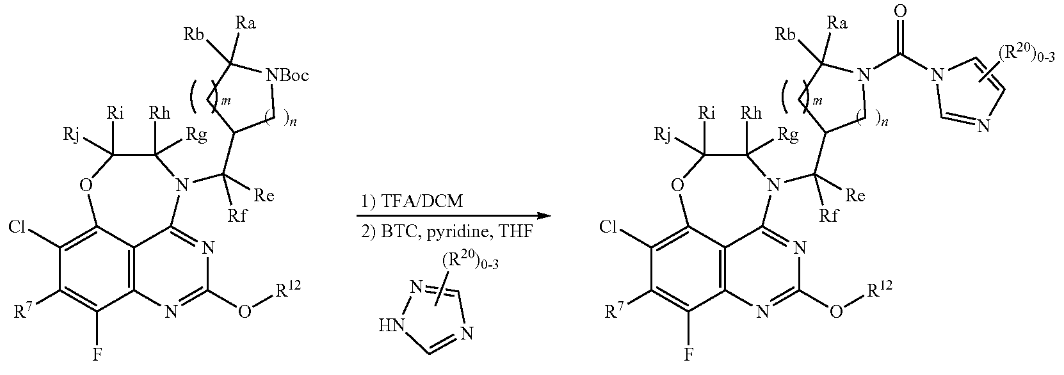
3-6 7 3-8
Scheme 4
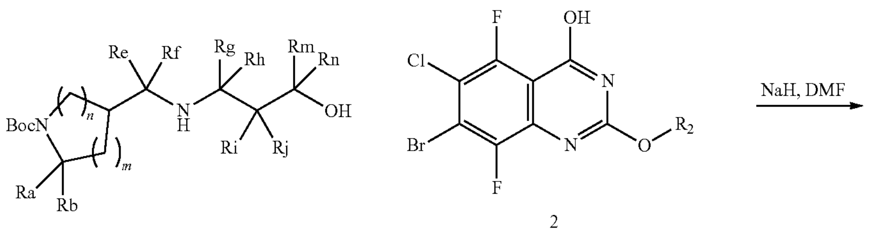
4-1 2
n = 0, 1, 2, 3, or 4
m = 0, 1, 2, 3, or 4

-continued

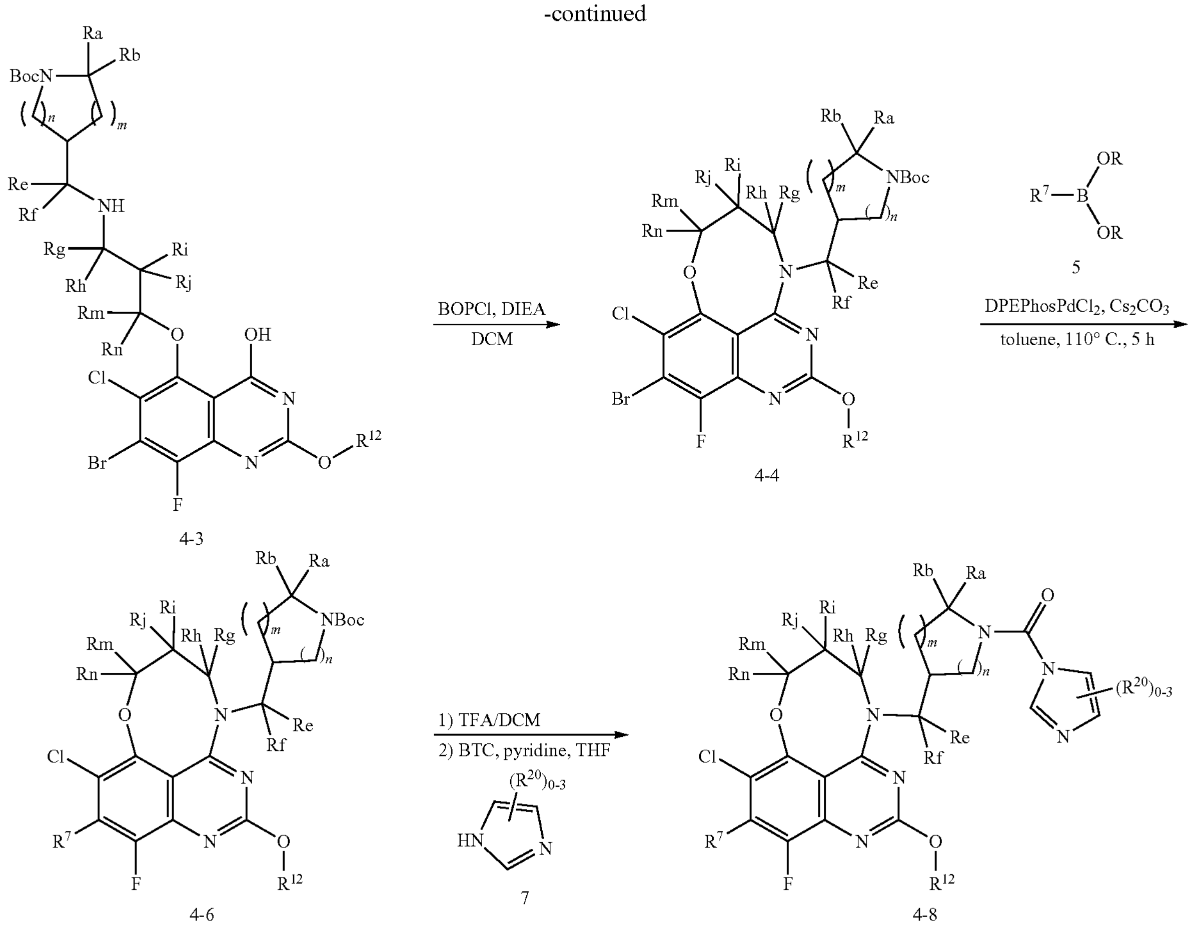

In some embodiments, a compound of Formula I, IA, IB, II, IIA, or V may be prepared according to Scheme 1 or 2. For example, addition of a substituent to bicyclic ring system, cyclization of the third ring of the ring system, and derivatization of one or more substituents of the tricyclic compound, to provide a compound of Formula I, IA, IB, II, IIA, or V.

In some embodiments, a compound of the present disclosure, for example, a compound of a formula given in Table 1, was synthesized according to one of the general routes outlined in Schemes 1 or 2, Example 1, or by methods generally known in the art. In some embodiments, exemplary compounds may include, but are not limited to, a compound selected from Table 1, or a salt or solvate thereof.

TABLE 1

| No. | Structure | Chemical Name | [M + H]+ |
|---|---|---|---|
| 401 | 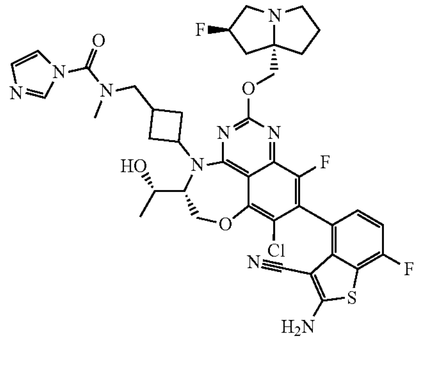 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1C1CC(CN(C)C(=O)n2ccnc2)C1] | N-((3-((5R)-9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-4-yl)cyclobutyl)methyl)-N-methyl-1H-imidazole-1-carboxamide | 822.2 |

TABLE 1-continued

| No. | Structure | Chemical Name | [M + H]+ |
| --- | --- | --- | --- |
| 402[4] | 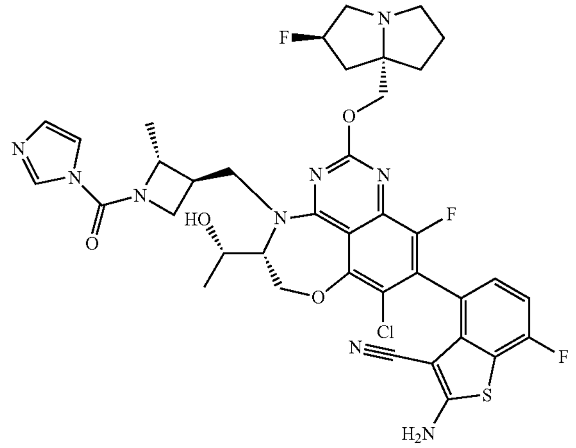 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1C[C@H]1CN(C(=O)n2ccnc2)[C@@H]1C] | 4-((5R)-4-(((2R,3S)-1-(1H-imidazole-1-carbonyl)-2-methylazetidin-3-yl)methyl)-8-chloro-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-9-yl)-2-amino-7-fluorobenzo[b]thiophene-3-carbonitrile | 808.2 |
| 403[4] | 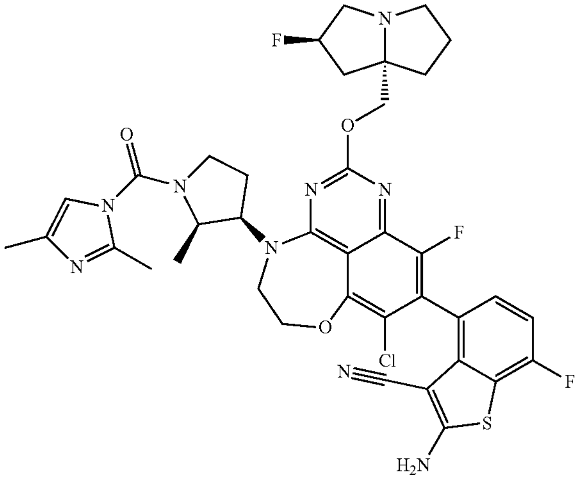 [SMILES: Cc1cn(C(=O)N2CC[C@@H](N3CCOc4c(Cl)c(-c5ccc(F)c6sc(N)c(C#N)c56)c(F)c5nc(OC[C@@]67CCCN6C[C@H](F)C7)nc3c45)[C@H]2C)c(C)n1] | 2-amino-4-(8-chloro-4-((2R,3R)-1-(2,4-dimethyl-1H-imidazole-1-carbonyl)-2-methylpyrrolidin-3-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 792.5 |
| 404[5] | 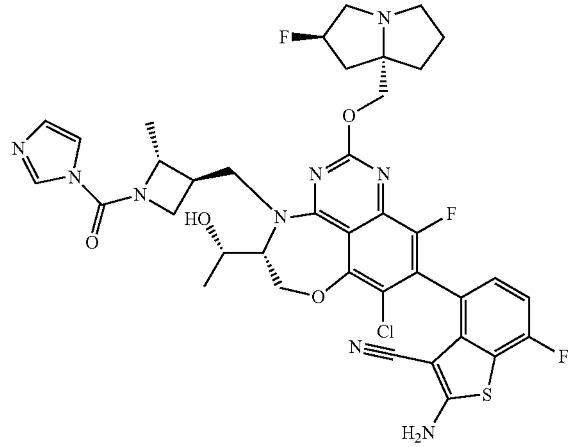 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1C[C@H]1CN(C(=O)n2ccnc2)[C@@H]1C] | 4-((5R)-4-(((2R,3S)-1-(1H-imidazole-1-carbonyl)-2-methylazetidin-3-yl)methyl)-8-chloro-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-9-yl)-2-amino-7-fluorobenzo[b]thiophene-3-carbonitrile | 808.2 |

TABLE 1-continued

| No. | Structure | Chemical Name | [M + H]+ |
|---|---|---|---|
| 405[1] | 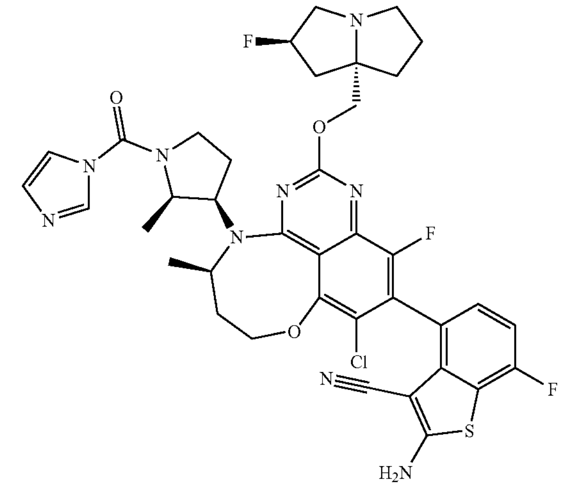 [SMILES: C[C@@H]1[C@H](N2c3nc(OC[C@@]45CCCN4C[C@H](F)C5)nc4c(F)c(-c5ccc(F)c6sc(N)c(C#N)c56)c(Cl)c(c34)OCC[C@H]2C)CCN1C(=O)n1ccnc1] | 4-((5R)-4-((2R,3R)-1-(1H-imidazole-1-carbonyl)-2-methylpyrrolidin-3-yl)-9-chloro-11-fluoro-2-(((2R,7aS)-2-fluorotetrahydro-1H-pyrrolizin-7a(5H)-yl)methoxy)-5-methyl-4,5,6,7-tetrahydro-[1,5]oxazocino[4,3,2-de]quinazolin-10-yl)-2-amino-7-fluorobenzo[b]thiophene-3-carbonitrile | 792.2 |
| 406[1] | 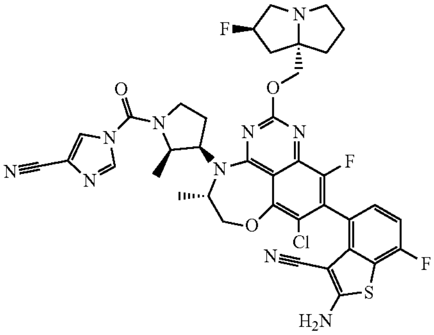 [SMILES: C[C@@H]1[C@H](N2c3nc(OC[C@@]45CCCN4C[C@H](F)C5)nc4c(F)c(-c5ccc(F)c6sc(N)c(C#N)c56)c(Cl)c(c34)OC[C@@H]2C)CCN1C(=O)n1cnc(C#N)c1] | 1-((2R,3R)-3-((5S)-9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5-methyl-5,6-dihydro-4H-[1,4]oxazepino[5,6,7-de]quinazolin-4-yl)-2-methylpyrrolidine-1-carbonyl)-1H-imidazole-4-carbonitrile | 803.2 |
| 407[4] | 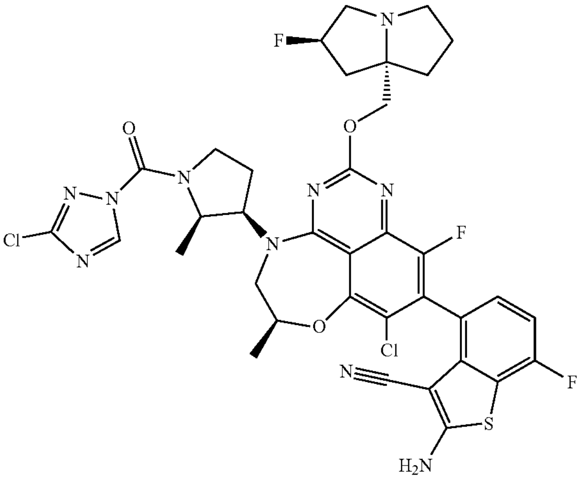 [SMILES: C[C@@H]1[C@H](N2C[C@H](C)Oc3c(Cl)c(-c4ccc(F)c5sc(N)c(C#N)c45)c(F)c4nc(OC[C@@]56CCCN5C[C@H](F)C6)nc2c34)CCN1C(=O)n1cnc(Cl)n1] | 2-amino-4-((6S)-8-chloro-4-((2R,3R)-1-(3-chloro-1H-1,2,4-triazole-1-carbonyl)-2-methylpyrrolidin-3-yl)-10-fluoro-2-(((2R,7aS)-2-fluorotetrahydro-1H-pyrrolizin-7a(5H)-yl)methoxy)-6-methyl-5,6-dihydro-4H-[1,4]oxazepino[5,6,7-de]quinazolin-9-yl)-7-fluorobenzo[b]thiophene-3-carbonitrile | 813.3 |

TABLE 1-continued

| No. | Structure | Chemical Name | [M + H]+ |
| --- | --- | --- | --- |
| 408[3] | 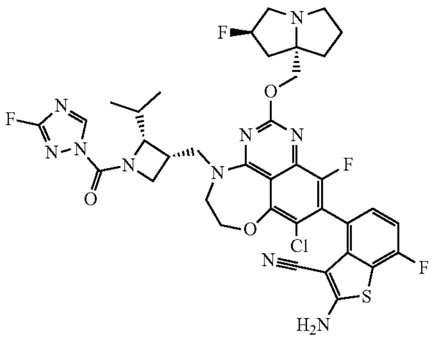 [SMILES: CC(C)[C@@H]1[C@H](CN2CCOc3c(Cl)c(-c4ccc(F)c5sc(N)c(C#N)c45)c(F)c4nc(OC[C@@]56CCCN5C[C@H](F)C6)nc2c34)CN1C(=O)n1cnc(F)n1] | 2-amino-4-(8-chloro-10-fluoro-4-(((2R,3R)-1-(3-fluoro-1H-1,2,4-triazole-1-carbonyl)-2-isopropylazetidin-3-yl) methyl)-2-(((2R,7aS)-2-fluorotetrahydro-1H-pyrrolizin-7a(5H)-yl) methoxy)-5,6-dihydro-4H-[1,4]oxazepino[5,6,7-de] quinazolin-9-yl)-7-fluorobenzo[b]thiophene-3-carbonitrile | 811.3 |
| 409 | 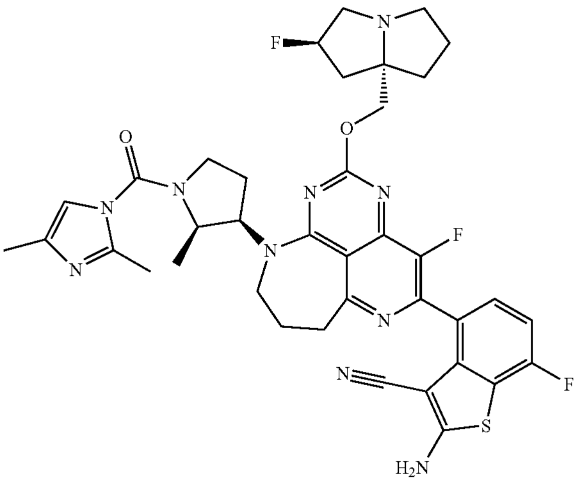 [SMILES: Cc1cn(C(=O)N2CC[C@@H](N3CCCc4nc(-c5ccc(F)c6sc(N)c(C#N)c56)c(F)c5nc(OC[C@@]67CCCN6C[C@H](F)C7)nc3c45)[C@H]2C)c(C)n1] | 2-amino-4-(10-((2R,3R)-1-(2,4-dimethyl-1H-imidazole-1-carbonyl)-2-methylpyrrolidin-3-yl)-4-fluoro-2-(((2R,7aS)-2-fluorotetrahydro-1H-pyrrolizin-7a(5H)-yl) methoxy)-7,8,9,10-tetrahydro-1,3,6,10-tetraazacyclohepta[de] naphthalen-5-yl)-7-fluorobenzo[b]thiophene-3-carbonitrile | 757.5 |
| 410[5] | 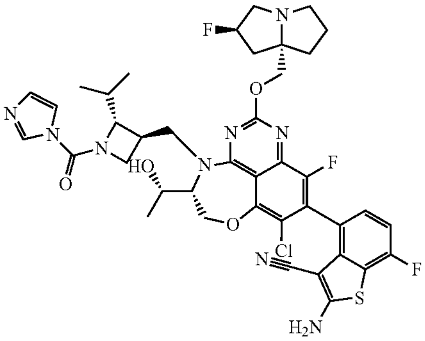 [SMILES: CC(C)[C@@H]1[C@@H](CN2c3nc(OC[C@@]45CCCN4C[C@H](F)C5)nc4c(F)c(-c5ccc(F)c6sc(N)c(C#N)c56)c(Cl)c(c34)OC[C@@H]2[C@H](C)O)CN1C(=O)n1ccnc1] | 4-((5R)-4-(((2R,3S)-1-(1H-imidazole-1-carbonyl)-2-isopropylazetidin-3-yl) methyl)-8-chloro-10-fluoro-2-(((2R,7aS)-2-fluorotetrahydro-1H-pyrrolizin-7a(5H)-yl) methoxy)-5-((S)-1-hydroxyethyl)-5,6-dihydro-4H-[1,4]oxazepino[5,6,7-de] quinazolin-9-yl)-2-amino-7-fluorobenzo[b]thiophene-3-carbonitrile | 836.2 |

TABLE 1-continued

| No. | Structure | Chemical Name | [M + H]+ |
| --- | --- | --- | --- |
| 411[1] | 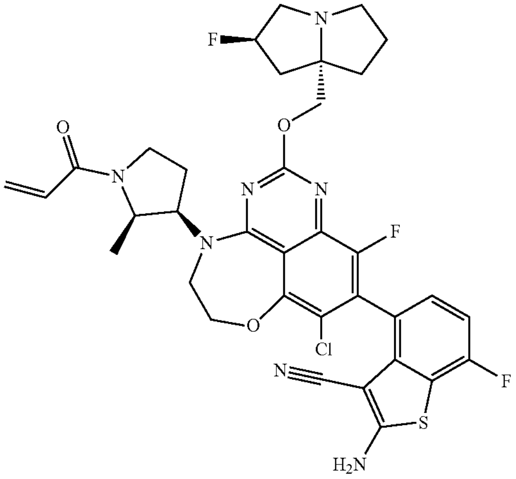 [SMILES: C=CC(=O)N1CC[C@@H](N2CCOc3c(Cl)c(-c4ccc(F)c5sc(N)c(C#N)c45)c(F)c4nc(OC[C@@]56CCCN5C[C@H](F)C6)nc2c34)[C@H]1C] | 4-(4-((2R,3R)-1-acryloyl-2-methylpyrrolidin-3-yl)-9-chloro-11-fluoro-2-(((2R,7aS)-2-fluorotetrahydro-1H-pyrrolizin-7a(5H)-yl) methoxy)-4,5,6,7-tetrahydro-[1,5]oxazocino[4,3,2-de] quinazolin-10-yl)-2-amino-7-fluorobenzo[b]thiophene-3-carbonitrile | 738.3 |
| 412[2,5] | 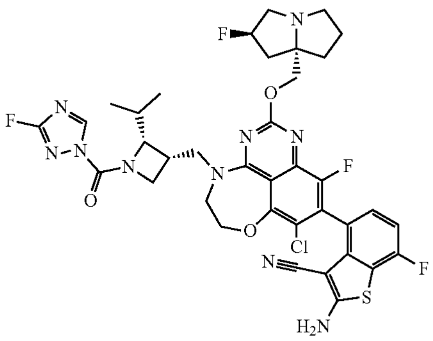 [SMILES: CC(C)[C@@H]1[C@H](CN2CCOc3c(Cl)c(-c4ccc(F)c5sc(N)c(C#N)c45)c(F)c4nc(OC[C@@]56CCCN5C[C@H](F)C6)nc2c34)CN1C(=O)n1cnc(F)n1] | 2-amino-4-(8-chloro-10-fluoro-4-(((2R,3R)-1-(3-fluoro-1H-1,2,4-triazole-1-carbonyl)-2-isopropylazetidin-3-yl) methyl)-2-(((2R,7aS)-2-fluorotetrahydro-1H-pyrrolizin-7a(5H)-yl) methoxy)-5,6-dihydro-4H-[1,4]oxazepino[5,6,7-de] quinazolin-9-yl)-7-fluorobenzo[b]thiophene-3-carbonitrile | 811.3 |
| 413[7] | 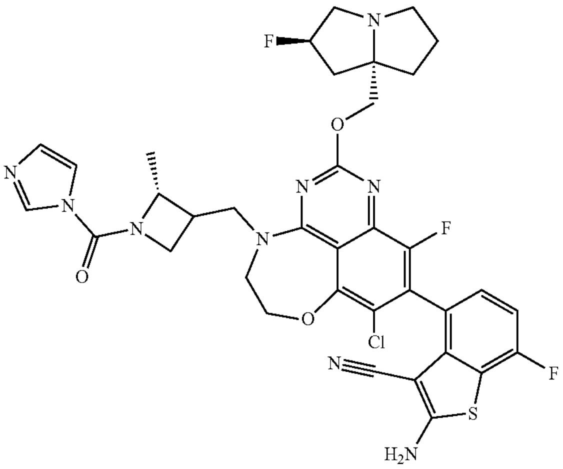 [SMILES: C[C@@H]1C(CN2CCOc3c(Cl)c(-c4ccc(F)c5sc(N)c(C#N)c45)c(F)c4nc(OC[C@@]56CCCN5C[C@H](F)C6)nc2c34)CN1C(=O)n1ccnc1] | 4-(4-(((2R)-1-(1H-imidazole-1-carbonyl)-2-methylazetidin-3-yl)methyl)-8-chloro-10-fluoro-2-(((2R,7aS)-2-fluorotetrahydro-1H-pyrrolizin-7a(5H)-yl) methoxy)-5,6-dihydro-4H-[1,4]oxazepino[5,6,7-de] quinazolin-9-yl)-2-amino-7-fluorobenzo[b]thiophene-3-carbonitrile | 764.2 |

TABLE 1-continued

| No. | Structure | Chemical Name | [M + H]+ |
|---|---|---|---|
| 414[7] | 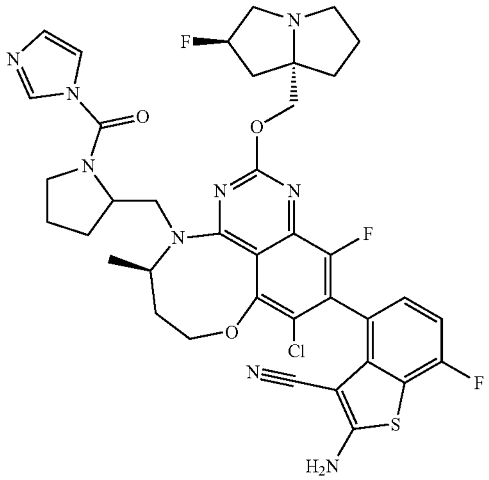 [SMILES: C[C@@H]1CCOc2c(Cl)c(-c3ccc(F)c4sc(N)c(C#N)c34)c(F)c3nc(OC[C@@]45CCCN4C[C@H](F)C5)nc(c23)N1CC1CCCN1C(=O)n1ccnc1] | 4-((5R)-4-((1-(1H-imidazole-1-carbonyl)pyrrolidin-2-yl)methyl)-9-chloro-11-fluoro-2-(((2R,7aS)-2-fluorotetrahydro-1H-pyrrolizin-7a(5H)-yl)methoxy)-5-methyl-4,5,6,7-tetrahydro-[1,5]oxazocino[4,3,2-de]quinazolin-10-yl)-2-amino-7-fluorobenzo[b]thiophene-3-carbonitrile | 792.2 |
| 415 | 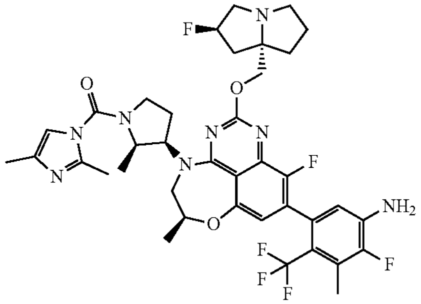 [SMILES: Cc1cn(C(=O)N2CC[C@@H](N3C[C@H](C)Oc4cc(-c5cc(N)c(F)c(C)c5C(F)(F)F)c(F)c5nc(OC[C@@]67CCCN6C[C@H](F)C7)nc3c45)[C@H]2C)c(C)n1] | ((2R,3R)-3-((S)-9-(5-amino-4-fluoro-3-methyl-2-(trifluoromethyl)phenyl)-10-fluoro-2-(((2R,7aS)-2-fluorotetrahydro-1H-pyrrolizin-7a(5H)-yl)methoxy)-6-methyl-5,6-dihydro-4H-[1,4]oxazepino[5,6,7-de]quinazolin-4-yl)-2-methylpyrrolidin-1-yl)(2,4-dimethyl-1H-imidazol-1-yl)methanone | 759.6 |
| 416[2,5] | 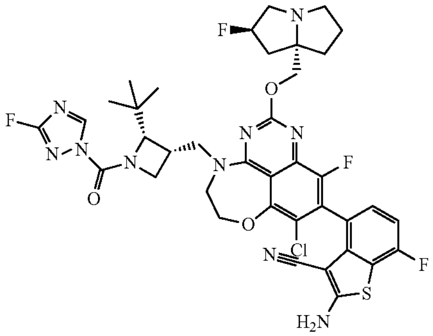 [SMILES: CC(C)(C)[C@@H]1[C@H](CN2CCOc3c(Cl)c(-c4ccc(F)c5sc(N)c(C#N)c45)c(F)c4nc(OC[C@@]56CCCN5C[C@H](F)C6)nc2c34)CN1C(=O)n1cnc(F)n1] | 2-amino-4-(4-(((2S,3R)-2-(tert-butyl)-1-(3-fluoro-1H-1,2,4-triazole-1-carbonyl)azetidin-3-yl)methyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 825.3 |
| 417[7] | 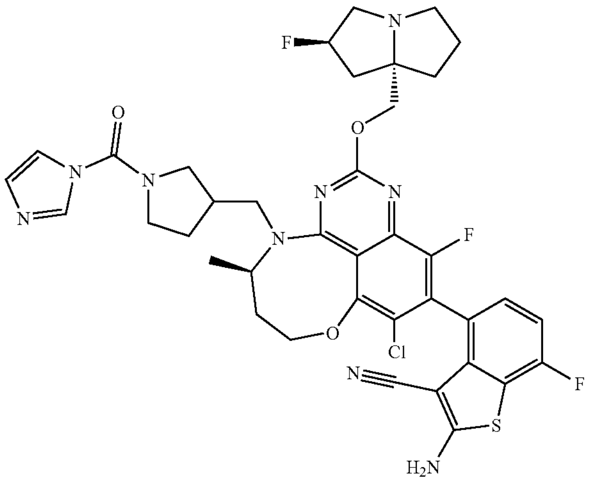 [SMILES: C[C@@H]1CCOc2c(Cl)c(-c3ccc(F)c4sc(N)c(C#N)c34)c(F)c3nc(OC[C@@]45CCCN4C[C@H](F)C5)nc(c23)N1CC1CCN(C(=O)n2ccnc2)C1] | 4-((5R)-4-((1-(1H-imidazole-1-carbonyl)pyrrolidin-3-yl)methyl)-9-chloro-11-fluoro-2-(((2R,7aS)-2-fluorotetrahydro-1H-pyrrolizin-7a(5H)-yl)methoxy)-5-methyl-4,5,6,7-tetrahydro-[1,5]oxazocino[4,3,2-de]quinazolin-10-yl)-2-amino-7-fluorobenzo[b]thiophene-3-carbonitrile | 792.2 |

TABLE 1-continued

| No. | Structure | Chemical Name | [M + H]+ |
|---|---|---|---|
| 418[1] | 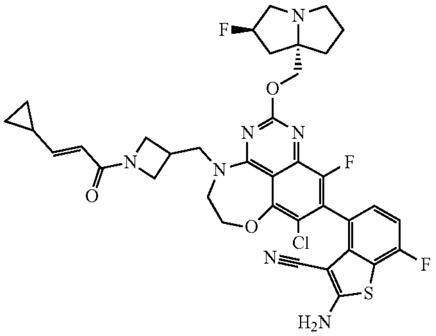 [SMILES: N#Cc1c(N)sc2c(F)ccc(-c3c(Cl)c4c5c(nc(OC[C@@]67CCCN6C[C@H](F)C7)nc5c3F)N(CC3CN(C(=O)/C=C/C5CC5)C3)CCO4)c12] | 2-amino-4-(8-chloro-4-((1-((E)-3-cyclopropylacryloyl)azetidin-3-yl)methyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 750.2 |
| 419[6,7] | 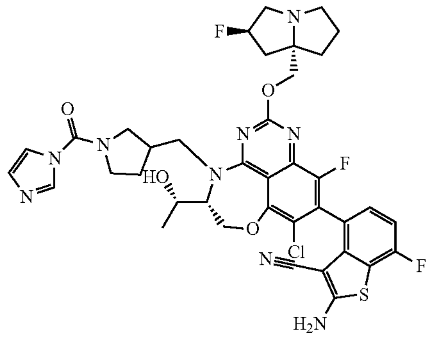 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1CC1CCN(C(=O)n2ccnc2)C1] | 4-((5R)-4-((1-(1H-imidazole-1-carbonyl)pyrrolidin-3-yl)methyl)-8-chloro-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-9-yl)-2-amino-7-fluorobenzo[b]thiophene-3-carbonitrile | 808.2 |
| 420[3] | 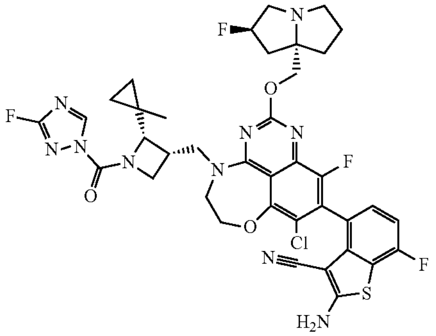 [SMILES: CC1([C@@H]2[C@H](CN3CCOc4c(Cl)c(-c5ccc(F)c6sc(N)c(C#N)c56)c(F)c5nc(OC[C@@]67CCCN6C[C@H](F)C7)nc3c45)CN2C(=O)n2cnc(F)n2)CC1] | 2-amino-4-(8-chloro-10-fluoro-4-(((2S,3R)-1-(3-fluoro-1H-1,2,4-triazole-1-carbonyl)-2-(1-methylcyclopropyl)azetidin-3-yl)methyl)-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 823.3 |
| 421[4] | 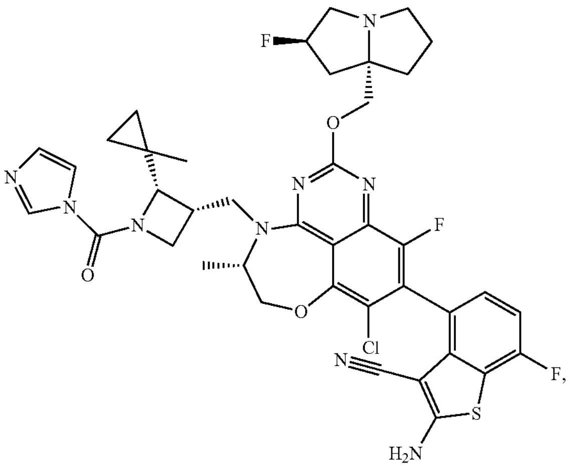 [SMILES: C[C@H]1COc2c(Cl)c(-c3ccc(F)c4sc(N)c(C#N)c34)c(F)c3nc(OC[C@@]45CCCN4C[C@H](F)C5)nc(c23)N1C[C@@H]1CN(C(=O)n2ccnc2)[C@@H]1C1(C)CC1], | 4-((5S)-4-(((2S,3R)-1-(1H-imidazole-1-carbonyl)-2-(1-methylcyclopropyl)azetidin-3-yl)methyl)-8-chloro-10-fluoro-2-(((2R,7aS)-2-fluorotetrahydro-1H-pyrrolizin-7a(5H)-yl)methoxy)-5-methyl-5,6-dihydro-4H-[1,4]oxazepino[5,6,7-de]quinazolin-9-yl)-2-amino-7-fluorobenzo[b]thiophene-3-carbonitrile | 818.2 |

TABLE 1-continued

| No. | Structure | Chemical Name | [M + H]+ |
|---|---|---|---|
| 422[4] | 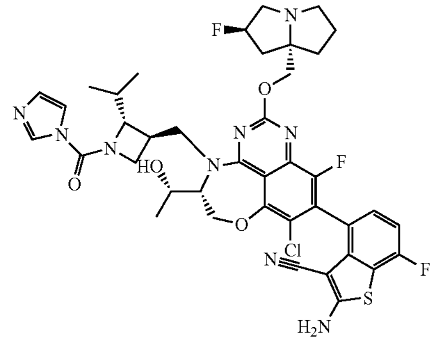 [SMILES: CC(C)[C@@H]1[C@@H](CN2c3nc(OC[C@@]45CCCN4C[C@H](F)C5)nc4c(F)c(-c5ccc(F)c6sc(N)c(C#N)c56)c(Cl)c(c34)OC[C@@H]2[C@H](C)O)CN1C(=O)n1ccnc1] | 4-((5R)-4-(((2R,3S)-1-(1H-imidazole-1-carbonyl)-2-isopropylazetidin-3-yl)methyl)-8-chloro-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-9-yl)-2-amino-7-fluorobenzo[b]thiophene-3-carbonitrile | 836.2 |
| 423[1] | 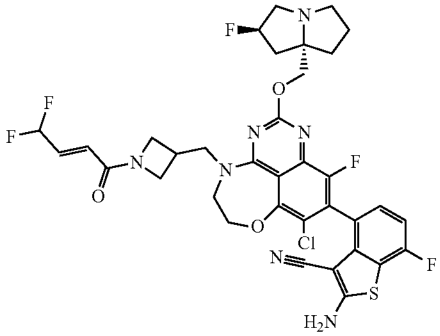 [SMILES: N#Cc1c(N)sc2c(F)ccc(-c3c(Cl)c4c5c(nc(OC[C@@]67CCCN6C[C@H](F)C7)nc5c3F)N(CC3CN(C(=O)/C=C/C(F)F)C3)CCO4)c12] | 2-amino-4-(8-chloro-4-((1-((E)-4,4-difluorobut-2-enoyl)azetidin-3-yl)methyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 760.2 |
| 424[7] | 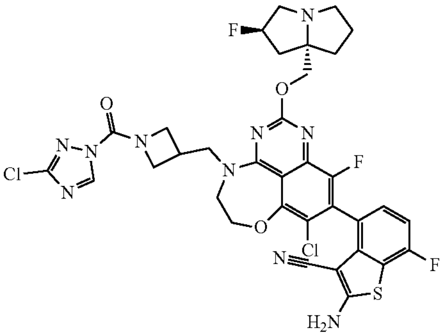 [SMILES: N#Cc1c(N)sc2c(F)ccc(-c3c(Cl)c4c5c(nc(OC[C@@]67CCCN6C[C@H](F)C7)nc5c3F)N(CC3CN(C(=O)n5cnc(Cl)n5)C3)CCO4)c12] | 2-amino-4-(8-chloro-10-fluoro-2-(((2R,7aS)-2-fluorotetrahydro-1H-pyrrolizin-7a(5H)-yl)methoxy)-4-((3-hydroxy-1-(4-methyl-1H-imidazole-1-carbonyl)azetidin-3-yl)methyl)-5,6-dihydro-4H-[1,4]oxazepino[5,6,7-de]quinazolin-9-yl)-7-fluorobenzo[b]thiophene-3-carbonitrile | 780.2 |
| 425 | 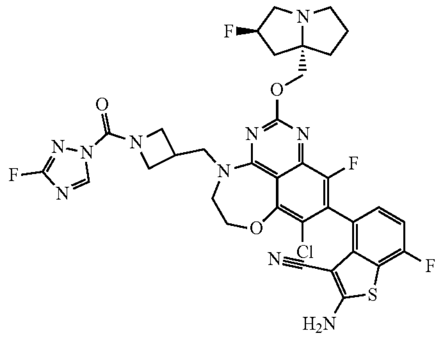 [SMILES: N#Cc1c(N)sc2c(F)ccc(-c3c(Cl)c4c5c(nc(OC[C@@]67CCCN6C[C@H](F)C7)nc5c3F)N(CC3CN(C(=O)n5cnc(F)n5)C3)CCO4)c12] | ((2R,3R)-3-(5-(5-amino-4-fluoro-3-methyl-2-(trifluoromethyl)phenyl)-4-fluoro-2-(((2R,7aS)-2-fluorotetrahydro-1H-pyrrolizin-7a(5H)-yl)methoxy)-8,9-dihydro-1,3,6,10-tetraazacyclohepta[de]naphthalen-10(7H)-yl)-2-methylpyrrolidin-1-yl)(3-chloro-1H-1,2,4-triazol-1-yl)methanone | 765.5 |

TABLE 1-continued

| No. | Structure | Chemical Name | [M + H]+ |
|---|---|---|---|
| 426[5] | 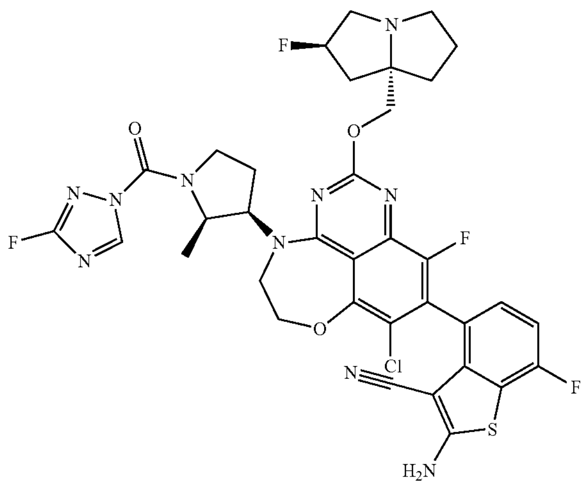 [SMILES: C[C@@H]1[C@H](N2CCOc3c(Cl)c(-c4ccc(F)c5sc(N)c(C#N)c45)c(F)c4nc(OC[C@@]56CCCN5C[C@H](F)C6)nc2c34)CCN1C(=O)n1cnc(F)n1] | 2-amino-4-(8-chloro-10-fluoro-4-((2R,3R)-1-(3-fluoro-1H-1,2,4-triazole-1-carbonyl)-2-methylpyrrolidin-3-yl)-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 783.2 |
| 427[1] | 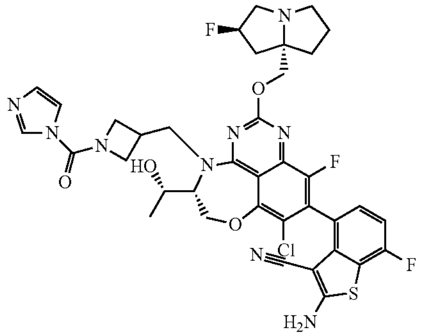 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1CC1CN(C(=O)n2ccnc2)C1] | 4-((5R)-4-((1-(1H-imidazole-1-carbonyl)azetidin-3-yl)methyl)-8-chloro-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-9-yl)-2-amino-7-fluorobenzo[b]thiophene-3-carbonitrile | 794.2 |
| 428 | 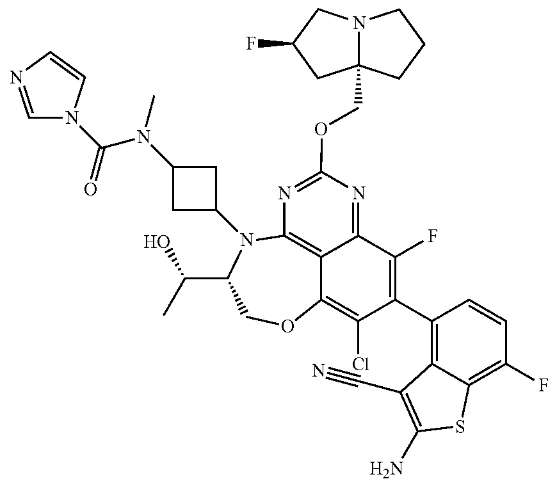 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1C1CC(N(C)C(=O)n2ccnc2)C1] | N-(3-((5R)-9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-4-yl)cyclobutyl)-N-methyl-1H-imidazole-1-carboxamide | 808.2 |

TABLE 1-continued

| No. | Structure | Chemical Name | [M + H]+ |
|---|---|---|---|
| 429 | 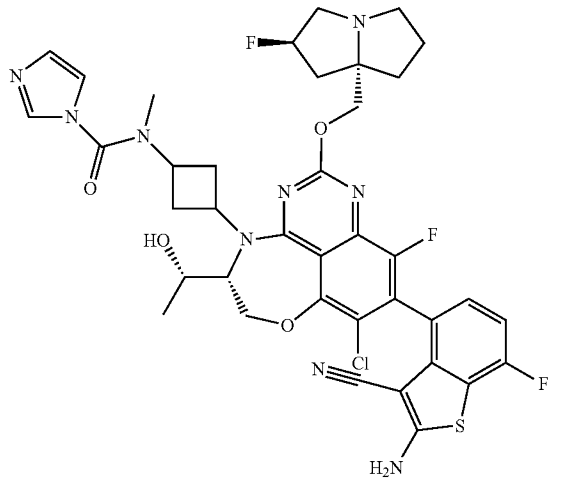 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1C1CC(N(C)C(=O)n2ccnc2)C1] | N-(3-((5R)-9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-4-yl)cyclobutyl)-N-methyl-1H-imidazole-1-carboxamide | 808.2 |
| 430 | 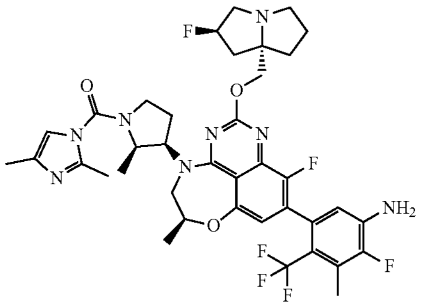 [SMILES: Cc1cn(C(=O)N2CC[C@@H](N3C[C@H](C)Oc4cc(-c5cc(N)c(F)c(C)c5C(F)(F)F)c(F)c5nc(OC[C@@]67CCCN6C[C@H](F)C7)nc3c45)[C@H]2C)c(C)n1] | ((2R,3R)-3-((S)-5-(5-amino-4-fluoro-3-methyl-2-(trifluoromethyl)phenyl)-4-fluoro-2-(((2R,7aS)-2-fluorotetrahydro-1H-pyrrolizin-7a(5H)-yl)methoxy)-8-methyl-8,9-dihydro-10H-7-oxa-1,3,6,10-tetraazacyclohepta[de]naphthalen-10-yl)-2-methylpyrrolidin-1-yl)(2,4-dimethyl-1H-imidazol-1-yl)methanone | 774.3 |
| 431 | 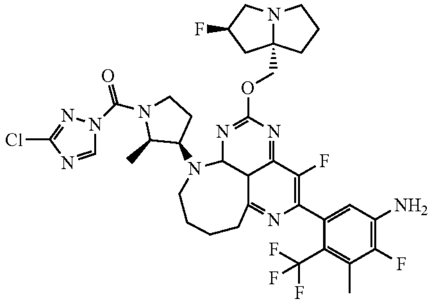 [SMILES: Cc1c(F)c(N)cc(C2=C(F)C3=NC(OC[C@@]45CCCN4C[C@H](F)C5)=NC4C3C(=N2)CCCCN4[C@@H]2CCN(C(=O)n3cnc(Cl)n3)[C@@H]2C)c1C(F)(F)F] | ((2R,3R)-3-(5-(5-amino-4-fluoro-3-methyl-2-(trifluoromethyl)phenyl)-4-fluoro-2-(((2R,7aS)-2-fluorotetrahydro-1H-pyrrolizin-7a(5H)-yl)methoxy)-7,8,9,10-tetrahydro-11H-1,3,6,11-tetraazacycloocta[de]naphthalen-11-yl)-2-methylpyrrolidin-1-yl)(3-chloro-1H-1,2,4-triazol-1-yl)methanone | 779.5 |
| 432[4] | 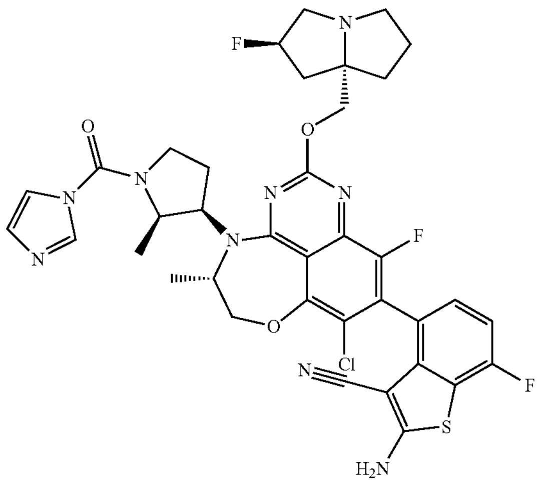 [SMILES: C[C@@H]1[C@H](N2c3nc(OC[C@@]45CCCN4C[C@H](F)C5)nc4c(F)c(-c5ccc(F)c6sc(N)c(C#N)c56)c(Cl)c(c34)OC[C@@H]2C)CCN1C(=O)n1ccnc1] | 4-((5S)-4-((2R,3R)-1-(1H-imidazole-1-carbonyl)-2-methylpyrrolidin-3-yl)-8-chloro-10-fluoro-2-(((2R,7aS)-2-fluorotetrahydro-1H-pyrrolizin-7a(5H)-yl)methoxy)-5-methyl-5,6-dihydro-4H-[1,4]oxazepino[5,6,7-de]quinazolin-9-yl)-2-amino-7-fluorobenzo[b]thiophene-3-carbonitrile | 778.2 |

TABLE 1-continued

| No. | Structure | Chemical Name | [M + H]+ |
|---|---|---|---|
| 433 | 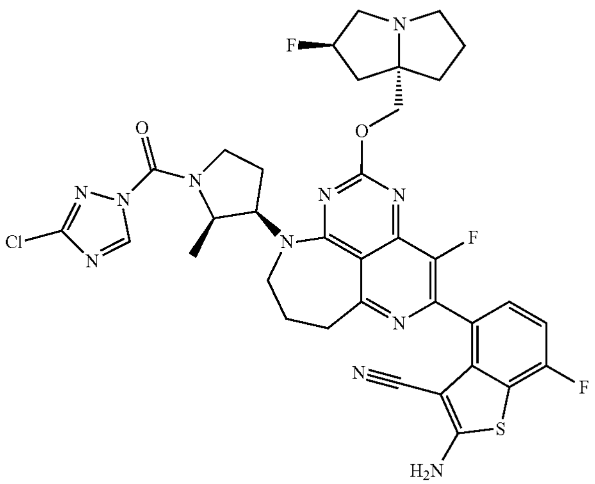 [SMILES: C[C@@H]1[C@H](N2CCCc3nc(-c4ccc(F)c5sc(N)c(C#N)c45)c(F)c4nc(OC[C@@]56CCCN5C[C@H](F)C6)nc2c34)CCN1C(=O)n1cnc(Cl)n1] | 2-amino-4-(10-((2R,3R)-1-(3-chloro-1H-1,2,4-triazole-1-carbonyl)-2-methylpyrrolidin-3-yl)-4-fluoro-2-(((2R,7aS)-2-fluorotetrahydro-1H-pyrrolizin-7a(5H)-yl) methoxy)-7,8,9,10-tetrahydro-1,3,6,10-tetraazacyclohepta[de] naphthalen-5-yl)-7-fluorobenzo[b]thiophene-3-carbonitrile | 764.5 |
| 434[3] | 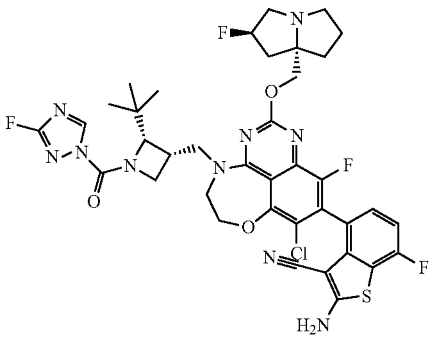 [SMILES: CC(C)(C)[C@@H]1[C@H](CN2CCOc3c(Cl)c(-c4ccc(F)c5sc(N)c(C#N)c45)c(F)c4nc(OC[C@@]56CCCN5C[C@H](F)C6)nc2c34)CN1C(=O)n1cnc(F)n1] | 2-amino-4-(4-(((2S,3R)-2-(tert-butyl)-1-(3-fluoro-1H-1,2,4-triazole-1-carbonyl)azetidin-3-yl)methyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de] quinazolin-9-yl)-7-fluorobenzo [b]thiophene-3-carbonitrile | 825.2 |
| 435 | 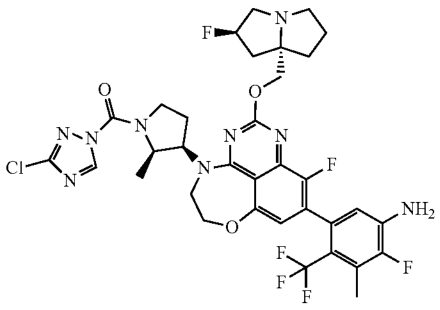 [SMILES: Cc1c(F)c(N)cc(-c2cc3c4c(nc(OC[C@@]56CCCN5C[C@H](F)C6)nc4c2F)N([C@@H]2CCN(C(=O)n4cnc(Cl)n4)[C@@H]2C)CCO3)c1C(F)(F)F] | ((2R,3R)-3-(9-(5-amino-4-fluoro-3-methyl-2-(trifluoromethyl) phenyl)-10-fluoro-2-(((2R,7aS)-2-fluorotetrahydro-1H-pyrrolizin-7a(5H)-yl) methoxy)-5,6-dihydro-4H-[1,4]oxazepino[5,6,7-de] quinazolin-4-yl)-2-methylpyrrolidin-1-yl) (3-chloro-1H-1,2,4-triazol-1-yl)methanone | 766.5 |
| 436[1] | 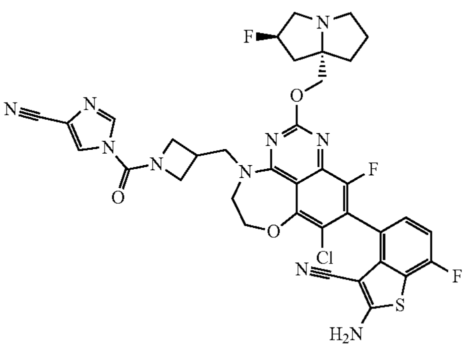 [SMILES: N#Cc1cn(C(=O)N2CC(CN3CCOc4c(Cl)c(-c5ccc(F)c6sc(N)c(C#N)c56)c(F)c5nc(OC[C@@]67CCCN6C[C@H](F)C7)nc3c45)C2)cn1] | 1-(3-((9-(2-amino-3-cyano-7-fluorobenzo[b] thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino [5,6,7-de]quinazolin-4-yl) methyl)azetidine-1-carbonyl)-1H-imidazole-4-carbonitrile | 775.2 |

TABLE 1-continued

| No. | Structure | Chemical Name | [M + H]+ |
|---|---|---|---|
| 437[5] | 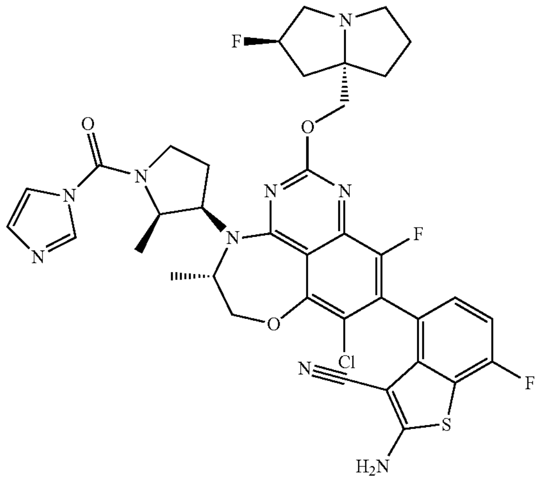 [SMILES: C[C@@H]1[C@H](N2c3nc(OC[C@@]45CCCN4C[C@H](F)C5)nc4c(F)c(-c5ccc(F)c6sc(N)c(C#N)c56)c(Cl)c(c34)OC[C@@H]2C)CCN1C(=O)n1ccnc1] | 4-((5S)-4-((2R,3R)-1-(1H-imidazole-1-carbonyl)-2-methylpyrrolidin-3-yl)-8-chloro-10-fluoro-2-(((2R,7aS)-2-fluorotetrahydro-1H-pyrrolizin-7a(5H)-yl)methoxy)-5-methyl-5,6-dihydro-4H-[1,4]oxazepino[5,6,7-de]quinazolin-9-yl)-2-amino-7-fluorobenzo[b]thiophene-3-carbonitrile | 778.2 |
| 438 | 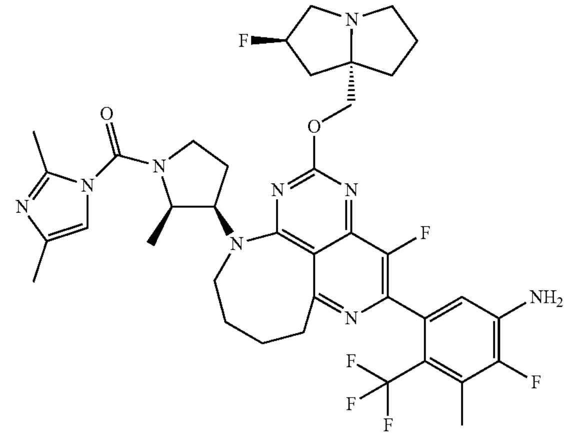 [SMILES: Cc1cn(C(=O)N2CC[C@@H](N3CCCCc4nc(-c5cc(N)c(F)c(C)c5C(F)(F)F)c(F)c5nc(OC[C@@]67CCCN6C[C@H](F)C7)nc3c45)[C@H]2C)c(C)n1] | ((2R,3R)-3-(5-(5-amino-4-fluoro-3-methyl-2-(trifluoromethyl)phenyl)-4-fluoro-2-(((2R,7aS)-2-fluorotetrahydro-1H-pyrrolizin-7a(5H)-yl)methoxy)-7,8,9,10-tetrahydro-11H-1,3,6,11-tetraazacycloocta[de]naphthalen-11-yl)-2-methylpyrrolidin-1-yl)(2,4-dimethyl-1H-imidazol-1-yl)methanone | 772.3 |
| 439[1] | 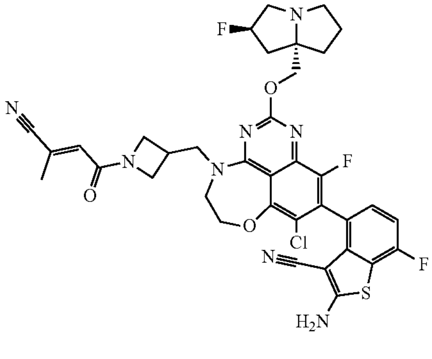 [SMILES: C/C(C#N)=C\C(=O)N1CC(CN2CCOc3c(Cl)c(-c4ccc(F)c5sc(N)c(C#N)c45)c(F)c4nc(OC[C@@]56CCCN5C[C@H](F)C6)nc2c34)C1] | 2-amino-4-(8-chloro-4-((1-((E)-3-cyanobut-2-enoyl)azetidin-3-yl)methyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 749.2 |
| 440 | 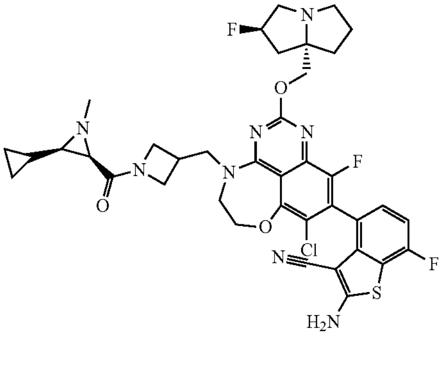 [SMILES: CN1[C@H](C2CC2)[C@@H]1C(=O)N1CC(CN2CCOc3c(Cl)c(-c4ccc(F)c5sc(N)c(C#N)c45)c(F)c4nc(OC[C@@]56CCCN5C[C@H](F)C6)nc2c34)C1] | 2-amino-4-(8-chloro-4-((1-((2R,3R)-3-cyclopropyl-1-methylaziridine-2-carbonyl)azetidin-3-yl)methyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 779.2 |

TABLE 1-continued

| No. | Structure | Chemical Name | [M + H]+ |
|---|---|---|---|
| 441[4] | 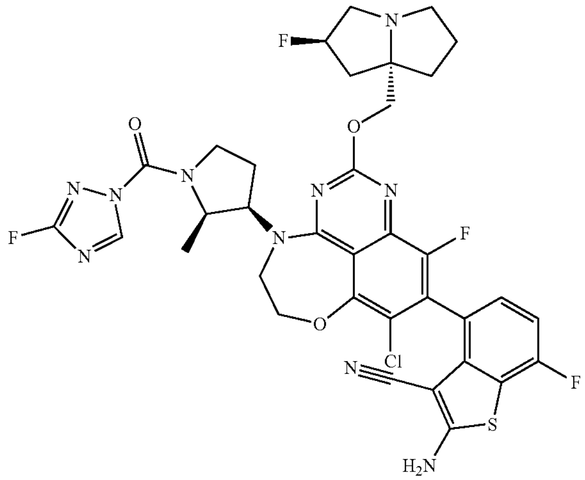 [SMILES: C[C@@H]1[C@H](N2CCOc3c(Cl)c(-c4ccc(F)c5sc(N)c(C#N)c45)c(F)c4nc(OC[C@@]56CCCN5C[C@H](F)C6)nc2c34)CCN1C(=O)n1cnc(F)n1] | 2-amino-4-(8-chloro-10-fluoro-4-((2R,3R)-1-(3-fluoro-1H-1,2,4-triazole-1-carbonyl)-2-methylpyrrolidin-3-yl)-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 783.2 |
| 442[1] | 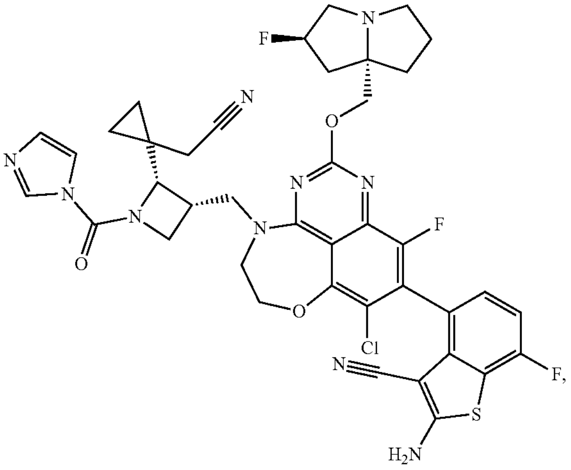 [SMILES: N#CCC1([C@@H]2[C@H](CN3CCOc4c(Cl)c(-c5ccc(F)c6sc(N)c(C#N)c56)c(F)c5nc(OC[C@@]67CCCN6C[C@H](F)C7)nc3c45)CN2C(=O)n2ccnc2)CC1] | 2-amino-4-(8-chloro-4-(((2S,3R)-2-(1-(cyanomethyl)cyclopropyl)-1-(1H-imidazole-1-carbonyl)azetidin-3-yl)methyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 829.2 |
| 443 | 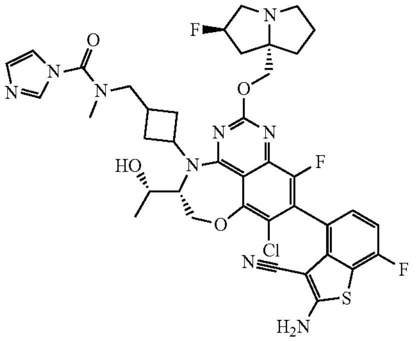 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1C1CC(CN(C)C(=O)n2ccnc2)C1] | N-((3-((5R)-9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-4-yl)cyclobutyl)methyl)-N-methyl-1H-imidazole-1-carboxamide | 822.2 |

TABLE 1-continued

| No. | Structure | Chemical Name | [M + H]+ |
| --- | --- | --- | --- |
| 444 | 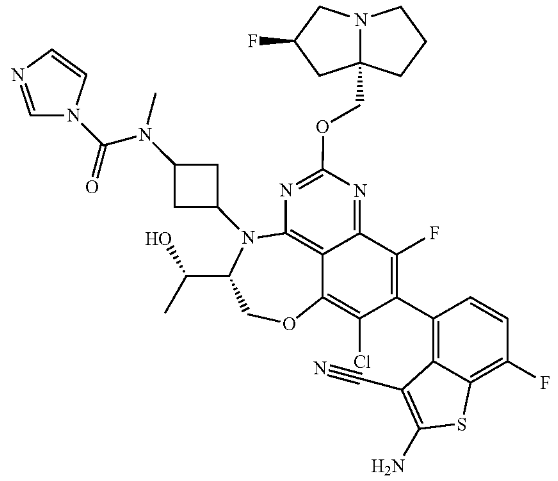 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1C1CC(N(C)C(=O)n2ccnc2)C1] | N-(3-((5R)-9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-4-yl)cyclobutyl)-N-methyl-1H-imidazole-1-carboxamide | 808.2 |
| 445[1] | 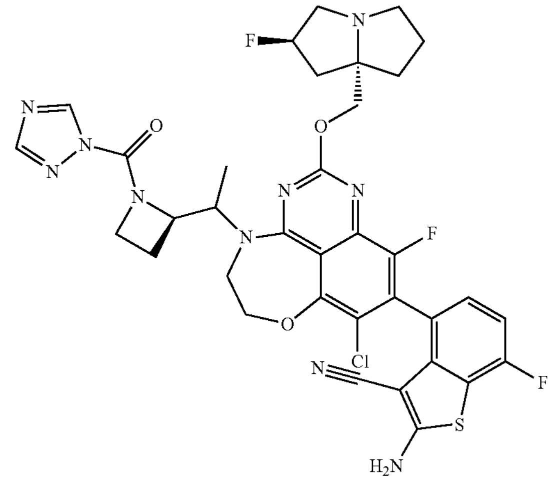 [SMILES: CC([C@H]1CCN1C(=O)n1cncn1)N1CCOc2c(Cl)c(-c3ccc(F)c4sc(N)c(C#N)c34)c(F)c3nc(OC[C@@]45CCCN4C[C@H](F)C5)nc1c23] | 4-(4-(1-((R)-1-(1H-1,2,4-triazole-1-carbonyl)azetidin-2-yl)ethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-2-amino-7-fluorobenzo[b]thiophene-3-carbonitrile | 765.1 |
| 446[4] | 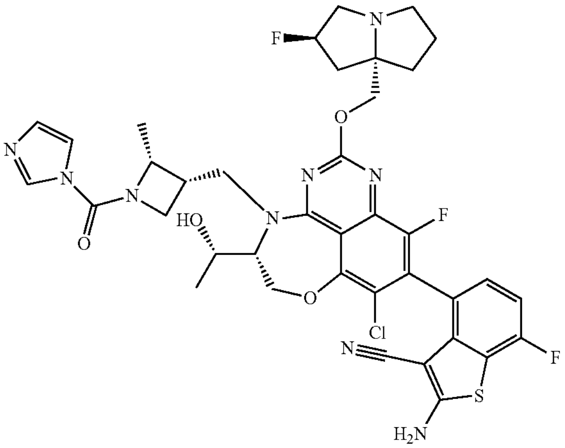 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1C[C@@H]1CN(C(=O)n2ccnc2)[C@@H]1C] | 4-((5R)-4-(((2R,3R)-1-(1H-imidazole-1-carbonyl)-2-methylazetidin-3-yl)methyl)-8-chloro-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-9-yl)-2-amino-7-fluorobenzo[b]thiophene-3-carbonitrile | 808.2 |

TABLE 1-continued

| No. | Structure | Chemical Name | [M + H]+ |
|---|---|---|---|
| 447[1] | 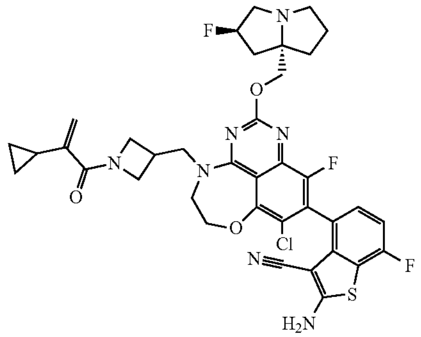 [SMILES: C=C(C(=O)N1CC(CN2CCOc3c(Cl)c(-c4ccc(F)c5sc(N)c(C#N)c45)c(F)c4nc(OC[C@@]56CCCN5C[C@H](F)C6)nc2c34)C1)C1CC1] | 2-amino-4-(8-chloro-4-((1-(2-cyclopropylacryloyl) azetidin-3-yl)methyl)-10-fluoro-2-(((2R,7aS)-2-fluorotetrahydro-1H-pyrrolizin-7a(5H)-yl)methoxy)-5,6-dihydro-4H-[1,4]oxazepino [5,6,7-de]quinazolin-9-yl)-7-fluorobenzo[b]thiophene-3-carbonitrile | 750.2 |
| 448[6] | 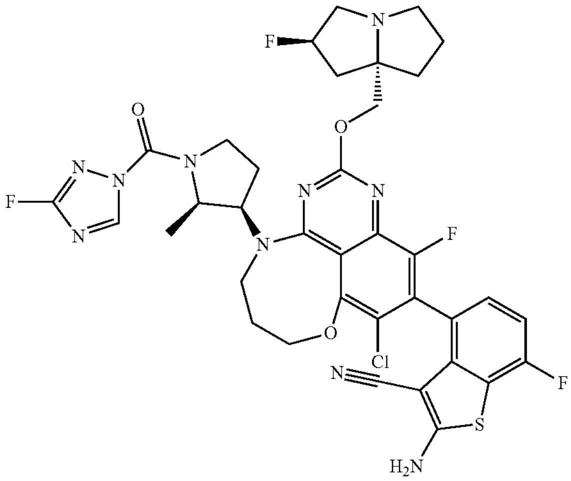 [SMILES: C[C@@H]1[C@H](N2CCCOc3c(Cl)c(-c4ccc(F)c5sc(N)c(C#N)c45)c(F)c4nc(OC[C@@]56CCCN5C[C@H](F)C6)nc2c34)CCN1C(=O)n1cnc(F)n1] | 2-amino-4-(9-chloro-11-fluoro-4-((2R,3R)-1-(3-fluoro-1H-1,2,4-triazole-1-carbonyl)-2-methylpyrrolidin-3-yl)-2-(((2R,7aS)-2-fluorotetrahydro-1H-pyrrolizin-7a(5H)-yl)methoxy)-4,5,6,7-tetrahydro-[1,5]oxazocino [4,3,2-de]quinazolin-10-yl)-7-fluorobenzo[b]thiophene-3-carbonitrile | 797.2 |
| 449[1] | 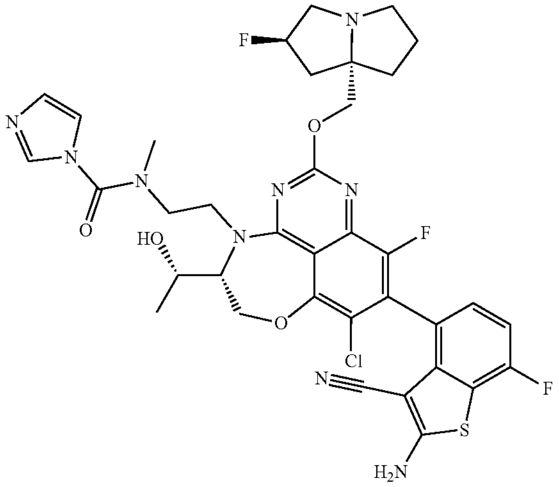 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1CCN(C)C(=O)n1ccnc1] | N-(2-((5R)-9-(2-amino-3-cyano-7-fluorobenzo[b] thiophen-4-yl)-8-chloro-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino [5,6,7-de]quinazolin-4-yl) ethyl)-N-methyl-1H-imidazole-1-carboxamide | 782.2 |

TABLE 1-continued

| No. | Structure | Chemical Name | [M + H]+ |
|---|---|---|---|
| 450[6,7] | 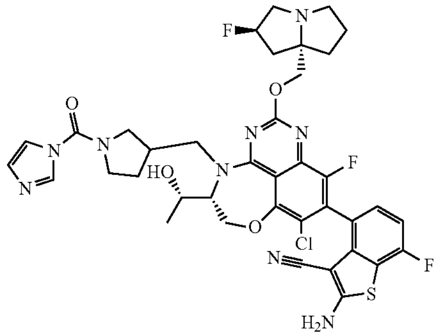 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1CC1CCN(C(=O)n2ccnc2)C1] | 4-((5R)-4-((1-(1H-imidazole-1-carbonyl)pyrrolidin-3-yl)methyl)-8-chloro-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino [5,6,7-de]quinazolin-9-yl)-2-amino-7-fluorobenzo[b] thiophene-3-carbonitrile | 808.2 |
| 451 | 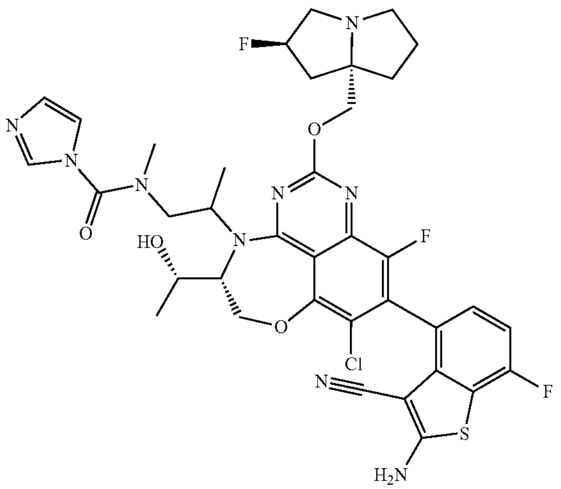 [SMILES: CC(CN(C)C(=O)n1ccnc1)N1c2nc(OC[C@@]34CCCN3C[C@H](F)C4)nc3c(F)c(-c4ccc(F)c5sc(N)c(C#N)c45)c(Cl)c(c23)OC[C@@H]1[C@H](C)O] | N-(2-((5R)-9-(2-amino-3-cyano-7-fluorobenzo[b] thiophen-4-yl)-8-chloro-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino [5,6,7-de]quinazolin-4-yl) propyl)-N-methyl-1H-imidazole-1-carboxamide | 796.2 |
| 452[3] | 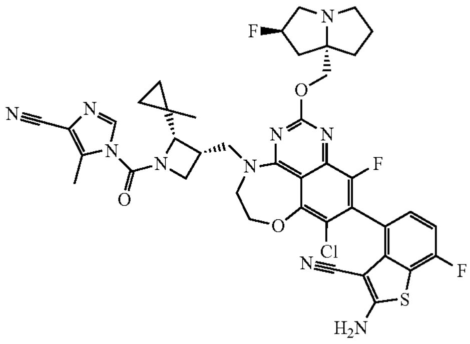 [SMILES: Cc1c(C#N)ncn1C(=O)N1C[C@@H](CN2CCOc3c(Cl)c(-c4ccc(F)c5sc(N)c(C#N)c45)c(F)c4nc(OC[C@@]56CCCN5C[C@H](F)C6)nc2c34)[C@H]1C1(C)CC1] | 1-((2S,3R)-3-((9-(2-amino-3-cyano-7-fluorobenzo[b] thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino [5,6,7-de]quinazolin-4-yl)methyl)-2-(1-methylcyclopropyl)azetidine-1-carbonyl)-5-methyl-1H-imidazole-4-carbonitrile | 843.2 |

TABLE 1-continued

| No. | Structure | Chemical Name | [M + H]+ |
|---|---|---|---|
| 453[5] | 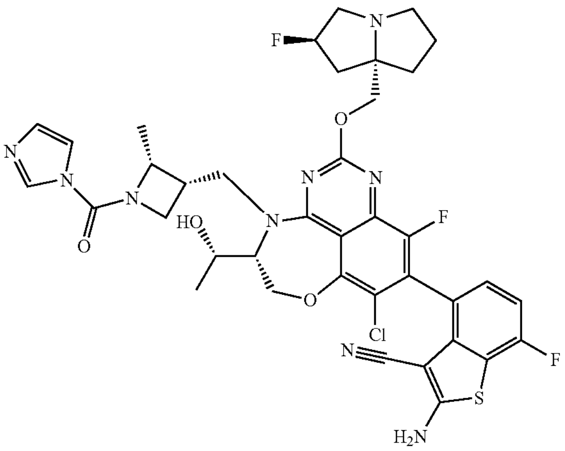 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1C[C@@H]1CN(C(=O)n2ccnc2)[C@@H]1C] | 4-((5R)-4-(((2R,3R)-1-(1H-imidazole-1-carbonyl)-2-methylazetidin-3-yl)methyl)-8-chloro-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-9-yl)-2-amino-7-fluorobenzo[b]thiophene-3-carbonitrile | 808.2 |
| 454 | 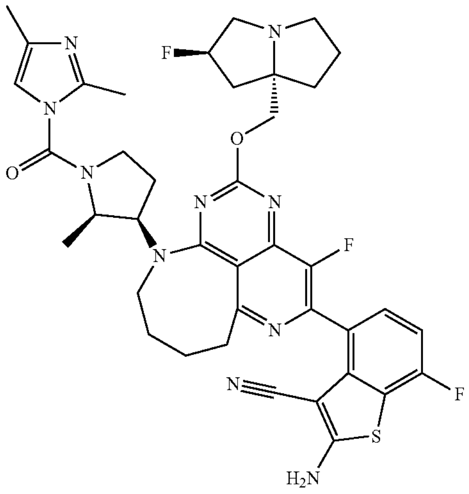 [SMILES: Cc1cn(C(=O)N2CC[C@@H](N3CCCCc4nc(-c5ccc(F)c6sc(N)c(C#N)c56)c(F)c5nc(OC[C@@]67CCCN6C[C@H](F)C7)nc3c45)[C@H]2C)c(C)n1] | 2-amino-4-(11-((2R,3R)-1-(2,4-dimethyl-1H-imidazole-1-carbonyl)-2-methylpyrrolidin-3-yl)-4-fluoro-2-(((2R,7aS)-2-fluorotetrahydro-1H-pyrrolizin-7a(5H)-yl)methoxy)-8,9,10,11-tetrahydro-7H-1,3,6,11-tetraazacycloocta[de]naphthalen-5-yl)-7-fluorobenzo[b]thiophene-3-carbonitrile | 771.3 |
| 455[1] | 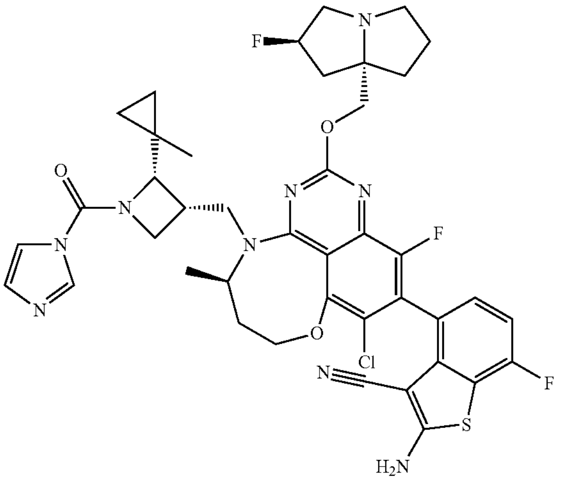 [SMILES: C[C@@H]1CCOc2c(Cl)c(-c3ccc(F)c4sc(N)c(C#N)c34)c(F)c3nc(OC[C@@]45CCCN4C[C@H](F)C5)nc(c23)N1C[C@@H]1CN(C(=O)n2ccnc2)[C@@H]1C1(C)CC1] | 4-((5R)-4-(((2S,3R)-1-(1H-imidazole-1-carbonyl)-2-(1-methylcyclopropyl)azetidin-3-yl)methyl)-9-chloro-11-fluoro-2-(((2R,7aS)-2-fluorotetrahydro-1H-pyrrolizin-7a(5H)-yl)methoxy)-5-methyl-4,5,6,7-tetrahydro-[1,5]oxazocino[4,3,2-de]quinazolin-10-yl)-2-amino-7-fluorobenzo[b]thiophene-3-carbonitrile | 832.2 |

TABLE 1-continued

| No. | Structure | Chemical Name | [M + H]+ |
|---|---|---|---|
| 456[1] | 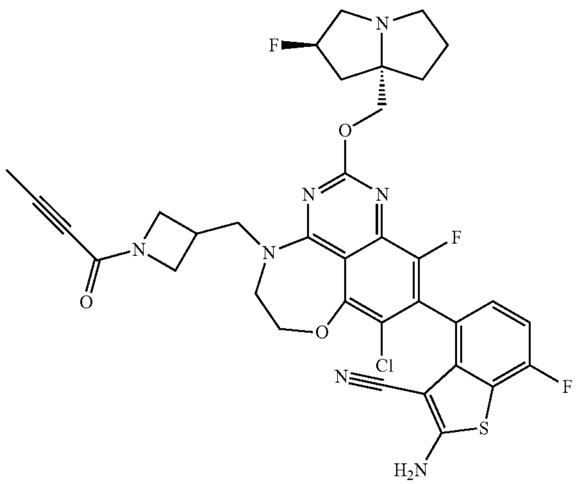 [SMILES: CC#CC(=O)N1CC(CN2CCOc3c(Cl)c(-c4ccc(F)c5sc(N)c(C#N)c45)c(F)c4nc(OC[C@@]56CCCN5C[C@H](F)C6)nc2c34)C1] | 2-amino-4-(4-((1-(but-2-ynoyl) azetidin-3-yl)methyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino [5,6,7-de]quinazolin-9-yl)-7-fluorobenzo[b]thiophene-3-carbonitrile | 722.2 |
| 457[7] | 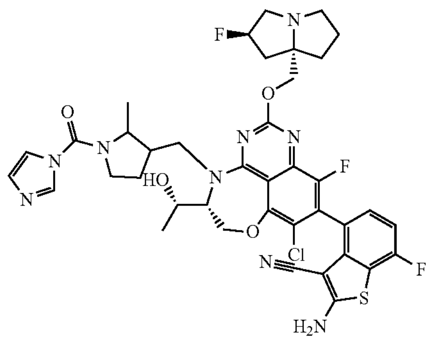 [SMILES: CC1C(CN2c3nc(OC[C@@]45CCCN4C[C@H](F)C5)nc4c(F)c(-c5ccc(F)c6sc(N)c(C#N)c56)c(Cl)c(c34)OC[C@@H]2[C@H](C)O)CCN1C(=O)n1ccnc1] | 4-((5R)-4-((1-(1H-imidazole-1-carbonyl)-2-methylpyrrolidin-3-yl)methyl)-8-chloro-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de] quinazolin-9-yl)-2-amino-7-fluorobenzo[b]thiophene-3-carbonitrile | 822.2 |
| 458[1] | 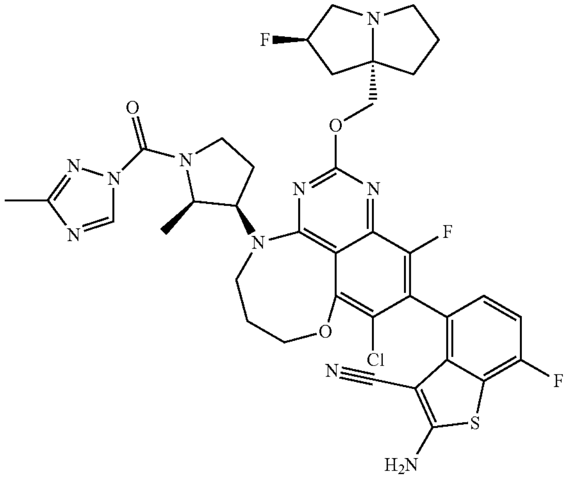 [SMILES: Cc1ncn(C(=O)N2CC[C@@H](N3CCCOc4c(Cl)c(-c5ccc(F)c6sc(N)c(C#N)c56)c(F)c5nc(OC[C@@]67CCCN6C[C@H](F)C7)nc3c45)[C@H]2C)n1] | 2-amino-4-(9-chloro-11-fluoro-2-(((2R,7aS)-2-fluorotetrahydro-1H-pyrrolizin-7a(5H)-yl) methoxy)-4-((2R,3R)-2-methyl-1-(4-methyl-1H-imidazole-1-carbonyl) pyrrolidin-3-yl)-4,5,6,7-tetrahydro-[1,5]oxazocino [4,3,2-de]quinazolin-10-yl)-7-fluorobenzo[b]thiophene-3-carbonitrile | 792.2 |

TABLE 1-continued

| No. | Structure | Chemical Name | [M + H]+ |
| --- | --- | --- | --- |
| 459[1] | 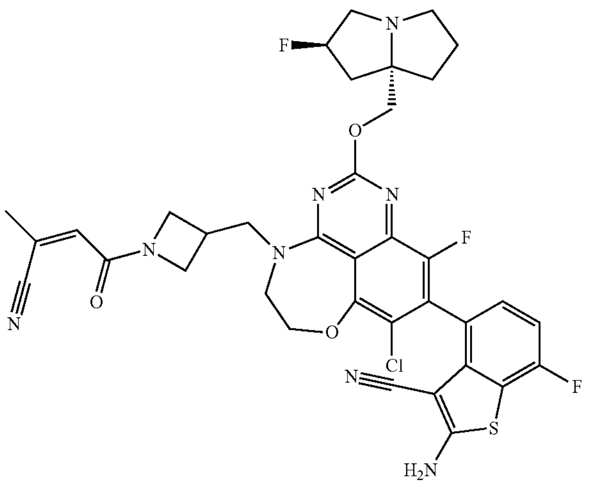 [SMILES: C/C(C#N)=C/C(=O)N1CC(CN2CCOc3c(Cl)c(-c4ccc(F)c5sc(N)c(C#N)c45)c(F)c4nc(OC[C@@]56CCCN5C[C@H](F)C6)nc2c34)C1] | 2-amino-4-(8-chloro-4-((1-((Z)-3-cyanobut-2-enoyl) azetidin-3-yl)methyl)-10-fluoro-2-(((2R, 7aS)-2-fluorotetrahydro-1H-pyrrolizin-7a(5H)-yl) methoxy)-5,6-dihydro-4H-[1,4]oxazepino[5,6,7-de] quinazolin-9-yl)-7-fluorobenzo [b]thiophene-3-carbonitrile | 749.2 |
| 460 | 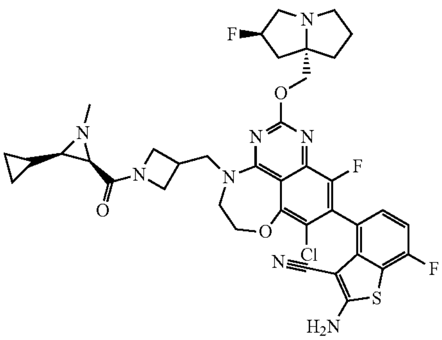 [SMILES: CN1[C@H](C2CC2)[C@@H]1C(=O)N1CC(CN2CCOc3c(Cl)c(-c4ccc(F)c5sc(N)c(C#N)c45)c(F)c4nc(OC[C@@]56CCCN5C[C@H](F)C6)nc2c34)C1] | 2-amino-4-(8-chloro-4-((1-((2R,3R)-3-cyclopropyl-1-methylaziridine-2-carbonyl) azetidin-3-yl)methyl)-10-fluoro-2-(((2R,7aS)-2-fluorotetrahydro-1H-pyrrolizin-7a(5H)-yl)methoxy)-5,6-dihydro-4H-[1,4]oxazepino [5,6,7-de]quinazolin-9-yl)-7-fluorobenzo[b]thiophene-3-carbonitrile | 779.2 |
| 461 | 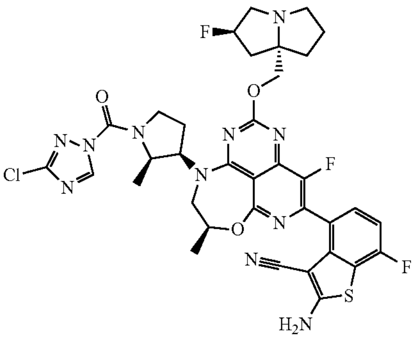 [SMILES: C[C@@H]1[C@H](N2C[C@H](C)Oc3nc(-c4ccc(F)c5sc(N)c(C#N)c45)c(F)c4nc(OC[C@@]56CCCN5C[C@H](F)C6)nc2c34)CCN1C(=O)n1cnc(Cl)n1] | 2-amino-4-((S)-10-((2R,3R)-1-(3-chloro-1H-1,2,4-triazole-1-carbonyl)-2-methylpyrrolidin-3-yl)-4-fluoro-2-(((2R,7aS)-2-fluorotetrahydro-1H-pyrrolizin-7a(5H)-yl)methoxy)-8-methyl-9,10-dihydro-8H-7-oxa-1,3,6,10-tetraazacyclohepta[de] naphthalen-5-yl)-7-fluorobenzo[b]thiophene-3-carbonitrile | 780.5 |

TABLE 1-continued

| No. | Structure | Chemical Name | [M + H]+ |
|---|---|---|---|
| 462[1] | 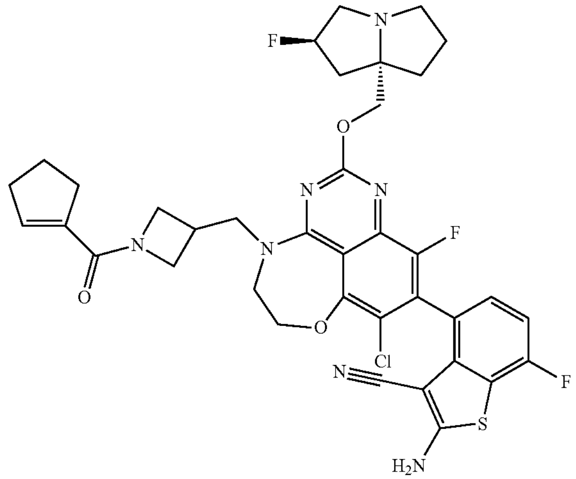 [SMILES: N#Cc1c(N)sc2c(F)ccc(-c3c(Cl)c4c5c(nc(OC[C@@]67CCCN6C[C@H](F)C7)nc5c3F)N(CC3CN(C(=O)C5=CCCC5)C3)CCO4)c12] | 2-amino-4-(8-chloro-4-((1-(cyclopent-1-ene-1-carbonyl) azetidin-3-yl)methyl)-10-fluoro-2-(((2R,7aS)-2-fluorotetrahydro-1H-pyrrolizin-7a(5H)-yl)methoxy)-5,6-dihydro-4H-[1,4]oxazepino [5,6,7-de]quinazolin-9-yl)-7-fluorobenzo[b]thiophene-3-carbonitrile | 750.2 |
| 463[7] | 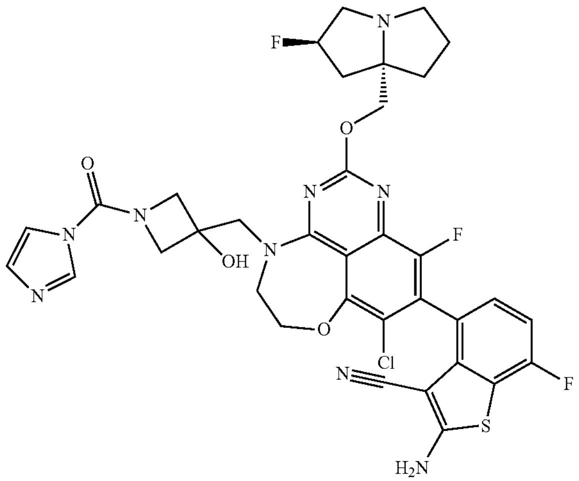 [SMILES: N#Cc1c(N)sc2c(F)ccc(-c3c(Cl)c4c5c(nc(OC[C@@]67CCCN6C[C@H](F)C7)nc5c3F)N(CC3(O)CN(C(=O)n5ccnc5)C3)CCO4)c12] | 2-amino-4-(8-chloro-10-fluoro-2-(((2R,7aS)-2-fluorotetrahydro-1H-pyrrolizin-7a(5H)-yl)methoxy)-4-((3-hydroxy-1-(1H-imidazole-1-carbonyl)azetidin-3-yl)methyl)-5,6-dihydro-4H-[1,4]oxazepino [5,6,7-de]quinazolin-9-yl)-7-fluorobenzo[b]thiophene-3-carbonitrile | 766.2 |
| 464[4] | 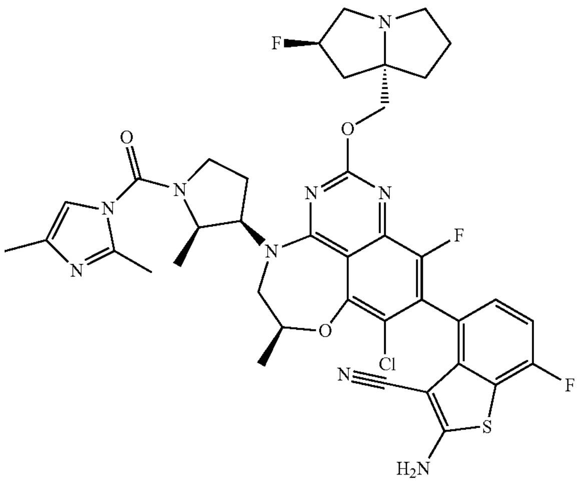 [SMILES: Cc1cn(C(=O)N2CC[C@@H](N3C[C@H](C)Oc4c(Cl)c(-c5ccc(F)c6sc(N)c(C#N)c56)c(F)c5nc(OC[C@@]67CCCN6C[C@H](F)C7)nc3c45)[C@H]2C)c(C)n1] | 2-amino-4-((6S)-8-chloro-4-((2R,3R)-1-(2,4-dimethyl-1H-imidazole-1-carbonyl)-2-methylpyrrolidin-3-yl)-10-fluoro-2-(((2R,7aS)-2-fluorotetrahydro-1H-pyrrolizin-7a(5H)-yl)methoxy)-6-methyl-5,6-dihydro-4H-[1,4] oxazepino[5,6,7-de]quinazolin-9-yl)-7-fluorobenzo[b] thiophene-3-carbonitrile | 806.2 |

TABLE 1-continued

| No. | Structure | Chemical Name | [M + H]+ |
|---|---|---|---|
| 465[3] | 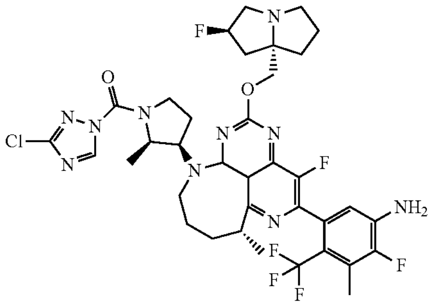 [SMILES: Cc1c(F)c(N)cc(C2=C(F)C3=NC(OC[C@@]45CCCN4C[C@H](F)C5)=NC4C3C(=N2)[C@H](C)CCCN4[C@@H]2CCN(C(=O)n3cnc(Cl)n3)[C@@H]2C)c1C(F)(F)F] | ((2R,3R)-3-((R)-5-(5-amino-4-fluoro-3-methyl-2-(trifluoromethyl)phenyl)-4-fluoro-2-(((2R,7aS)-2-fluorotetrahydro-1H-pyrrolizin-7a(5H)-yl)methoxy)-7-methyl-7,8,9,10-tetrahydro-11H-1,3,6,11-tetraazacycloocta[de]naphthalen-11-yl)-2-methylpyrrolidin-1-yl)(3-chloro-1H-1,2,4-triazol-1-yl)methanone | 793.3 |
| 466[1] | 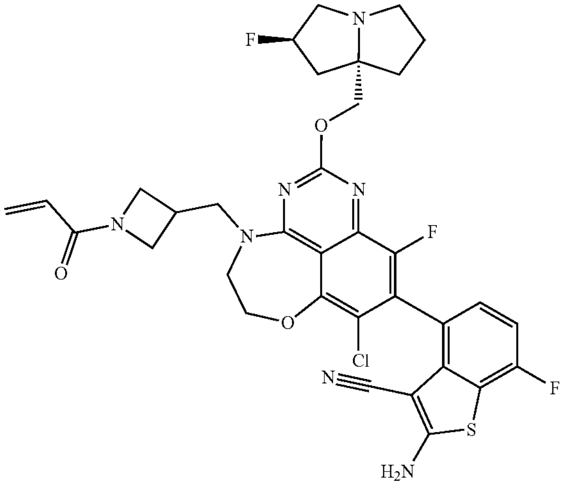 [SMILES: C=CC(=O)N1CC(CN2CCOc3c(Cl)c(-c4ccc(F)c5sc(N)c(C#N)c45)c(F)c4nc(OC[C@@]56CCCN5C[C@H](F)C6)nc2c34)C1] | 4-(4-((1-acryloylazetidin-3-yl)methyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-2-amino-7-fluorobenzo[b]thiophene-3-carbonitrile | 710.2 |
| 467[7] | 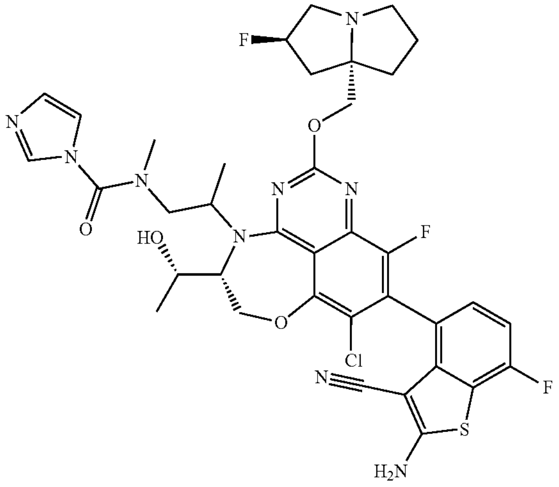 [SMILES: CC(CN(C)C(=O)n1ccnc1)N1c2nc(OC[C@@]34CCCN3C[C@H](F)C4)nc3c(F)c(-c4ccc(F)c5sc(N)c(C#N)c45)c(Cl)c(c23)OC[C@@H]1[C@H](C)O] | N-(2-((5R)-9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-4-yl)propyl)-N-methyl-1H-imidazole-1-carboxamide | 796.2 |
| 468 | 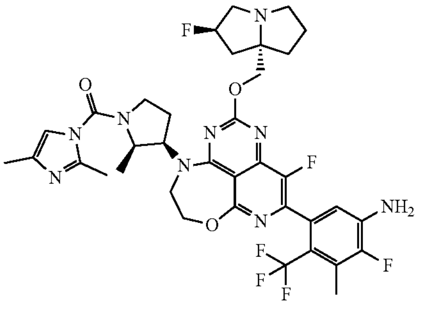 [SMILES: Cc1cn(C(=O)N2CC[C@@H](N3CCOc4nc(-c5cc(N)c(F)c(C)c5C(F)(F)F)c(F)c5nc(OC[C@@]67CCCN6C[C@H](F)C7)nc3c45)[C@H]2C)c(C)n1] | ((2R,3R)-3-(5-(5-amino-4-fluoro-3-methyl-2-(trifluoromethyl)phenyl)-4-fluoro-2-(((2R,7aS)-2-fluorotetrahydro-1H-pyrrolizin-7a(5H)-yl)methoxy)-8,9-dihydro-1,3,6,10-tetraazacyclohepta[de]naphthalen-10(7H)-yl)-2-methylpyrrolidin-1-yl)(2,4-dimethyl-1H-imidazol-1-yl)methanone | 758.3 |

TABLE 1-continued

| No. | Structure | Chemical Name | [M + H]+ |
|---|---|---|---|
| 469[1] | 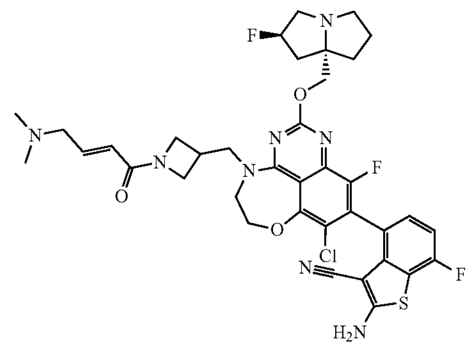 [SMILES: CN(C)C/C=C/C(=O)N1CC(CN2CCOc3c(Cl)c(-c4ccc(F)c5sc(N)c(C#N)c45)c(F)c4nc(OC[C@@]56CCCN5C[C@H](F)C6)nc2c34)C1] | 2-amino-4-(8-chloro-4-((1-((E)-4-(dimethylamino)but-2-enoyl)azetidin-3-yl) methyl)-10-fluoro-2-(((2R, 7aS)-2-fluorotetrahydro-1H-pyrrolizin-7a(5H)-yl) methoxy)-5,6-dihydro-4H-[1,4]oxazepino[5,6,7-de] quinazolin-9-yl)-7-fluorobenzo [b]thiophene-3-carbonitrile | 767.3 |
| 470[1] | 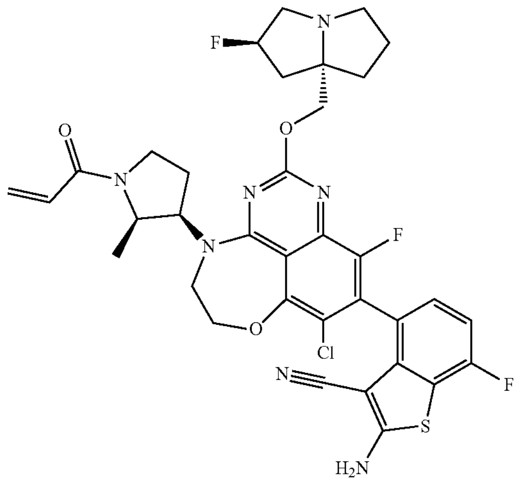 [SMILES: C=CC(=O)N1CC[C@@H](N2CCOc3c(Cl)c(-c4ccc(F)c5sc(N)c(C#N)c45)c(F)c4nc(OC[C@@]56CCCN5C[C@H](F)C6)nc2c34)[C@H]1C] | 4-(4-((2R,3R)-1-acryloyl-2-methylpyrrolidin-3-yl)-8-chloro-10-fluoro-2-(((2R, 7aS)-2-fluorotetrahydro-1H-pyrrolizin-7a(5H)-yl) methoxy)-5,6-dihydro-4H-[1,4]oxazepino[5,6,7-de] quinazolin-9-yl)-2-amino-7-fluorobenzo[b]thiophene-3-carbonitrile | 724.3 |
| 471[1] | 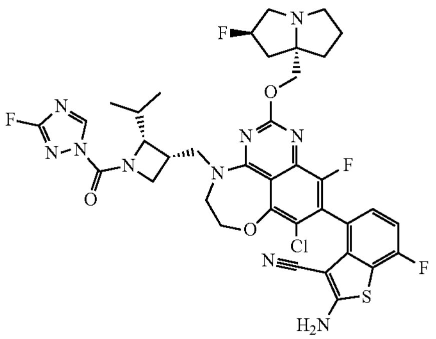 [SMILES: CC(C)[C@@H]1[C@H](CN2CCOc3c(Cl)c(-c4ccc(F)c5sc(N)c(C#N)c45)c(F)c4nc(OC[C@@]56CCCN5C[C@H](F)C6)nc2c34)CN1C(=O)n1cnc(F)n1] | 2-amino-4-(8-chloro-10-fluoro-4-(((2R,3R)-1-(3-fluoro-1H-1,2,4-triazole-1-carbonyl)-2-isopropylazetidin-3-yl)methyl)-2-(((2R,7aS)-2-fluorotetrahydro-1H-pyrrolizin-7a(5H)-yl)methoxy)-5,6-dihydro-4H-[1,4]oxazepino [5,6,7-de]quinazolin-9-yl)-7-fluorobenzo[b]thiophene-3-carbonitrile | 811.2 |
| 472[3] | 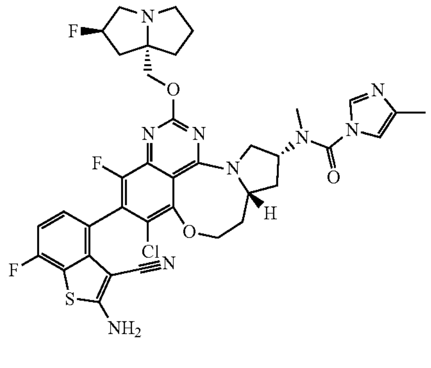 [SMILES: Cc1cn(C(=O)N(C)[C@@H]2C[C@@H]3CCOc4c(Cl)c(-c5ccc(F)c6sc(N)c(C#N)c56)c(F)c5nc(OC[C@@]67CCCN6C[C@H](F)C7)nc(c45)N3C2)cn1] | N-((2R,13aR)-9-(2-amino-3-cyano-7-fluorobenzo[b] thiophen-4-yl)-10-chloro-8-fluoro-6-(((2R,7aS)-2-fluorotetrahydro-1H-pyrrolizin-7a(5H)-yl) methoxy)-1,2,3,12,13,13a-hexahydropyrrolo[1',2':5,6] [1,5]oxazocino[4,3,2-de] quinazolin-2-yl)-N,4-dimethyl-1H-imidazole-1-carboxamide | 778.2 |

TABLE 1-continued

| No. | Structure | Chemical Name | [M + H]+ |
|---|---|---|---|
| 473[5] | 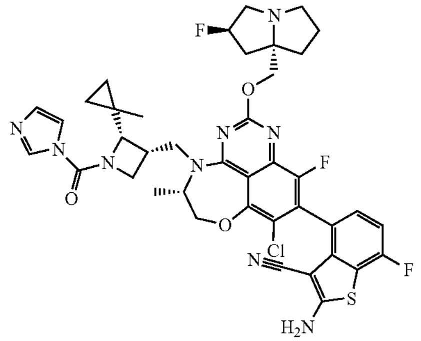 [SMILES: C[C@H]1COc2c(Cl)c(-c3ccc(F)c4sc(N)c(C#N)c34)c(F)c3nc(OC[C@@]45CCCN4C[C@H](F)C5)nc(c23)N1C[C@@H]1CN(C(=O)n2ccnc2)[C@@H]1C1(C)CC1] | 4-((5S)-4-(((2S,3R)-1-(1H-imidazole-1-carbonyl)-2-(1-methylcyclopropyl)azetidin-3-yl)methyl)-8-chloro-10-fluoro-2-(((2R,7aS)-2-fluorotetrahydro-1H-pyrrolizin-7a(5H)-yl) methoxy)-5-methyl-5,6-dihydro-4H-[1,4]oxazepino [5,6,7-de]quinazolin-9-yl)-2-amino-7-fluorobenzo[b] thiophene-3-carbonitrile | 818.2 |
| 474[3] | 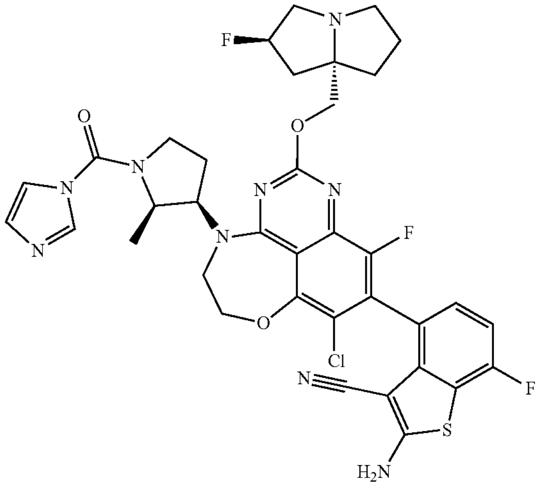 [SMILES: C[C@@H]1[C@H](N2CCOc3c(Cl)c(-c4ccc(F)c5sc(N)c(C#N)c45)c(F)c4nc(OC[C@@]56CCCN5C[C@H](F)C6)nc2c34)CCN1C(=O)n1ccnc1] | 4-(4-((2R,3R)-1-(1H-imidazole-1-carbonyl)-2-methylpyrrolidin-3-yl)-8-chloro-10-fluoro-2-(((2R,7aS)-2-fluorotetrahydro-1H-pyrrolizin-7a(5H)-yl) methoxy)-5,6-dihydro-4H-[1,4]oxazepino[5,6,7-de] quinazolin-9-yl)-2-amino-7-fluorobenzo[b]thiophene-3-carbonitrile | 764.2 |
| 475[1] | 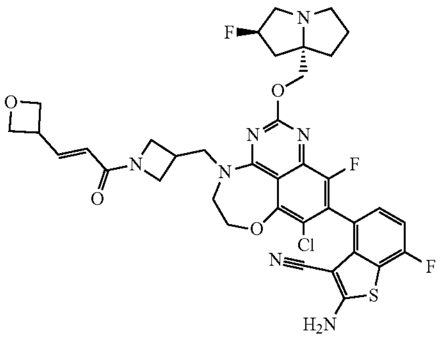 [SMILES: N#Cc1c(N)sc2c(F)ccc(-c3c(Cl)c4c5c(nc(OC[C@@]67CCCN6C[C@H](F)C7)nc5c3F)N(CC3CN(C(=O)/C=C/C5COC5)C3)CCO4)c12] | 2-amino-4-(8-chloro-10-fluoro-2-(((2R,7aS)-2-fluorotetrahydro-1H-pyrrolizin-7a(5H)-yl) methoxy)-4-((1-((E)-3-(oxetan-3-yl)acryloyl)azetidin-3-yl) methyl)-5,6-dihydro-4H-[1,4] oxazepino[5,6,7-de]quinazolin-9-yl)-7-fluorobenzo[b] thiophene-3-carbonitrile | 766.2 |
| 476[2] | 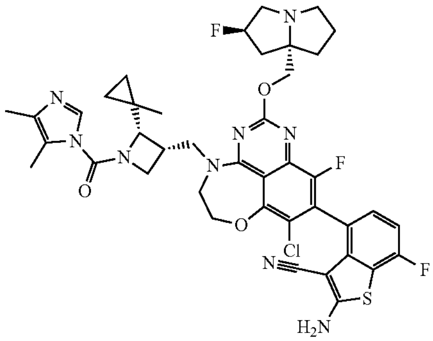 [SMILES: Cc1ncn(C(=O)N2C[C@@H](CN3CCOc4c(Cl)c(-c5ccc(F)c6sc(N)c(C#N)c56)c(F)c5nc(OC[C@@]67CCCN6C[C@H](F)C7)nc3c45)[C@H]2C2(C)CC2)c1C] | 2-amino-4-(8-chloro-4-(((2S,3R)-1-(4,5-dimethyl-1H-imidazole-1-carbonyl)-2-(1-methylcyclopropyl) azetidin-3-yl)methyl)-10-fluoro-2-(((2R,7aS)-2-fluorotetrahydro-1H-pyrrolizin-7a(5H)-yl)methoxy)-5,6-dihydro-4H-[1,4]oxazepino [5,6,7-de]quinazolin-9-yl)-7-fluorobenzo[b]thiophene-3-carbonitrile | 832.3 |

TABLE 1-continued

| No. | Structure | Chemical Name | [M + H]+ |
|---|---|---|---|
| 477[1] | 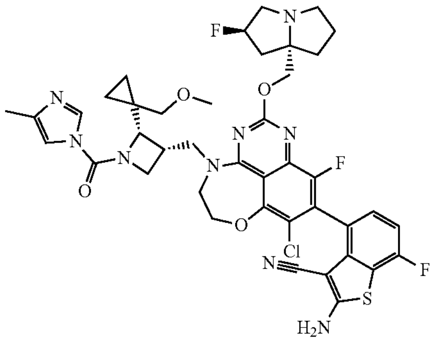 [SMILES: COCC1([C@@H]2[C@H](CN3CCOc4c(Cl)c(-c5ccc(F)c6sc(N)c(C#N)c56)c(F)c5nc(OC[C@@]67CCCN6C[C@H](F)C7)nc3c45)CN2C(=O)n2cnc(C)c2)CC1] | 2-amino-4-(8-chloro-10-fluoro-2-(((2R,7aS)-2-fluorotetrahydro-1H-pyrrolizin-7a(5H)-yl)methoxy)-4-(((2S,3R)-2-(1-(methoxymethyl)cyclopropyl)-1-(4-methyl-1H-imidazole-1-carbonyl)azetidin-3-yl)methyl)-5,6-dihydro-4H-[1,4]oxazepino[5,6,7-de]quinazolin-9-yl)-7-fluorobenzo[b]thiophene-3-carbonitrile | 848.2 |
| 478[1] | 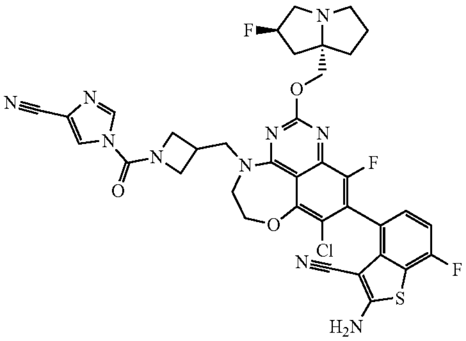 [SMILES: N#Cc1cn(C(=O)N2CC(CN3CCOc4c(Cl)c(-c5ccc(F)c6sc(N)c(C#N)c56)c(F)c5nc(OC[C@@]67CCCN6C[C@H](F)C7)nc3c45)C2)cn1] | 1-(3-((9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)methyl)azetidine-1-carbonyl)-1H-imidazole-4-carbonitrile | 775.5 |
| 479[2] | 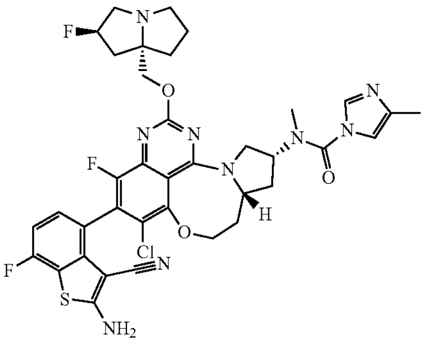 [SMILES: Cc1cn(C(=O)N(C)[C@@H]2C[C@@H]3CCOc4c(Cl)c(-c5ccc(F)c6sc(N)c(C#N)c56)c(F)c5nc(OC[C@@]67CCCN6C[C@H](F)C7)nc(c45)N3C2)cn1] | N-((2R,13aR)-9-(2-amino-3-cyano-7-fluorobenzo[b]thiophen-4-yl)-10-chloro-8-fluoro-6-(((2R,7aS)-2-fluorotetrahydro-1H-pyrrolizin-7a(5H)-yl)methoxy)-1,2,3,12,13,13a-hexahydropyrrolo[1',2':5,6][1,5]oxazocino[4,3,2-de]quinazolin-2-yl)-N,4-dimethyl-1H-imidazole-1-carboxamide | 778.1 |
| 480[6] | 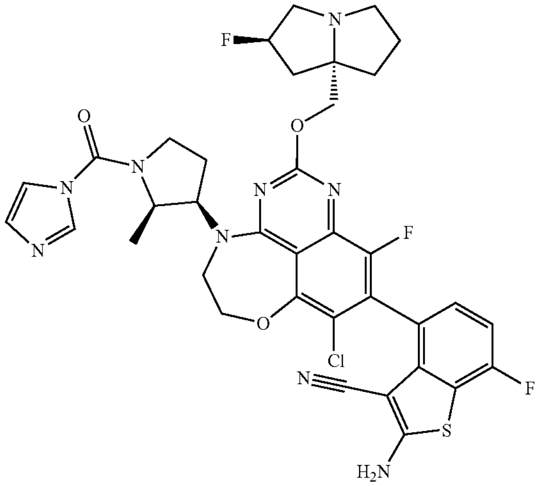 [SMILES: C[C@@H]1[C@H](N2CCOc3c(Cl)c(-c4ccc(F)c5sc(N)c(C#N)c45)c(F)c4nc(OC[C@@]56CCCN5C[C@H](F)C6)nc2c34)CCN1C(=O)n1ccnc1] | 4-(4-((2R,3R)-1-(1H-imidazole-1-carbonyl)-2-methylpyrrolidin-3-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-2-amino-7-fluorobenzo[b]thiophene-3-carbonitrile | 764.2 |

TABLE 1-continued

| No. | Structure | Chemical Name | [M + H]+ |
|---|---|---|---|
| 481[1] | 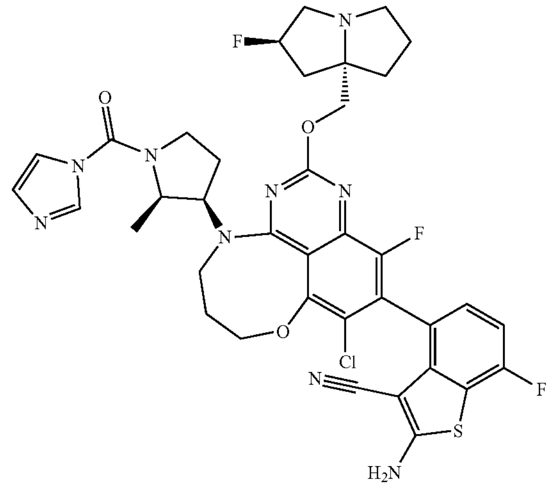 [SMILES: C[C@@H]1[C@H](N2CCCOc3c(Cl)c(-c4ccc(F)c5sc(N)c(C#N)c45)c(F)c4nc(OC[C@@]56CCCN5C[C@H](F)C6)nc2c34)CCN1C(=O)n1ccnc1] | 4-(4-((2R,3R)-1-(1H-imidazole-1-carbonyl)-2-methylpyrrolidin-3-yl)-9-chloro-11-fluoro-2-(((2R,7aS)-2-fluorotetrahydro-1H-pyrrolizin-7a(5H)-yl)methoxy)-4,5,6,7-tetrahydro-[1,5]oxazocino[4,3,2-de]quinazolin-10-yl)-2-amino-7-fluorobenzo[b]thiophene-3-carbonitrile | 778.2 |
| 482 | 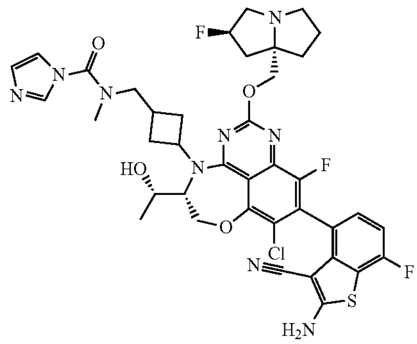 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1C1CC(CN(C)C(=O)n2ccnc2)C1] | N-((3-((5R)-9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-4-yl)cyclobutyl)methyl)-N-methyl-1H-imidazole-1-carboxamide | 822.3 |
| 483[2] | 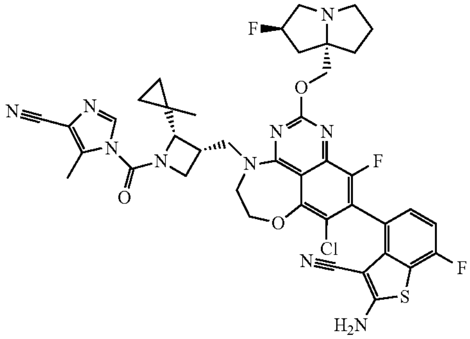 [SMILES: Cc1c(C#N)ncn1C(=O)N1C[C@@H](CN2CCOc3c(Cl)c(-c4ccc(F)c5sc(N)c(C#N)c45)c(F)c4nc(OC[C@@]56CCCN5C[C@H](F)C6)nc2c34)[C@H]1C1(C)CC1] | 1-((2S,3R)-3-((9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)methyl)-2-(1-methylcyclopropyl)azetidine-1-carbonyl)-5-methyl-1H-imidazole-4-carbonitrile | 843.2 |

TABLE 1-continued

| No. | Structure | Chemical Name | [M + H]+ |
| --- | --- | --- | --- |
| 484[1] | 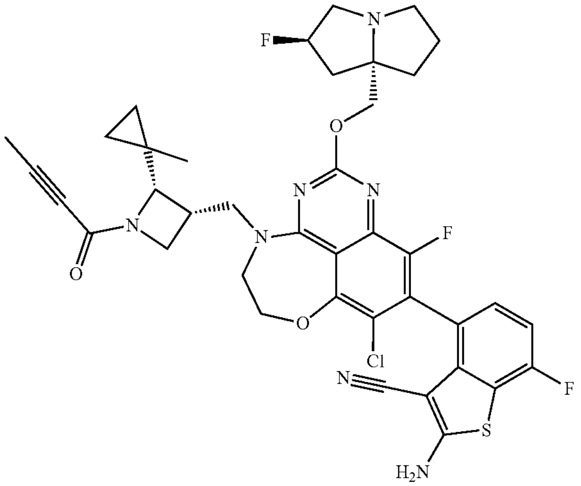 [SMILES: CC#CC(=O)N1C[C@@H](CN2CCOc3c(Cl)c(-c4ccc(F)c5sc(N)c(C#N)c45)c(F)c4nc(OC[C@@]56CCCN5C[C@H](F)C6)nc2c34)[C@H]1C1(C)CC1] | 2-amino-4-(4-(((2S,3R)-1-(but-2-ynoyl)-2-(1-methylcyclopropyl)azetidin-3-yl)methyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino [5,6,7-de]quinazolin-9-yl)-7-fluorobenzo[b]thiophene-3-carbonitrile | 776.3 |
| 485[4] | 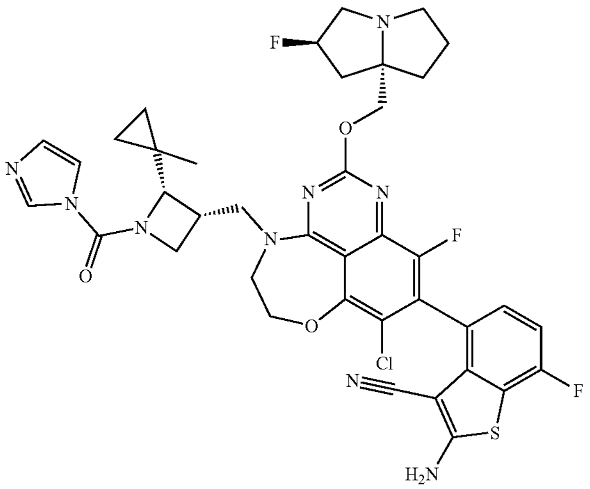 [SMILES: CC1([C@@H]2[C@H](CN3CCOc4c(Cl)c(-c5ccc(F)c6sc(N)c(C#N)c56)c(F)c5nc(OC[C@@]67CCCN6C[C@H](F)C7)nc3c45)CN2C(=O)n2ccnc2)CC1] | 4-(4-(((2S,3R)-1-(1H-imidazole-1-carbonyl)-2-(1-methylcyclopropyl)azetidin-3-yl)methyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino [5,6,7-de]quinazolin-9-yl)-2-amino-7-fluorobenzo[b] thiophene-3-carbonitrile | 804.2 |
| 486[6] | 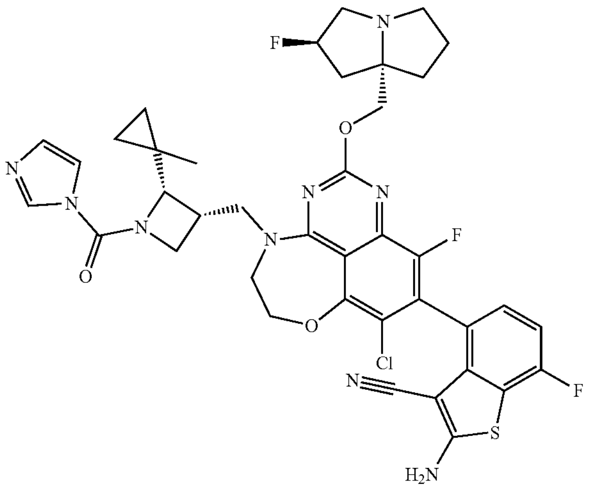 [SMILES: CC1([C@@H]2[C@H](CN3CCOc4c(Cl)c(-c5ccc(F)c6sc(N)c(C#N)c56)c(F)c5nc(OC[C@@]67CCCN6C[C@H](F)C7)nc3c45)CN2C(=O)n2ccnc2)CC1] | 4-(4-(((2S,3R)-1-(1H-imidazole-1-carbonyl)-2-(1-methylcyclopropyl)azetidin-3-yl)methyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino [5,6,7-de]quinazolin-9-yl)-2-amino-7-fluorobenzo[b] thiophene-3-carbonitrile | 804.2 |

TABLE 1-continued

| No. | Structure | Chemical Name | [M + H]+ |
| --- | --- | --- | --- |
| 487 | 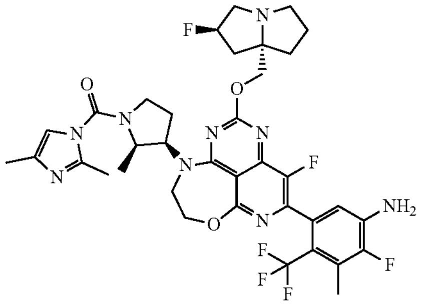 [SMILES: Cc1cn(C(=O)N2CC[C@@H](N3CCOc4nc(-c5cc(N)c(F)c(C)c5C(F)(F)F)c(F)c5nc(OC[C@@]67CCCN6C[C@H](F)C7)nc3c45)[C@H]2C)c(C)n1] | ((2R,3R)-3-(5-(5-amino-4-fluoro-3-methyl-2-(trifluoromethyl)phenyl)-4-fluoro-2-(((2R,7aS)-2-fluorotetrahydro-1H-pyrrolizin-7a(5H)-yl)methoxy)-8,9-dihydro-10H-7-oxa-1,3,6,10-tetraazacyclohepta[de]naphthalen-10-yl)-2-methylpyrrolidin-1-yl)(2,4-dimethyl-1H-imidazol-1-yl)methanone | 760.6 |
| 488 | 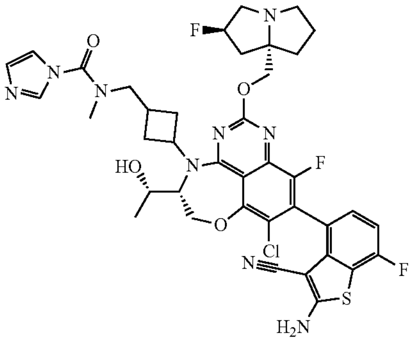 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1C1CC(CN(C)C(=O)n2ccnc2)C1] | N-((3-((5R)-9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-4-yl)cyclobutyl)methyl)-N-methyl-1H-imidazole-1-carboxamide | 822.2 |
| 489[3] | 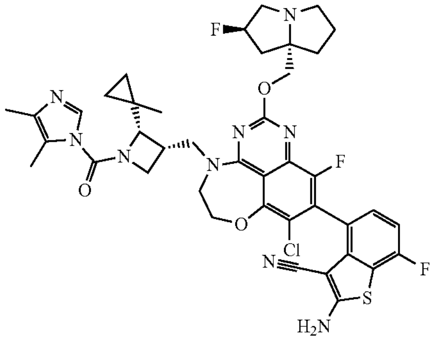 [SMILES: Cc1ncn(C(=O)N2C[C@@H](CN3CCOc4c(Cl)c(-c5ccc(F)c6sc(N)c(C#N)c56)c(F)c5nc(OC[C@@]67CCCN6C[C@H](F)C7)nc3c45)[C@H]2C2(C)CC2)c1C] | 2-amino-4-(8-chloro-4-(((2S,3R)-1-(4,5-dimethyl-1H-imidazole-1-carbonyl)-2-(1-methylcyclopropyl)azetidin-3-yl)methyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 832.2 |
| 490[2,5] | 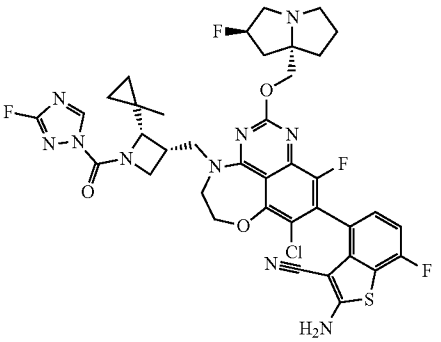 [SMILES: CC1([C@@H]2[C@H](CN3CCOc4c(Cl)c(-c5ccc(F)c6sc(N)c(C#N)c56)c(F)c5nc(OC[C@@]67CCCN6C[C@H](F)C7)nc3c45)CN2C(=O)n2cnc(F)n2)CC1] | 2-amino-4-(8-chloro-10-fluoro-4-(((2S,3R)-1-(3-fluoro-1H-1,2,4-triazole-1-carbonyl)-2-(1-methylcyclopropyl)azetidin-3-yl)methyl)-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 823.3 |

TABLE 1-continued

| No. | Structure | Chemical Name | [M + H]+ |
|---|---|---|---|
| 491[1] | 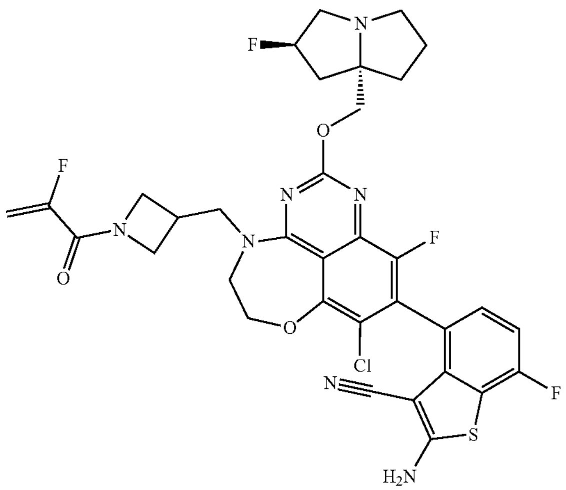 [SMILES: C=C(F)C(=O)N1CC(CN2CCOc3c(Cl)c(-c4ccc(F)c5sc(N)c(C#N)c45)c(F)c4nc(OC[C@@]56CCCN5C[C@H](F)C6)nc2c34)C1] | 2-amino-4-(8-chloro-10-fluoro-4-((1-(2-fluoroacryloyl) azetidin-3-yl)methyl)-2-(((2R,7aS)-2-fluorotetrahydro-1H-pyrrolizin-7a(5H)-yl) methoxy)-5,6-dihydro-4H-[1,4]oxazepino[5,6,7-de] quinazolin-9-yl)-7-fluorobenzo [b]thiophene-3-carbonitrile | 728.2 |
| 492 | 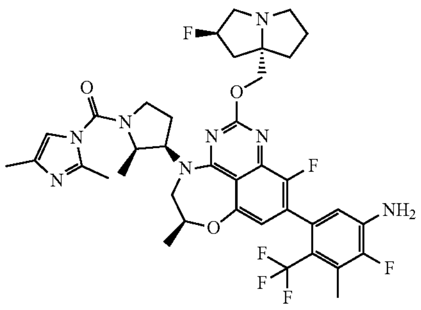 [SMILES: Cc1cn(C(=O)N2CC[C@@H](N3C[C@H](C)Oc4cc(-c5cc(N)c(F)c(C)c5C(F)(F)F)c(F)c5nc(OC[C@@]67CCCN6C[C@H](F)C7)nc3c45)[C@H]2C)c(C)n1] | ((2R,3R)-3-((S)-9-(5-amino-4-fluoro-3-methyl-2-(trifluoromethyl)phenyl)-10-fluoro-2-(((2R,7aS)-2-fluorotetrahydro-1H-pyrrolizin-7a(5H)-yl)methoxy)-6-methyl-5,6-dihydro-4H-[1,4]oxazepino [5,6,7-de]quinazolin-4-yl)-2-methylpyrrolidin-1-yl)(2,4-dimethyl-1H-imidazol-1-yl)methanone | 773.1 |
| 493[1] | 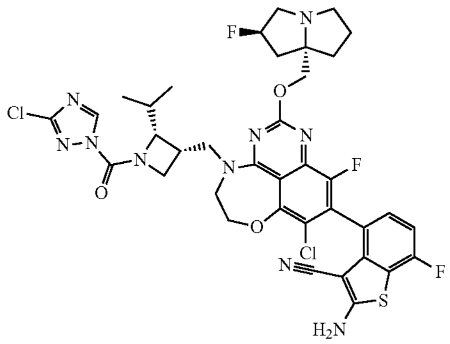 [SMILES: CC(C)[C@@H]1[C@H](CN2CCOc3c(Cl)c(-c4ccc(F)c5sc(N)c(C#N)c45)c(F)c4nc(OC[C@@]56CCCN5C[C@H](F)C6)nc2c34)CN1C(=O)n1cnc(Cl)n1] | 2-amino-4-(8-chloro-4-(((2R,3R)-1-(3-chloro-1H-1,2,4-triazole-1-carbonyl)-2-isopropylazetidin-3-yl) methyl)-10-fluoro-2-(((2R, 7aS)-2-fluorotetrahydro-1H-pyrrolizin-7a(5H)-yl) methoxy)-5,6-dihydro-4H-[1,4]oxazepino[5,6,7-de] quinazolin-9-yl)-7-fluorobenzo[b]thiophene-3-carbonitrile | 827.6 |

TABLE 1-continued

| No. | Structure | Chemical Name | [M + H]+ |
|---|---|---|---|
| 494[1] | 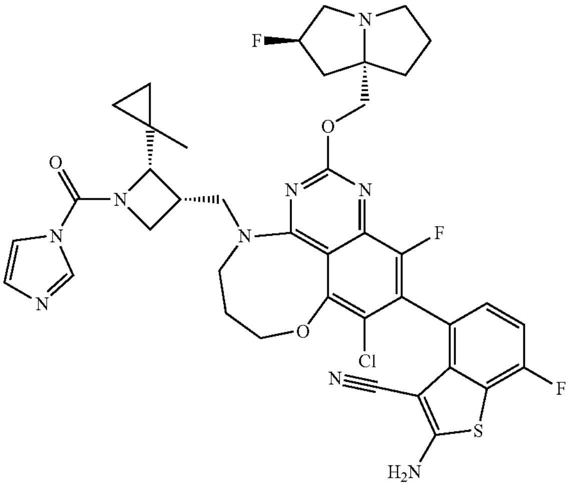 [SMILES: CC1([C@@H]2[C@H](CN3CCCOc4c(Cl)c(-c5ccc(F)c6sc(N)c(C#N)c56)c(F)c5nc(OC[C@@]67CCCN6C[C@H](F)C7)nc3c45)CN2C(=O)n2ccnc2)CC1] | 4-(4-(((2S,3R)-1-(1H-imidazole-1-carbonyl)-2-(1-methylcyclopropyl)azetidin-3-yl)methyl)-9-chloro-11-fluoro-2-(((2R,7aS)-2-fluorotetrahydro-1H-pyrrolizin-7a(5H)-yl)methoxy)-4,5,6,7-tetrahydro-[1,5]oxazocino[4,3,2-de]quinazolin-10-yl)-2-amino-7-fluorobenzo[b]thiophene-3-carbonitrile | 818.2 |
| 495[1] | 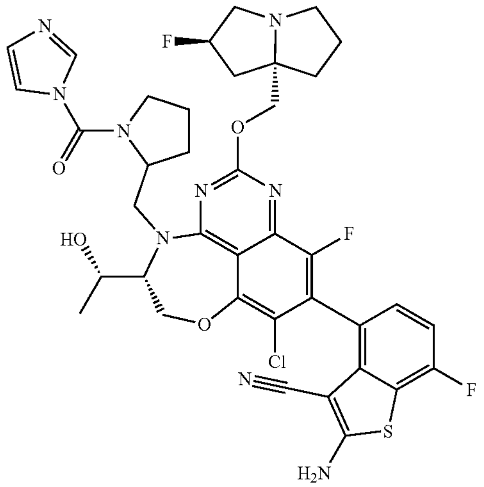 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1CC1CCCN1C(=O)n1ccnc1] | 4-((5R)-4-((1-(1H-imidazole-1-carbonyl)pyrrolidin-2-yl)methyl)-8-chloro-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-9-yl)-2-amino-7-fluorobenzo[b]thiophene-3-carbonitrile | 808.2 |

[1]compound provided as mixture of atropisomers
[2]compound provided as a single atropisomer (less polar P2 from chiral separation) at $X^7/R^7$ position
[3]compound provided as a single atropisomer (more polar P1 from chiral separation) at $X^7/R^7$ position
[4]compound provided as a single R atropisomer at $X^7/R^7$ position
[5]compound provided as a single S atropisomer at $X^7/R^7$ position
[6]compound provided as a single atropisomer at $X^7/R^7$ position
[7]compound provided as a diastereomer mixture Compounds of Table 1 are depicted with flat, wedged, and/or hashed wedged bonds. It is understood that compounds depicted in Table 1 encompass all possible stereoisomers, including atropisomers, of the compounds of Table 1. In some instances, the relative stereochemistry at one or more stereocenters of a compound has been determined; in some instances, the absolute stereochemistry has been determined. In some instances, a single compound number represents a mixture of stereoisomers, including atropisomers. In some instances, a single compound number represents a single stereoisomer, such as a single atropisomer. As such, it is understood that if two or more compound numbers in Table 1 are provided with the same depicted structure, then different stereoisomers or mixtures of stereoisomers of the depicted structure are represented by each compound number.

In some embodiments, the compounds of the present disclosure exhibit one or more functional characteristics disclosed herein. For example, a subject compound binds to a Ras protein, KRAS protein or a mutant form thereof. In some embodiments, a subject compound binds specifically and also inhibits a Ras protein, KRAS protein or a mutant form thereof. In some embodiments, a subject compound selectively inhibits a KRAS mutant relative to a wildtype KRAS. In some embodiments, the IC50 of a subject compound for a KRAS mutant (e.g., including G12S) is less than about 5 μM, less than about 1 μM, less than about 500 nM, less than 250 nM, less than 100 nM, less than 50 nM, or even less, as measured in an in vitro assay known in the art or exemplified herein. In some embodiments, a subject compound covalently binds to a KRAS mutant (e.g., KRAS G12S and/or KRAS G12C).

In some embodiments, a compound of the present disclosure is capable of reducing Ras signaling output. Such reduction may be evidenced by one or more of the following: (i) an increase in steady state level of GDP-bound Ras protein; (ii) a reduction in steady state level of GTP-bound Ras protein; (iii) a reduction of phosphorylated AKTs473, (iv) a reduction of phosphorylated ERKT202/y204, (v) a reduction of phosphorylated S6S235/236, and (vi) reduction (e.g., inhibition) of cell growth of Ras-driven tumor cells (e.g., those derived from a tumor cell line disclosed herein). In some cases, the reduction in Ras signaling output can be evidenced by two, three, four, five, or all of (i)-(vi) above.

It shall be understood that different aspects of the disclosure can be appreciated individually, collectively, or in combination with each other. Various aspects described herein may be applied to any of the particular applications disclosed herein. The compositions of matter, including compounds of any formulae disclosed in the compound section, of the present disclosure may be utilized in the method section, including methods of use and production disclosed herein, or vice versa.

Methods

The compounds described herein, or a pharmaceutically acceptable salt or solvate thereof, are Ras inhibitors capable of inhibiting a Ras protein, such as wild-type Ras or a Ras mutant protein (e.g., G12S, G12C, G12D, G12V, G13C, and/or G13D) from K-Ras, H-Ras or N-Ras. Compounds, including pharmaceutically acceptable salts or solvates thereof, disclosed herein have a wide range of applications in therapeutics, diagnostics, and other biomedical research.

In certain aspects, the present disclosure provides a method of treating cancer in a subject in need thereof, comprising administering to the subject a therapeutically effective amount of a compound described herein, or a pharmaceutically acceptable salt or solvate thereof.

In certain aspects, the present disclosure provides a method of treating a cancer comprising amplified wildtype Ras or a Ras mutant (e.g., G12S, G12C, G12D, G12V, G13C, and/or G13D) protein in a subject, comprising inhibiting amplified wildtype Ras or the Ras mutant protein of said subject by administering to said subject a compound, wherein the compound is characterized in that upon contacting the Ras protein, the Ras protein activity or function is inhibited (e.g., partially inhibited or completely inhibited), such that said inhibited Ras protein exhibits reduced Ras signaling output (e.g., compared to a corresponding Ras protein not contacted by the compound).

In certain aspects, the present disclosure provides a method of modulating activity of a Ras protein (e.g., K-Ras, mutant K-Ras, K-Ras G12S, K-Ras G12C, K-Ras G12D, K-Ras G12V, K-Ras G13C, and/or K-Ras G13D), comprising contacting a Ras protein with an effective amount of a compound described herein, or a pharmaceutically acceptable salt or solvate thereof, thereby modulating the activity of the Ras protein.

In certain aspects, the present disclosure provides a method of inhibiting cell growth, comprising administering an effective amount of a compound described herein, or a pharmaceutically acceptable salt or solvate thereof, to a cell expressing a Ras (e.g., K-Ras) protein, thereby inhibiting growth of said cells. In some embodiments, the subject method comprises administering an additional agent to said cell.

In certain aspects, the present disclosure provides a method of treating a disease mediated at least in part by a Ras protein, such as K-Ras or a mutant thereof, in a subject in need thereof, comprising administering to the subject an effective amount of a compound disclosed herein, or a pharmaceutically acceptable salt or solvate thereof. In some embodiments, the disease is cancer, such as a solid tumor or a hematological cancer. In some embodiments, the method further comprises administering an additional agent to the subject, such as a SHP2 inhibitor, a SOS inhibitor, an EGFR inhibitor, a MEK inhibitor, an ERK inhibitor, a CDK4/6 inhibitor, a BRAF inhibitor, or a combination thereof.

In certain aspects, the present disclosure provides a method of inhibiting activity of a Ras protein, such as K-Ras or a mutant thereof, comprising contacting the Ras protein with a compound disclosed herein, or a pharmaceutically acceptable salt or solvate thereof. In some embodiments, the compound exhibits an IC50 against the Ras protein of less than 10 μM, such as less than 5 μM, 1 μM, 500 nM, 100 nM, 50 nM, 10 nM, 5 nM, 1 nM, 500 μM, 50 μM, 10 μM or less.

In certain aspects, the present disclosure provides a method of treating a Ras-mediated cancer in a subject in need thereof, comprising administering to the subject a SHP2 inhibitor, a SOS inhibitor, an EGFR inhibitor, a MEK inhibitor, an ERK inhibitor, a CDK4/6 inhibitor, or a BRAF inhibitor and an effective amount of a compound disclosed herein, such as a compound of Formula I, IA, IB, II, IIA, or V, or a pharmaceutically acceptable salt or solvate thereof. In some embodiments, the cancer is a solid tumor. In some embodiments, the cancer is a hematological cancer.

In practicing any of the methods disclosed herein, the Ras target to which a subject compound binds, either covalently or reversibly, can be a Ras mutant (e.g., G12S, G12C, G12D, G12V, G13C, and/or G13D), including a mutant of K-Ras, H-Ras, or N-Ras. In some embodiments, the methods of treating cancer can be applied to treat a solid tumor or a hematological cancer. In some embodiments, the cancer being treated can be, without limitation, prostate cancer, brain cancer, colon cancer, rectal cancer, renal-cell carcinoma, liver cancer, various lung cancers including non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers. In some embodiments is a method of treating cancer in a subject in need thereof, comprising administering to the subject a therapeutically effective amount of a compound described herein, or a pharmaceutically acceptable salt or solvate thereof, wherein the cancer is a hematological cancer. In some embodiments is a method of treating cancer in a subject in need thereof, comprising administering to the subject a therapeutically effective amount of a compound described herein, or a pharmaceutically acceptable salt or solvate thereof, wherein the cancer is a hematological cancer selected from one or more of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, and preleukemia. In some embodiments is a method of treating cancer in a subject in need thereof, comprising administering to the subject a therapeutically effective amount of a compound described herein, or a pharmaceutically acceptable salt or solvate thereof, wherein the cancer is one or more cancers selected from the group consisting of chronic lymphocytic leukemia (CLL), acute myeloid leukemia (AML), T-cell acute lymphoblastic leukemia (T-ALL), B cell acute lymphoblastic leukemia (B-ALL), and/or acute lymphoblastic leukemia (ALL).

Any of the treatment methods disclosed herein can be administered alone or in combination or in conjunction with another therapy or another agent. By "combination" it is meant to include (a) formulating a subject composition containing a subject compound together with another agent, or (b) using the subject composition separate from the another agent as an overall treatment regimen. By "conjunction" it is meant that the another therapy or agent is administered either simultaneously, concurrently or sequentially with a subject composition comprising a compound disclosed herein, with no specific time limits, wherein such conjunctive administration provides a therapeutic effect.

In some embodiments, a subject treatment method is combined with surgery, cellular therapy, chemotherapy, radiation, and/or immunosuppressive agents. Additionally, compositions of the present disclosure can be combined with other therapeutic agents, such as other anti-cancer agents, anti-allergic agents, anti-nausea agents (or anti-emetics), pain relievers, cytoprotective agents, immunostimulants, and combinations thereof. In one embodiment, a subject treatment method is combined with a chemotherapeutic agent.

In some embodiments, a compound described herein, such as a compound, salt, or solvate of Formula I, IA, IB, II, IIA, or V, and one or more pharmacologically active agents are administered either simultaneously, concurrently or sequentially with no specific time limits, wherein such administration provides therapeutically effective levels of the two or more compounds in the body of the patient.

In some embodiments, a compound described herein, such as a compound, salt, or solvate of Formula I, IA, IB, II, IIA, or V, and one or more pharmacologically active agents are administered sequentially in any order by a suitable route, such as infusion or orally. The dosing regimen may vary depending upon the stage of the disease, physical fitness of the patient, safety profiles of the individual drugs, and tolerance of the individual drugs, as well as other criteria known to the attending physician and medical practitioner(s) administering the combination. The compound of the present disclosure and other pharmacologically active agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In some cases, a treatment regime may be dosed according to a body weight of a subject. In subjects who are determined obese (BMI>35) a practical weight may need to be utilized. BMI is calculated by: BMI=weight (kg)/[height (m)]$^2$. Body weight may be calculated for men as 50 kg+2.3*(number of inches over 60 inches) or for women 45.5 kg+2.3*(number of inches over 60 inches). An adjusted body weight may be calculated for subjects who are more than 20% of their ideal body weight. An adjusted body weight may be the sum of an ideal body weight+(0.4*(Actual body weight −ideal body weight)). In some cases, a body surface area may be utilized to calculate a dosage. A body surface area (BSA) may be calculated by: BSA (m$^2$) =√Height (cm)*Weight (kg)/3600.

In certain aspects, the present disclosure provides a method of modulating activity of a Ras (e.g., K-Ras) protein, comprising contacting a Ras protein with an effective amount of a compound described herein, or a pharmaceutically acceptable salt or solvate thereof, thereby modulating the activity of the Ras (e.g., K-Ras) protein. In some embodiments, the subject method comprises administering an additional agent or therapy.

In certain aspects, the present disclosure provides a method of modulating activity of a Ras protein, comprising contacting a Ras protein with an effective amount of a compound described, or a pharmaceutically acceptable salt or solvate thereof, wherein said modulating comprises inhibiting the Ras (e.g., K-Ras) protein activity. In certain aspects, the present disclosure provides a method of modulating activity of a Ras protein, such as Ras mutant (e.g., G12S, G12C, G12D, G12V, G13C, and/or G13D) proteins of K-Ras, H-Ras, and N-Ras, comprising contacting the Ras protein with an effective amount of a compound described herein, or a pharmaceutically acceptable salt or solvate thereof.

In certain aspects, the present disclosure provides a method of reducing Ras signaling output in a cell by contacting the cell with a compound described herein. A reduction in Ras signaling can be evidenced by one or more of the following: (i) an increase in steady state level of GDP-bound modified protein; (ii) a reduction in steady state level of GTP-bound Ras protein; (iii) a reduction of phosphorylated AKTs473, (iv) a reduction of phosphorylated ERKT202/y204, (v) a reduction of phosphorylated S6S235/236, (vi) a reduction of cell growth of a tumor cell expressing a Ras mutant (e.g., G12S, G12C, G12D, G12V, G13C, and/or G13D) protein, and (vii) a reduction in Ras interaction with a Ras-pathway signaling protein. Non-limiting examples of Ras-pathway signaling proteins include SOS (including SOS1 and SOS2), RAF, SHC, SHP (including SHP1 and SHP2), MEK, MAPK, ERK, GRB, RASA1, and GNAQ. In some embodiments, the reduction in Ras signaling output can be evidenced by two, three, four, five, six, or all of (i)-(vii) above. In some embodiments, the reduction of any one or more of (i)-(vii) can be 0.1-fold, 0.2-fold, 0.3-fold, 0.4-fold, 0.5-fold, 0.6-fold, 0.7-fold, 0.8-fold, 0.9-fold, 1-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, or more as compared to a control not treated with a subject compound. A reduction in cell growth can be demonstrated with the use of tumor cells or cell lines. A tumor cell line can be derived from a tumor in one or more tissues, e.g., pancreas, lung, ovary, biliary tract, intestine (e.g., small intestine, large intestine, colon), endometrium, stomach, hematopoietic tissue (e.g., lymphoid tissue), etc. Examples of tumor cell lines comprising a K-Ras mutation include, but are not limited to, A549 (e.g., K-Ras G12S), AGS (e.g., K-Ras G12D), ASPC1 (e.g., K-Ras G12D), Calu-6 (e.g., K-Ras Q61K), CFPAC-1 (e.g., K-Ras G12V), CL40 (e.g., K-Ras G12D), COL0678 (e.g., K-Ras G12D), COR-L23 (e.g., K-Ras G12V), DAN-G (e.g., K-Ras G12V), GP2D (e.g., K-Ras G12D), GSU (e.g., K-Ras G12F), HCT116 (e.g., K-Ras G13D), HEC1A (e.g., K-Ras G12D), HEC1B (e.g., K-Ras G12F), HEC50B (e.g., K-Ras G12F), HEYA8 (e.g., K-Ras G12D or G13D), HPAC (e.g., K-Ras G12D), HPAFII (e.g., K-Ras G12D), HUCCT1 (e.g., K-Ras G12D), KARPAS620 (e.g., K-Ras G13D), KOPN8 (e.g., K-Ras G13D), KP-3 (e.g., K-Ras G12V), KP-4 (e.g., K-Ras G12D), L3.3 (e.g., K-Ras G12D), LoVo (e.g., K-Ras G13D), LS180 (e.g., K-Ras G12D), LS513 (e.g., K-Ras G12D), MCAS (e.g., K-Ras G12D), NB4 (e.g., K-Ras A18D), NCI-H1355 (e.g., K-Ras G13C), NCI-H1573 (e.g., K-Ras G12A), NCI-H1944 (e.g., K-Ras G13D), NCI-H2009 (e.g., K-Ras G12A), NCI-H441 (e.g., K-Ras G12V), NCI-H747 (e.g., K-Ras G13D), NOMO-1 (e.g., K-Ras G12D), OV7 (e.g., K-Ras G12D), PANC0203 (e.g., K-Ras G12D), PANC0403 (e.g., K-Ras G12D), PANC0504 (e.g., K-Ras G12D), PANC0813 (e.g., K-Ras G12D), PANC1 (e.g., K-Ras G12D), Panc-10.05 (e.g., K-Ras G12D), PaTu-8902 (e.g., K-Ras G12V), PK1 (e.g., K-Ras G12D), PK45H (e.g., K-Ras G12D), PK59 (e.g., K-Ras G12D), SK-CO-1 (e.g., K-Ras G12V), SKLU1 (e.g., K-Ras G12D), SKM-1 (e.g., K-Ras K117N), SNU1 (e.g., K-Ras G12D), SNU1033 (e.g., K-Ras G12D), SNU1197 (e.g., K-Ras G12D), SNU407 (e.g., K-Ras G12D), SNU410 (e.g., K-Ras G12D), SNU601 (e.g., K-Ras G12D), SNU61 (e.g., K-Ras G12D), SNU8 (e.g., K-Ras G12D), SNU869 (e.g., K-Ras G12D), SNU-C2A (e.g., K-Ras G12D), SU.86.86 (e.g., K-Ras G12D), SUIT2 (e.g., K-Ras G12D), SW1990 (e.g., K-Ras G12D), SW403 (e.g., K-Ras G12V), SW480 (e.g., K-Ras G12V), SW620 (e.g., K-Ras G12V), SW948 (e.g., K-Ras Q61L), T3M10 (e.g., K-Ras G12D), TCC-PAN2 (e.g., K-Ras G12R), TGBC11TKB (e.g., K-Ras G12D), and MIA Pa-Ca (e.g., MIA Pa-Ca 2 (e.g., K-Ras G12C)).

In an aspect is provided a method of modifying a Ras mutant protein, comprising contacting the Ras mutant protein with an effective amount of the compound, salt, or solvate described herein.

In embodiments of a method described herein, the modified Ras mutant protein exhibits a reduced Ras signaling output.

In embodiments of a method described herein, the reduced Ras signaling output is evidenced by one or more output selected from (i) an increase in steady state level of GDP-bound modified protein; (ii) a reduction in steady state level of GTP-bound modified protein; (iii) a reduction of phosphorylated AKTs473; (iv) a reduction of phosphorylated ERK T202/Y204; (v) a reduction of phosphorylated S6 S235/236; (vi) a reduction of cell growth of a tumor cell expressing a Ras G12S mutant protein; and (vii) a reduction in Ras interaction with a Ras-pathway signaling protein.

In embodiments of a method described herein, the Ras mutant protein comprises an amino acid sequence in SEQ ID No. 4 having a serine residue corresponding to position 12 of SEQ ID No. 1.

In embodiments of a method described herein, the Ras mutant protein comprises an amino acid sequence of SEQ ID No. 4.

In embodiments of a method described herein, the modified Ras mutant protein comprises an amino acid sequence of SEQ ID No. 4, or a fragment thereof that comprises a serine residue corresponding to position 12 of SEQ ID No. 1, and wherein the compound selectively labels the serine residue as compared to (i) an aspartate residue of a K-Ras G12D mutant protein, said aspartate corresponding to position 12 of SEQ ID No. 2; (ii) a valine residue of a K-Ras G12V mutant protein, said valine corresponding to position 12 of SEQ ID No. 3; and/or (iii) a glycine residue of a K-Ras wildtype protein, said glycine corresponding to position 12 of SEQ ID No. 1.

In embodiments of a method described herein, the compound selectively labels the serine residue by at least 2-fold when assayed under comparable conditions.

In embodiments of a method described herein, the compound selectively labels the serine residue by at least 5-fold when assayed under comparable conditions.

In embodiments of a method described herein, the contacting occurs in vivo.

In an aspect is provided a method of treating cancer in a subject in need thereof, comprising administering to the subject a therapeutically effective amount of a compound described herein, or a pharmaceutically acceptable salt or solvate thereof.

In an aspect is provided a method of treating cancer in a subject comprising a Ras mutant protein, the method comprising: inhibiting the Ras mutant protein of said subject by administering to said subject a compound described herein, wherein the compound is characterized in that upon contacting the Ras mutant protein, said Ras mutant protein exhibits reduced Ras signaling output.

In embodiments of a method described herein, the cancer is a solid tumor or a hematological cancer.

In embodiments of a method described herein, the cancer comprises a K-Ras G12S mutant protein.

In an aspect is provided a method of modulating signaling output of a Ras protein, comprising contacting a Ras protein with an effective amount of a compound described herein, or a pharmaceutically acceptable salt or solvate thereof, thereby modulating the signaling output of the Ras protein.

In an aspect is provided a method of inhibiting cell growth, comprising administering an effective amount of a compound described herein, or a pharmaceutically acceptable salt or solvate thereof, to a cell expressing a Ras protein, thereby inhibiting growth of said cells.

In embodiments of a method described herein, the method comprises administering an additional agent.

In an aspect is provided a method of treating cancer in a subject comprising a Ras mutant protein (e.g., KRAS G12D, KRAS G12C, KRAS G12S, KRAS G12V, KRAS G13D, KRAS G13C, NRAS G12D, NRAS G12C, NRAS G12S, NRAS G13D, NRAS G13C, HRAS G12D, HRAS G12C, HRAS G12S, HRAS G13D, or HRAS G13C), the method comprising modifying the Ras mutant protein of said subject by administering to said subject a compound described herein, wherein the compound is characterized in that upon contacting a Ras mutant protein, said Ras mutant protein is modified covalently at a residue corresponding to residue 12 or 13 of SEQ ID No: 1, such that said modified Ras mutant protein exhibits reduced Ras signaling output (e.g., compared to a control, such as an unmodified Ras mutant protein not covalently bonded with any compound such as a compound disclosed herein).

In some aspects, a subject compound exhibits one or more of the following characteristics: it is capable of reacting with a mutant residue (.g., KRAS G12D, KRAS G12C, KRAS G12S, KRAS G12V, KRAS G13D, KRAS G13C, NRAS G12D, NRAS G12C, NRAS G12S, NRAS G13D, NRAS G13C, HRAS G12D, HRAS G12C, HRAS G12S, HRAS G13D, or HRAS G13C) of a Ras mutant protein and covalently modifying such Ras mutant and/or it comprises a moiety susceptible to reacting with a nucleophilic amino acid residue corresponding to position 12 or 13 of SEQ ID No: 1. In some embodiments, a subject compound, when used to modify a Ras mutant protein, reduces the signaling output of the Ras protein. In some embodiments, a subject compound exhibits an IC50 against a mutant Ras as ascertained by reduction of Ras::SOS1 interaction of less than 10 μM, such as less than 5 μM, 1 μM, 500 nM, 100 nM, 50 nM, 10 nM, 5 nM, 1 nM, 500 μM, 50 μM, 10 μM or less.

In some embodiments, a compound disclosed herein, such as a compound of Formula I, IA, IB, II, IIA, or V, exhibits selective and potent inhibition of K-Ras G12S relative to wildtype K-Ras or other K-Ras mutants (e.g., K-Ras G12V, K-Ras G12D, or K-Ras G12C). In some embodiments, a subject warhead exhibits selective engagement of K-Ras G12S relative to K-Ras G12D or wildtype K-Ras by at least 1-fold, and in some instances greater than 2-, 3-, 4-, 5-, 10-, 15-, or 20-fold, or even higher. In some embodiments, a subject warhead exhibits a selective and rapid engagement of K-Ras G12S yielding at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%, or even higher engagement of G12S within, 10 mins, 20 mins, 30 mins, 1 hr, 2 hrs, 3 hrs, 4 hrs, 5 hrs, 6 hrs, 7 hrs, 8 hrs, 9 hrs, 10 hrs, 20 hrs, or 24 hours. In some embodiments, a selective and rapid engagement of K-Ras G12S is evidenced by at least 50% engagement within 24 hours. In some embodiments, subject compounds specifically engage K-Ras G12S covalently with essentially no detectable labeling of K-Ras G12D when assayed under comparable conditions. In some embodiments, subject compounds specifically engage K-Ras G12S covalently with essentially no detectable labeling of K-Ras wildtype when assayed under comparable conditions.

In some embodiments, a compound of the present disclosure selectively labels (e.g., via covalent binding) the serine residue of an unmodified Ras G12S protein corresponding to position 12 of SEQ ID No: 4.

The compounds of Formula I, IA, IB, II, and IIA disclosed herein, or a pharmaceutically acceptable salt or solvate thereof, are K-Ras inhibitors and have a wide range of applications in therapeutics, diagnostics, and other biomedical research. In some embodiments, a compound disclosed herein covalently modifies a Ras protein, such as a K-Ras G12S protein. In some embodiments, a Ras protein, such as a K-Ras G12S protein, is contacted with a compound disclosed herein to form a modified Ras protein.

In some embodiments, the compounds described herein, or a pharmaceutically acceptable salt or solvate thereof, are Ras modulators (including Ras inhibitors) capable of covalently modifying a Ras protein. Ras proteins being modified can be Ras G12S mutants or G12C mutants from K-Ras, H-Ras or N-Ras. The compounds disclosed herein, or pharmaceutically acceptable salts or solvates thereof, have a wide range of applications in therapeutics, diagnostics, and other biomedical research.

In an aspect is provided a method of treating cancer in a subject comprising a Ras G12S mutant protein, comprising modifying the Ras G12S mutant protein of said subject by administering to said subject a compound described herein, wherein said compound is characterized in that upon contacting the Ras G12S mutant protein, the Ras G12S mutant protein is modified covalently at a serine residue corresponding to residue 12 of SEQ ID No: 4, such that said modified K-Ras G12S protein exhibits reduced Ras signaling output (e.g., compared to a corresponding unmodified Ras protein unbound to the covalent compound).

In an aspect is provided a method of treating cancer in a subject comprising a Ras G12C mutant protein, comprising modifying the Ras G12C mutant protein of said subject by administering to said subject a compound described herein, wherein said compound is characterized in that upon contacting the Ras G12C mutant protein, the Ras G12C mutant protein is modified covalently at the cysteine residue corresponding to residue 12 of SEQ ID No: 1 (in which glycine at position 12 is replaced with cysteine), such that said modified K-Ras G12C protein exhibits reduced Ras signaling output (e.g., compared to a corresponding unmodified Ras protein unbound to the covalent compound).

In an aspect is provided a method of modulating activity of a Ras protein (e.g., K-Ras, mutant K-Ras, K-Ras G12S, K-Ras G12C), comprising contacting a Ras protein with an effective amount of a compound described herein, or a pharmaceutically acceptable salt or solvate thereof, thereby modulating the activity of the Ras protein.

In practicing any of the methods disclosed herein, the Ras target to which a subject compound binds covalently can be a Ras mutant (e.g., KRAS G12D, KRAS G12C, KRAS G12S, KRAS G12V, KRAS G13D, KRAS G13C, NRAS G12D, NRAS G12C, NRAS G12S, NRAS G13D, NRAS G13C, HRAS G12D, HRAS G12C, HRAS G12S, HRAS G13D, or HRAS G13C).

Pharmaceutical Compositions and Methods of Administration

In an aspect is provided a pharmaceutical composition comprising a compound described herein, or a pharmaceutically acceptable salt or solvate thereof, and a pharmaceutically acceptable excipient.

In some embodiments, a compound described herein, or a pharmaceutically acceptable salt or solvate thereof, is administered to a subject in a biologically compatible form suitable for administration to treat or prevent diseases, disorders, or conditions. Administration of a compound described herein can be in any pharmacological form including a therapeutically effective amount of a compound described herein, or a pharmaceutically acceptable salt or solvate thereof, alone or in combination with a pharmaceutically acceptable carrier.

In some embodiments, a compound described herein is administered as a pure chemical. In some embodiments, the compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21$^{st}$ Ed. Mack Pub. Co., Easton, PA (2005)).

Accordingly, provided herein is a pharmaceutical composition comprising at least one compound described herein, or a pharmaceutically acceptable salt, together with one or more pharmaceutically acceptable excipients. The excipient(s) (or carrier(s)) is acceptable or suitable if the excipient is compatible with the other ingredients of the composition and not deleterious to the recipient (i.e., the subject) of the composition.

In some embodiments of the methods described herein, a compound described herein is administered either alone or in combination with pharmaceutically acceptable carriers, excipients or diluents, in a pharmaceutical composition. Administration of a compound or composition described herein can be affected by any method that enables delivery of the compound to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, a compound described herein can be administered locally to the area in need of treatment, by, for example, local infusion during surgery, topical application such as creams or ointments, injection, catheter, or implant. The administration can also be by direct injection at the site of a diseased tissue or organ. In some embodiments, a compound described herein, or a pharmaceutically acceptable salt or solvate thereof, is administered orally.

In some embodiments of the methods described herein, a pharmaceutical composition suitable for oral administration is presented as a discrete unit such as a capsule, cachet or tablet, each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary, or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments of the methods described herein, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compound which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long-acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

ADDITIONAL EMBODIMENTS

Embodiment 1 A compound of Formula (I):

(I)

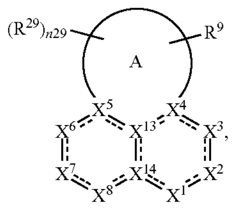

or a pharmaceutically acceptable salt or solvate thereof, wherein:

- Ring A is selected from a monocyclic $C_{7-10}$ carbocycle and monocyclic 7- to 10-membered heterocycle;
- $X^1$ is selected from C(R'), $C(R^1)_2$, N, $N(R^{1b})$, O, S, S(O), $S(O)_2$, and C(O);
- $X^2$ is selected from $C(R^2)$, $C(R^2)_2$, N, $N(R^{2b})$, O, S, S(O), $S(O)_2$, and C(O);
- $X^3$ is selected from $C(R^3)$, $C(R^3)_2$, N, $N(R^{3b})$, O, S, S(O), $S(O)_2$, and C(O);
- $X^4$ is selected from C, $C(R^4)$, and N;
- $X^5$ is selected from C, $C(R^5)$, and N;
- $X^6$ is selected from $C(R^6)$, $C(R^6)_2$, N, $N(R^{6b})$, O, S, S(O), $S(O)_2$, and C(O);
- $X^7$ is selected from $C(R^7)$, $C(R^{7a})(R^{7a})$, and N(Rh);

$X^8$ is selected from $C(R^8)$, $C(R^8)_2$, N, $N(R^{8b})$, O, S, S(O), $S(O)_2$, and C(O);

$X^{13}$ is selected from C, $C(R^{13a})$, and N;

$X^{14}$ is selected from C, $C(R^{14a})$, and N;

$R^7$ is $-L^{7a}-R^{17}$; $R^{7b}$ is $-L^{7b}-R^{17}$;

$L^{7a}$ is selected from a bond, $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, —$N(R^{12})$—, —C(O)—, —$N(R^{12})C(O)$—, —$C(O)N(R^{12})$—, —S—, —$S(O)_2$—, —S(O)—, —$P(O)(R^{12})$—, —$N(R^{12})S(O)_2$—, —$N(R^{12})S(O)$—, —$N(R^{12})P(O)(R^{12})$—, —$S(O)_2N(R^{12})$—, —$S(O)N(R^{12})$—, —$P(O)(R^{12})N(R^{12})$—, —$OP(O)(R^{12})$—, and —$P(O)(R^{12})O$—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$;

$L^{7b}$ is selected from a bond, $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —C(O)—, and —$C(O)N(R^{12})$—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$;

$R^9$ is $-L^{19}-R^{19}-L^{19a}-R^{19a}$;

$L^{19}$ is selected from a bond, $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, —$N(R^{12})$—, —C(O)—, —$N(R^{12})C(O)$—, —$C(O)N(R^{12})$—, —S—, —$S(O)_2$—, —S(O)—, —$P(O)(R^{12})$—, —$N(R^{12})S(O)_2$—, —$N(R^{12})S(O)$—, —$N(R^{12})P(O)(R^{12})$—, —$S(O)_2N(R^{12})$—, —$S(O)N(R^{12})$—, —$P(O)(R^{12})N(R^{12})$—, —$OP(O)(R^{12})$—, and —$P(O)(R^{12})O$—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$;

$R^{19}$ is selected from monocyclic $C_{3-8}$ carbocycle and monocyclic 3- to 8-membered heterocycle, wherein the monocyclic $C_{3-8}$ carbocycle and monocyclic 3- to 8-membered heterocycle are optionally substituted with one or more $R^{20}$;

$L^{19a}$ is selected from a bond, $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, —$N(R^{12})$—, —C(O)—, —$N(R^{12})C(O)$—, —$C(O)N(R^{12})$—, —S—, —$S(O)_2$—, —S(O)—, —$P(O)(R^{12})$—, —$N(R^{12})S(O)_2$—, —$N(R^{12})S(O)$—, —$N(R^{12})P(O)(R^{12})$—, —$S(O)_2N(R^{12})$—, —$S(O)N(R^{12})$—, —$P(O)(R^{12})N(R^{12})$—, —$OP(O)(R^{12})$—, and —$P(O)(R^{12})O$—, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$;

$R^{19a}$ is selected from:

i) 5-membered heteroaryl comprising one or more ring nitrogen atoms, wherein the 5-membered heteroaryl is directly bonded to $L^{19a}$ through an $R^{19a}$ ring nitrogen atom and wherein $R^{19a}$ is optionally substituted with one or more $R^{20}$; and ii) 5- to 12-membered heterocycle comprising three or four ring nitrogen atoms, wherein the 5- to 12-membered heterocycle is optionally substituted with one or more $R^{20}$;

$R^{1b}$, $R^{2b}$, $R^{3b}$, $R^{6b}$, and $R^{8b}$ are independently selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$C(O)OR^{12}$, —$C(O)R^{12}$, —$C(O)N(R^{12})(R^{13})$, —$C(O)C(O)N(R^{12})(R^{13})$, —$S(O)_2R^{12}$, —$S(O)(NR^{12})R^{12}$, —$S(O)_2N(R^{12})(R^{13})$, and —$S(=O)(=NR^{12})N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$;

$R^1$, $R^2$, $R^3$, $R^4$, $R^5$, $R^6$, $R^{7a}$, $R^8$, $R^{13a}$, $R^{14a}$, and $R^{17}$ are independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(=O)(=NR^{12})N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^2$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one or more $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one or more $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, $=NR^{22}$, $=C(R^{21})_2$, —C(O)

$OR^{22}$, $—OC(O)N(R^{22})(R^{23})$, $—N(R^{22})C(O)N(R^{22})(R^{23})$, $—N(R^{22})C(O)OR^{22}$, $—N(R^{22})S(O)_2R^{22}$, $—C(O)R^{22}$, $—S(O)R^{22}$, $—OC(O)R^{22}$, $—C(O)N(R^{22})(R^{23})$, $—C(O)C(O)N(R^{22})(R^{23})$, $—N(R^{22})C(O)R^{22}$, $—S(O)_2R^{22}$, $—S(O)(NR^{22})R^{22}$, $—S(O)_2N(R^{22})(R^{23})—$, and $—S(=O)(=NR^{22})N(R^{22})(R^{23})$; wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, $—C_{0-6}$ alkyl-($C_{3-12}$ carbocycle), -(2- to 6-membered heteroalkyl)-($C_{3-12}$ carbocycle), $—C_{0-6}$ alkyl-(3- to 12-membered heterocycle), and -(2- to 6-membered heteroalkyl)-(3- to 12-membered heterocycle) are optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, $—OR^{22}$, $—SR^{22}$, $—N(R^{22})(R^{23})$, $=NR^{22}$, $=C(R^{21})_2$, $—C(O)OR^{22}$, $—OC(O)N(R^{22})(R^{23})$, $—N(R^{22})C(O)N(R^{22})(R^{23})$, $—N(R^{22})C(O)OR^{22}$, $—N(R^{22})S(O)_2R^{22}$, $—C(O)R^{22}$, $—S(O)R^{22}$, $—OC(O)R^{22}$, $—C(O)N(R^{22})(R^{23})$, $—C(O)C(O)N(R^{22})(R^{23})$, $—N(R^{22})C(O)R^{22}$, $—S(O)_2R^{22}$, $—S(O)(NR^{22})R^{22}$, $—S(O)_2N(R^{22})(R^{23})$, and $—S(=O)(=NR^{22})N(R^{22})(R^{23})$;

$R^{21}$ is independently selected at each occurrence from hydrogen, halogen, $C_{1-6}$ alkyl, $C_{1-6}$ haloalkyl, $—C_{0-6}$ alkyl-($C_{3-12}$ carbocycle), and $—C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one or more substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, $—C_{0-6}$ alkyl-($C_{3-12}$ carbocycle), and $—C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle;

$R^{29}$ is independently selected at each occurrence from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, $—C_{0-6}$ alkyl-($C_{3-12}$ carbocycle), -(2- to 6-membered heteroalkyl)-($C_{3-12}$ carbocycle), $—C_{0-6}$ alkyl-(3- to 12-membered heterocycle), -(2- to 6-membered heteroalkyl)-(3- to 12-membered heterocycle), $—OR^{12}$, $—SR^{12}$, $—N(R^{12})(R^{13})$, $—C(O)OR^{12}$, $—OC(O)N(R^{12})(R^{13})$, $—N(R^{12})C(O)N(R^{12})(R^{13})$, $—N(R^{12})C(O)OR^{12}$, $—N(R^{12})S(O)_2R^{12}$, $—C(O)R^{12}$, $—S(O)R^{12}$, $—OC(O)R^{12}$, $—C(O)N(R^{12})(R^{13})$, $—C(O)C(O)N(R^{12})(R^{13})$, $—N(R^{12})C(O)R^{12}$, $—S(O)_2R^{12}$, $—S(O)(NR^{12})R^{12}$, $—S(O)_2N(R^{12})(R^{13})$, and $—S(=O)(=NR^{12})N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, $—C_{0-6}$ alkyl-($C_{3-12}$ carbocycle), -(2- to 6-membered heteroalkyl)-($C_{3-12}$ carbocycle), $—C_{0-6}$ alkyl-(3- to 12-membered heterocycle), and -(2- to 6-membered heteroalkyl)-(3- to 12-membered heterocycle) are optionally substituted with one or more $R^{20}$; and wherein two $R^{29}$ attached to the same atom are optionally joined to form oxo;

n29 is selected from 0, 1, 2, 3, 4, 5, 6, 7, 8, 9, 10, 11, 12, and 13; and each ⁼⁼⁼ independently indicates a single or double bond such that all valences are satisfied.

Embodiment 2 The compound of Embodiment 1, wherein $L^{19a}$ is selected from $C_{1-4}$ alkylene, $C_{2-4}$ alkenylene, $C_{2-4}$ alkynylene, 2- to 4-membered heteroalkylene, 3- to 4-membered heteroalkenylene, 3- to 4-membered heteroalkynylene, —O—, $—N(R^{12})—$, —C(O)—, $—N(R^{12})C(O)—$, $—C(O)N(R^{12})—$, —S—, $—S(O)_2—$, —S(O)—, $—P(O)(R^{12})—$, $—N(R^{12})S(O)_2—$, $—N(R^{12})S(O)—$, $—N(R^{12})P(O)(R^{12})—$, $—S(O)_2N(R^{12})—$, $—S(O)N(R^{12})—$, $—P(O)(R^{12})N(R^{12})—$, $—OP(O)(R^{12})—$, and $—P(O)(R^{12})O—$, wherein $C_{1-4}$ alkylene, $C_{2-4}$ alkenylene, $C_{2-4}$ alkynylene, 2- to 4-membered heteroalkylene, 3- to 4-membered heteroalkenylene, and 3- to 4-membered heteroalkynylene are optionally substituted with one or more $R^{20}$.

Embodiment 3 The compound of any one of Embodiments 1-2, having the formula (IA)

(IA)

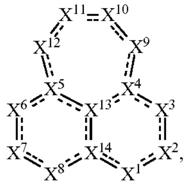

or a pharmaceutically acceptable salt or solvate thereof, wherein:

$X^9$ is selected from $C(R^9)$, $C(R^9)(R^{9a})$, and $N(R^9)$;

$X^{10}$ is selected from $C(R^{1i})$, $C(R^{10})_2$, N, $N(R^{10b})$, O, S, S(O), $S(O)_2$, and C(O);

$X^{11}$ is selected from $C(R^{11})$, $C(R^{11})_2$, N, $N(R^{11b})$, O, S, S(O), $S(O)_2$, and C(O);

$X^{12}$ is selected from $—X^{12a}—$, $—X^{12a}—X^{12b}—$, $—X^{12a}—X^{12b}—X^{12c}—$, and $—X^{12a}—X^{12b}—X^{12c}—X^{12d}—$; wherein $X^{12a}$ is directly bonded to $X^5$;

$X^{12a}$, $X^{12b}$, $X^{12c}$, and $X^{12d}$ are independently selected from $C(R^{12a})$, $C(R^{12a})_2$, N, $N(R^{12b})$, O, S, S(O), $S(O)_2$, and C(O);

$R^{19a}$ is 5-membered heteroaryl comprising one or more ring nitrogen atoms, wherein the 5-membered heteroaryl is directly bonded to $L^{19a}$ through an $R^{19a}$ ring nitrogen atom and wherein $R^{19a}$ is optionally substituted with one or more $R^{20}$;

$R^{10b}$, $R^{11b}$, and $R^{12b}$ are independently selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, $—C_{0-6}$ alkyl-($C_{3-12}$ carbocycle), -(2- to 6-membered heteroalkyl)-($C_{3-12}$ carbocycle), $—C_{0-6}$ alkyl-(3- to 12-membered heterocycle), -(2- to 6-membered heteroalkyl)-(3- to 12-membered heterocycle), $—C(O)OR^{12}$, $—C(O)R^{12}$, $—C(O)N(R^{12})(R^{13})$, $—C(O)C(O)N(R^{12})(R^{13})$, $—S(O)_2R^{12}$, $—S(O)(NR^{12})R^{12}$, $—S(O)_2N(R^{12})(R^{13})$, and $—S(=O)(=NR^{12})N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, $—C_{0-6}$ alkyl-($C_{3-12}$ carbocycle), -(2- to 6-membered heteroalkyl)-($C_{3-12}$ carbocycle), $—C_{0-6}$ alkyl-(3- to 12-membered heterocycle), and -(2- to 6-membered heteroalkyl)-(3- to 12-membered heterocycle) are optionally substituted with one or more $R^{20}$;

$R^{9a}$, $R^{10}$, $R^{11}$, and $R^{12a}$ are independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —S(═O)(═$NR^{12}$)$N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$; and each ═ independently indicates a single or double bond such that all valences are satisfied.

Embodiment 4 The compound of Embodiment 3, wherein $R^{19a}$ is 5-membered heteroaryl having one or two ring nitrogen atoms, wherein the 5-membered heteroaryl is directly bonded to $L^{19a}$ through an $R^{19a}$ ring nitrogen atom and wherein $R^{19a}$ is optionally substituted with one or more $R^{20}$.

Embodiment 5 The compound of any one of Embodiments 3-4, wherein $R^{19a}$ is pyrrolyl; wherein $R^{19a}$ is directly bonded to $L^{19a}$ through an $R^{19a}$ ring nitrogen atom; and wherein $R^{19a}$ is optionally substituted with one or more $R^{20}$.

Embodiment 6 The compound of any one of Embodiments 3-5, wherein $R^{19a}$ is selected from imidazolyl and pyrazolyl; wherein $R^{19a}$ is directly bonded to $L^{19a}$ through an $R^{19a}$ ring nitrogen atom; and wherein $R^{19a}$ is optionally substituted with one or more $R^{20}$.

Embodiment 7 The compound of any one of Embodiments 1-2 having the formula (IB):

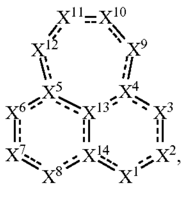

(IB)

or a pharmaceutically acceptable salt or solvate thereof, wherein:

$X^9$ is selected from $C(R^9)$, $C(R^9)(R^{9a})$, and $N(R^9)$;

$X^{10}$ is selected from $C(R^{10})$, $C(R^{10})_2$, N, $N(R^{10b})$, O, S, S(O), $S(O)_2$, and C(O);

$X^{II}$ is selected from $C(R^{11})$, $C(R^{11})_2$, N, $N(R^{11b})$, O, S, S(O), $S(O)_2$, and C(O);

$X^{12}$ is selected from —$X^{12a}$—, —$X^{12a}$—$X^{12b}$—, —$X^{12a}$—$X^{12b}$—$X^{12c}$—, and —$X^{12a}$—$X^{12b}$—$X^{12c}$—$X^{12d}$—; wherein $X^{12a}$ is directly bonded to $X^5$ $X^{12a}$, $X^{12b}$, $X^{12c}$, and $X^{12d}$ are independently selected from $C(R^{12a})$, $C(R^{12a})_2$, N, $N(R^{12b})$, O, S, S(O), $S(O)_2$, and C(O);

$R^{19a}$ is 5- to 12-membered heterocycle comprising three or four ring nitrogen atoms, wherein the 5- to 12-membered heterocycle is optionally substituted with one or more $R^{20}$;

$R^{10b}$, $R^{11b}$, and $R^{12b}$ are independently selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$C(O)OR^{12}$, —$C(O)R^{12}$, —$C(O)N(R^{12})(R^{13})$, —$C(O)C(O)N(R^{12})(R^{13})$, —$S(O)_2R^{12}$, —$S(O)(NR^{12})R^{12}$, —$S(O)_2N(R^{12})(R^{13})$, and —S(═O)(═$NR^{12}$)$N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$;

$R^{9a}$, $R^{10}$, $R^{11}$, and $R^{12a}$ are independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —S(═O)(═$NR^{12}$)$N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$; and each ═ independently indicates a single or double bond such that all valences are satisfied.

Embodiment 8 The compound of Embodiment 7, wherein $R^{19a}$ is a non-aromatic 5- to 12-membered heterocycle comprising three or four ring nitrogen atoms; wherein $R^{19a}$ is optionally substituted with one or more $R^{20}$.

Embodiment 9 The compound of Embodiment 7, wherein $R^{19a}$ is a 5- to 12-membered heteroaryl comprising three or four ring nitrogen atoms; wherein $R^{19a}$ is optionally substituted with one or more $R^{20}$.

Embodiment 10 The compound of Embodiment 7, wherein $R^{19a}$ is a 9- to 12-membered heteroaryl comprising three or four ring nitrogen atoms; wherein $R^{19a}$ is optionally substituted with one or more $R^{20}$.

Embodiment 11 The compound of any one of Embodiments 1 and 7, wherein $R^{19a}$ is a 5- to 6-membered heteroaryl comprising three or four ring nitrogen atoms; wherein $R^{19a}$ is optionally substituted with one or more $R^{20}$.

Embodiment 12 The compound of any one of Embodiments 1 and 7, wherein $R^{19a}$ is selected from triazolyl and tetrazolyl; wherein $R^{19a}$ is optionally substituted with one or more $R^{20}$.

Embodiment 13 The compound of any one of Embodiments 1 and 7, wherein $R^{19a}$ is selected from 1,2,3-triazolyl and 1,2,4-triazolyl; wherein $R^{19a}$ is optionally substituted with one or more $R^{20}$.

Embodiment 14 The compound of any one of Embodiments 1-13, wherein $R^{19a}$ is optionally substituted with one or more substituents independently selected from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, and 3- to 6-membered heteroalkynyl; wherein $C_{1-6}$ alkyl, $C_{2-6}$ alkenyl, $C_{2-6}$ alkynyl, 2- to 6-membered heteroalkyl, 3- to 6-membered heteroalkenyl, and 3- to 6-membered heteroalkynyl are optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, $—OR^{22}$, $—SR^{22}$, $—N(R^{22})(R^{23})$, $=NR^{22}$, $=C(R^{21})_2$, $—C(O)OR^{22}$, $—OC(O)N(R^{22})(R^{23})$, $—N(R^{22})C(O)N(R^{22})(R^{23})$, $—N(R^{22})C(O)OR^{22}$, $—N(R^{22})S(O)_2R^{22}$, $—C(O)R^{22}$, $—S(O)R^{22}$, $—OC(O)R^{22}$, $—C(O)N(R^{22})(R^{23})$, $—C(O)C(O)N(R^{22})(R^{23})$, $—N(R^{22})C(O)R^{22}$, $—S(O)_2R^{22}$, $—S(O)(NR^{22})R^{22}$, $—S(O)_2N(R^{22})(R^{23})$, and $—S(=O)(=NR^{22})N(R^{22})(R^{23})$.

Embodiment 15 The compound of any one of Embodiments 1-13, wherein $R^{19a}$ is optionally substituted with one or more substituents independently selected from halogen, —CN, and $C_{1-6}$ alkyl, wherein $C_{1-6}$ alkyl is optionally substituted with one or more substituents independently selected from halogen, oxo, —CN, $—OR^{22}$, $—SR^{22}$, and $—N(R^{22})(R^{23})$.

Embodiment 16 The compound of any one of Embodiments 1-13, wherein $R^{19a}$ is optionally substituted with one or more substituents independently selected from —F, —Cl, —Br, and —I.

Embodiment 17 The compound of any one of Embodiments 1-13, wherein $R^{19a}$ is optionally substituted with one $R^{20}$ selected from —F and —Cl.

Embodiment 18 The compound of any one of Embodiments 1-7, wherein $R^{19a}$ is selected from

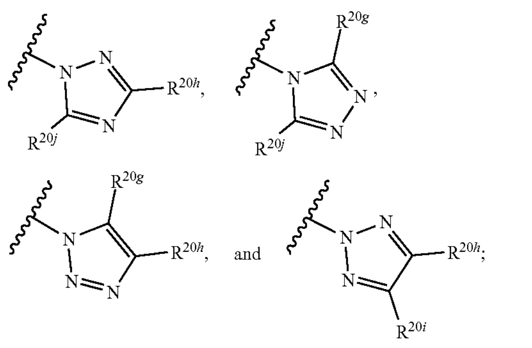

wherein $R^{20g}$, $R^{20h}$, $R^{20b}$, and $R^{20j}$ are independently selected at each occurrence from hydrogen and $R^{20}$.

Embodiment 19 The compound of any one of Embodiments 1-7, wherein $R^{19a}$ is selected from

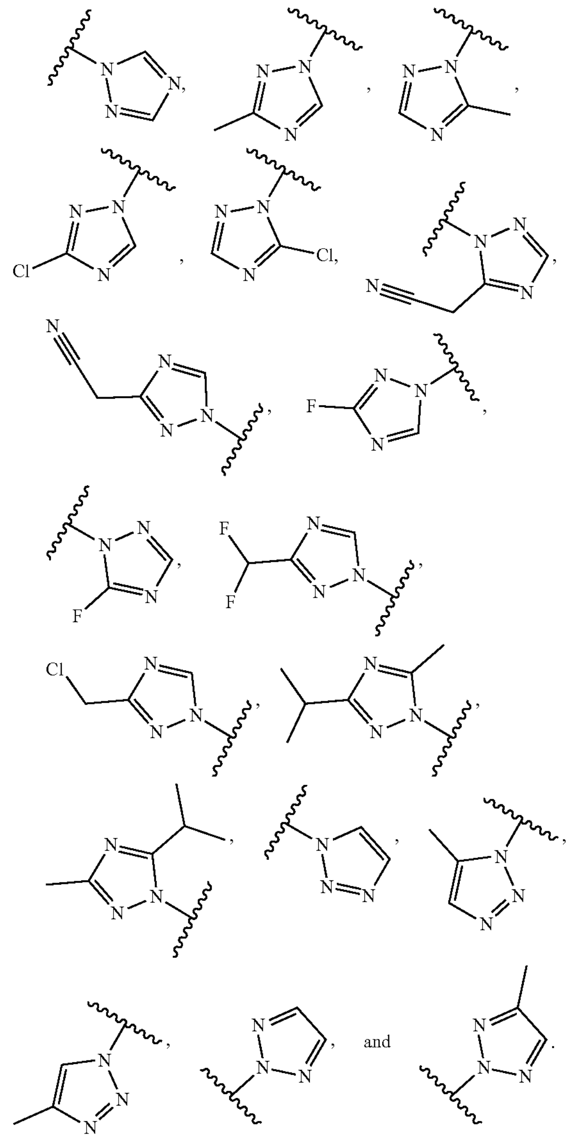

Embodiment 20 The compound of any one of Embodiments 1-19, wherein $L^{19a}$ is selected from —C(O)—, $—N(R^{12})C(O)—$, $—C(O)N(R^{12})—$, $—S(O)_2—$, —S(O)—, $—P(O)(R^{12})—$, $—N(R^{12})S(O)_2—$, $—N(R^{12})S(O)—$, $—N(R^{12})P(O)(R^{12})—$, $—S(O)_2N(R^{12})—$, $—S(O)N(R^{12})—$, and $—P(O)(R^{12})N(R^{12})—$.

Embodiment 21 The compound of any one of Embodiments 1-19, wherein $L^{19a}$ is selected from —C(O)—, $—S(O)_2—$, and —S(O)—.

Embodiment 22 The compound of any one of Embodiments 1-19, wherein $L^{19a}$ is selected from —C(O)— and $—N(R^{12})C(O)—$.

Embodiment 23 The compound of any one of Embodiments 1-19, wherein $L^{19a}$ is —C(O)—.

Embodiment 24 The compound of any one of Embodiments 1-23, wherein $R^{19}$ is a monocyclic $C_{3-8}$ carbocycle optionally substituted with one or more $R^{20}$.

Embodiment 25 The compound of any one of Embodiments 1-23, wherein $R^{19}$ is a monocyclic non-aromatic $C_{4-6}$ carbocycle optionally substituted with one or more $R^{20}$.

Embodiment 26 The compound of any one of Embodiments 1-23, wherein $R^{19}$ is a phenyl optionally substituted with one or more $R^{20}$.

Embodiment 27 The compound of any one of Embodiments 1-23, wherein $R^{19}$ is a monocyclic 3- to 8-membered heterocycle optionally substituted with one or more $R^{20}$.

Embodiment 28 The compound of any one of Embodiments 1-23, wherein $R^{19}$ is a monocyclic 5- to 6-membered heteroaryl optionally substituted with one or more $R^{20}$.

Embodiment 29 The compound of any one of Embodiments 1-23, wherein $R^{19}$ is a monocyclic, non-aromatic 4- to 5-membered heterocycle optionally substituted with one or more $R^{20}$.

Embodiment 30 The compound of any one of Embodiments 1-23, wherein $R^{19}$ is selected from azetidinyl and pyrrolidinyl; wherein the azetidinyl and pyrrolidinyl are optionally substituted with one or more $R^{20}$.

Embodiment 31 The compound of any one of Embodiments 24-30, wherein $R^{19}$ is optionally substituted with one or more substituents independently selected from $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), and —$C_{0-6}$ alkyl-(3- to 12-membered heterocycle); wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), and —$C_{0-6}$ alkyl-(3- to 12-membered heterocycle) are optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —$S(=O)(=NR^{22})N(R^{22})(R^{23})$.

Embodiment 32 The compound of any one of Embodiments 24-30, wherein $R^{19}$ is optionally substituted with one or more substituents independently selected from $C_{1-4}$ alkyl and $C_{3-4}$ carbocycle; wherein $C_{3-4}$ carbocycle is optionally substituted with one or more substituents independently selected from halogen and $C_{1-4}$ alkyl.

Embodiment 33 The compound of any one of Embodiments 24-30, wherein $R^{19}$ is optionally substituted with unsubstituted methyl.

Embodiment 34 The compound of any one of Embodiments 1-33, wherein $L^{19}$ is a bond.

Embodiment 35 The compound of any one of Embodiments 1-33, wherein $L^{19}$ is unsubstituted $C_{1-2}$ alkylene.

Embodiment 36 The compound of any one of Embodiments 1-33, wherein $L^{19}$ is unsubstituted methylene.

Embodiment 37 The compound of any one of Embodiments 3-36, wherein $X^9$ is $N(R^9)$.

Embodiment 38 The compound of any one of Embodiments 3-37, wherein $X^{10}$ is $C(R^{10})_2$.

Embodiment 39 The compound of any one of Embodiments 3-37, wherein $X^{10}$ is $CH(R^{11})$.

Embodiment 40 The compound of any one of Embodiments 3-37, wherein $X^{10}$ is $CH_2$.

Embodiment 41 The compound of any one of Embodiments 3-39, wherein $R^{10}$ is independently selected at each occurrence from $C_{1-6}$ alkyl, $C_{2-6}$ alkenyl, $C_{2-6}$ alkynyl, $C_{3-12}$ carbocycle, and 3- to 12-membered heterocycle, wherein $C_{1-6}$ alkyl, $C_{2-6}$ alkenyl, $C_{2-6}$ alkynyl, $C_{3-12}$ carbocycle, and 3- to 12-membered heterocycle are optionally substituted with one or more $R^{20}$.

Embodiment 42 The compound of any one of Embodiments 3-39, wherein $R^{10}$ is independently selected at each occurrence from $C_{1-4}$ alkyl, $C_{2-3}$ alkenyl, $C_{2-3}$ alkynyl, $C_{3-5}$ carbocycle, and 3- to 5-membered heterocycle, wherein $C_{1-4}$ alkyl, $C_{2-3}$ alkenyl, $C_{2-3}$ alkynyl, $C_{3-5}$ carbocycle, and 3- to 5-membered heterocycle are optionally substituted with one or more $R^{20}$.

Embodiment 43 The compound of any one of Embodiments 3-39, wherein $R^{10}$ is independently selected at each occurrence from $C_{1-4}$ alkyl, $C_{2-3}$ alkenyl, $C_{2-3}$ alkynyl, $C_{3-5}$ carbocycle, and 3- to 5-membered heterocycle, wherein $C_{1-4}$ alkyl, $C_{2-3}$ alkenyl, $C_{2-3}$ alkynyl, $C_{3-5}$ carbocycle, and 3- to 5-membered heterocycle are optionally substituted with one or more $R^{20}$ selected from halogen, —OH, and —CN.

Embodiment 44 The compound of any one of Embodiments 3-39, wherein $R^{10}$ is independently selected at each occurrence from unsubstituted $C_{1-4}$ alkyl, unsubstituted $C_{2-3}$ alkenyl, unsubstituted $C_{2-3}$ alkynyl, unsubstituted $C_{3-5}$ carbocycle, and unsubstituted 3- to 5-membered heterocycle.

Embodiment 45 The compound of any one of Embodiments 3-39, wherein $R^{10}$ is independently selected at each occurrence from

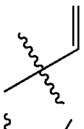, 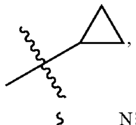, 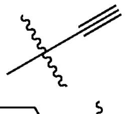, 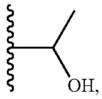, 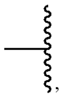, 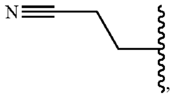, 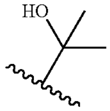, 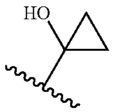, 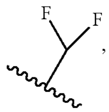, 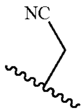, 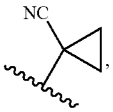, and 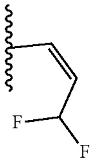.

Embodiment 46 The compound of any one of Embodiments 3-45, wherein $X^{11}$ is $C(R^{11})_2$.

Embodiment 47 The compound of any one of Embodiments 3-45, wherein $X^{11}$ is $CH(R^{11})$.

Embodiment 48 The compound of any one of Embodiments 3-45, wherein $X^{11}$ is $CH_2$.

Embodiment 49 The compound of any one of Embodiments 3-47, wherein $R^{11}$ is independently selected at each occurrence from $C_{1-6}$ alkyl, $C_{2-6}$ alkenyl, $C_{2-6}$ alkynyl, $C_{3-12}$ carbocycle, and 3- to 12-membered heterocycle, wherein $C_{1-6}$ alkyl, $C_{2-6}$ alkenyl, $C_{2-6}$ alkynyl, $C_{3-12}$ carbocycle, and 3- to 12-membered heterocycle are optionally substituted with one or more $R^{20}$.

Embodiment 50 The compound of any one of Embodiments 3-47, wherein $R^{11}$ is independently selected at each occurrence from $C_{1-4}$ alkyl, $C_{2-3}$ alkenyl, $C_{2-3}$ alkynyl, $C_{3-5}$ carbocycle, and 3- to 5-membered heterocycle, wherein $C_{1-4}$ alkyl, $C_{2-3}$ alkenyl, $C_{2-3}$ alkynyl, $C_{3-5}$ carbocycle, and 3- to 5-membered heterocycle are optionally substituted with one or more $R^{20}$.

Embodiment 51 The compound of any one of Embodiments 3-47, wherein $R^{11}$ is independently selected at each occurrence from unsubstituted $C_{1-4}$ alkyl, unsubstituted $C_{2-3}$ alkenyl, unsubstituted $C_{2-3}$ alkynyl, unsubstituted $C_{3-5}$ carbocycle, and unsubstituted 3- to 5-membered heterocycle.

Embodiment 52 The compound of any one of Embodiments 3-51, wherein $X^{12}$ is —$X^{12a}$—.

Embodiment 53 The compound of any one of Embodiments 3-52, wherein $X^{12a}$ is O.

Embodiment 54 The compound of any one of Embodiments 1-53, wherein $X^1$ is N.

Embodiment 55 The compound of any one of Embodiments 1-54, wherein $X^2$ is $C(R^2)$.

Embodiment 56 The compound of any one of Embodiments 1-55, wherein $R^2$ is —$OR^{12}$.

Embodiment 57 The compound of any one of Embodiments 1-55, wherein $R^2$ is —O($C_{1-3}$ alkylene)(4- to 10-membered heterocycle), wherein 4- to 10-membered heterocycle is optionally substituted with one, two, or three substituents independently selected from halogen, $C_{1-3}$ alkyl, $C_{1-3}$ haloalkyl, and $=C(R^{21})_2$.

Embodiment 58 The compound of any one of Embodiments 1-55, wherein $R^2$ is selected from

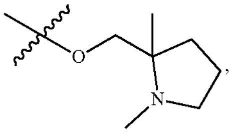
,
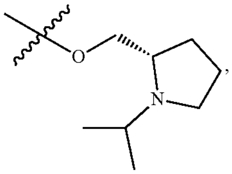
,
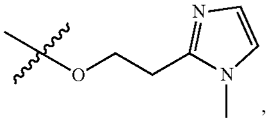
,
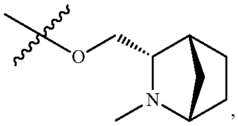
,
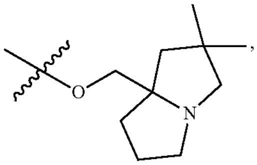
,
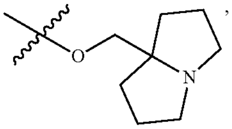
,
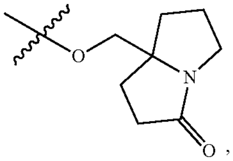
,
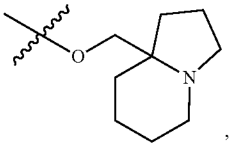
,
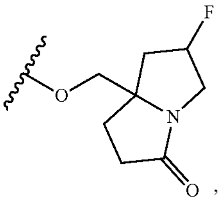
,
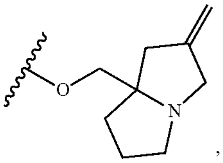
,
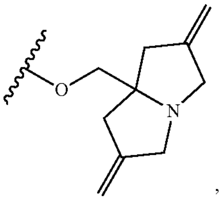
,
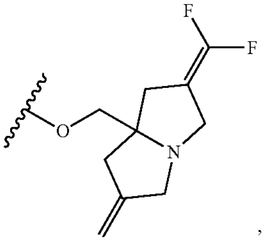
, -continued

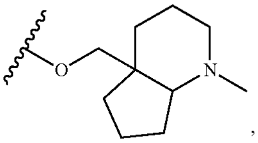
,
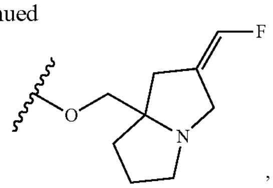
,
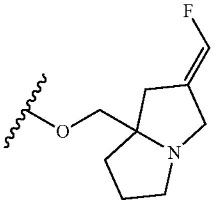
,
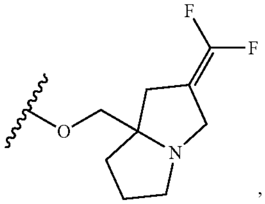
,
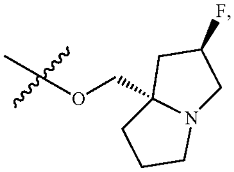
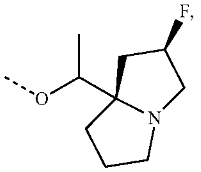
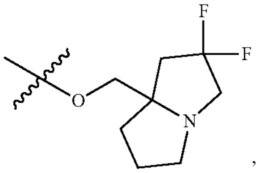
,
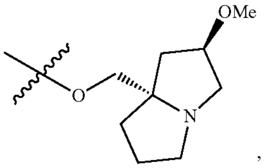
,
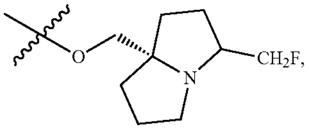
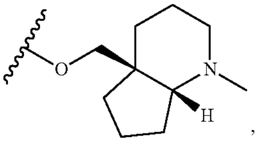
,
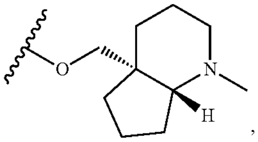
,
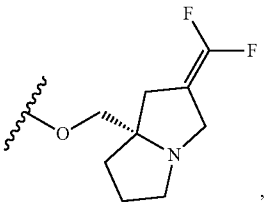
,
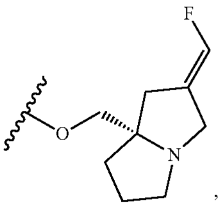
,
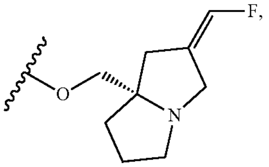
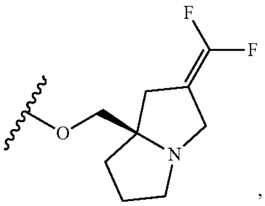
,
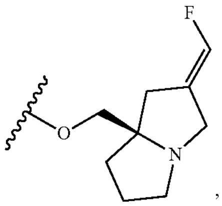
,
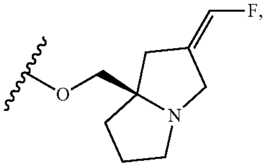

-continued
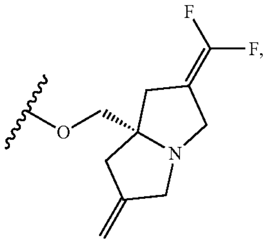
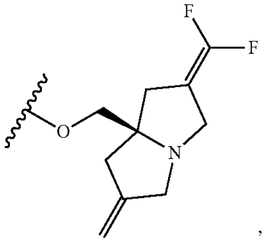
,
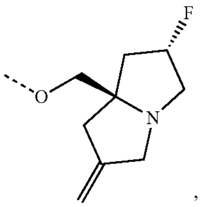
,
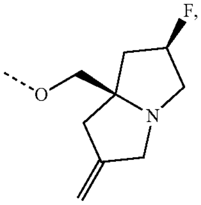
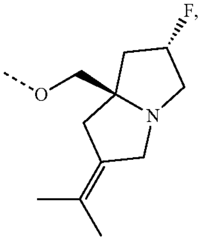
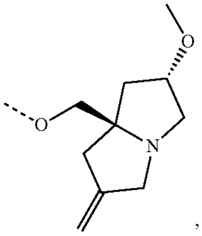
,
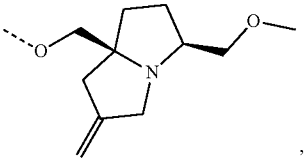
,
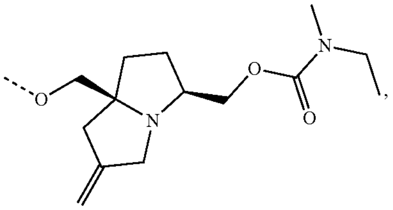
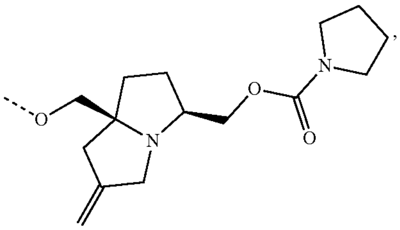
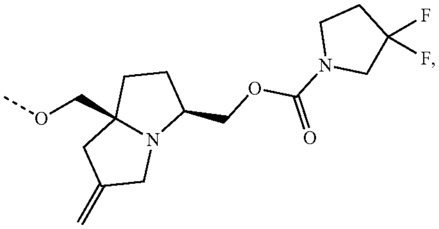
-continued
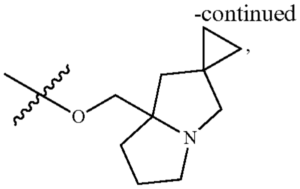
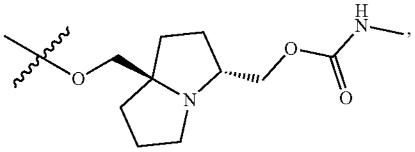
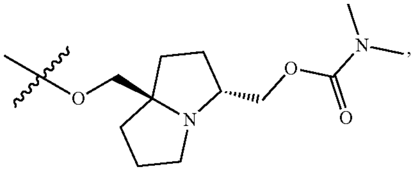
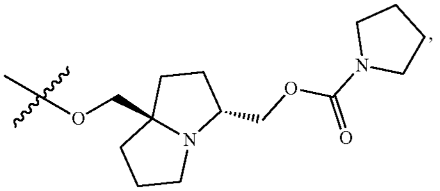
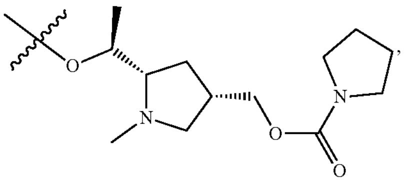
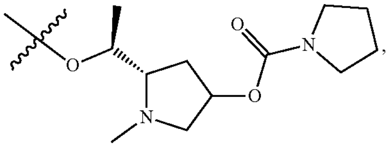
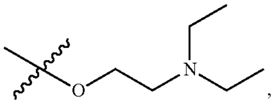
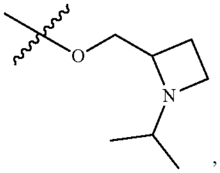
,
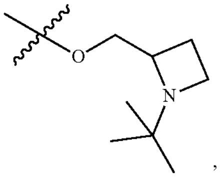
,
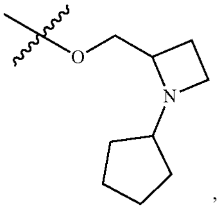
,
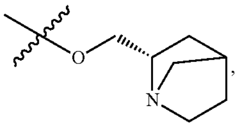
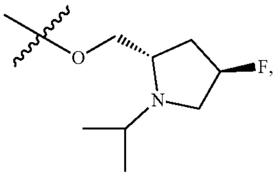
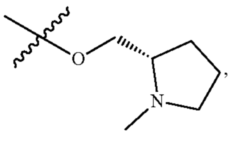
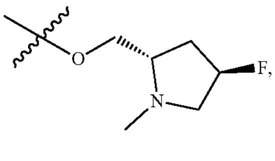

557
-continued
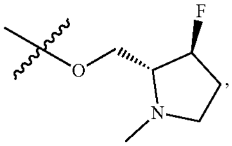
,
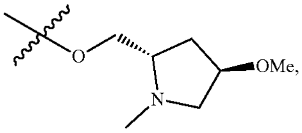
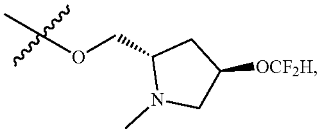
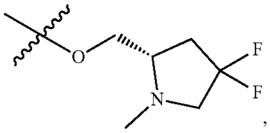
,
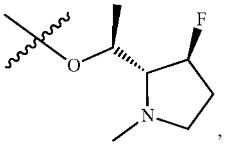
,
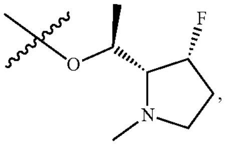
,
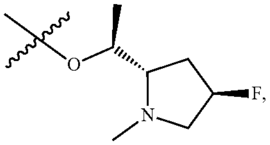
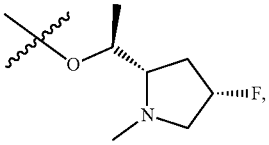
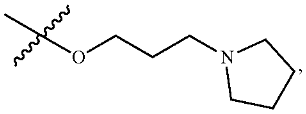
,
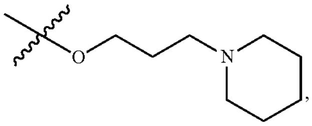
,
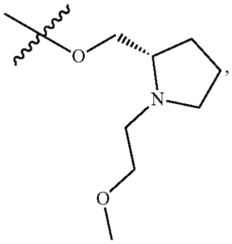
,
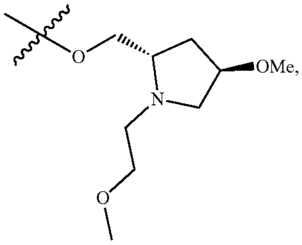
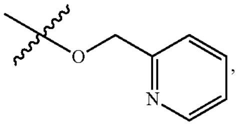
,
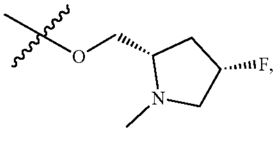
558
-continued
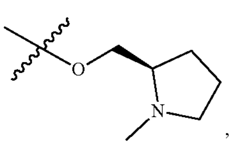
,
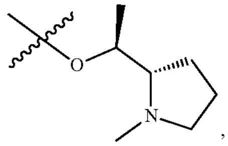
,
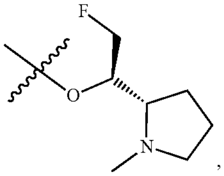
,
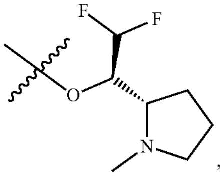
,
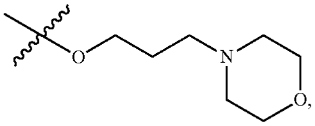
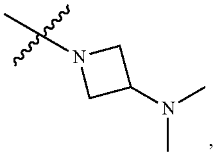
,
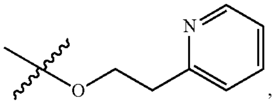
,
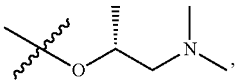
,
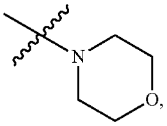
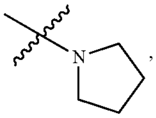
,
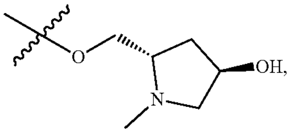
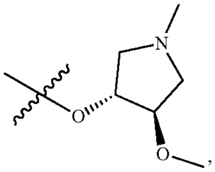
,
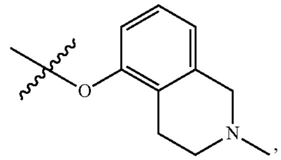
,
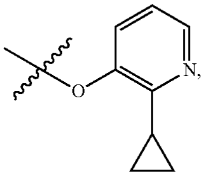
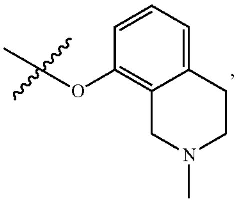
,
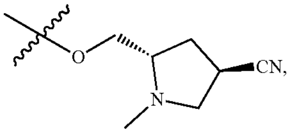
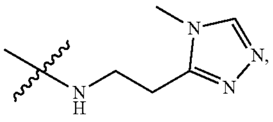
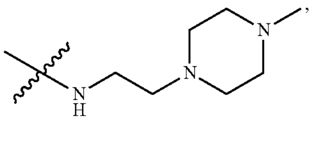

-continued
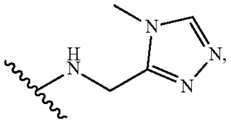
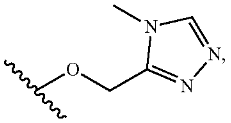
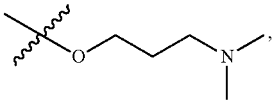
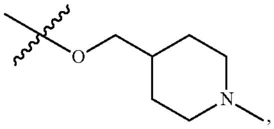
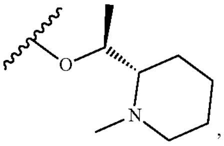,
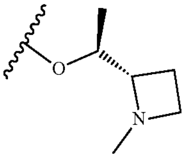,
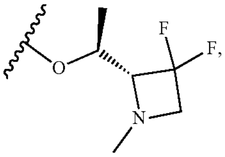
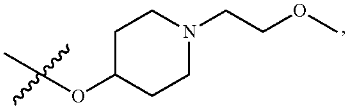
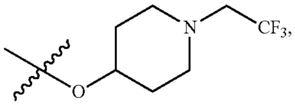
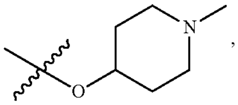,
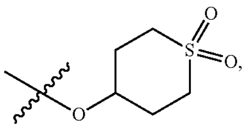
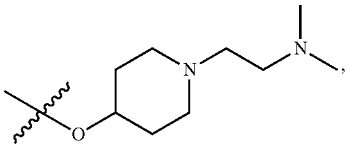
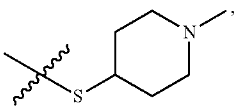
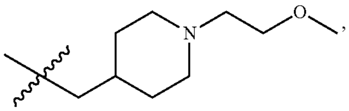
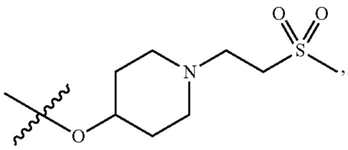
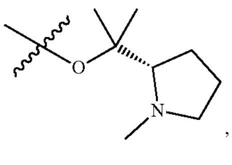,
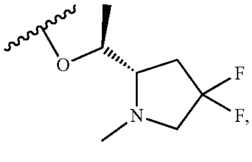
-continued
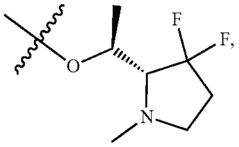
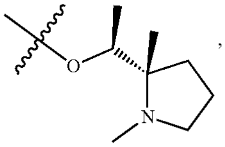,
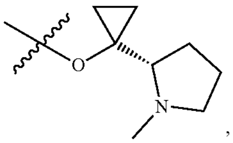,
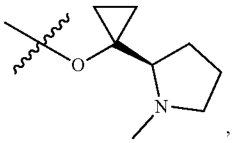,
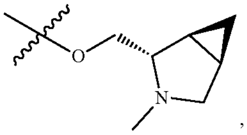,
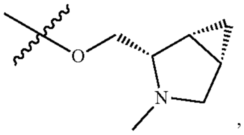,
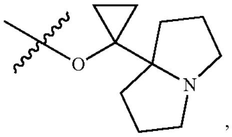,
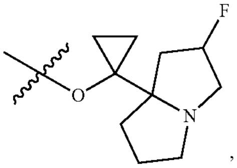,
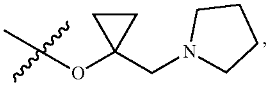
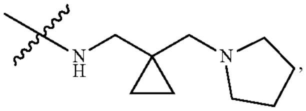
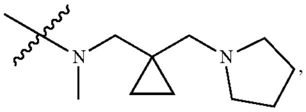
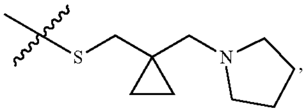
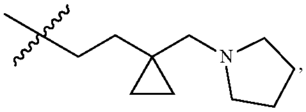
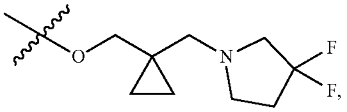
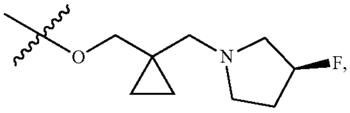
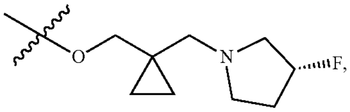
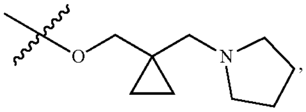
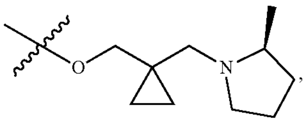

-continued
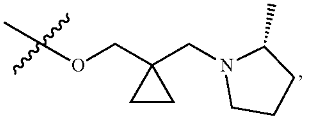,
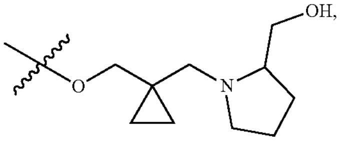,
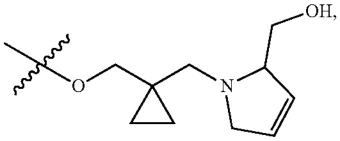,
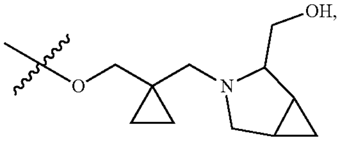,
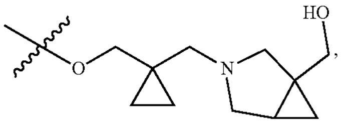,
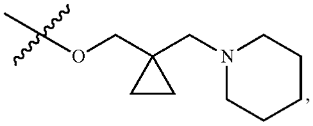,
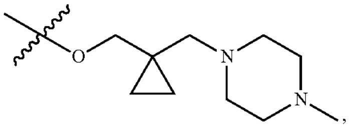,
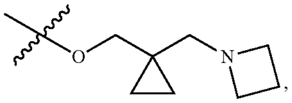,
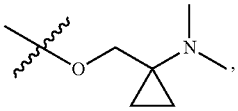, 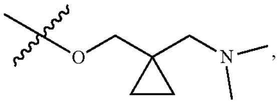,
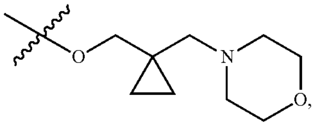,
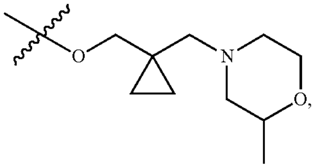,
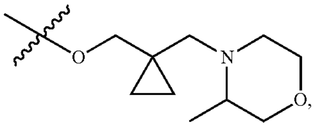,
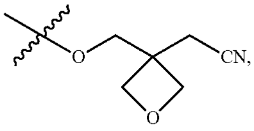,
-continued
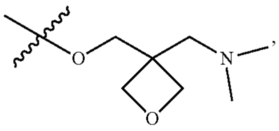, 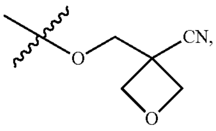,
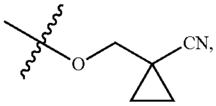, 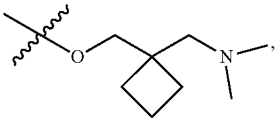,
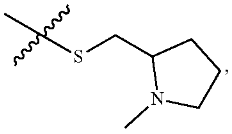, 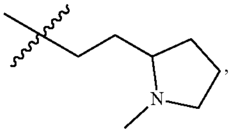,
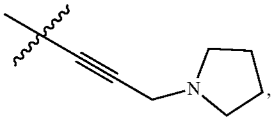, 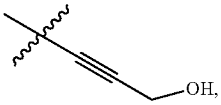,
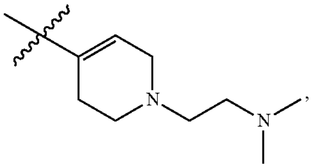,
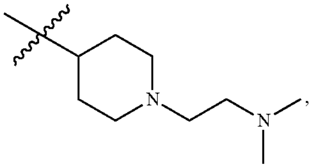,
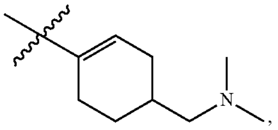,
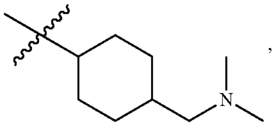, 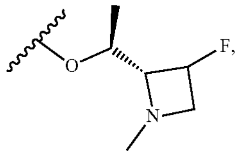,
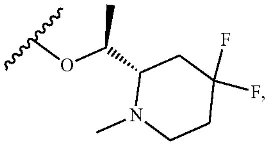, 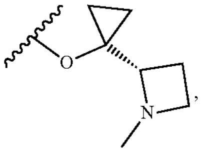,
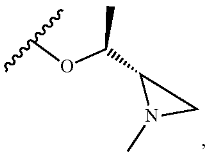, 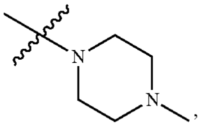,
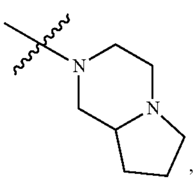, 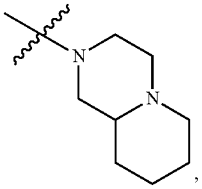, -continued

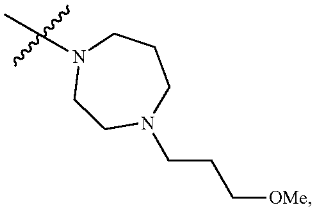

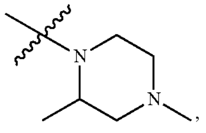

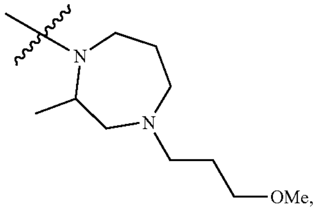

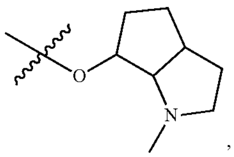

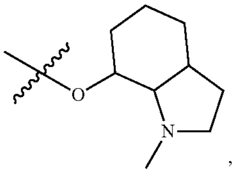

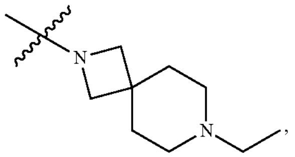

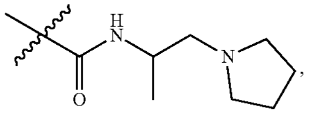

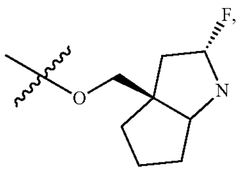

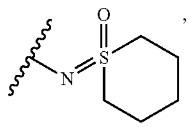

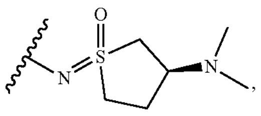

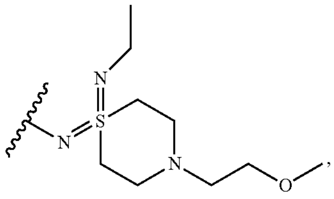

and

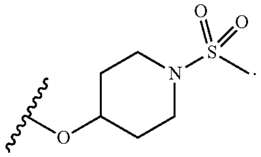

Embodiment 59 The compound of any one of Embodiments 1-55, wherein $R^2$ is selected from

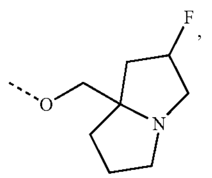

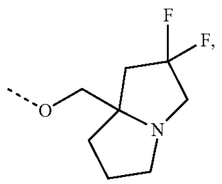

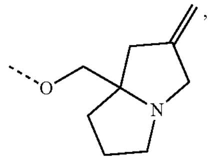

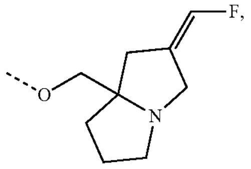

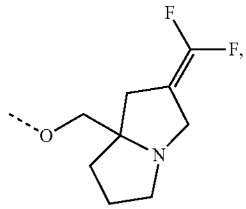

and

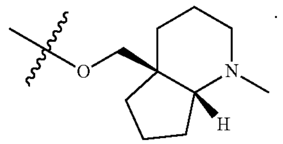

Embodiment 60 The compound of any one of Embodiments 1-55, wherein $R^2$ is selected from

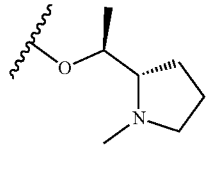

and

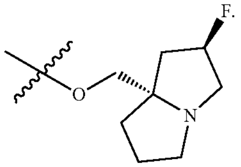

Embodiment 61 The compound of any one of Embodiments 1-60, wherein $X^3$ is N.

Embodiment 62 The compound of any one of Embodiments 1-61, wherein $X^4$ is C.

Embodiment 63 The compound of any one of Embodiments 1-62, wherein $X^5$ is C.

Embodiment 64 The compound of any one of Embodiments 1-63, wherein $X^6$ is $C(R^6)$.

Embodiment 65 The compound of any one of Embodiments 1-64, wherein $R^6$ is independently selected at each occurrence from hydrogen and halogen.

Embodiment 66 The compound of any one of Embodiments 1-63, wherein $X^6$ is N.

Embodiment 67 The compound of any one of Embodiments 1-63, wherein $X^6$ is $N(R^{6b})$.

Embodiment 68 The compound of any one of Embodiments 1-67, wherein $R^{6b}$ is unsubstituted cyclopropyl.

Embodiment 69 The compound of any one of Embodiments 1-68, wherein $X^7$ is $C(R^7)$.

Embodiment 70 The compound of any one of Embodiments 1-69, wherein $L^{7a}$ is a bond.

Embodiment 71 The compound of any one of Embodiments 1-70, wherein $R^{17}$ is selected from $C_{6-12}$ carbocycle and 5- to 12-membered heterocycle, wherein $C_{6-12}$ carbocycle and 5- to 12-membered heterocycle are optionally substituted with one or more $R^{20}$.

Embodiment 72 The compound of any one of Embodiments 1-70, wherein $R^{17}$ is selected from phenyl, pyridyl, naphthyl, quinolinyl, isoquinolinyl, benzothiazolyl, benzothienyl, indazolyl, and benzoxazolyl, wherein phenyl, pyridyl, naphthyl, quinolinyl, isoquinolinyl, benzothiazolyl, benzothienyl, indazolyl, and benzoxazolyl are optionally substituted with one or more $R^{20}$.

Embodiment 73 The compound of any one of Embodiments 1-70, wherein $R^{17}$ is selected from:

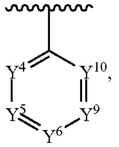, 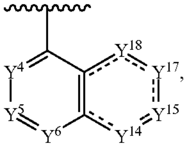,

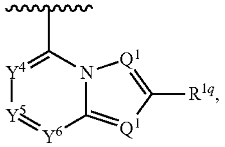, 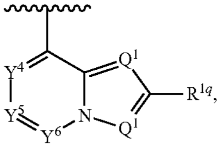,

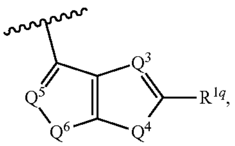, 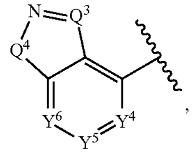,

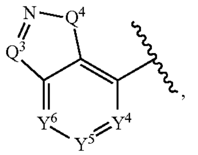, 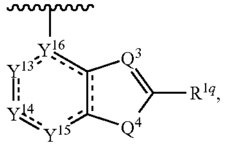,

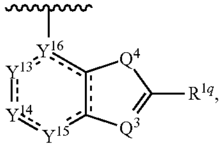, 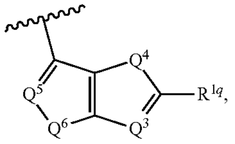,

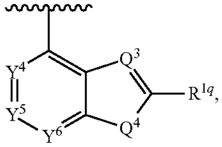, 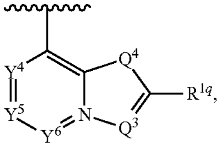,

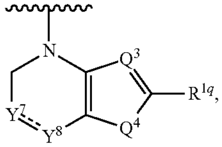, 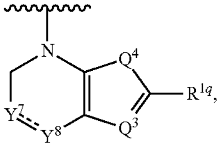,

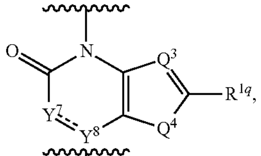, and

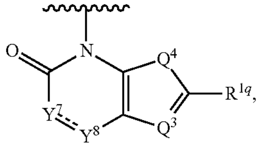, wherein:

$Q^1$, $Q^3$, and $Q^5$ are independently selected from N and $C(R^{1q})$;

$Q^4$ and $Q^6$ are independently selected from O, S, $C(R^{1q})_2$, and $N(R^{1r})$;

$Y^4$, $Y^5$, $Y^6$, $Y^9$, and $Y^{10}$ are independently selected from $C(R^{1q})$ and N;

$Y^7$ and $Y^8$ are independently selected from $C(R^{1q})$, $C(R^{1q})_2$, N, and $N(R^{1r})$;

$Y^{13}$ is selected from a bond, $C(R^{1q})$, N, C(O), $C(R^{1q})_2$, $C(O)C(R^{1q})_2$, $C(R^{1q})_2C(R^{1q})_2$, $C(R^{1q})_2N(R^{1r})$, and $N(R^{1r})$;

$Y^{14}$, $Y^{17}$, and $Y^{18}$ are independently selected from C(O), $C(R^{1q})$, N, $C(R^{1q})_2$, and $N(R^{1r})$;

$Y^{16}$ is selected from C, N, and $C(R^{1q})$;

each $R^{14}$ is independently selected from hydrogen, halogen, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(=O)(=NR^{12})N(R^{12})(R^{13})$, wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$; or two $R^{1q}$ bonded to the same carbon are joined to form 3- to 10-membered heterocycle or $C_{3-10}$ carbocycle, wherein 3- to 10-membered heterocycle and $C_{3-10}$ carbocycle are optionally substituted with one or more $R^{20}$; or two $R^{1q}$ bonded to adjacent atoms are joined to form 3- to 10-membered heterocycle or $C_{3-10}$ carbocycle, wherein 3- to 10-membered heterocycle and $C_{3-10}$ carbocycle are optionally substituted with one or more $R^{20}$; or one $R^{1q}$ and one $R^{1r}$ are joined to form 3- to 10-membered heterocycle or $C_{3-10}$ carbocycle, wherein 3- to 10-membered heterocycle and $C_{3-10}$ carbocycle are optionally substituted with one or more $R^{20}$;

each $R^{1r}$ is independently selected from hydrogen, $C_{1-6}$ alkyl, $C_{2-6}$ alkenyl, $C_{2-6}$ alkynyl, 3- to 10-membered heterocycle, and $C_{3-10}$ carbocycle, wherein $C_{1-6}$ alkyl, $C_{2-6}$ alkenyl, $C_{2-6}$ alkynyl, 3- to 10-membered heterocycle, and $C_{3-10}$ carbocycle are optionally substituted with one or more $R^{20}$; and each ═══ independently indicates a single or double bond such that all valences are satisfied.

Embodiment 74 The compound of any one of Embodiments 1-70, wherein $R^{17}$ is selected from

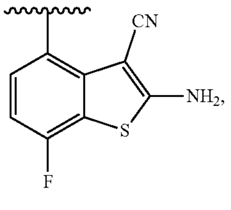, 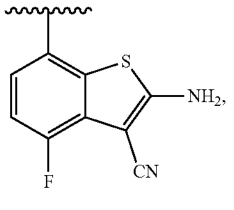,

-continued
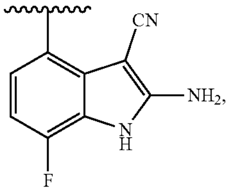
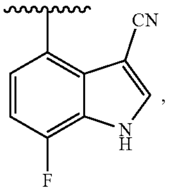
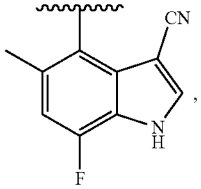
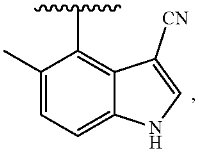
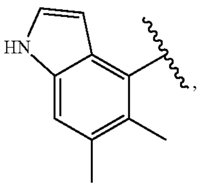
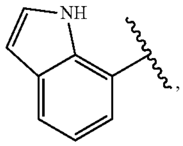
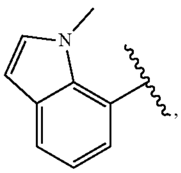
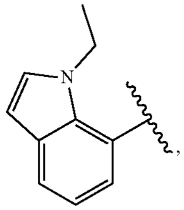
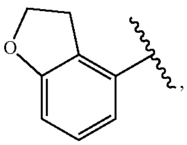
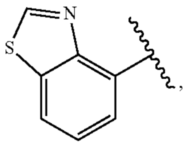
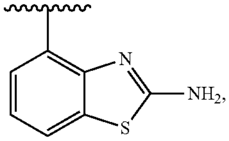
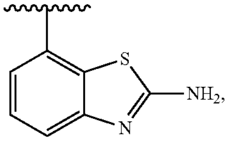
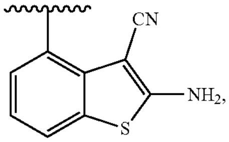
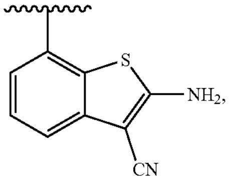
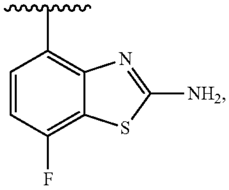
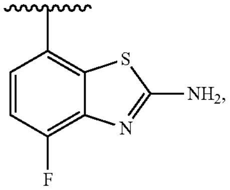
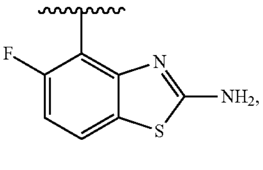
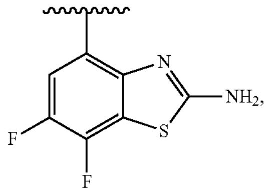
-continued
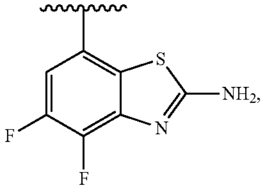
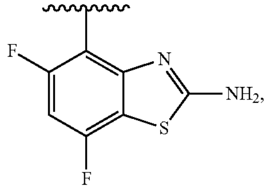
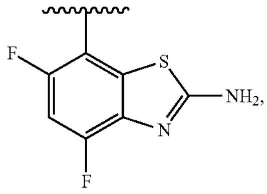
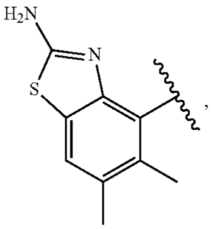
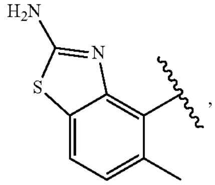
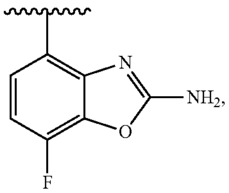
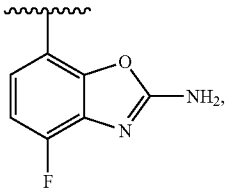
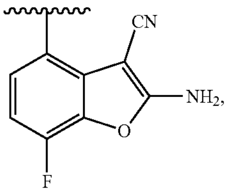
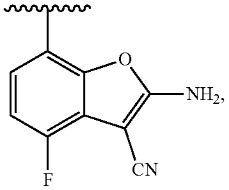
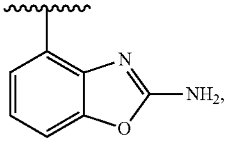
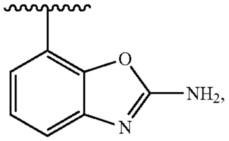
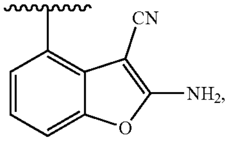
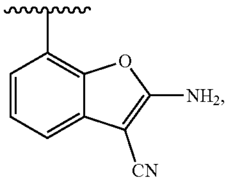
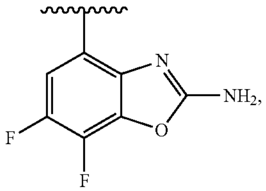
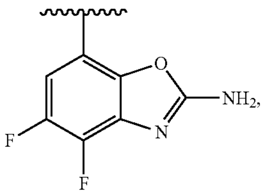
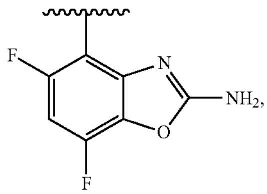
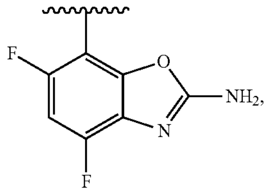
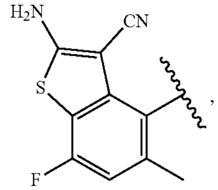

-continued
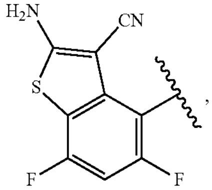,
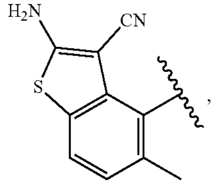,
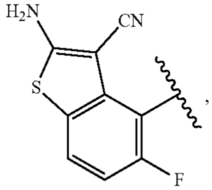,
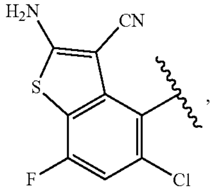,
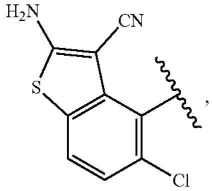,
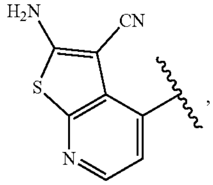,
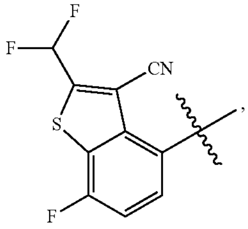,
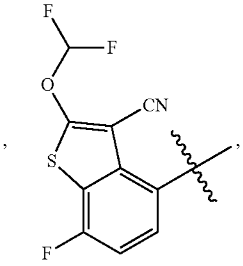,
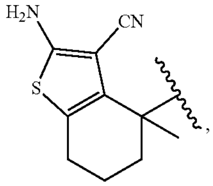,
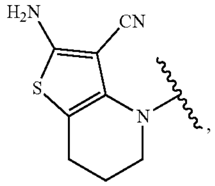,
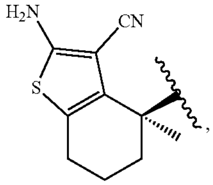,
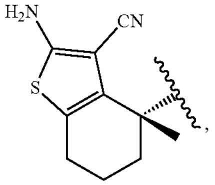,
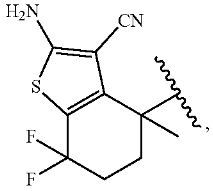,
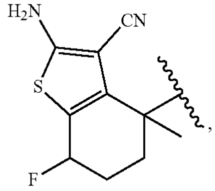,
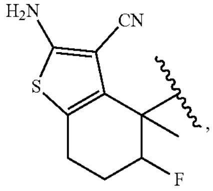,
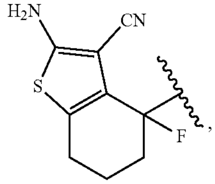,
-continued
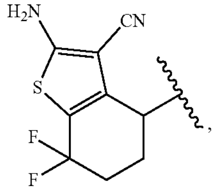,
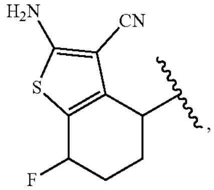,
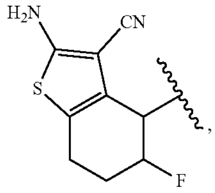,
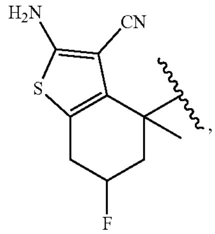,
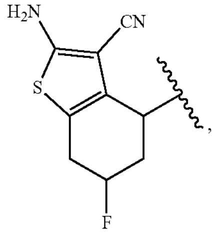,
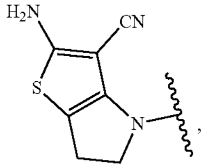,
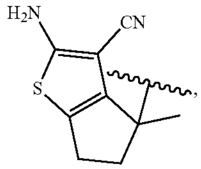,
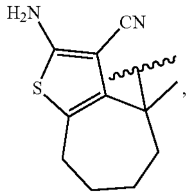,
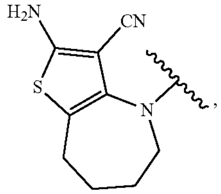,
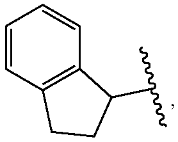,
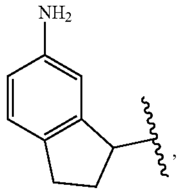,
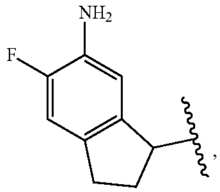,
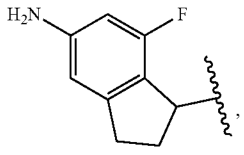,
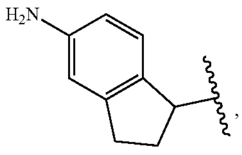,
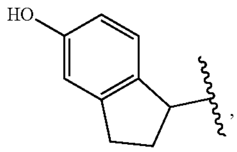,
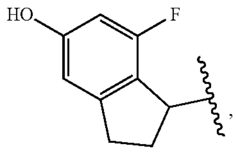, -continued
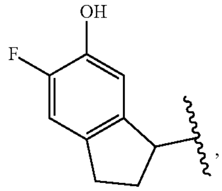,
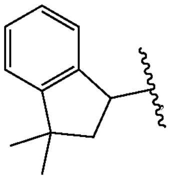
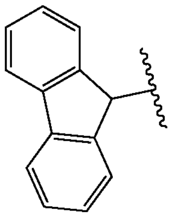,
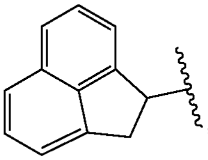,
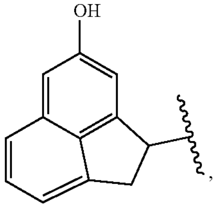,
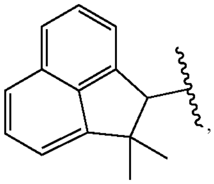,
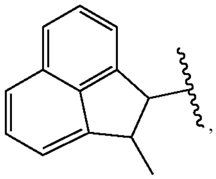,
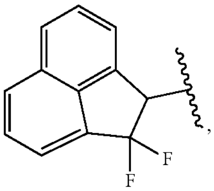,
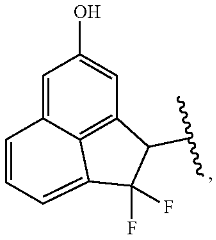,
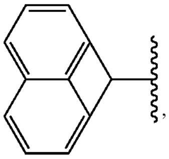,
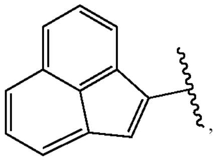,
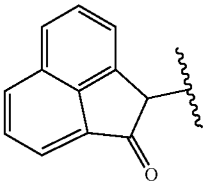,
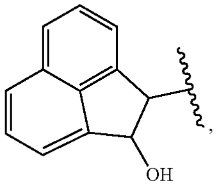,
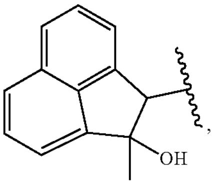,
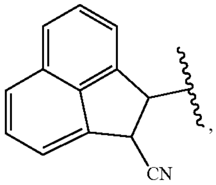,
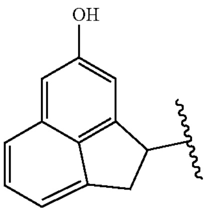,
-continued
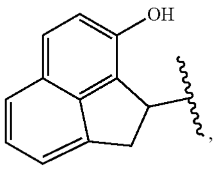,
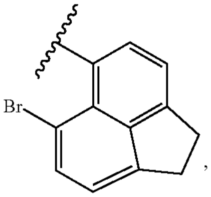,
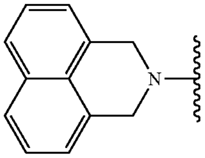,
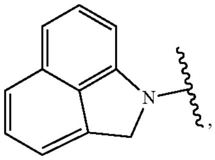,
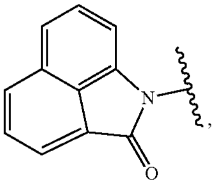,
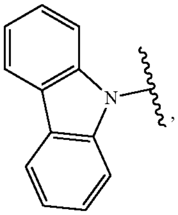,
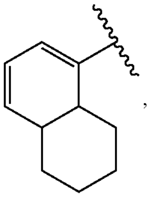,
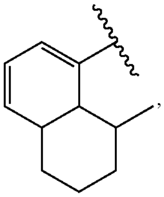,
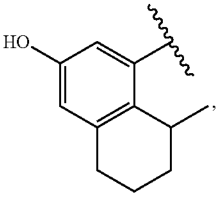,
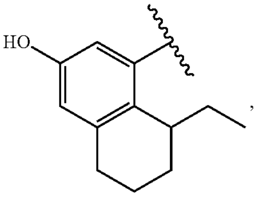,
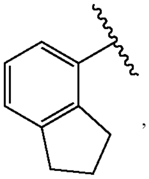,
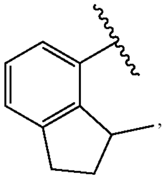,
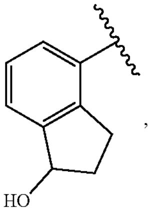,
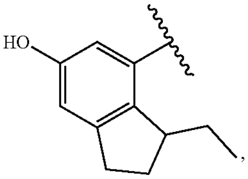,
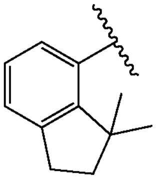,
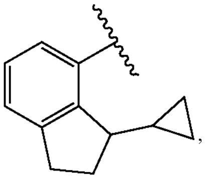,
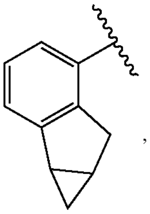, -continued
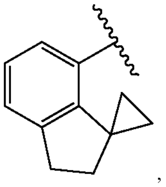
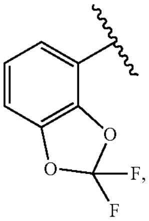
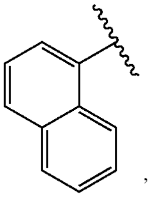
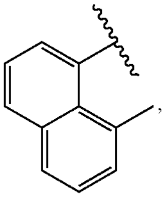
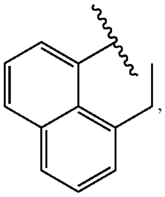
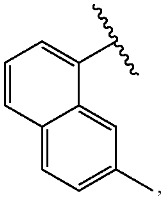
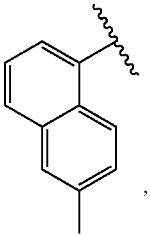
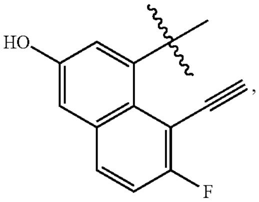
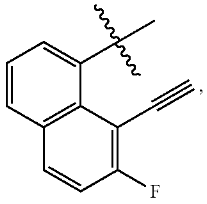
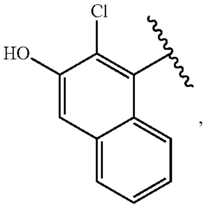
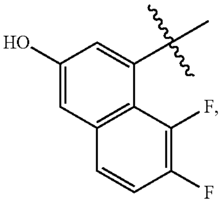
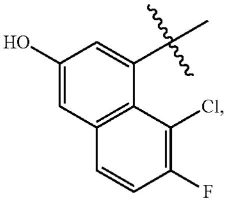
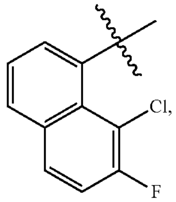
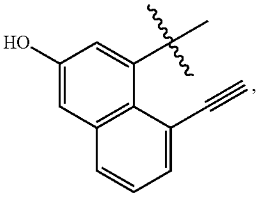
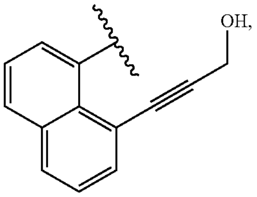
-continued
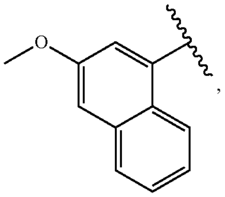
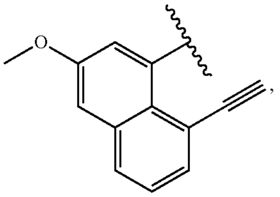
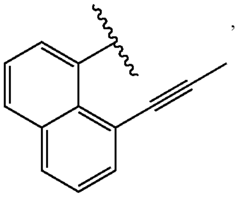
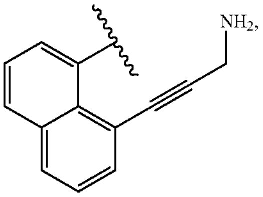
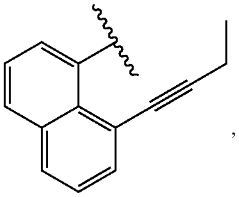
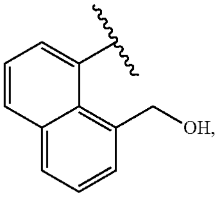
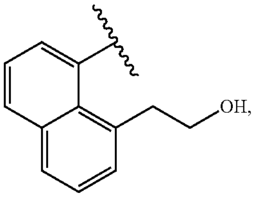
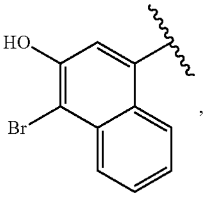
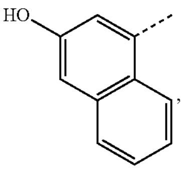
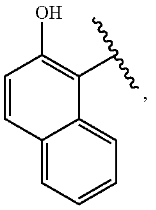
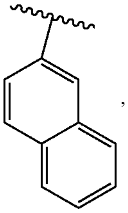
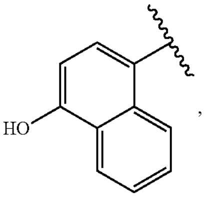
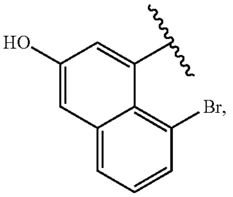
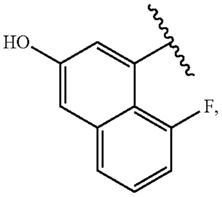
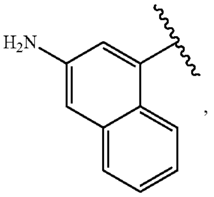
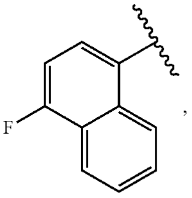
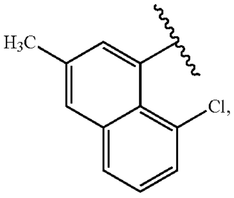

-continued
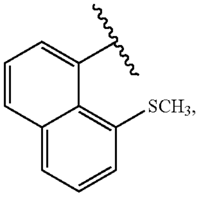
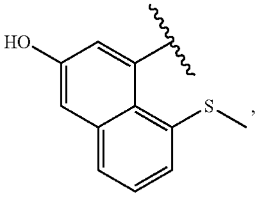
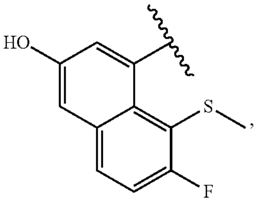
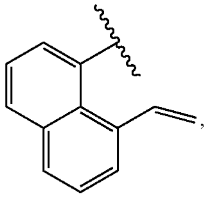
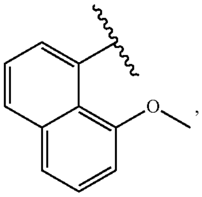
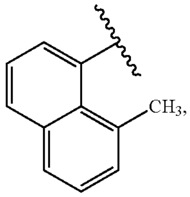
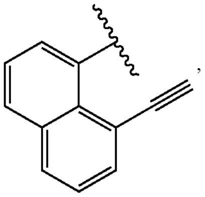
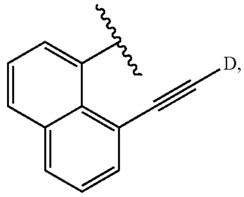
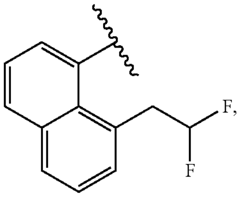
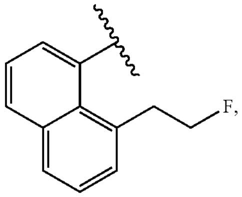
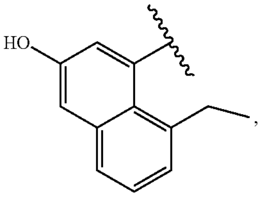
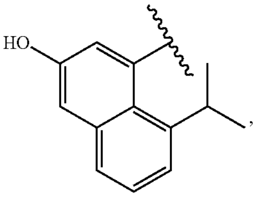
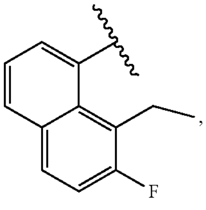
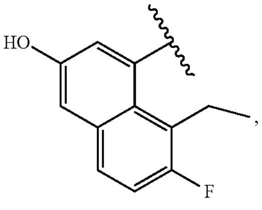
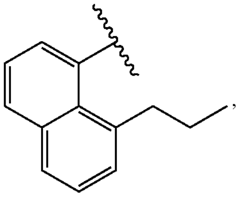
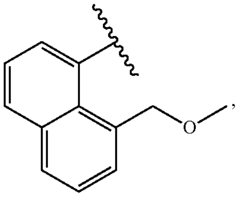
-continued
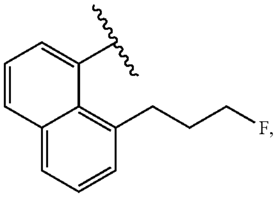
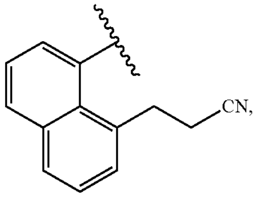
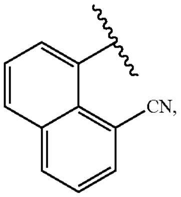
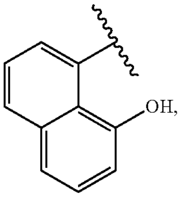
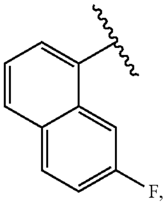
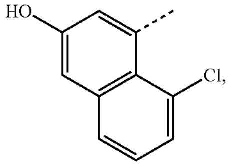
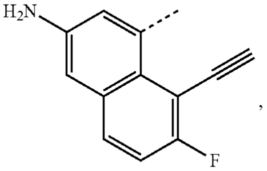
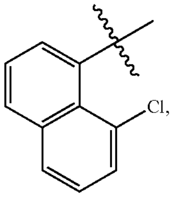
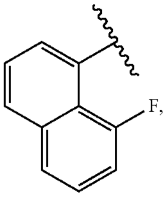
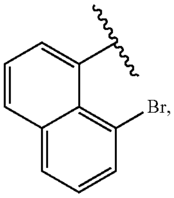
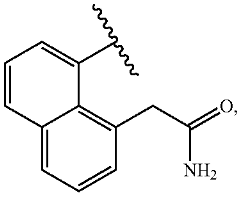
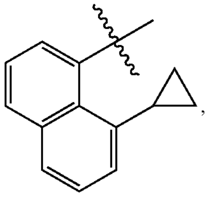
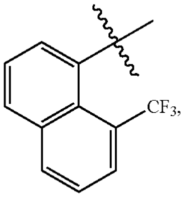
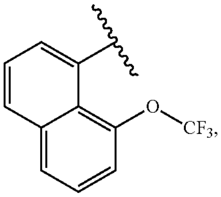
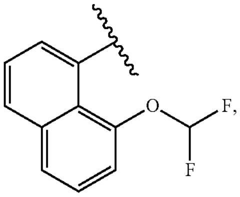
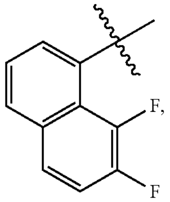

-continued
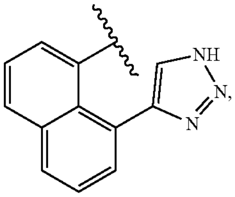, 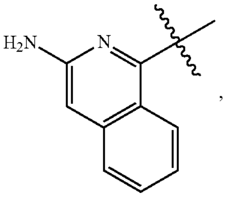,
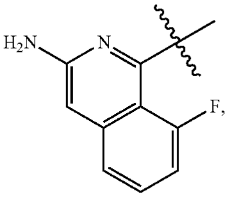, 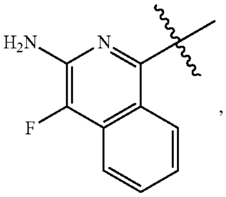,
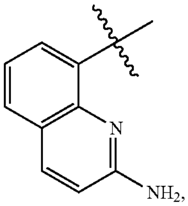, 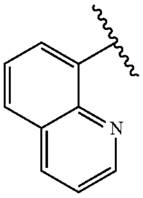,
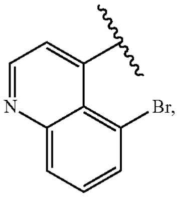, 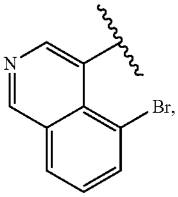, 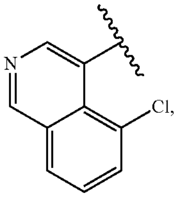,
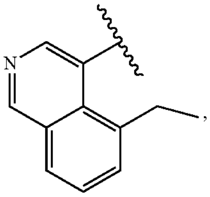, 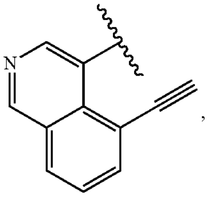,
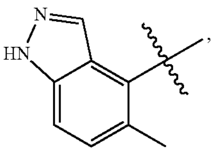, 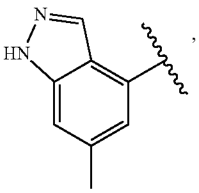,
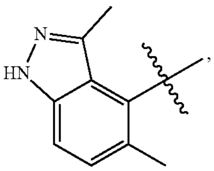, 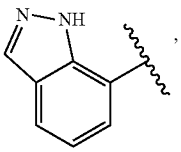,
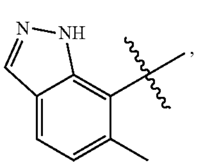, 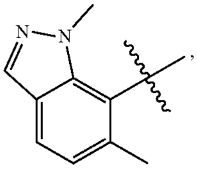,
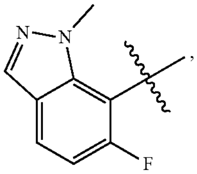, 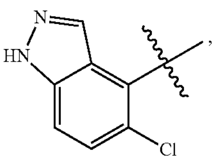,
-continued
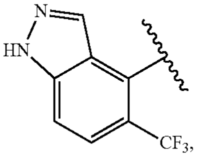, 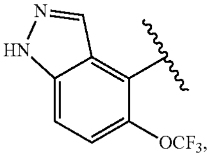,
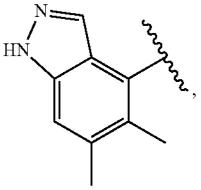, 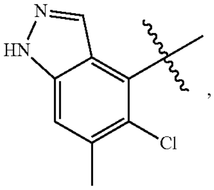,
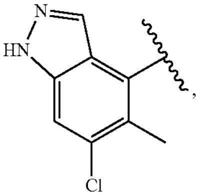, 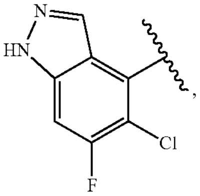,
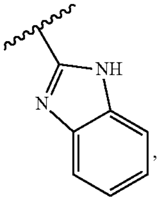, 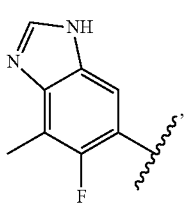, 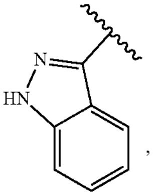,
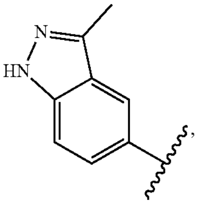, 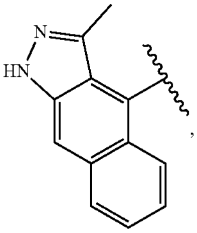,
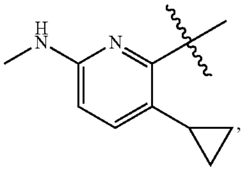, 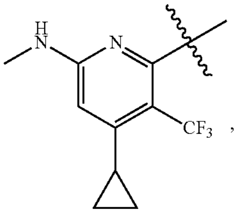,
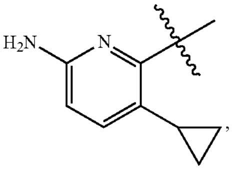, 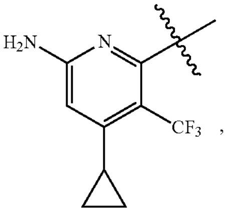,
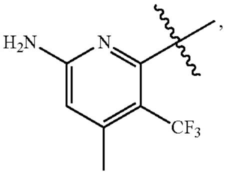, 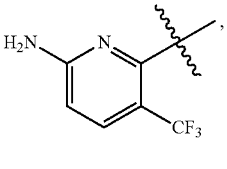, -continued
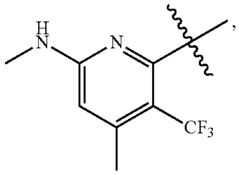, 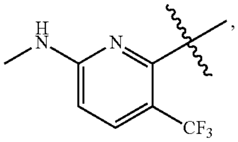,
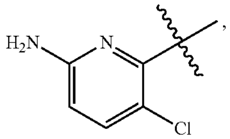, 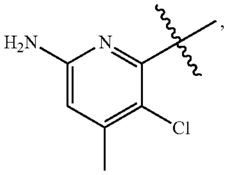,
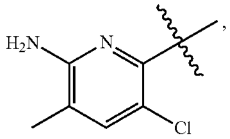, 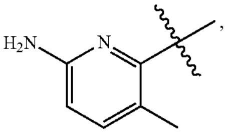,
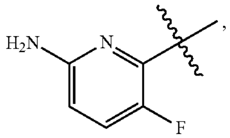, 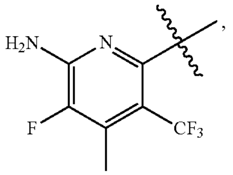,
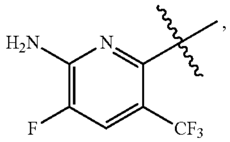, 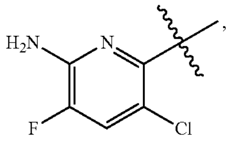,
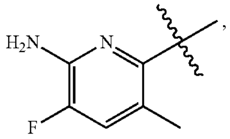, 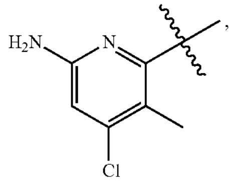,
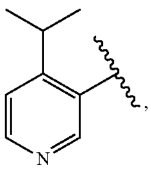, 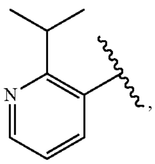, 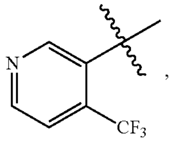,
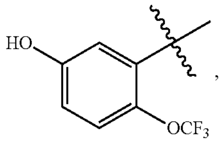, 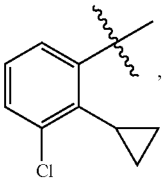,
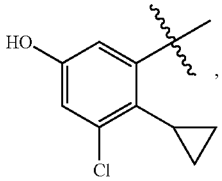, 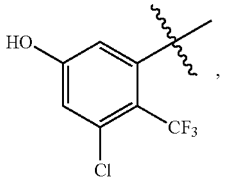,
-continued
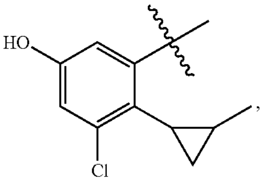, 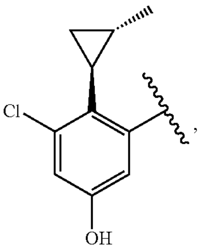,
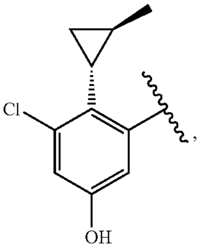, 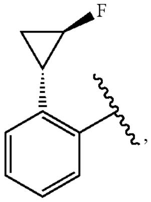, 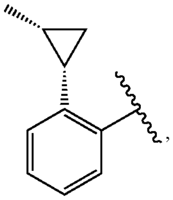,
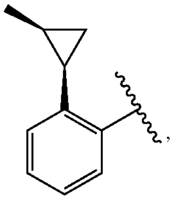, 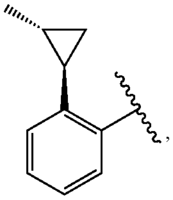, 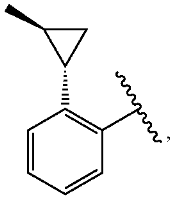,
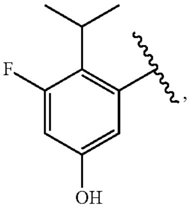, 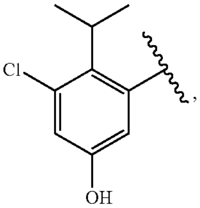,
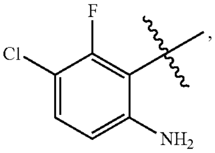, 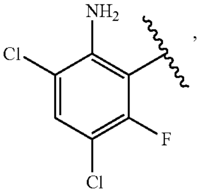,
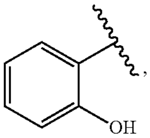, 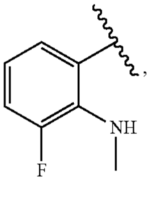, 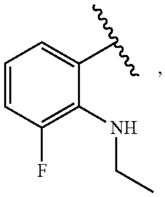,
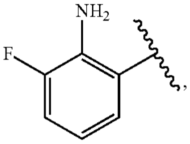, 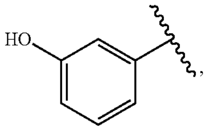,
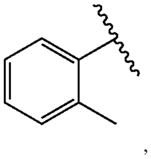, 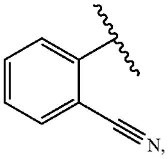, 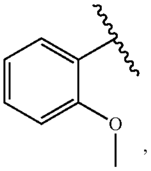, -continued
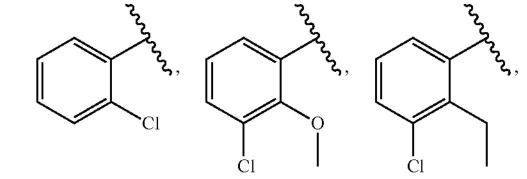
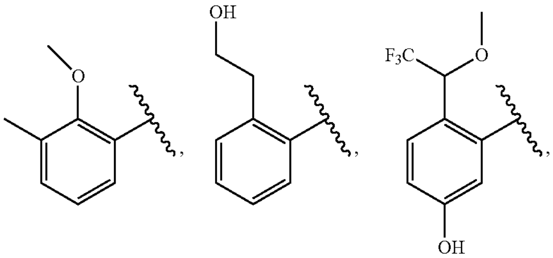
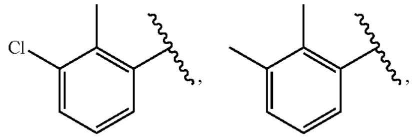
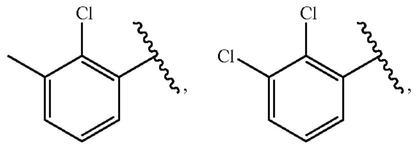
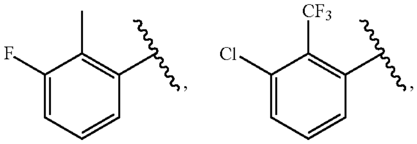
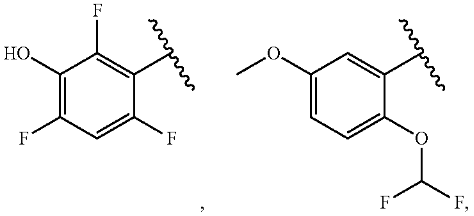
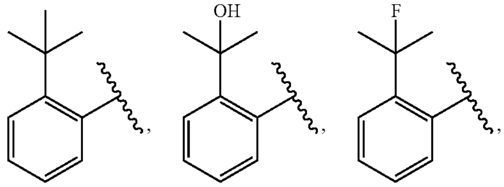
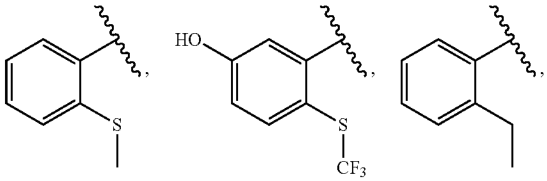
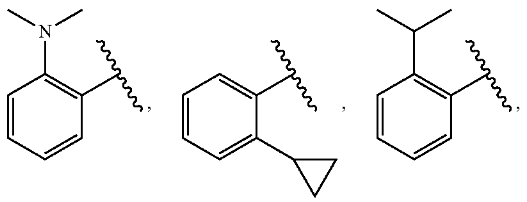
-continued
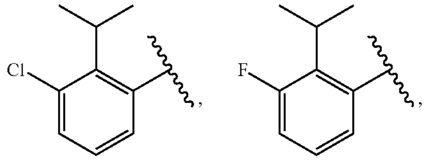
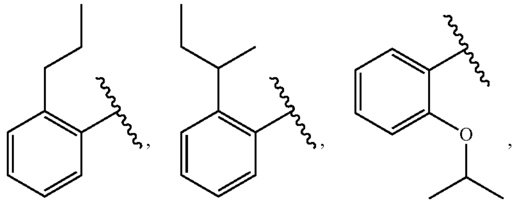
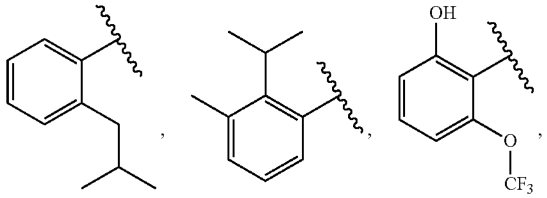
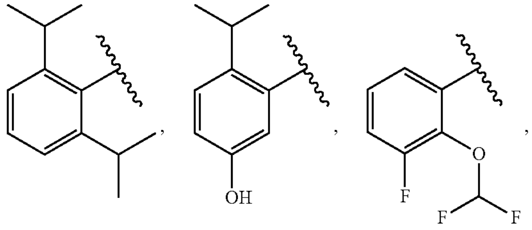
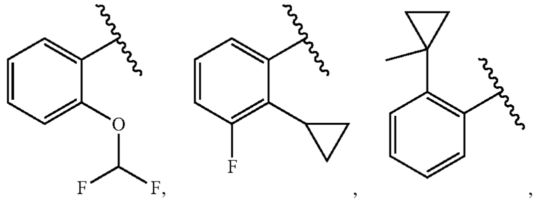
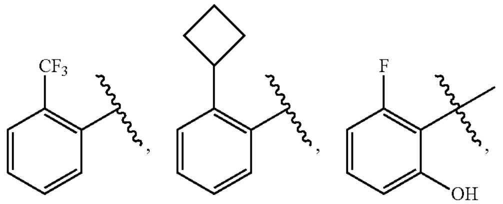
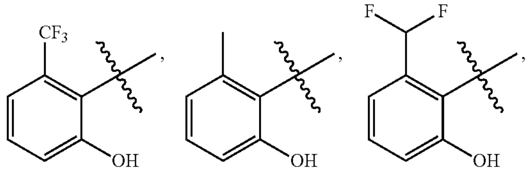
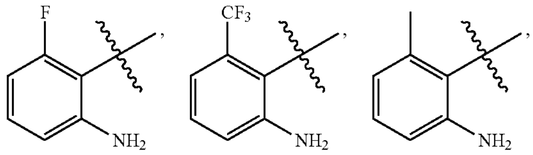
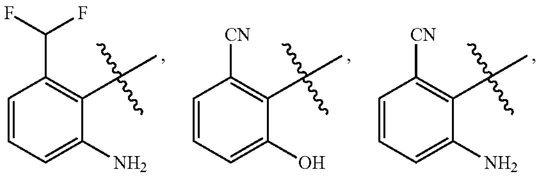

-continued
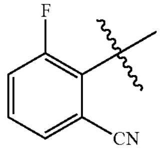, 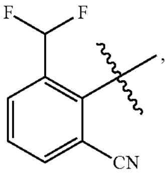,
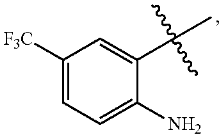, 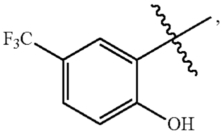,
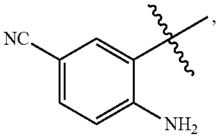, 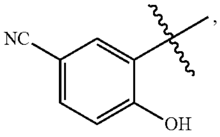,
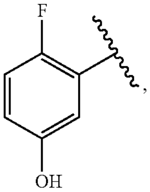, 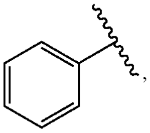, 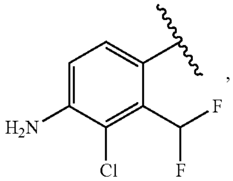,
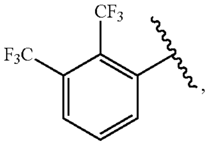, 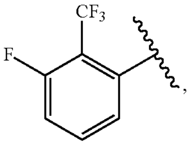,
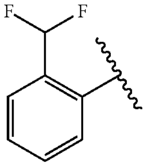, 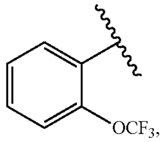, 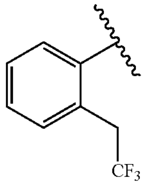,
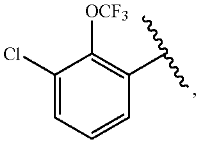, 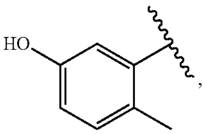,
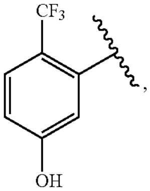, 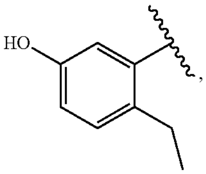,
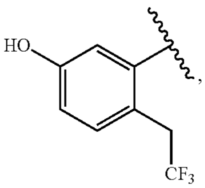, 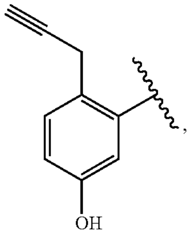,
-continued
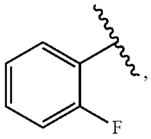, 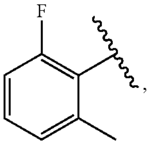, 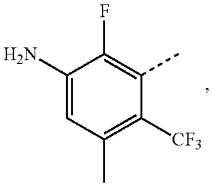,
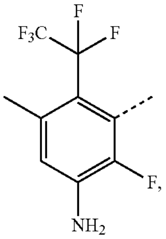 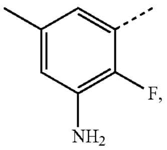 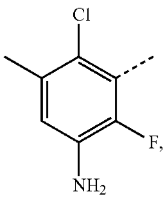
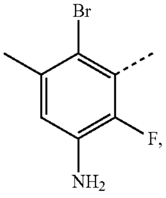 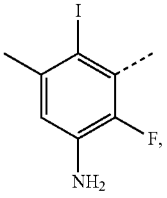 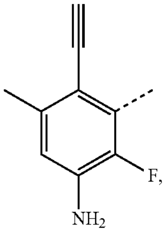
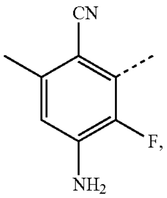 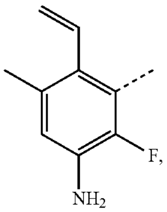 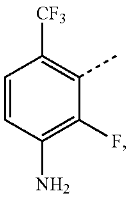
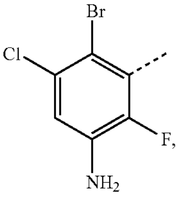 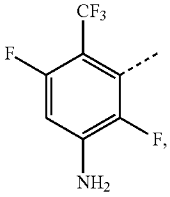
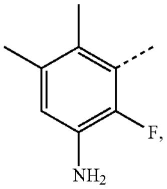 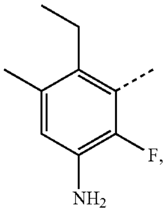
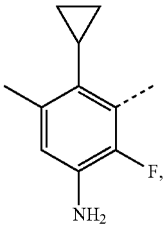 and 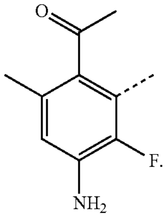
Embodiment 75 The compound of any one of Embodiments 1-70, wherein $R^{17}$ is selected from

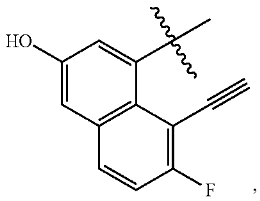
,
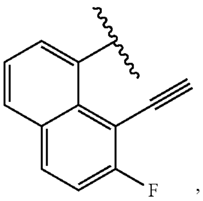
,
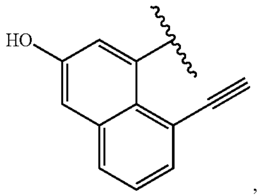
,
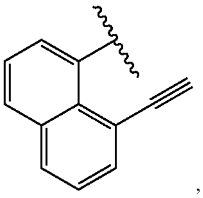
,
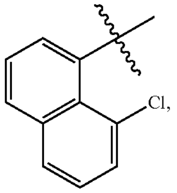
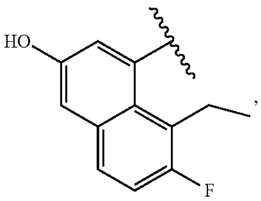
,
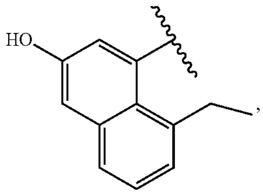
,
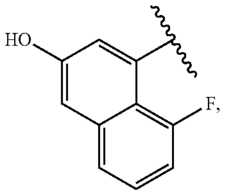
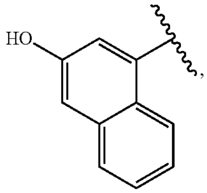
,
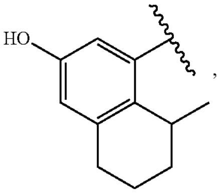
,
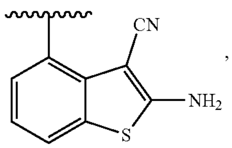
,
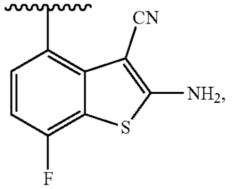
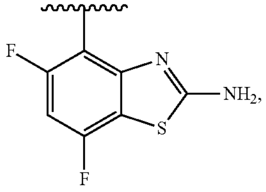
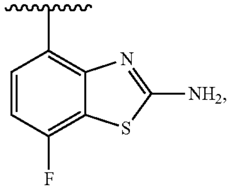
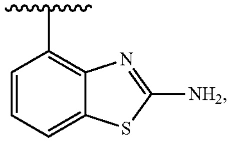
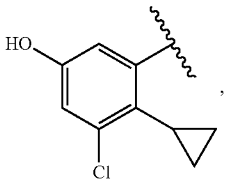
, -continued

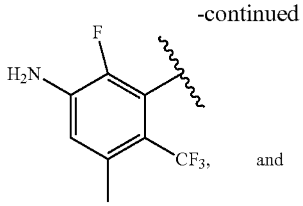
and
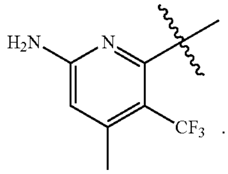
.

Embodiment 76 The compound of any one of Embodiments 1-75, wherein $X^8$ is $C(R^8)$.

Embodiment 77 The compound of any one of Embodiments 1-76, wherein $R^8$ is halogen.

Embodiment 78 The compound of any one of Embodiments 1-76, wherein $R^8$ is —F.

Embodiment 79 The compound of any one of Embodiments 3-78 having the formula:

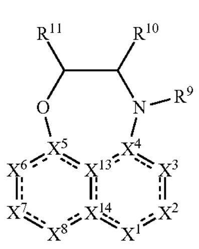
or
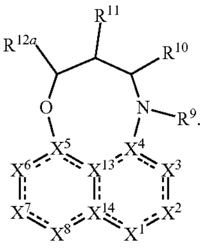

Embodiment 80 The compound of any one of Embodiments 3-78 having the formula:

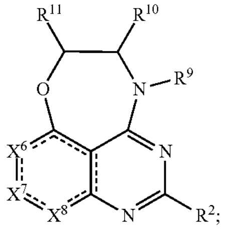

$X^6$ is selected from $C(R^6)$, $C(R^6)_2$, N, and $N(R^{6b})$;

$X^7$ is selected from $C(R^7)$ and $N(R^{7b})$;

$X^8$ is selected from $C(R^8)$ and $C(R^8)_2$; and $L^{7a}$ is a bond; $L^{7b}$ is a bond.

Embodiment 81 The compound of any one of Embodiments 3-53 having the formula:

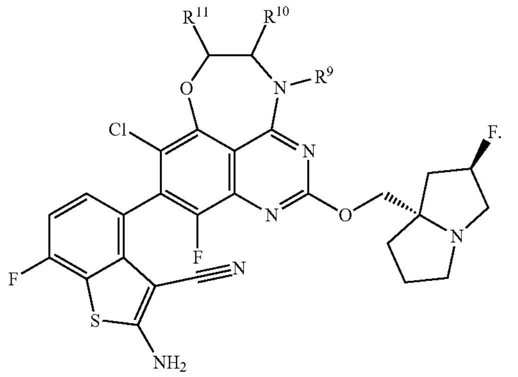

Embodiment 82 A compound having the formula B-$L^{BE}$-E wherein:

B is a monovalent form of a compound of one of Embodiments 1-81;

$L^{BE}$ is a covalent linker bonded to B and E; and

E is a monovalent form of a degradation enhancer.

Embodiment 83 The compound of Embodiment 82, wherein the degradation enhancer is capable of binding a protein selected from E3A, mdm2, APC, EDD1, SOCS/BC-box/eloBC/CUL5/RING, LNXp80, CBX4, CBLL1, HACE1, HECTD1, HECTD2, HECTD3, HECTD4, HECW1, HECW2, HERC1, HERC2, HERC3, HERC4, HER5, HERC6, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE3D, UBE4A, UBE4B, UBOX5, UBR5, VHL (von-Hippel-Lindau ubiquitin ligase), WWP1, WWP2, Parkin, MKRN1, CMA (chaperon-mediated autophage), SCFb-TRCP (Skip-Cullin-F box (Beta-TRCP) ubiquitin complex), b-TRCP (b-transducing repeat-containing protein), cIAP1 (cellular inhibitor of apoptosis protein 1), APC/C (anaphase-promoting complex/cyclosome), CRBN (cereblon), CUL4-RBX1-DDB1-CRBN ($CRL4^{CRBN}$) ubiquitin ligase, XIAP, IAP, KEAP1, DCAF15, RNF114, DCAF16, AhR, SOCS2, KLHL12, UBR2, SPOP, KLHL3, KLHL20, KLHDC2, SPSB1, SPSB2, SPSB4, SOCS6, FBXO4, FBXO31, BTRC, FBW7, CDC20, PML, TRIM21, TRIM24, TRIM33, GID4, avadomide, iberdomide, and CC-885.

Embodiment 84 The compound of Embodiment 82, wherein the degradation enhancer is capable of binding a protein selected from UBE2A, UBE2B, UBE2C, UBE2D1, UBE2D2, UBE2D3, UBE2DR, UBE2E1, UBE2E2, UBE2E3, UBE2F, UBE2G1, UBE2G2, UBE2H, UBE2I, UBE2J1, UBE2J2, UBE2K, UBE2L3, UBE2L6, UBE2L1, UBE2L2, UBE2L4, UBE2M, UBE2N, UBE20, UBE2Q1, UBE2Q2, UBE2R[1], UBE2R[2], UBE2S, UBE2T, UBE2U, UBE2V1, UBE2V2, UBE2W, UBE2Z, ATG3, BIRC6, and UFC1.

Embodiment 85 The compound of any one of Embodiments 82 to 84, wherein $L^{BE}$ is -$L^{BE1}$-$L^{BE2}$-$L^{BE3}$-$L^{BE4}$-$L^{BE5}$-;

$L^{BE1}$, $L^{BE2}$, $L^{BE3}$, $L^{BE4}$, and $L^{BE5}$ are independently a bond, —O—, —N($R^{12}$)—, —C(O)—, —N($R^{12}$)C(O)—, —C(O)N($R^{12}$)—, —S—, —S$(O)_2$—, —S(O)—, —S$(O)_2$N($R^{12}$)—, —S(O)N($R^{12}$)—, —N($R^{12}$)S(O)—, —N($R^{12}$)S$(O)_2$—, $C_{1-6}$ alkylene, (—O—$C_{1-6}$ alkyl$)_z$-, (—$C_{1-6}$ alkyl-O$)_z$—, $C_{2-6}$ alkenylene, $C_{2-6}$ alkynylene, $C_{1-6}$ haloalkylene, $C_{3-12}$ cycloalkylene, $C_{1-11}$ heterocycloalkylene, $C_{6-12}$ arylene, or $C_{1-11}$ heteroarylene, wherein $C_{1-6}$ alkylene, $C_{2-6}$ alkenylene, $C_{2-6}$ alkynylene, $C_{1-6}$ haloalkylene, $C_{3-12}$ cycloalkylene, $C_{1-11}$ heterocycloalkylene, $C_{6-12}$ arylene, or $C_{1-11}$ heteroarylene are optionally substituted with one, two, or three $R^{20}$; and wherein each $C_{1-6}$ alkyl of (—O—$C_{1-6}$ alkyl$)_z$- and (—$C_{1-6}$ alkyl-O$)_z$— is optionally substituted with one, two, or three $R^{20}$; and z is independently an integer from 0 to 10.

Embodiment 86 The compound of any one of Embodiments 82 to 85, wherein $L^{BE}$ is —(O—$C_2$ alkyl$)_z$- and z is an integer from 1 to 10.

Embodiment 87 The compound of any one of Embodiments 82 to 85, wherein $L^{BE}$ is —($C_2$ alkyl-O-$)_z$- and z is an integer from 1 to 10.

Embodiment 88 The compound of any one of Embodiments 82 to 85, wherein $L^{BE}$ is —$(CH_2)_{zz1}L^{BE2}(CH_2O)_{zz2}$—, wherein $L^{BE2}$ is a bond, a 5 or 6 membered heterocycloalkylene or heteroarylene, phenylene, —$C_{2-4}$alkynylene, —$SO_2$— or —NH—; and zz1 and zz2 are independently an integer from 0 to 10.

Embodiment 89 The compound of any one of Embodiments 82 to 85, wherein $L^{BE}$ is —$(CH_2)_{zz1}(CH_2O)_{zz2}$—, wherein zz1 and zz2 are each independently an integer from 0 to 10.

Embodiment 90 The compound of any one of Embodiments 82 to 85, wherein $L^{BE}$ is a PEG linker.

Embodiment 91 The compound of any one of Embodiments 82 to 90, wherein E is a monovalent form of a compound selected from

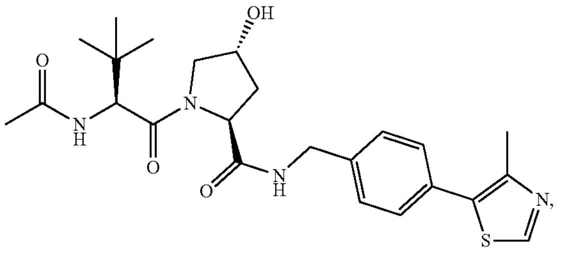

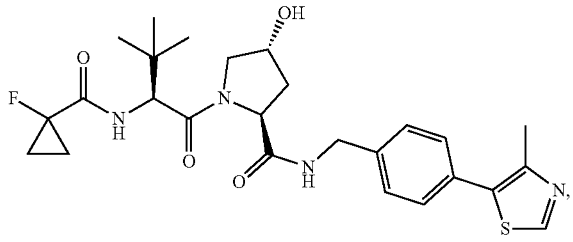

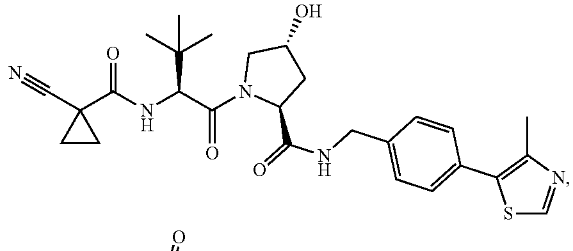

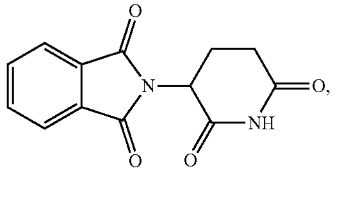

-continued

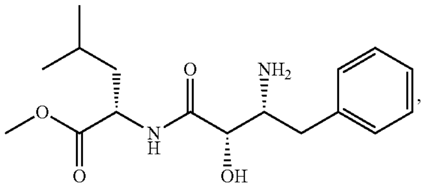

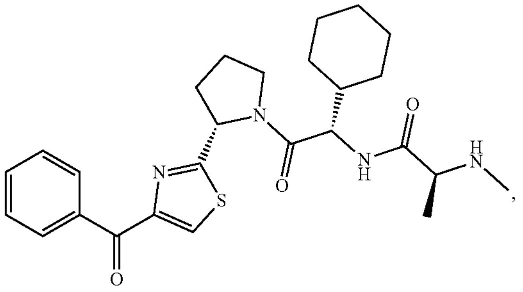

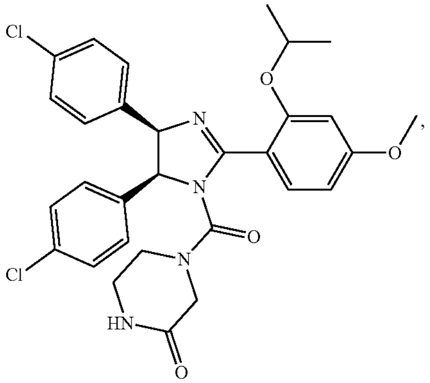

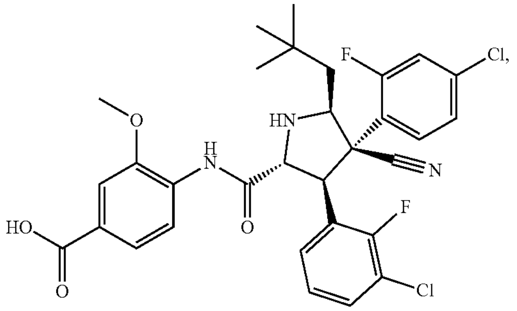

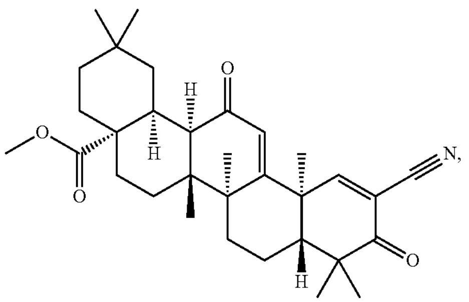

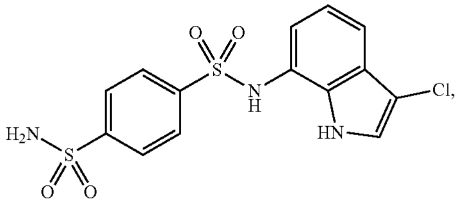

-continued

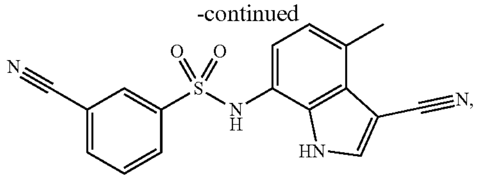

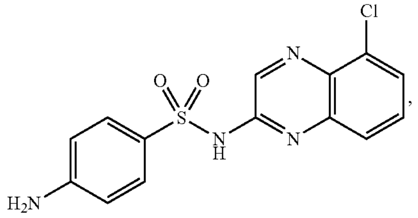

and

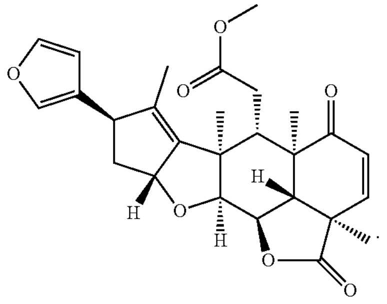

Embodiment 92 A pharmaceutical composition comprising a compound of any one of Embodiments 1-91, or a pharmaceutically acceptable salt or solvate thereof, and a pharmaceutically acceptable excipient.

Embodiment 93 A method of modifying a Ras mutant protein, comprising contacting the Ras mutant protein with an effective amount of the compound, salt, or solvate of any one of Embodiments 1-91.

Embodiment 94 The method of Embodiment 93, wherein the modified Ras mutant protein exhibits a reduced Ras signaling output.

Embodiment 95 The method of Embodiment 94, wherein the reduced Ras signaling output is evidenced by one or more output selected from (i) an increase in steady state level of GDP-bound modified protein; (ii) a reduction in steady state level of GTP-bound modified protein; (iii) a reduction of phosphorylated AKTs473; (iv) a reduction of phosphorylated ERK T202/Y204; (v) a reduction of phosphorylated S6 S235/236; (vi) a reduction of cell growth of a tumor cell expressing a Ras G12S mutant protein; and (vii) a reduction in Ras interaction with a Ras-pathway signaling protein.

Embodiment 96 The method of any one of Embodiments 93 to 95, wherein the Ras mutant protein comprises an amino acid sequence in SEQ ID No. 4 having a serine residue corresponding to position 12 of SEQ ID No. 1.

Embodiment 97 The method of any one of Embodiments 93 to 95, wherein the Ras mutant protein comprises an amino acid sequence of SEQ ID No. 4.

Embodiment 98 The method of any one of Embodiments 93 to 95, wherein the modified Ras mutant protein comprises an amino acid sequence of SEQ ID No. 1, or a fragment thereof that comprises the serine residue corresponding to position 12 of SEQ ID No. 1, and wherein the compound selectively labels the serine residue as compared to (i) an aspartate residue of a K-Ras G12D mutant protein, said aspartate corresponding to position 12 of SEQ ID No. 2; (ii) a valine residue of a K-Ras G12V mutant protein, said valine corresponding to position 12 of SEQ ID No. 3; and/or (iii) a glycine residue of a K-Ras wildtype protein, said glycine corresponding to position 12 of SEQ ID No. 1.

Embodiment 99 The method of Embodiment 98, wherein the compound selectively labels the serine residue by at least 2-fold when assayed under comparable conditions.

Embodiment 100 The method of Embodiment 98, wherein the compound selectively labels the serine residue by at least 5-fold when assayed under comparable conditions.

Embodiment 101 The method of any one of Embodiments 93 to 100, wherein the contacting occurs in vivo.

Embodiment 102 A method of treating cancer in a subject in need thereof, comprising administering to the subject a therapeutically effective amount of a compound of any one of Embodiments 1-91, or a pharmaceutically acceptable salt or solvate thereof.

Embodiment 103 A method of treating cancer in a subject comprising a Ras mutant protein, the method comprising: inhibiting the Ras mutant protein of said subject by administering to said subject a compound of any one of Embodiments 1-91, wherein the compound is characterized in that upon contacting the Ras mutant protein, said Ras mutant protein exhibits reduced Ras signaling output.

Embodiment 104 The method of Embodiment 102 or 103, wherein the cancer is a solid tumor or a hematological cancer.

Embodiment 105 The method of any one of Embodiments 102 to 104, wherein the cancer comprises a K-Ras G12S mutant protein.

Embodiment 106 A method of modulating signaling output of a Ras protein, comprising contacting a Ras protein with an effective amount of a compound of any one of Embodiments 1-91, or a pharmaceutically acceptable salt or solvate thereof, thereby modulating the signaling output of the Ras protein.

Embodiment 107 A method of inhibiting cell growth, comprising administering an effective amount of a compound of any one of Embodiments 1-91, or a pharmaceutically acceptable salt or solvate thereof, to a cell expressing a Ras protein, thereby inhibiting growth of said cells.

Embodiment 108 The method of any one of Embodiments 93 to 107, comprising administering an additional agent.

Embodiment 109 The method of Embodiment 108, wherein the additional agent comprises (1) an inhibitor of MEK; (2) an inhibitor of epidermal growth factor receptor (EGFR) and/or mutants thereof; (3) an immunotherapeutic agent; (4) a taxane; (5) an anti-metabolite; (6) an inhibitor of FGFR1 and/or FGFR2 and/or FGFR3 and/or mutants thereof; (7) a mitotic kinase inhibitor; (8) an anti-angiogenic drug; (9) a topoisomerase inhibitor; (10) a platinum-containing compound; (11) an inhibitor of c-MET and/or mutants thereof; (12) an inhibitor of BCR-ABL and/or mutants thereof; (13) an inhibitor of ErbB2 (Her2) and/or mutants thereof; (14) an inhibitor of AXL and/or mutants thereof; (15) an inhibitor of NTRK1 and/or mutants thereof; (16) an inhibitor of RET and/or mutants thereof; (17) an inhibitor of A-Raf and/or B-Raf and/or C-Raf and/or mutants thereof; (18) an inhibitor of ERK and/or mutants thereof; (19) an MDM2 inhibitor; (20) an inhibitor of mTOR; (21) an inhibitor of IGF1/2 and/or IGF1-R; (22) an inhibitor of CDK9; (23) an inhibitor of farnesyl transferase; (24) an inhibitor of SHIP pathway; (25) an inhibitor of SRC; (26) an inhibitor of JAK; (27) a PARP inhibitor, (28) a ROS1 inhibitor; (29) an inhibitor of SHP pathway; (30) an inhibitor of Src, FLT3, HDAC, VEGFR, PDGFR, LCK, Bcr-Abl or AKT; (31) an inhibitor of KRAS G12C; (32) an SHC inhibitor; (33) a GAB inhibitor; (34) a PI-3 kinase inhibitor; (35) a MARPK inhibitor; (36) a CDK4/6 inhibitor; (37) a MAPK inhibitor; (38) a SHP2 inhibitor; (39) a checkpoint immune blockade agent; (40) a SOS1 inhibitor; or (41) a SOS2 inhibitor.

Embodiment 110 The method of Embodiment 108, wherein the additional agent comprises an inhibitor of SHP2 selected from RMC-4630, ERAS-601,

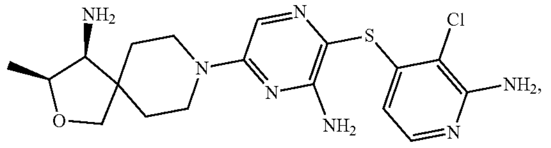

TNO155

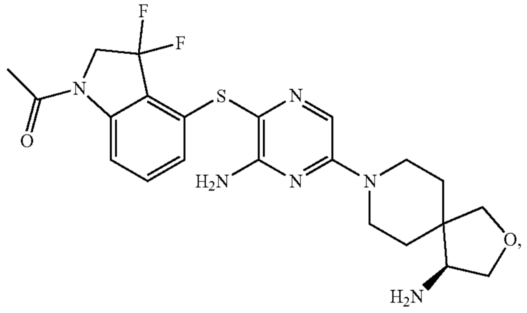

JAB-3068

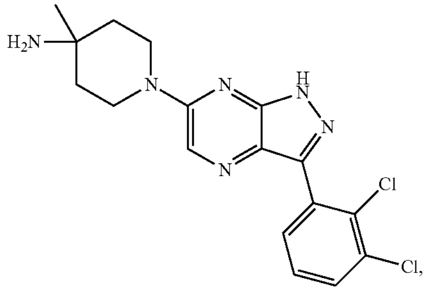

IACS-13909/BBP-398

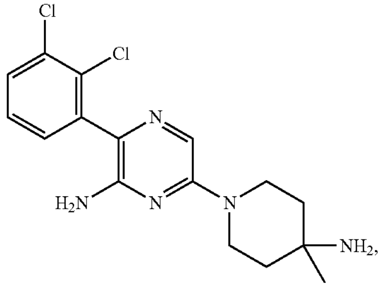

and

SHP099

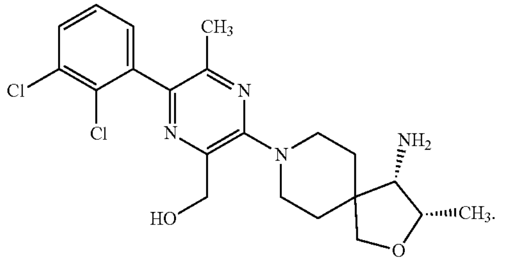

RMC-4550

Embodiment 111 The method of Embodiment 108, wherein the additional agent comprises an inhibitor of SOS selected from RMC-5845, BI-1701963,

BI-3406

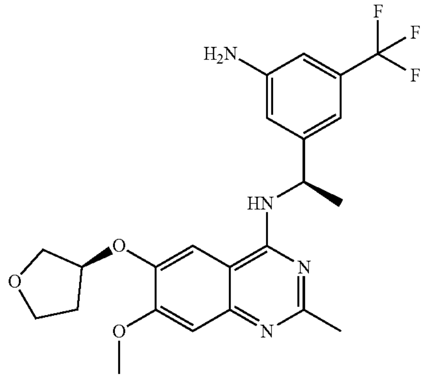

MRTX0902

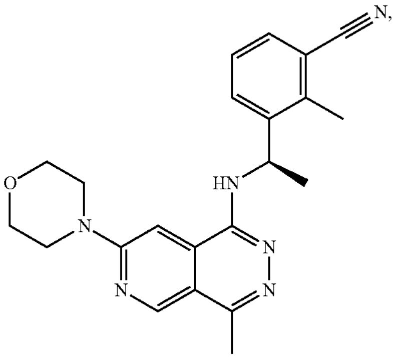

and

BAY 293

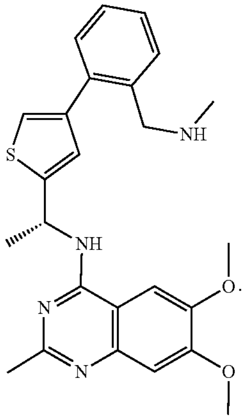

Embodiment 112 The method of Embodiment 108, wherein the additional agent comprises an inhibitor of EGFR selected from afatinib, erlotinib, gefitinib, lapatinib, cetuximab panitumumab, osimertinib, olmutinib, and EGF-816.

Embodiment 113 The method of Embodiment 108, wherein the additional agent comprises an inhibitor of MEK selected from trametinib, cobimetinib, binimetinib, selumetinib, refametinib, and AZD6244.

Embodiment 114 The method of Embodiment 108, wherein the additional agent comprises an inhibitor of ERK selected from ulixertinib, MK-8353, LTT462, AZD0364, SCH772984, BIX02189, LY3214996, and ravoxertinib.

Embodiment 115 The method of Embodiment 108, wherein the additional agent comprises an inhibitor of CDK4/6 selected from palbociclib, ribociclib, and abemaciclib.

Embodiment 116 The method of Embodiment 108, wherein the additional agent comprises an inhibitor of BRAF selected from Sorafenib, Vemurafenib, Dabrafenib, Encorafenib, regorafenib, and GDC-879.

EXAMPLES

The following examples are provided for illustrative purposes only and not to limit the scope of the claims provided herein. Unless noted otherwise, all materials, such as reagents, starting materials and solvents, were purchased from commercial suppliers, such as Sigma-Aldrich, VWR, and the like, and were used without further purification. Reactions were run under nitrogen atmosphere, unless noted otherwise. The progress of reactions was monitored by thin layer chromatography (TLC), analytical high performance liquid chromatography (anal. HPLC), and mass spectrometry, the details of which may be provided in specific examples.

Reactions were worked up as described specifically in each preparation; commonly, reaction mixtures were purified by extraction and other purification methods such as temperature- and solvent-dependent crystallization, and precipitation. In addition, reaction mixtures were routinely purified by preparative HPLC, for example, using Microsorb C18 or Microsorb BDS column packings and conventional eluents. Progress of reactions was typically monitored by liquid chromatography mass spectrometry (LCMS). Characterization of isomers was typically done by Nuclear Overhauser effect spectroscopy (NOE). Characterization of reaction products was routinely carried out by mass spectrometry and/or $^{1}$H-NMR spectroscopy. For NMR measurement, samples were dissolved in deuterated solvent ($CD_3OD$, $CDCl_3$, or DMSO-$d_6$).

Example 1: Synthetic Procedures

Example A: Synthesis of 2-amino-4-(8-chloro-10-fluoro-4-((1-(2-fluoroacryloyl)azetidin-3-yl)methyl)-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (491)

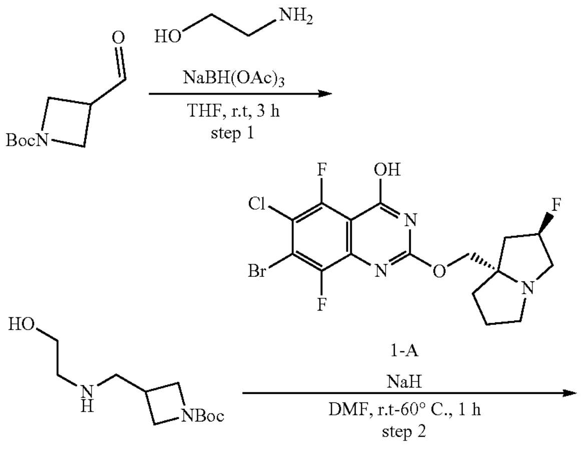

-continued

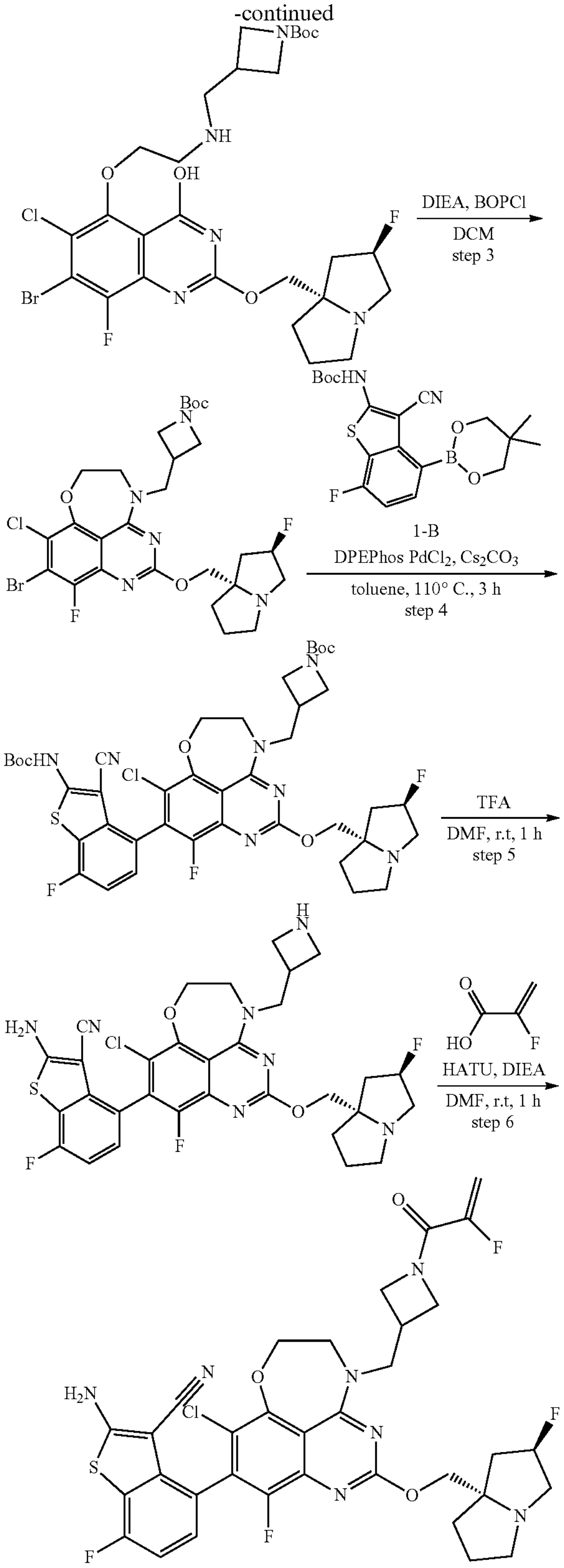

491

Step 1: A solution of tert-butyl 3-formylazetidine-1-carboxylate (5.6 g, 30 mmol) in MeOH (60 mL) was cooled to 0° C. 2-Aminoethan-1-ol (2.77 g, 45 mmol) and 4A molecular sieve powder was added. The mixture was stirred at room temperature for 16 h. The mixture was cooled to 0° C. and then $NaBH_4$ (3.43 g, 90 mmol) was added and the mixture was stirred at room temperature for 1 hour. After the reaction was completed, the reaction mixture was quenched with $NH_4Cl$ aqueous solution and extracted with EtOAc. The organic layer was dried over anhydrous $Na_2SO_4$, filtered and concentrated in vacuo. The crude product was purified by silica gel column to give the desired tert-butyl 3-(((2-hydroxyethyl)amino)methyl) azetidine-1-carboxylate (6 g, Yield: 87%) as a colorless oil. MS (ESI) m/z=231.1 $[M+H]^+$.

Step 2: To a solution of tert-butyl 3-(((2-hydroxyethyl)amino)methyl)azetidine-1-carboxylate (1.1 g, 4.8 mmol) in anhydrous DMF (14 mL) was added NaH (400 mg, 60% on mineral oil, 10 mmol) at room temperature under argon. After stirring at room temperature for 10 minutes, a solution of 7-bromo-6-chloro-5,8-difluoro-2-(((2R,7aS)-2-fluorotetrahydro-1H-pyrrolizin-7a(5H)-yl)methoxy)quina zolin-4-ol (1.45 g, 3.2 mmol) in anhydrous DMF (6 mL) was added. After the addition, the mixture was heated to 60° C. and stirred for 1 hour. The mixture was cooled to 0° C. The mixture was quenched with $NH_4Cl$ aqueous solution (15 mL) and extracted with EtOAc (3×10 mL). The organic layer was dried over anhydrous $Na_2SO_4$, filtered and concentrated in vacuo. The crude product was purified by silica gel column to give the desired product tert-butyl 3-(((2-((7-bromo-6-chloro-8-fluoro-2-(((2R,7aS)-2-fluorotetrahydro-1H-pyrrolizin-7a (5H)-yl)methoxy)-4-hydroxyquinazolin-5-yl)oxy)ethyl)amino)methyl)azetidine-1-carboxylate (1.6 g, yield 75.4%). MS (ESI) m/z=664.1 $[M+H]^+$.

Step 3: To a solution of tert-butyl 3-(((2-((7-bromo-6-chloro-8-fluoro-2-(((2R,7aS)-2-fluorotetrahydro-1H-pyrrolizin-7a (5H)-yl)methoxy)-4-hydroxyquinazolin-5-yl)oxy)ethyl)amino)methyl)azetidine-1-carboxylate (1.6 g, 2.4 mmol) in DCM (30 mL) was added DIEA (690 mg, 5.3 mmol) and BOPCl(1 g, 4 mmol) at room temperature under argon. The resulting mixture was stirred at room temperature for 1 hour. After completion, the reaction mixture was diluted with EtOAc and washed with brine. The organic layer was dried over anhydrous $Na_2SO_4$, filtered and concentrated in vacuo. The crude product was purified by silica gel column to give the desired product tert-butyl 3-((9-bromo-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-4-yl)methyl)azetidine-1-carboxylate as white solid (1.2 g, yield: 77%). MS (ESI) m/z=646.0 [M+H]+.

Step 4: To a solution of tert-butyl 3-((9-bromo-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-4-yl)methyl)azetidine-1-carboxylate (1.2 g, 1.86 mmol) in toluene (20 mL) was added tert-butyl (3-cyano-4-(5,5-dimethyl-1,3,2-dioxaborinan-2-yl)-7-fluorobenzo[b]thiophen-2-yl)carbamate (1.5 g, 3.72 mmol), $Cs_2CO_3$ (1.82 g, 5.6 mmol) and dichloro[bis(2-(diphenylphosphino)phenyl)ether]palladium(II) ($PdCl_2$ (DPEPhos), 266 mg, 0.37 mmol), the mixture was degassed and purged with $N_2$. The mixture was heated under $N_2$ at 110° C. with stirring for 3 hours and cooled down to room temperature. The mixture was treated with saturated $NH_4Cl$ (20 mL) and extracted with EtOAc (3×15 mL). Organic layers were collected and concentrated. The resulting residue was purified by silica gel column to provide desired tert-butyl 3-((9-(2-((tert-butoxycarbonyl)amino)-3-cyano-7-fluorobenzo[b]-thiophen-4-yl)-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-4-yl)methyl) azetidine-1-carboxylate as yellow solid (1.1 g, yield 69%). MS (ESI) m/z=856.2 $[M+H]^+$.

Step 5: To a solution of tert-butyl 3-((9-(2-((tert-butoxycarbonyl)amino)-3-cyano-7-fluorobenzo[b]-thiophen-4-yl)-8-chloro-10-fluoro-2-(((2R,7aS)-2-fluorotetrahydro-1H- pyrrolizin-7a (5H)-yl)methoxy)-5,6-dihydro-4H-[1,4]oxazepino[5,6,7-de]quinazolin-4-yl)methyl) azetidine-1-carboxylate (1.1 g, 1.2 mmol) in DCM (10 mL) was added TFA (4 mL) at room temperature. The mixture was stirred at room temperature for 1 hour. The solvent was removed under reduced pressure, diluted with DCM (30 mL), and washed with saturated $NaHCO_3$ aqueous solution (20 mL). The organic layer was concentrated and purified by silica gel column to afford 2-amino-4-(4-(azetidin-3-ylmethyl)-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-7-fluorobenzo[b]thiophene-3-carbonitrile (540 mg, 64.1%) as a yellow solid. MS (ESI) m/z=656.1 $[M+H]^+$ Step 6: To a solution of 2-fluoroacrylic acid (275 mg, 3.0 mmol) in DMF (20 mL) was added DIEA (785 mg, 6.08 mmol) and HATU(1740 mg, 4.52 mmol) at 0° C. under argon. The mixture was stirred at 0° C. for 30 min. followed by addition of 2-amino-4-(4-(azetidin-3-ylmethyl)-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-7-fluorobenzo[b]thiophene-3-carbonitrile (50 mg, 0.076 mmol) in DMF(2 mL) and stirring at room temperature for 1 hour. After the reaction was completed, the reaction mixture was purified by Prep-HPLC to give 2-amino-4-(8-chloro-10-fluoro-4-((1-(2-fluoroacryloyl)azetidin-3-yl)methyl)-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-7-fluorobenzo[b]thiophene-3-carbonitrile (24.54 mg, Yield: 44.6%) as a light red solid. MS (ESI) m/z=728.1 $[M+H]^+$. $^1H$ NMR (400 MHz, $d_6$-DMSO) δ 8.11 (s, 2H), 8.10 (s, 2H), 7.25-7.10 (m, 3H), 5.67-5.21 (m, 3H), 4.73-3.42 (m, 16H), 3.16 (s, 1H), 2.79 (dd, J=64.4, 12.0 Hz, 1H), 2.42-1.91 (m, 5H), 1.24 (s, 1H).

Example B Synthesis of 2-amino-4-(4-(((2S,3R)-2-(tert-butyl)-1-(3-fluoro-1H-1,2,4-triazole-1-carbonyl)azetidin-3-yl)methyl)-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-7-fluorobenzo[b]thiophene-3-carbonitrile (434 and 416)

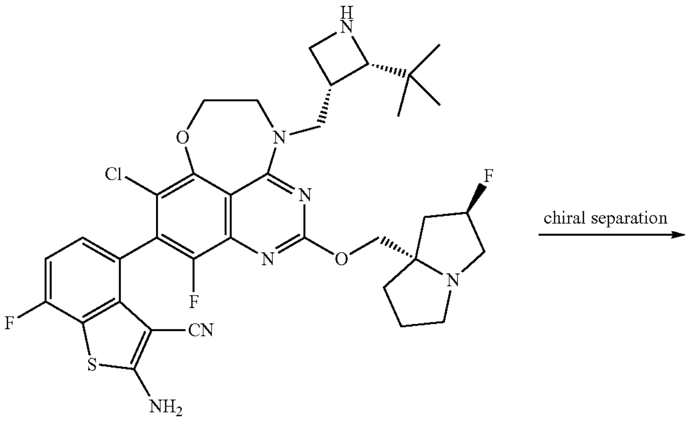

6-1

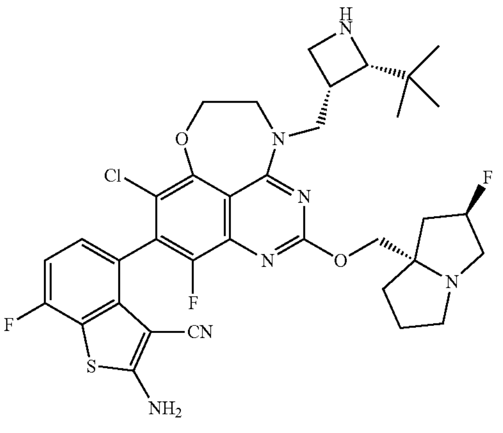

6-2-P1, polar peak

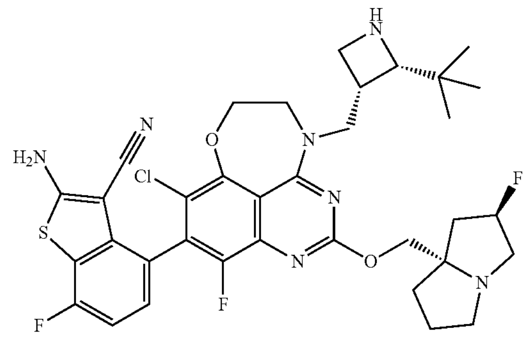

6-2-P2, less polar peak

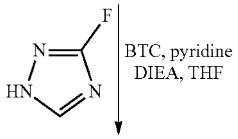

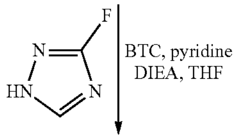

-continued

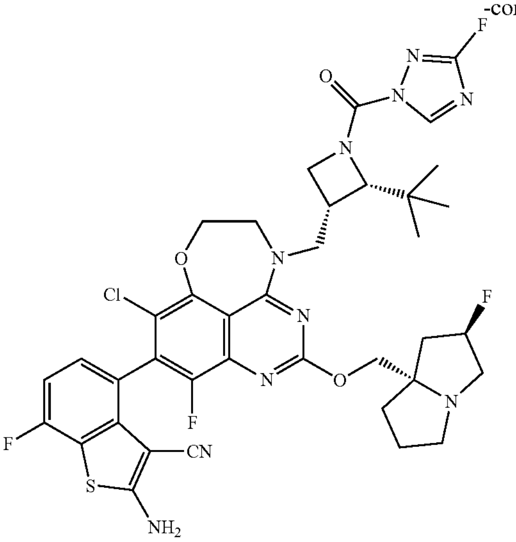

434

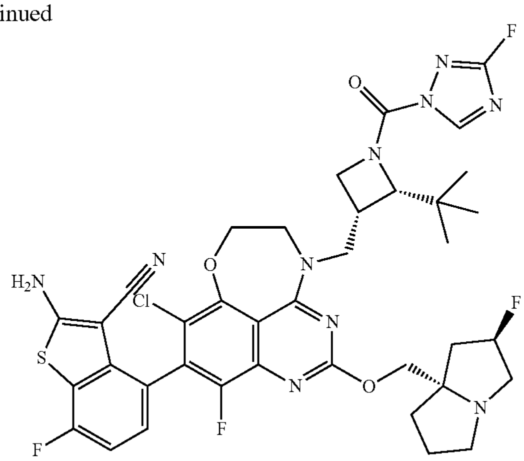

416

Preparation of 2-amino-4-(4-(((2S,3R)-2-(tert-butyl)-1-(3-fluoro-1H-1,2,4-triazole-1-carbonyl)azetidin-3-yl)methyl)-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-7-fluorobenzo[b]thiophene-3-carbonitrile (434 and 416) Atropoisomeric mixture Compound 6-1 (Prepared following the same procedure as described in Example D) was subjected to chiral separation to provide single atropisomer 6-2-P1 (polar peak) and single atropisomer 6-2-P2 (less polar peak) as HCl salts.

Following a similar procedure as described in Example D (step 5), 6-2-P1 and 6-2-P2 were converted to the corresponding desired products as single atropisomer compounds 434 and 416.

434: MS m/z (ESI): 825.2 $[M+H]^+$. $^1H$ NMR (500 MHz, $CDCl_3$) δ 8.58 (s, 1H), 7.14 (dd, J=3.3, 13.3 Hz, 1), 6.95 (t, J=8.7 Hz, 1H), 6.33 (s, 1H), 5.49 (d, J=52.5 Hz, 1H), 5.06 (d, J=11.9 Hz, 1H), 4.96 (s, 2H), 4.66-4.56 (m, 4H), 4.47-4.42 (m, 2H), 4.08-4.06 (m, 2H), 4.01-3.89 (m, 2H), 3.32-3.61 (m, 3H), 2.84-2.73 (m, 1H), 2.66 (s, 1H), 2.48-2.30 (m, 4H), 2.17 (s, 4H), 1.18 (s, 9H).

416: MS m/z (ESI): 825.2 $[M+H]^+$. $^1H$ NMR: 1H NMR (500 MHz, DMSO-d6) δ 9.04 (s, 1H), 7.19(m, 1H), 7.12 (m, 1H), 5.27 (d, J=55 Hz, 1H), 4.65-4.35 (m, 6H), 4.56-4.00 (m, 3H), 3.89 (m, 2H), 3.47 (m, 1H), 3.20-3.03 (m, 4H), 2.84 (m, 1H), 2.20-1.90 (m, 3H), 1.90-1.70 (m, 3H), 1.14 (s, 9H).

Example C: Synthesis of 2-amino-4-(8-chloro-4-((1-((E)-4,4-difluorobut-2-enoyl)azetidin-3-yl)methyl)-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-7-fluorobenzo[b]thiophene-3-carbonitrile (423)

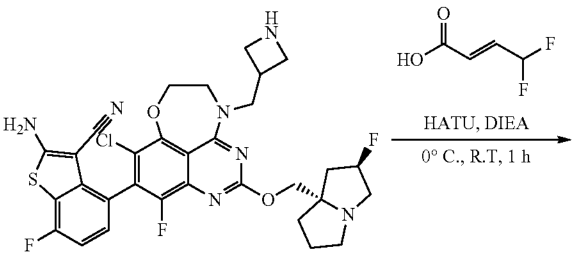

-continued

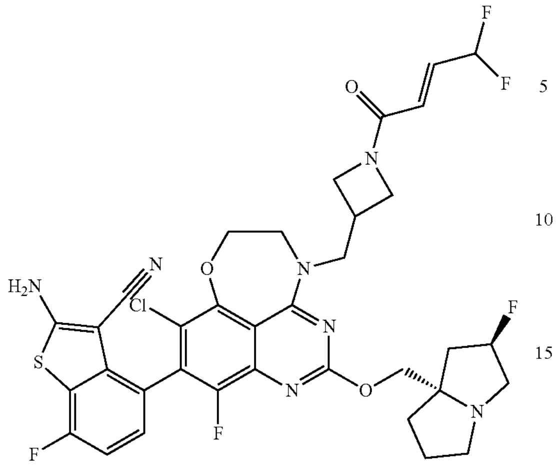

423

A mixture of (E)-4,4-difluorobut-2-enoic acid (46.5 mg, 0.38 mmol), HATU (217.5 mg, 0.57 mmol), and DIEA (98.5 mg, 0.76 mmol) in DMF (5 mL) was stirred at 25° C. for 1 hour. To a solution of 2-amino-4-(4-(azetidin-3-ylmethyl)-8-chloro-10-fluoro-2-(((2R,7aS)-2-fluorotetrahydro-1H-pyrrolizin-7a (5H)-yl)meth-oxy)-5,6-dihydro-4H-[1,4]oxazepino[5,6,7-de]quinazolin-9-yl)-7-fluorobenzo[b]thiophene-3-carbonitrile (50 mg, 0.07 mmol) in DMF (1 mL) was added the above reaction mixture (1 mL) at room temperature under $N_2$ atmosphere. The mixture was stirred at 25° C. for 0.5 hour. The crude was purified directly by prep-HPLC (formic acid as modifier) to give 2-amino-4-(8-chloro-4-((1-((E)-4,4-difluorobut-2-enoyl)azetidin-3-yl)methyl)-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-7-fluorobenzo[b]thiophene-3-carbonitrile (8.23 mg, Yield: 14.2%). MS m/z (ESI): 760.4 [M+H]. $^1H$ NMR (400 MHz, DMSO-$d_6$) δ 8.08 (s, 2H), 7.23-7.08 (m, 2H), 6.76-6.45 (m, 3H), 5.27 (d, J=54.4 Hz, 1H), 4.60-4.50 (m, 2H), 4.40-4.36 (m, 1H), 4.22-4.15 (m, 2H), 4.13-4.08 (m, 2H), 4.03-3.97 (m, 2H), 3.93-3.90 (m, 2H), 3.11-3.00 (m, 4H), 2.77-2.86 (m, 2H), 2.12-1.96 (m, 3H), 1.85-1.71 (m, 3H).

Example D: Synthesis of 2-amino-4-(8-chloro-10-fluoro-4-(((2R,3R)-1-(3-fluoro-1H-1,2,4-triazole-1-carbonyl)-2-isopropylazetidin-3-yl)methyl)-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-7-fluorobenzo[b]thiophene-3-carbonitrile (408 and 412)

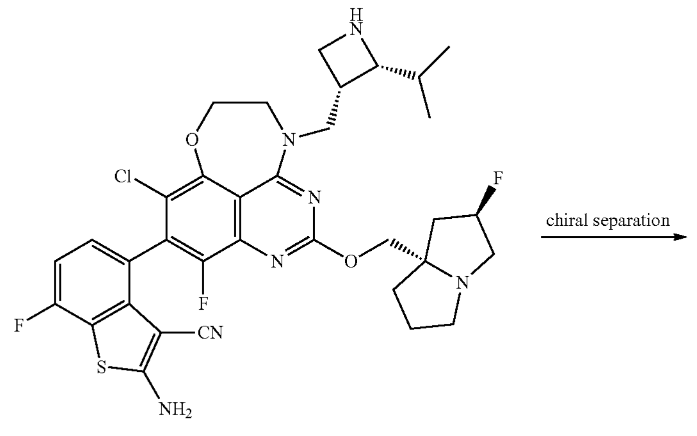

2-7

-continued

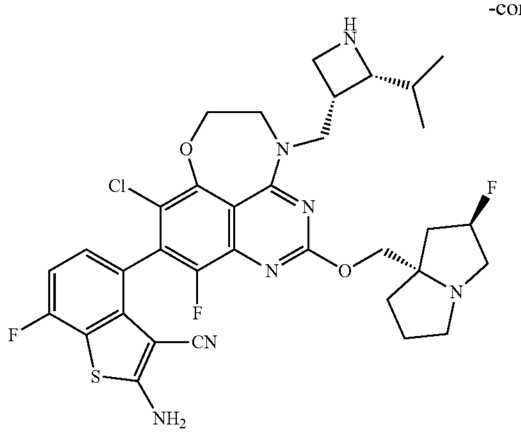

4-2-P1, polar peak

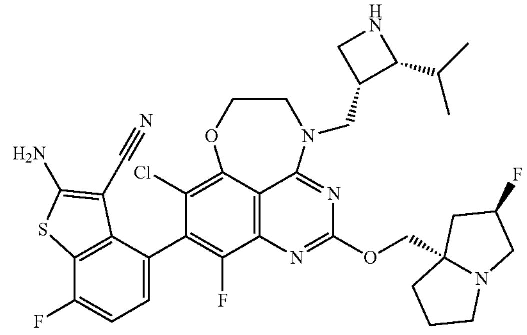

4-2-P2, less polar peak

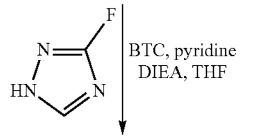

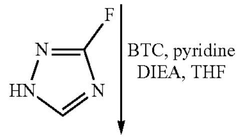

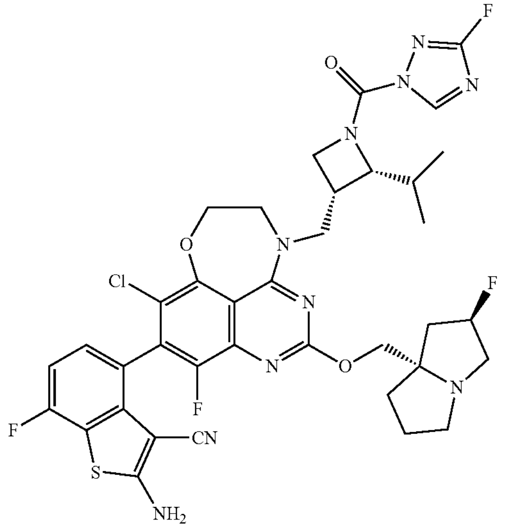

408

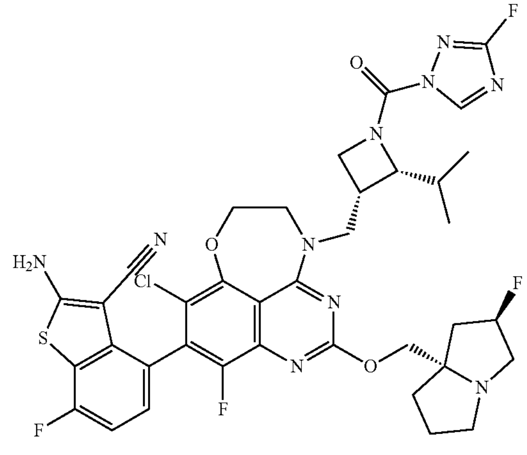

412

Preparation of 2-amino-4-(8-chloro-10-fluoro-4-(((2R, 3R)-1-(3-fluoro-1H-1,2,4-triazole-1-carbonyl)-2-isopropylazetidin-3-yl)methyl)-2-(((2R,7aS)-2-fluorotetrahydro-1H-pyrrolizin-7a (5H)-yl)methoxy)-5,6-dihydro-4H-[1,4] oxazepino[5,6,7-de]quinazolin-9-yl)-7-fluorobenzo[b] thiophene-3-carbonitrile (408 and 412). Atropoisomeric mixture Compound 2-7 was subjected to chiral separation to provide single atropisomer 4-2-P1 (polar peak) and single atropisomer 4-2-P2 (less polar peak) as HCl salts.

Following a similar procedure described in Example F (step 5), 4-2-Pt and 4-2-P2 were converted to the corresponding products as single atropisomer of desired compound 408 and 412.

408: MS m/z (ESI): 811.2 $[M+H]^+$. $^1H$ NMR (500 MHz, $CDCl_3$) δ 8.59 (s, 1H), 7.15 (m, 1H), 6.95 (m, 1H), 5.40 (d, J=55.0 Hz, 1H), 5.10 (br, 1H), 4.65-4.45 (m, 4H), 4.07 (m, 2H), 3.96 (m, 2H), 3.54 (m, 1H), 3.32 (br, 2H), 2.80-2.60 (m, 1H), 2.35-2.255 (m, 5H), 1.11 (m, 6H)

412: MS m/z (ESI): 811.2 $[M+H]^+$. $^1H$ NMR: $^1H$ NMR (500 MHz, DMSO-d6) δ 9.07 (s, 1H), 7.19 (m, 1H), 7.13 (m, 1H), 5.27 (d, J=55 Hz, 1H), 4.65-4.35 (m, 5H), 4.26 (m, 1H), 4.15 (m, 1H), 4.09 (d, J=10 Hz, 1H), 4.04 (d, J=10 Hz, 1H), 3.93 (m, 2H), 3.14-3.03 (m, 3H), 2.83 (m, 1H), 2.33 (m, 1H), 2.20-1.70 (m, 6H), 1.08 (d, J=10 Hz, 3H), 1.04 (d, J=10 Hz, 3H).

Example E: Synthesis of 4-(4-(1-((R)-1-(1H-1,2,4-triazole-1-carbonyl)azetidin-2-yl)ethyl)-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-2-amino-7-fluorobenzo[b]thiophene-3-carbonitrile (445)
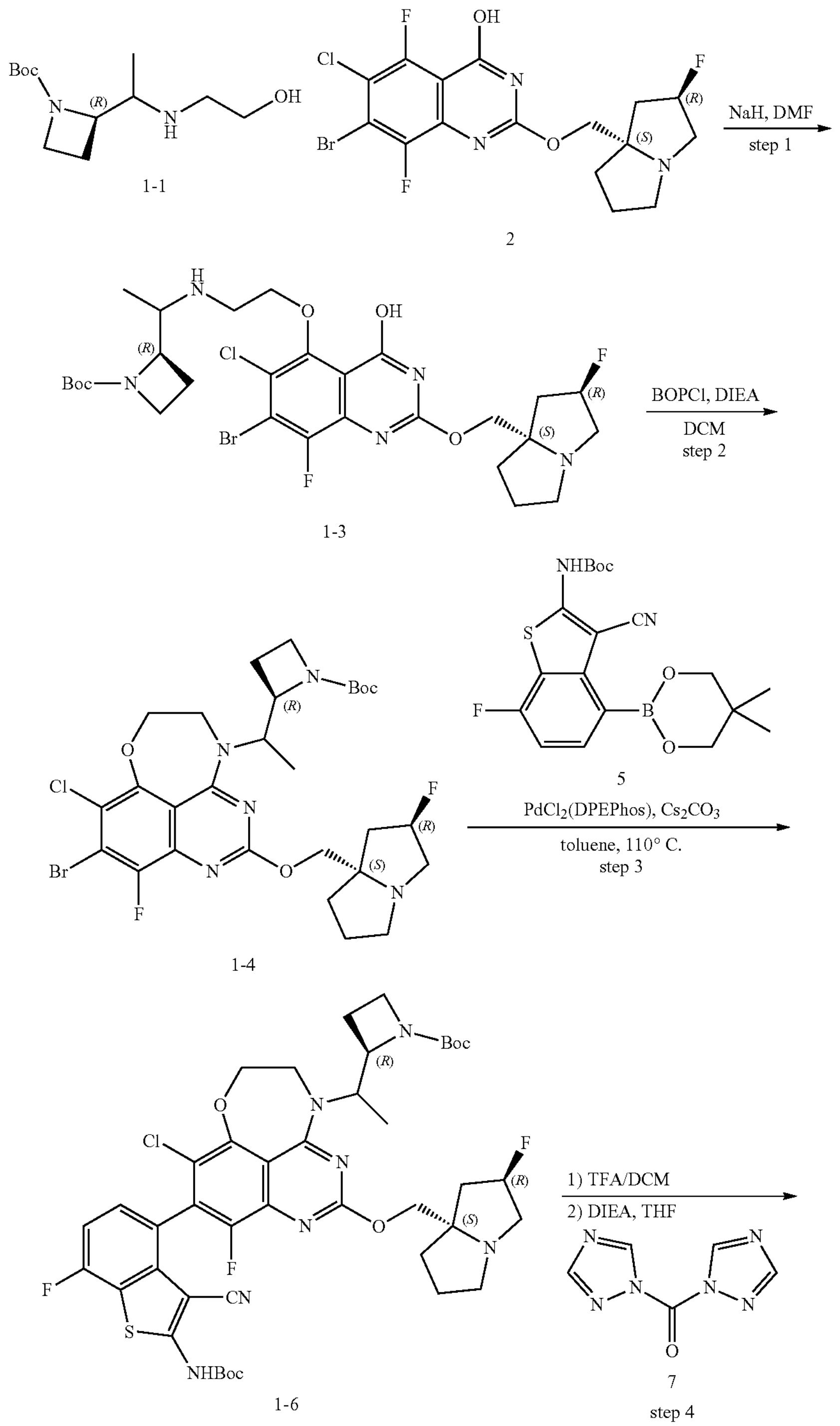

-continued

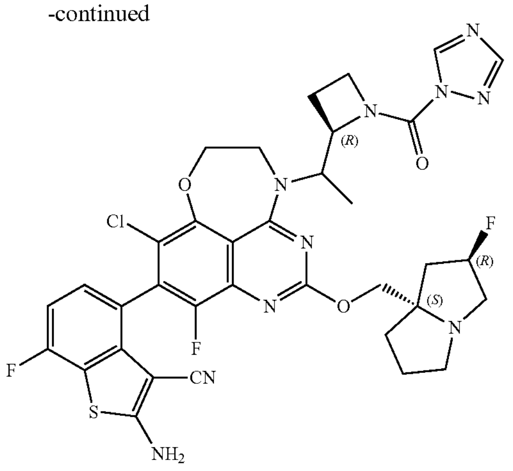

445

Step 1: Preparation of tert-butyl (2R)-2-(1-((2-((7-bromo-6-chloro-8-fluoro-2-(((2R,7aS)-2-fluorotetrahydro-1H-pyrrolizin-7a(5H)-yl)methoxy)-4-hydroxyquinazolin-5-yl)oxy)ethyl)amino)ethyl)-azetidine-1-carboxylate. To a solution of compound 1-1 (48 mg, 0.2 mmol) in anhydrous DMF (1 mL) was added NaH (12 mg, 60% on mineral oil, 0.3 mmol) at room temperature. After stirring at room temperature for 10 minutes, a solution of compound 2 (46 mg, 0.1 mmol) in anhydrous DMF (0.5 mL) was added. After the addition, the mixture was heated to 70° C. for 2 hours, and cooled to room temperature. It was then treated with sat. $NH_4Cl$ (15 mL) and extracted with EtOAc (3×10 mL). The organic layers were collected and concentrated, and the residue was purified by flash column chromatography (0-20% MeOH/DCM with 1% $NH_4OH$) to provide desired compound 1-3. MS m/z (ESI): 676.4 $[M+H]^+$.

Step 2: Preparation of tert-butyl (2R)-2-(1-(9-bromo-8-chloro-10-fluoro-2-(((2R,7aS)-2-fluorotetrahydro-1H-pyrrolizin-7a(5H)-yl)methoxy)-5,6-dihydro-4H-[1,4]oxazepino [5,6,7-de]quinazolin-4-yl)ethyl) azetidine-1-carboxylate. To a solution of compound 1-3 (54 mg, 0.08 mmol) in DCM (4 mL) was added DIEA (21 mg, 0.16 mmol) followed by bis(2-oxo-3-oxazolidinyl) phosphinic chloride (BOP-Cl, 41 mg, 0.16 mmol). The mixture was stirred at room temperature for 24 hours, treated with water (4 mL) and extracted with DCM (3×5 mL). Organic layers were collected and concentrated to provide residue which was purified by flash column chromatography (0-20% MeOH/DCM with 1% $NH_4OH$) to provide the desired compound 1-4 as white solid. MS m/z (ESI): 658.3 $[M+H]^+$.

Step 3: Preparation of tert-butyl (2R)-2-(1-(9-(2-((tert-butoxycarbonyl)amino)-3-cyano-7-fluorobenzo[b]thiophen-4-yl)-8-chloro-10-fluoro-2-(((2R,7aS)-2-fluorotetrahydro-1H-pyrrolizin-7a (5H)-yl)methoxy)-5,6-dihydro-4H-[1,4] oxazepino[5,6,7-de]quinazolin-4-yl)ethyl)azetidine-1-carboxylate. To a suspension of compound 1-4 (50 mg, 0.075 mmol), compound 5 (61 mg, 0.15 mmol), $PdCl_2$ (DPEPhos) (11 mg, 0.015 mmol) and $Cs_2CO_3$ (37 mg, 0.113 mmol) in toluene (1.5 mL) was evacuated and backfilled with $N_2$ three time to degas the system. The mixture was then sealed, heated to 110° C. for 8 hours and cooled down to room temperature. It was treated with saturated $NH_4Cl$ (2 mL) and extracted with EtOAc (3×5 mL). Organic layers were collected and concentrated, and the resulted residue was purified by flash column chromatography (0-20% MeOH/DCM with 1% $NH_4OH$) and then HPLC (10-80% ACN/water with 0.01% formic acid) to provide the desired compound 1-6 as white solid. MS m/z (ESI): 870.3 $[M+H]^+$.

Step 4: Preparation of 4-(4-(1-((R)-1-(1H-1,2,4-triazole-1-carbonyl)azetidin-2-yl)ethyl)-8-chloro-10-fluoro-2-(((2R, 7aS)-2-fluorotetrahydro-1H-pyrrolizin-7a (5H)-yl) methoxy)-5,6-dihydro-4H-[1,4]oxazepino[5,6,7-de] quinazolin-9-yl)-2-amino-7-fluorobenzo[b]thiophene-3-carbonitrile. Compound 1-6 (10 mg, 0.011 mmol) was treated with 5% TFA/DCM (1 mL) at room temperature. After stirring at room temperature for 2 hours, it was concentrated to provide crude material which was redissolved in THF. DIEA (15 uL) was added followed by compound 7 (3.5 mg, 0.022 mmol). After stirring at room temperature for 5 hours, the mixture was concentrated, and the residue thus obtained was purified by HPLC (10-60% ACN/water with 0.01% formic acid) to provide desired compound 445. MS m/z (ESI): 765.2 $[M+H]^+$.

Example F: Synthesis of 2-amino-4-(8-chloro-10-fluoro-4-(((2S,3R)-1-(3-fluoro-1H-1,2,4-triazole-1-carbonyl)-2-(1-methylcyclopropyl)azetidin-3-yl)methyl)-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-7-fluorobenzo[b]thiophene-3-carbonitrile (420 and 490)
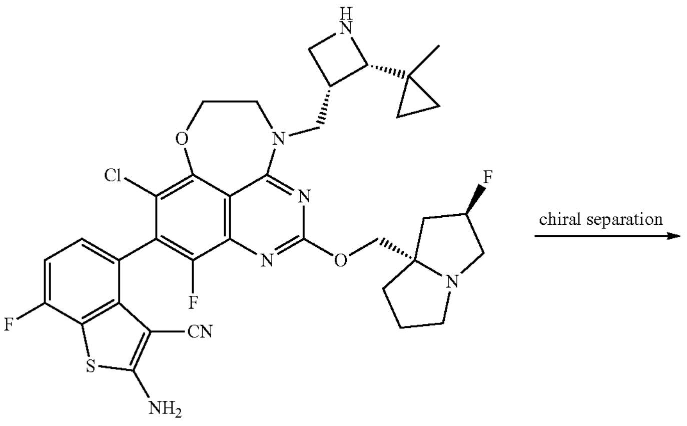
5-1
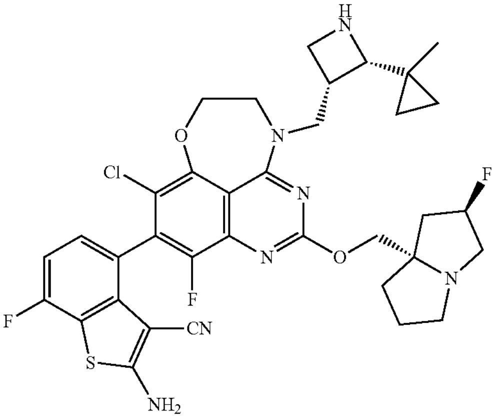
5-2-P1, polar peak
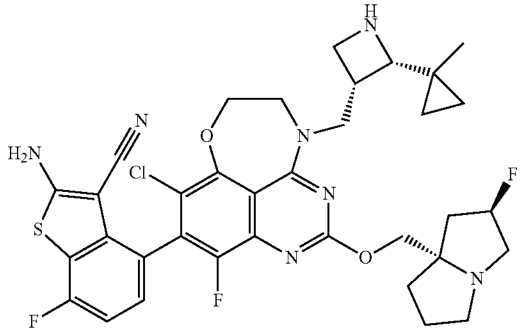
5-2-P2, less polar peak
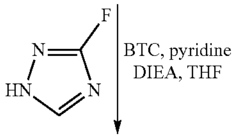
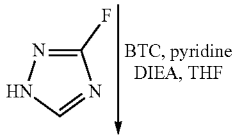

-continued

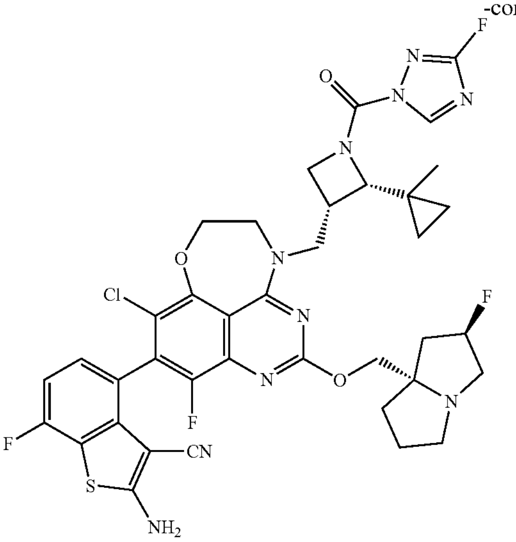

420

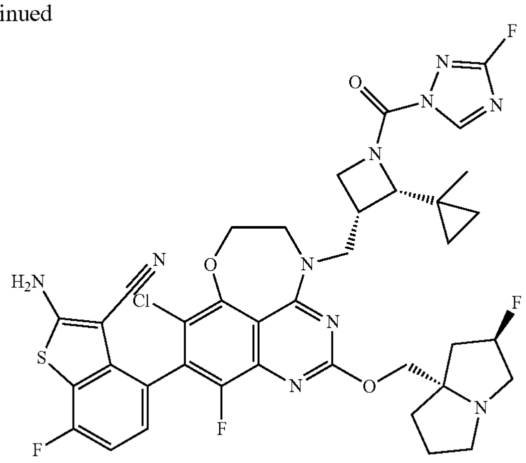

490

Preparation of 2-amino-4-(8-chloro-10-fluoro-4-(((2S, 3R)-1-(3-fluoro-1H-1,2,4-triazole-1-carbonyl)-2-(1-methylcyclopropyl)azetidin-3-yl)methyl)-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-7-fluorobenzo[b]thiophene-3-carbonitrile (420 and 490). Atropoisomeric mixture Compound 5-1 (Prepared following the same procedure described in Example G) was subjected to chiral separation to provide single atropisomer 5-2-Pt (polar peak) and single atropisomer 5-2-P2 (less polar peak) as HCl salts.

Following the same procedure as described in Example G (step 5), 5-2-P1 and 5-2-P2 were converted to the corresponding desired products as single atropisomer compound 420 and 490.

420: MS m/z (ESI): 823.2 $[M+H]^+$. $^1H$ NMR (500 MHz, $CDCl_3$) δ 8.62 (s, 1H), 7.19 (br, 1H), 6.98 (m, 1H), 6.26 (br, 2H), 5.47 (d, J=55.0 Hz, 1H), 5.07 (br, 1H), 4.65-4.45 (m, 6H), 4.30-3.80 (m, 4H), 3.96 (m, 2H), 3.56 (m, 1H), 3.30-3.10 (br, 2H), 2.80-2.60 (m, 11H), 2.45-2.25 (m, 4H), 1.28 (m, 3H), 0.82 (m, 1H), 0.60 (m, 2H), 0.53 (m, 1H).

490: MS m/z (ESI): 823.2 $[M+H]^+$. $^1H$ NMR: $^1H$ NMR (500 MHz, DMSO-d6) δ 9.08 (s, 1H), 7.20 (m, 1H), 7.13 (m, 1H), 5.26 (d, J=55 Hz, 1H), 4.65-4.35 (m, 5H), 4.26-4.10 (m, 2H), 4.05 (m, 2H), 3.94 (m, 2H), 3.20-3.03 (m, 4H), 2.20-1.90 (m, 3H), 1.90-1.70 (m, 3H), 1.23 (m, 4H), 0.72 (br, 1H), 0.61 (br, 1H), 0.48 (br, 2H).

Example G: Synthesis of 2-amino-4-(8-chloro-10-fluoro-4-(((2R,3R)-1-(3-fluoro-1H-1,2,4-triazole-1-carbonyl)-2-isopropylazetidin-3-yl)methyl)-2-(((2R, 7aS)-2-fluorotetrahydro-1H-pyrrolizin-7a (5H)-yl) methoxy)-5,6-dihydro-4H-[1,4]oxazepino[5,6,7-de] quinazolin-9-yl)-7-fluorobenzo[b]thiophene-3-carbonitrile (471)

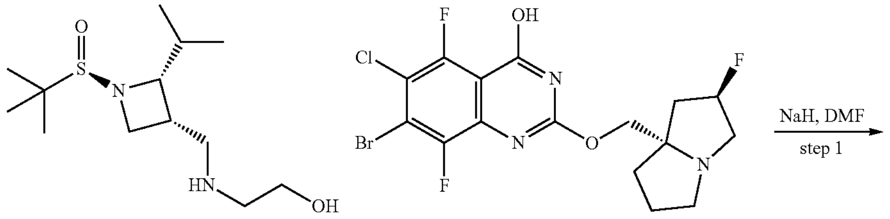

2-1 2

-continued
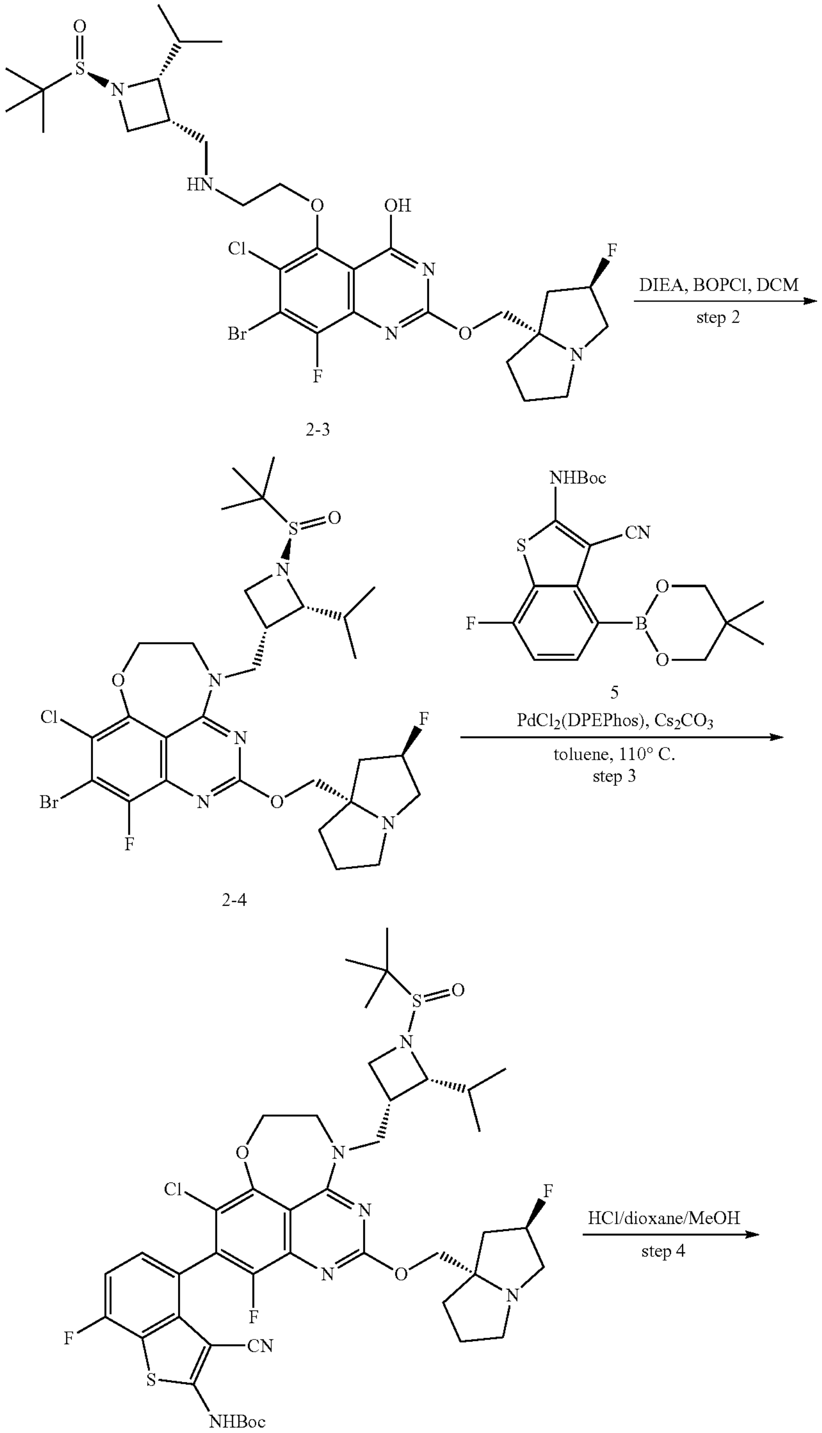
2-3
5
2-4
2-6

-continued

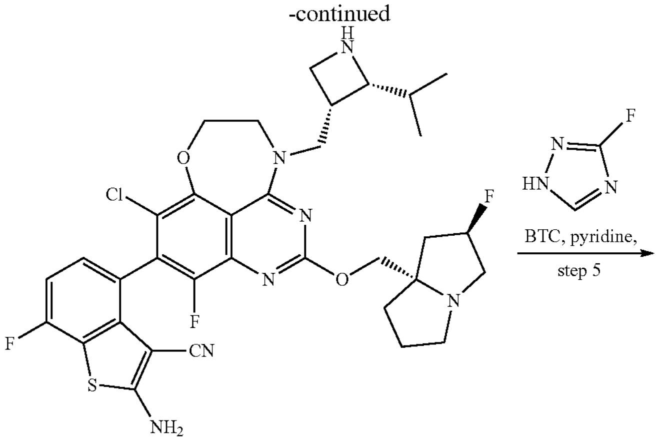

2-7

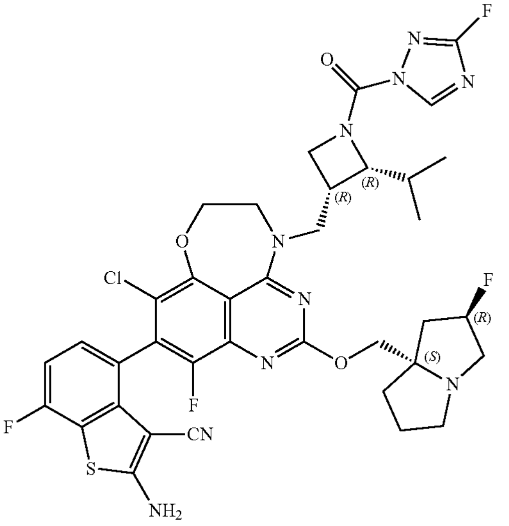

471

Step 1: Preparation of 7-bromo-5-(2-((((2R,3R)-1-((R)-tert-butylsulfinyl)-2-isopropylazetidin-3-yl)methyl)amino)ethoxy)-6-chloro-8-fluoro-2-(((2R,7aS)-2-fluorotetrahydro-1H-pyrrolizin-7a (5H)-yl)methoxy)quinazolin-4-ol. To a solution of compound 2-1 (60 mg, 0.22 mmol) in anhydrous DMF (1 mL) was added NaH (18 mg, 60% on mineral oil, 0.44 mmol) at room temperature. After stirring at room temperature for 10 minutes, a solution of compound 2 (65 mg, 0.14 mmol) in anhydrous DMF (0.5 mL) was added. After the addition, mixture was heated to 60° C. for 2 hours and cooled to room temperature. It was then treated with sat. $NH_4Cl$ (15 mL) and extracted with EtOAc (3×10 mL). The organic layers were collected and concentrated to give a residue. The residue was purified by flash column chromatography (0-20% MeOH/DCM with 1% $NH_4OH$) to provide desired compound 2-3. MS m/z (ESI): 708.3 $[M+H]^+$.

Step 2: Preparation of 9-bromo-4-(((2R,3R)-1-((R)-tert-butylsulfamoyl)-2-isopropylazetidin-3-yl)methyl)-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazoline. To a solution of compound 2-3 (66 mg, 0.09 mmol) in DCM (6 mL) was added DIEA (25 mg, 0.2 0 mmol) followed by bis(2-oxo-3-oxazolidinyl) phosphinic chloride (BOP-Cl, 38 mg, 0.15 mmol). The resulting mixture was stirred at room temperature for 24 hours, and then concentrated to provide residue which was purified by flash column chromatography (0-20% MeOH/DCM with 1% $NH_4OH$) to provide desired compound 2-4 as white solid MS m/z (ESI): 690.3 $[M+H]^+$.

Step 3: Preparation of tert-butyl (4-(4-(((2R,3R)-1-(tert-butylsulfamoyl)-2-isopropylazetidin-3-yl)methyl)-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-3-cyano-7-fluorobenzo[b]thiophen-2-yl)carbamate. To a suspension of compound 2-4 (40 mg, 0.058 mmol), compound 5 (47 mg, 0.116 mmol), $PdCl_2$ (DPEPhos) (8 mg, 0.012 mmol) and $Cs_2CO_3$ (28 mg, 0.087 mmol) in toluene (1 mL) was evacuated and backfilled with nitrogen three times to degas the system. The mixture was then sealed, heated to 110° C. with stirring for 16 hours and cooled down to room temperature. It was treated with saturated $NH_4Cl$ (2 mL) and extracted with EtOAc (3×5 mL). Organic layers were collected and concentrated. The resulting residue was purified by HPLC (10-80% ACN/water with 0.01% formic acid) to provide desired compound 2-6 as white solid. MS m/z (ESI): 902.4 $[M+H]^+$.

Step 4: Preparation of 2-amino-4-(8-chloro-10-fluoro-2-(((2R,7aS)-2-fluorotetrahydro-1H-pyrrolizin-7a (5H)-yl) methoxy)-4-(((2R,3S)-2-isopropylazetidin-3-yl)methyl)-5, 6-dihydro-4H-[1,4]oxazepino[5,6,7-de]quinazolin-9-yl)-7- fluorobenzo[b]thiophene-3-carbonitrile. To a solution of compound 2-6 (64 mg, 0.071 mmol) in dioxane/MeOH (9:1, 2 mL) was added HCl (4N in dioxane, 0.4 mL). The resulting mixture was stirred at 45° C. for 5 hours and then concentrated to give a residue. The residue was purified by HPLC (10~50% ACN/water with 0.1% formic acid). Pure fractions were concentrated with 0.5 mL 1N HCl to provide desired compound 2-7 as HCl salt. MS m/z (ESI): 698.3 $[M+H]^+$.

Step 5: Preparation of 2-amino-4-(8-chloro-10-fluoro-4-(((2R,3R)-1-(3-fluoro-1H-1,2,4-triazole-1-carbonyl)-2-isopropylazetidin-3-yl)methyl)-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-7-fluorobenzo[b]thiophene-3-carbonitrile. To a suspension of compound 2-7 (25 mg, 0.031 mmol, HCl salt) in THF (1 mL) was added pyridine (0.31 mmol) and DIEA (6 uL, 0.03 mmol). The resulting mixture was cooled to 0° C. before the addition of a solution of F-triazole (6.5 mg, 0.075 mmol), triphosgene (6.1 mg, 0.021 mmol) and pyridine (7.4 mg, 0.094 mmol) in THF (0.3 mL). After the addition, the mixture was warmed up to room temperature and stirred for 5 hours. The reaction mixture was then concentrated to give a residue which was purified by HPLC (30-60% ACN/water with 0.1% formic acid) to provide desired compound 471 as white solid. MS m/z (ESI): 811.2 $[M+H]^+$. $^1H$ NMR (500 MHz, MeOD) δ 8.82 (s, 1H), 7.17 (m, 1H), 7.02 (m, 1H), 5.27 (d, J=55.0 Hz, 1H), 4.65-4.45 (m, 4H), 4.39-4.27 (m, 3H), 4.15 (m, 1H), 3.97 (m, 2H), 3.60-3.45 (m, 2H), 3.05 (m, 1H), 2.45-1.85 (m, 8H), 1.16-1.12 (m, 6H)

Example H: Synthesis of 4-(4-((2R,3R)-1-acryloyl-2-methylpyrrolidin-3-yl)-9-chloro-11-fluoro-2-(((2R,7aS)-2-fluorotetrahydro-1H-pyrrolizin-7a (5H)-yl)methoxy)-4,5,6,7-tetrahydro-[1,5]oxazocino-[4,3,2-de]quinazolin-10-yl)-2-amino-7-fluorobenzo[b]thiophene-3-carbonitrile (4H)

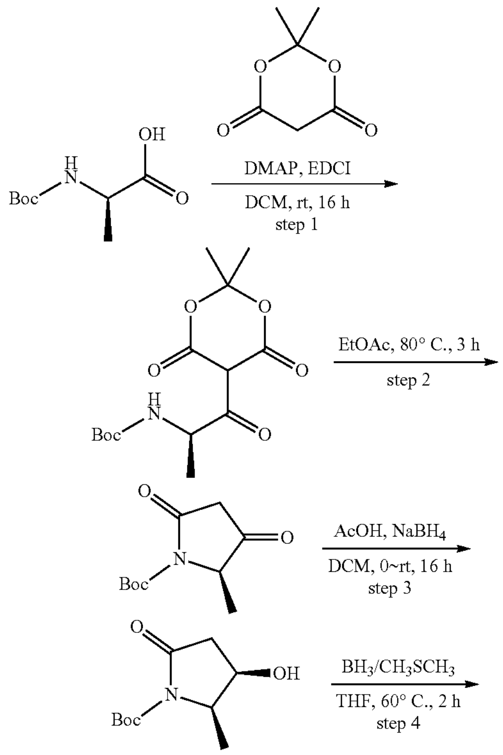

-continued

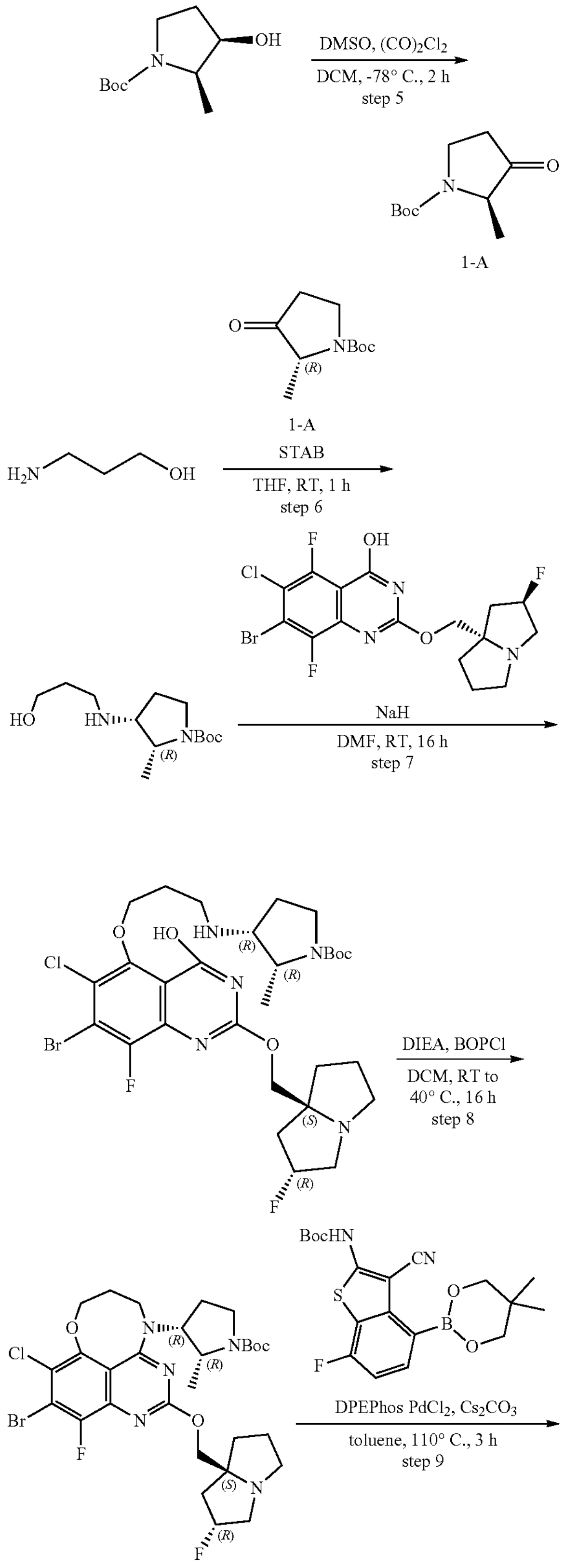

-continued

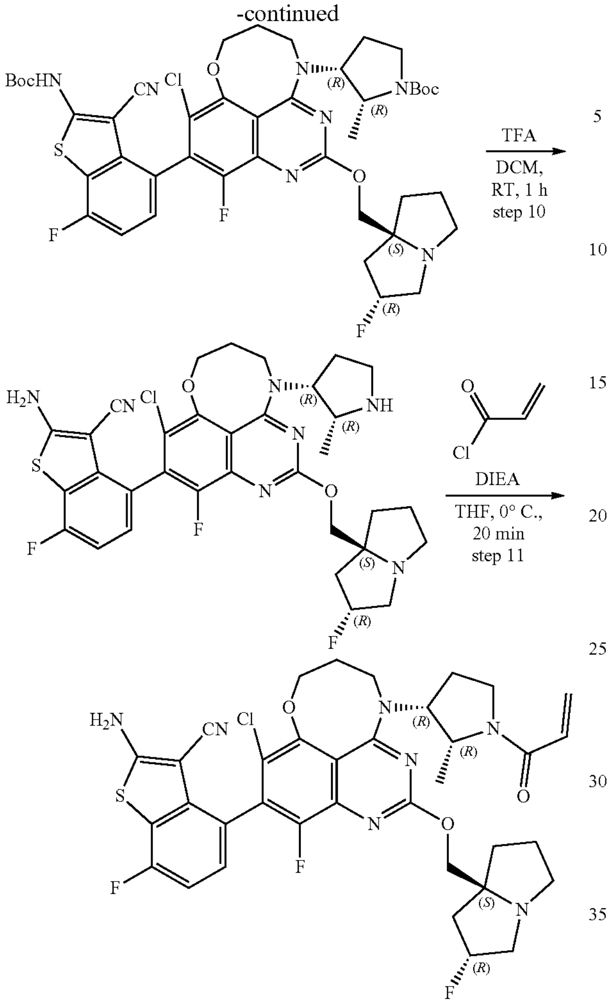

411

Step 1: To a stirred solution of 2,2-dimethyl-1,3-dioxane-4,6-dione (16.7 g, 116 mmol) in DCM (500 mL) was added N,N-dimethylpyridin-4-amine (19.4 g, 158.5 mmol). The reaction mixture was stirred at 0° C. for 10 minutes. Then (tert-butoxycarbonyl)-D-alanine (20.0 g, 106 mmol) and EDCI (48.6 g, 253.7 mmol) were added. The reaction mixture was stirred at room temperature for 16 hours. After the reaction was completed, the mixture was concentrated in vacuo, the mixture was diluted with DCM (100 mL) and washed with aqueous $KHSO_4$ solution (3×50 mL). The organic layer was dried over anhydrous $Na_2SO_4$, filtered and concentrated in vacuo. The crude product tert-butyl (R)-(1-(2,2-dimethyl-4,6-dioxo-1,3-dioxan-5-yl)-1-oxopropan-2-yl)carbamate was used directly for the next step without purification. (30 g, yield: 100%). MS (ESI) m/z=260.1 $[M+H-56]^+$ Step 2: A solution of tert-butyl (R)-(1-(2,2-dimethyl-4,6-dioxo-1,3-dioxan-5-yl)-1-oxopropan-2-yl) carbamate (30.0 g, 95.1 mmol) in EtOAc (300 mL) was stirred at 80° C. for 3 hours. After the reaction was completed, the mixture was concentrated in vacuo and the crude product was purified by silica gel column (petroleum ether:EtOAc=2:1) to give the desired product tert-butyl (R)-2-methyl-3,5-dioxopyrrolidine-1-carboxylate as a white solid (11 g, yield: 54.2%). MS (ESI) m/z 158.1 $[M+H-56]^+$ Step 3: To a stirred solution of tert-butyl (R)-2-methyl-3,5-dioxopyrrolidine-1-carboxylate (10.0 g, 46.9 mmol) in DCM (200 mL) was added AcOH (25.3 g, 422.1 mmol). The reaction mixture was stirred at 0° C. for 15 minutes. Then $NaBH_4$ (3.9 g, 103.2 mmol) was added. The reaction mixture was stirred at room temperature for 16 hours. After the reaction was completed, the reaction was quenched with sat. $NaHCO_3$ solution (100 mL) and extracted with DCM (100 mL). The organic layer was washed with brine (3×50 mL), dried over anhydrous $Na_2SO_4$, filtered and concentrated in vacuo. The crude product was purified by silica gel column (petroleum ether:EtOAc=1:1) to give the desired product tert-butyl (2R,3R)-3-hydroxy-2-methyl-5-oxopyrrolidine-1-carboxylate as a white solid (6.1 g, yield: 61%). MS (ESI) m/z=160.2 $[M+H-56]^+$ Step 4: To a solution of tert-butyl (2R,3R)-3-hydroxy-2-methyl-5-oxopyrrolidine-1-carboxylate (6.1 g, 28.3 mmol) in THF (60 mL) was added $BH_3/(CH_3)_2S$ (28.3 mL, 56.6 mmol). The mixture was stirred at 60° C. for 2 hours. After the reaction was completed, the reaction was quenched with MeOH (30 mL) and the mixture was concentrated in vacuo. The crude product was purified by silica gel column (petroleum ether:EtOAc=1:1) to give the desired product tert-butyl (2R,3R)-3-hydroxy-2-methylpyrrolidine-1-carboxylate as a white solid (5.0 g, yield: 87%). MS (ESI) m/z=187.2 $[M+H-56+41]^+$ Step 5: To a stirred solution of oxalyl chloride (3.148 g, 24.8 mmol) in DCM (10 mL) was added DMSO (3.87 g, 49.6 mmol) dropwise at −78° C. After stirring at −78° C. for 30 min, tert-butyl (2R,3R)-3-hydroxy-2-methylpyrrolidine-1-carboxylate (500 mg, 2.48 mmol) in DCM (2 mL) was added at −78° C. After stirring at −78° C. for 2 hours, TEA (7.5 g, 74.4 mmol) was added, and the reaction mixture was stirred at −78° C. for 20 min. After the completion of the reaction, the mixture was diluted with DCM (10 mL) and washed with brine (3×10 mL). The organic layer was dried over anhydrous $Na_2SO_4$, filtered and concentrated in vacuo. The crude product was purified by silica gel column (petroleum ether:EtOAc=5:1) to give the desired product tert-butyl (R)-2-methyl-3-oxopyrrolidine-1-carboxylate as a white solid (390 mg, yield: 79%).

$^1H$ NMR (400 MHz, $d_6$-DMSO) δ 3.79 (q, J=6.9 Hz, 1H), 3.70 (td, J=10.3, 4.9 Hz, 1H), 3.48 (d, J=7.4 Hz, 1H), 2.63 (dddd, J=17.4, 9.8, 7.5, 1.2 Hz, 1H), 2.56-2.52 (m, 1H), 1.43 (s, 9H), 1.20 (d, J=7.0 Hz, 3H).

Step 6: A solution of 3-aminopropan-1-ol (565 mg, 7.5 mmol), tert-butyl (R)-2-methyl-3-oxopyrrolidine-1-carboxylate (1.5 g, 7.5 mmol) and 4A molecular sieves (1 g) in THF (5 mL) was stirred at room temperature for 1 hour. Then STAB (3.3 g, 15 mmol) was added. After stirring at room temperature for 1 hour, the mixture was quenched with water (2 mL) and directly purified by silica gel column ($NH_3$-MeOH(7N):DCM=1:10) to give tert-butyl (2R)-3-((3-hydroxypropyl)amino)-2-methylpyrrolidine-1-carboxylate as a light yellow oil (1.5 g, 78%). MS (ESI) m/z=259.2 $[M+H]^+$ Step 7: To a solution of tert-butyl (2R)-3-((3-hydroxypropyl)amino)-2-methylpyrrolidine-1-carboxylate (630 mg, 2.44 mmol) in DMF (20 mL) was added NaH (488 mg, 12.2 mmol). The mixture was stirred at room temperature for 10 min. 7-bromo-6-chloro-5,8-difluoro-2-(((2R,7aS)-2-fluorotetrahydro-1H-pyrrolizin-7a (5H)-yl)methoxy)quinazolin-4-ol (1 g, 2.2 mmol) was added and the resulting mixture was stirred at room temperature for 16 hours. The mixture was quenched with water (40 mL) and extracted with EtOAc (2×50 mL). The organic layer was washed with brine (2×100 mL), dried ($Na_2SO_4$) and concentrated in vacuo. The residue was purified by silica gel column (10% $NH_3$-MeOH(7N) in DCM) to give tert-butyl (2R,3R)-3-((3-((7-bromo-6-chloro- 8-fluoro-2-(((2R,7aS)-2-fluorotetrahydro-1H-pyrrolizin-7a(5H)-yl)methoxy)-4-hydroxyquinazolin-5-yl)oxy)propyl)amino)-2-methylpyrrolidine-1-carboxylate as a white solid (1.2 g, 80%). MS (ESI) m/z=690.1 [M+H]$^+$.

Step 8: To a solution of tert-butyl (2R,3R)-3-((3-((7-bromo-6-chloro-8-fluoro-2-(((2R,7aS)-2-fluorotetrahydro-1H-pyrrolizin-7a(5H)-yl)methoxy)-4-hydroxyquinazolin-5-yl)oxy)propyl)amino)-2-methylpyrrolidine-1-carboxylate (1 g, 1.4 mmol) in DCM (20 mL) was added BOPCl (1.1 g, 4.3 mmol) and DIEA (930 mg, 7.2 mmol). The mixture was stirred at room temperature for 16 hours. The mixture was washed with water (5×10 mL). The organic layer was dried ($Na_2SO_4$), filtered and concentrated in vacuo. The residue was purified by silica gel column (10% MeOH in DCM) to give tert-butyl (2R,3R)-3-(10-bromo-9-chloro-11-fluoro-2-(((2R,7aS)-2-fluorotetrahydro-1H-pyrrolizin-7a (5H)-yl)methoxy)-6,7-dihydro-[1,5]oxazocino[4,3,2-de]quinazolin-4(5H)-yl)-2-methylpyrrolidine-1-carboxylate as a colorless oil (400 mg, 41%). MS (ESI) m/z=672.1 [M+H]$^+$.

Step 9: To a solution of tert-butyl (2R,3R)-3-(10-bromo-9-chloro-11-fluoro-2-(((2R,7aS)-2-fluorotetrahydro-1H-pyrrolizin-7a(5H)-yl)methoxy)-6,7-dihydro-[1,5][4,3,2-de]quinazolin-4(5H)-yl)-2-methylpyrrolidine-1-carboxylate (350 mg, 0.52 mmol) and tert-butyl (3-cyano-4-(5,5-dimethyl-1,3,2-dioxaborinan-2-yl)-7-fluorobenzo[b]thiophen-2-yl)carbamate (420 mg, 1.04 mmol) in toluene (20 mL) was added dichloro[bis(2-(diphenylphosphino)phenyl)ether]palladium(II) ($PdCl_2$(DPEPhos), 140 mg, 0.19 mmol) and $Cs_2CO_3$ (500 mg, 1.54 mmol). The mixture was degassed by applying vacuum and back filled with $N_2$ three times and stirred at 110° C. under $N_2$ for 3 hours. The mixture was cooled to room temperature and diluted with water (40 mL) and extracted with DCM (2×30 mL). The organic layer was dried ($Na_2SO_4$), filtered and concentrated in vacuo. The residue was purified by silica gel column (5% NH3-MeOH (7N) in DCM) to give tert-butyl (2R,3R)-3-(10-(2-((tert-butoxycarbonyl)amino)-3-cyano-7-fluorobenzo[b]thiophen-4-yl)-9-chloro-11-fluoro-2-(((2R,7aS)-2-fluorotetrahydro-1H-pyrrolizin-7a (5H)-yl)methoxy)-6,7-dihydro-[1,5]oxazocino[4,3,2-de]quinazolin-4(5H)-yl)-2-methylpyrrolidine-1-carboxylate as a yellow solid (400 mg, 87%). MS (ESI) m/z=884.2 [M+H]$^+$.

Step 10: To a solution of tert-butyl (2R,3R)-3-(10-(2-((tert-butoxycarbonyl)amino)-3-cyano-7-fluorobenzo[b]thiophen-4-yl)-9-chloro-11-fluoro-2-(((2R,7aS)-2-fluorotetrahydro-1H-pyrrolizin-7a (5H)-yl)methoxy)-6,7-dihydro-[1,5]oxazocino[4,3,2-de]quinazolin-4(5H)-yl)-2-methylpyrrolidine-1-carboxylate (400 mg, 0.45 mmol) in DCM (3 mL) was added TFA (3 mL) The mixture was stirred at room temperature for 1 hour. The mixture was concentrated in vacuo and pH was adjusted to 8 with NH3 in MeOH (7N, 10 mL). The mixture was concentrated in vacuo and purified by prep-TLC (10% NH3-MeOH in DCM) to give 2-amino-4-(9-chloro-11-fluoro-2-(((2R,7aS)-2-fluorotetrahydro-1H-pyrrolizin-7a (5H)-yl)methoxy)-4-((2R,3R)-2-methylpyrrolidin-3-yl)-4,5,6,7-tetrahydro-[1,5]oxazocino[4,3,2-de]quinazolin-10-yl)-7-fluorobenzo[b]thiophene-3-carbonitrile as a yellow solid (230 mg, 76%). MS (ESI) m/z=684.1 [M+H]$^+$ Step 11: To a stirred solution of 2-amino-4-(9-chloro-11-fluoro-2-(((2R,7aS)-2-fluorotetrahydro-1H-pyrrolizin-7a (5H)-yl)methoxy)-4-((2R,3R)-2-methylpyrrolidin-3-yl)-4,5,6,7-tetrahydro-[1,5]oxazocino[4,3,2-de]quinazolin-10-yl)-7-fluorobenzo[b]thiophene-3-carbonitrile (35 mg, 0.051 mmol) in THF (1 mL) was added DIEA (20 mg, 0.155 mmol) and acryloyl chloride (4.6 mg, 0.051 mmol). The reaction mixture was stirred at 0° C. for 20 min. The reaction mixture was purified directly by prep-HPLC to give 4-(4-((2R,3R)-1-acryloyl-2-methylpyrrolidin-3-yl)-9-chloro-11-fluoro-2-(((2R,7aS)-2-fluorotetra-hydro-1H-pyrrolizin-7a (5H)-yl)methoxy)-4,5,6,7-tetrahydro-[1,5]oxazocino[4,3,2-de]quinazolin-10-yl)-2-amino-7-fluorobenzo[b]thiophene-3-carbonitrile as an off white solid (19.06 mg, yield: 51%). MS (ESI) m/z=738.3 [M+H]$^+$. $^1$HNMR(400 MHz, $d_6$-DMSO) δ 8.09 (d, J=8.8 Hz, 2H), 7.40-7.23 (m, 1H), 7.16 (t, J=9.2 Hz, 1H), 6.66-6.54 (m, 1H), 6.23-6.16m, 1H), 5.72-5.65 (m, 1H), 5.28 (d, J=40.4 Hz, 1H), 5.00-3.95 (m, 6H), 3.89-3.34 (m, 5H), 3.13-3.01 (m, 3H), 2.84 (s, 1H), 2.44-2.35 (m, 1H), 2.25-1.78 (m, 8H), 1.06-0.88 (m, 3H).

Example I: Synthesis of 2-amino-4-(8-chloro-4-((1-((2R,3R)-3-cyclopropyl-1-methylaziridine-2-carbonyl)azetidin-3-yl)methyl)-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-7-fluorobenzo[b]thiophene-3-carbonitrile (440)

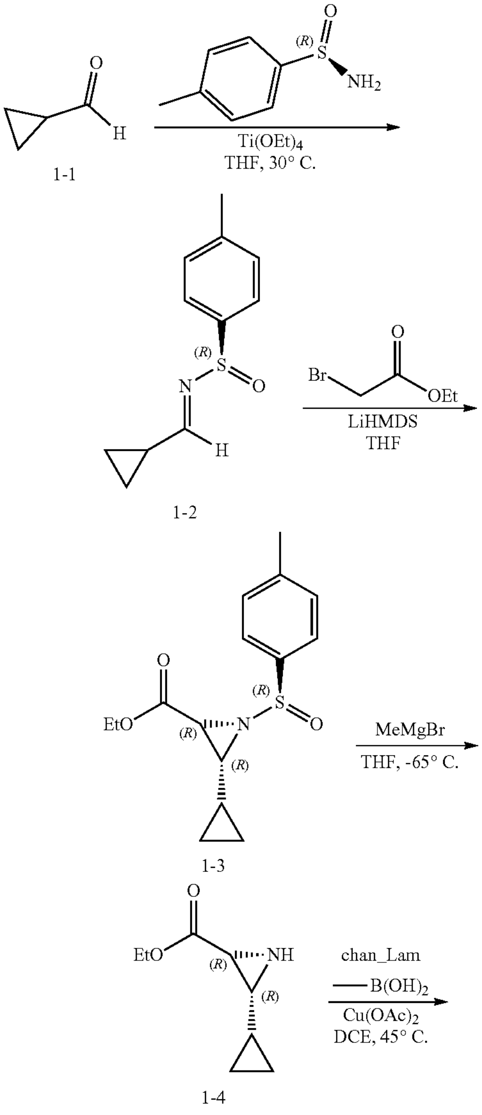

-continued

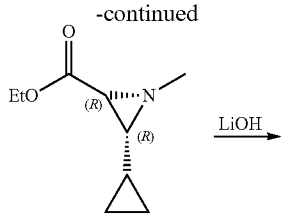

1-5

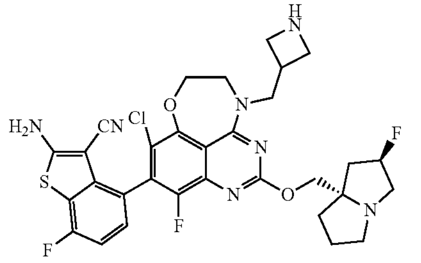

1-7

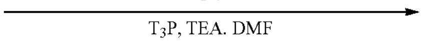

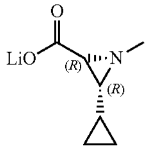

1-6

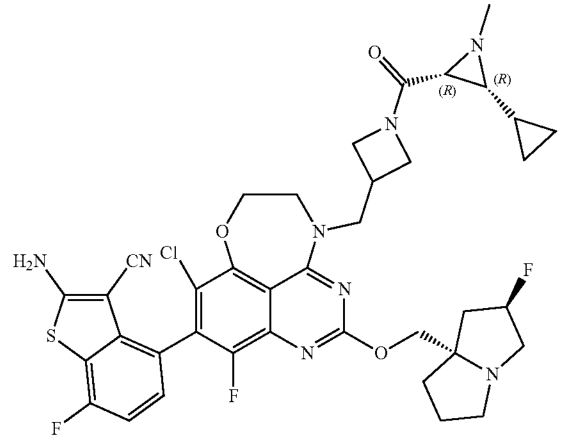

440

Step 1: To a solution of 1-1 (1.4 g, 20 mmol) in THF (30 mL) were added (R)-4-methylbenzenesulfinamide (3.1 g, 20 mmol) and $Ti(OEt)_4$ (9.12 g, 40 mmol) and the resulting mixture was stirred at 30° C. for 2 h. The reaction mixture was concentrated, and the residue was purified by flash column chromatography on silica gel (eluting with 0~10% of EA in PE) to give compound 1-2 (3.56 g). ESI-MS m/z: 208.2 $[M+H]^+$.

Step 2: To a solution of ethyl 2-bromoacetate (4.98 g, 30 mmol) in THF (150 mL) was added LiHMDS (1M, 30 mL) dropwise at −70° C. under $N_2$. The mixture was stirred at −70° C. for 30 min. A solution of 1-2 (3.1 g, 15 mmol) in THF (30 mL) was added into the mixture at −70° C., and the resulting mixture was stirred at −70° C. for 2 h. The mixture was poured into ice-water and extracted with ethyl acetate (100 mL×2). The combined extracts were concentrated in vacuo and the residue was purified by flash column chromatography on silica gel (eluting with 0~10% of EA in PE) to give compound 1-3 (1.9 g). ESI-MS m/z: 294.2 $[M+H]^+$.

Step 3: To a solution of 1-3 (1.9 g, 6.48 mmol) in THF (100 mL) was added dropwise MeMgBr (1M, 4.3 mL) at −65° C. under $N_2$. The mixture was stirred at −70° C. for 30 min. The mixture was quenched with saturated aqueous $NH_4Cl$ (50 mL) at −70° C., and extracted with ethyl acetate (100 mL×2). The combined extracts were concentrated in vacuo and the residue was purified by flash column chromatography on silica gel (eluting with 0-50% of EA in PE) to give compound 1-4 (570 mg). ESI-MS m/z: 156.0 $[M+H]^+$.

Step 4: To a solution of 1-4 (550 mg, 3.55 mmol) in dry DCE (20 mL) were added methylboronic acid (638 mg, 10.6 mmol), 2,2'-bipyridine (553 mg, 3.55 mmol), $Cu(OAc)_2$ (709 mg, 3.90 mmol) and $Na_2CO_3$ (1.1 g, 10.6 mmol). The mixture was stirred at 45° C. for 30 h. The mixture was poured into aqueous $NH_4Cl$ solution (50 mL) and extracted with DCM (100 mL×2). The combined extracts were concentrated in vacuo and the residue was purified by flash column chromatography on silica gel (eluting with 0-30% of EA in PE) to give compound 1-5 (600 mg). ESI-MS m/z: 170.1 $[M+H]^+$.

Step 5: To a solution of 1-5 (600 mg, 3.55 mmol) in THF (5 mL) was added a solution of $LiOH{\cdot}H_2O$ (298 mg, 7.10 mmol) in $H_2O$ (2 mL). The mixture was stirred at room temperature for 1 h. The mixture was concentrated, and the residue was dissolved in $H_2O$ (25 mL) and extracted with DCM (20 mL×2). The aqueous layer was lyophilized to give compound 1-6 (420 mg). ESI-MS m/z: 142.1 $[M+H]^+$.

Step 6: To a solution of 1-7 (20 mg, 0.031 mmol), and TEA (6 drops) in DMF (2 mL) was added 1-6 (9 mg, 0.061 mmol) at 0° C. The mixture was stirred at 0° C. for 5 min. $T_3P$ (50% in EA) (3 drops) was added at 0° C. The mixture was stirred for 30 min at 0° C. The reaction mixture was quenched with ice-water (2 mL) and the residue was extracted with EA (10 mL×3). The combined organic layer was concentrated in vacuo and the residue was purified by prep-HPLC to afford compounds 447 (1.07 mg) and 460 (0.2 mg). For 440, ESI-MS m/z: 779.2 $[M+H]^+$. For 460, ESI-MS m/z: 779.2 $[M+H]^+$.

Example J: Synthesis of 2-amino-4-(8-chloro-4-(((2R,3R)-1-(3-chloro-1H-1,2,4-triazole-1-carbonyl)-2-isopropylazetidin-3-yl)methyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (493)

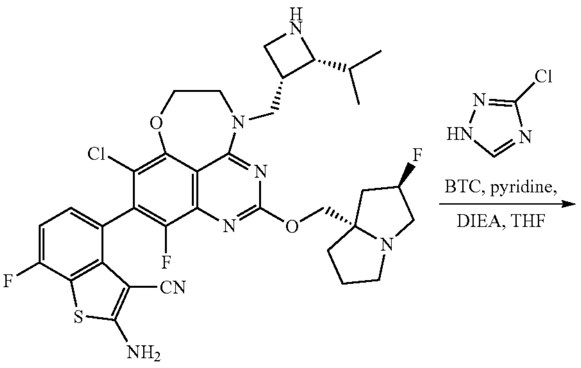

2-7

-continued

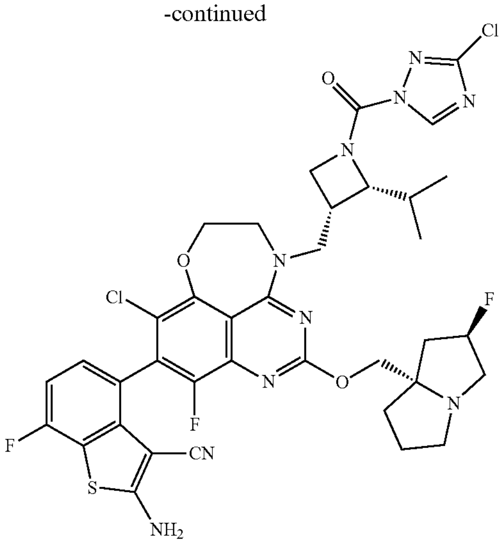

493

Preparation of 2-amino-4-(8-chloro-4-(((2R,3R)-1-(3-chloro-1H-1,2,4-triazole-1-carbonyl)-2-isopropylazetidin-3-yl)methyl)-10-fluoro-2-(((2R,7aS)-2-fluorotetrahydro-1H-pyrrolizin-7a (5H)-yl)methoxy)-5,6-dihydro-4H-[1,4] oxazepino[5,6,7-de]quinazolin-9-yl)-7-fluorobenzo[b] thiophene-3-carbonitrile. To a suspension of compound 2-7 (20 mg, 0.025 mmol, HCl salt) in THF (1 mL) was added pyridine (12 mg, 0.15 mmol) and DIEA (20 uL, 0.11 mmol). The resulting mixture was cooled to 0° C. before the addition of a solution of Cl-triazole (5 mg, 0.045 mmol), triphosgene (4 mg, 0.013 mmol) and pyridine (5 mg, 0.063 mmol) in THF (0.3 mL). After the addition, the mixture was warmed to room temperature and stirred for 5 hours. The reaction mixture was then concentrated to give a residue which was purified by HPLC (30~60% ACN/water with 0.1% formic acid) to provide desired compound 493 as white solid. MS m/z (ESI): 827.6 [M+H]$^+$. $^1$H NMR (500 MHz, MeOD) δ 8.97 (s, 1H), 7.18 (m, 1H), 7.02 (m, 1H), 5.34 (d, J=50.0 Hz, 1H), 4.65- 4.45 (m, 4H), 4.39-4.27 (m, 3H), 4.15 (m, 1H), 3.96 (m, 2H), 3.60-3.45 (m, 2H), 3.06 (m, 1H), 2.45-1.85 (m, 8H), 1.16-1.12 (m, 6H)

Example K: Synthesis of 2-amino-4-(4-((1-(but-2-ynoyl)azetidin-3-yl)methyl)-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-7-fluorobenzo[b]thiophene-3-carbonitrile (456)

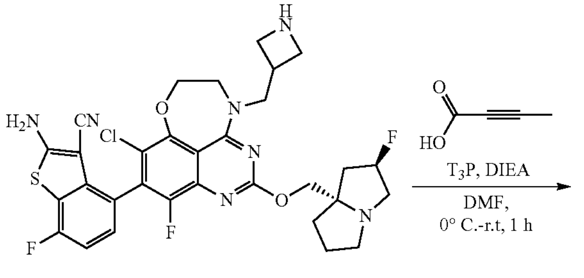

-continued

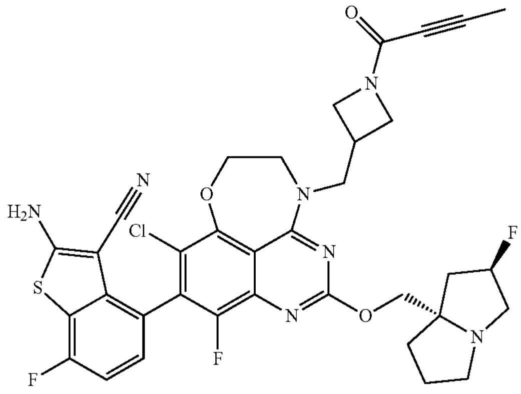

456

To a solution of 2-amino-4-(4-(azetidin-3-ylmethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino [5,6,7-de]quinazolin-9-yl)-7-fluorobenzo[b]thiophene-3-carbonitrile (50 mg, 0.076 mmol) in DMF was added but-2-ynoic acid (6.4 mg, 0.076 mmol) and DIEA (29.5 mg, 0.23 mmol) at 0° C. under argon. The mixture was stirred for 10 minutes, followed by addition of $T_3P$ (36.4 mg, 0.11 mmol) and stirring at room temperature for 1 hour. After the reaction was completed, the mixture was purified by prep-HPLC to give 2-amino-4-(4-((1-(but-2-ynoyl)azetidin-3-yl) methyl)-8-chloro-10-fluoro-2-(((2R,7aS)-2-fluorotetra-hydro-1H-pyrrolizin-7a (5H)-yl)methoxy)-5,6-dihydro-4H-[1,4]oxazepino[5,6,7-de]quinazolin-9-yl)-7-fluorobenzo[b]-thiophene-3-carbonitrile (10.27 mg, Yield: 18.67%) as a colorless oil. MS (ESI) m/z=722.4 [M+H]$^+$. $^1$H NMR (400 MHz, $d_6$-DMSO) δ 8.11 (d, J=22.4 Hz, 2H), 7.23-7.09 (m, 2H), 5.35 (d, J=52.8 Hz, 1H), 4.54 (d, J=21.6 Hz, 2H), 4.21-3.83 (m, 8H), 3.03 (d, J=70.8 Hz, 3H), 2.28-1.74 (m, 9H), 1.47 (s, 3H), 0.91 (t, J=6.8 Hz, 2H).

Example L: Synthesis of 2-amino-4-((6S,9R)-8-chloro-4-((2R,3R)-1-(3-chloro-1H-1,2,4-triazole-1-carbonyl)-2-methylpyrrolidin-3-yl)-10-fluoro-2-(((2R,7aS)-2-fluorotetrahydro-1H-pyrrolizin-7a (5H)-yl)methoxy)-6-methyl-5,6-dihydro-4H-[1,4] oxazepino[5,6,7-de]quinazolin-9-yl)-7-fluorobenzo [b]thiophene-3-carbonitrile (407)

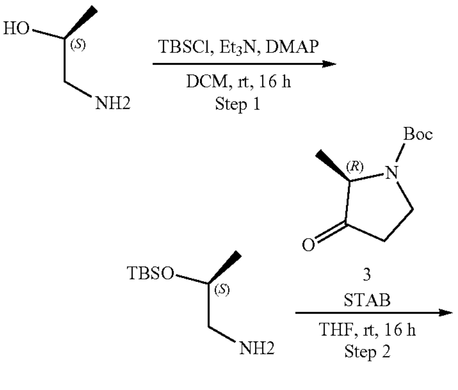

-continued

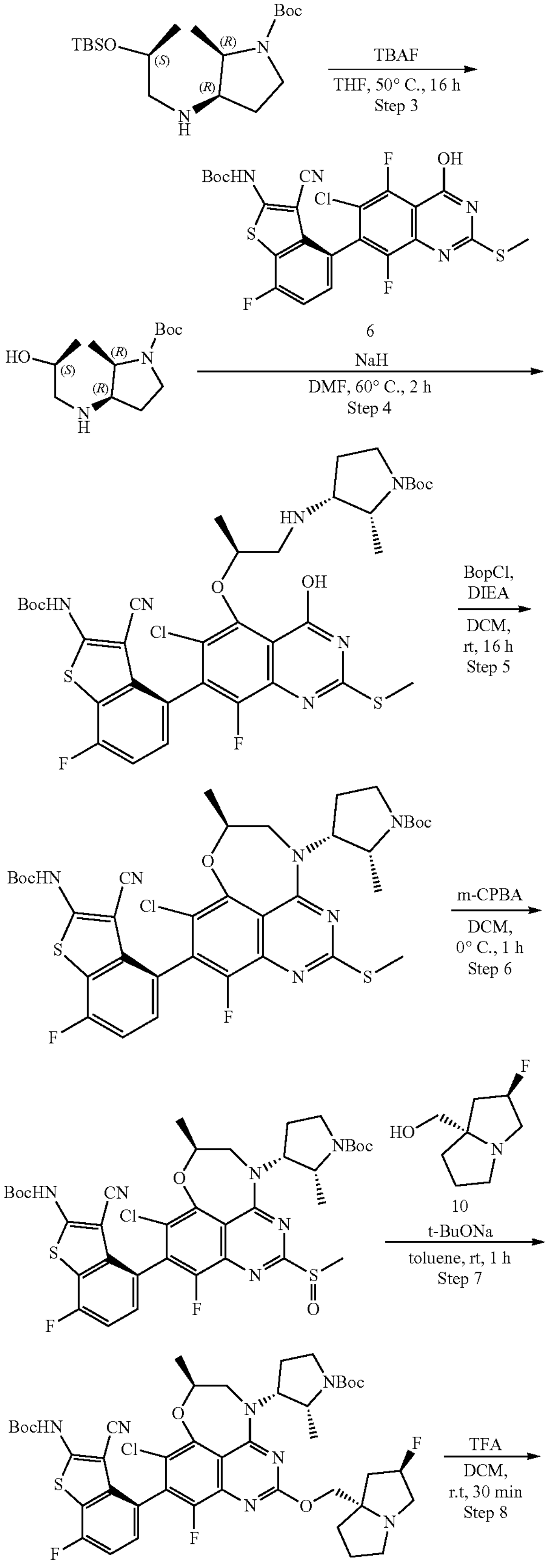

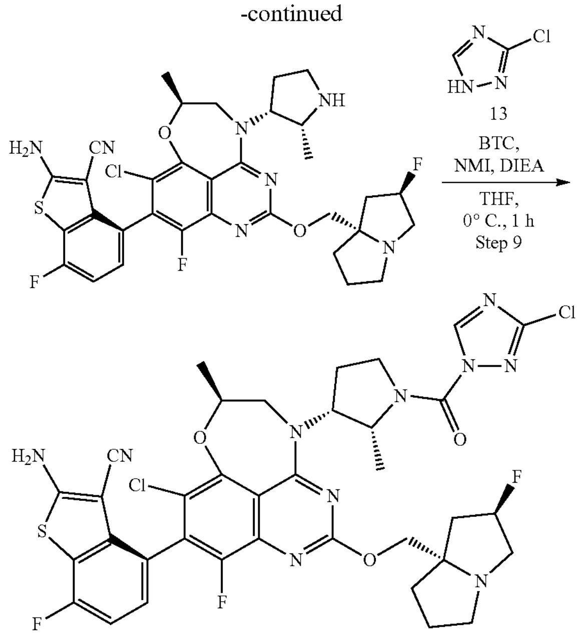

407

Step 1: To a solution of (S)-1-aminopropan-2-ol (5.0 g, 66.67 mmol) in DCM (80 ml) were added TEA (20.20 g, 200.0 mmol), DMAP (1.62 g, 13.3 mmol) and TBSCl (12.058 g, 80.0 mmol). The reaction mixture was stirred at room temperature for 16 h. LCMS showed the reaction was completed. The solution was diluted with DCM (100 mL) and washed with brine (80 mL). The organic layer was dried over anhydrous $Na_2SO_4$, filtered and concentrated in vacuo. The residue was purified by silica gel column (petroleum ether:EtOAc=1:1) to afford (S)-2-((tert-butyldimethylsilyl)oxy)propan-1-amine (6.1 g, Yield: 48%) as a yellow oil. MS (ESI) m/z=190.2 $[M+H]^+$.

Step 2: A solution of (S)-2-((tert-butyldimethylsilyl)oxy)propan-1-amine (5.700 g, 30.159 mmol) and tert-butyl (R)-2-methyl-3-oxopyrrolidine-1-carboxylate (5.001 g, 25.132 mmol) in THF (60 ml) was stirred at room temperature for 30 min. STAB (6.132 g, 50.265 mmol) was then added to the mixture. The reaction mixture was then stirred at room temperature for 16 h. LCMS showed the reaction was completed. The reaction was quenched by adding a saturated aqueous solution of $NaHCO_3$ (30 mL). The mixture was extracted with ethyl acetate (100 mL*3). The organic layer was washed with brine (100 mL), dried over anhydrous $Na_2SO_4$, filtered and concentrated in vacuo. The residue was purified by silica gel column (petroleum ether:EtOAc=2:1) to give compound tert-butyl (2R,3R)-3-(((S)-2-((tert-butyldimethylsilyl)oxy)propyl)amino)-2-methylpyrrolidine-1-carboxylate (5.7 g, Yield: 50.9%) as a yellow oil. MS (ESI) m/z=373.2 $[M+H]^+$.

Step 3: To a solution of tert-butyl (2R,3R)-3-(((S)-2-((tert-butyldimethylsilyl)oxy)propyl)amino)-2-methylpyrrolidine-1-carboxylate (5.2 g, 13.978 mmol) in THF (60 ml) was added TBAF (1 M in THF) (28.0 ml, 27.957 mmol). The mixture was stirred for 16 hours at room temperature. The mixture was diluted with EtOAc (200 mL) and washed with water (50 mL*3). The organic layer was washed with brine (100 mL), dried over anhydrous $Na_2SO_4$, filtered and concentrated in vacuo. The residue was purified by silica gel column (DCM: NH3 in MeOH(7N)=10:1) to afford compound tert-butyl (2R,3R)-3-(((S)-2-hydroxypropyl)amino)-

2-methylpyrrolidine-1-carboxylate (3.2 g, Yield: 80.8%) as white solid. MS (ESI) m/z=259.2 $[M+H]^+$.

Step 4: To a solution of tert-butyl (2R,3R)-3-(((S)-2-hydroxypropyl)amino)-2-methylpyrrolidine-1-carboxylate (1.0 g, 3.87 mmol) in DMF (10 mL) was added NaH (3.1 g, 77.5 mmol) at 0° C. The mixture was stirred at 0° C. for 0.5 hours under nitrogen. Then a solution of tert-butyl (R)-(4-(6-chloro-5,8-difluoro-4-hydroxy-2-(methylthio)quinazolin-7-yl)-3-cyano-7-fluorobenzo[b]thiophen-2-yl)carbamate (2.1 g, 3.87 mmol) was added at 0° C. The mixture was stirred at 60° C. for 1 hour under nitrogen. The mixture was quenched by iced cold $NH_4Cl$ aqueous solution (30 mL) and extracted with EtOAc (50 mL*3). The organic layer was washed with brine (50 mL), dried over anhydrous $Na_2SO_4$, filtered and concentrated in vacuo. The residue was purified by silica gel column (DCM/MeOH=10:1) to give compound tert-butyl (2R,3R)-3-(((S)-2-(((R)-7-(2-((tert-butoxycarbonyl)amino)-3-cyano-7-fluorobenzo[b]thiophen-4-yl)-6-chloro-8-fluoro-4-hydroxy-2-(methylthio)quinazolin-5-yl)oxy)propyl)amino)-2-methylpyrrolidine-1-carboxylate (2.5 g, Yield: 81.7%) as a yellow solid. MS (ESI) m/z=790.0 $[M+H]^+$.

Step 5: To a solution of tert-butyl (2R,3R)-3-(((S)-2-(((R)-7-(2-((tert-butoxycarbonyl)amino)-3-cyano-7-fluorobenzo[b]thiophen-4-yl)-6-chloro-8-fluoro-4-hydroxy-2-(methylthio)quinazolin-5-yl)oxy)propyl)amino)-2-methylpyrrolidine-1-carboxylate (2.5 g, 3.16 mmol) in DCM (25 mL) were added DIEA (2.0 g, 15.8 mmol) and BopCl (4.0 g, 15.8 mmol). The mixture was stirred at room temperature for 16 hours. The solution was diluted with DCM (50 mL*3) and washed with brine (50 mL). The organic layer was dried over anhydrous $Na_2SO_4$, filtered and concentrated in vacuo. The residue was purified by silica gel column (DCM/MeOH=10:1) to give compound tert-butyl (2R,3R)-3-((6S,9R)-9-(2-((tert-butoxycarbonyl)amino)-3-cyano-7-fluorobenzo[b]thiophen-4-yl)-8-chloro-10-fluoro-6-methyl-2-(methylthio)-5,6-dihydro-4H-[1,4]oxazepino[5,6,7-de]quinazolin-4-yl)-2-methylpyrrolidine-1-carboxylate (1.6 g, Yield: 65.6%) as a yellow solid. MS (ESI) m/z=772.9 $[M+H]^+$.

Step 6: To a solution of tert-butyl (2R,3R)-3-((6S,9R)-9-(2-((tert-butoxycarbonyl)amino)-3-cyano-7-fluorobenzo[b]thiophen-4-yl)-8-chloro-10-fluoro-6-methyl-2-(methylthio)-5,6-dihydro-4H-[1,4]oxazepino[5,6,7-de]quinazolin-4-yl)-2-methylpyrrolidine-1-carboxylate (1.6 g, 2.07 mmol) in DCM (25 mL) was added m-CPBA (500 mg, 2.90 mmol) at 0° C. The mixture was stirred at room temperature for 1 h. After the reaction completion, the reaction mixture was quenched with $Na_2S_2O_3$ aqueous solution and extracted with EtOAc (20 mL*3). The organic layer was washed with brine (100 mL), dried over anhydrous $Na_2SO_4$, filtered and concentrated in vacuo. The crude product tert-butyl (2R,3R)-3-((6S,9R)-9-(2-((tert-butoxycarbonyl)amino)-3-cyano-7-fluorobenzo[b]thiophen-4-yl)-8-chloro-10-fluoro-6-methyl-2-(methylsulfinyl)-5,6-dihydro-4H-[1,4]oxazepino[5,6,7-de]quinazolin-4-yl)-2-methylpyrrolidine-1-carboxylate was used in the next step without purification. MS (ESI) m/z=789.1$[M+H]^+$ Step 7: To a solution of ((2R,7aS)-2-fluorotetrahydro-1H-pyrrolizin-7a (5H)-yl)methanol (969 mg, 6.09 mmol) in toluene (5 mL), was added t-BuONa (585 mg, 6.09 mmol) at room temperature under argon. The mixture was stirred at room temperature for 10 min. Then tert-butyl (2R,3R)-3-((6S,9R)-9-(2-((tert-butoxycarbonyl)amino)-3-cyano-7-fluorobenzo[b]thiophen-4-yl)-8-chloro-10-fluoro-6-methyl-2-(methylsulfinyl)-5,6-dihydro-4H-[1,4]oxazepino[5,6,7-de]quinazolin-4-yl)-2-methylpyrrolidine-1-carboxylate (1.6 g, 2.03 mmol) was added at room temperature and the resulting mixture was stirred for another 16 h. After reaction completion, the mixture was diluted with DCM (20 mL) and washed with brine (20 mL*3). The organic layer was dried over anhydrous $Na_2SO_4$, filtered and concentrated in vacuo. The residue was purified by silica gel column to afford compound tert-butyl (2R,3R)-3-((6S,9R)-9-(2-((tert-butoxycarbonyl)amino)-3-cyano-7-fluorobenzo[b]thiophen-4-yl)-8-chloro-10-fluoro-2-(((2R,7aS)-2-fluorotetrahydro-1H-pyrrolizin-7a (5H)-yl)methoxy)-6-methyl-5,6-dihydro-4H-[1,4]oxazepino[5,6,7-de]quinazolin-4-yl)-2-methylpyrrolidine-1-carboxylate (1.2 g, Yield: 67.0%) as a yellow solid. MS (ESI) m/z=884.2 $[M+H]^+$ Step 8: To a solution of tert-butyl (2R,3R)-3-((6S,9R)-9-(2-((tert-butoxycarbonyl)amino)-3-cyano-7-fluorobenzo[b]thiophen-4-yl)-8-chloro-10-fluoro-2-(((2R,7aS)-2-fluorotetrahydro-1H-pyrrolizin-7a (5H)-yl)methoxy)-6-methyl-5,6-dihydro-4H-[1,4]oxazepino[5,6,7-de]quinazolin-4-yl)-2-methylpyrrolidine-1-carboxylate (1.2 g, 1.36 mmol) in DCM (5 ml) was added TFA (5 ml). The mixture was stirred at room temperature for 1 h. After the reaction reached completion, the mixture was concentrated, then diluted with DCM (100 mL) and washed with saturated $NaHCO_3$ aqueous solution (50 mL). The organic layer was concentrated and purified by silica gel column to afford compound 2-amino-4-((6S,9R)-8-chloro-10-fluoro-2-(((2R,7aS)-2-fluorotetrahydro-1H-pyrrolizin-7a (5H)-yl)methoxy)-6-methyl-4-((2R,3R)-2-methylpyrrolidin-3-yl)-5,6-dihydro-4H-[1,4]oxazepino[5,6,7-de]quinazolin-9-yl)-7-fluorobenzo[b]thiophene-3-carbonitrile (650 mg, Yield: 70.0%) as a yellow solid. MS (ESI) m/z=683.9 $[M+H]^+$ Step 9: Solution A: To a solution of 3-chloro-1H-1,2,4-triazole (75 mg, 0.732 mmol) in THF (5 mL) was added NMI (48 mg, 0.585 mmol) and BTC (43 mg, 0.146 mmol) at 0° C. The reaction mixture was stirred at 0° C. for 1 h under argon. To a solution of 2-amino-4-((6S,9R)-8-chloro-10-fluoro-2-(((2R, 7aS)-2-fluorotetrahydro-1H-pyrrolizin-7a (5H)-yl)methoxy)-6-methyl-4-((2R,3R)-2-methylpyrrolidin-3-yl)-5,6-dihydro-4H-[1,4]oxazepino[5,6,7-de]quinazolin-9-yl)-7-fluorobenzo[b]thiophene-3-carbonitrile (100 mg, 0.146 mmol) in THF (1 mL) was added DIEA (113 mg, 0.878 mmol) and solution A (1.2 mL) at 30° C. under $N_2$ atmosphere. The reaction mixture was stirring at 40° C. for 5 min. The reaction mixture was diluted with EtOAc (30 mL) and washed with brine (20 mL). The organic layer was dried over anhydrous sodium sulfate, filtered and concentrated in vacuo. The crude product was purified by prep-HPLC to give (R)-2-amino-4-((S)-8-chloro-4-((2R,3R)-1-(3-chloro-1H-1,2,4-triazole-1-carbonyl)-2-methylpyrrolidin-3-yl)-10-fluoro-2-(((2R, 7aS)-2-fluorotetrahydro-1H-pyrrolizin-7a (5H)-yl)methoxy)-6-methyl-5,6-dihydro-4H-[1,4]oxazepino[5,6,7-de]quinazolin-9-yl)-7-fluorobenzo[b]thiophene-3-carbonitrile (51.24 mg, Yield: 43.1%). MS (ESI) m/z=813.3 $[M+H]^+$. $^1H$ NMR (400 MHz, DMSO-$d_6$) δ 9.36-9.16 (m, 1H), 8.18-8.06 (m, 2H), 7.31-7.21 (m, 1H), 7.18-7.09 (m, 1H), 5.65-4.90 (m, 3H), 4.85-4.68 (m, 1H), 4.30-3.70 (m, 5H), 3.52-3.38 (m, 1H), 3.13-2.96 (m, 3H), 2.86-2.76 (m, 1H), 2.59-2.52 (m, 1H), 2.42-2.34 (m, 1H), 2.14-1.70 (m, 6H), 1.49-1.37 (m, 3H), 1.20-1.06 (s, 3H).

Example M: Synthesis of 2-amino-4-(10-((2R,3R)-1-(2,4-dimethyl-1H-imidazole-1-carbonyl)-2-methylpyrrolidin-3-yl)-4-fluoro-2-(((2R,7aS)-2-fluorotetrahydro-1H-pyrrolizin-7a (5H)-yl)methoxy)-7,8,9,10-tetrahydro-1,3,6,10-tetraazacyclohepta[de]naphthalen-5-yl)-7-fluorobenzo[b]thiophene-3-carbonitrile (409)
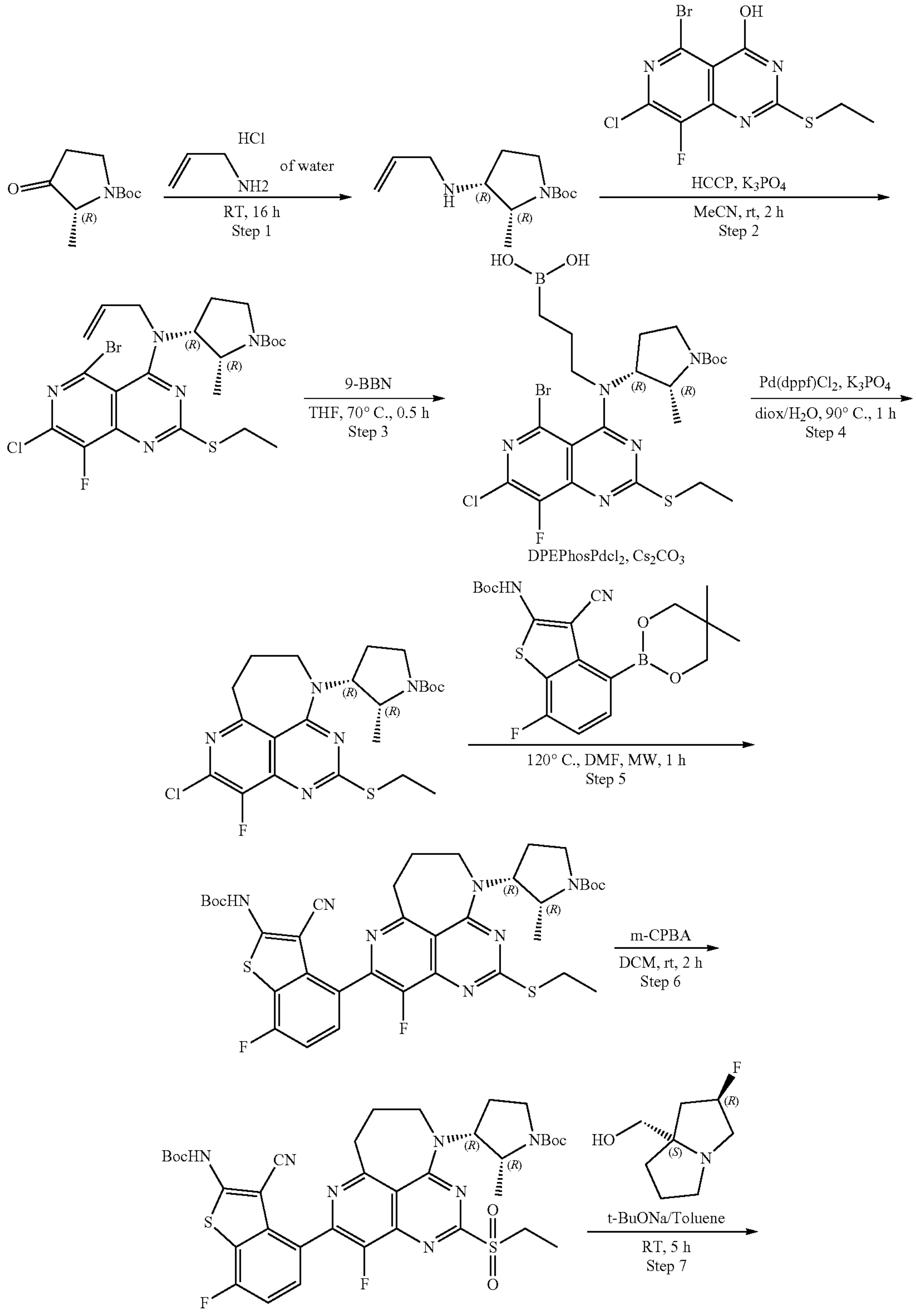

-continued

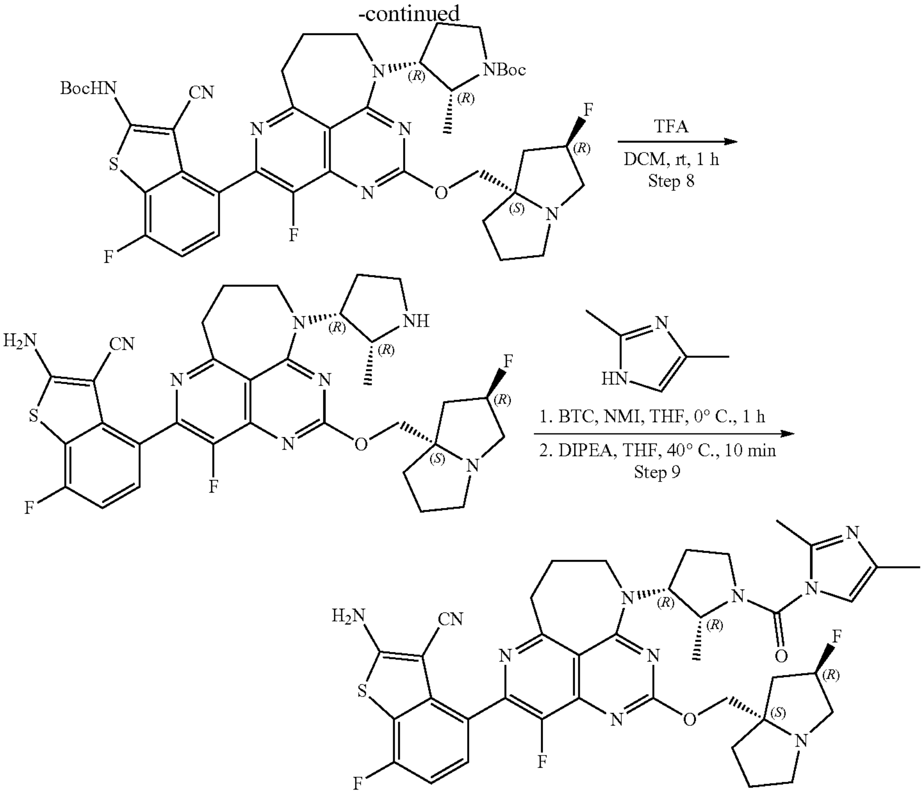

409

Step 1: To a solution of prop-2-en-1-amine hydrogen chloride (3 g, 20.1 mmol) in THF (60 mL) was added MeONa (1.08 g, 20.1 mmol) and tert-butyl (R)-2-methyl-3-oxopyrrolidine-1-carboxylate (2.0 g, 10 mmol) at 0° C., the mixture was stirred at room temperature for 1 h. The mixture was cooled to 0° C. followed by addition of $NaBH_4$(760 mg, 20.1 mmol) to the mixture. The resulting mixture was stirred at room temperature for 16 h. After the reaction was completed, the reaction mixture was quenched with saturated $NH_4Cl$ aqueous solution and extracted with EtOAc (80 mL*3). The organic layer was dried over anhydrous $Na_2SO_4$, filtered and concentrated in vacuo. The crude product was purified by silica gel column to give the desired product tert-butyl (2R,3R)-3-(allylamino)-2-methylpyrrolidine-1-carboxylate (2 g, Yield: 82.9%) as a colorless oil. MS (ESI) m/z=241.2 $[M+H]^+$.

Step 2: To a stirred solution of 5-bromo-7-chloro-2-(ethylthio)-8-fluoropyrido[4,3-d]pyrimidin-4-ol (1.0 g, 2.96 mmol) in MeCN (40 mL) was added HCCP (1.36 g, 3.25 mmol) and $K_3PO_4$ (1.35 g, 14.2 mmol) at room temperature. The mixture was stirred for 1 h and followed by addition of tert-butyl (2R,3R)-3-(allylamino)-2-methylpyrrolidine-1-carboxylate (1.02 g, 3.55 mol). The mixture was stirred for 16 h. After the reaction was completed, the mixture was poured to EtOAc (200 mL) and washed with water (200 mL). The organic was concentrated and purified by silica gel column (petroleum ether:EtOAc=1:1) to give product tert-butyl (2R,3R)-3-(allyl(5-bromo-7-chloro-2-(ethylthio)-8-fluoropyrido[4,3-d]pyrimidin-4-yl)amino)-2-methylpyrrolidine-1-carboxylate (1 g, yield: 60%) as a yellow solid.

Step 3: To a solution of tert-butyl (2R,3R)-3-(allyl(5-bromo-7-chloro-2-(ethylthio)-8-fluoropyrido[4,3-d]pyrimidin-4-yl)amino)-2-methylpyrrolidine-1-carboxylate (1.045 g, 1.87 mmol) in dioxane (22 mL) was added 9-BBN (913 mg, 7.48 mmol) at room temperature under argon. The mixture was stirred at 70° C. for 0.5 h. After the reaction was completed, the reaction mixture was cooled to room temperature and the crude product was used directly for the next step.

Step 4: To a solution of crude (3-((5-bromo-7-chloro-2-(ethylthio)-8-fluoropyrido[4,3-d]pyrimidin-4-yl)((2R,3R)-1-(tert-butoxy-carbonyl)-2-methylpyrrolidin-3-yl)amino) propyl)boronic acid (1.13 g, 1.87 mmol) in $H_2O$ (2 mL) and dioxane (22 mL) was added $Pd(dppf)Cl_2$ (137 mg, 0.19 mmol) and $K_3PO_4$ (1.19 g, 5.61 mmol) at room temperature under argon. The mixture was stirred at 90° C. under argon for 0.5 h. After the reaction was completed, the reaction mixture was cooled to room temperature, diluted with EtOAc (50 mL), and washed with water (50 mL*2). The organic layer was dried over anhydrous $Na_2SO_4$, filtered and concentrated in vacuo. The residue was purified by silica gel column to provide tert-butyl (2R,3R)-3-(5-chloro-2-(ethylthio)-4-fluoro-8,9-dihydro-1,3,6,10-tetraazacyclohepta[de]naphthalen-10(7H)-yl)-2-methylpyrrolidine-1-carboxylate as yellow solid (370 mg, yield 41%). MS (ESI) m/z=482.1 $[M+H]^+$.

Step 5: To a solution of tert-butyl (2R,3R)-3-(5-chloro-2-(ethylthio)-4-fluoro-8,9-dihydro-1,3,6,10-tetraazacyclohepta[de]naphthalen-10(7H)-yl)-2-methylpyrrolidine-1-carboxylate (370 mg, 0.77 mmol) in DMF (15 mL) was added tert-butyl (3-cyano-4-(5,5-dimethyl-1,3,2-dioxaborinan-2-yl)-7-fluorobenzo[b]thiophen-2-yl)carbamate (467 mg, 1.16 mmol), $Cs_2CO_3$ (753 mg, 2.31 mmol) and Dpetroleum etherPhos $PdCl_2$ (165 mg, 0.23 mmol) at room temperature under argon. The mixture was stirred at 120° C. for 1 hours with MW irradiation. After the reaction was completed, the mixture was diluted with EtOAc (50 mL) and washed with brine (50 mL*3). The organic layer was dried over anhydrous $Na_2SO_4$, filtered and concentrated in vacuo. The residue was purified by silica gel column to provide tert-butyl (2R,3R)-3-(5-(2-((tert-butoxycarbonyl)amino)-3-cyano-7-fluorobenzo[b]thiophen-4-yl)-2-(ethylthio)-4-fluoro-8,9-dihydro-1,3,6,10-tetraazacyclohepta[de]naphthalen-10(7H)-yl)-2-methylpyrrolidine-1-carboxylate as yellow solid (260 mg, yield 46%). MS (ESI) m/z=738.2 $[M+H]^+$.

Step 6: To a solution of tert-butyl (2R,3R)-3-(5-(2-((tert-butoxycarbonyl)amino)-3-cyano-7-fluorobenzo[b]thiophen-4-yl)-2-(ethylthio)-4-fluoro-8,9-dihydro-1,3,6,10-tetraazacyclohepta[de]naphthalen-10(7H)-yl)-2-methylpyrrolidine-1-carboxylate (260 mg, 0.35 mmol) in DCM (5 mL) was added m-CPBA (72 mg, 0.42 mmol) at 0° C. under argon. The mixture was stirred at 0° C. for 1 h under argon. After the reaction was completed, the mixture was quenched with $Na_2S_2O_3$ aqueous solution and extracted with EtOAc (20 mL*3). The organic layer was dried over anhydrous $Na_2SO_4$, filtered and concentrated in vacuo. The crude product tert-butyl (2R,3R)-3-(5-(2-((tert-butoxycarbonyl)amino)-3-cyano-7-fluorobenzo[b]thiophen-4-yl)-2-(ethylsulfonyl)-4-fluoro-8,9-dihydro-1,3,6,10-tetraazacyclohepta[de]naphthalen-10(7H)-yl)-2-methylpyrrolidine-1-carboxylate (260 mg, yield 96%) was used directly for the next step without further purification. MS (ESI) m/z=770.3 $[M+H]^+$.

Step 7: To a solution of ((2R,7aS)-2-fluorotetrahydro-1H-pyrrolizin-7a (5H)-yl)methanol (270 mg, 1.7 mmol) in toluene (5 mL) was added t-BuONa (163 mg, 1.7 mmol) at room temperature. The mixture was stirred at room temperature for 10 min. Then tert-butyl (2R,3R)-3-(5-(2-((tert-butoxycarbonyl)amino)-3-cyano-7-fluorobenzo[b]thiophen-4-yl)-2-(ethylsulfonyl)-4-fluoro-8,9-dihydro-1,3,6,10-tetraazacyclohepta[de]naphthalen-10(7H)-yl)-2-methylpyrrolidine-1-carboxylate (260 mg, 0.34 mmol) was added, the mixture was stirred at room temperature for 1 h. After the reaction was completed, the mixture was diluted with DCM (20 mL) and washed with brine (20 mL*3). The organic layer was dried over anhydrous $Na_2SO_4$, filtered and concentrated in vacuo. The residue was purified by silica gel column to afford tert-butyl (2R,3R)-3-(5-(2-((tert-butoxycarbonyl)amino)-3-cyano-7-fluorobenzo[b]thiophen-4-yl)-4-fluoro-2-(((2R, 7aS)-2-fluorotetrahydro-1H-pyrrolizin-7a (5H)-yl)methoxy)-8,9-dihydro-1,3,6,10-tetraazacyclohepta[de]naphthalen-10(7H)-yl)-2-methylpyrrolidine-1-carboxylate (150 mg, 52.9%) as a yellow solid. MS (ESI) m/z=835.3 $[M+H]^+$ Step 8: To a solution of tert-butyl (2R,3R)-3-(5-(2-((tert-butoxycarbonyl)amino)-3-cyano-7-fluorobenzo[b]thiophen-4-yl)-4-fluoro-2-(((2R,7aS)-2-fluorotetrahydro-1H-pyrrolizin-7a (5H)-yl)methoxy)-8,9-dihydro-1,3,6,10-tetraazacyclohepta[de]naphthalen-10(7H)-yl)-2-methylpyrrolidine-1-carboxylate (150 mg, 0.18 mmol) in DCM (2 mL) was added TFA (1 mL) at room temperature. The mixture was stirred at room temperature for 1 h. After the reaction was completed, the mixture was concentrated, then diluted with DCM (20 mL) and washed with saturated $NaHCO_3$ aqueous solution (10 mL). The organic layer was concentrated and purified by silica gel column to afford 2-amino-7-fluoro-4-(4-fluoro-2-(((2R, 7aS)-2-fluorotetrahydro-1H-pyrrolizin-7a (5H)-yl)methoxy)-10-((2R,3R)-2-methyl-pyrrolidin-3-yl)-7,8,9,10-tetrahydro-1,3,6,10-tetraazacyclohepta[de]naphthalen-5-yl)benzo[b]thiophene-3-carbonitrile (80 mg, 70.1%) as a yellow solid. MS (ESI) m/z=635.3 $[M+H]^+$ Step 9: Solution A: To a solution of 2,4-dimethyl-1H-imidazole (151 mg, 1.57 mmol) in THF (11 mL) was added NMI (51 mg, 0.63 mmol) and BTC (93 mg, 0.31 mmol,) at 0° C. The reaction mixture was stirred at 0° C. for 1 h under argon.

Solution B: To a solution of 2-amino-7-fluoro-4-(4-fluoro-2-(((2R,7aS)-2-fluorotetrahydro-1H-pyrrolizin-7a (5H)-yl)methoxy)-10-((2R,3R)-2-methylpyrrolidin-3-yl)-7,8,9,10-tetrahydro-1,3,6,10-tetraazacyclohepta[de]naphthalen-5-yl)benzo[b]thiophene-3-carbonitrile (20 mg, 0.031 mmol) in THF (1 mL) was added DIEA (37 mg, 0.28 mmol) and the solution A (5.5 mL, 0.79 mmol) at 40° C. The reaction mixture was stirring at 40° C. for 5 min. The reaction mixture was diluted with EtOAc (30 mL) and washed with brine (20 mL). The organic layer was dried over anhydrous sodium sulfate, filtered and concentrated in vacuo. The crude product was purified by prep-HPLC to give 2-amino-4-(10-((2R,3R)-1-(2,4-dimethyl-1H-imidazole-1-carbonyl)-2-methylpyrrolidin-3-yl)-4-fluoro-2-(((2R,7aS)-2-fluorotetrahydro-11H-pyrrolizin-7a (5H)-yl)methoxy)-7,8,9,10-tetrahydro-1,3,6,10-tetraazacyclohepta[de]naphthalen-5-yl)-7-fluorobenzo[b]thiophene-3-carbonitrile as white solid (1.03 mg, 4.3% yield). MS (ESI) m/z=757.5 $[M+H]^+$. $^1$HNMR(400 MHz, DMSO-d6) δ 8.05 (s, 2H), 7.43 (dd, J=8.8, 5.6 Hz, 1H), 7.19-7.02 (m, 2H), 5.30 (d, J=53.2 Hz, 1H), 4.95-4.72 (m, 2H), 4.18-4.06 (m, 2H), 3.71-3.40 (m, 5H), 3.15-2.97 (m, 5H), 2.87-2.80 (m, 1H), 2.40-2.26 (m, 6H), 2.18-1.97 (m, 6H), 1.89-1.73 (m, 3H), 0.99 (s, 3H).

Example N: Synthesis of 2-amino-4-(11-((2R,3R)-1-(2,4-dimethyl-1H-imidazole-1-carbonyl)-2-methylpyrrolidin-3-yl)-4-fluoro-2-(((2R,7aS)-2-fluorotetrahydro-1H-pyrrolizin-7a (5H)-yl)methoxy)-8,9,10,11-tetrahydro-7H-1,3,6,11-tetraazacycloocta[de]naphthalen-5-yl)-7-fluorobenzo[b]thiophene-3-carbonitrile (454)

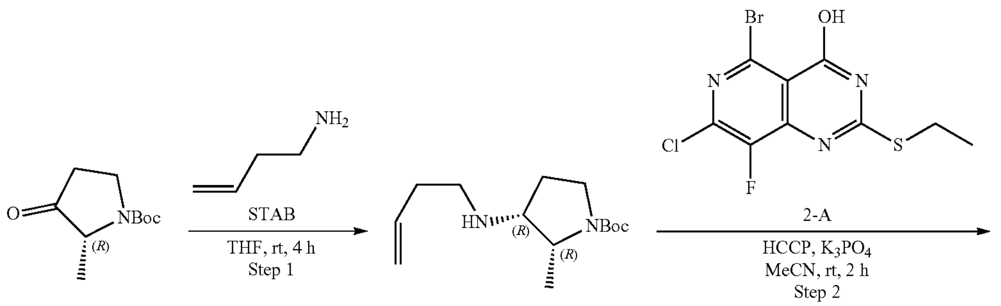

-continued
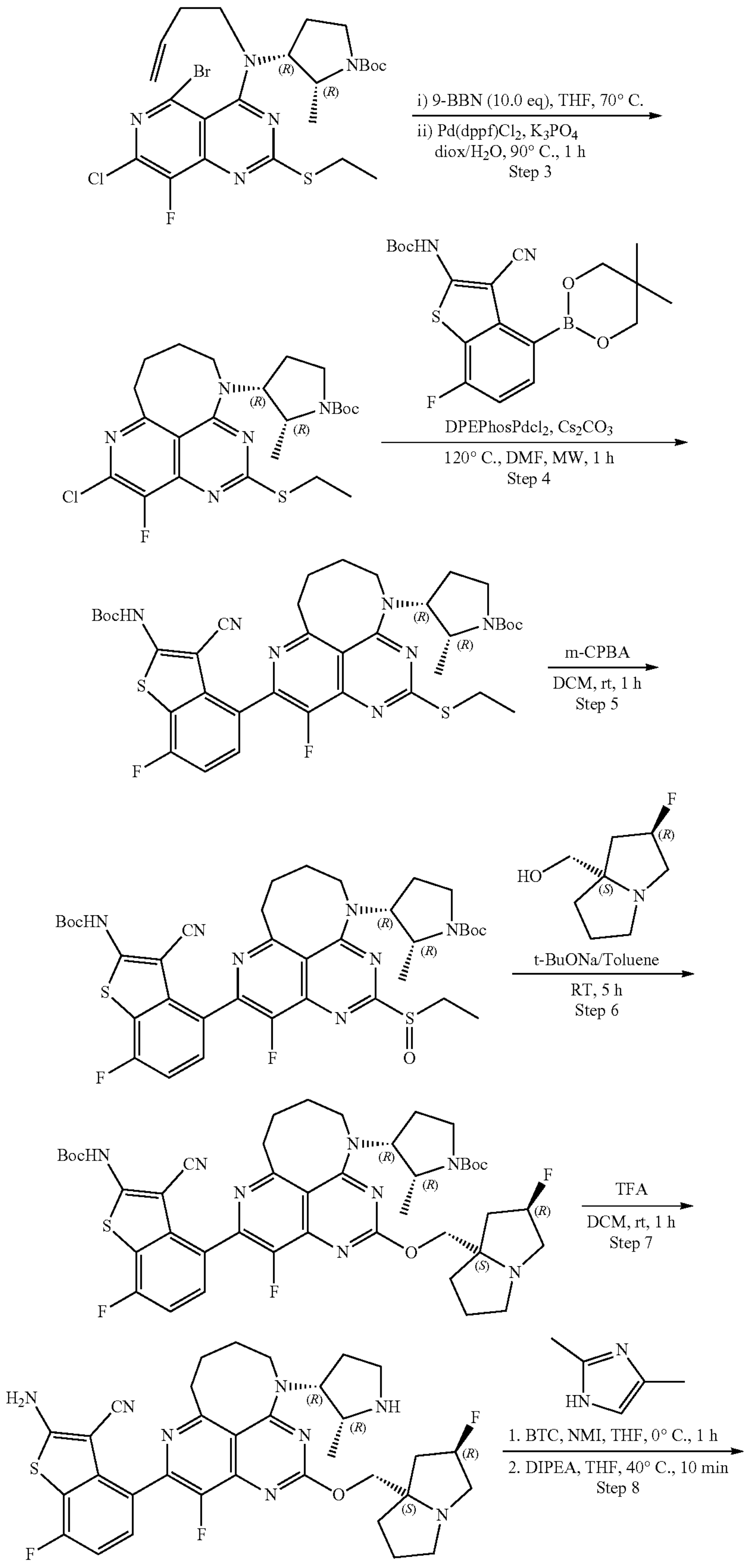

-continued

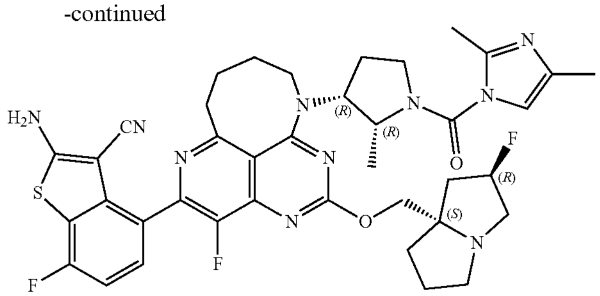

454

Step 1: To a solution of tert-butyl (R)-2-methyl-3-oxopyrrolidine-1-carboxylate (3 g, 20.1 mmol) in THF (60 mL) was added but-3-en-1-amine (1.4 g, 45 mmol), 4A powder at 0° C., the mixture was stirred at room temperature for 2 h under argon. The mixture was cooled to 0° C. and followed by addition of STAB (8.7 g, 40.2 mmol). The resulting mixture was stirred at room temperature for another 2 h. After the reaction was completed, the reaction mixture was quenched with saturated $NH_4Cl$ aqueous solution and extracted with EtOAc (50 mL*3). The organic layer was dried over anhydrous $Na_2SO_4$, filtered and concentrated in vacuo. The crude product was purified by silica gel column (petroleum ether:EtOAc=1:1) to give the desired tert-butyl (2R,3R)-3-(but-3-en-1-ylamino)-2-methylpyrrolidine-1-carboxylate (3 g, Yield: 58.8%) as a colorless oil. MS (ESI) m/z=255.2 $[M+H]^+$.

Step 2: To a stirred solution of 5-bromo-7-chloro-2-(ethylthio)-8-fluoropyrido[4,3-d]pyrimidin-4-ol (3.2 g, 9.46 mmol) in MeCN (40 mL) was added HCCP (3.29 g, 9.46 mmol) and $K_3PO_4$ (3 g, 14.2 mmol) at room temperature under argon. The mixture was stirred for 1 h followed by addition of tert-butyl (2R,3R)-3-(but-3-en-1-ylamino)-2-methylpyrrolidine-1-carboxylate (2.65 g, 10.4 mol). The resulting mixture was stirred at room temperature for 16 h. After the reaction was complete, the mixture was added to EtOAc (200 mL) and washed with water (200 mL) The organic was concentrated and purified by silica gel column (petroleum ether:EtOAc=1:1) to give tert-butyl (2R,3R)-3-((5-bromo-7-chloro-2-(ethylthio)-8-fluoropyrido[4,3-d]pyrimidin-4-yl)(but-3-en-1-yl)amino)-2-methylpyrrolidine-1-carboxylate (2.4 g, yield: 44.4%) as a yellow solid.

Step 3: To a solution of tert-butyl (2R,3R)-3-((5-bromo-7-chloro-2-(ethylthio)-8-fluoropyrido[4,3-d]pyrimidin-4-yl)(but-3-en-1-yl)amino)-2-methylpyrrolidine-1-carboxylate (2.2 g, 3.82 mmol) in dioxane (50 mL) was added 9-BBN (31 mL, 15.2 mmol) at room temperature under argon. The mixture was stirred at 70° C. for 0.5 h. After the reaction was completed, the reaction was cooled to room temperature and water (5 mL), Pd(dppf)$Cl_2$(279 mg, 0.38 mmol) and $K_3PO_4$ (2.4 g, 11.4 mmol) were added. The mixture was stirred at 90° C. under argon for 4 h. The reaction mixture was cooled to room temperature and diluted with EtOAc (100 mL). The mixture was washed with brine (50 mL*2). The organic layer was dried over anhydrous $Na_2SO_4$, filtered and concentrated in vacuo. The crude product was purified by silica gel column to give the desired product tert-butyl (2R,3R)-3-(5-chloro-2-(ethylthio)-4-fluoro-7,8,9,10-tetrahydro-11H-1,3,6,11-tetraazacycloocta[de]naphthalen-11-yl)-2-methylpyrrolidine-1-carboxylate as a white solid (600 mg, yield: 31.7%). MS (ESI) m/z=496.2 $[M+H]^+$.

Step 4: To a solution of tert-butyl (2R,3R)-3-(5-chloro-2-(ethylthio)-4-fluoro-7,8,9,10-tetrahydro-11H-1,3,6,11-tetraazacycloocta-[de]naphthalen-11-yl)-2-methylpyrrolidine-1-carboxylate (260 mg, 0.53 mmol) in DMF (8 mL) was added tert-butyl (3-cyano-4-(5,5-dimethyl-1,3,2-dioxaborinan-2-yl)-7-fluorobenzo[b]thiophen-2-yl)carbamate (321 mg, 0.80 mmol), $Cs_2CO_3$ (518 mg, 1.59 mmol) and DPEPhos $PdCl_2$ (114 mg, 0.16 mmol) at room temperature under argon. The mixture was stirred at 120° C. for 1 hours with MW irradiation. After the reaction was completed, the mixture was diluted with EtOAc (50 mL) and washed with brine (50 mL*3). The organic layer was dried over anhydrous $Na_2SO_4$, filtered and concentrated in vacuo. The resulting residue was purified by silica gel column to provide tert-butyl (2R,3R)-3-(5-(2-((tert-butoxycarbonyl)amino)-3-cyano-7-fluorobenzo[b]thiophen-4-yl)-2-(ethylthio)-4-fluoro-7,8,9,10-tetrahydro-11H-1,3,6,11-tetraazacycloocta[de]naphthalen-11-yl)-2-methylpyrrolidine-1-carboxylate as a yellow solid (224 mg, yield 56%). MS (ESI) m/z=752.4 $[M+H]^+$.

Step 5: To a solution of tert-butyl (2R,3R)-3-(5-(2-((tert-butoxycarbonyl)amino)-3-cyano-7-fluorobenzo[b]thiophen-4-yl)-2-(ethylthio)-4-fluoro-7,8,9,10-tetrahydro-11H-1,3,6,11-tetraazacycloocta[de]naphthalen-11-yl)-2-methylpyrrolidine-1-carboxylate (224 mg, 0.30 mmol) in DCM (5 mL) was added m-CPBA (62 mg, 0.36 mmol) at 0° C. under argon. The mixture was stirred at 0° C. for 1 h under argon. After the reaction was completed, the mixture was quenched with $Na_2S2O_3$ aqueous solution and extracted with EtOAc (20 mL*3). The organic layer was dried over anhydrous $Na_2SO_4$, filtered and concentrated in vacuo. The crude product tert-butyl (2R,3R)-3-(5-(2-((tert-butoxycarbonyl)amino)-3-cyano-7-fluorobenzo[b]thiophen-4-yl)-2-(ethylsulfnyl)-4-fluoro-7,8,9,10-tetrahydro-11H-1,3,6,11-tetraazacycloocta[de]naphthalen-11-yl)-2-methylpyrrolidine-1-carboxylate (224 mg, yield 97%) was used directly for the next step. MS (ESI) m/z=768.4 $[M+H]^+$.

Step 6: To a solution of ((2R,7aS)-2-fluorotetrahydro-1H-pyrrolizin-7a (5H)-yl)methanol (139 mg, 0.87 mmol) in toluene (5 mL) was added t-BuONa (84 mg, 0.87 mmol) at room temperature under argon. The mixture was stirred at room temperature for 10 min, followed by addition of tert-butyl (2R,3R)-3-(5-(2-((tert-butoxycarbonyl)amino)-3-cyano-7-fluorobenzo[b]thiophen-4-yl)-2-(ethylsulfinyl)-4-fluoro-7,8,9,10-tetrahydro-11H-1,3,6,11-tetraazacycloocta[de]naphthalen-11-yl)-2-methylpyrrolidine-1-carboxylate (224 mg, 0.29 mmol) at room temperature. The resulting mixture was stirred for another 1 h. After the reaction was completed, the mixture was diluted with DCM (20 mL) and washed with brine (20 mL*3). The organic layer was dried over anhydrous $Na_2SO_4$, filtered and concentrated in vacuo. The residue was purified by silica gel column to afford tert-butyl (2R,3R)-3-(5-(2-((tert-butoxycarbonyl)amino)-3-cyano-7-fluorobenzo[b]thiophen-4-yl)-4-fluoro-2-(((2R, 7aS)-2-fluorotetrahydro-1H-pyrrolizin-7a (5H)-yl) methoxy)-8,9-dihydro-1,3,6,10-tetraazacyclohepta[de] naphthalen-10(7H)-yl)-2-methylpyrrolidine-1-carboxylate (148 mg, 60.2%) as a yellow solid. MS (ESI) m/z=849.3 $[M+H]^+$ Step 7: To a solution of tert-butyl (2R,3R)-3-(5-(2-((tert-butoxycarbonyl)amino)-3-cyano-7-fluorobenzo[b]thiophen-4-yl)-4-fluoro-2-(((2R,7aS)-2-fluorotetrahydro-11H-pyrrolizin-7a (5H)-yl)methoxy)-8,9-dihydro-1,3,6,10-tetraazacyclohepta[de]naphthalen-10(7H)-yl)-2-methylpyrrolidine-1-carboxylate (148 mg, 0.17 mmol) in DCM (2 mL) was added TFA (1 mL) at room temperature. The mixture was stirred at room temperature for 1 h. After the reaction was completed, the mixture was concentrated, diluted with DCM (20 mL), and washed with $NaHCO_3$ aqueous solution (10 mL). The organic layer was concentrated and purified by silica gel column to afford 2-amino-7-fluoro-4-(4-fluoro-2-(((2R,7aS)-2-fluorotetrahydro-1H-pyrrolizin-7a (5H)-yl)methoxy)-11-((2R,3R)-2-methylpyrro-lidin-3-yl)-8,9,10,11-tetrahydro-7H-1,3,6,11-tetraazacycloocta[de]naphthalen-5-yl)benzo[b]thiophene-3-carbonitrile (100 mg, 90.8%) as a yellow solid. MS (ESI) m/z=649.3 $[M+H]^+$ Step 8: Solution A: To a solution of 3-fluoro-1H-1,2,4-triazole (55 mg, 0.63 mmol) in MeCN (2 mL) was added NMI (21 mg, 0.25 mmol) and BTC (37 mg, 0.13 mmol,) at 0° C. The reaction mixture was stirred at 0° C. for 1 h under argon. Solution B: To a solution of 2-amino-7-fluoro-4-(4-fluoro-2-(((2R, 7aS)-2-fluorotetrahydro-1H-pyrrolizin-7a (5H)-yl)methoxy)-11-((2R,3R)-2-methylpyrrolidin-3-yl)-8,9,10,11-tetrahydro-7H-1,3,6,11-tetraazacycloocta[de]naphthalen-5-yl)benzo[b]thiophene-3-carbonitrile (20 mg, 0.03 mmol) in THF (1 mL) was added DIEA (23 mg, 0.18 mmol) and the solution A (0.2 mL, 0.06 mmol) at 40° C. under argon. After the reaction mixture was stirring at 40° C. for 5 min., it was diluted with EtOAc (30 mL) and washed with brine (20 mL). The organic layer was dried over anhydrous sodium sulfate, filtered and concentrated in vacuo. The crude product was purified by prep-HPLC to give 2-amino-4-(11-((2R,3R)-1-(2,4-dimethyl-1H-imidazole-1-carbonyl)-2-methylpyrrolidin-3-yl)-4-fluoro-2-(((2R, 7aS)-2-fluorotetrahydro-1H-pyrrolizin-7a (5H)-yl)methoxy)-8,9,10,11-tetrahydro-7H-1,3,6,11-tetraazacycloocta[de]naphthalen-5-yl)-7-fluorobenzo[b]thiophene-3-carbonitrile as white solid (9.27 mg, 40.6% yield). MS (ESI) m/z=762.5 $[M+H]^+$. $^1H$ NMR (400 MHz, DMSO-d6) δ 9.14 (s, 1H), 8.06 (s, 2H), 7.52-7.37 (m, 1H), 7.18-7.08 (m, 1H), 5.32-5.17 (m, 2H), 4.21-4.10 (m, 2H), 3.92-3.73 (m, 2H), 3.07-3.01 (m, 6H), 2.81 (s, 1H), 2.01-1.79 (m, 10H), 1.24 (s, 4H), 1.10 (s, 3H).

Example 2: Ras Sequences

```
Human K-Ras Wildtype sequence
                                                    (SEQ ID NO. 1)
  1 MTEYKLVVVG AGGVGKSALT IQLIQNHFVD EYDPTIEDSY RKQVVIDGET

 51 CLLDILDTAG QEEYSAMRDQ YMRTGEGFLC VFAINNTKSF EDIHHYREQI

101 KRVKDSEDVP MVLVGNKCDL PSRTVDTKQA QDLARSYGIP FIETSAKTRQ

151 GVDDAFYTLV REIRKHKEKM SKDGKKKKKK SKTKCVIM

Human K-Ras G12D
                                                    (SEQ ID NO. 2)
  1 MTEYKLVVVG ADGVGKSALT IQLIQNHFVD EYDPTIEDSY RKQVVIDGET

 51 CLLDILDTAG QEEYSAMRDQ YMRTGEGFLC VFAINNTKSF EDIHHYREQI

101 KRVKDSEDVP MVLVGNKCDL PSRTVDTKQA QDLARSYGIP FIETSAKTRQ

151 GVDDAFYTLV REIRKHKEKM SKDGKKKKKK SKTKCVIM

Human K-Ras G12V
                                                    (SEQ ID NO. 3)
  1 MTEYKLVVVG AVGVGKSALT IQLIQNHFVD EYDPTIEDSY RKQVVIDGET

 51 CLLDILDTAG QEEYSAMRDQ YMRTGEGFLC VFAINNTKSF EDIHHYREQI

101 KRVKDSEDVP MVLVGNKCDL PSRTVDTKQA QDLARSYGIP FIETSAKTRQ

151 GVDDAFYTLV REIRKHKEKM SKDGKKKKKK SKTKCVIM

Human K-Ras G12S (SEQ ID NO. 4):
  1 MTEYKLVVVG ASGVGKSALT IQLIQNHFVD EYDPTIEDSY RKQVVIDGET

 51 CLLDILDTAG QEEYSAMRDQ YMRTGEGFLC VFAINNTKSF EDIHHYREQI

101 KRVKDSEDVP MVLVGNKCDL PSRTVDTKQA QDLARSYGIP FIETSAKTRQ

151 GVDDAFYTLV REIRKHKEKM SKDGKKKKKK SKTKCVIM

Human N-Ras wildtype
                                                    (SEQ ID NO. 5)
  1 MTEYKLVVVG AGGVGKSALT IQLIQNHFVD EYDPTIEDSY RKQVVIDGET

 51 CLLDILDTAG QEEYSAMRDQ YMRTGEGFLC VFAINNSKSF ADINLYREQI

101 KRVKDSDDVP MVLVGNKCDL PTRTVDTKQA HELAKSYGIP FIETSAKTRQ

151 GVEDAFYTLV REIRQYRMKK LNSSDDGTQG CMGLPCVVM
```

-continued

```
H-Ras G12D
                                                    (SEQ ID NO. 6)
  1 MTEYKLVVVG ADGVGKSALT IQLIQNHFVD EYDPTIEDSY RKQVVIDGET

 51 CLLDILDTAG QEEYSAMRDQ YMRTGEGFLC VFAINNTKSF EDIHQYREQI

101 KRVKDSDDVP MVLVGNKCDL AARTVESRQA QDLARSYGIP YIETSAKTRQ

151 GVEDAFYTLV REIRQHKLRK LNPPDESGPG CMSCKCVLS

H-Ras wildtype
                                                    (SEQ ID NO. 7)
  1 MTEYKLVVVG AGGVGKSALT IQLIQNHFVD EYDPTIEDSY RKQVVIDGET

 51 CLLDILDTAG QEEYSAMRDQ YMRTGEGFLC VFAINNTKSF EDIHQYREQI

101 KRVKDSDDVP MVLVGNKCDL AARTVESRQA QDLARSYGIP YIETSAKTRQ

151 GVEDAFYTLV REIRQHKLRK LNPPDESGPG CMSCKCVLS

Human N-Ras G12D
                                                    (SEQ ID NO. 8)
  1 MTEYKLVVVG ADGVGKSALT IQLIQNHFVD EYDPTIEDSY RKQVVIDGET

 51 CLLDILDTAG QEEYSAMRDQ YMRTGEGFLC VFAINNSKSF ADINLYREQI

101 KRVKDSDDVP MVLVGNKCDL PTRTVDTKQA HELAKSYGIP FIETSAKTRQ

151 GVEDAFYTLV REIRQYRMKK LNSSDDGTQG CMGLPCVVM
```

Example 3: Protein Expression

DNA expression constructs encoding one or more protein sequences of interest (e.g., KRAS fragments thereof, mutant variants thereof, etc.) and its corresponding DNA sequences are optimized for expression in *E. coli* and synthesized by, for example, the GeneArt Technology at Life Technologies. In some cases, the protein sequences of interest are fused with a tag (e.g., glutathione S-transferase (GST), histidine (His), or any other affinity tags) to facilitate recombinant expression and purification of the protein of interest. Such tag can be cleaved subsequent to purification. Alternatively, such tag may remain intact to the protein of interest and may not interfere with activities (e.g., target binding and/or phosphorylation) of the protein of interest A resulting expression construct is additionally encoded with (i) att-site sequences at the 5' and 3' ends for subcloning into various destination vectors using, for example, the Gateway Technology, as well as (ii) a Tobacco Etch Virus (TEV) protease site for proteolytic cleavage of one or more tag sequences. The applied destination vectors can be a pET vector series from Novagen (e.g., with ampicillin resistance gene), which provides an N-terminal fusion of a GST-tag to the integrated gene of interest and/or a pET vector series (e.g., with ampicillin resistance gene), which provides an N-terminal fusion of a HIS-tag to the integrated gene. To generate the final expression vectors, the expression construct of the protein of interest is cloned into any of the applied destination vectors. The expression vectors are transformed into an *E. coli* strain, e.g., BL21 (DE3). Cultivation of the transformed strains for expression is performed in a 10 L or 1 L fermenter. The cultures are grown, for example, in Terrific Broth media (MP Biomedicals, Kat. #1 13045032) with 200 μg/mL ampicillin at a temperature of 37° C. to a density of 0.6 (OD600), shifted to a temperature of ~27° C. (for K-Ras expression vectors) induced for expression with 100 mM IPTG, and further cultivated for 24 hours. After cultivation, the transformed *E. coli* cells are harvested by centrifugation and the resulting pellet is suspended in a lysis buffer, as provided below, and lysed by passing three-times through a high-pressure device. The lysate is centrifuged (49000 g, 45 min, 4° C.) and the supernatant is used for further purification.

Example 4: Ras Protein Purification

A Ras (e.g., K-Ras wildtype or a mutant such as K-Ras G12S, K-Ras G12D, K-Ras G12V or K-Ras G12C) construct or a variant thereof is tagged with GST. *E. coli* culture from a 1OL fermenter is lysed in lysis buffer (50 mM Tris HCl 7.5, 500 mM NaCl, 1 mM DTT, 0.5% CHAPS, Complete Protease Inhibitor Cocktail-(Roche)). As a first chromatography step, the centrifuged lysate is incubated with 50 mL Glutathione Agarose 4B (Macherey-Nagel; 745500.100) in a spinner flask (16 h, 10° C.). The Glutathione Agarose 4B loaded with protein is transferred to a chromatography column connected to a chromatography system, e.g., an Akta chromatography system. The column is washed with wash buffer (50 mM Tris HCl 7.5, 500 mM NaCl, 1 mM DTT) and the bound protein is eluted with elution buffer (50 mM Tris HCl 7.5, 500 mM NaCl, 1 mM DTT, 15 mM glutathione). The main fractions of the elution peak (monitored by OD280) are pooled. For further purification by size-exclusion chromatography, the above eluate volume is applied to a column Superdex 200 HR prep grade (GE Healthcare) and the resulting peak fractions of the eluted fusion protein is collected. Native mass spectrometry analyses of the final purified protein construct can be performed to assess its homogeneous load with GDP.

Example 5: HTRF (Homogenous Time-Resolved Fluorescence) Resonance Energy Transfer Assay The ability of a compound of the present disclosure to reduce Ras signaling output can be demonstrated by an HTRF assay. This assay can be also used to assess a selective inhibition or reduction of signaling output of a mutant Ras protein relative to a wildtype, or relative to a different mutant Ras protein. For example, the equilibrium interaction of wildtype KRAS or K-Ras mutant (e.g., wildtype or a mutant thereof) with SOS1 (e.g., hSOS1) can be assessed as a proxy or an indication for the ability of a subject compound to bind and inhibit Ras protein. The HTRF assay detects from (i) a fluorescence resonance energy transfer (FRET) donor (e.g., antiGST-Europium) that is bound to GST-tagged K-Ras mutant to (ii) a FRET acceptor (e.g., anti-6His-XL665) bound to a His-tagged hSOS1.

The assay buffer can contain ~5 mM HEPES pH 7.4, ~150 mM NaCl, ~1 mM DTT, 0.05% BSA and 0.0025% (v/v) Igepal. A Ras working solution is prepared in an assay buffer containing typically a suitable amount of the protein construct (e.g., GST-tagged K-Ras mutant) and the FRET donor (e.g., antiGST-Eu(K) from Cisbio, France). A SOS1 working solution is prepared in an assay buffer containing suitable amount of the protein construct (e.g., His-hSOS1) and the FRET acceptor (e.g., anti-6His-XL665 from Cisbio, France). A suitable amount of the protein construct will depend on the range of activity or range of IC50 values being detected or under investigation. For detecting an IC50 within a range of 500 nM, the protein constructs of the same range of molarity can be utilized. An inhibitor control solution is prepared in an assay buffer containing a comparable amount of the FRET acceptor without the SOS1 protein.

A fixed volume of DMSO with or without test compound is transferred into a 384-well plate. Ras working solution is added to all wells of the test plate. SOS1 working solution is added to all wells except for those that are subsequently filled with inhibitor control solution. Upon incubation for about 10 minutes or longer, the fluorescence is measured with a M1000Pro plate reader (Tecan) using HTRF detection (excitation 337 nm, emission 1: 620 nm, emission 2: 665 nm). Compounds are tested in duplicate at different concentrations (for example, 10 μM, 2.5 μM, 0.63 μM, 0.16 μM, 0.04 μM, 0.01 μM test compound). The ratiometric data (i.e., emission 2 divided by emission 1) is used to calculate IC50 values against Ras using GraphPad Prism (GraphPad software). Signaling output measured in terms of IC50 values can be obtained and a ratio of IC50 against one mutant relative to another mutant can be calculated. For instance, a selective reduction of K-Ras G12S signaling output can be evidenced by a ratio greater than one. In particular, a selective reduction of K-Ras G12S signaling relative to K-Ras WT signaling is evidenced if the ratio of IC50 (against K-Ras WT) to IC50 (against K-Ras G12S) is greater than 1. In some embodiments, one or more subject compounds disclosed herein exhibits selective inhibition of a Ras mutant (e.g., G12C or G12S) over WT. In some embodiments, subject compounds exhibit an IC50 against a KRas mutant (e.g., G12C or G12S) less than 500 nM, such as less than 100 nM, 50 nM, or even less.

The ability of one or more compounds exemplified in Table 1 to reduce Ras signaling output is demonstrated utilizing the procedures described above. Table 2 shows the resulting IC50 values of selected compounds against KRAS wildtype and KRAS G12S proteins using HTRF assays described herein. Compound numbers correspond to the numbers and structures provided in Table 1 and Example 1.

TABLE 2

| | <500 nM | 500 nM to 5 μM |
|---|---|---|
| Inhibition of KRAS WT ($IC_{50}$) | 401, 402, 403, 406, 407, 408, 409, 410, 411, 412, 413, 414, 415, 417, 418, 419, 420, 421, 422, 423, 424, 426, 427, 428, 429, 430, 432, 433, 434, 436, 437, 438, 439, 440, 441, 442, 444, 445, 446, 447, 448, 449, 450, 451, 452, 454, 455, 456, 457, 458, 459, 460, 461, 462, 463, 464, 466, 467, 469, 470, 471, 472, 473, 474, 475, 476, 477, 478, 479, 480, 481, 482, 484, 485, 486, 487, 488, 489, 491, 493, 494, 495 | 404, 405, 416, 425, 431, 435, 443, 453, 468, 483, 490, 492 |
| Inhibition of KRAS G12S ($IC_{50}$) | 401, 402, 403, 406, 407, 408, 409, 410, 411, 412, 413, 414, 417, 418, 419, 420, 421, 422, 423, 424, 426, 427, 428, 429, 430, 432, 433, 434, 436, 437, 438, 439, 440, 441, 442, 444, 445, 446, 447, 448, 449, 450, 451, 452, 454, 455, 456, 457, 458, 459, 460, 461, 462, 463, 464, 466, 467, 469, 470, 471, 472, 473, 474, 475, 476, 477, 478, 479, 480, 481, 482, 484, 486, 487, 488, 489, 491, 493, 494, 495 | 404, 405, 415, 416, 425, 431, 435, 443, 453, 465, 468, 483, 485, 490, 492 |

Example 6: GTPase Activity Assay

The ability of a compound of the present disclosure to inhibit Ras protein signaling can be demonstrated by a reduced GTPase activity. This assay can also be used to assess selective inhibition of a mutant Ras protein relative to a wildtype or different mutant Ras protein. For instance, the assay can be used to establish a subject compound's ability to selectively inhibit KRAS G12S relative to wildtype, KRAS G12S relative to KRAS G12V, KRAS G12S relative to KRAS G12D, KRAS G12C relative to KRAS G12D, or KRAS G12C relative to KRAS G12V or wildtype. In particular, intrinsic and GTPase-activating protein (GAP)-stimulated GTPase activity for a K-Ras construct or a mutant thereof can be measured using EnzCheck phosphate assay system (Life Technologies). For example, K-Ras WT, K-Ras D154Q mutant, K-Ras G12D mutant, K-Ras G12S mutant, and K-Ras G12D/D154Q mutant proteins (2.5 mg/mL) in buffer (20 mmol/L Tris, pH 8.0, 50 mM NaCl) are loaded with GTP at room temperature for 2 hours by exposing to exchange buffer containing EDTA. Proteins are buffer exchanged to assay buffer (30 mM Tris, pH 7.5, 1 mM DTT) and the concentration is adjusted to 2 mg/mL. GTP loading is verified by back extraction of nucleotide using 6M urea and evaluation of nucleotide peaks by HPLC using an ion-exchange column. The assay is performed in a clear 384-well plate (Costar) by combining GTP-loaded K-Ras proteins (50 mM final) with 2-amino-6-mercapto-7-methylpurine ribonucleoside (MESG) (200 mM final), and purine nucleotide phosphorylase (5 U/mL final). GTP hydrolysis is initiated by the addition of $MgCl_2$ at a working concentration of 40 mM. For GAP stimulation, Ras p21 protein activator 1 (P120GAP) can be included at 50 mM. Absorbance at 360 nm can be measured every 8 to 15 s for 1,000 s at 20° C. Samples are tested with or without a subject compound disclosed herein to assess the ability of each compound to inhibit signaling of a given Ras protein (e.g., a given mutant KRAS) of interest.

Example 7: Nucleotide Exchange Assay

The ability of a compound of the present disclosure to inhibit Ras protein signaling can be demonstrated by reduced nucleotide exchange activity. This assay can be also used to assess selective inhibition of a mutant Ras protein relative to a wildtype or different mutant Ras protein. For example, 250 nM or 500 nM GDP-loaded K-Ras protein (e.g., wildtype or a mutant thereof, including those mentioned in Example 4) is incubated with different concentrations of compounds (for example ~60 μM, ~20 μM, ~6.7 μM, ~2.2 μM, ~0.7 μM, or ~0.2 μM subject compound). A control reaction without subject compound is also included. SOS1 (catalytic domain) protein is added to the K-Ras protein solution. The nucleotide exchange reaction is initiated by adding fluorescent labelled GDP (guanosine 5'-diphosphate, BODIPY™ FL 2'-(or-3')-O—(N-(2-aminoethyl) urethane) to a final concentration of 0.36 μM. Fluorescence is measured every 30 s for 70 minutes at 490 nm/515 nm (excitation/emission) in a M1000Pro plate reader (Tecan). Data is exported and analyzed to calculate an IC50 using GraphPad Prism (GraphPad Software). Sample(s) can be tested with or without a subject compound disclosed herein to assess the ability of the compound to inhibit K-Ras signaling or its IC50 against a given Ras protein (e.g., a given mutant K-Ras) of interest.

Example 8: Testing for Modification of Ras Protein Via Covalent Binding

Test compounds are prepared as 10 mM stock solutions in DMSO (Fisher cat #BP231-100). KRAS protein (His-tagged GDP-loaded wildtype 1-169, His-tagged GDP-loaded G12S 1-169, His-tagged GDP-loaded G12C 1-169, or His-tagged GDP-loaded G12D 1-169) is diluted to ~2 μM in appropriate buffer (e.g., a Hepes buffer at physiological conditions). For testing KRAS modification, compounds are diluted to 50× final test concentration in DMSO in 96-well storage plates. 2 μL of the diluted 50× compounds are added to appropriate wells in the PCR plate (Fisher cat #AB-0800). ~49 μL of the stock protein solution is added to each well of the 96-well PCR plate. Reactions are mixed carefully. The plate is sealed well with aluminum plate seal and stored in a drawer at room temperature for 24 hrs. 5 μL of 2% formic acid (Fisher cat #A117-50) in MilliQ $H_2O$ is then added to each well followed by mixing with a pipette. The plate is then resealed with aluminum seal and stored until mass spectrometry analysis.

The extent of covalent modification of KRAS proteins can be determined by liquid chromatography electrospray mass spectrometry analysis of the intact proteins on a Thermo Q-Exactive Plus mass spectrometer. 20 μL of sample is injected onto a bioZen 3.6 μm Intact C4 column (Phenomenex cat #00B-4767-AN) placed in a column oven set to 40° C. and separated using a suitable LC gradient from ~20% to ~60% solvent B. Solvent A is 0.1% formic acid and solvent B is 0.1% formic acid in acetonitrile. HESI source settings are set to 40, 5 and 1 for the sheath, auxiliary and sweep gas flow, respectively. The spray voltage is 4 kV, and the capillary temperature is 320° C. S-lens RF level is 50 and auxiliary gas heater temperature is set to 200° C. The mass spectrometry is acquired using a scan range from 650 to 1750 m/z using positive polarity at a mass resolution of 70,000, AGC target of 1e6 ions and maximum injection time of 250 ms. The recorded protein mass spectrum is deconvoluted from the raw data file using Protein Deconvolution v4.0 (Thermo). The protein mass and adduct masses are exported with their peak intensities. The peak intensities for the unmodified and modified protein are used to calculate the percent covalent modification of the KRAS protein based on the following equation: % KRAS protein modification=((KRAS−compound)/(KRAS)+(KRAS−Compound))*100.

Example 9: Ras Cellular Assay

The ability of a compound of the present disclosure to inhibit Ras protein signaling can be demonstrated by inhibiting growth of a given KRAS mutant cell line. For example, this assay can be also used to assess selective growth inhibition of a mutant Ras protein relative to a wildtype or different mutant Ras protein.

a. Growth of Cells with K-Ras G12C Mutation

MIA PaCa-2 (ATCC CRL-1420) and NCI-H1792 (ATCC CRL-5895) cell lines comprise a G12C mutation and can be used to assess Ras cellular signaling in vitro, e.g., in response to an inhibitor compound of the present disclosure. This cellular assay can also be used to discern selective inhibition of a subject compound against certain types of KRAS mutants, e.g., more potent inhibition against KRAS G12C relative to KRAS G12D mutant, by comparing inhibition of MIA PaCa-2 (G12C driven tumor cell line) to inhibition of GP2d (G12D driven tumor cell line). MIA PaCa-2 culture medium is prepared with DMEM/Ham's F12 (e.g., with stable glutamine, 10% FCS, and 2.5% horse serum. NCI-H1792 culture medium is prepared with RPMI 1640 (e.g., with stable glutamine) and 10% FCS.

On a first day (e.g., Day 1), Softagar (Select Agar, Invitrogen, 3% in dd$H_2O$ autoclaved) is boiled and tempered at 48° C. Appropriate culture medium (i.e., medium) is tempered to 37° C. Agar (3%) is diluted 1:5 in medium (=0.6%) and plated into 96 well plates (Corning, #3904), then incubated at room temperature for agar solidification. A 3% agar is diluted to 0.25% in medium (1:12 dilution) and tempered at 42° C. Cells are trypsinized, counted, and tempered at 37° C. The cells (e.g., MIA PaCa-2 at about 125-150 cells, NCI-H1792 at about 1000 cells) are resuspended in 100 mL 0.25% Agar and plated, followed by incubation at room temperature for agar solidification. The wells are overlaid with 50 mL of the medium. Sister wells in a separate plate are plated for time zero determination. All plates are incubated overnight at 37° C. and 5% $CO_2$.

On a second day (e.g., Day 2), time zero values are measured. A 40 mL volume of Cell Titer 96 Aqueous Solution (Promega) is added to each well and incubated in the dark at 37° C. and 5% $CO_2$. Absorption can be measured at 490 nm and reference wavelength 660 nm. DMSO-prediluted test compounds are added to wells of interest, e.g., with HP Dispenser, to one or more desired concentrations (e.g., a final DMSO concentration of 0.3%).

On a tenth day (e.g., Day 10), absorption by wells treated with the test compounds and control wells are measured with, for example, Cell Titer 96 AQueous and analyzed in comparison to the time zero measurements. The IC50 values are determined using the four parameter fit. The resulting IC50 value is a measurement of the ability of the test compound to reduce cell growth of Ras-driven cells (e.g., tumor cell lines) in vitro and/or in vivo.

b. Growth of Cells with K-Ras G12D Mutation

ASPC-1 (ATCC CRL-1682), Panc-10.05 (ATCC CRL-2547), A427, and GP2d cell lines, or any other cell lines comprising a G12D mutation, can be used to assess Ras cellular signaling in vitro, e.g., in response to a compound described herein. For example, ASPC-1 culture medium is prepared with RPMI-1640 and 10% heat-inactivated FBS. Panc-10.05 culture medium is prepared with RPMI-1640, 10 units/mL human recombinant insulin, and 10% FBS. A427 cell culture is prepared with RPMI-1640 and 10% heat-inactivated FBS. A CellTiter-Glo (CTG) luminescent based assay (Promega) is used to assess growth of the cells, as a measurement of the ability of the compounds herein to inhibit Ras signaling in the cells. The cells (e.g., 800 per well) are seeded in their respective culture medium in standard tissue culture-treated 384-well format plates (Falcon #08-772-116) or ultra-low attachment surface 384-well format plates (S-Bio #MS-9384UZ). The day after plating, cells are treated with a dilution series (e.g., a 9 point, 3-fold dilution series) of the compounds herein (e.g., approximately 40 μL final volume per well). Cell viability can be monitored (e.g., approximately 5 days later) according to the manufacturer's recommended instructions, where CellTiter-Glo reagent is added (e.g., approximately 10 μL), vigorously mixed, covered, and placed on a plate shaker (e.g., approximately for 20 min) to ensure sufficient cell lysis prior to assessment of luminescent signal. The IC50 values are determined using the four-parameter fit. The resulting IC50 value is a measurement of the ability of the test compound to reduce cell growth of Ras-driven cells (e.g., tumor cell lines) in vitro and/or in vivo.

c. Growth of Cells with K-Ras G12S Mutation

A549 (ATCC CRL-185) and LS123 (ATCC CRL-255) cell lines comprise a G12S mutation and can be used to assess Ras cellular signaling in vitro, e.g., in response to treatment with a compound described herein. A549 culture medium is prepared with RPMI-1640 and 10% heat-inactivated FBS. LS123 culture medium is prepared with RPMI-1640 and 10% heat-inactivated FBS. A CellTiter-Glo (CTG) luminescent based assay (Promega) is used to assess growth of the cells, as a measurement of the ability of the compounds herein to inhibit Ras signaling in the cells. The cells (e.g., 800 per well) are seeded in their respective culture medium in standard tissue culture-treated 384-well format plates (Falcon #08-772-116) or ultra-low attachment surface 384-well format plates (S-Bio #MS-9384WZ). The day after plating, cells are treated with a dilution series (e.g., a 10 point, 3-fold dilution series) of the compounds herein (e.g., approximately 40 μL final volume per well). Cell viability can be monitored (e.g., approximately 6 days later) according to the manufacturer's recommended instructions, where CellTiter-Glo reagent is added (e.g., approximately 10 μL), vigorously mixed, covered, and placed on a plate shaker (e.g., approximately for 20 min) to ensure sufficient cell lysis prior to assessment of luminescent signal. The IC50 values are determined using the four parameter fit. The resulting IC50 value is a measurement of the ability of the test compound to reduce cell growth of Ras-driven cells (e.g., tumor cell lines) in vitro and/or in vivo. One or more compounds disclosed herein possess the ability to inhibit growth of KRAS G12S cell line (e.g., A549 or LS123) and/or KRAS G12C cell lines (e.g., MIA PaCa-2).

Example 10: In Vivo Ras Inhibition

The in vivo reduction in Ras signaling output by a compound of the present disclosure is determined in a mouse tumor xenograft model, particularly by using a mutant K-Ras model including without limitation a K-Ras G12S model, a K-Ras G12C model, a K-Ras G12D model, a K-Ras G13D model, and a K-Ras G13C model. These models can be generated by the methods and procedures described below. In particular, the methods disclosed below involving the use of a K-Ras G12S mutant cell line for generating a K-Ras G12S xenograft model can be applied to other K-Ras mutant animal models using the respective K-Ras mutant cell lines described above.

Xenograft with K-Ras G12D, G12C, or G12S Mutation

Tumor xenografts are established by administration of tumor cells with a K-Ras G12D mutation (e.g., ASPC-1 cells), a K-Ras G12C mutation (e.g., MIA PaCa-2 cells), or a K-Ras G12S mutation (e.g., A549 or LS123 cells) into mice. Female 6- to 8-week-old athymic BALB/c nude (NCr) nu/nu mice are used for xenografts. The tumor cells (e.g., approximately $5\times10^6$) are harvested on the day of use and injected in growth-factor-reduced Matrigel/PBS (e.g., 50% final concentration in 100 μL). One flank is inoculated subcutaneously per mouse. Mice are monitored daily, weighed twice weekly, and caliper measurements begin when tumors become visible. For efficacy studies, animals are randomly assigned to treatment groups by an algorithm that assigns animals to groups to achieve best case distributions of mean tumor size with lowest possible standard deviation. Tumor volume can be calculated by measuring two perpendicular diameters using the following formula: $(L\times w^2)/2$, in which L and w refer to the length and width of the tumor, respectively. Percent tumor volume change can be calculated using the following formula: $(V_{final}-V_{inital})/V_{inital}\times100$. Percent of tumor growth inhibition (% TGI) can be calculated using the following formula: % TGI=100×(1−(average $V_{final}-V_{inital}$ of treatment group)/(average $V_{final}-V_{inital}$ of control group). When tumors reach a threshold average size (e.g., approximately 200-400 $mm^3$), mice are randomized into 3-10 mice per group and are treated with vehicle (e.g., 100% Labrasol®) or a compound disclosed herein, using, for example, a daily schedule by oral gavage. Results can be expressed as mean and standard deviation of the mean.

Example 11: Metabolic (Microsomal) Stability Assay

The metabolic stability of a test compound is assayed at 37° C. using pooled liver microsomes (mouse or human liver microsomes). An aliquot of 10 μL of 50 μM test compound is mixed with 490 μL of 0.611 mg/mL liver microsomes, then 50 μL of the mixtures are dispensed to the 96 well tubes and warmed at 37° C. for 10 minutes. The reactions are initiated by adding 50 μL of the pre-warmed NADPH regeneration system solution (add 1.2 μL solution, 240 μL solution B, mix with 10.56 mL KPBS) and then incubated at 37° C. The final incubation solution contains 100 mM potassium phosphate (pH 7.4), 1.3 mM $NADP^+$, 3.3 mM glucose 6-phosphate, 0.4 unit/mL of glucose 6-phosphate dehydrogenase, 3.3 mM magnesium chloride, 0.3 mg/mL liver microsomes and 0.5 μM test article. After 0, 15, 30 and 60 minutes in a shaking incubator, the reactions are terminated by adding 100 μL of acetonitrile containing 200 nM buspirone as an internal standard. All incubations are conducted in duplicate. Plates are vortexed vigorously by using Fisher Scientific microplate vortex mixer (Henry Troemner, US). Samples are then centrifuged at 3500 rpm for 10 minutes (4° C.) using Sorvall Legend XRT Centrifuge (Thermo Scientific, GE). Supernatants (40 μL) are transferred into clean 96-deep well plates. To each well is added with 160 μL of ultrapure water (Milli-Q, Millipore Corporation) with 0.1% (v/v) formic acid (Fisher Chemical) and the resulting solutions mixed thoroughly and subjected to LC/MS/MS analysis in MRM positive ionization mode.

All samples are measured using a mass spectrometer (QTrap 5500 quadrupole/ion trap) coupled with a Shimadzu HPLC system. The HPLC system consists of a Shimadzu series degasser, binary quaternary gradient pumps, column heater coupled to an autosampler, and a Phenomenex Gemini-NX, C18, 3.0 μm or Phenomenex Lunar, C8, 5.0 μM HPLC column (Phenomenex, Torrance, CA), eluting with a mobile phase gradient consisting of Solution A (0.1% formic acid water) and Solution B (0.1% formic acid acetonitrile). The column temperature is maintained at 40° C. All the analytes are detected with positive-mode electrospray ionization (ES+).

The half-life for the metabolic degradation of the test compound is calculated by plotting the time-course disappearance of the test compound during the incubation with liver microsomes. Each plot is fitted to a first-order equation for the elimination of the test compound (% remaining compound) versus time using non-linear regression (Equation 1).

$$\frac{C_t}{C_0} = e^{-kt} \qquad \text{Equation 1}$$

where $C_t$ is the mean relative substrate concentration at time t and $C_0$ is the initial concentration (0.5 μM) at time 0. Note that the area ratio of the substrate peak to an internal standard peak is proportional to the analyte concentration and is used for regression analysis to derive a value of k.

The half-life $t_{1/2}$ for metabolic (microsome) stability is derived from the test compound elimination constant k using Equation 2 below.

$$t_{1/2} = \frac{0.693}{k} \qquad \text{Equation 2}$$

Example 12: CYP2C19 Inhibition Assay

Some xenobiotics can inhibit cytochrome P450 (CYP) enzyme function, which alters their ability to metabolize drugs. Administration of a CYP inhibitor with a drug whose clearance is dependent on CYP metabolism can result in increased plasma concentrations of this concomitant drug, leading to potential toxicity. The inhibition of CYP2C19 by a test compound is assayed in human liver microsomes using S-mephenytoin as a CYP2C19 substrate. The stock solution of the test compound or known CYP2C19 inhibitor as a positive control (10 mM) is diluted with KPBS to 40 μM. In a similar way, the stock solutions of the human liver microsomes and S-mephenytoin are diluted with KPBS buffer. The pre-incubations are started by incubating a plate containing 25 μL human liver microsomes (final concentration of 0.2 mg/mL), 25 μL NADPH-generating system, and a 25 μL test compound (final concentration 10 μM) or the positive control for 30 min at 37±1° C. After the pre-incubation, 25 μL S-mephenytoin (final concentration 200 μM) is added and incubated another 12 minutes at 37±1° C. for substrate metabolism. The reactions are terminated by addition of 100 μL of ice-cold acetonitrile containing an internal standard (buspirone). Precipitated proteins are removed by centrifugation at 3500 rpm for 10 minutes at 4° C. (Allegra 25R, Beckman Co. Fullerton, CA), then an aliquot of the supernatant is transferred to an assay plate.

All the samples are assessed using a mass spectrometer (QTrap 5500 quadrupole/ion trap) coupled with a Shimadzu HPLC system following the manufacturer's instructions. The metabolism of S-mephenytoin in human liver microsomes is monitored by LC/MS/MS as representative of CYP2C19 inhibitory activity. The amount of metabolite formed is assessed by the peak area ratio (metabolite/IS) and % inhibition at 10 μM is expressed as a percentage of the metabolite signal reduced compared to the control (i.e. an incubation that contained no inhibitor and represented 100% enzyme activity): % inhibition=(1−A/B)×100%, where A is the metabolite peak area ratio formed in the presence of test compound or inhibitor at 10 μM and B is the metabolite peak area ratio formed without test compound or inhibitor in the incubation.

Example 13: Mouse and Human Protein Binding Assay to Assess Free Drug Concentration This assay can be used to determine the plasma protein binding of the test compound in the plasma of human and animal species using a Rapid Equilibrium Dialysis (RED) device for equilibrium dialysis and LC-MS/MS for sample analysis. Test compound is spiked in. The stock solution of the test compound is prepared at 5 mM concentration. One μL of 5 mM working solution is added into 1000 μL plasma to achieve a final concentration of 5 μM. The spiked plasma is placed on a rocker and gently agitated for approximately 20 minutes. A volume of 300 μL of the plasma sample containing 5 μM test compound from each species is added to designated RED device donor chambers followed by addition of 500 μL of potassium phosphate buffer to the corresponding receiver chambers in duplicate. The RED device is then sealed with sealing tape and shaken at 150 RPM for 4 hours at 37° C. Post-dialysis donor and receiver compartment samples are prepared for LC-MS/MS analysis, including spiking samples with an internal standard for the bioanalytical analysis. Warfarin and propranolol are purchased from Sigma-Aldrich (St. Louis, MO), and used as positive controls for low and high plasma protein binding, respectively.

All the samples are analyzed using an Agilent Technologies 6430 Triple Quad LC/MS system. The HPLC system consists of an Agilent 1290 Infinity Liquid Chromatograph coupled to an autosampler (Agilent 1290 Infinity LC Injector HTC), and a Phenomenex Gemini-NX, C18, 3.0 μm or Phenomenex Lunar, C8, 5.0 μM HPLC column (Phenomenex, Torrance, CA), eluting with a mobile phase gradient consisting of Solution A (0.1% formic acid water) and Solution B (0.1% formic acid acetonitrile). The column temperature is maintained at 40° C. All the analytes are detected with positive-mode electrospray ionization (ES+). The percentage of the test compound bound to plasma is calculated following Equations 3 and 4.

Equation 3

$$\text{\% Free test compound} = \frac{\text{Peak ratio}\left(\frac{\text{test compound}}{\text{Internal standard}}\right)\text{, receiver component}}{\text{Peak ratio}\left(\frac{\text{test compound}}{\text{Internal standard}}\right)\text{, donor compartment}} * 100$$

$$\text{\% Plasma protein bound test compound} = 100 - \text{\% Free test compound} \qquad \text{Equation 4}$$

Example 14: HERG (Automated Patch-Clamp) Assay

The human ether-a-go-go related gene (hERG) encodes the voltage gated potassium channel in the heart (IKr) which is involved in cardiac repolarization. Inhibition of the hERG causes QT interval prolongation and can lead to potential fatal events in humans. It is thus important to assess hERG inhibition early in drug discovery. A hERG automated patch-clamp assay is done using a hERG CHO-K1 cell line using an incubation time of 5 min. The degree of hERG inhibition (%) is obtained by measuring the tail current amplitude, which is induced by a one second test pulse to −40 mV after a two second pulse to +20 mV, before and after drug incubation (the current difference is normalized to control and multiplied by 100 to obtain the percent of inhibition). The percent hERG inhibition is measured in the presence of 10 μM test compound.

Example 15: Rat Oral Exposure (% F)

A pharmacokinetic profile for a test compound is measured by single dosing in jugular vein cannulated male Sprague-Dawley rats. Animal weights are typically over 200 grams, and animals are allowed to acclimate to their new environment for at least 3 days prior to the initiation of any studies. One set of animals is dosed intravenously (IV) with test compound (2 mg/kg in 20% HP-beta-CD or 20% Captisol, pH adjusted to -4 by citric acid). The IV dosing solution concentration is 0.4 mg/mL test compound. Blood is sampled at 5 minutes, 15 minutes, 30 minutes, 90 minutes, 360 minutes, and 24 hours following IV dosing. Another set of animals is dosed oral (po) with test compound (10 mg/kg in 20% HP-beta-CD or 20% Captisol, pH adjusted to -4 by citric acid). The oral dosing solution concentration is 1 mg/mL test compound. Blood is sampled at 15 minutes, 30 minutes, 90 minutes, 180 minutes, 360 minutes and 24 hours following oral (po) dosing. Blood samples (~0.2 mL/sample) is collected via the jugular vein, placed in tubes containing EDTA-K2 and stored on ice until centrifuged. The blood samples are centrifuged at approximately 6800 g for 6 minutes at 2-8° C. and the resulting plasma is separated and stored frozen at approximately −80° C.

The plasma samples are analyzed using an Agilent Technologies 6430 Triple Quad LC/MS system, following the manufacturer's instructions. The analytes are detected with positive-mode electrospray ionization (ES+). A standard curve for each test compound is generated and used to measure test compound concentrations in the rat plasma samples. Based on the time course sampling, an area under the curve is calculated for the oral dose group and the intravenous dose group. Percentage rat bioavailability is calculated based on equation 5.

$$\% F(\text{rat}) = \frac{AUC_{po} * \text{Dose}_{IV}}{AUC_{IV} * \text{Dose}_{po}}, \quad \text{Equation 5}$$

where F is bioavailability, $AUC_{po}$ is area under curve of oral drug, $AUC_{IV}$ is area under curve of intravenous drug, $\text{Dose}_{IV}$ is the intravenous dose and $\text{Dose}_{po}$ is the oral dose.

What is claimed is:

1. A compound having the formula:

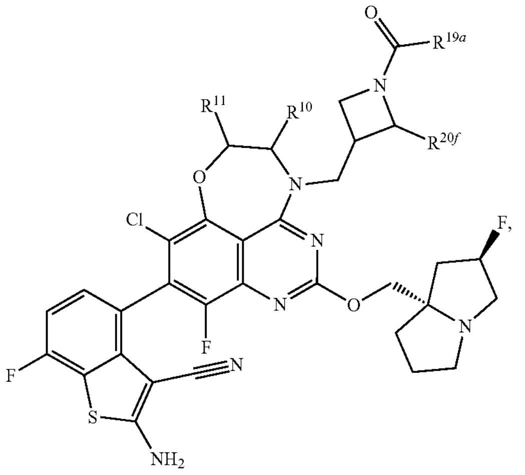

or a pharmaceutically acceptable salt or solvate thereof, wherein:

$R^{10}$ and $R^{11}$ are independently selected from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(=O)(=NR^{12})N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$;

$R^{19a}$ is imidazol-1-yl optionally substituted with one or more $R^{20}$;

$R^{20f}$ is selected from hydrogen and $R^{20}$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one or more $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one or more $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, $=NR^{22}$, $=C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —$S(=O)(=NR^{22})N(R^{22})(R^{23})$; wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, —$OR^{22}$, —$SR^{22}$, —$N(R^{22})(R^{23})$, $=NR^{22}$, $=C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —$S(=O)(=NR^{22})N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one or more substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle); and $R^{23}$ is independently selected at each occurrence from hydrogen and $C_{1-6}$ alkyl; or $R^{22}$ and $R^{23}$ attached to the same nitrogen atom form 3- to 10 membered heterocycle.

2. The compound, salt, or solvate of claim 1, wherein $R^{10}$ is selected from hydrogen, $C_{1-4}$ alkyl, $C_{2-3}$ alkenyl, $C_{2-3}$ alkynyl, $C_{3-5}$ carbocycle, and 3- to 5-membered heterocycle, wherein $C_{1-4}$ alkyl, $C_{2-3}$ alkenyl, $C_{2-3}$ alkynyl, $C_{3-5}$ carbocycle, and 3- to 5-membered heterocycle are optionally substituted with one or more substituents independently selected from halogen, —OH, and —CN.

3. The compound, salt, or solvate of claim 1, wherein $R^{11}$ is hydrogen.

4. The compound, salt, or solvate of claim 1, wherein $R^{19a}$ is selected from

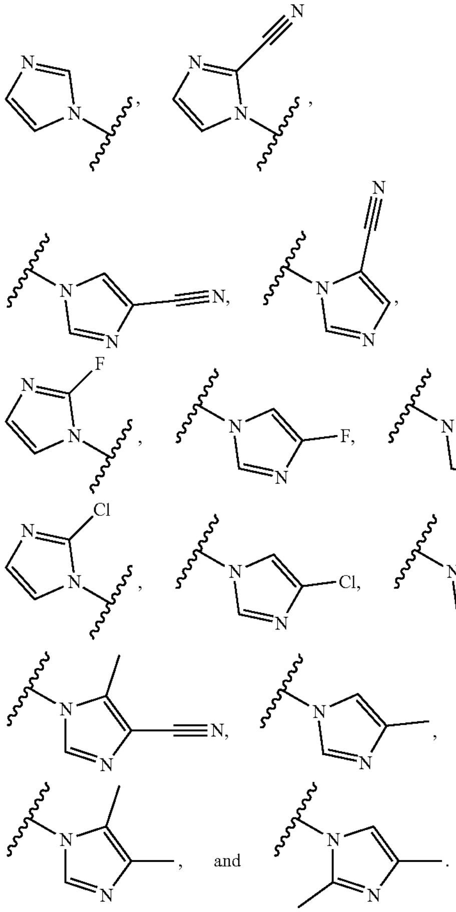

and

5. The compound, salt, or solvate of claim 1, wherein $R^{20f}$ is selected from hydrogen, halogen, —OH, —CN, $C_{1-6}$ alkyl, and $C_{3-6}$ cycloalkyl, wherein $C_{1-6}$ alkyl and $C_{3-6}$ cycloalkyl are optionally substituted with one or more substituents independently selected from halogen, —OH, —CN, $C_{1-3}$ alkyl, $C_{1-3}$ haloalkyl, and $C_{3-6}$ cycloalkyl.

6. The compound, salt, or solvate of claim 1, wherein the compound is selected from:

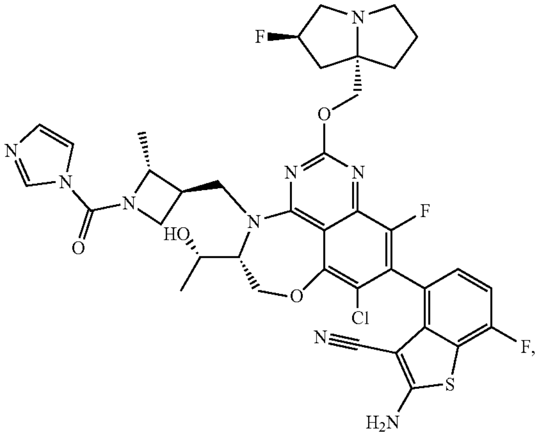

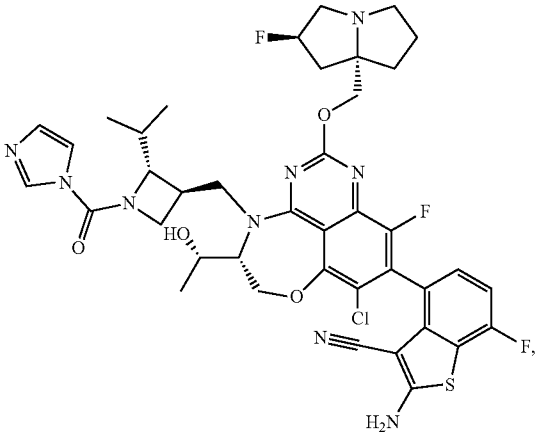

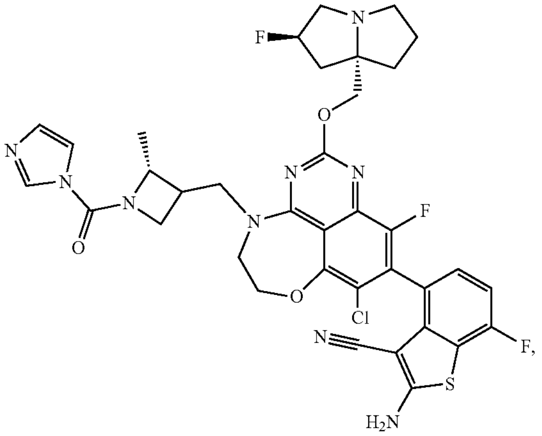

-continued
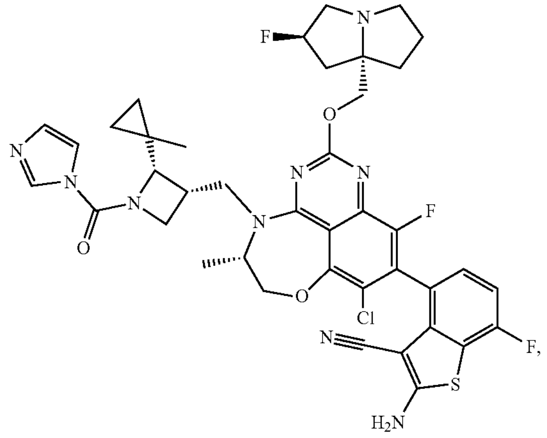
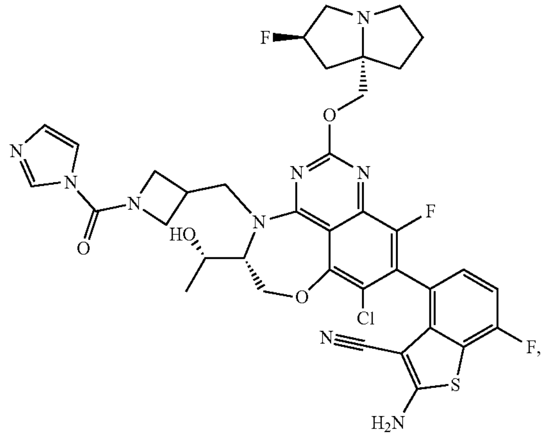
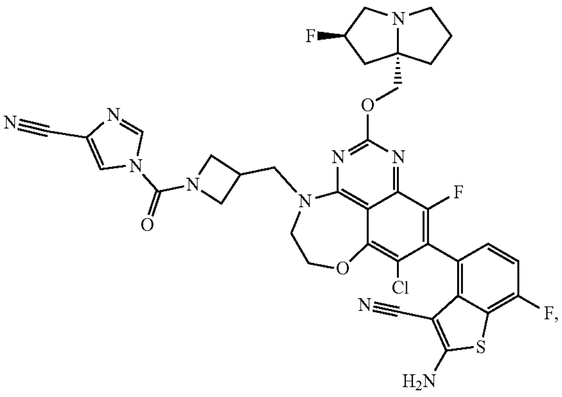
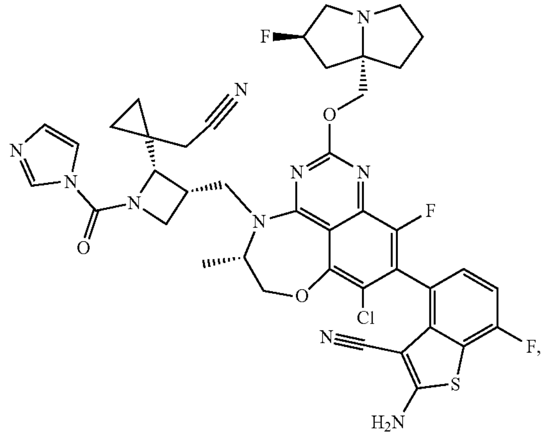
-continued
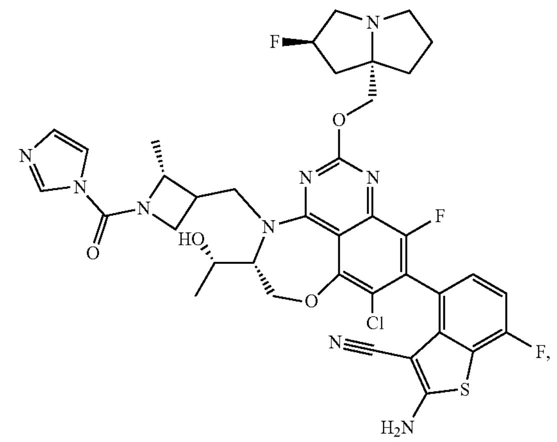
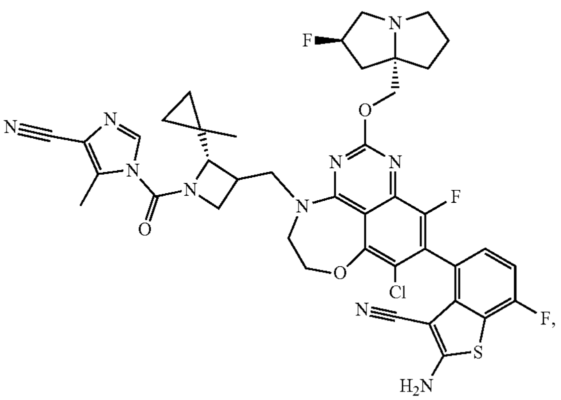
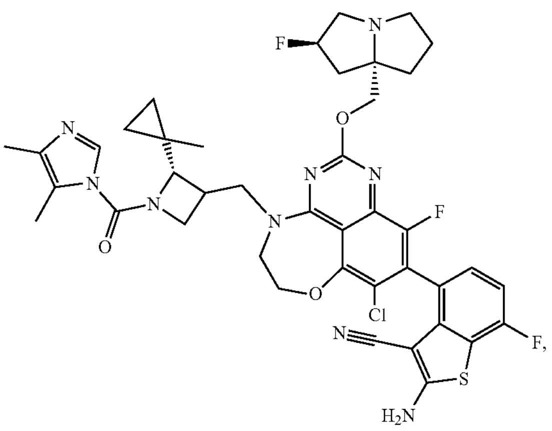
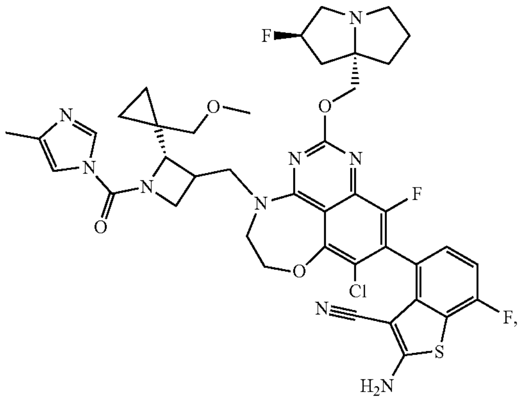
and -continued

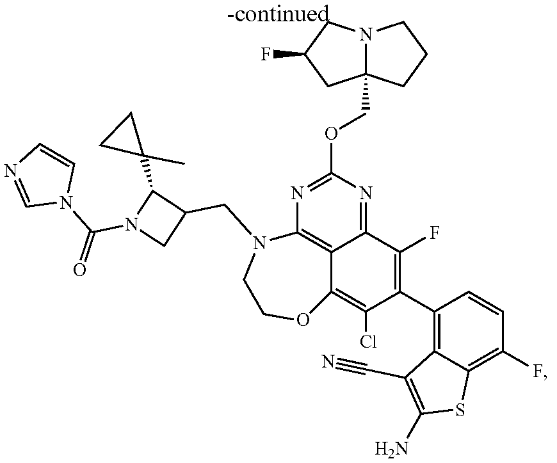

or a pharmaceutically acceptable salt or solvate thereof.

7. The compound, salt, or solvate of claim 1, wherein the compound is

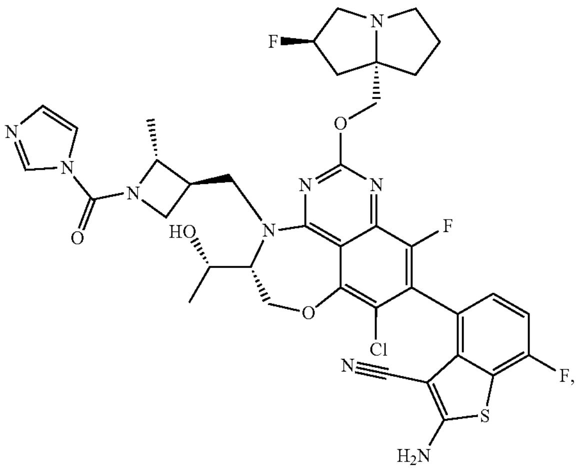 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1C[C@H]1CN(C(=O)n2ccnc2)[C@@H]1C]

or a pharmaceutically acceptable salt or solvate thereof.

8. The compound, salt, or solvate of claim 1, wherein the compound is

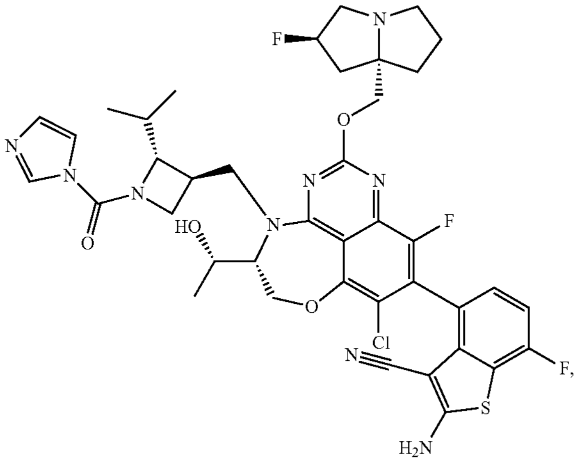 [SMILES: CC(C)[C@@H]1[C@@H](CN2c3nc(OC[C@@]45CCCN4C[C@H](F)C5)nc4c(F)c(-c5ccc(F)c6sc(N)c(C#N)c56)c(Cl)c(c34)OC[C@@H]2[C@H](C)O)CN1C(=O)n1ccnc1]

or a pharmaceutically acceptable salt or solvate thereof.

9. The compound, salt, or solvate of claim 1, wherein the compound is

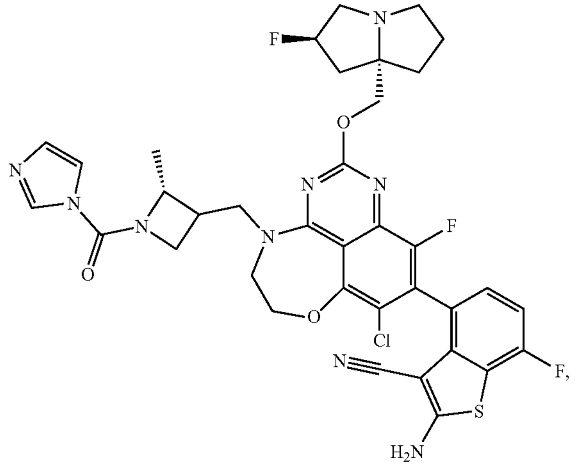 [SMILES: C[C@@H]1C(CN2CCOc3c(Cl)c(-c4ccc(F)c5sc(N)c(C#N)c45)c(F)c4nc(OC[C@@]56CCCN5C[C@H](F)C6)nc2c34)CN1C(=O)n1ccnc1]

or a pharmaceutically acceptable salt or solvate thereof.

10. The compound, salt, or solvate of claim 1, wherein the compound is

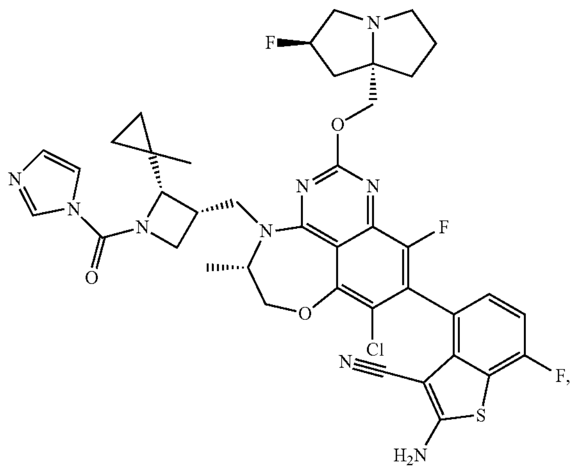 [SMILES: C[C@H]1COc2c(Cl)c(-c3ccc(F)c4sc(N)c(C#N)c34)c(F)c3nc(OC[C@@]45CCCN4C[C@H](F)C5)nc(c23)N1C[C@@H]1CN(C(=O)n2ccnc2)[C@@H]1C1(C)CC1]

or a pharmaceutically acceptable salt or solvate thereof.

11. The compound, salt, or solvate of claim 1, wherein the compound is

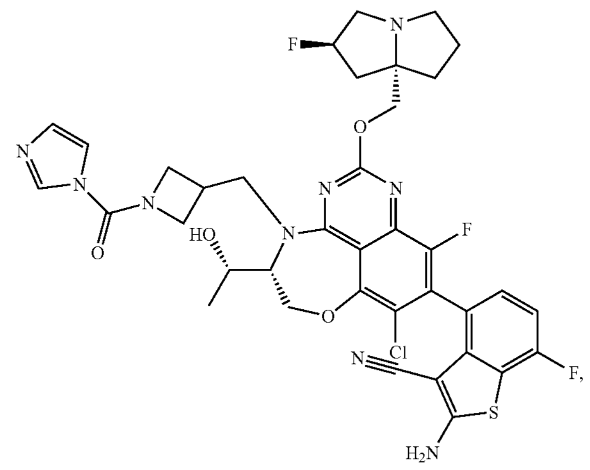 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1CC1CN(C(=O)n2ccnc2)C1]

or a pharmaceutically acceptable salt or solvate thereof.

12. The compound, salt, or solvate of claim 1, wherein the compound is

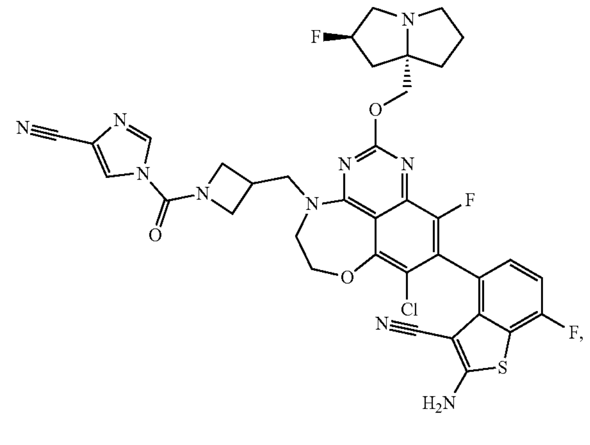 [SMILES: N#Cc1cn(C(=O)N2CC(CN3CCOc4c(Cl)c(-c5ccc(F)c6sc(N)c(C#N)c56)c(F)c5nc(OC[C@@]67CCCN6C[C@H](F)C7)nc3c45)C2)cn1]

or a pharmaceutically acceptable salt or solvate thereof.

13. The compound, salt, or solvate of claim 1, wherein the compound is

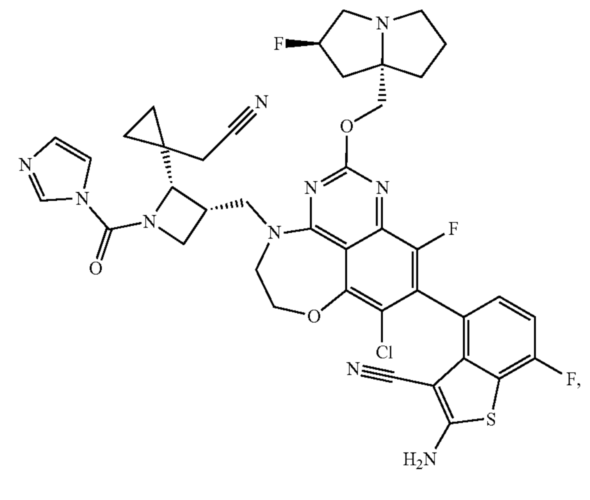 [SMILES: N#CCC1([C@@H]2[C@H](CN3CCOc4c(Cl)c(-c5ccc(F)c6sc(N)c(C#N)c56)c(F)c5nc(OC[C@@]67CCCN6C[C@H](F)C7)nc3c45)CN2C(=O)n2ccnc2)CC1]

or a pharmaceutically acceptable salt or solvate thereof.

14. The compound, salt, or solvate of claim 1, wherein the compound is

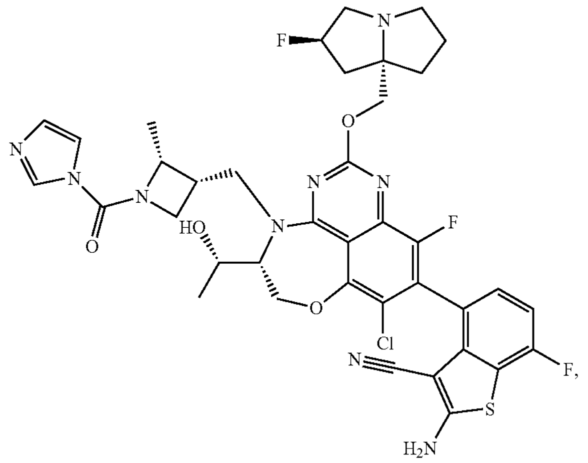 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1C[C@@H]1CN(C(=O)n2ccnc2)[C@@H]1C]

or a pharmaceutically acceptable salt or solvate thereof.

15. The compound, salt, or solvate of claim 1, wherein the compound is

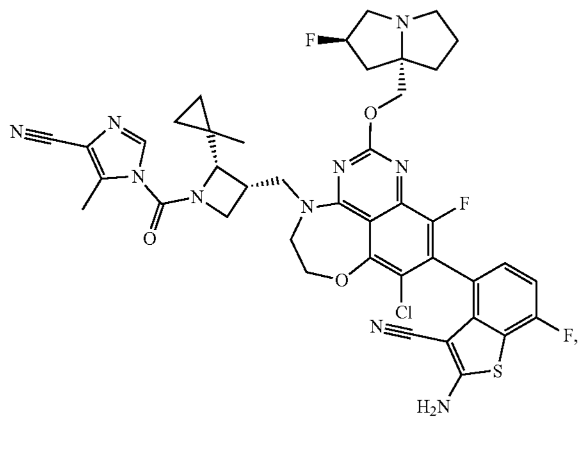 [SMILES: Cc1c(C#N)ncn1C(=O)N1C[C@@H](CN2CCOc3c(Cl)c(-c4ccc(F)c5sc(N)c(C#N)c45)c(F)c4nc(OC[C@@]56CCCN5C[C@H](F)C6)nc2c34)[C@H]1C1(C)CC1]

or a pharmaceutically acceptable salt or solvate thereof.

16. The compound, salt, or solvate of claim 1, wherein the compound is

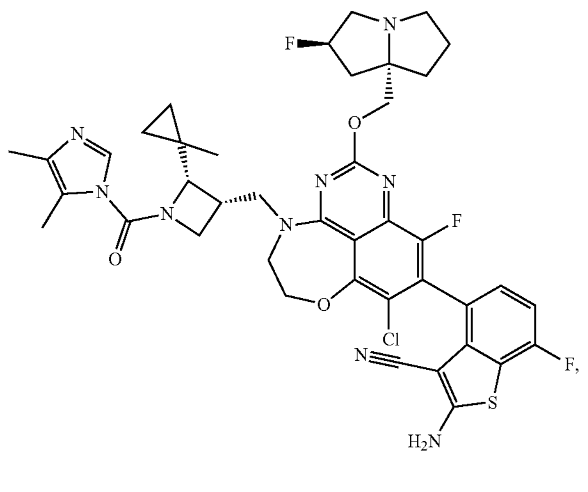 [SMILES: Cc1ncn(C(=O)N2C[C@@H](CN3CCOc4c(Cl)c(-c5ccc(F)c6sc(N)c(C#N)c56)c(F)c5nc(OC[C@@]67CCCN6C[C@H](F)C7)nc3c45)[C@H]2C2(C)CC2)c1C]

or a pharmaceutically acceptable salt or solvate thereof.

17. The compound, salt, or solvate of claim 1, wherein the compound is

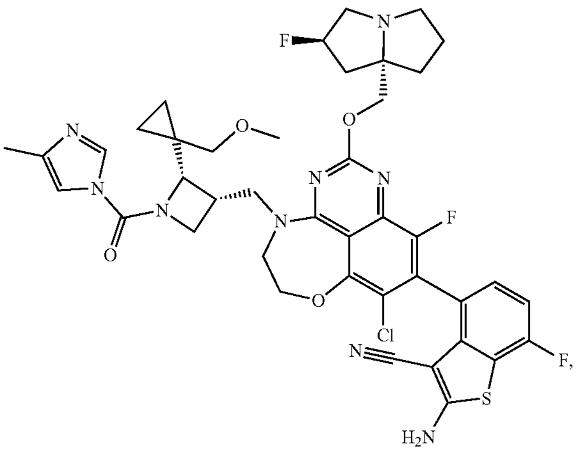 [SMILES: COCC1([C@@H]2[C@H](CN3CCOc4c(Cl)c(-c5ccc(F)c6sc(N)c(C#N)c56)c(F)c5nc(OC[C@@]67CCCN6C[C@H](F)C7)nc3c45)CN2C(=O)n2cnc(C)c2)CC1]

or a pharmaceutically acceptable salt or solvate thereof.

18. The compound, salt, or solvate of claim 1, wherein the compound is

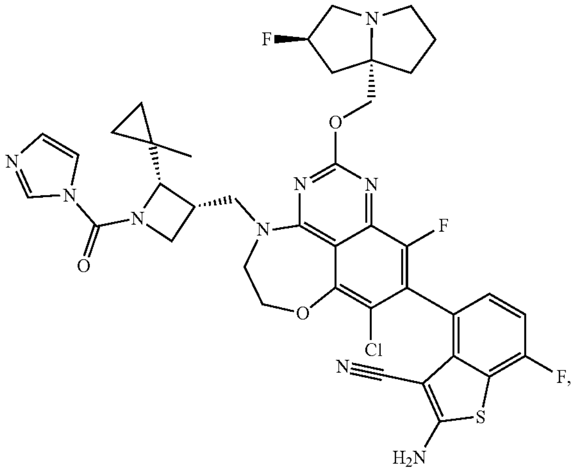 [SMILES: CC1([C@@H]2[C@H](CN3CCOc4c(Cl)c(-c5ccc(F)c6sc(N)c(C#N)c56)c(F)c5nc(OC[C@@]67CCCN6C[C@H](F)C7)nc3c45)CN2C(=O)n2ccnc2)CC1]

or a pharmaceutically acceptable salt or solvate thereof.

19. A pharmaceutical composition comprising a compound of claim 1, or a pharmaceutically acceptable salt or solvate thereof, and a pharmaceutically acceptable excipient.

20. A method of treating cancer comprising a K-Ras G12S mutant protein in a subject in need thereof, comprising administering to the subject a therapeutically effective amount of a compound having the formula:

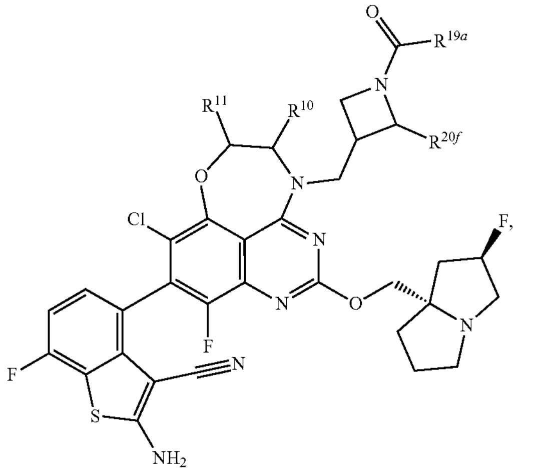

or a pharmaceutically acceptable salt or solvate thereof, wherein:

$R^{10}$ and $R^{11}$ are independently selected from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(=O)(=NR^{12})N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more $R^{20}$;

$R^{19a}$ is imidazol-1-yl optionally substituted with one or more $R^{20}$;

$R^{20f}$ is selected from hydrogen and $R^{20}$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one or more $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one or more $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —C(O)$OR^{22}$, —OC(O)$N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —S(=O)(=$NR^{22}$)$N(R^{22})(R^{23})$; wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one or more substituents independently selected from halogen, oxo, —CN, $C_{1-6}$ alkyl, $C_{1-6}$ haloalkyl, $C_{1-6}$ hydroxyalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —C(O)$OR^{22}$, —OC(O)$N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —S(=O)(=$NR^{22}$)$N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one or more substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle); and $R^{23}$ is independently selected at each occurrence from hydrogen and $C_{1-6}$ alkyl; or $R^{22}$ and $R^{23}$ attached to the same nitrogen atom form 3- to 10 membered heterocycle.

* * * * *